(12) United States Patent  
Tanaka et al.

(10) Patent No.: US 11,365,192 B2  
(45) Date of Patent: Jun. 21, 2022

(54) PYRIDINE COMPOUND SUBSTITUTED WITH AZOLE

(71) Applicant: TAISHO PHARMACEUTICAL CO., LTD., Tokyo (JP)

(72) Inventors: Hiroaki Tanaka, Tokyo (JP); Madoka Kawamura, Tokyo (JP); Makoto Hamada, Tokyo (JP); Yohei Kobashi, Tokyo (JP); Yuji Ito, Tokyo (JP); Kazuaki Suzuki, Tokyo (JP); Ayako Bohno, Tokyo (JP); Kosuke Funayama, Tokyo (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 31 days.

(21) Appl. No.: 16/637,595

(22) PCT Filed: Aug. 10, 2018

(86) PCT No.: PCT/JP2018/030456  
§ 371 (c)(1),  
(2) Date: Feb. 7, 2020

(87) PCT Pub. No.: WO2019/031618  
PCT Pub. Date: Feb. 14, 2019

(65) Prior Publication Data  
US 2021/0122741 A1 Apr. 29, 2021

(30) Foreign Application Priority Data  
Aug. 10, 2017 (JP) .............................. JP2017-171584

(51) Int. Cl.  
C07D 405/14 (2006.01)  
A61P 13/12 (2006.01)  
(Continued)

(52) U.S. Cl.  
CPC ............ *C07D 405/14* (2013.01); *A61P 13/12* (2018.01); *C07D 401/04* (2013.01); *C07D 401/14* (2013.01); *C07D 409/14* (2013.01)

(58) Field of Classification Search  
CPC .. C07D 401/04; C07D 401/14; C07D 405/14; C07D 409/14; A61P 13/12  
(Continued)

(56) References Cited

U.S. PATENT DOCUMENTS

| | | |
|---|---|---|
| 2004/0110830 A1 | 6/2004 | Sato et al. |
| 2006/0189673 A1 | 8/2006 | Mochizuki et al. |
| 2016/0157489 A1 | 6/2016 | Shioda et al. |

FOREIGN PATENT DOCUMENTS

| | | |
|---|---|---|
| EP | 1650206 A1 | 4/2006 |
| JP | 2004-262890 A | 9/2004 |

(Continued)

OTHER PUBLICATIONS

Harder, D.R., et al., "Role of Cytochrome P-450 Enzymes and Metabolites of Arachidonic Acid in the Control of Vascular Tone," *Journal of Vascular Research*, vol. 32, p. 79-92, 1955.

(Continued)

Primary Examiner — Kahsay Habte  
(74) Attorney, Agent, or Firm — Finnegan, Henderson, Farabow, Garrett & Dunner, LLP

(57) ABSTRACT

The present invention provides a compound represented by formula [I] shown below or a pharmaceutically acceptable salt thereof that has an inhibitory effect on 20-HETE producing enzyme.

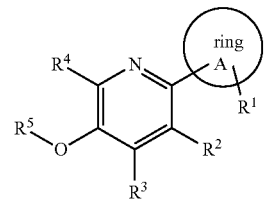

[I]

(in formula [I] above, the structure represented by formula [II] below:

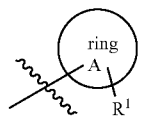

[II]

represents any of the structures represented by formula group [III] below:

[III]

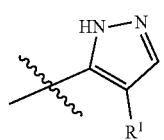

[III-1]

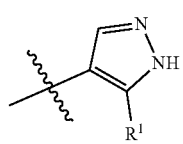

[III-2]

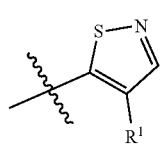

[III-3]

(Continued)

-continued

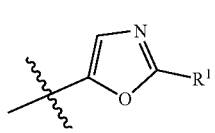

[III-4]

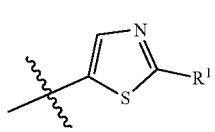

[III-5]

$R^1$, $R^2$, $R^3$, and $R^4$ independently represent a hydrogen atom, a fluorine atom, methyl, or the like, $R^5$ represents any of the structures represented by formula group [IV]:

[IV]

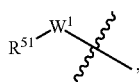

[IV-1]

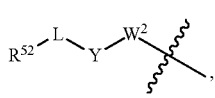

[IV-2]

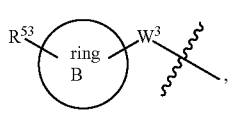

[IV-3]

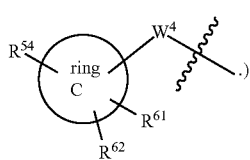

[IV-4]

23 Claims, No Drawings

(51) Int. Cl.
C07D 401/04 (2006.01)
C07D 401/14 (2006.01)
C07D 409/14 (2006.01)

(58) Field of Classification Search
USPC .................................................. 514/318
See application file for complete search history.

(56) References Cited

FOREIGN PATENT DOCUMENTS

| JP | 2012-527467 A | 11/2012 |
|---|---|---|
| JP | 2016-025878 | 12/2016 |
| WO | WO 01/32164 A1 | 5/2001 |
| WO | WO 03/022821 A1 | 3/2003 |
| WO | WO 2004/092163 A1 | 10/2004 |
| WO | WO 2005/012293 A1 | 2/2005 |
| WO | WO 2010/135360 A1 | 11/2010 |
| WO | WO 2015/016372 A1 | 2/2015 |
| WO | WO 2017/141927 A1 | 8/2017 |

OTHER PUBLICATIONS

McGiff, J. C. et al., "20-HETE and the kidney: resolution of old problems and new beginnings," *The American Journal of Physiology*, vol. 277, p. R607-R623, 1999.

Roman, R. J., "P-450 Metabolites of Arachidonic Acid in the Control of Cardiovascular Function," *Physiological Reviews*, vol. 82, p. 131-185, 2002.

Park, F. et al., "Chronic blockade of 20-HETE synthesis reduces polycystic kidney disease in an orthologous rat model of ARPKD," *American Journal of Physiology Renal Physiology*, vol. 296, p. F575-F582, 2009.

Klawitter, J., et al., "Bioactive lipid mediators in polycystic kidney disease," *Journal of Lipid Research*, vol. 55, p. 1139-1149, 2014.

Translation of Written Opinion of the International Search Authority for International Application No. PCT/JP2018/030456.

Extended European Search Report for European Patent Application No. EP 18843913.7, dated Feb. 23, 2021 (nine pages).

Ciapetti and Giethlen, "Molecular Variations Based on Isosteric Replacements," in The Practice of Medicinal Chemistry, Third Edition (C. G. Wermuth, Ed.) (2008) (pp. 290-342).

Patani, et al., "Bioisosterism: A Rational Approach in Drug Design," *Chem. Rev.*, 96, 3147-76 (1996).

Lassalas, et al., "Structure Property Relationships of Carboxylic Acid Isosteres," *J. Med. Chem.*, 59, 3183-3203 (2016).

PYRIDINE COMPOUND SUBSTITUTED WITH AZOLE

This application is a national stage filing under 35 U.S.C. § 371 of International Application No. PCT/JP2018/030456, filed on Aug. 10, 2018, which claims priority of Japanese Patent Application No. JP 2017-171584, filed on Aug. 10, 2017. The contents of each of these applications are incorporated herein by reference.

TECHNICAL FIELD

The present invention relates to an inhibitor of enzymes that produce 20-hydroxyeicosatetraenoic acid (hereinafter also referred to as "20-HETE"). More specifically, the present invention relates to an azole-substituted pyridine compound which is an inhibitor of 20-HETE producing enzymes.

BACKGROUND ART

Physiologically active substances produced from arachidonic acid conventionally include prostaglandins produced by cyclooxygenase and leukotrienes produced by lipoxygenase; in addition to these, 20-HETE produced from arachidonic acid by enzymes belonging to cytochrome P450 have recently been shown to display diverse functions in a living body. So far, 20-HETE has been demonstrated to control vascular tone or evoke cell growth in cerebral blood vessels and key organs such as kidney, suggesting that 20-HETE plays an important physiological role in a living body while being deeply involved in the pathology of various cerebro-vascular diseases, kidney diseases, cardio-vascular diseases, and others (Non Patent Literatures 1 to 3). Furthermore, it has been proven in recent years that 20-HETE is involved in the onset of polycystic kidney disease. Polycystic kidney disease is a hereditary cystic kidney disease, which is classified into autosomal dominant polycystic kidney disease and autosomal recessive polycystic kidney disease, in which a great number of cysts are formed in the kidney to cause impaired renal function. It is suggested that when administered to pathologic animals developing polycystic kidney disease, 20-HETE inhibitors not only block intracellular growth signals but also exhibit an ameliorating effect on renal cysts (Non Patent Literature 4). Moreover, increased renal volume and decreased renal function are shown to correlate with increased plasma 20-HETE levels in patients with autosomal dominant polycystic kidney disease, suggesting that 20-HETE is associated with the progression of polycystic kidney disease (Non Patent Literature 5).

Previously reported inhibitors of 20-HETE producing enzymes include, for example, a hydroxyformamidine derivative (Patent Literature 1), a heterocycle derivative as a compound having the phenylazoleskeleton (Patent Literature 2), and a phenylazole compound (Patent Literature 3). Patent Literature 2 discloses a heteroaryl-substituted pyridine compound that is substituted with heteroaryl such as pyrazolyl at the 3-position of pyridine. However, the compound of the present invention or an azole-substituted pyridine compound that is a compound substituted with azole such as pyrazolyl at the 2-position of pyridine is yet to be disclosed.

CITATION LIST

Patent Literature

PTL 1: WO01/032164
PTL 2: WO03/022821
PTL 3: WO2004/092163

Non Patent Literature

NPL 1: Journal of Vascular Research, Vol. 32, p. 79, 1995
NPL 2: The American Journal of Physiology, Vol. 277, p. R607, 1999
NPL 3: Physiological Reviews, Vol. 82, p. 131, 2002
NPL 4: American Journal of Physiology Renal Physiology, Vol. 296, p. F575, 2009
NPL 5: Journal of Lipid Research, Vol. 55, p. 1139, 2013

SUMMARY OF INVENTION

Technical Problem

An object of the present invention is to provide a novel compound that inhibits 20-HETE producing enzymes.

Solution to Problem

As a result of intensive studies to solve the above problem, the present inventors found that a compound represented by formula [I] shown below (hereinafter also referred to as the compound [I]) has an inhibitory effect on 20-HETE producing enzymes.

The present invention will be described in detail below.

Briefly, the following are embodiments of the present invention.

(1) In one embodiment, the present invention provides a compound represented by formula [I] shown below:

[Formula 1]

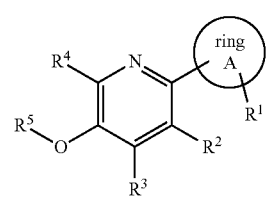

[I]

wherein
the structure represented by formula [II] shown below:

[Formula 2]

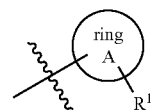

[II]

represents any of the structures represented by formula group [III] shown below:

[Formula 3] [III]

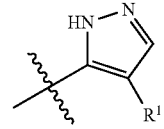

[III-1]

[III-2]

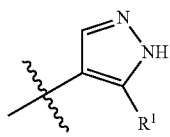

[III-3]

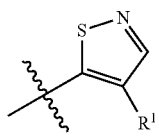

[III-4]

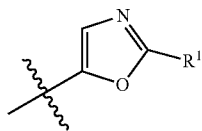

[III-5]

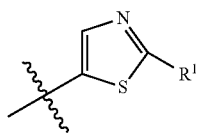

$R^1$ represents a hydrogen atom, a fluorine atom, a chlorine atom, methyl, or difluoromethyl;

$R^2$, $R^3$, and $R^4$ each independently represent a hydrogen atom, a fluorine atom, or methyl;

$R^5$ represents any of the structures represented by formula group [IV] shown below:

[Formula 4]

[IV]

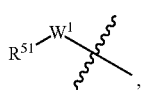

[IV-1]

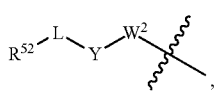

[IV-2]

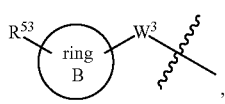

[IV-3]

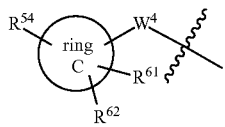

[IV-4]

(A)

when $R^5$ represents the structure represented by formula [IV-1], $R^{51}$ represents any of the structures represented by formula group [V] shown below:

[Formula 5]   [V]

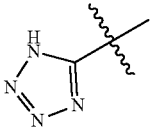

[V-1]

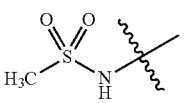

[V-2]

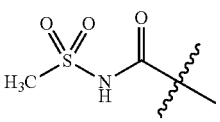

[V-3]

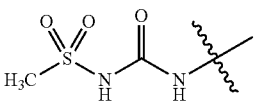

[V-4]

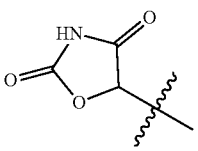

[V-5]

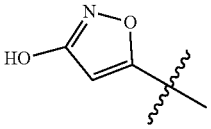

[V-6]

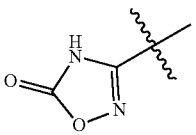

[V-7]

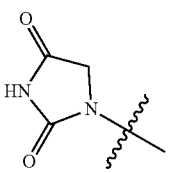

[V-8]

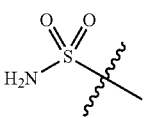

[V-10]

$W^1$ represents $C_{4-10}$ alkanediyl;

(B)

when $R^5$ represents the structure represented by formula [IV-2], $R^{52}$ represents carboxy;

L represents any of the structures represented by formula group [VI] shown below:

[Formula 6]

[VI]

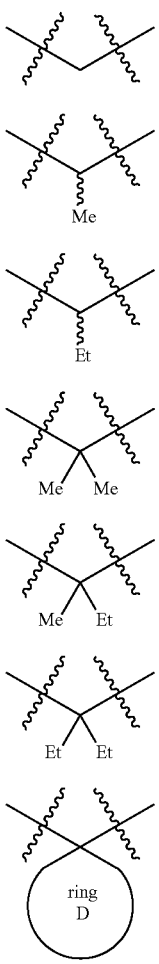

[VI-1]
[VI-2]
[VI-3]
[VI-4]
[VI-5]
[VI-6]
[VI-7]

wherein
ring D represents
(i) $C_{3-6}$cycloalkane,
(ii) 4- to 6-membered saturated oxygen-containing hetero ring,
(iii) 4- to 6-membered saturated sulfur-containing hetero ring (the sulfur atom of the 4- to 6-membered saturated sulfur-containing hetero ring may be substituted with one or two oxo),
(iv) 4- to 6-membered saturated nitrogen-containing hetero ring (the nitrogen atom of the 4- to 6-membered nitrogen-containing hetero ring may be substituted with one $C_{1-4}$alkylcarbonyl);
Y represents the formula —$CH_2$—, the formula —$CMe_2$-, the formula —O—, the formula —NHCO—, the formula —NMeCO—, the formula —CONH—, or the formula —CONMe-;
$W^2$ represents $C_{2-10}$alkanediyl, wherein one of the carbon atoms that constitute the $C_{2-10}$ alkanediyl represented by $W^2$ may be replaced with an oxygen atom;
(C)
when $R^5$ represents the structure represented by formula [IV-3] above,
$R^{53}$ represents carboxy, carboxymethyl, or carboxymethoxy, wherein the methylene moiety of the carboxymethyl or carboxymethoxy that is represented by $R^{53}$ may be replaced with a structure selected from structure group α below, structure group α represents any of the structures represented by formula group [VII] below:

[Formula 7]

[VII]

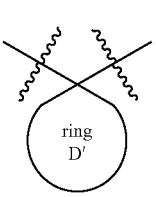

[VII-1]
[VII-2]
[VII-3]

wherein
ring D' represents
(i) $C_{3-6}$cycloalkane,
(ii) 4- to 6-membered saturated oxygen-containing hetero ring,
(iii) 4- to 6-membered saturated sulfur-containing hetero ring (the sulfur atom of the 4- to 6-membered saturated sulfur-containing hetero ring may be substituted with one or two oxo),
(iv) 4- to 6-membered saturated nitrogen-containing hetero ring (the nitrogen atom of the 4- to 6-membered saturated nitrogen-containing hetero ring may be substituted with one $C_{1-4}$alkylcarbonyl);
ring B represents any of the structures represented by formula group [VIII] below:

[Formula 8]   [VIII]

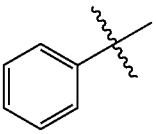

[VIII-1]
[VIII-2]
[VIII-3]

-continued

[VIII-4]
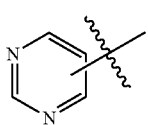

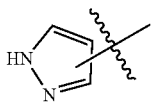
[VIII-5]

[VIII-6]
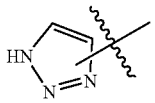

[VIII-7]
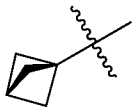

$W^3$ represents $C_{4-8}$alkanediyl, the formula —O—$W^{31}$—, or the formula —$SO_2$—$W^{33}$—, wherein $W^{31}$ represents $C_{3-7}$alkanediyl, $W^{33}$ represents $C_{3-7}$alkanediyl;

(D)
when $R^5$ represents the structure represented by formula [IV-4] above,
ring C represents
(a) $C_{3-6}$ cycloalkyl,
(b) 4- to 6-membered saturated nitrogen-containing heterocyclyl,
(c) phenyl,
(d) pyridyl,
(e) pyrazolyl,
(l) triazolyl,
(g) tetrahydronaphthyl,
(h) chromanyl,
(j) indazolyl,
(k) tetrahydroisoquinolyl,
(m) 2-oxotetrahydroisoquinolyl,
(n) the structure represented by formula [IX-1] below,
(p) the structure represented by formula [IX-2] below,
(q) the structure represented by formula [IX-3] below, or
(r) the structure represented by formula [IX-4] below:

[Formula 9] [IX]

[IX-1]

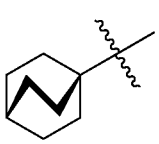
[IX-2]

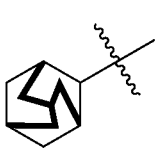
[IX-3]

[IX-4]
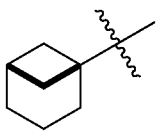

(a) when ring C represents $C_{3-6}$cycloalkyl,
$R^{54}$ is selected from the group consisting of:
(i) carboxy,
(ii) $C_{1-4}$alkylsulfonylamino,
(iii) $C_{1-4}$alkylsulfonyl($C_{1-4}$alkyl)amino, and
(iv) $C_{1-4}$alkyl substituted with carboxy;
$R^{61}$ and $R^{62}$ represent a hydrogen atom;
(b) when ring C represents 4- to 6-membered saturated nitrogen-containing heterocyclyl,
$R^{54}$ is selected from the group consisting of:
(i) $C_{1-4}$ alkylcarbonyl substituted with carboxy,
(ii) $C_{1-4}$ alkylcarbonyl substituted with sulfamoyl,
(iii) $C_{1-4}$ alkylcarbonyl substituted with $C_{1-4}$ alkylsulfonylamino,
(iv) phenylmethylcarbonyl substituted with carboxy,
(v) phenylcarbonyl substituted with sulfamoyl,
(vi) dihydopyridinylcarbonyl substituted with oxo,
(vii) phenylsulfonyl substituted with carboxy,
(viii) mono$C_{1-4}$ alkylaminocarbonyl substituted with carboxy,
(ix) the structure represented by formula [X-1] below, which is substituted with carboxy,
(x) the structure represented by formula [X-2] below, which is substituted with carboxy,
(xi) the structure represented by formula [X-3] below, which is substituted with carboxy,

[Formula 10] [X]

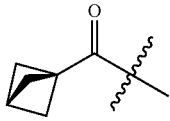
[X-1]

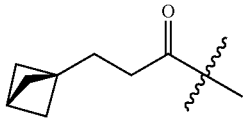
[X-2]

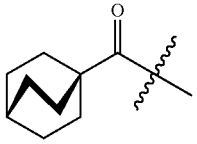
[X-3]

when position α of the carboxy of the $C_{1-4}$alkylcarbonyl substituted with carboxy, the $C_{1-4}$alkylsulfonyl substituted with carboxy, or the mono$C_{1-4}$alkylaminocarbonyl substituted with carboxy is a methylene moiety, said methylene moiety may be replaced with a structure selected from structure group α above;
wherein $R^{61}$ and $R^{62}$ represent a hydrogen atom;
(c) when ring C is phenyl,
$R^{54}$ is selected from the group consisting of:
(i) carboxy,
(ii) carbamoyl, (iii) monoC$_{1-4}$ alkylaminocarbonyl (the C$_{1-4}$ alkyl of the monoC$_{1-4}$ alkylaminocarbonyl may be substituted with one hydroxy),
(iv) monoC$_{1-4}$ alkylaminosulfonyl (the C$_{1-4}$ alkyl of the monoC$_{1-4}$alkylaminosulfonyl may be substituted with one indolyl),
(v) di(C$_{1-4}$ alkyl)aminosulfonyl (one C$_{1-4}$ alkyl of the di(C$_{1-4}$ alkyl)aminosulfonyl may be substituted with one phenyl, and the phenyl may be substituted with one monoC$_{1-4}$ alkylaminosulfonyl),
(vi) phenylaminosulfonyl (the phenyl of the phenylaminosulfonyl may be substituted with one fluorine atom),
(vii) C$_{1-4}$ alkylsulfonylamino,
(viii) C$_{1-4}$ alkylsulfonylaminocarbonyl,
(ix) C$_{1-4}$ alkylsulfonyl(C$_{1-4}$ alkyl)aminocarbonyl,
(x) C$_{1-4}$ alkyl substituted with carboxy (when position α of the carboxy of the C$_{1-4}$ alkyl substituted with carboxy is a methylene moiety, said methylene moiety may be replaced with a structure selected from structure group α above),
(xi) C$_{1-4}$ alkyl substituted with methylsulfonylaminocarbonyl,
(xii) C$_{1-4}$ alkyl substituted with trifluoromethylsulfonylamino,
(xiii) C$_{1-4}$ alkyl substituted with methylsulfonyl(methyl)aminocarbonyl,
(xiv) C$_{1-4}$ alkyl substituted with monoC$_{1-4}$ alkylaminocarbonyl (the C$_{1-4}$ alkyl of the monoC$_{1-4}$ alkylaminocarbonyl of the C$_{1-4}$ alkyl substituted with monoC$_{1-4}$ alkylaminocarbonyl may be substituted with one group selected from the group consisting of hydroxy, C$_{1-4}$ alkoxy, 4- to 6-membered saturated oxygen-containing heterocyclyl, di(C$_{1-4}$ alkyl) amino, and 4- to 6-membered saturated nitrogen-containing heterocyclylcarbonyl),
(xv) C$_{1-4}$ alkyl substituted with di(C$_{1-4}$ alkyl)aminocarbonyl (one C$_{1-4}$ alkyl of the di(C$_{1-4}$ alkyl)aminocarbonyl of the C$_{1-4}$ alkyl substituted with di(C$_{1-4}$ alkyl)aminocarbonyl may be substituted with one hydroxy),
(xvi) C$_{1-4}$ alkyl substituted with 4- to 6-membered saturated oxygen-containing heterocyclylaminocarbonyl,
(xvii) C$_{1-4}$ alkyl substituted with 4- to 6-membered saturated nitrogen-containing heterocyclylcarbonyl (the 4- to 6-membered saturated nitrogen-containing heterocyclyl of the C$_{1-4}$ alkyl substituted with 4- to 6-membered saturated nitrogen-containing heterocyclylcarbonyl may be substituted with one to two groups selected from the group consisting of hydroxy and a fluorine atom),
(xviii) halo-C$_{1-4}$ alkyl substituted with carboxy,
(xix) C$_{2-4}$ alkenyl substituted with carboxy,
(xx) C$_{2-4}$ alkenyl substituted with di(C$_{1-4}$ alkyl)aminocarbonyl,
(xxi) C$_{3-6}$ cycloalkyl substituted with carboxy,
(xxii) C$_{3-6}$ cycloalkyl substituted with di(C$_{1-4}$ alkyl)aminocarbonyl,
(xxiii) 4- to 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl (the methylene moiety at position α of the carboxy of the pyrazolyl substituted with carboxymethyl may be replaced with a structure selected from structure group c above),
(xxviii) pyrimidinyl substituted with carboxy,
(xxix) pyrazinyl substituted with carboxy,
(xxx) 2-oxodihydropyridinyl substituted with carboxymethyl (the methylene moiety at position α of the carboxy of the 2-oxodihydropyridinyl substituted with carboxymethyl may be replaced with a structure selected from structure group c above),
(xxxi) monoC$_{1-4}$ alkylaminocarbonyl substituted with carboxy (the C$_{1-4}$ alkyl of the monoC$_{1-4}$ alkylaminocarbonyl substituted with carboxy may be substituted with one group selected from the group consisting of phenyl and benzyl, and when position α of the carboxy of the monoC$_{1-4}$ alkylaminocarbonyl substituted with carboxy is a methylene moiety, said methylene moiety may be replaced with a structure selected from formula group α above),
(xxxii) phenylC$_{1-4}$ alkylaminocarbonyl substituted with carboxy,
(xxxiii) monoC$_{1-4}$ alkylaminocarbonyl substituted with the structure represented by formula [V-6] below,

[Formula 11]

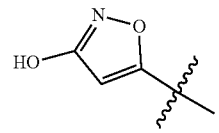

[V-6]

(xxxiv) di(C$_{1-4}$alkyl)aminocarbonyl substituted with carboxy (when position α of the carboxy of the di(C$_{1-4}$alkyl)aminocarbonyl substituted with carboxy is a methylene moiety, said methylene moiety may be replaced with a structure selected from formula group α above),
(xxxv) C$_{3-6}$cycloalkylaminocarbonyl substituted with carboxy,
(xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
(xxxvii) 4- to 6-membered saturated nitrogen-containing heterocyclylcarbonyl substituted with carboxymethyl (the methylene moiety at position α of the carboxy of the 4- to 6-membered saturated nitrogen-containing heterocyclylcarbonyl substituted with carboxymethyl may be replaced with a structure selected from structure group α above),
(xxxviii) the structure represented by formula [XI-1] below, which is substituted with carboxy,
(xxxix) the structure represented by formula [XI-2] below, which is substituted with carboxy,
(xxxx) the structure represented by formula [XI-3] below, which is substituted with carboxy,
(xxxxi) the structure represented by formula [XI-4] below, which is substituted with carboxy,
(xxxxii) the structure represented by formula [XI-5] below, which is substituted with carboxy,
(xxxxiii) the structure represented by formula [XI-6] below, which is substituted with carboxy,

[Formula 12] [XI]

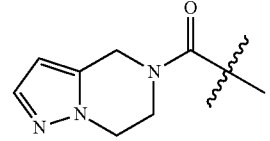

[XI-1]

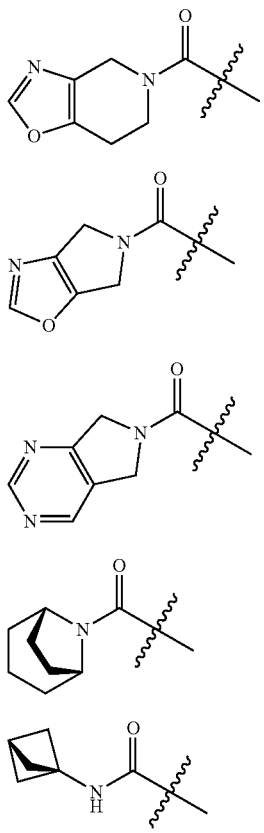

(xxxxiv) $C_{1-4}$ alkylsulfonyl substituted with carboxy (when position α of the carboxy of the $C_{1-4}$ alkylsulfonyl substituted with carboxy is a methylene moiety, said methylene moiety may be replaced with a structure selected from structure group c above),
(xxxxv) mono$C_{1-4}$ alkylaminosulfonyl substituted with carboxy (when position α of the carboxy of the mono$C_{1-4}$ alkylaminosulfonyl substituted with carboxy is a methylene moiety, said methylene moiety may be replaced with a structure selected from structure group c above),
(xxxxvi) di($C_{1-4}$ alkyl)aminosulfonyl substituted with carboxy (when position α of the carboxy of the di($C_{1-4}$ alkyl) aminosulfonyl substituted with carboxy is a methylene moiety, said methylene moiety may be replaced with the structure selected from structure group c above),
(xxxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
(xxxxviii) $C_{1-4}$ alkoxy substituted with carboxy (when position α of the carboxy of the $C_{1-4}$ alkoxy substituted with carboxy is a methylene moiety, said methylene moiety may be replaced with a structure selected from structure group α above),
(xxxxix) hydroxy,
(xxxxx) $C_{1-4}$ alkylsulfonyloxy,
(xxxxxi) $C_{1-4}$ alkyl substituted with hydroxy,
(xxxxxii) halo-$C_{1-4}$ alkyl substituted with hydroxy,
(xxxxxiii) $C_{1-4}$ alkylsulfonyl substituted with hydroxy,
(xxxxxiv) $C_{3-6}$ cycloalkyl substituted with hydroxy (the $C_{3-6}$ cycloalkyl of the $C_{3-6}$ cycloalkyl substituted with hydroxy may be substituted with one group selected from the group consisting of carboxy and di($C_{1-4}$alkyl)aminocarbonyl), or
(xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$ alkylcarbonyl, $C_{1-4}$ alkoxycarbonyl, and di($C_{1-4}$alkyl)aminocarbonyl), wherein $R^{61}$ and $R^{62}$ each independently represent a hydrogen atom, a fluorine atom, a chlorine atom, methyl, methoxy, or methylsulfonyl;
(d) when ring C is pyridyl,
$R^{54}$ is selected from the group consisting of:
(i) carboxy,
(ii) carbamoyl,
(iii) $C_{1-4}$ alkyl substituted with carboxy,
(iv) $C_{1-4}$ alkoxy substituted with carboxy,
(v) mono$C_{1-4}$ alkylaminocarbonyl substituted with carboxy, and
(vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
wherein when position α of the carboxy of the $C_{1-4}$ alkyl substituted with carboxy, the $C_{1-4}$ alkoxy substituted with carboxy, or the mono$C_{1-4}$ alkylaminocarbonyl substituted with carboxy is a methylene moiety, said methylene moiety may be replaced with a structure selected from structure group α above);
and wherein $R^{61}$ and $R^{62}$ represent a hydrogen atom;
(e) when ring C is pyrazolyl,
$R^{54}$ represents carboxy;
wherein $R^{61}$ and $R^{62}$ represent a hydrogen atom;
(f) when ring C is triazolyl,
$R^{54}$ represents $C_{1-4}$ alkyl substituted with carboxy,
wherein when position α of the carboxy of the $C_{1-4}$ alkyl substituted with carboxy is a methylene moiety, said methylene moiety may be replaced with a structure selected from structure group α above;
wherein $R^{61}$ and $R^{62}$ represent a hydrogen atom;
(g) when ring C is tetrahydronaphthyl,
$R^{54}$ is carboxy;
wherein $R^{61}$ and $R^{62}$ represent a hydrogen atom;
(h) when ring C is chromanyl,
$R^{54}$ is carboxy;
wherein $R^{61}$ and $R^{62}$ represent a hydrogen atom;
(j) when ring C is indazolyl,
$R^{54}$ represents $C_{1-4}$ alkyl substituted with carboxy,
wherein when position α of the carboxy of the $C_{1-4}$ alkyl substituted with carboxy is a methylene moiety, said methylene moiety may be replaced with a structure selected from structure group α above;
wherein $R^{61}$ and $R^{62}$ represent a hydrogen atom;
(k) when ring C is tetrahydroisoquinolyl,
$R^{54}$ represents $C_{1-4}$ alkylcarbonyl substituted with carboxy,
wherein position α of the carboxy of the $C_{1-4}$ alkylcarbonyl substituted with carboxy is a methylene moiety, said methylene moiety may be replaced with a structure selected from structure group α above;
wherein $R^{61}$ and $R^{62}$ represent a hydrogen atom;
(m) when ring C is 2-oxotetrahydroisoquinolyl,
$R^{54}$ represents $C_{1-4}$ alkyl substituted with carboxy,
wherein position α of the carboxy of the $C_{1-4}$ alkyl substituted with carboxy is a methylene moiety, said methylene moiety may be replaced with a structure selected from structure group α above;
wherein $R^{61}$ and $R^{62}$ represent a hydrogen atom;

(n) when ring C is the structure represented by formula [IX-1] above, $R^{54}$ is selected from the group consisting of:
(i) carboxy,
(ii) $C_{1-4}$ alkyl substituted with $C_{1-4}$ alkylsulfonylamino, and
(iii) $C_{1-4}$ alkyl substituted with $C_{1-4}$ alkylsulfonyl($C_{1-4}$ alkyl) amino
wherein when $R^{54}$ represents (ii) $C_{1-4}$ alkyl substituted with $C_{1-4}$ alkylsulfonylamino and the $C_{1-4}$ alkyl of the $C_{1-4}$ alkylsulfonylamino of the $C_{1-4}$ alkyl substituted with $C_{1-4}$ alkylsulfonylamino is substituted with one carboxy and if position α of the carboxy of the $C_{1-4}$ alkylsulfonylamino substituted with carboxy is a methylene moiety, said methylene moiety may be replaced with a structure selected from structure group α above;
wherein $R^{61}$ and $R^{62}$ represent a hydrogen atom;

(p) when ring C is the structure represented by formula [IX-2] above,
$R^{54}$ is selected from the group consisting of:
(i) carboxy, and
(ii) $C_{1-4}$ alkyl substituted with carboxy,
wherein when position α of the carboxy of the $C_{1-4}$ alkyl substituted with carboxy is a methylene moiety, said methylene moiety may be replaced with a structure selected from structure group α above;
and wherein $R^{61}$ and $R^{62}$ represent a hydrogen atom;

(q) when ring C is the structure represented by formula [IX-3] above,
$R^{54}$ represents carboxy;
wherein $R^{61}$ and $R^{62}$ represent a hydrogen atom;

(r) when ring C is the structure represented by formula [IX-4] above,
$R^{54}$ represents carboxy;
wherein $R^{61}$ and $R^{62}$ represent a hydrogen atom;
$W^4$ represents a single bond, $C_{1-3}$ alkanediyl, or the formula —O—CH$_2$CH$_2$—; or a pharmaceutically acceptable salt thereof.

(2) In another embodiment, the present invention provides the compound according to (1), wherein as regards $R^5$ of formula [I] above,
(A)
when $R^5$ is the structure represented by formula [IV-1] above,
$R^{51}$ represents any of the structures represented by formula group [V″] below:

[Formula 13]   [V″]

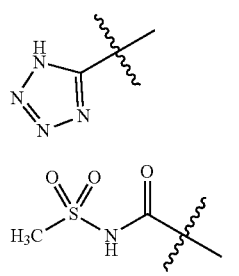

[V-1]

[V-3]

[V-4]

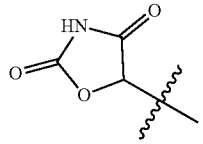

[V-5]

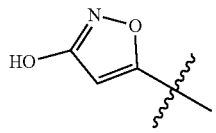

[V-6]

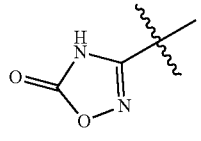

[V-7]

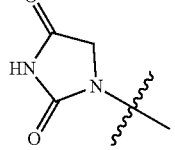

[V-8]

$W^1$ represents $C_{4-10}$ alkanediyl;

(B)
when $R^5$ represents the structure represented by formula [IV-2] above,
$R^{52}$ represents carboxy,
L represents any of the structures represented by formula group [VI'] below:

[Formula 14]
[VI']

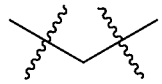

[VI-1]

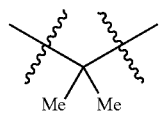

[VI-4]

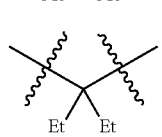

[VI-6]

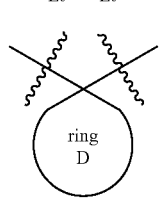

[VI-7]

wherein ring D is $C_{3-6}$cycloalkane, 4- to 6-membered saturated oxygen-containing hetero ring, or 4- to 6-membered saturated nitrogen-containing hetero ring (the nitrogen atom of the 4- to 6-membered saturated nitrogen-containing hetero ring may be substituted with $C_{1-4}$alkylcarbonyl);

Y represents the formula —CH$_2$—, the formula —CMe$_2$-, the formula —O—, the formula —NHCO—, the formula —CONH—, or the formula —CONMe-, W$^2$ represents C$_{2-8}$alkanediyl, wherein one of the carbon atoms that constitute the C$_{2-8}$alkanediyl represented by W$^2$ may be replaced with an oxygen atom;

(C)

when R$^5$ represents the structure represented by formula [IV-3] above,

R$^{53}$ represents carboxy, carboxymethyl, or carboxymethoxy, wherein the methylene moiety of the carboxymethyl and carboxymethoxy represented by R$^{53}$ may be replaced with propane-2,2-diyl;

ring B represents any of the structures represented by formula group [VIII] below:

[Formula 15]     [VIII]

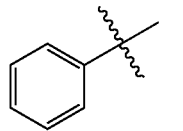
[VIII-1]

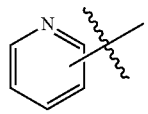
[VIII-2]

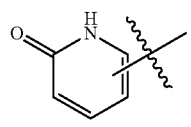
[VIII-3]

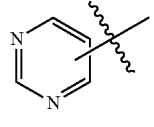
[VIII-4]

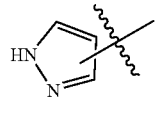
[VIII-5]

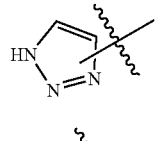
[VIII-6]

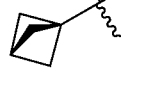
[VIII-7]

W$^3$ represents C$_{4-8}$alkanediyl, or the formula —SO$_2$—W$^{33}$—,

W$^{33}$ represents C$_{3-7}$ alkanediyl;

(D)

when R$^5$ is the structure represented by formula [IV-4] above, ring C represents:
(a) C$_{3-6}$ cycloalkyl,
(b) 4- to 6-memred saturated nitrogen-containing heterocyclyl,
(c) phenyl,
(d) pyridyl,
(e) pyrazolyl,
(g) tetrahydronaphthyl,
(h) chromanyl,
(j) indazolyl,
(n) the structure represented by formula [IX-1] below,
(p) the structure represented by formula [IX-2] below,
(q) the structure represented by formula [IX-3] below, or
(r) the structure represented by formula [IX-4] below,

[Formula 16]     [IX]

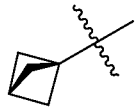
[IX-1]

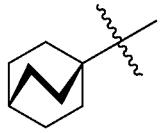
[IX-2]

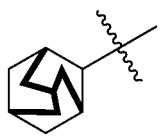
[IX-3]

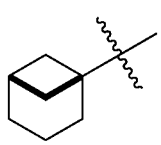
[IX-4]

wherein
(a) when ring C represents C$_{3-6}$cycloalkyl,
R$^{54}$ represents
(i) carboxy or
(iv) C$_{1-4}$alkyl substituted with carboxy,
wherein R$^{61}$ and R$^{62}$ represent a hydrogen atom;

(b) when ring C represents 4- to 6-membered saturated nitrogen-containing heterocyclyl,
R$^{54}$ represents:
(i) C$_{1-4}$ alkylcarbonyl substituted with carboxy (when position α of the carboxy of the C$_{1-4}$ alkylcarbonyl substituted with carboxy is a methylene moiety, said methylene moiety may be replaced with C$_5$cycloalkanediyl),
(ii) C$_{1-4}$ alkylcarbonyl substituted with sulfamoyl,
(iv) phenylmethylcarbonyl substituted with carboxy,
(v) phenylcarbonyl substituted with sulfamoyl,
(vi) dihydropyridinylcarbonyl substituted with oxo,
(vii) phenylsulfonyl substituted with carboxy,
(viii) mono-C$_{1-4}$alkylaminocarbonyl substituted with carboxy (when position α of the carboxy of mono-C$_{1-4}$alkylaminocarbonyl substituted with carboxy is a methylene moiety, said methylene moiety may be replaced with propane-2,2-diyl), and
(x) the structure represented by formula [X-2] below, which is substituted with carboxy:

[Formula 17]

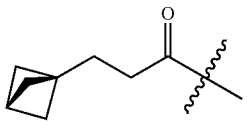

wherein R$^{61}$ and R$^{62}$ represent a hydrogen atom;
(c) when ring C is phenyl,
R$^{54}$ represents:
(i) carboxy,
(ii) carbamoyl,
(iii) mono-C$_{1-4}$alkylaminocarbonyl (the C$_{1-4}$alkyl of the mono-C$_{1-4}$alkylaminocarbonyl may be substituted with one hydroxy),
(iv) mono-C$_{1-4}$ alkylaminosulfonyl,
(v) di(C$_{1-4}$ alkyl)aminosulfonyl (one C$_{1-4}$ alkyl of the di(C$_{1-4}$ alkyl)aminosulfonyl is substituted with one phenyl, wherein said phenyl may be substituted with one mono-C$_{1-4}$ alkylaminosulfonyl),
(vi) phenylaminosulfonyl (the phenyl of the phenylaminosulfonyl may be substituted with one fluorine atom),
(vii) C$_{1-4}$ alkylsulfonylamino,
(viii) C$_{1-4}$ alkylsulfonylaminocarbonyl,
(ix) C$_{1-4}$ alkylsulfonyl(C$_{1-4}$ alkyl)aminocarbonyl,
(x) C$_{1-4}$ alkyl substituted with carboxy (when position α of the carboxy of the C$_{1-4}$ alkyl substituted with carboxy is a methylene moiety, said methylene moiety may be replaced with a structure selected from the group consisting of ethane-1,1-diyl, propane-2,2-diyl, cyclopropane-1,1-diyl, tetrahydropyran-4,4-diyl, and piperidine-4,4-diyl (the nitrogen atom of the piperidine-4,4-diyl is substituted with methylcarbonyl)),
(xi) C$_{1-4}$ alkyl substituted with methylsulfonylaminocarbonyl,
(xii) C$_{1-4}$ alkyl substituted with trifluoromethylsulfonylamino,
(xiii) C$_{1-4}$ alkyl substituted with methylsulfonyl(methyl)aminocarbonyl,
(xiv) C$_{1-4}$ alkyl substituted with mono-C$_{1-4}$ alkylaminocarbonyl (the C$_{1-4}$ alkyl of the mono-C$_{1-4}$ alkylaminocarbonyl of the C$_{1-4}$ alkyl substituted with mono-C$_{1-4}$ alkylaminocarbonyl may be substituted with one group selected from the group consisting of hydroxy, C$_{1-4}$ alkoxy, 4- to 6-membered saturated oxygen-containing heterocyclyl, di(C$_{1-4}$ alkyl)amino, and 4- to 6-membered saturated nitrogen-containing heterocyclylcarbonyl),
(xv) C$_{1-4}$ alkyl substituted with di(C$_{1-4}$ alkyl)aminocarbonyl (one C$_{1-4}$ alkyl of the di(C$_{1-4}$ alkyl)aminocarbonyl of the C$_{1-4}$ alkyl substituted with di(C$_{1-4}$ alkyl)aminocarbonyl may be substituted with one hydroxy),
(xvi) C$_{1-4}$ alkyl substituted with 4- to 6-membered saturated oxygen-containing heterocyclylaminocarbonyl,
(xvii) C$_{1-4}$ alkyl substituted with 4- to 6-membered saturated nitrogen-containing heterocyclylcarbonyl (the 4- to 6-membered saturated nitrogen-containing heterocyclyl of the C$_{1-4}$ alkyl substituted with 4- to 6-membered saturated nitrogen-containing heterocyclylcarbonyl may be substituted with one to two groups selected from the group consisting of hydroxy and a fluorine atom),
(xviii) halo-C$_{1-4}$ alkyl substituted with carboxy,
(xix) C$_{2-4}$ alkenyl substituted with carboxy,
(xx) C$_{2-4}$ alkenyl substituted with di(C$_{1-4}$ alkyl)aminocarbonyl,
(xxi) C$_{3-6}$ cycloalkyl substituted with carboxy,
(xxii) C$_{3-6}$ cycloalkyl substituted with di(C$_{1-4}$ alkyl)aminocarbonyl,
(xxiii) 4- to 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxviii) pyrimidinyl substituted with carboxy,
(xxix) pyrazinyl substituted with carboxy,
(xxx) 2-oxodihydropyridinyl substituted with carboxymethyl,
(xxxi) mono-C$_{1-4}$ alkylaminocarbonyl substituted with carboxy (the C$_{1-4}$ alkyl of the mono-C$_{1-4}$ alkylaminocarbonyl substituted with carboxy may be substituted with one group selected from the group consisting of phenyl and benzyl, wherein when position α of the carboxy of the mono-C$_{1-4}$ alkylaminocarbonyl substituted with carboxy is a methylene moiety, said methylene moiety may be replaced with a structure selected from the group consisting of ethane-1,1-diyl, propane-2,2-diyl, cyclopropane-1,1-diyl, cyclopentane-1,1-diyl, and tetrahydropyran-4,4-diyl),
(xxxii) phenylC$_{1-4}$ alkylaminocarbonyl substituted with carboxy,
(xxxiii) mono-C$_{1-4}$ alkylaminocarbonyl substituted with the structure represented by formula [V-6] below:

[Formula 18]

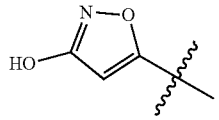

(xxxiv) di(C$_{1-4}$alkyl)aminocarbonyl substituted with carboxy (when position α of the carboxy of the di(C$_{1-4}$alkyl) aminocarbonyl substituted with carboxy is a methylene moiety, said methylene moiety may be replaced with propane-2,2-diyl),
(xxxv) C$_{3-6}$cycloalkylaminocarbonyl substituted with carboxy,
(xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
(xxxvii) 4- to 6-membered saturated nitrogen-containing heterocyclylcarbonyl substituted with carboxymethyl,
(xxxviii) the structure represented by formula [XI-1] below, which is substituted with carboxy,
(xxxix) the structure represented by formula [XI-2] below, which is substituted with carboxy,
(xxxx) the structure represented by formula [XI-3] below, which is substituted with carboxy,
(xxxxiii) the structure represented by formula [XI-6] below, which is substituted with carboxy,

[Formula 19] [XI']

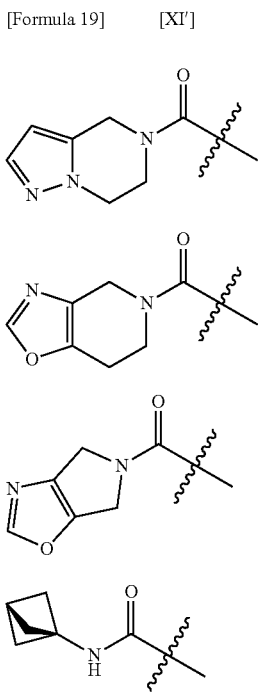

[XI-1]

[XI-2]

[XI-3]

[XI-6]

(xxxxiv) $C_{1-4}$alkylsulfonyl substituted with carboxy (when position α of the carboxy of the $C_{1-4}$alkylsulfonyl substituted with carboxy is a methylene moiety, said methylene moiety may be replaced with propane-2,2-diyl),
(xxxxv) mono-$C_{1-4}$alkylaminosulfonyl substituted with carboxy (when position α of the carboxy of the mono-$C_{1-4}$ alkylaminosulfonyl substituted with carboxy is a methylene moiety, said methylene moiety may be replaced with propane-2,2-diyl),
(xxxxvi) di($C_{1-4}$alkyl)aminosulfonyl substituted with carboxy (when position α of the carboxy of the di($C_{1-4}$alkyl) aminosulfonyl substituted with carboxy is a methylene moiety, said methylene moiety may be replaced with propane-2,2-diyl),
(xxxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
(xxxxviii) $C_{1-4}$ alkoxy substituted with carboxy (when position α of the carboxy of the $C_{1-4}$ alkoxy substituted with carboxy is a methylene moiety, said methylene moiety may be replaced with propane-2,2-diyl),
(xxxxix) hydroxy,
(xxxxx) $C_{1-4}$ alkylsulfonyloxy,
(xxxxxi) $C_{1-4}$ alkyl substituted with hydroxy,
(xxxxxii) halo-$C_{1-4}$ alkyl substituted with hydroxy,
(xxxxxiii) $C_{1-4}$ alkylsulfonyl substituted with hydroxy,
(xxxxxiv) $C_{3-6}$ cycloalkyl substituted with hydroxy (the $C_{3-6}$ cycloalkyl of the $C_{3-6}$ cycloalkyl substituted with hydroxy may be substituted with one group selected from the group consisting of carboxy and di($C_{1-4}$alkyl)aminocarbonyl), or
(xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$ alkylcarbonyl, $C_{1-4}$ alkoxycarbonyl, and di($C_{1-4}$alkyl)aminocarbonyl),
wherein $R^{61}$ and $R^{62}$ each independently represent a hydrogen atom, a fluorine atom, a chlorine atom, methyl, methoxy, or methylsulfonyl;
    (d) when ring C is pyridyl,
$R^{54}$ represents:
(i) carboxy,
(ii) carbamoyl,
(iii) $C_{1-4}$ alkyl substituted with carboxy (when position α of the carboxy of the $C_{1-4}$ alkyl substituted with carboxy is a methylene moiety, said methylene moiety may be replaced with propane-2,2-diyl),
(iv) $C_{1-4}$alkoxy substituted with carboxy (when position α of the carboxy of the $C_{1-4}$alkoxy substituted with carboxy is a methylene moiety, said methylene moiety may be replaced with propane-2,2-diyl),
(v) mono-$C_{1-4}$alkylaminocarbonyl substituted with carboxy (when position α of the carboxy of the mono-$C_{1-4}$alkylaminocarbonyl substituted with carboxy is a methylene moiety, said methylene moiety may be replaced with propane-2,2-diyl), or
(vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
wherein $R^{61}$ and $R^{62}$ represent a hydrogen atom;
    (e) when ring C is pyrazolyl,
$R^{54}$ represents carboxy,
wherein $R^{61}$ and $R^{62}$ represent a hydrogen atom;
    (g) when ring C is tetrahydronaphthyl,
$R^{54}$ represents carboxy,
wherein $R^{61}$ and $R^{62}$ represent a hydrogen atom;
    (h) when ring C is chromanyl,
$R^{54}$ represents carboxy,
wherein $R^{61}$ and $R^{62}$ represent a hydrogen atom;
    (j) when ring C is indazolyl,
$R^{54}$ represents $C_{1-4}$ alkyl substituted with carboxy,
wherein $R^{61}$ and $R^{62}$ represent a hydrogen atom;
    (n) when ring C is the structure represented by formula [IX-1] above,
$R^{54}$ represents:
(i) carboxy,
(ii) $C_{1-4}$ alkyl substituted with $C_{1-4}$ alkylsulfonylamino, or
(iii) $C_{1-4}$ alkyl substituted with $C_{1-4}$ alkylsulfonyl($C_{1-4}$ alkyl) amino,
wherein $R^{61}$ and $R^{62}$ represent a hydrogen atom;
    (p) when ring C is the structure represented by formula [IX-2] above,
$R^{54}$ is selected from the group consisting of:
(i) carboxy, and
(ii) $C_{1-4}$ alkyl substituted with carboxy,
wherein $R^{61}$ and $R^{62}$ represent a hydrogen atom;
    (q) when ring C is the structure represented by formula [IX-3] above,
$R^{54}$ represents carboxy,
wherein $R^{61}$ and $R^{62}$ represent a hydrogen atom;
    (r) when ring C is the structure represented by formula [IX-4] above,
$R^{54}$ represents carboxy,
wherein $R^{61}$ and $R^{62}$ represent a hydrogen atom;
    $W^4$ is $C_{1-3}$ alkanediyl or the formula —O—$CH_2CH_2$—;
or a pharmaceutically acceptable salt thereof.

(3) In another embodiment, the present invention provides the compound according to (1) or (2),
wherein as regards $R^5$ of formula [I] above, (A)

when $R^5$ represents the structure represented by formula [IV-1] above, $R^{51}$ represents any of the structures represented by formula group [V′′′] below,

[Formula 20]

[V′′′ ]

[V-1]
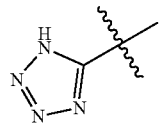

[V-3]
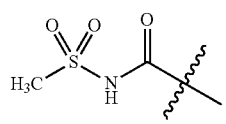

[V-4]
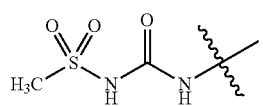

[V-5]
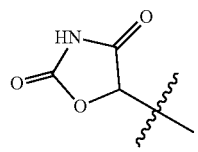

[V-6]
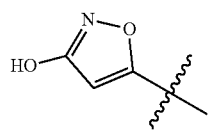

[V-7]
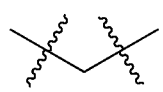

$W^1$ represents butane-1,4-diyl, or pentane-1,5-diyl;

(B)

when $R^5$ represents the structure represented by formula [IV-2] above, $R^{52}$ represents carboxy, L represents the structure represented by formula [VI-1], formula [VI-4], formula [VI-8], formula [VI-9], formula [VI-10], or formula [VI-12] below:

[Formula 21]

[VI-1]
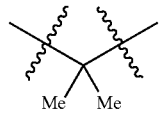

[VI-4]
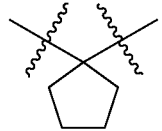

[VI-8]
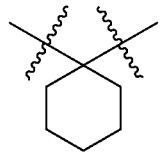

[VI-9]
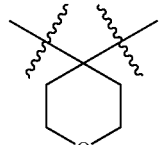

[VI-10]
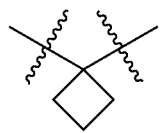

[VI-12]
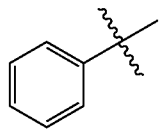

Y represents the formula —CH$_2$—, the formula —CMe$_2$-, the formula —O—, the formula —NHCO—, or the formula —CONMe-, $W^2$ represents propane-1,3-diyl, butane-1,4-diyl, pentane-1,5-diyl, hexane-1,6-diyl, heptane-1,7-diyl, or the formula —O—(CH$_2$)$_6$—;

(C)

when $R^5$ represents the structure represented by formula [IV-3] above, $R^{53}$ represents carboxy, carboxymethyl (the methylene moiety of the carboxymethyl may be replaced with propane-2,2-diyl), or carboxymethoxy (the methylene moiety of the carboxymethoxy is substituted with propane-2,2-diyl);

ring B represents the structure represented by formula [VIII-1], formula [VIII-8], formula [VIII-9], formula [VIII-11], formula [VIII-12], formula [VIII-14], formula [VIII-B], or formula [VIII-7] below,

[Formula 22]

[VIII-1]
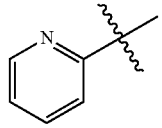

[VIII-8]

-continued

[VIII-9]
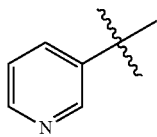

[VIII-11]
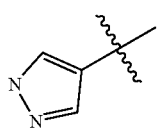

[VIII-12]
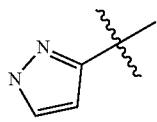

[VI-14]
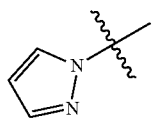

[VIII-13]
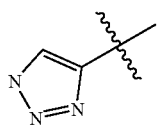

[VIII-7]
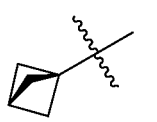

$W^3$ represents butane-1,4-diyl, or hexane-1,6-diyl;

(D)
when $R^5$ represents the structure represented by formula [IV-4] above,
ring C represents:
(a) $C_{3-6}$ cycloalkyl,
(b) 4- to 6-membered saturated nitrogen-containing heterocyclyl,
(c) phenyl,
(d) pyridyl,
(g) tetrahydronaphthyl,
(h) chromanyl,
(j) indazolyl,
(p) the structure represented by formula [IX-2] below,
(q) the structure represented by formula [IX-3] below, or
(r) the structure represented by formula [IX-4] below,

[Formula 23]

[IX']

[IX-2]
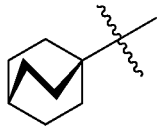

[IX-3]
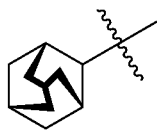

[IX-4]
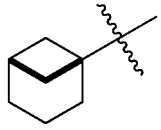

wherein
(a) when ring C is $C_{3-6}$ cycloalkyl,
ring C is cyclopropyl, cyclobutyl, or cyclohexyl,
$R^{54}$ represents:
(i) carboxy, or
(iv) methyl substituted with carboxy, or ethyl substituted with carboxy,
wherein $R^{61}$ and $R^{62}$ represent a hydrogen atom;
(b) when ring C is 4- to 6-membered saturated nitrogen-containing heterocyclyl, ring C is pipieridin-3-yl;
$R^{54}$ represents:
(i) ethylcarbonyl substituted with carboxy, n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy;
wherein $R^{61}$ and $R^{62}$ represent a hydrogen atom;
(c) when ring C is phenyl,
$R^{54}$ represents:
(i) carboxy,
(ii) carbamoyl,
(iii) n-propylaminocarbonyl,
(iv) methylaminosulfonyl,
(v) dimethylaminosulfonyl (one methyl of the dimethylaminosuflonyl is substituted with one phenyl, wherein the phenyl is substituted with one methylaminosulfonyl),
(vii) isopropylsulfonylamino,
(viii) methylsulfonylaminocarbonyl,
(x) methyl substituted with carboxy (the methylene moiety at position α of the carboxy of the methyl substituted with carboxy may be replaced with ethane-1,1-diyl, propane-2,2-diyl, cyclopropane-1,1-diyl, tetrahydropyran-4,4-diyl, or piperidine-4,4-diyl, wherein the nitrogen atom of the piperidine-4,4-diyl is substituted with one methylcarbonyl), ethyl substituted with carboxy, n-propyl substituted with carboxy, or n-butyl substituted with carboxy,
(xi) methyl substituted with methylsulfonylaminocarbonyl, or ethyl substituted with methylsulfonylaminocarbonyl,
(xii) methyl substituted with trifluoromethylsulfonylamino,
(xiv) ethyl substituted with methylaminocarbonyl (the methyl of the ethyl substituted with methylaminocarbonyl may be substituted with tetrahydrofuranyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl may be substituted with one group selected from the group consisting of hydroxy and methoxy), or ethyl substituted with isopropylaminocarbonyl (the isopropyl of the ethyl substituted with isopropylaminocarbonyl is substituted with one hydroxy),
(xv) ethyl substituted with dimethylaminocarbonyl, (xvi) ethyl substituted with oxetanylaminocarbonyl, (xvii) ethyl substituted with azetidinylcarbonyl (the azetidinyl of the ethyl substituted with azetidinylcarbonyl may be substituted with one to two groups selected from the group consisting of hydroxy and a fluorine atom) or ethyl substituted with pyrrolidinylcarbonyl, (xviii) halo-methyl substituted with carboxy, (xix) ethenyl substituted with carboxy, (xxi) cyclopropyl substituted with carboxy, or cyclohexyl substituted with carboxy, (xxii) cyclopropyl substituted with dimethylaminocarbonyl, (xxiii) piperidinyl substituted with carboxy, (xxiv) phenyl substituted with carboxy, (xxv) pyridyl substituted with carboxy, (xxvi) pyrazolyl substituted with carboxy, (xxvii) pyrazolyl substituted with carboxymethyl, (xxviii) pyrimidinyl substituted with carboxy, (xxix) pyrazinyl substituted with carboxy, (xxx) 2-oxodihydropyridinyl substituted with carboxymethyl, (xxxi) methylaminocarbonyl substituted with carboxy (the methyl of the methylaminocarbonyl substituted with carboxy may be substituted with one benzyl, and the methylene moiety at position α of the carboxy of the methylaminocarbonyl substituted with carboxy may be replaced with ethane-1,1-diyl), ethylaminocarbonyl substituted with carboxy (the ethyl of the ethylaminocarbonyl substituted with carboxy may be substituted with one phenyl, and the methylene moiety at position α of the carboxy of the ethylaminocarbonyl substituted with carboxy may be replaced with a structure selected from the group consisting of propane-2,2-diyl, cyclopropane-1,1-diyl, and cyclopentane-1,1-diyl), or n-propylaminocarbonyl substituted with carboxy (the methylene moiety at position α of the carboxy of the n-propylaminocarbonyl substituted with carboxy is replaced with propane-2,2-diyl), (xxxii) phenylmethylaminocarbonyl substituted with carboxy, (xxxiii) monomethylaminocarbonyl substituted with the structure represented by formula [V-6] below,

[Formula 24]

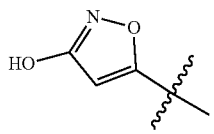

[V-6]

(xxxiv) ethyl(methyl)aminocarbonyl substituted with carboxy, (xxxv) cyclobutylaminocarbonyl substituted with carboxy, (xxxvi) pyrrolidinylcarbonyl substituted with carboxy (the pyrrolidinyl of the pyrrolidinylcarbonyl substituted with carboxy is substituted with one fluorine atom), or piperidinylcarbonyl substituted with carboxy, (xxxviii) the structure represented by formula [XI-1] below, which is substituted with carboxy, (xxxix) the structure represented by formula [XI-2] below, which is substituted with carboxy,

[Formula 25] [XI″]

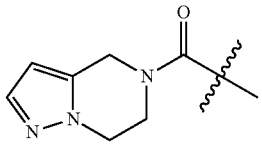

[XI-1]

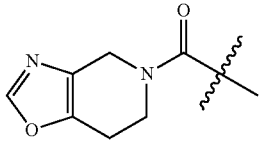

[XI-2]

(xxxxiv) ethylsulfonyl substituted with carboxy, or n-butylsulfonyl substituted with carboxy (the methylene moiety at position α of carboxy of the n-butylsulfonyl substituted with carboxy is replaced with propane-2,2-diyl), (xxxxv) mono-n-propylaminosulfonyl substituted with carboxy (the methylene moiety at position α of the carboxy of the mono-n-propylaminosuflonyl substituted with carboxy is replaced with propane-2,2-diyl), (xxxxvi) n-propyl(methyl)aminosulfonyl substituted with carboxy (the methylene moiety at position α of the carboxy of the n-propyl(methyl)aminosulfonyl substituted with carboxy is replaced with propane-2,2-diyl), (xxxxvii) pyrrolidinylsulfonyl substituted with carboxy (the pyrrolidinyl of the pyrrolidinylsulfonyl substituted with carboxy may be substituted with one fluorine atom), piperidinylsulfonyl substituted with carboxy, or morpholinylsulfonyl substituted with carboxy, (xxxxviii) methoxy substituted with carboxy (the methylene moiety at position α of the carboxy of the methoxy substituted with carboxy may be replaced with propane-2,2-diyl), (xxxxix) hydroxy, (xxxxxi) isopropyl substituted with hydroxy, (xxxxxii) haloethyl substituted with hydroxy, halo-n-propyl substituted with hydroxy, or haloisopropyl substituted with hydroxy, (xxxxxiii) ethylsulfonyl substituted with hydroxy, isobutylsulfonyl substituted with hydroxy, or (xxxxxiv) cyclobutyl substituted with hydroxy (the cyclobutyl of the cyclobutyl substituted with hydroxy may be substituted with one carboxy), cyclopentyl substituted with hydroxy, wherein $R^{61}$ and $R^{62}$ each independently represent a hydrogen atom, a fluorine atom, methyl, methoxy, or methylsulfonyl;

(d) when ring C is pyridyl, ring C is pyridin-2-yl or pyridin-4-yl;

$R^{54}$ represents:

(i) carboxy, (iii) n-propyl substituted with carboxy (the methylene moiety at position α of the carboxy of the n-propyl substituted with carboxy is replaced with propane-2,2-diyl), (iv) ethoxy substituted with carboxy (the methylene moiety at position α of the carboxy of the ethoxy substituted with carboxy is replaced with propane-2,2-diyl), (v) mono-n-propylaminocarbonyl substituted with carboxy (the methylene moiety at position α of the carboxy of the mono-n-propylaminocarbonyl substituted with carboxy is replaced with propane-2,2-diyl);
wherein $R^{61}$ and $R^{62}$ represent a hydrogen atom;
(g) when ring C is tetrahydronaphthyl,
ring C represents the structure represented by formula [XII-1], formula [XII-2], or formula [XII-3] below,

[Formula 26]

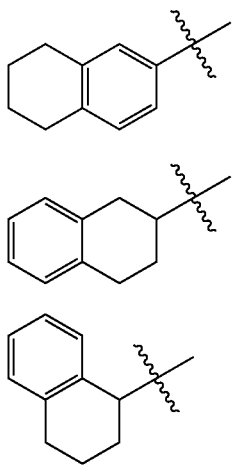

[XII-1]

[XII-2]

[XII-3]

$R^{54}$ represents carboxy, wherein $R^{61}$ and $R^{62}$ represent a hydrogen atom;
(h) when ring C is chromanyl,
ring C represents the structure represented by formula [XIII-1] or formula [XIII-2] below

[Formula 27]

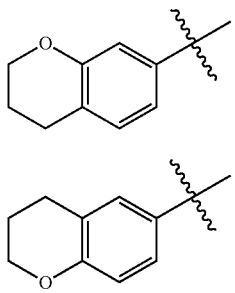

[XIII-1]

[XIII-2]

$R^{54}$ represents carboxy, wherein $R^{61}$ and $R^{62}$ represent a hydrogen atom;
(j) when ring C is indazolyl,
$R^{54}$ represents methyl substituted with carboxy, wherein $R^{61}$ and $R^{62}$ represent a hydrogen atom;
(p) when ring C is the structure represented by formula [IX-2] above,
$R^{54}$ represents
(i) carboxy, or
(ii) ethyl substituted with carboxy, wherein $R^{61}$ and $R^{62}$ represent a hydrogen atom;
(q) when ring C is the structure represented by formula [IX-3] above,
$R^{54}$ represents carboxy, wherein $R^{61}$ and $R^{62}$ represent a hydrogen atom;

(r) when ring C is the structure represented by formula [IX-4] above,
$R^{54}$ represents carboxy, wherein $R^{61}$ and $R^{62}$ represent a hydrogen atom;
$W^4$ represents methanediyl, ethane-1,2-diyl, propane-1,3-diyl, or the formula —O—CH$_2$CH$_2$—,
or pharmaceutically acceptable salt thereof.

(4) In another embodiment, the present invention provides the compound according to any one of (1) to (3), wherein the structure represented by formula [II] below is the structure represented by formula [III-1] below:

[Formula 28]

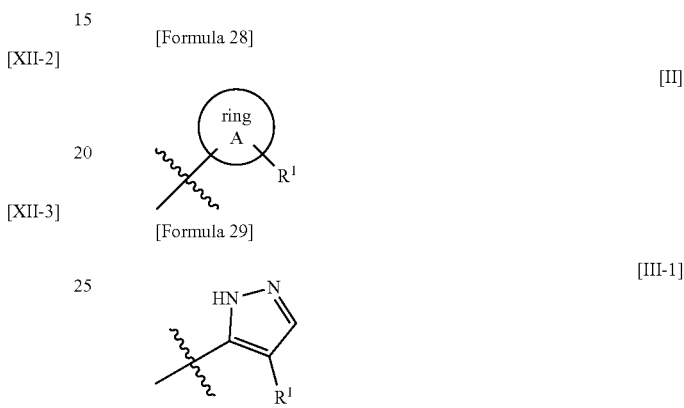

[II]

[Formula 29]

[III-1]

or a pharmaceutically acceptable salt thereof.

(5) In another embodiment, the present invention provides the compound according to (1), wherein
$R^1$ represents a hydrogen atom;
$R^2$ represents a hydrogen atom;
$R^3$ represents a hydrogen atom;
$R^4$ represents a hydrogen atom;
wherein
(B)
when $R^5$ represents the structure represented by formula [IV-2] below

[Formula 30]

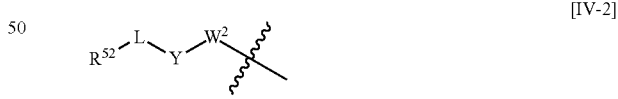

[IV-2]

$R^{52}$ represents carboxy,
L represents the structure represented by formula [VI-4] or formula [VI-7] below

[Formula 31]

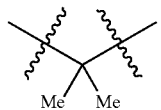

[VI-4]

-continued

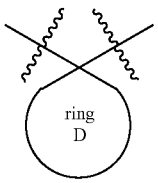

[VI-7]

wherein ring D represents (ii) 4- to 6-membered saturated oxygen-containing hetero ring,
Y represents the formula —$CH_2$—, or the formula —O—,
$W^2$ represents $C_{7-8}$alkanediyl, wherein one of the carbon atoms that constitute the $C_{7-8}$alkanediyl represented by $W^2$ may be replaced with one oxygen atom;
(C)
when $R^5$ represents the structure represented by formula [IV-3] below

[Formula 32]

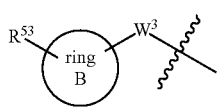

[IV-3]

$R^{53}$ represents carboxy,
ring B represents the structure represented by formula [VIII-7] below

[Formula 33]

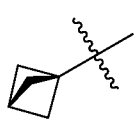

[VIII-7]

$W^3$ represents hexane-1,6-diyl;
(D)
when $R^5$ represents the structure represented by formula [IV-4] below

[Formula 34]

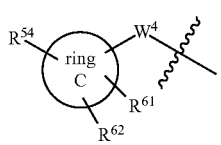

[IV-4]

ring C represents (c) phenyl, (d) pyridyl, (g) tetrahydronaphthyl or (h) chromanyl,
$W^4$ represents methanediyl;
(c) when ring C is phenyl,
$R^{54}$ represents
(xxi) $C_{3-6}$ cycloalkyl substituted with carboxy, or (xxxxvii) 4- to 6-membered saturated nitrogen-containing heterocyclylsulfonyl, which is substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
wherein $R^{61}$ represents a hydrogen atom and $R^{62}$ represents a hydrogen atom;
(d) when ring C is pyridyl,
$R^{54}$ represents
(iv) $C_{1-4}$ alkoxy substituted with carboxy,
wherein $R^{61}$ represents a hydrogen atom and $R^{62}$ represents a hydrogen atom;
(g) when ring C is tetrahydronaphthyl,
$R^{54}$ represents carboxy,
wherein $R^{61}$ represents a hydrogen atom and $R^{62}$ represents a hydrogen atom;
(h) when ring C is chromanyl,
$R^{54}$ represents carboxy,
wherein $R^{61}$ represents a hydrogen atom and $R^{62}$ represents a hydrogen atom; or a pharmaceutically acceptable salt thereof.
(6) In another embodiment, the present invention provides the compound according to (1),
wherein formula [I] is formula [I-D'] below,

[Formula 35]

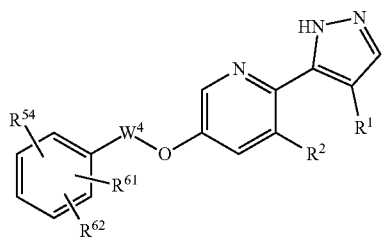

[I-D']

wherein
$R^1$ represents a hydrogen atom;
$R^2$ represents a hydrogen atom;
$R^{54}$ represents $C_{3-6}$cycloalkyl substituted with carboxy,
wherein $R^{61}$ and $R^{62}$ each independently represent a hydrogen atom, a fluorine atom, methyl, or methylsulfonyl;
$W^4$ represents $C_{1-3}$alkanediyl;
or a pharmaceutically acceptable salt thereof.
(7) In another embodiment, the present invention provides the compound according to (6), wherein formula [I] is formula [I-D'] below,

[Formula 36]

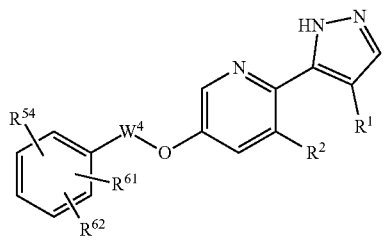

[I-D']

wherein
$R^1$ represents a hydrogen atom;
$R^2$ represents a hydrogen atom;
$R^{54}$ represents cyclopropyl substituted with carboxy,
wherein
$R^{61}$ represents a fluorine atom that substitutes the benzene ring at ortho position with respect to —$W^4$—, $R^{62}$ represents a hydrogen atom;
$W^4$ represents methanediyl or ethane-1,2-diyl;
or a pharmaceutically acceptable salt thereof.

(8) In another embodiment, the present invention provides the compound according to (7), wherein formula [I] is formula [I-D'] below,

[Formula 37]

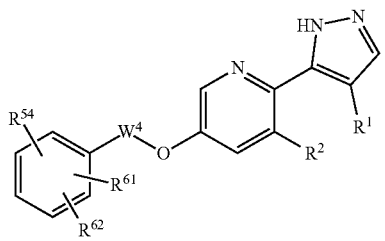

[I-D']

wherein
$R^1$ represents a hydrogen atom;
$R^2$ represents a hydrogen atom;
$R^{54}$ represents cyclopropyl substituted with carboxy, which substitutes the benzene ring at meta position with respect to —$W^4$—,
wherein $R^{61}$ represents a fluorine atom that substitutes the benzene ring at ortho position with respect to —$W^4$—,
$R^{62}$ represents a hydrogen atom;
$W^4$ represents methanediyl or ethane-1,2-diyl;
or a pharmaceutically acceptable salt thereof.

(9) In another embodiment, the present invention provides the compound according to (6), wherein formula [I] is formula [I-D'] below,

[Formula 38]

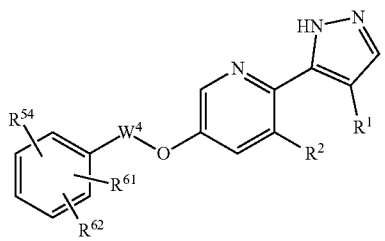

[I-D']

wherein
$R^1$ represents a hydrogen atom;
$R^2$ represents a hydrogen atom;
$R^{54}$ represents cyclopropyl substituted with carboxy, which substitutes the benzene ring at meta position with respect to —$W^4$—,
wherein $R^{61}$ and $R^{62}$ each independently represent a hydrogen atom or a fluorine atom;
$W^4$ represents ethane-1,2-diyl;
or a pharmaceutically acceptable salt thereof.

(10) In another embodiment, the present invention provides the compound according to (9), wherein formula [I] is formula [I-D'] below,

[Formula 39]

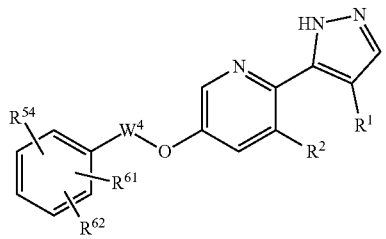

[I-D']

wherein
$R^1$ represents a hydrogen atom;
$R^2$ represents a hydrogen atom;
$R^{54}$ represents cyclopropyl substituted with carboxy, which substitutes the benzene ring at meta position with respect to —$W^4$—, wherein $R^{61}$ represents a fluorine atom,
$R^{62}$ represents a hydrogen atom;
$W^4$ represents ethane-1,2-diyl;
or a pharmaceutically acceptable salt thereof.

(11) In another embodiment, the present invention provides the compound according to (6), wherein formula [I] is formula [I-D'] below,

[Formula 40]

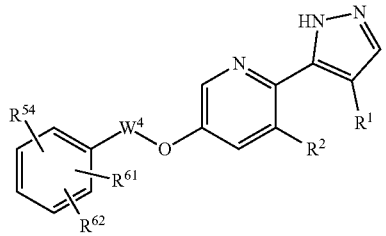

[I-D']

wherein
$R^1$ represents a hydrogen atom;
$R^2$ represents a hydrogen atom;
$R^{54}$ represents cyclopropyl substituted with carboxy,
wherein $R^{61}$ and $R^{62}$ each identically represent a hydrogen atom;
$W^4$ represents ethane-1,2-diyl;
or a pharmaceutically acceptable salt thereof.

(12) In another embodiment, the present invention provides the compound according to (1),
wherein formula [I] is formula [I-B] below,

[Formula 41]

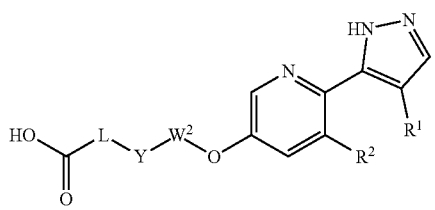

[I-B]

wherein
$R^1$ represents a hydrogen atom;
$R^2$ represents a hydrogen atom;

L is the structure represented by formula [VI-1], formula [VI-4], or [VI-7] below,

[Formula 42]

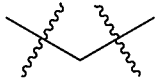
[VI-1]

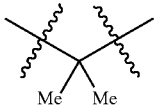
[VI-4]

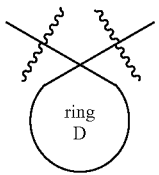
[VI-7]

wherein ring D represents
(i) $C_{3-6}$ cycloalkane,
(ii) 4- to 6-membered saturated oxygen-containing hetero ring, or
(iv) 6-membered saturated nitrogen-containing hetero ring (the nitrogen atom of the 6-membered saturated nitrogen-containing hetero ring may be substituted with one $C_{1-4}$ alkylcarbonyl);
Y represents the formula —CH$_2$—, the formula —O—, or the formula —CONMe-;
W$^2$ represents $C_{2-10}$alkanediyl,
wherein one of the carbon atoms that constitute $C_{2-10}$alkanediyl represented by W$^2$ may be replaced with one oxygen atom;
or a pharmaceutically acceptable salt thereof.

(13) In another embodiment, the present invention provides the compound according to (12),
wherein formula [I] is formula [I-B] below,

[Formula 43]

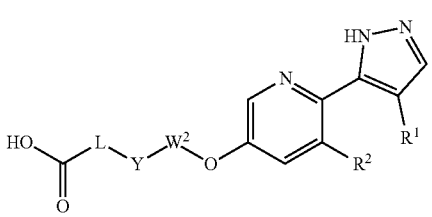
[I-B]

wherein
R$^1$ represents a hydrogen atom;
R$^2$ represents a hydrogen atom;
L represents the structure represented by formula [VI-7] below

[Formula 44]

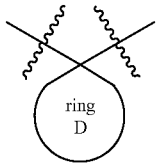
[VI-7]

wherein ring D represents
(i) $C_4$cycloalkane, or
(ii) 4-membered saturated oxygen-containing hetero ring;
Y represents the formula —CH$_2$— or the formula —O—;
W$^2$ represents heptane-1,7-diyl, or a pharmaceutically salt thereof;
or a pharmaceutically acceptable salt thereof.

(14) In another embodiment, the invention provides the compound according to (1), wherein formula [I] is formula [I-B] below,

[Formula 45]

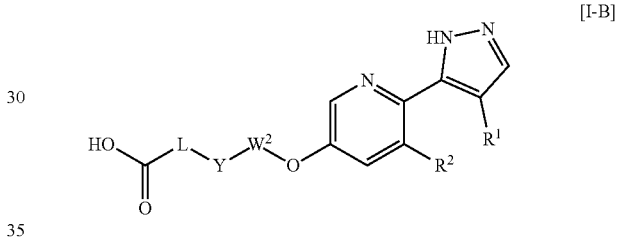
[I-B]

wherein
R$^1$ represents a hydrogen atom;
R$^2$ represents a hydrogen atom;
L represents the structure represented by formula [VI-7] below

[Formula 46]

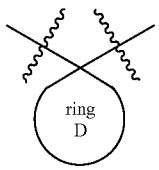
[VI-7]

wherein ring D represents
(i) $C_4$cycloalkane,
(ii) 4-membered saturated oxygen-containing hetero ring, or
(iii) 4-membered saturated sulfur-containing hetero ring (the sulfur atom of the 4-membered saturated sulfur-containing hetero ring is substituted with two oxo),
Y represents the formula —CH$_2$— or the formula —O—;
W$^2$ represents heptane-1,7-diyl;
or a pharmaceutically salt thereof.

(15) In another embodiment, the present invention provides the compound according to any one of (1) to (5), which is shown below:

[Formula 47]
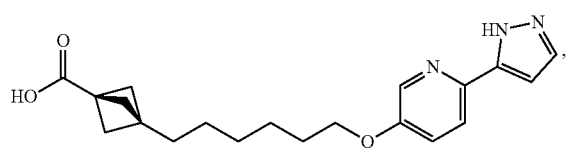
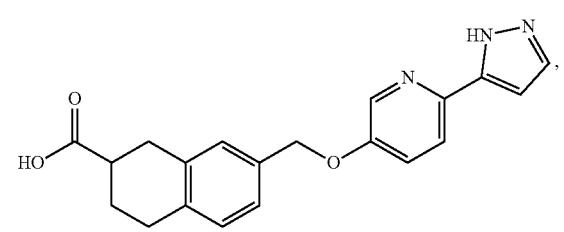
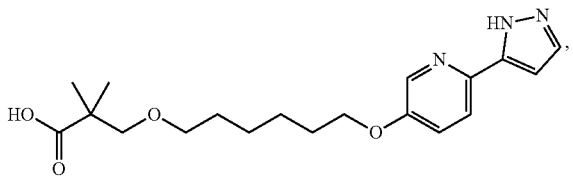
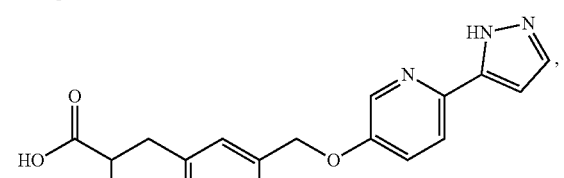
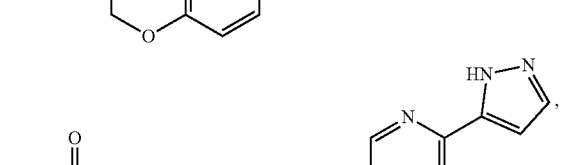
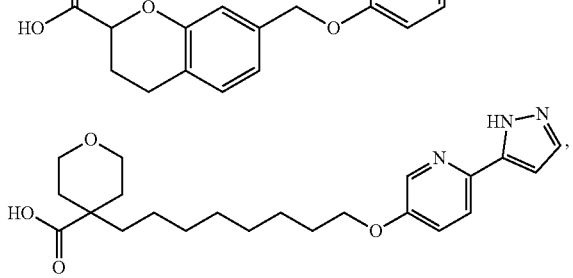
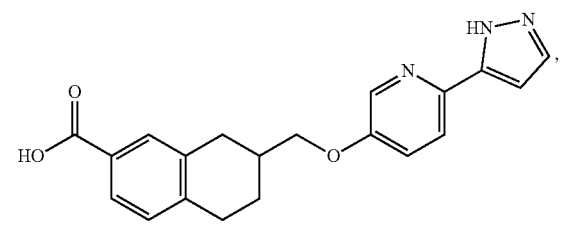
[Formula 48]
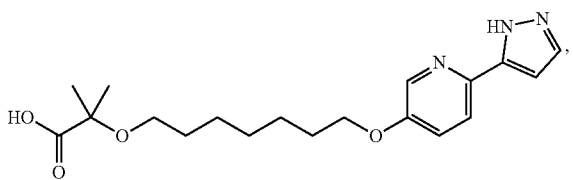
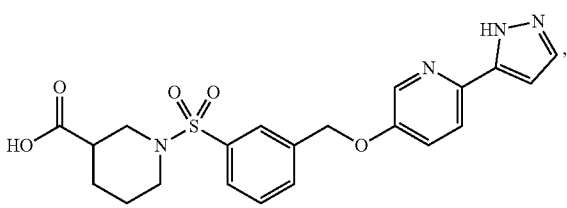
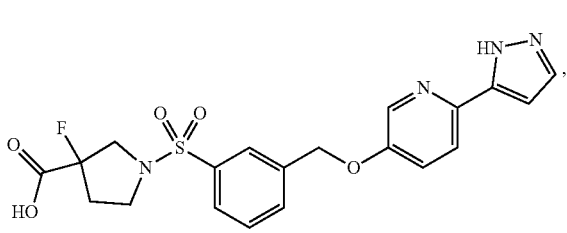
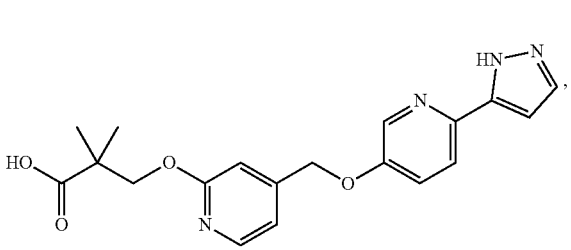
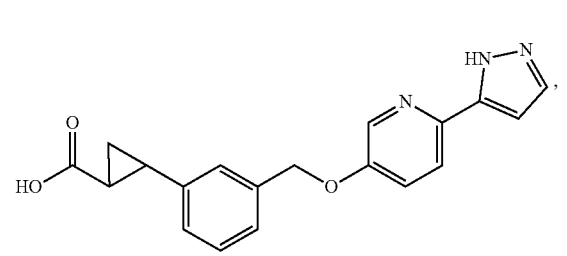
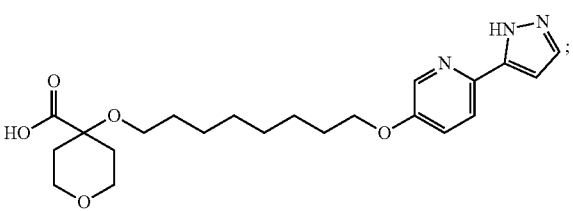
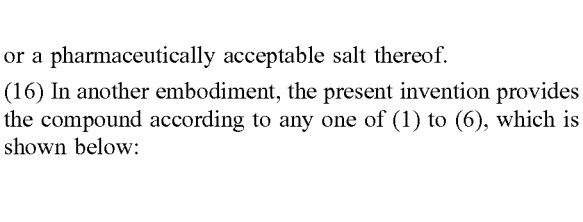
or a pharmaceutically acceptable salt thereof.
(16) In another embodiment, the present invention provides the compound according to any one of (1) to (6), which is shown below:
[Formula 49]
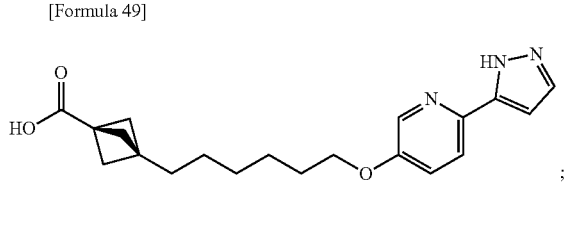
or a pharmaceutically acceptable salt thereof.
(17) In another embodiment, the present invention provides the compound according to any one of (1) to (6), which is shown below:

[Formula 50]

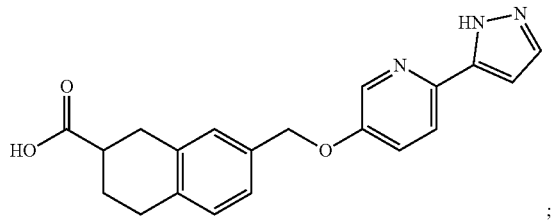

;

or a pharmaceutically acceptable salt thereof.
(18) In another embodiment, the present invention provides the compound according to any one of (1) to (6), which is shown below:

[Formula 51]

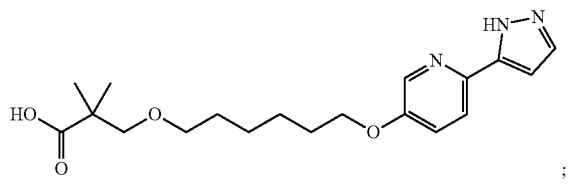

;

or a pharmaceutically acceptable salt thereof.
(19) In another embodiment, the present invention provides the compound according to any one of (1) to (6), which is shown below:

[Formula 52]

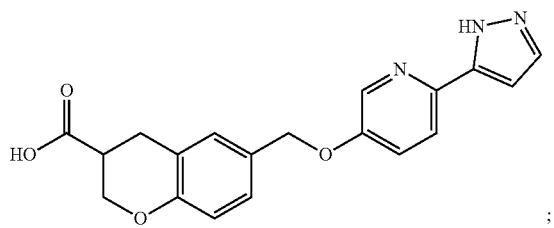

;

or a pharmaceutically acceptable salt thereof.
(20) In another embodiment, the present invention provides the compound according to any one of (1) to (6), which is shown below:

[Formula 53]

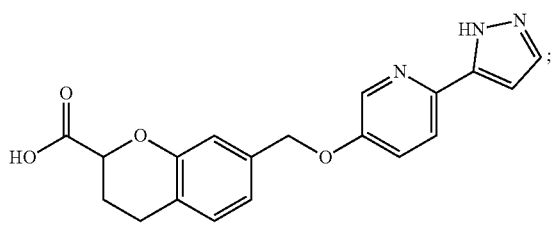

;

or a pharmaceutically acceptable salt thereof.
(21) In another embodiment, the present invention provides the compound according to any one of (1) to (6), which is shown below:

[Formula 54]

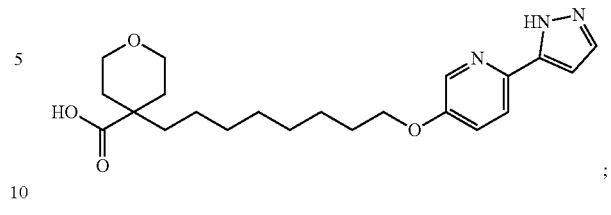

;

or a pharmaceutically acceptable salt thereof.
(22) In another embodiment, the present invention provides the compound according to any one of (1) to (6), which is shown below:

[Formula 55]

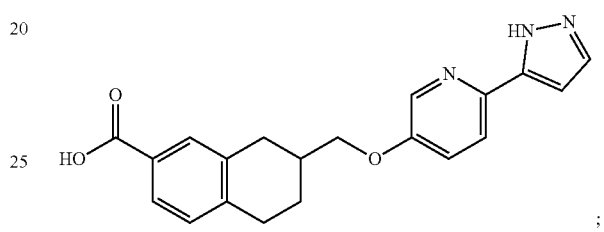

;

or a pharmaceutically acceptable salt thereof.
(23) In another embodiment, the present invention provides the compound according to any one of (1) to (6), which is shown below:

[Formula 56]

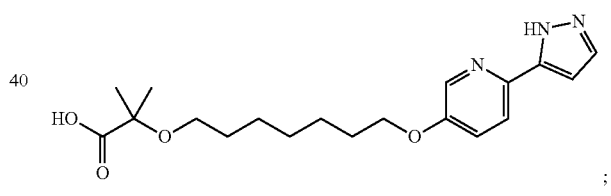

;

or a pharmaceutically acceptable salt thereof.
(24) In another embodiment, the present invention provides the compound according to any one of (1) to (6), which is shown below:

[Formula 57]

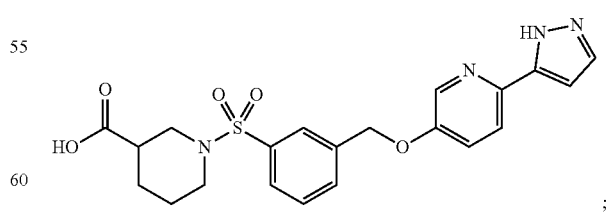

;

or a pharmaceutically acceptable salt thereof.
(25) In another embodiment, the present invention provides the compound according to any one of (1) to (6), which is shown below:

[Formula 58]

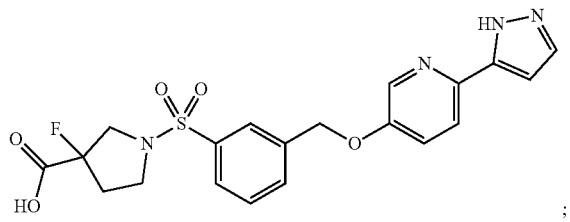

or a pharmaceutically acceptable salt thereof.
(26) In another embodiment, the present invention provides the compound according to any one of (1) to (6), which is shown below:

[Formula 59]

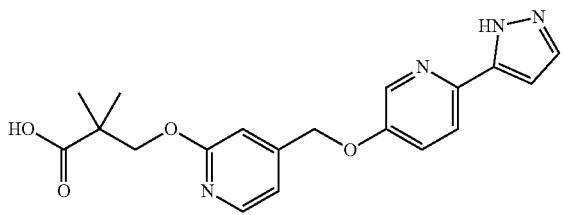

or a pharmaceutically acceptable salt thereof.
(27) In another embodiment, the present invention provides the compound according to any one of (1) to (6), which is shown below:

[Formula 60]

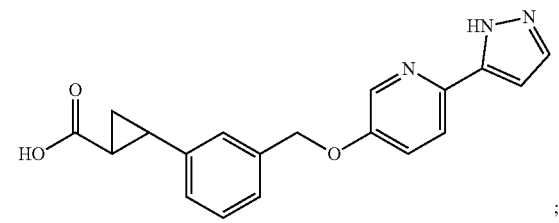

or a pharmaceutically acceptable salt thereof.
(28) In another embodiment, the present invention provides the compound according to any one of (1) to (6), which is shown below:

[Formula 61]

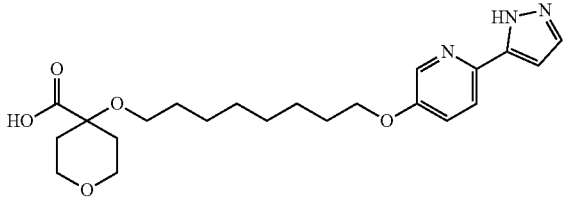

or a pharmaceutically acceptable salt thereof.
(29) In another embodiment, the present invention provides the compound according to (1), which is shown below:

[Formula 62]

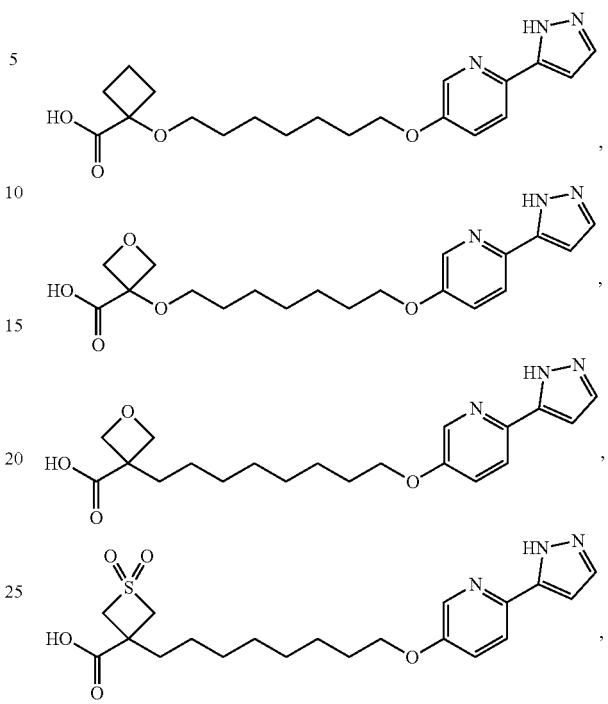

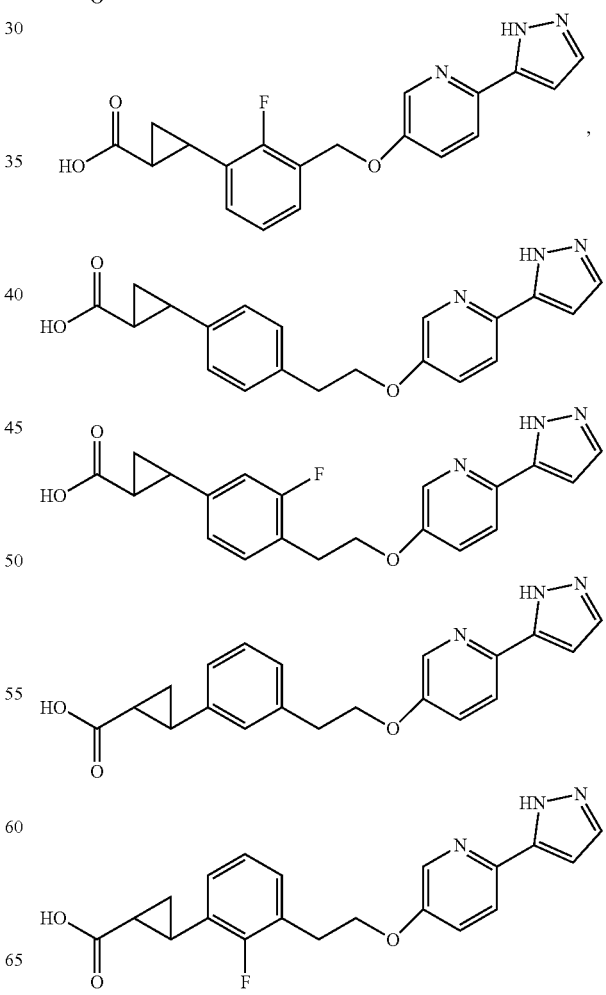

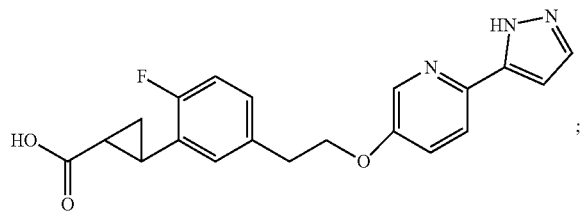

or a pharmaceutically acceptable salt thereof.

(30) In another embodiment, the present invention provides the compound according to (1), which is shown below:

[Formula 63]

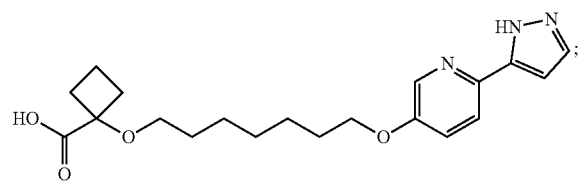

or a pharmaceutically acceptable salt thereof.

(31) In another embodiment, the present invention provides the compound according to (1), which is shown below:

[Formula 64]

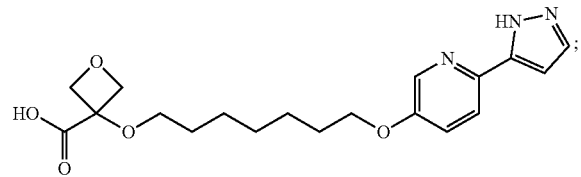

or a pharmaceutically acceptable salt thereof.

(32) In another embodiment, the present invention provides the compound according to (1), which is shown below:

[Formula 65]

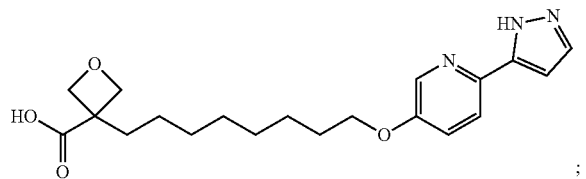

or a pharmaceutically acceptable salt thereof.

(33) In another embodiment, the present invention provides the compound according to (1), which is shown below:

[Formula 66]

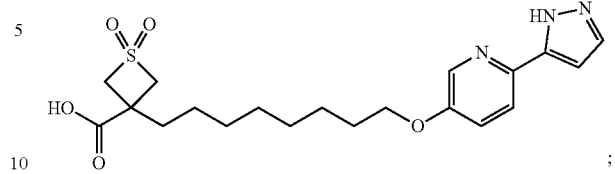

or a pharmaceutically acceptable salt thereof.

(34) In another embodiment, the present invention provides the compound according to (1), which is shown below:

[Formula 67]

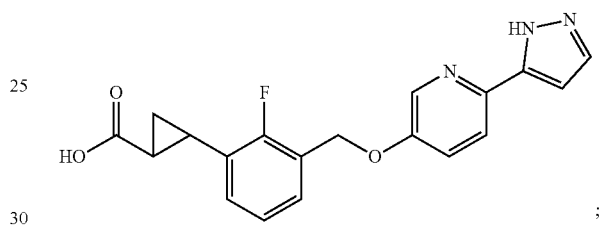

or a pharmaceutically acceptable salt thereof.

(35) In another embodiment, the present invention provides the compound according to (1), which is shown below:

[Formula 68]

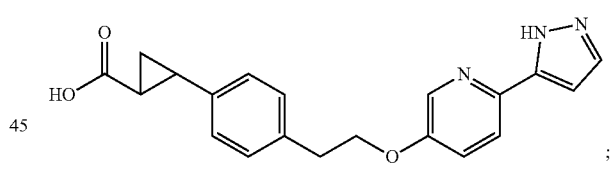

or a pharmaceutically acceptable salt thereof.

(36) In another embodiment, the present invention provides the compound according to (1), which is shown below:

[Formula 69]

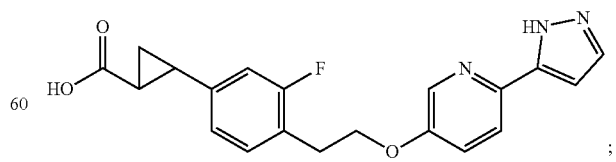

or a pharmaceutically acceptable salt thereof.

(37) In another embodiment, the present invention provides the compound according to (1), which is shown below:

[Formula 70]

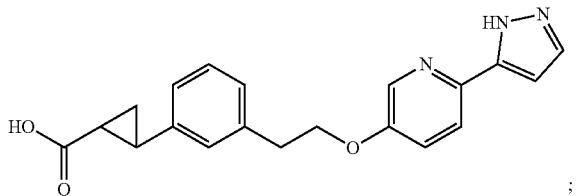

or a pharmaceutically acceptable salt thereof.
(38) In another embodiment, the present invention provides the compound according to (1), which is shown below:

[Formula 71]

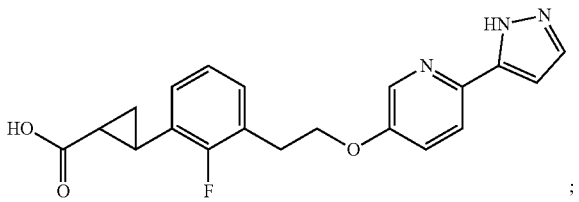

or a pharmaceutically acceptable salt thereof.
(39) In another embodiment, the present invention provides the compound according to (1), which is shown below:

[Formula 72]

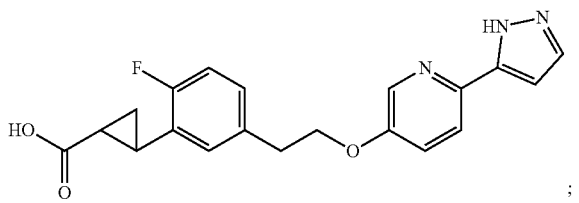 [SMILES: O=C(O)C1CC1c1cc(CCOc2ccc(-c3ccn[nH]3)nc2)ccc1F]

or a pharmaceutically acceptable salt thereof.
(40) In another embodiment, the present invention provides a pharmaceutical comprising the compound or pharmaceutically acceptable salt thereof according to any one of (1) to (39) as an active ingredient.
(41) In another embodiment, the present invention provides an agent that inhibits 20-HETE producing enzyme, wherein the agent comprises the compound or pharmaceutically acceptable salt thereof according to any one of (1) to (39) as an active ingredient.
(42) In another embodiment, the present invention provides an agent that prevents or ameliorates polycystic kidney disease, wherein the agent comprises the compound or pharmaceutically acceptable salt thereof according to any one of (1) to (39) as an active ingredient.

Advantageous Effects of Invention

The compound of the present invention (hereinafter also referred to as "the inventive compound") has an inhibitory effect on 20-HETE producing enzymes.

DESCRIPTION OF EMBODIMENTS

The present invention provides a compound represented by formula [I] shown above that has an inhibitory effect on 20-HETE producing enzymes or a pharmaceutically acceptable salt thereof.

The compounds of the present invention will be described in more detail below, but the present invention is not limited to the exemplary embodiments.

As used herein, the term "methylene moiety at position α of carboxy" has the same meaning as the carbon atom at position α of carboxy. Similarly, the terms "methylene moiety of carboxymethyl" and "methylene moiety of carboxymethoxy" have the same meaning as the carbon atom of methyl of carboxymethyl and the carbon atom of methoxy of carboxymethoxy, respectively.

The term "halogen atom" refers to a fluorine atom, a chlorine atom, a bromine atom, or an iodine atom.

The term "$C_{1-4}$ alkyl" refers to a straight or branched alkyl group having one to four carbon atoms. Examples of $C_{1-4}$ alkyl include methyl, ethyl, n-propyl, isopropyl, n-butyl, isobutyl, sec-butyl, and tert-butyl.

The term "halo-$C_{1-4}$ alkyl" refers to a straight or branched alkyl group that is substituted with a halogen atom and has one to four carbon atoms. The halo-$C_{1-4}$ alkyl is preferably substituted with one to five halogen atoms, and the halogen atom is preferably a fluorine atom. Examples of halo-$C_{1-4}$ alkyl include monofluoromethyl, difluoromethyl, trifluoromethyl, 1-fluoroethyl, 1,1-difluoroethyl, 2-fluoroethyl, 2-fluoro-2-methylpropyl, 2,2-difluoropropyl, 1-fluoro-2-methylpropan-2-yl, 1,1-difluoro-2-methylpropan-2-yl, 2,2,2-trifluoro-1-methylethyl, and the like.

The term "$C_{2-4}$ alkenyl" refers to a straight or branched alkenyl group having two to four carbon atoms. Examples of $C_{2-4}$ alkenyl include ethenyl, (E)-prop-1-en-1-yl, (Z)-prop-1-en-1-yl, prop-2-en-1-yl, (Z)-but-2-en-1-yl, and the like.

The term "$C_{3-6}$ cycloalkane" refers to a hydrocarbon ring having three to six carbon atoms. Examples of $C_{3-6}$ cycloalkane include cyclopropane, cyclobutane, cyclopentane, and cyclohexane.

The term "$C_{3-6}$ cycloalkyl" refers to a cyclic alkyl group having three to six carbon atoms. Examples of $C_{3-6}$ cycloalkyl include cyclopropyl, cyclobutyl, cyclopentyl, and cyclohexyl.

The term "aryl" refers to a monocyclic or fused polycyclic aromatic hydrocarbon group having 6 to 14 carbon atoms. Examples of aryl include phenyl, naphthyl, anthryl, and the like.

Also, partially-saturated aryl groups are included in "aryl". The term "partially-saturated aryl group" refers to a partially-saturated fused polycyclic heterocyclic group among the monocyclic or fused polycyclic aromatic hydrocarbon group having 6 to 14 carbon atoms. Examples of partially-saturated aryl groups include dihydroindenyl and the like.

The term "saturated hetero ring" refers to a 3- to 8-membered monocyclic saturated heterocyclic group consisting of one to seven carbon atoms and one or more atoms which may be the same or different and are selected from the group consisting of an oxygen atom, a sulfur atom, and a nitrogen atom. Examples of saturated hetero ring include oxetane, tetrahydrofuran, tetrahydropyran, oxepane, azetidine, pyrrolidine, piperidine, azepane, thietane, tetrahydrothiophenyl, tetrahydrothiopyran, piperazine, pyrazolidine, morpholine, piperazine, thiomorpholine, 1,3-oxadinane, isothiazolidine, and the like.

The term "saturated heterocyclyl" refers to a 3- to 8-membered monocyclic saturated heterocyclic group consisting of one to seven carbon atoms and one or more atoms which may be the same or different and are selected from the group consisting of an oxygen atom, a sulfur atom, and a nitrogen atom. Examples of saturated heterocyclyl include oxetanyl, tetrahydrofuranyl, tetrahydropyranyl, oxepanyl, azetidinyl, pyrrolidinyl, piperidinyl, azepanyl, thietanyl, tetrahydrothiophenyl, tetrahydrothiopyranyl, piperazinyl, pyrazolidinyl, morpholinyl, piperazinyl, thiomorpholinyl, 1,3-oxazinanyl, isothiazolidinyl, and the like.

The term "4- to 6-membered saturated oxygen-containing hetero ring" refers to a 4- to 6-membered monocyclic saturated heterocyclic ring consisting of one oxygen atom and 3 to 5 carbon atoms. Examples of 4- to 6-membered saturated oxygen-containing hetero ring include oxetan, tetrahydrofuran, tetrahydropyrane, and the like.

The term "4- to 6-membered saturated oxygen-containing heterocyclyl" refers to a 4- to 6-membered monocyclic saturated heterocyclic group consisting of one oxygen atom and 3 to 5 carbon atoms. Examples of 4- to 6-membered saturated oxygen-containing heterocyclyl include oxetanyl, tetrahydrofuranyl, tetrahydropyranyl, and the like.

The term "4- to 6-membered saturated sulfur-containing hetero ring" refers to a 4- to 6-membered monocyclic saturated heterocyclic ring consisting of one sulfur atom and 3 to 5 carbon atoms. Examples of 4- to 6-membered saturated sulfur-containing hetero ring include thiethane, tetrahydrothiophene, tetrahydrothiopyrane, and the like.

The term "4- to 6-membered saturated sulfur-containing heterocyclyl" refers to a 4- to 6-membered monocyclic saturated heterocyclic group consisting of one sulfur atom and 3 to 5 carbon atoms. Examples of 4- to 6-membered saturated sulfur-containing heterocyclyl include thietanyl, tetrahydrothiophenyl, tetrahydrothiopyranyl, and the like.

The term "4- to 6-membered saturated nitrogen-containing hetero ring" refers to a 4- to 6-membered monocyclic saturated heterocyclic ring that consists of one nitrogen atom and 3 to 5 carbon atoms, and may further contain one heteroatom selected from the group consisting of a nitrogen atom, an oxygen atom, and a sulfur atom. Examples of 4- to 6-membered saturated nitrogen-containing hetero ring include azetidine, pyrrolidine, piperidine, piperazine, morpholine, thiomorpholine, and the like.

The term "4- to 6-membered saturated nitrogen-containing heterocyclyl" refers to a 4- to 6-membered monocyclic saturated heterocyclic group that consists of one nitrogen atom and 3 to 5 carbon atoms, and may further contain one heteroatom selected from the group consisting of a nitrogen atom, an oxygen atom, and a sulfur atom. Examples of 4- to 6-membered saturated nitrogen-containing heterocyclyl include azetidinyl, pyrrolidinyl, piperidinyl, piperazinyl, morpholinyl, thiomorpholinyl, and the like.

The term "heteroaryl" refers to a 5- to 7-membered monocyclic aromatic heterocyclic group consisting of one to six carbon atoms and one or more atoms which may be the same or different and are selected from the group consisting of an oxygen atom, a sulfur atom, and a nitrogen atom or a fused polycyclic aromatic heterocyclic group that is composed of 9 to 14 atoms consisting of 1 to 13 carbon atoms and one or more atoms which may be the same or different and are selected from the group consisting of an oxygen atom, a sulfur atom, and a nitrogen atom. Examples of heteroaryl include imidazolyl, pyrazolyl, thiazolyl, isothiazolyl, thiadiazolyl, oxazolyl, isooxazolyl, oxadiazolyl, pyrrolyl, triazolyl, tetrazolyl, pyridyl, pyrimidinyl, pyrazinyl, pyridazinyl, triazinyl, indolyl, benzopyrazolyl, benzotriazolyl, benzofuranyl, benzothiophenyl, quinolyl, isoquinolyl, quinoxalyl, and the like.

Also, partially-saturated heteroaryl groups are included in "heteroaryl". The term "partially-saturated heteroaryl group" refers to a 5- to 7-membered partially-saturated monocyclic heterocyclic group consisting of one to six carbon atoms and one or more atoms which may be the same or different and are selected from the group consisting of an oxygen atom, a sulfur atom, and a nitrogen atom or a partially-saturated fused polycyclic heterocyclic group that is composed of 9 to 14 atoms consisting of 1 to 13 carbon atoms and one or more atoms which may be the same or different and are selected from the group consisting of an oxygen atom, a sulfur atom, and a nitrogen atom. Examples of partially-saturated heteroaryl group include oxazolidinyl, thiazolinyl, dihydropyridinyl, dihydrobenzofuranyl, chromanyl, dihydropyranopyridinyl, dihydrofuropyridinyl, tetrahydroquinolyl, tetrahydroisoquinolyl, dihydrobenzodioxinyl, tetrahydrotriazoloazepinyl, and the like.

The term "$C_{1-4}$ alkoxy" refers to a straight or branched alkoxy group having one to four carbon atoms. Examples of $C_{1-4}$ alkoxy include methoxy, ethoxy, n-propoxy, isopropoxy, n-butoxy, isobutoxy, sec-butoxy, and tert-butoxy.

The term "mono$C_{1-4}$ alkylamino" refers to an amino group having, as a substituent, one "$C_{1-4}$ alkyl" group mentioned above. Examples of mono$C_{1-4}$ alkylamino include methylamino, ethylamino, n-propylamino, isopropylamino, n-butylamino, isobutylamino, sec-butylamino, and tert-butylamino The term "di($C_{1-4}$ alkyl)amino" refers to an amino group having, as substituents, two "$C_{1-4}$ alkyl" groups mentioned above, wherein the $C_{1-4}$ alkyl groups may be the same or different. Examples of di($C_{1-4}$ alkyl)amino include dimethylamino, diethylamino, di(n-propyl)amino, di(isopropyl)amino, ethylmethylamino, methyl(n-propyl)amino, and the like.

The term "$C_{1-4}$ alkylcarbonyl" refers to a group consisting of the above-mentioned "$C_{1-4}$ alkyl" which is bound to carbonyl. Examples of $C_{1-4}$ alkylcarbonyl include acetyl, ethylcarbonyl, n-propylcarbonyl, isopropylcarbonyl, n-butylcarbonyl, isobutylcarbonyl, sec-butylcarbonyl, and tert-butylcarbonyl.

The term "saturated heterocyclylcarbonyl" refers to a group consisting of the above-mentioned "saturated heterocyclyl" which is bound to carbonyl. Examples of saturated heterocyclylcarbonyl include oxetanylcarbonyl, tetrahydrofuranylcarbonyl, tetrahydropyranylcarbonyl, oxepanylcarbonyl, azetidinylcarbonyl, pyrrolidinylcarbonyl, piperidinylcarbonyl, azepanylcarbonyl, tetrahydrothiopyranylcarbonyl, morpholinylcarbonyl, piperazinylcarbonyl, thiomorpholinylcarbonyl, isothiazolidinylcarbonyl, and the like.

The "4- to 6-membered saturated oxygen-containing heterocyclylcarbonyl" refers to a group consisting of the above-mentioned "4- to 6-membered saturated oxygen-containing heterocyclyl" which is bound to carbonyl. Examples of 4- to 6-membered saturated oxygen-containing heterocyclylcarbonyl include oxetanylcarbonyl, tetrahydrofuranylcarbonyl, tetrahydropyranylcarbonyl, and the like.

The "4- to 6-membered saturated nitrogen-containing heterocyclylcarbonyl" refers to a group consisting of the above-mentioned "4- to 6-membered saturated nitrogen-containing heterocyclyl" which is bound to carbonyl. Examples of 4- to 6-membered saturated nitrogen-containing heterocyclylcarbonyl include azetidinylcarbonyl, pyrrolidinylcarbonyl, piperidinylcarbonyl, azepanylcarbonyl, morpholinylcarbonyl, piperazinylcarbonyl, thiomorpholinylcarbonyl, isothiazolidinylcarbonyl, and the like.

The term "$C_{1-4}$ alkylsulfonyl" refers to a group consisting of the above-mentioned "$C_{1-4}$ alkyl" which is bound to sulfonyl. Examples of $C_{1-4}$ alkylsulfonyl include methylsulfonyl, ethylsulfonyl, n-propylsulfonyl, isopropylsulfonyl, n-butylsulfonyl, isobutylsulfonyl, sec-butylsulfonyl, and tert-butylsulfonyl.

The term "$C_{1-4}$ alkylsulfonyloxy" refers to a group consisting of the above-mentioned "$C_{1-4}$ alkylsulfonyl" which is bound to an oxygen atom. Examples of $C_{1-4}$ alkylsulfonyloxy include methylsulfonyloxy, ethylsulfonyloxy, n-propylsulfonyloxy, isopropylsulfonyloxy, n-butylsulfonyloxy, isobutylsulfonyloxy, sec-butylsulfonyloxy, and tert-butylsulfonyloxy.

The term "saturated heterocyclylsulfonyl" refers to a group consisting of the above-mentioned "saturated heterocyclyl" which is bound to sulfonyl. Examples of saturated heterocyclylsulfonyl include azetidinylsulfonyl, pyrrolidinylsulfonyl, piperidinylsulfonyl, morpholinylsulfonyl, and the like.

The term "4- to 6-membered saturated nitrogen-containing heterocyclylsulfonyl" refers to a group consisting of the above-mentioned "4- to 6-membered saturated nitrogen-containing heterocyclyl" which is bound to sulfonyl. Examples of 4- to 6-membered saturated nitrogen-containing heterocyclylsulfonyl include azetidinylsulfonyl, pyrrolidinylsulfonyl, piperidinylsulfonyl, morpholinylsulfonyl, piperazinylsulfonyl, thiomorpholinylsulfonyl, isothiazolidinylsulfonyl, and the like.

The term "$C_{1-4}$ alkylsulfonylamino" refers to an amino group having, as a substituent, one "$C_{1-4}$ alkylsulfonyl" mentioned above. Examples of $C_{1-4}$ alkylsulfonylamino include methylsulfonylamino, ethylsulfonylamino, n-propylsulfonylamino, isopropylsulfonylamino, n-butylsulfonylamino, isobutylsulfonylamino, sec-butylsulfonylamino, and tert-butylsulfonylamino The term "$C_{1-4}$ alkylsulfonyl($C_{1-4}$ alkyl)amino" refers to an amino group having, as substituents, one "$C_{1-4}$ alkylsulfonyl" mentioned above and one "$C_{1-4}$ alkyl" mentioned above. Examples of $C_{1-4}$ alkylsulfonyl($C_{1-4}$ alkyl)amino include methylsulfonyl(methyl)amino, methylsulfonyl(ethyl)amino, ethylsulfonyl(methyl)amino, n-propylsulfonyl(methyl)amino, isopropylsulfonyl(methyl)amino, n-butylsulfonyl(methyl)amino, isobutylsulfonyl(methyl)amino, sec-butylsulfonyl(methyl)amino, and tert-butylsulfonyl(methyl)amino The term "$C_{1-4}$ alkylsulfonylaminocarbonyl" refers to a group consisting of the above-mentioned "$C_{1-4}$ alkylsulfonylamino" which is bound to carbonyl. Examples of $C_{1-4}$alkylsulfonylaminocarbonyl include methylsulfonylaminocarbonyl, ethylsulfonylaminocarbonyl, n-propylsulfonylaminocarbonyl, isopropylsulfonylaminocarbonyl, n-butylsulfonylaminocarbonyl, isobutylsulfonylaminocarbonyl, sec-butylsulfonylaminocarbonyl, and tert-butylsulfonylaminocarbonyl.

The term "$C_{1-4}$ alkylsulfonyl($C_{1-4}$ alkyl)aminocarbonyl" refers to a group consisting of the above-mentioned "$C_{1-4}$ alkylsulfonyl($C_{1-4}$ alkyl)amino" which is bound to carbonyl. Examples of $C_{1-4}$ alkylsulfonyl($C_{1-4}$ alkyl)aminocarbonyl include methylsulfonyl(methyl)aminocarbonyl, methylsulfonyl(ethyl)aminocarbonyl, ethylsulfonyl(methyl)aminocarbonyl, n-propylsulfonyl(methyl)aminocarbonyl, isopropylsulfonyl(methyl)aminocarbonyl, n-butylsulfonyl(methyl)aminocarbonyl, isobutylsulfonyl(methyl)aminocarbonyl, sec-butylsulfonyl(methyl)aminocarbonyl, and tert-butylsulfonyl(methyl)aminocarbonyl.

The term "$C_{1-4}$ alkoxycarbonyl" refers to a group consisting of the above-mentioned "$C_{1-4}$ alkoxy" which is bound to carbonyl. The $C_{1-4}$ alkoxycarbonyl includes methoxycarbonyl, ethoxycarbonyl, n-propoxycarbonyl, isopropoxycarbonyl, n-butoxycarbonyl, isobutoxycarbonyl, sec-butoxycarbonyl, and tert-butoxycarbonyl.

The term "mono$C_{1-4}$ alkylaminocarbonyl" refers to a group consisting of the above-mentioned "mono$C_{1-4}$ alkylamino" which is bound to carbonyl. The mono$C_{1-4}$alkylaminocarbonyl includes methylaminocarbonyl, ethylaminocarbonyl, n-propylaminocarbonyl, isopropylaminocarbonyl, n-butylaminocarbonyl, isobutylaminocarbonyl, sec-butylaminocarbonyl, and tert-butylaminocarbonyl.

The term "di($C_{1-4}$ alkyl)aminocarbonyl" refers to a group consisting of the above-mentioned "di($C_{1-4}$ alkyl)amino" which is bound to carbonyl. Examples of di($C_{1-4}$alkyl) aminocarbonyl include dimethylaminocarbonyl, diethylaminocarbonyl, di(n-propyl)aminocarbonyl, di(isopropyl)aminocarbonyl, ethylmethylaminocarbonyl, methyl(n-propyl)aminocarbonyl, and the like.

The term "$C_{3-6}$ cycloalkylaminocarbonyl" refers to a group consisting of an amino group that has, as a substituent, one "$C_{3-6}$ cycloalkyl" mentioned above and which is bound to carbonyl. Examples of $C_{3-6}$ cycloalkylaminocarbonyl include cyclopropylaminocarbonyl, cyclobutylaminocarbonyl, cyclopentylaminocarbonyl, and cyclohexylaminocarbonyl.

The term "saturated heterocyclylaminocarbonyl" refers to a group consisting of an amino group that has, as a substituent, one "saturated heterocyclyl" mentioned above and which is bound to carbonyl. The saturated heterocyclylaminocarbonyl includes oxetanylaminocarbonyl, tetrahydrofuranylaminocarbonyl, tetrahydropyranylaminocarbonyl, oxepanylaminocarbonyl, azetidinylaminocarbonyl, pyrrolidinylaminocarbonyl, piperidinylaminocarbonyl, azepanylaminocarbonyl, tetrahydrothiopyranylaminocarbonyl, morpholinylaminocarbonyl, piperazinylaminocarbonyl, thiomorpholinylaminocarbonyl, and the like.

The term "4- to 6-membered saturated oxygen-containing heterocyclylaminocarbonyl" refers to a group consisting of an amino group that has, as a substituent, one "4- to 6-membered saturated oxygen-containing heterocyclyl" mentioned above and which is bound to carbonyl. Examples of 4- to 6-membered saturated oxygen-containing heterocyclylaminocarbonyl include oxetanylaminocarbonyl, tetrahydrofuranylaminocarbonyl, tetrahydropyranylaminocarbonyl, and the like.

The term "mono$C_{1-4}$ alkylaminosulfonyl" refers to a group consisting of the above-mentioned "mono$C_{1-4}$ alkylamino" which is bound to sulfonyl. The mono$C_{1-4}$alkylaminosulfonyl includes methylaminosulfonyl, ethylaminosulfonyl, n-propylaminosulfonyl, isopropylaminosulfonyl, n-butylaminosulfonyl, isobutylaminosulfonyl, sec-butylaminosulfonyl, and tert-butylaminosulfonyl.

The term "di($C_{1-4}$ alkyl)aminosulfonyl" refers to a group consisting of the above-mentioned "di($C_{1-4}$ alkyl)amino" which is bound to sulfonyl. Examples of di($C_{1-4}$alkyl) aminosulfonyl include dimethylaminosulfonyl, diethylaminosulfonyl, di(n-propyl)aminosulfonyl, di(isopropyl)aminosulfonyl, ethylmethylaminosulfonyl, methyl(n-propyl)aminosulfonyl, and the like.

The term "oxo" refers to a substituent (=O) which involves substitution of the oxygen atom via a double bond. Accordingly, when an oxo group is substituted by a carbon atom, the oxo group and the carbon atom taken together form carbonyl. When one oxo group is substituted by one sulfur atom, the oxo group and the sulfur atom taken together form sulfinyl. When two oxo groups are substituted by one sulfur atom, the oxo groups and the sulfur atom taken together form sulfonyl.

When oxo is substituted with saturated heterocyclyl in the present invention, oxo-substituting saturated heterocyclyl forms and specific examples of such oxo-substituting saturated heterocyclyl include 2-oxopyrrolidinyl, 2-oxopiperidinyl, 2-oxopiperazinyl, 3-oxopiperazinyl, 1,1-dioxidotetrahydrothiophenyl, 1-oxidotetrahydro-2H-thiopyranyl, 1,1-dioxidotetrahydro-2H-thiopyranyl, 1,1-dioxidoisothiazolidinyl, 2-oxo-1,3-oxazolidinyl, 2-oxo-1,3-oxazinanyl, 6-oxo-1,6-dihydropyridinyl, 6-oxo-1,1-dihydropyridazinyl, 1-oxo-1,2,3,4-tetrahydroisoquinolyl-7-yl, and the like.

The term "$C_{1-3}$ alkanediyl" refers to a divalent hydrocarbon group formed by removing one hydrogen atom from alkyl having 1 to 3 carbon atoms. The $C_{1-3}$ alkanediyl includes methanediyl, ethane-1,1-diyl, ethane-1,2-diyl, propane-1,1-diyl, propane-1,2-diyl, propane-1,3-diyl, and propane-2,2-diyl.

The term "$C_{2-6}$ alkanediyl" refers to a divalent hydrocarbon group formed by removing one hydrogen atom from alkyl having 2 to 6 carbon atoms. Examples of $C_{2-6}$ alkanediyl include ethane-1,1-diyl, ethane-1,2-diyl, propane-1,3-diyl, butane-1,4-diyl, pentane-1,5-diyl, hexane-1,6-diyl, and the like.

The term "$C_{3-7}$ alkanediyl" refers to a divalent hydrocarbon group formed by removing one hydrogen atom from alkyl having 3 to 7 carbon atoms. Examples of $C_{3-7}$ alkanediyl include propane-1,3-diyl, butane-1,4-diyl, pentane-1,5-diyl, hexane-1,6-diyl, heptane-1,7-diyl, and the like.

The term "$C_{4-5}$ alkanediyl" refers to a divalent hydrocarbon group formed by removing one hydrogen atom from alkyl having 4 or 5 carbon atoms. Examples of $C_{4-5}$ alkanediyl include butane-1,4-diyl, pentane-1,5-diyl, and the like.

The term "$C_{4-8}$ alkanediyl" refers to a divalent hydrocarbon group formed by removing one hydrogen atom from alkyl having 4 to 8 carbon atoms. Examples of $C_{4-8}$ alkanediyl include butane-1,4-diyl, pentane-1,5-diyl, hexane-1,6-diyl, heptane-1,7-diyl, octane-1,8-diyl, 3,3-dimethyl-propane-1,3-diyl, and the like.

The term "$C_{4-10}$ alkanediyl" refers to a divalent hydrocarbon group formed by removing one hydrogen atom from alkyl having 4 to 10 carbon atoms. Examples of $C_{4-10}$ alkanediyl include butane-1,4-diyl, pentane-1,5-diyl, hexane-1,6-diyl, heptane-1,7-diyl, octane-1,8-diyl, nonane-1,9-diyl, decane-1,10-diyl, 3,3-dimethyl-propane-1,3-diyl, 8,8-dimethyl-octane-1,8-diyl, and the like.

The term "$C_{5-10}$ alkanediyl" refers to a divalent hydrocarbon group formed by removing one hydrogen atom from alkyl having 5 to 10 carbon atoms. Examples of $C_{5-10}$ alkanediyl include pentane-1,5-diyl, hexane-1,6-diyl, heptane-1,7-diyl, octane-1,8-diyl, nonane-1,9-diyl, decane-1,10-diyl, 3,3-dimethyl-propane-1,3-diyl, 8,8-dimethyl-octane-1,8-diyl, and the like.

The term "benzyl-based protecting group" refers to a group that is benzyl in which the phenyl may be substituted or benzyl in which the methylene may be substituted and that protects a functional group. Examples of the benzyl-based protecting group include benzyl, 4-methoxybenzyl, and the like.

Examples of functional groups to be protected by such a benzyl-based protecting group include hydroxy, carboxy, and the like.

When hydroxy is protected, the group is also referred to as "benzyl ether-based protecting group". Similarly, when carboxy is protected, the group is also referred to as "benzyl ester-based protecting group".

The term "acetal-based protecting group" refers to a group that forms an acetal structure together with hydroxy to protect a functional group. Examples of the acetal-based protecting group include methoxymethyl and tetrahydropyranyl.

Examples of functional groups to be protected by such an acetal-based protecting group include hydroxy and the like.

The term "silyl-based protecting group" refers to a group that is silyl substituted with three groups selected from alkyl and aryl and that protects a functional group. Examples of the silyl-based protecting group include trimethylsilyl, triisopropylsilyl, tert-butyldimethylsilyl, and the like.

Examples of functional groups to be protected by such a silyl-based protecting group include hydroxy and the like.

The following is one preferred embodiment of compounds of the present invention.

Among the structures represented by formula [II] shown below,

[Formula 73]

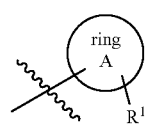

[II]

preferred is any of the structures represented by formula group [III] shown below:

[Formula 74]

[III]

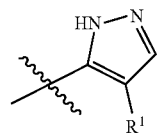

[III-1]

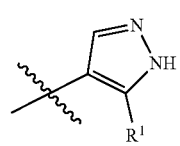

[III-2]

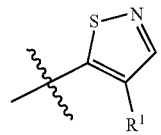

[III-3]

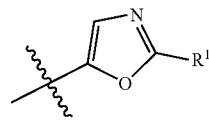

[III-4]

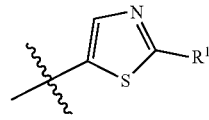

[III-5]

More preferred is any of the structures represented by formula group [III-1] shown below:

[Formula 75]

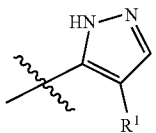

[III-1]

Preferably, $R^1$ is a hydrogen atom, a chlorine atom, or methyl. More preferably, $R^1$ is a hydrogen atom or a chlorine atom. Even more preferably, $R^1$ is a hydrogen atom.

Preferably, $R^2$ is a hydrogen atom, a fluorine atom, or methyl. More preferably, $R^2$ is a hydrogen atom or a fluorine atom. Even more preferably, $R^2$ is a hydrogen atom.

Preferably, $R^3$ is a hydrogen atom. Preferably, $R^4$ is a hydrogen atom.

Preferably, $R^5$ is as follows:

(A)

when $R^5$ is the structure represented by formula [IV-1], preferably, $R^{51}$ is any of the structures represented by formula group [V'] shown below:

[Formula 76]

[V' ]

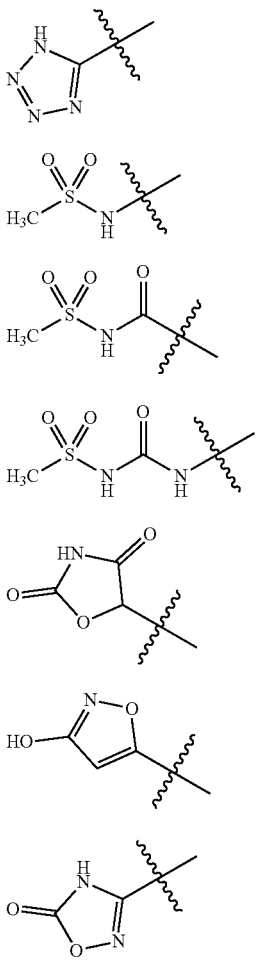

[V-1]

[V-2]

[V-3]

[V-4]

[V-5]

[V-6]

[V-7]

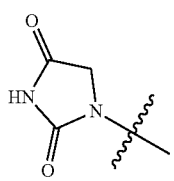

[V-8]

preferably, $W^1$ is $C_{4-10}$alkanediyl;

(B)

when $R^5$ is the structure represented by formula [IV-2], preferably, $R^{52}$ is carboxy;

preferably, L is any of the structures represented by formula group [VI'] shown below:

[Formula 77]

[VI' ]

[VI-1]

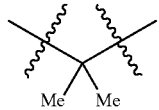

[VI-4]

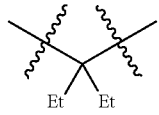

[VI-6]

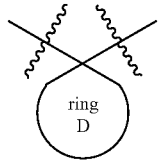

[VI-7]

wherein
preferably, ring D is
(i) $C_{3-6}$cycloalkane,
(ii) 4- to 6-membered saturated oxygen-containing hetero ring, or
(iv) 4- to 6-membered saturated nitrogen-containing hetero ring (the nitrogen atom of the 4- to 6-membered saturated nitrogen-containing hetero ring may be substituted with one $C_{1-4}$alkylcarbonyl);

preferably, Y is the formula —$CH_2$—, the formula —$CMe_2$-, the formula —O—, the formula —NHCO—, the formula —CONH—, or the formula —CONMe-;

preferably, $W^2$ is $C_{2-8}$alkanediyl, wherein one of the carbon atoms that constitute $C_{2-8}$ alkanediyl represented by $W^2$ may be replaced with an oxygen atom;

(C)

when $R^5$ is the structure represented by formula [IV-3], preferably, $R^{53}$ is carboxy, carboxymethyl, or carboxymethoxy, wherein the methylene moiety of the carboxymethyl or carboxymethoxy that is represented by $R^{53}$ may be replaced with propane-2,2-diyl;

preferably, ring B is any of the structures represented by formula group [VIII] shown below:

[Formula 78] [VIII]

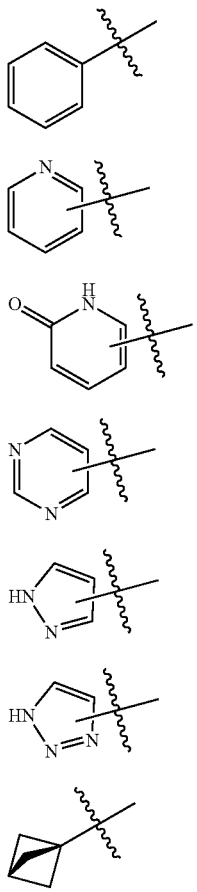

preferably, W³ is C₄₋₈alkanediyl or the formula —SO₂—W³³—, wherein preferably, W³³ is C₃₋₇alkanediyl;

(D)
when R⁵ is the structure represented by formula [IV-4], preferably, ring C is
(a) C₃₋₆cycloalkyl,
(b) 4- to 6-membered saturated nitrogen-containing heterocyclyl,
(c) phenyl,
(d) pyridyl,
(e) pyrazolyl,
(g) tetrahydronaphthyl,
(h) chromanyl,
(j) indazolyl,
(k) tetrahydroisoquinolyl,
(m) 2-oxotetrahydroisoquinolyl,
(n) the structure represented by formula [IX-1] below,
(p) the structure represented by formula [IX-2] below,
(q) the structure represented by formula [IX-3] below, or
(r) the structure represented by formula [IX-4] below:

[Formula 79] [IX]

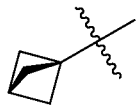 [IX-1]

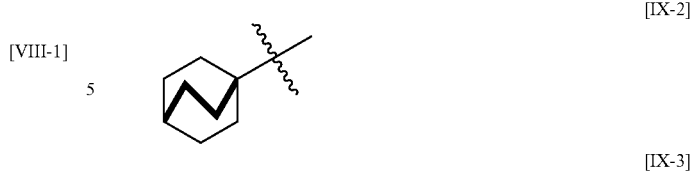 [IX-2]

 [IX-3]

 [IX-4]

(a) when ring C is C₃₋₆ cycloalkyl,
preferably, R⁵⁴ is
(i) carboxy, or
(iv) C₁₋₄ alkyl substituted with carboxy;
preferably, R⁶¹ and R⁶² are each a hydrogen atom;
(b) when ring C is 4- to 6-membered saturated nitrogen-containing heterocyclyl, preferably, R⁵⁴ is
(i) C₁₋₄ alkylcarbonyl substituted with carboxy (when position α of the carboxy of the C₁₋₄alkylcarbonyl substituted with carboxy is a methylene moiety, the methylene moiety may be replaced with propane-2,2-diyl or cyclopentane-1,1-diyl),
(ii) C₁₋₄ alkylcarbonyl substituted with sulfamoyl,
(iii) C₁₋₄ alkylcarbonyl substituted with C₁₋₄ alkylsulfonylamino,
(iv) phenylmethylcarbonyl substituted with carboxy,
(v) phenylcarbonyl substituted with sulfamoyl,
(vi) dihydropyridinylcarbonyl substituted with oxo,
(vii) phenylsulfonyl substituted with carboxy,
(viii) monoC₁₋₄ alkylaminocarbonyl substituted with carboxy (when position α of the carboxy of the monoC₁₋₄ alkylaminocarbonyl substituted with carboxy is a methylene moiety, the methylene moiety may be replaced with propane-2,2-diyl), or
(x) the structure represented by formula [X-2] below, which is substituted with carboxy:

[Formula 80]

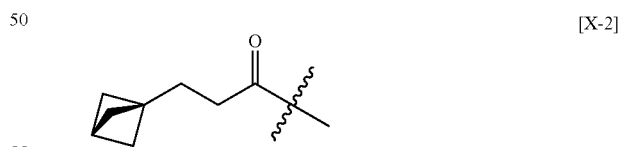 [X-2]

wherein preferably, R⁶¹ and R⁶² are each a hydrogen atom;
(c) when ring C is phenyl,
preferably, R⁵⁴ is
(i) carboxy,
(ii) carbamoyl,
(iii) monoC₁₋₄alkylaminocarbonyl (the C₁₋₄alkyl of the monoC₁₋₄alkylaminocarbonyl may be substituted with one hydroxy),
(iv) monoC₁₋₄alkylaminosulfonyl (the C₁₋₄alkyl of the monoC₁₋₄alkylaminosulfonyl may be substituted with one indolyl), (v) di($C_{1-4}$alkyl)aminosulfonyl (one $C_{1-4}$alkyl of the di($C_{1-4}$ alkyl)aminosulfonyl may be substituted with one phenyl, wherein the phenyl may be substituted with one mono$C_{1-4}$ alkylaminosulfonyl), (vi) phenylaminosulfonyl (the phenyl of the phenylaminosulfonyl may be substituted with one fluorine atom), (vii) $C_{1-4}$ alkylsulfonylamino, (viii) $C_{1-4}$alkylsulfonylaminocarbonyl, (ix) $C_{1-4}$ alkylsulfonyl($C_{1-4}$alkyl)aminocarbonyl, (x) $C_{1-4}$alkyl substituted with carboxy (when position α of the carboxy of the $C_{1-4}$alkyl substituted with carboxy is a methylene moiety, the methylene moiety may be replaced with a structure selected from the group consisting of ethane-1,1-diyl, propane-2,2-diyl, cyclopropane-1,1-diyl, tetrahydropyran-4,4-diyl, and piperidine-4,4-diyl (the nitrogen atom of the piperidine-4,4-diyl is substituted with methylcarbonyl), (xi) $C_{1-4}$ alkyl substituted with methylsulfonylaminocarbonyl, (xii) $C_{1-4}$ alkyl substituted with trifluoromethylsulfonylamino, (xiii) $C_{1-4}$ alkyl substituted with methylsulfonyl(methyl) aminocarbonyl, (xiv) $C_{1-4}$ alkyl substituted with mono$C_{1-4}$ alkylaminocarbonyl (the $C_{1-4}$ alkyl of the mono$C_{1-4}$alkylaminocarbonyl of the $C_{1-4}$ alkyl substituted with mono$C_{1-4}$ alkylaminocarbonyl may be substituted with one group selected from the group consisting of hydroxy, $C_{1-4}$ alkoxy, 4- to 6-membered saturated oxygen-containing heterocyclyl, di($C_{1-4}$ alkyl) amino, and 4- to 6-membered saturated nitrogen-containing heterocyclylcarbonyl), (xv) $C_{1-4}$ alkyl substituted with di($C_{1-4}$ alkyl)aminocarbonyl (one $C_{1-4}$ alkyl of the di($C_{1-4}$alkyl)aminocarbonyl of the $C_{1-4}$ alkyl substituted with di($C_{1-4}$ alkyl)aminocarbonyl may be substituted with one hydroxy), (xvi) $C_{1-4}$ alkyl substituted with 4- to 6-membered saturated oxygen-containing heterocyclylaminocarbonyl, (xvii) $C_{1-4}$ alkyl substituted with 4- to 6-membered saturated nitrogen-containing heterocyclylcarbonyl (the 4- to 6-membered saturated nitrogen-containing heterocyclyl of the $C_{1-4}$ alkyl substituted with 4- to 6-membered saturated nitrogen-containing heterocyclylcarbonyl may be substituted with one or two groups selected from the group consisting of hydroxy and a fluorine atom), (xviii) halo-$C_{1-4}$ alkyl substituted with carboxy, (xix) $C_{2-4}$ alkenyl substituted with carboxy, (xx) $C_{2-4}$ alkenyl substituted with di($C_{1-4}$ alkyl)aminocarbonyl, (xxi) $C_{3-6}$ cycloalkyl substituted with carboxy, (xxii) $C_{3-6}$ cycloalkyl substituted with di($C_{1-4}$ alkyl)aminocarbonyl, (xxiii) 4- to 6-membered saturated nitrogen-containing heterocyclyl substituted with carboxy, (xxiv) phenyl substituted with carboxy, (xxv) pyridyl substituted with carboxy, (xxvi) pyrazolyl substituted with carboxy, (xxvii) pyrazolyl substituted with carboxymethyl, (xxviii) pyrimidinyl substituted with carboxy, (xxix) pyrazinyl substituted with carboxy, (xxx) 2-oxodihydropyridinyl substituted with carboxymethyl, (xxxi) mono$C_{1-4}$ alkylaminocarbonyl substituted with carboxy (the $C_{1-4}$ alkyl of the mono$C_{1-4}$alkylaminocarbonyl substituted with carboxy may be substituted with one group selected from the group consisting of phenyl and benzyl, and when position α of the carboxy of the mono$C_{1-4}$ alkylaminocarbonyl substituted with carboxy is a methylene moiety, the methylene moiety may be replaced with a structure selected from the group consisting of ethane-1,1-diyl, propane-2,2-diyl, cyclopropane-1,1-diyl, cyclopentane-1,1-diyl, and tetrahydropyran-4,4-diyl), (xxxii) phenyl$C_{1-4}$ alkylaminocarbonyl substituted with carboxy, (xxxiii) mono$C_{1-4}$ alkylaminocarbonyl substituted with the structure represented by formula [V-6] below,

[Formula 81]

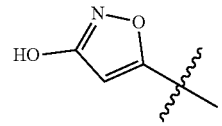

[V-6]

(xxxiv) di($C_{1-4}$alkyl)aminocarbonyl substituted with carboxy (when position α of the carboxy of the di($C_{1-4}$alkyl) aminocarbonyl substituted with carboxy is a methylene moiety, the methylene moiety may be replaced with propane-2,2-diyl), (xxxv) $C_{3-6}$cycloalkylaminocarbonyl substituted with carboxy, (xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), (xxxvii) 4- to 6-membered saturated nitrogen-containing heterocyclylcarbonyl substituted with carboxymethyl, (xxxviii) the structure represented by formula [XI-1] below, which is substituted with carboxy, (xxxix) the structure represented by formula [XI-2] below, which is substituted with carboxy, (xxxx) the structure represented by formula [XI-3] below, which is substituted with carboxy, (xxxxiii) the structure represented by formula [XI-6] below, which is substituted with carboxy,

[Formula 82]

[XI' ]

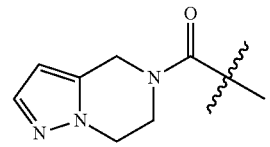

[XI-1]

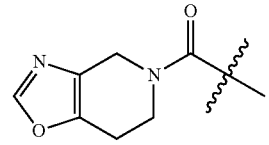

[XI-2]

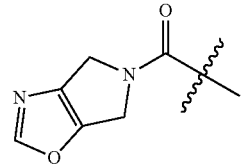

[XI-3]

-continued

[XI-6]

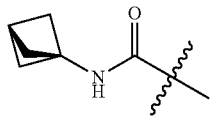

(xxxiv) $C_{1-4}$alkylsulfonyl substituted with carboxy (when position α of the carboxy of the $C_{1-4}$alkylsulfonyl substituted with carboxy is a methylene moiety, the methylene moiety may be replaced with propane-2,2-diyl),
(xxxv) monoC$_{1-4}$alkylaminosulfonyl substituted with carboxy (when position α of the carboxy of the monoC$_{1-4}$ alkylaminosulfonyl substituted with carboxy is a methylene moiety, the methylene moiety may be replaced with propane-2,2-diyl),
(xxxvi) di($C_{1-4}$alkyl)aminosulfonyl substituted with carboxy (when position α of the carboxy of the di($C_{1-4}$alkyl) aminosulfonyl substituted with carboxy is a methylene moiety, the methylene moiety may be replaced with propane-2,2-diyl),
(xxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
(xxxviii) $C_{1-4}$alkoxy substituted with carboxy (when position α of the carboxy of the $C_{1-4}$alkoxy substituted with carboxy is a methylene moiety, the methylene moiety may be replaced with propane-2,2-diyl),
(xxxix) hydroxy,
(xxxxx) $C_{1-4}$alkylsulfonyloxy,
(xxxxxi) $C_{1-4}$alkyl substituted with hydroxy,
(xxxxxii) halo-$C_{1-4}$alkyl substituted with hydroxy,
(xxxxxiii) $C_{1-4}$alkylsulfonyl substituted with hydroxy,
(xxxxxiv) $C_{3-6}$ cycloalkyl substituted with hydroxy (the $C_{3-6}$ cycloalkyl of the $C_{3-6}$ cycloalkyl substituted with hydroxy may be substituted with one group selected from the group consisting of carboxy and di($C_{1-4}$alkyl)aminocarbonyl), or
(xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$ alkylcarbonyl, $C_{1-4}$ alkoxycarbonyl and di($C_{1-4}$alkyl)aminocarbonyl), wherein preferably, $R^{61}$ and $R^{62}$ are each independently a hydrogen atom, a fluorine atom, a chlorine atom, methyl, methoxy, or methylsulfonyl;
(d) when ring C is pyridyl,
preferably, $R^{54}$ is
(i) carboxy,
(ii) carbamoyl,
(iii) $C_{1-4}$ alkyl substituted with carboxy (when position α of the carboxy of the $C_{1-4}$ alkyl substituted with carboxy is a methylene moiety, the methylene moiety may be replaced with propane-2,2-diyl),
(iv) $C_{1-4}$ alkoxy substituted with carboxy (when position α of the carboxy of the $C_{1-4}$ alkoxy substituted with carboxy is a methylene moiety, the methylene moiety may be replaced with propane-2,2-diyl),
(v) monoC$_{1-4}$ alkylaminocarbonyl substituted with carboxy (when position α of the carboxy of the monoC$_{1-4}$ alkylaminocarbonyl substituted with carboxy is a methylene moiety, the methylene moiety may be replaced with propane-2,2-diyl), or (vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), wherein preferably, $R^{61}$ and $R^{62}$ are each a hydrogen atom;
(e) when ring C is pyrazolyl,
preferably, $R^{54}$ is carboxy,
wherein preferably, $R^{61}$ and $R^{62}$ are each a hydrogen atom;
(g) when ring C is tetrahydronaphthyl,
preferably, $R^{54}$ is carboxy,
wherein preferably, $R^{61}$ and $R^{62}$ are each a hydrogen atom;
(h) when ring C is chromanyl,
preferably, $R^{54}$ is carboxy,
wherein $R^{61}$ and $R^{62}$ are each a hydrogen atom;
(j) when ring C is indazolyl,
preferably, $R^{54}$ is $C_{1-4}$ alkyl substituted with carboxy,
wherein preferably, $R^{61}$ and $R^{62}$ are each a hydrogen atom;
(k) when ring C is tetrahydroisoquinolyl,
preferably, $R^{54}$ is $C_{1-4}$ alkylcarbonyl substituted with carboxy,
wherein when position α of the carboxy of the $C_{1-4}$ alkylcarbonyl substituted with carboxy is a methylene moiety, the methylene moiety may be replaced with propane-2,2-diyl,
wherein preferably, $R^{61}$ and $R^{62}$ are each a hydrogen atom;
(m) when ring C is 2-oxotetrahydroisoquinolyl,
preferably, $R^{54}$ is $C_{1-4}$ alkyl substituted with carboxy,
wherein when position α of the carboxy of the $C_{1-4}$ alkyl substituted with carboxy is a methylene moiety, the methylene moiety may be replaced with propane-2,2-diyl,
wherein preferably, $R^{61}$ and $R^{62}$ are each a hydrogen atom;
(n) when ring C is the structure represented by formula [IX-1] above, preferably, $R^{54}$ is
(i) carboxy,
(ii) $C_{1-4}$ alkyl substituted with $C_{1-4}$ alkylsulfonylamino, or
(iii) $C_{1-4}$ alkyl substituted with $C_{1-4}$ alkylsulfonyl($C_{1-4}$alkyl) amino, wherein preferably, $R^{61}$ and $R^{62}$ are each a hydrogen atom;
(p) when ring C is the structure represented by formula [IX-2] above,
preferably, $R^{54}$ is
(i) carboxy, or
(ii) $C_{1-4}$ alkyl substituted with carboxy,
wherein preferably, $R^{61}$ and $R^{62}$ are each a hydrogen atom;
(q) when ring C is the structure represented by formula [IX-3] above, preferably, $R^{54}$ is carboxy,
wherein preferably, $R^{61}$ and $R^{62}$ are each a hydrogen atom;
(r) when ring C is the structure represented by formula [IX-4] above, preferably, $R^{54}$ is carboxy,
wherein preferably, $R^{61}$ and $R^{62}$ are each a hydrogen atom;
preferably, $W^4$ is $C_{1-3}$ alkanediyl or the formula —O—CH$_2$CH$_2$—.

The following are other preferred embodiments of the compounds of the present invention.

Preferred embodiments of $R^1$, $R^2$, $R^3$, $R^4$, and ring A in formula [1] above are as described above.

Another preferred examples of $R^5$ are as follows:
(A)
when $R^5$ is the structure represented by formula [IV-1], another preferred example of $R^{51}$ is any of the structures represented by formula group [V'''] shown below:

[Formula 83] [V″]

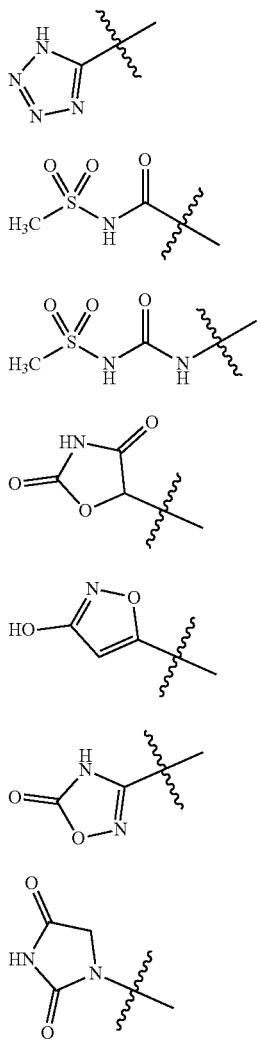

another preferred example of $W^1$ is $C_{4-10}$alkanediyl;

(B)

when $R^5$ is the structure represented by formula [IV-2], another preferred example of $R^{52}$ is carboxy;

another preferred example of L is any of the structures represented by formula group [VI'] shown below:

[Formula 84]

[VI' ]

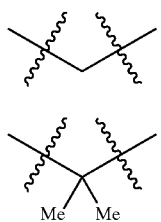

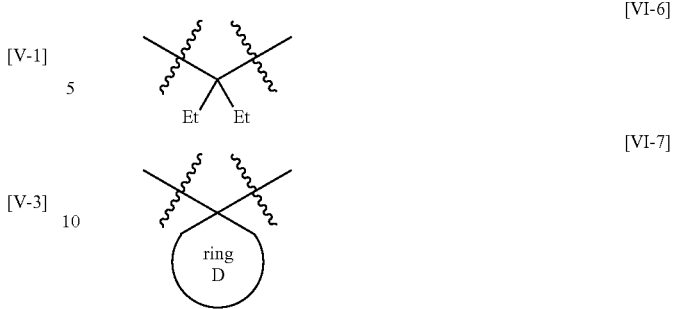

wherein another preferred example of ring D is (i) $C_{3-6}$cycloalkane, (ii) 4- to 6-membered saturated oxygen-containing hetero ring, or (iv) 4- to 6-membered saturated nitrogen-containing hetero ring (the nitrogen atom of the 4- to 6-membered saturated nitrogen-containing hetero ring may be substituted with one $C_{1-4}$alkylcarbonyl;

another preferred example of Y is the formula —CH$_2$—, the formula —CMe$_2$-, the formula —O—, the formula —NHCO—, the formula —CONH—, or the formula —CONMe-;

another preferred example of $W^2$ is $C_{2-8}$ alkanediyl, wherein one of the carbon atoms that constitute $C_{2-8}$ alkanediyl represented by $W^2$ may be replaced with an oxygen atom;

(C)

when $R^5$ is the structure represented by formula [IV-3], another preferred example of $R^{53}$ is carboxy, carboxymethyl, or carboxymethoxy, wherein the methylene moiety of the carboxymethyl or carboxymethoxy that is represented by $R^{53}$ may be replaced with propane-2,2-diyl;

another preferred example of ring B is any of the structures represented by formula group [VIII] shown below:

[Formula 85]

[VIII]

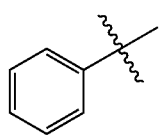

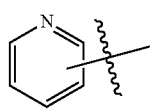

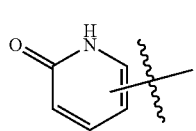

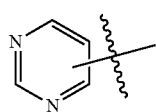

-continued

[VIII-5]

[VIII-6]

[VIII-7]

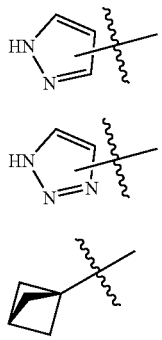

another preferred example of $W^3$ is $C_{4-8}$alkanediyl or the formula —$SO_2$—$W^{33}$—, wherein another preferred example of $W^3$ is $C_{3-7}$alkanediyl;

(D) when $R^5$ is the structure represented by formula [IV-4], another preferred example of ring C is (a) $C_{3-6}$cycloalkyl,
(b) 4- to 6-membered saturated nitrogen-containing heterocyclyl,
(c) phenyl,
(d) pyridyl,
(e) pyrazolyl,
(g) tetrahydronaphthyl,
(h) chromanyl,
(j) indazolyl,
(n) the structure represented by formula [IX-1] below,
(p) the structure represented by formula [IX-2] below,
(q) the structure represented by formula [IX-3] below, or
(r) the structure represented by formula [IX-4] below

[Formula 86]

[IX]

[IX-1]

[IX-2]

[IX-3]

[IX-4]

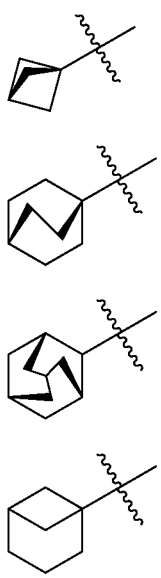

wherein
(a) when ring C is $C_{3-6}$ cycloalkyl,
another preferred example of $R^{54}$ is
(i) carboxy, or
(iv) $C_{1-4}$alkyl substituted with carboxy;

wherein another preferred example of $R^{61}$ and $R^{62}$ is a hydrogen atom;

(b) when ring C is 4- to 6-membered saturated nitrogen-containing heterocyclyl, another preferred example of $R^{54}$ is (i) $C_{1-4}$ alkylcarbonyl substituted with carboxy (when position α of the carboxy of the $C_{1-4}$alkylcarbonyl substituted with carboxy is a methylene moiety, the methylene moiety may be replaced with cyclopentane-1,1-diyl),
(ii) $C_{1-4}$ alkylcarbonyl substituted with sulfamoyl,
(iv) phenylmethylcarbonyl substituted with carboxy,
(v) phenylcarbonyl substituted with sulfamoyl,
(vi) dihydropyridinylcarbonyl substituted with oxo,
(vii) phenylsulfonyl substituted with carboxy,
(viii) mono$C_{1-4}$ alkylaminocarbonyl substituted with carboxy (when position α of the carboxy of the mono$C_{1-4}$ alkylaminocarbonyl substituted with carboxy is a methylene moiety, the methylene moiety may be replaced with propane-2,2-diyl), or
(x) the structure represented by formula [X-2] below, which is substituted with carboxy:

[Formula 87]

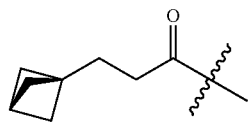

[X-2]

wherein another preferred example of $R^{61}$ and $R^{62}$ is a hydrogen atom;

(c) when ring C is phenyl,
another preferred example of $R^{54}$ is
(i) carboxy,
(ii) carbamoyl,
(iii) mono$C_{1-4}$alkylaminocarbonyl (the $C_{1-4}$alkyl of the mono$C_{1-4}$alkylaminocarbonyl may be substituted with one hydroxy),
(iv) mono$C_{1-4}$ alkylaminosulfonyl,
(v) di($C_{1-4}$alkyl)aminosulfonyl (one $C_{1-4}$alkyl of the di($C_{1-4}$ alkyl)aminosulfonyl may be substituted with one phenyl, wherein the phenyl may be substituted with one mono$C_{1-4}$ alkylaminosulfonyl),
(vi) phenylaminosulfonyl (the phenyl of the phenylaminosulfonyl may be substituted with one fluorine atom),
(vii) $C_{1-4}$ alkylsulfonylamino,
(viii) $C_{1-4}$alkylsulfonylaminocarbonyl,
(ix) $C_{1-4}$ alkylsulfonyl($C_{1-4}$ alkyl)aminocarbonyl,
(x) $C_{1-4}$ alkyl substituted with carboxy (when position α of the carboxy of the $C_{1-4}$ alkyl substituted with carboxy is a methylene moiety, the methylene moiety may be replaced with a structure selected from the group consisting of ethane-1,1-diyl, propane-2,2-diyl, cyclopropane-1,1-diyl, tetrahydropyran-4,4-diyl, and piperidine-4,4-diyl (the nitrogen atom of the piperidine-4,4-diyl is substituted with methylcarbonyl),
(xi) $C_{1-4}$ alkyl substituted with methylsulfonylaminocarbonyl,
(xii) $C_{1-4}$ alkyl substituted with trifluoromethylsulfonylamino,
(xiii) $C_{1-4}$ alkyl substituted with methylsulfonyl(methyl)aminocarbonyl, (xiv) $C_{1-4}$ alkyl substituted with mono$C_{1-4}$ alkylaminocarbonyl (the $C_{1-4}$ alkyl of the mono$C_{1-4}$alkylaminocarbonyl of the $C_{1-4}$ alkyl substituted with mono$C_{1-4}$ alkylaminocarbonyl may be substituted with one group selected from the group consisting of hydroxy, $C_{1-4}$ alkoxy, 4- to 6-membered saturated oxygen-containing heterocyclyl, di($C_{1-4}$ alkyl)amino, and 4- to 6-membered saturated nitrogen-containing heterocyclylcarbonyl), (xv) $C_{1-4}$ alkyl substituted with di($C_{1-4}$ alkyl)aminocarbonyl (one $C_{1-4}$ alkyl of the di($C_{1-4}$alkyl)aminocarbonyl of the $C_{1-4}$ alkyl substituted with di($C_{1-4}$ alkyl)aminocarbonyl may be substituted with one hydroxy), (xvi) $C_{1-4}$ alkyl substituted with 4- to 6-membered saturated oxygen-containing heterocyclylaminocarbonyl, (xvii) $C_{1-4}$ alkyl substituted with 4- to 6-membered saturated nitrogen-containing heterocyclylcarbonyl (the 4- to 6-membered saturated nitrogen-containing heterocyclyl of the $C_{1-4}$ alkyl substituted with 4- to 6-membered saturated nitrogen-containing heterocyclylcarbonyl may be substituted with one or two groups selected from the group consisting of hydroxy and a fluorine atom), (xviii) halo-$C_{1-4}$ alkyl substituted with carboxy,
(xix) $C_{2-4}$ alkenyl substituted with carboxy,
(xx) $C_{2-4}$ alkenyl substituted with di($C_{1-4}$ alkyl)aminocarbonyl,
(xxi) $C_{3-6}$ cycloalkyl substituted with carboxy,
(xxii) $C_{3-6}$ cycloalkyl substituted with di($C_{1-4}$ alkyl)aminocarbonyl,
(xxiii) 4- to 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxviii) pyrimidinyl substituted with carboxy,
(xxix) pyrazinyl substituted with carboxy,
(xxx) 2-oxodihydropyridinyl substituted with carboxymethyl,
(xxxi) mono$C_{1-4}$ alkylaminocarbonyl substituted with carboxy (the $C_{1-4}$ alkyl of the mono$C_{1-4}$alkylaminocarbonyl substituted with carboxy may be substituted with one group selected from the group consisting of phenyl and benzyl, and when position α of the carboxy of the mono$C_{1-4}$ alkylaminocarbonyl substituted with carboxy is a methylene moiety, the methylene moiety may be replaced with a structure selected from the group consisting of ethane-1,1-diyl, propane-2,2-diyl, cyclopropane-1,1-diyl, cyclopentane-1,1-diyl, and tetrahydropyran-4,4-diyl),
(xxxii) phenyl$C_{1-4}$ alkylaminocarbonyl substituted with carboxy,
(xxxiii) mono$C_{1-4}$ alkylaminocarbonyl substituted with the structure represented by formula [V-6] below,

[Formula 88]

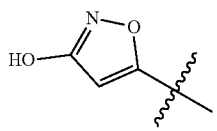

[V-6]

(xxxiv) di($C_{1-4}$alkyl)aminocarbonyl substituted with carboxy (when position α of the carboxy of the di($C_{1-4}$alkyl) aminocarbonyl substituted with carboxy is a methylene moiety, the methylene moiety may be replaced with propane-2,2-diyl), (xxxv) $C_{3-6}$cycloalkylaminocarbonyl substituted with carboxy, (xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), (xxxvii) 4- to 6-membered saturated nitrogen-containing heterocyclylcarbonyl substituted with carboxymethyl, (xxxviii) the structure represented by formula [XI-1] below, which is substituted with carboxy, (xxxix) the structure represented by formula [XI-2] below, which is substituted with carboxy, (xxxx) the structure represented by formula [XI-3] below, which is substituted with carboxy, (xxxxiii) the structure represented by formula [XI-6] below, which is substituted with carboxy,

[Formula 89]

[XI' ]

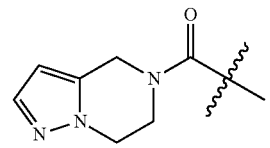

[XI-1]

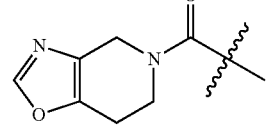

[XI-2]

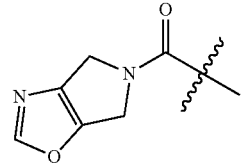

[XI-3]

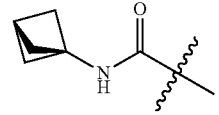

[XI-6]

(xxxxiv) $C_{1-4}$alkylsulfonyl substituted with carboxy (when position α of the carboxy of the $C_{1-4}$alkylsulfonyl substituted with carboxy is a methylene moiety, the methylene moiety may be replaced with propane-2,2-diyl), (xxxxv) mono$C_{1-4}$alkylaminosulfonyl substituted with carboxy (when position α of the carboxy of the mono$C_{1-4}$ alkylaminosulfonyl substituted with carboxy is a methylene moiety, the methylene moiety may be replaced with propane-2,2-diyl), (xxxxvi) di($C_{1-4}$alkyl)aminosulfonyl substituted with carboxy (when position α of the carboxy of the di($C_{1-4}$alkyl) aminosulfonyl substituted with carboxy is a methylene moiety, the methylene moiety may be replaced with propane-2,2-diyl), (xxxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
(xxxxviii) $C_{1-4}$alkoxy substituted with carboxy (when position α of the carboxy of the $C_{1-4}$alkoxy substituted with carboxy is a methylene moiety, the methylene moiety may be replaced with propane-2,2-diyl),
(xxxxix) hydroxy,
(xxxxx) $C_{1-4}$ alkylsulfonyloxy,
(xxxxxi) $C_{1-4}$ alkyl substituted with hydroxy,
(xxxxxii) halo-$C_{1-4}$ alkyl substituted with hydroxy,
(xxxxxiii) $C_{1-4}$ alkylsulfonyl substituted with hydroxy,
(xxxxxiv) $C_{3-6}$ cycloalkyl substituted with hydroxy (the $C_{3-6}$ cycloalkyl of the $C_{3-6}$ cycloalkyl substituted with hydroxy may be substituted with one group selected from the group consisting of carboxy and di($C_{1-4}$ alkyl)aminocarbonyl), or
(xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$ alkylcarbonyl, $C_{1-4}$ alkoxycarbonyl and di($C_{1-4}$ alkyl)aminocarbonyl), wherein another preferred example of $R^{61}$ and $R^{62}$ is each independently a hydrogen atom, a fluorine atom, a chlorine atom, methyl, methoxy, or methylsulfonyl;
(d) when ring C is pyridyl,
another preferred example of $R^{54}$ is
(i) carboxy,
(ii) carbamoyl,
(iii) $C_{1-4}$ alkyl substituted with carboxy (when position α of the carboxy of the $C_{1-4}$ alkyl substituted with carboxy is a methylene moiety, the methylene moiety may be replaced with propane-2,2-diyl),
(iv) $C_{1-4}$ alkoxy substituted with carboxy (when position α of the carboxy of the $C_{1-4}$ alkoxy substituted with carboxy is a methylene moiety, the methylene moiety may be replaced with propane-2,2-diyl),
(v) mono$C_{1-4}$ alkylaminocarbonyl substituted with carboxy (when position α of the carboxy of the mono$C_{1-4}$ alkylaminocarbonyl substituted with carboxy is a methylene moiety, the methylene moiety may be replaced with propane-2,2-diyl), or
(vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
wherein another preferred example of $R^{61}$ and $R^{62}$ is a hydrogen atom;
(e) when ring C is pyrazolyl,
another preferred example of $R^{54}$ is carboxy,
wherein another preferred example of $R^{61}$ and $R^{62}$ is a hydrogen atom;
(g) when ring C is tetrahydronaphthyl,
another preferred example of $R^{54}$ is carboxy,
wherein another preferred example of $R^{61}$ and $R^{62}$ is a hydrogen atom;
(h) when ring C is chromanyl,
another preferred example of $R^{54}$ is carboxy,
wherein another preferred example of $R^{61}$ and $R^{62}$ is a hydrogen atom;

(j) when ring C is indazolyl,
another preferred example of $R^{54}$ is $C_{1-4}$ alkyl substituted with carboxy,
wherein another preferred example of $R^{61}$ and $R^{62}$ is a hydrogen atom;
(n) when ring C is the structure represented by formula [IX-1] above, another preferred example of $R^{54}$ is
(i) carboxy,
(ii) $C_{1-4}$ alkyl substituted with $C_{1-4}$ alkylsulfonylamino, or
(iii) $C_{1-4}$ alkyl substituted with $C_{1-4}$ alkylsulfonyl($C_{1-4}$alkyl)amino,
wherein another preferred example of $R^{61}$ and $R^{62}$ is a hydrogen atom;
(p) when ring C is the structure represented by formula [IX-2] above, another preferred example of $R^{54}$ is
(i) carboxy, or
(ii) $C_{1-4}$ alkyl substituted with carboxy,
wherein another preferred example of $R^{61}$ and $R^{62}$ is a hydrogen atom;
(q) when ring C is the structure represented by formula [IX-3] above, another preferred example of $R^{54}$ is carboxy, wherein another preferred example of $R^{61}$ and $R^{62}$ is a hydrogen atom;
(r) when ring C is the structure represented by formula [IX-4] above, another preferred example of $R^{54}$ is carboxy, wherein another preferred example of $R^{61}$ and $R^{62}$ is a hydrogen atom;
Another preferred example of $W^4$ is $C_{1-3}$ alkanediyl, or the formula —O—$CH_2CH_2$—.
Here, more preferably, $R^5$ is,
(A)
when $R^5$ represents the structure represented by formula [IV-1],
more preferably, $R^{51}$ represents any of the structures represented by formula group [VI'] shown below:

[Formula 90]

[V'']

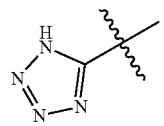

[V-1]

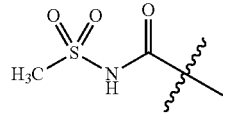

[V-3]

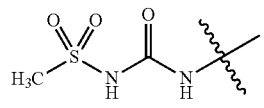

[V-4]

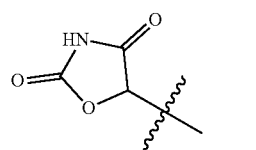

[V-5]

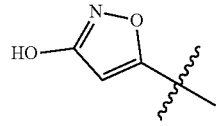

[V-6]

-continued

[V-7]

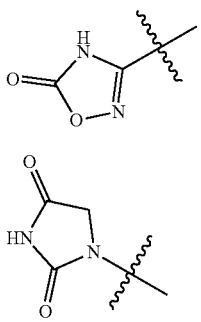

[V-8]

more preferably, $W^1$ represents $C_{4-5}$ alkanediyl;

(B)
when $R^5$ represents the structure represented by formula [IV-2],
more preferably, $R^{52}$ represents carboxy;
more preferably, L represents any of the structures represented by formula group [VI] below:

[Formula 91]

[VI']

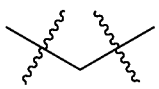
[VI-1]

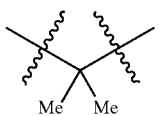
[VI-4]

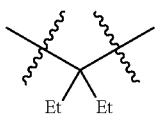
[VI-6]

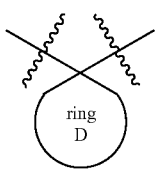
[VI-7]

wherein more preferably, ring D represents
(i) $C_{4-6}$cycloalkane,
(ii) 6-membered saturated oxygen-containing hetero ring, or
(iv) 5- to 6-membered saturated nitrogen-containing hetero ring (the nitrogen atom of the 5- to 6-membered saturated nitrogen-containing hetero ring is substituted with $C_1$alkylcarbonyl);
more preferably, Y represents the formula —$CH_2$—, the formula —$CMe_2$-, the formula —O—, the formula —NHCO—, the formula —CONH—, or the formula —CONMe-;
more preferably, $W^2$ represents $C_{2-8}$alkanediyl,
wherein one of the carbon atoms that constitute $C_{2-8}$alkanediyl represented by $W^2$ may be replaced with an oxygen atom;

(C)
When $R^5$ is the structure represented by formula [IV-3];
more preferably, $R^{53}$ represents carboxy, carboxymethyl (the methylene moiety of the carboxymethyl may be replaced with propane-2,2-diyl), or carboxymethoxy (the methylene moiety of the carboxymethoxy is replaced with propane-2,2-diyl);
more preferably, ring B represents any of the structures represented by formula group [VIII] below:

[Formula 92] [VIII]

[VIII-1]

[VIII-2]

[VIII-3]

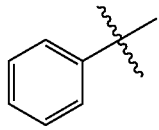
[VIII-4]

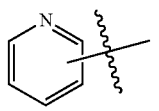
[VIII-5]

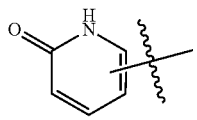
[VIII-6]

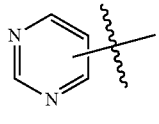
[VIII-7]

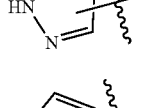

more preferably, $W^3$ represents $C_{4-6}$alkanediyl or the formula —$SO_2$—$W^{33}$—,
wherein more preferably, $W^{33}$ represents $C_4$alkanediyl;
(D)
when $R^5$ is the structure represented by formula [IV-4],
more preferably, ring C is
(a) $C_{3-6}$cycloalkyl,
(b) 6-membered saturated nitrogen-containing heterocyclyl,
(c) phenyl,
(d) pyridyl,
(e) pyrazolyl,
(g) tetrahydronaphthyl,
(h) chromanyl,
(j) indazolyl,
(n) the structure represented by formula [IX-1] below,
(p) the structure represented by formula [IX-2] below,
(q) the structure represented by formula [IX-3] below, or
(r) the structure represented by formula [IX-4] below,

[Formula 93] [IX]

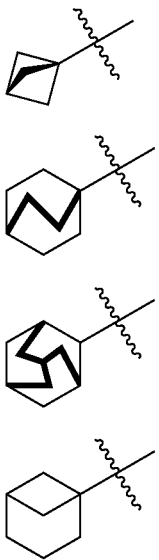

[IX-1]

[IX-2]

[IX-3]

[IX-4]

wherein
(a) when ring C represents $C_{3-6}$ cycloalkyl,
more preferably, ring C represents $C_{3-6}$ cycloalkyl;
more preferably, $R^{54}$ is
(i) carboxy, or
(iv) $C_{1-2}$ alkyl substituted with carboxy,
wherein more preferably, $R^{61}$ and $R^{62}$ represent a hydrogen atom;
(b) when ring C is 4- to 6-membered saturated nitrogen-containing heterocyclyl, more preferably, ring C is 6-membered saturated nitrogen-containing heterocyclyl, more preferably, $R^{54}$ is
(i) $C_{2-4}$ alkylcarbonyl substituted with carboxy (when position α of the carboxy of the $C_{2-4}$alkylcarbonyl substituted with carboxy is a methylene moiety, the methylene moiety may be replaced with cyclopentane-1,1-diyl),
(ii) $C_3$alkylcarbonyl substituted with sulfamoyl,
(iv) phenylmethylcarbonyl substituted with carboxy,
(v) phenylcarbonyl substituted with sulfamoyl,
(vi) dihydopyridinylcarbonyl substituted with oxo,
(vii) phenylsulfonyl substituted with carboxy,
(viii) monoC$_3$alkylaminocarbonyl substituted with carboxy (when position α of the carboxy of the monoC$_3$alkylaminocarbonyl substituted with carboxy is a methylene moiety, the methylene moiety is replaced with propane-2,2-diyl), or
(x) the structure represented by formula [X-2] below, which is substituted with carboxy:

[Formula 94]

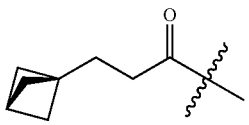

[X-2]

wherein more preferably, $R^{61}$ and $R^{62}$ represent a hydrogen atom;
(c) when ring C is phenyl,
more preferably, $R^{54}$ is
(i) carboxy,
(ii) carbamoyl,
(iii) monoC$_{1-3}$ alkylaminocarbonyl (the $C_{1-3}$ alkyl of the monoC$_{1-3}$ alkylaminocarbonyl may be substituted with one hydroxy),
(iv) monoC$_1$alkylaminosulfonyl,
(v) di(C$_1$alkyl)aminosulfonyl (one C$_1$alkyl of the di(C$_1$alkyl)aminosulfonyl is substituted with one phenyl, wherein the phenyl is substituted with one monoC$_1$alkylaminosulfonyl),
(vi) phenylaminosulfonyl (the phenyl of the phenylaminosulfonyl is substituted with one fluorine atom),
(vii) C$_3$alkylsulfonylamino,
(viii) C$_1$alkylsulfonylaminocarbonyl,
(ix) C$_1$alkylsulfonyl(C$_1$alkyl)aminocarbonyl,
(x) $C_{1-4}$alkyl substituted with carboxy (when position α of the carboxy of the $C_{1-4}$alkyl substituted with carboxy is a methylene moiety, the methylene moiety may be replaced with ethane-1,1-diyl, propane-2,2-diyl, cyclopropane-1,1-diyl, tetrahydropyran-4,4-diyl, or piperidine-4,4-diyl, wherein the nitrogen atom of the piperidine-4,4-diyl is substituted with one methylcarbonyl),
(xi) $C_{1-2}$ alkyl substituted with methylsulfonylaminocarbonyl,
(xii) C$_1$alkyl substituted with trifluoromethylsulfonylamino,
(xiii) $C_{1-2}$ alkyl substituted with methylsulfonyl(methyl)aminocarbonyl,
(xiv) $C_{1-2}$ alkyl substituted with monoC$_{1-3}$ alkylaminocarbonyl (the $C_{1-3}$ alkyl of the monoC$_{1-3}$alkylaminocarbonyl of the $C_{1-2}$ alkyl substituted with monoC$_{1-3}$ alkylaminocarbonyl may be substituted with one group selected from the group consisting of hydroxy, C$_1$alkoxy, 5-membered saturated oxygen-containing heterocyclyl, di(C$_1$alkyl)amino, and 5-membered saturated nitrogen-containing heterocyclylcarbonyl),
(xv) $C_{1-2}$ alkyl substituted with di(C$_{1-2}$ alkyl)aminocarbonyl (one $C_{1-2}$ alkyl of the di(C$_{1-2}$alkyl)amino of the di(C$_{1-2}$ alkyl)aminocarbonyl may be substituted with one hydroxy),
(xvi) C$_2$alkyl substituted with 4-membered saturated oxygen-containing heterocyclylaminocarbonyl,
(xvii) C$_2$alkyl substituted with 4- to 6-membered saturated nitrogen-containing heterocyclylcarbonyl (the 4- to 6-membered saturated nitrogen-containing heterocyclyl of the C$_2$alkyl substituted with 4- to 6-membered saturated nitrogen-containing heterocyclylcarbonyl may be substituted with one or two groups selected from the group consisting of hydroxy and a fluorine atom),
(xviii) halo-C$_1$alkyl substituted with carboxy,
(xix) C$_2$alkenyl substituted with carboxy,
(xx) C$_2$alkenyl substituted with di(C$_1$alkyl)aminocarbonyl,
(xxi) $C_{3-6}$ cycloalkyl substituted with carboxy,
(xxii) C$_3$cycloalkyl substituted with di(C$_1$alkyl)aminocarbonyl,
(xxiii) 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxviii) pyrimidinyl substituted with carboxy,
(xxix) pyrazinyl substituted with carboxy,
(xxx) 2-oxodihydropyridinyl substituted with carboxymethyl,
(xxxi) monoC$_{1-3}$ alkylaminocarbonyl substituted with carboxy (the $C_{1-3}$ alkyl of the monoC$_{1-3}$alkylaminocarbonyl substituted with carboxy may be substituted with one group selected from the group consisting of phenyl and benzyl, and when position α of the carboxy of the monoC$_{1-3}$ alkylaminocarbonyl substituted with carboxy is a methylene moiety, the methylene moiety may be replaced with a structure selected from the group consisting of ethane-1,1-diyl, propane-2,2-diyl, cyclopropane-1,1-diyl, cyclopentane-1,1-diyl, and tetrahydropyran-4,4-diyl), (xxxii) phenylC$_1$alkylaminocarbonyl substituted with carboxy, (xxxiii) monoC$_1$alkylaminocarbonyl substituted with the structure represented by formula [V-6] below,

[Formula 95]

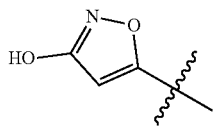

[V-6]

(xxxiv) di(C$_{1-3}$alkyl)aminocarbonyl substituted with carboxy (when position α of the carboxy of the di(C$_{1-3}$alkyl)aminocarbonyl substituted with carboxy is a methylene moiety, the methylene moiety may be replaced with propane-2,2-diyl), (xxxv) C$_{4-6}$cycloalkylaminocarbonyl substituted with carboxy, (xxxvi) 5- to 6-membered saturated nitrogen-containing heterocyclylcarbonyl substituted with carboxy (the 5- to 6-membered saturated nitrogen-containing heterocyclyl of the 5- to 6-membered saturated nitrogen-containing heterocyclylcarbonyl may be substituted with one fluorine atom), (xxxvii) 4- to 6-membered saturated nitrogen-containing heterocyclylcarbonyl substituted with carboxymethyl, (xxxviii) the structure represented by formula [XI-1] below, which is substituted with carboxy, (xxxix) the structure represented by formula [XI-2] below, which is substituted with carboxy, (xxxx) the structure represented by formula [XI-3] below, which is substituted with carboxy, (xxxxiii) the structure represented by formula [XI-6] below, which is substituted with carboxy,

[Formula 96]

[XI' ]

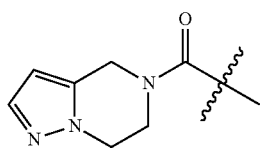

[XI-1]

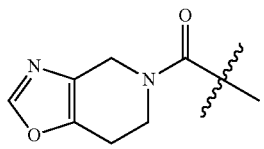

[XI-2]

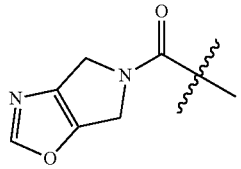

[XI-3]

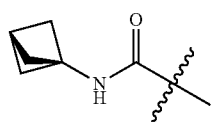

[XI-6]

(xxxxiv) C$_{2-4}$alkylsulfonyl substituted with carboxy (when position α of the carboxy of the C$_{2-4}$alkylsulfonyl substituted with carboxy is a methylene moiety, the methylene moiety may be replaced with propane-2,2-diyl), (xxxxv) monoC$_3$alkylaminosulfonyl substituted with carboxy (when position α of the carboxy of the monoC$_3$alkylaminosulfonyl substituted with carboxy is a methylene moiety, the methylene moiety is replaced with propane-2,2-diyl), (xxxxvi) di(C$_{1-3}$alkyl)aminosulfonyl substituted with carboxy (when position α of the carboxy of the di(C$_{1-3}$alkyl)aminosulfonyl substituted with carboxy is a methylene moiety, the methylene moiety is replaced with propane-2,2-diyl), (xxxxvii) 5- to 6-membered saturated nitrogen-containing heterocyclylsulfonyl substituted with carboxy (the 5- to 6-membered saturated nitrogen-containing heterocyclyl of the 5- to 6-membered saturated nitrogen-containing heterocyclylsulfonyl substituted with carboxy may be substituted with one fluorine atom), (xxxxviii) C$_1$alkoxy substituted with carboxy (when position α of the carboxy of the C$_1$alkoxy substituted with carboxy is a methylene moiety, the methylene moiety may be replaced with propane-2,2-diyl), (xxxxix) hydroxy, (xxxxx) C$_1$alkylsulfonyloxy, (xxxxxi) C$_{1-3}$alkyl substituted with hydroxy, (xxxxxii) halo-C$_{2-3}$alkyl substituted with hydroxy, (xxxxxiii) C$_{2-4}$alkylsulfonyl substituted with hydroxy, (xxxxxiv) C$_{4-5}$cycloalkyl substituted with hydroxy (the C$_{4-5}$cycloalkyl of the C$_{4-5}$ cycloalkyl substituted with hydroxy may be substituted with one group selected from the group consisting of carboxy and di(C$_1$alkyl)aminocarbonyl), or (xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy is substituted with one group selected from the group consisting of C$_1$alkylcarbonyl, C$_1$alkoxycarbonyl, and di(C$_1$alkyl)aminocarbonyl), wherein more preferably, R$^{61}$ and R$^{62}$ each independently represent a hydrogen atom, a fluorine atom, a chlorine atom, methyl, methoxy, or methylsulfonyl;

(d) when ring C is pyridyl,
more preferably, R$^{54}$ is
(i) carboxy,
(ii) carbamoyl,
(iii) C$_{1-3}$ alkyl substituted with carboxy (when position α of the carboxy of the C$_{1-3}$ alkyl substituted with carboxy is a methylene moiety, the methylene moiety may be replaced with propane-2,2-diyl), (iv) $C_2$alkoxy substituted with carboxy (when position α of the carboxy of the $C_2$alkoxy substituted with carboxy is a methylene moiety, the methylene moiety is replaced with propane-2,2-diyl),
(v) mono$C_3$alkylaminocarbonyl substituted with carboxy (when position α of the carboxy of the mono$C_3$alkylaminocarbonyl substituted with carboxy is a methylene moiety, the methylene moiety is replaced with propane-2,2-diyl), or
(vi) 5-membered saturated nitrogen-containing heterocyclylcarbonyl substituted with carboxy (the 5-membered saturated nitrogen-containing heterocyclyl of the 5-membered saturated nitrogen-containing heterocyclylcarbonyl substituted with carboxy is substituted with one fluorine atom),
wherein more preferably, $R^{61}$ and $R^{62}$ are each a hydrogen atom;
　　(e) when ring C is pyrazolyl,
more preferably, $R^{54}$ is carboxy,
wherein more preferably, $R^{61}$ and $R^{62}$ are each a hydrogen atom;
　　(g) when ring C is tetrahydronaphthyl,
more preferably, $R^{54}$ is carboxy,
wherein more preferably, $R^{61}$ and $R^{62}$ are each a hydrogen atom;
　　(h) when ring C is chromanyl,
more preferably, $R^{54}$ is carboxy,
wherein more preferably, $R^{61}$ and $R^{62}$ are each a hydrogen atom;
　　(j) when ring C is indazolyl,
more preferably, $R^{54}$ is $C_1$alkyl substituted with carboxy,
wherein more preferably, $R^{61}$ and $R^{62}$ are each a hydrogen atom;
　　(n) when ring C is the structure represented by formula [IX-1] above,
more preferably, $R^{54}$ is
(i) carboxy,
(ii) $C_1$alkyl substituted with $C_1$alkylsulfonylamino, or
(iii) $C_1$alkyl substituted with $C_1$alkylsulfonyl($C_1$alkyl)amino;
wherein more preferably, $R^{61}$ and $R^{62}$ represent a hydrogen atom;
　　(p) when ring C is the structure represented by formula [IX-2] above,
more preferably, $R^{54}$ is
(i) carboxy, or
(ii) $C_2$alkyl substituted with carboxy,
wherein more preferably, $R^{61}$ and $R^{62}$ represent a hydrogen atom;
　　(q) when ring C is the structure represented by formula [IX-3] above,
more preferably, $R^{54}$ represents carboxy;
wherein more preferably, $R^{61}$ and $R^{62}$ represent a hydrogen atom;
　　(r) when ring C is the structure represented by formula [IX-4] above,
more preferably, $R^{54}$ represents carboxy;
wherein more preferably, $R^{61}$ and $R^{62}$ represent a hydrogen atom;
　　more preferably, $W^4$ is $C_{1-3}$ alkanediyl, or the formula —O—$CH_2CH_2$—.
　Wherein, one even more preferred $R^5$ is as follows:
　　(A)
when $R^5$ represents the structure represented by formula [IV-1],
even more preferably, $R^{51}$ represents any of the structures represented by formula group [V'''] below:

[Formula 97]

[V''']

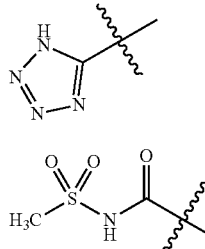   [V-1]

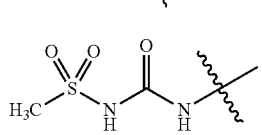   [V-3]

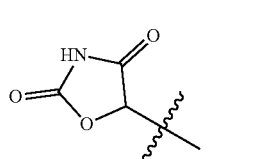   [V-4]

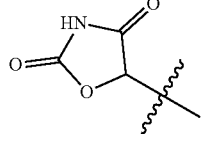   [V-5]

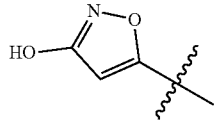   [V-6]

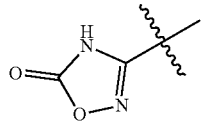   [V-7]

even more preferably, $W^1$ represents butane-1,4-diyl or pentane-1,5-diyl;
　(B)
when $R^5$ represents the structure represented by formula [IV-2],
even more preferably, $R^{52}$ represents carboxy;
even more preferably, L represents the structure represented by formula [VI-1], formula [VI-4], formula [VI-8], formula [VI-9], formula [VI-10], or formula [VI-12] below:

[Formula 98]

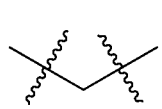   [VI-1]

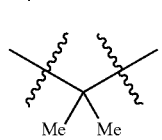   [VI-4]

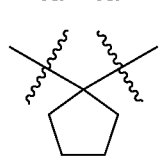   [VI-8]

-continued

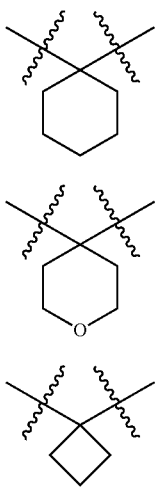

[VI-9]

[VI-10]

[VI-12]

even more preferably, Y represents the formula —CH$_2$—, the formula —CMe$_2$-, the formula —O—, the formula —NHCO—, or the formula —CONMe-, even more preferably, W$^2$ represents propane-1,3-diyl, butane-1,4-diyl, pentane-1,5-diyl, hexane-1,6-diyl, heptane-1,7-diyl, or the formula —O—(CH$_2$)$_6$—;

(C)

when R$^5$ is the structure represented by formula [IV-3];

even more preferably, R$^{53}$ represents carboxy, carboxymethyl (the methylene moiety of the carboxymethyl may be replaced with propane-2,2-diyl), or carboxymethoxy (the methylene moiety of the carboxymethoxy is replaced with propane-2,2-diyl);

even more preferably, ring B represents the structure represented by formula [VIII-1], formula [VIII-8], formula [VIII-9], formula [VIII-11], formula [VIII-12], formula [VIII-14], formula [VIII-B], or formula [VIII-7] below:

[Formula 99]

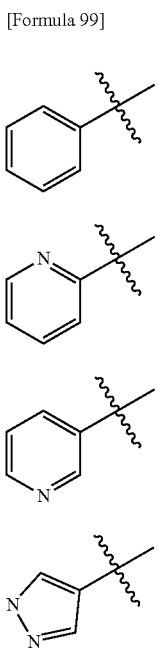

[VIII-1]

[VIII-8]

[VIII-9]

[VIII-11]

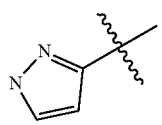

[VIII-12]

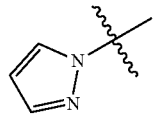

[VI-14]

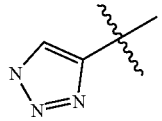

[VIII-13]

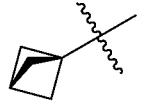

[VIII-7]

even more preferably, W$^3$ represents butane-1,4-diyl or hexane-1,6-diyl;

(D)

when R$^5$ is the structure represented by formula [IV-4], even more preferably, ring C represents:
(a) C$_{3-6}$cycloalkyl,
(b) 4- to 6-membered saturated nitrogen-containing heterocyclyl,
(c) phenyl,
(d) pyridyl,
(g) tetrahydronaphthyl,
(h) chromanyl,
(j) indazolyl,
(p) the structure represented by formula [IX-2] below,
(q) the structure represented by formula [IX-3] below, or
(r) the structure represented by formula [IX-4] below:

[Formula 100]

[IX']

[IX-2]

[IX-3]

[IX-4]

wherein
(a) when ring C represents C$_{3-6}$cycloalkyl,
even more preferably, ring C is cyclopropyl, cyclobutyl, or cyclohexyl;

even more preferably, $R^{54}$ represents:
(i) carboxy,
(iv) methyl substituted with carboxy, or ethyl substituted with carboxy,
wherein even more preferably, $R^{61}$ and $R^{62}$ represent a hydrogen atom;
(b) when ring C is 4- to 6-membered saturated nitrogen-containing heterocyclyl,
even more preferably, ring C is pipieridin-3-yl;
even more preferably, $R^{54}$ represents:
(i) ethylcarbonyl substituted with carboxy, n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy;
wherein even more preferably, $R^{61}$ and $R^{62}$ represent a hydrogen atom;
(c) when ring C is phenyl,
even more preferably, $R^{54}$ represents:
(i) carboxy,
(ii) carbamoyl,
(iii) n-propylaminocarbonyl,
(iv) methylaminosulfonyl,
(v) dimethylaminosulfonyl (one methyl of the dimethylaminosuflonyl is substituted with one phenyl,
wherein the phenyl is substituted with one methylaminosulfonyl),
(vii) isopropylsulfonylamino,
(viii) methylsulfonylaminocarbonyl,
(x) methyl substituted with carboxy (the methylene moiety at position α of the carboxy of the methyl substituted with carboxy may be replaced with ethane-1,1-diyl, propane-2,2-diyl, cyclopropane-1,1-diyl, tetrahydropyran-4,4-diyl, or piperidine-4,4-diyl,
wherein the nitrogen atom of the piperidine-4,4-diyl is substituted with one methylcarbonyl), ethyl substituted with carboxy, n-propyl substituted with carboxy, or n-butyl substituted with carboxy,
(xi) methyl substituted with methylsulfonylaminocarbonyl, or ethyl substituted with methylsulfonylaminocarbonyl,
(xii) methyl substituted with trifluoromethylsulfonylamino,
(xiv) ethyl substituted with methylaminocarbonyl (the methyl of the ethyl substituted with methylaminocarbonyl may be substituted with tetrahydrofuranyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl may be substituted with one group selected from the group consisting of hydroxy and methoxy), or ethyl substituted with isopropylaminocarbonyl (the isopropyl of the ethyl substituted with isopropylaminocarbonyl is substituted with one hydroxy),
(xv) ethyl substituted with dimethylaminocarbonyl,
(xvi) ethyl substituted with oxetanylaminocarbonyl,
(xvii) ethyl substituted with azetidinylcarbonyl (the azetidinyl of the ethyl substituted with azetidinylcarbonyl may be substituted with one to two groups selected from the group consisting of hydroxy and a fluorine atom), or ethyl substituted with pyrrolidinylcarbonyl,
(xviii) halo-methyl substituted with carboxy,
(xix) ethenyl substituted with carboxy,
(xxi) cyclopropyl substituted with carboxy, or cyclohexyl substituted with carboxy,
(xxii) cyclopropyl substituted with dimethylaminocarbonyl,
(xxiii) piperidinyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxviii) pyrimidinyl substituted with carboxy,
(xxix) pyrazinyl substituted with carboxy,
(xxx) 2-oxodihydropyridinyl substituted with carboxymethyl,
(xxxi) methylaminocarbonyl substituted with carboxy (the methyl of the methylaminocarbonyl substituted with carboxy may be substituted with one benzyl, and the methylene moiety at position α of the carboxy of the methylaminocarbonyl substituted with carboxy may be replaced with ethane-1,1-diyl), ethylaminocarbonyl substituted with carboxy (the ethyl of the ethylaminocarbonyl substituted with carboxy may be substituted with one phenyl, and the methylene moiety at position α of the carboxy of the ethylaminocarbonyl substituted with carboxy may be replaced with a structure selected from the group consisting of propane-2,2-diyl, cyclopropane-1,1-diyl, and cyclopentane-1,1-diyl), or n-propylaminocarbonyl substituted with carboxy (the methylene moiety at position α of the carboxy of the n-propylaminocarbonyl substituted with carboxy is replaced with propane-2,2-diyl),
(xxxii) phenylmethylaminocarbonyl substituted with carboxy,
(xxxiii) monomethylaminocarbonyl substituted with the structure represented by formula [V-6] below:

[Formula 101]

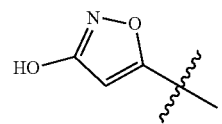

[V-6]

(xxxiv) ethyl(methyl)aminocarbonyl substituted with carboxy,
(xxxv) cyclobutylaminocarbonyl substituted with carboxy,
(xxxvi) pyrrolidinylcarbonyl substituted with carboxy (the pyrrolidinyl of the pyrrolidinylcarbonyl substituted with carboxy is substituted with one fluorine atom), or piperidinylcarbonyl substituted with carboxy,
(xxxviii) the structure represented by formula [XI-1] below, which is substituted with carboxy,
(xxxix) the structure represented by formula [XI-2] below, which is substituted with carboxy:

[Formula 102]

[XI'']

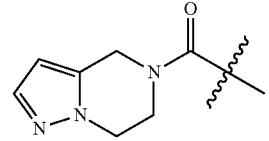

[XI-1]

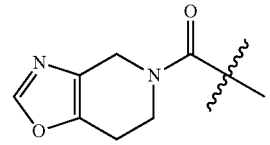

[XI-2]

(xxxxiv) ethylsulfonyl substituted with carboxy, or n-butylsulfonyl substituted with carboxy (the methylene moiety at position α of carboxy of the n-butylsulfonyl substituted with carboxy is replaced with propane-2,2-diyl),
(xxxxv) mono-n-propylaminosulfonyl substituted with carboxy (the methylene moiety at position α of the carboxy of the mono-n-propylaminosuflonyl substituted with carboxy is replaced with propane-2,2-diyl),
(xxxxvi) n-propyl(methyl)aminosulfonyl substituted with carboxy (the methylene moiety at position α of the carboxy of the n-propyl(methyl)aminosulfonyl substituted with carboxy is replaced with propane-2,2-diyl),
(xxxxvii) pyrrolidinylsulfonyl substituted with carboxy (the pyrrolidinyl of the pyrrolidinylsulfonyl substituted with carboxy may be substituted with one fluorine atom), piperidinylsulfonyl substituted with carboxy, morpholinylsulfonyl substituted with carboxy,
(xxxxviii) methoxy substituted with carboxy (the methylene moiety at position α of the carboxy of the methoxy substituted with carboxy may be replaced with propane-2,2-diyl),
(xxxxix) hydroxy,
(xxxxxi) isopropyl substituted with hydroxy,
(xxxxxii) haloethyl substituted with hydroxy, halo-n-propyl substituted with hydroxy, haloisopropyl substituted with hydroxy,
(xxxxxiii) ethylsulfonyl substituted with hydroxy, isobutylsulfonyl substituted with hydroxy, or
(xxxxxiv) cyclobutyl substituted with hydroxy (the cyclobutyl of the cyclobutyl substituted with hydroxy may be substituted with one carboxy), cyclopentyl substituted with hydroxy; wherein even more preferably, $R^{61}$ and $R^{62}$ each independently represent a hydrogen atom, a fluorine atom, methyl, methoxy, or methylsulfonyl;
(d) when ring C is pyridyl,
even more preferably, ring C is pyridin-2-yl or pyridin-4-yl,
even more preferably, $R^{54}$ represents:
(i) carboxy,
(iii) n-propyl substituted with carboxy (the methylene moiety at position α of the carboxy of the n-propyl substituted with carboxy is replaced with propane-2,2-diyl),
(iv) ethoxy substituted with carboxy (the methylene moiety at position α of the carboxy of the ethoxy substituted with carboxy is replaced with propane-2,2-diyl), or
(v) mono-n-propylaminocarbonyl substituted with carboxy (the methylene moiety at position α of the carboxy of the mono-n-propylaminocarbonyl substituted with carboxy is replaced with propane-2,2-diyl);
wherein even more preferably, $R^{61}$ and $R^{62}$ represent a hydrogen atom;
(g) when ring C is tetrahydronaphthyl,
even more preferably, ring C represents the structure represented by formula [XII-1], formula [XII-2], or formula [XII-3] below:

[Formula 103]

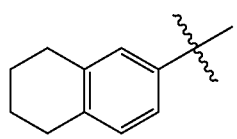
[XII-1]

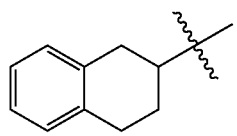
[XII-2]

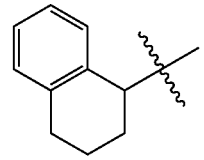
[XII-3]

even more preferably, $R^{54}$ represents carboxy;
wherein even more preferably, $R^{61}$ and $R^{62}$ represent a hydrogen atom;
(h) when ring C is chromanyl,
even more preferably, ring C represents the structure represented by formula [XIII-1] or formula [XIII-2] below:

[Formula 104]

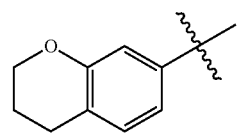
[XIII-1]

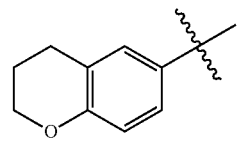
[XIII-2]

even more preferably, $R^{54}$ represents carboxy;
wherein even more preferably, $R^{61}$ and $R^{62}$ represent a hydrogen atom;
(j) when ring C is indazolyl,
even more preferably, $R^{54}$ represents methyl substituted with carboxy,
wherein even more preferably, $R^{61}$ and $R^{62}$ represent a hydrogen atom;
(p) when ring C is the structure represented by formula [IX-2] above,
even more preferably, $R^{54}$ represents:
(i) carboxy, or
(ii) ethyl substituted with carboxy,
wherein even more preferably, $R^{61}$ and $R^{62}$ represent a hydrogen atom;
(q) when ring C is the structure represented by formula [IX-3] above,
even more preferably, $R^{54}$ represents carboxy;
wherein even more preferably, $R^{61}$ and $R^{62}$ represent a hydrogen atom;
(r) when ring C is the structure represented by formula [IX-4] above,
even more preferably, $R^{54}$ represents carboxy;
wherein even more preferably, $R^{61}$ and $R^{62}$ represent a hydrogen atom;
even more preferably, $W^4$ represents methanediyl, ethane-1,2-diyl, propane-1,3-diyl, or the formula —O—CH$_2$CH$_2$—.
Wherein, another even more preferred $R^5$ is as follows:
(A)
when $R^5$ represents the structure represented by formula [IV-1],
even more preferably, $R^{51}$ represents the structure represented by formula [V-6] below:

[Formula 105]

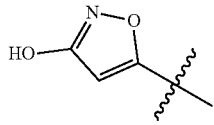

[V-6]

even more preferably, $W^1$ represents butane-1,4-diyl;

(B)

when $R^5$ represents the structure represented by formula [IV-2], even more preferably, $R^{52}$ represents carboxy;

even more preferably, L represents the structure represented by formula [VI-1], formula [VI-4], formula [VI-8], formula [VI-9], or formula [VI-10] below:

[Formula 106]

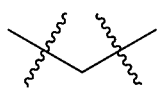

[VI-1]

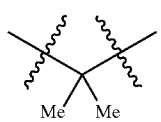

[VI-4]

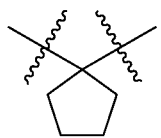

[VI-8]

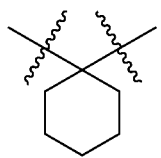

[VI-9]

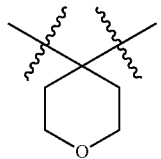

[VI-10]

even more preferably, Y represents the formula —CH$_2$—, the formula —O—, or the formula —CONMe-;

even more preferably, $W^2$ represents pentane-1,5-diyl, hexane-1,6-diyl, heptane-1,7-diyl, or the formula —O—(CH$_2$)$_6$—;

(C)

when $R^5$ is the structure represented by formula [IV-3];

even more preferably, $R^{53}$ represents carboxy;

even more preferably, ring B represents the structure represented by formula [VIII-1], formula [VIII-8], formula [VIII-9], or formula [VIII-7] below:

[Formula 107]

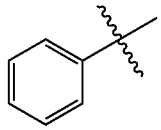

[VIII-1]

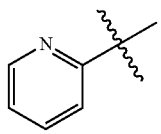

[VIII-8]

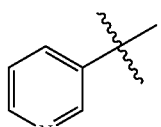

[VIII-9]

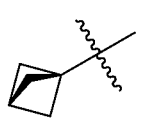

[VIII-7]

even more preferably, $W^3$ represents butane-1,4-diyl, or hexane-1,6-diyl;

(D)

when $R^5$ is the structure represented by formula [IV-4], even more preferably, ring C represents:
(a) $C_{3-6}$cycloalkyl,
(b) 4- to 6-membered saturated nitrogen-containing heterocyclyl,
(c) phenyl,
(d) pyridyl,
(g) tetrahydronaphthyl, or
(h) chromanyl;
wherein
(a) when ring C represents $C_{3-6}$cycloalkyl,
even more preferably, ring C is cyclohexyl;
even more preferably, $R^{54}$ represents carboxy;
wherein even more preferably, $R^{61}$ and $R^{62}$ represent a hydrogen atom;
(b) when ring C is 4- to 6-membered saturated nitrogen-containing heterocyclyl, even more preferably, ring C is pipieridin-3-yl;
even more preferably, $R^{54}$ represents:
(i) n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy;
wherein even more preferably, $R^{61}$ and $R^{62}$ represent a hydrogen atom;
(c) when ring C is phenyl,
even more preferably, $R^{54}$ represents:
(i) carboxy,
(ii) carbamoyl,
(iii) n-propylaminocarbonyl,
(iv) methylaminosulfonyl,
(v) dimethylaminosulfonyl (one methyl of the dimethylaminosuflonyl is substituted with one phenyl,
wherein the phenyl is substituted with one methylaminosulfonyl),
(vii) isopropylsulfonylamino,
(x) methyl substituted with carboxy, ethyl substituted with carboxy, or n-propyl substituted with carboxy, (xii) methyl substituted with trifluoromethylsulfonylamino, (xiv) ethyl substituted with methylaminocarbonyl (the methyl of the ethyl substituted with methylaminocarbonyl may be substituted with one tetrahydrofuranyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl may be substituted with one group selected from the group consisting of hydroxy and methoxy), or ethyl substituted with isopropylaminocarbonyl (the isopropyl of the ethyl substituted with isopropylaminocarbonyl is substituted with one group selected from the group consisting of hydroxy and methoxy), (xv) ethyl substituted with dimethylaminocarbonyl, (xvi) $C_{1-4}$alkylethyl substituted with oxetanylaminocarbonyl, (xvii) ethyl substituted with azetidinylcarbonyl (the azetidinyl of the ethyl substituted with azetidinylcarbonyl may be substituted with one hydroxy or one to two fluorine atoms), or ethyl substituted with pyrrolidinylcarbonyl, (xix) ethenyl substituted with carboxy, (xxi) cyclopropyl substituted with carboxy, or cyclohexyl substituted with carboxy, (xxii) cyclopropyl substituted with dimethylaminocarbonyl, (xxiv) phenyl substituted with carboxy, (xxv) pyridyl substituted with carboxy, (xxvi) pyrazolyl substituted with carboxy, (xxvii) pyrazolyl substituted with carboxymethyl, (xxix) pyrazinyl substituted with carboxy, (xxx) 2-oxodihydropyridinyl substituted with carboxymethyl, (xxxi) ethylaminocarbonyl substituted with carboxy (the methylene moiety at position α of the carboxy of the ethylaminocarbonyl substituted with carboxy is replaced with cyclopentane-1,1-diyl), n-propylaminocarbonyl substituted with carboxy (the methylene moiety at position α of the carboxy of the n-propylaminocarbonyl substituted with carboxy is replaced with propane-2,2-diyl), (xxxii) phenylmethylaminocarbonyl substituted with carboxy, (xxxiii) methylaminocarbonyl substituted with the structure represented by formula [V-6] below:

[Formula 108]

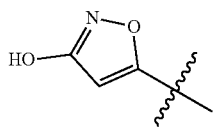
[V-6]

(xxxvi) pyrrolidinylcarbonyl substituted with carboxy (the pyrrolidinyl of the pyrrolidinylcarbonyl substituted with carboxy is substituted with one fluorine atom), (xxxix) the structure represented by formula [XI-2] below, which is substituted with carboxy:

[Formula 109]

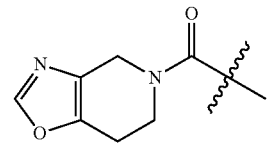
[XI-2]

(xxxiv) n-butylsulfonyl substituted with carboxy (the methylene moiety at position α of carboxy of the n-butylsulfonyl substituted with carboxy is replaced with propane-2,2-diyl), (xxxxvi) n-propyl(methyl)aminosulfonyl substituted with carboxy (the methylene moiety at position α of the carboxy of the n-propyl(methyl)aminosulfonyl substituted with carboxy is replaced with propane-2,2-diyl), (xxxxvii) piperidinylsulfonyl substituted with carboxy, pyrrolidinylsulfonyl substituted with carboxy (the pyrrolidinyl of the pyrrolidinylsulfonyl substituted with carboxy is substituted with one fluorine atom), (xxxxix) hydroxy, (xxxxxi) isopropyl substituted with hydroxy, (xxxxxii) haloethyl substituted with hydroxy, halo-n-propyl substituted with hydroxy, haloisopropyl substituted with hydroxy, (xxxxxiii) ethylsulfonyl substituted with hydroxy, isobutylsulfonyl substituted with hydroxy, or (xxxxxiv) cyclobutyl substituted with hydroxy (the cyclobutyl of the cyclobutyl substituted with hydroxy may be substituted with one carboxy), cyclopentyl substituted with hydroxy; wherein even more preferably, $R^{61}$ and $R^{62}$ each independently represent a hydrogen atom, a fluorine atom, or methylsulfonyl;

(d) when ring C is pyridyl, even more preferably, ring C is pyridin-4-yl;

even more preferably, $R^{54}$ represents ethoxy substituted with carboxy (the methylene moiety at position α of the carboxy of the ethoxy substituted with carboxy is replaced with propane-2,2-diyl);

wherein even more preferably, $R^{61}$ and $R^{62}$ represent a hydrogen atom;

(g) when ring C is tetrahydronaphthyl, even more preferably, ring C represents the structure represented by formula [XII-1] or formula [XII-2] below:

[Formula 110]

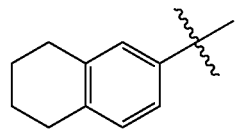
[XII-1]

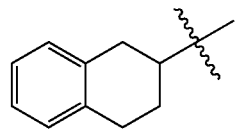
[XII-2]

even more preferably, $R^{54}$ represents carboxy;

wherein even more preferably, $R^{61}$ and $R^{62}$ represent a hydrogen atom;

(h) when ring C is chromanyl, even more preferably, ring C represents the structure represented by formula [XIII-1] or formula [XIII-2] below:

[Formula 111]

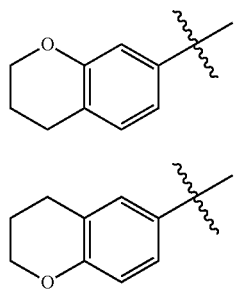

[XIII-1]

[XIII-2]

even more preferably, $R^{54}$ represents carboxy;

wherein even more preferably, $R^{61}$ and $R^{62}$ represent a hydrogen atom;

even more preferably, $W^4$ represents methanediyl, ethane-1,2-diyl, or propane-1,3-diyl.

Other preferred embodiments of the compounds of the present invention are as follows:

Preferred embodiments of $R^1$, $R^2$, $R^3$, $R^4$, and ring A in formula [1] above are as described above.

Other preferred examples of $R^5$ are as follows:

(A)

when $R^5$ is the structure represented by formula [IV-1], another preferred example of $R^{51}$ is any of the structures represented by formula group [V-b] shown below:

[Formula 112] [V-b]

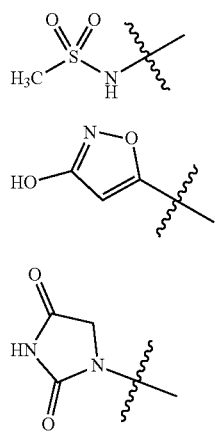

[V-2]

[V-6]

[V-8]

another preferred example of $W^1$ is $C_{4-10}$alkanediyl;

(B)

when $R^5$ is the structure represented by formula [IV-2], another preferred example of $R^{52}$ is carboxy;

another preferred example of L is any of the structures represented by formula group [VI-b] shown below:

[Formula 113]

[VI-b]

[VI-1]

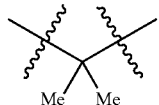

[VI-4]

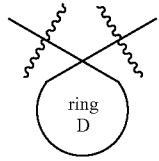

[VI-7]

wherein another preferred example of ring D is (i) $C_{5-6}$ cycloalkane, (ii) 4- to 6-membered saturated oxygen-containing hetero ring, or (iv) 4- to 6-membered saturated nitrogen-containing hetero ring (the nitrogen atom of the 4- to 6-membered saturated nitrogen-containing hetero ring may be substituted with one $C_{1-4}$alkylcarbonyl);

another preferred example of Y is the formula —$CH_2$—, the formula —O—, the formula —CONH—, or the formula —CONMe-;

another preferred example of $W^2$ is $C_{5-8}$ alkanediyl, wherein one of the carbon atoms that constitute $C_{5-8}$ alkanediyl represented by $W^2$ may be replaced with an oxygen atom;

(C)

when $R^5$ is the structure represented by formula [IV-3], another preferred example of $R^{53}$ is carboxy or carboxymethoxy;

another preferred example of ring B is any of the structures represented by formula group [VIII"] shown below:

[Formula 114]

[VIII" ]

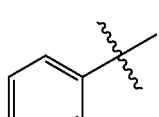

[VIII-1]

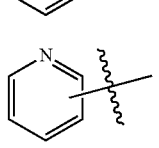

[VIII-2]

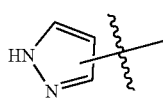

[VIII-4]

-continued

[VIII-7]

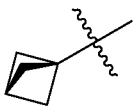

another preferred example of W³ is C₄₋₈alkanediyl;

(D)
when $R^5$ is the structure represented by formula [IV-4], another preferred example of ring C is
(a) $C_{3-6}$cycloalkyl,
(b) 4- to 6-membered saturated nitrogen-containing heterocyclyl,
(c) phenyl,
(d) pyridyl,
(g) tetrahydronaphthyl,
(h) chromanyl,
(k) tetrahydroisoquinolyl,
(m) 2-oxotetrahydroisoquinolyl, or
(n) the structure represented by formula [IX-1] below:

[Formula 115]

[IX-1]

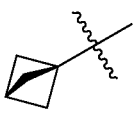
;

wherein (a) when ring C is $C_{3-6}$cycloalkyl,
another preferred example of $R^{54}$ is
(i) carboxy;
wherein another preferred example of $R^{61}$ and $R^{62}$ is a hydrogen atom;
(b) when ring C is 4- to 6-membered saturated nitrogen-containing heterocyclyl, another preferred example of $R^{54}$ is
(i) $C_{1-4}$alkylcarbonyl substituted with carboxy (when position α of the carboxy of the $C_{1-4}$alkylcarbonyl substituted with carboxy is a methylene moiety, the methylene moiety may be replaced with propane-2,2-diyl or cyclopentane-1,1-diyl),
(ii) $C_{1-4}$ alkylcarbonyl substituted with sulfamoyl,
(iii) $C_{1-4}$alkylcarbonyl substituted with $C_{1-4}$alkylsulfonylamino,
(v) phenylcarbonyl substituted with sulfamoyl,
(vii) phenylsulfonyl substituted with carboxy, or
(x) the structure represented by formula [X-2] below, which is substituted with carboxy:

[Formula 116]

[X-2]

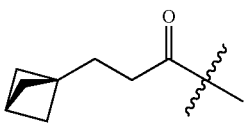

wherein another preferred example of $R^{61}$ and $R^{62}$ is a hydrogen atom;
(c) when ring C is phenyl,
another preferred example of $R^{54}$ is
(i) carboxy,
(ii) carbamoyl, (iii) mono$C_{1-4}$ alkylaminocarbonyl (the $C_{1-4}$ alkyl of the mono$C_{1-4}$ alkylaminocarbonyl may be substituted with one hydroxy),
(iv) mono$C_{1-4}$ alkylaminosulfonyl (the $C_{1-4}$ alkyl of the mono$C_{1-4}$ alkylaminosulfonyl may be substituted with one indolyl),
(v) di($C_{1-4}$ alkyl)aminosulfonyl (one $C_{1-4}$ alkyl of the di($C_{1-4}$ alkyl)aminosulfonyl may be substituted with one phenyl, wherein the phenyl may be substituted with one mono$C_{1-4}$alkylaminosulfonyl),
(vi) phenylaminosulfonyl (the phenyl of the phenylaminosulfonyl may be substituted with one fluorine atom),
(vii) $C_{1-4}$alkylsulfonylamino,
(ix) $C_{1-4}$alkylsulfonyl($C_{1-4}$ alkyl)aminocarbonyl,
(x) $C_{1-4}$ alkyl substituted with carboxy,
(xii) $C_{1-4}$ alkyl substituted with trifluoromethylsulfonylamino,
(xiii) $C_{1-4}$ alkyl substituted with methylsulfonyl(methyl)aminocarbonyl,
(xiv) $C_{1-4}$ alkyl substituted with mono$C_{1-4}$ alkylaminocarbonyl (the $C_{1-4}$ alkyl of the mono$C_{1-4}$alkylaminocarbonyl of the $C_{1-4}$ alkyl substituted with mono$C_{1-4}$ alkylaminocarbonyl may be substituted with one group selected from the group consisting of hydroxy, $C_{1-4}$ alkoxy, 4- to 6-membered saturated oxygen-containing heterocyclyl, di($C_{1-4}$ alkyl)amino, and 4- to 6-membered saturated nitrogen-containing heterocyclylcarbonyl),
(xv) $C_{1-4}$ alkyl substituted with di($C_{1-4}$ alkyl)aminocarbonyl (one $C_{1-4}$ alkyl of di($C_{1-4}$alkyl)aminocarbonyl of the $C_{1-4}$ alkyl substituted with di($C_{1-4}$ alkyl)aminocarbonyl may be substituted with one hydroxy),
(xvi) $C_{1-4}$ alkyl substituted with 4- to 6-membered saturated oxygen-containing heterocyclylaminocarbonyl,
(xvii) $C_{1-4}$ alkyl substituted with 4- to 6-membered saturated nitrogen-containing heterocyclylcarbonyl (the 4- to 6-membered saturated nitrogen-containing heterocyclyl of the $C_{1-4}$ alkyl substituted with 4- to 6-membered saturated nitrogen-containing heterocyclylcarbonyl may be substituted with one or two groups selected from the group consisting of hydroxy and a fluorine atom),
(xix) $C_{2-4}$ alkenyl substituted with carboxy,
(xx) $C_{2-4}$ alkenyl substituted with di($C_{1-4}$ alkyl)aminocarbonyl,
(xxi) $C_{3-6}$ cycloalkyl substituted with carboxy,
(xxii) $C_{3-6}$ cycloalkyl substituted with di($C_{1-4}$ alkyl)aminocarbonyl,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxix) pyrazinyl substituted with carboxy,
(xxx) 2-oxodihydropyridinyl substituted with carboxymethyl,
(xxxi) mono$C_{1-4}$ alkylaminocarbonyl substituted with carboxy (the $C_{1-4}$ alkyl of the mono$C_{1-4}$alkylaminocarbonyl substituted with carboxy may be substituted with benzyl, and when position α of the carboxy of the mono$C_{1-4}$ alkylaminocarbonyl substituted with carboxy is a methylene moiety, the methylene moiety may be replaced with a structure selected from the group consisting of propane-2,2-diyl and cyclopentane-1,1-diyl),
(xxxii) phenyl$C_{1-4}$ alkylaminocarbonyl substituted with carboxy,
(xxxiii) mono$C_{1-4}$ alkylaminocarbonyl substituted with the structure represented by formula [V-6] below:

[Formula 117]

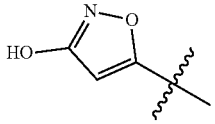

[V-6]

(xxxiv) di($C_{1-4}$alkyl)aminocarbonyl substituted with carboxy (when position α of the carboxy of the di($C_{1-4}$alkyl) aminocarbonyl substituted with carboxy is a methylene moiety, the methylene moiety may be replaced with propane-2,2-diyl), (xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), (xxxix) the structure represented by formula [XI-2] below, which is substituted with carboxy, (xxxx) the structure represented by formula [XI-3] below, which is substituted with carboxy:

[Formula 118]

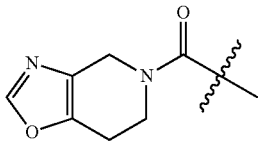

[XI-2]

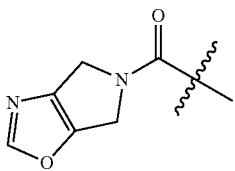

[XI-3]

(xxxxiv) $C_{1-4}$alkylsulfonyl substituted with carboxy (when position α of the carboxy of the $C_{1-4}$alkylsulfonyl substituted with carboxy is a methylene moiety, the methylene moiety may be replaced with propane-2,2-diyl), (xxxxvi) di($C_{1-4}$alkyl)aminosulfonyl substituted with carboxy (when position α of the carboxy of the di($C_{1-4}$alkyl) aminosulfonyl substituted with carboxy is a methylene moiety, the methylene moiety may be replaced with propane-2,2-diyl), (xxxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom), (xxxix) hydroxy, (xxxxx) $C_{1-4}$alkylsulfonyloxy, (xxxxxi) $C_{1-4}$alkyl substituted with hydroxy, (xxxxxii) halo-$C_{1-4}$alkyl substituted with hydroxy, (xxxxxiii) $C_{1-4}$alkylsulfonyl substituted with hydroxy, (xxxxxiv) $C_{3-6}$cycloalkyl substituted with hydroxy (the $C_{3-6}$cycloalkyl of the $C_{3-6}$cycloalkyl substituted with hydroxy may be substituted with one group selected from the group consisting of carboxy and di($C_{1-4}$alkyl)aminocarbonyl), or (xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$alkylcarbonyl, $C_{1-4}$alkoxycarbonyl, and di($C_{1-4}$alkyl)aminocarbonyl), wherein another preferred example of $R^{61}$ and $R^{62}$ is each independently a hydrogen atom, a fluorine atom, methyl, or methylsulfonyl;

(d) when ring C is pyridyl,
another preferred example of $R^{54}$ is
(ii) carbamoyl,
(iii) $C_{1-4}$ alkyl substituted with carboxy,
(iv) $C_{1-4}$ alkoxy substituted with carboxy (when position α of the carboxy of the $C_{1-4}$ alkoxy substituted with carboxy is a methylene moiety, the methylene moiety may be replaced with propane-2,2-diyl),
(v) mono$C_{1-4}$alkylaminocarbonyl substituted with carboxy (when position α of the carboxy of the mono$C_{1-4}$alkylaminocarbonyl substituted with carboxy is a methylene moiety, the methylene moiety may be replaced with propane-2,2-diyl), or
(vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom);
wherein another preferred example of $R^{61}$ and $R^{62}$ is a hydrogen atom;

(g) when ring C is tetrahydronaphthyl,
another preferred example of $R^{54}$ is carboxy,
wherein another preferred example of $R^{61}$ and $R^{62}$ is a hydrogen atom;

(h) when ring C is chromanyl,
another preferred example of $R^{54}$ is carboxy,
wherein another preferred example of $R^{61}$ and $R^{62}$ is a hydrogen atom;

(k) when ring C is tetrahydroisoquinolyl,
another preferred example of $R^{54}$ is $C_{1-4}$ alkylcarbonyl substituted with carboxy (when c position of the carboxy of the $C_{1-4}$ alkylcarbonyl substituted with carboxy is a methylene moiety, the methylene moiety may be replaced with propane-2,2-diyl),
wherein another preferred example of $R^{61}$ and $R^{62}$ is a hydrogen atom;

(m) when ring C is 2-oxotetrahydroisoquinolyl,
another preferred example of $R^{54}$ is $C_{1-4}$ alkyl substituted with carboxy (when position α of the carboxy of the $C_{1-4}$ alkyl substituted with carboxy is a methylene moiety, the methylene moiety may be replaced with propane-2,2-diyl);
wherein another preferred example of $R^{61}$ and $R^{62}$ is a hydrogen atom;

(n) when ring C is the structure represented by formula [IX-1] above, another preferred example of $R^{54}$ is
(ii) $C_{1-4}$ alkyl substituted with $C_{1-4}$ alkylsulfonylamino, or
(iii) $C_{1-4}$ alkyl substituted with $C_{1-4}$ alkylsulfonyl($C_{1-4}$ alkyl) amino;
wherein another preferred example of $R^{61}$ and $R^{62}$ is a hydrogen atom;
another preferred example of $W^4$ is $C_{1-3}$ alkanediyl.
Here, more preferably, $R^5$ is as follows:
(A)
when $R^5$ is the structure represented by formula [IV-1], more preferably, $R^{51}$ is any of the structures represented by formula group [V-b] shown below:

[Formula 119]

[V-b]

[V-2]

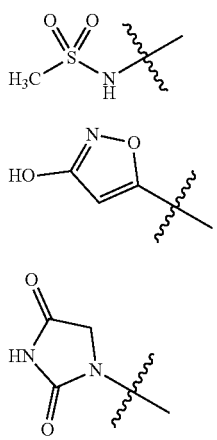

[V-6]

[V-8]

more preferably, $W^1$ is $C_{4-6}$alkanediyl;

(B)
when $R^5$ is the structure represented by formula [IV-2], more preferably, $R^{52}$ is carboxy;
more preferably, L is any of the structures represented by formula group [VI-b] shown below:

[Formula 120]

[VI-b]

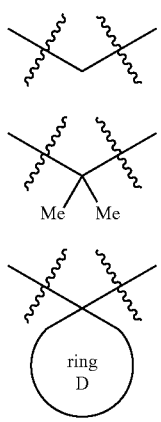

[VI-1]

[VI-4]

[VI-7]

wherein
more preferably, ring D is
(i) $C_{5-6}$cycloalkane,
(ii) 6-membered saturated oxygen-containing hetero ring, or
(iv) 6-membered saturated nitrogen-containing hetero ring (the nitrogen atom of the 6-membered saturated nitrogen-containing hetero ring is substituted with one $C_1$alkylcarbonyl);
more preferably, Y is the formula —$CH_2$—, the formula —O—, the formula —CONH—, or the formula —CONMe—;
more preferably, $W^2$ is $C_{5-8}$alkanediyl, wherein one of the carbon atoms that constitute $C_{5-8}$alkanediyl represented by $W^2$ may be replaced with an oxygen atom;

(C)
when $R^5$ is the structure represented by formula [IV-3], more preferably, $R^{53}$ is carboxy;
more preferably, ring B is any of the structures represented by formula group [VIII-b] shown below:

[Formula 121]

[VIII-b]

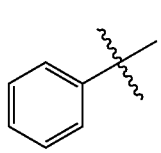

[VIII-1]

[VIII-2]

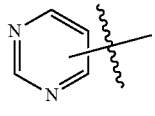

[VIII-3]

[VIII-7]

more preferably, $W^3$ is $C_{4-6}$alkanediyl;
(D)
when $R^5$ is the structure represented by formula [IV-4], more preferably, ring C is
(a) $C_{3-6}$ cycloalkyl,
(b) 4- to 6-membered saturated nitrogen-containing heterocyclyl,
(c) phenyl,
(d) pyridyl,
(g) tetrahydronaphthyl,
(h) chromanyl,
(k) tetrahydroisoquinolyl,
(m) 2-oxotetrahydroisoquinolyl, or
(n) the structure represented by formula [IX-1] below:

[Formula 122]

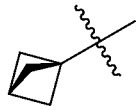

[IX-1]

wherein (a) when ring C is $C_{3-6}$cycloalkyl,
more preferably, ring C is $C_6$cycloalkyl;
more preferably, $R^{54}$ is carboxy;
wherein more preferably, $R^{61}$ and $R^{62}$ are each a hydrogen atom;
(b) when ring C is 4- to 6-membered saturated nitrogen-containing heterocyclyl, more preferably, ring C is 6-membered saturated nitrogen-containing heterocyclyl; more preferably, $R^{54}$ is
(i) $C_{2-4}$alkylcarbonyl substituted with carboxy (when position α of the carboxy of the $C_{2-4}$alkylcarbonyl substituted with carboxy is a methylene moiety, the methylene moiety is replaced with a structure selected from the group consisting of propane-1,1-diyl and cyclopentane-1,1-diyl),
(ii) C$_3$alkylcarbonyl substituted with sulfamoyl,
(iii) C$_1$alkylcarbonyl substituted with C$_2$alkylsulfonylamino,
(v) phenylcarbonyl substituted with sulfamoyl,
(vii) phenylsulfonyl substituted with carboxy, or
(x) the structure represented by formula [X-2] below, which is substituted with carboxy:

[Formula 123]

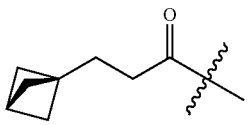

[X-2]

wherein more preferably, R$^{61}$ and R$^{62}$ are each a hydrogen atom;

(c) when ring C is phenyl,
more preferably, R$^{54}$ is
(i) carboxy,
(ii) carbamoyl,
(iii) monoC$_{1-3}$ alkylaminocarbony (the C$_{1-3}$ alkyl of the monoC$_{1-3}$ alkylaminocarbonyl may be substituted with one hydroxy),
(iv) monoC$_{1-2}$alkylaminosulfonyl (the C$_{1-2}$alkyl of the monoC$_{1-2}$alkylaminosulfonyl may be substituted with one indolyl),
(iv) monoC$_2$alkylaminosulfonyl (the C$_2$alkyl of the monoC$_2$alkylaminosulfonyl is substituted with one indolyl),
(v) di(C$_1$alkyl)aminosulfonyl (the one C$_1$alkyl of the di(C$_1$alkyl)aminosulfonyl is substituted with one phenyl, wherein the phenyl is substituted with one monoC$_1$alkylaminosulfonyl),
(vi) phenylaminosulfonyl (the phenyl of the phenylaminosulfonyl is substituted with one fluorine atom),
(vii) C$_3$alkylsulfonylamino,
(ix) C$_1$alkylsulfonyl(C$_1$alkyl)aminocarbonyl,
(x) C$_{1-3}$alkyl substituted with carboxy,
(xii) C$_1$alkyl substituted with trifluoromethylsulfonylamino,
(xiii) C$_{1-2}$alkyl substituted with methylsulfonyl(methyl)aminocarbonyl,
(xiv) C$_{1-2}$alkyl substituted with monoC$_{1-3}$alkylaminocarbonyl (the C$_{1-3}$alkyl of the monoC$_{1-3}$alkylaminocarbonyl of the C$_{1-2}$ alkyl substituted with monoC$_{1-3}$alkylaminocarbonyl may be substituted with one group selected from the group consisting of hydroxy, C$_1$alkoxy, 5-membered saturated oxygen-containing heterocyclyl, di(C$_1$alkyl)amino, and 5-membered saturated nitrogen-containing heterocyclylcarbonyl),
(xv) C$_{1-2}$ alkyl substituted with di(C$_{1-2}$ alkyl)aminocarbonyl (one C$_{1-2}$ alkyl of the di(C$_{1-2}$alkyl)aminocarbonyl may be substituted with one hydroxy),
(xvi) C$_2$alkyl substituted with 4-membered saturated oxygen-containing heterocyclylaminocarbonyl,
(xvii) C$_2$alkyl substituted with 4- to 6-membered saturated nitrogen-containing heterocyclylcarbonyl (the 4- to 6-membered saturated nitrogen-containing heterocyclyl of the C$_2$alkyl substituted with 4- to 6-membered saturated nitrogen-containing heterocyclylcarbonyl may be substituted with one hydroxy or one or two fluorine atoms),
(xix) C$_2$alkenyl substituted with carboxy,
(xx) C$_2$alkenyl substituted with di(C$_1$alkyl)aminocarbonyl,
(xxi) C$_{3-6}$ cycloalkyl substituted with carboxy,
(xxii) C$_3$cycloalkyl substituted with di(C$_1$alkyl)aminocarbonyl,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxix) pyrazinyl substituted with carboxy,
(xxx) 2-oxodihydropyridinyl substituted with carboxymethyl,
(xxxi) monoC$_{1-3}$ alkylaminocarbonyl substituted with carboxy (the C$_{1-3}$ alkyl of the monoC$_{1-3}$alkylaminocarbonyl substituted with carboxy may be substituted with one benzyl, and when position α of the carboxy of the monoC$_{1-3}$ alkylaminocarbonyl substituted with carboxy is a methylene moiety, the methylene moiety may be replaced with a structure selected from the group consisting of propane-2,2-diyl and cyclopentane-1,1-diyl),
(xxxii) phenylC$_1$alkylaminocarbonyl substituted with carboxy,
(xxxiii) monoC$_1$alkylaminocarbonyl substituted with the structure represented by formula [V-6] below:

[Formula 124]

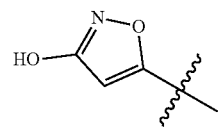

[V-6]

(xxxiv) di(C$_{1-3}$alkyl)aminocarbonyl substituted with carboxy (when position α of the carboxy of the di(C$_{1-3}$alkyl) aminocarbonyl substituted with carboxy is a methylene moiety, the methylene moiety is replaced with propane-2,2-diyl),
(xxxvi) 5-membered saturated nitrogen-containing heterocyclylcarbonyl substituted with carboxy (the 5-membered saturated nitrogen-containing heterocyclyl of the 5-membered saturated nitrogen-containing heterocyclylcarbonyl substituted with carboxy is substituted with one fluorine atom),
(xxxix) the structure represented by formula [XI-2] below, which is substituted with carboxy,
(xxxx) the structure represented by formula [XI-3] below, which is substituted with carboxy,

[Formula 125]

[XI-b]

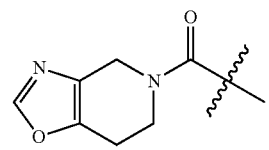

[XI-2]

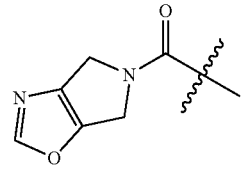

[XI-3]

(xxxxiv) $C_4$alkylsulfonyl substituted with carboxy (when position α of the carboxy of the $C_4$alkylsulfonyl substituted with carboxy is a methylene moiety, the methylene moiety is replaced with propane-2,2-diyl),
(xxxxvi) di($C_{1-3}$alkyl)aminosulfonyl substituted with carboxy (when position α of the carboxy of the di($C_{1-3}$alkyl) aminosulfonyl substituted with carboxy is a methylene moiety, the methylene moiety is replaced with propane-2,2-diyl),
(xxxxvii) 5- to 6-membered saturated nitrogen-containing heterocyclylsulfonyl substituted with carboxy (the 5- to 6-membered saturated nitrogen-containing heterocyclyl of the 5- to 6-membered saturated nitrogen-containing heterocyclylsulfonyl substituted with carboxy may be substituted with one fluorine atom),
(xxxxix) hydroxy,
(xxxxx) $C_1$alkylsulfonyloxy,
(xxxxxi) $C_{1-3}$alkyl substituted with hydroxy,
(xxxxxii) halo-$C_{2-3}$ alkyl substituted with hydroxy,
(xxxxxiii) $C_{2-4}$ alkylsulfonyl substituted with hydroxy,
(xxxxxiv) $C_{4-5}$ cycloalkyl substituted with hydroxy (the $C_{4-5}$ cycloalkyl of the $C_{4-5}$ cycloalkyl substituted with hydroxy may be substituted with one group selected from the group consisting of carboxy and di($C_1$alkyl)aminocarbonyl), or
(xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy is substituted with one group selected from the group consisting of $C_1$alkylcarbonyl, $C_1$alkoxycarbonyl, and di($C_1$alkyl)aminocarbonyl); wherein more preferably, $R^{61}$ and $R^{62}$ are each independently a hydrogen atom, a fluorine atom, methyl, or methylsulfonyl;
(d) when ring C is pyridyl,
more preferably, $R^{54}$ is
(ii) carbamoyl,
(iii) $C_1$alkyl substituted with carboxy,
(iv) $C_2$alkoxy substituted with carboxy (when position α of the carboxy of the $C_2$alkoxy substituted with carboxy is a methylene moiety, the methylene moiety is replaced with propane-2,2-diyl),
(v) mono$C_3$alkylaminocarbonyl substituted with carboxy (when position α of the carboxy of the mono$C_3$alkylaminocarbonyl substituted with carboxy is a methylene moiety, the methylene moiety is replaced with propane-2,2-diyl), or
(vi) 5-membered saturated nitrogen-containing heterocyclylcarbonyl substituted with carboxy (the 5-membered saturated nitrogen-containing heterocyclyl of the 5-membered saturated nitrogen-containing heterocyclylcarbonyl substituted with carboxy is substituted with one fluorine atom);
wherein more preferably, $R^{61}$ and $R^{62}$ are each a hydrogen atom;
(g) when ring C is tetrahydronaphthyl,
more preferably, $R^{54}$ is carboxy;
wherein more preferably, $R^{61}$ and $R^{62}$ are each a hydrogen atom;
(h) when ring C is chromanyl,
more preferably, $R^{54}$ is carboxy;
wherein more preferably, $R^{61}$ and $R^{62}$ are a hydrogen atom;
(k) when ring C is tetrahydroisoquinolyl,
more preferably, $R^{54}$ is $C_1$alkylcarbonyl substituted with carboxy (the methylene moiety at position α of the carboxy of the $C_1$alkylcarbonyl substituted with carboxy is replaced with propane-2,2-diyl);

wherein more preferably, $R^{61}$ and $R^{62}$ are each a hydrogen atom;
(m) when ring C is 2-oxotetrahydroisoquinolyl,
more preferably, $R^{54}$ is $C_3$alkyl substituted with carboxy (when position α of the carboxy of the $C_3$alkyl substituted with carboxy is a methylene moiety, the methylene moiety is replaced with propane-2,2-diyl);
wherein more preferably, $R^{61}$ and $R^{62}$ are each a hydrogen atom;
(n) when ring C is the structure represented by formula [IX-1] above, more preferably, $R^{54}$ is
(ii) $C_1$alkyl substituted with $C_1$alkylsulfonylamino, or
(iii) $C_1$alkyl substituted with $C_1$alkylsulfonyl($C_1$alkyl)amino;
wherein more preferably, $R^{61}$ and $R^{62}$ are each a hydrogen atom;
more preferably, $W^4$ is $C_{1-3}$ alkanediyl.
Here, even more preferably, $R^5$ is as follows:
(A)
when $R^5$ is the structure represented by formula [IV-1],
even more preferably, $R^{51}$ is the structure represented by formula [V-2] shown below:

[Formula 126]

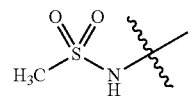

[V-2]

even more preferably, $W^1$ is hexane-1,6-diyl;
(B)
when $R^5$ is the structure represented by formula [IV-2],
even more preferably, $R^{52}$ is carboxy;
even more preferably, L is a structure represented by formula [VI-1], formula [VI-4], formula [VI-8], formula [VI-10], or formula [VI-11] shown below:

[Formula 127]

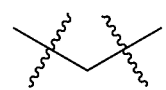

[VI-1]

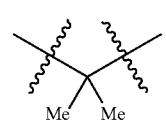

[VI-4]

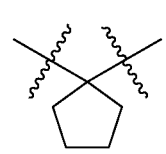

[VI-8]

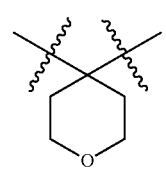

[VI-10]

-continued

[VI-11]

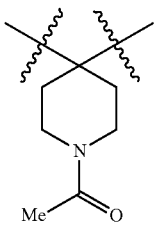

even more preferably, Y is the formula —CH$_2$— or the formula —O—;
even more preferably, W$^2$ is hexane-1,6-diyl, heptane-1,7-diyl, or octane-1,8-diyl;
(C)
when R$^5$ is the structure represented by formula [IV-3], even more preferably, R$^{53}$ is carboxy;
even more preferably, ring B is the structure represented by formula [VIII-10] shown below:

[Formula 128]

[VIII-10]

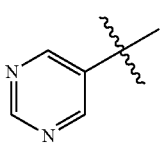

even more preferably, W$^3$ is butane-1,4-diyl;
(D)
when R$^5$ is the structure represented by formula [IV-4], even more preferably, ring C is
(b) 4- to 6-membered saturated nitrogen-containing heterocyclyl,
(c) phenyl,
(d) pyridyl,
(g) tetrahydronaphthyl,
(h) chromanyl,
(k) tetrahydroisoquinolyl,
(m) 2-oxotetrahydroisoquinolyl, or
(n) the structure represented by formula [IX-1] below:

[Formula 129]

[IX-1]

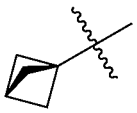

(b) when ring C is 4- to 6-membered saturated nitrogen-containing heterocyclyl, even more preferably, ring C is piperidine-3-yl or piperidine-4-yl;
even more preferably, R$^{54}$ is
(i) ethylcarbonyl substituted with carboxy (the methylene moiety at position α of the carboxy of the ethylcarbonyl substituted with carboxy is replaced with propane-2,2-diyl), n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy, wherein even more preferably, R$^{61}$ and R$^{62}$ are each a hydrogen atom;
(c) when ring C is phenyl,
even more preferably, R$^{54}$ is
(ii) carbamoyl,
(iii) methylaminocarbonyl, n-propylaminocarbonyl,
(iv) ethylaminosulfonyl (the ethyl of the ethylaminosulfonyl is substituted with one indolyl),
(v) dimethylaminosulfonyl (one methyl of the dimethylaminosulfonyl is substituted with one phenyl, wherein the phenyl is substituted with one methylaminosulfonyl),
(vi) phenylaminosulfonyl (the phenyl of the phenylaminosulfonyl is substituted with one fluorine atom),
(ix) methylsulfonyl(methyl)aminocarbonyl,
(x) n-propyl substituted with carboxy,
(xii) methyl substituted with trifluoromethylsulfonylamino,
(xiii) ethyl substituted with methylsulfonyl(methyl)aminocarbonyl,
(xiv) methyl substituted with methylaminocarbonyl, methyl substituted with n-propylaminocarbonyl, ethyl substituted with methylaminocarbonyl (the methyl of the ethyl substituted with methylaminocarbonyl may be substituted with one group selected from the group consisting of tetrahydrofuranyl and piperidinylcarbonyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl may be substituted with one group selected from the group consisting of hydroxy and methoxy), ethyl substituted with isopropylaminocarbonyl (the isopropyl of the ethyl substituted with isopropylaminocarbonyl is substituted with one group selected from the group consisting of hydroxy and methoxy),
(xv) ethyl substituted with dimethylaminocarbonyl, ethyl substituted with ethyl(methyl)aminocarbonyl (the ethyl of the ethyl(methyl)aminocarbonyl of the ethyl substituted with ethyl(methyl)aminocarbonyl is substituted with one hydroxy),
(xvi) ethyl substituted with oxetanylaminocarbonyl,
(xvii) ethyl substituted with azetidinylcarbonyl (the azetidinyl of the ethyl substituted with azetidinylcarbonyl may be substituted with one hydroxy or one or two fluorine atoms), ethyl substituted with pyrrolidinylcarbonyl, ethyl substituted with piperidinylcarbonyl, ethyl substituted with morpholinylcarbonyl,
(xix) ethenyl substituted with carboxy,
(xx) ethenyl substituted with dimethylaminocarbonyl,
(xxii) cyclopropyl substituted with dimethylaminocarbonyl,
(xxiv) phenyl substituted with carboxy,
(xxv) pyridin-3-yl substituted with carboxy, pyridin-4-yl substituted with carboxy,
(xxxix) the structure represented by formula [XI-2] below, which is substituted with carboxy,
(xxxx) the structure represented by formula [XI-3] below, which is substituted with carboxy:

[Formula 130]

[XI-b]

[XI-2]

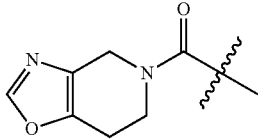

-continued

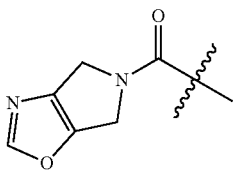

[XI-3]

(xxxxiv) n-butylsulfonyl substituted with carboxy (the methylene moiety at position α of the carboxy of the n-butylsulfonyl substituted with carboxy is replaced with propane-2,2-diyl),
(xxxxvii) piperidinylsulfonyl substituted with carboxy,
(xxxxix) hydroxy,
(xxxxx) methylsulfonyloxy,
(xxxxxi) methyl substituted with hydroxy,
(xxxxxii) haloethyl substituted with hydroxy, halo-n-propyl substituted with hydroxy,
(xxxxxiii) isobutylsulfonyl substituted with hydroxy,
(xxxxxiv) cyclobutyl substituted with hydroxy (the cyclobutyl of the cyclobutyl substituted with hydroxy is substituted with one dimethylaminocarbonyl), cyclopentyl substituted with hydroxy, or
(xxxxxv) azetidinyl substituted with hydroxy (the nitrogen atom of the azetidinyl substituted with hydroxy is substituted with one methylcarbonyl), piperidinyl substituted with hydroxy (the nitrogen atom of the piperidinyl substituted with hydroxy is substituted with one group selected from the group consisting of methylcarbonyl, methoxycarbonyl, and dimethylaminocarbonyl),
wherein even more preferably, $R^{61}$ and $R^{62}$ are each independently a hydrogen atom, a fluorine atom, methyl, or methylsulfonyl;
  (d) when ring C is pyridyl,
even more preferably, ring C is pyridin-4-yl;
even more preferably, $R^{54}$ is
(ii) carbamoyl, or
(v) n-propylaminocarbonyl substituted with carboxy (the methylene moiety at position α of the carboxy of the n-propylaminocarbonyl substituted with carboxy is replaced with propane-2,2-diyl);
wherein even more preferably, $R^{61}$ and $R^{62}$ are each a hydrogen atom;
  (g) when ring C is tetrahydronaphthyl,
even more preferably, ring C is a structure represented by formula [XII-1] or formula [XII-2] below:

[Formula 131]

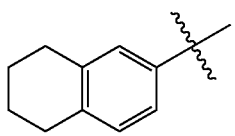

[XII-1]

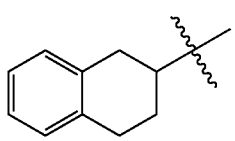

[XII-2]

even more preferably, $R^{54}$ is carboxy, wherein even more preferably, $R^{61}$ and $R^{62}$ are each a hydrogen atom;
  (h) when ring C is chromanyl,
even more preferably, ring C is the structure represented by formula [XIII-1] below:

[Formula 132]

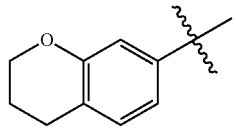

[XIII-1]

even more preferably, $R^{54}$ is carboxy,
wherein even more preferably, $R^{61}$ and $R^{62}$ are each a hydrogen atom;
  (k) when ring C is tetrahydroisoquinolyl,
even more preferably, ring C is the structure represented by formula [XIV-1] below:

[Formula 133]

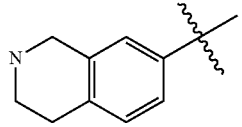

[XIV-1]

even more preferably, $R^{54}$ is methylcarbonyl substituted with carboxy (the methylene moiety at position α of the carboxy of the methylcarbonyl substituted with carboxy is replaced with propane-2,2-diyl),
wherein even more preferably, $R^{61}$ and $R^{62}$ are each a hydrogen atom;
  (m) when ring C is 2-oxotetrahydroisoquinolyl,
even more preferably, ring C is the structure represented by formula [XV-1] below:

[Formula 134]

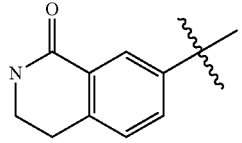

[XV-1]

even more preferably, $R^{54}$ is n-propyl substituted with carboxy (the methylene moiety at position α of the carboxy of the n-propyl substituted with carboxy is replaced with propane-2,2-diyl),
wherein even more preferably, $R^{61}$ and $R^{62}$ are each a hydrogen atom;
  (n) when ring C is the structure represented by formula [IX-1] above,
even more preferably, $R^{54}$ is
(ii) methyl substituted with methylsulfonylamino, or
(iii) methyl substituted with methylsulfonyl(methyl)amino,
wherein even more preferably, $R^{61}$ and $R^{62}$ are each a hydrogen atom;
    even more preferably, $W^4$ is methanediyl, ethane-1,2-diyl or propane-1,3-diyl.
  Here, other even more preferred examples of $R^5$ are as follows:

(B)
when $R^5$ is the structure represented by formula [IV-2],
even more preferably, $R^{52}$ is carboxy;
even more preferably, L is a structure represented by formula [VI-1], formula [VI-4], formula [VI-8], formula [VI-10], or formula [VI-11] shown below:

[Formula 135]

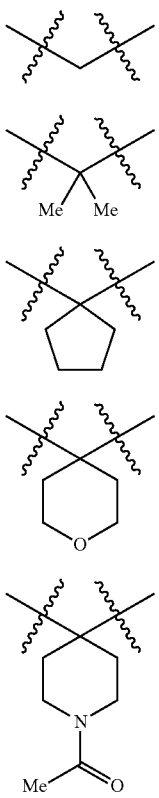

[VI-1]

[VI-4]

[VI-8]

[VI-10]

[VI-11]

even more preferably, Y is the formula —$CH_2$— or the formula —O—;
even more preferably, $W^2$ is hexane-1,6-diyl, heptane-1,7-diyl, or octane-1,8-diyl;
(C)
when $R^5$ is the structure represented by formula [IV-3],
even more preferably, $R^{53}$ is carboxy;
even more preferably, ring B is the structure represented by formula [VIII-10] shown below:

[Formula 136]

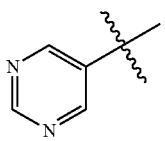

[VIII-10]

even more preferably, $W^3$ is butane-1,4-diyl;
(D)
when $R^5$ is the structure represented by formula [IV-4],
even more preferably, ring C is
(b) 4- to 6-membered saturated nitrogen-containing heterocyclyl,
(c) phenyl,
(d) pyridyl,
(g) tetrahydronaphthyl,
(h) chromanyl, or
(n) the structure represented by formula [IX-1] below:

[Formula 137]

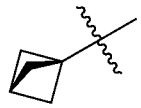

[IX-1]

wherein (b) when ring C is 4- to 6-membered saturated nitrogen-containing heterocyclyl,
even more preferably, ring C is piperidine-3-yl or piperidine-4-yl;
even more preferably, $R^{54}$ is
(i) n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy,
wherein even more preferably, $R^{61}$ and $R^{62}$ are each a hydrogen atom;
(c) when ring C is phenyl,
even more preferably, $R^{54}$ is
(ii) carbamoyl,
(iii) methylaminocarbonyl, n-propylaminocarbonyl,
(v) dimethylaminosulfonyl (one methyl of the dimethylaminosulfonyl is substituted with one phenyl, wherein the phenyl is substituted with one methylaminosulfonyl),
(vi) phenylaminosulfonyl (the phenyl of the phenylaminosulfonyl is substituted with one fluorine atom),
(ix) methylsulfonyl(methyl)aminocarbonyl,
(x) n-propyl substituted with carboxy,
(xii) methyl substituted with trifluoromethylsulfonylamino,
(xiii) ethyl substituted with methylsulfonyl(methyl)aminocarbonyl,
(xiv) methyl substituted with methylaminocarbonyl, methyl substituted with n-propylaminocarbonyl, ethyl substituted with methylaminocarbonyl (the methyl of the ethyl substituted with methylaminocarbonyl may be substituted with one group selected from the group consisting of tetrahydrofuranyl and piperidinylcarbonyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl may be substituted with one group selected from the group consisting of hydroxy and methoxy), ethyl substituted with isopropylaminocarbonyl (the isopropyl of the ethyl substituted with isopropylaminocarbonyl is substituted with one group selected from the group consisting of hydroxy and methoxy),
(xv) ethyl substituted with dimethylaminocarbonyl, ethyl substituted with ethyl(methyl)aminocarbonyl (the ethyl of the ethyl(methyl)aminocarbonyl of the ethyl substituted with ethyl(methyl)aminocarbonyl is substituted with one hydroxy),
(xvi) ethyl substituted with oxetanylaminocarbonyl,
(xvii) ethyl substituted with azetidinylcarbonyl (the azetidinyl of the ethyl substituted with azetidinylcarbonyl may be substituted with one hydroxy or one or two fluorine atoms), ethyl substituted with pyrrolidinylcarbonyl, ethyl substituted with piperidinylcarbonyl, ethyl substituted with morpholinylcarbonyl,
(xix) ethenyl substituted with carboxy,
(xx) ethenyl substituted with dimethylaminocarbonyl,
(xxii) cyclopropyl substituted with dimethylaminocarbonyl,
(xxiv) phenyl substituted with carboxy,
(xxv) pyridin-3-yl substituted with carboxy, pyridin-4-yl substituted with carboxy,
(xxxix) the structure represented by formula [XI-2] below, which is substituted with carboxy,
(xxxx) the structure represented by formula [XI-3] below, which is substituted with carboxy:

[Formula 138]

[XI-b]

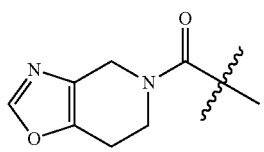

[XI-2]

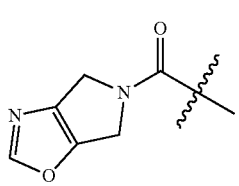

[XI-3]

(xxxxiv) n-butylsulfonyl substituted with carboxy (the methylene moiety at position α of the carboxy of the n-butylsulfonyl substituted with carboxy is replaced with propane-2,2-diyl),
(xxxxvii) piperidinylsulfonyl substituted with carboxy,
(xxxxix) hydroxy,
(xxxxx) methylsulfonyloxy,
(xxxxxi) methyl substituted with hydroxy,
(xxxxxii) haloethyl substituted with hydroxy, halo-n-propyl substituted with hydroxy,
(xxxxxiii) isobutylsulfonyl substituted with hydroxy,
(xxxxxiv) cyclobutyl substituted with hydroxy (the cyclobutyl of the cyclobutyl substituted with hydroxy is substituted with one dimethylamino), cyclopentyl substituted with hydroxy, or
(xxxxxv) azetidinyl substituted with hydroxy (the nitrogen atom of the azetidinyl substituted with hydroxy is substituted with one methylcarbonyl), piperidinyl substituted with hydroxy (the nitrogen atom of the piperidinyl substituted with hydroxy is substituted with one group selected from the group consisting of methylcarbonyl, methoxycarbonyl, and dimethylcarbonyl),
wherein even more preferably, $R^{61}$ and $R^{62}$ are each independently a hydrogen atom, a fluorine atom, methyl, or methylsulfonyl;
(d) when ring C is pyridyl,
even more preferably, ring C is pyridin-4-yl;
even more preferably, $R^{54}$ is carbamoyl,
wherein even more preferably, $R^{61}$ and $R^{62}$ are each a hydrogen atom;
(g) when ring C is tetrahydronaphthyl,
even more preferably, ring C is a structure represented by formula [XII-1] or formula [XII-2] below:

[Formula 139]

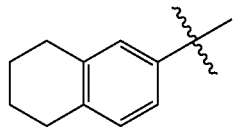
[XII-1]

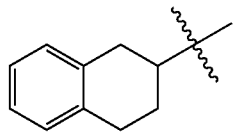
[XII-2]

even more preferably, $R^{54}$ is carboxy,
wherein even more preferably, $R^{61}$ and $R^{62}$ are each a hydrogen atom;
(h) when ring C is chromanyl,
even more preferably, ring C is the structure represented by formula [XIII-1] below:

[Formula 140]

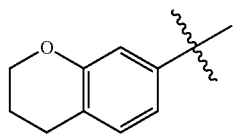
[XIII-1]

even more preferably, $R^{54}$ is carboxy,
wherein even more preferably, $R^{61}$ and $R^{62}$ are each a hydrogen atom;
(n) when ring C is the structure represented by formula [IX-1] above, even more preferably, $R^{54}$ is
(ii) methyl substituted with methylsulfonylamino, or
(iii) methyl substituted with methylsulfonyl(methyl)amino;
even more preferably, $W^4$ is methanediyl, ethane-1,2-diyl, or propane-1,3-diyl.

The following are other preferred embodiments of the compounds of the present invention.

Preferred embodiments of $R^1$, $R^2$, $R^3$, $R^4$, and ring A in formula [1] above are as described above.

Other preferred examples of $R^5$ are as follows:
(A)
when $R^5$ is the structure represented by formula [IV-1], another preferred example of $R^5$ is such that
$R^{51}$ is the structure represented by formula [V-6] shown below:

[Formula 141]

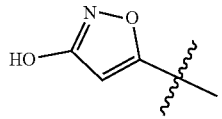
[V-6]

$W^1$ is $C_{4-10}$ alkanediyl;
wherein more preferably, $R^5$ is such that
$R^{51}$ is the structure represented by formula [V-6] shown below:

[Formula 142]

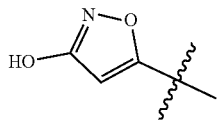

[V-6]

$W^1$ is $C_4$alkanediyl;
wherein even more preferably, $R^5$ is such that
$R^{51}$ is the structure represented by formula [V-6] shown below:

[Formula 143]

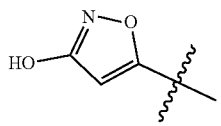

[V-6]

$W^1$ is butane-1,4-diyl;
(B)
when $R^5$ is the structure represented by formula [IV-2], another preferred example of $R^5$ is such that
$R^{52}$ is carboxy;
L is a structure represented by formula [VI-1], formula [VI-4], or formula [VI-7] shown below:

[Formula 144]

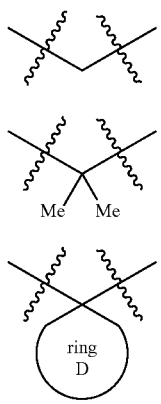

[VI-1]

[VI-4]

[VI-7]

wherein
ring D is
(i) $C_{3-6}$cycloalkane,
(ii) 4- to 6-membered saturated oxygen-containing hetero ring, or
(iv) 6-membered saturated nitrogen-containing hetero ring (the nitrogen atom of the 6-membered saturated nitrogen-containing hetero ring may be substituted with one $C_{1-4}$alkylcarbonyl),
Y is the formula —CH$_2$—, the formula —O—, or the formula —CONMe-;
$W^2$ is $C_{2-10}$alkanediyl, wherein one of the carbon atoms that constitute $C_{2-10}$alkanediyl represented by $W^2$ may be replaced with an oxygen atom;

wherein more preferably, $R^5$ is such that
$R^{52}$ is carboxy;
L is a structure represented by formula [VI-1] shown below, formula [VI-4] shown below, or formula [VI-7] shown below:

[Formula 145]

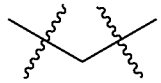

[VI-1]

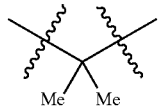

[VI-4]

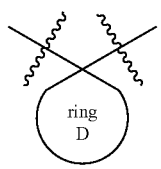

[VI-7]

wherein ring D is
$C_{5-6}$ cycloalkane,
6-membered saturated oxygen-containing hetero ring, or
6-membered saturated nitrogen-containing hetero ring
(the nitrogen atom of the 6-membered saturated nitrogen-containing hetero ring is substituted with one $C_1$alkylcarbonyl),
Y is the formula —CH$_2$—, the formula —O—, or the formula —CONMe-;
$W^2$ is $C_{5-8}$alkanediyl, wherein one of the carbon atoms that constitute $C_{5-8}$alkanediyl represented by $W^2$ may be replaced with an oxygen atom;
wherein even more preferably, $R^5$ is such that
$R^{52}$ is carboxy;
L is a structure represented by formula [VI-1], formula [VI-4], formula [VI-8], formula [VI-9], formula [VI-10], or formula [VI-11] shown below:

[Formula 146]

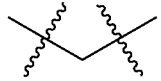

[VI-1]

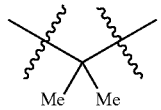

[VI-4]

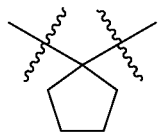

[VI-8]

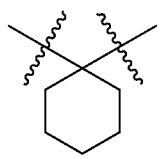

[VI-9]

-continued

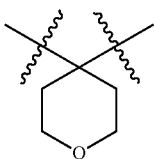
[VI-10]

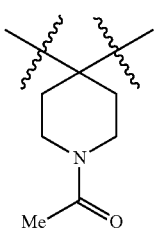
[VI-11]

Y is the formula —CH$_2$—, the formula —O—, or the formula —CONMe-;

W$^2$ is pentane-1,5-diyl, hexane-1,6-diyl, heptane-1,7-diyl, octane-1,8-diyl, or the formula —O—(CH$_2$)$_6$—;

(C)

when R$^5$ is the structure represented by formula [IV-3], another preferred example of R$^5$ is such that R$^{53}$ is carboxy;

ring B is a structure represented by formula [VIII-1], formula [VIII-2], formula [VIII-4], or formula [VIII-7] shown below:

[Formula 147]

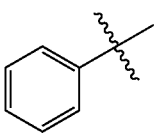
[VIII-1]

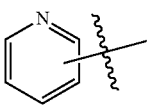
[VIII-2]

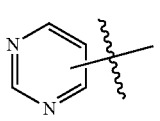
[VIII-4]

[VIII-7]

W$^3$ is C$_{3-7}$alkanediyl;

wherein more preferably, R$^5$ is such that

R$^{53}$ is carboxy;

ring B is a structure represented by formula [VIII-1], formula [VIII-2], formula [VIII-4], or formula [VIII-7] shown below:

[Formula 148]

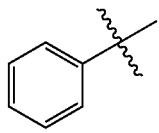
[VIII-1]

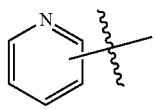
[VIII-2]

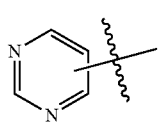
[VIII-4]

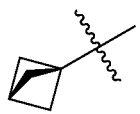
[VIII-7]

W$^3$ is C$_{4-6}$alkanediyl;

wherein even more preferably, R$^5$ is such that

R$^{53}$ is carboxy;

ring B is a structure represented by formula [VIII-1], formula [VIII-8], formula [VIII-9], formula [VIII-10], or formula [VIII-7] shown below:

[Formula 149]

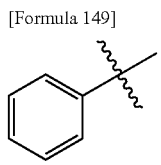
[VIII-1]

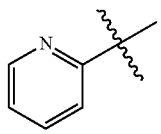
[VIII-8]

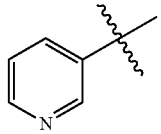
[VIII-9]

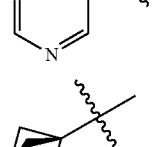
[VIII-10]

[VIII-7]

W$^3$ is butane-1,4-diyl or hexane-1,6-diyl;

(D)

when R$^5$ is the structure represented by formula [IV-4], another preferred example of ring C is (a) C$_{3-6}$cycloalkyl, (b) 4- to 6-membered saturated nitrogen-containing heterocyclyl, (c) phenyl,
(d) pyridyl,
(g) tetrahydronaphthyl,
(h) chromanyl, or
(n) the structure represented by formula [IX-1] below:

[Formula 150]

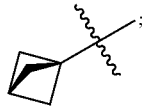

[IX-1]

wherein
(a) when ring C is $C_{3-6}$cycloalkyl,
another preferred example of $R^5$ is such that
$R^{54}$ is carboxy;
$R^{61}$ is a hydrogen atom;
$R^{62}$ is a hydrogen atom;
$W^4$ is $C_{1-3}$alkanediyl;
wherein more preferably, $R^5$ is such that
ring C is $C_6$cycloalkyl;
$R^{54}$ is carboxy;
$R^{61}$ is a hydrogen atom;
$R^{62}$ is a hydrogen atom;
$W^4$ is $C_3$alkanediyl;
wherein even more preferably, $R^5$ is such that
ring C is cyclohexyl,
$R^{54}$ is carboxy;
$R^{61}$ is a hydrogen atom;
$R^{62}$ is a hydrogen atom;
$W^4$ is propane-1,3-diyl;
(b) when ring C is 4- to 6-membered saturated nitrogen-containing heterocyclyl, another preferred example of $R^5$ is such that
$R^{54}$ is
  $C_{1-4}$ alkylcarbonyl substituted with carboxy (when position α of the carboxy of the $C_{1-4}$alkylcarbonyl substituted with carboxy is a methylene moiety, the methylene moiety may be replaced with cyclopentane-1,1-diyl), or
  phenylsulfonyl substituted with carboxy;
$R^{61}$ is a hydrogen atom;
$R^{62}$ is a hydrogen atom;
$W^4$ is $C_{1-3}$alkanediyl;
wherein more preferably, $R^5$ is such that
ring C is 5-membered saturated nitrogen-containing heterocyclyl;
$R^{54}$ is
(i) $C_4$alkylcarbonyl substituted with carboxy (when position α of the carboxy of the $C_4$alkylcarbonyl substituted with carboxy is a methylene moiety, the methylene moiety may be replaced with cyclopentane-1,1-diyl), or
(vii) phenylsulfonyl substituted with carboxy,
$R^{61}$ is a hydrogen atom;
$R^{62}$ is a hydrogen atom;
$W^4$ is $C_1$alkanediyl;
wherein even more preferably, $R^5$ is such that
ring C is piperidine-3-yl or piperidine-4-yl;
$R^{54}$ is
(i) n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy;
$R^{61}$ is a hydrogen atom;
$R^{62}$ is a hydrogen atom;
$W^4$ is methanediyl;
(c) when ring C is phenyl,
another preferred example of $R^5$ is such that
$R^{54}$ is
  carboxy,
  carbamoyl,
  mono$C_{1-4}$ alkylaminocarbonyl,
  mono$C_{1-4}$ alkylaminosulfonyl,
  di($C_{1-4}$ alkyl)aminosulfonyl (one $C_{1-4}$ alkyl of the di($C_{1-4}$ alkyl)aminosulfonyl may be substituted with one phenyl, and the phenyl is substituted with one mono$C_{1-4}$ alkylaminosulfonyl),
  phenylaminosulfonyl (the phenyl of the phenylaminosulfonyl may be substituted with one fluorine atom),
  $C_{1-4}$ alkylsulfonylamino,
  $C_{1-4}$ alkylsulfonyl($C_{1-4}$ alkyl)aminocarbonyl,
  $C_{1-4}$ alkyl substituted with carboxy,
  $C_{1-4}$ alkyl substituted with trifluoromethylsulfonylamino,
  $C_{1-4}$ alkyl substituted with methylsulfonyl(methyl)aminocarbonyl,
  $C_{1-4}$ alkyl substituted with mono$C_{1-4}$ alkylaminocarbonyl (the $C_{1-4}$ alkyl of the mono$C_{1-4}$alkylaminocarbonyl of the $C_{1-4}$ alkyl substituted with mono$C_{1-4}$ alkylaminocarbonyl may be substituted with one group selected from the group consisting of hydroxy, $C_{1-4}$ alkoxy, 4- to 6-membered saturated oxygen-containing heterocyclyl, and 4- to 6-membered saturated nitrogen-containing heterocyclylcarbonyl),
  $C_{1-4}$ alkyl substituted with di($C_{1-4}$ alkyl)aminocarbonyl (one $C_{1-4}$ alkyl of the di($C_{1-4}$alkyl)aminocarbonyl of the $C_{1-4}$ alkyl substituted with di($C_{1-4}$ alkyl)aminocarbonyl may be substituted with one hydroxy),
  $C_{1-4}$ alkyl substituted with 4- to 6-membered saturated oxygen-containing heterocyclylaminocarbonyl,
  $C_{1-4}$ alkyl substituted with 4- to 6-membered saturated nitrogen-containing heterocyclylcarbonyl (the 4- to 6-membered saturated nitrogen-containing heterocyclyl of the $C_{1-4}$ alkyl substituted with 4- to 6-membered saturated nitrogen-containing heterocyclylcarbonyl may be substituted with one or two groups selected from the group consisting of hydroxy and a fluorine atom),
  $C_{2-4}$ alkenyl substituted with carboxy,
  $C_{2-4}$ alkenyl substituted with di($C_{1-4}$ alkyl)aminocarbonyl,
  $C_{3-6}$ cycloalkyl substituted with carboxy,
  $C_{3-6}$ cycloalkyl substituted with di($C_{1-4}$ alkyl)aminocarbonyl,
  phenyl substituted with carboxy,
  pyridyl substituted with carboxy,
  pyrazolyl substituted with carboxy,
  pyrazolyl substituted with carboxymethyl,
  pyrazinyl substituted with carboxy,
  2-oxodihydropyridinyl substituted with carboxymethyl,
  mono$C_{1-4}$ alkylaminocarbonyl substituted with carboxy (when position α of the carboxy of the mono$C_{1-4}$ alkylaminocarbonyl substituted with carboxy is a methylene moiety, the methylene moiety may be replaced with propane-2,2-diyl or cyclopentane-1,1-diyl),
  phenyl$C_{1-4}$ alkylaminocarbonyl substituted with carboxy,
  mono$C_{1-4}$ alkylaminocarbonyl substituted with the structure represented by formula [V-6] below:

[Formula 151]

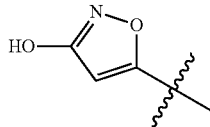

[V-6]

4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
the structure represented by formula [XI-2] below, which is substituted with carboxy,
the structure represented by formula [XI-3] below, which is substituted with carboxy:

[Formula 152]

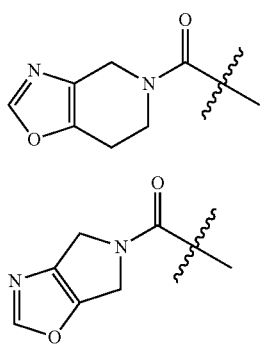

[XI-2]

[XI-3]

$C_{1-4}$alkylsulfonyl substituted with carboxy (when position α of the carboxy of the $C_{1-4}$alkylsulfonyl substituted with carboxy is a methylene group, the methylene moiety may be replaced with propane-2,2-diyl),
di($C_{1-4}$alkyl)aminosulfonyl substituted with carboxy (when position α of the carboxy of the di($C_{1-4}$alkyl)aminosulfonyl substituted with carboxy is a methylene moiety, the methylene moiety may be replaced with propane-2,2-diyl),
4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom),
hydroxy,
$C_{1-4}$ alkylsulfonyloxy,
$C_{1-4}$ alkyl substituted with hydroxy,
halo-$C_{1-4}$ alkyl substituted with hydroxy,
$C_{1-4}$ alkylsulfonyl substituted with hydroxy,
$C_{3-6}$ cycloalkyl substituted with hydroxy (the $C_{3-6}$ cycloalkyl of the $C_{3-6}$ cycloalkyl substituted with hydroxy may be substituted with one group selected from the group consisting of carboxy and di($C_{1-4}$alkyl)aminocarbonyl), or
4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_{1-4}$alkylcarbonyl, $C_{1-4}$ alkoxycarbonyl, and di($C_{1-4}$alkyl)aminocarbonyl);
$R^{61}$ and $R^{62}$ are each independently a hydrogen atom, a fluorine atom, methyl, or methylsulfonyl;
$W^4$ is $C_{1-3}$alkanediyl;
wherein more preferably, $R^5$ is such that
$R^{54}$ is
carboxy,
carbamoyl,
mono$C_{1-3}$ alkylaminocarbonyl (the $C_{1-3}$ alkyl of the mono$C_{1-3}$ alkylaminocarbonyl may be substituted with one hydroxy),
mono$C_1$alkylaminosulfonyl,
di($C_1$alkyl)aminosulfonyl (one $C_1$alkyl of the di($C_1$alkyl)aminosulfonyl is substituted with one phenyl, wherein the phenyl is substituted with one $C_1$alkylaminosulfonyl),
phenylaminosulfonyl (the phenyl of the phenylaminosulfonyl is substituted with one fluorine atom),
$C_3$alkylsulfonylamino,
$C_1$alkylsulfonyl($C_1$alkyl)aminocarbonyl,
$C_{1-3}$ alkyl substituted with carboxy,
$C_1$alkyl substituted with trifluoromethylsulfonylamino,
$C_2$alkyl substituted with methylsulfonyl(methyl)aminocarbonyl,
$C_{1-2}$alkyl substituted with mono$C_{1-3}$alkylaminocarbonyl (the $C_{1-3}$alkyl of the mono$C_{1-3}$alkylaminocarbonyl of the $C_{1-2}$ alkyl substituted with mono$C_{1-3}$ alkylaminocarbonyl may be substituted with one group selected from the group consisting of hydroxy, $C_1$alkoxy, 5-membered saturated oxygen-containing heterocyclyl, di($C_1$alkyl)amino, and 5-membered saturated nitrogen-containing heterocyclylcarbonyl),
$C_{1-2}$ alkyl substituted with di($C_1$alkyl)aminocarbonyl,
$C_2$alkyl substituted with 4-membered saturated oxygen-containing heterocyclylaminocarbonyl,
$C_2$alkyl substituted with 4- to 6-membered saturated nitrogen-containing heterocyclylcarbonyl (the 4- to 6-membered saturated nitrogen-containing heterocyclyl of the $C_2$alkyl substituted with 4- to 6-membered saturated nitrogen-containing heterocyclylcarbonyl may be substituted with one or two groups selected from the group consisting of hydroxy and a fluorine atom),
$C_2$alkenyl substituted with carboxy,
$C_2$alkenyl substituted with di($C_1$alkyl)aminocarbonyl,
$C_{3-6}$ cycloalkyl substituted with carboxy,
$C_3$cycloalkyl substituted with di($C_1$alkyl)aminocarbonyl,
phenyl substituted with carboxy,
pyridyl substituted with carboxy,
pyrazolyl substituted with carboxy,
pyrazolyl substituted with carboxymethyl,
pyrazinyl substituted with carboxy,
2-oxodihydropyridinyl substituted with carboxymethyl,
$C_{2-3}$ alkylaminocarbonyl substituted with carboxy (when position α of the carboxy of the $C_{2-3}$alkylaminocarbonyl substituted with carboxy is a methylene moiety, the methylene moiety may be replaced with propane-2,2-diyl or cyclopentane-1,1-diyl),
phenyl$C_1$alkylaminocarbonyl substituted with carboxy,
$C_1$alkylaminocarbonyl substituted with the structure represented by formula [V-6] below:

[Formula 153]

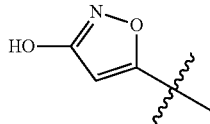

[V-6]

5-membered saturated nitrogen-containing heterocyclyl-carbonyl substituted with carboxy (the 5-membered saturated nitrogen-containing heterocyclyl of the 5-membered saturated nitrogen-containing heterocyclylcarbonyl is substituted with one fluorine atom),
the structure represented by formula [XI-2], which is substituted with carboxy,
the structure represented by formula [XI-3], which is substituted with carboxy:

[Formula 154]

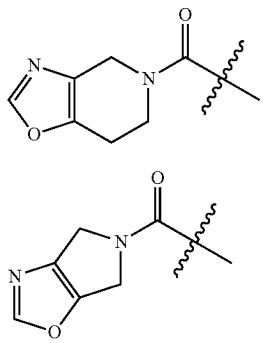

[XI-2]

[XI-3]

$C_4$alkylsulfonyl substituted with carboxy (when position α of the carboxy of the $C_4$alkylsulfonyl substituted with carboxy is a methylene moiety, the methylene moiety is replaced with propane-2,2-diyl),
di($C_{1-3}$alkyl)aminosulfonyl substituted with carboxy (when position α of the carboxy of the di($C_{1-3}$alkyl) aminosulfonyl substituted with carboxy is a methylene moiety, the methylene moiety may be replaced with propane-2,2-diyl),
5- or 6-membered saturated nitrogen-containing heterocyclylsulfonyl substituted with carboxy (the 5- or 6-membered saturated nitrogen-containing heterocyclyl of the 5- or 6-membered saturated nitrogen-containing heterocyclylsulfonyl substituted with carboxy may be substituted with one fluorine atom),
hydroxy,
$C_1$sulfonyloxy,
$C_{1-3}$ alkyl substituted with hydroxy,
halo-$C_{2-3}$alkyl substituted with hydroxy,
$C_{2-4}$ alkylsulfonyl substituted with hydroxy,
$C_{4-5}$ cycloalkyl substituted with hydroxy (the $C_{4-5}$ cycloalkyl of the $C_{4-5}$ cycloalkyl substituted with hydroxy may be substituted with one group selected from the group consisting of carboxy and di($C_1$alkyl) aminocarbonyl), or
4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_1$alkylcarbonyl, $C_1$alkoxycarbonyl, and di($C_1$alkyl) aminocarbonyl),
wherein $R^{61}$ and $R^{62}$ are each independently a hydrogen atom, a fluorine atom, methyl, or methylsulfonyl;
$W^4$ is $C_{1-3}$alkanediyl;
wherein even more preferably, $R^5$ is such that
$R^{54}$ is
carboxy,
carbamoyl,
methylaminocarbonyl, ethylaminocarbonyl (the ethyl of the ethylaminocarbonyl is substituted with one hydroxy), n-propylaminocarbonyl,
methylaminosulfonyl,
dimethylaminosulfonyl (one methyl of the dimethylaminosulfonyl is substituted with one phenyl, wherein the phenyl is substituted with one methylaminosulfonyl),
phenylaminosulfonyl (the phenyl of the phenylaminosulfonyl is substituted with one fluorine atom),
isopropylsulfonylamino,
methylsulfonyl(methyl)aminocarbonyl,
methyl substituted with carboxycarboxy, ethyl substituted with carboxy, n-propyl substituted with carboxy,
methyl substituted with trifluoromethylsulfonylamino,
ethyl substituted with methylsulfonyl(methyl)aminocarbonyl,
methyl substituted with methylaminocarbonyl, methyl substituted with propylaminocarbonyl, ethyl substituted with methylaminocarbonyl (the methyl of the ethyl substituted with methylaminocarbonyl may be substituted with one group selected from the group consisting of tetrahydrofuranyl and pyrrolidinylcarbonyl), ethyl substituted with ethylaminocarbonyl (the ethyl of the ethylaminocarbonyl of the ethyl substituted with ethylaminocarbonyl is substituted with one group selected from the group consisting of hydroxy, methoxy, and dimethylamino), ethyl substituted with n-propylaminocarbonyl (the n-propyl of the ethyl substituted with n-propylaminocarbonyl may be substituted with one group selected from the group consisting of hydroxy and methoxy),
methyl substituted with dimethylaminocarbonyl, ethyl substituted with dimethylaminocarbonyl,
ethyl substituted with oxetanylaminocarbonyl,
ethyl substituted with azetidinylcarboxy (the azetidinyl of the ethyl substituted with azetidinylcarboxy may be substituted with one hydroxy or one or two fluorine atoms), ethyl substituted with pyrrolidinylcarboxy, ethyl substituted with piperidinylcarboxy, ethyl substituted with morpholinylcarboxy,
$C_2$alkenyl substituted with carboxy,
ethenyl substituted with dimethylaminocarbonyl,
cyclopropyl substituted with carboxy, cyclohexyl substituted with carboxy,
cyclopropyl substituted with dimethylaminocarbonyl,
phenyl substituted with carboxy,
pyridyl substituted with carboxy,
pyrazolyl substituted with carboxy,
pyrazolyl substituted with carboxymethyl,
pyrazinyl substituted with carboxy,
2-oxodihydropyridinyl substituted with carboxymethyl,
ethylaminocarbonyl substituted with carboxy (the methylene moiety at position α of the carboxy of the ethylaminocarbonyl substituted with carboxy is replaced with cyclopentane-1,1-diyl), n-propylaminocarbonyl substituted with carboxy (the methylene moiety at position α of the carboxy of the n-propylaminocarbonyl substituted with carboxy is replaced with propane-2,2-diyl), 2-carboxyphenylmethylaminocarbonyl, 3-carboxyphenylmethylaminocarbonyl, 4-carboxyphenylmethylaminocarbonyl, methylaminocarbonyl substituted with the structure represented by formula [V-6] below:

[Formula 155]

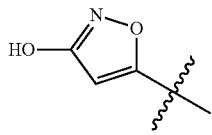

[V-6]

pyrrolidinylcarbonyl substituted with carboxy (the pyrrolidinyl of the pyrrolidinylcarbonyl substituted with carboxy is substituted with one fluorine atom), the structure represented by formula [XI-2] below, which is substituted with carboxy, the structure represented by formula [XI-3] below, which is substituted with carboxy:

[Formula 156]

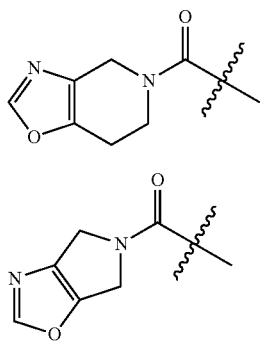

[XI-2]

[XI-3]

n-butylsulfonyl substituted with carboxy (the methylene moiety at position α of the carboxy of the n-butylsulfonyl substituted with carboxy is replaced with propane-2,2-diyl), n-propyl(methyl)aminosulfonyl substituted with carboxy (the methylene moiety at position α of the carboxy of the n-propyl(methyl)aminosulfonyl substituted with carboxy is replaced with propane-2,2-diyl), piperidinylsulfonyl substituted with carboxy, pyrrolidinylsulfonyl substituted with carboxy (the pyrrolidinyl of the pyrrolidinylsulfonyl substituted with carboxy is substituted with one fluorine atom), hydroxy, methylsulfonyloxy, methyl substituted with hydroxy, isopropyl substituted with hydroxy, haloethyl substituted with hydroxy, halo-n-propyl substituted with hydroxy, ethylsulfonyl substituted with hydroxy, isobutylsulfonyl substituted with hydroxy, cyclobutyl substituted with hydroxy (the cyclobutyl of the cyclobutyl substituted with hydroxy may be substituted with one group selected from the group consisting of carboxy and dimethylaminocarbonyl), cyclopentyl substituted with hydroxy, or azetidinyl substituted with hydroxy (the nitrogen atom of the azetidinyl substituted with hydroxy is substituted with one methylcarbonyl), or piperidinyl substituted with hydroxy (the nitrogen atom of the piperidinyl substituted with hydroxy is substituted with one group selected from the group consisting of methylcarbonyl, methoxycarbonyl, and dimethylaminocarbonyl), wherein $R^{61}$ and $R^{62}$ are each independently a hydrogen atom, a fluorine atom, methyl, or methylsulfonyl;

$W^4$ is methanediyl, ethane-1,2-diyl, or propane-1,3-diyl;

(d) when ring C is pyridyl, another preferred example of $R^5$ is such that $R^{54}$ is carbamoyl, or $C_{1-4}$ alkoxy substituted with carboxy (when position α of the carboxy of the $C_{1-4}$ alkoxy substituted with carboxy is a methylene moiety, the methylene moiety may be replaced with propane-2,2-diyl);

$R^{61}$ is a hydrogen atom;

$R^{62}$ is a hydrogen atom;

$W^4$ is $C_{1-3}$alkanediyl;

wherein more preferably, $R^5$ is such that $R^{54}$ is (ii) carbamoyl, or (iv) $C_2$alkoxy substituted with carboxy (when position α of the carboxy of the $C_2$alkoxy substituted with carboxy is a methylene moiety, the methylene moiety is replaced with propane-2,2-diyl);

$R^{61}$ is a hydrogen atom;

$R^{62}$ is a hydrogen atom;

$W^4$ is $C_1$alkanediyl;

wherein even more preferably, $R^5$ is such that ring C is pyridin-4-yl, $R^{54}$ is (ii) carbamoyl, or (iv) ethoxy substituted with carboxy (the methylene moiety at position α of the carboxy of the ethoxy substituted with carboxy is replaced with propane-2,2-diyl);

$R^{61}$ is a hydrogen atom;

$R^{62}$ is a hydrogen atom;

$W^4$ is methanediyl;

(g) when ring C is tetrahydronaphthyl, another preferred example of $R^5$ is such that $R^{54}$ is carboxy;

$R^{61}$ is a hydrogen atom;

$R^{62}$ is a hydrogen atom;

$W^4$ is $C_{1-3}$alkanediyl;

wherein more preferably, $R^5$ is such that $R^{54}$ is carboxy;

$R^{61}$ is a hydrogen atom;

$R^{62}$ is a hydrogen atom;

$W^4$ is $C_1$alkanediyl;

wherein even more preferably, $R^5$ is such that ring C is a structure represented by formula [XII-1] or formula [XII-2] below:

[Formula 157]

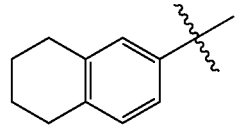

[XII-1]

-continued

[XII-2]

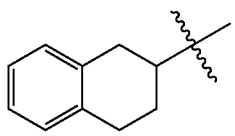

R⁵⁴ is carboxy;
R⁶¹ is a hydrogen atom;
R⁶² is a hydrogen atom;
W⁴ is methanediyl;
(h) when ring C is chromanyl,
another preferred example of R⁵ is such that
R⁵⁴ is carboxy;
R⁶¹ is a hydrogen atom;
R⁶² is a hydrogen atom;
W⁴ is $C_{1-3}$alkanediyl;
wherein even more preferably, R⁵ is such that
R⁵⁴ is carboxy;
R⁶¹ is a hydrogen atom;
R⁶² is a hydrogen atom;
W⁴ is $C_1$alkanediyl;
wherein even more preferably, R⁵ is such that
ring C is a structure represented by formula [XIII-1] or formula [XIII-2] below:

[Formula 158]

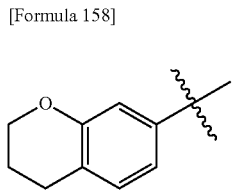

[XIII-1]

[XIII-2]

R⁵⁴ is carboxy;
R⁶¹ is a hydrogen atom;
R⁶² is a hydrogen atom;
W⁴ is methanediyl;
(n) when ring C is the structure represented by formula [IX-1] below:

[Formula 159]

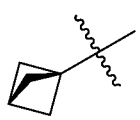

[IX-1]

another preferred example of R⁵ is such that
R⁵⁴ is
  $C_{1-4}$ alkyl substituted with $C_{1-4}$alkylsulfonylamino, or
  $C_{1-4}$ alkyl substituted with $C_{1-4}$ alkylsulfonyl($C_{1-4}$alkyl) amino;
R⁶¹ is a hydrogen atom;
R⁶² is a hydrogen atom;
W⁴ is $C_{1-3}$alkanediyl;

wherein more preferably, R⁵ is such that
ring C is the structure represented by formula [IX-1] above,
R⁵⁴ is
(ii) $C_1$alkyl substituted with $C_1$alkylsulfonylamino, or
(iii) $C_1$alkyl substituted with $C_1$alkylsulfonyl($C_1$alkyl) amino,
R⁶¹ is a hydrogen atom;
R⁶² is a hydrogen atom;
W⁴ is $C_1$alkanediyl;
wherein even more preferably, R⁵ is such that
ring C is the structure represented by formula [IX-1] above,
R⁵⁴ is
(ii) methyl substituted with methylsulfonylamino, or
(iii) methyl substituted with methylsulfonyl(methyl)amino,
R⁶¹ is a hydrogen atom;
R⁶² is a hydrogen atom;
W⁴ is methanediyl.

The "preferred embodiments" described above include compounds or pharmaceutically acceptable salts thereof below:

[Formula 160]

,

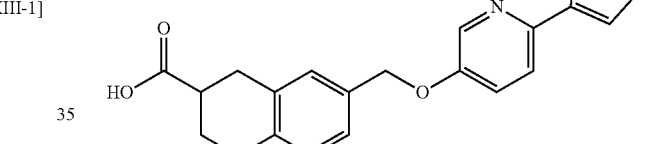

,

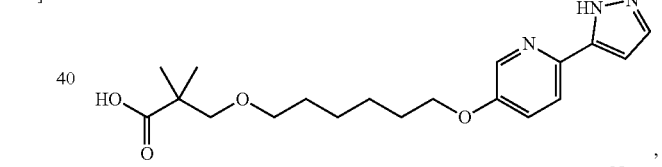

,

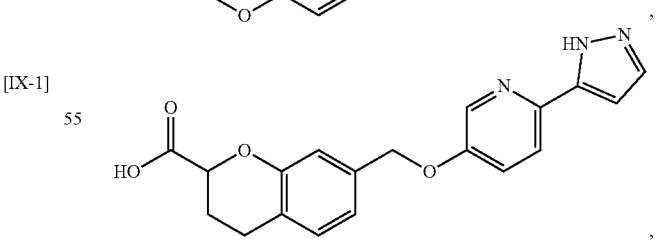

,

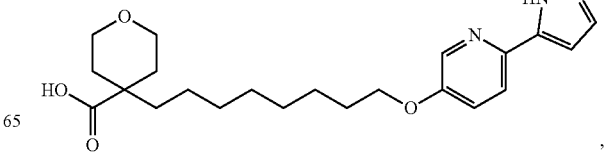

,

-continued
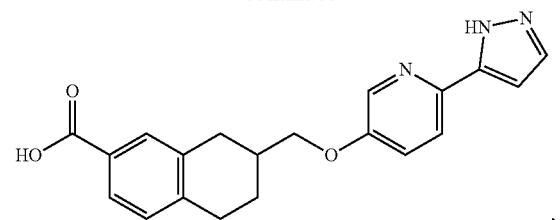
[Formula 161]
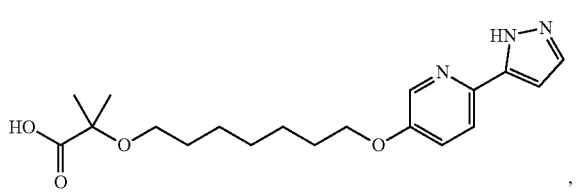
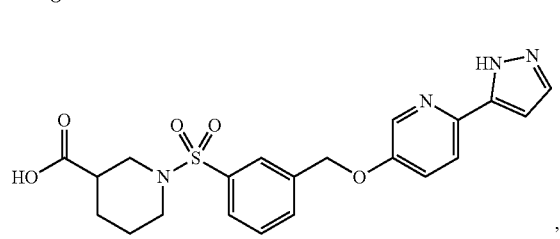
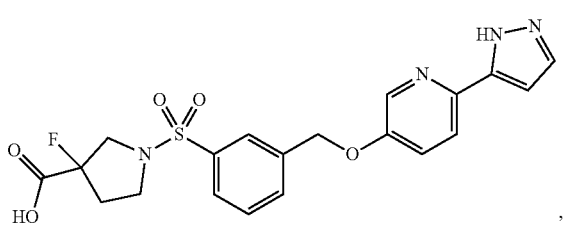
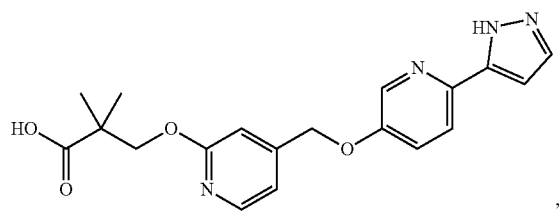
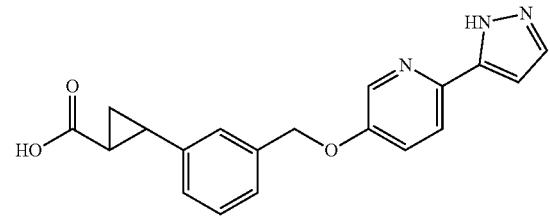
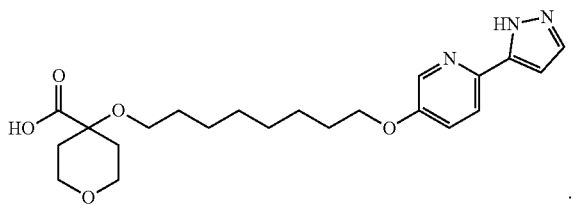
[Formula 162]
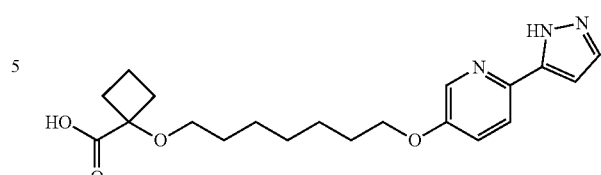
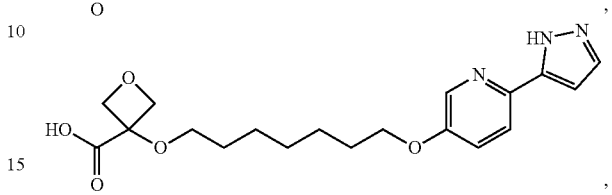
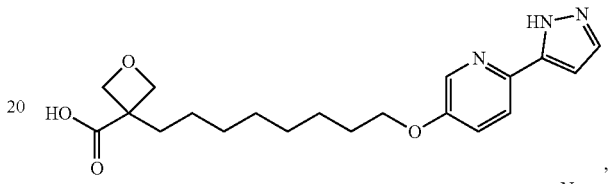
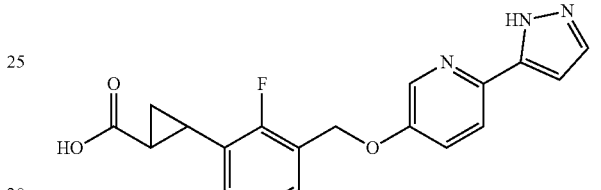
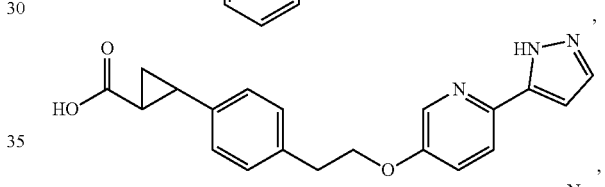

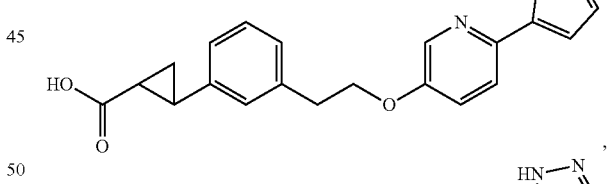
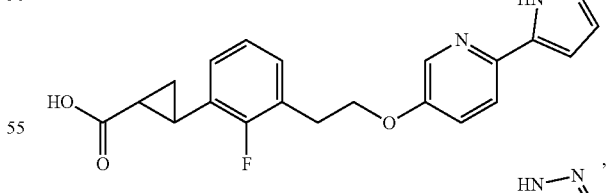
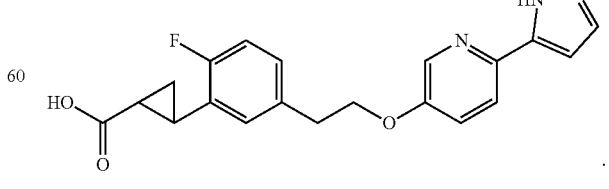
The "preferred embodiments" described above further include compounds or pharmaceutically acceptable salts thereof below:
One preferred embodiment of compounds of the present invention is a compound represented by formula [I-A] below or a pharmaceutically acceptable salt thereof:

[Formula 163]

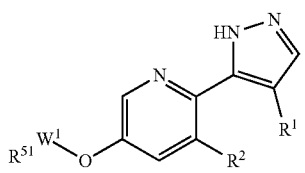

[I-A]

wherein preferred embodiments of $R^1$, $R^2$, $R^{51}$, and $W^1$ are as described above.

One more preferred embodiment of formula [I-A] above is such that
$R^1$ is a hydrogen atom;
$R^2$ is a hydrogen atom;
$R^{51}$ is a structure represented by formula [V-6] or formula [V-8] below:

[Formula 164]

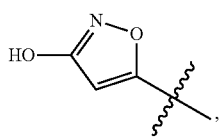

[V-6]

[V-8]

$W^1$ is $C_4$alkanediyl;
wherein an even more preferred embodiment is such that
$R^1$ is a hydrogen atom;
$R^2$ is a hydrogen atom;
$R^{51}$ is a structure represented by formula [V-6] or formula [V-8] below:

[Formula 165]

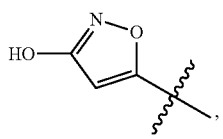

[V-6]

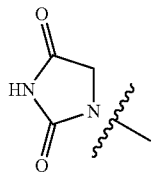

[V-8]

$W^1$ is butane-1,4-diyl.
Another more preferred embodiment of formula [I-A] above is such that
$R^1$ is a hydrogen atom;
$R^2$ is a hydrogen atom;
$R^{51}$ is the structure represented by formula [V-6] below:

[Formula 166]

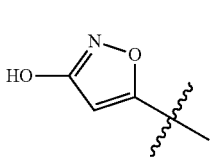

[V-6]

$W^1$ is $C_4$alkanediyl;
wherein an even more preferred embodiment is such that
$R^1$ is a hydrogen atom;
$R^2$ is a hydrogen atom;
$R^{51}$ is the structure represented by formula [V-6] below:

[Formula 167]

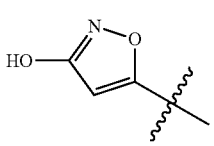

[V-6]

$W^1$ is butane-1,4-diyl;
wherein a particularly preferred embodiment is such that the compound represented by formula [I-A] is as follows:

[Formula 168]

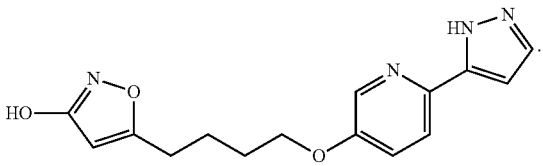

Another preferred embodiment of compounds of the present invention is a compound represented by formula [I-B] below or a pharmaceutically acceptable salt thereof:

[Formula 169]

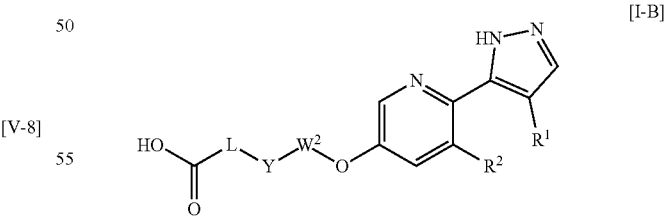

[I-B]

wherein preferred embodiments of $R^1$, $R^2$, L, Y, and $W^2$ are as described above.

One more preferred embodiment of formula [I-B] above is such that
$R^1$ is a hydrogen atom;
$R^2$ is a hydrogen atom;
L is a structure represented by formula [VI-1], formula [VI-4], or formula [VI-7] below:

[Formula 170]

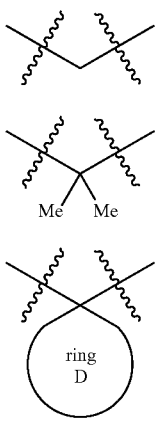

wherein
ring D is
(i) $C_{5-6}$cycloalkane,
(ii) 6-membered saturated oxygen-containing hetero ring, or
(iv) 6-membered saturated nitrogen-containing hetero ring
(the nitrogen atom of the 6-membered saturated nitrogen-containing hetero ring is substituted with one $C_1$alkylcarbonyl);
Y is the formula —CH$_2$—, the formula —O—, the formula —CONH—, or the formula —CONMe-;
W$^2$ is $C_{5-8}$alkanediyl,
wherein one of the carbon atoms that constitute $C_{5-8}$alkanediyl represented by W$^2$ may be replaced with an oxygen atom;
wherein an even more preferred embodiment is such that
R$^1$ is a hydrogen atom;
R$^2$ is a hydrogen atom;
L is a structure represented by formula [VI-1], formula [VI-4], formula [VI-8], formula [VI-9], formula [VI-10], or formula [VI-11] below:

[Formula 171]

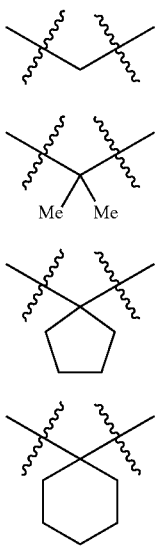

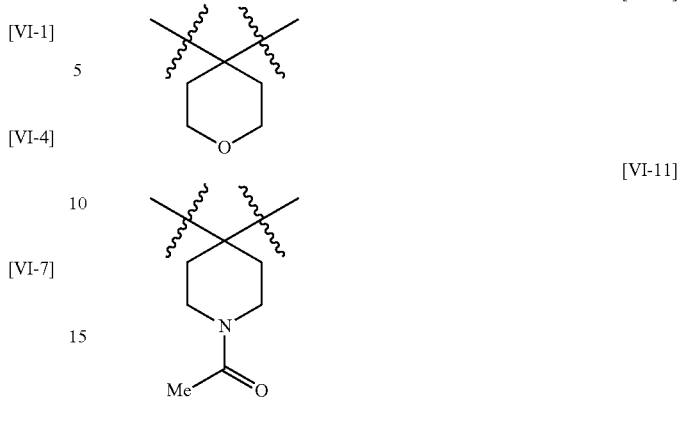

Y is the formula —CH$_2$—, the formula —O—, the formula —CONH—, or the formula —CONMe-;
W$^2$ is pentane-1,5-diyl, hexane-1,6-diyl, heptane-1,7-diyl, octane-1,8-diyl, or the formula —O—(CH$_2$)$_6$—.
Another more preferred embodiment of formula [I-B] above is such that
R$^1$ is a hydrogen atom;
R$^2$ is a hydrogen atom;
L is a structure represented by formula [VI-1], formula [VI-4], or formula [VI-7] below:

[Formula 172]

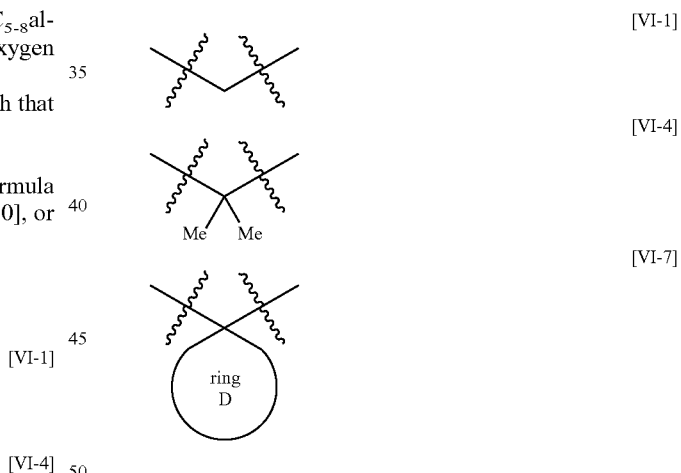

wherein
ring D is
(i) $C_{5-6}$cycloalkane,
(ii) 6-membered saturated oxygen-containing hetero ring, or
(iv) 6-membered saturated nitrogen-containing hetero ring
(the nitrogen atom of the 6-membered saturated nitrogen-containing hetero ring is substituted with one $C_1$alkylcarbonyl);
Y is the formula —CH$_2$—, the formula —O—, or the formula —CONMe-;
W$^2$ is $C_{5-8}$alkanediyl,
wherein one of the carbon atoms that constitute $C_{5-8}$alkanediyl represented by W$^2$ may be replaced with an oxygen atom;
wherein an even more preferred embodiment is such that
R$^1$ is a hydrogen atom;
R$^2$ is a hydrogen atom;

L is a structure represented by formula [VI-1], formula [VI-4], formula [VI-8], formula [VI-9], formula [VI-10], or formula [VI-11] below:

[Formula 173]

[VI-1]
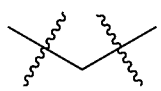

[VI-4]
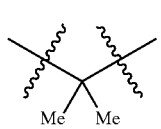

[VI-8]
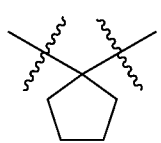

[VI-9]
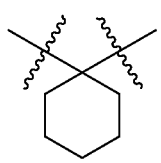

[VI-10]
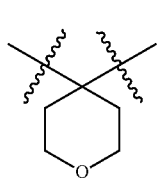

[VI-11]
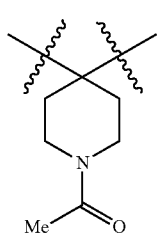

Y is the formula —CH$_2$—, the formula —O—, or the formula —CONMe—;

W$^2$ is pentane-1,5-diyl, hexane-1,6-diyl, heptane-1,7-diyl, octane-1,8-diyl, or the formula —O—(CH$_2$)$_6$—, wherein a particularly preferred embodiment is such that the compound represented by formula [I-B] is any of the following:

[Formula 174]

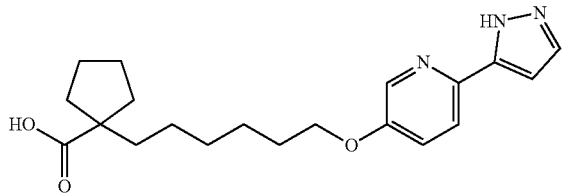

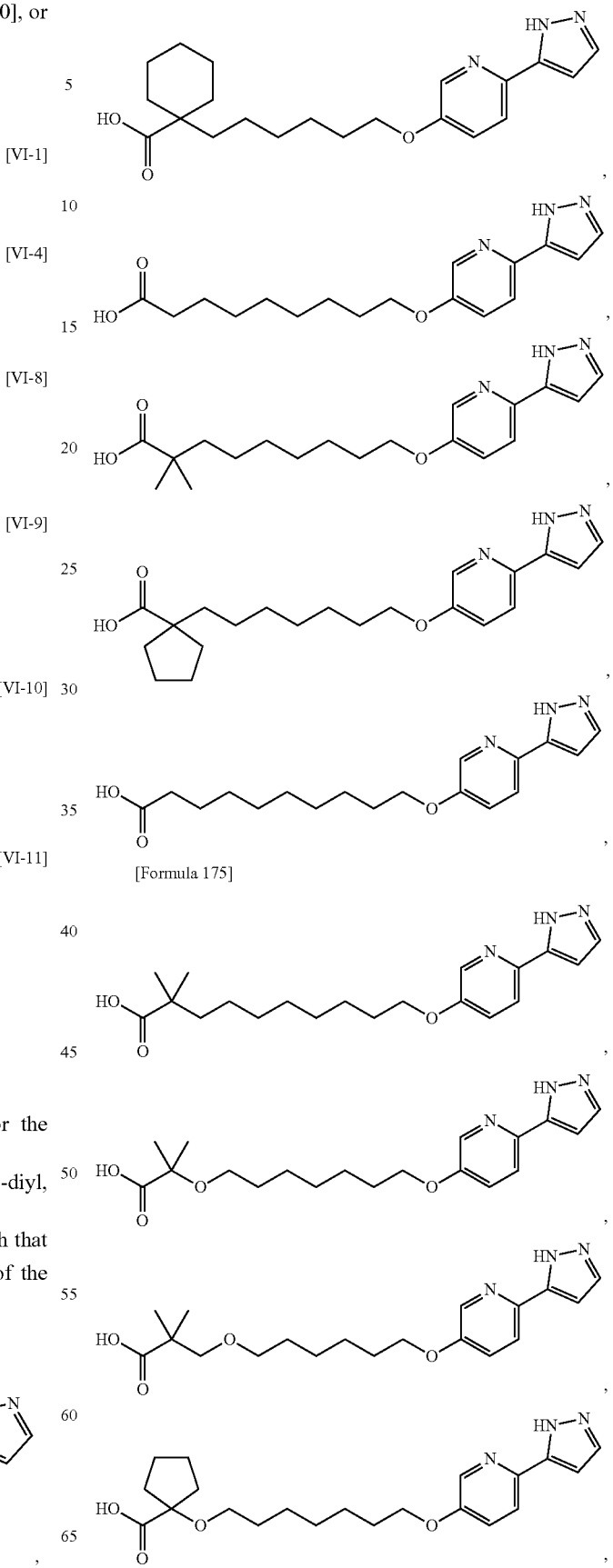

[Formula 175]

[Formula 176]

Another preferred embodiment of compounds of the present invention is a compound represented by formula [I-C] below or a pharmaceutically acceptable salt thereof:

[Formula 177]

[I-C]

wherein preferred embodiments of $R^1$, $R^2$, $R^{53}$, ring B, and $W^3$ are as described above.

One more preferred embodiment of formula [I-C] above is such that
$R^1$ is a hydrogen atom;
$R^2$ is a hydrogen atom;
ring B is a structure represented by formula [VIII-1], formula [VIII-2], formula [VIII-4], or formula [VIII-7] below:

[Formula 178]

[VIII-1]

[VIII-2]

[VIII-4]

[VIII-7]

$R^{53}$ is carboxy;
$W^3$ is $C_{4-6}$ alkanediyl;
wherein an even more preferred embodiment is such that
$R^1$ is a hydrogen atom;
$R^2$ is a hydrogen atom;
ring B is a structure represented by formula [VIII-1], formula [VIII-8], formula [VIII-9], formula [VIII-10], or formula [VIII-7] below:

[Formula 179]

[VIII-1]

[VIII-8]

[VIII-9]

[VIII-10]

[VIII-7]

$R^{53}$ is carboxy;
$W^3$ is butane-1,4-diyl or hexane-1,6-diyl.

Another more preferred embodiment of formula [I-C] above is such that
$R^1$ is a hydrogen atom;
$R^2$ is a hydrogen atom;
ring B is a structure represented by formula [VIII-1], formula [VIII-2], formula [VIII-4], or formula [VIII-7] below:

[Formula 180]

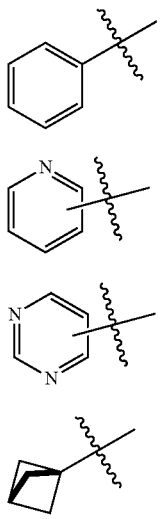

R⁵³ is carboxy;
W³ is C₄₋₆alkanediyl;
wherein an even more preferred embodiment is such that,
R¹ is a hydrogen atom;
R² is a hydrogen atom;
ring B is a structure represented by formula [VIII-1], formula [VIII-8], formula [VIII-9], formula [VIII-10], or formula [VIII-7] below:

[Formula 181]

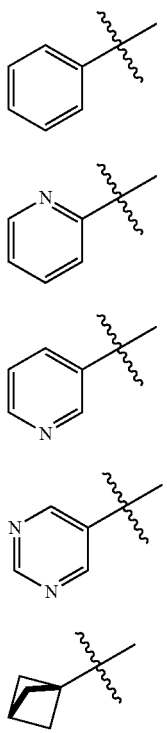

R⁵³ is carboxy;
W³ is butane-1,4-diyl or hexane-1,6-diyl;

wherein a particularly preferred embodiment is such that the compound represented by formula [1-C] is any of the following:

[Formula 182]

Another preferred embodiment of compounds of the present invention is a compound represented by formula [I-D] below or a pharmaceutically acceptable salt thereof:

[Formula 183]

wherein preferred embodiments of R¹, R², R⁵⁴, ring C, and W⁴ are as described above.
In formula [I-D] above,
(a) when ring C is C₃₋₆cycloalkyl, one more preferred embodiment is such that $R^1$ is a hydrogen atom;
$R^2$ is a hydrogen atom;
ring C is $C_6$cycloalkyl;
$R^{54}$ is carboxy;
$W^4$ is $C_3$alkanediyl;
wherein an even more preferred embodiment is such that
$R^1$ is a hydrogen atom;
$R^2$ is a hydrogen atom;
ring C is cyclohexyl;
$R^{54}$ is carboxy;
$W^4$ is propane-1,3-diyl.

In formula [I-D] above,
(a) when ring C is $C_{3-6}$cycloalkyl, another more preferred embodiment is such that
$R^1$ is a hydrogen atom;
$R^2$ is a hydrogen atom;
ring C is $C_6$cycloalkyl;
$R^{54}$ is carboxy;
$W^4$ is $C_3$alkanediyl;
wherein an even more preferred embodiment is such that
$R^1$ is a hydrogen atom;
$R^2$ is a hydrogen atom;
ring C is cyclohexyl;
$R^{54}$ is carboxy;
$W^4$ is propane-1,3-diyl;
wherein a particularly preferred embodiment is such that the compound represented by formula [I-D] is as follows:

[Formula 184]

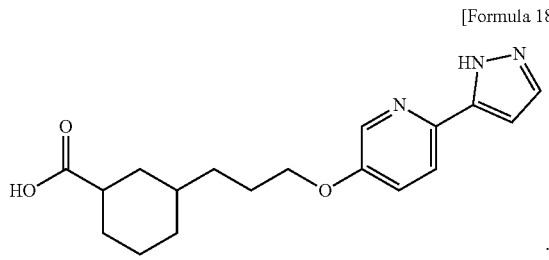

In formula [I-D] above,
(b) when ring C is 4- to 6-membered saturated nitrogen-containing heterocyclyl, one more preferred embodiment is such that
$R^1$ is a hydrogen atom;
$R^2$ is a hydrogen atom;
ring C is 6-membered saturated nitrogen-containing heterocyclyl;
$R^{54}$ is
(i) $C_4$alkylcarbonyl substituted with carboxy (when position α of the carboxy of the $C_4$alkylcarbonyl substituted with carboxy is a methylene moiety, the methylene moiety is replaced with $C_5$alkanediyl),
(ii) $C_3$alkylcarbonyl substituted with sulfamoyl,
(v) phenylcarbonyl substituted with sulfamoyl,
(vii) phenylsulfonyl substituted with carboxy, or
(x) the structure represented by formula [X-2] below, which is substituted with carboxy:

[Formula 185]

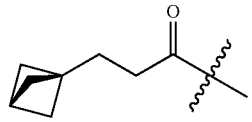

$W^4$ is $C_1$alkanediyl;
wherein an even more preferred embodiment is such that
$R^1$ is a hydrogen atom;
$R^2$ is a hydrogen atom;
ring C is piperidine-3-yl or piperidine-4-yl;
$R^{54}$ is
(i) n-butylcarbonyl substituted with carboxy (the methylene moiety at position α of the carboxy of the n-butylcarbonyl substituted with carboxy may be replaced with cyclopentane-1,1-diyl),
(ii) n-propylcarbonyl substituted with sulfamoyl,
(v) phenylcarbonyl substituted with sulfamoyl,
(vii) phenylsulfonyl substituted with carboxy, or
(x) the structure represented by formula [X-2] below, which is substituted with carboxy:

[Formula 186]

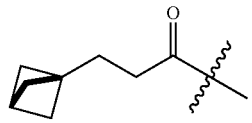

$W^4$ is methanediyl.
In formula [I-D] above,
(b) when ring C is 4- to 6-membered saturated nitrogen-containing heterocyclyl, another more preferred embodiment is such that
$R^1$ is a hydrogen atom;
$R^2$ is a hydrogen atom;
ring C is 6-membered saturated nitrogen-containing heterocyclyl;
$R^{54}$ is
(i) $C_4$alkylcarbonyl substituted with carboxy (when position α of the carboxy of the $C_4$alkylcarbonyl substituted with carboxy is a methylene moiety, the methylene moiety is replaced with cyclopentane-1,1-diyl), or
(vii) phenylsulfonyl substituted with carboxy, and
$W^4$ is $C_1$alkanediyl;
wherein an even more preferred embodiment is such that
$R^1$ is a hydrogen atom;
$R^2$ is a hydrogen atom;
ring C is piperidine-3-yl or piperidine-4-yl;
$R^{54}$ is
(i) n-butylcarbonyl substituted with carboxy (the methylene moiety at position α of the carboxy of the n-butylcarbonyl substituted with carboxy is replaced with cyclopentane-1,1-diyl), or
(vii) phenylsulfonyl substituted with carboxy, and
$W^4$ is methanediyl;
wherein a particularly preferred embodiment is such that the compound represented by formula [I-D] is any of the following:

[Formula 187]

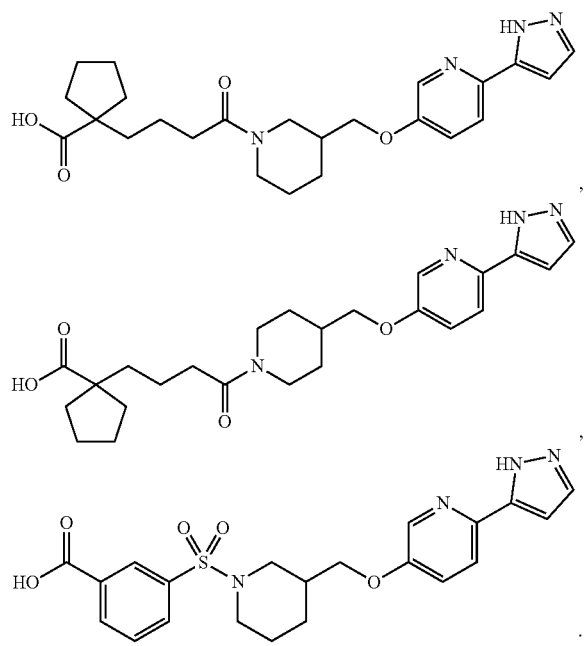

In formula [I-D] above,
(d) when ring C is pyridyl, one more preferred embodiment is such that
$R^1$ is a hydrogen atom;
$R^2$ is a hydrogen atom;
$R^{54}$ is
(ii) carbamoyl,
(iii) $C_1$alkyl substituted with carboxy,
(iv) $C_2$alkoxy substituted with carboxy (when position α of the carboxy of the $C_2$alkoxy substituted with carboxy is a methylene moiety, the methylene moiety may be replaced with propane-2,2-diyl), or
(vi) 5-membered saturated heterocyclylcarbonyl substituted with carboxy (the 5-membered saturated heterocyclyl of the 5-membered saturated heterocyclylcarbonyl substituted with carboxy is substituted with one fluorine atom);
$W^4$ is $C_1$alkanediyl;
wherein an even more preferred embodiment is such that
$R^1$ is a hydrogen atom;
$R^2$ is a hydrogen atom;
$R^{54}$ is
(ii) carbamoyl,
(iii) methyl substituted with carboxy,
(iv) ethoxy substituted with carboxy (the methylene moiety at position α of the carboxy of the ethoxy substituted with carboxy is replaced with propane-2,2-diyl),
(vi) n-propylaminocarbonyl substituted with carboxy (the methylene moiety at position α of the carboxy of the n-propylaminocarbonyl substituted with carboxy is replaced with propane-2,2-diyl), or
pyrrolidinylcarbonyl substituted with carboxy (the pyrrolidinyl of the pyrrolidinylcarbonyl substituted with carboxy is substituted with one fluorine atom);
$W^4$ is methanediyl.
In formula [I-D] above,
(d) when ring C is pyridyl, another more preferred embodiment is such that
$R^1$ is a hydrogen atom;
$R^2$ is a hydrogen atom;

$R^{54}$ is
(ii) carbamoyl, or
(iv) $C_2$alkoxy substituted with carboxy (when position α of the carboxy of the $C_2$alkoxy substituted with carboxy is a methylene moiety, the methylene moiety is replaced with propane-2,2-diyl);
$W^4$ is $C_1$alkanediyl;
wherein an even more preferred embodiment is such that
$R^1$ is a hydrogen atom;
$R^2$ is a hydrogen atom;
ring C is pyridin-4-yl;
$R^{54}$ is
(ii) carbamoyl, or
(iv) ethoxy substituted with carboxy (the methylene moiety at position α of the carboxy of the ethoxy substituted with carboxy is replaced with propane-2,2-diyl);
$W^4$ is methanediyl;
wherein a particularly preferred embodiment is such that the compound represented by formula [I-D] is any of the following:

[Formula 188]

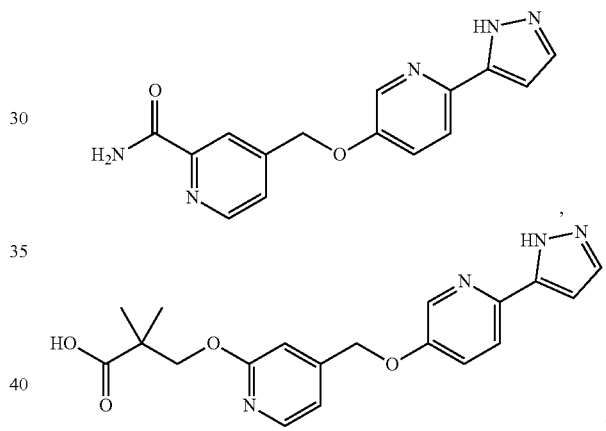

In formula [I-D] above,
(g) when ring C is tetrahydronaphthyl, one more preferred embodiment is such that
$R^1$ is a hydrogen atom;
$R^2$ is a hydrogen atom;
$R^{54}$ is carboxy;
$W^4$ is $C_1$alkanediyl;
wherein an even more preferred embodiment is such that
$R^1$ is a hydrogen atom;
$R^2$ is a hydrogen atom;
ring C is a structure represented by formula [XII-1] or formula [XII-2] below:

[Formula 189]

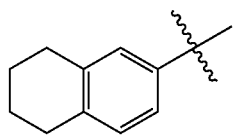

[XII-1]

[XII-2]

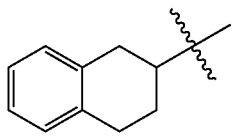

$R^{54}$ is carboxy;
$W^4$ is methanediyl.
In formula [I-D] above,
(g) when ring C is tetrahydronaphthyl, another more preferred embodiment is such that
$R^1$ is a hydrogen atom;
$R^2$ is a hydrogen atom;
$R^{54}$ is carboxy;
$W^4$ is $C_1$alkanediyl;
wherein an even more preferred embodiment is such that
$R^1$ is a hydrogen atom;
$R^2$ is a hydrogen atom;
ring C is a structure represented by formula [XII-1] or formula [XII-2] below:

[Formula 190]

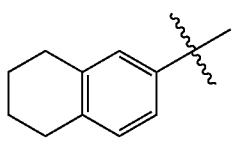

[XII-1]

[XII-2]

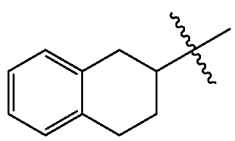

$R^{54}$ is carboxy;
$W^4$ is methanediyl;
wherein a particularly preferred embodiment is such that the compound represented by formula [I-D] is any of the following:

[Formula 191]

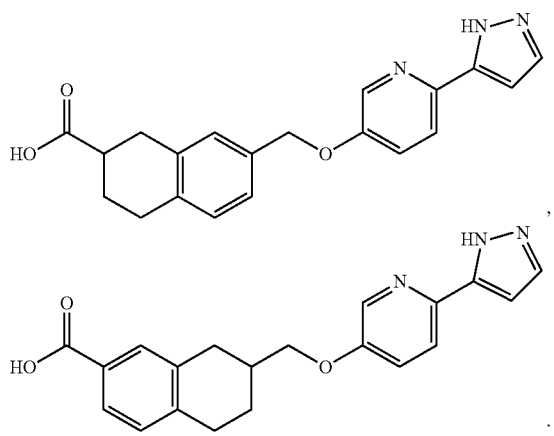

In formula [I-D] above,
(h) when ring C is chromanyl, one more preferred embodiment is such that
$R^1$ is a hydrogen atom;
$R^2$ is a hydrogen atom;
$R^{54}$ is carboxy;
$W^4$ is $C_1$alkanediyl;
wherein an even more preferred embodiment is such that
$R^1$ is a hydrogen atom;
$R^2$ is a hydrogen atom;
ring C is a structure represented by formula [XIII-1] or formula [XIII-2] below:

[Formula 192]

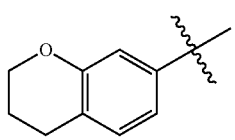

[XIII-1]

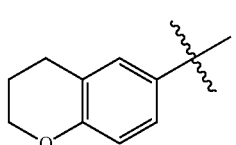

[XIII-2]

$R^{54}$ is carboxy;
$W^4$ is methanediyl.
In formula [I-D] above,
(h) when ring C is chromanyl, another more preferred embodiment is such that
$R^1$ is a hydrogen atom;
$R^2$ is a hydrogen atom;
$R^{54}$ is carboxy;
$W^4$ is $C_1$alkanediyl;
wherein an even more preferred embodiment is such that
$R^1$ is a hydrogen atom;
$R^2$ is a hydrogen atom;
ring C is a structure represented by formula [XIII-1] or formula [XIII-2] below:

[Formula 193]

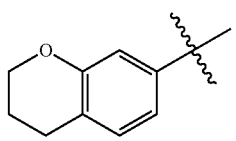

[XIII-1]

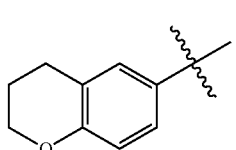

[XIII-2]

$R^{54}$ is carboxy;
$W^4$ is methanediyl;
wherein a particularly preferred embodiment is such that the compound represented by formula [I-D] is any of the following:

[Formula 194]

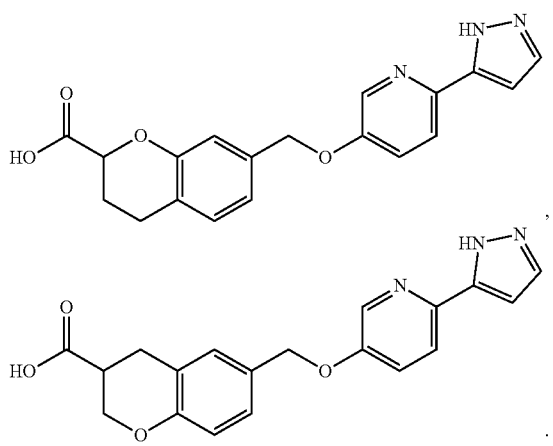

In formula [I-D] above,
(n) when ring C is the structure represented by formula [IX-1] below:

[Formula 195]

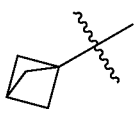

[IX-1]

one more preferred embodiment is such that
$R^1$ is a hydrogen atom;
$R^2$ is a hydrogen atom;
$R^{54}$ is
(ii) $C_1$alkyl substituted with $C_1$alkylsulfonylamino, or
(iii) $C_1$alkyl substituted with $C_1$alkylsulfonyl($C_1$alkyl)amino;
$W^4$ is $C_1$alkanediyl;
 wherein an even more preferred embodiment is such that
$R^1$ is a hydrogen atom;
$R^2$ is a hydrogen atom;
$R^{54}$ is
(ii) methyl substituted with methylsulfonylamino, or
(iii) methyl substituted with methylsulfonyl(methyl)amino, and
$W^4$ is methanediyl.
In formula [I-D] above,
(n) when ring C is the structure represented by formula [IX-1] below:

[Formula 196]

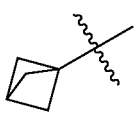

[IX-1]

another more preferred embodiment is such that
$R^1$ is a hydrogen atom;
$R^2$ is a hydrogen atom;
$R^{54}$ is
(ii) $C_1$alkyl substituted with $C_1$alkylsulfonylamino, or
(iii) $C_1$alkyl substituted with $C_1$alkylsulfonyl($C_1$alkyl)amino;
$W^4$ is $C_1$alkanediyl;
 wherein an even more preferred embodiment is such that
$R^1$ is a hydrogen atom;
$R^2$ is a hydrogen atom;
$R^{54}$ is
(ii) methyl substituted with methylsulfonylamino, or
(iii) methyl substituted with methylsulfonyl(methyl)amino, and
$W^4$ is methanediyl;
 wherein a particularly preferred embodiment is such that the compound represented by formula [I-D] is any of the following:

[Formula 197]

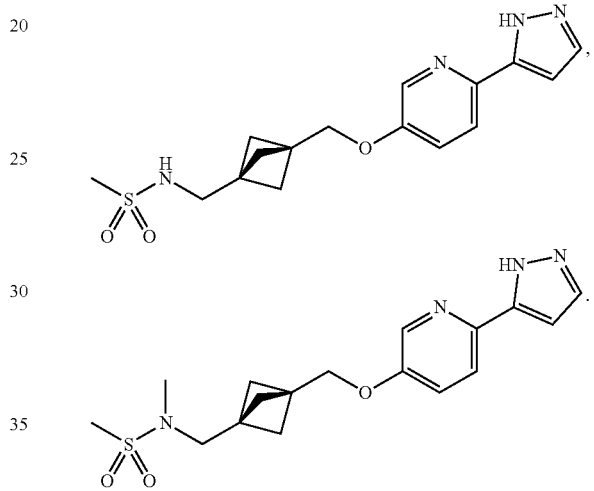

Another preferred embodiment of compounds of the present invention is a compound represented by formula [I-D'] below or a pharmaceutically acceptable salt thereof.

[Formula 198]

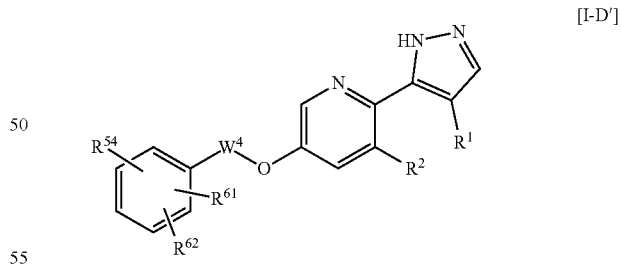

[I-D']

wherein preferred embodiments of $R^1$, $R^2$, $R^{54}$, $R^{61}$, $R^{62}$, and $W^4$ are as described above.
In formula [I-D'] above, one more preferred embodiment is such that
$R^1$ is a hydrogen atom;
$R^2$ is a hydrogen atom;
$R^{54}$ is
carboxy,
carbamoyl,
mono$C_{1-3}$ alkylaminocarbonyl (the $C_{1-3}$ alkyl of the mono$C_{1-3}$ alkylaminocarbonyl may be substituted with one hydroxy), $C_1$alkylaminosulfonyl,
di($C_1$alkyl)aminosulfonyl (one $C_1$alkyl of the di($C_1$alkyl) aminosulfonyl is substituted with one phenyl, wherein the phenyl is substituted with one $C_1$alkylaminosulfonyl),
phenylaminosulfonyl (the phenyl of the phenylaminosulfonyl may be substituted with one fluorine atom),
$C_3$alkylsulfonylamino,
$C_1$alkylsulfonyl($C_1$alkyl)aminocarbonyl,
$C_{1-3}$ alkyl substituted with carboxy,
$C_1$alkyl substituted with trifluoromethylsulfonylamino,
$C_{1-2}$ alkyl substituted with methylsulfonyl(methyl)aminocarbonyl,
$C_{1-2}$alkyl substituted with mono$C_{1-3}$alkylaminocarbonyl (the $C_{1-3}$alkyl of the mono$C_{1-3}$alkylaminocarbonyl of the $C_{1-2}$ alkyl substituted with mono$C_{1-3}$ alkylaminocarbonyl may be substituted with one group selected from the group consisting of hydroxy, $C_1$alkoxy, 5-membered saturated oxygen-containing heterocyclyl, di($C_1$alkyl)amino, and 5-membered saturated nitrogen-containing heterocyclylcarbonyl),
$C_{1-2}$ alkyl substituted with di($C_{1-2}$ alkyl)aminocarbonyl (one $C_{1-2}$ alkyl of the di($C_{1-2}$alkyl)amino of the $C_{1-2}$ alkyl substituted with di($C_{1-2}$ alkyl)aminocarbonyl may be substituted with one hydroxy),
$C_2$alkyl substituted with 4-membered saturated oxygen-containing heterocyclylaminocarbonyl,
$C_2$alkyl substituted with 4- to 6-membered saturated nitrogen-containing heterocyclylcarbonyl (the 4- to 6-membered saturated nitrogen-containing heterocyclyl of the $C_2$alkyl substituted with 4- to 6-membered saturated nitrogen-containing heterocyclylcarbonyl may be substituted with one or two groups selected from the group consisting of hydroxy and a fluorine atom),
$C_2$alkenyl substituted with carboxy,
$C_2$alkenyl substituted with di($C_1$alkyl)aminocarbonyl,
$C_{3-6}$ cycloalkyl substituted with carboxy,
$C_3$cycloalkyl substituted with di($C_1$alkyl)aminocarbonyl,
phenyl substituted with carboxy,
pyridyl substituted with carboxy,
pyrazolyl substituted with carboxy,
pyrazolyl substituted with carboxymethyl,
pyrazinyl substituted with carboxy,
2-oxodihydropyridinyl substituted with carboxymethyl,
mono$C_{1-3}$ alkylaminocarbonyl substituted with carboxy (the $C_{1-3}$ alkyl of the mono$C_{1-3}$alkylaminocarbonyl substituted with carboxy may be substituted with one benzyl, and when position α of the carboxy of the mono$C_{1-3}$ alkylaminocarbonyl substituted with carboxy is a methylene moiety, the methylene moiety may be replaced with propane-2,2-diyl or cyclopentane-1,1-diyl),
phenyl$C_1$alkylaminocarbonyl substituted with carboxy,
$C_1$alkylaminocarbonyl substituted with the structure represented by formula [V-6] below:

[Formula 199]

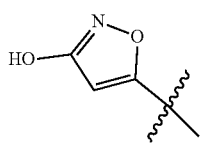

[V-6]

di($C_{1-3}$alkyl)aminocarbonyl substituted with carboxy (when position α of the carboxy of the di($C_{1-3}$alkyl) aminocarbonyl substituted with carboxy is a methylene moiety, the methylene moiety may be replaced with propane-2,2-diyl),
5-membered saturated nitrogen-containing heterocyclylcarbonyl substituted with carboxy (the 5-membered saturated nitrogen-containing heterocyclyl of the 5-membered saturated nitrogen-containing heterocyclylcarbonyl substituted with carboxy may be substituted with one fluorine atom),
the structure represented by formula [XI-2] below, which is substituted with carboxy,
the structure represented by formula [XI-3] below, which is substituted with carboxy:

[Formula 200]

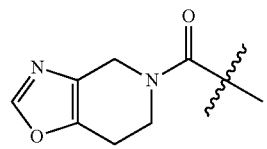

[XI-2]

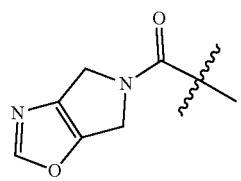

[XI-3]

$C_4$alkylsulfonyl substituted with carboxy (when position α of the carboxy of the $C_4$alkylsulfonyl substituted with carboxy is a methylene moiety, the methylene moiety may be replaced with propane-2,2-diyl),
di($C_{1-3}$ alkyl)aminosulfonyl substituted with carboxy (when position α of the carboxy of the di($C_{1-3}$ alkyl) aminosulfonyl substituted with carboxy is a methylene moiety, the methylene moiety may be replaced with propane-2,2-diyl),
5- or 6-membered saturated nitrogen-containing heterocyclylsulfonyl substituted with carboxy (the 5- or 6-membered saturated nitrogen-containing heterocyclyl of the 5- or 6-membered saturated nitrogen-containing heterocyclylsulfonyl substituted with carboxy may be substituted with one fluorine atom),
hydroxy,
$C_1$sulfonyloxy,
$C_{1-3}$ alkyl substituted with hydroxy,
halo-$C_{2-3}$ alkyl substituted with hydroxy,
$C_{2-4}$ alkylsulfonyl substituted with hydroxy,
$C_{4-5}$ cycloalkyl substituted with hydroxy (the $C_{4-5}$ cycloalkyl of the $C_{4-5}$ cycloalkyl substituted with hydroxy may be substituted with one group selected from the group consisting of carboxy and di($C_1$alkyl) aminocarbonyl), or
4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_1$alkylcarbonyl, $C_1$alkoxycarbonyl, and di($C_1$alkyl) aminocarbonyl), wherein $R^{61}$ and $R^{62}$ are each independently a hydrogen atom, a fluorine atom, methyl, or methylsulfonyl;

$W^4$ is $C_{1-3}$alkanediyl;

wherein an even more preferred embodiment is such that $R^1$ is a hydrogen atom;

$R^2$ is a hydrogen atom;

$R^{54}$ is carboxy,
carbamoyl,
methylaminocarbonyl, n-propylaminocarbonyl, methylaminosulfonyl,
dimethylaminosulfonyl (one methyl of the dimethylaminosulfonyl is substituted with one phenyl, wherein the phenyl is substituted with one methylaminosulfonyl),
phenylaminosulfonyl (the phenyl of the phenylaminosulfonyl may be substituted with one fluorine atom),
phenylaminosulfonyl (the phenyl of the phenylaminosulfonyl may be substituted with one fluorine atom),
isopropylsulfonylamino,
methylsulfonyl(methyl)aminocarbonyl,
methyl substituted with carboxy, ethyl substituted with carboxy, n-propyl substituted with carboxy,
methyl substituted with trifluoromethylsulfonylamino,
methyl substituted with methylsulfonyl(methyl)aminocarbonyl, ethyl substituted with methylsulfonyl(methyl)aminocarbonyl,
methyl substituted with methylaminocarbonyl, ethyl substituted with methylaminocarbonyl (the methyl of the ethyl substituted with methylaminocarbonyl may be substituted with one group selected from the group consisting of tetrahydrofuranyl and pyrrolidinylcarbonyl), ethyl substituted with ethylaminocarbonyl (the ethyl of the ethylaminocarbonyl of the ethyl substituted with ethylaminocarbonyl is substituted with one group selected from the group consisting of hydroxy and methoxy), methyl substituted with n-propylaminocarbonyl, ethyl substituted with n-propylaminocarbonyl (the n-propyl of the ethyl substituted with n-propylaminocarbonyl is substituted with one group selected from the group consisting of hydroxy and methoxy), n-propyl substituted with n-propylaminocarbonyl,
ethyl substituted with dimethylaminocarbonyl, ethyl substituted with ethyl(methyl)aminocarbonyl (the ethyl of the ethyl(methyl)aminocarbonyl of the ethyl substituted with ethyl(methyl)aminocarbonyl is substituted with one hydroxy),
ethyl substituted with oxetanylaminocarbonyl,
ethyl substituted with azetidinylcarbonyl, ethyl substituted with azetidinylcarbonyl (the azetidinyl of the ethyl substituted with azetidinylcarbonyl is substituted with one hydroxy or one or two fluorine atoms), ethyl substituted with pyrrolidinylcarbonyl, ethyl substituted with piperidinylcarbonyl, ethyl substituted with morpholinylcarbonyl,
ethenyl substituted with carboxy,
ethenyl substituted with dimethylaminocarbonyl,
cyclopropyl substituted with carboxy, cyclohexyl substituted with carboxy,
cyclopropyl substituted with dimethylaminocarbonyl,
phenyl substituted with carboxy,
pyridyl substituted with carboxy,
pyrazolyl substituted with carboxy,
pyrazolyl substituted with carboxymethyl,
pyrazinyl substituted with carboxy,
2-oxodihydropyridinyl substituted with carboxymethyl,
methylaminocarbonyl substituted with carboxy (the methyl of the methylaminocarbonyl substituted with carboxy may be substituted with one benzyl), ethylaminocarbonyl substituted with carboxy (the methylene moiety at position α of the carboxy of the ethylaminocarbonyl substituted with carboxy may be replaced with cyclopentane-1,1-diyl), n-propylaminocarbonyl substituted with carboxy (the methylene moiety at position α of the carboxy of the n-propylaminocarbonyl substituted with carboxy may be replaced with propane-2,2-diyl), phenylmethylaminocarbonyl substituted with carboxy, methylaminocarbonyl substituted with the structure represented by formula [V-6] below:

[Formula 201]

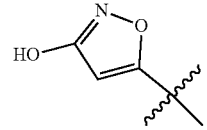

[V-6]

n-propyl(methyl)aminocarbonyl substituted with carboxy (the methylene moiety at position α of the carboxy of the n-propyl of the n-propyl(methyl)aminocarbonyl substituted with carboxy may be replaced with propane-2,2-diyl), pyrrolidinylcarbonyl substituted with carboxy (the pyrrolidinyl of the pyrrolidinylcarbonyl substituted with carboxy may be substituted with one fluorine atom), the structure represented by formula [XI-2] below, which is substituted with carboxy, the structure represented by formula [XI-3] below, which is substituted with carboxy,

[Formula 202]

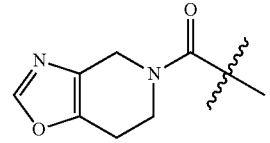

[XI-2]

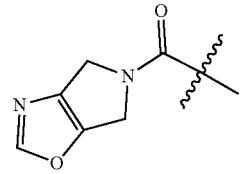

[XI-3]

n-butylsulfonyl substituted with carboxy (the methylene moiety at position α of the carboxy of the n-butylsulfonyl substituted with carboxy may be replaced with propane-2,2-diyl), n-propyl(methyl)aminosulfonyl substituted with carboxy (the methylene moiety at position α of the carboxy of the n-propyl of the n-propyl(methyl)aminosulfonyl substituted with carboxy may be replaced with propane-2,2-diyl), piperidinylsulfonyl substituted with carboxy, pyrrolidinylsulfonyl substituted with carboxy (the pyrrolidinyl of the pyrrolidinylsulfonyl substituted with carboxy is substituted with one fluorine atom), hydroxy,
methylsulfonyloxy,
methyl substituted with hydroxy, isopropyl substituted with hydroxy,
halomethyl substituted with hydroxy, haloethyl substituted with hydroxy,
ethylsulfonyl substituted with hydroxy, isobutyl substituted with hydroxy,
cyclobutyl substituted with hydroxy (the cyclobutyl of the cyclobutyl substituted with hydroxy may be substituted with one group selected from the group consisting of carboxy and dimethylamino), cyclopentyl substituted with hydroxy, or
azetidinyl substituted with hydroxy (the nitrogen atom of the azetidinyl substituted with hydroxy is substituted with one methylcarbonyl), piperidinyl substituted with hydroxy (the nitrogen atom of the piperidinyl substituted with hydroxy is substituted with one group selected from the group consisting of methylcarbonyl, methoxycarbonyl, or dimethylaminocarbonyl),
wherein $R^{61}$ and $R^{62}$ are each independently a hydrogen atom, a fluorine atom, methyl, or methylsulfonyl;
$W^4$ is methanediyl, ethane-1,2-diyl, or propane-1,3-diyl;
in formula [I-D'] above, another more preferred embodiment is such that
$R^1$ is a hydrogen atom;
$R^2$ is a hydrogen atom;
$R^{54}$ is
  carboxy,
  carbamoyl,
  mono$C_{1-3}$alkylaminocarbonyl (the $C_{1-3}$alkyl of the mono$C_{1-3}$alkylaminocarbonyl may be substituted with one hydroxy),
  $C_1$alkylaminosulfonyl,
  di($C_1$alkyl)aminosulfonyl (one $C_1$alkyl of the di($C_1$alkyl)aminosulfonyl is substituted with one phenyl, wherein the phenyl is substituted with one $C_1$alkylaminosulfonyl),
  phenylaminosulfonyl (the phenyl of the phenylaminosulfonyl is substituted with one fluorine atom),
  $C_3$alkylsulfonylamino,
  $C_1$alkylsulfonyl($C_1$alkyl)aminocarbonyl,
  $C_{1-3}$ alkyl substituted with carboxy,
  $C_1$alkyl substituted with trifluoromethylsulfonylamino,
  $C_2$alkyl substituted with methylsulfonyl(methyl)aminocarbonyl,
  $C_{1-2}$ alkyl substituted with mono$C_{1-3}$alkylaminocarbonyl (the $C_{1-3}$alkyl of the mono$C_{1-3}$alkylaminocarbonyl of the $C_{1-2}$ alkyl substituted with mono$C_{1-3}$alkylaminocarbonyl may be substituted with one group selected from the group consisting of hydroxy, $C_1$alkoxy, 5-membered saturated oxygen-containing heterocyclyl, di($C_1$alkyl)amino, and 5-membered saturated nitrogen-containing heterocyclylcarbonyl),
  $C_{1-2}$ alkyl substituted with di($C_1$alkyl)aminocarbonyl,
  $C_2$alkyl substituted with 4-membered saturated oxygen-containing heterocyclylaminocarbonyl,
  $C_2$alkyl substituted with 4- to 6-membered saturated nitrogen-containing heterocyclylcarbonyl (the 4- to 6-membered saturated nitrogen-containing heterocyclyl of the 4- to 6-membered saturated nitrogen-containing heterocyclylcarbonyl may be substituted with one or two groups selected from the group consisting of hydroxy and a fluorine atom),
  $C_2$alkenyl substituted with carboxy,
  $C_2$alkenyl substituted with di($C_1$alkyl)aminocarbonyl,
  $C_{3-6}$ cycloalkyl substituted with carboxy,
  $C_3$cycloalkyl substituted with di($C_1$alkyl)aminocarbonyl,
  phenyl substituted with carboxy,
  pyridyl substituted with carboxy,
  pyrazolyl substituted with carboxy,
  pyrazolyl substituted with carboxymethyl,
  pyrazinyl substituted with carboxy,
  2-oxodihydropyridinyl substituted with carboxymethyl,
  $C_{2-3}$ alkylaminocarbonyl substituted with carboxy (when position α of the carboxy of the $C_2$-3alkylaminocarbonyl substituted with carboxy is a methylene moiety, the methylene moiety may be replaced with propane-2,2-diyl or cyclopentane-1,1-diyl),
  phenyl$C_1$alkylaminocarbonyl substituted with carboxy,
  $C_1$alkylaminocarbonyl substituted with the structure represented by formula [V-6] below:

[Formula 203]

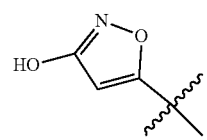

[V-6]

5-membered saturated nitrogen-containing heterocyclylcarbonyl substituted with carboxy (the 5-membered saturated nitrogen-containing heterocyclyl of the 5-membered saturated nitrogen-containing heterocyclylcarbonyl is substituted with one fluorine atom),
  the structure represented by formula [XI-2], which is substituted with carboxy,
  the structure represented by formula [XI-3], which is substituted with carboxy:

[Formula 204]

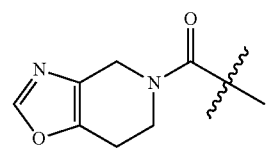

[XI-2]

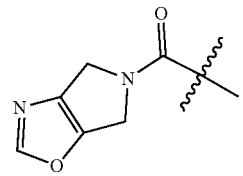

[XI-3]

$C_4$alkylsulfonyl substituted with carboxy (when position α of the carboxy of the $C_4$alkylsulfonyl substituted with carboxy is a methylene moiety, the methylene moiety is replaced with propane-2,2-diyl),
  di($C_{1-3}$alkyl)aminosulfonyl substituted with carboxy (when position α of the carboxy of the di($C_{1-3}$alkyl)aminosulfonyl substituted with carboxy is a methylene moiety, the methylene moiety may be replaced with propane-2,2-diyl),
  5- or 6-membered saturated nitrogen-containing heterocyclylsulfonyl substituted with carboxy (the 5- or 6-membered saturated nitrogen-containing heterocyclyl of the 5- or 6-membered saturated nitrogen-containing heterocyclylsulfonyl substituted with carboxy may be substituted with one fluorine atom),
hydroxy,
$C_1$sulfonyloxy,
$C_{1-3}$alkyl substituted with hydroxy,
halo-$C_{2-3}$alkyl substituted with hydroxy,
$C_{2-4}$alkylsulfonyl substituted with hydroxy,
$C_{4-5}$cycloalkyl substituted with hydroxy (the $C_{4-5}$cycloalkyl of the $C_{4-5}$cycloalkyl substituted with hydroxy may be substituted with one group selected from the group consisting of carboxy and di($C_1$alkyl)aminocarbonyl), or
4- to 6-membered saturated nitrogen-containing heterocyclyl substituted with hydroxy (the nitrogen atom of the 4- to 6-membered saturated nitrogen-containing heterocyclyl substituted with hydroxy may be substituted with one group selected from the group consisting of $C_1$alkylcarbonyl, $C_1$alkoxycarbonyl, and di($C_1$alkyl)aminocarbonyl),
wherein $R^{61}$ and $R^{62}$ are each independently a hydrogen atom, a fluorine atom, methyl, or methylsulfonyl;
$W^4$ is $C_{1-3}$ alkanediyl;
wherein an even more preferred embodiment is such that
$R^1$ is a hydrogen atom;
$R^2$ is a hydrogen atom;
$R^{54}$ is
  carboxy,
  carbamoyl,
  methylaminocarbonyl, ethylaminocarbonyl (the ethyl of the ethylaminocarbonyl is substituted with one hydroxy), n-propylaminocarbonyl,
  methylaminosulfonyl,
  dimethylaminosulfonyl (one methyl of the dimethylaminosulfonyl is substituted with one phenyl, wherein the phenyl is substituted with one methylaminosulfonyl),
  phenylaminosulfonyl (the phenyl of the phenylaminosulfonyl is substituted with one fluorine atom),
  isopropylsulfonylamino,
  methylsulfonyl(methyl)aminocarbonyl,
  methyl substituted with carboxycarboxy, ethyl substituted with carboxy, n-propyl substituted with carboxy,
  methyl substituted with trifluoromethylsulfonylamino,
  ethyl substituted with methylsulfonyl(methyl)aminocarbonyl,
  methyl substituted with methylaminocarbonyl, methyl substituted with propylaminocarbonyl, ethyl substituted with methylaminocarbonyl (the methyl of the ethyl substituted with methylaminocarbonyl may be substituted with one group selected from the group consisting of tetrahydrofuranyl and pyrrolidinylcarbonyl), ethyl substituted with ethylaminocarbonyl (the ethyl of the ethylaminocarbonyl of the ethyl substituted with ethylaminocarbonyl is substituted with one group selected from the group consisting of hydroxy, methoxy, and dimethylamino), ethyl substituted with n-propylaminocarbonyl (the n-propyl of the ethyl substituted with n-propylaminocarbonyl may be substituted with one group selected from the group consisting of hydroxy and methoxy),
  methyl substituted with dimethylaminocarbonyl, ethyl substituted with dimethylaminocarbonyl,
  ethyl substituted with oxetanylaminocarbonyl,
  ethyl substituted with azetidinylcarboxy (the azetidinyl of the ethyl substituted with azetidinylcarboxy may be substituted with one hydroxy or one or two fluorine atoms), ethyl substituted with pyrrolidinylcarboxy,
  ethyl substituted with piperidinylcarboxy, ethyl substituted with morpholinylcarboxy,
  ethenyl substituted with carboxy,
  ethenyl substituted with dimethylaminocarbonyl,
  cyclopropyl substituted with carboxy, cyclohexyl substituted with carboxy,
  cyclopropyl substituted with dimethylaminocarbonyl,
  phenyl substituted with carboxy,
  pyridyl substituted with carboxy,
  pyrazolyl substituted with carboxy,
  pyrazolyl substituted with carboxymethyl,
  pyrazinyl substituted with carboxy,
  2-oxodihydropyridinyl substituted with carboxymethyl,
  ethylaminocarbonyl substituted with carboxy (the methylene moiety at position α of the carboxy of the ethylaminocarbonyl substituted with carboxy is replaced with cyclopentane-1,1-diyl), n-propylaminocarbonyl substituted with carboxy (the methylene moiety at position α of the carboxy of the n-propylaminocarbonyl substituted with carboxy is replaced with propane-2,2-diyl),
  2-carboxyphenylmethylaminocarbonyl, 3-carboxyphenylmethylaminocarbonyl, 4-carboxyphenylmethylaminocarbonyl,
  methylaminocarbonyl substituted with the structure represented by formula [V-6] below:

[Formula 205]

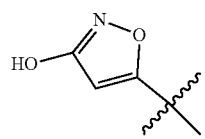

[V-6]

pyrrolidinylcarbonyl substituted with carboxy (the pyrrolidinyl of the pyrrolidinylcarbonyl substituted with carboxy is substituted with one fluorine atom),
  the structure represented by formula [XI-2] below, which is substituted with carboxy,
  the structure represented by formula [XI-3] below, which is substituted with carboxy:

[Formula 206]

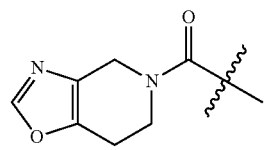

[XI-2]

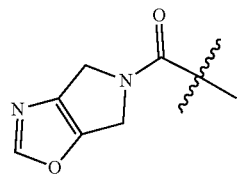

[XI-3]

n-butylsulfonyl substituted with carboxy (the methylene moiety at position α of the carboxy of the n-butylsulfonyl substituted with carboxy is replaced with propane-2,2-diyl), n-propyl(methyl)aminosulfonyl substituted with carboxy (the methylene moiety at position α of the carboxy of the n-propyl(methyl)aminosulfonyl substituted with carboxy may be replaced with propane-2,2-diyl),
piperidinylsulfonyl substituted with carboxy, pyrrolidinylsulfonyl substituted with carboxy (the pyrrolidinyl of the pyrrolidinylsulfonyl substituted with carboxy is substituted with one fluorine atom),
hydroxy,
methylsulfonyloxy,
methyl substituted with hydroxy, isopropyl substituted with hydroxy,
haloethyl substituted with hydroxy, halo-n-propyl substituted with hydroxy,
ethylsulfonyl substituted with hydroxy, isobutylsulfonyl substituted with hydroxy,
cyclobutyl substituted with hydroxy (the cyclobutyl of the cyclobutyl substituted with hydroxy may be substituted with one group selected from the group consisting of carboxy and dimethylaminocarbonyl), cyclopentyl substituted with hydroxy, or
azetidinyl substituted with hydroxy (the nitrogen atom of the azetidinyl substituted with hydroxy is substituted with one methylcarbonyl) or piperidinyl substituted with hydroxy (the nitrogen atom of the piperidinyl substituted with hydroxy is substituted with one group selected from the group consisting of methylcarbonyl, methoxycarbonyl, and dimethylaminocarbonyl),
wherein $R^{61}$ and $R^{62}$ are each independently a hydrogen atom, a fluorine atom, methyl, or methylsulfonyl;
$W^4$ is methanediyl, ethane-1,2-diyl, or propane-1,3-diyl;
wherein a particularly preferred embodiment is such that the compound represented by formula [I-D] is any of the following:

[Formula 207]

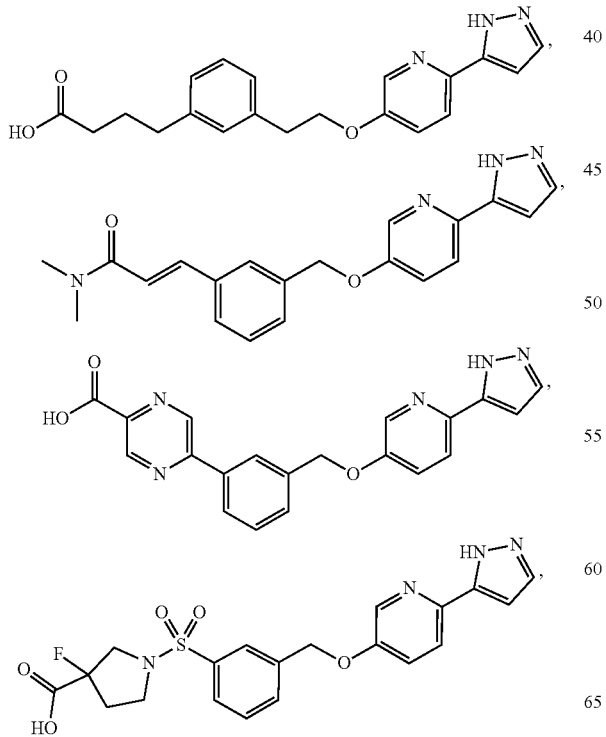

[Formula 208]

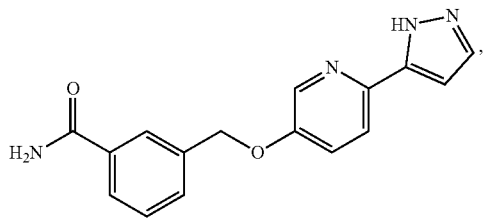

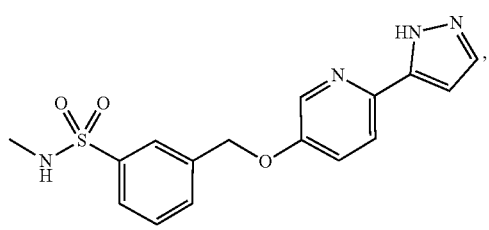

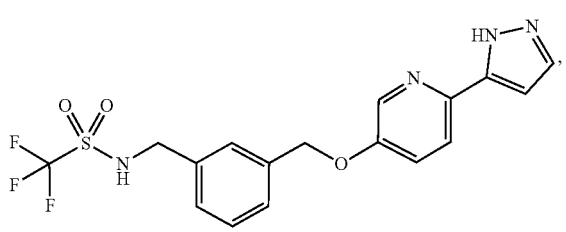

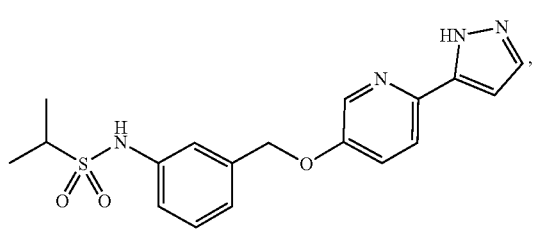

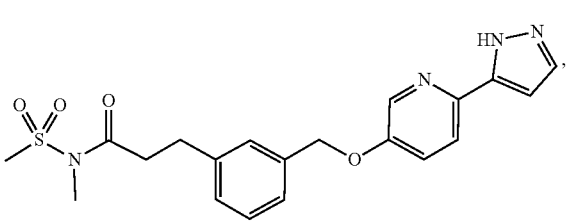

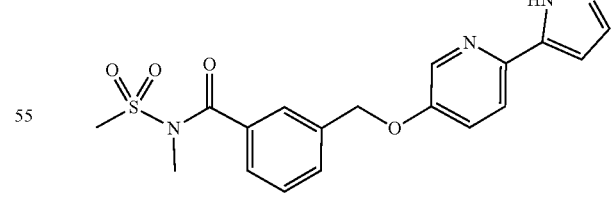

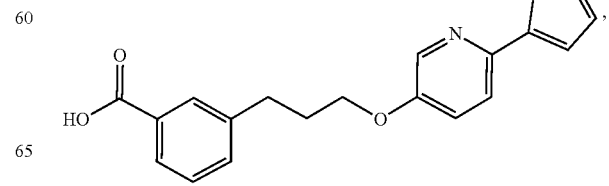

-continued
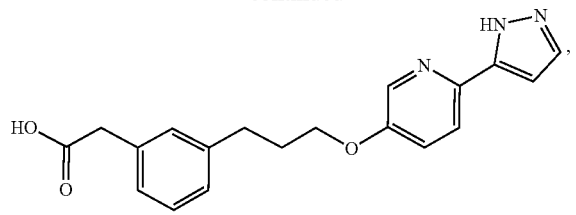
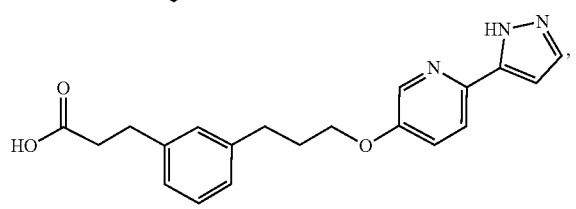
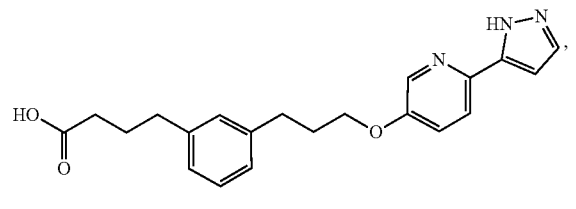
[Formula 209]
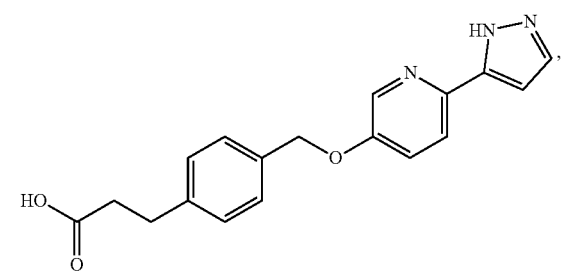
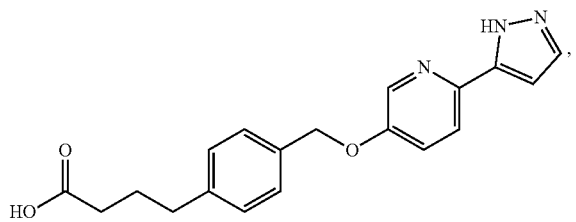
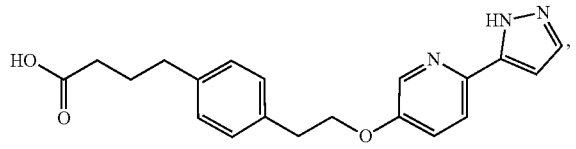
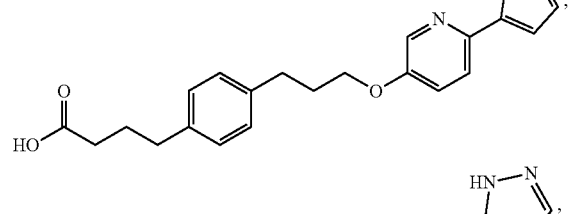
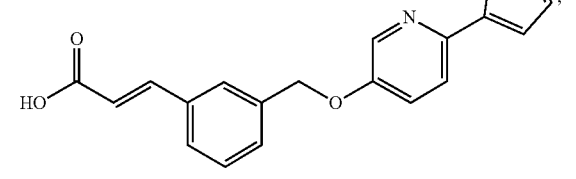
-continued
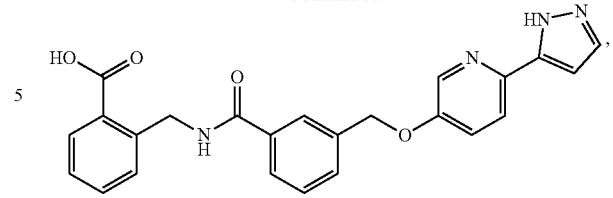
[Formula 210]
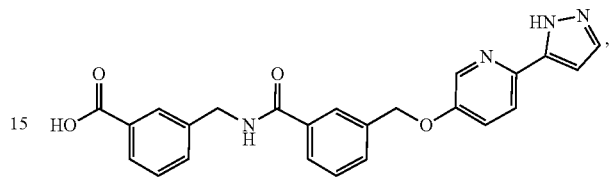
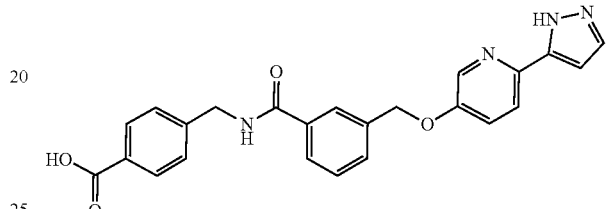
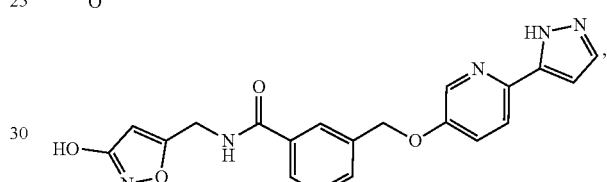
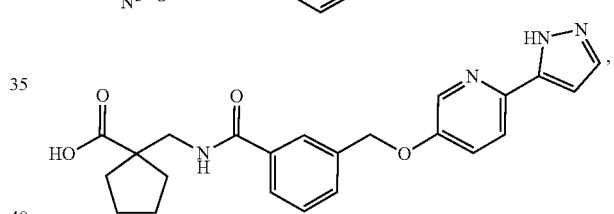
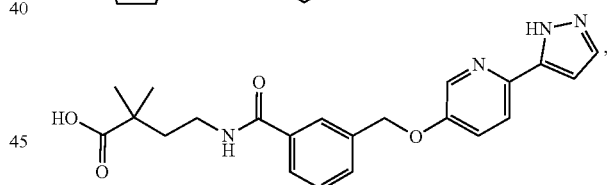
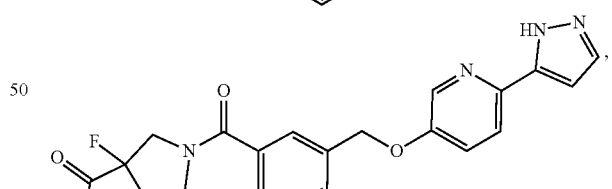
[Formula 211]
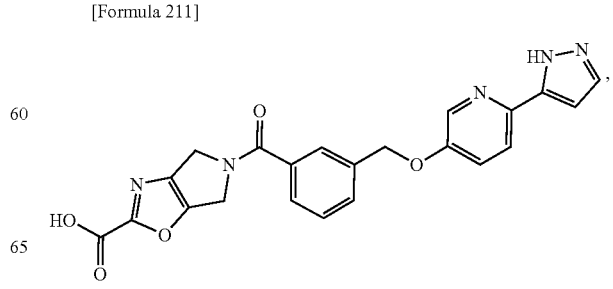

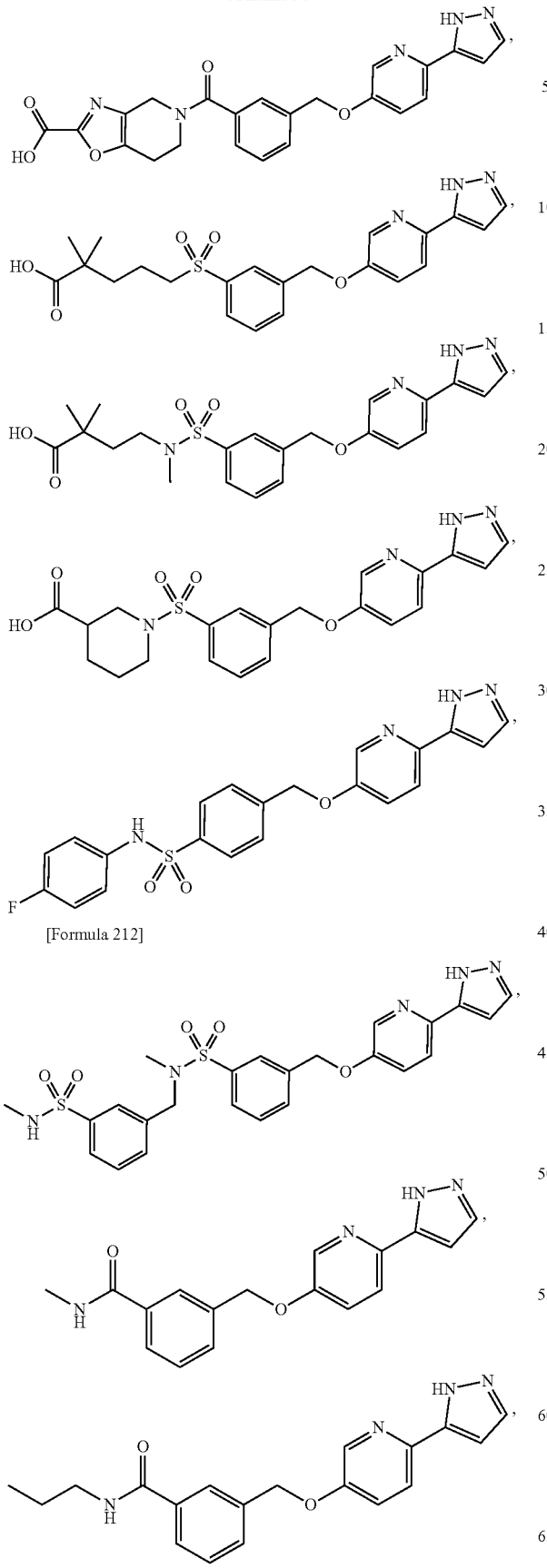
[Formula 212]
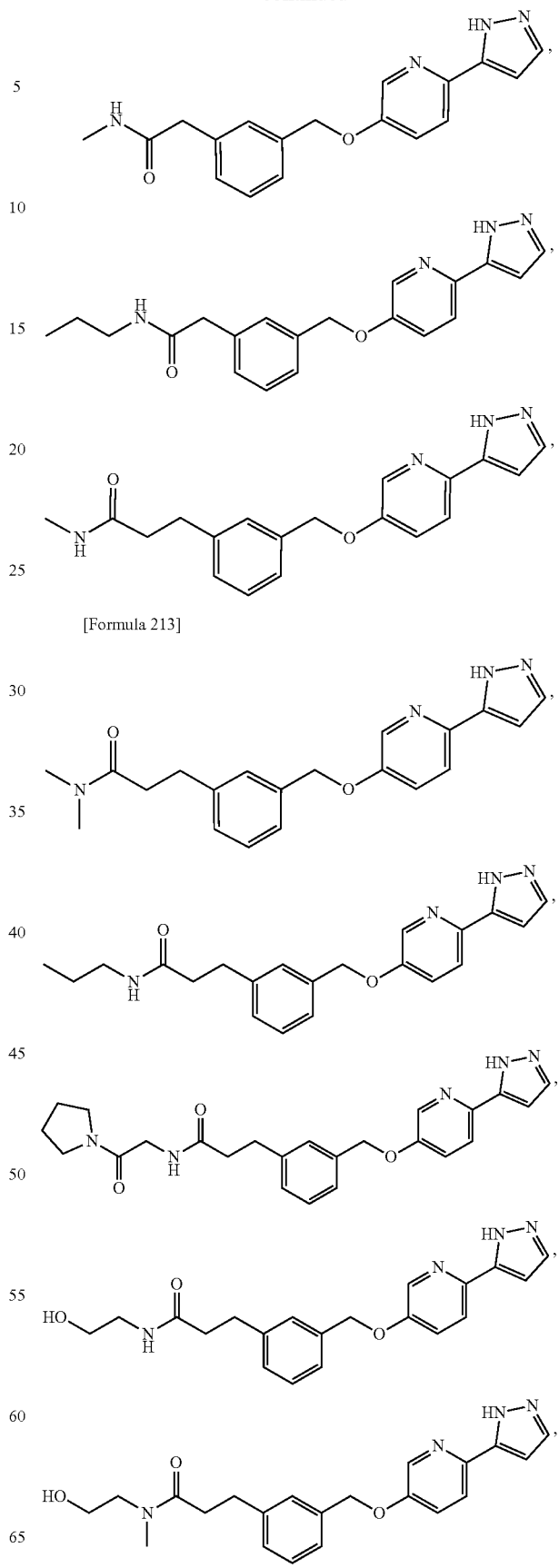
[Formula 213]

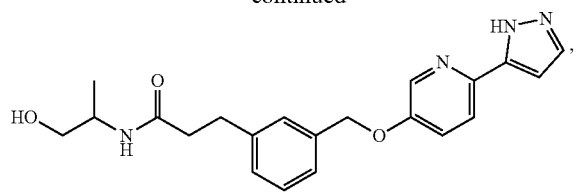
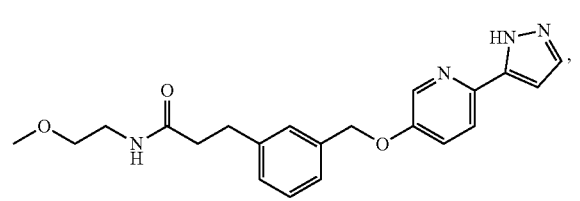
[Formula 214]
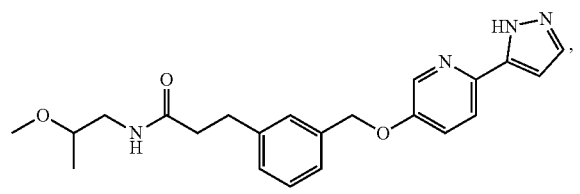
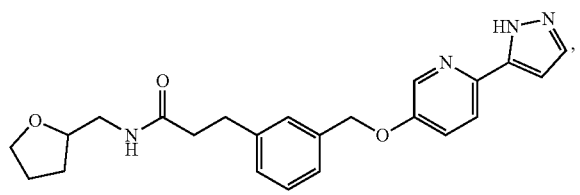
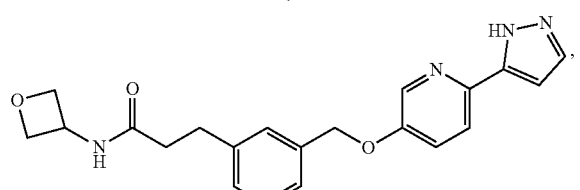
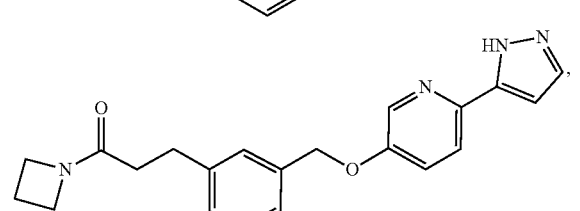
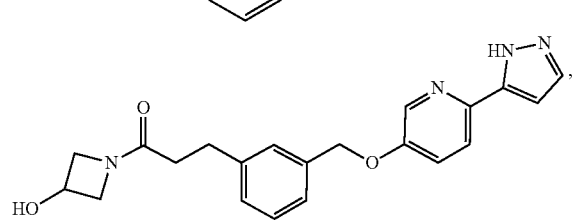
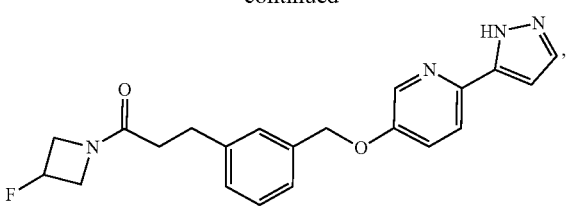
[Formula 215]
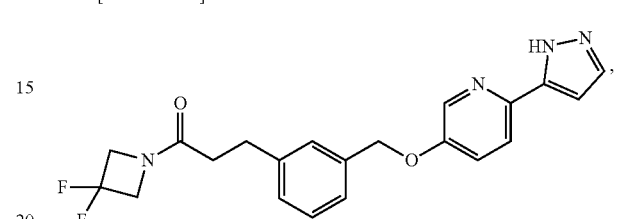
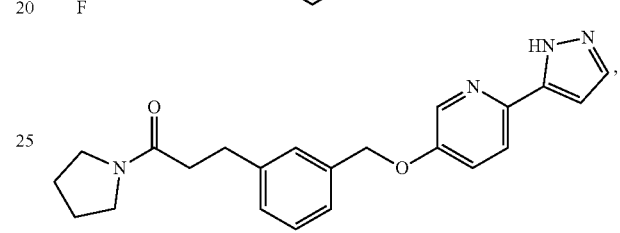
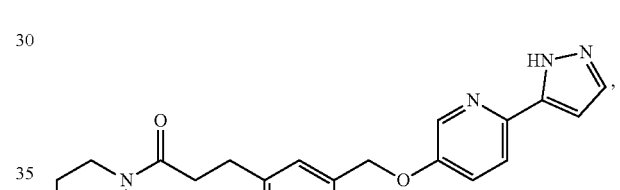
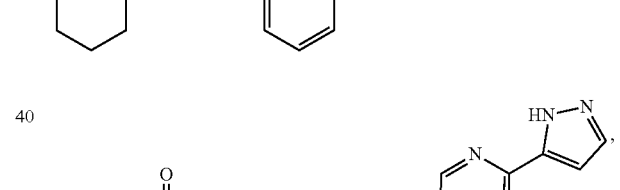
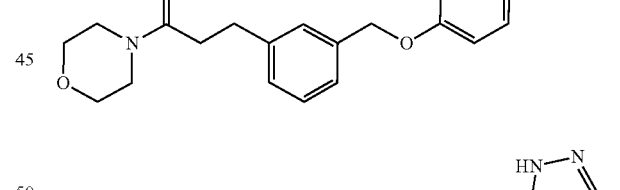
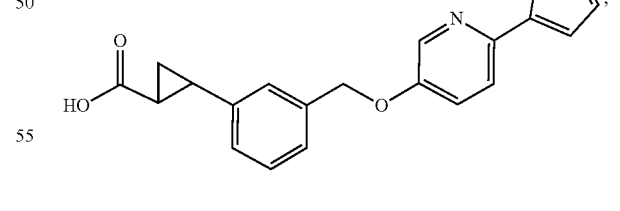
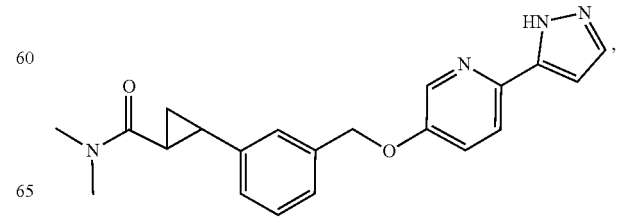

-continued
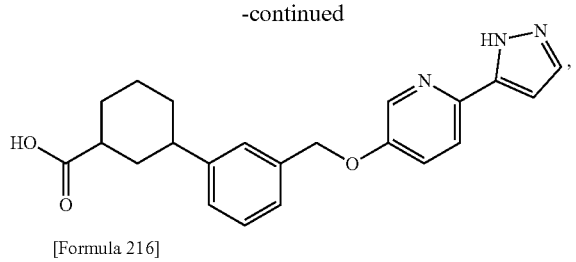
[Formula 216]
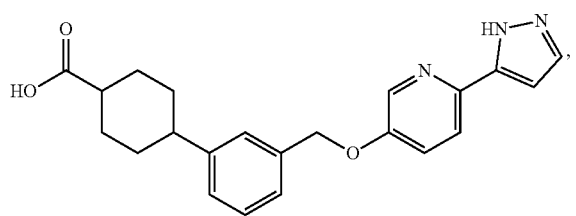
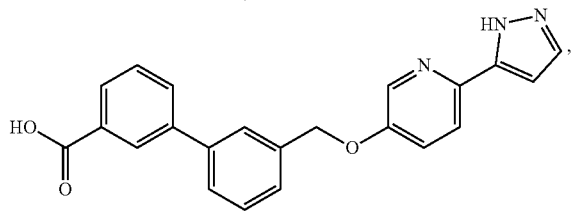
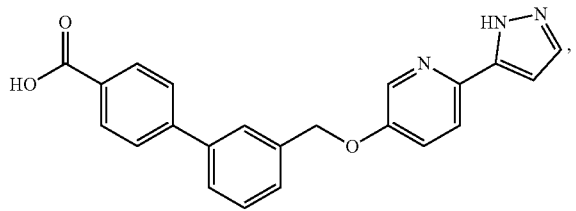
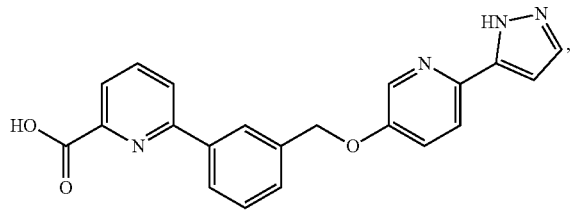
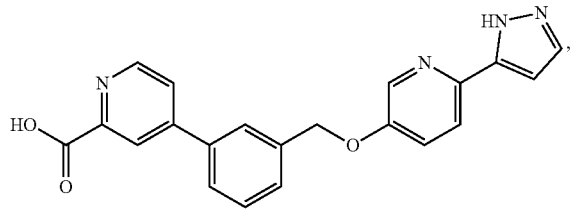
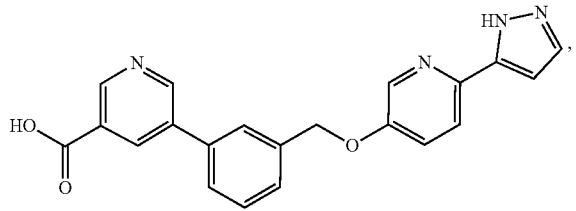
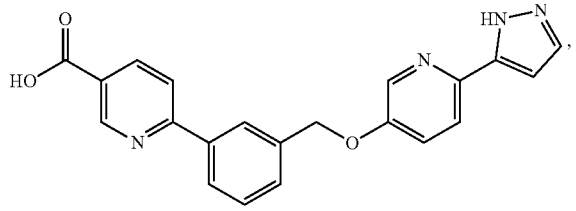
-continued
[Formula 217]
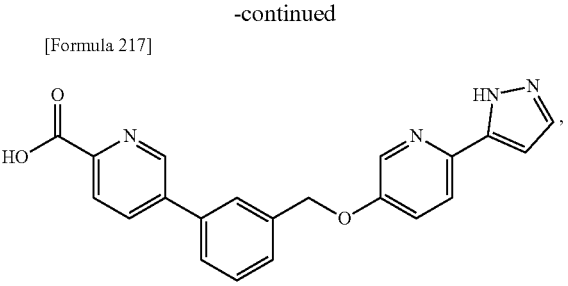
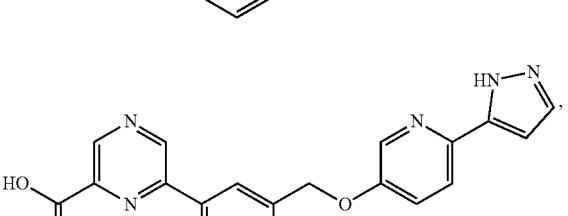
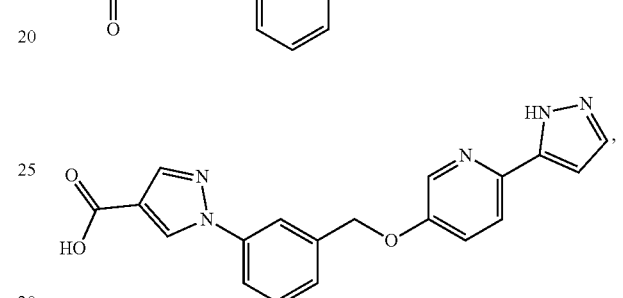
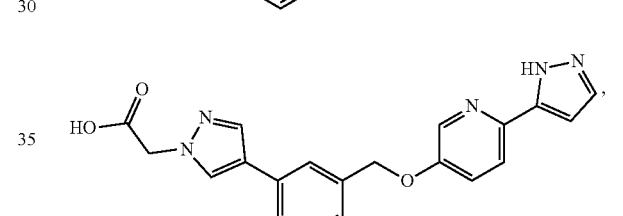
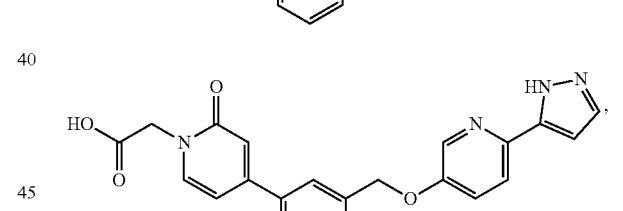
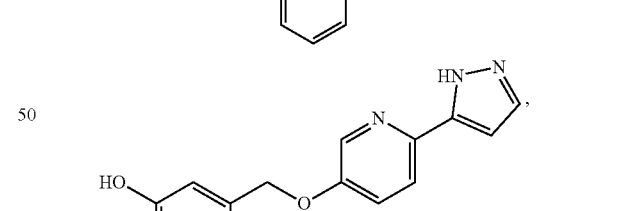
[Formula 218]
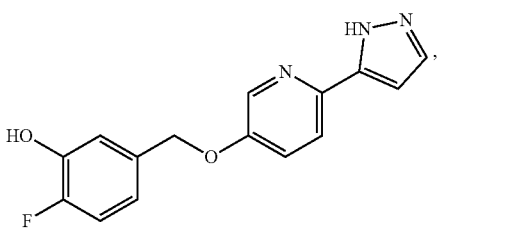

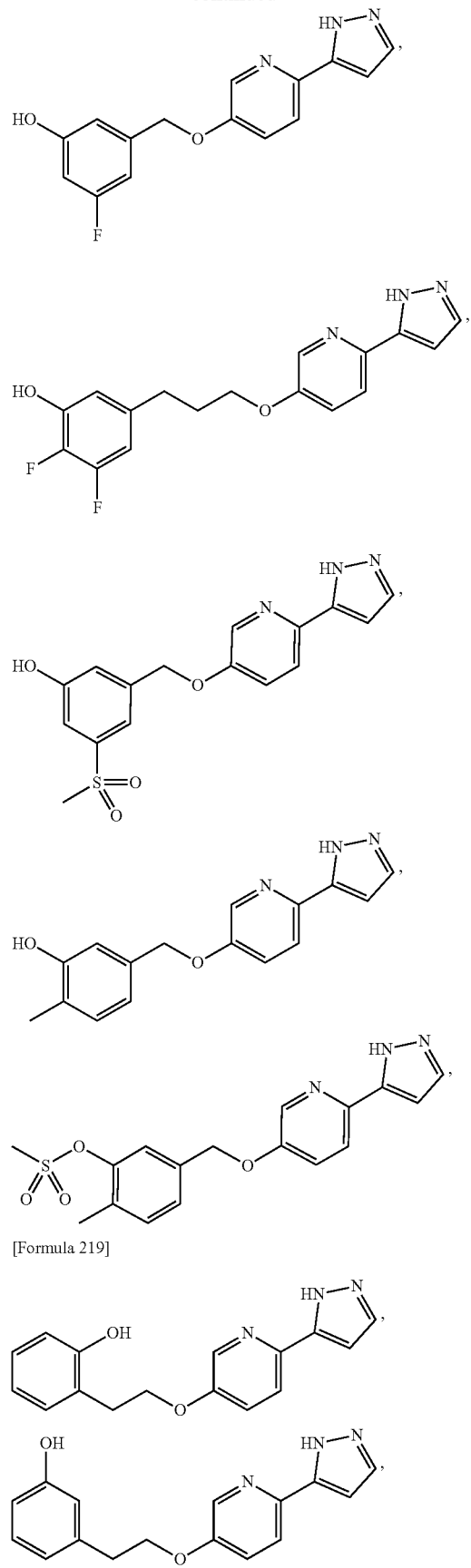
[Formula 219]
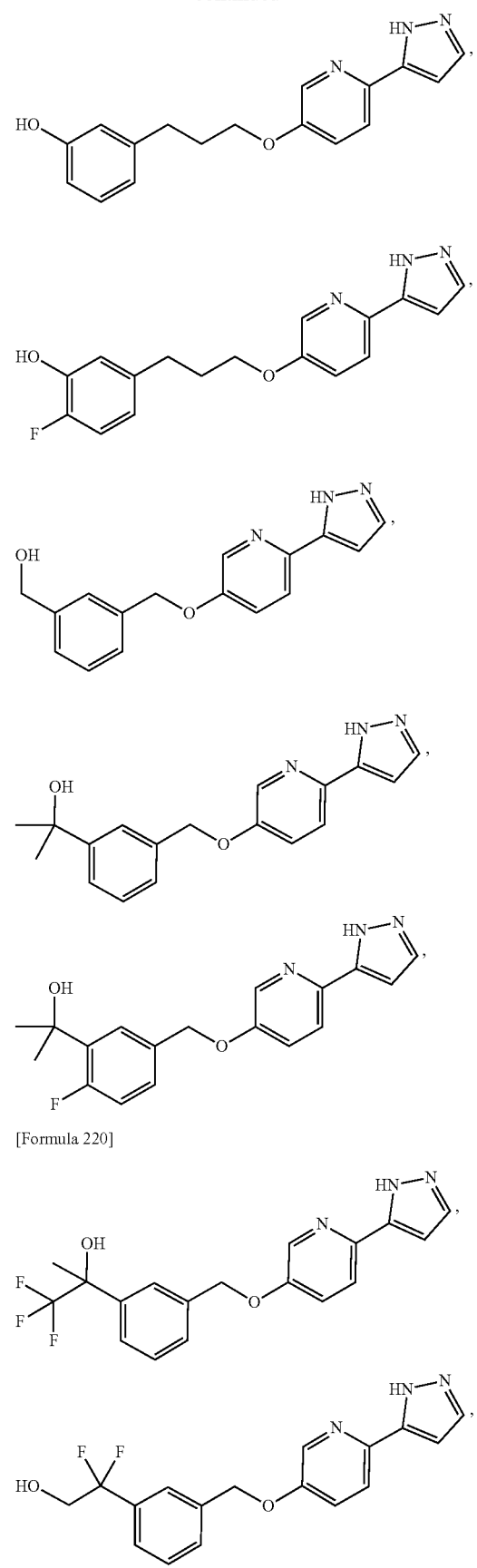
[Formula 220]

The "preferred embodiments" described above include compounds or pharmaceutically acceptable salts thereof below:

[Formula 221]

[Formula 222]

[Formula 225]

[VI-4]

[VI-7]

Another preferred embodiment of compounds of the present invention is a compound represented by formula [1-E] below or a pharmaceutically acceptable salt thereof:

[Formula 223]

[I-E]

wherein preferred embodiments of $R^1$, $R^2$, and $R^5$ are as described above.

In formula [I-E] above, one more preferred embodiment is such that $R^1$ is a hydrogen atom;
$R^2$ is a hydrogen atom;

(B)
when $R^5$ is the structure represented by formula [IV-2] below:

[Formula 224]

[IV-2]

L is a structure represented by formula [VI-4] or formula [VI-7] below:

wherein
ring D is (ii) 6-membered saturated oxygen-containing hetero ring;
$R^{52}$ is carboxy;
Y is the formula —$CH_2$—, or the formula —O—;
$W^2$ is $C_{7-8}$ alkanediyl,
wherein one of the carbon atoms that constitute $C_{7-8}$ alkanediyl represented by $W^2$ may be replaced with an oxygen atom;

(C)
when $R^5$ is the structure represented by formula [IV-3] below:

[Formula 226]

[IV-3]

ring B is the structure represented by formula [VIII-7] below:

[Formula 227]

[VIII-7]

$R^{53}$ is carboxy;
$W^3$ is $C_6$alkanediyl;

(D)
when $R^5$ is the structure represented by formula [IV-4] below:

[Formula 228]

[IV-4]

ring C is
(c) phenyl,
(d) pyridyl,
(g) tetrahydronaphthyl, or
(h) chromanyl;
wherein
(c)
when ring C is phenyl,
$R^{54}$ is
(xxi) $C_3$cycloalkyl substituted with carboxy, or
(xxxxvii) 5- or 6-membered saturated nitrogen-containing heterocyclylsulfonyl substituted with carboxy (the 5- or 6-membered saturated nitrogen-containing heterocyclyl of the 5- or 6-membered saturated nitrogen-containing heterocyclylsulfonyl substituted with carboxy may be substituted with one fluorine atom);
$R^{61}$ is a hydrogen atom;
$R^{62}$ is a hydrogen atom;
$W^4$ is $C_1$alkanediyl;
(d)
when ring C is pyridyl,
$R^{54}$ is (iv) $C_2$alkoxy substituted with carboxy (when position α of the carboxy of the $C_2$alkoxy substituted with carboxy is a methylene moiety, the methylene moiety is replaced with propane-2,2-diyl);
$R^{61}$ is a hydrogen atom;
$R^{62}$ is a hydrogen atom;
$W^4$ is $C_1$alkanediyl;
(g)
when ring C is tetrahydronaphthyl,
$R^{54}$ is carboxy;
$R^{61}$ is a hydrogen atom;
$R^{62}$ is a hydrogen atom;
$W^4$ is $C_1$alkanediyl;
(h)
when ring C is chromanyl,
$R^{54}$ is carboxy;
$R^{61}$ is a hydrogen atom;
$R^{62}$ is a hydrogen atom;
$W^4$ is $C_1$alkanediyl;
wherein in formula [1-E] above, an even more preferred embodiment is such that
$R^1$ is a hydrogen atom;
$R^2$ is a hydrogen atom;
(B)
when $R^5$ is the structure represented by formula [IV-2] below:

[Formula 229]

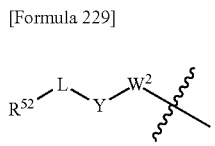

[IV-2]

L is a structure represented by formula [VI-4] or formula [VI-10] below:

[Formula 230]

[VI-4]

-continued

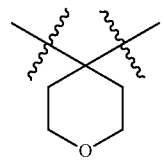

[VI-10]

$R^{52}$ is carboxy;
Y is the formula —$CH_2$— or the formula —O—;
$W^2$ is heptane-1,7-diyl, octane-1,8-diyl, or the formula —O—$(CH_2)_6$—;
(C)
when $R^5$ is the structure represented by formula [IV-3] below:

[Formula 231]

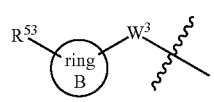

[IV-3]

ring B is the structure represented by formula [VIII-7] below:

[Formula 232]

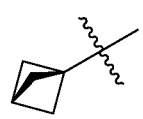

[VIII-7]

$R^{53}$ is carboxy;
$W^3$ is hexane-1,6-diyl;
(D)
when $R^5$ is the structure represented by formula [IV-4] below:

[Formula 233]

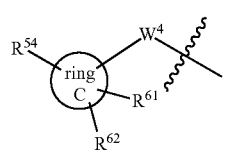

[IV-4]

ring C is
(c) phenyl,
(d) pyridyl,
(g) tetrahydronaphthyl, or
(h) chromanyl,
(c)
when ring C is phenyl,
$R^{54}$ is
(xxi) cyclopropyl substituted with carboxy, or
(xxxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom), piperidinylsulfonyl substituted with carboxy, pyrrolidinylsulfonyl substituted with carboxy (the pyrrolidinyl of the pyrrolidinylsulfonyl substituted with carboxy is substituted with one fluorine atom);
$R^{61}$ is a hydrogen atom;
$R^{62}$ is a hydrogen atom;
$W^4$ is methanediyl;
(d)
when ring C is pyridyl,
ring C is pyridin-4-yl;
$R^{54}$ is (iv) ethoxy substituted with carboxy (the methylene moiety at position α of the carboxy of the ethoxy substituted with carboxy is replaced with propane-2,2-diyl);
$R^{61}$ is a hydrogen atom;
$R^{62}$ is a hydrogen atom;
$W^4$ is methanediyl;
(g)
when ring C is tetrahydronaphthyl,
ring C is a structure represented by formula [XII-1] or formula [XII-2] below:

[Formula 234]

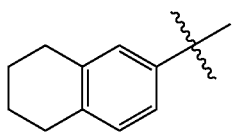
[XII-1]

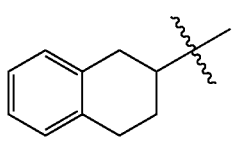
[XII-2]

$R^{54}$ is carboxy;
$R^{61}$ is a hydrogen atom;
$R^{62}$ is a hydrogen atom;
$W^4$ is methanediyl;
(h)
when ring C is chromanyl,
ring C is a structure represented by formula [XIII-1] or formula [XIII-2] below:

[Formula 235]

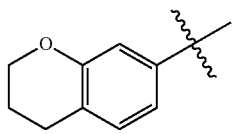
[XIII-1]

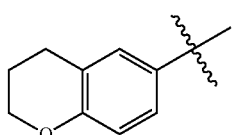
[XIII-2]

$R^{54}$ is carboxy;
$R^{61}$ is a hydrogen atom;
$R^{62}$ is a hydrogen atom;
$W^4$ is methanediyl.

In formula [I-E] above, one particularly preferred embodiment is such that the compound represented by formula [I-E] is any of the following:

[Formula 236]

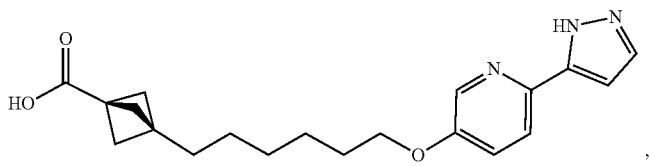
,

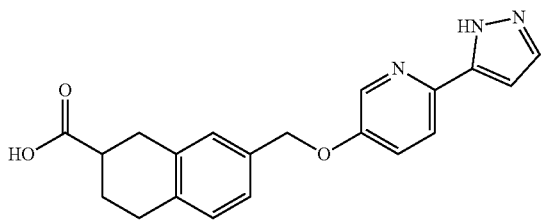
,

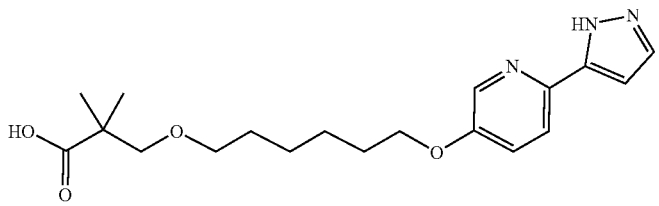
,

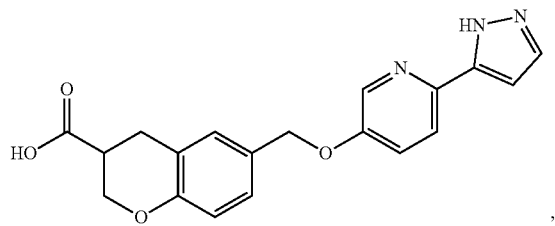
,
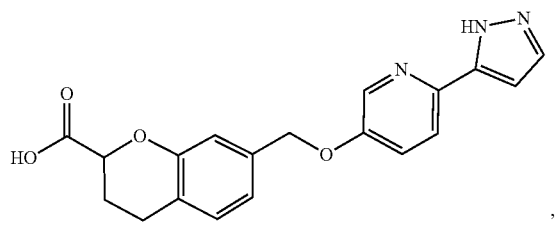
,
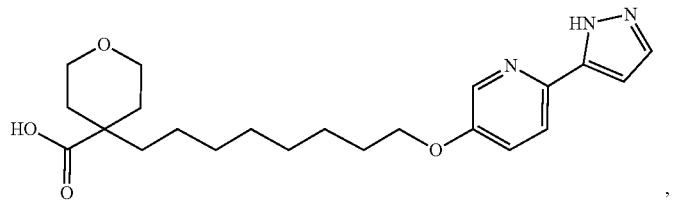
,
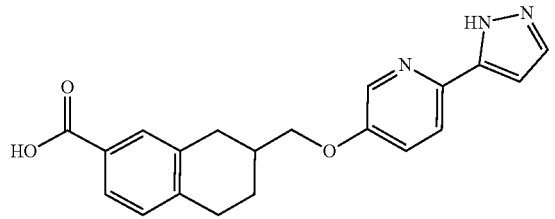
,
[Formula 237]
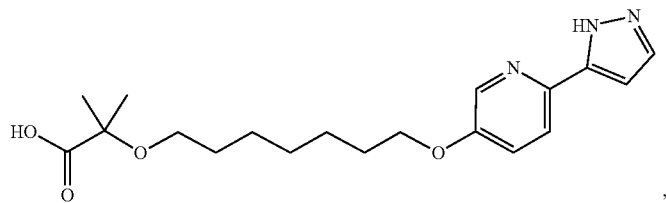
,
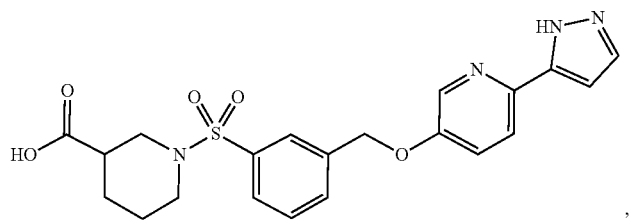
,
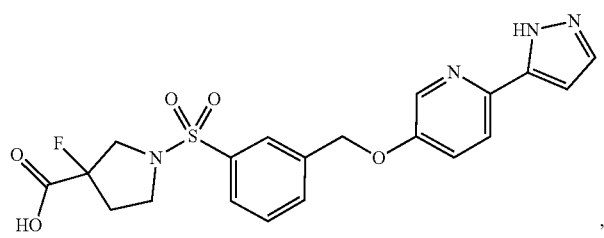
,

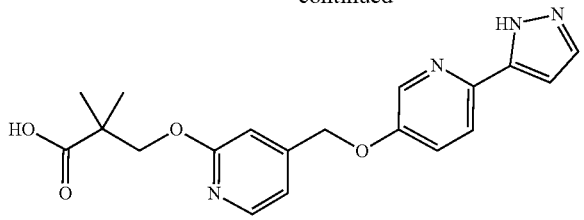

,

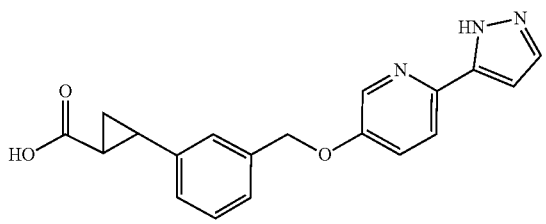

,

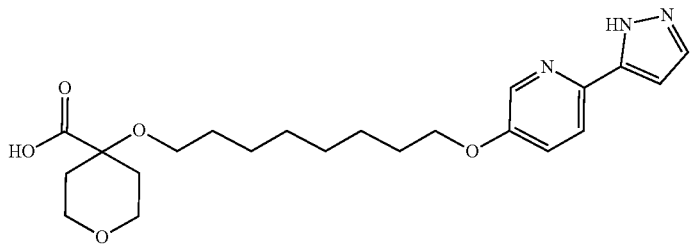

.

In formula [I-E] above, another particularly preferred embodiment is such that the compound represented by formula [I-E] is as follows:

[Formula 238]

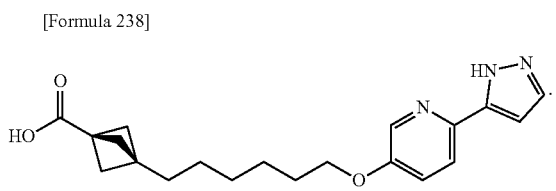

In formula [I-E] above, another particularly preferred embodiment is such that the compound represented by formula [I-E] is as follows:

[Formula 239]

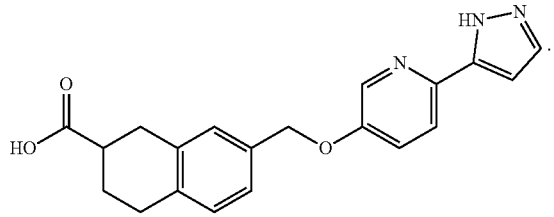

In formula [I-E] above, another particularly preferred embodiment is such that the compound represented by formula [I-E] is as follows:

[Formula 240]

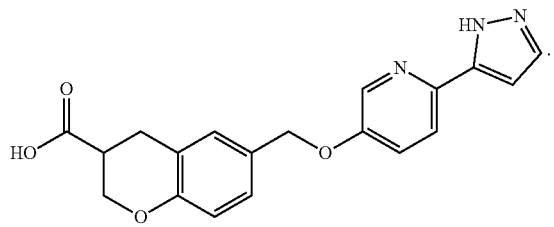

In formula [I-E] above, another particularly preferred embodiment is such that the compound represented by formula [I-E] is as follows:

[Formula 241]

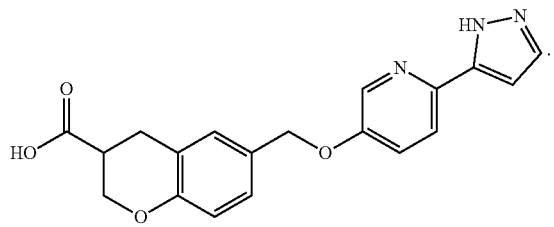

In formula [I-E] above, another particularly preferred embodiment is such that the compound represented by formula [I-E] is as follows:

[Formula 242]

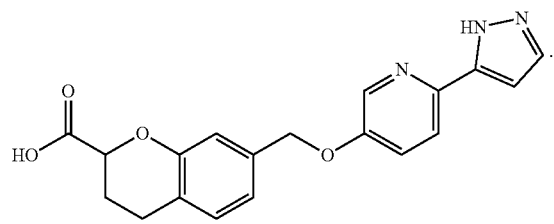

In formula [I-E] above, another particularly preferred embodiment is such that the compound represented by formula [I-E] is as follows:

[Formula 243]

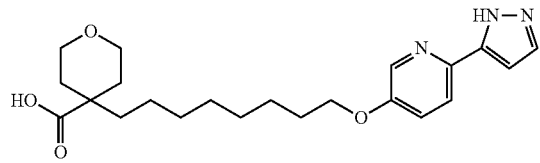

In formula [I-E] above, another particularly preferred embodiment is such that the compound represented by formula [I-E] is as follows:

[Formula 244]

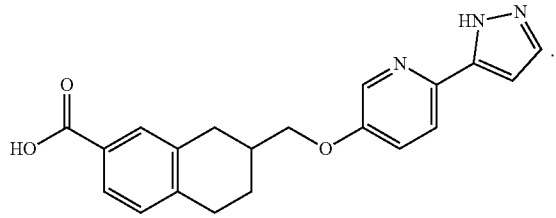

In formula [I-E] above, another particularly preferred embodiment is such that the compound represented by formula [I-E] is as follows:

[Formula 245]

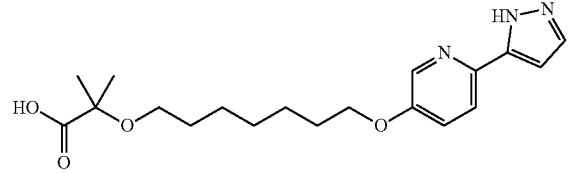

In formula [I-E] above, another particularly preferred embodiment is such that the compound represented by formula [I-E] is as follows:

[Formula 246]

In formula [I-E] above, another particularly preferred embodiment is such that the compound represented by formula [I-E] is as follows:

[Formula 247]

In formula [I-E] above, another particularly preferred embodiment is such that the compound represented by formula [I-E] is as follows:

[Formula 248]

In formula [I-E] above, another particularly preferred embodiment is such that the compound represented by formula [I-E] is as follows:

[Formula 249]

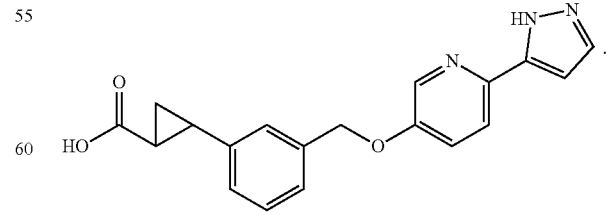

In formula [I-E] above, another particularly preferred embodiment is such that the compound represented by formula [I-E] is as follows:

[Formula 250]

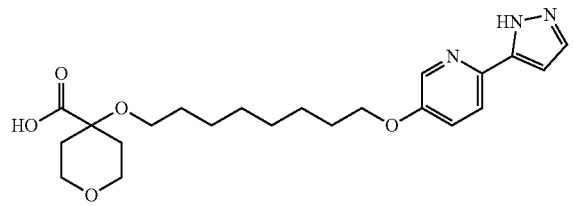

Other preferred embodiments of the compound represented by formula [I-D'], among compounds of the present invention, or a pharmaceutically acceptable salt thereof are (101) to (106) below.

(101) A compound, wherein formula [I] is formula [I-D'] below:

[Formula 251]

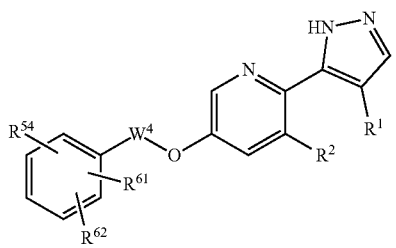

[I-D']

wherein
$R^1$ is a hydrogen atom;
$R^2$ is a hydrogen atom;
$R^{54}$ is $C_{3-6}$ cycloalkyl substituted with carboxy,
wherein $R^{61}$ and $R^{62}$ are each independently a hydrogen atom, a fluorine atom, methyl, or methylsulfonyl;
$W^4$ is $C_{1-3}$alkanediyl.

(102) A compound or a pharmaceutically acceptable salt thereof, wherein formula [I] is formula [I-D'] below:

[Formula 252]

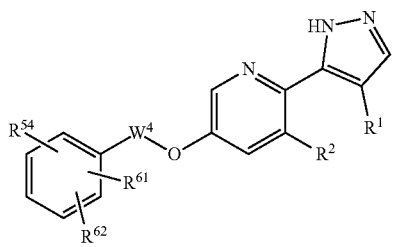

[I-D']

wherein
$R^1$ is a hydrogen atom;
$R^2$ is a hydrogen atom;
$R^{54}$ is cyclopropyl substituted with carboxy,
wherein
$R^{61}$ is a fluorine atom that substitutes the benzene ring at ortho position with respect to —$W^4$—,
$R^{62}$ is a hydrogen atom;
$W^4$ is methanediyl or ethane-1,2-diyl.

(103) A compound or a pharmaceutically acceptable salt thereof, wherein formula [I] is formula [I-D'] below:

[Formula 253]

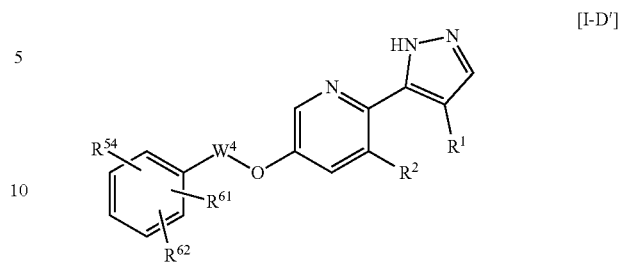

[I-D']

wherein
$R^1$ is a hydrogen atom;
$R^2$ is a hydrogen atom;
$R^{54}$ is cyclopropyl substituted with carboxy, which substitutes the benzene ring at meta position with respect to —$W^4$—,
wherein
$R^{61}$ is a fluorine atom that substitutes the benzene ring at ortho position with respect to —$W^4$—,
$R^{62}$ is a hydrogen atom;
$W^4$ is methanediyl or ethane-1,2-diyl.

(104) A compound or a pharmaceutically acceptable salt thereof, wherein formula [I] is formula [I-D'] below:

[Formula 254]

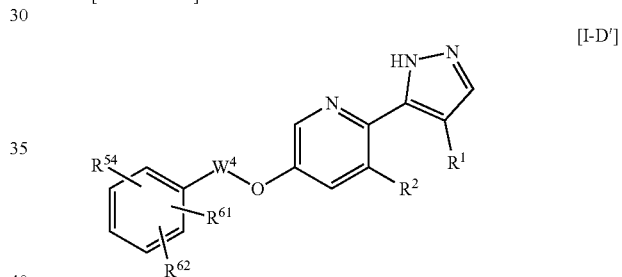

[I-D']

wherein
$R^1$ is a hydrogen atom;
$R^2$ is a hydrogen atom;
$R^{54}$ is cyclopropyl substituted with carboxy, which substitutes the benzene ring at meta position with respect to —$W^4$—,
wherein $R^{61}$ and $R^{62}$ are each independently a hydrogen atom or a fluorine atom;
$W^4$ is ethane-1,2-diyl.

(105) A compound or a pharmaceutically acceptable salt thereof, wherein formula [I] is formula [I-D'] below:

[Formula 255]

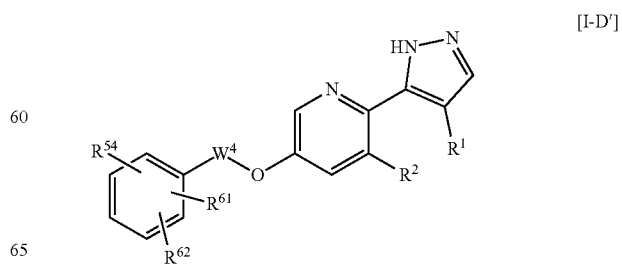

[I-D']

wherein
R¹ is a hydrogen atom;
R² is a hydrogen atom;
R⁵⁴ is cyclopropyl substituted with carboxy, which substitutes the benzene ring at meta position with respect to —W⁴—,
wherein
R⁶¹ is a fluorine atom,
R⁶² is a hydrogen atom;
W⁴ is ethane-1,2-diyl.
(106) A compound or a pharmaceutically acceptable salt thereof, wherein formula [I] is formula [I-D'] below:

[Formula 256]

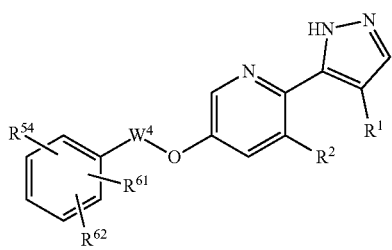

[I-D']

wherein
R¹ is a hydrogen atom;
R² is a hydrogen atom;
R⁵⁴ is cyclopropyl substituted with carboxy,
wherein R⁶¹ and R⁶² are each identically a hydrogen atom;
W⁴ is ethane-1,2-diyl.

Other preferred embodiments of the compound represented by formula [I-B], among compounds of the present invention, or a pharmaceutically acceptable salt thereof are (201) to (203) below.
(201) A compound or a pharmaceutically acceptable salt thereof, wherein formula [I] is formula [I-B] below:

[Formula 257]

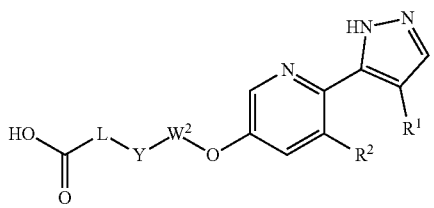

[I-B]

wherein
R¹ is a hydrogen atom;
R² is a hydrogen atom;
L is a structure represented by formula [VI-1], formula [VI-4], or formula [VI-7] below:

[Formula 258]

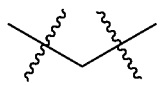

[VI-1]

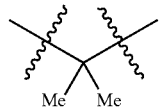

[VI-4]

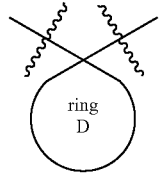

[VI-7]

wherein ring D is
(i) $C_{3-6}$ cycloalkane,
(ii) 4- to 6-membered saturated oxygen-containing hetero ring, or
(iv) 6-membered saturated nitrogen-containing hetero ring (the nitrogen atom of the 6-membered saturated nitrogen-containing hetero ring may be substituted with one $C_{1-4}$alkylcarbonyl);
Y is the formula —CH₂—, the formula —O—, or the formula —CONMe—;
W² is $C_{2-10}$alkanediyl,
wherein one of the carbon atoms that constitute $C_{2-10}$alkanediyl represented by W² may be replaced with one oxygen atom.
(202) A compound or a pharmaceutically acceptable salt thereof, wherein formula [I] is formula [I-B] below:

[Formula 259]

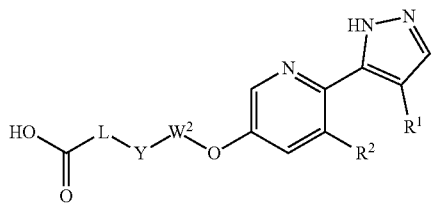

[I-B]

wherein
R¹ is a hydrogen atom;
R² is a hydrogen atom;
L is the structure represented by formula [VI-7] below:

[Formula 260]

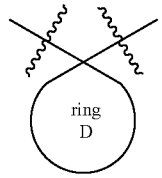

[VI-7]

wherein ring D is
(i) C₄cycloalkane, or
(ii) 4-membered saturated oxygen-containing hetero ring;
Y is the formula —CH₂— or the formula —O—;
W² is heptane-1,7-diyl.
(203) A compound or a pharmaceutically acceptable salt thereof, wherein formula [I] is formula [I-B] below:

[Formula 261]

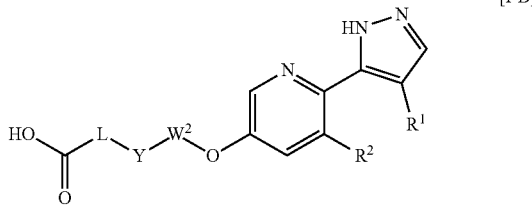

[I-B]

wherein
R[1] is a hydrogen atom;
R[2] is a hydrogen atom;
L is the structure represented by formula [VI-7] below:

[Formula 262]

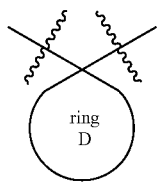

[VI-7]

wherein ring D is
(i) $C_4$cycloalkane,
(ii) 4-membered saturated oxygen-containing hetero ring, or
(iii) 4-membered saturated sulfur-containing hetero ring (the sulfur atom of the 4-membered saturated sulfur-containing hetero ring is substituted with two oxo);
Y is the formula —$CH_2$— or the formula —O—;
$W^2$ is heptane-1,7-diyl.

The compounds of the present invention are those having the basic skeleton of which is pyridine substituted with an azole such as pyrazolyl, and pharmaceutically acceptable salt of such compounds may also be used.

The compounds of the present invention also include tautomers. To give an example of tautomersism, the structure represented by formula [II] shown below:

[Formula 263]

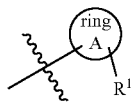

[II]

assumes the structure represented by formula [III-1] shown below:

[Formula 264]

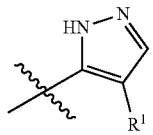

[III-1]

to form a compound (hereinafter referred to as compound [I-1]) and a tautomer thereof (hereinafter referred to as a compound [I-1-α]), both being shown below.

[Formula 265]

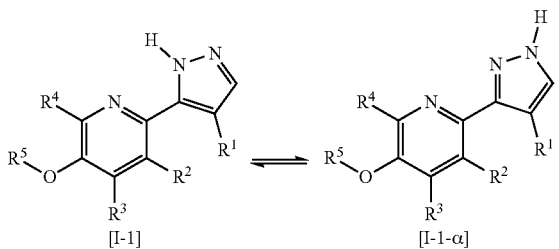

[I-1]     [I-1-α]

Examples of the pharmaceutically acceptable salt include: acid addition salts such as mineral acid salts such as hydrochloride, hydrobromide, hydroiodide, phosphate, sulfate, and nitrate, sulfonic acid salts such as methanesulfonate, ethanesulfonate, benzenesulfonate, p-toluenesulfonate, and trifluoromethanesulfonate, and organic acid salts such as oxalate, tartrate, citrate, maleate, succinate, acetate, trifluoroacetate, benzoate, mandelate, ascorbate, lactate, gluconate, and malate; amino acid salts such as glycine salt, lysine salt, arginine salt, ornithine salt, glutamate, and aspartate; or inorganic salts such as lithium salt, sodium salt, potassium salt, calcium salt, and magnesium salt or salts formed with organic bases, such as ammonium salt, triethylamine salt, diisopropylamine salt, and cyclohexylamine salt. Note that salts include hydrous salts.

The compound of the present invention may have an asymmetric center, and in that case, various optical isomers occur. Accordingly, the compound of the present invention may occur as a separate optically active substance (R) or (S), and as a racemate or an (RS) mixture. Also, when the compound has two or more asymmetric centers, diastereomers also result from the respective optical isomerisms. The compound of the present invention also includes mixtures containing all these forms in any proportions. For example, a diastereomer can be separated by methods well known to those skilled in the art such as a fractional crystallization method, and, also, an optically active substance can be obtained by techniques in organic chemistry that are well known for this purpose. Also, the compound of the present invention may occur as geometric isomers such as a cis and a trans form. Moreover, the compound of the present invention has tautomerism and occurs as various tautomers. The compound of the present invention also includes those isomers as well as mixtures containing those isomers in any proportions.

Moreover, when the compound of the present invention or a salt thereof forms a hydrate or a solvate, these are also included within the scope of the compound of the present invention or a salt thereof.

The 20-HETE producing enzymes refer to cytochrome P450 4A11 and 4F2 that catalyze hydroxylation at ω-position of arachidonic acid to produce 20-HETE using arachidonic acid as a substrate.

Now, as already described above, 20-HETE displays diverse functions in a living body and is involved in the onset of polycystic kidney disease and the pathologies of various cerebrovascular diseases, renal diseases, cardiovascular diseases, and the like.

Accordingly, by inhibiting the 20-HETE producing enzymes, it is possible to prevent or ameliorate polycystic kidney disease, diseases associated with polycystic kidney disease, and symptoms associated with polycystic kidney disease. Also, it is possible to prevent or ameliorate hypertension, cerebrovascular diseases, ischemic heart diseases, chronic renal failure, arteriosclerosis, fatty liver, and cancer.

The compound of the present invention acts to inhibit the 20-HETE producing enzymes. Thus, the compound of the present invention can be used as a 20-HETE producing enzyme inhibitor or an active ingredient of a prophylactic or ameliorating agent for polycystic kidney disease.

Also, it is possible to use the compound of the present invention as an active ingredient of a prophylactic or ameliorating agent for hypertension, cerebrovascular diseases, ischemic heart diseases, chronic renal failure, arteriosclerosis, fatty liver, and cancer.

Here, "polycystic kidney disease" includes "autosomal dominant polycystic kidney disease" and "autosomal recessive polycystic kidney disease", and in which a great number of cysts progressively develop and increase in both kidneys due to genetic mutation. Examples of "diseases associated with polycystic kidney disease" include chronic renal failure, hypertension, vascular disorders, hepatic and pancreatic cysts, urinary tract infections, hepatobiliary infections, urolithiasis, and the like. Also, "symptoms associated with polycystic kidney disease" include pain, hematuria, and abdominal distention.

The action of the compound of the present invention for inhibiting the 20-HETE producing enzymes can be evaluated by known procedures such as the method described in the following Test Examples of the present specification.

Concerning the pharmaceutical according to the present invention, the contained inventive compound, i.e., the compound inhibiting the 20-HETE producing enzymes, or a pharmaceutically acceptable salt thereof, can be administered either alone or in combination with a pharmaceutically or pharmacologically acceptable additive.

Additives that can be used include excipients or diluents in common use, and if necessary, binders, disintegrants, lubricants, coating agents, sugar coating agents, pH adjusters, solubilizers, or aqueous or nonaqueous solvents that are in general use. Specific examples include water, lactose, dextrose, fructose, sucrose, sorbitol, mannitol, polyethylene glycol, propylene glycol, starch, cornstarch, gum, gelatin, alginate, calcium silicate, calcium phosphate, cellulose, water syrup, methylcellulose, polyvinylpyrrolidone, alkylparahydroxybenzoate, talc, stearic acid, magnesium stearate, agar, pectin, gum arabic, glycerin, sesame oil, olive oil, soybean oil cacao butter, ethylene glycol, low viscosity hydroxypropylcellulose (HPC-L), microcrystalline cellulose, carboxymethylcellulose (CMC), sodium carboxymethylcellulose (CMC-Na), and other commonly used additives.

The pharmaceutical according to the present invention may be in any form selected from a solid composition, a liquid composition, and other compositions, and an optimum form is selected as necessary.

The pharmaceutical according to the present invention can be produced by adding the above-mentioned additives to the compound of the present invention and preparing a tablet, pill, capsule, granule, dust, powder, liquid, emulsion, suspension, injection, or the like by a commonly used formulating technique.

Also, the pharmaceutical according to the present invention can be formulated by forming a clathrate from the compound of the present invention and α, β, or γ-cyclodextrin or methylated cyclodextrin or the like.

The pharmaceutical according to the present invention can be a single preparation (a combined drug) containing the compound of the present invention and concomitantly usable compound(s), or two or more preparations (combination drugs) obtained by separately formulating the respective compounds.

When these compounds are separately formulated as two or more preparations, the individual preparations can be administered simultaneously or at certain time intervals. In the latter case, whichever may be administered earlier. The two or more preparations can each be administered a different number of times a day. Also, the two or more preparations can be administered through different routes as well.

When these compounds are separately formulated as two preparations, they may be administered simultaneously or at extremely short intervals, and in such a case, it is preferred that a package insert, a sales brochure, or the like of a commercially available pharmaceutical state to the effect that the preparations are used in combination.

It is also preferred to formulate these active ingredients separately and form a kit composed of two preparations.

When the compound of the present invention is used as a 20-HETE producing enzyme inhibitor or the like, the compound of the present invention may be orally administered as it is. Alternatively, the compound of the present invention may be orally administered in the form of an agent containing the compound as an active ingredient.

When the compound of the present invention is used as a prophylactic or ameliorating agent or the like for polycystic kidney disease, the compound of the present invention may be orally administered as it is. Alternatively, the compound of the present invention may be orally administered in the form of an agent containing the compound as an active ingredient.

The dosage of the compound of the present invention varies with the subject to which it is administered, the route of administration, the disease to be treated, the symptoms, and the like; take, for example, the case of oral administration to an adult patient, and the dosage is normally 0.1 mg to 1000 mg, preferably 1 mg to 200 mg, as a single dose and this dosage is desirably administered 1 to 3 times a day or once every 2 to 3 days.

Examples of producing preparations of the compound of the present invention are described below.

Preparation Example 1

Granules containing the following ingredients are produced.

Ingredients: Compound represented by formula [I] or pharmaceutically acceptable salt thereof, lactose, cornstarch, and HPC-L.

The compound represented by formula [I] or a pharmaceutically acceptable salt thereof and lactose are sieved. Cornstarch is sieved. These are mixed in a mixer. An aqueous solution of HPC-L is added to the mixed powder, and the mixture is kneaded, granulated (extrusion-granulated), and then dried. The resulting dried granules are passed through a vibrating sieve to give granules.

Preparation Example 2

A powder for encapsulation containing the following ingredients is produced.

Ingredients: Compound represented by formula [I] or pharmaceutically acceptable salt thereof, lactose, cornstarch, and magnesium stearate.

The compound represented by formula [I] or a pharmaceutically acceptable salt thereof and lactose are sieved. Cornstarch is sieved. These and magnesium stearate are mixed in a mixer to give a powder. Capsules can be filled with the resulting powder.

Preparation Example 3

Granules for encapsulation containing the following ingredients are produced.
Ingredients: Compound represented by formula [I] or pharmaceutically acceptable salt thereof, lactose, cornstarch, and HPC-L.
The compound represented by formula [I] or a pharmaceutically acceptable salt thereof and lactose are sieved. Cornstarch is sieved. These are mixed in a mixer. An aqueous solution of HPC-L is added to the mixed powder, and the mixture is kneaded, granulated, and then dried. The resulting dried granules are passed through a vibrating sieve for classification to give granules. Capsules can be filled with the resulting granules.

Preparation Example 4

A tablet containing the following ingredients is produced.
Ingredients: Compound represented by formula [I] or pharmaceutically acceptable salt thereof, lactose, microcrystalline cellulose, magnesium stearate, and CMC-Na.
The compound represented by formula [I] or a pharmaceutically acceptable salt thereof, lactose, microcrystalline cellulose, and CMC-Na are sieved and mixed. Magnesium stearate is added to the mixed powder to give a mixed powder for pharmaceutical preparation. This mixed powder is directly pressed to give a tablet.

Hereinafter, the production method for compound [I] according to the present invention will be described in detail, but the production method is not particularly limited to the examples given below. The solvent which is used in the reaction may be any solvent as long as it does not interfere with the respective reactions, and it is not particularly limited to the following description.

Compound [I] of the present invention can be produced by methods known per se, for example, production methods 1 to 44 shown below, or modifications thereof.

In addition, in the production of compound [I] of the present invention, the order of the respective steps in each production method can be appropriately changed.

In each of the following production methods, starting compounds may be used in a salt form thereof; and examples of the salt include the previously described "pharmaceutically acceptable salts".

Among compound [I] of the present invention, methods for producing the compound in which the structure represented by formula [II] below is a structure of formula [III-1] below (hereinafter also referred to as compound [I-1]) are shown in production methods 1 to 35; methods for producing the compound in which the structure represented by formula [II] below is a structure of formula [III-2] below (hereinafter also referred to as compound [I-2]) are shown in production methods 36 to 38; methods for producing the compound in which the structure represented by formula [II] below is a structure of formula [III-3] below (hereinafter also referred to as compound [I-3]) are shown in production methods 39 to 41; and methods for producing the compound in which the structure represented by formula [II] below is a structure of formula [III-4] or formula [III-5] below (hereinafter also referred to as compound [I-4] and compound [I-5], respectively) are shown in production methods 42 to 44.

[Formula 266]

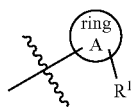

[II]

[Formula 267]

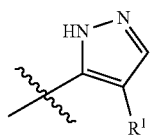

[III-1]

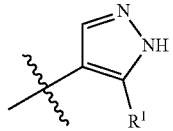

[III-2]

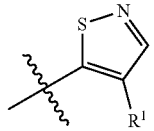

[III-3]

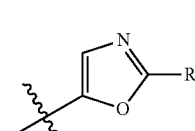

[III-4]

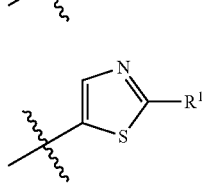

[III-5]

Compound [1-e] which is an intermediate in the production of compound [I-1] of the present invention can be produced, for example, by production method 1 below or a method pursuant thereto.

Production Method 1

[Formula 268]

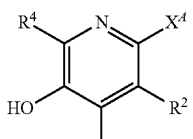

[1-a]

step 1-1

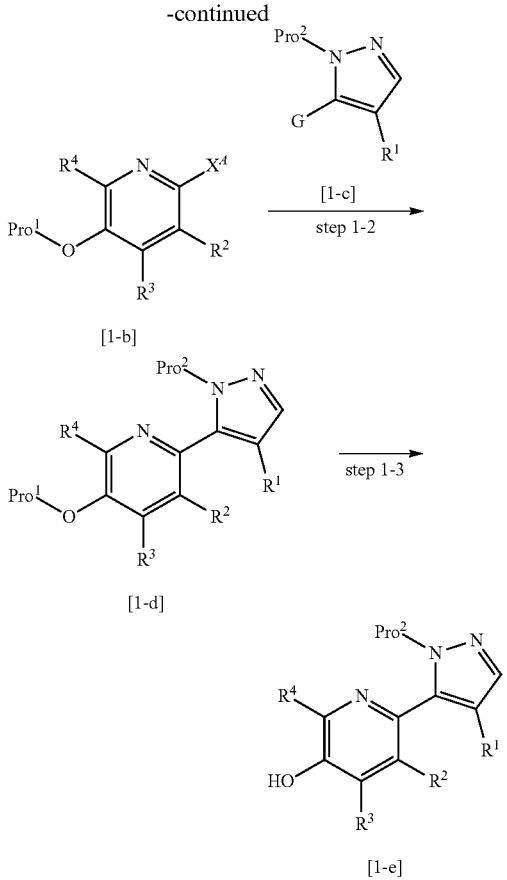

[In the scheme,
R¹, R², R³, and R⁴ are the same as defined above;
$X^A$ represents a chlorine atom or a bromine atom; and
G represents a boronic acid group or a boronic acid ester group, and
$Pro^1$ represents a protecting group for hydroxy, as exemplified by:
(i) benzyl, 4-methoxybenzyl, and the like (protecting groups which form a benzyl ether structure together with the hydroxy, and herein also referred to as "benzyl ether-based protecting group");
(ii) methoxymethyl, tetrahydropyranyl, and the like (protecting groups which form an acetal structure together with the hydroxy, and herein also referred to as "acetal-based protecting group");
(iii) trimethylsilyl, triisopropylsilyl, tert-butyldimethylsilyl, and the like (protecting groups which form a silyl ether structure together with the hydroxy, and herein also referred to as "silyl ether-based protecting group"); and
$Pro^2$ represents a protecting group for azoles which are typified by pyrazolyl, for example, tetrahydropyranyl, triphenylmethyl, and the like]

[Step 1-1]

This step is a method of producing compound [1-b] by protecting the hydroxy of compound [1-a] with protecting group Pro'.

This reaction can be carried out by the method described in the literature (Protective Groups in Organic Synthesis, 4th edition, 2007, edited by G. M. Wuts and T. W. Greene), or a method pursuant thereto.

[Step 1-2]

This step is a method of producing compound [1-d] by reacting compound [1-b] with compound [1-c].

This reaction is a so-called Suzuki-Miyaura coupling reaction that can be carried out by a process which is described in the literature (Tetrahedron Letters, Vol. 20, page 3437, 1979, Chemical Reviews, Volume 95, page 2457, 1995) in the presence of a palladium catalyst and a base, or a process pursuant thereto.

The amount of compound [1-c] which is used in the present reaction is 1 to 5 equivalents, and preferably 1 to 3 equivalents, with respect to 1 equivalent of compound [1-b].

Examples of the palladium catalysts include tetrakis(triphenylphosphine)palladium(0), a [1,1'-bis(diphenylphosphino)ferrocene]palladium(II) dichloride dichloromethane adduct, and bis(triphenylphosphine)palladium(II) dichloride. The amount of the palladium catalyst to be used is usually 0.001 to 0.5 equivalents, and preferably 0.001 to 0.3 equivalents, with respect to 1 equivalent of compound [1-b].

Examples of the base include: alkali metal carbonates such as potassium carbonate, cesium carbonate, and sodium carbonate, or aqueous solutions thereof; potassium fluoride; cesium fluoride; and triethylamine. The amount of the base to be used is usually 1 to 5 equivalents, and preferably 1 to 3 equivalents, with respect to 1 equivalent of compound [1-b].

Examples of the reaction solvent include solvents that do not interfere with reactions, such as N,N-dimethylformamide, dimethylsulfoxide, toluene, 1,4-dioxane, tetrahydrofuran, 1,2-dimethoxyethane, ethanol, and water; and these solvents may be mixed with each other at an appropriate ratio and used.

These reactions can be carried out usually at room temperature to reflux temperature for 1 to 24 hours, and can be also carried out under microwave irradiation.

As described above, as compound [I'] of the present invention includes a tautomer thereof, compound [1-d] and the like, which are substituted with protecting group $Pro^2$ of pyrazolyl, may include an isomer thereof. As examples of the isomers, compound [1-d] and its isomer [1-d-α] are shown below.

[Formula 269]

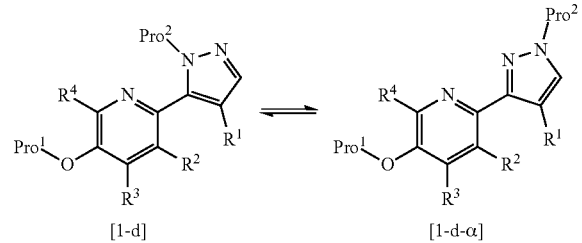

[Step 1-3]

This step is a method of producing compound [1-e] by deprotecting the hydroxy of compound [1-d] by removing protecting group Pro'.

(i) When Pro' is a benzyl ether-based protecting group such as benzyl and 4-methoxybenzyl, the present reaction can be carried out in a solvent which does not interfere with the reaction, in the presence of a metal catalyst and a hydrogen source.

Examples of the metal catalyst which is used in the present reaction include palladium carbon and palladium hydroxide carbon. The amount of the metal catalyst to be used is 0.001 to 1 equivalent, and preferably 0.01 to 0.5 equivalents, with respect to 1 equivalent of compound A hydrogen pressure which is used in the present reaction is ordinary pressure to 10 atm, and preferably ordinary pressure to 4 atm.

Examples of the solvent which is used in the present reaction include methanol, ethanol, water, tetrahydrofuran, and ethyl acetate; and these solvents may be mixed with each other at an appropriate ratio and used.

The present reaction can be carried out usually at room temperature to reflux temperature for 1 to 24 hours.

(ii) When $Pro^1$ is an acetal-based protecting group such as methoxymethyl and tetrahydropyranyl, the present reaction can be carried out in a solvent which does not interfere with the reaction in the presence of an acid.

Examples of the acid which is used in the present reaction include hydrochloric acid and trifluoroacetic acid. The amount of the acid to be used is 1 to 5 equivalents, and preferably 1 to 3 equivalents, with respect to 1 equivalent of compound Examples of the solvent which is used in the present reaction include solvents that do not interfere with reactions, such as methanol, ethanol, water, dichloromethane, and chloroform; and these solvents may be mixed with each other at an appropriate ratio and used.

The present reaction can be carried out usually at room temperature to reflux temperature for 1 to 24 hours.

(iii) When $Pro^1$ is a silyl ether-based protecting group such as trimethylsilyl, triisopropylsilyl, and tert-butyldimethylsilyl, the present reaction can be carried out in a solvent which does not interfere with the reaction in the presence of an acid.

Examples of the acid which is used in the present reaction include hydrochloric acid, acetic acid, and trifluoroacetic acid. The amount of the acid to be used is 1 to 5 equivalents, and preferably 1 to 3 equivalents, with respect to 1 equivalent of compound [1-d].

Examples of the solvent which is used in the present reaction include solvents that do not interfere with reactions, such as tetrahydrofuran, methanol, ethanol, and water; and these solvents may be mixed with each other at an appropriate ratio and used.

The present reaction can be carried out usually at room temperature to reflux temperature for 1 to 24 hours.

In addition, the present reaction can also be carried out in a solvent which does not interfere with the reaction in the presence of a fluoride ion.

Examples of the fluoride ion source which is used in the present reaction include potassium fluoride and tetrabutylammonium fluoride. The amount of the fluoride ion source to be used is 1 to 5 equivalents, and preferably 1 to 3 equivalents, with respect to 1 equivalent of compound [1-d].

Examples of the solvent which is used in the present reaction include solvents that do not interfere with reactions, such as tetrahydrofuran, N,N-dimethylformamide, methanol, and ethanol; and these solvents may be mixed with each other at an appropriate ratio and used.

The present reaction can be carried out usually at room temperature to reflux temperature for 1 to 24 hours.

Compound [1-e] thus obtained can be isolated and purified by known separation and purification means such as concentration, concentration under reduced pressure, reprecipitation, solvent extraction, crystallization, and chromatography.

Incidentally, compounds [1-a] and [1-c] which are used as starting compounds in production method 1 above can be produced by a method known per se, or can be obtained by purchasing commercial products.

Among compound [1-e] which is an intermediate in the production of compound [I] of the present invention, compound [2-b] in which $R^1$ is a chlorine atom or a bromine atom can be produced, for example, by production method 2 below or a method pursuant thereto.

Production Method 2

[Formula 270]

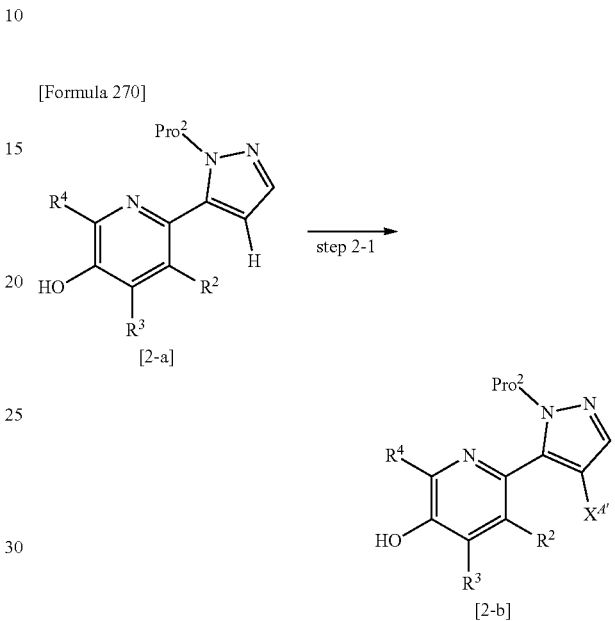

[In the scheme,
$R^2$, $R^3$, $R^4$, and $Pro^2$ are the same as defined above; and
$X^{4'}$ represents a chlorine atom or a bromine atom.]

[Step 2-1]

This step is a method of producing compound [2-b] by reacting compound [2-a] which is that type of compound [1-e] in which $R^1$ is a hydrogen atom with a halogenating agent.

Examples of the halogenating agent which is used in the present reaction include N-chlorosuccinimide (NCS) and N-bromosuccinimide (NBS). The amount of the reagent to be used is 1 to 5 equivalents, and preferably 1 to 1.1 equivalents, with respect to 1 equivalent of compound [2-a].

Examples of the solvent which is used in the present reaction include solvents that do not interfere with reactions, such as chloroform, dichloromethane, carbon tetrachloride, acetonitrile, ethyl acetate, N,N-dimethylformamide, and water; and these solvents may be mixed with each other at an appropriate ratio and used.

The present reaction can be carried out usually at 0° C. to reflux temperature for 1 to 48 hours.

In addition, the present reaction can be similarly carried out for an unprotected substrate, that is, when $Pro^2$ is a hydrogen atom.

Compound [2-a] which is used as a starting compound in production method 2 above can be produced by production method 1 above, a method pursuant thereto, or a method known per se.

Among compound [1-e] which is an intermediate in the production of compound [I] of the present invention, compound [3-e] in which $R^1$ is difluoromethyl can be produced, for example, by production method 3 below or a method pursuant thereto.

Production Method 3

[Formula 271]

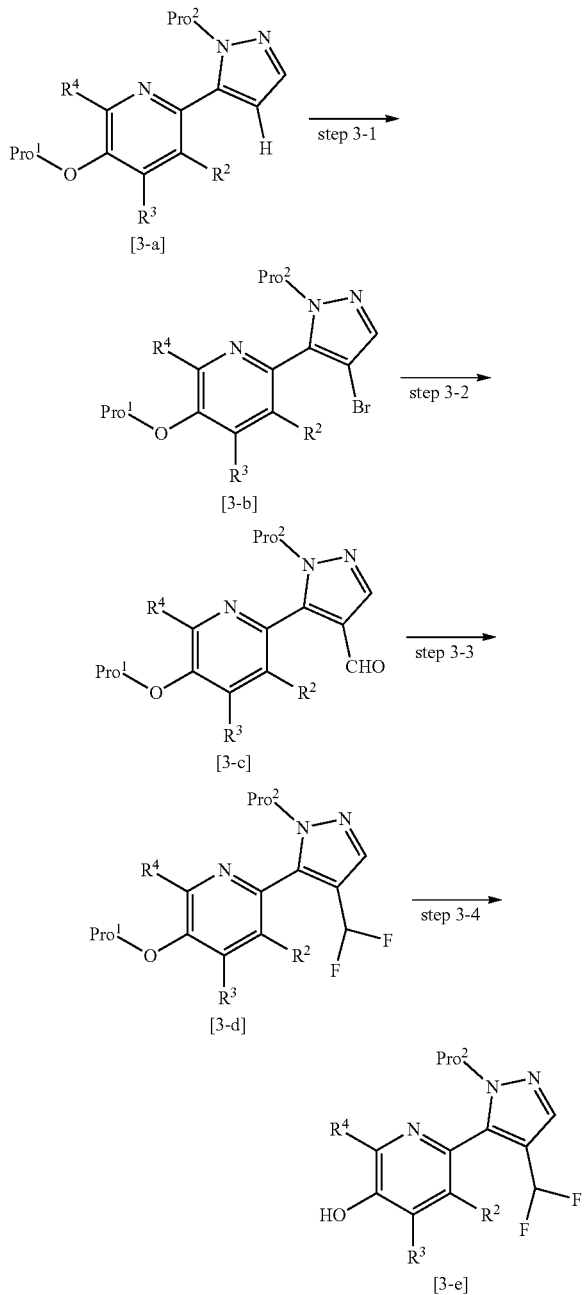

[In the scheme,

R², R³, R⁴, Pro¹, and Pro² are the same as defined above.]

[Step 3-1]

This step is a method of producing compound [3-b] by regioselectively brominating compound [3-a] which is that type of compound [1-d] in which R¹ is a hydrogen atom.

The present reaction can be carried out by the method described in step 2-1 of production method 2 or a method pursuant thereto.

[Step 3-2]

This step is a method of producing compound [3-c] by reacting compound [3-b] with an alkyl lithium compound and then reacting the resulting reaction intermediate with a formamide compound.

Examples of the alkyl lithium compound which is used in the reaction with compound [3-b] include n-butyl lithium. The amount of the alkyl lithium compound to be used is 1 to 5 equivalents, and preferably 1 to 3 equivalents, with respect to 1 equivalent of compound [3-b].

Examples of the solvent which is used in the present reaction include solvents that do not interfere with reactions, such as diethyl ether, tetrahydrofuran, 1,4-dioxane, toluene, and xylene; and these solvents may be mixed with each other at an appropriate ratio and used.

The present reaction can be carried out usually at −80° C. to −50° C. for 0.1 to 1 hour.

Examples of the formamide compound which is used in the reaction with the reaction intermediate to be generated include N,N-dimethyl formamide and N-methoxy-N-methylformamide. The amount of the formamide compound to be used is 1 to 5 equivalents, and preferably 1 to 3 equivalents, with respect to 1 equivalent of compound [3-b].

The present reaction can be carried out usually at −80° C. to room temperature for 0.1 to 24 hours.

[Step 3-3]

This step is a method of producing compound [3-d] by converting the formyl of compound [3-c] to difluoromethyl.

Examples of the fluorinating reagent which is used in the reaction with compound [3-c] include tetrafluoro sulfur (IV), (N,N-diethylamino)sulfur trifluoride (DAST), and bis(2-methoxyethyl)aminosulfur trifluoride (BAST). The amount of the fluorinating reagent to be used is 1 to 5 equivalents, and preferably 1 to 3 equivalents, with respect to 1 equivalent of compound [3-c].

Examples of the solvent to be used in the present reaction include solvents that do not interfere with reactions, such as dichloromethane, chloroform, acetonitrile, tetrahydrofuran, 1,4-dioxane, toluene, and xylene; and these solvents may be mixed with each other at an appropriate ratio and used.

The present reaction can be carried out usually at room temperature to reflux temperature for 1 to 24 hours.

[Step 3-4]

This step is a method of producing compound [3-e] by deprotecting compound [3-d] by removing protecting group Pro¹.

This step can be carried out by step 1-3 of production method 1 or a method pursuant thereto.

Compound [3-e] thus obtained can be isolated and purified by known separation and purification means such as concentration, concentration under reduced pressure, reprecipitation, solvent extraction, crystallization, and chromatography.

Incidentally, compound [3-a] which is used as a starting compound in production method 3 can be obtained by steps 1-1 and 1-2 of production method 1 or a method pursuant thereto.

Compound [4-c] which is an intermediate in the production of that type of compound [I-1] of the present invention in which the structure represented by R⁵ is a structure shown in formula [IV-1] below can be produced, for example, by production method 4 below or a method pursuant thereto.

[Formula 272]

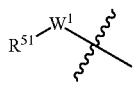

[IV-1]

Production Method 4

[Formula 273]

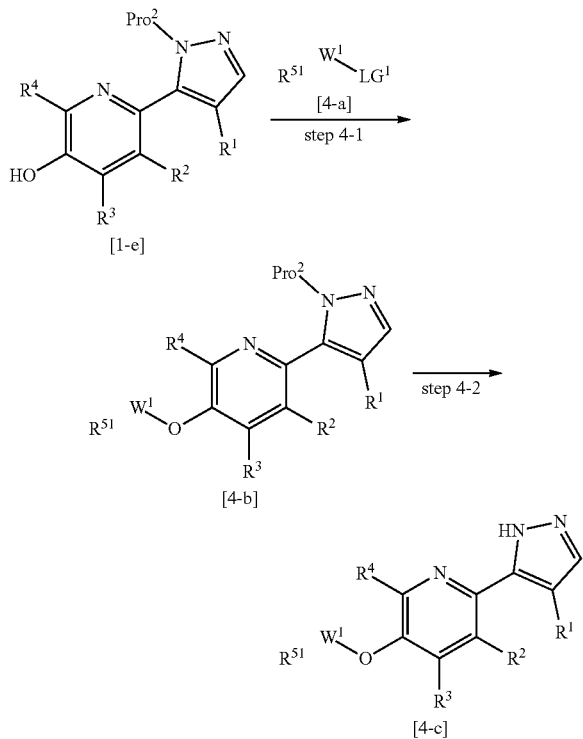

[In the scheme,
$R^1$, $R^2$, $R^3$, $R^4$, $Pro^2$, $R^{51}$, and $W^1$ are the same as defined above; $LG^1$ represents hydroxy or a leaving group; and the "leaving group" represented by $LG^1$ refers to, for example, a halogen atom such as a chlorine atom and a bromine atom, $C_{1-4}$ alkylsulfonyloxy such as methanesulfonyloxy, or arylsulfonyloxy such as p-toluenesulfonyloxy.]

[Step 4-1]

This step is a method of producing compound [4-b] by reacting compound [1-e] with compound [4-a].

(i) When $LG^1$ in compound [4-a] is hydroxy, the present reaction can be carried out by a known method, i.e., the so-called "Mitsunobu reaction" (page 1, Synthesis, 1981).

The amount of compound [4-a] which is used in the present reaction is 1 to 5 equivalents, and preferably 1 to 3 equivalents, with respect to 1 equivalent of compound [1-e].

Examples of the azo compound which is used in the present reaction include bis(2-methoxyethyl) azodicarboxylate, diisopropyl azodicarboxylate, and 1,1'-azobis(N,N-dimethylformamide). The amount of the azo compound to be used is 1 to 5 equivalents, and preferably 1 to 3 equivalents, with respect to 1 equivalent of compound [1-e].

Examples of the phosphine compound which is used in the present reaction include triphenylphosphine and tributylphosphine. The amount of the phosphine compound to be used is 1 to 5 equivalents, and preferably 1 to 3 equivalents, with respect to 1 equivalent of compound [1-e].

Examples of the solvent which is used in the present reaction include solvents that do not interfere with reactions, such as tetrahydrofuran, 1,4-dioxane, diethyl ether, chloroform, dichloromethane, toluene, N,N-dimethylformamide, and dimethyl sulfoxide; and these solvents may be mixed with each other at an appropriate ratio and used.

The present reaction can be carried out usually at room temperature to reflux temperature for 1 to 24 hours.

The present reaction may also be carried out by the method described in Tetrahedron Letters, Vol. 36, page 2531, 1995 or Tetrahedron Letters, Vol. 37, page 2463, 1996.

Examples of the reagent which is used in the present reaction include cyanomethylenetrimethylphosphorane and cyanomethylenetributylphosphorane. The amount of the reagent to be used is 1 to 5 equivalents, and preferably 1 to 3 equivalents, with respect to 1 equivalent of compound [1-e].

Examples of the solvent which is used in the present reaction are the same as those used in the Mitsunobu reaction described above.

The present reaction can be carried out usually at room temperature to reflux temperature for 1 to 24 hours.

(ii) When $LG^1$ in compound [4-a] is a leaving group, the present reaction can be carried out in the presence of a base.

The amount of compound [4-a] which is used in the present reaction is 1 to 5 equivalents, and preferably 1 to 3 equivalents, with respect to 1 equivalent of compound [1-e].

Examples of the base which is used in the present reaction include amines such as triethylamine, N,N-diisopropylethylamine, and 1,8-diazabicyclo[4,3,0]undec-7-ene, alkali metal hydrides such as sodium hydride, alkali metal hydroxides such as potassium hydroxide, alkali metal carbonates such as cesium carbonate, potassium carbonate, and sodium carbonate, and alkoxy alkali metal such as potassium tert-butoxide. The amount of the base to be used is 1 to 5 equivalents, and preferably 1 to 3 equivalents, with respect to 1 equivalent of compound [1-e].

Examples of the solvent which is used in the present reaction include solvents that do not interfere with reactions, such as tetrahydrofuran, dimethyl sulfoxide, N,N-dimethylformamide, N, N-dimethylacetamide, and N-methylpyrrolidone; and these solvents may be mixed with each other at an appropriate ratio and used.

The present reaction can be carried out usually at room temperature to reflux temperature for 1 to 24 hours.

When $LG^1$ in compound [4-a] is hydroxy, the present reaction can also be carried out after hydroxy is converted to a leaving group.

The hydroxy may be converted to a leaving group by a usual method. For example, compound [4-a] in which $LG^1$ is a leaving group may be prepared by the reaction with (a) a halogenating reagent or (b) a sulfonate esterification reagent in the presence of a base in a solvent which does not interfere with the reaction.

Examples of (a) halogenating reagent used in the present reaction include thionyl chloride, phosphoryl chloride, N-chlorosuccinimide, bromine, and N-bromosuccinimide. The amount of the halogenating reagent to be used is 1 to 5 equivalents, and preferably 1 to 3 equivalents, with respect to 1 equivalent of the compound having hydroxy.

Examples of the solvent which is used in the present reaction include solvents that do not interfere with reactions, such as chloroform and dichloromethane; and these solvents may be mixed with each other at an appropriate ratio and used.

The present reaction can be carried out usually at room temperature to reflux temperature for 1 to 24 hours.

Furthermore, examples of (b) sulfonate esterification reagent used in the present reaction include methanesulfonyl chloride, trifluoromethanesulfonyl chloride, and p-toluenesulfonyl chloride. The amount of the sulfonate esterification reagent to be used is 1 to 5 equivalents, and preferably 1 to 3 equivalents, with respect to 1 equivalent of the compound having hydroxy.

Examples of the base which is used in the present reaction include triethylamine, N,N-diisopropylethylamine, pyridine, and 4-dimethylaminopyridine. The amount of the base to be used is 1 to 5 equivalents, and preferably 1 to 3 equivalents, with respect to 1 equivalent of the sulfonate esterification reagent to be used.

Examples of the solvent which is used in the present reaction include solvents that do not interfere with reactions, such as chloroform and dichloromethane; and these solvents may be mixed with each other at an appropriate ratio and used.

The present reaction can be carried out usually at room temperature to reflux temperature for 1 to 24 hours.

[Step 4-2]

This step is a method of producing compound [4-c] by deprotecting the pyrazolyl of compound [4-b] by removing protecting group $Pro^2$ under an acidic condition.

Examples of the acid which is used in the present reaction include hydrochloric acid, formic acid, and trifluoroacetic acid. The amount of the acid to be used is 1 equivalent to a solvent amount, and preferably 1 to 10 equivalents, with respect to 1 equivalent of compound [4-b].

Examples of the solvent which is used in the present reaction include solvents that do not interfere with reactions, such as methanol, ethanol, tetrahydrofuran, water, ethyl acetate, and 1,4-dioxane; and these solvents may be mixed with each other at an appropriate ratio and used.

The present reaction can be carried out usually at 0° C. to reflux temperature for 1 to 24 hours.

Compound [4-c] thus obtained can be isolated and purified by known separation and purification means such as concentration, concentration under reduced pressure, reprecipitation, solvent extraction, crystallization, and chromatography.

Compounds [1-e] and [4-a] which are used as starting compounds in production method 4 above can be produced by production method 1 above, a method pursuant thereto, or a method known per se, or can be obtained by purchasing commercial products.

Among compound [I-1] of the present invention, compound [5-e] in which the structure represented by $R^5$ is a structure shown in formula [IV-2] below and $R^{52}$ is carboxy can be produced, for example, by production method 5 below or a method pursuant thereto.

[Formula 274]

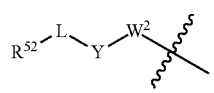

[IV-2]

Production Method 5

[Formula 275]

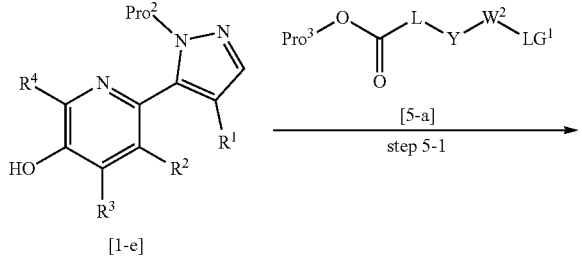

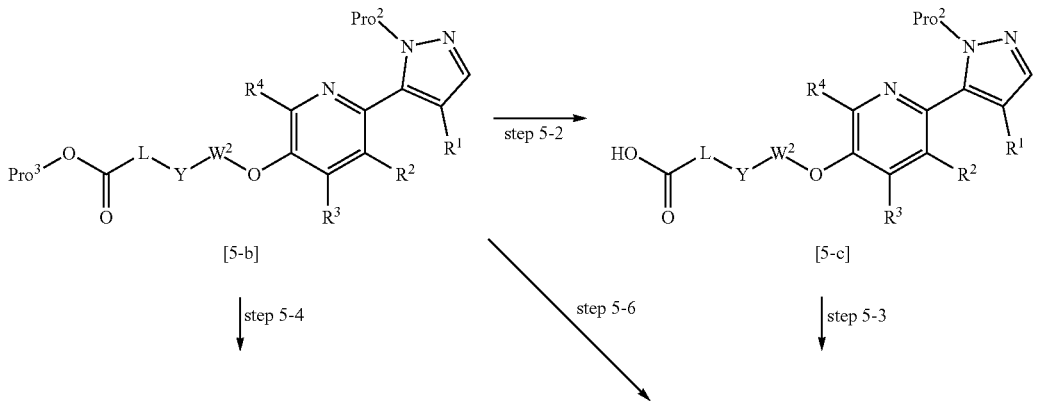

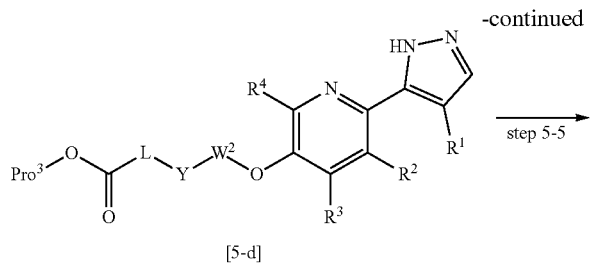
[5-d]

→ step 5-5

[5-e]

[In the scheme,
$R^1$, $R^2$, $R^3$, $R^4$, $Pro^2$, L, Y, $W^2$, and $LG^1$ are the same as defined above; and
$Pro^3$ represents primary or secondary alkyl such as methyl, ethyl, and 2-propyl; a benzyl-based protecting group such as benzyl and 4-methoxybenzyl; or tert-butyl]

[Step 5-1]

This step is a method of producing compound [5-b] by reacting compound [1-e] with compound [5-a].

This reaction can be carried out by the method described in step 4-1 of production method 4 or a method pursuant thereto.

There are several synthesis pathways for production of compound [5-e]. Steps 5-2 to 5-6 therefor will be sequentially described.

(i) When $Pro^3$ in compound [5-b] is primary or secondary alkyl such as methyl, ethyl, and 2-propyl, or (ii) when $Pro^3$ in compound [5-b] is a benzyl-based protecting group such as benzyl and 4-methoxybenzyl, compound [5-e] can be produced via compound [5-c] by methods described in steps 5-2 and 5-3.

[Step 5-2]

This step is a method of producing compound [5-c] by deprotecting compound [5-b] by removing protecting group $Pro^3$.

(i) When $Pro^3$ in compound [5-b] is primary or secondary alkyl such as methyl, ethyl, and 2-propyl, the present reaction can be carried out under a basic condition.

Examples of the base which is used in the present reaction include alkali metal hydroxides such as sodium hydroxide and potassium hydroxide. The amount of the base to be used is 1 to 100 equivalents, and preferably 1 to 10 equivalents, with respect to 1 equivalent of compound [5-b].

Examples of the solvent which is used in the present reaction include solvents that do not interfere with reactions, such as methanol, ethanol, 2-propanol, acetone, tetrahydrofuran, 1,4-dioxane, and water; and these solvents may be mixed with each other at an appropriate ratio and used.

The present reaction can be carried out usually at 0° C. to reflux temperature for 1 to 24 hours.

(ii) When $Pro^3$ in compound [5-b] is a benzyl-based protecting group such as benzyl and 4-methoxybenzyl, the present reaction can be carried out by the method described in (i) or the method described in step 1-3 (i) of production method 1, or a method pursuant thereto.

[Step 5-3]

This step is a method of producing compound [5-e] by deprotecting the pyrazolyl of compound [5-c] by removing protecting group $Pro^2$ under an acidic condition.

This reaction can be carried out by the method described in step 4-2 of production method 4 or a method pursuant thereto.

(i) When $Pro^3$ in compound [5-b] is primary or secondary alkyl such as methyl, ethyl, and 2-propyl, (ii) when $Pro^3$ in compound [5-b] is a protecting group such as benzyl and 4-methoxybenzyl, or (iii) when $Pro^3$ in compound [5-b] is tert-butyl, compound [5-e] can be produced via compound [5-d] by methods described in steps 5-4 and 5-5.

[Step 5-4]

This step is a method of producing compound [5-d] by deprotecting the pyrazolyl of compound [5-b] by removing protecting group $Pro^2$ under an acidic condition.

(i) When $Pro^3$ in compound [5-b] is primary or secondary alkyl such as methyl, ethyl, and 2-propyl, or (ii) when $Pro^3$ in compound [5-b] is a benzyl-based protecting group such as benzyl and 4-methoxybenzyl, the present reaction can be carried out by the method described in step 4-2 of production method 4 or a method pursuant thereto.

(iii) When $Pro^3$ in compound [5-b] is tert-butyl, the present reaction can be carried out under a relatively moderately acidic condition.

Examples of the acid which is used in the present reaction include hydrochloric acid, formic acid, and trifluoroacetic acid. The amount of the acid to be used is 1 equivalent to a solvent amount, and preferably 1 to 10 equivalents, with respect to 1 equivalent of compound [5-b].

Examples of the solvent which is used in the present reaction include solvents that do not interfere with reactions, such as methanol, ethanol, tetrahydrofuran, water, ethyl acetate, and 1,4-dioxane; and these solvents may be mixed with each other at an appropriate ratio and used.

The present reaction can be carried out usually at 0° C. to room temperature for 1 to 24 hours.

[Step 5-5]

This step is a method of producing compound [5-e] by deprotecting compound [5-d] by removing protecting group $Pro^3$.

(i) When $Pro^3$ in compound [5-d] is primary or secondary alkyl such as methyl, ethyl, and 2-propyl, the present reaction can be carried out by the method described in step 5-2 (i) of production method 5 or a method pursuant thereto.

(ii) When $Pro^3$ in compound [5-d] is a benzyl-based protecting group such as benzyl and 4-methoxybenzyl, the present reaction can be carried out by the method described in (i) or the method described in step 1-3 of production method 1, or a method pursuant thereto.

(iii) When $Pro^3$ in compound [5-d] is tert-butyl, the present reaction can be carried out under an acidic condition.

Examples of the acid which is used in the present reaction include hydrochloric acid and trifluoroacetic acid. The amount of the acid to be used is 1 equivalent to a solvent amount, and preferably 1 to 10 equivalents, with respect to 1 equivalent of compound [5-d].

Examples of the solvent which is used in the present reaction include solvents that do not interfere with reactions, such as methanol, ethanol, tetrahydrofuran, water, ethyl acetate, and 1,4-dioxane; and these solvents may be mixed with each other at an appropriate ratio and used.

The present reaction can be carried out usually at 50° C. to reflux temperature for 1 to 24 hours.

When Pro³ in compound [5-b] is 4-methoxybenzyl or tert-butyl, compound [5-e] can be produced by step 5-6.

[Step 5-6]

This step is a method of producing compound [5-e] by deprotecting compound [5-b] by removing protecting groups Pro² and Pro³ under an acidic condition.

This reaction can be carried out by the method described in step 5-5 (iii) of production method 5 or a method pursuant thereto.

Compound [5-e] thus obtained can be isolated and purified by known separation and purification means such as concentration, concentration under reduced pressure, reprecipitation, solvent extraction, crystallization, and chromatography.

Compounds [1-e] and [5-a] which are used as starting compounds in production method 5 above can be produced by production method 1 above, a method pursuant thereto, or a method known per se, or can be obtained by purchasing commercial products.

Alternatively, compound [5-e] can be produced, for example, by production method 6 below or a method pursuant thereto.

Production Method 6

[Formula 276]

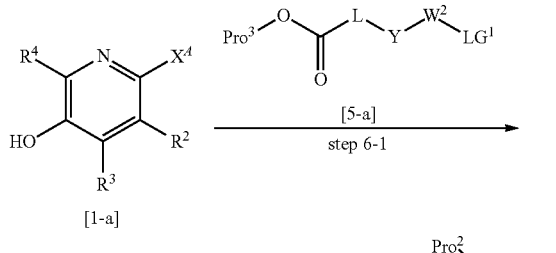

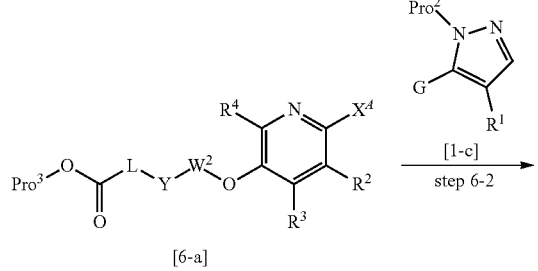

[In the scheme,
R¹, R², R³, R⁴, X⁴, Pro², Pro³, W², Y, L, LG¹, and G are the same as defined above.]

[Step 6-1]

This step is a method of producing compound [6-a] by reacting compound [1-a] with compound [5-a].

This reaction can be carried out by the method described in step 4-1 of production method 4 or a method pursuant thereto.

[Step 6-2]

This step is a method of producing compound [5-b] by reacting compound [6-a] with compound [1-c].

This reaction can be carried out by the method described in step 1-2 of production method 1 or a method pursuant thereto.

Compound [5-e] may be derived from compound [5-b] thus obtained by the method described in steps 5-2 to 5-6 of production method 5 or a method pursuant thereto.

Compounds [1-a], [5-a], and [1-c] which are used as starting compounds in production method 6 above can be produced by a method known per se, or can be obtained by purchasing commercial products.

Among compound [I-1] of the present invention, compound [7-f] which is that type of compound [5-e] in which Y is the formula —O— can be produced, for example, by production method 7 below or a method pursuant thereto.

Production Method 7

[Formula 277]

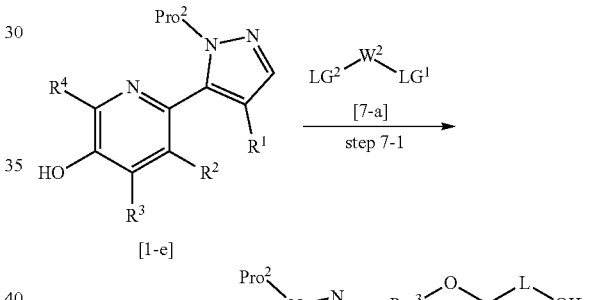

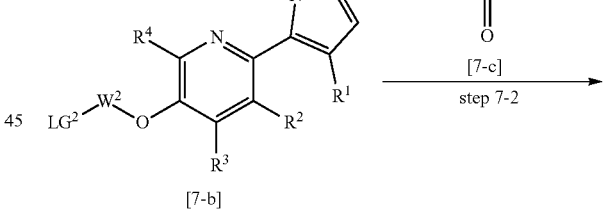

197
-continued

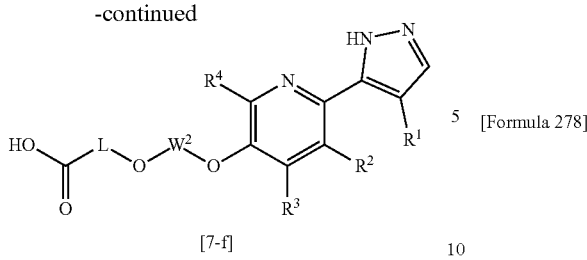

[7-f]

[In the scheme,
$R^1$, $R^2$, $R^3$, $R^4$, $Pro^2$, $Pro^3$, $LG^1$, $W^2$, and L are the same as defined above;
$LG^2$ represents, independently of $LG^1$, a leaving group such as hydroxy; a halogen atom such as a chlorine atom and a bromine atom; $C_{1-4}$ alkylsulfonyloxy such as methanesulfonyloxy; and arylsulfonyloxy such as p-toluenesulfonyloxy.]

[Step 7-1]

This step is a method of producing compound [7-b] by reacting compound [1-e] with compound [7-a].

This reaction can be carried out by the method described in step 4-1 of production method 4 or a method pursuant thereto.

[Step 7-2]

This step is a method of producing compound [7-d] by reacting compound [7-b] with compound [7-c].

This reaction can be carried out by the method described in step 4-1(ii) of production method 4 or a method pursuant thereto.

[Step 7-3]

This step is a method of producing compound [7-e] by deprotecting the pyrazolyl of compound [7-d] by removing protecting group $Pro^2$ under an acidic condition.

This reaction can be carried out by the method described in step 4-2 of production method 4 or the method described in step 5-4 of production method 5, or a method pursuant thereto.

[Step 7-4]

This step is a method of producing compound [7-f] by deprotecting compound [7-e] by removing protecting group $Pro^3$.

This reaction can be carried out by the method described in step 5-5 of production method 5 or a method pursuant thereto.

Steps 7-3 and 7-4 above may be carried out in the reversed order.

Compound [7-f] thus obtained can be isolated and purified by known separation and purification means such as concentration, concentration under reduced pressure, reprecipitation, solvent extraction, crystallization, and chromatography.

Incidentally, compounds [1-e], [7-a], and [7-c] which are used as starting compounds in production method 7 above can be produced by the method described in production method 1 above, a method pursuant thereto, or a method known per se, or can be obtained by purchasing commercial products.

Among compound [I-1] of the present invention, compound [8-g] which is that type of compound [5-e] in which Y is the formula —NHCO— can be produced, for example, by production method 8 below or a method pursuant thereto.

198
Production Method 8

[Formula 278]

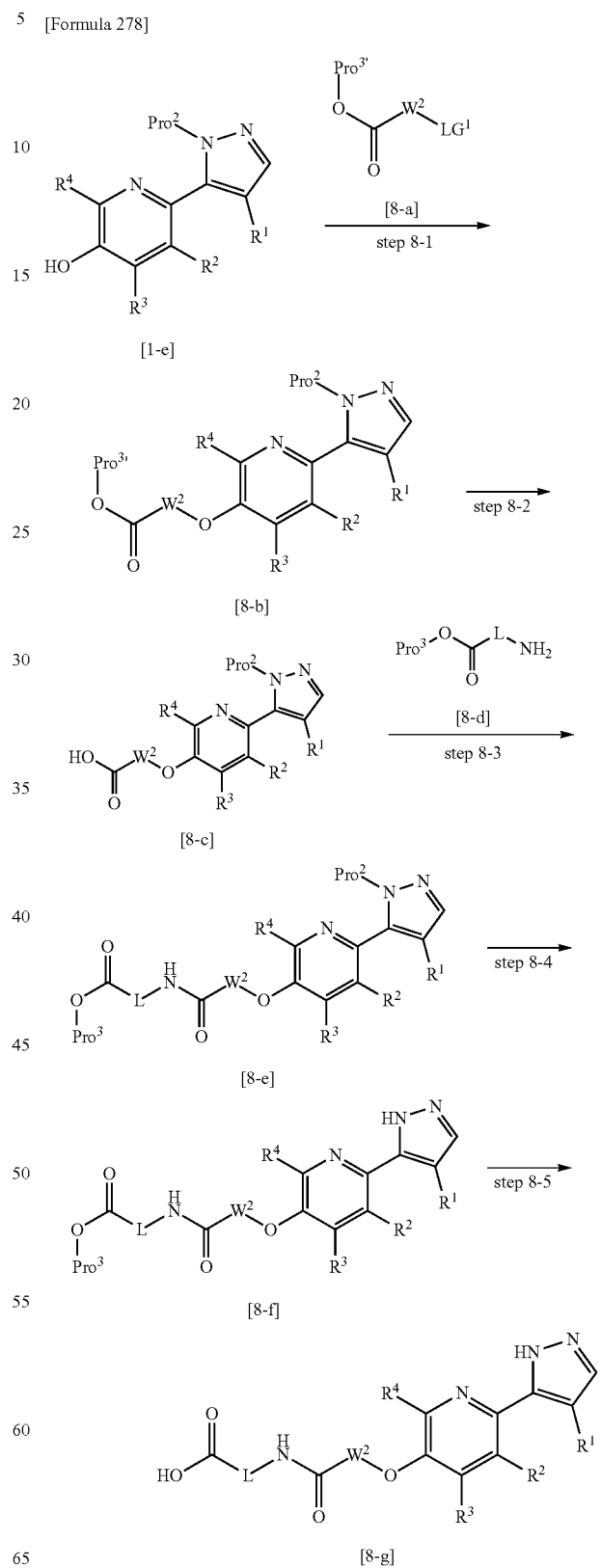

[In the scheme,
$R^1$, $R^2$, $R^3$, $R^4$, $Pro^2$, $Pro^3$, $LG^1$, $W^2$, and L are the same as defined above; and
$Pro^{3'}$ represents primary or secondary alkyl such as methyl, ethyl, and isopropyl; or a benzyl-based protecting group such as benzyl and 4-methoxybenzyl.]

[Step 8-1]
This step is a method of producing compound [8-b] by reacting compound [1-e] with compound [8-a].
This reaction can be carried out by the method described in step 4-1 of production method 4 or a method pursuant thereto.

[Step 8-2]
This step is a method of producing compound [8-c] by removing $Pro^{3'}$ in compound [8-b] under a basic condition.
This reaction can be carried out by the method described in step 5-2 (i) of production method 5 or a method pursuant thereto.

[Step 8-3]
This step is a method of producing compound [8-e] by reacting compound [8-c] with compound [8-d].
This reaction is a so-called condensation reaction that can be carried out by a known method, for example, by using a condensation agent in the presence or absence of a base and an additive.
The amount of compound [8-d] to be used in the present reaction is 1 to 5 equivalents, and preferably 1 to 3 equivalents, with respect to 1 equivalent of compound [8-c].
Examples of the condensation agent include O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), 1-(3-dimethylaminopropyl)-3-ethylcarbodiimide hydrochloride (EDCI), dicyclohexylcarbodiimide (CDI), (1H-benzotriazol-1-yloxy)(tripyrrolidin-1-yl)phosphonium hexafluorophosphate (PyBOP), propylphosphonic anhydride (T3P), and 4-(4,6-dimethoxy-1,3,5-triazin-2-yl)-4-methylmorpholinium chloride (DMT-MM). The amount of the condensation agent to be used is 1 to 5 equivalents, and preferably 1 to 3 equivalents, with respect to 1 equivalent of compound [8-c].
Examples of the additive which is used in the present reaction include N-hydroxybenzotriazole monohydrate (HOBt) and N-hydroxysuccinimide. The amount of the additive to be used is 1 to 5 equivalents, and preferably 1 to 2 equivalents, with respect to 1 equivalent of compound [8-c].
Examples of the base which is used in the present reaction include tertiary aliphatic amines such as N,N-diisopropylethylamine and triethylamine, and pyridine. The amount of the base to be used is 1 to 5 equivalents, and preferably 1 to 2 equivalents, with respect to 1 equivalent of compound [8-c].

Examples of the solvent which is used in the present reaction include solvents that do not interfere with reactions, such as N,N-dimethylformamide, dichloromethane, chloroform, 1,2-dichloroethane, toluene, tetrahydrofuran, and water; and these solvents may be mixed with each other at an appropriate ratio and used.
The present reaction can be carried out usually at 0° C. to reflux temperature for 1 to 24 hours.

[Step 8-4]
This step is a method of producing compound [8-f] by deprotecting the pyrazolyl of compound [8-e] by removing protecting group $Pro^2$ under an acidic condition.
This reaction can be carried out by the method described in step 4-2 of production method 4 or the method described in step 5-4 of production method 5, or a method pursuant thereto.

[Step 8-5]
This step is a method of producing compound [8-g] by deprotecting compound [84] by removing protecting group $Pro^3$.
This reaction can be carried out by the method described in step 5-5 of production method 5 or a method pursuant thereto.
Steps 8-4 and 8-5 above may be carried out in the reversed order.
Compound [8-g] thus obtained can be isolated and purified by known separation and purification means such as concentration, concentration under reduced pressure, reprecipitation, solvent extraction, crystallization, and chromatography.
Incidentally, compounds [1-e], [8-a], and [8-d] which are used as starting compounds in production method 8 above can be produced by production method 1 above, a method pursuant thereto, or a method known per se, or can be obtained by purchasing commercial products.
Among compound [I-1] of the present invention, compound [9-e] in which the structure represented by $R^5$ is a structure represented by formula [IV-3] below and $R^{53}$ is the formula $HOC(=O)-L^1-$ can be produced, for example, by production method 9 below or a method pursuant thereto.

[Formula 279]

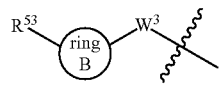

[IV-3]

Production Method 9

[Formula 280]

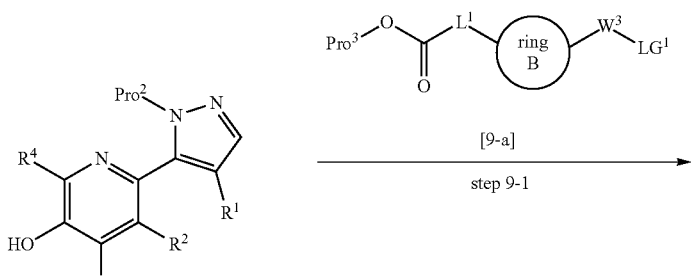

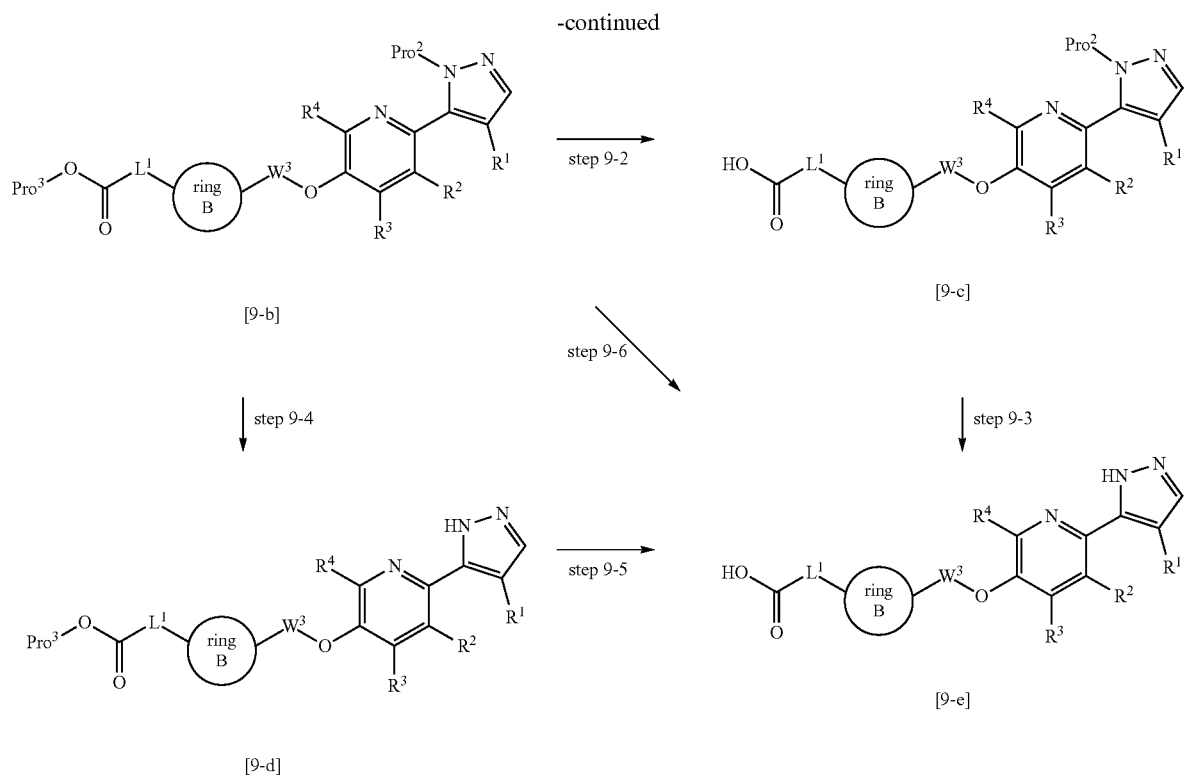

[In the scheme,
$R^1$, $R^2$, $R^3$, $R^4$, $Pro^2$, $Pro^3$, $LG^1$, ring B, and $W^3$ are the same as defined above; and
$L^1$ represents a single bond, the formula —$CH_2$—, or the formula —$CH_2O$— (in these formulas, methanediyl may be replaced with any of the structures represented by formula group [VII].]

[Step 9-1]

This step is a method of producing compound [9-b] by reacting compound [1-e] with compound [9-a].

This reaction can be carried out by the method described in step 4-1 of production method 4 or a method pursuant thereto.

There are several synthesis pathways for production of compound [9-e]. Steps 9-2 to 9-6 therefor will be sequentially described.

(i) When $Pro^3$ in compound [9-b] is primary or secondary alkyl such as methyl, ethyl, and 2-propyl, or (ii) when $Pro^3$ in compound [9-b] is a benzyl-based protecting group such as benzyl and 4-methoxybenzyl, compound [9-e] can be produced via compound [9-c] by methods described in steps 9-2 and 9-3.

[Step 9-2]

This step is a method of producing compound [9-c] by deprotecting compound [9-b] by removing protecting group $Pro^3$.

This reaction can be carried out by the method described in step 5-2 of production method 5 or a method pursuant thereto.

[Step 9-3]

This step is a method of producing compound [9-e] by deprotecting the pyrazolyl of compound [9-c] by removing protecting group $Pro^2$ under an acidic condition.

This reaction can be carried out by the method described in step 4-2 of production method 4 or a method pursuant thereto.

(i) When $Pro^3$ in compound [9-b] is primary or secondary alkyl such as methyl, ethyl, and 2-propyl, (ii) when $Pro^3$ in compound [9-b] is a benzyl-based protecting group such as benzyl and 4-methoxybenzyl, or (iii) when $Pro^3$ in compound [9-b] is tert-butyl, compound [9-e] can be produced via compound [9-d] by methods described in steps 9-4 and 9-5.

[Step 9-4]

This step is a method of producing compound [9-d] by deprotecting the pyrazolyl of compound [9-b] by removing protecting group $Pro^2$ under an acidic condition.

This reaction can be carried out by the method described in step 5-4 of production method 5, or a method pursuant thereto.

[Step 9-5]

This step is a method of producing compound [9-e] by deprotecting compound [9-d] by removing protecting group $Pro^3$.

This reaction can be carried out by the method described in step 5-5 of production method 5 or a method pursuant thereto.

When $Pro^3$ in compound [9-b] is 4-methoxybenzyl or tert-butyl, compound [9-e] can be produced by a method described in step 9-6.

[Step 9-6]

This step is a method of producing compound [9-e] by deprotecting compound [9-b] by removing protecting groups $Pro^2$ and $Pro^3$ under an acidic condition.

This reaction can be carried out by the method described in step 5-5 (iii) of production method 5 or a method pursuant thereto.

Compound [9-e] thus obtained can be isolated and purified by known separation and purification means such as concentration, concentration under reduced pressure, reprecipitation, solvent extraction, crystallization, and chromatography.

Compounds [1-e] and [9-a] which are used as starting compounds in production method 9 above can be produced by production method 1 above, a method pursuant thereto, or a method known per se, or can be obtained by purchasing commercial products.

Alternatively, compound [9-b] can be produced, for example, by production method 10 below or a method pursuant thereto.

Production Method 10

[Formula 281]

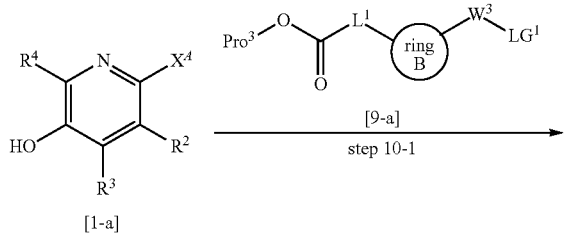

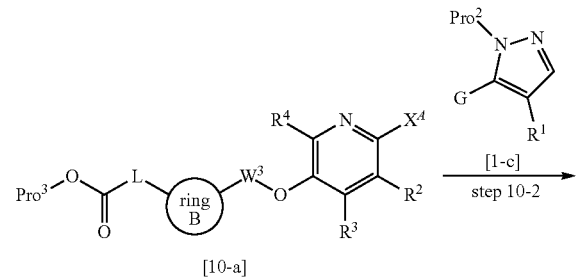

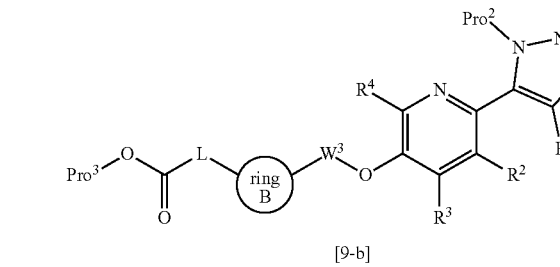

[In the scheme,
$R^1$, $R^2$, $R^3$, $R^4$, $X^4$, $Pro^2$, $Pro^3$, $W^3$, ring B, $L^1$, $LG^1$, and G are the same as defined above.]

[Step 10-1]

This step is a method of producing compound [10-a] by reacting compound [1-a] with compound [9-a].

This reaction can be carried out by the method described in step 4-1 of production method 4 or a method pursuant thereto.

[Step 10-2]

This step is a method of producing compound [9-b] by reacting compound [10-a] with compound [1-c].

This reaction can be carried out by the method described in step 1-2 of production method 1 or a method pursuant thereto.

Compound [9-e] may be derived from compound [9-b] thus obtained by the method described in steps 9-2 to 9-6 of production method 9 or a method pursuant thereto.

Compounds [1-a], [9-a], and [1-c] which are used as starting compounds in production method 10 above can be produced by a method known per se, or can be obtained by purchasing commercial products.

Among compound [I-1] of the present invention, compound [11-g] can be produced, for example, by production method 11 below or a method pursuant thereto.

Production Method 11

[Formula 282]

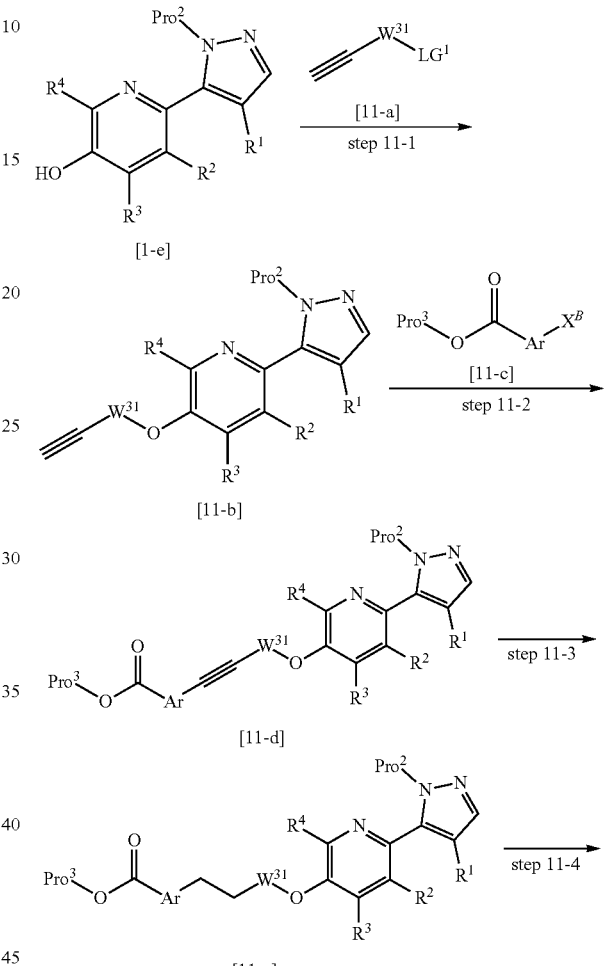

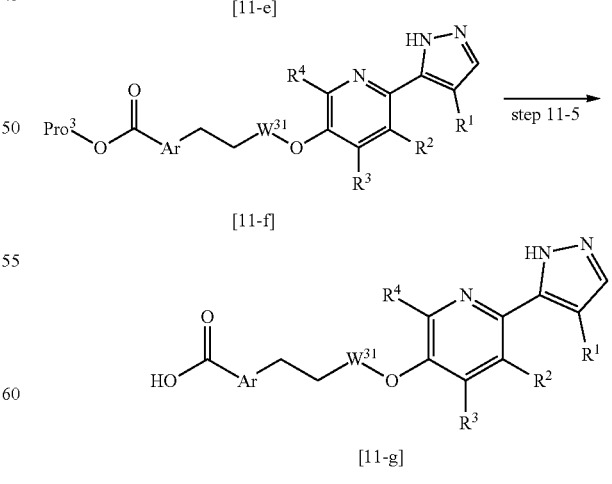

[In the scheme,
$R^1$, $R^2$, $R^3$, $R^4$, $Pro^2$, $Pro^3$, and $LG^1$ are the same as defined above;

$W^{31}$ represents $C_{2-6}$alkanediyl;

Ar represents aryl or heteroaryl; and $X^B$ represents a bromine atom or an iodine atom.]

[Step 11-1]

This step is a method of producing compound [11-b] by reacting compound [1-e] with compound [11-a].

This reaction can be carried out by the method described in step 4-1 of production method 4 or a method pursuant thereto.

[Step 11-2]

This step is a method of producing compound [11-d] by reacting compound [11-b] with compound [11-c].

This reaction is a so-called Sonogashira reaction ("Handbook of Organopalladium Chemistry for Organic Synthesis", Chapter III.2.8., pp 493-535) that can be carried out in the presence of a palladium catalyst, a copper(I) salt, and a base by a process which is described in the literature or a process pursuant thereto.

The amount of compound [11-c] to be used in the present reaction is usually 1 to 5 equivalents, and preferably 1 to 2 equivalents, with respect to 1 equivalent of compound [11-b].

Examples of the palladium catalyst which is used in the present reaction include tetrakis(triphenylphosphine)palladium(0), [1,1'-bis(diphenylphosphino)ferrocene]palladium(II) dichloride dichloromethane complex, and bis(triphenylphosphine)palladium(II) dichloride. The amount of the palladium catalyst to be used is usually 0.001 to 0.5 equivalents, and preferably 0.005 to 0.3 equivalents, with respect to 1 equivalent of compound [11-b].

Examples of the copper(I) salt which is used in the present reaction include copper(I) iodide. The amount of the copper(I) salt to be used is usually 0.01 to 1 equivalent, and preferably 0.02 to 0.3 equivalents, with respect to 1 equivalent of compound [11-b].

Examples of the base which is used in the present reaction include amine such as triethylamine and N,N-diisopropylethylamine. The amount of the base to be used is usually 2 equivalents to a solvent amount, and preferably 2 to 5 equivalents, with respect to 1 equivalent of compound [11-b].

Examples of the reaction solvent which is used in the present reaction include solvents that do not interfere with reactions, such as N,N-dimethylformamide, diethyl ether, 1,4-dioxane, tetrahydrofurane, and 1,2-dimethoxyethane; and these solvents may be mixed with each other at an appropriate ratio and used.

These reactions can be carried out usually at room temperature to reflux temperature for 1 to 24 hours, and can be also carried out under microwave irradiation.

[Step 11-3]

This step is a method of producing compound [11-e] by catalytic hydrogenation of the alkyne of compound [11-d].

This reaction can be carried out in a solvent which does not interfere with the reaction, in the presence of a metal catalyst and a hydrogen source.

Examples of the metal catalyst which is used in the present reaction include palladium carbon, palladium hydroxide carbon, palladium (ethylenediamine complex) carbon, and tris(triphenylphosphine)rhodium(I) chloride. The amount of the metal catalyst to be used is 0.001 to 1 equivalent, and preferably 0.01 to 0.5 equivalents, with respect to 1 equivalent of compound [11-d].

A hydrogen pressure which is used in the present reaction is ordinary pressure to 10 atm, and preferably ordinary pressure to 4 atm.

Examples of the solvent which is used in the present reaction include methanol, ethanol, water, tetrahydrofuran, chloroform, and ethyl acetate; and these solvents may be mixed with each other at an appropriate ratio and used.

The present reaction can be carried out usually at room temperature to reflux temperature for 1 to 24 hours.

[Step 11-4]

This step is a method of producing compound [11-f] by deprotecting the pyrazolyl of compound [11-e] by removing protecting group $Pro^2$ under an acidic condition.

This reaction can be carried out by the method described in step 4-2 of production method 4 or the method described in step 5-4 of production method 5, or a method pursuant thereto.

[Step 11-5]

This step is a method of producing compound [11-g] by deprotecting compound [11-f] by removing protecting group $Pro^3$.

This reaction can be carried out by the method described in step 5-5 of production method 5 or a method pursuant thereto.

Steps 11-4 and 11-5 above may be carried out in the reversed order.

Compound [11-g] thus obtained can be isolated and purified by known separation and purification means such as concentration, concentration under reduced pressure, reprecipitation, solvent extraction, crystallization, and chromatography.

Compounds [1-e], [11-a], and [11-c] which are used as starting compounds in production method 11 above can be produced by production method 1 above, a method pursuant thereto, or a method known per se, or can be obtained by purchasing commercial products.

Among compound [I-1] of the present invention, compound [12-f] can be produced, for example, by production method 12 below or a method pursuant thereto.

Production Method 12

[Formula 283]

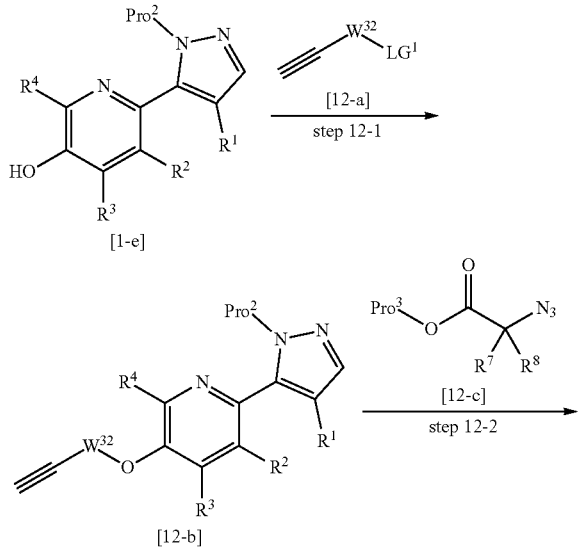

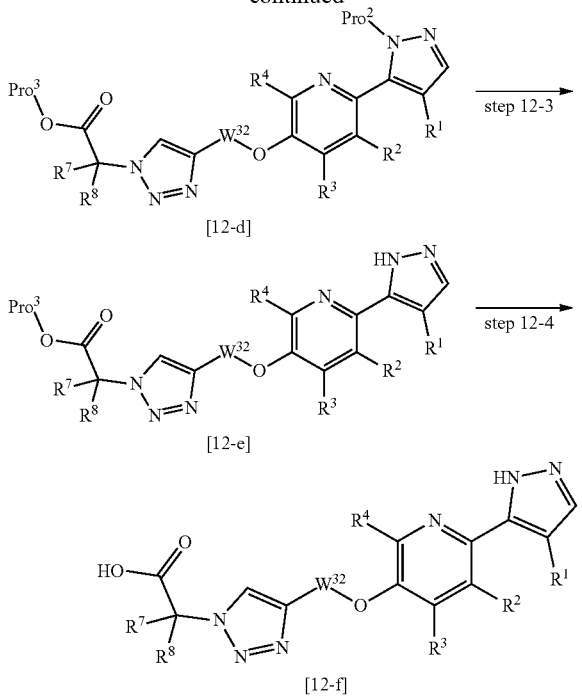

[In the scheme,
R$^1$, R$^2$, R$^3$, R$^4$, Pro$^2$, Pro$^3$, and LG$^1$ are the same as defined above;
R$^7$ and R$^8$ each independently represent a hydrogen atom or methyl,
wherein R$^7$ and R$^8$ may form, together with the adjacent carbon atom, C$_{3-6}$cycloalkane, 4- to 6-membered saturated oxygen-containing hetero ring, 4- to 6-membered saturated sulfur-containing hetero ring (the sulfur atom of the 4- to 6-membered saturated sulfur-containing hetero ring may be substituted with 1 or 2 oxo), or 4- to 6-membered saturated nitrogen-containing hetero ring (the nitrogen atom of the 4- to 6-membered saturated nitrogen-containing hetero ring may be substituted with one C$_{1-4}$alkylcarbonyl); and
W$^{32}$ represents C$_{4-8}$ alkanediyl.]

[Step 12-1]
This step is a method of producing compound [12-b] by reacting compound [1-e] with compound [12-a].
This reaction can be carried out by the method described in step 4-1 of production method 4 or a method pursuant thereto.

[Step 12-2]
This step is a method of producing compound [12-d] by reacting compound [12-b] with compound [12-c].
This reaction is a so-called Huisgen cyclization reaction (Angew. Chem., Int. Ed. Engl. 1963, 2, 565.) that can be carried out using a copper catalyst in the presence or absence of an additive by a process which is described in the literature or a process pursuant thereto.
The amount of compound [12-c] to be used in the present reaction is usually 1 to 5 equivalents, and preferably 1 to 2 equivalents, with respect to compound [12-b].
Examples of the copper catalyst which is used in the present reaction include copper sulfate, copper iodide, copper acetate, and copper trifluoromethanesulfonate-benzene complex. The amount of the copper catalyst to be used is usually 0.01 to 0.5 equivalents, and preferably 0.05 to 0.2 equivalents, with respect to 1 equivalent of compound [12-b].

Examples of the additive which is used in the present reaction include sodium ascorbate. The amount of the additive to be used is usually 0.02 to 1 equivalent, and preferably 0.1 to 0.4 equivalents, with respect to 1 equivalent of compound [12-b].
Examples of the reaction solvent which is used in the present reaction include solvents that do not interfere with reactions, such as N,N-dimethylformamide, ethanol, methanol, 1,4-dioxane, tetrahydrofurane, and water; and these solvents may be mixed with each other at an appropriate ratio and used.
These reactions can be carried out usually at room temperature to reflux temperature for 1 to 24 hours.

[Step 12-3]
This step is a method of producing compound [12-e] by deprotecting the pyrazolyl of compound [12-d] by removing protecting group Pro$^2$ under an acidic condition.
This reaction can be carried out by the method described in step 4-2 of production method 4 or the method described in step 5-4 of production method 5, or a method pursuant thereto.

[Step 12-4]
This step is a method of producing compound [124] by deprotecting compound [12-e] by removing protecting group Pro$^3$.
This reaction can be carried out by the method described in step 5-5 of production method 5 or a method pursuant thereto.

Steps 12-3 and 12-4 above may be carried out in the reversed order.

Compound [124] thus obtained can be isolated and purified by known separation and purification means such as concentration, concentration under reduced pressure, reprecipitation, solvent extraction, crystallization, and chromatography.

Compounds [1-e], [12-a], and [12-c] which are used as starting compounds in production method 12 above can be produced by production method 1 above, a method pursuant thereto, or a method known per se, or can be obtained by purchasing commercial products.

Compound [13-f] as compound [I-1] of the present invention can be produced, for example, by production method 13 below or a method pursuant thereto.

Production Method 13

[Formula 284]

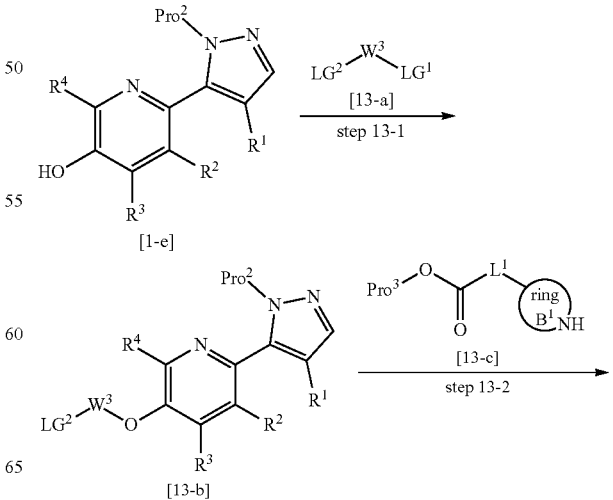

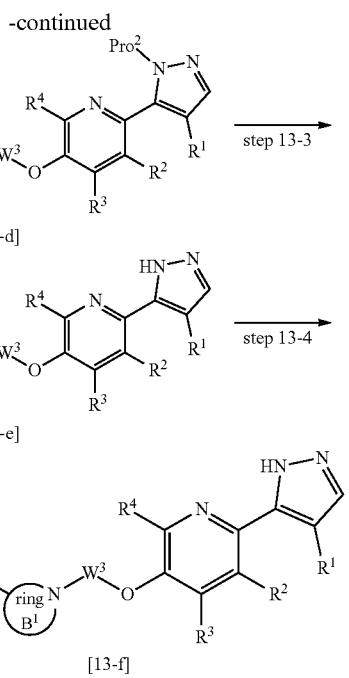

[In the scheme,
R$^1$, R$^2$, R$^3$, R$^4$, Pro$^2$, Pro$^3$, LG$^1$, LG$^2$, W$^3$, and L$^1$ are the same as defined above; and ring B$^1$ represents nitrogen-containing heterocyclyl.]

[Step 13-1]

This step is a method of producing compound [13-b] by reacting compound [1-e] with compound [13-a].

This reaction can be carried out by the method described in step 4-1 of production method 4 or a method pursuant thereto.

[Step 13-2]

This step is a method of producing compound [13-d] by reacting compound [13-b] with compound [13-c].

When LG$^2$ in compound [13-b] is a leaving group, the present reaction can be carried out in the presence of a base.

The amount of compound [13-c] which is used in the present reaction is 1 to 5 equivalents, and preferably 1 to 3 equivalents, with respect to 1 equivalent of compound [13-b].

Examples of the base which is used in the present reaction include amines such as triethylamine, N,N-diisopropylethylamine, and 1,8-diazabicyclo[4,3,0]undec-7-ene, alkali metal hydrides such as sodium hydride, alkali metal hydroxides such as potassium hydroxide, alkali metal carbonates such as cesium carbonate, potassium carbonate, and sodium carbonate, and alkoxy alkali metal such as potassium tert-butoxide. The amount of the base to be used is 1 to 5 equivalents, and preferably 1 to 3 equivalents, with respect to 1 equivalent of compound [13-b].

Examples of the solvent which is used in the present reaction include solvents that do not interfere with reactions, such as tetrahydrofuran, dimethyl sulfoxide, N,N-dimethylformamide, N,N-dimethylacetamide, and N-methylpyrrolidone; and these solvents may be mixed with each other at an appropriate ratio and used.

The present reaction can be carried out usually at room temperature to reflux temperature for 1 to 24 hours.

When LG$^2$ in compound [13-b] is hydroxy, the present reaction can also be carried out after hydroxy is converted to a leaving group.

The hydroxy may be converted to a leaving group by a usual method. For example, compound [13-b] in which LG$^2$ is a leaving group may be prepared by the reaction with (a) a halogenating reagent or (b) a sulfonate esterification reagent in the presence of a base in a solvent which does not interfere with the reaction.

Examples of (a) halogenating reagent used in the present reaction include thionyl chloride, phosphoryl chloride, N-chlorosuccinimide, bromine, and N-bromosuccinimide. The amount of the halogenating reagent to be used is 1 to 5 equivalents, and preferably 1 to 3 equivalents, with respect to 1 equivalent of the compound having hydroxy.

Examples of the solvent which is used in the present reaction include solvents that do not interfere with reactions, such as chloroform and dichloromethane; and these solvents may be mixed with each other at an appropriate ratio and used.

The present reaction can be carried out usually at room temperature to reflux temperature for 1 to 24 hours.

Furthermore, examples of (b) sulfonate esterification reagent used in the present reaction include methanesulfonyl chloride, trifluoromethanesulfonyl chloride, and p-toluenesulfonyl chloride. The amount of the sulfonate esterification reagent to be used is 1 to 5 equivalents, and preferably 1 to 3 equivalents, with respect to 1 equivalent of the compound having hydroxy.

Examples of the base which is used in the present reaction include triethylamine, N,N-diisopropylethylamine, pyridine, and 4-dimethylaminopyridine. The amount of the base to be used is 1 to 5 equivalents, and preferably 1 to 3 equivalents, with respect to 1 equivalent of the sulfonate esterification reagent to be used.

Examples of the solvent which is used in the present reaction include solvents that do not interfere with reactions, such as chloroform and dichloromethane; and these solvents may be mixed with each other at an appropriate ratio and used.

The present reaction can be carried out usually at room temperature to reflux temperature for 1 to 24 hours.

[Step 13-3]

This step is a method of producing compound [13-e] by deprotecting the pyrazolyl of compound [13-d] by removing protecting group Pro$^2$ under an acidic condition.

This reaction can be carried out by the method described in step 4-2 of production method 4 or the method described in step 5-4 of production method 5, or a method pursuant thereto.

[Step 13-4]

This step is a method of producing compound [134] by deprotecting compound [13-e] by removing protecting group Pro$^3$.

This reaction can be carried out by the method described in step 5-5 of production method 5 or a method pursuant thereto.

Steps 13-3 and 13-4 above may be carried out in the reversed order.

Compound [134] thus obtained can be isolated and purified by known separation and purification means such as concentration, concentration under reduced pressure, reprecipitation, solvent extraction, crystallization, and chromatography.

Compounds [1-e], [13-a], and [13-c] which are used as starting compounds in production method 13 above can be produced by production method 1 above, a method pursuant thereto, or a method known per se, or can be obtained by purchasing commercial products.

Among compound [I-1] of the present invention, compound [14-e] in which the structure represented by $R^5$ is a structure represented by formula [1V-4] below and $R^{54}$ is the formula $HOC(=O)-R^{54'}-$ can be produced, for example, by production method 14 below or a method pursuant thereto.

[In the scheme,
$R^1, R^2, R^3, R^4, Pro^2, Pro^3, LG^1$, ring C, $W^4, R^{61}$, and $R^{62}$ are the same as defined above; and a group represented by formula [IV-4'] below represents a group below selected from $R^{54}$;

[Formula 285]

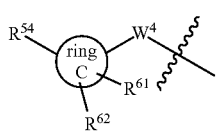

[IV-4]

[Formula 287]

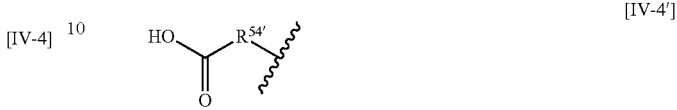

[IV-4']

wherein
(a) when ring C is $C_{3-6}$cycloalkyl,
the group represented by formula [IV-4'] above is carboxy, or
$C_{1-4}$ alkyl substituted with carboxy;

Production Method 14

[Formula 286]

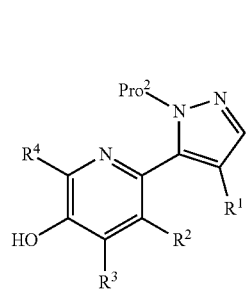

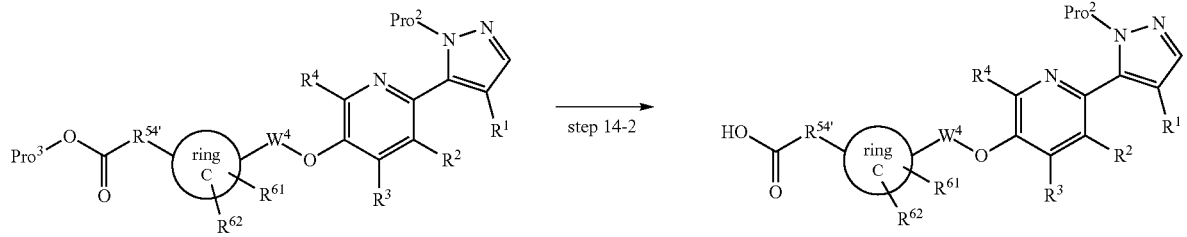

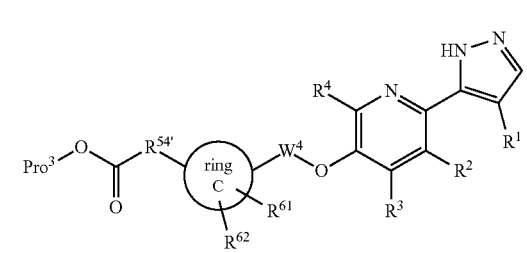

(b) when ring C is 4- to 6-membered saturated nitrogen-containing heterocyclyl, the group represented by formula [IV-4'] above is $C_{1-4}$ alkylcarbonyl substituted with carboxy,
phenylmethylcarbonyl substituted with carboxy,
phenylsulfonyl substituted with carboxy,
mono$C_{1-4}$alkylaminocarbonyl substituted with carboxy,
the structure represented by formula [X-1] below, which is substituted with carboxy,
the structure represented by formula [X-2] below, which is substituted with carboxy, or
the structure represented by formula [X-3] below, which is substituted with carboxy,

[Formula 288]
[X]

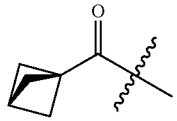
[X-1]

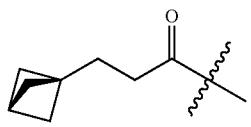
[X-2]

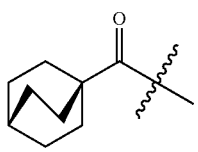
[X-3]

wherein when position α of the carboxy of the $C_{1-4}$alkylcarbonyl substituted with carboxy, $C_{1-4}$alkylsulfonyl substituted with carboxy, and mono$C_{1-4}$alkylaminocarbonyl substituted with carboxy is a methylene moiety, the methylene moiety may be replaced with a structure selected from structure group α above;

(c) when ring C is phenyl,
the group represented by formula [IV-4'] above is
carboxy,
$C_{1-4}$ alkyl substituted with carboxy (when position α of the carboxy of the $C_{1-4}$ alkyl substituted with carboxy is a methylene moiety, the methylene moiety may be replaced with a structure selected from structure group α above),
halo-$C_{1-4}$alkyl substituted with carboxy,
$C_{2-4}$ alkenyl substituted with carboxy,
$C_{3-6}$cycloalkyl substituted with carboxy,
4- to 6-membered saturated nitrogen-containing heterocyclyl substituted with carboxy,
phenyl substituted with carboxy,
pyridyl substituted with carboxy,
pyrazolyl substituted with carboxy,
pyrazolyl substituted with carboxymethyl (the methylene moiety at position α of the carboxy of the pyrazolyl substituted with carboxymethyl may be replaced with a structure selected from structure group α above),
pyrimidinyl substituted with carboxy,
pyrazinyl substituted with carboxy, 2-oxodihydropyridinyl substituted with carboxymethyl (the methylene moiety at position α of the carboxy of the 2-oxodihydropyridinyl substituted with carboxymethyl may be replaced with a structure selected from structure group α above),
mono$C_{1-4}$ alkylaminocarbonyl substituted with carboxy (the $C_{1-4}$ alkyl of the mono$C_{1-4}$alkylaminocarbonyl substituted with carboxy may be substituted with one group selected from the group consisting of phenyl and benzyl, and when position α of the carboxy of the mono$C_{1-4}$ alkylaminocarbonyl substituted with carboxy is a methylene moiety, the methylene moiety may be replaced with a structure selected from structure group α above),
phenyl$C_{1-4}$ alkylaminocarbonyl substituted with carboxy,
di($C_{1-4}$ alkyl)aminocarbonyl substituted with carboxy (when position α of the carboxy of the di($C_{1-4}$ alkyl) aminocarbonyl substituted with carboxy is a methylene moiety, the methylene moiety may be replaced with a structure selected from structure group α above),
$C_{3-6}$ cycloalkylaminocarbonyl substituted with carboxy,
4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom),
4- to 6-membered saturated nitrogen-containing heterocyclylcarbonyl substituted with carboxymethyl (the methylene moiety at position α of the carboxy of the 4- to 6-membered saturated nitrogen-containing heterocyclylcarbonyl substituted with carboxymethyl may be replaced with a structure selected from structure group α above),
the structure represented by formula [XI-1] below, which is substituted with carboxy,
the structure represented by formula [XI-2] below, which is substituted with carboxy,
the structure represented by formula [XI-3] below, which is substituted with carboxy,
the structure represented by formula [XI-4] below, which is substituted with carboxy,
the structure represented by formula [XI-5] below, which is substituted with carboxy,
the structure represented by formula [XI-6] below, which is substituted with carboxy,

[Formula 289]
[XI]

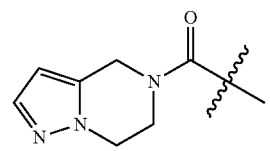
[XI-1]

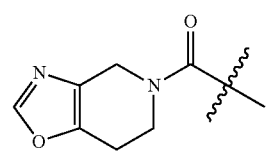
[XI-2]

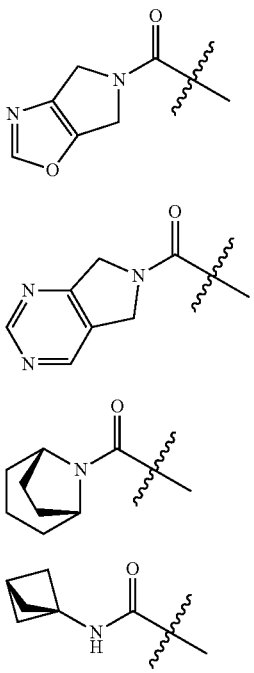

[XI-3]

[XI-4]

[XI-5]

[XI-6]

C$_{1-4}$alkylsulfonyl substituted with carboxy (when position α of the carboxy of the C$_{1-4}$alkylsulfonyl substituted with carboxy is a methylene moiety, the methylene moiety may be replaced with a structure selected from structure group α above), monoC$_{1-4}$alkylaminosulfonyl substituted with carboxy (when position α of the carboxy of the monoC$_{1-4}$alkylaminosulfonyl substituted with carboxy is a methylene moiety, the methylene moiety may be replaced with a structure selected from structure group α above), di(C$_{1-4}$alkyl)aminosulfonyl substituted with carboxy (when position α of the carboxy of the di(C$_{1-4}$alkyl)aminosulfonyl substituted with carboxy is a methylene moiety, the methylene moiety may be replaced with a structure selected from structure group α above), 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy may be substituted with one fluorine atom), C$_{1-4}$ alkoxy substituted with carboxy (when position α of the carboxy of the C$_{1-4}$ alkoxy substituted with carboxy is a methylene moiety, the methylene moiety may be replaced with a structure selected from structure group α above), or C$_{3-6}$ cycloalkyl substituted with hydroxy (the C$_{3-6}$cycloalkyl of the C$_{3-6}$cycloalkyl substituted with hydroxy is substituted with one carboxy);

(d) when ring C is pyridyl,
the group represented by formula [IV-4'] above is
(i) carboxy,
(iii) C$_{1-4}$ alkyl substituted with carboxy,
(iv) C$_{1-4}$ alkoxy substituted with carboxy,
(v) monoC$_{1-4}$ alkylaminocarbonyl substituted with carboxy, or (vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), wherein when position α of the carboxy of the C$_{1-4}$ alkyl substituted with carboxy, C$_{1-4}$ alkoxy substituted with carboxy, and monoC$_{1-4}$ alkylaminocarbonyl substituted with carboxy is a methylene moiety, the methylene moiety may be replaced with a structure selected from structure group α above;

(e) when ring C is pyrazolyl,
the group represented by formula [IV-4'] above is carboxy;
(f) when ring C is triazolyl,
the group represented by formula [IV-4] above is C$_{1-4}$ alkyl substituted with carboxy, wherein when position α of the carboxy of the C$_{1-4}$ alkyl substituted with carboxy is a methylene moiety, the methylene moiety may be replaced with a structure selected from structure group α above;

(g) when ring C is tetrahydronaphthyl,
the group represented by formula [IV-4'] above is carboxy;
(h) when ring C is chromanyl,
the group represented by formula [IV-4'] above is carboxy;
(j) when ring C is indazolyl,
the group represented by formula [IV-4] above is C$_{1-4}$ alkyl substituted with carboxy, wherein when position α of the carboxy of the C$_{1-4}$ alkyl substituted with carboxy is a methylene moiety, the methylene moiety may be replaced with a structure selected from structure group α above;

(k) when ring C is tetrahydroisoquinolyl,
the group represented by formula [IV-4] above is C$_{1-4}$ alkylcarbonyl substituted with carboxy, wherein when position α of the carboxy of the C$_{1-4}$ alkylcarbonyl substituted with carboxy is a methylene moiety, the methylene moiety may be replaced with a structure selected from structure group α above;

(m) when ring C is 2-oxotetrahydroisoquinolyl,
the group represented by formula [IV-4] above is C$_{1-4}$ alkyl substituted with carboxy, wherein when position α of the carboxy of the C$_{1-4}$ alkyl substituted with carboxy is a methylene moiety, the methylene moiety may be replaced with a structure selected from structure group α above;

(n) when ring C is the group represented by formula [IX-1] above, the group represented by formula [IV-4] above is
carboxy, or
C$_{1-4}$ alkyl substituted with C$_{1-4}$ alkylsulfonylamino (the C$_{1-4}$ alkyl of the C$_{1-4}$alkylsulfonylamino of the C$_{1-4}$ alkyl substituted with C$_{1-4}$ alkylsulfonylamino is substituted with one carboxy), wherein when the group represented by formula [IV-4] above is (ii) C$_{1-4}$ alkyl substituted with C$_{1-4}$ alkylsulfonylamino, and the C$_{1-4}$ alkyl of the C$_{1-4}$ alkylsulfonylamino of the C$_{1-4}$ alkyl substituted with C$_{1-4}$ alkylsulfonylamino is substituted with one carboxy, and if position α of the carboxy of C$_{1-4}$ alkylsulfonylamino substituted with carboxy is a methylene moiety, the methylene moiety may be replaced with a structure selected from structure group α above;

(p) when ring C is the group represented by formula [IX-2] above, the group represented by formula [IV-4] above is carboxy;

(q) when ring C is the group represented by formula [IX-3] above, the group represented by formula [IV-4] above is
carboxy, or
C$_{1-4}$ alkyl substituted with carboxy, wherein when position α of the carboxy of the $C_{1-4}$ alkyl substituted with carboxy is a methylene moiety, the methylene moiety may be replaced with a structure selected from structure group α above;

(r) when ring C is the group represented by formula [IX-4] above, the group represented by formula [IV-4] above is carboxy.]

[Step 14-1]

This step is a method of producing compound [14-b] by reacting compound [1-e] with compound [14-a].

This reaction can be carried out by the method described in step 4-1 of production method 4 or a method pursuant thereto.

There are several synthesis pathways for production of compound [14-e]. Steps 14-2 to 14-6 therefor will be sequentially described.

(i) When $Pro^3$ in compound [14-b] is primary or secondary alkyl such as methyl, ethyl, and 2-propyl, or (ii) when $Pro^3$ in compound [14-b] is a protecting group such as benzyl and 4-methoxybenzyl, compound [14-e] can be produced via compound [14-c] by methods described in steps 14-2 and 14-3.

[Step 14-2]

This step is a method of producing compound [14-c] by deprotecting compound [14-b] by removing protecting group $Pro^3$.

This reaction can be carried out by the method described in step 5-2 of production method 5 or a method pursuant thereto.

[Step 14-3]

This step is a method of producing compound [14-e] by deprotecting the pyrazolyl of compound [14-c] by removing protecting group $Pro^2$ under an acidic condition.

This reaction can be carried out by the method described in step 4-2 of production method 4 or a method pursuant thereto.

(i) When $Pro^3$ in compound [14-b] is primary or secondary alkyl such as methyl, ethyl, and 2-propyl, (ii) when $Pro^3$ in compound [14-b] is a protecting group such as benzyl and 4-methoxybenzyl, or (iii) when $Pro^3$ in compound [14-b] is tert-butyl, compound [14-e] can be produced via compound [14-d] by methods described in steps 14-4 and 14-5.

[Step 14-4]

This step is a method of producing compound [14-d] by deprotecting the pyrazolyl of compound [14-b] by removing protecting group $Pro^2$ under an acidic condition.

This reaction can be carried out by the method described in step 5-4 of production method 5 or a method pursuant thereto.

[Step 14-5]

This step is a method of producing compound [14-e] by deprotecting compound [14-d] by removing protecting group $Pro^3$.

This reaction can be carried out by the method described in step 5-5 of production method 5 or a method pursuant thereto.

When $Pro^3$ in compound [14-b] is 4-methoxybenzyl or tert-butyl, compound [14-e] can be produced by step 14-6.

[Step 14-6]

This step is a method of producing compound [14-e] by deprotecting compound [14-b] by removing protecting groups $Pro^2$ and $Pro^3$ under an acidic condition.

This reaction can be carried out by the method described in step 5-5 (iii) of production method 5 or a method pursuant thereto.

Compound [14-e] thus obtained can be isolated and purified by known separation and purification means such as concentration, concentration under reduced pressure, reprecipitation, solvent extraction, crystallization, and chromatography.

Compounds [1-e] and [14-a] which are used as starting compounds in production method 14 above can be produced by production method 1 above, a method pursuant thereto, or a method known per se, or can be obtained by purchasing commercial products.

Alternatively, compound [14-b] can be produced, for example, by production method 15 below or a method pursuant thereto.

Production Method 15

[Formula 290]

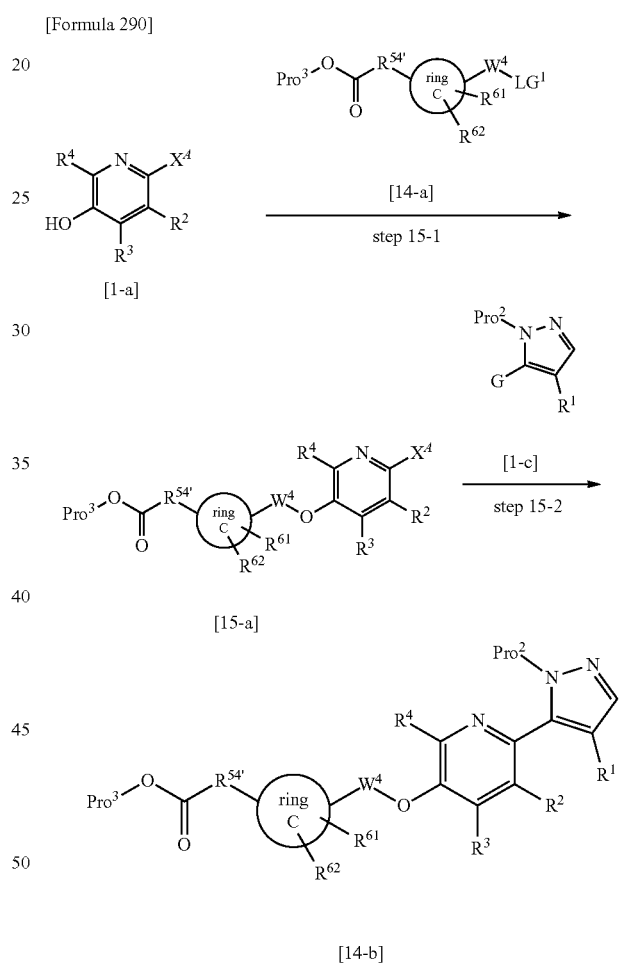

[In the scheme,
$R^1$, $R^2$, $R^3$, $R^4$, $R^{54'}$, $R^{61}$, $R^{62}$, $X^4$, $Pro^2$, $Pro^3$, $W^4$, ring C, $LG^1$, and G are the same as defined above.]

[Step 15-1]

This step is a method of producing compound [15-a] by reacting compound [1-a] with compound [14-a].

This reaction can be carried out by the method described in step 4-1 of production method 4 or a method pursuant thereto.

[Step 15-2]

This step is a method of producing compound [14-b] by reacting compound [15-a] with compound [1-c].

This reaction can be carried out by the method described in step 1-2 of production method 1 or a method pursuant thereto.

Compound [14-e] may be derived from compound [14-b] thus obtained by the method described in steps 14-2 to 14-6 of production method 14 or a method pursuant thereto.

Compounds [1-a], [14-a], and [1-c] which are used as starting compounds in production method 15 above can be produced by a method known per se, or can be obtained by purchasing commercial products.

Among compound [I-1] of the present invention, compound [16-f] can be produced, for example, by production method 16 below or a method pursuant thereto.

Production Method 16

[Formula 291]

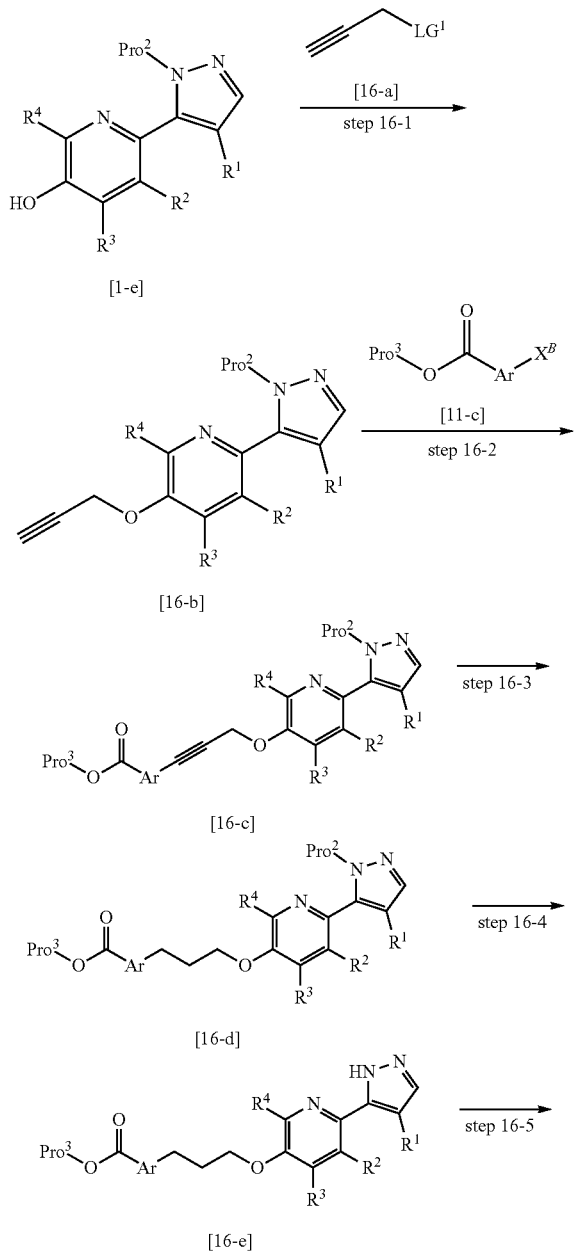

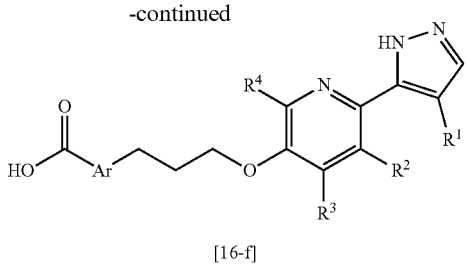

[In the scheme,
$R^1$, $R^2$, $R^3$, $R^4$, $Pro^2$, $Pro^3$, $LG^1$, Ar and $X^B$ are the same as defined above.]

[Step 16-1]

This step is a method of producing compound [16-b] by reacting compound [1-e] with compound [16-a].

This reaction can be carried out by the method described in step 4-1 of production method 4 or a method pursuant thereto.

[Step 16-2]

This step is a method of producing compound [16-c] by reacting compound [16-b] with compound [11-c].

This reaction can be carried out by the method described in step 11-2 of production method 11 or a method pursuant thereto.

[Step 16-3]

This step is a method of producing compound [16-d] by catalytic hydrogenation of the alkyne of compound [16-c].

This reaction can be carried out by the method described in step 11-3 of production method 11 or a method pursuant thereto.

[Step 16-4]

This step is a method of producing compound [16-e] by deprotecting the pyrazolyl of compound [16-d] by removing protecting group $Pro^2$ under an acidic condition.

This reaction can be carried out by the method described in step 4-2 of production method 4 or the method described in step 5-4 of production method 5, or a method pursuant thereto.

[Step 16-5]

This step is a method of producing compound [164] by deprotecting compound [16-e] by removing protecting group $Pro^3$.

This reaction can be carried out by the method described in step 5-5 of production method 5 or a method pursuant thereto.

Steps 16-4 and 16-5 above may be carried out in the reversed order.

Compound [164] thus obtained can be isolated and purified by known separation and purification means such as concentration, concentration under reduced pressure, reprecipitation, solvent extraction, crystallization, and chromatography.

Compounds [1-e], [11-c], and [16-a] which are used as starting compounds in production method 16 above can be produced by production method 1 above, a method pursuant thereto, or a method known per se, or can be obtained by purchasing commercial products.

Among compound [I-1] of the present invention, compound [17-g] can be produced, for example, by production method 17 below or a method pursuant thereto.

Production Method 17

[Formula 292]

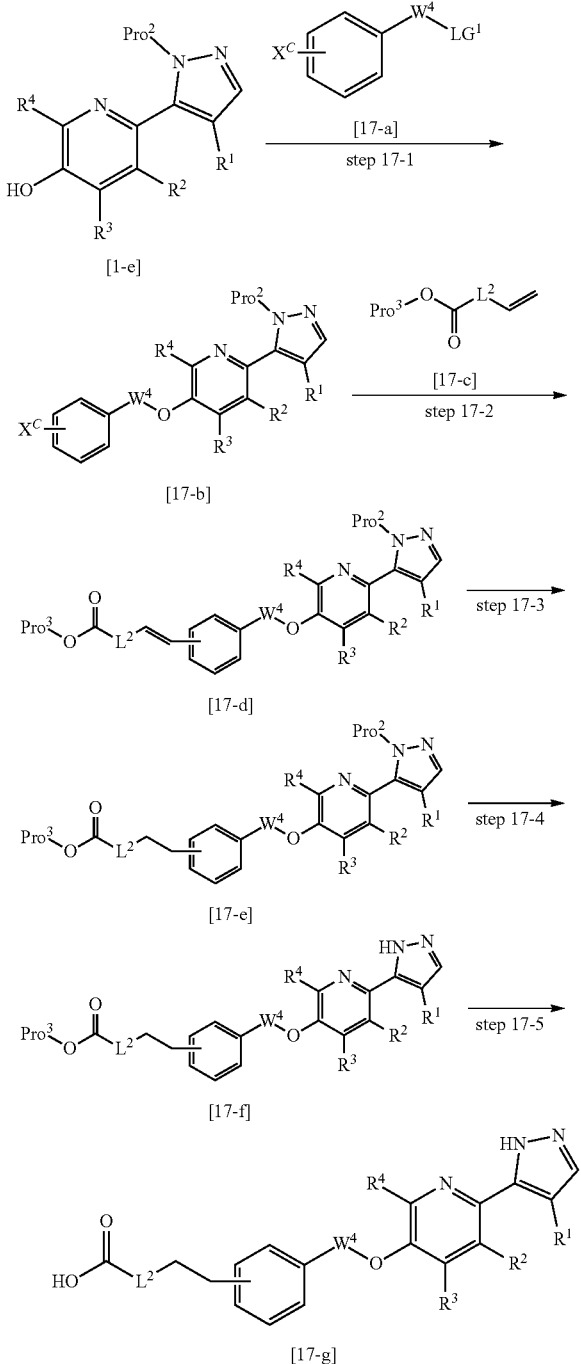

R¹, R², R³, R⁴, Pro², Pro³, W⁴, LG¹, and Pro³ are the same as defined above;

$X^C$ represents a bromine atom or an iodine atom; and $L^2$ represents a single bond or methanediyl.]

[Step 17-1]

This step is a method of producing compound [17-b] by reacting compound [1-e] with compound [17-a].

This reaction can be carried out by the method described in step 4-1 of production method 4 or a method pursuant thereto.

[Step 17-2]

This step is a method of producing compound [17-d] by reacting compound [17-b] with compound [17-c].

This reaction is a so-called Heck reaction that can be carried out in the presence of a palladium catalyst and a base by a process which is described in the literature (Angewandte Chemie International Edition in English, Volume 33, page 2379, 1995) or a process pursuant thereto.

The amount of compound [17-c] to be used in the present reaction is usually 1 to 5 equivalents, and preferably 1 to 1.5 equivalents, with respect to 1 equivalent of compound [17-b].

Examples of the palladium catalyst which is used in the present reaction include tetrakis(triphenylphosphine)palladium(0), [1,1'-bis(diphenylphosphino)ferrocene]palladium(II) dichloride dichloromethane adduct, and bis(triphenylphosphine)palladium(II) dichloride. The amount of the palladium catalyst to be used in the present reaction is usually 0.01 to 0.2 equivalents, and preferably 0.01 to 0.1 equivalents, with respect to 1 equivalent of compound [17-b].

Examples of the base which is used in the present reaction include triethylamine, N-ethyl-N,N-diisopropylamine, potassium carbonate, calcium carbonate, cesium carbonate, potassium t-butoxide, and potassium acetate. The amount of the base to be used in the present reaction is usually 1 to 5 equivalents, and preferably 1 to 3 equivalents, with respect to 1 equivalent of compound [17-b].

Examples of the solvent which is used in the present reaction include solvents that do not interfere with reactions, such as acetonitrile, toluene, tetrahydrofuran, and N,N-dimethylformamide; and these solvents may be mixed with each other at an appropriate ratio and used.

These reactions can be carried out usually at room temperature to reflux temperature for 1 to 24 hours, and can be also carried out under microwave irradiation.

[Step 17-3]

This step is a method of producing compound [17-e] by catalytic hydrogenation of the alkene of compound [17-d].

This reaction can be carried out by the method described in step 11-3 of production method 11 or a method pursuant thereto.

[Step 17-4]

This step is a method of producing compound [174] by deprotecting the pyrazolyl of compound [17-e] by removing protecting group Pro² under an acidic condition.

This reaction can be carried out by the method described in step 4-2 of production method 4 or the method described in step 5-4 of production method 5, or a method pursuant thereto.

[Step 17-5]

This step is a method of producing compound [17-g] by deprotecting compound [17-f] by removing protecting group Pro³.

This reaction can be carried out by the method described in step 5-5 of production method 5 or a method pursuant thereto.

Steps 17-4 and 17-5 above may be carried out in the reversed order.

Compound [17-g] thus obtained can be isolated and purified by known separation and purification means such as concentration, concentration under reduced pressure, reprecipitation, solvent extraction, crystallization, and chromatography.

Compounds [1-e], [17-a], and [17-c] which are used as starting compounds in production method 17 above can be produced by production method 1 above, a method pursuant thereto, or a method known per se, or can be obtained by purchasing commercial products.

Among compound [I-1] of the present invention, compound [18-d] can be produced, for example, by production method 18 below or a method pursuant thereto.

Production Method 18

[Formula 293]

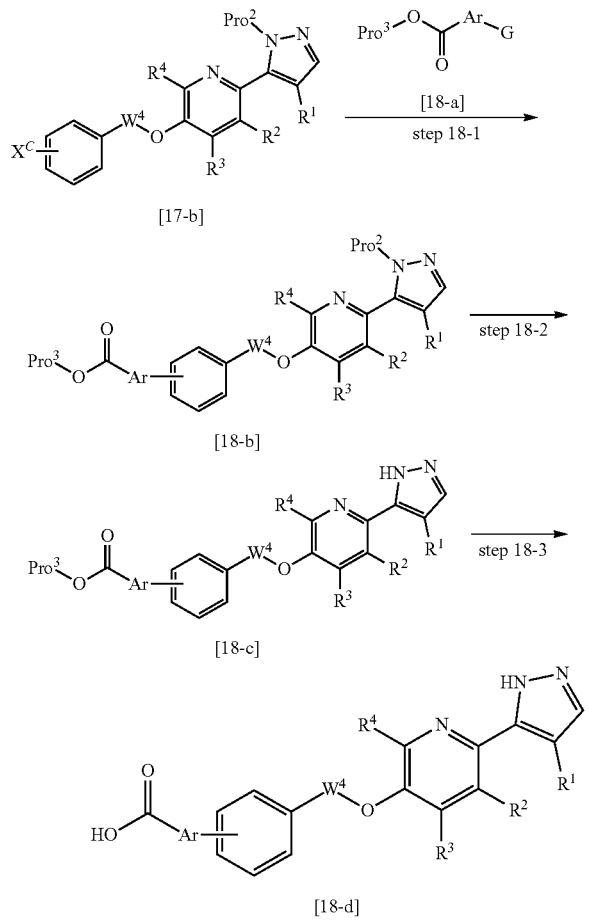

[In the scheme,
$R^1$, $R^2$, $R^3$, $R^4$, $Pro^2$, $Pro^3$, $W^4$, $X^C$, Ar, and G are the same as defined above.]

[Step 18-1]
This step is a method of producing compound [18-b] by reacting compound [17-b] with compound [18-a].

This reaction can be carried out by the method described in step 1-2 of production method 1 or a method pursuant thereto.

[Step 18-2]
This step is a method of producing compound [18-c] by deprotecting the pyrazolyl of compound [18-b] by removing protecting group $Pro^2$ under an acidic condition.

This reaction can be carried out by the method described in step 4-2 of production method 4 or the method described in step 5-4 of production method 5, or a method pursuant thereto.

[Step 18-3]
This step is a method of producing compound [18-d] by deprotecting compound [18-c] by removing protecting group $Pro^3$.

This reaction can be carried out by the method described in step 5-5 of production method 5 or a method pursuant thereto.

Steps 18-2 and 18-3 above may be carried out in the reversed order.

Compound [18-d] thus obtained can be isolated and purified by known separation and purification means such as concentration, concentration under reduced pressure, reprecipitation, solvent extraction, crystallization, and chromatography.

Compounds [17-b] and [18-a] which are used as starting compounds in production method 18 above can be produced by production method 17 above, a method pursuant thereto, or a method known per se, or can be obtained by purchasing commercial products.

Among compound [I-1] of the present invention, compound [19-d] can be produced, for example, by production method 19 below or a method pursuant thereto.

Production Method 19

[Formula 294]

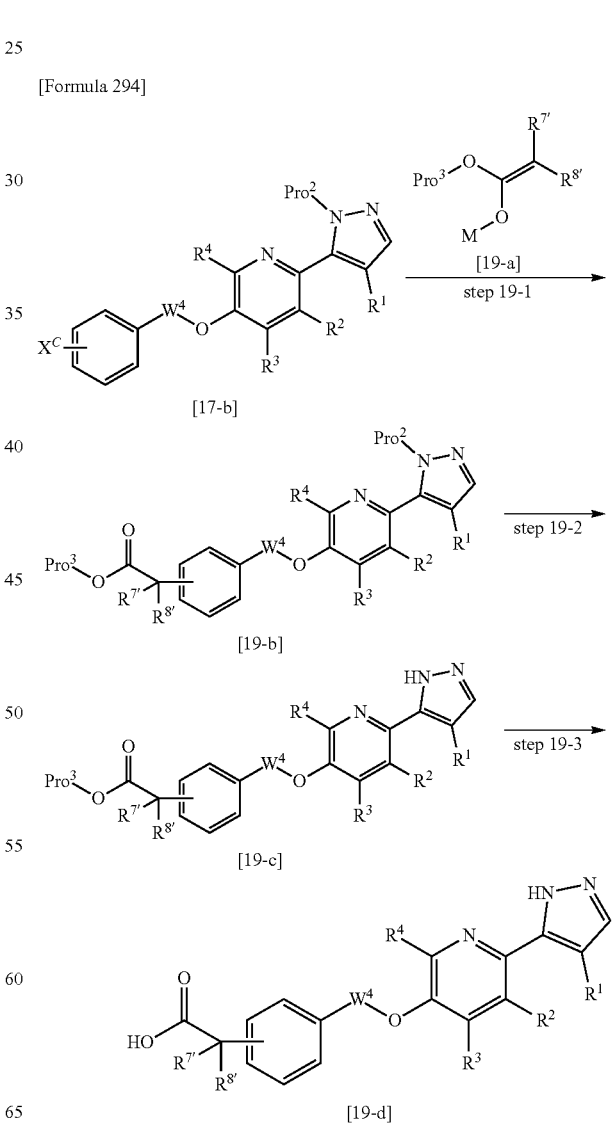

[In the scheme,
R$^1$, R$^2$, R$^3$, R$^4$, Pro$^2$, Pro$^3$, W$^4$, and X$^C$ are the same as defined above;
R$^{7'}$ and R$^{8'}$ each independently represent a hydrogen atom or methyl,
wherein R$^{7'}$ and R$^{8'}$ may form, together with the adjacent carbon atom, C$_{3-6}$cycloalkane, 4- to 6-membered saturated oxygen-containing hetero ring, or 4- to 6-membered saturated sulfur-containing hetero ring (the sulfur atom of the 4- to 6-membered saturated sulfur-containing hetero ring may be substituted with 1 or 2 oxo); and
M represents a metal such as lithium and zinc.]

[Step 19-1]

This step is a method of producing compound [19-b] by reacting compound [17-b] with compound [19-a].

This reaction can be carried out by reacting compound [19-a] with compound [17-b] in the presence of a palladium catalyst, wherein compound [19-a] is (i) generated by allowing a metal fluoride to react with a silylenol ether, or (ii) generated by allowing a metal amide to react with an ester.

(i) When compound [19-a] is generated by allowing a metal fluoride to react with a silylenol ether, the amount of the silylenol ether to be used in the present reaction is 1 to 5 equivalents, and preferably 1 to 2 equivalents, with respect to 1 equivalent of compound [17-b].

Examples of the metal fluoride which is used in the present reaction include cesium fluoride and zinc fluoride. The amount of the metal fluoride to be used is 1 to 5 equivalents, and preferably 1 to 2 equivalents, with respect to 1 equivalent of compound [17-b].

(ii) When compound [19-a] is generated by allowing a metal amide to react with an ester, the amount of the ester to be used in the present reaction is 1 to 5 equivalents, and preferably 1 to 2 equivalents, with respect to 1 equivalent of compound [17-b].

Examples of the metal amide which is used in the present reaction include lithium diisopropylamide (LDA) and lithium bis(trimethylsilyl)amide (LHMDS). The amount of the metal amide to be used is 1 to 5 equivalents, and preferably 1 to 2 equivalents, with respect to 1 equivalent of compound [17-b].

Examples of the reaction solvent which is used in the present reaction include solvents that do not interfere with reactions, such as toluene, 1,4-dioxane, tetrahydrofuran, and 1,2-dimethoxyethane; and these solvents may be mixed with each other at an appropriate ratio and used.

These reactions can be carried out usually at room temperature to reflux temperature for 1 to 24 hours, and can be also carried out under microwave irradiation.

[Step 19-2]

This step is a method of producing compound [19-c] by deprotecting the pyrazolyl of compound [19-b] by removing protecting group Pro$^2$ under an acidic condition.

This reaction can be carried out by the method described in step 4-2 of production method 4 or the method described in step 5-4 of production method 5, or a method pursuant thereto.

[Step 19-3]

This step is a method of producing compound [19-d] by deprotecting compound [19-c] by removing protecting group Pro$^3$.

This reaction can be carried out by the method described in step 5-5 of production method 5 or a method pursuant thereto.

Steps 19-2 and 19-3 above may be carried out in the reversed order.

Compound [19-d] thus obtained can be isolated and purified by known separation and purification means such as concentration, concentration under reduced pressure, reprecipitation, solvent extraction, crystallization, and chromatography.

Compound [17-b] which is used as a starting compound in production method 19 above, and the silylenol ether and the ester which are used to generate compound [19-a] can be produced by production method 17 above, a method pursuant thereto, or a method known per se, or can be obtained by purchasing commercial products.

Among compound [I-1] of the present invention, compound [20-f] can be produced, for example, by production method 20 below or a method pursuant thereto.

Production Method 20

[Formula 295]

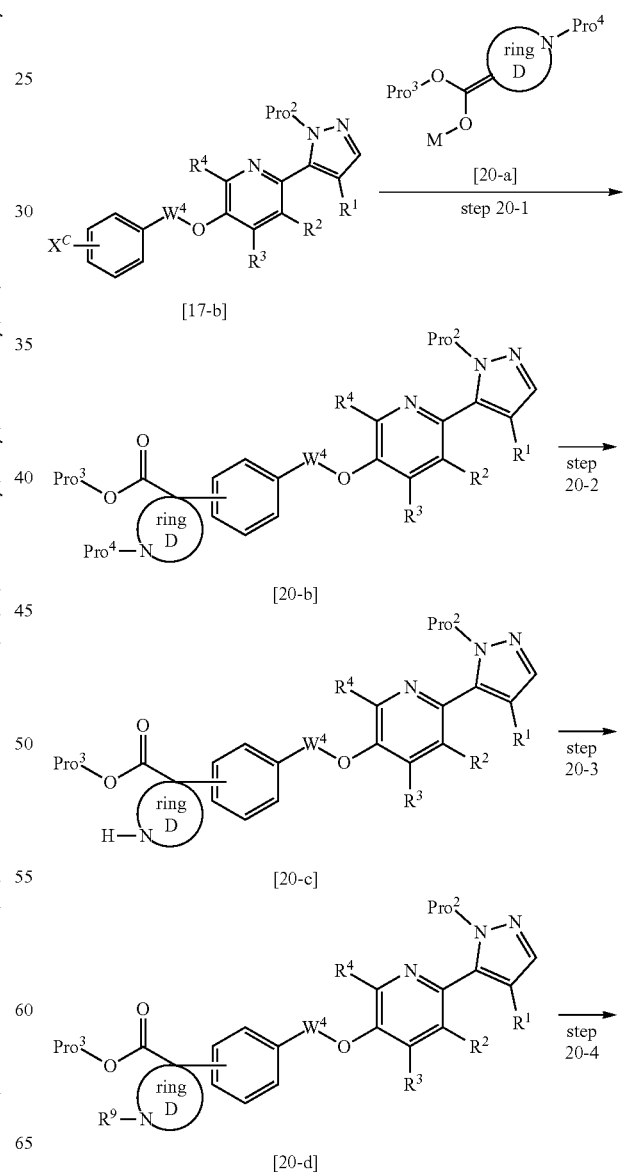

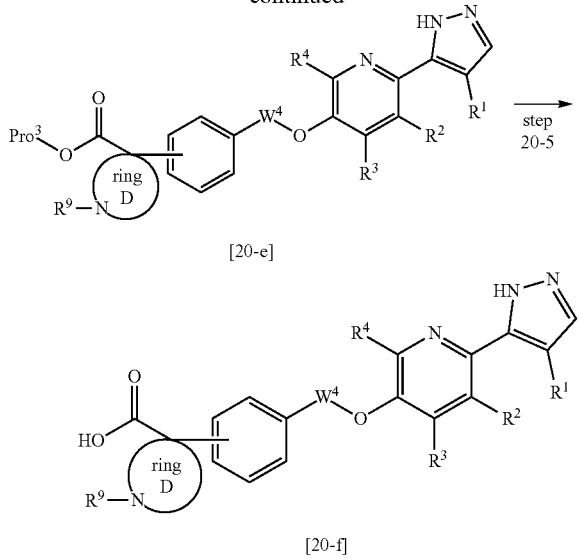

[In the scheme,
R[1], R[2], R[3], R[4], Pro[2], Pro[3], W[4], X[C], and M are the same as defined above; ring D represents 4- to 6-membered saturated nitrogen-containing heterocyclyl;
R[9] represents $C_{1-4}$ alkylcarbonyl, $C_{1-4}$alkoxycarbonyl, mono$C_{1-4}$alkylaminocarbonyl, or di($C_{1-4}$alkyl)aminocarbonyl; and
Pro[4] represents a protecting group for amino, as exemplified by tert-butoxycarbonyl, benzyloxycarbonyl, and the like.

[Step 20-1]

This step is a method of producing compound [20-b] by reacting compound [17-b] with compound [20-a].

This reaction can be carried out by the method described in step 19-1 of production method 19 or a method pursuant thereto.

[Step 20-2]

This step is a method of producing compound [20-c] by deprotecting the nitrogen atom in 4- to 6-membered saturated nitrogen-containing heterocyclyl of compound [20-b] by removing protecting group Pro[4].

(i) When protecting group Pro[4] is tert-butoxycarbonyl, the present reaction can be carried out in a solvent which does not interfere with the reaction, in the presence of an acid.

Examples of the reagent which is used in the present reaction include mineral acid such as hydrochloric acid and organic acid such as trifluoroacetic acid. The amount of the reagent to be used is 1 to 5 equivalents, and preferably 1 to 3 equivalents, with respect to 1 equivalent of compound [20-b].

Examples of the solvent which is used in the present reaction include methanol, ethanol, water, tetrahydrofuran, and ethyl acetate; and these solvents may be mixed with each other at an appropriate ratio and used.

The present reaction can be carried out usually at room temperature to reflux temperature for 1 to 24 hours.

The present reaction can also be carried out in a solvent which does not interfere with the reaction in the presence of a Lewis acid.

Examples of the reagent which is used in the present reaction include trimethylsilyl trifluoromethanesulfonate and tert-butyldimethylsilyl trifluoromethanesulfonate. The amount of the reagent to be used is 1 to 5 equivalents, and preferably 1 to 3 equivalents, with respect to 1 equivalent of compound [20-b].

For example, 2,6-lutidine may be used as an additive in the present reaction. The amount to be used is 1 to 10 equivalents, and preferably 2 to 5 equivalents, with respect to 1 equivalent of compound [20-b].

Examples of the solvent which is used in the present reaction include dichloromethane, chloroform, and toluene; and these solvents may be mixed with each other at an appropriate ratio and used.

The present reaction can be carried out usually at −80° C. to room temperature for 1 to 24 hours.

(ii) When protecting group Pro[4] is benzyloxycarbonyl, this step can be carried out in a solvent which does not interfere with the reaction, in the presence of a metal and a hydrogen source.

Examples of the metal which is used in the present reaction include palladium. The amount of the metal to be used is 0.1 to 1 equivalent, and preferably 0.1 to 0.5 equivalents, with respect to 1 equivalent of compound [20-b].

A hydrogen pressure which is used in the present reaction is ordinary pressure to 10 atm, and preferably ordinary pressure to 4 atm.

Examples of the solvent which is used in the present reaction include methanol, ethanol, water, tetrahydrofuran, chloroform, and ethyl acetate; and these solvents may be mixed with each other at an appropriate ratio and used.

The present reaction can be carried out usually at room temperature to reflux temperature for 1 to 24 hours.

[Step 20-3]

This step is a method of producing compound [20-d] by reacting compound [20-c] with a carboxylic acid, acid halide, acid anhydride, active ester, isocyanate, or amine corresponding to R[9].

(i) When the reagent to be used in the present reaction is a carboxylic acid, the present reaction can be carried out by the method described in step 8-3 of production method 8 or a method pursuant thereto.

(ii) When the reagent to be used in the present step is an acid chloride, an acid anhydride, or an active ester such as succinimide ester, the present reaction can be carried out by a known method, for example, in the presence of a base.

The amount of the acid chloride to be used in the present reaction is 1 to 5 equivalents, and preferably 1 to 3 equivalents, with respect to 1 equivalent of compound [20-c].

Examples of the base which is used in the present reaction include triethylamine, pyridine, 4-dimethylaminopyridine, and N,N-diisopropylethylamine. The amount of the base to be used is usually 1 to 5 equivalents, and preferably 1 to 3 equivalents, with respect to 1 equivalent of compound [20-c].

Examples of the solvent which is used in the present reaction include solvents that do not interfere with reactions, such as chloroform, dichloromethane, toluene, diethyl ether, tetrahydrofuran, ethyl acetate, N,N-dimethylformamide, and acetonitrile; and these solvents may be mixed with each other at an appropriate ratio and used.

The present reaction can be carried out usually at 0° C. to room temperature for 1 to 24 hours.

(iii) When the reagent to be used in the present step reaction is isocyanate, the present reaction can be carried out in a solvent which does not interfere with the reaction, in the presence or absence of a base.

The amount of the isocyanate to be used in the present reaction is 1 to 5 equivalents, and preferably 1 to 3 equivalents, with respect to 1 equivalent of compound [20-c].

Examples of the base which is used in the present reaction include triethylamine, pyridine, 4-dimethylaminopyridine, and N,N-diisopropylethylamine. The amount of the base to be used is usually 1 to 5 equivalents, and preferably 1 to 3 equivalents, with respect to 1 equivalent of compound [20-c].

Examples of the solvent which is used in the present reaction include solvents that do not interfere with reactions, such as chloroform, dichloromethane, diethyl ether, tetrahydrofuran, ethyl acetate, N,N-dimethylformamide, and dimethyl sulfoxide; and these solvents may be mixed with each other at an appropriate ratio and used.

The present reaction can be carried out usually at 0° C. to room temperature for 1 to 24 hours.

(iv) When the reagent to be used in the present step allows amine to react, the present reaction can be carried out by allowing 4-nitrophenyl chloroformate, dicyclohexylcarbodiimide (CDI), triphosgene, etc., to act in a solvent which does not interfere with the reaction, in the presence of a base.

The amount of the amine to be used in the present reaction is 1 to 5 equivalents, and preferably 1 to 3 equivalents, with respect to 1 equivalent of compound [20-c].

Examples of the base which is used in the present reaction include triethylamine, pyridine, 4-dimethylaminopyridine, and N,N-diisopropylethylamine. The amount of the base to be used is usually 1 to 5 equivalents, and preferably 1 to 3 equivalents, with respect to 1 equivalent of compound [20-c].

The amount of 4-nitrophenyl chloroformate or dicyclohexylcarbodiimide (CDI) to be used in the present reaction is 1 to 5 equivalents, and preferably 1 to 3 equivalents, with respect to 1 equivalent of compound [20-c].

Examples of the solvent which is used in the present reaction include solvents that do not interfere with reactions, such as chloroform, dichloromethane, diethyl ether, tetrahydrofuran, ethyl acetate, and acetonitrile; and these solvents may be mixed with each other at an appropriate ratio and used.

The present reaction can be carried out usually at 0° C. to reflux temperature for 1 to 24 hours.

[Step 20-4]

This step is a method of producing compound [20-e] by deprotecting the pyrazolyl of compound [20-d] by removing protecting group Pro² under an acidic condition.

This reaction can be carried out by the method described in step 4-2 of production method 4 or the method described in step 5-4 of production method 5, or a method pursuant thereto.

[Step 20-5]

This step is a method of producing compound [20-f] by deprotecting compound [20-e] by removing protecting group Pro³.

This reaction can be carried out by the method described in step 5-5 of production method 5 or a method pursuant thereto.

Steps 20-4 and 20-5 above may be carried out in the reversed order.

Compound [204] thus obtained can be isolated and purified by known separation and purification means such as concentration, concentration under reduced pressure, reprecipitation, solvent extraction, crystallization, and chromatography.

Compound [17-b] which is used as a starting compound in production method 20 above, and the silylenol ether and the ester which are used to generate compound [20-a] can be produced by production method 17 above, a method pursuant thereto, or a method known per se, or can be obtained by purchasing commercial products.

Among compound [I-1] of the present invention, compound [21-d] can be produced, for example, by production method 21 below or a method pursuant thereto.

Production Method 21

[Formula 296]

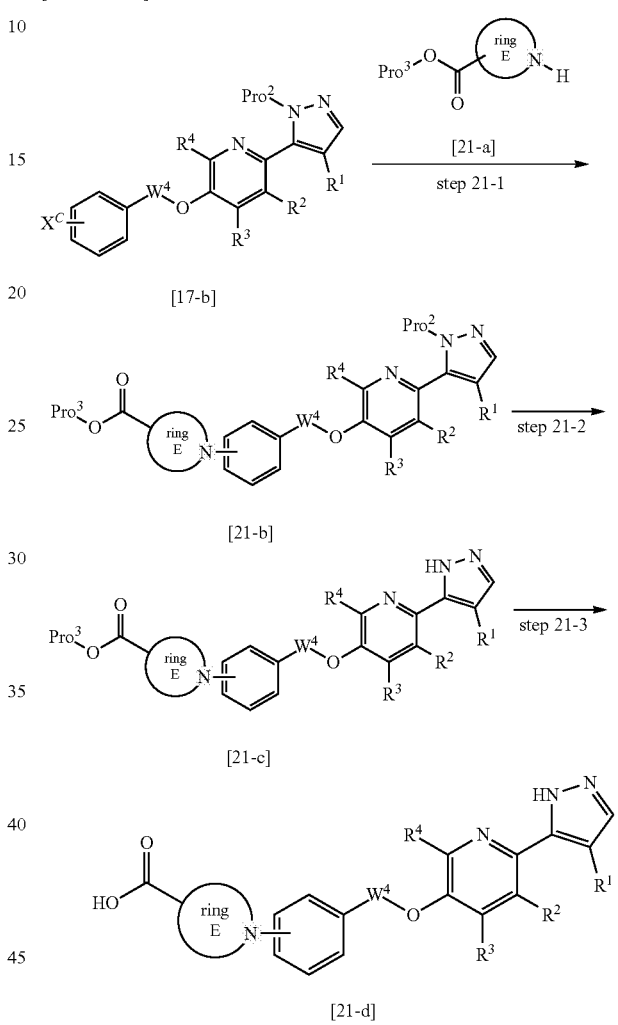

[In the scheme,
$R^1$, $R^2$, $R^3$, $R^4$, $Pro^2$, $Pro^3$, $W^4$, and $X^C$ are the same as defined above; and ring E represents 4- to 6-membered saturated nitrogen-containing heterocyclyl or nitrogen-containing heteroaryl.]

[Step 21-1]

This step is a method of producing compound [21-b] by reacting compound [17-b] with compound [21-a].

This reaction is a so-called Ullmann-type coupling reaction that can be carried out in a solvent which does not interfere with the reaction, in the presence of a copper salt, a ligand, and a base.

Examples of the copper salt which is used in the present reaction include copper(I) iodide, copper(I) bromide, copper (I) chloride, copper(I) oxide, and copper(I) trifluoromethanesulfonate-benzene complex. The amount of the copper salt to be used is 0.1 to 2 equivalents, and preferably 0.1 to 0.5 equivalents, with respect to 1 equivalent of compound [17-b].

Examples of the ligand which is used in the present reaction include 2-isobutyrylcyclohexanone, L-proline, and trans-N,N'-dimethylcyclohexane-1,2-diamine. The amount of the ligand to be used is 0.1 to 2 equivalents, and preferably 0.1 to 0.5 equivalents, with respect to 1 equivalent of compound [17-b].

Examples of the base which is used in the present reaction include potassium carbonate, potassium phosphate, cesium carbonate, N,N-diisopropylethylamine, and triethylamine. The amount of the base to be used is 1 to 5 equivalents, and preferably 1 to 2 equivalents, with respect to 1 equivalent of compound [17-b].

Examples of the solvent which is used in the present reaction include solvents that do not interfere with reactions, such as dimethyl sulfoxide, N,N-dimethylformamide, N-methylpyrrolidone, 1,4-dioxane, acetonitrile, and toluene; and these solvents may be mixed with each other at an appropriate ratio and used.

The present reaction can be carried out usually at reflux temperature for 1 to 24 hours.

[Step 21-2]

This step is a method of producing compound [21-c] by deprotecting the pyrazolyl of compound [21-b] by removing protecting group $Pro^2$ under an acidic condition.

This reaction can be carried out by the method described in step 4-2 of production method 4 or the method described in step 5-4 of production method 5, or a method pursuant thereto.

[Step 21-3]

This step is a method of producing compound [21-d] by deprotecting compound [21-c] by removing protecting group $Pro^3$.

This reaction can be carried out by the method described in step 5-5 of production method 5 or a method pursuant thereto.

Steps 21-2 and 21-3 above may be carried out in the reversed order.

Compound [21-d] thus obtained can be isolated and purified by known separation and purification means such as concentration, concentration under reduced pressure, reprecipitation, solvent extraction, crystallization, and chromatography.

Compounds [17-b] and [21-a] which are used as starting compounds in production method 21 above can be produced by production method 17 above, a method pursuant thereto, or a method known per se, or can be obtained by purchasing commercial products.

Among compound [I-1] of the present invention, compound [22-e] can be produced, for example, by production method 22 below or a method pursuant thereto.

Production Method 22

[Formula 297]

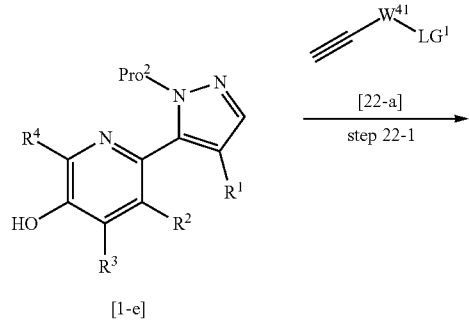

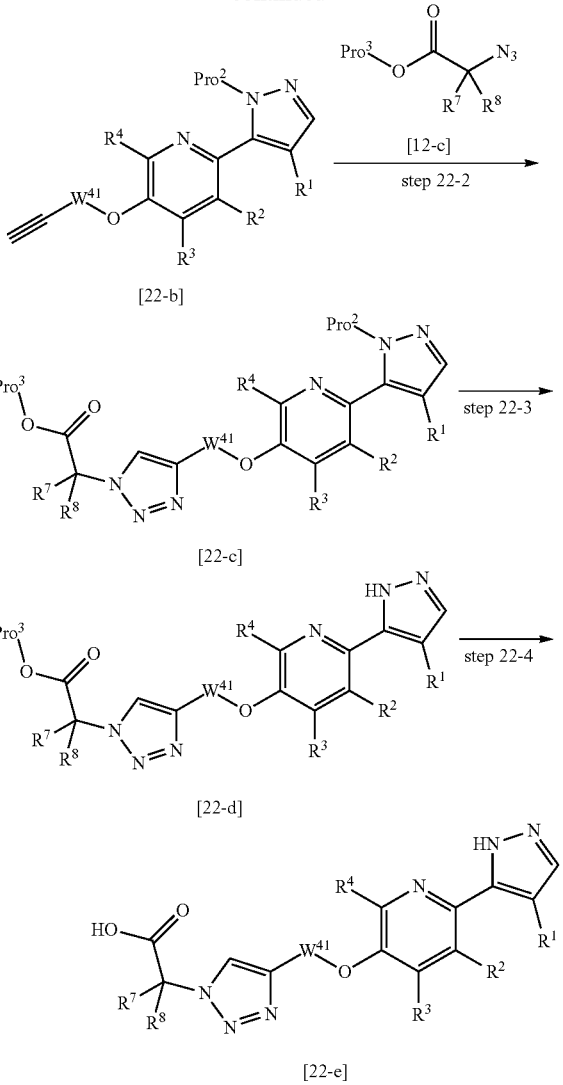

[In the scheme, $R^1$, $R^2$, $R^3$, $R^4$, $R^7$, $R^8$, $Pro^2$, $Pro^3$, and $LG^1$ are the same as defined above; and $W^{41}$ represents $C_{1-3}$alkanediyl.]

[Step 22-1]

This step is a method of producing compound [22-b] by reacting compound [1-e] with compound [22-a].

This reaction can be carried out by the method described in step 4-1 of production method 4 or a method pursuant thereto.

[Step 22-2]

This step is a method of producing compound [22-c] by reacting compound [22-b] with compound [12-c].

This reaction can be carried out by the method described in step 12-2 of production method 12 or a method pursuant thereto.

[Step 22-3]

This step is a method of producing compound [22-d] by deprotecting the pyrazolyl of compound [22-c] by removing protecting group $Pro^2$ under an acidic condition.

This reaction can be carried out by the method described in step 4-2 of production method 4 or the method described in step 5-4 of production method 5, or a method pursuant thereto.

[Step 22-4]

This step is a method of producing compound [22-e] by deprotecting compound [22-d] by removing protecting group Pro³.

This reaction can be carried out by the method described in step 5-5 of production method 5 or a method pursuant thereto.

Steps 22-3 and 22-4 above may be carried out in the reversed order.

Compound [22-e] thus obtained can be isolated and purified by known separation and purification means such as concentration, concentration under reduced pressure, reprecipitation, solvent extraction, crystallization, and chromatography.

Compounds [1-e], [22-a], and [12-c] which are used as starting compounds in production method 22 above can be produced by production method 1 above, a method pursuant thereto, or a method known per se, or can be obtained by purchasing commercial products.

Among compound [I-1] of the present invention, compound [23-e] can be produced, for example, by production method 23 below or a method pursuant thereto.

Production Method 23

[Formula 298]

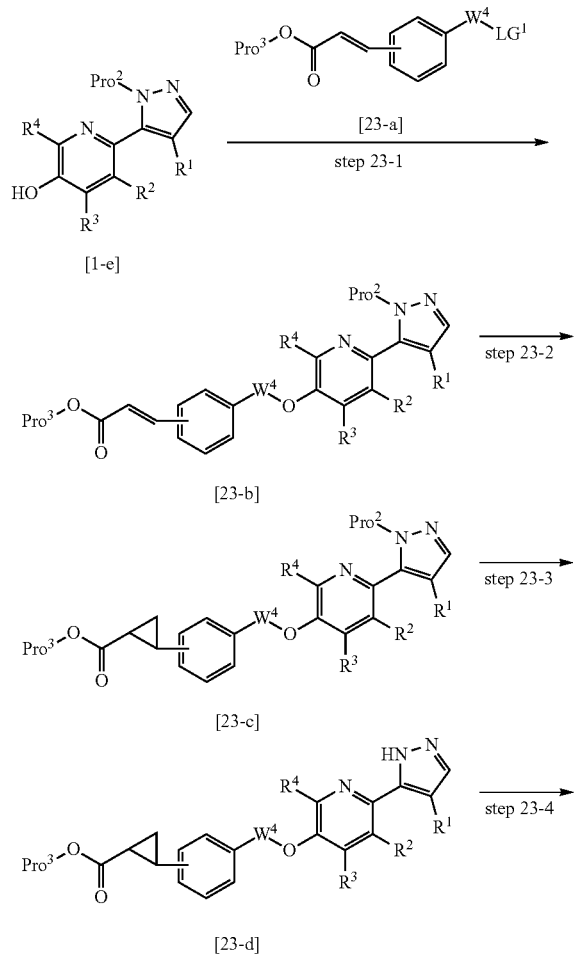

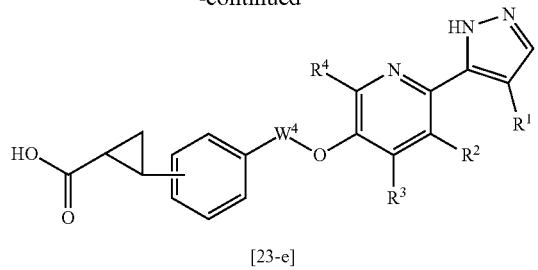

[In the scheme,
$R^1$, $R^2$, $R^3$, $R^4$, $W^4$, $LG^1$, $Pro^2$, and $Pro^3$ are the same as defined above.]

[Step 23-1]

This step is a method of producing compound [23-b] by reacting compound [1-e] with compound [23-a].

This reaction can be carried out by the method described in step 4-1 of production method 4 or a method pursuant thereto.

[Step 23-2]

This step is a method of producing compound [23-c] by reacting trimethylsulfoxonium iodide with a base and then with compound [23-b].

The reaction of trimethylsulfoxonium iodide with a base can be carried out by a known method, for example, the method described in WO2002/002522 or a method pursuant thereto.

The amount of the trimethylsulfoxonium iodide to be used in the present reaction is usually 1 to 10 equivalents, and preferably 1 to 5 equivalents, with respect to 1 equivalent of compound [23-b].

Examples of the base which is used in the present reaction include sodium hydride, potassium tert-butoxide, lithium bis(trimethylsilyl)amide, sodium bis(trimethylsilyl)amide, potassium bis(trimethylsilyl)amide, sodium methoxide, and sodium ethoxide. The amount of the base to be used is usually 1 to 10 equivalents, and preferably 1 to 5 equivalents, with respect to 1 equivalent of compound [23-b].

Examples of the solvent which is used in the present reaction include dimethyl sulfoxide, tetrahydrofuran, dimethoxyethane, 1,4-dioxane, diethyl ether, N,N-dimethylformamide, N,N-dimethylacetamide, acetonitrile, and dichloromethane; and these solvents may be mixed with each other at an appropriate ratio and used.

The present reaction can be carried out usually at 0° C. to reflux temperature for 0.5 to 72 hours.

[Step 23-3]

This step is a method of producing compound [23-d] by deprotecting the pyrazolyl of compound [23-c] by removing protecting group Pro² under an acidic condition.

This reaction can be carried out by the method described in step 4-2 of production method 4 or the method described in step 5-4 of production method 5, or a method pursuant thereto.

[Step 23-4]

This step is a method of producing compound [23-e] by deprotecting compound [23-d] by removing protecting group Pro³.

This reaction can be carried out by the method described in step 5-5 of production method 5 or a method pursuant thereto.

Steps 23-3 and 23-4 above may be carried out in the reversed order.

Compound [23-e] thus obtained can be isolated and purified by known separation and purification means such as concentration, concentration under reduced pressure, reprecipitation, solvent extraction, crystallization, and chromatography.

Compounds [1-e] and [23-a] which are used as starting compounds in production method 23 above can be produced by production method 1 above, a method pursuant thereto, or a method known per se, or can be obtained by purchasing commercial products.

Among compound [I-1] of the present invention, compound [24-e] can be produced, for example, by production method 24 below or a method pursuant thereto.

Production Method 24

[Formula 299]

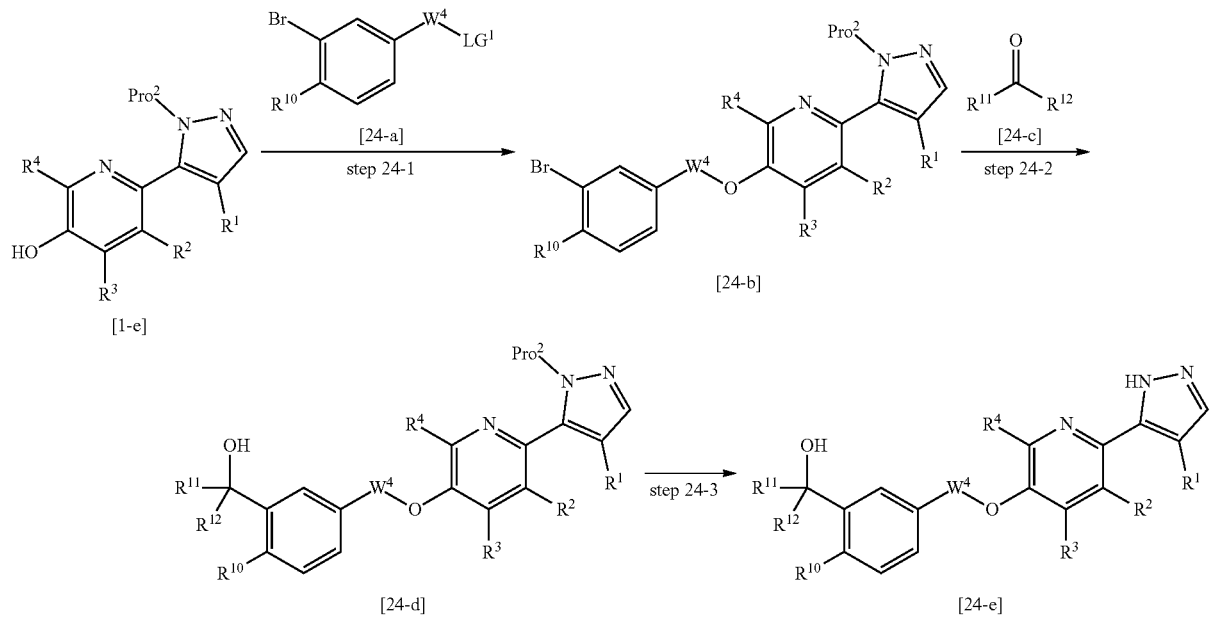

[In the scheme,
$R^1$, $R^2$, $R^3$, $R^4$, $Pro^2$, $W^4$, and $LG^1$ are the same as defined above;
$R^{10}$ represents a hydrogen atom or a fluorine atom;
$R^{11}$ represents $C_{1-4}$ alkyl, halo-$C_{1-4}$ alkyl, or aryl; and
$R^{12}$ represents a hydrogen atom, $C_{1-4}$alkyl, halo-$C_{1-4}$alkyl, or aryl.]

[Step 24-1]
This step is a method of producing compound [24-b] by reacting compound [1-e] with compound [24-a].

This reaction can be carried out by the method described in step 4-1 of production method 4 or a method pursuant thereto.

[Step 24-2]
This step is a method of producing compound [24-d] by reacting compound [24-b] with an alkyl lithium compound and then reacting the resulting reaction intermediate with a carbonyl compound represented by compound [24-c].

Examples of the alkyl lithium compound which is used in the reaction with compound [24-b] include n-butyl lithium. The amount of the alkyl lithium compound to be used is 1 to 5 equivalents, and preferably 1 to 3 equivalents, with respect to 1 equivalent of compound [24-b].

Examples of the solvent to be used in the present reaction include solvents that do not interfere with reactions, such as diethyl ether, tetrahydrofuran, 1,4-dioxane, toluene, and xylene; and these solvents may be mixed with each other at an appropriate ratio and used.

The present reaction can be carried out usually at −80° C. to −50° C. for 0.1 to 1 hour.

The amount of compound [24-c] to be used in the reaction with the reaction intermediate to be generated is 1 to 5 equivalents, and preferably 1 to 3 equivalents, with respect to 1 equivalent of compound [24-b].

The present reaction can be carried out usually at −80° C. to room temperature for 0.1 to 24 hours.

[Step 24-3]
This step is a method of producing compound [24-e] by deprotecting the pyrazolyl of compound [24-d] by removing protecting group $Pro^2$ under an acidic condition.

This reaction can be carried out by the method described in step 4-2 of production method 4 or a method pursuant thereto.

Compound [24-e] thus obtained can be isolated and purified by known separation and purification means such as concentration, concentration under reduced pressure, reprecipitation, solvent extraction, crystallization, and chromatography.

Incidentally, compounds [1-e], [24-a], and [24-c] which are used as starting compounds in production method 24 above can be produced by production method 1 above, a method pursuant thereto, or a method known per se, or can be obtained by purchasing commercial products.

Among compound [I-1] of the present invention, compound [25-f] can be produced, for example, by production method 25 below or a method pursuant thereto.

Production Method 25
[Formula 300]
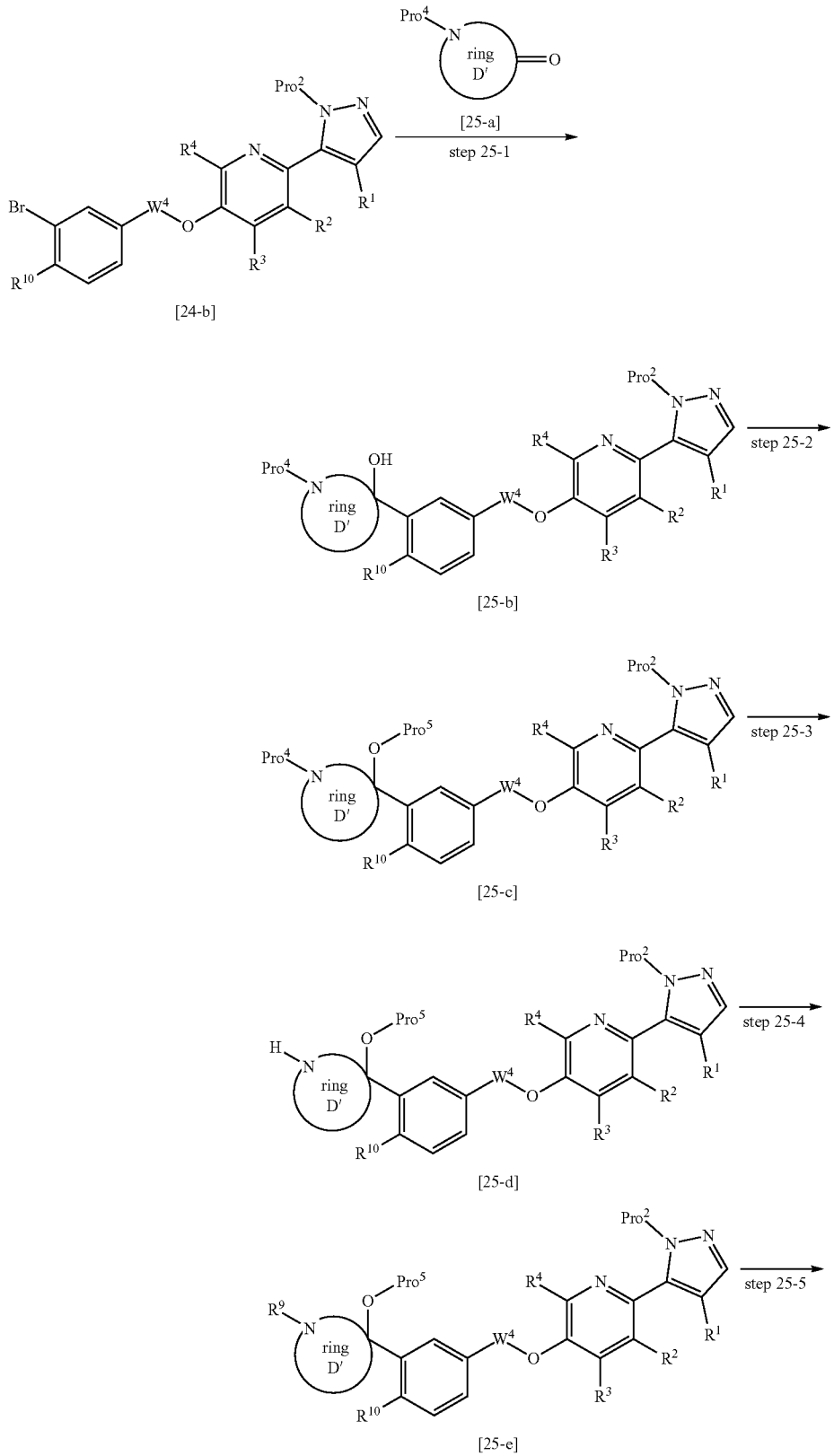

-continued

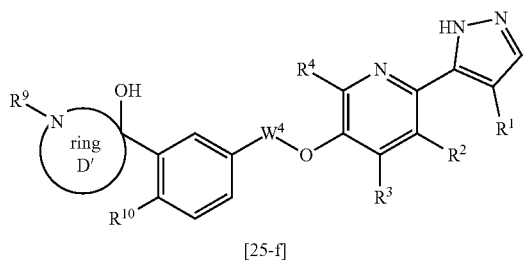

[25-f]

[In the scheme,
$R^1$, $R^2$, $R^3$, $R^4$, $R^9$, $R^{10}$, $Pro^2$, $Pro^4$, and $W^4$ are the same as defined above;
ring D' represents 4- to 6-membered saturated nitrogen-containing heterocyclyl (the 4- to 6-membered saturated nitrogen-containing heterocyclyl is substituted with one oxo at a carbon atom not adjacent to the nitrogen atom); and $Pro^5$ represents a protecting group for hydroxy, as exemplified by a silyl-based protecting group or the like such as trimethylsilyl, triisopropylsilyl, and tert-butyldimethylsilyl.]

[Step 25-1]

This step is a method of producing compound [25-b] by reacting compound [24-b] with an alkyl lithium compound and then reacting the resulting reaction intermediate with a carbonyl compound represented by compound [25-a].

This reaction can be carried out by the method described in step 24-2 of production method 24 or a method pursuant thereto.

[Step 25-2]

This step is a method of producing compound [25-c] by protecting the hydroxy of compound [25-b] with protecting group $Pro^5$.

Examples of the reagent which is used in the present reaction include trimethylsilyl chloride and trimethylsilyl triflate. The amount of the reagent to be used is 1 to 5 equivalents, and preferably 1 to 3 equivalents, with respect to 1 equivalent of compound [25-b].

Examples of the base which is used in the present reaction include imidazole, triethylamine, pyridine, and 2,6-lutidine. The amount of the base to be used is 1 to 5 equivalents, and preferably 1 to 3 equivalents, with respect to 1 equivalent of compound [25-b].

Examples of the solvent which is used in the present reaction include solvents that do not interfere with reactions, such as chloroform, dichloromethane, 1,4-dioxane, ethyl acetate, tetrahydrofuran, and N,N-dimethylformamide; and these solvents may be mixed with each other at an appropriate ratio and used.

The present reaction can be carried out usually at 0° C. to room temperature for 1 to 24 hours.

[Step 25-3]

This step is a method of producing compound [25-d] by deprotecting the nitrogen atom in 4- to 6-membered saturated nitrogen-containing heterocyclyl of compound [25-c] by removing protecting group $Pro^4$.

This reaction can be carried out by the method described in step 20-2 of production method 20 or a method pursuant thereto.

[Step 25-4]

This step is a method of producing compound [25-e] by reacting compound [25-d] with a carboxylic acid, acid halide, acid anhydride, active ester, isocyanate, or amine corresponding to $R^9$.

This reaction can be carried out by the method described in step 20-3 of production method 20 or a method pursuant thereto.

[Step 25-5]

This step is a method of producing compound [254] by deprotecting the pyrazolyl of compound [25-e] by removing protecting group $Pro^2$ under an acidic condition.

This reaction can be carried out by the method described in step 4-2 of production method 4 or a method pursuant thereto.

Compound [254] thus obtained can be isolated and purified by known separation and purification means such as concentration, concentration under reduced pressure, reprecipitation, solvent extraction, crystallization, and chromatography.

Compounds [24-b] and [25-a] which are used as starting compounds in production method 25 above can be produced by production method 24 above, a method pursuant thereto, or a method known per se, or can be obtained by purchasing commercial products.

Among compound [I-1] of the present invention, compound [26-d] can be produced, for example, by production method 26 below or a method pursuant thereto.

Production Method 26

[Formula 301]

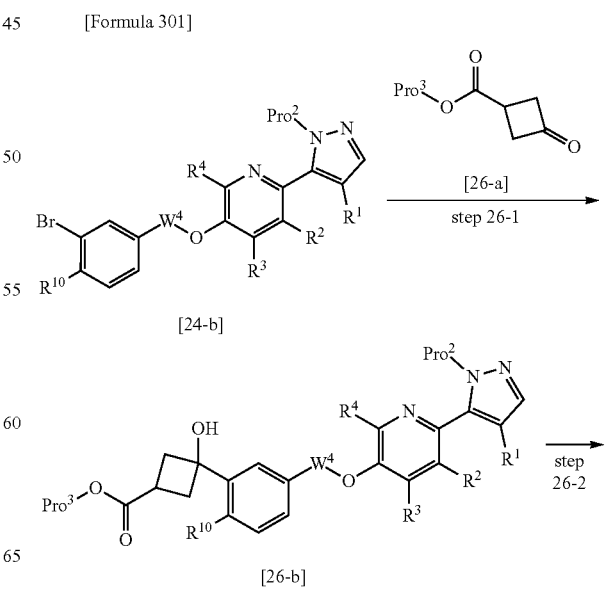

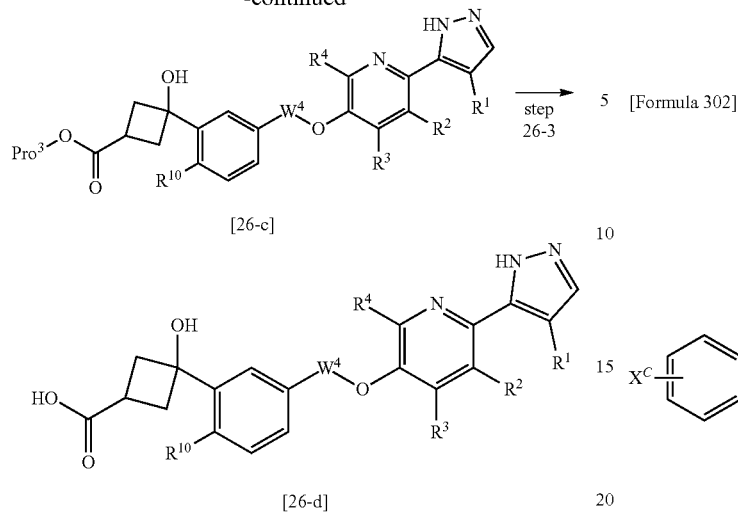

[In the scheme,
R[1], R[2], R[3], R[4], R[10], Pro[2], Pro[3], and W[4] are the same as defined above.]

[Step 26-1]

This step is a method of producing compound [26-b] by reacting compound [24-b] with an alkyl lithium compound and then reacting the resulting reaction intermediate with a carbonyl compound represented by compound [26-a].

This reaction can be carried out by the method described in step 24-2 of production method 24 or a method pursuant thereto.

[Step 26-2]

This step is a method of producing compound [26-c] by deprotecting the pyrazolyl of compound [26-b] by removing protecting group Pro[2] under an acidic condition.

This reaction can be carried out by the method described in step 4-2 of production method 4 or the method described in step 5-4 of production method 5, or a method pursuant thereto.

[Step 26-3]

This step is a method of producing compound [26-d] by deprotecting compound [26-c] by removing protecting group Pro[3].

This reaction can be carried out by the method described in step 5-5 of production method 5 or a method pursuant thereto.

Steps 26-2 and 26-3 above may be carried out in the reversed order.

Compound [26-d] thus obtained can be isolated and purified by known separation and purification means such as concentration, concentration under reduced pressure, reprecipitation, solvent extraction, crystallization, and chromatography.

Compounds [24-b] and [26-a] which are used as starting compounds in production method 26 above can be produced by production method 24 above, a method pursuant thereto, or a method known per se, or can be obtained by purchasing commercial products.

Among compound [I-1] of the present invention, compound [27-c] can be produced, for example, by production method 27 below or a method pursuant thereto.

Production Method 27

[Formula 302]

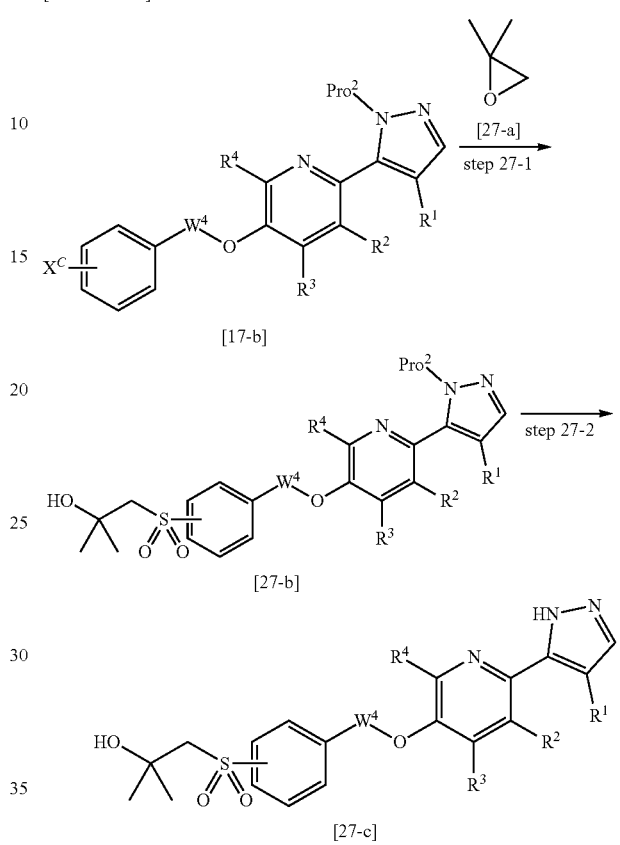

[In the scheme,
R[1], R[2], R[3], R[4], Pro[2], W[4], and X[C] are the same as defined above.]

[Step 27-1]

This step is a method of producing compound [27-b] by reacting compound [17-b] with potassium disulfite and sodium formate in the presence of a palladium catalyst and then reacting the resulting sodium sulfinate intermediate with compound [27-a] as an epoxide.

(i) Preparation of the sodium sulfinate intermediate in the present reaction can be carried out by a known method, for example, the method described in Organic Letters, 2013, 15, 6226 or a method pursuant thereto.

Examples of the palladium catalyst which is used in the present reaction include palladium(II) acetate, and the amount is 0.01 to 0.1 equivalents, and preferably 0.03 to 0.07 equivalents, with respect to 1 equivalent of compound [17-b].

Examples of the solvent which is used in the present reaction include solvents that do not interfere with reactions, such as N,N-dimethylformamide, dimethyl sulfoxide, and acetonitrile; and these solvents may be mixed with each other at an appropriate ratio and used.

The present reaction can be carried out usually at 50° C. to 100° C. for 1 to 24 hours, and can be also carried out under microwave irradiation.

(ii) The reaction of the sodium sulfinate intermediate generated and epoxide [27-a] can be carried out by a known method, for example, the method described in. The Journal of Organic Chemistry, 1985, 50, 1327 or Tetrahedron Letters, 2009, 50, 5009, or a method pursuant thereto.

The amount of the epoxide to be used in the present reaction is 1 to 5 equivalents, and preferably 1 to 3 equivalents, with respect to 1 equivalent of compound [17-b].

Examples of the solvent which is used in the present reaction include solvents that do not interfere with reactions, such as water, toluene, N,N-dimethylformamide, dimethyl sulfoxide, and acetonitrile; and these solvents may be mixed with each other at an appropriate ratio and used.

The present reaction can be carried out usually at room temperature to 100° C. for 1 to 24 hours.

[Step 27-2]

This step is a method of producing compound [27-c] by reacting compound [27-b] under an acidic condition to deprotect the pyrazolyl by removing protecting group $Pro^2$.

This reaction can be carried out by the method described in step 4-2 of production method 4 or a method pursuant thereto.

Compound [27-c] thus obtained can be isolated and purified by known separation and purification means such as concentration, concentration under reduced pressure, reprecipitation, solvent extraction, crystallization, and chromatography.

Incidentally, compounds [17-b] and [27-a] which are used as starting compounds in production method 27 above can be produced by production method 17 above, a method pursuant thereto, or a method known per se, or can be obtained by purchasing commercial products.

Among compound [I-1] of the present invention, compound [28-d] can be produced, for example, by production method 28 below or a method pursuant thereto.

Production Method 28

[Formula 303]

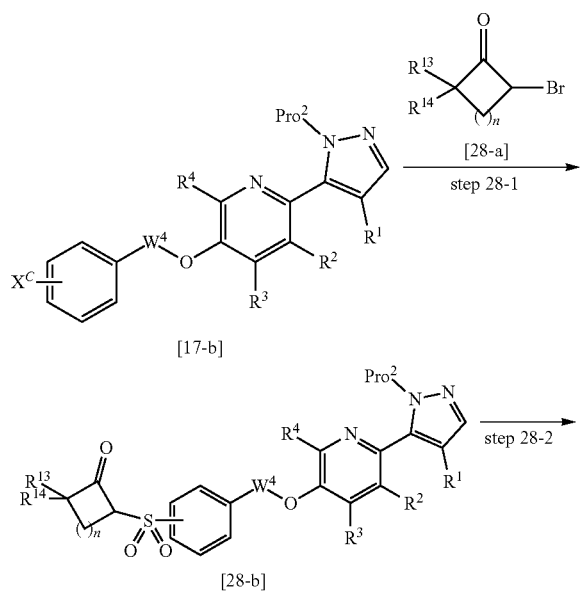

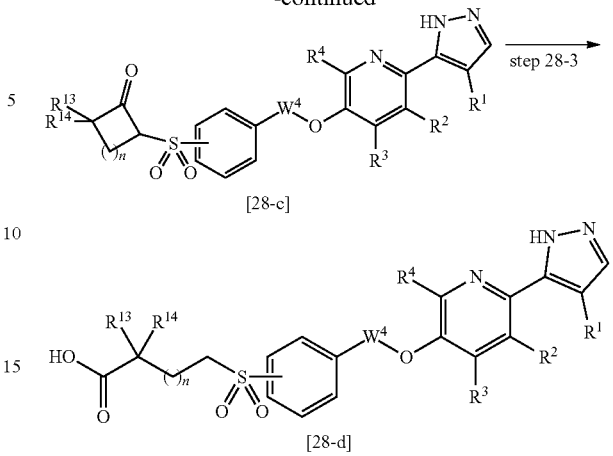

[In the scheme,
$R^1$, $R^2$, $R^3$, $R^4$, $Pro^2$, $W^4$, and $X^C$ are the same as defined above;
n represents an integer of 0 to 2; and
$R^{13}$ and $R^{14}$ each independently represent a hydrogen atom or methyl.]

[Step 28-1]

This step is a method of producing compound [28-b] by reacting compound [17-b] with potassium disulfite and sodium formate in the presence of a palladium catalyst and then reacting the resulting sodium sulfinate intermediate with compound [28-a] as an alkyl bromide.

(i) Preparation of the sodium sulfinate intermediate in the present reaction can be carried out by the method described in step 27-1 (i) of production method 27 or a method pursuant thereto.

(ii) The reaction of the sodium sulfinate intermediate generated and alkyl bromide [28-a] can be carried out by mixing them in a solvent which does not interfere with the reaction.

Examples of the solvent which is used in the present reaction include solvents that do not interfere with reactions, such as N,N-dimethylformamide and dimethyl sulfoxide; and these solvents may be mixed with each other at an appropriate ratio and used.

The present reaction can be carried out usually at room temperature to 100° C. for 1 to 24 hours.

[Step 28-2]

This step is a method of producing compound [28-c] by deprotecting the pyrazolyl of compound [28-b] by removing protecting group $Pro^2$ under an acidic condition.

This reaction can be carried out by the method described in step 4-2 of production method 4 or the method described in step 5-4 of production method 5, or a method pursuant thereto.

[Step 28-3]

This step is a method of producing compound [28-d] by ring-opening the 2-sulfonylcycloalkanone of compound [28-c].

This reaction is a so-called retro-Aldol reaction that can be carried out in the presence of a base under heating.

Examples of the base which is used in the present reaction include sodium hydroxide and potassium hydroxide. The amount of the base to be used is 1 to 5 equivalents, and preferably 1 to 3 equivalents, with respect to 1 equivalent of compound [28-c].

Examples of the solvent which is used in the present reaction include solvents that do not interfere with reactions, such as water, N,N-dimethylformamide, dimethyl sulfoxide, and tetrahydrofuran; and these solvents may be mixed with each other at an appropriate ratio and used.

The present reaction can be carried out usually at 50° C. to reflux temperature for 1 to 24 hours.

Compound [28-d] thus obtained can be isolated and purified by known separation and purification means such as concentration, concentration under reduced pressure, reprecipitation, solvent extraction, crystallization, and chromatography.

Incidentally, compound [17-b] and compound [28-a] which are used as starting compounds in production method 28 above can be produced by production method 17 above, a method pursuant thereto, or a method known per se, or can be obtained by purchasing commercial products.

Among compound [I-1] of the present invention, compounds [29-f] and [29-j] can be produced, for example, by production method 29 below or a method pursuant thereto.

Production Method 29

[Formula 304]

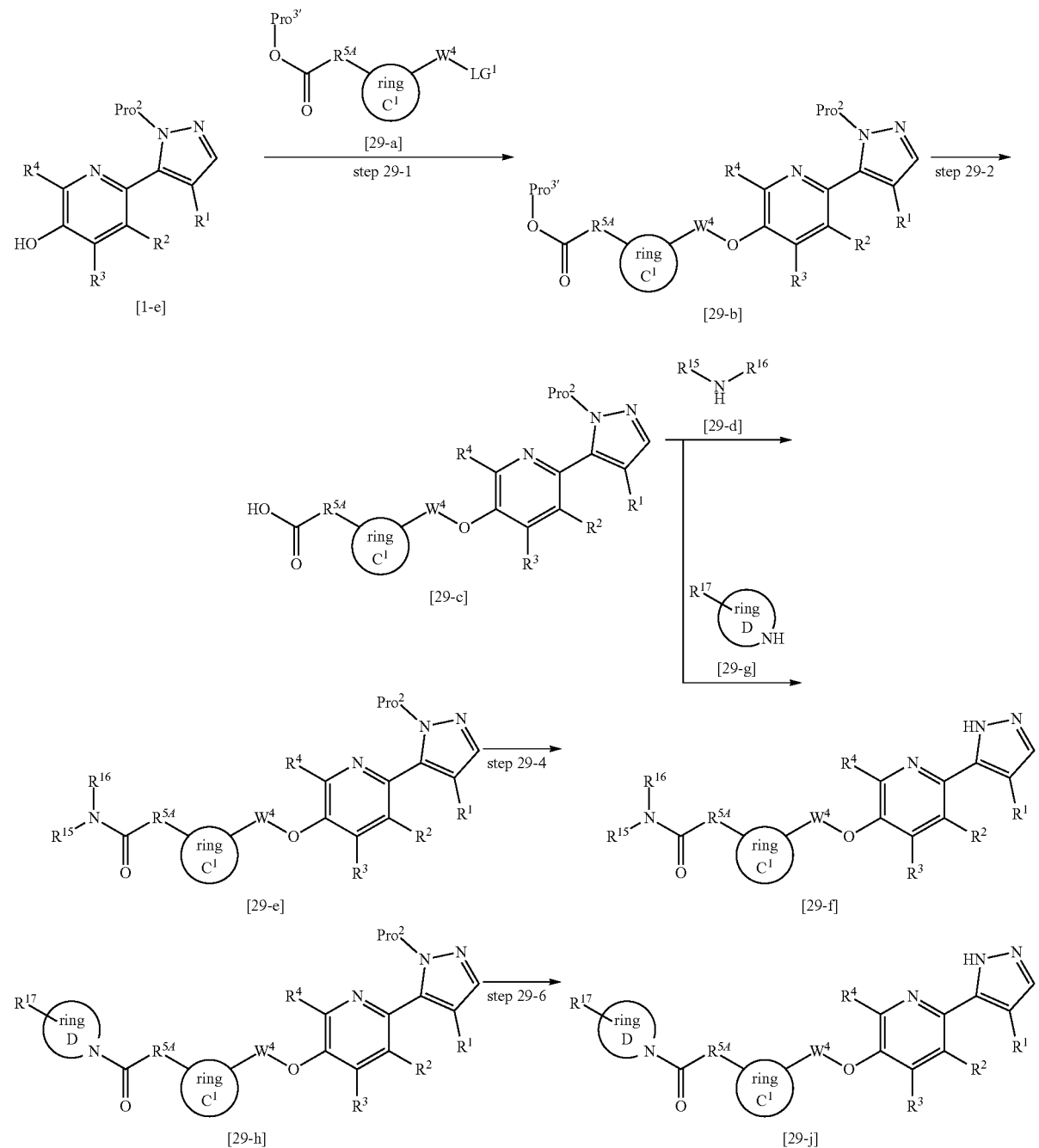

[In the scheme,
$R^1$, $R^2$, $R^3$, $R^4$, $Pro^2$, $Pro^{3'}$, $LG^1$, $W^4$, and ring D are the same as defined above;
a group represented by formula [IV-4"-1] below:

[Formula 305]

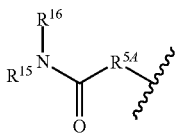

[IV-4"-1]

represents a group below selected from $R^{54}$
carbamoyl,
mono$C_{1-4}$alkylaminocarbonyl (the $C_{1-4}$alkyl of the mono$C_{1-4}$alkylaminocarbonyl may be substituted with one hydroxy),
$C_{1-4}$alkyl substituted with mono$C_{1-4}$alkylaminocarbonyl (the $C_{1-4}$alkyl of the mono$C_{1-4}$alkylaminocarbonyl of the $C_{1-4}$alkyl substituted with mono$C_{1-4}$alkylaminocarbonyl may be substituted with one group selected from the group consisting of hydroxy, $C_{1-4}$alkoxy, 4- to 6-membered saturated oxygen-containing heterocyclyl, di($C_{1-4}$alkyl)amino, and 4- to 6-membered saturated nitrogen-containing heterocyclylcarbonyl),
$C_{2-4}$ alkenyl substituted with di($C_{1-4}$alkyl)aminocarbonyl,
$C_{3-6}$cycloalkyl substituted with di($C_{1-4}$alkyl)aminocarbonyl,
$C_{1-4}$ alkylsulfonylaminocarbonyl,
$C_{1-4}$ alkyl substituted with $C_{1-4}$alkylsulfonylaminocarbonyl,
$C_{1-4}$ alkylsulfonyl($C_{1-4}$ alkyl)aminocarbonyl,
$C_{1-4}$ alkyl substituted with $C_{1-4}$alkylsulfonyl($C_{1-4}$alkyl)aminocarbonyl,
$C_{1-4}$alkyl substituted with di($C_{1-4}$ alkyl)aminocarbonyl (one $C_{1-4}$ alkyl of the di($C_{1-4}$alkyl)aminocarbonyl of the $C_{1-4}$alkyl substituted with di($C_{1-4}$alkyl)aminocarbonyl may be substituted with one hydroxy), or
$C_{1-4}$ alkyl substituted with 4- to 6-membered saturated oxygen-containing heterocyclylaminocarbonyl;
a group represented by formula [IV-4"-2] below:

[Formula 306]

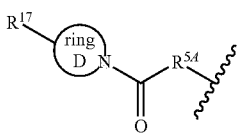

[IV-4"-2]

represents a group below selected from $R^{54}$
$C_{1-4}$ alkyl substituted with 4- to 6-membered saturated nitrogen-containing heterocyclylcarbonyl (the 4- to 6-membered saturated nitrogen-containing heterocyclyl of the $C_{1-4}$ alkyl substituted with 4- to 6-membered saturated nitrogen-containing heterocyclylcarbonyl may be substituted with one or two groups selected from the group consisting of hydroxy and a fluorine atom),
$C_{1-4}$ alkyl substituted with 4- to 6-membered saturated oxygen- and nitrogen-containing heterocyclylcarbonyl;

$R^{5A}$ represents
a single bond,
$C_{1-4}$ alkyl,
halo-$C_{1-4}$ alkyl,
$C_{2-4}$ alkenyl, or
$C_{3-6}$ cycloalkyl (the $C_{3-6}$ cycloalkyl may be substituted with one hydroxy); ring $C^1$ represents phenyl (the phenyl may be substituted with one fluorine atom) or pyridyl;
$R^{15}$ represents a hydrogen atom, $C_{1-4}$ alkyl (the $C_{1-4}$ alkyl may be substituted with one group selected from the group consisting of hydroxy, $C_{1-4}$ alkoxy, 4- to 6-membered saturated oxygen-containing heterocyclyl, di($C_{1-4}$ alkyl)amino, and 4- to 6-membered saturated nitrogen-containing heterocyclylcarbonyl), $C_{1-4}$ alkylsulfonyl, or oxetanyl;
$R^{16}$ represents a hydrogen atom or $C_{1-4}$ alkyl; and
$R^{17}$ represents a hydrogen atom, a fluorine atom, or hydroxy.]

[Step 29-1]
This step is a method of producing compound [29-b] by reacting compound [1-e] with compound [29-a].
This reaction can be carried out by the method described in step 4-1 of production method 4 or a method pursuant thereto.

[Step 29-2]
This step is a method of producing compound [29-c] by removing $Pro^{3'}$ in compound [29-b] under a basic condition.
This reaction can be carried out by the method described in step 5-2 of production method 5 or a method pursuant thereto.

[Step 29-3]
This step is a method of producing compound [29-e] by reacting compound [29-c] with compound [29-d].
This reaction can be carried out by the method described in step 8-3 of production method 8 or a method pursuant thereto.

[Step 29-4]
This step is a method of producing compound [294] by reacting compound [29-e] under an acidic condition to deprotect the pyrazolyl by removing protecting group $Pro^2$.
This reaction can be carried out by the method described in step 4-2 of production method 4 or a method pursuant thereto.

[Step 29-5]
This step is a method of producing compound [29-b] by reacting compound [29-c] with compound [29-g].
This reaction can be carried out by the method described in step 8-3 of production method 8 or a method pursuant thereto.

[Step 29-6]
This step is a method of producing compound [29-j] by reacting compound [29-b] under an acidic condition to deprotect the pyrazolyl by removing protecting group $Pro^2$.
This reaction can be carried out by the method described in step 4-2 of production method 4 or a method pursuant thereto.

Compounds [29-f] and [29-j] thus obtained can be isolated and purified by known separation and purification means such as concentration, concentration under reduced pressure, reprecipitation, solvent extraction, crystallization, and chromatography.

Compounds [1-e], [29-a], [29-d], and [29-g] which are used as starting compounds in production method 29 above can be produced by production method 1 above, a method pursuant thereto, or a method known per se, or can be obtained by purchasing commercial products.

Among compound [I-1] of the present invention, compounds [30-g] and [30-m] can be produced, for example, by production method 30 below or a method pursuant thereto.

Production Method 30
[Formula 307]
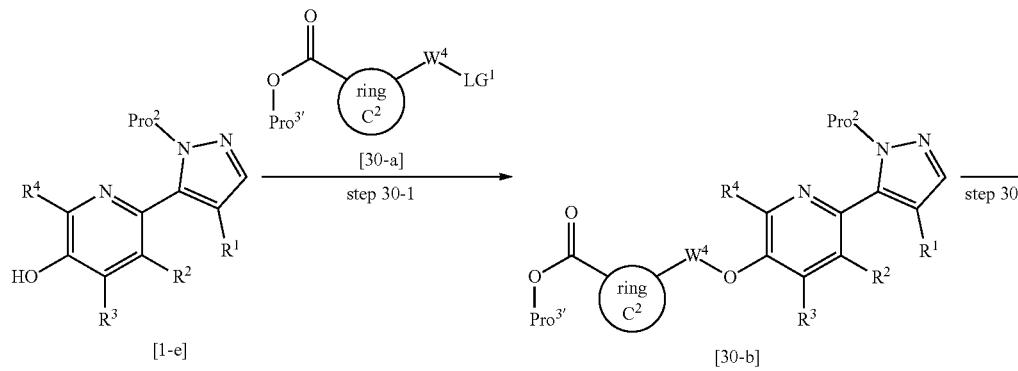
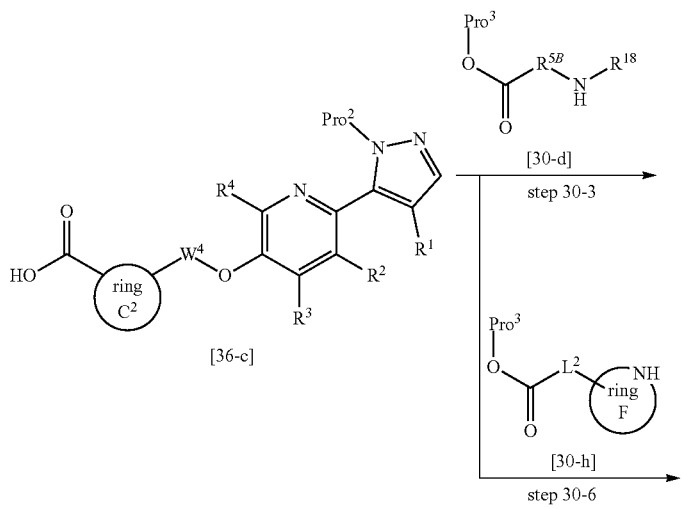
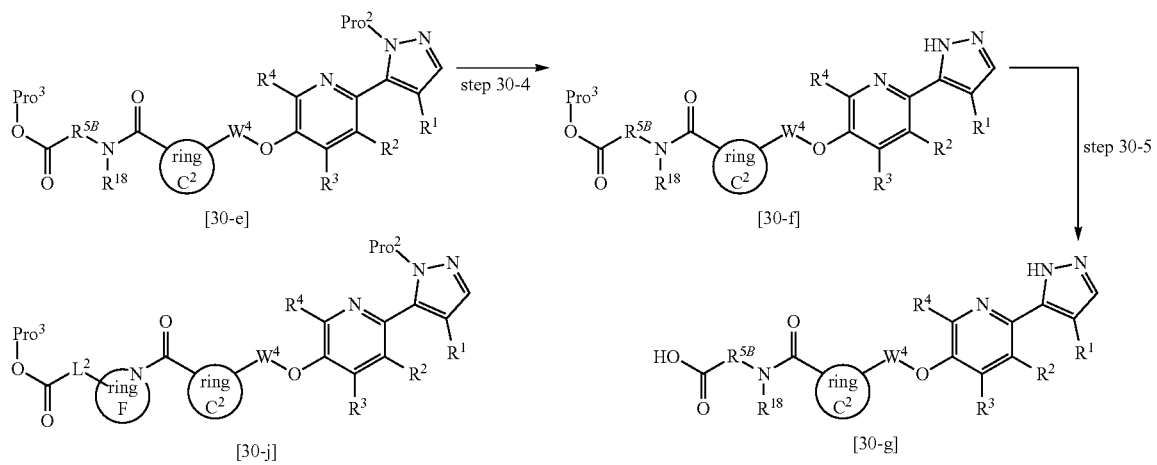

-continued

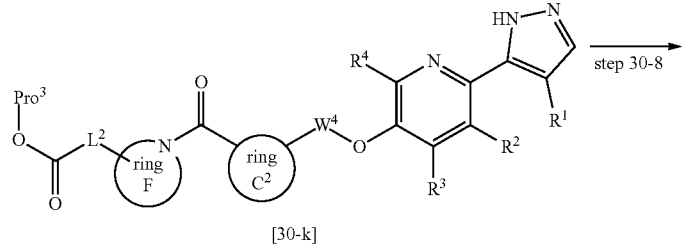

[30-k]

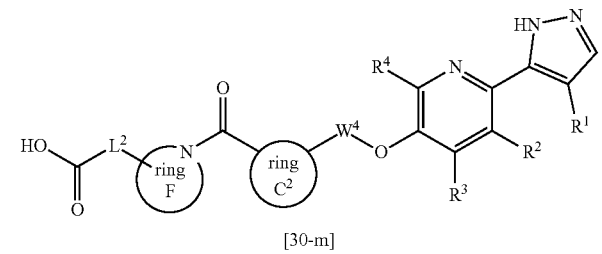

[30-m]

[In the scheme, $R^1$, $R^2$, $R^3$, $R^4$, $W^4$, $Pro^2$, $Pro^3$, $Pro^{3'}$, $LG^1$, and $L^2$ are the same as defined above;

a group represented by formula [IV-4″-3] below:

[Formula 308]

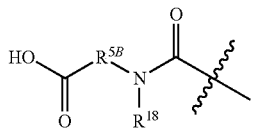

[IV-4″-3]

represents a group below selected from $R^{54}$ mono$C_{1-4}$ alkylaminocarbonyl substituted with carboxy (the $C_{1-4}$ alkyl of the mono$C_{1-4}$ alkylaminocarbonyl substituted with carboxy may be substituted with one phenyl, and when position α of the carboxy of the mono$C_{1-4}$ alkylaminocarbonyl substituted with carboxy is a methylene moiety, the methylene moiety may be replaced with a structure selected from structure group α above), di($C_{1-4}$ alkyl)aminocarbonyl substituted with carboxy, phenylmethylaminocarbonyl substituted with carboxy, $C_{3-6}$ cycloalkylaminocarbonyl substituted with carboxy, or the structure represented by formula [VIII-7] below, which is substituted with carboxy;

[Formula 309]

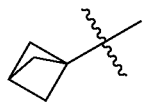

[VIII-7]

a group represented by formula [IV-4″-4] below:

[Formula 310]

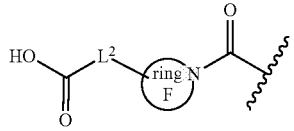

[IV-4″-4]

represents a group below selected from $R^{54}$ 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy may be substituted with one fluorine atom), 4- to 6-membered saturated nitrogen-containing heterocyclylcarbonyl substituted with carboxymethyl, the structure represented by formula [XI-1] below, which is substituted with carboxy, the structure represented by formula [XI-2] below, which is substituted with carboxy, the structure represented by formula [XI-3] below, which is substituted with carboxy, the structure represented by formula [XI-4] below, which is substituted with carboxy, the structure represented by formula [XI-5] below, which is substituted with carboxy;

[Formula 311]

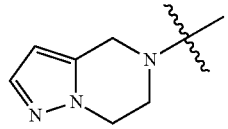

[XI-1]

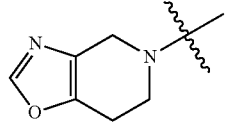

[XI-2]

-continued

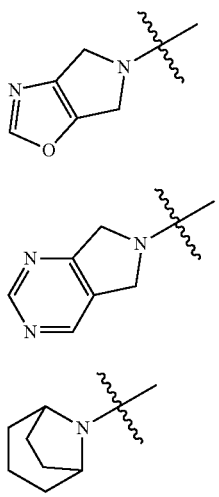

[XI-3]

[XI-4]

[XI-5]

$R^{5B}$ represents $C_{1-4}$ alkyl (the $C_{1-4}$ alkyl may be substituted with one phenyl, and when position α of the carboxy is a methylene moiety, the methylene moiety may be replaced with a structure selected from structure group α above), $C_{3-6}$cycloalkyl, phenylmethyl, the structure represented by formula [VIII-7] below;

[Formula 312]

[VIII-7]

ring $C^2$ represents phenyl or pyridyl;
$R^{18}$ represents a hydrogen atom or $C_{1-4}$alkyl;
ring F represents
4- to 6-membered nitrogen-containing heterocyclyl (the 4- to 6-membered nitrogen-containing heterocyclyl may be substituted with one fluorine atom),
the structure represented by formula [XI-1] above,
the structure represented by formula [XI-2] above,
the structure represented by formula [XI-3] above,
the structure represented by formula [XI-4] above, or
the structure represented by formula [XI-5] above.]

[Step 30-1]

This step is a method of producing compound [30-b] by reacting compound [1-e] with compound [30-a].

This reaction can be carried out by the method described in step 4-1 of production method 4 or a method pursuant thereto.

[Step 30-2]

This step is a method of producing compound [30-c] by removing $Pro^{3'}$ in compound [30-b] under a basic condition.

This reaction can be carried out by the method described in step 5-2 of production method 5 or a method pursuant thereto.

[Step 30-3]

This step is a method of producing compound [30-e] by reacting compound [30-c] with compound [30-d].

This reaction can be carried out by the method described in step 8-3 of production method 8 or a method pursuant thereto.

[Step 30-4]

This step is a method of producing compound [304] by reacting compound [30-e] under an acidic condition to deprotect the pyrazolyl by removing protecting group $Pro^2$.

This reaction can be carried out by the method described in step 4-2 of production method 4 or the method described in step 5-4 of production method 5, or a method pursuant thereto.

[Step 30-5]

This step is a method of producing compound [30-g] by deprotecting compound [30-f] by removing protecting group $Pro^3$.

This reaction can be carried out by the method described in step 5-5 of production method 5 or a method pursuant thereto.

[Step 30-6]

This step is a method of producing compound [30-j] by reacting compound [30-c] with compound [30-h].

This reaction can be carried out by the method described in step 8-3 of production method 8 or a method pursuant thereto.

[Step 30-7]

This step is a method of producing compound [30-k] by reacting compound [30-j] under an acidic condition to deprotect the pyrazolyl by removing protecting group $Pro^2$.

This reaction can be carried out by the method described in step 4-2 of production method 4 or the method described in step 5-4 of production method 5, or a method pursuant thereto.

[Step 30-8]

This step is a method of producing compound [30-m] by deprotecting compound [30-k] by removing protecting group $Pro^3$.

This reaction can be carried out by the method described in step 5-5 of production method 5 or a method pursuant thereto.

Steps 30-4 and 30-5, and steps 30-7 and 30-8 above may be carried out in the reversed order.

Compounds [30-g] and [30-m] thus obtained can be isolated and purified by known separation and purification means such as concentration, concentration under reduced pressure, reprecipitation, solvent extraction, crystallization, and chromatography.

Compounds [1-e], [30-a], [30-d], and [30-b] which are used as starting compounds in production method 30 above can be produced by production method 1 above, a method pursuant thereto, or a method known per se, or can be obtained by purchasing commercial products.

Among compound [I-1] of the present invention, compound [31-f] can be produced, for example, by production method 31 below or a method pursuant thereto.

Production Method 31

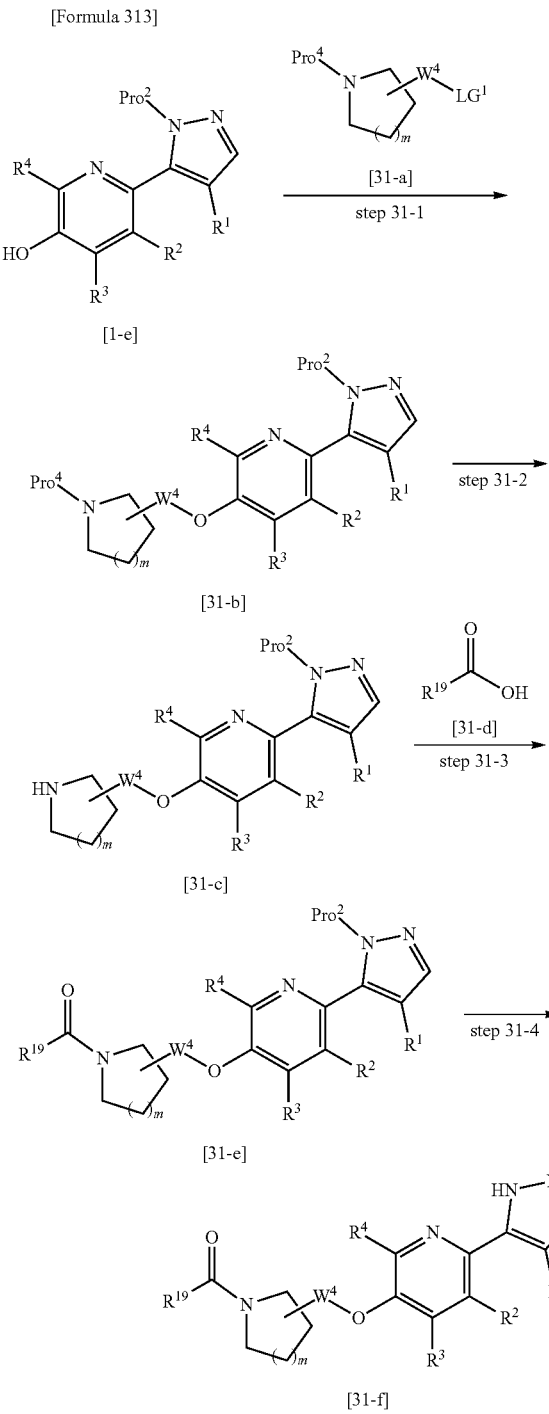

[Formula 313]

[In the scheme,
R¹, R², R³, R⁴, W⁴, Pro², Pro⁴, and LG¹ are the same as defined above; m represents an integer of 0 to 2; and R¹⁹ represents $C_{1-4}$alkyl substituted with sulfamoyl, $C_{1-4}$alkyl substituted with $C_{1-4}$alkylsulfonylamino, phenyl substituted with sulfamoyl, or dihydropyridine substituted with oxo.]

[Step 31-1]

This step is a method of producing compound [31-b] by reacting compound [1-e] with compound [31-a].

This reaction can be carried out by the method described in step 4-1 of production method 4 or a method pursuant thereto.

[Step 31-2]

This step is a method of producing compound [31-c] by deprotecting the nitrogen atom in 4- to 6-membered saturated nitrogen-containing heterocyclyl of compound [31-b] by removing protecting group Pro⁴.

This reaction can be carried out by the method described in step 20-2 of production method 20 or a method pursuant thereto.

[Step 31-3]

This step is a method of producing compound [31-e] by reacting compound [31-c] with compound [31-d].

This reaction can be carried out by the method described in step 8-3 of production method 8 or a method pursuant thereto.

[Step 31-4]

This step is a method of producing compound [314] by reacting compound [31-e] under an acidic condition to deprotect the pyrazolyl by removing protecting group Pro².

This reaction can be carried out by the method described in step 4-2 of production method 4 or a method pursuant thereto.

Compound [314] thus obtained can be isolated and purified by known separation and purification means such as concentration, concentration under reduced pressure, reprecipitation, solvent extraction, crystallization, and chromatography.

Compounds [1-e], [31-a] and [31-d] which are used as starting compounds in production method 31 above can be produced by production method 1 above, a method pursuant thereto, or a method known per se, or can be obtained by purchasing commercial products.

Among compound [I-1] of the present invention, compound [32-d] can be produced, for example, by production method 32 below or a method pursuant thereto.

Production Method 32

[Formula 314]

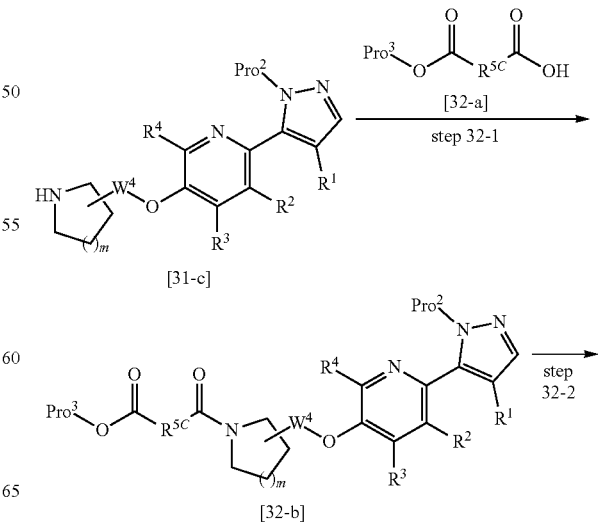

257
-continued

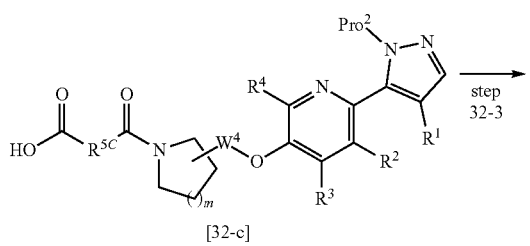

[32-c]

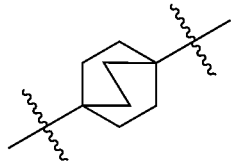

[32-d]

[In the scheme,
$R^1, R^2, R^3, R^4, W^4, Pro^2, Pro^3$, and m are the same as defined above; and
$R^{5C}$ represents $C_{1-4}$ alkanediyl, the formula —($C_{1-4}$ alkane)-NH—, the formula —($C_6H_4$)—$CH_2$—, a structure represented by formula [X-1'], formula [X-2'], or formula [X-3'] below.]

[Formula 315]

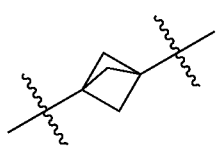 [X-1']

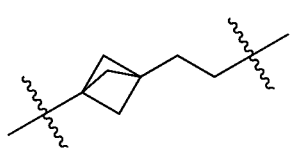 [X-2']

258
-continued

[X-3']

[Step 32-1]
This step is a method of producing compound [32-b] by reacting compound [31-c] with compound [32-a] or the corresponding alkylamine (the alkyl of the alkylamine is substituted with alkoxycarbonyl).
This reaction can be carried out by the method described in step 20-3 of production method 20 or a method pursuant thereto.

[Step 32-2]
This step is a method of producing compound [32-c] by reacting compound [32-b] under an acidic condition to deprotect the pyrazolyl by removing protecting group $Pro^2$.
This reaction can be carried out by the method described in step 4-2 of production method 4 or the method described in step 5-4 of production method 5, or a method pursuant thereto.

[Step 32-3]
This step is a method of producing compound [32-d] by deprotecting compound [32-c] by removing protecting group $Pro^3$.
This reaction can be carried out by the method described in step 5-5 of production method 5 or a method pursuant thereto.
Steps 32-2 and 32-3 above may be carried out in the reversed order.
Compound [32-d] thus obtained can be isolated and purified by known separation and purification means such as concentration, concentration under reduced pressure, reprecipitation, solvent extraction, crystallization, and chromatography.
Compounds [31-c] and [32-a] which are used as starting compounds in production method 32 above can be produced by production method 31 above, a method pursuant thereto, or a method known per se, or can be obtained by purchasing commercial products.
Among compound [I-1] of the present invention, compound [33-e] can be produced, for example, by production method 33 below or a method pursuant thereto.

Production Method 33

[Formula 316]

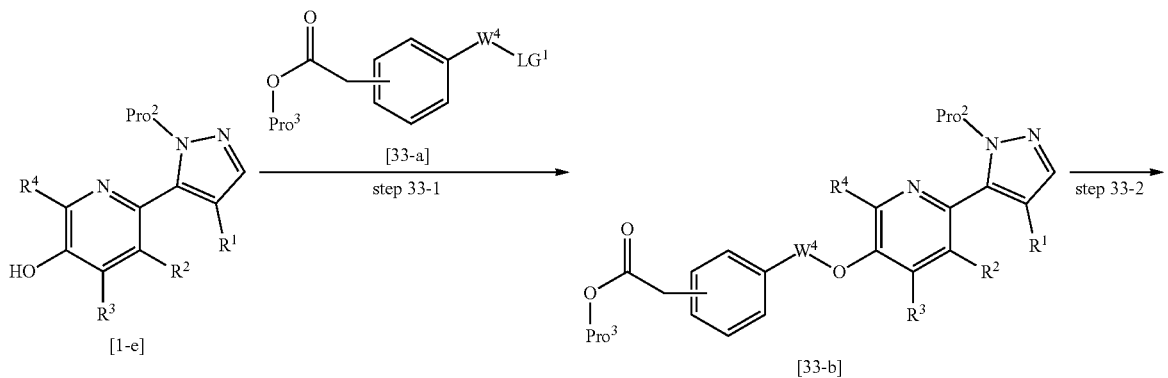

-continued

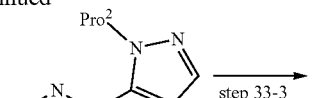
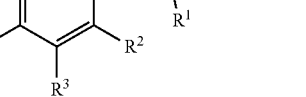

[In the scheme,
$R^1$, $R^2$, $R^3$, $R^4$, $W^4$, $LG^1$, $Pro^2$, and $Pro^3$ are the same as defined above; and
$R^{20}$ represents a hydrogen atom or methyl.]

[Step 33-1]

This step is a method of producing compound [33-b] by reacting compound [1-e] with compound [33-a].

This reaction can be carried out by the method described in step 4-1 of production method 4 or a method pursuant thereto.

[Step 33-2]

This step is a method of producing compound [33-c] by methylating position α of the carbonyl of the ester of compound [33-b].

This reaction can be carried out by using methyl iodide and sodium hydride, and (i) when slightly excessive amounts of the reagents are used, a monomethyl form in which $R^{20}$ is a hydrogen atom is obtained as a main product, and (ii) when highly excessive amounts of the reagents are used, a dimethyl form in which $R^{20}$ is methyl is obtained as a main product.

(i) When the monomethyl form is obtained as a main product, the amount of the methyl iodide to be used in the present reaction is 1 to 1.5 equivalents, and preferably 1 to 1.1 equivalents, with respect to 1 equivalent of compound [33-b].

The amount of the sodium hydride to be used in the present reaction is 1 to 2 equivalents, and preferably 1 to 1.2 equivalents, with respect to 1 equivalent of compound [33-b].

(ii) When the dimethyl form is obtained as a main product, the amount of the methyl iodide to be used in the present reaction is 2 to 5 equivalents, and preferably 2 to 4 equivalents, with respect to 1 equivalent of compound [33-b].

The amount of the sodium hydride to be used in the present reaction is 2 to 5 equivalents, and preferably 2 to 4.2 equivalents, with respect to 1 equivalent of compound [33-b].

Examples of the solvent which is used in the present reaction include tetrahydrofuran, N,N-dimethylformamide, and dimethyl sulfoxide; and these solvents may be mixed with each other at an appropriate ratio and used.

The present reaction can be carried out usually at 0° C. to room temperature for 1 to 24 hours.

[Step 33-3]

This step is a method of producing compound [33-d] by reacting compound [33-c] under an acidic condition to deprotect the pyrazolyl by removing protecting group $Pro^2$.

This reaction can be carried out by the method described in step 4-2 of production method 4 or the method described in step 5-4 of production method 5, or a method pursuant thereto.

[Step 33-4]

This step is a method of producing compound [33-e] by deprotecting compound [33-d] by removing protecting group $Pro^3$.

This reaction can be carried out by the method described in step 5-5 of production method 5 or a method pursuant thereto.

Steps 33-3 and 33-4 above may be carried out in the reversed order.

Compound [33-e] thus obtained can be isolated and purified by known separation and purification means such as concentration, concentration under reduced pressure, reprecipitation, solvent extraction, crystallization, and chromatography.

Compounds [1-e] and [33-a] which are used as starting compounds in production method 33 above can be produced by production method 1 above, a method pursuant thereto, or a method known per se, or can be obtained by purchasing commercial products.

Among compound [I-1] of the present invention, compound [34-e] can be produced, for example, by production method 34 below or a method pursuant thereto.

Production Method 34

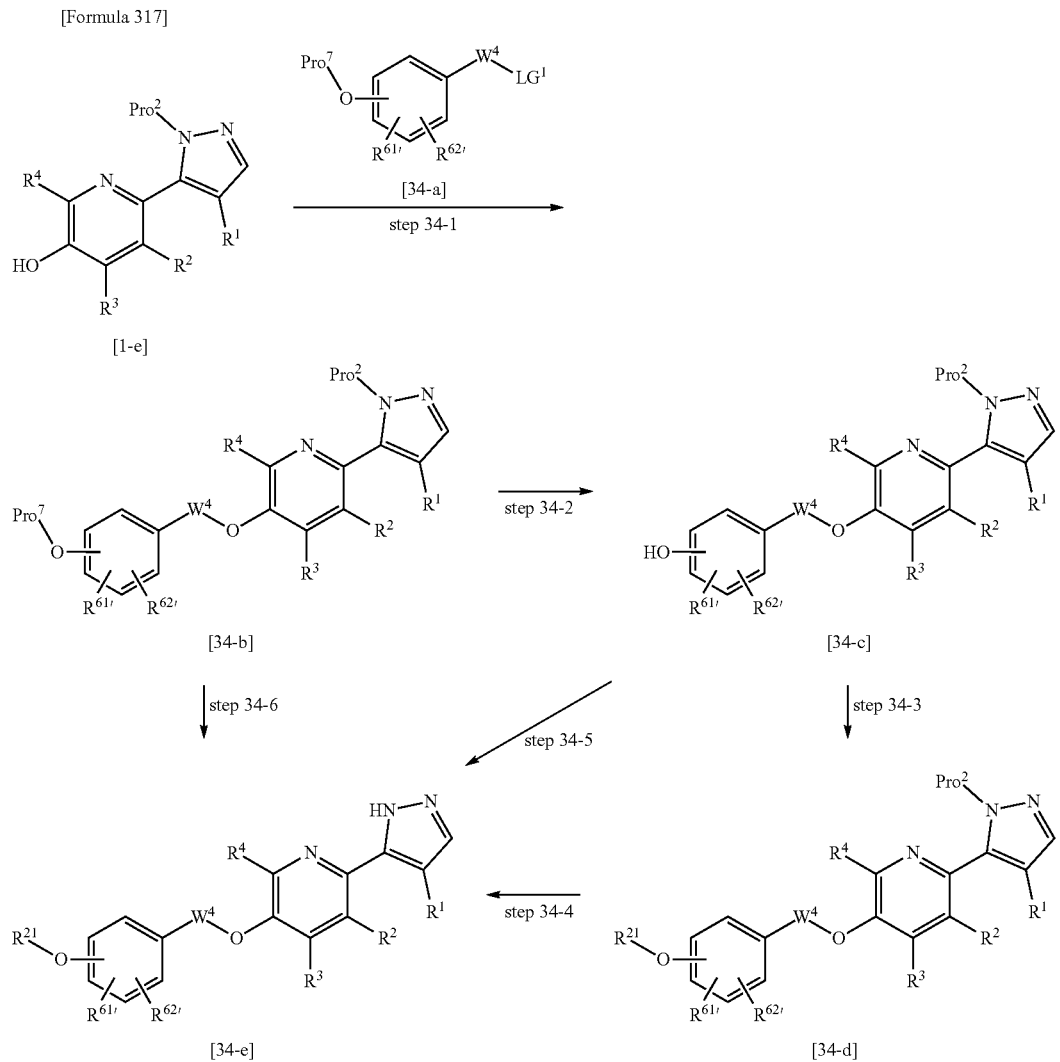

[In the scheme,
$R^1$, $R^2$, $R^3$, $R^4$, $W^4$, $LG^1$, and $Pro^2$ are the same as defined above;
$R^{61'}$ represents a hydrogen atom, a fluorine atom, methylsulfonyl, or methyl;
$R^{62'}$ represents a hydrogen atom or a fluorine atom;
$R^{21}$ represents a hydrogen atom or $C_{1-4}$ alkylsulfonyl; and
$Pro^6$ represents a protecting group for hydroxy, as exemplified by acetyl, or a benzyl-based protecting group such as benzyl and 4-methoxybenzyl.]

[Step 34-1]

This step is a method of producing compound [34-b] by reacting compound [1-e] with compound [34-a].

This reaction can be carried out by the method described in step 4-1 of production method 4 or a method pursuant thereto.

[Step 34-2]

This step is a method of producing compound [34-c] by deprotecting the hydroxy of compound [34-b] by removing protecting group $Pro^6$.

(i) When protecting group $Pro^6$ is acetyl or the like, this reaction can be carried out by the method described in step 5-2 of production method 5 or a method pursuant thereto.

(ii) When protecting group $Pro^6$ is a benzyl-based protecting group such as benzyl and 4-methoxybenzyl, this reaction can be carried out by the method described in step 1-3 of production method 1 or a method pursuant thereto.

[Step 34-3]

This step is a method of producing compound [34-d] by reacting compound [34-c] with the corresponding sulfonyl chloride.

The amount of the sulfonyl chloride to be used in the present reaction is 1 to 5 equivalents, and preferably 1 to 3 equivalents, with respect to 1 equivalent of compound [34-c].

Examples of the base which is used in the present reaction include triethylamine, pyridine, 4-dimethylaminopyridine, and N,N-diisopropylethylamine. The amount of the base to be used is usually 1 to 5 equivalents, and preferably 1 to 3 equivalents, with respect to 1 equivalent of compound [34-c].

Examples of the solvent which is used in the present reaction include solvents that do not interfere with reactions, such as chloroform, dichloromethane, toluene, diethyl ether, tetrahydrofuran, ethyl acetate, N,N-dimethylformamide, and acetonitrile; and these solvents may be mixed with each other at an appropriate ratio and used.

The present reaction can be carried out usually at 0° C. to room temperature for 1 to 24 hours.

[Step 34-4]

This step is a method of producing compound [34-e] by reacting compound [34-d] under an acidic condition to deprotect the pyrazolyl by removing protecting group $Pro^2$.

This reaction can be carried out by the method described in step 4-2 of production method 4 or a method pursuant thereto.

[Step 34-5]

This step is a method of producing compound [34-e] in which $R^{21}$ is a hydrogen atom from compound [34-c].

This reaction can be carried out by the method described in step 4-2 of production method 4 or a method pursuant thereto.

When that type of compound [34-e] in which $R^{21}$ is a hydrogen atom is produced, steps 34-2 and 34-5 above may be carried out in the reversed order.

[Step 34-6]

This step is a method of producing compound [34-e] in which $R^{21}$ is a hydrogen atom from compound [34-c] in which $Pro^6$ is 4-methoxybenzyl.

This reaction can be carried out by the method described in step 4-2 of production method 4 or the method described in step 5-5 of production method 5, or a method pursuant thereto.

Compound [34-e] thus obtained can be isolated and purified by known separation and purification means such as concentration, concentration under reduced pressure, reprecipitation, solvent extraction, crystallization, and chromatography.

Incidentally, compounds [1-e] and [34-a] which are used as starting compounds in production method 34 above can be produced by production method 1 above, a method pursuant thereto, or a method known per se, or can be obtained by purchasing commercial products.

Among compound [I-1] of the present invention, compound [35-g] can be produced, for example, by production method 35 below or a method pursuant thereto.

Production Method 35

[Formula 318]

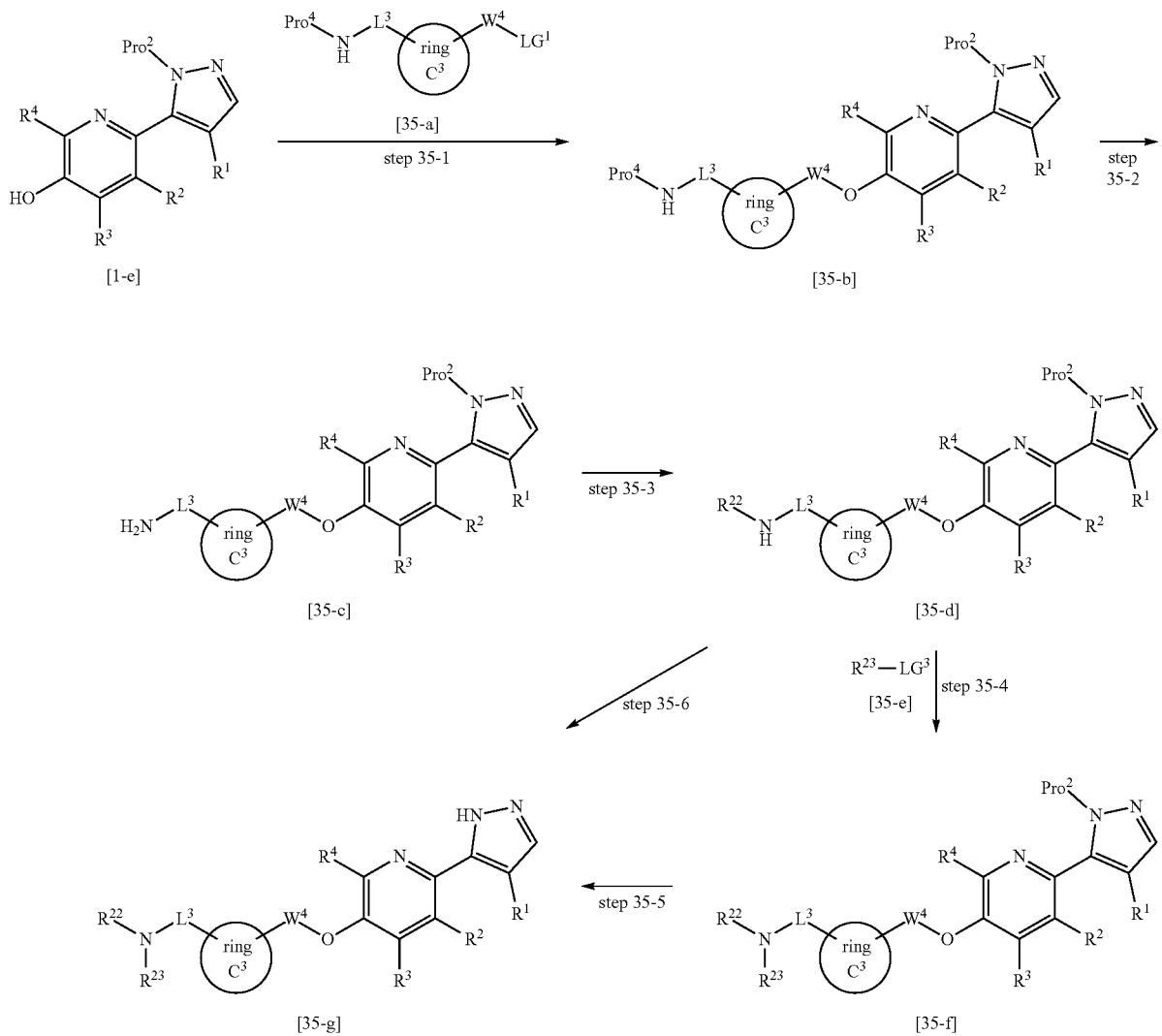

[In the scheme, $R^1$, $R^2$, $R^3$, $R^4$, $W^4$, $LG^1$, $Pro^2$, and $Pro^4$ are the same as defined above;

$L^3$ represents a single bond or $C_{1-4}$ alkyl;

ring $C^3$ represents phenyl, $C_{3-6}$ cycloalkyl, or the structure represented by formula [IX-1] below:

[Formula 319]

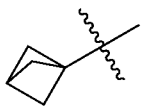

[IX-1]

$R^{22}$ represents $C_{1-4}$ alkylsulfonyl;

$R^{23}$ represents a hydrogen atom or $C_{1-4}$ alkyl; and $LG^3$ represents a leaving group selected from the group consisting of a halogen atom such as a chlorine atom and a bromine atom, $C_{1-4}$ alkylsulfonyloxy such as methanesulfonyloxy, and arylsulfonyloxy such as p-toluenesulfonyloxy.]

[Step 35-1]

This step is a method of producing compound [35-b] by reacting compound [1-e] with compound [35-a].

This reaction can be carried out by the method described in step 4-1 of production method 4 or a method pursuant thereto.

[Step 35-2]

This step is a method of producing compound [35-c] by deprotecting the amino of compound [35-b] by removing protecting group $Pro^4$.

This reaction can be carried out by the method described in step 20-2 of production method 20 or a method pursuant thereto.

[Step 35-3]

This step is a method of producing compound [35-d] by reacting compound [35-c] with the corresponding sulfonyl chloride.

This reaction can be carried out by the method described in step 34-3 of production method 34 or a method pursuant thereto.

[Step 35-4]

This step is a method of producing compound [35-f] by reacting compound [35-d] with compound [35-e].

This reaction can be carried out by the method described in step 7-2 of production method 7 or a method pursuant thereto.

[Step 35-5]

This step is a method of producing compound [35-g] by reacting compound [34-f] under an acidic condition to deprotect the pyrazolyl by removing protecting group $Pro^2$.

This reaction can be carried out by the method described in step 4-2 of production method 4 or a method pursuant thereto.

[Step 35-6]

This step is a method of producing compound [35-g] in which $R^{23}$ is a hydrogen atom from compound [35-d].

This reaction can be carried out by the method described in step 4-2 of production method 4 or a method pursuant thereto.

Compound [35-g] thus obtained can be isolated and purified by known separation and purification means such as concentration, concentration under reduced pressure, reprecipitation, solvent extraction, crystallization, and chromatography.

Compounds [1-e] and [35-a] which are used as starting compounds in production method 35 above can be produced by production method 1 above, a method pursuant thereto, or a method known per se, or can be obtained by purchasing commercial products.

Among compound [I-2] of the present invention, compound [36-e] in which the structure represented by $R^5$ is a structure shown in formula [IV-2] below and $R^{52}$ is carboxy can be produced, for example, by production method 36 below or a method pursuant thereto.

[Formula 320]

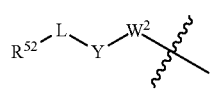

[IV-2]

Production Method 36

[Formula 321]

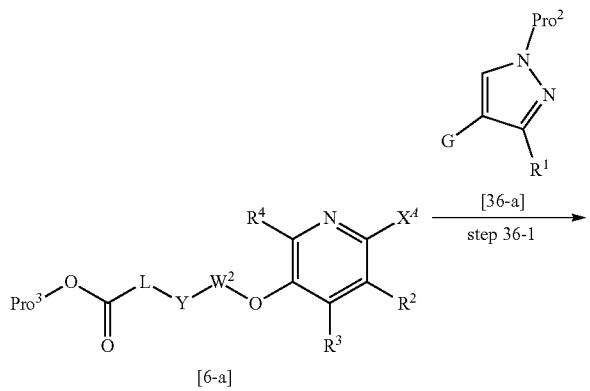

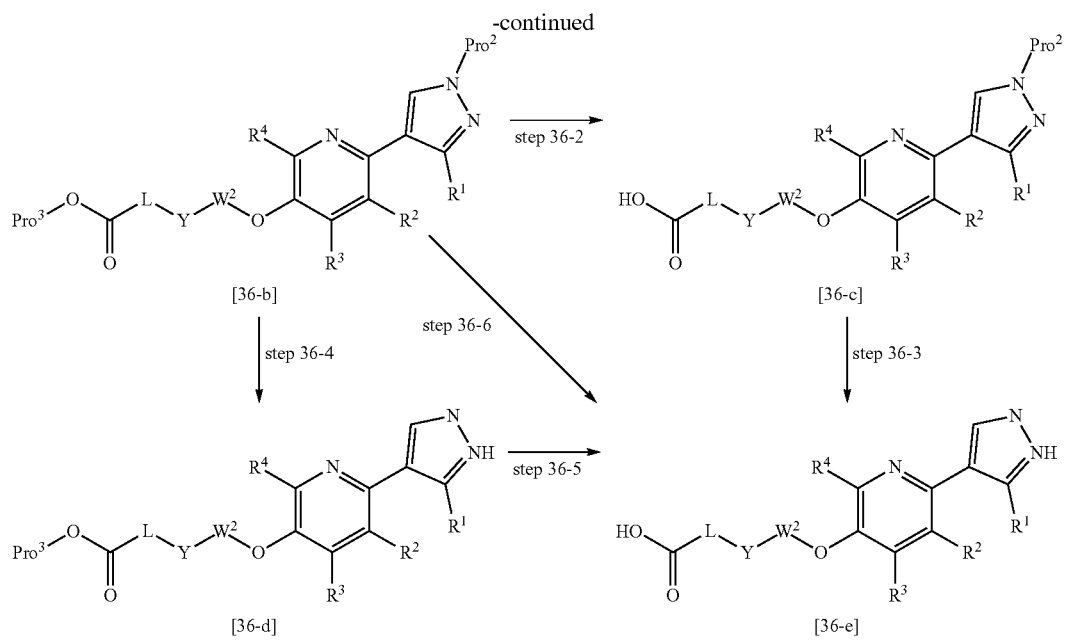

[In the scheme,
$R^1$, $R^2$, $R^3$, $R^4$, $X^A$, $Pro^2$, $Pro^3$, $W^2$, Y, L, and G are the same as defined above.]

[Step 36-1]

This step is a method of producing compound [36-b] by reacting compound [6-a] with compound [36-a].

This reaction can be carried out by the method described in step 1-2 of production method 1 or a method pursuant thereto.

There are several synthesis pathways for production of compound [36-e]. Steps 36-2 to 36-6 therefor will be sequentially described.

(i) When $Pro^3$ in compound [36-b] is primary or secondary alkyl such as methyl, ethyl, and 2-propyl, or (ii) when $Pro^3$ in compound [36-b] is a benzyl-based protecting group such as benzyl and 4-methoxybenzyl, compound [36-e] can be produced via compound [36-c] by methods described in steps 36-2 and 36-3.

[Step 36-2]

This step is a method of producing compound [36-c] by deprotecting compound [36-b] by removing protecting group $Pro^3$.

This reaction can be carried out by the method described in step 5-2 of production method 5 or a method pursuant thereto.

[Step 36-3]

This step is a method of producing compound [36-e] by deprotecting the pyrazolyl of compound [36-c] by removing protecting group $Pro^2$ under an acidic condition.

This reaction can be carried out by the method described in step 4-2 of production method 4 or a method pursuant thereto.

(i) When $Pro^3$ in compound [36-b] is primary or secondary alkyl such as methyl, ethyl, and 2-propyl, (ii) when $Pro^3$ in compound [36-b] is a benzyl-based protecting group such as benzyl and 4-methoxybenzyl, or (iii) when $Pro^3$ in compound [36-b] is tert-butyl, compound [36-e] can be produced via compound [36-d] by methods described in steps 36-4 and 36-5.

[Step 36-4]

This step is a method of producing compound [36-d] by deprotecting the pyrazolyl of compound [36-b] by removing protecting group $Pro^2$ under an acidic condition.

This reaction can be carried out by the method described in step 5-4 of production method 5 or a method pursuant thereto.

[Step 36-5]

This step is a method of producing compound [36-e] by deprotecting compound [36-d] by removing protecting group $Pro^3$.

This reaction can be carried out by the method described in step 5-5 of production method 5 or a method pursuant thereto.

When $Pro^3$ in compound [36-b] is 4-methoxybenzyl or tert-butyl, compound [36-e] can be produced by a method described in step 36-6.

[Step 36-6]

This step is a method of producing compound [36-e] by deprotecting compound [36-b] by removing protecting groups $Pro^2$ and $Pro^3$ under an acidic condition.

This reaction can be carried out by the method described in step 5-5 (iii) of production method 5 or a method pursuant thereto.

Compound [36-e] thus obtained can be isolated and purified by known separation and purification means such as concentration, concentration under reduced pressure, reprecipitation, solvent extraction, crystallization, and chromatography.

Incidentally, compounds [6-a] and [36-a] which are used as starting compounds in production method 36 above can be produced by production method 6 above, a method pursuant thereto, or a method known per se, or can be obtained by purchasing commercial products.

Among compound [I-2] of the present invention, compound [37-d] in which the structure represented by $R^5$ is a structure represented by formula [IV-3] below and $R^{53}$ is the formula $HOC(=O)-L^1-$ can be produced, for example, by production method 37 below or a method pursuant thereto.

[Formula 322]

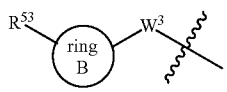

Production Method 37

[Formula 323]

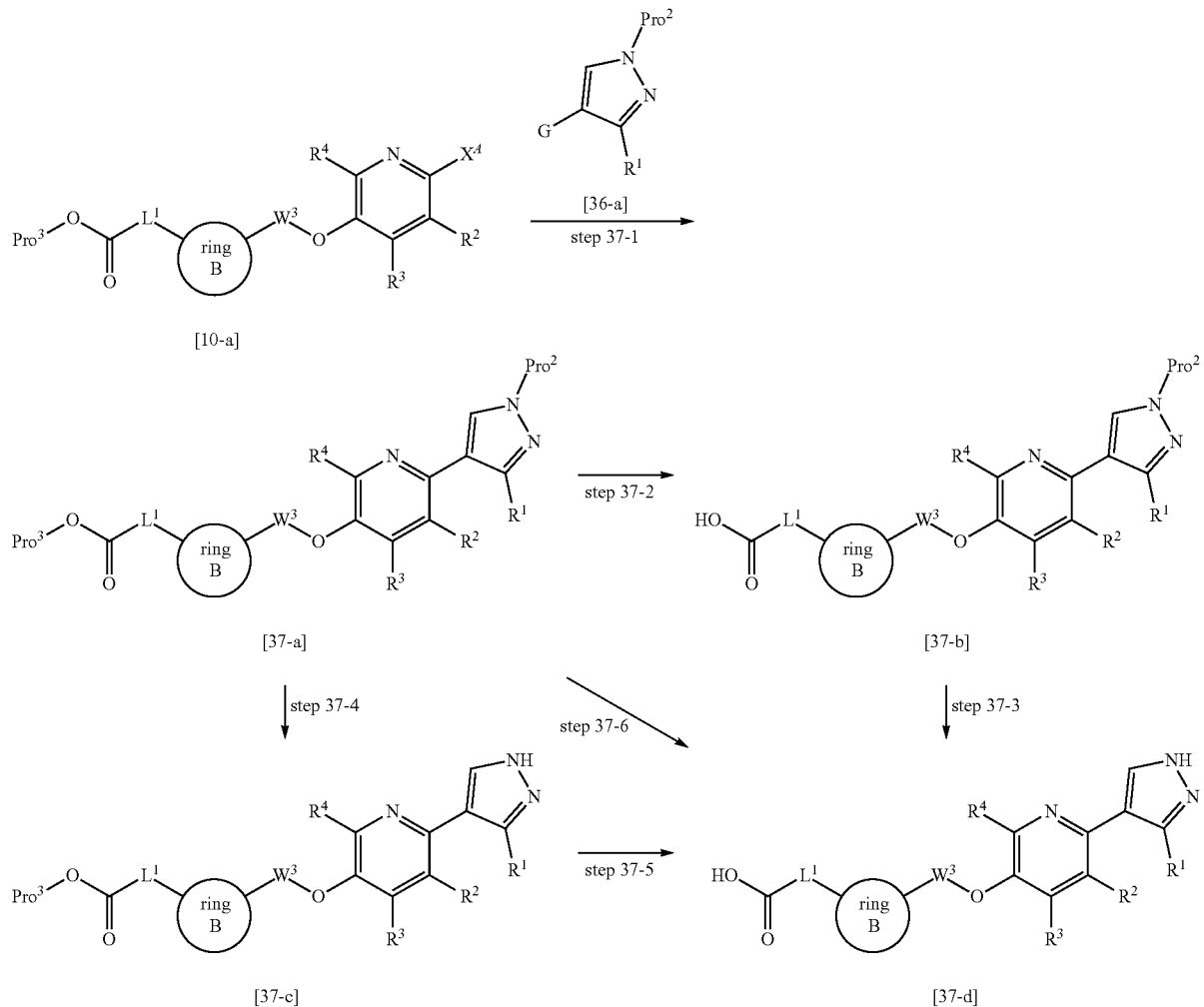

[In the scheme,
$R^1$, $R^2$, $R^3$, $R^4$, $X^4$, $Pro^2$, $Pro^3$, $W^3$, ring B, $L^1$, and G are the same as defined above.]

[Step 37-1]

This step is a method of producing compound [37-a] by reacting compound [10-a] with compound [36-a].

This reaction can be carried out by the method described in step 1-2 of production method 1 or a method pursuant thereto.

There are several synthesis pathways for production of compound [37-d]. Steps 37-2 to 37-6 therefor will be sequentially described.

(i) When $Pro^3$ in compound [37-a] is primary or secondary alkyl such as methyl, ethyl, and 2-propyl, or (ii) when $Pro^3$ in compound [37-a] is a benzyl-based protecting group such as benzyl and 4-methoxybenzyl, compound [37-d] can be produced via compound [37-b] by methods described in steps 37-2 and 37-3.

[Step 37-2]

This step is a method of producing compound [37-b] by deprotecting compound [37-a] by removing protecting group $Pro^3$.

This reaction can be carried out by the method described in step 5-2 of production method 5 or a method pursuant thereto.

[Step 37-3]

This step is a method of producing compound [37-d] by deprotecting the pyrazolyl of compound [37-b] by removing protecting group $Pro^2$ under an acidic condition.

This reaction can be carried out by the method described in step 4-2 of production method 4 or a method pursuant thereto.

(i) When $Pro^3$ in compound [37-a] is primary or secondary alkyl such as methyl, ethyl, and 2-propyl, (ii) when $Pro^3$ in compound [37-a] is a benzyl-based protecting group such as benzyl and 4-methoxybenzyl, or (iii) when $Pro^3$ in compound [37-a] is tert-butyl, compound [37-d] can be produced via compound [37-c] by methods described in steps 37-4 and 37-5.

[Step 37-4]

This step is a method of producing compound [37-c] by deprotecting the pyrazolyl of compound [37-a] by removing protecting group Pro$^2$ under an acidic condition.

This reaction can be carried out by the method described in step 5-4 of production method 5 or a method pursuant thereto.

[Step 37-5]

This step is a method of producing compound [37-d] by deprotecting compound [37-c] by removing protecting group Pro$^3$.

This reaction can be carried out by the method described in step 5-5 of production method 5 or a method pursuant thereto.

When Pro$^3$ in compound [37-a] is 4-methoxybenzyl or tert-butyl, compound [37-d] can be produced by a method described in step 37-6.

[Step 37-6]

This step is a method of producing compound [37-d] by deprotecting compound [37-a] by removing protecting groups Pro$^2$ and Pro$^3$ under an acidic condition.

This reaction can be carried out by the method described in step 5-5 (iii) of production method 5 or a method pursuant thereto.

Compound [37-d] thus obtained can be isolated and purified by known separation and purification means such as concentration, concentration under reduced pressure, reprecipitation, solvent extraction, crystallization, and chromatography.

Incidentally, compounds [10-a] and [36-a] which are used as starting compounds in production method 37 above can be produced by production method 10 above, a method pursuant thereto, or a method known per se, or can be obtained by purchasing commercial products.

Among compound [I-2] of the present invention, compound [38-d] in which the structure represented by R$^5$ is a structure represented by formula [IV-4] below and R$^{54}$ is the formula HOC(=O)—R$^{54'}$— can be produced, for example, by production method 38 below or a method pursuant thereto.

[Formula 324]

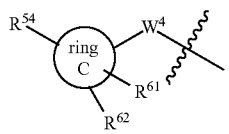

[IV-4]

Production Method 38

[Formula 325]

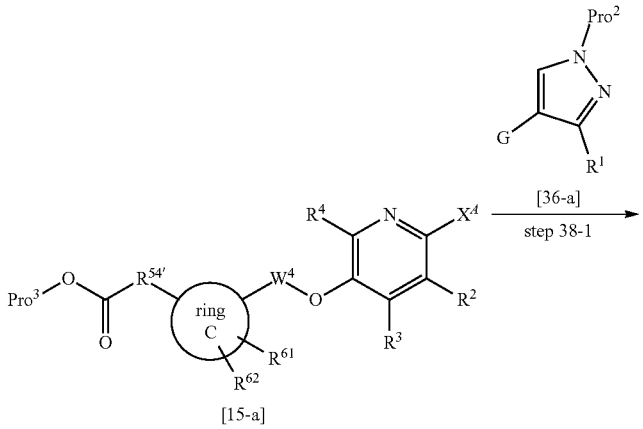

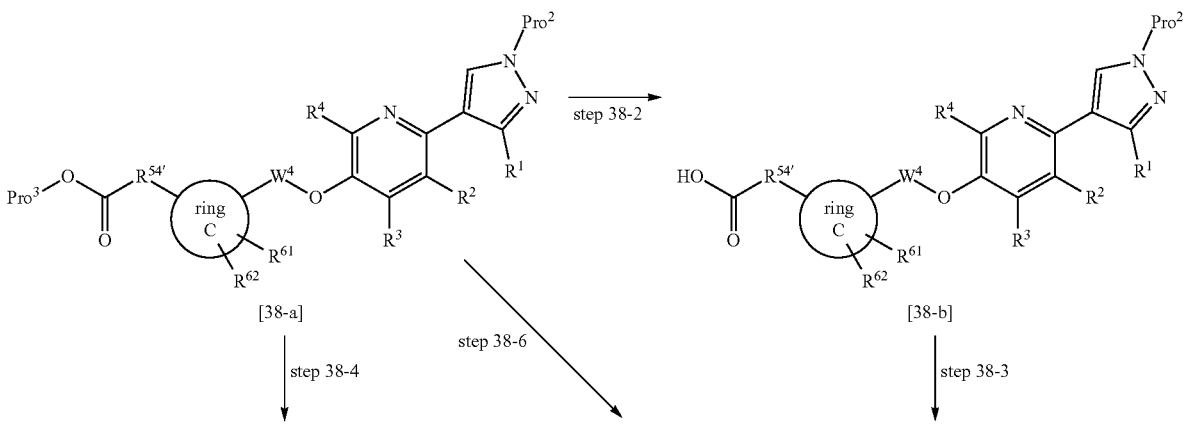

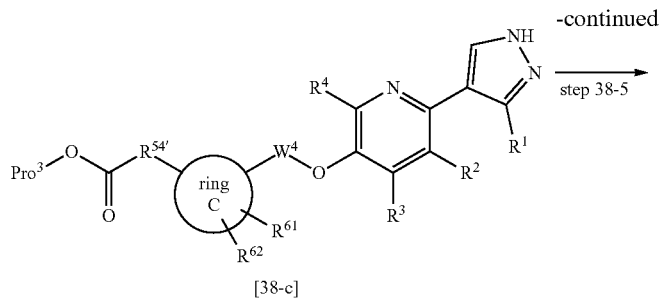

[38-c]

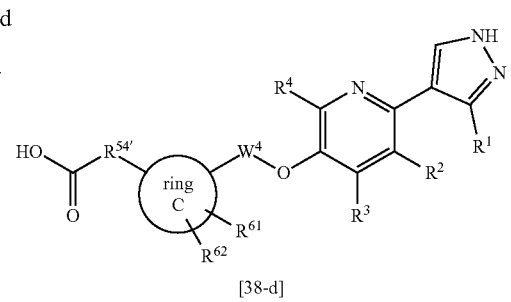

[38-d]

[In the scheme,
$R^1$, $R^2$, $R^3$, $R^4$, $X^4$, $R^{54'}$, $R^{61}$, $R^{62}$, $Pro^2$, $Pro^3$, $W^4$, ring C, and G are the same as defined above.]

[Step 38-1]

This step is a method of producing compound [38-a] by reacting compound [15-a] with compound [36-a].

This reaction can be carried out by the method described in step 1-2 of production method 1 or a method pursuant thereto.

There are several synthesis pathways for production of compound [38-d]. Steps 38-2 to 38-6 therefor will be sequentially described.

(i) When $Pro^3$ in compound [38-a] is primary or secondary alkyl such as methyl, ethyl, and 2-propyl, or (ii) when $Pro^3$ in compound [38-a] is a benzyl-based protecting group such as benzyl and 4-methoxybenzyl, compound [38-d] can be produced via compound [38-b] by methods described in steps 38-2 and 38-3.

[Step 38-2]

This step is a method of producing compound [38-b] by deprotecting compound [38-a] by removing protecting group $Pro^3$.

This reaction can be carried out by the method described in step 5-2 of production method 5 or a method pursuant thereto.

[Step 38-3]

This step is a method of producing compound [38-d] by deprotecting the pyrazolyl of compound [38-b] by removing protecting group $Pro^2$ under an acidic condition.

This reaction can be carried out by the method described in step 4-2 of production method 4 or a method pursuant thereto.

(i) When $Pro^3$ in compound [38-a] is primary or secondary alkyl such as methyl, ethyl, and 2-propyl, (ii) when $Pro^3$ in compound [38-a] is a benzyl-based protecting group such as benzyl and 4-methoxybenzyl, or (iii) when $Pro^3$ in compound [38-a] is tert-butyl, compound [38-d] can be produced via compound [38-c] by methods described in steps 38-4 and 38-5.

[Step 38-4]

This step is a method of producing compound [38-c] by deprotecting the pyrazolyl of compound [38-a] by removing protecting group $Pro^2$ under an acidic condition.

This reaction can be carried out by the method described in step 5-4 of production method 5 or a method pursuant thereto.

[Step 38-5]

This step is a method of producing compound [38-d] by deprotecting compound [38-c] by removing protecting group $Pro^3$.

This reaction can be carried out by the method described in step 5-5 of production method 5 or a method pursuant thereto.

When $Pro^3$ in compound [38-a] is 4-methoxybenzyl or tert-butyl, compound [38-d] can be produced by step 38-6.

[Step 38-6]

This step is a method of producing compound [38-d] by deprotecting compound [38-a] by removing protecting groups $Pro^2$ and $Pro^3$ under an acidic condition.

This reaction can be carried out by the method described in step 5-5 (iii) of production method 5 or a method pursuant thereto.

Compound [38-d] thus obtained can be isolated and purified by known separation and purification means such as concentration, concentration under reduced pressure, precipitation, solvent extraction, crystallization, and chromatography.

Incidentally, compounds [15-a] and [36-a] which are used as starting compounds in production method 38 above can be produced by production method 15 above, a method pursuant thereto, or a method known per se, or can be obtained by purchasing commercial products.

Among compound [I-3] of the present invention, compound [39-c] in which the structure represented by $R^5$ is a structure represented by formula [IV-2] below and $R^{52}$ is carboxy can be produced, for example, by production method 39 below or a method pursuant thereto.

[Formula 326]

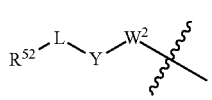

[IV-2]

Production Method 39

[Formula 327]

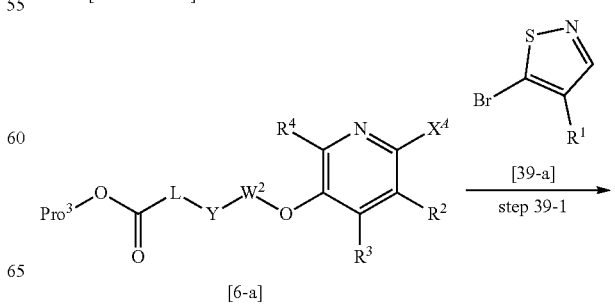

[6-a]    [39-a]    step 39-1

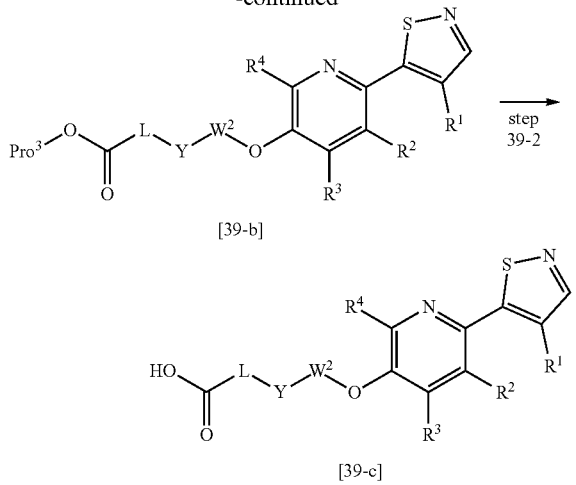

[39-b]

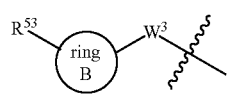

[39-c]

[In the scheme,
R$^1$, R$^2$, R$^3$, R$^4$, X$^A$, Pro$^3$, W$^2$, Y, and L are the same as defined above.]

[Step 39-1]

This step is a method of producing compound [39-b] by reacting compound [6-a] with compound [39-a].

This reaction applies a so-called Stille-Kelly reaction to intermolecular heterocoupling, and can be carried out in the presence of a palladium catalyst and an organodistannane.

The type and amount of the catalyst to be used in the present reaction is the same as those in step 1-2 of production method 1 or those pursuant thereto.

Examples of the organodistannane which is used in the present reaction include bis(trimethylstannane) and bis(tributylstannane). The amount of the organodistannane to be used is 1 to 3 equivalents, and preferably 1 to 1.5 equivalents, with respect to compound [6-a].

Examples of the reaction solvent which is used in the present reaction include solvents that do not interfere with reactions, such as toluene, xylene, 1,4-dioxane, tetrahydrofuran, and 1,2-dimethoxyethane; and these solvents may be mixed with each other at an appropriate ratio and used.

These reactions can be carried out usually at room temperature to reflux temperature for 1 to 24 hours, and can be also carried out under microwave irradiation.

[Step 39-2]

This step is a method of producing compound [39-c] by deprotecting compound [39-b] by removing protecting group Pro$^3$.

This reaction can be carried out by the method described in step 5-5 of production method 5 or a method pursuant thereto.

Compound [39-c] thus obtained can be isolated and purified by known separation and purification means such as concentration, concentration under reduced pressure, reprecipitation, solvent extraction, crystallization, and chromatography.

Compounds [6-a] and [39-a] which are used as starting compounds in production method 39 above can be produced by production method 6 above, a method pursuant thereto, or a method known per se, or can be obtained by purchasing commercial products.

Among compound [I-3] of the present invention, compound [40-b] in which the structure represented by R$^5$ is a structure represented by formula [IV-3] below and R$^{53}$ is the formula HOC(=O)-L$^1$- can be produced, for example, by production method 40 below or a method pursuant thereto.

[Formula 328]

[IV-3]

R$^{53}$—(ring B)—W$^3$—

Production Method 40

[Formula 329]

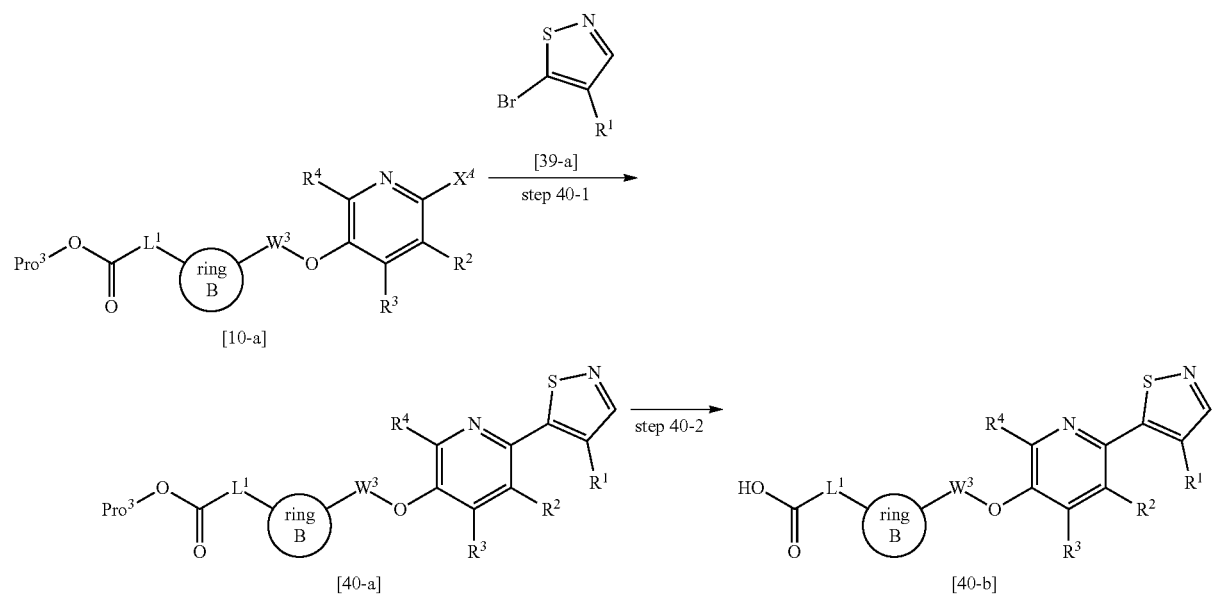

[In the scheme, $R^1$, $R^2$, $R^3$, $R^4$, $X^4$, $Pro^3$, $W^3$, ring B, and $L^1$ are the same as defined above.]

[Step 40-1]

This step is a method of producing compound [40-a] by reacting compound [10-a] with compound [39-a].

This reaction can be carried out by the method described in step 39-1 of production method 39 or a method pursuant thereto.

[Formula 331]

[Step 40-2]

This step is a method of producing compound [40-b] by deprotecting compound [40-a] by removing protecting group $Pro^3$.

This reaction can be carried out by the method described in step 5-5 of production method 5 or a method pursuant thereto.

Compound [40-b] thus obtained can be isolated and purified by known separation and purification means such as concentration, concentration under reduced pressure, reprecipitation, solvent extraction, crystallization, and chromatography.

Incidentally, compounds [10-a] and [39-a] which are used as starting compounds in production method 40 above can be produced by production method 10 above, a method pursuant thereto, or a method known per se, or can be obtained by purchasing commercial products.

Among compound [I-3] of the present invention, compound [41-b] in which the structure represented by $R^5$ is a structure represented by formula [IV-4] below and $R^{54}$ is the formula $HOC(=O)-R^{54'}$— can be produced, for example, by production method 41 below or a method pursuant thereto.

[Formula 330]

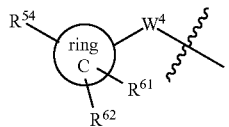

[IV-4]

Production Method 41

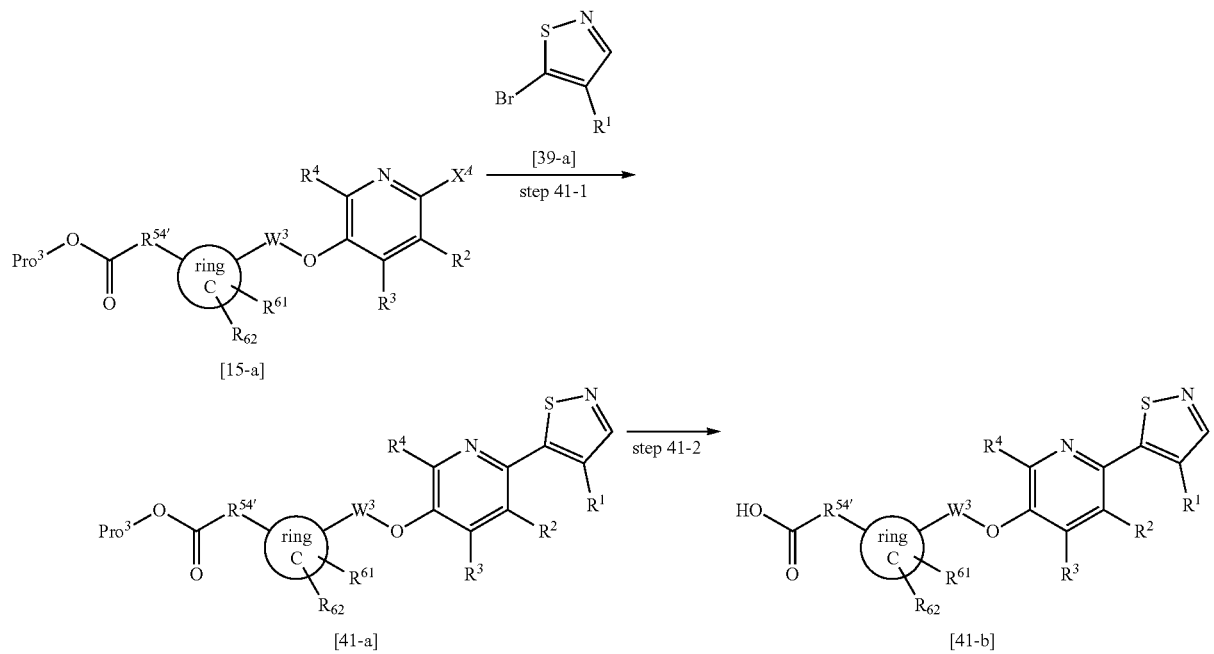

[In the scheme, $R^1$, $R^2$, $R^3$, $R^4$, $X^4$, $R^{54'}$, $R^{61}$, $R^{62}$, $PRO^3$, $W^4$, and ring C are the same as defined above.]

[Step 41-1]

This step is a method of producing compound [41-a] by reacting compound [15-a] with compound [39-a].

This reaction can be carried out by the method described in step 39-1 of production method 39 or a method pursuant thereto.

[Step 41-2]

This step is a method of producing compound [41-b] by deprotecting compound [41-a] by removing protecting group $Pro^3$.

This reaction can be carried out by the method described in step 5-5 of production method 5 or a method pursuant thereto.

Compound [41-b] thus obtained can be isolated and purified by known separation and purification means such as concentration, concentration under reduced pressure, reprecipitation, solvent extraction, crystallization, and chromatography.

Incidentally, compounds [15-a] and [39-a] which are used as starting compounds in production method 41 above can be produced by production method 15 above, a method pursuant thereto, or a method known per se, or can be obtained by purchasing commercial products.

Among compound [I-4] or [I-5] of the present invention, compound [42-c] in which the structure represented by $R^5$ is a structure represented by formula [IV-2] below and $R^{52}$ is carboxy can be produced, for example, by production method 42 below or a method pursuant thereto.

[Formula 332]

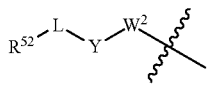

[IV-2]

Production Method 42

[Formula 333]

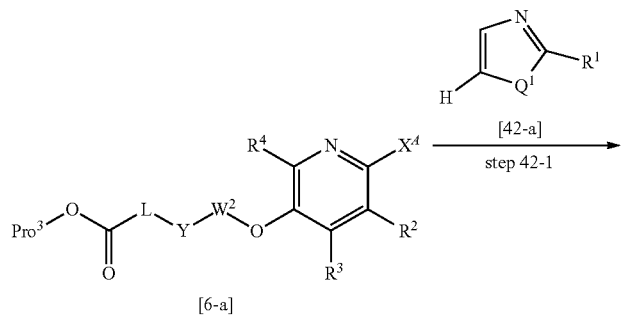

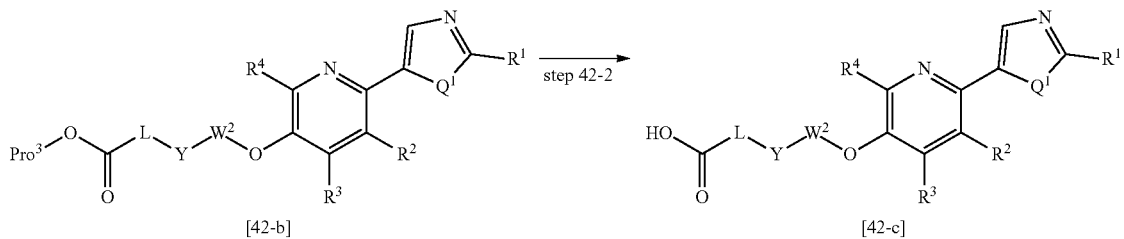

[In the scheme,
$R^1$, $R^2$, $R^3$, $R^4$, $Pro^3$, $W^2$, Y, and L are the same as defined above; and
$Q^1$ represents an oxygen atom or a sulfur atom.]

[Step 42-1]

This step is a method of producing compound [42-b] by reacting compound [6-a] with compound [42-a].

This reaction is a so-called Heck-type reaction that can be carried out in the presence of a palladium catalyst and a base.

The type and amount of the palladium catalyst to be used in the present reaction are the same as those in step 17-2 of production example 17 or those pursuant thereto.

Examples of the base which is used in the present reaction include potassium acetate, tetrabutylammonium acetate, and cesium pivalate. The amount of the base to be used is 1 to 3 equivalents, and preferably 1 to 1.5 equivalents, with respect to compound [6-a].

Examples of the reaction solvent to be used in the present reaction include solvents that do not interfere with reactions, such as toluene, N,N-dimethylacetamide, 1,4-dioxane, and water; and these solvents may be mixed with each other at an appropriate ratio and used.

These reactions can be carried out usually at reflux temperature for 1 to 24 hours, and can be also carried out under microwave irradiation.

[Step 42-2]

This step is a method of producing compound [42-c] by deprotecting compound [42-b] by removing protecting group $Pro^3$.

This reaction can be carried out by the method described in step 5-5 of production method 5 or a method pursuant thereto.

Compound [42-c] thus obtained can be isolated and purified by known separation and purification means such as concentration, concentration under reduced pressure, reprecipitation, solvent extraction, crystallization, and chromatography.

Compounds [6-a] and [42-a] which are used as starting compounds in production method 42 above can be produced by production method 6 above, a method pursuant thereto, or a method known per se, or can be obtained by purchasing commercial products.

Among compound [I-4] or [I-5] of the present invention, compound [43-b] in which the structure represented by $R^5$ is a structure represented by formula [IV-3] below and $R^{53}$ is the formula $HOC(\!=\!O)\text{-}L^1\text{-}$ can be produced, for example, by production method 43 below or a method pursuant thereto.

[Formula 334]

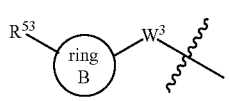

[IV-3]

Production Method 43

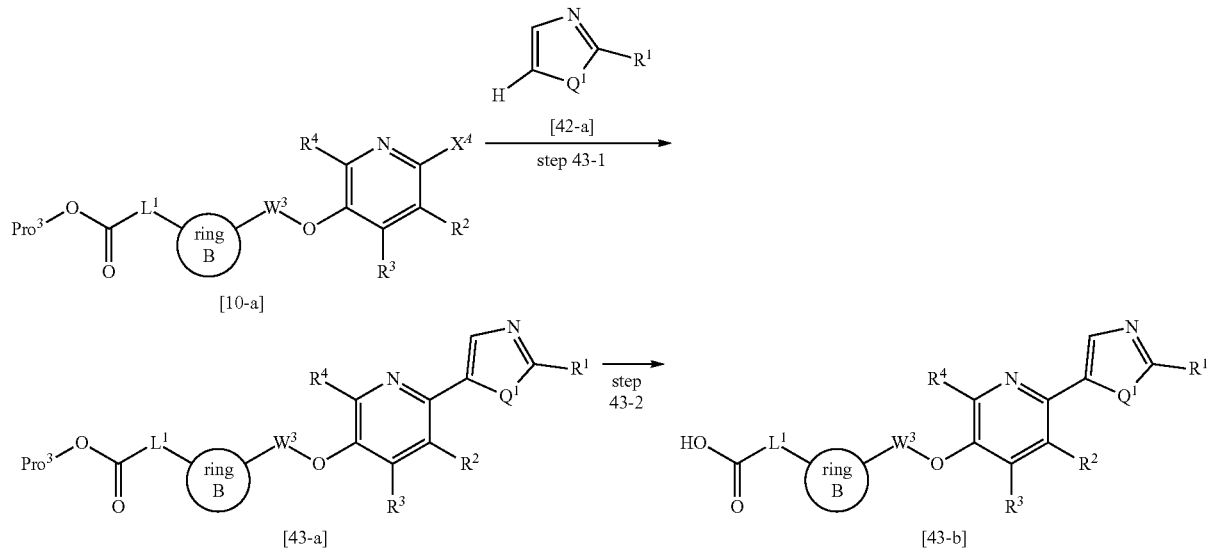

[In the scheme,
$R^1, R^2, R^3, R^4, Pro^3, X^4, W^3$, ring B, $L^1$, and $Q^1$ are the same as defined above.]

[Step 43-1]
This step is a method of producing compound [43-a] by reacting compound [10-a] with compound [42-a].
This reaction can be carried out by the method described in step 42-1 of production method 42 or a method pursuant thereto.

[Step 43-2]
This step is a method of producing compound [43-b] by deprotecting compound [43-a] by removing protecting group $Pro^3$.
This reaction can be carried out by the method described in step 5-5 of production method 5 or a method pursuant thereto.
Compound [43-b] thus obtained can be isolated and purified by known separation and purification means such as concentration, concentration under reduced pressure, precipitation, solvent extraction, crystallization, and chromatography.
Compounds [10-a] and [42-a] which are used as starting compounds in production method 43 above can be produced by production method 10 above, a method pursuant thereto, or a method known per se, or can be obtained by purchasing commercial products.

Among compound [I-4] or [I-5] of the present invention, compound [44-b] in which the structure represented by $R^5$ is a structure represented by formula [IV-4] below and $R^{54}$ is the formula $HOC(=O)-R^{54'}-$ can be produced, for example, by production method 44 below or a method pursuant thereto.

[Formula 336]

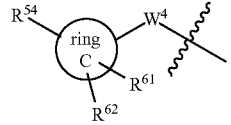

[IV-4]

Production Method 44

[Formula 337]

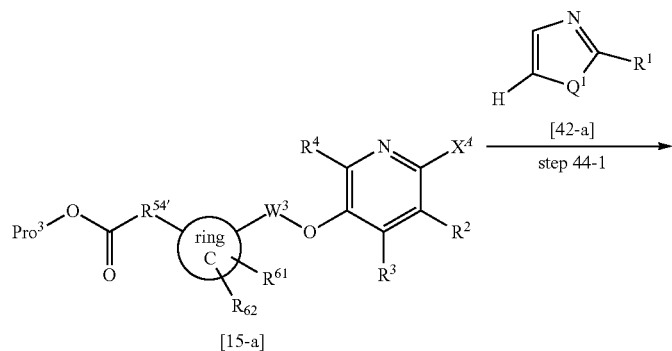

[In the scheme,
$R^1$, $R^2$, $R^3$, $R^4$, $R^{54'}$, $R^{61}$, $R^{62}$, $Pro^3$, $X^A$, $W^4$, ring C, and $Q^1$ are the same as defined above.]

[Step 44-1]

This step is a method of producing compound [44-a] by reacting compound [15-a] with compound [42-a].

This reaction can be carried out by the method described in step 42-1 of production method 42 or a method pursuant thereto.

[Step 44-2]

This step is a method of producing compound [44-b] by deprotecting compound [44-a] by removing protecting group $Pro^3$.

This reaction can be carried out by the method described in step 5-5 of production method 5 or a method pursuant thereto.

Compound [44-b] thus obtained can be isolated and purified by known separation and purification means such as concentration, concentration under reduced pressure, reprecipitation, solvent extraction, crystallization, and chromatography.

Compounds [15-a] and [42-a] which are used as starting compounds in production method 44 above can be produced by production method 15 above, a method pursuant thereto, or a method known per se, or can be obtained by purchasing commercial products.

The present invention will be described in more detail with reference to the following Reference Examples, Examples, and Test Examples, but these examples do not limit the present invention, and may be varied in such a range as not to deviate from the scope of the present invention.

In the following Reference Examples and Examples, packed columns (Reveleris (registered trademark) Flash Cartridges Silica manufactured by Grace or Biotage (registered trademark) SNAP Cartridge HP-Sphere manufactured by Biotage AB) were used for silica gel column chromatography. Packed columns (Reveleris (registered trademark) Flash Cartridges Amino manufactured by Grace or Biotage (registered trademark) SNAP Cartridge KP-NH manufactured by Biotage AB) were used for NH silica gel column chromatography. PLC plate 20×20 cm silica gel 60F254, 2 mm manufactured by Merck KGaA was used for preparative thin-layer chromatography. Unless otherwise stated, the ratio of eluent solvents is expressed as a volume ratio. The phase separator used was ISOLUTE (registered trademark) Phase Separator manufactured by Biotage AB.

Abbreviations used herein have the following meanings:
s: singlet
d: doublet
t: triplet
q: quartet
quin: quintet
sxt: sextet
spt: septet
dd: double doublet
dt: double triplet
td: triple doublet
tt: triple triplet
qd: quarter doublet
m: multiplet
br: broad
J: coupling constant
Hz: Hertz
CHLOROFORM-d: deuterated chloroform
DMSO-$d_6$: deuterated dimethyl sulfoxide
MeOH-$d_4$: deuterated methanol
ACETONE-$d_6$: deuterated acetone
$D_2O$: deuterated water
THP: tetrahydropyranyl
TMS: trimethylsilyl
Rf: retardation factor
$^1$H-NMR (proton nuclear magnetic resonance spectrum) was measured using tetramethylsilane as an internal standard with Fourier transformed NMR as described below, and all δ values are expressed in ppm.
200 MHz: Gemini2000 (Agilent Technologies, Inc.)
300 MHz: Inova300 (Agilent Technologies, Inc.)
400 MHz: AVANCE III HD400 (Bruker Corporation)
500 MHz: JNM-ECA500 (JEOL Ltd.)
600 MHz: JNM-ECA600 (JEOL Ltd.)

ACD/Spectrus Processor 2015 ACD/Labs 2015 Release (File Version S30S41, Build 76327, 28 Feb. 2015) (trade name) or the like was used for analysis. Very broad proton peaks shown by hydroxy, amino, amide, pyrazole, or the like are not indicated in some cases.

In analysis of compounds, there may be a proton unidentifiable because of overlapping with a peak from water or a solvent.

Mass Spectrum (MS) was measured on the following devices:
PlatformLC (Waters Corporation)
LCMS-2010EV (Shimadzu Corporation)
LCMS-IT-TOF (Shimadzu Corporation)
Agilent 6130 (Agilent Technologies, Inc.)
Agilent 6150 (Agilent Technologies, Inc.)

Ionization techniques used were Electrospray Ionization (ESI), Electron Ionization (EI), and dual ionization of ESI and Atmospheric Pressure Chemical Ionization (APCI). The values actually measured (which are described as "Found") are reported. Generally, molecular ion peaks are detected. However, for compounds having tert-butoxycarbonyl (-Boc), fragment ion peaks, which are peaks derived from the compounds that have lost tert-butoxycarbonyl or tert-butyl, may be also detected. For compounds having tetrahydropyranyl (THP), fragment ion peaks, which are peaks derived from the compounds that have lost tetrahydropyranyl, may be also detected. For compounds having hydroxy (—OH), fragment peaks, which are peaks derived from compounds that have lost $H_2O$ or an OH radical, may be also detected. For salts, molecular ion peaks of free forms or fragment ion peaks are typically observed.

LC-MS was performed in the Examples and Reference Examples under the following conditions:
HPLC: Agilent 1290 Infinity
MS: Agilent 6130 or 6150
[HPLC Conditions]
Column: Acquity UPLC CSH C18, 1.7 µm, 2.1x×50 mm (WATERS Corporation)
Solvent: solution A; water with 0.1% formic acid, solution B; acetonitrile with 0.1% formic acid
 (Method A)
Gradient: 0.00 min (solution A/solution B=80/20), 1.20 min (solution A/solution B=1/99), 1.40 min (solution A/solution B=1/99), 1.41 min (solution A/solution B=80/20), 1.50 min (solution A/solution B=80/20)
 (Method B)
Gradient: 0.00 min (solution A/solution B=95/5), 0.80 min (solution A/solution B=60/40), 1.08 min (solution A/solution B=1/99), 1.38 min (solution A/solution B=1/99), 1.41 min (solution A/solution B=95/5), 1.50 min (solution A/solution B=80/20) (Method C)
Gradient: 0.00 min (solution A/solution B=70/30), 0.80 min (solution A/solution B=1/99), 1.40 min (solution A/solution B=1/99), 1.42 min (solution A/solution B=70/30), 1.50 min (solution A/solution B=70/30)
Injection volume: 0.5 µL; Flow rate: 0.8 mL/min
Detection: UV 210 nm, 254 nm
HPLC equipped with evaporative light scattering detector (ELSD): Agilent 385-ELSD
MS condition
 Ionization: ESI or ESI/APCI multimode
Purification by preparative HPLC was performed in the Examples and Reference Examples under the following conditions:
Equipment: High-throughput purification system from Gilson, Inc.
Column: Triart C18, 5 µm, 30×50 mm (YMC Co., Ltd.) or X-Bridge Prep C18 5 um OBD,
30×50 (Waters Corporation)
Solvent: solution A; water with 0.1% formic acid, solution B; acetonitrile with 0.1% formic acid, or solution A; water with 0.1% trifluoroacetic acid, solution B; acetonitrile with 0.1% trifluoroacetic acid
 (Method A)
Gradient: 0.00 min (solution A/solution B=90/10), 2.00 min (solution A/solution B=90/10), 11.0 min (solution A/solution B=20/80), 12.0 min (solution A/solution B=5/95), 13.52 min (solution A/solution B=5/95), 15.0 min (solution A/solution B=90/10) (Method B)
Gradient: 0.00 min (solution A/solution B=95/5), 3.00 min (solution A/solution B=95/5), 8.53 min (solution A/solution B=80/20), 10.0 min (solution A/solution B=80/20), 11.0 min (solution A/solution B=50/50), 12.02 min (solution A/solution B=5/95), 13.5 min (solution A/solution B=5/95), 13.65 min (solution A/solution B=95/5), 15.0 min (solution A/solution B=95/5) (Method C)
Gradient: 0.00 min (solution A/solution B=80/20), 2.00 min (solution A/solution B=80/20), 10.0 min (solution A/solution B=5/95), 11.5 min (solution A/solution B=1/99), 13.5 min (solution A/solution B=1/99), 13.55 min (solution A/solution B=80/20), 15.0 min (solution A/solution B=5/95), 15.0 min (solution A/solution B=95/5)
Flow rate: 40 mL/min
Detection: UV 210 nm, UV 254 nm
HPLC equipped with ELSD: SofTA MODEL 300S ELSD
Purification by preparative LC-MS was performed in the Examples and Reference Examples under the following conditions:
HPLC: Agilent 1260 Infinity
[HPLC Conditions]
Column: X-SELECT CSH C18, 5 µm, OBD, 30×50 (Waters Corporation)
Solvent: solution A; water with 0.1% formic acid, solution B; acetonitrile with 0.1% formic acid, or solution A; water with 0.1% trifluoroacetic acid, solution B; acetonitrile with 0.1% trifluoroacetic acid
 (Method A)
Gradient: 0.00 min (solution A/solution B=90/10), 0.50 min (solution A/solution B=90/10), 7.50 min (solution A/solution B=20/80), 7.95 min (solution A/solution B=20/80), 8.00 min (solution A/solution B=5/95), 9.00 min (solution A/solution B=5/95), 9.05 min (solution A/solution B=90/10), 10.0 min (solution A/solution B=90/10)
 (Method B)
Gradient: 0.00 min (solution A/solution B=95/5), 0.50 min (solution A/solution B=95/5), 7.50 min (solution A/solution B=50/50), 7.95 min (solution A/solution B=50/50), 8.00 min (solution A/solution B=5/95), 9.00 min (solution A/solution B=5/95), 9.05 min (solution A/solution B=95/5), 10.00 min (solution A/solution B=95/5)
 (Method C)
Gradient: 0.00 min (solution A/solution B=80/20), 0.50 min (solution A/solution B=80/20), 7.00 min (solution A/solution B=5/95), 7.45 min (solution A/solution B=5/95), 7.50 min (solution A/solution B=1/99), 9.00 min (solution A/solution B=1/99), 9.20 min (solution A/solution B=80/20), 10.0 min (solution A/solution B=80/20)
Flow rate: 50 mL/min
Detection: UV 210 nm, UV 254 nm
MS: Agilent 6130
HPLC equipped with ELSD: Agilent 385 ELSD
MS condition
 Ionization: ESI or ESI/APCI multimode
Chiral HPLC analysis was performed in the Examples and Reference Examples under the following conditions:
HPLC: Agilent 1260 Infinity or 1100 Series
[HPLC Conditions]

TABLE 1-1

| | Conditions |
|---|---|
| Reference Example 90-1-(1) | Column: CHIRALPAK IB-3, 3 µm, 4.6 × 150 mm<br>Solvent: solution A; ethanol, solution B; n-hexane<br>Elution condition: solution A/solution B = 20/80<br>Flow rate: 1 mL/min, temperature: 40° C. |
| Reference Example 110-4 | Column: CHIRALPAK AY-3, 3 µm, 4.6 × 150 mm<br>Solvent: solution A; ethanol, solution B; n-hexane<br>Elution condition: solution A/solution B = 10/90<br>Flow rate: 1 mL/min, temperature: 40° C. |
| Reference Example 111-4 | |
| Reference Example 110-5 | Column: CHIRALPAK IB-3, 3 µm, 4.6 × 150 mm<br>Solvent: solution A; ethanol, solution B; n-hexane<br>Elution condition: solution A/solution B = 10/90<br>Flow rate: 1 mL/min, temperature: 40° C. |
| Reference Example 111-2 | Column: CHIRALPAK AY-3, 3 µm, 4.6 × 150 mm<br>Solvent: solution A; ethanol, solution B; n-hexane<br>Elution condition: solution A/solution B = 5/95<br>Flow rate: 1 mL/min, temperature: 40° C. |

TABLE 1-1-continued

| | Conditions |
|---|---|
| Example 26-2-(3) | Column: CHIRALPAK OD-3, 3 μm, 4.6 × 150 mm<br>Solvent: solution A; n-hexane, solution B; ethanol<br>Elution condition: solution A/solution B = 80/20<br>Flow rate: 1 mL/min, temperature: 40° C. |
| Example 69-2-(1) | Column: CHIRALCEL OZ-3, 3 μm, 4.6 × 150 mm<br>Solvent: solution A; ethanol, solution B; n-hexane<br>Elution condition: solution A/solution B = 80/20<br>Flow rate: 1 mL/min, temperature: 40° C. |
| Example 70-10 | Column: CHIRALCEL OZ-3, 3 μm, 4.6 × 150 mm<br>Solvent: solution A; ethanol, solution B; n-hexane<br>Elution condition: solution A/solution B = 50/50<br>Flow rate: 1 mL/min, temperature: 40° C. |
| Example 71-2 | Column: CHIRALPAK AD-3, 3 μm, 4.6 × 150 mm<br>Solvent: solution A; 2-propanol, solution B; n-hexane<br>Elution condition: solution A/solution B = 40/60<br>Flow rate: 1 mL/min, temperature: 40° C. |
| Example 74-4 Example 74-5 | Column: CHIRALCEL OZ-3, 3 μm, 4.6 × 150 mm<br>Solvent: solution A; ethanol, solution B; n-hexane<br>Elution condition: solution A/solution B = 40/60<br>Flow rate: 1 mL/min, temperature: 60° C. |

Detection: UV 210 nm, 254 nm

Preparative chiral HPLC was performed in the Examples and Reference Examples under the following conditions:

HPLC: High-throughput purification system from Gilson, Inc. or preparative LC system from Waters Corporation

[HPLC Conditions]

TABLE 1-2

| | Conditions |
|---|---|
| Reference Example 90-1-(1) | Column: CHIRALPAK IB, 5 μm, 20 × 250 mm<br>Solvent: solution A; ethanol, solution B; n-hexane<br>Elution condition: solution A/solution B = 10/90<br>Flow rate: 10 mL/min, temperature: 40° C. |
| Reference Example 110-4 Reference Example 111-4 | Column: CHIRALPAK AY-H, 5 μm, 20 × 250 mm<br>Solvent: solution A; ethanol, solution B; n-hexane<br>Elution condition: solution A/solution B = 10/90<br>Flow rate: 10 mL/min, temperature: room temperature |
| Reference Example 110-5 | Column: CHIRALPAK ID, 5 μm, 20 × 250 mm<br>Solvent: solution A; ethanol, solution B; n-hexane<br>Elution condition: solution A/solution B = 10/90<br>Flow rate: 10 mL/min, temperature: room temperature |
| Reference Example 111-2 | Column: CHIRALPAK AY-H, 5 μm, 20 × 250 mm<br>Solvent: solution A; ethanol, solution B; n-hexane<br>Elution condition: solution A/solution B = 5/95<br>Flow rate: 10 mL/min, temperature: room temperature |
| Example 26-2-(3) | Column: CHIRALCEL OD, 10 μm, 20 × 250 mm<br>Solvent: solution A; n-hexane, solution B; ethanol<br>Elution condition: solution A/solution B = 70/30<br>Flow rate: 10 mL/min, temperature: room temperature |
| Example 69-2-(1) | Column: CHIRALCEL OZ-H, 5 μm, 20 × 250 mm<br>Solvent: solution A; ethanol, solution B; n-hexane<br>Elution condition: solution A/solution B = 80/20<br>Flow rate: 10 mL/min, temperature: room temperature |
| Example 71-2 | Column: CHIRALPAK AD-H, 5 μm, 20 × 250 mm<br>Solvent: solution A; ethanol, solution B; n-hexane<br>Elution condition: solution A/solution B = 40/60<br>Flow rate: 10 mL/min, temperature: room temperature |

Detection: UV 210 nm, 254 nm

Chiral suprecritical fluid chromatography (SFC) analysis was performed in the Examples and Reference Examples under the following conditions:

SFC: UPC$^2$ from Waters Corporation

[SFC Conditions]

TABLE 1-3

| | Conditions |
|---|---|
| Reference Example 109-2-(2) | Column: CHIRALPAK IF, 5 μm, 4.6 × 250 mm<br>Solvent: solution A; methanol, solution B; n-hexane<br>Elution condition: solution A/solution B = 7/93<br>Flow rate: 3 mL/min, temperature: 40° C. |
| Example 69-1 | Column: CHIRALCEL OD-H, 5 μm, 4.6 × 250 mm<br>Solvent: solution A; methanol, solution B; carbon dioxide<br>Elution condition: solution A/solution B = 40/60<br>Flow rate: 3 mL/min, temperature: 40° C. |
| Example 69-2 | Column: CHIRALCEL OD-3, 3 μm, 4.6 × 250 mm<br>Solvent: solution A; ethanol, solution B; carbon dioxide<br>Elution condition: solution A/solution B = 25/75<br>Flow rate: 3 mL/min, temperature: 40° C. |
| Example 69-3 | Column: CHIRALCEL OD-3, 3 μm, 4.6 × 250 mm<br>Solvent: solution A; methanol, solution B; carbon dioxide<br>Elution condition: solution A/solution B = 50/50<br>Flow rate: 3 mL/min, temperature: 40° C. |
| Example 69-4 | Column: CHIRALPAK AY-H, 5 μm, 4.6 × 250 mm<br>Solvent: solution A; methanol, solution B; carbon dioxide<br>Elution condition: solution A/solution B = 40/60<br>Flow rate: 3 mL/min, temperature: 40° C. |
| Example 69-5 | Column: CHIRALPAK AD-H, 5 μm, 4.6 × 250 mm<br>Solvent: solution A; methanol, solution B; carbon dioxide<br>Elution condition: solution A/solution B = 60/40<br>Flow rate: 3 mL/min, temperature: 40° C. |
| Example 71-8 | Column: CHIRALCEL OD-H, 5 μm, 4.6 × 250 mm<br>Solvent: solution A; methanol, solution B; carbon dioxide<br>Elution condition: solution A/solution B = 50/50<br>Flow rate: 3 mL/min, temperature: 40° C. |
| Example 71-17 Example 71-18 | Column: CHIRALPAK IA, 5 μm, 4.6 × 250 mm<br>Solvent: solution A; methanol, solution B; carbon dioxide<br>Elution condition: solution A/solution B = 60/40<br>Flow rate: 3 mL/min, temperature: 40° C. |
| Example 71-22 | Column: CHIRALPAK AY-H, 5 μm, 4.6 × 250 mm<br>Solvent: solution A; methanol, solution B; carbon dioxide<br>Elution condition: solution A/solution B = 60/40<br>Flow rate: 3 mL/min, temperature: 40° C. |
| Example 71-45 Example 71-46 | Column: CHIRALPAK IA, 5 μm, 4.6 × 250 mm<br>Solvent: solution A; methanol, solution B; carbon dioxide<br>Elution condition: solution A/solution B = 60/40<br>Flow rate: 3 mL/min, temperature: 40° C. |
| Example 75-7 Example 75-8 | Column: CHIRALCEL OD-H, 5 μm, 4.6 × 250 mm<br>Solvent: solution A; methanol, solution B; carbon dioxide<br>Elution condition: solution A/solution B = 50/50<br>Flow rate: 3 mL/min, temperature: 40° C. |

Detection: UV 210 nm, 254 nm

Preparative chiral SFC was performed in the Examples and Reference Examples under the following conditions:

SFC: SFC 30 from Waters Corporation

[SFC Conditions]

TABLE 1-4

| | Conditions |
|---|---|
| Reference Example 109-2-(2) | Column: CHIRALPAK IF, 5 μm, 20 × 250 mm<br>Solvent: solution A; methanol, solution B; carbon dioxide<br>Elution condition: solution A/solution B = 7/93<br>Flow rate: 30 mL/min, temperature: 40° C. |
| Example 69-1-(1) | Column: CHIRALCEL OD, 10 μm, 20 × 250 mm<br>Solvent: solution A; methanol, solution B; carbon dioxide<br>Elution condition: solution A/solution B = 30/70<br>Flow rate: 30 mL/min, temperature: 40° C. |

TABLE 1-4-continued

| | Conditions |
|---|---|
| Example 69-3 | Column: CHIRALPAK AY-H, 5 μm, 20 × 250 mm<br>Solvent: solution A; methanol, solution B; carbon dioxide<br>Elution condition: solution A/solution B = 40/60<br>Flow rate: 30 mL/min, temperature: 40° C. |
| Example 70-10 | Column: CHIRALCEL OD, 10 μm, 20 × 250 mm<br>Solvent: solution A; methanol, solution B; carbon dioxide<br>Elution condition: solution A/solution B = 30/70<br>Flow rate: 30 mL/min, temperature: 40° C. |
| Example 71-8 | Column: CHIRALCEL OD, 10 μm, 20 × 250 mm<br>Solvent: solution A; methanol, solution B; carbon dioxide<br>Elution condition: solution A/solution B = 50/50<br>Flow rate: 30 mL/min, temperature: 40° C. |
| Example 71-22 | Column: CHIRALCEL OD, 10 μm, 20 × 250 mm<br>Solvent: solution A; methanol, solution B; carbon dioxide<br>Elution condition: solution A/solution B = 50/50<br>Flow rate: 30 mL/min, temperature: 40° C. |

Detection: UV 210 nm, 254 nm

The polarimeter used was Autopol V from Rudolph Research Analytical, and the sodium D line (589 nm) was used as a light source.

The microwave reactor used was Initiator from Biotage AB or MONOWAVE 300 from Anton-Paar GmbH.

Compound names were designated using Molecular to Chemical Name (version 1), as a component of PipelinePilot 9.5 from OpenEye Scientific Software.

Conformations of compounds in the Reference Examples and Examples are shown in the absolute configuration of its asymmetric carbon. A compound with the designation of absolute configuration of its asymmetric carbon is an optically active substance.

The present invention will be described in more detail with reference to the following Reference Examples, Examples, Test Examples, and Preparation Examples, but these examples do not limit the present invention, and may be varied in such a range as not to deviate from the scope of the present invention.

Reference Example 1-1

6-[2-(2-Oxanyl)-3-pyrazolyl]-3-pyridinol

[Formula 338]

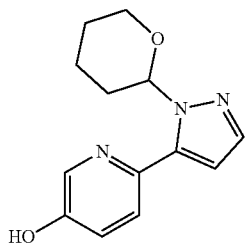

(1) Potassium carbonate (20.65 g) and benzyl bromide (10.6 mL) were added to a solution of commercially available 2-bromo-5-hydroxypyridine (13.00 g) in acetone (250 mL) under ice cooling, and the mixture was stirred at room temperature for 2 hours. After the solvent was distilled off under reduced pressure, water was added to the residue, and the mixture was extracted with ethyl acetate. The organic layer was separated by a phase separator, and the solvent was distilled off under reduced pressure. The obtained residue was purified by silica gel column chromatography (n-hexane:ethyl acetate=9:1 to 4:1) to give 2-bromo-5-(benzyloxy)pyridine (16.71 g) as a colorless powder.

(2) To the compound (10.00 g) obtained in (1) above, 1-(2-tetrahydropyranyl)1H-pyrazole-5-boronic acid pinacol ester (15.80 g), sodium carbonate (12.04 g), and 1,1'-bis(diphenylphosphino)ferrocene palladium(II) dichloromethane complex (1.55 g), 1,2-dimethoxyethane (120 mL) and water (60 mL) were added, and the resultant mixture was heated to reflux at 100° C. under a nitrogen atmosphere for 7 hours. After cooling to room temperature, the resultant solution was passed through Celite (registered trademark) to remove insolubles, and the filtrate was concentrated under reduced pressure, and water was added to the residue, and the mixture was extracted with chloroform. The organic layer was separated by a phase separator, and the solvent was distilled off under reduced pressure. The obtained residue was purified by silica gel column chromatography (n-hexane:ethyl acetate=7:3 to 1:1) to give 2-[2-(2-oxanyl)-3-pyrazolyl]-5-phenylmethoxypyridine (11.04 g) as a light orange oil.

(3) To a solution of the compound (11.04 g) obtained in (2) above in ethanol (40 mL) and ethyl acetate (40 mL), palladium carbon (1.10 g) was added, and the mixture was stirred under a hydrogen atmosphere at room temperature for 2 hours. After the reaction solution was filtered through Celite (registered trademark), the filtrate was concentrated, the obtained residue was purified by silica gel column chromatography (chloroform only to chloroform:methanol=92:8), and was powdered from diethyl ether/hexane to give the title compound (6.18 g) as a colorless powder.

$^1$H NMR (400 MHz, DMSO-d$_6$) δ ppm 1.43-1.70 (m, 3H) 1.83-1.91 (m, 1H) 1.94-2.03 (m, 1H) 2.30-2.42 (m, 1H) 3.41-3.54 (m, 1H) 3.81-3.88 (m, 1H) 6.11-6.17 (m, 1H) 6.56-6.60 (m, 1H) 7.24-7.29 (m, 1H) 7.48-7.59 (m, 2H) 8.20-8.24 (m, 1H) 10.21 (s, 1H).

MS ESI/APCI Multi posi: 246[M+H]$^+$.

The compounds of Reference Examples 1-2 and 1-3 below were synthesized using a commercially available compound, according to the method described in Reference Example 1-1. The structures, NMR data, and MS data of these compounds are shown in Table 1-5.

TABLE 1-5

| Reference Example No. | Structure | Analytical Data |
|---|---|---|
| 1-2 | 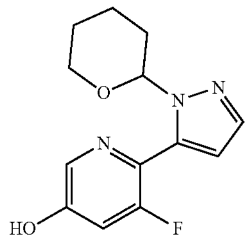 [SMILES: Oc1cnc(-c2ccnn2C2CCCCO2)c(F)c1] | $^1$H NMR (400 MHz, DMSO-d$_6$) δ ppm 1.42-1.68 (m, 3 H) 1.85-2.03 (m, 2 H) 2.26-2.39 (m, 1 H) 3.34-3.43 (m, 1 H) 3.73-3.81 (m, 1 H) 5.91-5.97 (m, 1H) 6.52-6.57 (m, 1 H) 7.18-7.25 (m, 1 H) 7.56-7.60 (m, 1 H) 8.12-8.17 (m, 1 H) 10.81 (br s, 1 H). MS ESI mega: 262[M − H]$^-$. |
| 1-3 | 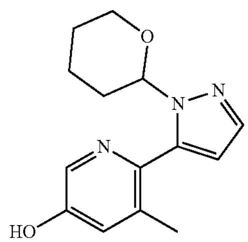 [SMILES: Cc1cc(O)cnc1-c1ccnn1C1CCCCO1] | $^1$H NMR (600 MHz, CHLOROFORM-d) δ ppm 1.45-1.50 (m, 1 H) 1.51-1.69 (m, 2 H) 1.92-2.07 (m, 2 H) 2.19 (s, 3 H) 2.37-2.47 (m, 1 H) 3.34-3.41 (m, 1 H) 3.91-3.95 (m, 1 H) 5.21-5.24 (m, 1 H) 6.33 (d, J = 1.7 Hz, 1 H) 7.06 (d, J = 2.5 Hz, 1 H) 7.63 (d, J = 1.7 Hz, 1 H) 8.13 (d, J = 2.5 Hz, 1 H). MS ESI/APCI Multi posi: 260[M + H]$^+$. MS ESI/APCI Multi nega: 258[M − H]$^-$. |

Reference Example 2-1

6-[4-(Difluoromethyl)-2-(2-oxanyl)-3-pyrazolyl]-3-pyridinol

[Formula 339]

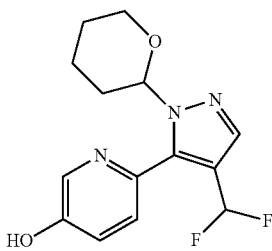

(1) To a solution of the compound (700 mg) obtained in Reference Example 1-1-(2) in chloroform (10 mL), N-bromosuccinimide (557 mg) was added at room temperature, and the mixture was stirred for 1 hour. The reaction solution was poured into a saturated aqueous solution of sodium hydrogen carbonate and extracted with chloroform. The organic layer was separated by a phase separator and concentrated under reduced pressure. The residue was purified by silica gel column chromatography (n-hexane:ethyl acetate=7:3) to give 2-[4-bromo-2-(2-oxanyl)-3-pyrazolyl]-5-phenylmethoxypyridine (710 mg) as a pale yellow oil.

(2) A solution of the compound (710 mg) obtained in (1) above in tetrahydrofuran (10 mL) was cooled to −78° C. under a nitrogen atmosphere, and n-butyl lithium (1.60 mol/L n-hexane solution, 1.18 mL) was added dropwise thereto and the mixture was stirred for 45 minutes. To the reaction solution, N,N-dimethylformamide (0.15 mL) was added dropwise. The temperature of the solution was gradually increased to room temperature and the solution was stirred for 1 hour. Water was added to the reaction solution, and the mixture was extracted with ethyl acetate. The organic layer was separated by a phase separator, and concentrated under reduced pressure. The residue was purified by silica gel column chromatography (n-hexane:ethyl acetate=4:1 to 1:1) to give a mixture (630 mg) containing 1-(2-oxanyl)-5-(5-phenylmethoxy-2-pyridinyl)-4-pyrazole-carboxaldehyde as a pale yellow oil.

(3) Bis(2-methoxyethyl)aminosulfur trifluoride (BAST) (491 μL) and ethanol (7 μL) were added to a solution of the compound (622 mg) obtained in (2) above in chloroform (10 mL), and the mixture was stirred at room temperature for 1 hour, and then at 50° C. for 3 hours. The reaction solution was added dropwise to a saturated aqueous solution of sodium hydrogen carbonate and extracted with chloroform. The organic layer was separated by a phase separator, and concentrated under reduced pressure. The residue was purified by silica gel column chromatography (n-hexane:ethyl acetate=9:1 to 13:7) to give 2-[4-(difluoromethyl)-2-(2-oxanyl)-3-pyrazolyl]-5-phenylmethoxypyridine (196 mg) as a pale yellow oil.

(4) The compound (196 mg) obtained in (3) above was used to perform the synthesis process according to the method described in Reference Example 1-1-(3) thereby giving the title compound (149 mg) as a colorless amorphous substance.

$^1$H NMR (400 MHz, CHLOROFORM-d) δ ppm 1.50-1.80 (m, 3H) 1.89-2.15 (m, 2H) 2.44-2.55 (m, 1H) 3.47-3.58 (m, 1H) 4.00-4.09 (m, 1H) 5.41-5.52 (m, 1H) 6.50-6.83 (m, 1H) 7.28-7.33 (m, 1H) 7.49-7.55 (m, 1H) 7.83 (s, 1H) 8.36-8.42 (m, 1H).

MS ESI/APCI Multi posi: 296[M+H]$^+$.
MS ESI/APCI Multi nega: 294[M−H]$^-$.

Reference Example 3-1

6-[4-Chloro-2-(2-oxanyl)-3-pyrazolyl]-3-pyridinol

[Formula 340]

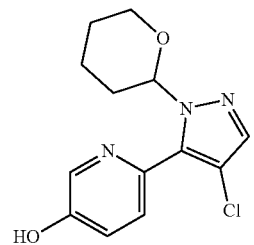

To a solution of the compound (300 mg) obtained in Reference Example 1-1 in chloroform (6.2 mL), N-chlorosuccinimide (109 mg) was added, and the mixture was stirred at 70° C. for 6 hours. The reaction solution was concentrated under reduced pressure, and the residue was purified by silica gel column chromatography (n-hexane:ethyl acetate=5:1 to 1:1) to give the title compound (217 mg) as a colorless powder.

$^1$H NMR (400 MHz, CHLOROFOLM-d) δ ppm 1.47-1.74 (m, 4H) 1.93-2.14 (m, 2H) 2.37-2.51 (m, 1H) 3.48 (td, J=11.3, 2.4 Hz, 1H) 3.93-4.00 (m, 1H) 5.75 (dd, J=9.8, 2.4 Hz, 1H) 7.24-7.30 (m, 1H) 7.59 (d, J=8.4 Hz, 2H) 8.35 (d, J=2.8 Hz, 1H).

MS ESI/APCI Multi posi: 280[M+H]$^+$.
MS ESI/APCI Multi nega: 278[M−H]$^−$.

Reference Example 4-1

2-[2-(2-Oxanyl)-3-pyrazolyl]-5-(4-piperidinylmethoxy)pyridine

[Formula 341]

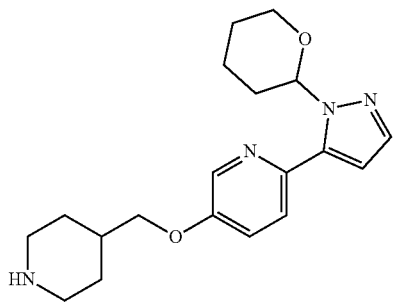

(1) To a solution of the compound (1.00 g) obtained in Reference Example 1-1 in tetrahydrofuran (40 mL), (phenylmethyl) 4-(hydroxymethyl)-1-piperidinecarboxylate (1.11 g), tributylphosphine (1.50 mL), and 1,1′-azobis(N,N-dimethylformamide) (1.04 g) were added, and the mixture was stirred at 60° C. for 3 hours, and then at room temperature overnight. After the reaction solution was concentrated, water was added to the concentrated solution, and the mixture was extract with ethyl acetate. After the extracted substance was dried over anhydrous sodium sulfate, the drying agent was filtered off, and the solvent was distilled off under reduced pressure. The obtained residue was purified by silica gel column chromatography (n-hexane:ethyl acetate=9:1 to ethyl acetate only) to give (phenylmethyl) 4-[[6-[2-(2-oxanyl)-3-pyrazolyl]-3-pyridinyl]oxymethyl]-1-piperidinecarboxylate (1.01 g) as a colorless oil.

(2) To a solution of the compound (1.01 g) obtained in (1) above in methanol (15 mL), palladium carbon (200 mg) was added, and the mixture was stirred under a hydrogen atmosphere at room temperature for 30 minutes. After the reaction solution was filtered through Celite (registered trademark), the filtrate was concentrated, the obtained residue was purified by NH silica gel column chromatography (hexane:ethyl acetate=1:1 to ethyl acetate only to chloroform:methanol=19:1 to 9:1) to give the title compound (561 mg) as a colorless oil.

$^1$H NMR (600 MHz, CHLOROFORM-d) δ ppm 1.23-1.38 (m, 3H) 1.51-1.80 (m, 3H) 1.82-1.87 (m, 2H) 1.93-2.04 (m, 2H) 2.06-2.12 (m, 1H) 2.49-2.57 (m, 1H) 2.67 (td, J=12.2, 2.5 Hz, 2H) 3.12-3.17 (m, 2H) 3.59 (td, J=11.6, 2.5 Hz, 1H) 3.89 (d, J=6.6 Hz, 2H) 4.02-4.07 (m, 1H) 6.08 (dd, J=9.9, 2.5 Hz, 1H) 6.49 (d, J=1.7 Hz, 1H) 7.23-7.27 (m, 1H) 7.53 (d, J=8.7 Hz, 1H) 7.59 (d, J=1.7 Hz, 1H) 8.36 (d, J=2.9 Hz, 1H).

MS ESI/APCI Multi posi: 343[M+H]$^+$.

The compounds of Reference Examples 4-2 to 4-4 below were synthesized using a commercially available compound, according to the method described in Reference Example 4-1. The structures, NMR data, and MS data of them are shown in Table 2-1.

TABLE 2-1

| Reference Example No. | Structure | Analytical Data |
| --- | --- | --- |
| 4-2 | 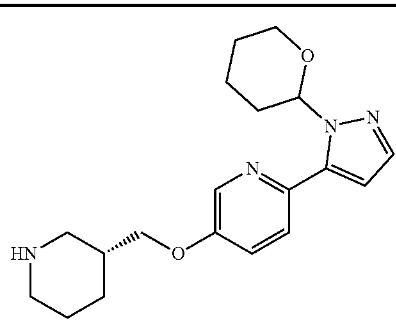 | $^1$H NMR (600 MHz, CHLOROFORM-d) δ ppm 1.23-1.35 (m, 1 H) 1.49-1.80 (m, 5 H) 1.87-1.96 (m, 1H) 1.99-2.11 (m, 3 H) 2.47-2.57 (m, 2 H) 2.59-2.66 (m, 1 H) 3.00- 3.08 (m, 1 H) 3.21-3.29 (m, 1 H) 3.55-3.63 (m, 1 H) 3.86-3.94 (m, 2 H) 4.00-4.09 (m, 1 H) 6.04-6.10 (m, 1H) 6.49 (d, J = 1.9 Hz, 1 H) 7.25 (dd, J = 8.7, 3.1 Hz, 1H) 7.52 (d, J = 8.7 Hz, 1H) 7.59 (d, J = 1.9 Hz, 1H) 8.36 (d, J = 3.1 Hz, 1 H). MS ESI/APCI Multi posi: 343[M + H]$^+$. |

TABLE 2-1-continued

| Reference Example No. | Structure | Analytical Data |
|---|---|---|
| 4-3 | 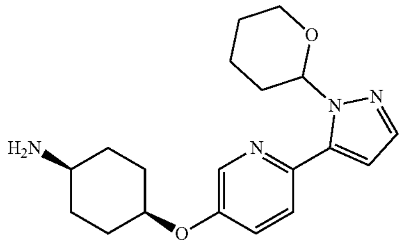 [SMILES: N[C@H]1CC[C@@H](Oc2ccc(-c3ccnn3C3CCCCO3)nc2)CC1] | $^1$H NMR (400 MHz, CHLOROFORM-d) δ ppm 1.46-2.24 (m, 13 H) 2.47-2.58 (m, 1 H) 3.18-3.26 (m, 1 H) 3.56-3.64 (m, 1 H) 4.01-4.07 (m, 1 H) 4.59-4.63 (m, 1 H) 6.07-6.12 (m, 1 H) 6.48 (d, J = 1.8 Hz, 1 H) 7.28 (dd, J = 8.7, 2.5 Hz, 1 H) 7.52 (d, J = 8.7 Hz, 2 H) 7.58 (d, J = 1.8 Hz, 1 H) 8.39 (d, J = 2.5 Hz, 1 H). MS ESI/APCI Multi posi: 343[M + H]$^+$. |
| 4-4 | 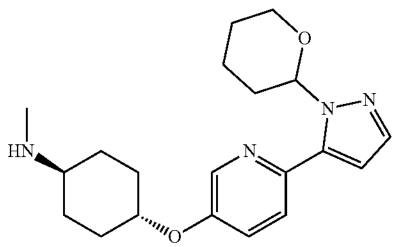 [SMILES: CN[C@H]1CC[C@H](Oc2ccc(-c3ccnn3C3CCCCO3)nc2)CC1] | $^1$H NMR (400 MHz, CHLOROFORM-d) δ ppm 1.44-2.29 (m, 13 H) 2.48-2.61 (m, 4 H) 2.67-2.77 (m, 1 H) 3.53-3.70 (m, 1 H) 3.98-4.08 (m, 1 H) 4.21-4.40 (m, 1 H) 6.07-6.12 (m, 1 H) 6.49 (d, J = 1.8 Hz, 1 H) 7.25 (dd, J = 8.8, 2.8 Hz, 1 H) 7.53 (d, J = 8.8 Hz, 1 H) 7.58 (d, J = 1.8 Hz, 1 H) 8.35 (d, J = 2.8 Hz, 1 H). MS ESI/APCI Multi posi: 357[M + H]$^+$. |

Reference Example 5-1

5-[[(3R)-3-Piperidinyl]methoxy]-2-(1H-pyrazol-5-yl)pyridine

[Formula 342]

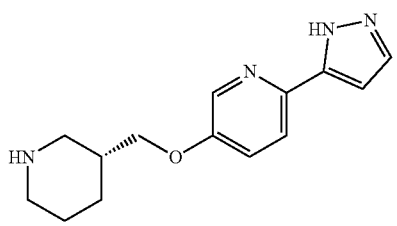

Water (4 mL) and trifluoroacetic acid (1 mL) were added to a solution of the compound (2.00 g) obtained in Reference Example 4-2 in methanol (20 mL), and the mixture was stirred at 60° C. for 3 hours. After the reaction solution was concentrated, the residue was neutralized with saturated sodium hydrogen carbonate and was concentrated again. The obtained residue was purified by NH silica gel column chromatography (n-hexane:ethyl acetate=1:1 to ethyl acetate only to chloroform:methanol=9:1) to give the title compound (625 mg) as a colorless powder.

$^1$H NMR (600 MHz, DMSO-d$_6$) δ ppm 1.15-1.25 (m, 1H) 1.30-1.42 (m, 1H) 1.53-1.61 (m, 1H) 1.76-1.89 (m, 2H) 2.07 (br s, 1H) 2.33 (dd, J=11.8, 9.7 Hz, 1H) 2.41-2.47 (m, 1H) 2.82 (dt, J=11.9, 3.6 Hz, 1H) 3.02 (dd, J=11.8, 2.7 Hz, 1H) 3.91 (d, J=6.6 Hz, 2H) 6.72 (d, J=2.1 Hz, 1H) 7.37-7.47 (m, 1H) 7.60-7.76 (m, 1H) 7.78-7.88 (m, 1H) 8.26 (d, J=2.9 Hz, 1H) 12.94 (br s, 1H).

MS ESI/APCI Multi posi: 259[M+H]$^+$.

Reference Example 6-1

5-[(3-Bromophenyl)methoxy]-2-[2-(2-oxanyl)-3-pyrazolyl]pyridine

[Formula 343]

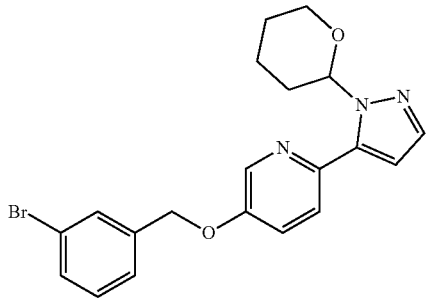

To a solution of the compound (3.00 g) obtained in Reference Example 1-1 in toluene (31 mL), 3-bromobenzyl alcohol (2.73 g) and cyanomethylene tributylphosphorane (9.63 mL) were added, and the mixture was stirred at 100° C. for 1.5 hours. The reaction mixture was concentrated, and the obtained residue was purified by silica gel column chromatography (n-hexane only to ethyl acetate only) to give the title compound (4.70 g) as a brown oil.

$^1$H NMR (300 MHz, CHLOROFORM-d) δ ppm 1.51-1.83 (m, 3H) 1.97-2.13 (m, 2H) 2.45-2.61 (m, 1H) 3.52-3.68 (m, 1H) 3.97-4.08 (m, 1H) 5.13 (s, 2H) 5.99-6.21 (m, 1H) 6.50 (d, J=1.9 Hz, 1H) 7.23-7.42 (m, 3H) 7.47-7.52 (m, 1H) 7.52-7.57 (m, 1H) 7.59 (d, J=1.9 Hz, 1H) 7.60-7.65 (m, 1H) 8.41-8.46 (m, 1H).

MS ESI/APCI Multi posi: 414[M+H]$^+$.

Reference Example 6-2

5-[3-(3-Bromophenyl)propoxy]-2-[2-(2-oxanyl)-3-pyrazolyl]pyridine

[Formula 344]

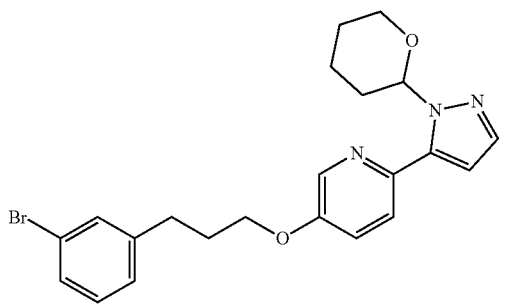

The compound (500 mg) obtained in Reference Example 1-1, 3-(3-bromophenyl)-1-propanol (515 mg), and triphenylphosphine (762 mg) were dissolved in tetrahydrofuran (6.45 mL). Bis(2-methoxyethyl) azodicarboxylate (680 mg) was added to the solution under ice cooling, the air in the flask was purged with nitrogen, and the solution was then stirred at room temperature overnight. After the reaction solution was concentrated under reduced pressure, the obtained residue was purified by silica gel column chromatography (n-hexane:ethyl acetate=9:1 to 7:13) to give a mixture containing the title compound (636 mg) as a colorless oil.

$^1$H NMR (400 MHz, CHLOROFORM-d) δ ppm 1.50-1.60 (m, 1H) 1.61-1.81 (m, 2H) 1.97-2.21 (m, 4H) 2.48-2.60 (m, 1H) 2.78-2.88 (m, 2H) 3.55-3.65 (m, 1H) 4.01-4.09 (m, 3H) 6.09 (dd, J=10.0, 2.3 Hz, 1H) 6.50 (s, 1H) 7.13-7.25 (m, 4H) 7.28-7.39 (m, 2H) 7.50-7.55 (m, 1H) 7.57-7.61 (m, 1H) 8.37 (d, J=2.9 Hz, 1H).

MS ESI/APCI Multi posi: 442[M+H]$^+$.

The compounds of Reference Examples 6-2 to 6-7 below were synthesized using a commercially available compound, according to the method described in Reference Example 6-2. The structures, NMR data, and MS data of them are shown in Table 3-1.

TABLE 3-1

| Reference Example No. | Structure | Analytical Data |
|---|---|---|
| 6-3 | 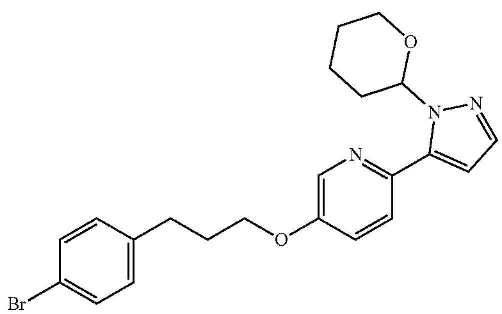 [SMILES: Brc1ccc(CCCOc2ccc(-c3ccnn3C3CCCCO3)nc2)cc1] | $^1$H NMR (400 MHz, CHLOROFORM-d) δ ppm 1.50-1.60 (m, 1 H) 1.61-1.81 (m, 2 H) 1.97-2.19 (m, 4 H) 2.48-2.60 (m, 1 H) 2.77-2.84 (m, 2 H) 3.56-3.64 (m, 1 H) 4.01-4.08 (m, 3 H) 6.09 (dd, J = 10.0, 2.4 Hz, 1 H) 6.50 (d, J = 1.8 Hz, 1 H) 7.10 (d, J = 8.5 Hz, 2 H) 7.21-7.25 (m, 1 H) 7.40-7.44 (m, 2 H) 7.53 (d, J = 8.5 Hz, 1 H) 7.59 (d, J = 1.8 Hz, 1 H) 8.36 (d, J = 2.7 Hz, 1 H). MS ESI/APCI Multi posi: 442 [M + H]$^+$. |
| 6-4 | 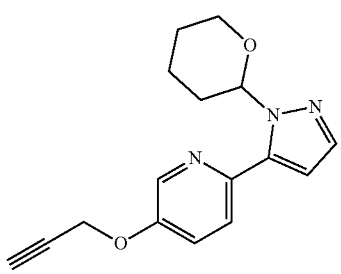 [SMILES: C#CCOc1ccc(-c2ccnn2C2CCCCO2)nc1] | $^1$H NMR (400 MHz, CHLOROFORM-d) δ ppm 1.48-1.83 (m, 3 H) 1.97-2.16 (m, 2 H) 2.46-2.63 (m, 2 H) 3.53-3.66 (m, 1 H) 3.98-4.09 (m, 1 H) 4.76-4.83 (m, 2 H) 6.05-6.16 (m, 1 H) 6.48-6.55 (m, 1 H) 7.32-7.41 (m, 1 H) 7.53-7.61 (m, 2 H) 8.41-8.49 (m, 1 H). MS ESI/APCI Multi posi: 284 [M + H]$^+$. |
| 6-5 | 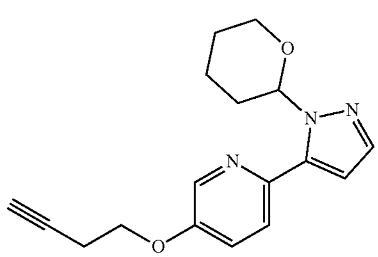 [SMILES: C#CCCOc1ccc(-c2ccnn2C2CCCCO2)nc1] | $^1$H NMR (400 MHz, CHLOROFORM-d) δ ppm 1.50-1.57 (m, 1H) 1.64-1.83 (m, 2 H) 1.96-2.15 (m, 3 H) 2.46-2.60 (m, 1 H) 2.71-2.79 (m, 2 H) 3.54-3.65 (m, 1 H) 4.00-4.08 (m, 1 H) 4.20 (t, J = 6.8 Hz, 2 H) 6.07-6.12 (m, 1 H) 6.47-6.51 (m, 1 H) 7.28 (dd, J = 8.7, 2.8 Hz, 1 H) 7.54 (d, J = 8.7 Hz, 1 H) 7.59 (d, J = 1.7 Hz, 1 H) 8.39 (d, J = 2.8 Hz, 1 H). MS ESI posi: 298 [M + H]$^+$. |

TABLE 3-1-continued

| Reference Example No. | Structure | Analytical Data |
|---|---|---|
| 6-6 | 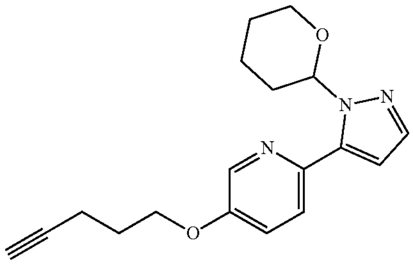 [SMILES: C#CCCCOc1ccc(-c2ccnn2C2CCCCO2)nc1] | $^1$H NMR (400 MHz, CHLOROFORM-d) δ ppm 1.57-2.62 (m, 11 H) 3.52-3.66 (m, 1 H) 3.99-4.09 (m, 1 H) 4.14-4.24 (m, 2 H) 6.02-6.14 (m, 1 H) 6.45-6.55 (m, 1 H) 7.19-7.32 (m, 1 H) 7.49-7.63 (m, 2 H) 8.34-8.42 (m, 1 H). MS ESI posi: 312 [M + H]$^+$. |
| 6-7 | 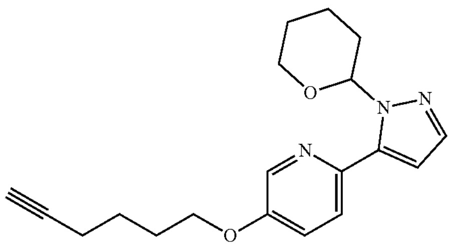 [SMILES: C#CCCCCOc1ccc(-c2ccnn2C2CCCCO2)nc1] | $^1$H NMR (400 MHz, CHLOROFORM-d) δ ppm 1.59-1.85 (m, 5 H) 1.89-2.14 (m, 5 H) 2.26-2.38 (m, 2 H) 2.47-2.64 (m, 1 H) 3.52-3.66 (m, 1 H) 3.95-4.21 (m, 3 H) 6.06-6.11 (m, 1 H) 6.49 (d, J = 1.6 Hz, 1 H) 7.14-7.35 (m, 1 H) 7.53 (d, J = 8.7 Hz, 1 H) 7.59 (d, J = 1.6 Hz, 1 H) 8.37 (d, J = 2.8 Hz, 1 H). MS ESI posi: 326 [M + H]$^+$. |

Reference Example 7-1

[3-[[6-[2-(2-Oxanyl)-3-pyrazolyl]-3-pyridinyl]oxymethyl]-1-bicyclo[1.1.1]pentanyl]methanamine

[Formula 345]

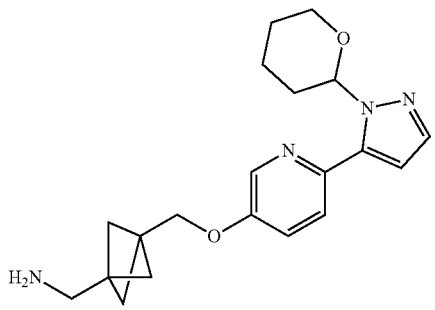

(1) The compound (421 mg) obtained in Reference Example 1-1 and methyl 1-(hydroxymethyl)bicyclo[1.1.1]pentane-3-carboxylate (295 mg) were used to perform the synthesis process according to the method described in Reference Example 6-1 thereby giving methyl 3-[[[6-[1-(oxan-2-yl)-1H-pyrazol-5-yl]pyridin-3-yl]oxy]methyl]bicyclo[1.1.1]pentane-1-carboxylate (684 mg) as a colorless oil.

(2) To a solution of the compound (684 mg) obtained in (1) above in methanol (10 mL), lithium borohydride (148 mg) was added, and the mixture was stirred at room temperature for 17 hours. Lithium borohydride (74.0 mg) was further added thereto, and the mixture was stirred at room temperature for 2 hours. A saturated aqueous solution of ammonium chloride was added to the reaction solution, and the solvent was distilled off. The resultant was extracted with chloroform, and the organic layer was separated by a phase separator and then was concentrated under reduced pressure to give [3-[[[6-[1-(oxan-2-yl)-1H-pyrazol-5-yl]pyridin-3-yl]oxy]methyl]bicyclo[1.1.1]pentan-1-yl]methanol (495 mg) as a colorless oil. The obtained compound was used for the next reaction without being purified.

(3) Triethylamine (201 μL) and methanesulfonyl chloride (94.8 μL) were added to a solution of the compound (395 mg) obtained in (2) above in ethyl acetate (2 mL), and the mixture was stirred at room temperature for 1 hour. After impurities were filtered off, the filtrate was concentrated to give [3-[[[6-[1-(oxan-2-yl)-1H-pyrazol-5-yl]pyridin-3-yl]oxy]methyl]bicyclo[1.1.1]pentan-1-yl]methyl methanesulfonate (481 mg) as a colorless oil. The obtained compound was used for the next reaction without being purified.

(4) Sodium azide (216 mg) was added to a solution of the compound (481 mg) obtained in (3) above in N,N-dimethylformamide (5 mL), and the mixture was stirred at 80° C. for 1 hour. Water was added to the reaction mixture, and the resultant mixture was extracted with ethyl acetate. The organic layer was washed with water and brine, and then dried over anhydrous magnesium sulfate. The drying agent was filtered off, and the filtrate was concentrated under reduced pressure to give 5-[[3-(azidomethyl)bicyclo[1.1.1]pentan-1-yl]methoxy]-2-[1-(oxan-2-yl)-1H-pyrazol-5-yl]pyridine (422 mg) as a brown oil. The obtained compound was used for the next reaction without being purified.

(5) To a solution of the compound (422 mg) obtained in (4) above in methanol (6 mL), palladium carbon (42.2 mg) was added, and the mixture was stirred under a hydrogen atmosphere at room temperature for 2 hours. The reaction mixture was filtered through Celite (registered trademark), and then the filtrate was concentrated under reduced pressure. The obtained residue was purified by NH silica gel column chromatography (chloroform only to chloroform:methanol=9:1) to give the title compound (358 mg) as a brown oil.

$^1$H NMR (400 MHz, CHLOROFORM-d) δ ppm 1.49-1.58 (m, 1H) 1.62-1.80 (m, 7H) 1.87-2.25 (m, 3H) 2.47-2.60 (m, 1H) 2.72-2.79 (m, 2H) 3.54-3.63 (m, 1H) 4.02-4.09 (m, 3H) 6.05-6.10 (m, 1H) 6.49 (d, J=1.8 Hz, 1H) 7.24 (dd, J=8.7, 3.0 Hz, 1H) 7.52 (d, J=8.7 Hz, 1H) 7.59 (d, J=1.8 Hz, 1H) 8.37 (d, J=3.0 Hz, 1H).
MS ESI/APCI Multi posi: 355 [M+H]$^+$.

301

Reference Example 8-1

5-[(3-Bromo-4-fluorophenyl)methoxy]-2-[2-(2-oxanyl)-3-pyrazolyl]pyridine

[Formula 346]

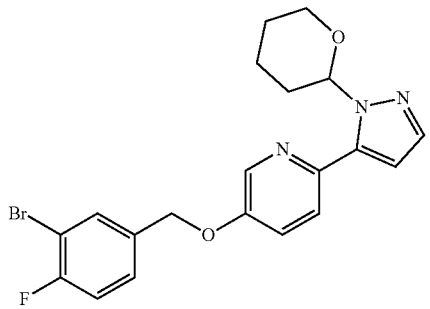

To a solution of the compound (872 mg) obtained in Reference Example 1-1 in N,N-dimethylformamide (10 mL), potassium carbonate (983 mg), 3-bromo-4-fluorobenzyl bromide (1.00 g) and sodium iodide (53.3 mg) were added, and the mixture was stirred at 60° C. for 2 hours. Water was added to the reaction mixture, and the resultant mixture was extracted with ethyl acetate. The organic layer was washed with water and brine, and then dried over anhydrous magnesium sulfate. The drying agent was filtered off, and the filtrate was concentrated under reduced pressure. The obtained residue was purified by silica gel column chromatography (n-hexane only to n-hexane:ethyl acetate=7:3) to give the title compound (1.51 g) as a yellow oil.

$^1$H NMR (600 MHz, CHLOROFORM-d) δ ppm 1.51-1.57 (m, 1H) 1.64-1.79 (m, 2H) 1.99-2.05 (m, 1H) 2.07-2.12 (m, 1H) 2.50-2.57 (m, 1H) 3.57-3.62 (m, 1H) 4.02-4.06 (m, 1H) 5.10 (s, 2H) 6.08-6.11 (m, 1H) 6.51 (d, J=1.7 Hz, 1H) 7.14-7.20 (m, 1H) 7.31 (dd, J=8.7, 2.9 Hz, 1H) 7.34-7.39 (m, 1H) 7.56 (d, J=8.7 Hz, 1H) 7.59 (d, J=1.7 Hz, 1H) 7.65-7.70 (m, 1H) 8.43 (d, J=2.9 Hz, 1H).

MS ESI/APCI Multi posi: 432[M+H]$^+$.

302

Reference Example 8-2

5-[(4-Iodophenyl)methoxy]-2-[2-(2-oxanyl)-3-pyrazolyl]pyridine

[Formula 347]

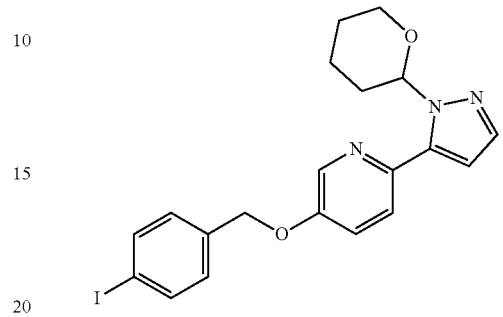

To a solution of the compound (500 mg) obtained in Reference Example 1-1 in N,N-dimethylformamide (1.41 mL), 4-iodobenzyl bromide (150 mg) and potassium carbonate (87.5 mg) were added, and the mixture was stirred at room temperature overnight. The reaction solution was poured into water, and the resultant mixture was extracted three times with ethyl acetate. The organic layers were combined, washed with brine, separated from the aqueous layer by a phase separator, and then concentrated under reduced pressure. The obtained residue was purified by silica gel column chromatography (n-hexane:ethyl acetate=19:1 to 2:3) to give the title compound (195 mg) as a pale yellow gum-like substance.

$^1$H NMR (400 MHz, CHLOROFORM-d) δ ppm 1.50-1.60 (m, 1H) 1.61-1.80 (m, 2H) 1.96-2.14 (m, 2H) 2.47-2.60 (m, 1H) 3.55-3.64 (m, 1H) 4.00-4.08 (m, 1H) 5.11 (s, 2H) 6.09 (dd, J=10.1, 2.4 Hz, 1H) 6.50 (d, J=1.8 Hz, 1H) 7.16-7.24 (m, 2H) 7.28-7.34 (m, 1H) 7.50-7.64 (m, 2H) 7.75 (d, J=8.3 Hz, 2H) 8.42 (d, J=2.7 Hz, 1H).

MS ESI/APCI Multi posi: 462[M+H]$^+$.

The compound of Reference Example 8-3 below was synthesized using 3-iodobenzyl bromide, according to the method described in Reference Example 8-2. The structure, NMR data, and MS data of it are shown in Table 4-1.

TABLE 4-1

| Reference Example No. | Structure | Analytical Data |
|---|---|---|
| 8-3 | 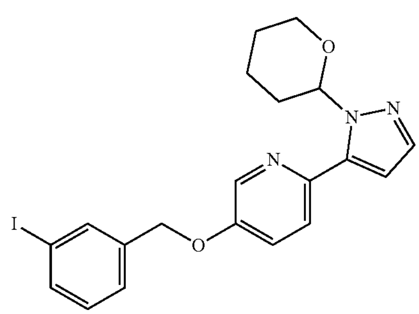 [SMILES: Ic1cccc(COc2ccc(-c3ccnn3C3CCCCO3)nc2)c1] | $^1$H NMR (400 MHz, CHLOROFORM-d) δ ppm 1.50-1.60 (m, 1 H) 1.61-1.81 (m, 2 H) 1.99-2.13 (m, 2 H) 2.48-2.60 (m, 1 H) 3.56-3.64 (m, 1 H) 4.01-4.08 (m, 1 H) 5.10 (s, 2 H) 6.10 (dd, J = 10.1, 2.4 Hz, 1 H) 6.50 (d, J = 1.8 Hz, 1 H) 7.12-7.18 (m, 1 H) 7.28-7.34 (m, 1 H) 7.41 (d, J = 7.8 Hz, 1 H) 7.55 (d, J = 8.7 Hz, 1 H) 7.59 (d, J = 1.8 Hz, 1 H) 7.70 (d, J = 7.8 Hz, 1 H) 7.82 (s, 1 H) 8.43 (d, J = 2.8 Hz, 1 H). MS ESI/APCI Multi posi: 462 [M + H]$^+$. |

Reference Example 9-1

Trimethyl-[[4 [3-[[6-[2-(2-oxanyl)-3-pyrazolyl]-3-pyridinyl][oxymethyl]phenyl]-4-piperidinyl]oxy]silane

[Formula 348]

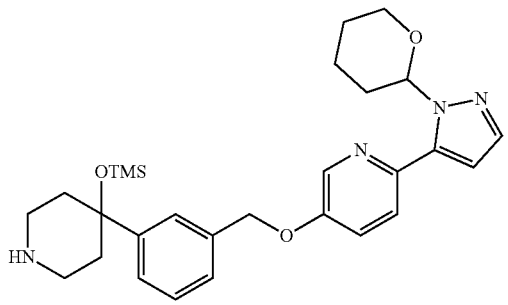

(1) To a suspension of the compound (421 mg) obtained in Reference Example 6-1 and molecular sieves of 4 angstroms (200 mg) in tetrahydrofuran (5 mL), n-butyl lithium (2.6 mol/L n-hexane solution, 508 µL) was added dropwise at −78° C., and the mixture was stirred for 10 minutes. To the mixture, 1-(tert-butoxycarbamoyl)-4-piperidone (405 mg) was added all at once at −78° C., the temperature of the mixture was gradually increased, and the mixture was stirred at room temperature for 1 hour. A saturated aqueous solution of ammonium chloride was added to the reaction mixture, the resultant mixture was extracted with ethyl acetate, and the organic layer was then washed with brine and dried over anhydrous magnesium sulfate. After the drying agent was filtered off, the filtrate was concentrated under reduced pressure, and the obtained residue was purified by silica gel column chromatography (n-hexane:ethyl acetate=9:1 to 1:9) to give tert-butyl 4-hydroxy-4-{3-[({6-[1-(oxan-2-yl)-1H-pyrazol-5-yl]pyridin-3-yl}oxy)methyl]phenyl}piperidine-1-carboxylate (402 mg) as a yellow amorphous substance.

(2) To a solution of the compound (348 mg) obtained in (1) above in chloroform (6 mL), 2,6-lutidine (754 µL) and trimethylsilyl trifluoromethanesulfonate (470 µL) were added under ice cooling, and the mixture was stirred at the same temperature for 30 minutes. A saturated aqueous solution of sodium hydrogen carbonate was added to the reaction mixture, and the resultant mixture was extracted with chloroform. The organic layer was separated by a phase separator, and the solvent was distilled off under reduced pressure. The obtained residue was purified by silica gel column chromatography (n-hexane only to n-hexane:ethyl acetate=3:2) to give the title compound (200 mg) as a colorless oil.

$^1$H NMR (600 MHz, CHLOROFORM-d) δ ppm −0.12 (s, 9H) 1.50-2.11 (m, 9H) 2.50-2.56 (m, 1H) 2.90-2.97 (m, 2H) 3.09-3.15 (m, 2H) 3.56-3.61 (m, 1H) 4.02-4.06 (m, 1H) 5.17 (s, 2H) 6.09 (dd, J=10.1, 2.3 Hz, 1H) 6.48-6.50 (m, 1H) 7.28-7.44 (m, 4H) 7.49-7.59 (m, 3H) 8.45 (d, J=2.9 Hz, 1H).

MS ESI/APCI Multi posi: 507[M+H]$^+$.

The compound of Reference Example 9-2 below was synthesized using the compound obtained in Reference Example 6-1, according to the method described in Reference Example 9-1. The structure, NMR data, and MS data of it are shown in Table 5-1.

TABLE 5-1

| Reference Example No. | Structure | Analytical Data |
|---|---|---|
| 9-2 | 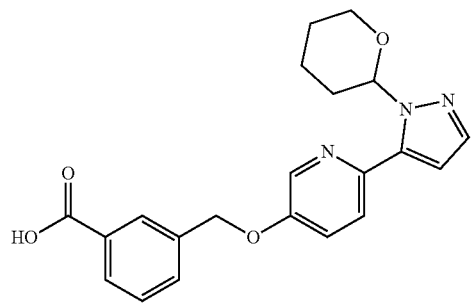 | $^1$H NMR (600 MHz, CHLOROFORM-d) δ ppm −0.04-0.07 (m, 9 H) 1.49-1.59 (m, 1 H) 1.61-1.78 (m, 2 H) 1.98-2.06 (m, 1 H) 2.06-2.13 (m, 1 H) 2.43-2.61 (m, 1 H) 3.55-3.65 (m, 1 H) 3.81-3.86 (m, 1 H) 3.89-3.96 (m, 1 H) 4.02-4.17 (m, 3 H) 5.16-5.23 (m, 2 H) 6.06-6.10 (m, 1 H) 6.47-6.51 (m, 1 H) 7.30-7.46 (m, 4 H) 7.52-7.56 (m, 1 H) 7.56-7.61 (m, 2 H) 7.66-7.69 (m, 1 H) 8.43-8.46 (m, 1 H). MS ESI/APCI Multi posi: 479 [M + H]$^+$. |

Reference Example 10-1

3-[[6-[2-(2-Oxanyl)-3-pyrazolyl]-3-pyridinyl]oxymethyl]benzoic Acid

[Formula 349]

(1) The compound (1.14 g) obtained in Reference Example 1-1 and commercially available methyl (3-bromomethyl)benzoate (1.17 g) were used to perform the synthesis process according to the method described in Reference Example 1-1-(1) thereby giving methyl 3-[[6-[2-(2-oxanyl)-3-pyrazolyl]-3-pyridinyl]oxymethyl]benzoate (1.83 g) as a colorless amorphous substance.

(2) To a solution of the compound (1.83 g) obtained in (1) above in methanol (10 mL) and tetrahydrofuran (10 mL), an aqueous solution of 1 mol/L sodium hydroxide (5.6 mL) was added, and the mixture was stirred at room temperature for 20 hours. A saturated aqueous solution of ammonium chloride was added to the reaction solution, the resultant mixture was extracted with chloroform, and the organic layer was separated by a phase separator. The solvent was distilled off under reduced pressure, and the obtained residue was purified by silica gel column chromatography (hexane:ethyl acetate=1:1 to ethyl acetate only to chloroform:methanol=9:1) to give the title compound (1.70 g) as a colorless solid.

$^1$H NMR (400 MHz, CHLOROFORM-d) δ ppm 1.51-1.60 (m, 1H) 1.61-1.82 (m, 2H) 1.97-2.15 (m, 2H) 2.47-2.61 (m, 1H) 3.55-3.66 (m, 1H) 4.01-4.09 (m, 1H) 5.23 (s, 2H) 6.07 (dd, J=10.0, 2.3 Hz, 1H) 6.51 (d, J=1.7 Hz, 1H) 7.35 (dd, J=8.7, 3.1 Hz, 1H) 7.52-7.63 (m, 3H) 7.72 (d, J=7.7 Hz, 1H) 8.11 (d, J=7.7 Hz, 1H) 8.21 (s, 1H) 8.48 (d, J=2.8 Hz, 1H).

MS ESI/APCI Multi posi: 380[M+H]$^+$.
MS ESI/APCI Multi nega: 378[M–H]$^-$.

The compounds of Reference Examples 10-2 and 10-3 below were synthesized using a commercially available compound, according to the method described in Reference Example 10-1. The structures, NMR data, and MS data of them are shown in Table 6-1.

Reference Example 11-1

Ethyl 2-[3-(bromomethyl)phenyl]acetate

[Formula 350]

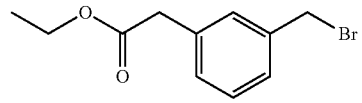

To a solution of ethyl m-toluylacetate (5.00 g) in acetonitrile (15 mL), 2,2'-azobis(isobutyronitrile) (46 mg) was added, and the mixture was stirred under heating at 90° C. A solution of N-bromosuccinimide (5.24 g) and 2,2'-azobis(isobutyronitrile) (46 mg) in acetonitrile (40 mL), which had been separately prepared, were added dropwise to the reaction solution, and the resultant mixture was stirred at the same temperature for 30 minutes. The solvent was distilled off under reduced pressure, and diethyl ether was added to the residue. The precipitate was filtered off, and the solvent was distilled off under reduced pressure. The obtained residue was purified by silica gel column chromatography (n-hexane only to n-hexane:ethyl acetate=4:1) to give the title compound (2.30 g) as a pale yellow oil.

$^1$H NMR (200 MHz, CHLOROFORM-d) δ ppm 1.26 (t, J=7.2 Hz, 3H) 3.61 (s, 2H) 4.16 (q, J=7.2 Hz, 2H) 4.48 (s, 2H) 7.19-7.38 (m, 4H).

MS ESI/APCI Multi posi: 257[M+H]$^+$.

TABLE 6-1

| Reference Example No. | Structure | Analytical Data |
|---|---|---|
| 10-2 | 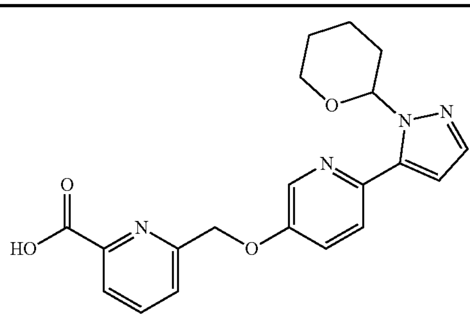 | $^1$H NMR (400 MHz, DMSO-d$_6$) δ ppm 1.41-1.70 (m, 3 H) 1.83-2.04 (m, 2 H) 2.27-2.41 (m, 1 H) 3.44-3.53 (m, 1 H) 3.79-3.88 (m, 1 H) 5.40 (s, 2 H) 6.15-6.21 (m, 1 H) 6.64-6.70 (m, 1 H) 7.51-7.56 (m, 1 H) 7.60-7.73 (m, 2 H) 7.77-7.83 (m, 1 H) 7.98-8.10 (m, 2 H) 8.52 (d, J = 2.7 Hz, 1 H). MS ESI posi: 381 [M + H]$^+$. MS ESI nega: 379 [M – H]$^-$. |
| 10-3 | 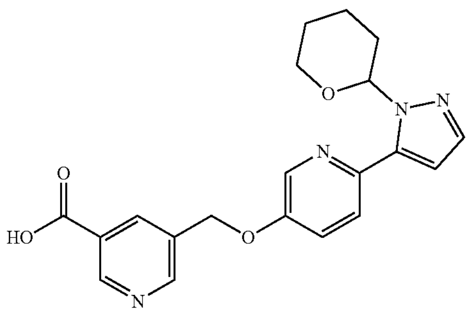 [SMILES: O=C(O)c1cncc(COc2ccc(-c3ccnn3C3CCCCO3)nc2)c1] | $^1$H NMR (400 MHz, DMSO-d$_6$) δ ppm 1.26-1.78 (m, 3 H) 1.84-2.04 (m, 2 H) 2.28-2.41 (m, 1 H) 3.37-3.58 (m, 1 H) 3.75-3.91 (m, 1 H) 5.40 (s, 2 H) 6.15-6.21 (m, 1 H) 6.65-6.70 (m, 1 H) 7.51-7.73 (m, 4 H) 8.35-8.42 (m, 2 H) 8.89-8.95 (m, 1 H). MS ESI posi: 381 [M + H]$^+$. MS ESI nega: 379 [M – H]$^-$. |

Reference Example 11-2

Ethyl 5-(bromomethyl)-2-fluorobenzoate

[Formula 351]

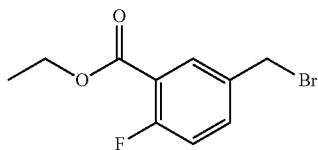

To a solution of ethyl 2-fluoro-5-methylbenzoate (243 mg) in carbon tetrachloride (6.7 mL), N-bromosuccinimide (261 mg) and 2,2'-azobis(isobutyronitrile) (22 mg) were added, and the mixture was stirred at an outer temperature of 65° C. for 2 hours. After the reaction solution was concentrated under reduced pressure, the obtained residue was purified by silica gel column chromatography (n-hexane:ethyl acetate=49:1 to 17:3) to give the title compound (208 mg) as a colorless oil.

$^1$H NMR (400 MHz, CHLOROFORM-d) δ ppm 1.36-1.46 (m, 3H) 4.34-4.45 (m, 2H) 4.48 (s, 2H) 7.07-7.16 (m, 1H) 7.48-7.58 (m, 1H) 7.92-7.98 (m, 1H).

MS ESI/APCI Multi posi: 283[M+Na]$^+$.

The compound of Reference Example 11-3 below was synthesized using a commercially available compound, according to the method described in Reference Example 11-2. The structure, NMR data, and MS data of it are shown in Table 7-1.

TABLE 7-1

| Reference Example No. | Structure | Analytical Data |
|---|---|---|
| 11-3 | 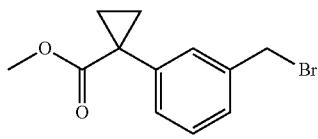 | $^1$H NMR (400 MHz, CHLOROFORM-d) δ ppm 1.36-1.46 (m, 3 H) 4.33-4.51 (m, 4 H) 7.41-7.46 (m, 2 H) 7.83 (s, 1 H). MS ESI/APCI Multi posi: 299 [M + Na]$^+$. |

Reference Example 12-1

Methyl 1-[3-(bromomethyl)phenyl]-1-cyclopropanecarboxylate

[Formula 352]

(1) A solution of commercially available 1-(3-methylphenyl)-1-cyclopropanecarboxylic acid (150 mg) in toluene:methanol (1:1, 1.70 mL) was ice-cooled under a nitrogen atmosphere, trimethylsilyldiazomethane (2.0 mol/L diethyl ether solution, 1.10 mL) was added to the solution, and the mixture was stirred at room temperature for 3 hours. Acetic acid was added thereto under ice cooling to stop the reaction, and the solution was concentrated under reduced pressure to give methyl 1-(3-methylphenyl)-1-cyclopropanecarboxylate (160 mg).

(2) To a solution of the compound (160 mg) obtained in (1) above in carbon tetrachloride (1.7 mL), N-bromosuccinimide (180 mg) and 2,2'-azobis(isobutyronitrile) (126 mg) were added, and the mixture was stirred under a nitrogen atmosphere at 80° C. for 4 hours. The reaction mixture was cooled to room temperature, and water was added thereto and the reaction mixture was extracted with chloroform. The organic layer was passed through a phase separator, and concentrated under reduced pressure. The obtained residue was purified by silica gel column chromatography (hexane:ethyl acetate=10:1 to 1:1) to give the title compound (74 mg).

$^1$H NMR (400 MHz, CHLOROFORM-d) δ ppm 1.18-1.25 (m, 2H) 1.60-1.67 (m, 2H) 3.63 (s, 3H) 4.49 (s, 2H) 7.23-7.38 (m, 4H).

Reference Example 13-1

Methyl[2-(3-bromomethyl)phenyl]-5-pyrimidinecarboxylate

[Formula 353]

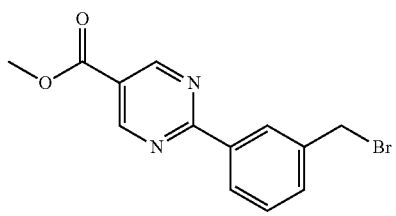 [SMILES: COC(=O)c1ncc(-c2cccc(CBr)c2)cn1]

(1) A solution of methyl 2-chloro-5-pyrimidinecarboxylate (170 mg), (3-methylphenyl)boronic acid (174 mg), [1,1'-bis(diphenylphosphino)ferrocene]palladium(II) dichloride dichloromethane adduct (80 mg), and potassium carbonate (272 mg) in 1,4-dioxane:water (5:1, 6 mL) was stirred at an outer temperature of 90° C. for 5 hours. After cooling to room temperature, the solution was diluted with ethyl acetate and filtered through Celite (registered trademark), and concentrated under reduced pressure. The obtained residue was purified by silica gel chromatography (hexane:ethyl acetate) to give methyl 2-(3-methylphenyl)-5-pyrimidinecarboxylate (100 mg) as a colorless solid.

(2) The compound (100 mg) obtained in (2) above was used to perform the synthesis process according to the method described in Reference Example 12-1-(2) thereby giving the title compound (70 mg) as a colorless solid.

$^1$H NMR (400 MHz, CHLOROFORM-d) δ ppm 4.07 (s, 3H) 4.61 (s, 2H) 7.44-7.60 (m, 2H) 7.87 (d, J=4.9 Hz, 1H) 8.47 (d, J=7.6 Hz, 1H) 8.55 (s, 1H) 9.04 (d, J=4.9 Hz, 1H).

MS ESI posi: 307[M+H]$^+$.

Reference Example 13-2

Methyl 2-[3-(bromomethyl)phenyl]-4-pyrimidinecarboxylate

[Formula 354]

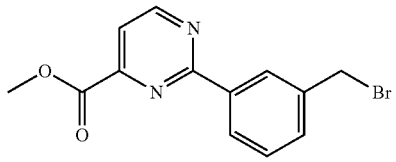

(1) A solution of methyl 2-chloro-4-pyrimidinecarboxylate (150 mg), (3-methylphenyl)boronic acid (122 mg), [1,1'-bis(diphenylphosphino)ferrocene]palladium(II) dichloride dichloromethane adduct (56 mg), and potassium carbonate (191 mg) in N,N-dimethylformamide (3.5 mL) was stirred under heating at an outer temperature of 90° C. for 2 hours. After cooling to room temperature, the solution was diluted with ethyl acetate and filtered through Celite (registered trademark), and concentrated under reduced pressure. The obtained residue was purified by silica gel chromatography (hexane:ethyl acetate) to give methyl 5-(3-methylphenyl)-2-pyrimidinecarboxylate (135 mg) as a pale red solid.

(2) The compound (130 mg) obtained in (1) above was used to perform the synthesis process according to the method described in Reference Example 12-1-(2) thereby giving the title compound (106 mg) as a colorless solid.

$^1$H NMR (400 MHz, CHLOROFORM-d) δ ppm 4.07 (s, 3H) 4.61 (s, 2H) 7.44-7.62 (m, 2H) 7.87 (d, J=4.9 Hz, 1H) 8.47 (d, J=7.8 Hz, 1H) 8.54-8.57 (m, 1H) 9.04 (d, J=5.0 Hz, 1H).

MS ESI posi: 307[M+H]$^+$.

The compound of Reference Example 13-3 below was synthesized using a commercially available compound, according to the method described in Reference Example 13-2. The structure, NMR data, and MS data of it are shown in Table 8-1.

Reference Example 14-1

Ethyl 2-[[4-(bromomethyl)-2-pyridinyl]oxy]-2-methylpropanoate

[Formula 355]

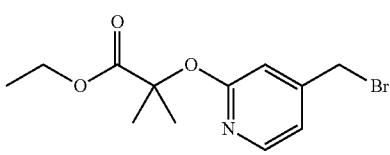

(1) 4-Methyl-2-pyridinol (300 mg) and ethyl 2-hydroxy-2-methylpropanoate (550 μL) were used to perform the synthesis process according to the method described in Reference Example 6-2 thereby giving ethyl 2-methyl-2-[(4-methyl-2-pyridinyl)oxy]propanoate (409 mg) as a colorless oil.

(2) To a solution of the compound (409 mg) obtained in (1) above in carbon tetrachloride (15 mL), N-bromosuccinimide (652 mg) and 2,2'-azobis(isobutyronitrile) (30 mg) were added, and the mixture was stirred at 80° C. for 9 hours. A saturated aqueous solution of sodium hydrogen carbonate was added to the reaction solution, and the resultant mixture was extracted with chloroform. The organic layer was separated by a phase separator, and concentrated under reduced pressure. The obtained residue was dissolved in tetrahydrofuran (10 mL), N,N-diisopropylethylamine (957 μL) and diethyl phosphite (709 μL) were added thereto, and the resultant mixture was stirred at room temperature for 8 hours. Water was added to the reaction solution, and the resultant mixture was extracted with chloroform. The organic layer was separated by a phase separator, and concentrated under reduced pressure. The residue was purified by silica gel column chromatography (n-hexane:ethyl acetate=4:1). The purified residue was dried under reduced pressure to give the title compound (395 mg) as a pale yellow oil.

$^1$H NMR (400 MHz, CHLOROFORM-d) δ ppm 1.12 (t, J=7.1 Hz, 3H) 1.66 (s, 6H) 4.14 (q, J=7.1 Hz, 2H) 4.32 (s, 2H) 6.75 (s, 1H) 6.84 (d, J=5.3 Hz, 1H) 8.00 (d, J=5.3 Hz, 1H).

MS ESI posi: 302[M+H]$^+$.

The compound of Reference Example 14-2 below was synthesized using a commercially available compound, according to the method described in Reference Example 14-1. The structure, NMR data, and MS data of the compound are shown in Table 9-1.

TABLE 8-1

| Reference Example No. | Structure | Analytical Data |
|---|---|---|
| 13-3 | ![structure] | $^1$H NMR (400 MHz, CHLOROFORM-d) δ ppm 4.11 (s, 3 H) 4.58 (s, 2 H) 7.50-7.69 (m, 4 H) 9.12 (s, 2 H). MS ESI posi: 307 [M + H]$^+$. |

TABLE 9-1

| Reference Example No. | Structure | Analytical Data |
|---|---|---|
| 14-2 | 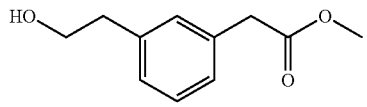 | $^1$H NMR (400 MHz, CHLOROFORM-d) δ ppm 1.31 (s, 6 H) 3.69 (s, 3 H) 4.29-4.37 (m, 4 H) 6.75 (s, 1 H) 6.88 (d, J = 5.2 Hz, 1 H) 8.11 (d, J = 5.2 Hz, 1 H). MS ESI posi: 302 [M + H]$^+$. |

Reference Example 15-1

Methyl 2-[3-(2-hydroxyethyl)phenyl]acetate

[Formula 356]

(1) A borane-tetrahydrofuran complex (0.90 mol/L tetrahydrofuran solution, 6.0 mL) was added to a solution of 2-[3-(carboxymethyl)phenyl]acetic acid (1.00 g) in tetrahydrofuran (10 mL) under a nitrogen atmosphere with ice cooling, and the mixture was stirred at room temperature for 1 hour. A saturated aqueous solution of sodium dihydrogen phosphate (15 mL) was added to stop the reaction, and the resultant mixture was extracted with ethyl acetate. The obtained organic layer was separated from the aqueous layer by passing through a phase separator, and then concentrated under reduced pressure to give 2-[3-(2-hydroxyethyl)phenyl]acetic acid as a crude product.

(2) The crude product obtained in (1) above was used to perform the synthesis process according to the method described in Reference Example 12-1-(1), and the product was purified by silica gel column chromatography (n-hexane:ethyl acetate=10:1 to 1:1) to give the title compound (130 mg) as a colorless oil.

$^1$H NMR (400 MHz, CHLOROFORM-d) δ ppm 2.86 (t, J=6.4 Hz, 2H) 3.62 (s, 2H) 3.70 (s, 3H) 3.86 (t, J=6.4 Hz, 2H) 7.12-7.19 (m, 3H) 7.26-7.32 (m, 1H).

The compound of Reference Example 15-2 below was synthesized using a commercially available compound, according to the method described in Reference Example 15-1. The structure, NMR data, and MS data of the compound are shown in Table 10-1.

Reference Example 16-1

Methyl 3-[[(3R)-3-(hydroxymethyl)-1-piperidinyl]sulfonyl]benzoate

[Formula 357]

(1) Triethylamine (0.13 mL) and 3-chlorosulfonylbenzoic acid (100 mg) were added to a solution of commercially available [(3R)-3-piperidinyl]methanol (55 mg) in chloroform (4.5 mL) under ice cooling, and the mixture was stirred at room temperature for 2.5 hours. A saturated aqueous solution of sodium dihydrogen phosphate was added to stop the reaction, and the resultant mixture was extracted with ethyl acetate. The obtained organic layer was separated from the aqueous layer by passing through a phase separator, and concentrated under reduced pressure to give 3-[[(3R)-3-(hydroxymethyl)-1-piperidinyl]sulfonyl]benzoic acid as a crude product.

(2) The crude product obtained in (1) above was used to perform the synthesis process according to the method described in Reference Example 12-1-(1) thereby giving the title compound (30 mg) as a colorless oil.

$^1$H NMR (400 MHz, CHLOROFOLM-d) δ ppm 1.00-1.14 (m, 1H) 1.61-1.82 (m, 4H) 1.84-1.96 (m, 1H) 2.35 (t, J=10.5 Hz, 1H) 2.44-2.57 (m, 1H) 3.49-3.62 (m, 3H) 3.62-3.77 (m, 1H) 3.97 (s, 3H) 7.63 (t, J=7.8 Hz, 1H) 7.95 (d, J=7.8 Hz, 1H) 8.26 (d, J=7.8 Hz, 1H) 8.41 (s, 1H).

MS ESI/APCI Multi posi: 314[M+H]$^+$, 336[M+Na]$^+$.

TABLE 10-1

| Reference Example No. | Structure | Analytical Data |
|---|---|---|
| 15-2 | 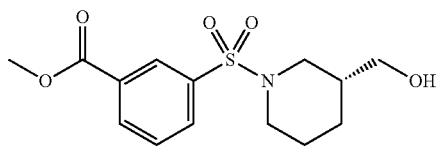 | $^1$H NMR (400 MHz, CHLOROFOLM-d) δ ppm 2.86 (t, J = 6.5 Hz, 2 H) 3.61 (s, 2 H) 3.69 (s, 3 H) 3.85 (t, J = 6.5 Hz, 2 H) 7.17-7.21 (m, 2 H) 7.21-7.25 (m, 2 H). |

Reference Example 17-1

Methyl 4-[[3-(bromomethyl)phenyl]sulfonylamino]-2,2-dimethylbutanoic Acid

[Formula 358]

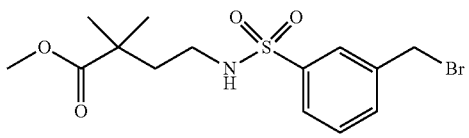

Triethylamine (0.08 mL) and 3-(bromomethyl)benzenesulfonyl chloride (78 mg) were added to a solution of methyl 4-amino-2,2-dimethylbutanoate hydrochloride (50 mg) in chloroform (2.8 mL) under a nitrogen atmosphere, and the mixture was stirred at room temperature for 2 hours. A saturated aqueous solution of ammonium chloride was added to stop the reaction, and the reaction mixture was extracted with chloroform. The obtained organic layer was separated from the aqueous layer by passing through a phase separator, and then concentrated under reduced pressure. The obtained residue was purified by silica gel column chromatography (n-hexane:ethyl acetate=4:1 to 2:3) to give the title compound (64 mg).

$^1$H NMR (400 MHz, CHLOROFOLM-d) δ ppm 1.15 (s, 6H) 1.74 (t, J=7.4 Hz, 2H) 2.97-3.03 (m, 2H) 3.66 (s, 3H) 4.51 (s, 2H) 4.53-4.60 (m, 1H) 7.48-7.55 (m, 1H) 7.61 (d, J=7.8 Hz, 1H) 7.78 (d, J=7.8 Hz, 1H) 7.87 (s, 1H).

MS ESI/APCI Multi posi: 378[M+H]$^+$, 400[M+Na]$^+$.
MS ESI/APCI Multi nega: 376[M−H]$^-$.

The compounds of Reference Examples 17-2 to 17-4 below were synthesized using a commercially available compound, according to the method described in Reference Example 17-1. The structures and MS data of the compounds are shown in Table 11-1.

Reference Example 17-5 Ethyl 1-[3-(bromomethyl)phenyl]sulfonyl-4-piperidinecarboxylate

[Formula 359]

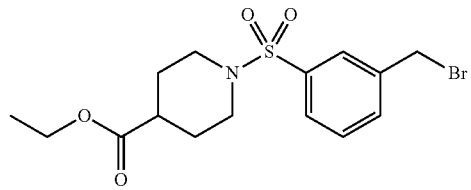

To a solution of ethyl 4-piperidinecarboxylate (245 mg) in chloroform (3 mL), 3-(bromomethyl)benzenesulfonyl chloride (400 mg) was added, and the mixture was stirred at room temperature for 2 hours. To the reaction solution, 2 mol/L hydrochloric acid was added, and the resultant mixture was extracted with chloroform. The organic layer was separated by a phase separator, and concentrated under reduced pressure to give a mixture (573 mg) containing the title compound.

MS ESI posi: 390[M+H]$^+$.

The compound of Reference Example 17-6 below was synthesized using a commercially available compound, according to the method described in Reference Example 17-5. The structure and MS data of the compound are shown in Table 11-2.

TABLE 11-1

| Reference Example No. | Structure | Analytical Data |
|---|---|---|
| 17-2 | 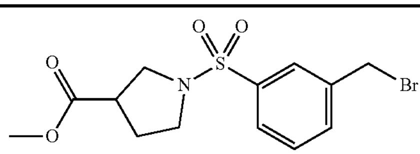 | MS ESI posi: 362 [M + H]$^+$. |
| 17-3 | 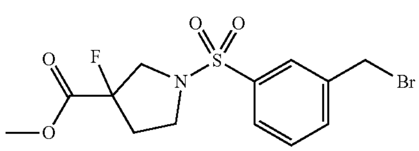 [SMILES: COC(=O)C1(F)CCN(S(=O)(=O)c2cccc(CBr)c2)C1] | MS ESI posi: 380 [M + H]$^+$. |
| 17-4 | 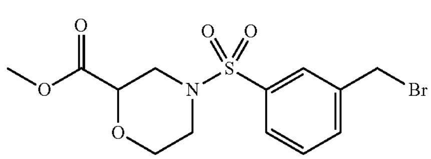 [SMILES: COC(=O)C1CN(S(=O)(=O)c2cccc(CBr)c2)CCO1] | MS ESI posi: 378 [M + H]$^+$. |

TABLE 11-2

| Reference Example No. | Structure | Analytical Data |
|---|---|---|
| 17-6 | 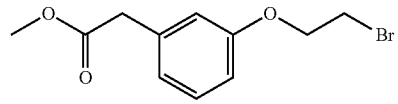 | MS ESI posi: 390 [M + H]+. |

Reference Example 18-1

Methyl 4-[[3-(bromomethyl)phenyl]sulfonyl-methylamino]-2,2-dimethylbutanoate

[Formula 360]

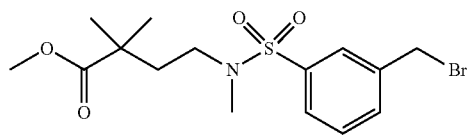

(1) Sodium hydride (60% mineral oil dispersion, 156 mg) was added to a solution of 2,2-dimethyl-4-[[(2-methylpropan-2-yl)oxy-oxomethyl]amino]butanoic acid (300 mg) in tetrahydrofuran (4.3 mL) under a nitrogen atmosphere, and the mixture was stirred at room temperature for 30 minutes, and methyl iodide (0.24 mL) was then added thereto, and the mixture was stirred at room temperature for 22 hours. A saturated aqueous solution of ammonium chloride was added to stop the reaction, and the resultant mixture was extracted with ethyl acetate. The obtained organic layer was passed through a phase separator, and concentrated under reduced pressure. The obtained residue was purified by silica gel column chromatography (n-hexane:ethyl acetate=9:1 to 1:4) to give 2,2-dimethyl-4-[methyl-[(2-methylpropan-2-yl) oxy-oxomethyl]amino]butanoic acid (185 mg) as a colorless oil.

(2) To a solution of the compound (185 mg) obtained in (1) above in methanol (1.5 mL), 2 mol/L hydrogen chloride-methanol solution (1.9 mL) was added, and the mixture was stirred at 70° C. for 2 hours. The reaction mixture was cooled to room temperature and concentrated under reduced pressure to give methyl 2,2-dimethyl-4-(methylamino)butanoate hydrochloride (137 mg) as a colorless powder.

(3) The compound (60 mg) obtained in (2) above and 3-(bromomethyl)benzenesulfonyl chloride were used to perform the synthesis process according to the method described in Reference Example 16-1-(1) thereby giving the title compound (63 mg) as a colorless oil.

$^1$H NMR (400 MHz, CHLOROFORM-d) δ ppm 1.21 (s, 6H) 1.77-1.84 (m, 2H) 2.73 (s, 3H) 3.01-3.07 (m, 2H) 3.67 (s, 3H) 4.63 (s, 2H) 7.52 (t, J=7.9 Hz, 1H) 7.59-7.63 (m, 1H) 7.68-7.76 (m, 1H) 7.80 (s, 1H).

Reference Example 19-1

Methyl 2-[3-(2-bromoethoxy)phenyl]acetate

[Formula 361]

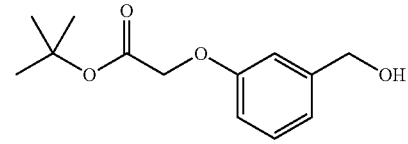

To a solution of methyl 2-(3-hydroxyphenyl)acetate (1.12 g) in N,N-dimethylformamide (6.61 mL), 1,2-dibromoethane (8.54 mL) and cesium carbonate (3.23 g) were added, and the mixture was stirred at an outer temperature of 90° C. for 6.5 hours, and then at an outer temperature of 120° C. for 1 hour. After cooling to room temperature, the reaction solution was poured into water, and the resultant mixture was extracted with ethyl acetate three times. The organic layers were combined, washed twice with brine, separated from the aqueous layer by a phase separator, and then concentrated under reduced pressure. The obtained residue was purified by silica gel column chromatography (n-hexane only to n-hexane:ethyl acetate=7:3) to give the title compound (811 mg) as a pale yellow oil.

$^1$H NMR (400 MHz, CHLOROFORM-d) δ ppm 3.58-3.66 (m, 4H) 3.70 (s, 3H) 4.26-4.32 (m, 2H) 6.79-6.93 (m, 3H) 7.22-7.27 (m, 1H).

Reference Example 19-2 tert-Butyl 2-[3-(hydroxymethyl)phenoxy]acetate

[Formula 362]

Potassium carbonate (5.57 g) and tert-butyl 2-bromoacetate (3.93 mL) were added to a solution of 3-(hydroxymethyl)phenol (2.50 g) in acetone (100 mL), and the mixture was stirred at room temperature for 2 days. Insolubles were filtered off, and the filtrate was concentrated under reduced pressure. The residue was purified by silica gel column chromatography (chloroform:methanol=19:1). The purified residue was dried under reduced pressure to give the title compound (3.36 g) as a light orange oil.

$^1$H NMR (400 MHz, CHLOROFORM-d) δ ppm 1.49 (s, 9H) 4.52 (s, 2H) 4.67 (d, J=6.1 Hz, 2H) 6.80-6.85 (m, 1H) 6.91-7.00 (m, 2H) 7.24-7.30 (m, 1H).

MS ESI/APCI Multi posi: 261 [M+Na]+.

Reference Example 19-3

Ethyl 2-[3-(hydroxymethyl)phenoxy]-2-methylpropanoate

[Formula 363]

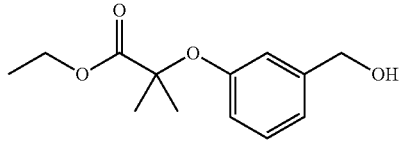

Ethyl 2-bromo-2-methylpropanoate (1.04 g) and cesium carbonate (2.17 g) were added to a solution of 3-(hydroxymethyl)phenol (550 mg) in acetonitrile (5 mL), and the mixture was stirred at 85° C. for 8 hours. The reaction solution was poured into 2 mol/L hydrochloric acid, and the resultant mixture was extracted with chloroform. The organic layer was separated by a phase separator, and concentrated under reduced pressure. The residue was purified by silica gel column chromatography (n-hexane:ethyl acetate=9:1 to 3:2). The purified residue was dried under reduced pressure to give the title compound (642 mg) as a colorless oil.

$^1$H NMR (400 MHz, CHLOROFORM-d) δ ppm 1.25 (t, J=7.1 Hz, 3H) 1.60 (s, 6H) 4.24 (q, J=7.1 Hz, 2H) 4.64 (s, 2H) 6.72-6.78 (m, 1H) 6.88 (s, 1H) 6.99 (d, J=7.5 Hz, 1H) 7.19-7.25 (m, 1H).

MS ESI/APCI Multi posi: 261 [M+Na]$^+$.

Reference Example 20-1

Methyl 8-hydroxyoctanoate

[Formula 364]

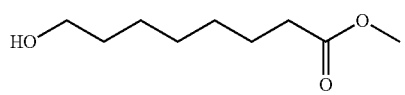

8-Hydroxyoctanoic acid (719 mg) was used to perform the synthesis process according to the method described in Reference Example 12-1-(1) thereby giving the title compound (694 mg) as a colorless oil.

$^1$H NMR (400 MHz, CHLOROFORM-d) δ ppm 1.28-1.42 (m, 6H) 1.49-1.69 (m, 4H) 2.25-2.36 (m, 2H) 3.57-3.71 (m, 5H).

MS ESI/APCI Multi posi: 175[M+H]$^+$, 197[M+Na]$^+$.

The compound of Reference Example 20-2 below was synthesized using a commercially available compound, according to the method described in Reference Example 20-1. The structure, NMR data, and MS data of the compound are shown in Table 12-1.

Reference Example 21-1 tert-Butyl 5-hydroxypentanoate

[Formula 365]

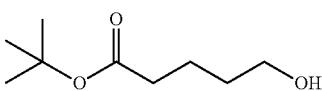

(1) To a solution of oxane-2,6-dione (6.85 g), N-hydroxysuccinimide (2.07 g), and 4-(dimethylamino)pyridine (0.73 g) in toluene (30 mL), tert-butanol (5.78 g) and triethylamine (2.51 mL) were added, and the mixture was heated to reflux for 17 hours. The reaction solution was diluted with ethyl acetate, and sequentially washed with an aqueous solution of 10% citric acid and brine. The organic layer was dried over anhydrous magnesium sulfate, the solid was filtered off, and the filtrate was then concentrated under reduced pressure. Diethyl ether was added to the residue, petroleum ether was added thereto with stirring at −20° C., and the precipitated solid was filtered off. The filtrate was concentrated, and the obtained residue was purified by silica gel column chromatography (n-hexane only to n-hexane: diethyl ether=7:3) to give 5-[(2-methylpropan-2-yl)oxy]-5-oxopentanoic acid (2.88 g) as a colorless oil.

(2) The compound (1.44) obtained in (1) above was used to perform the synthesis process according to the method described in Reference Example 15-1-(1) thereby giving the title compound (1.32 g) as a colorless oil.

$^1$H NMR (400 MHz, CHLOROFORM-d) δ ppm 1.45 (s, 9H) 1.57-1.71 (m, 4H) 2.26 (t, J=7.0 Hz, 2H) 3.65 (t, J=6.1 Hz, 2H).

MS ESI posi: 197[M+Na]$^+$.

Reference Example 22-1 tert-Butyl 4-hydroxy-4-oxanecarboxylate

[Formula 366]

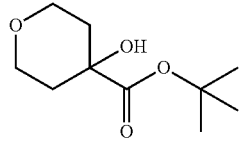

(1) Boc$_2$O (13 mL) and 4-(dimethylamino)pyridine (1.4 g) were added to a solution of tetrahydropyran-4-carboxylic

TABLE 12-1

| Reference Example No. | Structure | Analytical Data |
|---|---|---|
| 20-2 | ![structure](methyl 3-(2-hydroxyethyl)benzoate) | $^1$H NMR (400 MHz, CHLOROFOLM-d) δ ppm 2.93 (t, J = 6.5 Hz, 2 H) 3.86-3.95 (m, 5 H) 7.36-7.47 (m, 2 H) 7.88-7.96 (m, 2 H). MS ESI/APCI Multi posi: 181 [M + H]$^+$. | acid (5 g) in tert-butanol (38 mL), and the mixture was stirred at room temperature for 2 hours. The reaction mixture was concentrated under reduced pressure, and the obtained residue was purified by silica gel column chromatography (n-hexane only to n-hexane:ethyl acetate=3:1) to give tert-butyl 4-oxanecarboxylate (6.65 g) as a colorless oil.

(2) n-Butyl lithium (1.6 mol/L n-hexane solution, 18 mL) was added dropwise to a solution of diisopropylamine (6.8 mL) in tetrahydrofuran (70 mL) under a nitrogen atmosphere at a temperature of −60° C. or lower, and the mixture was stirred at the same temperature for 40 minutes. Subsequently, a solution of the compound (5 g) obtained in (1) above in tetrahydrofuran (19 mL) was added dropwise thereto, the mixture was stirred at the same temperature for 40 minutes, and triethyl phosphite (14 mL) was then added dropwise thereto, and oxygen gas was passed therethrough at a temperature of −60° C. or lower for 1.5 hours, and at room temperature for 1.5 hours. An aqueous solution of potassium hydrogen sulfate was added thereto under ice cooling, and the resultant mixture was extracted with ethyl acetate. The organic layer was sequentially washed with a saturated aqueous solution of sodium hydrogen carbonate, water, and brine, and then dried over anhydrous magnesium sulfate. The drying agent was filtered off, and the filtrate was concentrated under reduced pressure. The residue was purified by silica gel column chromatography (n-hexane:ethyl acetate=17:3 to 1:1) to give the title compound (3.75 g) as a colorless powder.

¹H NMR (400 MHz, CHLOROFORM-d) δ ppm 1.39-1.61 (m, 11H) 2.00-2.19 (m, 2H) 3.16 (s, 1H) 3.72-3.91 (m, 4H).

MS ESI/APCI Multi posi: 225 [M+Na]⁺.

Reference Example 23-1

5-(Hydroxymethyl)-2-methylphenyl Acetate

[Formula 367]

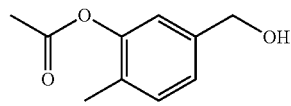

(1) Acetic anhydride (2.00 mL) was added to a solution of commercially available 3-hydroxy-4-methylbenzoic acid (500 mg) in pyridine (2.00 mL), and the mixture was stirred at room temperature for 30 minutes. The reaction solution was diluted with ethyl acetate, and washed twice with 2 mol/L hydrochloric acid, and then with brine. The organic layer was dried over anhydrous magnesium sulfate and then filtered, and the filtrate was concentrated under reduced pressure. The obtained residue was recrystallized from a n-hexane:chloroform mixed solution to give 3-acetyloxy-4-methylbenzoic acid (313 mg).

(2) The compound (300 mg) obtained in (1) above was used to perform the synthesis process according to the method described in Reference Example 15-1-(1) thereby giving the title compound (235 mg).

¹H NMR (600 MHz, CHLOROFORM-d) δ ppm 2.17 (s, 3H) 2.32 (s, 3H) 4.64 (s, 2H) 7.02 (d, J=1.4 Hz, 1H) 7.13 (dd, J=7.8, 1.4 Hz, 1H) 7.21 (d, J=7.8 Hz, 1H).

The compounds of Reference Examples 23-2 and 23-3 below were synthesized using the corresponding commercially available benzoic acid, according to the method described in Reference Example 23-1. The structures and NMR data of them are shown in Table 13-1.

TABLE 13-1

| Reference Example No. | Structure | Analytical Data |
|---|---|---|
| 23-2 | ![structure] | ¹H NMR (600 MHz, CHLOROFORM-d) δ ppm ppm 1.79 (t, J = 6.0 Hz, 1 H) 2.34 (s, 3 H) 4.66 (d, J = 6.0 Hz, 2 H) 7.12-7.17 (m, 2 H) 7.17-7.21 (m, 1 H). |
| 23-3 | ![structure] | ¹H NMR (600 MHz, CHLOROFORM-d) δ ppm 2.30 (s, 3 H) 4.69 (s, 2 H) 6.75-6.79 (m, 1 H) 6.89-6.92 (m, 1 H) 6.95-6.99 (m, 1 H). |

Reference Example 24-1

2-(2-Phenylmethoxyphenyl)ethanol

[Formula 368]

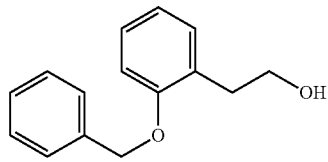

(1) Potassium hydroxide (477 mg) was added to a suspension of commercially available 2-(2-hydroxyphenyl)acetic acid (500 mg) in ethanol (3 mL), and the mixture was stirred at room temperature for 10 minutes. Benzyl bromide (468 μL) was added to this solution, and the resultant mixture was stirred at 60° C. for 2 hours. After cooling to room temperature, water was added to the reaction solution, pH was adjusted to 2 with 2 mol/L hydrochloric acid, then, the resultant solution was further diluted with water, and the diluted solution was extracted twice with chloroform. The organic layer was dried over magnesium sulfate, the drying agent was filtered off, and the filtrate was then concentrated under reduced pressure. The obtained residue was purified by silica gel column chromatography (chloroform:methanol=99:1 to 19:1) to give 2-(2-phenylmethoxyphenyl)acetic acid (313 mg).

(2) The compound (310 mg) obtained in (1) above was used to perform the synthesis process according to the method described in Reference Example 15-1-(1) thereby giving the title compound (250 mg) as a colorless oily compound.

$^1$H NMR (600 MHz, CHLOROFORM-d) δ ppm 2.96 (t, J=6.3 Hz, 2H) 3.86 (t, J=6.3 Hz, 2H) 5.09 (s, 2H) 6.90-6.96 (m, 2H) 7.18-7.23 (m, 2H) 7.31-7.35 (m, 1H) 7.36-7.44 (m, 4H).

The compound of Reference Example 24-2 below was synthesized using the corresponding commercially available phenylacetic acid, according to the method described in Reference Example 24-1. The structure and NMR data of it are shown in Table 14-1.

mL) was further added to the mixture, and the mixture was then stirred at an outer temperature of 60° C. for 2 hours. After cooling to room temperature, the reaction solution was diluted with water, and the diluted solution was extracted three times with ethyl acetate. The organic layers were combined, washed with brine, separated from the aqueous layer by a phase separator, and then concentrated under reduced pressure. The obtained residue was purified by silica gel column chromatography (n-hexane:ethyl acetate=9:1 to 1:4) to give the title compound (680 mg) as a colorless oil.

$^1$H NMR (400 MHz, CHLOROFORM-d) δ ppm 1.85-1.93 (m, 2H) 2.66-2.71 (m, 2H) 3.67 (t, J=6.4 Hz, 2H) 3.82 (s, 3H) 4.98 (s, 2H) 6.78-6.85 (m, 3H) 6.89-6.95 (m, 2H) 7.17-7.23 (m, 1H) 7.36 (d, J=8.7 Hz, 2H).

TABLE 14-1

| Reference Example No. | Structure | Analytical Data |
|---|---|---|
| 24-2 | 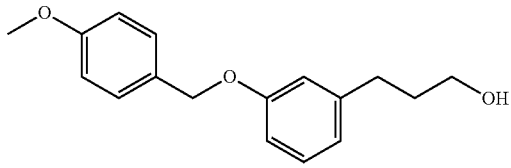 | $^1$H NMR (600 MHz, CHLOROFORM-d) δ ppm 1.37 (t, J = 5.8 Hz, 1 H) 2.84 (t, J = 6.6 Hz, 2 H) 3.82-3.88 (m, 2 H) 5.06 (s, 2 H) 6.81-6.87 (m, 3 H) 7.23 (t, J = 8.1 Hz, 1 H) 7.30-7.34 (m, 1 H) 7.36-7.40 (m, 2 H) 7.41-7.45 (m, 2 H). |

Reference Example 25-1

3-[3-[(4-Methoxyphenyl)methoxy]phenyl]-1-propanol

[Formula 369]

Reference Example 26-1

3-(Chloromethyl)-N-methylbenzenesulfonamide

[Formula 370]

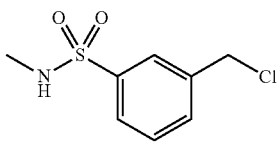

(1) Potassium carbonate (641 mg) was added to a solution of methyl 3-(3-hydroxyphenyl)propanoate (588 mg) in acetone (10.3 mL). The mixture was ice-cooled, to which 4-methoxybenzyl chloride (501 μL) was added, and the mixture was stirred at room temperature overnight. The mixture was heated to an outer temperature of 60° C., to which potassium carbonate (641 mg) and 4-methoxybenzyl chloride (501 μL) were then added, and the resultant mixture was stirred for 3.5 hours. After cooling to room temperature, insolubles were filtered off, and the solvent was distilled off under reduced pressure. The residue was purified by NH silica gel column chromatography (n-hexane only to n-hexane:ethyl acetate=4:1) to give methyl 3-[3-[(4-methoxyphenyl)methoxy]phenyl]propanoate (756 mg) as a colorless oil.

(2) Lithium borohydride (3 mol/L tetrahydrofuran solution, 1.66 mL) was added to a solution of the compound (756 mg) obtained in (1) above in tetrahydrofuran (6.22 mL), and the mixture was stirred at room temperature overnight. Lithium borohydride (3 mol/L tetrahydrofuran solution, 1.66

(1) To a solution of commercially available 3-chlorosulfonylbenzoic acid (2.01 g) in chloroform (30 mL), N,N-diisopropylethylamine (2.38 mL) and methylamine (9.8 mol/L methanol solution, 980 μL) were added, and the mixture was stirred at room temperature for 2 hours. Thereto, N,N-diisopropylethylamine (2.38 mL) and methylamine (9.8 mol/L methanol solution, 980 μL) were further added, and the mixture was stirred for 2 hours. Water and 2 mol/L hydrochloric acid were added thereto under ice cooling, and the resultant mixture was extracted with ethyl acetate. After the organic layer was dried over anhydrous magnesium sulfate, the drying agent was filtered off, and the filtrate was concentrated under reduced pressure to give 3-(methylsulfamoyl)benzoic acid (1.54 g) as a yellow powder. The obtained compound was used for the next reaction without being purified.

(2) The compound (1.54 g) obtained in (1) above was used to perform the synthesis process according to the method described in Reference Example 15-1-(1) thereby giving 3-(hydroxymethyl)-N-methylbenzene-1-sulfonamide (1.53 g) as a colorless oil.

(3) Thionyl chloride (778 μL) was added to a solution of the compound (1.53 g) obtained in (2) above in chloroform (20 mL), and the mixture was stirred at room temperature for 2 hours. Thionyl chloride (778 μL) was further added thereto, and the mixture was stirred at room temperature for 1 hour, and at 50° C. for 2 hours. The solvent was distilled off, and the obtained residue was purified by silica gel column chromatography (n-hexane only to n-hexane:ethyl acetate=7:3) to give the title compound (769 mg) as a colorless oil.

$^1$H NMR (300 MHz, CHLOROFORM-d) δ ppm 2.67-2.71 (m, 3H) 4.44 (br s, 1H) 4.63 (s, 2H) 7.48-7.59 (m, 1H) 7.59-7.69 (m, 1H) 7.78-7.86 (m, 1H) 7.86-7.94 (m, 1H).

MS ESI/APCI Multi posi: 242[M+Na]$^+$.

Reference Example 27-1

Methyl 2-[3-(hydroxymethyl)phenyl]benzoate

[Formula 371]

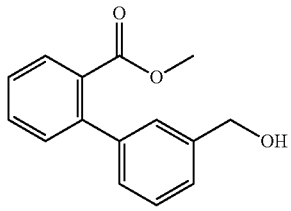

(1) 2-(3-Methoxycarbonylphenyl)benzoic acid (535 mg) was used to perform the synthesis process according to the method described in Reference Example 25-1-(2) thereby giving a mixture (361 mg) containing 2-[3-(hydroxymethyl)phenyl]benzoic acid.

(2) Potassium carbonate (433 mg) and methyl iodide (143 μL) were added to a solution of the mixture (361 mg) obtained in (1) above in acetone (5.22 mL), and the resultant mixture was stirred at an outer temperature of 60° C. for 2 hours. After cooling to room temperature, potassium carbonate (433 mg) and methyl iodide (143 μL) were further added thereto, and the resultant mixture was stirred at room temperature for 2 days. The solvent was distilled off under reduced pressure, and the residue was distributed into diethyl ether and water. The aqueous layer was extracted with diethyl ether. The organic layers were combined, sequentially washed with an aqueous solution of 1 mol/L potassium hydroxide and brine, separated from the aqueous layer by a phase separator, and then concentrated under reduced pressure. The obtained residue was purified by silica gel column chromatography (n-hexane:ethyl acetate=19:1 to 3:2) to give a mixture (141 mg) containing the title compound as a colorless oil.

$^1$H NMR (400 MHz, CHLOROFORM-d) δ ppm 1.26 (t, J=5.9 Hz, 1H) 3.65 (s, 3H) 4.74 (d, J=5.9 Hz, 2H) 7.22-7.26 (m, 1H) 7.32-7.44 (m, 5H) 7.50-7.56 (m, 1H) 7.81-7.86 (m, 1H).

MS ESI/APCI Multi posi: 225[M-OH]$^+$.

Reference Example 28-1

Methyl 5-(hydroxymethyl)-2-methoxybenzoate

[Formula 372]

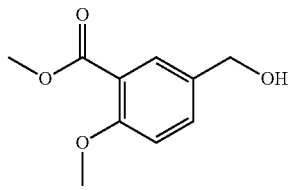

Sodium borohydride (184 mg) was added to a solution of methyl 5-formyl-2-methoxybenzoate (860 mg) in methanol (18 mL) under ice cooling, and the mixture was stirred at the same temperature for 2.5 hours. Water and a saturated aqueous solution of ammonium chloride were added thereto, and methanol was distilled off under reduced pressure. The obtained aqueous layer was extracted with chloroform, and the organic layer was separated by a phase separator and concentrated under reduced pressure. The residue was purified by silica gel column chromatography (n-hexane:ethyl acetate=1:1 to 1:4) to give the title compound (870 mg) as a colorless oil.

$^1$H NMR (400 MHz, CHLOROFORM-d) δ ppm 1.60-1.69 (m, 1H) 3.89 (s, 3H) 3.91 (s, 3H) 4.60-4.69 (m, 2H) 6.94-7.02 (m, 1H) 7.43-7.52 (m, 1H) 7.75-7.84 (m, 1H).

MS ESI/APCI Multi posi: 197[M+H]$^+$.

Reference Example 29-1 tert-Butyl 4-(8-hydroxyoctyl)-4-oxanecarboxylate

[Formula 373]

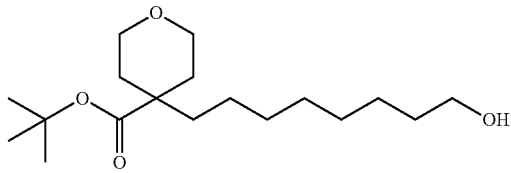

(1) To a solution of diisopropylamine (300 μL) in tetrahydrofuran (5 mL), n-butyl lithium (2.67 mol/L n-hexane solution, 790 μL) was added dropwise under a nitrogen atmosphere with ice cooling, and the mixture was stirred at the same temperature for 30 minutes. A solution of the compound (300 mg) obtained in Reference Example 22-1-(1) in tetrahydrofuran (2 mL) was added dropwise thereto at a temperature of −60° C. or lower, and the mixture was stirred at the same temperature for 45 minutes. Subsequently, a solution of 2-(8-bromooctoxy)oxane (620 mg) in tetrahydrofuran (1 mL) was added dropwise thereto at the same temperature, and the mixture was stirred at room temperature overnight. A saturated aqueous solution of ammonium chloride was added dropwise thereto under ice cooling, and the resultant mixture was extracted with diethyl ether. After the organic layer was washed with brine, the organic layer was dried over anhydrous magnesium sulfate, the drying agent was filtered off, and the filtrate was then concentrated under reduced pressure. The residue was purified by silica gel column chromatography (n-hexane:ethyl acetate=49:1 to 3:1) to give tert-butyl 4-[8-(2-oxanyloxy)octyl]-4-oxanecarboxylate (314 mg) as a colorless oil.

(2) To a solution of the compound (311 mg) obtained in (1) above in methanol (3.9 mL), p-toluenesulfonic acid monohydrate (15 mg) was added, and the mixture was stirred at room temperature overnight. A saturated aqueous solution of sodium hydrogen carbonate was added to the reaction solution, and the resultant mixture was extracted with chloroform. The organic layer was separated by a phase separator, and concentrated under reduced pressure. The residue was purified by silica gel column chromatography (n-hexane:ethyl acetate=3:1 to 1:1) to give the title compound (237 mg) as a colorless oil.

$^1$H NMR (400 MHz, CHLOROFORM-d) δ ppm 1.13-1.63 (m, 25H) 1.95-2.06 (m, 2H) 3.39-3.51 (m, 2H) 3.58-3.69 (m, 2H) 3.76-3.86 (m, 2H).

MS ESI/APCI Multi posi: 337[M+Na]$^+$.

Reference Example 30-1 tert-Butyl 1-acetyl-4-(6-hydroxyhexyl)-4-piperidinecarboxylate

[Formula 374]

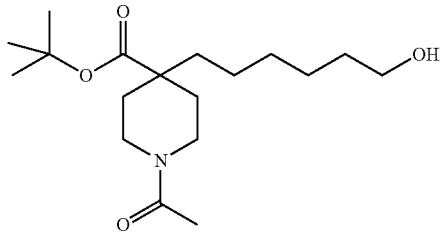

(1) Boc$_2$O (6.0 mL) and 4-dimethylaminopyridine (799 mg) were added to a solution of 1-[(2-methylpropan-2-yl)oxy-oxomethyl]-4-piperidinecarboxylic acid (5.0 g) in t-butanol (22 mL), and the mixture was stirred at room temperature for 14 hours. A saturated aqueous solution of sodium hydrogen carbonate (10 mL) was added to stop the reaction, and the resultant mixture was extracted with hexane. The obtained organic layer was separated from the aqueous layer by passing through a phase separator, and concentrated under reduced pressure. The obtained residue was purified by silica gel column chromatography (n-hexane only to n-hexane:ethyl acetate=9:1) to give ditert-butyl piperidine-1,4-dicarboxylate (5.6 g) as a colorless solid.

(2) The compound (571 mg) obtained in (1) above and 2-(6-bromohexoxy)oxane (530 mg) were used to perform the synthesis process according to the method described in Reference Example 29-1-(1) thereby giving ditert-butyl 4-[6-(2-oxanyloxy)hexyl]piperidine-1,4-dicarboxylate (362 mg) as a colorless oil.

(3) A solution of 4 mol/L hydrogen chloride-1,4-dioxane (1.9 mL) was added to a solution of the compound (362 mg) obtained in (2) above in 1,4-dioxane (3.8 mL) under ice cooling, and the mixture was stirred at room temperature for 4.5 hours. Triethylamine (2.0 mL) was added to stop the reaction. The resultant solution was filtered through Celite (registered trademark), and the filtrate was concentrated under reduced pressure. The residue was dissolved in chloroform (7.7 mL), and triethylamine (0.22 mL) and acetic anhydride (0.11 mL) were added thereto, and the resultant mixture was stirred at room temperature for 14 hours. A saturated aqueous solution of ammonium chloride (8 mL) was added to stop the reaction, and the resultant mixture was extracted with chloroform. The obtained organic layer was separated from the aqueous layer by passing through a phase separator, and concentrated under reduced pressure. The obtained residue was dissolved in methanol (1.5 mL), water (0.50 mL) and trifluoroacetic acid (0.25 mL) were added thereto under ice cooling, and the resultant mixture was stirred at room temperature for 4 hours. A saturated aqueous solution of sodium hydrogen carbonate (5 mL) was added to stop the reaction, and the resultant mixture was extracted with ethyl acetate. The obtained organic layer was separated from the aqueous layer by passing through a phase separator, and concentrated under reduced pressure. The obtained residue was purified by silica gel column chromatography (n-hexane:ethyl acetate=7:3 to 1:9 to chloroform:methanol=17:3) to give the title compound (70 mg) as a colorless oil.

MS ESI posi: 328[M+H]$^+$, 350[M+Na]$^+$.

The compound of Reference Example 30-2 below was synthesized using a commercially available compound, according to the method described in Reference Example 30-1. The structure, NMR data, and MS data of the compound are shown in Table 15-1.

TABLE 15-1

| Reference Example No. | Structure | Analytical Data |
|---|---|---|
| 30-2 | 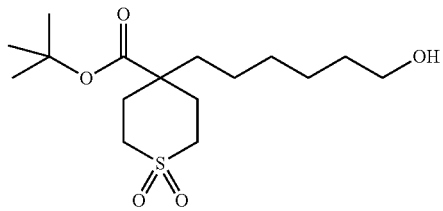 | $^1$H NMR (400 MHz, CHLOROFOLM-d) δ ppm 1.20-1.40 (m, 6 H) 1.45 (d, J = 3.3 Hz, 9 H) 1.50-1.86 (m, 6 H) 1.97-2.07 (m, 3 H) 2.26-2.44 (m, 1 H) 2.65 (d, J = 9.2 Hz, 1 H) 3.12-3.29 (m, 1 H) 3.60-3.69 (m, 2 H) 3.86-4.03 (m, 1 H). MS ESI posi: 314 [M + H]$^+$, 336 [M + Na]$^+$. |

Reference Example 31-1 tert-Butyl 4-(6-hydroxyhexyl)-1,1-dioxo-4-thiancarboxylate

[Formula 375]

(1) 4-Thiancarboxylic acid (1.0 g) was used to perform the synthesis process according to the method described in Reference Example 30-1-(1) thereby giving tert-butyl 4-thiancarboxylate (1.53 g) as a colorless oil.

(2) The compound (400 mg) obtained in (1) above was used to perform the synthesis process according to the method described in Reference Example 29-1-(1) thereby giving tert-butyl 4-[6-(2-oxanyloxy)hexyl]-4-thiancarboxylate (463 mg) as a colorlessoil.

(3) To a solution of the compound (463 mg) obtained in (2) above in chloroform (6.0 mL), meta-chloroperbenzoic acid (650 mg) was added under ice cooling, and the mixture was stirred at room temperature for 12 hours. A mixed solution of saturated aqueous solution of sodium thiosulfate: saturated aqueous solution of sodium hydrogen carbonate (1:1) was added to stop the reaction, and the reaction mixture was extracted with chloroform. The obtained organic layer was separated from the aqueous layer by passing through a phase separator, and concentrated under reduced pressure to give tert-butyl 4-[6-(2-oxanyloxy)hexyl]-1,1-dioxo-4-thiancarboxylate as a crude product.

(4) Water (0.5 mL) and trifluoroacetic acid (0.25 mL) were added to a solution of the crude product obtained in (3) above in methanol (1.5 mL) under ice cooling, and the mixture was stirred at room temperature for 4.5 hours. A saturated aqueous solution of sodium hydrogen carbonate (5 mL) was added to stop the reaction, and the resultant mixture was extracted with ethyl acetate. The obtained organic layer was separated from the aqueous layer by passing through a phase separator, and concentrated under reduced pressure. The obtained residue was purified by silica gel column chromatography (n-hexane:ethyl acetate=7:3 to 1:4) to give the title compound (372 mg) as a colorless oil.

$^1$H NMR (400 MHz, CHLOROFOLM-d) δ ppm 1.19-1.40 (m, 5H) 1.48 (s, 9H) 1.50-1.63 (m, 6H) 1.92-2.07 (m, 2H) 2.40-2.49 (m, 2H) 2.88-3.14 (m, 4H) 3.64 (t, J=6.5 Hz, 2H).

MS ESI posi: 357[M+Na]$^+$.

Reference Example 32-1

Ethyl 9-hydroxy-2,2-dimethylnonanoate

[Formula 376]

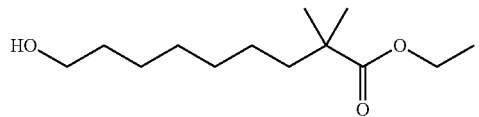

(1) To a solution of 7-bromo-1-heptanol (1.5 g) in chloroform (15 mL), 3,4-dihydro-2H-pyran (840 μL) and p-toluenesulfonic acid monohydrate (150 mg) were added, and the mixture was stirred at room temperature overnight. A saturated aqueous solution of sodium hydrogen carbonate was added to the reaction solution, and the resultant mixture was extracted with diethyl ether and washed with brine. The organic layer was separated by a phase separator, and concentrated under reduced pressure. The residue was purified by silica gel column chromatography (n-hexane:ethyl acetate=49:1 to 9:1) to give 2-(7-bromoheptoxy)oxane (1.1 g) as a colorless oil.

(2) The compound (865 mg) obtained in (1) above and ethyl isobutyrate (345 μL) were used to perform the synthesis process according to the method described in Reference Example 29-1-(1) thereby giving ethyl 2,2-dimethyl-9-(2-oxanyloxy)nonanoate (722 mg) as a colorless oil.

(3) To a solution of the compound obtained in (2) above in ethanol (23 mL), p-toluenesulfonic acid monohydrate (87 mg) was added, and the mixture was stirred at room temperature overnight. A saturated aqueous solution of sodium hydrogen carbonate was added to the reaction solution, and the resultant mixture was extracted with ethyl acetate. After the organic layer was washed with brine, the organic layer was dried over anhydrous magnesium sulfate, the drying agent was filtered off, and the filtrate was then concentrated under reduced pressure. The residue was purified by silica gel column chromatography (n-hexane:ethyl acetate=17:3 to 3:2) to give the title compound (469 mg) as a colorless oil.

$^1$H NMR (400 MHz, CHLOROFORM-d) δ ppm 1.10-1.67 (m, 21H) 3.60-3.68 (m, 2H) 4.05-4.17 (m, 2H).

MS ESI/APCI Multi posi: 231[M+H]$^+$.

Reference Example 33-1

Ethyl 6-hydroxy-2,2-dimethylhexanoate

[Formula 377]

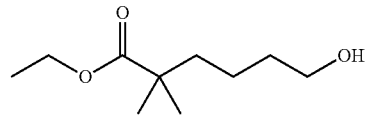

(1) 2-(4-Bromobutoxy)oxane (735 mg) was used to perform the synthesis process according to the method described in Reference Example 32-1-(2) thereby giving ethyl 2,2-dimethyl-6-(2-oxanyloxy)hexanoate (411 mg) as a colorless oil.

(2) The compound (411 mg) obtained in (1) above was used to perform the synthesis process according to the method described in Reference Example 32-1-(3) thereby giving the title compound (266 mg) as a colorless oil.

$^1$H NMR (400 MHz, CHLOROFORM-d) δ ppm 1.17 (s, 6H) 1.20-1.61 (m, 10H) 3.60-3.69 (m, 2H) 4.12 (q, J=7.1 Hz, 2H).

MS ESI/APCI Multi posi: 189[M+H]$^+$.

The compounds of Reference Examples 33-2 and 33-3 below were synthesized using a commercially available compound, according to the method described in Reference Example 33-1. The structures, NMR data, and MS data of the compounds are shown in Table 16-1.

TABLE 16-1

| Reference Example No. | Structure | Analytical Data |
|---|---|---|
| 33-2 | 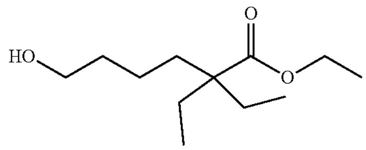 | $^1$H NMR (400 MHz, CHLOROFORM-d) δ ppm 0.77 (t, J = 7.5 Hz, 6 H) 1.15-1.66 (m, 13 H) 3.60-3.69 (m, 2 H) 4.13 (q, J = 7.1 Hz, 2 H). MS ESI/APCI Multi posi: 217 [M + H]$^+$. |
| 33-3 | 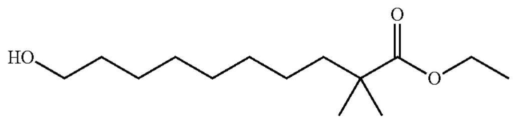 [SMILES: CCOC(=O)C(C)(C)CCCCCCCCO] | $^1$H NMR (400 MHz, CHLOROFORM-d) δ ppm 1.11-1.64 (m, 24 H) 3.59-3.68 (m, 2 H) 4.11 (q, J = 7.2 Hz, 2 H). MS ESI/APCI Multi posi: 245 [M + H]$^+$. |

Reference Example 33-4

Methyl 1-(4-hydroxybutyl)-1-cyclopentanecarboxylate

[Formula 378]

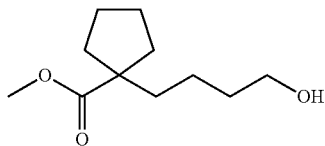

(1) Methyl cyclopentanecarboxylate (200 mg) and 2-(4-bromobutoxy)oxane (389 mg) were used to perform the synthesis process according to the method described in Reference Example 29-1-(1) thereby giving methyl 1-[4-(2-oxanyloxy)butyl]-1-cyclopentanecarboxylate (250 mg) as a colorless oil.

(2) The compound obtained in (1) above was used to perform, under ice cooling, the synthesis process according to the method described in Reference Example 31-1-(4) thereby giving the title compound (152 mg) as a colorless oil.

$^1$H NMR (400 MHz, CHLOROFORM-d) δ ppm 1.21-1.33 (m, 2H) 1.40-1.58 (m, 4H) 1.59-1.69 (m, 6H) 2.05-2.15 (m, 2H) 3.63 (t, J=6.5 Hz, 2H) 3.67 (s, 3H).

The compounds of Reference Examples 33-5 to 33-8 below were synthesized using a commercially available compound, according to the method described in Reference Example 33-4. The structures, NMR data, and MS data of the compounds are shown in Table 16-2.

TABLE 16-2

| Reference Example No. | Structure | Analytical Data |
|---|---|---|
| 33-5 | 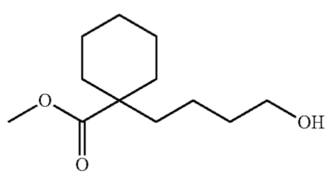 | $^1$H NMR (400 MHz, CHLOROFOLM-d) δ ppm 1.14-1.39 (m, 8 H) 1.45-1.63 (m, 6 H) 2.02-2.12 (m, 2 H) 3.62 (t, J = 6.6 Hz, 2 H) 3.68 (s, 3 H). |
| 33-6 | 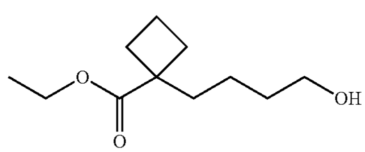 | $^1$H NMR (400 MHz, CHLOROFOLM-d) δ ppm 1.20-1.32 (m, 5 H) 1.53-1.61 (m, 3 H) 1.74-1.95 (m, 6 H) 2.33-2.47 (m, 2 H) 3.64 (t, J = 6.5 Hz, 2 H) 4.15 (q, J = 7.1 Hz, 2 H). |
| 33-7 | 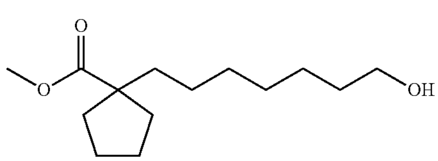 [SMILES: COC(=O)C1(CCCCCCCO)CCCC1] | $^1$H NMR (400 MHz, CHLOROFOLM-d) δ ppm 1.12-1.35 (m, 8 H) 1.41-1.53 (m, 4 H) 1.57-1.65 (m, 6 H) 2.04-2.15 (m, 2 H) 3.57-3.71 (m, 5 H). |

TABLE 16-2-continued

| Reference Example No. | Structure | Analytical Data |
|---|---|---|
| 33-8 | 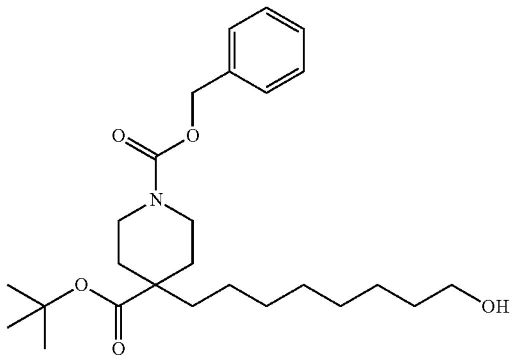 [SMILES: CC(C)(C)OC(=O)C1(CCCCCCCCO)CCN(C(=O)OCc2ccccc2)CC1] | $^1$H NMR (400 MHz, CHLOROFORM-d) δ ppm 1.09-1.65 (m, 25 H) 1.99-2.13 (m, 2 H) 2.86-3.06 (m, 2 H) 3.56-3.69 (m, 2 H) 3.86-4.06 (m, 2 H) 5.12 (s, 2 H) 7.27-7.43 (m, 5 H). MS ESI/APCI Multi posi: 470 [M + Na]$^+$. |

Reference Example 34-1

Ethyl 7-hydroxy-2,2-dimethylheptanoate

[Formula 379]

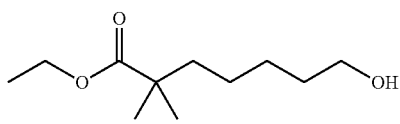

(1) Ethyl 2-methylpropanoate (0.12 mL) and 5-bromopentoxymethylbenzene (120 mg) were used to perform the synthesis process according to the method described in Reference Example 29-1-(1) thereby giving ethyl 2,2-dimethyl-7-phenylmethoxyheptanoate (72 mg) as a colorless oil.

(2) The compound (72 mg) obtained in (1) above was used to perform the synthesis process according to the method described in Reference Example 1-1-(3) thereby giving the title compound (35 mg) as a colorless oil.

$^1$H NMR (400 MHz, CHLOROFOLM-d) δ ppm 1.16 (s, 6H) 1.20-1.40 (m, 7H) 1.48-1.63 (m, 4H) 3.63 (q, J=6.2 Hz, 2H) 4.11 (q, J=7.2 Hz, 2H).

The compounds of Reference Examples 34-2 to 34-4 below were synthesized using a commercially available compound, according to the method described in Reference Example 34-1. The structures, NMR data, and MS data of the compounds are shown in Table 17-1.

TABLE 17-1

| Reference Example No. | Structure | Analytical Data |
|---|---|---|
| 34-2 | 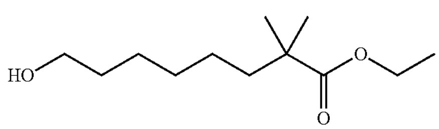 | $^1$H NMR (400 MHz, CHLOROFORM-d) δ ppm 1.15 (s, 6 H) 1.18-1.66 (m, 14 H) 3.58-3.69 (m, 2 H) 4.11 (q, J = 7.2 Hz, 2 H). MS ESI/APCI Multi posi: 217 [M + H]$^+$. |
| 34-3 | 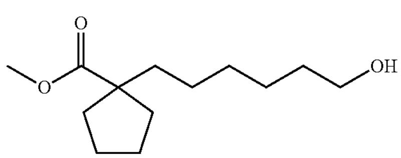 [SMILES: COC(=O)C1(CCCCCCO)CCCC1] | $^1$H NMR (400 MHz, CHLOROFOLM-d) δ ppm 1.15-1.39 (m, 7 H) 1.41-1.65 (m, 9 H) 2.04-2.16 (m, 2 H) 3.60-3.70 (m, 5 H). |
| 34-4 | 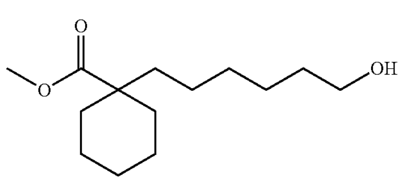 [SMILES: COC(=O)C1(CCCCCCO)CCCCC1] | $^1$H NMR (400 MHz, CHLOROFOLM-d) δ ppm 1.15-1.37 (m, 12 H) 1.43-1.61 (m, 6 H) 2.00-2.09 (m, 2 H) 3.58-3.70 (m, 5 H). |

Reference Example 35-1 tert-Butyl 1-acetyl-4-(7-hydroxyheptyl)-4-piperidinecarboxylate

[Formula 380]

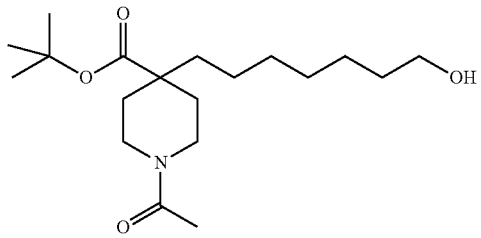

(1) The compound (570 g) obtained in Reference Example 30-1-(1) and the compound (560 mg) obtained in Reference Example 32-1-(1) were used to perform the synthesis process according to the method described in Reference Example 31-1-(2) thereby giving ditert-butyl 4-[7-(2-oxanyloxy)heptyl]piperidine-1,4-dicarboxylate (557 mg) as a colorless oil.

(2) The compound (557 mg) obtained in (1) above was used to perform the synthesis process according to the method described in Reference Example 30-1-(3) thereby giving the title compound (231 mg) as a colorless oil.

$^1$H NMR (400 MHz, CHLOROFOLM-d) δ ppm 1.21-1.67 (m, 24H) 2.00-2.18 (m, 5H) 2.73 (t, J=11.7 Hz, 1H) 3.17 (t, J=11.7 Hz, 1H) 3.56-3.73 (m, 3H) 4.29-4.41 (m, 1H).

MS ESI posi: 342[M+H]$^+$.

Reference Example 36-1

(Phenylmethyl) 1-(7-hydroxyheptoxy)-1-cyclopentanecarboxylate

[Formula 381]

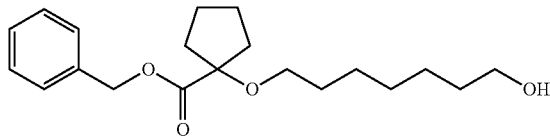

(1) 1-Hydroxy-1-cyclopentanecarboxylic acid (1 g) was used to perform the synthesis process according to the method described in Reference Example 8-2 thereby giving (phenylmethyl) 1-hydroxy-1-cyclopentanecarboxylate (888 mg) as a colorless oil.

(2) Sodium iodide (983 mg) was added to a solution of the compound (916 mg) obtained in Reference Example 32-1-(1) in acetone (6.6 mL), and the mixture was stirred while being heated to reflux for 8 hours. The reaction solution was concentrated under reduced pressure, and the residue was diluted with diethyl ether, and sequentially washed with water and brine. The organic layer was dried over anhydrous magnesium sulfate, the drying agent was filtered off, and the filtrate was then concentrated under reduced pressure. The residue was purified by silica gel column chromatography (n-hexane:ethyl acetate=49:1 to 91:9) to give 2-(7-iodoheptoxy)oxane (953 mg) as a colorless oil.

(3) Sodium hydride (60% mineral oil dispersion, 124 mg) was added to a solution of the compound (682 mg) obtained in (1) above in N,N-dimethylformamide (9 mL) under ice cooling, and the mixture was stirred at room temperature for 45 minutes. A solution of the compound (841 mg) obtained in (2) above in N,N-dimethylformamide (1.3 mL) was added thereto under ice cooling, and the resultant mixture was stirred at room temperature overnight. Water was added to the reaction solution under ice cooling, the resultant mixture was extracted with a n-hexane:ethyl acetate mixed solution, and the organic layer was sequentially washed with water and brine. After the organic layer was dried over anhydrous magnesium sulfate, the drying agent was filtered off, and the filtrate was then concentrated under reduced pressure. The residue was purified by silica gel column chromatography (n-hexane:ethyl acetate=49:1 to 17:3) to give (phenylmethyl) 1-[7-(2-oxanyloxy)heptoxy]-1-cyclopentanecarboxylate (140 mg) as a colorless oil.

(4) The compound (135 mg) obtained in (3) above was used to perform the synthesis process according to the method described in Reference Example 29-1-(2) thereby giving the title compound (96 mg) as a colorless oil.

$^1$H NMR (400 MHz, CHLOROFORM-d) δ ppm 1.09-1.62 (m, 10H) 1.63-1.84 (m, 4H) 1.88-2.09 (m, 4H) 3.23-3.36 (m, 2H) 3.56-3.69 (m, 2H) 5.18 (s, 2H) 7.28-7.43 (m, 5H).

MS ESI/APCI Multi posi: 357[M+Na]$^+$.

Reference Example 37-1

Methyl 3-(6-hydroxyhexoxy)-2,2-dimethylpropanoate

[Formula 382]

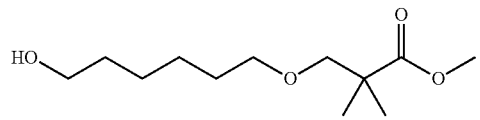

(1) Methyl 3-hydroxy-2,2-dimethylpropanoate (490 μL) and 6-bromohexoxymethylbenzene (800 mg) were used to perform the synthesis process according to the method described in Reference Example 36-1-(3) thereby giving methyl 2,2-dimethyl-3-(6-phenylmethoxyhexoxy)propanoate (252 mg) as a colorless oil.

(2) The compound (250 mg) obtained in (1) above was used to perform the synthesis process according to the method described in Reference Example 1-1-(3) by giving the title compound (142 mg) as a colorless oil.

$^1$H NMR (400 MHz, CHLOROFORM-d) δ ppm 1.18 (s, 6H) 1.30-1.64 (m, 8H) 3.30-3.48 (m, 4H) 3.57-3.75 (m, 5H).

MS ESI/APCI Multi posi: 255 [M+Na]$^+$.

Reference Example 38-1

Ethyl 2-[3-(4-hydroxybutoxy)propoxy]-2-methyl-propanoate

[Formula 383]

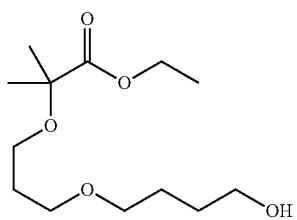

(1) Propane-1,3-diol (3.7 mL) and 2-(4-bromobutoxy)oxane (1.5 g) were used to perform the synthesis process according to the method described in Reference Example 36-1-(3) thereby giving 3-[4-(2-oxanyloxy)butoxy]-1-propanol (870 mg) as a colorless oil.

(2) Triethylamine (1 mL) and trimethylamine hydrochloride (36 mg) were added to a solution of the compound (870 mg) obtained in (1) above and p-toluenesulfonyl chloride (928 mg) in toluene (18 mL) under ice cooling, and the mixture was stirred at room temperature for 12 hours. The reaction solution was diluted with ethyl acetate, and the organic layer was washed with a saturated aqueous solution of ammonium chloride and water, and then concentrated under reduced pressure. The obtained residue was purified by silica gel column chromatography (chloroform:methanol) to give 3-[4-(2-oxanyloxy)butoxy]propyl 4-methylbenzenesulfonate (1.4 g) as a colorless oil.

(3) Sodium hydride (60% mineral oil dispersion, 124 mg) was added to a solution of ethyl 2-hydroxy-2-methylpropanoate (616 mg) in N,N-dimethylformamide (10 mL) under ice cooling, and the mixture was stirred at the same temperature for 30 minutes. A solution of the compound (600 mg) obtained in (2) above in N,N-dimethylformamide (5 mL) was slowly added dropwise to that mixed solution, and the resultant mixture was stirred at 35° C. for 7 hours, and at room temperature for 10 hours. The reaction solution was diluted with diethyl ether, and washed with a saturated aqueous solution of ammonium chloride. The organic layers were collected and concentrated, and the obtained residue was purified by silica gel column chromatography (hexane:ethyl acetate) to give a mixture (60 mg) containing ethyl 2-methyl-2-[4-[4-(2-oxanyloxy)butoxy]butoxy]propanoate.

(4) To a solution of the mixture (130 mg) obtained in (3) above in ethanol (0.5 mL), 2 mol/L hydrochloric acid (0.16 mL) was added, and the mixture was stirred at room temperature for 2 hours. The reaction solution was diluted with water, and the diluted reaction solution was extracted with ethyl acetate, and the extracted substance was then concentrated under reduced pressure to give the title compound (100 mg) as a colorless oil.

$^1$H NMR (400 MHz, CHLOROFORM-d) δ ppm 1.28 (t, J=7.2 Hz, 3H) 1.41 (s, 6H) 1.61-1.73 (m, 4H) 1.84 (t, J=6.4 Hz, 2H) 2.23-2.36 (m, 1H) 3.40-3.49 (m, 4H) 3.54 (t, J=6.4 Hz, 2H) 3.59-3.72 (m, 2H) 4.19 (q, J=7.1 Hz, 2H).

The compound of Reference Example 38-2 below was synthesized using a commercially available compound, according to the method described in Reference Example 38-1. The structure and NMR data of the compound are shown in Table 18-1.

TABLE 18-1

| Reference Example No. | Structure | Analytical Data |
|---|---|---|
| 38-2 | 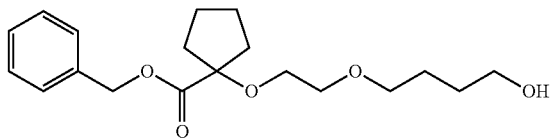 | $^1$H NMR (400 MHz, CHLOROFORM-d) δ ppm 1.28 (t, J = 7.2 Hz, 3 H) 1.41 (s, 6 H) 1.58-1.82 (m, 8 H) 2.31-2.50 (m, 1 H) 3.31-3.56 (m, 6 H) 3.56-3.75 (m, 2 H) 4.18 (q, J = 7.2 Hz, 2 H). |

Reference Example 38-3

(Phenylmethyl) 1-[2-(4-hydroxybutoxy)ethoxy]-1-cyclopentanecarboxylate

[Formula 384]

(1) Sodium hydride (60% mineral oil dispersion, 1.93 g) was added to a solution of ethane-1,2-diol (6.0 mL) in N,N-dimethylformamide (21 mL) under ice cooling, the mixture was stirred at the same temperature for 30 minutes, 2-(4-bromobutoxy)oxane (1.94 mL) was subsequently added thereto, and the resultant mixture was stirred at room temperature overnight. A saturated aqueous solution of ammonium chloride was added thereto under ice cooling, and the resultant mixture was extracted with ethyl acetate. The organic layer was sequentially washed with water and brine, and the organic layer was separated by a phase separator, and concentrated under reduced pressure. The residue was purified by silica gel column chromatography (n-hexane:ethyl acetate=1:1 to 1:9) to give 2-[4-(2-oxanyloxy)butoxy]ethanol (1.76 g) as a colorless oil.

(2) Triethylamine (2.3 mL), trimethylamine hydrochloride (77 mg), and p-toluenesulfonyl chloride (2.0 g) were added to a solution of the compound (1.8 g) obtained in (1) above in toluene (40 mL), and the mixture was stirred at room temperature overnight. Water was added to the reaction solution under ice cooling, the resultant mixture was extracted with diethyl ether, and the organic layer was sequentially washed with water and brine. The organic layer was dried over anhydrous magnesium sulfate, the drying agent was filtered off, and the filtrate was then concentrated under reduced pressure. The residue was purified by silica gel column chromatography (n-hexane:ethyl acetate=19:1 to 7:3) to give 2-[4-(2-oxanyloxy)butoxy]ethyl 4-methylbenzenesulfonate (2.4 g) as a colorless oil.

(3) The compound (202 mg) obtained in (2) above and the compound (100 mg) obtained in Reference Example 36-1-(1) were used to perform the synthesis process according to the method described in Reference Example 36-1-(3) thereby giving a crude product (81 mg) containing (phenylmethyl) 1-[2-[4-(2-oxanyloxy)butoxy]ethoxy]-1-cyclopentanecarboxylate as a colorless oil.

(4) The compound (275 mg) obtained in (3) above was used to perform the synthesis process according to the method described in Reference Example 29-1-(2) thereby giving the title compound (180 mg) as a colorless oil.

$^1$H NMR (400 MHz, CHLOROFORM-d) δ ppm 1.37-2.17 (m, 12H) 3.41-3.72 (m, 8H) 5.11-5.24 (m, 2H) 7.22-7.46 (m, 5H).

MS ESI/APCI Multi posi: 359[M+Na]$^+$.

Reference Example 38-4

Ethyl 2-[2-(4-hydroxybutoxy)ethoxy]-2-methylpropanoate

[Formula 385]

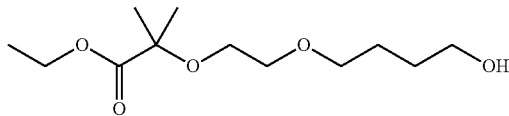

(1) The compound (500 mg) obtained in Reference Example 38-3-(2) and ethyl 2-hydroxy-2-methylpropanoate (540 µL) were used to perform the synthesis process according to the method described in Reference Example 36-1-(3) thereby giving ethyl 2-methyl-2-[2-[4-(2-oxanyloxy)butoxy]ethoxy]propanoate (372 mg) as a colorless oil.

(2) The compound (372 mg) obtained in (1) above was used to perform the synthesis process according to the method described in Reference Example 29-1-(2) thereby giving the title compound (48 mg) as a colorless oil.

$^1$H NMR (400 MHz, CHLOROFORM-d) δ ppm 1.28 (t, J=7.1 Hz, 3H) 1.43 (s, 6H) 1.49-1.79 (m, 4H) 3.44-3.79 (m, 8H) 4.19 (q, J=7.1 Hz, 2H).

MS ESI/APCI Multi posi: 271 [M+Na]$^+$.

Reference Example 39-1

Ethyl 2-[6-(hydroxymethyl)-2-pyridinyl]acetate

[Formula 386]

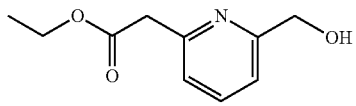

(1) Potassium cyanide (354 mg) was added to a solution of [6-(bromomethyl)-2-pyridinyl]methanol (544 mg) in ethanol:water (2:1, 8.07 mL), and the mixture was heated to reflux for 3 hours. After the mixture was cooled to room temperature, the solvent was distilled off under reduced pressure. The residue was suspended in ethanol and insolubles were filtered off, and the filtrate was then concentrated under reduced pressure. The obtained residue was purified by silica gel column chromatography (chloroform:ethyl acetate=19:1 to 3:2) to give 2-[6-(hydroxymethyl)-2-pyridinyl]acetonitrile (309 mg) as a pale gray solid.

(2) Water (1.42 mL) and potassium hydroxide (654 mg) were added to a solution of the compound (309 mg) obtained in (1) above in ethanol (1.42 mL), and the mixture was heated to reflux for 3.5 hours. After the mixture was cooled to room temperature, the solvent was distilled off under reduced pressure. The residue was adjusted to acidic condition (about pH 2) with concentrated hydrochloric acid, and volatile components were distilled off under reduced pressure. The residue was suspended in ethanol, insolubles were filtered off, and the obtained filtrate was concentrated under reduced pressure to give a mixture (430 mg) containing 2-[6-(hydroxymethyl)-2-pyridinyl]acetic acid.

(3) Cesium carbonate (969 mg) and ethyl iodide (174 µL) were added to a solution of the mixture (430 mg) obtained in (2) above in N,N-dimethylformamide (3.97 mL), and the mixture was stirred at room temperature overnight. Water was added to the mixture, and the resultant mixture was extracted four times with ethyl acetate. The organic layers were combined, washed with brine, separated from the aqueous layer by a phase separator, and then concentrated under reduced pressure. The obtained residue was purified by NH silica gel column chromatography (n-hexane:ethyl acetate=9:1 to 2:3) to give the title compound (326 mg) as a pale yellow oil.

$^1$H NMR (400 MHz, CHLOROFORM-d) δ ppm 1.27 (t, J=7.2 Hz, 3H) 3.75-3.82 (m, 1H) 3.85 (s, 2H) 4.19 (q, J=7.2 Hz, 2H) 4.74 (d, J=3.2 Hz, 2H) 7.13 (d, J=7.8 Hz, 1H) 7.21 (d, J=7.8 Hz, 1H) 7.66 (dd, J=7.8 Hz, 1H).

MS ESI/APCI Multi posi: 196[M+H]$^+$.

Reference Example 40-1

Propan-2-yl 2-(2-hydroxyethyl)benzoate

[Formula 387]

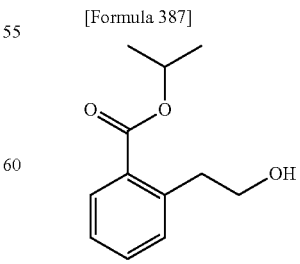

(1) Imidazole (677 mg) and tert-butyldimethylchlorosilane (825 mg) were added to a solution of commercially available 2-(2-bromophenyl)ethanol (1.0 g) in N,N-dimethylformamide (8.3 mL), and the mixture was stirred at room temperature for 3 hours. A saturated aqueous solution of ammonium chloride (10 mL) was added to stop the reaction, and the resultant mixture was extracted with diethyl ether. The obtained organic layer was passed through a phase separator, and then concentrated under reduced pressure. The obtained residue was purified by silica gel column chromatography (n-hexane:ethyl acetate=99:1 to 10:1) to give 2-(2-bromophenyl)ethoxy-tert-butyl-dimethylsilane (1.2 g).

(2) A solution of the compound (300 mg) obtained in (1) above in tetrahydrofuran (12 mL) was cooled to −78° C. under a nitrogen atmosphere, n-butyl lithium (1.6 mol/L n-hexane solution, 0.80 mL) was added thereto, and the mixture was stirred at −78° C. for 30 minutes. Isopropyl chloroformate (0.34 mL) was added thereto, and the resultant mixture was stirred at −78° C. for 1.5 hours. A saturated aqueous solution of ammonium chloride (10 mL) was added to stop the reaction, and the resultant mixture was extracted with ethyl acetate. The obtained organic layer was passed through a phase separator, and then concentrated under reduced pressure. The obtained residue was purified by silica gel column chromatography (n-hexane:ethyl acetate=99:1 to 2:1) to give propan-2-yl 2-[2-[tert-butyl(dimethyl)silyl]oxyethyl]benzoate (229 mg).

(3) A solution of the compound (229 mg) obtained in (2) above in tetrahydrofuran (14 mL) was ice-cooled, acetic acid (0.22 mL) and tetrabutylammonium fluoride (1.0 mol/L tetrahydrofuran solution, 0.78 mL) were added thereto, and the mixture was stirred at room temperature for 22 hours. A saturated aqueous solution of ammonium chloride (10 mL) was added to stop the reaction, and the resultant mixture was extracted with ethyl acetate. The obtained organic layer was passed through a phase separator, and then concentrated under reduced pressure. The obtained residue was purified by silica gel column chromatography (n-hexane:ethyl acetate=4:1 to 1:1) to give the title compound (121 mg) as a colorless oil.

$^1$H NMR (400 MHz, CHLOROFOLM-d) δ ppm 1.38 (d, J=6.3 Hz, 6H) 3.19 (t, J=6.3 Hz, 2H) 3.91 (t, J=6.3 Hz, 2H) 5.24 (spt, J=6.3 Hz, 1H) 7.20-7.33 (m, 2H) 7.42-7.48 (m, 1H) 7.85 (d, J=7.9 Hz, 1H).

MS ESI/APCI Multi posi: 209[M+H]$^+$.

The compound of Reference Example 40-2 below was synthesized using a commercially available compound, according to the method described in Reference Example 40-1. The structure and NMR data of the compound are shown in Table 19-1.

Reference Example 41-1

(Phenylmethyl) (E)-3-[2-(2-hydroxyethyl)phenyl]-2-propenoate

[Formula 388]

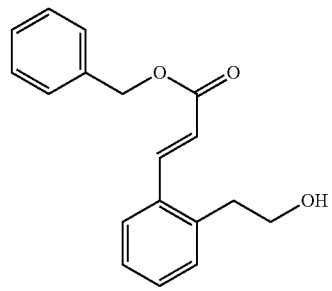

Triethylamine (0.17 mL), tri(o-toluyl)phosphine (60 mg), and palladium(II) acetate (22 mg) were added to a solution of commercially available 2-(2-bromophenyl)ethanol (200 mg) and commercially available (phenylmethyl) 2-propenoate (0.17 mL) in N,N-dimethylformamide (5.0 mL) under a nitrogen atmosphere, and the mixture was stirred at 60° C. for 1.5 hours, and at 80° C. for 2 hours. The reaction mixture was cooled to room temperature and filtered through Celite (registered trademark), and the filtrate was concentrated under reduced pressure. A saturated aqueous solution of ammonium chloride was added to the residue, and the resultant mixture was extracted with diethyl ether. The obtained organic layer was passed through a phase separator, and then concentrated under reduced pressure. The obtained residue was purified by silica gel column chromatography (n-hexane:ethyl acetate=5:1 to 1:2) to give the title compound (180 mg).

$^1$H NMR (400 MHz, CHLOROFOLM-d) δ ppm 3.04 (t, J=6.7 Hz, 2H) 3.83 (t, J=6.7 Hz, 2H) 5.26 (s, 2H) 6.43 (d, J=15.8 Hz, 1H) 7.23-7.45 (m, 8H) 7.59 (d, J=7.6 Hz, 1H) 8.07 (d, J=15.8 Hz, 1H).

The compounds of Reference Examples 41-2 and 41-3 below were synthesized using a commercially available compound, according to the method described in Reference Example 41-1. The structures, NMR data, and MS data of the compounds are shown in Table 20-1.

TABLE 19-1

| Reference Example No. | Structure | Analytical Data |
|---|---|---|
| 40-2 | ![structure] | $^1$H NMR (400 MHz, CHLOROFOLM-d) δ ppm 1.36 (d, J = 6.2 Hz, 6 H) 2.93 (t, J = 6.5 Hz, 2 H) 3.89 (t, J = 6.5 Hz, 2 H) 5.25 (spt, J = 6.2 Hz, 1 H) 7.30 (d, J = 8.3 Hz, 2 H) 7.98 (d, J = 8.3 Hz, 2 H). |

TABLE 20-1

| Reference Example No. | Structure | Analytical Data |
|---|---|---|
| 41-2 | ![structure] | $^1$H NMR (400 MHz, CHLOROFOLM-d) δ ppm 1.38 (t, J = 5.9 Hz, 1 H) 2.86 (t, J = 6.5 Hz, 2 H) 3.26 (dd, J = 7.1, 1.1 Hz, 2 H) 3.72 (s, 3 H) 3.82-3.90 (m, 2 H) 6.30 (dt, J = 15.9, 7.1 Hz, 1 H) 6.44-6.53 (m, 1 H) 7.22-7.27 (m, 4 H). |
| 41-3 | ![structure] | $^1$H NMR (400 MHz, CHLOROFOLM-d) δ ppm 1.36 (t, J = 5.9 Hz, 1 H) 2.86 (t, J = 6.5 Hz, 2 H) 3.25 (dd, J = 7.1, 1.2 Hz, 2 H) 3.72 (s, 3 H) 3.82-3.91 (m, 2 H) 6.27 (dt, J = 15.9, 7.1 Hz, 1 H) 6.47 (d, J = 15.9 Hz, 1 H) 7.18 (d, J = 8.1 Hz, 2 H) 7.32 (d, J = 8.1 Hz, 2 H).<br>MS ESI/APCI Multi posi: 221 [M + H]$^+$. |

Reference Example 42-1

Ethyl (E)-3-[3-(methylsulfonyloxymethyl)phenyl]-2-propenoate

[Formula 389]

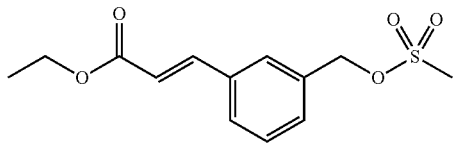

(1) Triethylamine (15 mL), ethyl acrylate (17 mL), palladium(II) acetate (360 mg), and tri(o-toluyl)phosphine (1.95 g) were added to a solution of 3-bromobenzyl alcohol (10.0 g) in acetonitrile (100 mL), and the mixture was heated to 95° C. and stirred for 3 hours. The solvent was distilled off under reduced pressure, water was added to the residue, and the resultant mixture was extracted with ethyl acetate. The organic layer was dried over anhydrous sodium sulfate, and the drying agent was filtered off. The solvent was distilled off under reduced pressure, and the obtained residue was purified by silica gel column chromatography (n-hexane:ethyl acetate=7:3 to 1:1) to give ethyl (E)-3-[3-(hydroxymethyl)phenyl]-2-propenoate (11.41 g) as a pale yellow oil.

(2) Methanesulfonyl chloride (619 μL) was added to a mixed solution of the compound (1.50 g) obtained in (1) above, triethylamine (1.11 mL), and ethyl acetate (10 mL) under ice cooling, and the mixture was stirred at room temperature for 30 minutes. The reaction solution was filtered through Celite (registered trademark) to separate precipitates. The solvent was distilled off under reduced pressure to give the title compound (2.68 g) as a pale yellow oil.

$^1$H NMR (200 MHz, CHLOROFORM-d) δ ppm 1.30-1.40 (m, 3H) 2.97 (s, 3H) 4.27 (q, J=7.3 Hz, 2H) 5.25 (s, 2H) 6.47 (d, J=16.0 Hz, 1H) 7.39-7.47 (m, 2H) 7.51-7.60 (m, 2H) 7.68 (d, J=16.0 Hz, 1H).

Reference Example 43-1

Ethyl 3-[3-(methylsulfonyloxymethyl)phenyl]propanoate

[Formula 390]

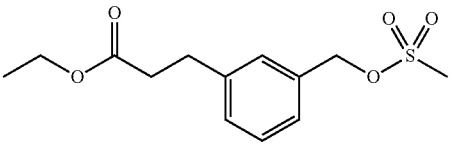

(1) Tris(triphenylphosphine)rhodium(I) chloride (449 mg) was added to a solution of the compound (1.00 g) obtained in Reference Example 42-1-(1) in ethanol (10 mL), and the mixture was stirred under a hydrogen atmosphere at room temperature for 4 hours. The reaction solution was filtered through Celite (registered trademark), and the filtrate was concentrated under reduced pressure. The obtained residue was purified by silica gel column chromatography (n-hexane:ethyl acetate=3:2) to give ethyl 3-[3-(hydroxymethyl)phenyl]propanoate (1.24 g) as a pale yellow oil.

(2) Methanesulfonyl chloride (413 μL) was added to a mixed solution of the compound (1.01 g) obtained in (1) above, triethylamine (1.01 mL), and ethyl acetate (15 mL) under ice cooling, and the mixture was stirred at room temperature for 30 minutes. The reaction solution was filtered through Celite (registered trademark) to separate precipitates. The solvent was distilled off under reduced pressure to give the title compound (2.00 g) as a reddish brown oil.

$^1$H NMR (200 MHz, CHLOROFORM-d) δ ppm 1.24 (t, J=7.2 Hz, 3H) 2.57-2.68 (m, 2H) 2.90-3.03 (m, 5H) 4.13 (q, J=7.2 Hz, 2H) 5.22 (s, 2H) 7.19-7.36 (m, 4H).

Reference Example 44-1

Ethyl 3-[4-(hydroxymethyl)phenyl]propanoate

[Formula 391]

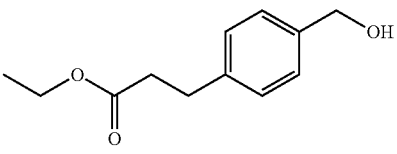

(1) Commercially available (4-iodophenyl)methanol (520 mg) and commercially available ethyl acrylate (0.29 mL) were used to perform the synthesis process according to the method described in Reference Example 41-1 thereby giving ethyl (E)-3-[4-(hydroxymethyl)phenyl]-2-propenoate (630 mg) as a crude product.

(2) The crude product (200 mg) obtained in (1) above was used to perform the synthesis process according to the method described in Reference Example 43-1-(1) thereby giving the title compound (104 mg) as a colorless oil.

$^1$H NMR (400 MHz, CHLOROFOLM-d) δ ppm 1.24 (t, J=7.2 Hz, 3H) 2.61 (t, J=7.8 Hz, 2H) 2.88 (s, 1H) 2.95 (t, J=7.8 Hz, 2H) 4.13 (q, J=7.2 Hz, 2H) 4.66 (s, 2H) 7.20 (d, J=8.0 Hz, 2H) 7.29 (d, J=8.0 Hz, 2H).

The compound of Reference Example 44-2 below was synthesized using a commercially available compound, according to the method described in Reference Example 44-1. The structure and NMR data of the compound are shown in Table 21-1.

(1) Triethylamine (0.14 mL), tri(o-toluyl)phosphine (52 mg), and palladium(II) acetate (19 mg) were added to a solution of (2-iodophenyl)methanol (200 mg) and methyl 3-butenoate (0.11 mL) in acetonitrile (4.3 mL) under a nitrogen atmosphere, and the mixture was stirred at 60° C. for 2 hours. The reaction mixture was cooled to room temperature and filtered through Celite (registered trademark), and the filtrate was concentrated under reduced pressure. A saturated aqueous solution of ammonium chloride (8 mL) was added to the residue, and the resultant mixture was extracted with diethyl ether. The obtained organic layer was passed through a phase separator, and then concentrated under reduced pressure. The obtained residue was purified by silica gel column chromatography

TABLE 21-1

| Reference Example No. | Structure | Analytical Data |
|---|---|---|
| 44-2 | ![structure] | $^1$H NMR (400 MHz, CHLOROFOLM-d) δ ppm 1.22 (t, J = 7.2 Hz, 3 H) 2.68 (t, J = 7.6 Hz, 2 H) 3.03 (t, J = 7.6 Hz, 2 H) 4.08-4.14 (m, 2 H) 4.73 (s, 2 H) 7.19-7.28 (m, 3 H) 7.34-7.39 (m, 1H). |

Reference Example 44-3

Methyl 4-[2-(hydroxymethyl)phenyl]butanoate

[Formula 392]

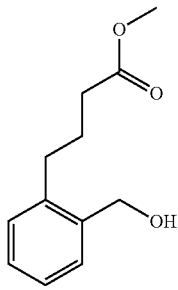

(n-hexane:ethyl acetate=3:1 to 1:1) to give methyl (E)-4-[2-(hydroxymethyl)phenyl]-3-butenoate (56 mg).

(2) The compound (56 mg) obtained in (1) above was used to perform the synthesis process according to the method described in Reference Example 43-1-(1) thereby giving the title compound (47 mg) as a light yellow oil.

$^1$H NMR (400 MHz, CHLOROFOLM-d) δ ppm 1.85-2.06 (m, 2H) 2.40 (t, J=7.2 Hz, 2H) 2.68-2.80 (m, 2H) 3.66 (s, 3H) 4.65-4.82 (m, 2H) 7.17-7.41 (m, 4H).

The compound of Reference Example 44-4 below was synthesized using a commercially available compound, according to the method described in Reference Example 44-3. The structure and NMR data of the compound are shown in Table 21-2.

TABLE 21-2

| Reference Example No. | Structure | Analytical Data |
|---|---|---|
| 44-4 | ![structure] | $^1$H NMR (400 MHz, CHLOROFOLM-d) δ ppm 1.15-1.36 (m, 3 H) 1.59-1.81 (m, 2 H) 2.34 (t, J = 7.2 Hz, 2 H) 2.39-2.63 (m, 2 H) 2.64-2.77 (m, 2 H) 4.08-4.19 (m, 2 H) 4.69-4.76 (m, 2 H) 7.14-7.49 (m, 4 H). |

Reference Example 44-5

Ethyl 3-[3-(2-hydroxyethyl)phenyl]propanoate

[Formula 393]

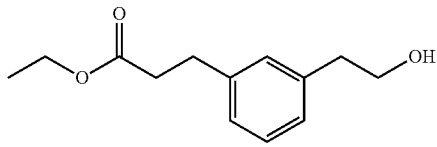

(1) Commercially available 2-(3-bromophenyl)ethanol (300 mg) and commercially available ethyl acrylate (0.18 mL) were used to perform the synthesis process according to the method described in Reference Example 41-1 thereby giving ethyl (E)-3-[3-(2-hydroxyethyl)phenyl]-2-propenoate (236 mg) as a yellow oil.

(2) The compound (236 mg) obtained in (1) above was used to perform the synthesis process according to the method described in Reference Example 1-1-(3) thereby giving the title compound (214 mg) as a yellow oil.

$^1$H NMR (400 MHz, CHLOROFOLM-d) δ ppm 1.15-1.31 (m, 5H) 2.55-2.69 (m, 3H) 2.80-3.00 (m, 3H) 4.13 (q, J=7.1 Hz, 2H) 6.95-7.40 (m, 4H).

The compound of Reference Example 44-6 below was synthesized using a commercially available compound, according to the method described in Reference Example 44-5. The structure and NMR data of the compound are shown in Table 21-3.

5-bromo-1,2-difluoro-3-[(4-methoxyphenyl)methoxy]benzene (464 mg) as a colorless solid.

(2) The compound (200 mg) obtained in (1) above, palladium(II) acetate (6.82 mg), and tris(o-toluyl)phosphine (18.5 mg) were weighted in a pressure-resistant tube and dissolved in N,N-dimethylformamide (1.22 mL), and the air in the container was purged with nitrogen and the container was then sealed. Triethylamine (119 µL) and ethyl acrylate (132 µL) were added to the mixture with a syringe, and the resultant mixture was stirred at an outer temperature of 90° C. overnight. After cooling to room temperature, the container was opened, and palladium(II) acetate (13.6 mg), tris(o-toluyl)phosphine (37.0 mg), triethylamine (119 µL), and ethyl acrylate (132 µL) were added thereto, and the air in the container was purged with nitrogen and the container was then sealed. After stirring at an outer temperature of 120° C. for 2.5 hours, the mixture was cooled to room temperature. The mixture was poured into water, and the formed precipitate was collected by filtration, washed with water, and then dissolved in chloroform. After separating from the aqueous layer by a phase separator, the resultant was concentrated under reduced pressure. The obtained residue was purified by silica gel column chromatography (n-hexane only to n-hexane:ethyl acetate=4:1). The obtained crude product was dissolved in a n-hexane:ethyl acetate (1:2) mixed solution, and insolubles were filtered off. The filtrate was concentrated under reduced pressure to give

TABLE 21-3

| Reference Example No. | Structure | Analytical Data |
|---|---|---|
| 44-6 | 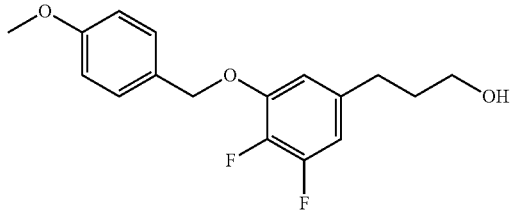 | $^1$H NMR (400 MHz, CHLOROFOLM-d) δ ppm 1.14-1.32 (m, 3 H) 2.56-2.65 (m, 2 H) 2.75-2.98 (m, 4 H) 3.85 (t, J = 6.5 Hz, 2 H) 4.13 (q, J = 7.1 Hz, 2 H) 7.09-7.19 (m, 4 H). |

Reference Example 45-1

3-[3,4-Difluoro-5-[(4-methoxyphenyl)methoxy]phenyl]-1-propanol

[Formula 394]

(1) 5-Bromo-2,3-difluorophenol (588 mg) was used to perform the synthesis process according to the method described in Reference Example 25-1-(1) thereby giving ethyl (E)-3-[3,4-difluoro-5-[(4-methoxyphenyl)methoxy]phenyl]-2-propenoate (184 mg) as a colorless solid.

(3) A palladium carbon-ethylenediamine complex (8.40 mg) was added to a solution of the compound (84.0 mg) obtained in (2) above in tetrahydrofuran:methanol=1:1 (1.58 mL), and the mixture was stirred under a hydrogen atmosphere at room temperature overnight. The catalyst was filtered off, and the filtrate was concentrated under reduced pressure. The obtained residue was purified by NH silica gel column chromatography (n-hexane only to n-hexane:ethyl acetate=4:1) to give ethyl 3-[3,4-difluoro-5-[(4-methoxyphenyl)methoxy]phenyl]propanoate (35.9 mg) as a colorless oil.

(4) The compound (35.9 mg) obtained in (3) above was used to perform the synthesis process according to the method described in Reference Example 25-1-(2) thereby giving the title compound (30.5 mg) as a colorless oil.

$^1$H NMR (400 MHz, CHLOROFORM-d) δ ppm 1.78-1.87 (m, 2H) 2.58-2.67 (m, 2H) 3.59-3.67 (m, 2H) 3.82 (s, 3H) 5.06 (s, 2H) 6.58-6.65 (m, 2H) 6.89-6.94 (m, 2H) 7.31-7.39 (m, 2H).

Reference Example 46-1

Ethyl 2-(3-hydroxypropyl)benzoate

[Formula 395]

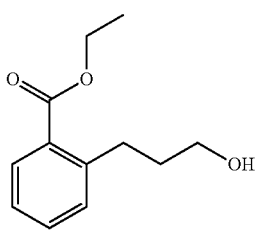

method described in Reference Example 1-1-(3) thereby giving the title compound (387 mg) as a light yellow oil.

$^1$H NMR (400 MHz, CHLOROFOLM-d) δ ppm 1.39 (t, J=7.2 Hz, 3H) 1.86-1.97 (m, 2H) 2.25 (t, J=5.9 Hz, 1H) 3.06 (t, J=7.4 Hz, 2H) 3.56-3.70 (m, 2H) 4.36 (q, J=7.2 Hz, 2H) 7.22-7.32 (m, 2H) 7.37-7.50 (m, 1H) 7.87 (dd, J=7.8, 1.3 Hz, 1H).

MS ESI/APCI Multi posi: 209[M+H]$^+$.

The compounds of Reference Examples 46-2 to 46-5 below were synthesized using a commercially available compound, according to the method described in Reference Example 46-1. The structures, NMR data, and MS data of the compounds are shown in Table 22-1.

TABLE 22-1

| Reference Example No. | Structure | Analytical Data |
|---|---|---|
| 46-2 | 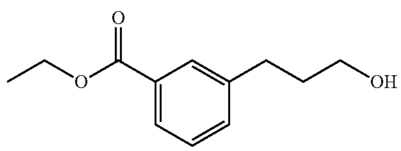 | $^1$H NMR (400 MHz, CHLOROFOLM-d) δ ppm 1.36-1.44 (m, 3 H) 1.87-1.97 (m, 2 H) 2.72-2.82 (m, 2 H) 3.68 (t, J = 6.4 Hz, 2 H) 4.32-4.46 (m, 3 H) 7.30-7.46 (m, 2 H) 7.83-7.95 (m, 2 H). MS ESI/APCI Multi posi: 209 [M + H]$^+$. |
| 46-3 | 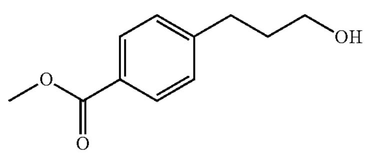 | $^1$H NMR (400 MHz, CHLOROFOLM-d) δ ppm 1.28 (t, J = 5.2 Hz, 1 H) 1.87-1.95 (m, 2 H) 2.74-2.80 (m, 2 H) 3.65-3.72 (m, 2 H) 3.90 (s, 3 H) 7.24-7.31 (m, 2 H) 7.96 (d, J = 8.3 Hz, 2 H). MS ESI/APCI Multi posi: 195 [M + H]$^+$. |
| 46-4 | 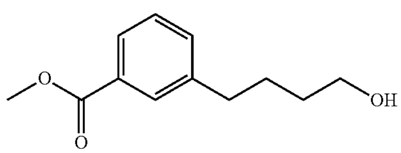 | $^1$H NMR (400 MHz, CHLOROFOLM-d) δ ppm 1.50-1.77 (m, 4 H) 2.70 (t, J = 7.6 Hz, 2 H) 3.61-3.75 (m, 2 H) 3.88-3.95 (m, 3 H) 7.32-7.46 (m, 2 H) 7.83-7.96 (m, 2 H). |
| 46-5 | 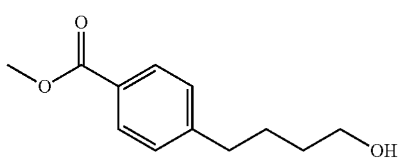 | $^1$H NMR (400 MHz, CHLOROFOLM-d) δ ppm 1.50-1.79 (m, 4 H) 2.70 (t, J = 7.6 Hz, 2 H) 3.62-3.72 (m, 2 H) 3.90 (s, 3 H) 7.23-7.26 (m, 2 H) 7.95 (d, J = 8.2 Hz, 2 H). MS ESI/APCI Multi posi: 237 [M + H]$^+$. |

(1) Triethylamine (1.51 mL), copper(I) iodide (55 mg), and bis(triphenylphosphine)palladium(II) dichloride (140 mg) were added to a solution of ethyl 2-iodobenzoate (1.0 g) and 2-propyn-1-ol (0.25 mL) in acetonitrile (7.2 mL) under a nitrogen atmosphere, and the mixture was stirred at 60° C. for 4 hour. The reaction solution was cooled to room temperature and filtered through Celite (registered trademark), and the filtrate was concentrated under reduced pressure. A saturated aqueous solution of ammonium chloride (8 mL) was added to the residue, and the resultant mixture was extracted with ethyl acetate. The obtained organic layer was passed through a phase separator, and then concentrated under reduced pressure. The obtained residue was purified by silica gel column chromatography (n-hexane:ethyl acetate=2:1 to 1:1) to give ethyl 2-(3-hydroxyprop-1-inyl)benzoate (732 mg).

(2) The compound (732 mg) obtained in (1) above was used to perform the synthesis process according to the

Reference Example 46-6

(Phenylmethyl) 4-[6-(hydroxymethyl)-2-pyridinyl]-2,2-dimethylbutanoate

[Formula 396]

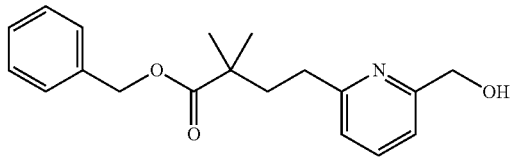

(1) Triethylamine (0.69 mL), copper(I) iodide (9.4 mg), and bis(triphenylphosphine)palladium(II) dichloride (35 mg) were added to a solution of (6-bromo-2-pyridinyl)methanol (195 mg) and (phenylmethyl) 2,2-dimethyl-3-butynoate (0.19 mL) in N,N-dimethylformamide (4.9 mL) under a nitrogen atmosphere, and the mixture was stirred at 60° C. for 3 hours. The temperature of the mixture was returned to room temperature, a saturated aqueous solution of ammonium chloride (8 mL) was added to the mixture, the resulting mixture was filtered through Celite (registered trademark), and the filtrate was extracted with ethyl acetate. The obtained organic layer was passed through a phase separator, and then concentrated under reduced pressure. The obtained residue was purified by silica gel column chromatography (n-hexane:ethyl acetate=3:2 to 1:9) to give (phenylmethyl) 4-[6-(hydroxymethyl)-2-pyridinyl]-2,2-dimethyl-3-butynoate (206 mg).

(2) Tris(triphenylphosphine)rhodium(I) chloride (50 mg) was added to a solution of the compound (206 mg) obtained in (1) above in ethanol (6.7 mL), and the mixture was stirred under a hydrogen atmosphere at room temperature for 14 hours, and at 80° C. for 22 hours. The reaction mixture was concentrated under reduced pressure, and the obtained residue was purified by silica gel column chromatography (n-hexane:ethyl acetate=7:3 to 1:4) to give the title compound (80 mg) as a colorless oil.

$^1$H NMR (400 MHz, CHLOROFOLM-d) δ ppm 1.29 (s, 6H) 1.91-2.05 (m, 2H) 2.62-2.74 (m, 2H) 4.70 (s, 2H) 5.13 (s, 2H) 6.82-7.10 (m, 2H) 7.29-7.40 (m, 4H) 7.42-7.72 (m, 2H).

MS ESI posi: 314[M+H]$^+$.

Reference Example 47-1

(Phenylmethyl) 4-[4-(hydroxymethyl)-2-pyridinyl]-2,2-dimethylbutanoate

[Formula 397]

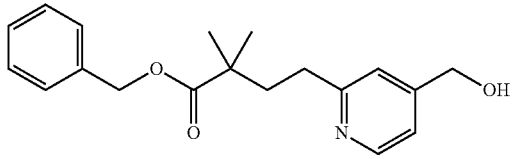

(1) Pyridinium p-toluenesulfonate (103 mg) and 3,4-dihydro-2H-pyran (0.74 mL) were added to a solution of (2-bromo-4-pyridinyl)methanol (784 mg) in chloroform (8.2 mL), and the mixture was stirred at room temperature for 17 hours. The reaction mixture was concentrated under reduced pressure, and the residue was purified by silica gel column chromatography (n-hexane only to n-hexane:ethyl acetate=3:2) to give 2-bromo-4-(2-oxanyloxymethyl)pyridine (1.1 g) as a colorless oil.

(2) The compound (283 mg) obtained in (1) above and commercially available (phenylmethyl) 2,2-dimethyl-3-butynoate (0.19 mL) were used to perform the synthesis process according to the method described in Reference Example 46-6-(1) thereby giving (phenylmethyl) 2,2-dimethyl-4-[4-(2-oxanyloxymethyl)-2-pyridinyl]-3-butynoate (250 mg) as a colorless oil.

(3) The compound (250 mg) obtained in (2) above was used to perform the synthesis process according to the method described in Reference Example 43-1-(1) thereby giving (phenylmethyl) 2,2-dimethyl-4-[4-(2-oxanyloxymethyl)-2-pyridinyl]butanoate (152 mg) as a colorless oil.

(4) A 4 mol/L hydrogen chloride-1,4-dioxane solution (0.96 mL) was added to a solution of the compound (152 mg) obtained in (3) above in 1,4-dioxane (1.9 mL), and the mixture was stirred at room temperature for 14 hours. A saturated aqueous solution of sodium hydrogen carbonate (5 mL) was added to stop the reaction, and the resultant mixture was extracted with ethyl acetate. The obtained organic layer was passed through a phase separator, and then concentrated under reduced pressure. The obtained residue was purified by silica gel column chromatography (n-hexane:ethyl acetate=7:3 to 1:4) to give the title compound (61 mg) as a colorless oil.

$^1$H NMR (400 MHz, CHLOROFOLM-d) δ ppm 1.28 (s, 6H) 1.95-2.02 (m, 2H) 2.67-2.75 (m, 2H) 4.68 (s, 2H) 5.12 (s, 2H) 7.03 (s, 1H) 7.08 (d, J=5.0 Hz, 1H) 7.26-7.56 (m, 5H) 8.46 (d, J=5.0 Hz, 1H).

MS ESI posi: 314[M+H]$^+$.

Reference Example 48-1

Ethyl 6-[3-(hydroxymethyl)phenyl]-2-pyridinecarboxylate

[Formula 398]

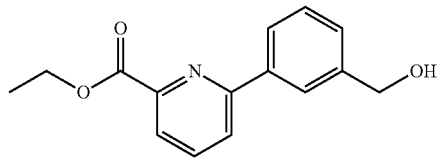

Ethyl 6-bromo-2-pyridinecarboxylate (600 mg) and [3-(hydroxymethyl)phenyl]boronic acid (515 mg) were used to perform the synthesis process according to the method described in Reference Example 13-1-(1) thereby giving the title compound (680 mg) as a pale red oil.

$^1$H NMR (600 MHz, CHLOROFORM-d) δ ppm 1.44 (t, J=7.0 Hz, 3H) 1.70-1.79 (m, 1H) 4.47 (q, J=7.0 Hz, 2H) 4.78 (d, J=6.2 Hz, 2H) 7.41-7.50 (m, 2H) 7.84-7.91 (m, 2H) 7.95 (d, J=7.4 Hz, 1H) 8.03 (dd, J=7.0, 1.2 Hz, 1H) 8.06 (s, 1H).

MS ESI/APCI Multi posi: 258[M+H]$^+$.

The compounds of Reference Examples 48-2 to 48-6 below were synthesized using a commercially available compound, according to the method described in Reference Example 48-1. The structures, NMR data, and MS data of the compounds are shown in Table 23-1.

TABLE 23-1

| Reference Example No. | Structure | Analytical Data |
|---|---|---|
| 48-2 | 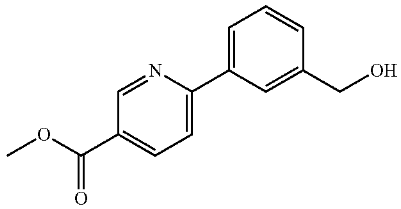 [SMILES: COC(=O)c1ccc(-c2cccc(CO)c2)nc1] | ¹H NMR (600 MHz, CHLOROFORM-d) δ ppm 1.72-1.80 (m, 1 H) 3.97 (d, J = 0.8 Hz, 3 H) 4.80 (d, J = 6.2 Hz, 2 H) 7.45-7.56 (m, 2 H) 7.83 (d, J = 8.3 Hz, 1 H) 7.93-8.01 (m, 1 H) 8.08 (d, J = 0.8 Hz, 1 H) 8.31-8.40 (m, 1 H) 9.24-9.30 (m, 1 H). MS ESI/APCI Multi posi: 244 [M + H]⁺. |
| 48-3 | 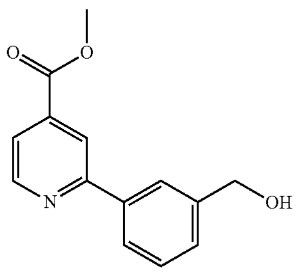 [SMILES: COC(=O)c1ccnc(-c2cccc(CO)c2)c1] | ¹H NMR (400 MHz, CHLOROFORM-d) δ ppm 1.71-1.84 (m, 1 H) 4.00 (s, 3 H) 4.81 (d, J = 6.1 Hz, 2 H) 7.39-7.59 (m, 2 H) 7.73-7.83 (m, 1 H) 7.94-8.01 (m, 1 H) 8.08 (s, 1 H) 8.32 (s, 1 H) 8.84 (d, J = 5.0 Hz, 1 H). MS ESI/APCI Multi posi: 244 [M + H]⁺. |
| 48-4 | 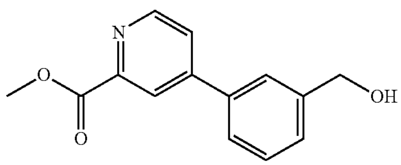 [SMILES: COC(=O)c1cc(-c2cccc(CO)c2)ccn1] | ¹H NMR (400 MHz, CHLOROFORM-d) δ ppm 1.75-1.87 (m, 1 H) 4.05 (s, 3 H) 4.82 (d, J = 5.9 Hz, 2 H) 7.46-7.55 (m, 2 H) 7.63 (d, J = 7.3 Hz, 1 H) 7.69-7.76 (m, 2 H) 8.40 (d, J = 1.2 Hz, 1 H) 8.79 (d, J = 5.0 Hz, 1 H). MS ESI/APCI Multi posi: 244 [M + H]⁺. |
| 48-5 | 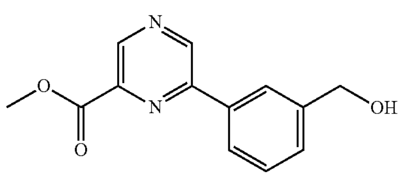 [SMILES: COC(=O)c1cncc(-c2cccc(CO)c2)n1] | ¹H NMR (400 MHz, CHLOROFORM-d) δ ppm 1.79-1.92 (m, 1 H) 4.07 (s, 3 H) 4.83 (d, J = 5.9 Hz, 2 H) 7.51-7.55 (m, 2 H) 7.94-8.04 (m, 1 H) 8.11 (s, 1 H) 9.18-9.25 (m, 2 H). MS ESI/APCI Multi posi: 245 [M + H]⁺. |
| 48-6 | 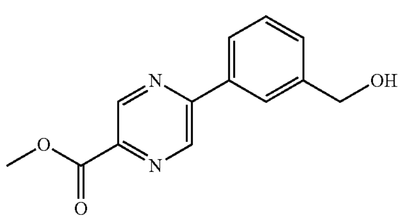 [SMILES: COC(=O)c1cnc(-c2cccc(CO)c2)cn1] | ¹H NMR (400 MHz, CHLOROFORM-d) δ ppm 1.76-1.86 (m, 1 H) 4.07 (s, 3 H) 4.83 (d, J = 6.0 Hz, 2 H) 7.55 (d, J = 5.0 Hz, 2 H) 7.97-8.06 (m, 1 H) 8.13 (s, 1 H) 9.14 (d, J = 1.3 Hz, 1 H) 9.34 (d, J = 1.3 Hz, 1 H). MS ESI/APCI Multi posi: 245 [M + H]⁺. |

Reference Example 49-1 tert-Butyl 2-[4-[3-(hydroxymethyl)phenyl]-1-pyrazolyl]acetate

[Formula 399]

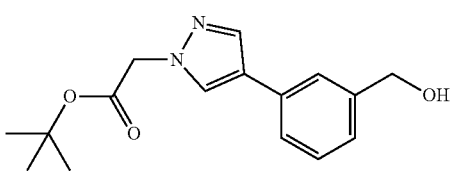

(1) Cesium carbonate (5.3 g) was added to a solution of 4-bromo-1H-pyrazole (2 g) in N,N-dimethylformamide (40 mL), and the mixture was stirred at room temperature. To this mixture, tert-butyl 2-bromoacetate (3.2 g) was slowly added under ice cooling, and the resultant mixture was stirred at room temperature 14 hours. Water was added to the reaction solution, and the resultant mixture was extracted with ethyl acetate. The organic layer was washed twice with water and concentrated under reduced pressure, and the obtained residue was purified by silica gel column chromatography (n-hexane:ethyl acetate=9:1) to give tert-butyl 2-(4-bromo-1-pyrazolyl)acetate (3.2 g) as a colorless oil.

(2) The compound (300 mg) synthesized in (1) above and [3-(hydroxymethyl)phenyl]boronic acid (227 mg) were used to perform the synthesis process according to the method described in Reference Example 13-1-(1) thereby giving the title compound (260 mg) as a dark brown oil.

¹H NMR (400 MHz, CHLOROFORM-d) δ ppm 1.49 (s, 9H) 1.60-1.67 (m, 1H) 4.72 (d, J=6.0 Hz, 2H) 4.84 (s, 2H) 7.20-7.25 (m, 1H) 7.32-7.39 (m, 1H) 7.40-7.45 (m, 1H) 7.51 (s, 1H) 7.74 (s, 1H) 7.84 (s, 1H).

MS ESI/APCI Multi posi: 289[M+H]⁺.

Reference Example 49-2

Propan-2-yl 2-[5-[3-(hydroxymethyl)phenyl]-2-oxo-1-pyridinyl]acetate

[Formula 400]

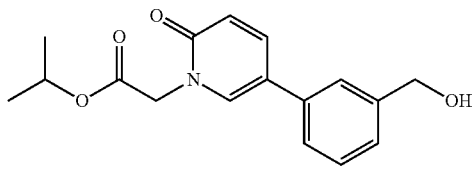

(1) Potassium carbonate (1.3 g) and isopropyl bromoacetate (1.2 mL) were added to a solution of 5-bromo-1H-pyridin-2-one (1.50 g) in N,N-dimethylformamide (8.6 mL), and the mixture was stirred at room temperature for 1 hour. A saturated aqueous solution of ammonium chloride (10 mL) was added to stop the reaction, and the resultant mixture was extracted with ethyl acetate. The obtained organic layer was passed through a phase separator, and then concentrated under reduced pressure. The obtained residue was purified by silica gel column chromatography (n-hexane:ethyl acetate=7:3 to 3:7) to give propan-2-yl 2-(5-bromo-2-oxo-1-pyridinyl)acetate (1.2 g) as a colorless solid.

(2) Potassium carbonate (100 mg) and tetrakis(triphenylphosphine)palladium(0) (42 mg) were added to a solution of the compound (100 mg) obtained in (1) above and commercially available [3-(hydroxymethyl)phenyl]boronic acid (58 mg) in dimethoxyethane:water (4:1, 4.5 mL) under a nitrogen atmosphere, and the mixture was stirred at 120° C. for 30 minutes under microwave irradiation. The reaction mixture was filtered through Celite (registered trademark), a saturated aqueous solution of ammonium chloride (5 mL) was added to the filtrate, and the resultant mixture was extracted with ethyl acetate. The obtained organic layer was passed through a phase separator, and then concentrated under reduced pressure. The obtained residue was purified by silica gel column chromatography (n-hexane:ethyl acetate=7:3 to 1:9) to give the title compound (73 mg) as a brown amorphous substance.

$^1$H NMR (400 MHz, CHLOROFOLM-d) δ ppm 1.29 (d, J=6.3 Hz, 6H) 1.86 (t, J=5.7 Hz, 1H) 4.68 (s, 2H) 4.75 (d, J=5.7 Hz, 2H) 5.11 (spt, J=6.3 Hz, 1H) 6.67 (d, J=9.4 Hz, 1H) 7.29-7.50 (m, 5H) 7.62-7.74 (m, 1H).

MS ESI posi: 302[M+H]$^+$.

Reference Example 49-3 Propan-2-yl 2-[4-[3-(hydroxymethyl)phenyl]-2-oxo-1-pyridinyl]acetate

[Formula 401]

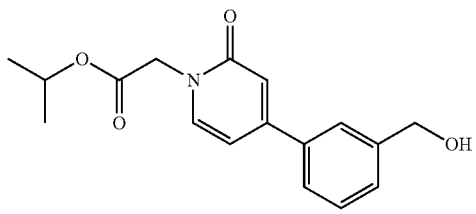

(1) 4-Iodo-1H-pyridin-2-one (1.0 g) was used to perform the synthesis process according to the method described in Reference Example 49-2-(1) thereby giving propan-2-yl 2-(4-iodo-2-oxo-1-pyridinyl)acetate (1.2 g) as a colorless solid.

(2) The compound (150 mg) obtained in (1) above and [3-(hydroxymethyl)phenyl]boronic acid (75 mg) were used to perform the synthesis process according to the method described in Reference Example 49-2-(2) thereby giving the title compound (93 mg) as a colorless oil.

$^1$H NMR (400 MHz, CHLOROFOLM-d) δ ppm 1.29 (d, J=6.3 Hz, 6H) 1.94 (t, J=5.8 Hz, 1H) 4.65 (s, 2H) 4.77 (d, J=5.8 Hz, 2H) 5.12 (spt, J=6.3 Hz, 1H) 6.48 (dd, J=7.1, 2.0 Hz, 1H) 6.78 (d, J=1.8 Hz, 1H) 7.28 (s, 1H) 7.42-7.54 (m, 3H) 7.59 (s, 1H).

MS ESI posi: 302[M+H]$^+$.

Reference Example 50-1 tert-Butyl 2-[4-(4-hydroxybutyl)-1-pyrazolyl]acetate

[Formula 402]

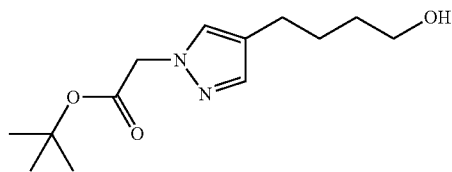

(1) The compound (500 mg) synthesized in Reference Example 49-1-(1) and tert-butyl-dimethyl-[(E)-4-(4,4,5,5-tetramethyl-1,3,2-dioxaborolan-2-yl)but-3-enoxy]silane (777 mg) were used to perform the synthesis process according to the method described in Reference Example 13-1-(1) thereby giving tert-butyl 2-[4-[(E)-4-[tert-butyl(dimethyl)silyl]oxybut-1-enyl]-1-pyrazolyl]acetate (520 mg) as a pale yellow oil.

(2) Palladium hydroxide carbon (115 mg) was added to a solution of the compound (200 mg) obtained in (1) above in ethyl acetate (5.5 mL), and the mixture was stirred under a hydrogen atmosphere at room temperature for 4 hours. The resultant mixture was diluted with ethyl acetate, filtered through Celite (registered trademark), and then concentrated under reduced pressure to give a mixture containing tert-butyl 2-[4-[4-[tert-butyl(dimethyl)silyl]oxybutyl]-1-pyrazolyl]acetate.

(3) Tetrabutylammonium fluoride (1 mol/L tetrahydrofuran solution, 0.54 mL) was added to a solution of the mixture obtained in (2) above in tetrahydrofuran (2 mL), and the resultant mixture was stirred at room temperature for 2 hours. The reaction solution was concentrated under reduced pressure, and purified by silica gel column chromatography (hexane:ethyl acetate) to give the title compound (95 mg) as a pale yellow oil.

$^1$H NMR (400 MHz, CHLOROFORM-d) δ ppm 1.47 (s, 9H) 1.60-1.70 (m, 5H) 2.46-2.58 (m, 2H) 3.60-3.75 (m, 2H) 4.72-4.77 (m, 2H) 7.24 (s, 1H) 7.37 (s, 1H).

MS ESI/APCI Multi posi: 255 [M+H]$^+$.

The compound of Reference Example 50-2 below was synthesized using a commercially available compound, according to the method described in Reference Example 50-1. The structure, NMR data, and MS data of the compound are shown in Table 24-1.

TABLE 24-1

| Reference Example No. | Structure | Analytical Data |
|---|---|---|
| 50-2 | ![structure] | 1H NMR (400 MHz, CHLOROFORM-d) δ ppm 1.26-1.32 (m, 6 H) 1.58-1.77 (m, 5 H) 2.49 (t, J = 7.5 Hz, 2 H) 3.67 (q, J = 5.8 Hz, 2 H) 4.58 (s, 2 H) 4.99-5.15 (m, 1 H) 6.07 (d, J = 7.0 Hz, 1 H) 6.36-6.44 (m, 1 H) 7.11 (d, J = 7.0 Hz, 1 H). MS ESI posi: 268 [M + H]+. |

Reference Example 51-1

Ethyl 2-[4-(4-hydroxybutyl)-1-pyrazolyl]-2-methyl-propanoate

[Formula 403]

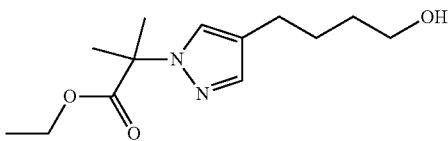 [SMILES: CCOC(=O)C(C)(C)n1ccc(CCCCO)n1]

Reference Example 50-1-(3) thereby giving the title compound (47 mg) as a colorless oil.

1H NMR (400 MHz, CHLOROFORM-d) δ ppm 1.21 (t, J=7.2 Hz, 3H) 1.60-1.68 (m, 4H) 1.83 (s, 6H) 2.51 (t, J=7.0 Hz, 2H) 3.64-3.71 (m, 2H) 4.16 (q, J=7.2 Hz, 2H) 7.34 (s, 1H) 7.38 (s, 1H).

The compound of Reference Example 51-2 below was synthesized using a commercially available compound, according to the method described in Reference Example 51-1. The structure and NMR data of the compound are shown in Table 25-1.

TABLE 25-1

| Reference Example No. | Structure | Analytical Data |
|---|---|---|
| 51-2 | ![structure] | 1H NMR (400 MHz, CHLOROFORM-d) δ ppm 1.11-1.24 (m, 3 H) 1.58-1.79 (m, 4 H) 1.82 (s, 6 H) 1.80-1.81 (m, 1 H) 2.68 (t, J = 7.4 Hz, 2 H) 3.62-3.69 (m, 2 H) 4.15 (q, J = 7.0 Hz, 2 H) 5.92-6.37 (m, 1 H) 7.43-7.59 (m, 1 H). |

(1) 3-Bromo-1H-pyrazole (500 mg) and ethyl 2-bromo-2-methylpropanoate (796 mg) were used to perform the synthesis process according to the method described in Reference Example 49-1-(1) thereby giving ethyl 2-(4-bromo-1-pyrazolyl)-2-methylpropanoate (839 mg) as a colorless oil.

(2) The compound (100 mg) obtained in (1) above was used to perform the synthesis process according to the method described in Reference Example 50-1-(1) thereby giving ethyl 2-[3-[(E)-4-[tert-butyl(dimethyl)silyl]oxybut-1-enyl]-1-pyrazolyl]-2-methylpropanoate (95 mg) as a colorless oil.

(3) The compound (90 mg) obtained in (2) above was used to perform the synthesis process according to the method described in Reference Example 50-1-(2) thereby giving a mixture containing ethyl 2-[3-[4-[tert-butyl(dimethyl)silyl]oxybutyl]-1-pyrazolyl]-2-methylpropanoate.

(4) The mixture obtained in (3) above was used to perform the synthesis process according to the method described in

Reference Example 52-1

Methyl 4-[7-(hydroxymethyl)-1-oxo-3,4-dihydroisoquinolin-2-yl]-2,2-dimethylbutanoate

[Formula 404]

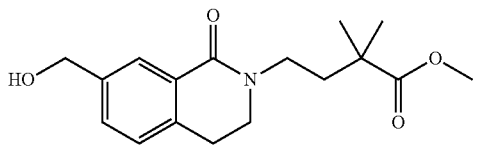

(1) Sodium hydride (60% mineral oil dispersion, 50 mg) was added to a solution of 7-bromo-3,4-dihydro-2H-isoquinolin-1-one (216 mg) in N,N-dimethylformamide (3 mL) under ice cooling, and the mixture was stirred at room temperature for 1 hour. A solution of methyl 4-bromo-2,2-dimethylbutanoate (250 mg) in N,N-dimethylformamide (1 mL) was added to the reaction solution, and the resultant mixture was stirred at 90° C. for 2.5 hours. A saturated aqueous solution of ammonium chloride was added thereto, the resultant mixture was extracted with ethyl acetate, and the organic layers were collected and washed with brine. After concentrating under reduced pressure, the concentrated solution was purified by silica gel column chromatography (n-hexane:ethyl acetate=19:1 to 13:7) to give methyl 4-(7-bromo-1-oxo-3,4-dihydroisoquinolin-2-yl)-2,2-dimethylbutanoate (163 mg) as a colorless oil.

(2) The compound (160 mg) obtained in (1) above and potassium vinyltrifluoroborate (109 mg) were used to perform the synthesis process according to the method described in Reference Example 13-1-(1) thereby giving methyl 4-(7-ethenyl-1-oxo-3,4-dihydroisoquinolin-2-yl)-2,2-dimethylbutanoate (110 mg) as a colorless oil.

(3) The compound (105 mg) obtained in (2) above and N-methylmorpholine-N-oxide (102 mg) were dissolved in tert-butyl alcohol (1.7 mL), tetrahydrofuran (1.7 mL), and water (0.35 mL), and an aqueous solution of 4% osmium tetroxide (45 μL) was added thereto, and the mixture was stirred at room temperature for 2 hours. A saturated aqueous solution of sodium thiosulfate was added to the reaction solution, and the resultant mixture was extracted with ethyl acetate. The organic layer was concentrated under reduced pressure to give a mixture (110 mg) containing methyl 4-[7-(1,2-dihydroxyethyl)-1-oxo-3,4-dihydroisoquinolin-2-yl]-2,2-dimethylbutanoate.

(4) Sodium periodate (77 mg) was added to a solution of the mixture (110 mg) obtained in (3) above in tetrahydrofuran (1.6 mL), and the mixture was stirred at room temperature 30 minutes. The mixture was diluted with water, and extracted with ethyl acetate. The organic layer was concentrated under reduced pressure to give a mixture containing methyl 4-(7-formyl-1-oxo-3,4-dihydroisoquinolin-2-yl)-2,2-dimethylbutanoate.

(5) Sodium borohydride (15 mg) was added to a solution of the mixture obtained in (4) above in methanol (1.6 mL) at −20° C., and the mixture was stirred for 30 minutes. The mixture was diluted with water, and extracted with ethyl acetate. The extracted substance was concentrated under reduced pressure, and the obtained residue was purified by silica gel column chromatography (chloroform:methanol) to give the title compound (80 mg) as a colorless oil.

$^1$H NMR (400 MHz, CHLOROFORM-d) δ ppm 1.27 (s, 6H) 1.62-1.72 (m, 1H) 1.81-1.93 (m, 2H) 2.98 (t, J=6.6 Hz, 2H) 3.50-3.61 (m, 4H) 3.67 (s, 3H) 4.68-4.74 (m, 2H) 7.18 (d, J=7.7 Hz, 1H) 7.45 (d, J=7.7 Hz, 1H) 8.03 (s, 1H).

MS ESI posi: 306[M+H]$^+$.

Reference Example 53-1

Ethyl 7-(hydroxymethyl)-3,4-dihydro-2H-1-benzopyran-2-carboxylate

[Formula 405]

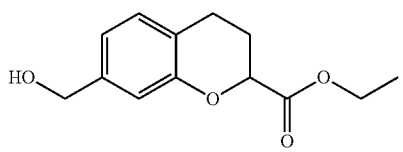

(1) Palladium carbon (981 mg) was added to a solution of commercially available ethyl 7-hydroxy-4-oxo-1-benzopyran-2-carboxylate (3.27 g) in acetic acid (30 mL), and the mixture was stirred under a hydrogen atmosphere (50 psi) at 30° C. for 12 hours. After the reaction solution was filtered through Celite (registered trademark), the filtrate was concentrated. Ethyl acetate was added to the obtained residue, which was sequentially washed with a saturated aqueous solution of sodium hydrogen carbonate and brine. The organic layer was separated by a phase separator, and concentrated under reduced pressure. Diethyl ether and n-hexane were added to the obtained residue, and the precipitated solid was collected by filtration to give ethyl 7-hydroxy-3,4-dihydro-2H-1-benzopyran-2-carboxylate (2.91 g) as a colorless powder.

(2) Pyridine (730 μL) was added to a solution of the compound (1.00 g) obtained in (1) above in chloroform (15 mL), and trifluoromethanesulfonic anhydride (910 μL) was added dropwise thereto under ice cooling. The temperature of the mixture was increased to room temperature, and the mixture was stirred for 1 hour. To the reaction solution, 1 mol/L hydrochloric acid (20 mL) and water (5 mL) were added under ice cooling, and the resultant mixture was stirred. The organic layer was separated by a separatory funnel, and washed with a saturated aqueous solution of sodium hydrogen carbonate. After passing through a phase separator, the resultant was concentrated under reduced pressure, and the obtained residue was purified by silica gel column chromatography (n-hexane:ethyl acetate=9:1 to 1:1) to give ethyl 7-(trifluoromethylsulfonyloxy)-3,4-dihydro-2H-1-benzopyran-2-carboxylate (1.61 g) as a colorless oil.

(3) The compound (400 mg) obtained in (2) above and potassium vinyltrifluoroborate (272 mg) were used to perform the synthesis process according to the method described in Reference Example 13-1-(1) thereby giving ethyl 7-ethenyl-3,4-dihydro-2H-1-benzopyran-2-carboxylate (212 mg) as a colorless oil.

(4) The compound (212 mg) obtained in (3) above and N-methylmorpholine-N-oxide (267 mg) were dissolved in tert-butyl alcohol (4.6 mL), tetrahydrofuran (4.6 mL), and water (0.91 mL), and an aqueous solution of 4% osmium tetroxide (118 μL) was added thereto, and the mixture was stirred at room temperature for 2 hours, and then at 60° C. for 20 minutes. A saturated aqueous solution of sodium thiosulfate was added to the reaction solution, and the resultant mixture was extracted with ethyl acetate. After passing through a phase separator, the resultant was concentrated under reduced pressure to give a mixture (271 mg) containing ethyl 7-(1,2-dihydroxyethyl)-3,4-dihydro-2H-1-benzopyran-2-carboxylate.

(5) The compound (271 mg) obtained in (4) above was used to perform the synthesis process according to the method described in Reference Example 52-1-(4) thereby giving a mixture (217 mg) containing ethyl 7-formyl-3,4-dihydro-2H-1-benzopyran-2-carboxylate.

(6) Sodium borohydride (46 mg) was added to a solution of the mixture obtained in (5) above in ethanol (4.6 mL) under ice cooling, and the mixture was stirred at the same temperature for 30 minutes. A saturated aqueous solution of ammonium chloride and water were added thereto, and the resultant mixture was extracted with ethyl acetate. The organic layer was separated by a phase separator, and concentrated under reduced pressure. The obtained residue was purified by silica gel column chromatography (n-hexane:ethyl acetate=9:1 to 1:1) to give the title compound (170 mg) as a colorless oil.

$^1$H NMR (400 MHz, CHLOROFORM-d) δ ppm 1.29 (t, J=7.1 Hz, 3H) 2.13-2.33 (m, 2H) 2.68-2.88 (m, 2H) 4.25 (q, J=7.1 Hz, 2H) 4.62 (d, J=6.0 Hz, 2H) 4.69-4.76 (m, 1H) 6.88 (d, J=7.7 Hz, 1H) 6.94 (s, 1H) 7.02 (d, J=7.7 Hz, 1H).

MS ESI posi: 259[M+Na]$^+$.

Reference Example 54-1

Ethyl 3-[3-(hydroxymethyl)phenyl]-1-cyclohexanecarboxylate

[Formula 406]

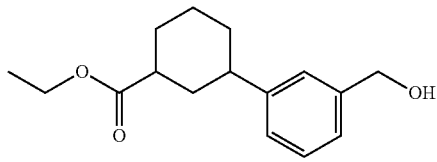

(1) Trifluoromethanesulfonic anhydride (562 µL) was added to a solution of ethyl 3-oxo-1-cyclohexanecarboxylate (500 µL) and 2,4,6-tri-tert-butylpyridine (905 mg) in chloroform (6.36 mL) under ice cooling, and the mixture was stirred at room temperature overnight. The mixture was diluted with chloroform, and sequentially washed with 1 mol/L hydrochloric acid and brine. The organic layer was separated by a phase separator, and concentrated under reduced pressure. The obtained residue was purified by silica gel column chromatography (n-hexane only to n-hexane:ethyl acetate=93:7) to give ethyl 3-(trifluoromethylsulfonyloxy)-1-cyclohex-3-enecarboxylate (529 mg) as a colorless oil.

(2) The compound (136 mg) obtained in (1) above, [1,1'-bis(diphenylphosphino)ferrocene]palladium(II) dichloride dichloromethane adduct (18.4 mg), and potassium fluoride (91.5 mg) were weighed in a three-necked flask, the container was sealed, and the air in the container was then purged with nitrogen. To this mixture, a solution of [3-(hydroxymethyl)phenyl]boronic acid (88.9 mg) in tetrahydrofuran (2.93 mL) was added, and the mixture was stirred at room temperature for 3 days. The mixture was diluted with ethyl acetate, and sequentially washed with a saturated aqueous solution of sodium hydrogen carbonate and brine. The organic layer was separated by a phase separator, and concentrated under reduced pressure. The obtained residue was purified by silica gel column chromatography (n-hexane only to n-hexane:ethyl acetate=7:3) to give ethyl 3-[3-(hydroxymethyl)phenyl]-1-cyclohex-3-enecarboxylate (92.1 mg) as a yellow oil.

(3) The compound (87.9 mg) obtained in (2) above was used to perform the synthesis process according to the method described in Reference Example 45-1-(3) thereby giving the title compound (73.6 mg) as a colorless oil.

$^1$H NMR (400 MHz, CHLOROFORM-d) δ ppm 1.20-1.34 (m, 3H) 1.41-1.77 (m, 5H) 1.83-2.34 (m, 4H) 2.41-2.84 (m, 2H) 4.08-4.24 (m, 2H) 4.65-4.73 (m, 2H) 7.14-7.32 (m, 4H).

Reference Example 54-2

Ethyl 4-[3-(hydroxymethyl)phenyl]-1-cyclohexanecarboxylate

[Formula 407]

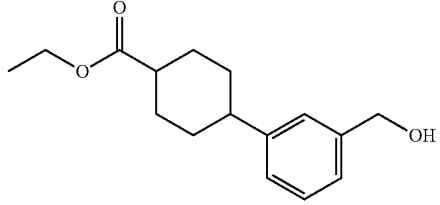

(1) Ethyl 4-(trifluoromethylsulfonyloxy)-1-cyclohex-3-enecarboxylate (131 mg) was used to perform the synthesis process according to the method described in Reference Example 54-1-(2) thereby giving ethyl 4-[3-(hydroxymethyl)phenyl]-1-cyclohex-3-enecarboxylate (77.5 mg) as a yellow oil.

(2) The compound (92.2 mg) obtained in (1) above was used to perform the synthesis process according to the method described in Reference Example 45-1-(3) thereby giving the title compound (85.1 mg) as a white oil.

$^1$H NMR (400 MHz, CHLOROFORM-d) δ ppm 1.23-1.32 (m, 3H) 1.42-1.83 (m, 6H) 1.93-2.15 (m, 2H) 2.21-2.72 (m, 3H) 4.11-4.24 (m, 2H) 4.64-4.71 (m, 2H) 7.11-7.33 (m, 4H).

MS ESI/APCI Multi posi: 245[M-OH]$^+$.

Reference Example 55-1

(3-Methylsulfonyl-5-phenylmethoxyphenyl)methanol

[Formula 408]

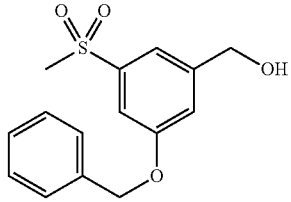

(1) Potassium carbonate (1.63 g) and benzyl bromide (842 µL) were added to a solution of 3-bromo-5-(hydroxymethyl)phenol (1.20 g) in acetone (20 mL), and the mixture was stirred at room temperature for 5 hours. The reaction solution was filtered through Celite (registered trademark), and the filtrate was then concentrated under reduced pressure. The residue was purified by silica gel column chromatography (n-hexane:ethyl acetate=4:1 to 2:3). The purified residue was dried under reduced pressure to give (3-bromo-5-phenylmethoxyphenyl)methanol (1.71 g) as a pale yellow oil.

(2) The compound (200 mg) obtained in (1) above, copper(I) iodide (26 mg), L-proline (31 mg), sodium hydroxide (11 mg), sodium methanesulfinate (139 mg), and dimethyl sulfoxide (3 mL) were mixed, and the mixture was stirred at 150° C. for 50 minutes under microwave irradiation. A saturated aqueous solution of ammonium chloride was added to the reaction solution, and the resultant mixture was extracted with ethyl acetate. The organic layer was separated by a phase separator, and concentrated under reduced pressure. The resultant was dried under reduced pressure to give the title compound (210 mg) as a light orange oil.

$^1$H NMR (400 MHz, CHLOROFORM-d) δ ppm 3.03 (s, 3H) 4.74-4.78 (m, 2H) 5.13 (s, 2H) 7.28 (s, 1H) 7.32-7.45 (m, 6H) 7.53 (s, 1H).

MS ESI/APCI Multi nega: 201[M-Bn]$^-$.

Reference Example 56-1

[4-[(4-Methoxyphenyl)methoxy]-3-methylsulfonylphenyl]methanol

[Formula 409]

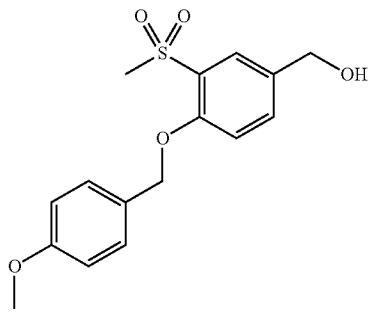

(1) Sodium hydride (60% mineral oil dispersion, 811 mg) was added to a solution of 3-bromo-4-hydroxybenzoic acid (2.00 g) in N,N-dimethylformamide (18 mL) under ice cooling, and the mixture was stirred at room temperature for 30 minutes. At the same temperature, 4-methoxybenzyl chloride (2.61 mL) was slowly added thereto, and the resultant mixture was stirred at room temperature for 65 hours. A saturated aqueous solution of ammonium chloride was added thereto under ice cooling, the resultant mixture was extracted with ethyl acetate, and the extracted substance was sequentially washed with water and brine. After drying over anhydrous sodium sulfate, the drying agent was filtered off, and the filtrate was concentrated. The resultant was recrystallized from a diethyl ether:n-hexane mixed solution to give (4-methoxyphenyl)methyl 3-bromo-4-[(4-methoxyphenyl)methoxy]benzoate (3.10 g) as a colorless powder.

(2) In a test tube for a microwave reaction, sodium methanesulfinate (66.9 mg), a copper(I) trifluoromethanesulfonate benzene complex (33.0 mg), and N,N'-dimethylethylenediamine (14.1 μL) were added to a solution of the compound (100 mg) obtained in (1) above in dimethyl sulfoxide (2 mL), and the test tube was sealed. The mixture was stirred at 150° C. for 1 hour under microwave irradiation. After extraction with ethyl acetate, the extracted substance was sequentially washed with water and brine, and the organic layer was separated by a phase separator and then concentrated. The resultant was purified by preparative thin layer chromatography (n-hexane:ethyl acetate=1:1, Rf=0.4) to give (4-methoxyphenyl)methyl 4-[(4-methoxyphenyl)methoxy]-3-methylsulfonylbenzoate (20.1 mg) as a colorless solid.

(3) Lithium borohydride (59.5 mg) and methanol (1 mL) were added to a solution of the compound (416 mg) obtained in (2) above in tetrahydrofuran (9 mL), and the mixture was stirred at 60° C. for 30 minutes. A saturated aqueous solution of ammonium chloride was added thereto under ice cooling, and the resultant mixture was stirred until generation of bubbles ceased. Chloroform was added thereto, and the organic layer was separated by a phase separator and then concentrated. The residue was purified by silica gel column chromatography (n-hexane only to ethyl acetate only) to give the title compound (239 mg) as a colorless powder.

$^1$H NMR (400 MHz, CHLOROFORM-d) δ ppm 3.17 (s, 3H) 3.82 (s, 3H) 4.69 (s, 2H) 5.19 (s, 2H) 6.93 (d, J=8.6 Hz, 2H) 7.10 (d, J=8.6 Hz, 1H) 7.42 (d, J=8.6 Hz, 2H) 7.59 (dd, J=8.6, 2.1 Hz, 1H) 7.98 (d, J=2.1 Hz, 1H).

MS ESI/APCI Multi posi: 345 [M+Na]$^+$.

Reference Example 57-1

Methyl 2-[3-(4-hydroxybutylsulfonyl)phenyl]-2-methylpropanoate

[Formula 410]

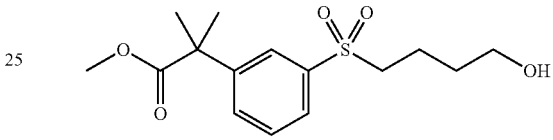

(1) Sodium hydride (60% mineral oil dispersion, 119 mg) was added to a solution of methyl 2-(3-iodophenyl)acetate (210 mg) in N,N-dimethylformamide (2.48 mL), and the mixture was stirred at room temperature for 5 minutes. To this mixture, methyl iodide (162 μL) was added, and the resultant mixture was stirred at room temperature overnight. Sodium hydride (60% mineral oil dispersion, 119 mg) and methyl iodide (162 μL) were further added thereto, and the resultant mixture was further stirred for 2 hours. The reaction was stopped with a saturated aqueous solution of ammonium chloride, and the mixture was extracted three times with ethyl acetate. The organic layers were combined, washed with brine, passed through a phase separator, and concentrated under reduced pressure. The obtained residue was purified by silica gel column chromatography (n-hexane only to n-hexane:ethyl acetate=9:1) to give methyl 2-(3-iodophenyl)-2-methylpropanoate (156 mg) as a colorless oil.

(2) In a test tube for a microwave reaction, the compound (156 mg) obtained in (1) above, potassium disulfite (205 mg), tetrabutylammonium bromide (164 mg), sodium formate (69.1 mg), palladium(II) acetate (5.18 mg), triphenylphosphine (18.2 mg), 1,10-phenanthroline (12.5 mg), and dimethyl sulfoxide (2.31 mL) were mixed, and nitrogen gas was passed therethrough for 20 minutes. After the test tube was sealed, the mixture was stirred at 100° C. for 30 minutes under microwave irradiation. After cooling to room temperature, the test tube was opened, 2-(4-bromobutoxy)oxane (93.3 μL) was added to the mixture, and the resultant mixture was stirred at room temperature overnight. This mixture was poured into water, and the resultant mixture was extracted three times with ethyl acetate. The organic layers were combined and washed with brine, the organic layer was separated by a phase separator, and the solvent was then distilled off under reduced pressure. The obtained residue was purified by silica gel column chromatography (n-hexane only to n-hexane:ethyl acetate=1:3) to give methyl 2-methyl-2-[3-[4-(2-oxanyloxy)butylsulfonyl]phenyl]propanoate (103 mg) as a pale yellow oil.

(3) Pyridinium p-toluenesulfonate (6.07 mg) was added to a solution of the compound (103 mg) obtained in (2) above in methanol (1.21 mL), and the mixture was heated to reflux for 3 hours. The mixture was cooled to room temperature and poured into a saturated aqueous solution of sodium hydrogen carbonate, and the resultant mixture was extracted twice with ethyl acetate. The organic layers were combined and washed with brine, the organic layer was separated by a phase separator, and the solvent was then distilled off under reduced pressure. The obtained residue was purified by silica gel column chromatography (n-hexane:ethyl acetate=9:1 to 3:7) to give the title compound (68.4 mg) as a colorless oil.

$^1$H NMR (400 MHz, CHLOROFORM-d) δ ppm 1.60-1.69 (m, 8H) 1.81-1.90 (m, 2H) 3.09-3.21 (m, 2H) 3.61-3.72 (m, 5H) 7.50-7.56 (m, 1H) 7.61-7.65 (m, 1H) 7.78-7.82 (m, 1H) 7.87-7.91 (m, 1H).

MS ESI/APCI Multi posi: 315 [M+H]$^+$.

Reference Example 58-1

[3-[2-(2-Oxanyloxy)ethylsulfonyl]phenyl]methanol

[Formula 411]

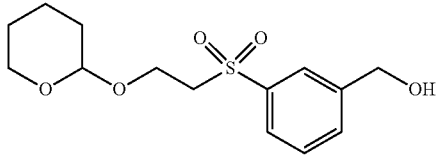

(1) Ethyl 3-iodobenzoate (1 g) and 2-(2-bromoethoxy)tetrahydro-2H-pyran (604 μL) were used to perform the synthesis process according to the method described in Reference Example 57-1-(2) thereby giving ethyl 3-[2-(2-oxanyloxy)ethylsulfonyl]benzoate (643 mg).

(2) The compound (643 mg) obtained in (1) above was used to perform the synthesis process according to the method described in Reference Example 25-1-(2) thereby giving a crude product containing the title compound (353 mg).

$^1$H NMR (400 MHz, CHLOROFORM-d) δ ppm 1.23-1.65 (m, 5H) 1.88-2.03 (m, 1H) 3.08-3.17 (m, 2H) 3.41-3.50 (m, 1H) 3.68-3.84 (m, 2H) 4.01-4.16 (m, 1H) 4.46-4.51 (m, 1H) 4.77-4.84 (m, 2H) 7.51-7.60 (m, 1H) 7.62-7.69 (m, 1H) 7.80-7.87 (m, 1H) 7.90-7.96 (m, 1H).

MS ESI/APCI Multi posi: 323 [M+Na]$^+$.

Reference Example 59-1

Ethyl 7-(hydroxymethyl)-1,2,3,4-tetrahydronaphthalene-2-carboxylate

[Formula 412]

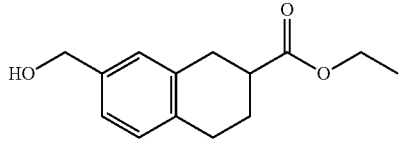

(1) In a microwave reaction container, tetrakis(triphenylphosphine)palladium(0) (920 mg) and zinc cyanide (2.4 g) were added to a suspension of 7-bromo-3,4-dihydro-2H-naphthalen-1-one (1.8 g) in N,N-dimethylformamide (16 mL), the air in the test tube was purged with nitrogen and the test tube was then sealed, and the mixture was stirred at 150° C. for 30 minutes under microwave irradiation. Tetrakis(triphenylphosphine)palladium(0) (460 mg) was further added thereto, the air in the test tube was purged with nitrogen and the test tube was then sealed, and the mixture was stirred at 150° C. for 30 minutes under microwave irradiation. The same operations were performed in another container, the obtained reaction solutions from them were combined. Ethyl acetate and water were added to the combined reaction solution, and the resultant mixture was filtered through Celite (registered trademark), and the filtrate was extracted with ethyl acetate. The organic layer was sequentially washed with water and brine, passed through a phase separator, and concentrated under reduced pressure. The residue was purified by silica gel column chromatography (n-hexane:ethyl acetate=3:1 to 2:3) to give a crude product (2.2 g) containing 8-oxo-6,7-dihydro-5H-naphthalene-2-carbonitrile as a pale yellow solid.

(2) Sodium hydride (60% mineral oil dispersion, 192 mg) was added to a suspension of the crude product (547 mg) obtained in (1) above in diethyl carbonate (3.9 mL) at room temperature, and the mixture was stirred for 3 hours while being heated to reflux. Under ice cooling, 1 mol/L hydrochloric acid was added thereto, and the resultant mixture was extracted with ethyl acetate. The organic layer was sequentially washed with water and brine, passed through a phase separator, and concentrated under reduced pressure. The residue was purified by silica gel column chromatography (n-hexane:ethyl acetate=9:1 to 3:1), and the obtained crude product was recrystallized from a n-hexane:ethyl acetate mixed solution to give ethyl 7-cyano-1-oxo-3,4-dihydro-2H-naphthalene-2-carboxylate (442 mg) as a pale brown solid.

(3) Triethylsilane (1.25 mL) was added to a solution of the compound (315 mg) obtained in (2) above in trifluoroacetic acid (4.3 mL) at room temperature, and the mixture was stirred for 3 days. After the reaction solution was concentrated under reduced pressure, a saturated aqueous solution of sodium hydrogen carbonate was added thereto, and the resultant mixture was extracted with chloroform. The organic layer was separated by a phase separator, and concentrated under reduced pressure. The residue was purified by silica gel column chromatography (n-hexane:ethyl acetate=9:1 to 13:7) to give ethyl 7-cyano-1-hydroxy-1,2,3,4-tetrahydronaphthalene-2-carboxylate (258 mg) as a colorless powder.

(4) To a solution of the compound (156 mg) obtained in (3) above in toluene (1.3 mL), p-toluenesulfonic acid monohydrate (12 mg) was added, and the mixture was stirred for 10 hours while being heated to reflux. A saturated aqueous solution of sodium hydrogen carbonate was added to the reaction solution, and the resultant mixture was extracted with ethyl acetate. The obtained organic layer was washed with brine, and the organic layer was separated by a phase separator, and concentrated under reduced pressure. The residue was purified by silica gel column chromatography (n-hexane:ethyl acetate=9:1 to 7:3) to give ethyl 7-cyano-3,4-dihydronaphthalene-2-carboxylate (82 mg) as a colorless powder.

(5) The compound (467 mg) obtained in (4) above and ethyl acetate (21 mL) were used to perform the synthesis process according to the method described in Reference Example 1-1-(3) thereby giving a crude product (459 mg) containing ethyl 7-cyano-1,2,3,4-tetrahydronaphthalene-2-carboxylate.

(6) Pyridine (5.2 mL), acetic acid (5.2 mL), Raney nickel (aqueous suspension, 5 mL), and sodium dihydrogen phosphate (1.5 g) were added to the compound (459 mg) obtained in (5) above, and the mixture was stirred under a hydrogen atmosphere at 50° C. for 1.5 hours, at 80° C. for 1.5 hours, and at 100° C. for 30 minutes. The reaction solution was filtered through Celite (registered trademark), and washed with ethanol. The filtrate was concentrated under reduced pressure, and azeotroped with toluene. The residue was diluted with a n-hexane:ethyl acetate mixed solution, sequentially washed with 1 mol/L hydrochloric acid, a saturated aqueous solution of sodium hydrogen carbonate, and brine, and dried over anhydrous magnesium sulfate. The drying agent was filtered off, and the filtrate was concentrated under reduced pressure. The residue was purified by silica gel column chromatography (n-hexane:ethyl acetate=9:1 to 3:1) to give a crude product (396 mg) containing ethyl 7-formyl-1,2,3,4-tetrahydronaphthalene-2-carboxylate.

(7) The compound (387 mg) obtained in (6) above was used to perform the synthesis process according to the method described in Reference Example 53-1-(6) thereby giving the title compound (218 mg).

(2) The compound (510 mg) obtained in (1) above was used to perform the synthesis process according to the method described in Reference Example 59-1-(1) thereby giving ethyl 6-cyano-3,4-dihydro-2H-1-benzopyran-3-carboxylate (147 mg) as a colorless solid.

(3) The compound (147 mg) obtained in (2) above was used to perform the synthesis process according to the method described in Reference Example 59-1-(6) thereby giving ethyl 6-formyl-3,4-dihydro-2H-1-benzopyran-3-carboxylate (86 mg) as a colorless oil.

(4) The compound (82 mg) obtained in (3) above was used to perform the synthesis process according to the method described in Reference Example 53-1-(6) thereby giving the title compound (81 mg) as a colorless oil.

$^1$H NMR (400 MHz, CHLOROFORM-d) δ ppm 1.29 (t, J=7.2 Hz, 3H) 2.94-3.15 (m, 3H) 4.07-4.25 (m, 3H) 4.39-4.48 (m, 1H) 4.58 (s, 2H) 6.76-6.87 (m, 1H) 7.03-7.16 (m, 2H).

MS ESI posi: 219[M-OH]$^+$.

The compound of Reference Example 60-2 below was synthesized using a commercially available compound, according to the method described in Reference Example 60-1. The structure, NMR data, and MS data of the compound are shown in Table 26-1.

TABLE 26-1

| Reference Example No. | Structure | Analytical Data |
|---|---|---|
| 60-2 | 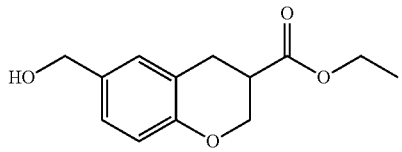 | $^1$H NMR (400 MHz, CHLOROFORM-d) δ ppm 1.29 (t, J = 7.1 Hz, 3 H) 2.13-2.34 (m, 2 H) 2.69-2.89 (m, 2 H) 4.25 (q, J = 7.1 Hz, 2 H) 4.58 (s, 2 H) 4.68-4.74 (m, 1 H) 6.92 (d, J = 8.3 Hz, 1 H) 7.03-7.15 (m, 2 H). MS ESI posi: 259 [M + Na]+. |

$^1$H NMR (400 MHz, CHLOROFORM-d) δ ppm 1.23-1.34 (m, 3H) 1.77-1.93 (m, 1H) 2.15-2.25 (m, 1H) 2.65-2.93 (m, 3H) 2.95-3.07 (m, 2H) 4.13-4.25 (m, 2H) 4.57-4.69 (m, 2H) 7.03-7.16 (m, 3H).

MS ESI/APCI Multi posi: 257[M+Na]$^+$.

Reference Example 60-1

Ethyl 6-(hydroxymethyl)-3,4-dihydro-2H-1-benzopyran-3-carboxylate

[Formula 413]

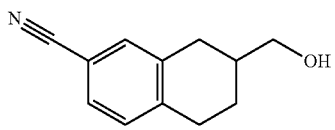

(1) To commercially available 6-bromo-3,4-dihydro-2H-1-benzopyran-3-carboxylic acid (500 mg), a 2 mol/L hydrogen chloride-ethanol solution (9.7 mL) was added, and the mixture was stirred at 75° C. for 18 hours. The reaction solution was concentrated under reduced pressure to give ethyl 6-bromo-3,4-dihydro-2H-1-benzopyran-3-carboxylate (510 mg).

Reference Example 61-1

7-(Hydroxymethyl)-5,6,7,8-tetrahydronaphthalene-2-carbonitrile

[Formula 414]

The compound (66 mg) obtained in Reference Example 59-1-(5) was used to perform the synthesis process according to the method described in Reference Example 25-1-(2) thereby giving the title compound (29 mg) as a colorless oil.

$^1$H NMR (400 MHz, CHLOROFORM-d) δ ppm 1.32-1.59 (m, 2H) 1.90-2.12 (m, 2H) 2.45-2.60 (m, 1H) 2.76-3.01 (m, 3H) 3.56-3.73 (m, 2H) 7.05-7.21 (m, 1H) 7.31-7.46 (m, 2H).

MS ESI/APCI Multi posi: 210[M+Na]$^+$.

Reference Example 62-1

8-(2-Hydroxyethyl)-5,6,7,8-tetrahydronaphthalene-2-carbonitrile

[Formula 415]

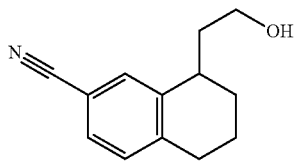

(1) A solution of triethyl phosphonoacetate (590 μL) in tetrahydrofuran (10 mL) was added dropwise to a suspension of sodium hydride (60% mineral oil dispersion, 120 mg) in tetrahydrofuran (10 mL) under ice cooling. The mixture was stirred at the same temperature for 30 minutes, subsequently a solution of the compound (423 mg) obtained in Reference Example 59-1-(1) in tetrahydrofuran (7 mL) was added dropwise thereto, and the resultant mixture was stirred at room temperature for 2 hours, and for 14 hours while being heated to reflux. A saturated aqueous solution of ammonium chloride was added to the reaction solution under ice cooling, and the resultant mixture was extracted with ethyl acetate. The organic layer was washed with brine, and the organic layer was separated by a phase separator, and concentrated under reduced pressure. The residue was purified by silica gel column chromatography (n-hexane:ethyl acetate=17:3 to 3:2) to give ethyl (2E)-2-(7-cyano-3,4-dihydro-2H-naphthalen-1-ylidene)acetate (402 mg) as a colorless oil.

(2) The compound (397 mg) obtained in (1) above was used to perform the synthesis process according to the method described in Reference Example 1-1-(3) thereby giving ethyl 2-(7-cyano-1,2,3,4-tetrahydronaphthalen-1-yl)acetate (304 mg) as a colorless oil.

(3) The compound (304 mg) obtained in (2) above was used to perform the synthesis process according to the method described in Reference Example 25-1-(2) thereby giving the title compound (180 mg) as a brown oil.

$^1$H NMR (400 MHz, CHLOROFORM-d) δ ppm 1.19-1.45 (m, 1H) 1.65-2.01 (m, 6H) 2.71-2.90 (m, 2H) 2.96-3.06 (m, 1H) 3.72-3.83 (m, 2H) 7.10-7.19 (m, 1H) 7.33-7.40 (m, 1H) 7.49 (s, 1H).

MS ESI/APCI Multi posi: 224[M+Na]$^+$.

Reference Example 63-1

3-(3-Methoxycarbonyl-1-bicyclo[1.1.1]pentanyl)propanoic Acid

[Formula 416]

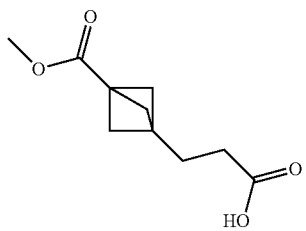

(1) A solution of methyl 1-(hydroxymethyl)-3-bicyclo[1.1.1]pentanecarboxylate (500 mg) in chloroform (13 mL) was ice-cooled under a nitrogen atmosphere, Dess-Martin periodinane (1.63 g) was added thereto, and the mixture was stirred at room temperature for 3 hours. A mixed solution (10 mL) of saturated aqueous solution of sodium thiosulfate: saturated aqueous solution of sodium hydrogen carbonate: water (1:1:1) was added to stop the reaction, and the resultant mixture was extracted with diethyl ether. The obtained organic layer was separated from the aqueous layer by passing through a phase separator, and concentrated under reduced pressure to give methyl 1-formyl-3-bicyclo[1.1.1]pentanecarboxylate as a crude product.

(2) Benzyl(triphenylphosphoranylidene)acetate (2.03 g) was added to a solution of the crude product obtained in (1) above in tetrahydrofuran (5.3 mL), and the mixture was stirred at room temperature for 19 hours. The reaction mixture was concentrated under reduced pressure, and the residue was purified by silica gel column chromatography (n-hexane:ethyl acetate=7:3 to 3:7) to give methyl 1-[(E)-3-oxo-3-phenylmethoxyprop-1-enyl]-3-bicyclo[1.1.1]pentanecarboxylate (400 mg).

(3) The compound (400 mg) obtained in (2) above was used to perform the synthesis process according to the method described in Reference Example 1-1-(3) thereby giving the title compound (38 mg) as a colorless oil.

$^1$H NMR (400 MHz, CHLOROFOLM-d) δ ppm 1.84 (t, J=7.6 Hz, 2H) 1.93 (s, 6H) 2.34 (t, J=7.6 Hz, 2H) 3.66 (s, 3H).

MS ESI posi: 199[M+H]$^+$.
MS ESI nega: 197[M–H]$^-$.

Reference Example 64-1

Ethyl 3-(2-hydroxyethyl)-1-cyclobutanecarboxylate

[Formula 417]

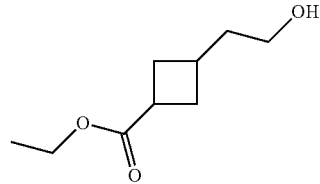

(1) Ethyl 3-oxo-1-cyclobutanecarboxylate (500 mg) was used to perform the synthesis process according to the method described in Reference Example 63-1-(2) thereby giving ethyl 3-(2-oxo-2-phenylmethoxyethylidene)-1-cyclobutanecarboxylate (882 mg) as a colorless oil.

(2) The compound (223 mg) obtained in (1) above was used to perform the synthesis process according to the method described in Reference Example 1-1-(3) thereby giving 2-(3-ethoxycarbonylcyclobutyl)acetic acid (150 mg) as a colorless oil.

(3) To a solution of the compound (85 mg) obtained in (2) above in tetrahydrofuran (1.1 mL), 4-methylmorpholine (0.10 mL) and isobutyl chloroformate (0.12 mL) were added under ice cooling, and the mixture was stirred at room temperature for 3.5 hours. The reaction mixture was filtrated, and thoroughly washed with tetrahydrofuran (0.91 mL). A solution of sodium borohydride (35 mg) in water (1.0 mL) was added to the filtrate under ice cooling, and the resultant mixture was stirred at room temperature for 30 minutes. A saturated aqueous solution of ammonium chloride (5 mL) was added to stop the reaction, and the reaction mixture was extracted with diethyl ether. The obtained organic layer was passed through a phase separator, and concentrated under reduced pressure. The obtained residue The compound of Reference Example 65-2 below was synthesized using a commercially available compound, according to the method described in Reference Example 65-1. The structure and NMR data of the compound are shown in Table 27-1.

TABLE 27-1

| Reference Example No. | Structure | Analytical Data |
|---|---|---|
| 65-2 | 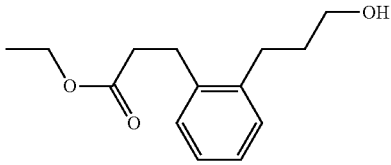 | $^1$H NMR (400 MHz, CHLOROFOLM-d) δ ppm 0.78-0.95 (m, 1 H) 0.99-1.13 (m, 1 H) 1.18-1.39 (m, 6 H) 1.71-1.84 (m, 2 H) 1.90-2.03 (m, 2 H) 2.24-2.37 (m, 1 H) 3.59-3.70 (m, 5 H). | was purified by silica gel column chromatography (n-hexane:ethyl acetate=10:1 to 1:1) to give the title compound (86 mg) as a colorless oil.

$^1$H NMR (400 MHz, CHLOROFOLM-d) δ ppm 1.18-1.33 (m, 3H) 1.64-1.78 (m, 2H) 1.87-2.00 (m, 2H) 2.26-2.53 (m, 2H) 2.67-2.76 (m, 1H) 2.93-3.12 (m, 1H) 3.56-3.80 (m, 2H) 4.08-4.18 (m, 2H).

Reference Example 65-1

Ethyl 3-[2-(3-hydroxypropyl)phenyl]propanoate

[Formula 418]

(1) The compound (224 mg) synthesized in Reference Example 44-2 was used to perform the synthesis process according to the method described in Reference Example 63-1-(1) thereby giving ethyl 3-(2-formylphenyl)propanoate (293 mg) as a light yellow oil.

(2) The compound (293 mg) synthesized in (1) above was used to perform the synthesis process according to the method described in Reference Example 63-1-(2) thereby giving ethyl 3-[2-[(E)-3-oxo-3-phenylmethoxyprop-1-enyl]phenyl]propanoate (319 mg) as a colorless oil.

(3) The compound (319 mg) synthesized in (2) above was used to perform the synthesis process according to the method described in Reference Example 1-1-(3) thereby giving 3-[2-(3-ethoxy-3-oxopropyl)phenyl]propanoic acid (158 mg) as a colorless oil.

(4) The compound (158 mg) synthesized in (3) above was used to perform the synthesis process according to the method described in Reference Example 15-1-(1) thereby giving the title compound (130 mg) as a colorless oil.

$^1$H NMR (400 MHz, CHLOROFOLM-d) δ ppm 1.25 (t, J=7.1 Hz, 3H) 1.83-1.92 (m, 1H) 2.56-2.78 (m, 4H) 2.94-3.03 (m, 3H) 3.72 (t, J=6.4 Hz, 2H) 4.14 (q, J=7.1 Hz, 2H) 7.13-7.20 (m, 4H).

MS ESI/APCI Multi posi: 237[M+H]$^+$.

Reference Example 65-3

Methyl 1-(3-hydroxypropyl)-4-bicyclo[2.2.2]octanecarboxylate

[Formula 419]

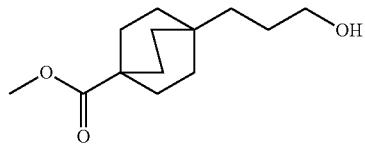

(1) Methyl 1-(hydroxymethyl)-4-bicyclo[2.2.2]octanecarboxylate (200 mg) was used to perform the synthesis process according to the method described in Reference Example 63-1-(1) thereby giving methyl 1-formyl-4-bicyclo[2.2.2]octanecarboxylate (182 mg) as a colorless oil.

(2) To a solution of benzyl dimethylphosphonoacetate (359 mg) in tetrahydrofuran (9.3 mL), n-butyl lithium (1.6 mol/L n-hexane solution, 0.87 mL) was added under a nitrogen atmosphere at −20° C., and the mixture was stirred at the same temperature. The compound (182 mg) synthesized in (1) above was added to the reaction solution, the temperature of the resultant mixture was increased to room temperature, and the mixture was stirred for 5 hours. A saturated aqueous solution of ammonium chloride (10 mL) was added to stop the reaction, and the resultant mixture was extracted with ethyl acetate. The obtained organic layer was passed through a phase separator, and concentrated under reduced pressure. The obtained residue was purified by silica gel column chromatography (n-hexane:ethyl acetate=10:1 to 1:1) to give methyl 1-[(E)-3-oxo-3-phenylmethoxyprop-1-enyl]-4-bicyclo[2.2.2]octanecarboxylate (184 mg) as a colorless oil.

(3) The compound (168 mg) synthesized in (2) above was used to perform the synthesis process according to the method described in Reference Example 1-1-(3) thereby giving 3-(4-methoxycarbonyl-1-bicyclo[2.2.2]octanyl)propanoic acid (131 mg) as a colorless oil.

(4) The compound (131 mg) synthesized in (3) above was used to perform the synthesis process according to the method described in Reference Example 15-1-(1) thereby giving the title compound (83 mg) as a colorless oil.

¹H NMR (400 MHz, CHLOROFOLM-d) δ ppm 1.11-1.18 (m, 2H) 1.30-1.51 (m, 9H) 1.72-1.83 (m, 6H) 3.55-3.70 (m, 5H).

Reference Example 66-1

Ethyl trans-2-(3-hydroxypropyl)-1-cyclopropanecarboxylate

[Formula 420]

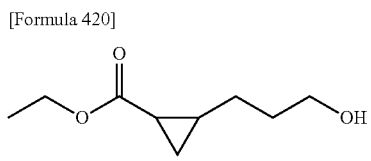

(1) trans-2-Ethoxycarbonyl-1-cyclopropanecarboxylic acid (100 mg) was used to perform the synthesis process according to the method described in Reference Example 15-1-(1) thereby giving ethyl trans-2-(hydroxymethyl)-1-cyclopropanecarboxylate (62 mg) as a colorless oil.

(2) The compound (63 mg) obtained in (1) above was used to perform the synthesis process according to the method described in Reference Example 63-1-(1) thereby giving ethyl trans-2-formyl-1-cyclopropanecarboxylate (57 mg) as a colorless oil.

(3) The compound (57 mg) synthesized in (2) above was used to perform the synthesis process according to the method described in Reference Example 63-1-(2) thereby giving ethyl trans-2-[(E)-3-oxo-3-phenylmethoxyprop-1-enyl]-1-cyclopropanecarboxylate (75 mg) as a colorless oil.

(4) The compound (75 mg) synthesized in (3) above was used to perform the synthesis process according to the method described in Reference Example 1-1-(3) thereby giving trans-3-(2-ethoxycarbonylcyclopropyl)propanoic acid (45 mg) as a colorless oil.

(5) The compound (45 mg) synthesized in (4) above was used to perform the synthesis process according to the method described in Reference Example 15-1-(1) thereby giving the title compound (20 mg) as a colorless oil.

¹H NMR (400 MHz, CHLOROFOLM-d) δ ppm 0.67-0.75 (m, 1H) 1.14-1.31 (m, 5H) 1.32-1.48 (m, 4H) 1.64-1.73 (m, 2H) 3.68 (t, J=6.5 Hz, 2H) 4.12 (q, J=7.1 Hz, 2H).

The compound of Reference Example 66-2 below was synthesized using a commercially available compound, according to the method described in Reference Example 66-1. The structure and NMR data of the compound are shown in Table 28-1.

Reference Example 67-1

Ethyl 2-[3-(4-hydroxybutyl)phenoxy]-2-methylpropanoate

[Formula 421]

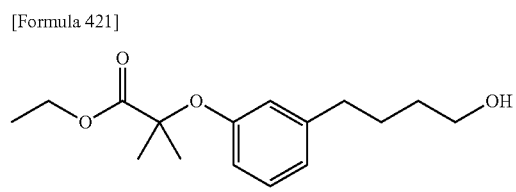 [SMILES: CCOC(=O)C(C)(C)Oc1cccc(CCCCO)c1]

(1) Potassium carbonate (330 mg) and ethyl 2-bromo-2-methylpropanoate (0.36 mL) were added to a solution of 3-(2-hydroxyethyl)phenol (300 mg) in acetonitrile (4.3 mL), and the mixture was stirred at 100° C. for 2 hours under microwave irradiation. A saturated aqueous solution of ammonium chloride was added thereto, and the resultant mixture was extracted with ethyl acetate. The obtained organic layer was passed through a phase separator, and concentrated under reduced pressure. The obtained residue was purified by silica gel column chromatography (n-hexane:ethyl acetate=4:1 to 3:7) to give ethyl 2-[3-(2-hydroxyethyl)phenoxy]-2-methylpropanoate (137 mg) as a colorless oil.

(2) The compound (137 mg) obtained in (1) above was used to perform the synthesis process according to the method described in Reference Example 63-1-(1) thereby giving ethyl 2-methyl-2-[3-(2-oxoethyl)phenoxy]propanoate as a crude product.

(3) The crude product synthesized in (2) above was used to perform the synthesis process according to the method described in Reference Example 63-1-(2) thereby giving ethyl 2-methyl-2-[3-[(E)-4-oxo-4-phenylmethoxybut-2-enyl]phenoxy]propanoate (140 mg) as a colorless oil.

(4) The compound (140 mg) synthesized in (3) above was used to perform the synthesis process according to the method described in Reference Example 1-1-(3) thereby giving 4-[3-(1-ethoxy-2-methyl-1-oxopropan-2-yl)oxyphenyl]butanoic acid as a crude product.

(5) The crude product synthesized in (4) above was used to perform the synthesis process according to the method described in Reference Example 15-1-(1) thereby giving the title compound (53 mg) as a colorless oil.

¹H NMR (400 MHz, CHLOROFOLM-d) δ ppm 1.20-1.30 (m, 4H) 1.55-1.72 (m, 10H) 2.59 (t, J=7.5 Hz, 2H) 3.60-3.70 (m, 2H) 4.23 (q, J=7.1 Hz, 2H) 6.62-6.72 (m, 2H) 6.81 (d, J=7.5 Hz, 1H) 7.08-7.17 (m, 1H).

MS ESI posi: 303[M+Na]⁺.

TABLE 28-1

| Reference Example No. | Structure | Analytical Data |
|---|---|---|
| 66-2 | (structure shown) | シス体<br>¹H NMR (400 MHz, CHLOROFOLM-d) δ ppm 0.90-0.98 (m, 1 H) 1.00-1.09 (m, 1 H) 1.29-1.33 (m, 1 H) 1.34-1.45 (m, 1 H) 1.55-1.75 (m, 4 H) 3.60-3.70 (m, 5 H). |

Reference Example 68-1

(Phenylmethyl) (E)-3-[3-(hydroxymethyl)cyclohexyl]-2-propenoate

[Formula 422]

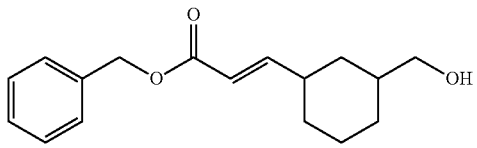

(1) Triethylamine (0.47 mL), tert-butyldiphenylchlorosilane (648 mg), and 4-dimethylaminopyridine (102 mg) were added to a solution of methyl 3-(hydroxymethyl)-1-cyclohexanecarboxylate (267 mg) in chloroform (1.1 mL), and the mixture was stirred at room temperature for 21 hours. A saturated aqueous solution of ammonium chloride (5 mL) was added to stop the reaction, and the resultant mixture was extracted with chloroform. The obtained organic layer was passed through a phase separator, and concentrated under reduced pressure. The obtained residue was purified by silica gel column chromatography (n-hexane:ethyl acetate=10:1 to 5:1) to give methyl 3-[[tert-butyl(diphenyl)silyl]oxymethyl]-1-cyclohexanecarboxylate (543 mg).

(2) The compound (543 mg) obtained in (1) above was used to perform the synthesis process according to the method described in Reference Example 25-1-(2) thereby giving [3-[[tert-butyl(diphenyl)silyl]oxymethyl]cyclohexyl]methanol (555 mg) as a colorless oil.

(3) The compound (506 mg) obtained in (2) above was used to perform the synthesis process according to the method described in Reference Example 63-1-(1) thereby giving 3-[[tert-butyl(diphenyl)silyl]oxymethyl]-1-cyclohexanecarboxaldehyde as a crude product.

(4) The crude product synthesized in (3) above was used to perform the synthesis process according to the method described in Reference Example 63-1-(2) thereby giving (phenylmethyl) (E)-3-[3-[[tert-butyl(diphenyl)silyl]oxymethyl]cyclohexyl]-2-propenoate (243 mg) as a colorless oil.

(5) The compound (243 mg) obtained in (4) above was used to perform the synthesis process according to the method described in Reference Example 50-1-(3) thereby giving the title compound (108 mg) as a colorless oil.

$^1$H NMR (400 MHz, CHLOROFOLM-d) δ ppm 0.78-0.96 (m, 2H) 1.00-1.15 (m, 1H) 1.22-1.41 (m, 2H) 1.50-1.64 (m, 1H) 1.72-1.94 (m, 4H) 2.11-2.25 (m, 1H) 3.39-3.55 (m, 2H) 5.17 (s, 2H) 5.83 (d, J=15.9 Hz, 1H) 6.96 (dd, J=15.9, 6.7 Hz, 1H) 7.26-7.48 (m, 5H).

Reference Example 68-2

(Phenylmethyl) (E)-3-[1-(hydroxymethyl)-4-bicyclo[2.2.2]octanyl]-2-propenoate

[Formula 423]

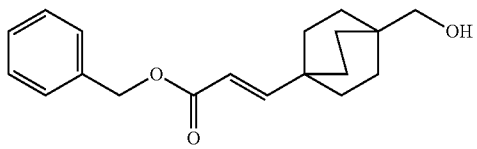

(1) Methyl 1-(hydroxymethyl)-4-bicyclo[2.2.2]octanecarboxylate (500 mg) was used to perform the synthesis process according to the method described in Reference Example 68-1-(1) thereby giving methyl 1-[[tert-butyl(diphenyl)silyl]oxymethyl]-4-bicyclo[2.2.2]octanecarboxylate as a crude product.

(2) The crude product obtained in (1) above was used to perform the synthesis process according to the method described in Reference Example 25-1-(2) thereby giving [4-[[tert-butyl(diphenyl)silyl]oxymethyl]-1-bicyclo[2.2.2]octanyl]methanol (500 mg) as a colorless oil.

(3) The compound (500 mg) obtained in (2) above was used to perform the synthesis process according to the method described in Reference Example 63-1-(1) thereby giving 1-[[tert-butyl(diphenyl)silyl]oxymethyl]-4-bicyclo[2.2.2]octanecarboxaldehyde (373 mg) as a colorless oil.

(4) The compound (200 mg) obtained in (3) above was used to perform the synthesis process according to the method described in Reference Example 65-3-(2) thereby giving (phenylmethyl) (E)-3-[1-[[tert-butyl(diphenyl)silyl]oxymethyl]-4-bicyclo[2.2.2]octanyl]-2-propenoate (216 mg) as a colorless oil.

(5) The compound (216 mg) obtained in (4) above was used to perform the synthesis process according to the method described in Reference Example 40-1-(3) thereby giving the title compound (30 mg) as a colorless oil.

$^1$H NMR (400 MHz, CHLOROFOLM-d) δ ppm 1.40-1.70 (m, 6H) 3.29 (s, 2H) 5.17 (s, 2H) 5.72 (d, J=15.9 Hz, 1H) 6.92 (d, J=15.9 Hz, 1H) 7.29-7.45 (m, 5H).

Reference Example 69-1

3-[4-Fluoro-3-[(4-methoxyphenyl)methoxy]phenyl]-1-propanol

[Formula 424]

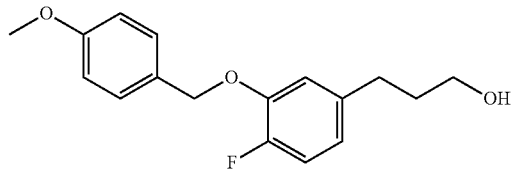

(1) Methyl 4-fluoro-3-hydroxybenzoate (2.17 g) was used to perform the synthesis process according to the method described in Reference Example 25-1-(1) thereby giving methyl 4-fluoro-3-[(4-methoxyphenyl)methoxy]benzoate (3.28 g) as a colorless solid.

(2) The compound (1.31 g) obtained in (1) above was used to perform the synthesis process according to the method described in Reference Example 25-1-(2) thereby giving [4-fluoro-3-[(4-methoxyphenyl)methoxy]phenyl]methanol (1.16 g) as a colorless solid.

(3) Sodium hydrogen carbonate (1.86 g) and Dess-Martin periodinane (2.81 g) were added to a solution of the compound (1.16 g) obtained in (2) above in chloroform (11.1 mL), and the mixture was stirred at room temperature for 2 hours. To this mixture, a saturated aqueous solution of sodium thiosulfate and a saturated aqueous solution of sodium hydrogen carbonate were added, and the resultant mixture was vigorously stirred for 1 hour. The organic layer was separated, and the aqueous layer was extracted twice with chloroform. The organic layers were combined, sequentially washed with water and brine, and passed through a phase separator, and the solvent was then distilled off under reduced pressure. The obtained residue was purified by silica gel column chromatography (n-hexane:ethyl acetate=97:3 to 7:3) to give 4-fluoro-3-[(4-methoxyphenyl)methoxy]benzaldehyde (522 mg) as a pale yellow solid.

(4) Triethyl phosphonoacetate (591 µL) and 1,8-diazabicyclo[5.4.0]undec-7-ene (444 µL) were added to a solution of the compound (522 mg) obtained in (3) above in acetonitrile (9.93 mL) under ice cooling, and the mixture was then stirred at room temperature overnight. The mixture was poured into a saturated aqueous solution of ammonium chloride, and the resultant mixture was extracted three times with a n-hexane:ethyl acetate (2:1) mixed solution. The organic layers were combined, washed with brine, and passed through a phase separator, and the solvent was then distilled off under reduced pressure. The obtained residue was purified by silica gel column chromatography (n-hexane only to n-hexane:ethyl acetate=4:1) to give ethyl (E)-3-[4-fluoro-3-[(4-methoxyphenyl)methoxy]phenyl]-2-propenoate (597 mg) as a colorless solid.

(5) The compound (200 mg) obtained in (4) above was used to perform the synthesis process according to the method described in Reference Example 45-1-(3) thereby giving ethyl 3-[4-fluoro-3-[(4-methoxyphenyl)methoxy]phenyl]propanoate (159 mg) as a colorless oil.

(6) The compound (159 mg) obtained in (5) above was used to perform the synthesis process according to the method described in Reference Example 25-1-(2) thereby giving the title compound (121 mg) as a pale brown oil.

$^1$H NMR (400 MHz, CHLOROFORM-d) δ ppm 1.79-1.88 (m, 2H) 2.61-2.67 (m, 2H) 3.63 (t, J=6.4 Hz, 2H) 3.81 (s, 3H) 5.05 (s, 2H) 6.69-6.74 (m, 1H) 6.82-6.86 (m, 1H) 6.88-6.93 (m, 2H) 6.95-7.01 (m, 1H) 7.34-7.38 (m, 2H).

Reference Example 70-1

Methyl 2-[4-(3-hydroxypropyl)phenyl]acetate

[Formula 425]

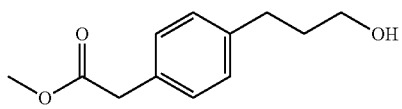

(1) 2-[4-(Hydroxymethyl)phenyl]acetic acid (5.12 g) was used to perform the synthesis process according to the method described in Reference Example 1-1-(1) thereby giving (phenylmethyl) 2-[4-(hydroxymethyl)phenyl]acetate (7.31 g) as a colorless oil.

(2) Manganese(IV) oxide (24.3 g) was added to a solution of the compound (7.31 g) obtained in (1) above in diisopropyl ether (55.8 mL), and the mixture was stirred at room temperature for 1.5 hours. The catalyst was filtered off, and washed with a n-hexane:ethyl acetate (1:1) mixed solution. The filtrate and the washing solution were combined, and the solvent was distilled off under reduced pressure. The obtained residue was purified by silica gel column chromatography (n-hexane only to n-hexane:ethyl acetate=4:1) to give (phenylmethyl) 2-(4-formylphenyl)acetate (6.47 g) as a pale yellow oil.

(3) Methyl diethylphosphonoacetate (4.82 mL) and 1,8-diazabicyclo[5.4.0]undec-7-ene (4.26 µL) were added to a solution of the compound (6.47 g) obtained in (2) above in tetrahydrofuran (47.6 mL) under ice cooling, and the mixture was stirred at room temperature overnight, and then at an outer temperature of 50° C. for 1 hour. To this mixture, methyl diethylphosphonoacetate (1.32 mL) and 1,8-diazabicyclo[5.4.0]undec-7-ene (1.42 µL) were added, and the resultant mixture was further stirred at the same temperature for 2.5 hours. After cooling to room temperature, the mixture was diluted with toluene, and sequentially washed with water, 1 mol/L hydrochloric acid, and brine. After the organic layer was separated by a phase separator, the solvent was distilled off under reduced pressure. The obtained residue was purified by silica gel column chromatography (n-hexane:ethyl acetate=9:1 to 4:1) to give methyl (E)-3-[4-(2-oxo-2-phenylmethoxyethyl)phenyl]-2-propenoate (4.92 g) as a colorless solid.

(4) The compound (4.92 g) obtained in (3) above was used to perform the synthesis process according to the method described in Reference Example 1-1-(3) thereby giving a mixture (3.15 g) containing 2-[4-(3-methoxy-3-oxopropyl)phenyl]acetic acid.

(5) The mixture (3.15 g) obtained in (4) above was used to perform the synthesis process according to the method described in Reference Example 25-1-(2) thereby giving a mixture (1.95 g) containing 2-[4-(3-hydroxypropyl)phenyl]acetic acid.

(6) Concentrated sulfuric acid (10 mL) was slowly added to methanol (33.5 mL) with the mixture (1.95 g) obtained in (5) above under ice cooling, and the mixture was heated to reflux for 3.5 hours. The mixture was cooled to room temperature, and the solvent was distilled off under reduced pressure. The residue was distributed into ethyl acetate and water, and the aqueous layer was extracted with ethyl acetate. The organic layers were combined, sequentially washed with a saturated aqueous solution of sodium hydrogen carbonate and brine, and passed through a phase separator, and the solvent was then distilled off under reduced pressure. The obtained residue was purified by silica gel column chromatography (n-hexane:ethyl acetate=9:1 to 3:7) to give the title compound (1.41 g) as a colorless oil.

$^1$H NMR (400 MHz, CHLOROFORM-d) δ ppm 1.84-1.93 (m, 2H) 2.66-2.73 (m, 2H) 3.60 (s, 2H) 3.65-3.71 (m, 5H) 7.13-7.23 (m, 4H).

Reference Example 71-1

Methyl 3-[4-(3-hydroxypropyl)phenyl]propanoate

[Formula 426]

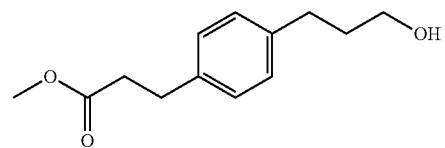

(1) (E)-3-(4-Formylphenyl)-2-propenic acid (1.05 g) was used to perform the synthesis process according to the method described in Reference Example 1-1-(1) thereby giving (phenylmethyl) (E)-3-(4-formylphenyl)-2-propenoate (1.26 g) as a pale gray solid.

(2) The compound (1.26 g) obtained in (1) above was used to perform the synthesis process according to the method described in Reference Example 70-1-(3) thereby giving methyl (E)-3-[4-[(E)-3-oxo-3-phenylmethoxyprop-1-enyl]phenyl]-2-propenoate (964 mg) as a colorless solid.

(3) The compound (964 mg) obtained in (2) above was used to perform the synthesis process according to the method described in Reference Example 1-1-(3) thereby giving a mixture (661 mg) containing 3-[4-(3-methoxy-3-oxopropyl)phenyl]propanoic acid.

(4) The mixture (661 mg) obtained in (3) above was used to perform the synthesis process according to the method described in Reference Example 25-1-(2) thereby giving a mixture (465 mg) containing 3-[4-(3-hydroxypropyl)phenyl]propanoic acid.

(5) The mixture (465 mg) obtained in (3) above was used to perform the synthesis process according to the method described in Reference Example 70-1-(6) thereby giving the title compound (340 mg) as a colorless solid.

$^1$H NMR (400 MHz, CHLOROFORM-d) δ ppm 1.83-1.93 (m, 2H) 2.58-2.73 (m, 4H) 2.88-2.97 (m, 2H) 3.63-3.72 (m, 5H) 7.07-7.17 (m, 4H).

Reference Example 72-1

(Phenylmethyl) 4-(hydroxymethyl)-1-adamantanecarboxylate

[Formula 427]

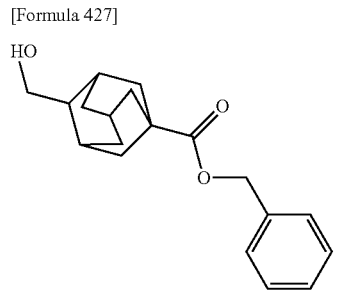

(1) To a solution of 4-oxo-1-adamantanecarboxylic acid (260 mg) in chloroform (4.5 mL), 4-dimethylaminopyridine (14 mg), triethylamine (0.12 mL), and benzyl chloroformate (0.12 mL) were added, and the mixture was stirred at room temperature for 2 hours, and at 60° C. for 2 hours. The temperature of the mixture was returned to room temperature, a saturated aqueous solution of ammonium chloride (7 mL) was added to stop the reaction, and the resultant mixture was extracted with ethyl acetate. The obtained organic layer was separated from the aqueous layer by passing through a phase separator, and concentrated under reduced pressure. The obtained residue was purified by silica gel column chromatography (n-hexane only to n-hexane:ethyl acetate=2:1) to give (phenylmethyl) 4-oxo-1-adamantanecarboxylate (90 mg) as a colorless oil.

(2) A solution of (methoxymethyl)triphenylphosphonium chloride (213 mg) in tetrahydrofuran (3.5 mL) was cooled to −78° C. under a nitrogen atmosphere, n-butyl lithium (1.6 mol/L n-hexane solution, 0.37 mL) was added thereto, and the mixture was stirred at −78° C. for 30 minutes. The compound (100 mg) obtained in (1) above was added thereto, and the resultant mixture was stirred at room temperature for 14 hours, and at 60° C. for 3 hours. The temperature of the mixture was returned to room temperature, a saturated aqueous solution of ammonium chloride (5 mL) was added to stop the reaction, and the resultant mixture was extracted with ethyl acetate. The obtained organic layer was passed through a phase separator, and concentrated under reduced pressure. The obtained residue was purified by silica gel column chromatography (n-hexane:ethyl acetate=10:1 to 1:1) to give (phenylmethyl) 4-(methoxymethylidene)-1-adamantanecarboxylate (40 mg) as a colorless oil.

(3) Water (0.06 mL) and concentrated hydrochloric acid (0.01 mL) were added to a solution of the compound (40 mg) obtained in (2) above in acetone (1.3 mL) under ice cooling, the mixture was stirred for 4 hours with ice cooling continued, the temperature of the mixture was increased to room temperature, and the mixture was stirred for 30 minutes. A saturated aqueous solution of sodium hydrogen carbonate (5 mL) was added to stop the reaction, and the reaction mixture was extracted with diethyl ether. The obtained organic layer was passed through a phase separator, and concentrated under reduced pressure to give (phenylmethyl) 4-formyl-1-adamantanecarboxylate as a crude product.

(4) Sodium borohydride (5 mg) was added to a solution of the crude product obtained in (3) above in tetrahydrofuran (0.8 mL) and methanol (0.8 mL) under ice cooling, and the mixture was stirred at the same temperature for 10 minutes. Water (5 mL) was added thereto, and the resultant mixture was extracted with diethyl ether. The obtained organic layer was passed through a phase separator, and concentrated under reduced pressure. The obtained residue was purified by silica gel column chromatography (n-hexane:ethyl acetate=3:1 to 1:2) to give the title compound (32 mg) as a colorless oil.

$^1$H NMR (400 MHz, CHLOROFOLM-d) δ ppm 1.68-2.09 (m, 15H) 3.69-3.78 (m, 2H) 5.08-5.13 (m, 2H) 7.29-7.44 (m, 5H).

Reference Example 73-1

Methyl 1-(6-hydroxyhexyl)-3-bicyclo[1.1.1]pentanecarboxylate

[Formula 428]

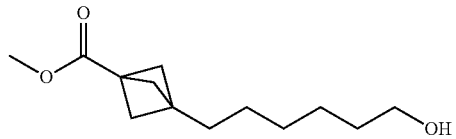

(1) Potassium carbonate (1.6 g) and benzyl 5-bromoamyl ether (1.28 mL) were added to a solution of 1-phenyl-5-tetrazolethiol (1 g) in N,N-dimethylformamide (11 mL) at room temperature, and the mixture was stirred at the same temperature overnight. Water was added thereto, the resultant mixture was extracted with ethyl acetate, and the organic layer was sequentially washed with water and brine, and dried over anhydrous magnesium sulfate. The drying agent was filtered off, and the filtrate was concentrated under reduced pressure. The residue was purified by silica gel column chromatography (n-hexane:ethyl acetate=17:3 to 3:2) to give 1-phenyl-5-(5-phenylmethoxypentylthio)tetrazole (1.80 g) as a colorless oil.

(2) The compound (1.8 g) obtained in (1) above and sodium hydrogen carbonate were used to perform the synthesis process according to the method described in Reference Example 31-1-(3) thereby giving 1-phenyl-5-(5-phenylmethoxypentylsulfonyl)tetrazole (1.11 g) as a colorless oil.

(3) Sodium bis(trimethylsilyl)amide (1.14 mol/L tetrahydrofuran solution, 1.34 mL) was added dropwise to a solution of the compound (590 mg) obtained in (2) above in tetrahydrofuran (3.4 mL) under a nitrogen atmosphere at a temperature of −60° C. or lower, and the mixture was stirred at the same temperature for 30 minutes. Subsequently, a solution of the compound (196 mg) obtained in Reference Example 63-1-(1) in tetrahydrofuran (2.0 mL) was added dropwise thereto, and the resultant mixture was stirred at room temperature overnight. A saturated aqueous solution of ammonium chloride was added to the reaction solution under ice cooling, and the resultant mixture was extracted with ethyl acetate. The organic layer was washed with brine and dried over anhydrous magnesium sulfate, and the drying agent was filtered off. The filtrate was concentrated under reduced pressure, and the residue was purified by silica gel column chromatography (n-hexane:ethyl acetate=19:1 to 3:1) to give methyl 1-[(E)-6-phenylmethoxyhex-1-enyl]-3-bicyclo[1.1.1]pentanecarboxylate (198 mg) as a colorless oil.

(4) The compound (196 mg) obtained in (3) above was used to perform the synthesis process according to the method described in Reference Example 1-1-(3) thereby giving the title compound (140 mg) as a colorless oil.

$^1$H NMR (400 MHz, CHLOROFORM-d) δ ppm 1.10-1.67 (m, 10H) 1.89 (s, 6H) 3.56-3.73 (m, 5H).

MS ESI/APCI Multi posi: 249[M+Na]$^+$.

Reference Example 74-1

Ethyl 1-(3-hydroxypropyl)-5-bicyclo[3.1.1]heptanecarboxylate

[Formula 429]

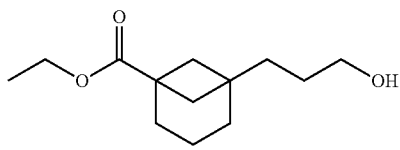

(1) To a solution of diisopropylamine (1.6 mL) in tetrahydrofuran (34 mL), n-butyl lithium (2.67 mol/L n-hexane solution, 4.3 mL) was added dropwise under a nitrogen atmosphere with ice cooling, and the mixture was stirred at the same temperature for 30 minutes. Subsequently, a solution of diethyl cyclohexane-1,3-dicarboxylate (2 g) in tetrahydrofuran (10 mL) was added dropwise thereto at a temperature of −60° C. or lower, the resultant mixture was stirred at the same temperature for 45 minutes, diiodomethane (920 μL) was then added thereto, and the resultant mixture was stirred at room temperature overnight. A saturated aqueous solution of ammonium chloride was added thereto under ice cooling, and the resultant mixture was extracted with diethyl ether. After the organic layer was washed with brine, the organic layer was dried over anhydrous magnesium sulfate, the drying agent was filtered off, and the filtrate was then concentrated under reduced pressure. The residue was purified by silica gel column chromatography (n-hexane:ethyl acetate=49:1 to 17:3) to give a crude product (2.27 g) containing diethyl 1-(iodomethyl)cyclohexane-1,3-dicarboxylate as a colorless oil. To a solution of diisopropylamine (1.2 mL) in tetrahydrofuran (20 mL), n-butyl lithium (2.67 mol/L n-hexane solution, 3 mL) was added dropwise under a nitrogen atmosphere with ice cooling, and the mixture was stirred at the same temperature for 30 minutes. Subsequently, a solution of the crude product (2.27 g) obtained above in tetrahydrofuran (10 mL) was added dropwise thereto at a temperature of −60° C. or lower, and the resultant mixture was stirred at room temperature overnight. A saturated aqueous solution of ammonium chloride was added thereto under ice cooling, and the resultant mixture was extracted with diethyl ether. After the organic layer was washed with brine, the organic layer was dried over anhydrous magnesium sulfate, the drying agent was filtered off, and the filtrate was then concentrated under reduced pressure. The residue was purified by silica gel column chromatography (n-hexane:ethyl acetate=49:1 to 17:3) to give a crude product (665 mg) containing diethyl bicyclo[3.1.1]heptane-1,5-dicarboxylate as a colorless oil.

(2) Potassium hydroxide (2.5 mol/L tetrahydrofuran solution, 1.22 mL) was added to a solution of the crude product (665 mg) obtained in (1) above in tetrahydrofuran (5.5 mL) under ice cooling, and the mixture was stirred at room temperature overnight. Water was added to the reaction solution, the resultant mixture was washed with diethyl ether, and the aqueous layer was neutralized with 2 mol/L hydrochloric acid. Subsequently, the resultant mixture was extracted with chloroform, and the organic layer was separated by a phase separator, and concentrated under reduced pressure. The residue was purified by silica gel column chromatography (chloroform:methanol=99:1 to 47:3) to give 5-ethoxycarbonyl-1-bicyclo[3.1.1]heptanecarboxylic acid (322 mg).

(3) The compound (320 mg) obtained in (2) above was used to perform the synthesis process according to the method described in Reference Example 15-1-(1) thereby giving ethyl 1-(hydroxymethyl)-5-bicyclo[3.1.1]heptanecarboxylate (250 mg) as a colorless oil.

(4) The compound (250 mg) obtained in (3) above was used to perform the synthesis process according to the method described in Reference Example 63-1-(1) thereby giving ethyl 1-formyl-5-bicyclo[3.1.1]heptanecarboxylate (219 mg) as a colorless oil.

(5) Benzyl dimethylphosphonoacetate (300 μL) was added to a suspension of sodium hydride (60% mineral oil dispersion, 57 mg) in N,N-dimethylformamide (6 mL) under ice cooling, and the mixture was stirred at the same temperature for 30 minutes. Subsequently, a solution of the compound (215 mg) obtained in (4) above in N,N-dimethylformamide (6 mL) was added dropwise thereto, and the mixture was stirred at room temperature overnight. A saturated aqueous solution of ammonium chloride was added to the reaction solution under ice cooling, and the resultant mixture was extracted with diethyl ether. The organic layer was washed with brine, passed through a phase separator, and then concentrated under reduced pressure. The residue was purified by silica gel column chromatography (n-hexane:ethyl acetate=49:1 to 17:3) to give ethyl 1-[(E)-3-oxo-3-phenylmethoxyprop-1-enyl]-5-bicyclo[3.1.1]heptanecarboxylate (304 mg) as a colorless oil.

(6) The compound (304 mg) obtained in (5) above was used to perform the synthesis process according to the method described in Reference Example 1-1-(3) thereby giving a crude product (224 mg) containing 3-(5-ethoxycarbonyl-1-bicyclo[3.1.1]heptanyl)propanoic acid as a colorless oil.

(7) The compound (220 mg) obtained in (6) above was used to perform the synthesis process according to the method described in Reference Example 15-1-(1) thereby giving the title compound (207 mg) as a colorless oil.

$^1$H NMR (400 MHz, CHLOROFORM-d) δ ppm 1.17-1.30 (m, 4H) 1.32-1.41 (m, 2H) 1.42-1.54 (m, 2H) 1.57-1.68 (m, 4H) 1.77-1.99 (m, 6H) 3.56-3.68 (m, 2H) 4.10 (q, J=7.1 Hz, 2H).

MS ESI/APCI Multi posi: 227[M+H]$^+$.

Reference Example 75-1

Ethyl 6-hydroxy-3,3-dimethylhexanoate

[Formula 430]

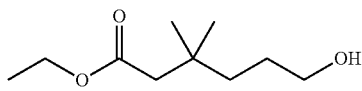

(1) Propionic acid (260 μL) was added to a solution of 3-methyl-2-buten-1-ol (3.0 g) in trimethyl orthoacetate (42 mL), and the mixture was stirred while being heated to reflux for 6 hours, with removing generated water by a Dean-Stark apparatus. After cooling to room temperature, the reaction solution was extracted with diethyl ether, sequentially washed with 1 mol/L hydrochloric acid, water, a saturated aqueous solution of sodium hydrogen carbonate, and brine, and then dried over anhydrous magnesium sulfate. After the drying agent was filtered off, the filtrate was concentrated under reduced pressure to give a crude product (5.45 g) containing ethyl 3,3-dimethyl-4-pentenoate as a colorless oil.

(2) Ozone was passed through a solution of the compound (1.5 g) obtained in (1) above in methanol (70 mL) at a temperature of −60° C. or lower for 1 hour. Subsequently, oxygen was passed therethrough for 1 hour, dimethyl sulfide (3.5 mL) was added thereto, and the mixture was stirred at room temperature overnight. The reaction solution was concentrated under reduced pressure, water was added to the residue, and the resultant mixture was extracted with diethyl ether. The organic layer was washed with brine, and then dried over anhydrous magnesium sulfate. After the drying agent was filtered off, the filtrate was concentrated under reduced pressure to give a crude product (1.16 g) containing ethyl 3,3-dimethyl-4-oxobutanoate as a colorless oil.

(3) Lithium chloride (342 mg) and 1,8-diazabicyclo[5.4.0]-7-undecene (1.2 mL) were added to a solution of tert-butyl diethylphosphonoacetate (2.07 mL) in tetrahydrofuran (27 mL), and the mixture was stirred for a while. Subsequently, a solution of the compound (1.16 g) obtained in (2) above in tetrahydrofuran (10 mL) was added dropwise thereto under ice cooling, and the resultant mixture was stirred at room temperature overnight. A saturated aqueous solution of ammonium chloride was added to the reaction solution, and the resultant mixture was extracted with ethyl acetate. The organic layer was washed with brine and dried over anhydrous magnesium sulfate, the drying agent was filtered off, and the resultant was then concentrated under reduced pressure. The residue was purified by silica gel column chromatography (n-hexane:ethyl acetate=97:3 to 4:1) to give a crude product (970 mg) containing O1-tert-butyl O6-ethyl (E)-4,4-dimethyl-2-hexenedioate as a colorless oil.

(4) The compound (970 mg) obtained in (3) above was used to perform the synthesis process according to the method described in Reference Example 1-1-(3) thereby giving O6-tert-butyl O1-ethyl 3,3-dimethylhexanedioate (247 mg) as a colorless oil.

(5) A 4 mol/L hydrogen chloride-1,4-dioxane solution (1.9 mL) was added to a solution of the compound (243 mg) obtained in (4) above in 1,4-dioxane (1.9 mL), and the mixture was stirred at room temperature overnight, and then stirred while being heated to reflux for 1 hour. The reaction solution was concentrated under reduced pressure, and trifluoroacetic acid (1.5 mL) was added to a solution of the residue in chloroform (4.7 mL), and the resultant mixture was stirred while being heated to reflux for 4 hours. The reaction solution was concentrated under reduced pressure, and the residue was azeotroped with toluene to give a crude product (215 mg) containing 6-ethoxy-4,4-dimethyl-6-oxohexanoic acid.

(6) The compound (215 mg) obtained in (5) above was used to perform the synthesis process according to the method described in Reference Example 15-1-(1) thereby giving the title compound (180 mg) as a colorless oil.

$^1$H NMR (400 MHz, CHLOROFORM-d) δ ppm 1.01 (s, 6H) 1.20-1.29 (m, 3H) 1.31-1.44 (m, 3H) 1.51-1.64 (m, 2H) 2.21 (s, 2H) 3.57-3.70 (m, 2H) 4.12 (q, J=7.2 Hz, 2H).

MS ESI/APCI Multi posi: 189[M+H]$^+$.

Reference Example 76-1

3,3-Dimethyl-4-penten-1-ol

[Formula 431]

A solution of the compound (1 g) obtained in Reference Example 75-1-(1) in tetrahydrofuran (10 mL) was added dropwise to a suspension of lithium aluminum hydride (292 mg) in tetrahydrofuran (33 mL) under ice cooling, and the mixture was stirred at room temperature overnight. Sodium sulfate decahydrate was added thereto under ice cooling, and the resultant mixture was stirred at room temperature for a while. The solid was filtered off through Celite (registered trademark), and the filtrate was concentrated under reduced pressure to give a crude product (560 mg) containing the title compound as a colorless oil.

$^1$H NMR (400 MHz, CHLOROFORM-d) δ ppm 1.04 (s, 6H) 1.57-1.79 (m, 3H) 3.61-3.69 (m, 2H) 4.90-5.01 (m, 2H) 5.78-5.92 (m, 1H).

MS ESI/APCI Multi posi: 115 [M+H]$^+$.

Reference Example 77-1

4-[1-[(2-Methylpropan-2-yl)oxy-oxomethyl]cyclopentyl]butanoic Acid

[Formula 432]

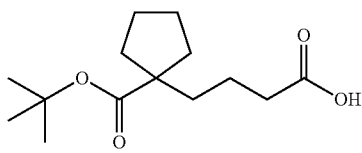

(1) Cyclopentanecarboxylic acid (3.67 g) was used to perform the synthesis process according to the method described in Reference Example 22-1-(1) thereby giving tert-butyl cyclopentanecarboxylate (5.60 g) as a colorless oil.

(2) The compound (930 mg) obtained in (1) above and 2-(4-bromobutoxy)oxane (1.0 g) were used to perform the synthesis process according to the method described in Reference Example 29-1-(1) thereby giving tert-butyl 1-[4-(2-oxanyloxy)butyl]-1-cyclopentanecarboxylate (1.2 g) as a colorless oil.

(3) The compound (1.2 g) obtained in (2) above was used to perform the synthesis process according to the method described in Reference Example 29-1-(2) thereby giving tert-butyl 1-(4-hydroxybutyl)-1-cyclopentanecarboxylate (570 mg) as a colorless oil.

(4) To a solution of the compound (100 mg) obtained in (3) above in acetonitrile:phosphate buffer (pH 7.0) (1:1, 2.8 mL), 2-hydroxy-2-azaadamantane (6 mg), sodium chlorite (140 mg), and sodium hypochlorite pentahydrate (20 mg) were added under ice cooling, and the mixture was stirred at room temperature for 4.5 hours. A saturated aqueous solution of sodium thiosulfate (5 mL) was added to stop the reaction, and the resultant mixture was extracted with ethyl acetate. The obtained organic layer was passed through a phase separator, and concentrated under reduced pressure. The obtained residue was purified by silica gel column chromatography (n-hexane:ethyl acetate=4:1 to 1:1) to give the title compound (64 mg) as a colorless oil.

$^1$H NMR (400 MHz, CHLOROFORM-d) δ ppm 1.38-1.48 (m, 11H) 1.55-1.66 (m, 8H) 2.01-2.14 (m, 2H) 2.34 (t, J=6.2 Hz, 2H).

MS ESI/APCI Multi posi: 279[M+Na]$^+$.

MS ESI/APCI Multi nega: 255[M−H]$^−$.

Reference Example 77-2 tert-Butyl 1-[4-[(3R)-3-(hydroxymethyl)-1-piperidinyl]-4-oxobutyl]-1-cyclopentanecarboxylate

[Formula 433]

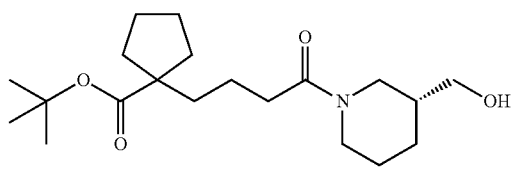

To a solution of the compound (85 mg) obtained in Reference Example 77-1 and N,N-diisopropylethylamine (173 μL) in N,N-dimethylformamide (3.3 mL), O-(7-azabenzotriazol-1-yl)-N,N,N',N'-tetramethyluronium hexafluorophosphate (HATU) (151 mg) was added under ice cooling, and the mixture was stirred at the same temperature for a while. Thereto, (3R)-3-piperidinemethanol (46 mg) was added, and the resultant mixture was stirred at room temperature overnight. Saturated ammonium chloride was added to the reaction mixture, and the resultant mixture was extracted with ethyl acetate. The organic layer was sequentially washed with water and brine, passed through a phase separator, and then concentrated under reduced pressure. The obtained residue was purified by silica gel column chromatography (chloroform:methanol=99:1 to 47:3) to give the title compound (110 mg) as a pale brown oil.

MS ESI/APCI Multi posi: 354[M+H]$^+$.

Reference Example 77-3 tert-Butyl 1-[3-[4-(2-hydroxyethyl)-1-piperidinyl]-3-oxopropyl]-1-cyclopentanecarboxylate

[Formula 434]

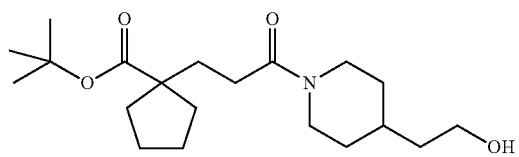

(1) The compound (500 mg) obtained in Reference Example 77-1-(1) and 3-bromopropoxymethylbenzene (740 mg) were used to perform the synthesis process according to the method described in Reference Example 29-1-(1) thereby giving tert-butyl 1-(3-phenylmethoxypropyl)-1-cyclopentanecarboxylate (386 mg) as a colorless oil.

(2) The compound obtained in (1) above was used to perform the synthesis process according to the method described in Reference Example 1-1-(3) thereby giving tert-butyl 1-(3-hydroxypropyl)-1-cyclopentanecarboxylate (265 mg) as a colorless oil.

(3) The compound (265 mg) obtained in (2) above was used to perform the synthesis process according to the method described in Reference Example 77-1-(4) thereby giving 3-[1-[(2-methylpropan-2-yl)oxy-oxomethyl]cyclopentyl]propanoic acid (240 mg) as a colorless oil.

(4) The compound (70 mg) obtained in (3) above and 2-(4-piperidyl)ethanol (45 mg) were used to perform the synthesis process according to the method described in Reference Example 77-2 thereby giving the title compound (89 mg) as a colorless oil.

$^1$H NMR (400 MHz, METHANOL-$d_4$) δ ppm 0.96-1.34 (m, 2H) 1.36-1.56 (m, 13H) 1.60-1.90 (m, 10H) 2.02-2.14 (m, 2H) 2.25-2.36 (m, 2H) 2.55-2.67 (m, 1H) 3.09 (td, J=13.0, 2.6 Hz, 1H) 3.62 (t, J=6.5 Hz, 2H) 3.87-3.94 (m, 1H) 4.46-4.53 (m, 1H).

MS ESI posi: 354[M+H]$^+$.

Reference Example 78-1 tert-Butyl 1-[(6-hydroxyhexylamino)-oxomethyl]-1-cyclopentanecarboxylate

[Formula 435]

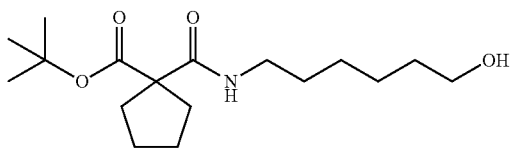

(1) Sodium hydride (60% mineral oil dispersion, 639 mg) was added to a solution of O3-tert-butyl O1-(phenylmethyl) propanedioate (2.0 g) in tetrahydrofuran (20 mL) under a nitrogen atmosphere with ice cooling, and the mixture was stirred at the same temperature for 1 hour. Thereto, 1,4-dibromobutane (1.05 mL) was added, and the resultant mixture was stirred at 65° C. for 4.5 hours. A saturated aqueous solution of ammonium chloride (15 mL) was added to stop the reaction, and the resultant mixture was extracted with ethyl acetate. The obtained organic layer was passed through a phase separator, and concentrated under reduced pressure. The obtained residue was purified by silica gel column chromatography (n-hexane:ethyl acetate=10:1 to 2:1) to give O1'-tert-butyl O1-(phenylmethyl) cyclopentane-1,1-dicarboxylate (975 mg) as a colorless oil.

(2) The compound (622 mg) obtained in (1) above was used to perform the synthesis process according to the method described in Reference Example 1-1-(3) thereby giving 1-[(2-methylpropan-2-yl)oxy-oxomethyl]-1-cyclopentanecarboxylic acid (392 mg) as an orange powder.

(3) The compound (60 mg) obtained in (2) above and 6-amino-1-hexanol (43 mg) were used to perform the synthesis process according to the method described in Reference Example 77-2 thereby giving the title compound (69 mg) as a colorless oil.

$^1$H NMR (400 MHz, CHLOROFOLM-d) δ ppm 1.28-1.76 (m, 24H) 2.04-2.20 (m, 4H) 3.22-3.28 (m, 2H) 3.63 (t, J=6.5 Hz, 2H).

MS ESI posi: 336[M+H]$^+$.

Reference Example 78-2 tert-Butyl 1-[[6-hydroxyhexyl(methyl)amino]-oxomethyl]-1-cyclopentanecarboxylate

[Formula 436]

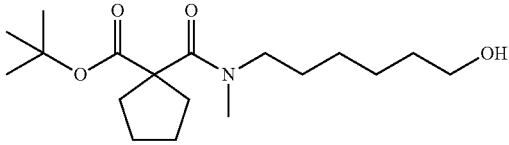

The compound (60 mg) obtained in Reference Example 78-1-(2) and 6-(methylamino)-1-hexanol (55 mg) were used to perform the synthesis process according to the method described in Reference Example 77-2 thereby giving the title compound (92 mg) as a colorless oil.

$^1$H NMR (400 MHz, CHLOROFOLM-d) δ ppm 1.27-1.50 (m, 13H) 1.52-1.71 (m, 8H) 2.04-2.15 (m, 2H) 2.17-2.27 (m, 2H) 2.85 (s, 3H) 3.36 (t, J=7.2 Hz, 2H) 3.63 (t, J=6.4 Hz, 2H).

MS ESI posi: 350[M+Na]$^+$.

Reference Example 79-1

Methyl 4-[3-(3-hydroxypropyl)-1-piperidinyl]-2,2-dimethyl-4-oxobutanoate

[Formula 437]

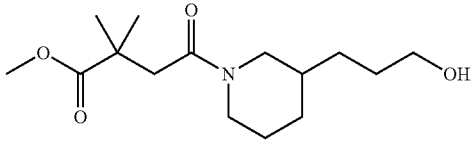

(1) 3-[1-[(2-Methylpropan-2-yl)oxy-oxomethyl]-3-piperidinyl]propanoic acid (382 mg) was used to perform the synthesis process according to the method described in Reference Example 15-1-(1) thereby giving tert-butyl 3-(3-hydroxypropyl)-1-piperidinecarboxylate (320 mg) as a colorless oil.

(2) A 4 mol/L hydrogen chloride-1,4-dioxane solution (3.3 mL) was added to a solution of the compound (320 mg) obtained in (2) above in 1,4-dioxane (1.3 mL), and the mixture was stirred at room temperature for 20 hours. The reaction mixture was concentrated under reduced pressure to give 3-(3-piperidinyl)-1-propanol hydrochloride (210 mg) as a colorless solid.

(3) The compound (70 mg) obtained in (2) above and 4-methoxy-3,3-dimethyl-4-oxobutanoic acid (68 mg) were used to perform the synthesis process according to the method described in Reference Example 77-2 thereby giving the title compound (30 mg) as a colorless oil.

¹H NMR (400 MHz, METHANOL-d₄) δ ppm 1.24 (s, 6H) 1.13-1.80 (m, 15H) 1.83-1.97 (m, 1H) 2.59-2.82 (m, 3H) 2.94-3.15 (m, 1H) 3.54 (dt, J=13.6, 6.6 Hz, 2H) 3.64 (s, 3H) 3.76-3.87 (m, 1H) 4.16-4.32 (m, 1H).

MS ESI posi: 286[M+H]⁺.

Reference Example 80-1

(Phenylmethyl) 4-[(3S)-3-(hydroxymethyl)-1-piperidinyl]-4-oxobutanoate

[Formula 438]

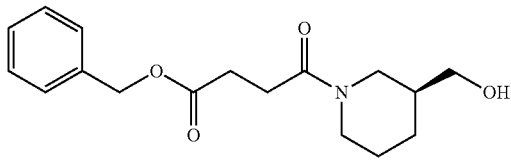

To a solution of 4-oxo-4-phenylmethoxybutanoic acid (100 mg) and [(3S)-3-piperidinyl]methanol hydrochloride (73 mg) in chloroform (4.8 mL), N,N-diisopropylethylamine (0.17 mL) and bromotripyrrolidinophosphonium hexafluorophosphate (223 mg) were added, and the mixture was stirred at room temperature for 17 hours. A saturated aqueous solution of sodium hydrogen carbonate (5 mL) was added to stop the reaction. The resultant mixture was extracted with ethyl acetate, and the organic layer was passed through a phase separator, and then concentrated under reduced pressure. The obtained residue was purified by silica gel column chromatography (n-hexane:ethyl acetate=10:1 to 1:1) to give the title compound (200 mg) as a colorless oil.

MS ESI/APCI Multi posi: 306[M+H]⁺.

Reference Example 80-2

(Phenylmethyl) 4-[(3R)-3-(hydroxymethyl)-1-piperidinyl]-4-oxobutanoate

[Formula 439]

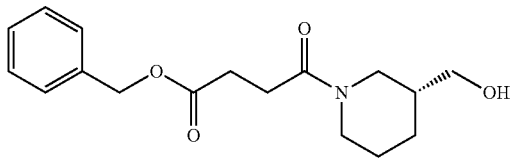

To a solution of 4-oxo-4-phenylmethoxybutanoic acid (190 mg) and [(3R)-3-piperidinyl]methanol (100 mg) in chloroform (8.7 mL), N,N-diisopropylethylamine (0.18 mL), N-(3-dimethylaminopropyl)-N'-ethylcarbodiimide hydrochloride (200 mg), and 1-hydroxybenzotriazole monohydrate (173 mg) were added, and the mixture was stirred at room temperature for 18 hours. A saturated aqueous solution of ammonium chloride (8 mL) was added to stop the reaction, and the resultant mixture was extracted with chloroform. The organic layer was passed through a phase separator, and then concentrated under reduced pressure. The obtained residue was purified by silica gel column chromatography (chloroform only to chloroform:methanol=10:1) to give the title compound (164 mg) as a colorless oil.

MS ESI/APCI Multi posi: 306[M+H]⁺.

Reference Example 80-3

Methyl 4-[4-(3-hydroxypropyl)-1-piperidinyl]-2,2-dimethyl-4-oxobutanoate

[Formula 440]

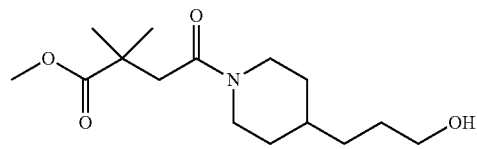

To a solution of 4-methoxy-3,3-dimethyl-4-oxobutanoic acid (94 mg) in N,N-dimethylformamide (5.6 mL), N,N-diisopropylethylamine (0.58 mL), O-(7-azabenzotriazol-1-yl)-N,N,N',N'-tetramethyluronium hexafluorophosphate (HATU) (233 mg), and 3-(4-piperidinyl)-1-propanol hydrochloride (100 mg) were added under a nitrogen atmosphere with ice cooling, and the mixture was stirred at room temperature for 13 hours. A saturated aqueous solution of ammonium chloride (8 mL) was added to stop the reaction, and the resultant mixture was extracted with diethyl ether. The obtained organic layer was passed through a phase separator, and concentrated under reduced pressure. The obtained residue was purified by silica gel column chromatography (n-hexane:ethyl acetate=1:1 to 1:4 to chloroform:methanol=9:1 to 1:4) to give the title compound (122 mg) as a colorless oil.

¹H NMR (400 MHz, METHANOL-d₄) δ ppm 0.95-1.18 (m, 2H) 1.23 (s, 6H) 1.27-1.37 (m, 2H) 1.46-1.63 (m, 3H) 1.68-1.83 (m, 2H) 2.52-2.62 (m, 1H) 2.68 (s, 2H) 2.98-3.07 (m, 1H) 3.54 (t, J=6.5 Hz, 2H) 3.64 (s, 3H) 3.88-3.96 (m, 1H) 4.32-4.48 (m, 1H).

MS ESI posi: 286[M+H]⁺, 308[M+Na]⁺.

The compound of Reference Example 80-4 below was synthesized using a commercially available compound, according to the method described in Reference Example 80-3. The structure and MS data of the compound are shown in Table 29-1.

TABLE 29-1

| Reference Example No. | Structure | Analytical Data |
|---|---|---|
| 80-4 | 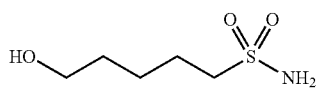 | MS ESI posi: 354[M + H]+. |

Reference Example 81-1

Ethyl 2-[[6-(hydroxymethyl)-2-pyridinyl]oxy]-2-methylpropanoate

[Formula 441]

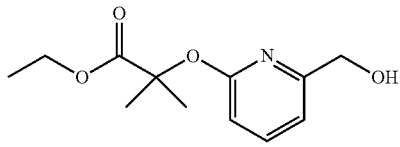

(1) 6-Methyl-2-pyridinol (300 mg) and ethyl 2-hydroxy-2-methylpropanoate (550 μL) were used to perform the synthesis process according to the method described in Reference Example 6-2 thereby giving ethyl 2-methyl-2-[(6-methyl-2-pyridinyl)oxy]propanoate (365 mg) as a colorless oil.

(2) The compound (365 mg) obtained in (1) above was used to perform the synthesis process according to the method described in Reference Example 31-1-(3) thereby giving ethyl 2-methyl-2-[(6-methyl-1-oxide-2-pyridin-1-iumyl)oxy]propanoate (146 mg) as a colorless oil.

(3) A solution of the compound (146 mg) obtained in (2) above in acetic anhydride (610 μL) was stirred while being heated to reflux for 4 hours. The reaction solution was concentrated under reduced pressure, a saturated aqueous solution of sodium hydrogen carbonate was added to the residue, and the resultant mixture was extracted with chloroform. The organic layer was separated by a phase separator, and concentrated under reduced pressure to give a crude product (170 mg) containing ethyl 2-[[6-(acetyloxymethyl)-2-pyridinyl]oxy]-2-methylpropanoate.

(4) Potassium carbonate (93 mg) was added to a solution of the compound (171 mg) obtained in (3) above in ethanol:water (5:1, 7.3 mL) under ice cooling, and the mixture was stirred at room temperature overnight. Water was added to the reaction solution, the resultant mixture was extracted with chloroform, and the organic layer was separated by a phase separator, and concentrated under reduced pressure. The residue was purified by silica gel column chromatography (n-hexane:ethyl acetate=4:1 to 1:1) to give the title compound (105 mg) as a colorless oil.

$^1$H NMR (400 MHz, CHLOROFORM-d) δ ppm 1.13 (t, J=7.1 Hz, 3H) 1.67 (s, 6H) 3.14-3.22 (m, 1H) 4.15 (q, J=7.1 Hz, 2H) 4.55-4.67 (m, 2H) 6.60-6.68 (m, 1H) 6.70-6.78 (m, 1H) 7.49-7.61 (m, 1H).

MS ESI/APCI Multi posi: 240[M+H]+.

Reference Example 82-1

5-Hydroxy-1-pentanesulfonamide

[Formula 442]

(1) 5-Phenylmethoxy-1-pentanol (2.0 g) was used to perform the synthesis process according to the method described in Reference Example 38-1-(2) thereby giving a crude product (4.03 g) containing 5-phenylmethoxypentyl 4-methylbenzenesulfonate.

(2) Thiourea (723 mg) was added to a solution of the compound (4.03 g) obtained in (1) above in ethanol (50 mL), and the mixture was stirred at 60° C. for 1.5 hours, and then stirred for 3 hours while being heated to reflux. The reaction solution was concentrated under reduced pressure, ethyl acetate was added to the residue to suspend, and the suspension was stirred. The solid was collected by filtration to give a crude product (2.0 g) containing 5-phenylmethoxypentyl carbamidethioate.

(3) An aqueous solution of 1 mol/L sodium hydroxide (9.5 mL) was added to the compound (2.0 g) obtained in (2) above, and the mixture was stirred at room temperature overnight. To the reaction solution, 2 mol/L hydrochloric acid was added to neutralize, and the resultant mixture was extracted with diethyl ether. The organic layer was washed with brine, and dried over anhydrous magnesium sulfate. The drying agent was filtered off, and the resultant was concentrated under reduced pressure to give a crude product (790 mg) containing 5-phenylmethoxy-1-pentanethiol as a colorless oil.

(4) To a solution of the compound (790 mg) obtained in (3) above in chloroform (32 mL), N-chlorosuccinimide (4.2 g) and water (16 mL) were sequentially added, and the mixture was stirred at room temperature overnight. The reaction solution was extracted with chloroform, and the organic layer was sequentially washed with a saturated aqueous solution of sodium hydrogen carbonate, water, and brine. The organic layer was separated by a phase separator, and concentrated under reduced pressure. The residue was purified by silica gel column chromatography (n-hexane:ethyl acetate=19:1 to 3:1) to give 5-phenylmethoxy-1-pentanesulfonyl chloride (553 mg) as a pale yellow oil.

(5) To a solution of the compound (553 mg) obtained in (4) above in chloroform (5 mL), 25% aqueous ammonia (2 mL) was added at room temperature, and the mixture was stirred at the same temperature overnight. The reaction solution was concentrated under reduced pressure, and a saturated aqueous solution of ammonium chloride was added to the residue. The resultant mixture was extracted with chloroform, and the organic layer was separated by a phase separator, and concentrated under reduced pressure. The residue was purified by silica gel column chromatography (n-hexane:ethyl acetate=3:2 to 1:3) to give 5-phenylmethoxy-1-pentanesulfonamide (342 mg) as a colorless oil.

(6) The compound (342 mg) obtained in (5) above was used to perform the synthesis process according to the method described in Reference Example 1-1-(3) thereby giving a crude product (245 mg) containing the title compound as a black oil.

MS ESI/APCI Multi posi: 190[M+Na]⁺.

Reference Example 83-1

5-Bromo-2,2-dimethyl-1-cyclopentanone

[Formula 443]

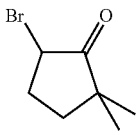

Trimethylphenylammonium tribromide (1.84 g) was added to a solution of 2,2-dimethyl-1-cyclopentanone (500 mg) in tetrahydrofuran (45 mL) under ice cooling, and the mixture was stirred at room temperature for 5 hours. Water was added to the reaction solution, and the resultant mixture was extracted with diethyl ether. The organic layer was washed with brine, and dried over anhydrous magnesium sulfate. After the drying agent was filtered off, the filtrate was concentrated under reduced pressure, and the residue was purified by silica gel column chromatography (n-hexane:ethyl acetate=49:1 to 17:3) to give the title compound (592 mg) as a colorless oil.

MS EI posi: 190[M]⁺.

Reference Example 84-1

Ethyl 2-azido-2-methylpropanoate

[Formula 444]

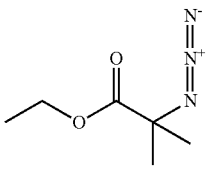

Sodium azide (0.5 g) was added to a solution of ethyl 2-bromo-2-methylpropanoate (1 g) in N,N-dimethylformamide (17 mL), and the mixture was stirred at room temperature for 25 hours. The reaction solution was diluted with diethyl ether, and the organic layer was washed five times with water. The organic layer was concentrated under reduced pressure to give the title compound (710 mg) as a colorless oil.

¹H NMR (400 MHz, CHLOROFORM-d) δ ppm 1.32 (t, J=7.1 Hz, 3H) 1.47 (s, 6H) 4.24 (q, J=7.1 Hz, 2H).

Reference Example 85-1

Ethyl 2-[3-[(6-bromo-3-pyridinyl)oxymethyl]phenyl]acetate

[Formula 445]

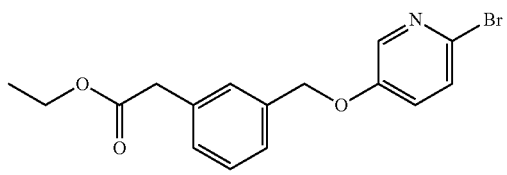

2-Bromo-4-hydroxypyridine (160 mg) and ethyl 2-[3-(bromomethyl)phenyl] acetate (497 mg) were used to perform the synthesis process according to the method described in Reference Example 1-1-(1) thereby giving the title compound (302 mg) as a colorless oil.

¹H NMR (400 MHz, CHLOROFORM-d) δ ppm 1.25 (t, J=7.1 Hz, 3H) 3.63 (s, 2H) 4.15 (q, J=7.1 Hz, 2H) 5.08 (s, 2H) 7.15 (dd, J=8.7, 3.1 Hz, 1H) 7.26-7.38 (m, 5H) 8.13 (d, J=3.1 Hz, 1H).

MS ESI/APCI Multi posi: 350[M+H]⁺.

Reference Example 86-1

Methyl 1-[(6-bromo-3-pyridinyl)oxymethyl]-4-bicyclo[2.2.2]octanecarboxylate

[Formula 446]

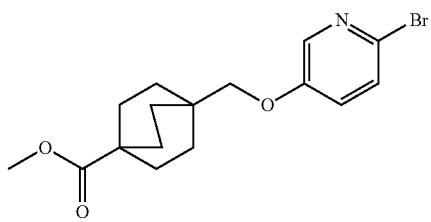

2-Bromo-4-hydroxypyridine (184 mg) and methyl 1-(hydroxymethyl)-4-bicyclo[2.2.2]octanecarboxylate (200 mg) were used to perform the synthesis process according to the method described in Reference Example 6-1 thereby giving the title compound (174 mg) as a colorless solid.

¹H NMR (400 MHz, CHLOROFOLM-d) δ ppm 1.55-1.62 (m, 6H) 1.80-1.88 (m, 6H) 3.59 (s, 2H) 3.66 (s, 3H) 7.07 (dd, J=8.7, 3.1 Hz, 1H) 7.34 (d, J=8.7 Hz, 1H) 8.03 (d, J=3.1 Hz, 1H).

MS ESI/APCI Multi posi: 354[M+H]⁺.

Reference Example 87-1

(2R)-2-Methoxy-1-propanamine

[Formula 447]

(1) Triethylamine (8.35 mL) was added to a solution of (2R)-1-aminopropan-2-ol (3.00 g) and Boc₂O (9.59 g) in tetrahydrofuran (50 mL), and the mixture was stirred at room temperature for 20 hours. The solvent was distilled off under reduced pressure, an aqueous solution of 20% citric acid was added thereto, and the resultant mixture was extracted with ethyl acetate. The organic layer was washed with a saturated aqueous solution of sodium hydrogen carbonate, and passed through a phase separator. The filtrate was concentrated under reduced pressure to give tert-butyl N-[(2R)-2-hydroxypropyl]carbamate (8.30 g) as a pale yellow oil.

(2) Sodium hydride (60% mineral oil dispersion, 1.10 g) and methyl iodide (1.56 mL) were added to a solution of the compound (4.00 g) obtained in (1) above in tetrahydrofuran (50 mL) under ice cooling, and the mixture was stirred at the same temperature for 2 hours. Water was added to the reaction solution, and the resultant mixture was extracted with ethyl acetate. The organic layer was washed with water, and passed through a phase separator. The filtrate was concentrated under reduced pressure, and the obtained residue was purified by silica gel column chromatography (n-hexane:ethyl acetate=4:1 to 1:1) to give tert-butyl N-[(2R)-2-methoxypropyl]carbamate (700 mg) as a pale yellow oil.

(3) A solution of 4 mol/L hydrogen chloride-ethyl acetate (5 mL) was added to a solution of the compound (700 mg) obtained in (2) above in ethyl acetate (5 mL), and the mixture was stirred at room temperature for 20 hours. The solvent was distilled off under reduced pressure, an aqueous solution of 1 mol/L sodium hydroxide was added to the residue, and the resultant mixture was extracted with a chloroform:methanol (9:1) mixed solution. The organic layer was separated by a phase separator, and the solvent was distilled off under reduced pressure to give the title compound (435 mg) as a pale yellow amorphous substance.

¹H NMR (600 MHz, CHLOROFORM-d) δ ppm 1.21 (d, J=6.2 Hz, 3H) 2.88-2.93 (m, 1H) 3.11-3.16 (m, 1H) 3.40 (s, 3H) 3.72-3.78 (m, 1H).

MS ESI/APCI Multi posi: 90[M+H]⁺.

Reference Example 88-1

2-Amino-1-(1-pyrrolidinyl)ethanone

[Formula 448]

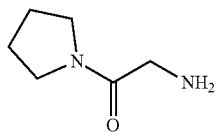

(1) Pyrrolidine (614 μL), N,N-diisopropylethylamine (1.46 mL), and a propylphosphonic anhydride-ethyl acetate solution (5.04 mL) were added to a solution of N-(tert-butoxycarbonyl)glycine (1.00 g) in ethyl acetate (20 mL), and the mixture was stirred at room temperature for 20 hours. To the reaction solution, 0.5 mol/L hydrochloric acid was added, and the resultant mixture was extracted with ethyl acetate. The organic layer was sequentially washed with 0.5 mol/L hydrochloric acid, an aqueous solution of 1 mol/L sodium hydroxide, and water, and passed through a phase separator. The solvent was distilled off under reduced pressure to give tert-butyl N-[2-oxo-2-(1-pyrrolidinyl)ethyl]carbamate (1.00 g) as a colorless powder.

(2) A 4 mol/L hydrogen chloride-ethyl acetate solution (5 mL) was added to a solution of the compound (1.00 g) obtained in (1) above in ethyl acetate (5 mL), and the mixture was stirred at room temperature for 20 hours. The solvent was distilled off under reduced pressure, an aqueous solution of 1 mol/L sodium hydroxide was added to the residue, and the resultant mixture was extracted with a chloroform:methanol (9:1) solution. The organic layer was separated by a phase separator, and the solvent was distilled off under reduced pressure to give the title compound (98 mg) as a pale yellow oil.

¹H NMR (600 MHz, CHLOROFORM-d) δ ppm 1.81-1.91 (m, 2H) 1.92-2.01 (m, 2H) 3.33 (t, J=6.8 Hz, 2H) 3.37 (s, 2H) 3.50 (t, J=6.8 Hz, 2H).

MS ESI/APCI Multi posi: 129[M+H]⁺.

Reference Example 89-1

2-[[6-(1H-Pyrazol-5-yl)-3-pyridinyl]oxymethyl]benzoic Acid

[Formula 449]

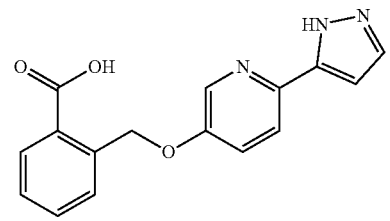

(1) The compound (50 mg) obtained in Reference Example 1-1 and methyl 2-(chloromethyl)benzoate (41 mg) were used to perform the synthesis process according to the method described in Reference Example 8-2 thereby giving methyl 2-[[6-[2-(2-oxanyl)-3-pyrazolyl]-3-pyridinyl]oxymethyl]benzoate (74 mg) as a colorless oil.

(2) An aqueous solution of 1 mol/L sodium hydroxide (0.41 mL) was added to a solution of the compound obtained in (1) above in tetrahydrofuran (1.9 mL), and the mixture was stirred at 65° C. for 5 hours. The temperature of the mixture was returned to room temperature, methanol (1.5 mL), water (0.5 mL), and trifluoroacetic acid (0.25 mL) were added thereto, and the resultant mixture was stirred at room temperature for 1.5 hours. The reaction mixture was concentrated under reduced pressure, the residue was dissolved in methanol and recrystallized therefrom, and the recrystallized residue was thoroughly washed with diethyl ether and collected by filtration to give the title compound (14 mg) as a colorless powder.

$^1$H NMR (400 MHz, DMSO-d$_6$) δ ppm 5.55 (s, 2H) 6.72-6.77 (m, 1H) 7.45-7.54 (m, 2H) 7.59-7.71 (m, 3H) 7.84-7.91 (m, 1H) 7.94 (d, J=7.5 Hz, 1H) 8.31-8.35 (m, 1H).
MS ESI/APCI Multi posi: 296[M+H]$^+$.

Reference Example 90-1

Ethyl 7-(bromomethyl)-3,4-dihydro-2H-chromene-2-carboxylate (Optically Active Substance)

[Formula 450]

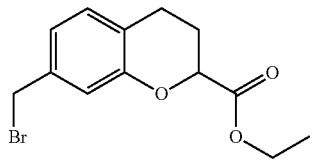

(1) Optical isomers of the compound (540 mg) in Reference Example 53-1 were separated from each other by using preparative HPLC equipped with a chiral column. A compound (236 mg) of Reference Example 90-1-(1)-1, which was a component having a short retention time, was obtained as a colorless oil, and a compound (233 mg) of Reference Example 90-1-(1)-2, which was a component having a long retention time, was obtained as a colorless oil.

(2) A solution of the above-obtained compound (101 mg) of Reference Example 90-1-(1)-1 in chloroform (2 mL) was added to a solution of triphenylphosphine (224 mg) and tetrabromo carbon (354 mg) in chloroform (2 mL) under ice cooling, the temperature of the mixture was then increased, and the mixture was stirred at room temperature for 1 hour. Triphenylphosphine (224 mg) and tetrabromo carbon (354 mg) were added thereto under ice cooling, and the resultant mixture was stirred at the same temperature for 15 minutes. The reaction solution was washed with a saturated aqueous solution of sodium hydrogen carbonate, and the organic layer was separated by a phase separator, and concentrated under reduced pressure. The obtained residue was purified by silica gel column chromatography (n-hexane only to n-hexane:ethyl acetate=4:1) to give the title compound (123 mg) as a colorless oil.

$^1$H NMR (400 MHz, CHLOROFORM-d) δ ppm 1.29 (t, J=7.0 Hz, 3H) 2.12-2.33 (m, 2H) 2.68-2.88 (m, 2H) 4.26 (q, J=7.0 Hz, 2H) 4.42 (s, 2H) 4.69-4.75 (m, 1H) 6.87-6.93 (m, 1H) 6.95-7.03 (m, 2H).
MS ESI posi: 321[M+Na]$^+$.

Reference Example 90-2

Ethyl 7-(bromomethyl)-3,4-dihydro-2H-chromene-2-carboxylate (Optically Active Substance, Enantiomer of Reference Example 90-1)

The compound of Reference Example 90-1-(1)-2 (70 mg) was used to perform the reaction according to the method described in Reference Example 90-1-(2) thereby giving the title compound (68 mg) as a colorless oil.
MS ESI posi: 321[M+Na]$^+$.

Reference Example 91-1

Ethyl (3R)-1-[3-(hydroxymethyl)phenyl]sulfonylpiperidine-3-carboxylate

[Formula 451]

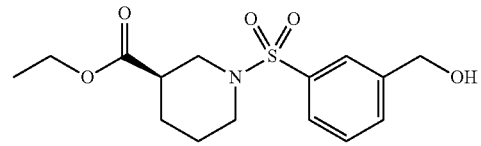 [SMILES: CCOC(=O)[C@H]1CCCN(S(=O)(=O)c2cccc(CO)c2)C1]

(1) Ethyl (3R)-piperidinecarboxylate (5.06 g) and 3-(carboxy)benzenesulfonyl chloride (6.50 g) were used to perform the reaction according to the method described in Reference Example 5-1-(3) thereby giving 3-[(3R)-3-ethoxycarbonylpiperidin-1-yl]sulfonylbenzoic acid (8.34 g) as a pale yellow solid.

(2) The compound (1.34 g) obtained in (1) above was used to perform the reaction according to the method described in Reference Example 15-1-(1) thereby giving the title compound (1.02 g) as a colorless oil.

$^1$H NMR (400 MHz, CHLOROFORM-d) δ ppm 1.26 (t, J=6.9 Hz, 3H) 1.33-1.46 (m, 1H) 1.59-1.72 (m, 1H) 1.75-1.89 (m, 2H) 1.93-2.06 (m, 1H) 2.34-2.44 (m, 1H) 2.51-2.67 (m, 2H) 3.58-3.68 (m, 1H) 3.79-3.89 (m, 1H) 4.14 (q, J=6.9 Hz, 2H) 4.80 (d, J=5.9 Hz, 2H) 7.49-7.57 (m, 1H) 7.59-7.64 (m, 1H) 7.67-7.72 (m, 1H) 7.77 (s, 1H).
MS ESI posi: 328[M+H]$^+$, 350[M+Na]$^+$.

The compound of Reference Example 91-2 below was synthesized using ethyl (3S)-piperidinecarboxylate, according to the method described in Reference Example 91-1. The structure, NMR data, and MS data of the compound are shown in Table 29-2.

TABLE 29-2

| Reference Example No. | Structure | Analytical Data |
|---|---|---|
| 91-2 | 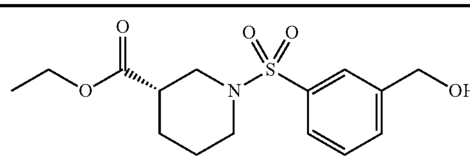 | $^1$H NMR (400 MHz, CHLOROFORM-d) δ ppm 1.26 (t, J = 6.9 Hz, 3 H) 1.33-1.46 (m, 1 H) 1.59-1.72 (m, 1 H) 1.75-1.89 (m, 2 H) 1.93-2.06 (m, 1 H) 2.34-2.44 (m, 1 H) 2.51-2.67 (m, 2 H) 3.58-3.68 (m, 1 H) 3.79-3.89 (m, 1 H) 4.14 (q, J = 6.9 Hz, 2 H) 4.80 (d, J = 5.9 Hz, 2 H) 7.49-7.57 (m, 1 H) 7.59-7.64 (m, 1 H) 7.67-7.72 (m, 1 H) 7.77 (s, 1 H). MS ESI posi: 328[M = H]$^+$, 350 [M + Na]$^+$. |

Reference Example 92-1

Ethyl 2-[[3-(chloromethyl)phenyl]sulfonylamino]-2-methylpropanoate

[Formula 452]

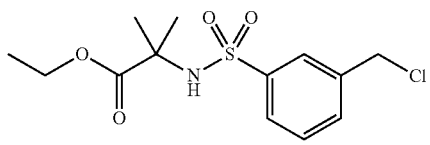

To a solution of ethyl 2-amino-2-methylpropanoate hydrochloride (75 mg) in chloroform (3.0 mL), 2,6-dimethylpyridine (172 μL) was added under a nitrogen atmosphere, and the mixture was ice-cooled. Thereto, 3-(bromomethyl) benzenesulfonyl chloride (100 mg) was added, and the resultant mixture was stirred at room temperature for 3 days. A saturated aqueous solution of ammonium chloride was added to stop the reaction, and the resultant mixture was extracted with chloroform. The organic layers were combined, passed through a phase separator, and concentrated under reduced pressure. The obtained residue was purified by silica gel column chromatography (n-hexane only to n-hexane:ethyl acetate=1:1) to give the title compound (99 mg) as a colorless oil.

$^1$H NMR (400 MHz, CHLOROFORM-d) δ ppm 1.20-1.29 (m, 3H) 1.46 (s, 6H) 4.08-4.16 (m, 2H) 4.62 (s, 2H) 5.39 (s, 1H) 7.46-7.54 (m, 1H) 7.56-7.60 (m, 1H) 7.79-7.89 (m, 1H) 7.89-7.92 (m, 1H).

MS ESI nega: 318[M−H]$^-$.

The compounds of Reference Examples 92-2 and 92-3 below were synthesized using 3-(bromomethyl)benzenesulfonyl chloride and commercially available amine hydrochloride, according to the method described in Reference Example 16-1-(1). The structures, NMR data, and MS data of the compounds are shown in Table 29-3.

Reference Example 93-1

Ethyl 3-[[3-(bromomethyl)phenyl]sulfonyl-methyl-amino]-2,2-dimethylpropanoate

[Formula 453]

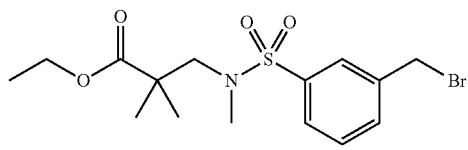 [SMILES: CCOC(=O)C(C)(C)CNS(=O)(=O)c1cccc(CBr)c1]

(1) Ethyl 2-amino-2-methylpropanoate hydrochloride (200 mg) was used to perform the reaction according to the method described in Reference Example 87-1-(1) thereby giving ethyl 2,2-dimethyl-3-[(2-methylpropan-2-yl)oxycarbonylamino]propanoate (257 mg) as a colorless oil.

(2) Silver(I) oxide (711 mg) and methyl iodide (190 μL) were added to a solution of the compound (251 mg) obtained in (1) above in N,N-dimethylformamide (3 mL), and the mixture was stirred at 90° C. for 3 hours. Silver(I) oxide (356 mg) and methyl iodide (95 μL) were further added thereto, and the resultant mixture was stirred at 90° C. for 2 hours. The reaction solution was filtered through Celite, and the solid was washed with ethyl acetate. The filtrate and the washing solution were combined, and the resultant was concentrated under reduced pressure. The residue was dissolved in ethyl acetate, and washed twice with a saturated aqueous solution of ammonium chloride. The organic layer was dried over anhydrous sodium sulfate, the drying agent was filtered off, and the organic layer was concentrated under reduced pressure. The obtained residue was purified by NH silica gel column chromatography (n-hexane only to n-hexane:ethyl acetate=9:1) to give ethyl 2,2-dimethyl-3-[methyl-[(2-methylpropan-2-yl)oxycarbonyl] amino]propanoate (154 mg) as a colorless oil.

(3) The compound (154 mg) obtained in (2) above was used to perform the reaction according to the method

TABLE 29-3

| Reference Example No. | Structure | Analytical Data |
|---|---|---|
| 92-2 | 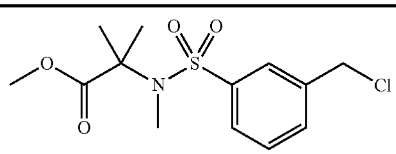 | MS ESI posi: 320[M + H]$^+$, 342[M + Na]$^+$. |
| 92-3 | | $^1$H NMR (400 MHz, CHLOROFORM-d) δ ppm 1.14-1.30 (m, 9 H) 2.97 (d, J = 7.0 Hz, 2 H) 4.07-4.17 (m, 2 H) 4.51 (s, 2 H) 5.11-5.21 (m, 1 H) 7.45-7.54 (m, 1 H) 7.57-7.63 (m, 1 H) 7.74-7.81 (m, 1 H) 7.85-7.90 (m, 1 H). MS ESI posi: 320[M + H]$^+$, 342[M + Na]$^+$. | described in Reference Example 79-1-(2) thereby giving ethyl 2,2-dimethyl-3-(methylamino)propanoate hydrochloride (115 mg) as a grayish white solid.

(4) The compound (32 mg) obtained in (3) above was used to perform the reaction according to the method described in Reference Example 16-1-(1) thereby giving the title compound (40 mg) as a colorless oil.

MS ESI posi: 392[M+H]$^+$, 414[M+Na]$^+$.

Reference Example 94-1

Ethyl 2-[3-(2-hydroxyethyl)phenoxy]-2-methylpropanoate

[Formula 454]

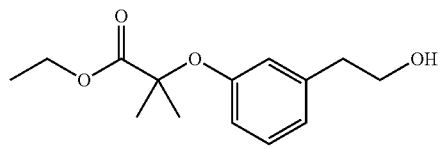

3-(2-Hydroxyethyl)phenol (300 mg) and ethyl 2-bromo-2-methylpropanoate (356 μL) were used to perform the reaction according to the method described in Reference Example 67-1-(1) thereby giving the title compound (137 mg) as a colorless oil.

$^1$H NMR (400 MHz, CHLOROFORM-d) δ ppm 1.25 (t, J=7.1 Hz, 3H) 1.57-1.62 (m, 1H) 1.60 (s, 6H) 2.78-2.85 (m, 2H) 3.79-3.88 (m, 2H) 4.23 (q, J=7.1 Hz, 2H) 6.66-6.72 (m, 1H) 6.73-6.77 (m, 1H) 6.80-6.90 (m, 1H) 7.14-7.20 (m, 1H).

MS ESI posi: 253 [M+H]$^+$, 275 [M+Na]$^+$.

The compound of Reference Example 94-2 below was synthesized using 4-(2-hydroxyethyl)phenol, according to the method described in Reference Example 94-1. The structure, NMR data, and MS data of the compound are shown in Table 29-4.

(1) 2-(3-Bromophenyl)ethanol (1.0 g) was used to perform the reaction according to the method described in Reference Example 32-1-(1) thereby giving 2-[2-(3-bromophenyl)ethoxy]oxane (1.3 g) as a colorless oil.

(2) The compound (620 mg) obtained in (1) above and ethyl 3-oxocyclobutanecarboxylate (300 mg) were used to perform the reaction according to the method described in Reference Example 9-1-(1) thereby giving ethyl 3-hydroxy-3-[3-[2-(oxan-2-yloxy)ethyl]phenyl]cyclobutane-1-carboxylate (250 mg) as a brown oil.

(3) The compound (250 mg) obtained in (2) above was used to perform the reaction according to the method described in Reference Example 1-1-(3) thereby giving the title compound (100 mg) as a colorless oil.

$^1$H NMR (400 MHz, CHLOROFORM-d) δ ppm 1.27 (t, J=7.1 Hz, 3H) 1.37 (t, J=5.9 Hz, 1H) 2.34-2.49 (m, 2H) 2.54-2.68 (m, 2H) 2.86 (t, J=6.4 Hz, 2H) 3.03-3.17 (m, 1H) 3.37-3.51 (m, 1H) 3.87 (td, J=6.4, 5.9 Hz, 2H) 4.15 (q, J=7.1 Hz, 2H) 7.02-7.16 (m, 3H) 7.22-7.31 (m, 1H).

MS ESI posi: 271[M+Na]$^+$, 231[M-OH]$^+$.

Reference Example 95-2

Ethyl 3-[4-(2-hydroxyethyl)phenyl]cyclobutane-1-carboxylate

[Formula 456]

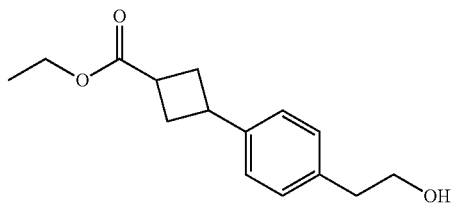

TABLE 29-4

| Reference Example No. | Structure | Analytical Data |
|---|---|---|
| 94-2 | 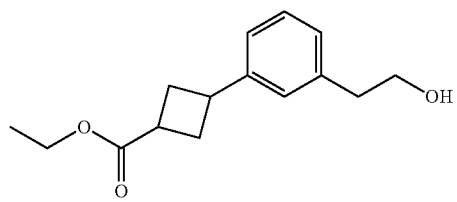 | $^1$H NMR (400 MHz, CHLOROFORM-d) δ ppm 1.26 (t, J = 7.1 Hz, 3 H) 2.80 (t, J = 6.5 Hz, 2 H) 3.82 (t, J = 6.5 Hz, 2 H) 4.24 (q, J = 7.1 Hz, 2 H) 6.80 (d, J = 8.6 Hz, 2 H) 7.09 (d, J = 8.6 Hz, 2 H).<br>MS ESI post: 253[M + H]$^+$, 275[M + Na]$^+$. |

Reference Example 95-1

Ethyl 3-[3-(2-hydroxyethyl)phenyl]cyclobutane-1-carboxylate

[Formula 455]

2-(4-Bromophenyl)ethanol was used to perform the synthesis process according to the method described in Reference Example 95-1 thereby giving a compound (56 mg) of Reference Example 95-2-1, which was the cis form of the title compound, as a colorless oil, and a compound (59 mg) of Reference Example 95-2-2, which was the trans form, as a colorless oil.

Reference Example 95-2-1

Cis Form $^1$H NMR (400 MHz, CHLOROFORM-d) δ ppm 0.88-0.93 (m, 1H) 1.27 (t, J=7.1 Hz, 3H) 2.33-2.47 (m, 2H) 2.52-2.66 (m, 2H) 2.85 (t, J=6.5 Hz, 2H) 3.03-3.16 (m, 1H) 3.34-3.52 (m, 1H) 3.78-3.91 (m, 2H) 4.15 (q, J=7.1 Hz, 2H) 7.15-7.23 (m, 4H).

MS ESI posi: 249[M+H]$^+$.

Reference Example 95-2-2

Trans Form
¹H NMR (400 MHz, CHLOROFORM-d) δ ppm 0.87-0.95 (m, 1H) 1.33-1.40 (m, 3H) 2.26-2.43 (m, 2H) 2.49-2.71 (m, 2H) 2.83-2.88 (m, 2H) 3.08-3.20 (m, 1H) 3.36-3.47 (m, 1H) 3.81-3.91 (m, 2H) 4.10-4.19 (m, 2H) 7.04-7.22 (m, 4H).

The compounds of Reference Examples 96-1 and 96-2 below were synthesized using the corresponding commercially available compound, according to the method described in Reference Example 30-1. The structures, NMR data, and MS data of the compounds are shown in Table 29-5.

Reference Example 98-1

3-(8-Hydroxyoctyl)-1,1-dioxothietane-3-carbonitrile

[Formula 457]

TABLE 29-5

| Reference Example No. | Structure | Analytical Data |
|---|---|---|
| 96-1 | (structure) | ¹H NMR (400 MHz, CHLOROFORM-d) δ ppm 1.17-1.60 (m, 19 H) 1.68-1.89 (m, 3 H) 1.98-2.11 (m, 3 H) 2.17 (s, 2 H) 2.27-2.46 (m, 1 H) 3.12-3.30 (m, 1 H) 3.32-3.59 (m, 2 H) 3.64 (t, J = 6.5 Hz, 2 H) 3.88-3.98 (m, 1 H). |
| 96-2 | (structure) | ¹H NMR (400 MHz, CHLOROFORM-d) δ ppm 1.15-1.41 (m, 14 H) 1.87 (s, 3 H) 2.23 (s, 2 H) 3.64 (t, J = 6.5 Hz, 2 H) 3.76 (s, 3 H) 3.78-3.89 (m, 2 H) 4.19 (d, J = 10.3 Hz, 1 H) 4.39 (d, J = 8.4 Hz, 1 H). MS ESI posi: 286[M + H]⁺. |

The compound of Reference Example 97-1 below was synthesized using the corresponding commercially available compound, according to the method described in Reference Example 31-1. The structure and MS data of the compound are shown in Table 29-6.

(1) Methyl cyanoacetate (1.22 mL) and potassium carbonate (2.83 g) were added to a solution of 2-(8-bromooctoxy)oxane (2.0 g) in N,N-dimethylformamide (27 mL), and the mixture was stirred at 75° C. for 3 hours. A saturated aqueous solution of ammonium chloride was added to the

TABLE 29-6

| Reference Example No. | Structure | Analytical Data |
|---|---|---|
| 97-1 | (structure) | ¹H NMR (400 MHz, CHLOROFORM-d) δ ppm 1.09-1.45 (m, 14 H) 1.48 (s, 9 H) 1.50-1.62 (m, 2 H) 1.93-2.03 (m, 2 H) 2.45 (d, J = 13.9 Hz, 2 H) 2.86-2.99 (m, 2 H) 3.00-3.16 (m, 2 H) 3.64 (t, J = 6.5 Hz, 2 H). MS ESI posi: 385 [M + Na]⁺. | reaction solution, and the resultant mixture was extracted with diethyl ether. The organic layer was sequentially washed with water and brine, and dried over anhydrous magnesium sulfate. After the drying agent was filtered off, the filtrate was concentrated under reduced pressure. The obtained residue was purified by silica gel column chromatography (n-hexane:ethyl acetate=9:1 to 7:3) to give methyl 2-cyano-10-(oxan-2-yloxy)decanoate (1.40 g) as a colorless oil.

(2) To a solution of the compound (1.40 g) obtained in (1) above in acetonitrile (15 mL), 37% formalin (1.52 mL) and triethylamine (63 μL) were added, and the mixture was stirred at 65° C. for 5 hours. The reaction solution was concentrated under reduced pressure, water was added to the obtained residue, and the resultant mixture was extracted with ethyl acetate. The organic layer was washed with brine, and then dried over anhydrous magnesium sulfate. The drying agent was filtered off, and the filtrate was concentrated under reduced pressure. The obtained residue was purified by silica gel column chromatography (n-hexane:ethyl acetate=7:3 to 9:11) to give methyl 2-cyano-2-(hydroxymethyl)-10-(oxan-2-yloxy)decanoate (1.5 g) as a colorless oil.

(3) The compound (1.5 g) obtained in (2) above was used to perform the reaction according to the method described in Reference Example 25-1-(2) thereby giving 2,2-bis(hydroxymethyl)-10-(oxan-2-yloxy)decanenitrile (1.09 g) as a colorless oil.

(4) To a solution of the compound (546 mg) obtained in (3) above in ethyl acetate (8.7 mL), N,N-diisopropylethylamine (1.2 mL) and methanesulfonyl chloride (410 μL) were added under ice cooling, and the mixture was stirred at room temperature overnight. Saturated sodium bicarbonate water was added under ice cooling to stop the reaction, and the resultant mixture was extracted with ethyl acetate. The organic layer was washed with brine, then passed through a phase separator, and concentrated under reduced pressure. The obtained residue was purified by silica gel column chromatography (n-hexane:ethyl acetate=7:3 to 3:7) to give [2-cyano-2-(methylsulfonyloxymethyl)-10-(oxan-2-yloxy) decyl]methanesulfonate (750 mg) as a colorless oil.

(5) Sodium sulfide nonahydrate (1.92 g) and tetrabutylammonium iodide (118 mg) were added to a solution of the compound (750 mg) obtained in (4) above in N,N-dimethylformamide (16 mL), and the mixture was stirred under a nitrogen atmosphere at 50° C. overnight. Water was added to the reaction solution, the resultant mixture was extracted with ethyl acetate, and then the organic layer was sequentially washed with water and brine, passed through a phase separator, and concentrated under reduced pressure. The obtained residue was purified by silica gel column chromatography (n-hexane:ethyl acetate=19:1 to 4:1) to give 3-[8-(oxan-2-yloxy)octyl]thietane-3-carbonitrile (36 mg) as a colorless oil.

(6) The compound (36 mg) obtained in (5) above was used to perform the reaction according to the method described in Reference Example 31-1-(3) thereby giving 3-[8-(oxan-2-yloxy)octyl]-1,1-dioxothietane-3-carbonitrile (28 mg) as a colorless oil.

(7) The compound (28 mg) obtained in (6) above was used to perform the reaction according to the method described in Reference Example 31-1-(4) thereby giving the title compound (16 mg) as a colorless solid.

$^1$H NMR (600 MHz, CHLOROFORM-d) δ ppm 1.18-1.61 (m, 13H) 2.00-2.06 (m, 2H) 3.62-3.69 (m, 2H) 4.09-4.15 (m, 2H) 4.57-4.63 (m, 2H).

MS ESI/APCI Multi posi: 282[M+Na]$^+$.

MS ESI/APCI Multi nega: 294[M+Cl]$^-$.

Reference Example 99-1 tert-Butyl 3-(8-hydroxyoctyl)oxolane-3-carboxylate

[Formula 458]

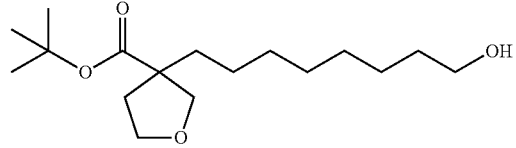

(1) A solution of tert-butyl 3-tetrahydrofurancarboxylate (5.00 g) and 2-(8-bromooctoxy)oxane (8.51 g) in tetrahydrofuran (97 mL) was cooled to −78° C. under a nitrogen atmosphere, and potassium hexamethyldisilazane (0.5 mol/L toluene solution, 90 mL) was added dropwise thereto. The mixture was stirred for 4 hours while the temperature of the mixture was increased to room temperature. A saturated aqueous solution of ammonium chloride was added to the mixture, and the resultant mixture was extracted with diethyl ether. The organic layer was washed with brine, passed through a phase separator, and concentrated under reduced pressure. The obtained residue was purified by silica gel column chromatography (n-hexane:ethyl acetate=19:1 to 3:2) to give a mixture (750 mg) containing tert-butyl 3-[8-(oxan-2-yloxy)octyl]oxolane-3-carboxylate.

(2) The mixture (750 mg) obtained in (1) above was used to perform the reaction according to the method described in Reference Example 31-1-(4) thereby giving the title compound (500 mg) as a colorless oil.

$^1$H NMR (400 MHz, CHLOROFORM-d) δ ppm 1.11-1.40 (m, 12H) 1.45 (s, 9H) 1.42-1.48 (m, 1H) 1.65-1.77 (m, 2H) 2.35-2.46 (m, 2H) 3.51 (d, J=8.7 Hz, 1H) 3.64 (t, J=6.6 Hz, 2H) 3.77-3.91 (m, 2H) 4.07 (d, J=8.7 Hz, 1H).

MS ESI posi: 323 [M+H]$^+$.

The compound of Reference Example 99-2 below was synthesized using 2-tetrahydrofurancarboxylic acid, according to the method described in Reference Example 29-1. The compound of Reference Example 99-3 below was synthesized using methyl oxetane-2-carboxylate, according to the method described in Reference Example 99-1. The structures, NMR data, and MS data of the compounds are shown in Table 29-7.

TABLE 29-7

| Reference Example No. | Structure | Analytical Data |
|---|---|---|
| 99-2 | (structure) | ¹H NMR (400 MHz, CHLOROFORM-d) δ ppm 1.17-1.42 (m, 12 H) 1.47 (s, 9 H) 1.69-1.93 (m, 5 H) 2.15-2.25 (m, 1 H) 3.58-3.68 (m, 2H) 3.93 (t, J = 6.8 Hz, 2 H). MS ESI posi: 323[M + Na]⁺. |
| 99-3 | (structure) | ¹H NMR (400 MHz, CHLOROFORM-d) δ ppm 1.10-1.40 (m, 12 H) 1.94-2.02 (m, 2 H) 3.64 (t, J = 6.6 Hz, 2 H) 3.76 (s, 3 H) 4.43 (d, J = 6.1 Hz, 2 H) 4.89 (d, J = 6.1 Hz, 2 H). MS ESI posi: 245 [M + H]⁺. |

Reference Example 100-1

Ethyl 3-[4-(hydroxymethyl)phenyl]-2,2-dimethyl-propanoate

[Formula 459]

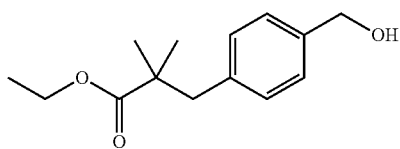

(1) 4-(Bromomethyl)benzoic acid (1.0 g) was used to perform the reaction according to the method described in Reference Example 15-1-(1) thereby giving [4-(bromomethyl)phenyl]methanol (931 mg) as a colorless solid.

(2) The compound (931 mg) obtained in (1) above was used to perform the reaction according to the method described in Reference Example 32-1-(1) thereby giving 2-[[4-(bromomethyl)phenyl]methoxy]oxane (1.14 g) as a colorless oil.

(3) The compound (300 mg) obtained in (2) above was used to perform the reaction according to the method described in Reference Example 29-1-(1) thereby giving ethyl 2,2-dimethyl-3-[4-(oxan-2-yloxymethyl)phenyl]propanoate (300 mg) as a colorless oil.

(4) The compound (300 mg) obtained in (3) above was used to perform the reaction according to the method described in Reference Example 38-1-(4) thereby giving the title compound (164 mg) as a colorless oil.

¹H NMR (400 MHz, CHLOROFORM-d) δ ppm 1.17 (s, 6H) 1.24 (t, J=7.1 Hz, 3H) 1.59 (t, J=5.8 Hz, 1H) 2.85 (s, 2H) 4.12 (q, J=7.1 Hz, 2H) 4.66 (d, J=5.8 Hz, 2H) 7.11 (d, J=7.9 Hz, 2H) 7.26 (d, J=7.9 Hz, 2H).

MS ESI posi: 259[M+Na]⁺, 219[M-OH]⁺.

Reference Example 101-1

Methyl 3-[[4-(2-hydroxyethyl)phenyl]methyl]oxetane-3-carboxylate

[Formula 460]

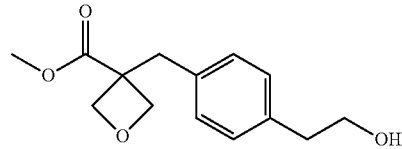

(1) 2-[4-(Bromomethyl)phenyl]acetic acid (2.34 g) was used to perform the reaction according to the method described in Reference Example 15-1-(1) thereby giving 2-[4-(bromomethyl)phenyl]ethanol (2.17 g) as a colorless solid.

(2) The compound (2.17 g) obtained in (1) above was used to perform the reaction according to the method described in Reference Example 32-1-(1) thereby giving 2-[2-[4-(bromomethyl)phenyl]ethoxy]oxane (2.53 g) as a colorless oil.

(3) The compound (349 mg) obtained in (2) above and methyl oxetane-3-carboxylate (100 μL) were used to perform the reaction according to the method described in Reference Example 29-1-(1) thereby giving methyl 3-[[4-[2-(oxan-2-yloxy)ethyl]phenyl]methyl]oxetane-3-carboxylate (104 mg) as a colorless oil.

(4) The compound (104 mg) obtained in (3) above was used to perform the reaction according to the method described in Reference Example 57-1-(3) thereby giving the title compound (72.8 mg) as a colorless oil.

¹H NMR (400 MHz, CHLOROFORM-d) δ ppm 2.83 (t, J=6.4 Hz, 2H) 3.33 (s, 2H) 3.72 (s, 3H) 3.80-3.89 (m, 2H) 4.59 (d, J=6.4 Hz, 2H) 4.90 (d, J=6.4 Hz, 2H) 7.05 (d, J=7.7 Hz, 2H) 7.14 (d, J=7.7 Hz, 2H).

MS ESI posi: 251 [M+H]⁺, 273 [M+Na]⁺.

Reference Example 101-2

Ethyl 1-[[4-(2-hydroxyethyl)phenyl]methyl]cyclopropane-1-carboxylate

[Formula 461]

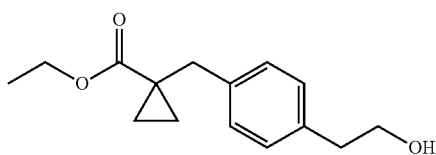

(1) The compound (488 mg) obtained in Reference Example 101-1-(2) and cyclopropanecarbonitrile (100 µL) were used to perform the reaction according to the method described in Reference Example 29-1-(1) thereby giving 1-[[4-[2-(oxan-2-yloxy)ethyl]phenyl]methyl]cyclopropane-1-carbonitrile (172 mg) as a colorless oil.

(2) The compound (172 mg) obtained in (1) above was used to perform the reaction according to the method described in Reference Example 39-1-(2) thereby giving a mixture (165 mg) containing 1-[[4-[2-(oxan-2-yloxy)ethyl]phenyl]methyl]cyclopropane-1-carboxylic acid.

(3) The mixture (165 mg) obtained in (2) above was used to perform the reaction according to the method described in Reference Example 60-1-(1) thereby giving the title compound (45.5 mg) as a colorless oil.

$^1$H NMR (400 MHz, CHLOROFORM-d) δ ppm 0.77-0.82 (m, 2H) 1.18 (t, J=7.1 Hz, 3H) 1.24-1.29 (m, 2H) 2.84 (t, J=6.4 Hz, 2H) 2.95 (s, 2H) 3.80-3.89 (m, 2H) 4.08 (q, J=7.1 Hz, 2H) 7.10-7.15 (m, 2H) 7.17-7.21 (m, 2H).

MS ESI posi: 249[M+H]$^+$, 271 [M+Na]$^+$.

Reference Example 102-1

Methyl 3-[[2-fluoro-3-(hydroxymethyl)phenyl]methyl]oxetane-3-carboxylate

[Formula 462]

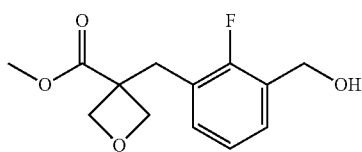

(1) 3-Bromo-2-fluorobenzoic acid (10.4 g) was used to perform the reaction according to the method described in Reference Example 18-1-(2) thereby giving methyl 3-bromo-2-fluorobenzoate (11.0 g) as a colorless oil.

(2) The compound (11.0 g) obtained in (1) above was used to perform the reaction according to the method described in Reference Example 52-1-(2) thereby giving methyl 3-ethenyl-2-fluorobenzoate (7.0 g) as an orange oil.

(3) The compound (7.0 g) obtained in (2) above was used to perform the reaction according to the method described in Reference Example 52-1-(3) thereby giving methyl 3-(1,2-dihydroxyethyl)-2-fluorobenzoate (7.3 g) as a colorless solid.

(4) Water (30 mL) and sodium periodate (7.6 g) were added to a solution of the compound (3.8 g) obtained in (3) above in 1,4-dioxane (59 mL), and the mixture was stirred at room temperature for 1 hour. The mixture was ice-cooled, sodium borohydride (1.0 g) was added thereto, and the resultant mixture was stirred at the same temperature for 15 minutes. A saturated aqueous solution of ammonium chloride was added to stop the reaction, and the resultant mixture was extracted with ethyl acetate. The organic layer was passed through a phase separator, and concentrated under reduced pressure. The obtained residue was purified by silica gel column chromatography (n-hexane:ethyl acetate=9:1 to 1:1) to give methyl 2-fluoro-3-(hydroxymethyl)benzoate (3.3 g) as a brown oil.

(5) The compound (3.3 g) obtained in (4) above was used to perform the reaction according to the method described in Reference Example 32-1-(1) thereby giving methyl 2-fluoro-3-(oxan-2-yloxymethyl)benzoate (4.2 g) as a colorless oil.

(6) The compound (4.2 g) obtained in (5) above was used to perform the reaction according to the method described in Reference Example 25-1-(2) thereby giving [2-fluoro-3-(oxan-2-yloxymethyl)phenyl]methanol (3.3 g) as a colorless oil.

(7) The compound (3.3 g) obtained in (6) above was used to perform the reaction according to the method described in Reference Example 90-1-(2) thereby giving 2-[[3-(bromomethyl)-2-fluorophenyl]methoxy]oxane (1.2 g) as a colorless oil.

(8) The compound (649 mg) obtained in (7) above and methyl oxetane-3-carboxylate (200 mg) were used to perform the reaction according to the method described in Reference Example 29-1-(1) thereby giving methyl 3-[[2-fluoro-3-(oxan-2-yloxymethyl)phenyl]methyl]oxetane-3-carboxylate (161 mg) as a colorless oil.

(9) The compound (161 mg) obtained in (8) above was used to perform the reaction according to the method described in Reference Example 31-1-(4) thereby giving the title compound (100 mg) as a colorless oil.

$^1$H NMR (400 MHz, CHLOROFORM-d) δ ppm 3.38 (s, 2H) 3.71 (s, 3H) 4.62 (d, J=6.4 Hz, 2H) 4.75 (d, J=5.9 Hz, 2H) 4.90 (d, J=6.4 Hz, 2H) 6.97-7.12 (m, 2H) 7.29-7.37 (m, 1H).

MS ESI posi: 277[M+Na]$^+$.

The compound of Reference Example 102-2 below was synthesized using the compound obtained in Reference Example 102-1-(7) and tert-butyl cyclopropanecarboxylate, according to the methods described in Reference Example 29-1-(1) and Reference Example 31-1-(4). The structure, NMR data, and MS data of the compound are shown in Table 29-8.

TABLE 29-8

| Reference Example No. | Structure | Analytical Data |
|---|---|---|
| 102-2 | 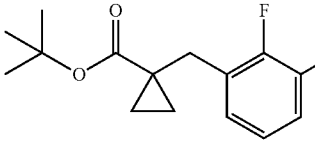 | $^1$H NMR (400 MHz, CHLOROFORM-d) δ ppm 0.72-0.80 (m, 2 H) 1.19-1.26 (m, 2 H) 1.35 (s, 9 H) 2.98 (s, 2 H) 4.75 (s, 2 H) 7.02-7.10 (m, 1 H) 7.20-7.36 (m, 2 H). MS ESI posi: 303 [M + Na]$^+$. |

Reference Example 102-3 Methyl 3-[[2-fluoro-3-(2-hydroxyethyl)phenyl]methyl]oxetane-3-carboxylate

[Formula 463]

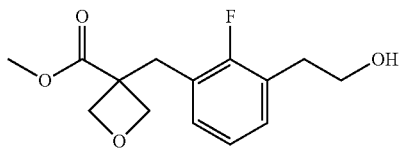

(1) To a solution of the compound (3.5 g) obtained in Reference Example 102-1-(3) in acetone (16 mL), 2,2-dimethoxypropane (16 mL) and pyridinium p-toluenesulfonate (410 mg) were added, and the mixture was stirred at room temperature for 3 hours. A saturated aqueous solution of sodium hydrogen carbonate was added to stop the reaction, and the resultant mixture was extracted with chloroform. The organic layer was separated by a phase separator, and concentrated under reduced pressure. The obtained residue was purified by silica gel column chromatography (n-hexane only to n-hexane:ethyl acetate=4:1) to give methyl 3-(2,2-dimethyl-1,3-dioxolan-4-yl)-2-fluorobenzoate (4.2 g) as a colorless oil.

(2) The compound (4.2 g) obtained in (1) above was used to perform the reaction according to the method described in Reference Example 25-1-(2) thereby giving [3-(2,2-dimethyl-1,3-dioxolan-4-yl)-2-fluorophenyl]methanol (3.6 g) as a colorless oil.

(3) The compound (3.6 g) obtained in (2) above was used to perform the reaction according to the method described in Reference Example 90-1-(2) thereby giving 4-[3-(bromomethyl)-2-fluorophenyl]-2,2-dimethyl-1,3-dioxolane (2.5 g) as a colorless oil.

(4) The compound (747 mg) obtained in (3) above and methyl oxetane-3-carboxylate (300 mg) were used to perform the reaction according to the method described in Reference Example 29-1-(2) thereby giving methyl 3-[[2-fluoro-3-[2-(oxan-2-yloxy)ethyl]phenyl]methyl]oxetane-3-carboxylate (170 mg) as a colorless oil.

(5) The compound (170 mg) obtained in (4) above was used to perform the reaction according to the method described in Reference Example 1-1-(3) thereby giving the title compound (57 mg) as a colorless oil.

$^1$H NMR (400 MHz, CHLOROFORM-d) δ ppm 2.90 (t, J=6.4 Hz, 2H) 3.36 (s, 2H) 3.72 (s, 3H) 3.85 (q, J=6.4 Hz, 2H) 4.61 (d, J=6.4 Hz, 2H) 4.89 (d, J=6.4 Hz, 2H) 6.93-7.04 (m, 2H) 7.11-7.18 (m, 1H).

MS ESI posi: 269[M+H]$^+$, 291 [M+Na]$^+$.

The compound of Reference Example 102-4 below was synthesized using the compound obtained in Reference Example 102-2-(3) and tert-butyl cyclopropanecarboxylate, according to the methods described in Reference Example 29-1-(1) and Reference Example 1-1-(3). The structure, NMR data, and MS data of the compound are shown in Table 29-9.

TABLE 29-9

| Reference Example No. | Structure | Analytical Data |
|---|---|---|
| 102-4 | 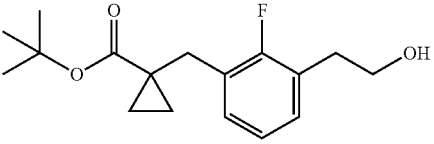 [SMILES: CC(C)(C)OC(=O)C1(Cc2cccc(CCO)c2F)CC1] | $^1$H NMR (400 MHz, CHLOROFORM-d) δ ppm 0.71-0.78 (m, 2 H) 1.18-1.26 (m, 2 H) 1.36 (s, 9 H) 2.91 (t, J = 6.5 Hz, 2 H) 2.98 (s, 2 H) 3.86 (t, J = 6.5 Hz, 2 H) 6.97-7.03 (m, 1 H) 7.05-7.11 (m, 1 H) MS ESI posi: 317 [M + Na]$^+$. |

The compound of Reference Example 103-1 below was synthesized using the compound obtained in Reference Example 32-1-(1) and methyl 2-hydroxypropionate, according to the method described in Reference Example 38-4. The structure, NMR data, and MS data of the compound are shown in Table 29-10.

TABLE 29-10

| Reference Example No. | Structure | Analytical Data |
|---|---|---|
| 103-1 | 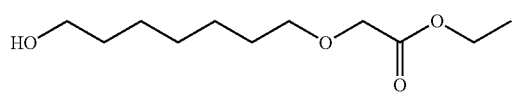 | $^1$H NMR (400 MHz, CHLOROFORM-d) δ ppm 1.22-1.75 (m, 13 H) 2.98-3.42 (m, 1 H) 3.48-3.59 (m, 1 H) 3.60-3.68 (m, 2 H) 3.75 (s, 3 H) 3.96 (q, J = 6.9 Hz, 1 H). MS ESI posi: 219[M + H]$^+$. |

Reference Example 104-1

Ethyl 2-(7-hydroxyheptoxy)acetate

[Formula 464]

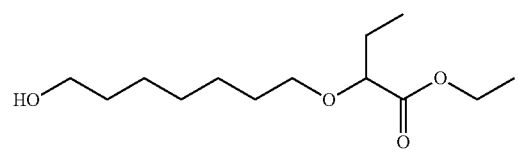

(1) Triethylamine (52.7 mL), N,N-dimethylaminopyridine (1.85 g), and p-toluenesulfonyl chloride (37.9 g) were added to a suspension of heptane-1,7-diol (25 g) in toluene (378 mL) under ice cooling, and the mixture was then stirred at room temperature overnight. A saturated aqueous solution of ammonium chloride was added to this mixture under ice cooling, and the resultant mixture was extracted with ethyl acetate. The organic layer was washed with brine, dried over anhydrous magnesium sulfate, and then filtered. The filtrate was concentrated under reduced pressure, and the obtained residue was purified by silica gel column chromatography (n-hexane:ethyl acetate=3:2 to 1:3) to give 7-hydroxyheptyl 4-methylbenzenesulfonate (31.4 g) as a colorless oil.

(2) The compound (31.4 g) obtained in (1) above was used to perform the reaction according to the method described in Reference Example 32-1-(1) thereby giving 7-(oxan-2-yloxy)heptyl 4-methylbenzenesulfonate (35.8 g) as a pale yellow oil.

(3) The compound (200 mg) obtained in (2) above was used to perform the reaction according to the method described in Reference Example 36-1-(3) at 70° C. thereby giving ethyl 2-[7-(oxan-2-yloxy)heptoxy]acetate (46 mg) as a colorless oil.

(4) The compound (120 mg) obtained in (3) above was used to perform the reaction according to the method described in Reference Example 31-1-(4) thereby giving the title compound (65 mg) as a colorless oil.

$^1$H NMR (400 MHz, CHLOROFORM-d) δ ppm 1.25-1.31 (m, 3H) 1.32-1.45 (m, 6H) 1.56-1.69 (m, 4H) 3.52 (t, J=6.6 Hz, 2H) 3.59-3.68 (m, 2H) 4.06 (s, 2H) 4.22 (q, J=7.1 Hz, 2H).

Reference Example 104-2

Ethyl 2-(7-hydroxyheptoxy)butanoate

[Formula 465]

(1) A solution of the compound (200 mg) obtained in Reference Example 104-1-(3) in tetrahydrofuran (2.2 mL) was cooled to −78° C., lithium hexamethyldisilazane (1.3 mol/L tetrahydrofuran solution, 0.61 mL) was added thereto, the mixture was stirred at the same temperature for 30 minutes, and then ethyl iodide (63.5 μL) was added dropwise thereto. After the end of the dropwise addition, the mixture was stirred for 15 hours while the temperature of the mixture was slowly increased to room temperature. To this mixture, a saturated aqueous solution of ammonium chloride was added, and the resultant mixture was extracted with ethyl acetate. The organic layer was passed through a phase separator, and concentrated under reduced pressure. The obtained residue was purified by silica gel column chromatography (n-hexane:ethyl acetate=49:1 to 4:1) to give a mixture (100 mg) containing ethyl 2-[7-(oxan-2-yloxy)heptoxy]butanoate.

(2) The mixture (100 mg) obtained in (1) above was used to perform the reaction according to the method described in Reference Example 31-1-(4) thereby giving the title compound (55 mg) as a colorless oil.

$^1$H NMR (400 MHz, CHLOROFORM-d) δ ppm 0.97 (t, J=7.5 Hz, 3H) 1.29 (t, J=7.2 Hz, 3H) 1.32-1.42 (m, 6H) 1.57-1.68 (m, 4H) 1.68-1.81 (m, 2H) 3.26-3.37 (m, 1H) 3.50-3.70 (m, 3H) 3.73 (dd, J=7.3, 5.4 Hz, 1H) 4.18-4.28 (m, 2H).

MS ESI posi: 247[M+H]$^+$.

The compounds of Reference Examples 104-3 to 104-5 below were synthesized using the compound obtained in Reference Example 104-1-(2) and the corresponding commercially available alcohol, according to the methods described in Reference Example 104-1-(3) and (4). The compound of Reference Example 104-6 below was synthesized using the corresponding commercially available diol, according to the method described in Reference Example 104-1. The structures, NMR data, and MS data of the compounds are shown in Table 29-11.

TABLE 29-11

| Reference Example No. | Structure | Analytical Data |
|---|---|---|
| 104-3 | HO~~~~~~O-C(=O)-C(CH3)2-O-C(CH3)3 | $^1$H NMR (400 MHz, CHLOROFORM-d) δ ppm 1.32-1.39 (m, 10 H) 1.47 (s, 9 H) 1.55 (s, 6 H) 3.35 (t, J = 6.5 Hz, 2 H) 3.64 (t, J = 6.5 Hz, 2 H). MS ESI/APCI Multi posi: 275[M + H]$^+$. |
| 104-4 | HO~~~~~~~O-C(cyclobutyl)-C(=O)-O-C(CH3)3 | $^1$H NMR (400 MHz, CHLOROFORM-d) δ ppm 1.29-1.43 (m, 6 H) 1.50 (s, 9 H) 1.55-1.64 (m, 4 H) 1.76-1.89 (m, 2 H) 2.09-2.23 (m, 2 H) 2.36-2.46 (m, 2 H) 3.28 (t, J = 6.6 Hz, 2 H) 3.60-3.69 (m, 2 H). MS ESI posi: 309[M + Na]$^+$. |
| 104-5 | HO~~~~~~O-C(cyclopropyl)-C(=O)-O-CH3 | $^1$H NMR (400 MHz, CHLOROFORM-d) δ ppm 1.27-1.43 (m, 4 H) 1.55-1.63 (m, 4 H) 3.57 (t, J = 6.5 Hz, 2 H) 3.58-3.70 (m, 2 H) 3.73 (s, 3 H). MS ESI posi: 231[M + H]$^+$. |
| 104-6 | HO~~~~~~~O-C(CH3)2-C(=O)-O-C(CH3)3 | $^1$H NMR (400 MHz, CHLOROFORM-d) δ ppm 1.29-1.36 (m, 8 H) 1.37 (s, 6 H) 1.47 (s, 9 H) 1.56-1.59 (m, 2 H) 3.35 (t, J = 6.7 Hz, 2 H) 3.58-3.70 (m, 2 H). MS ESI posi: 311[M + Na]$^+$. |

Reference Example 105-1

Methyl 3-(7-hydroxyheptoxy)oxetane-3-carboxylate

[Formula 466]

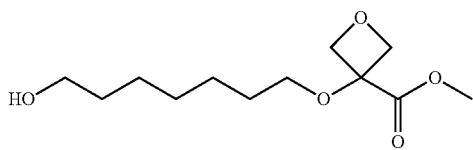

(1) Heptane-1,7-diol (10.0 g) was used to perform the reaction according to the method described in Reference Example 32-1-(1) thereby giving 7-(oxan-2-yloxy)heptan-1-ol (8 g) as a colorless oil.

(2) Rhodium(II) acetate (71.5 mg) was added to a solution of the compound (7.0 g) obtained in (1) above in chloroform (50 mL) while the reaction container was cooled in a water bath. After the mixture was stirred for 5 minutes, a solution of dimethyl diazomalonate (5.1 g) in chloroform (20 mL) was added dropwise thereto over 5 minutes. After the end of the dropwise addition, the mixture was stirred at room temperature for 2 days, a saturated aqueous solution of sodium hydrogen carbonate was added thereto, the resultant mixture was shaken, and the organic layer was separated by a phase separator. The organic layer was concentrated under reduced pressure, and the obtained residue was purified by silica gel column chromatography (n-hexane:ethyl acetate=19:1 to 3:2) to give dimethyl 2-[7-(oxan-2-yloxy)heptoxy]propanedioate (11.5 g) as a colorless oil.

(3) Formalin (37%, 2.4 mL) was slowly added to a solution of the compound (10 g) obtained in (2) above and sodium hydrogen carbonate (243 mg) in methanol (29 mL)/water (14 mL) under ice cooling. After the mixture was stirred at room temperature for 1 hour, triethylamine (4.0 mL) was added thereto, and the resultant mixture was stirred at room temperature for 18 hours. The mixture was concentrated under reduced pressure, and the obtained residue was purified by silica gel column chromatography (n-hexane:ethyl acetate=23:2 to 1:2) to give dimethyl 2-(hydroxymethyl)-2-[7-(oxan-2-yloxy)heptoxy]propanedioate (5.6 g) as a colorless oil.

(4) The compound (5.6 g) obtained in (3) above and tert-butyldiphenylchlorosilane (6.1 g) were used to perform the reaction according to the method described in Reference Example 40-1-(1) thereby giving dimethyl 2-[[tert-butyl (diphenyl)silyl]oxymethyl]-2-[7-(oxan-2-yloxy)heptoxy] propanedioate (10 g) as a colorless oil.

(5) The compound (5.0 g) obtained in (4) above was used to perform the reaction according to the method described in Reference Example 25-1-(2) thereby giving 2-[[tert-butyl (diphenyl)silyl]oxymethyl]-2-[7-(oxan-2-yloxy)heptoxy] propane-1,3-diol (3.5 g) as a colorless oil.

(6) To a solution of the compound (1.0 g) obtained in (5) above in tetrahydrofuran (7.2 mL), n-butyl lithium (1.6 mol/L hexane solution, 1.2 mL) was slowly added under ice cooling, and the mixture was stirred at the same temperature for 20 minutes. To this mixture, a solution of p-toluenesulfonyl chloride (380 mg) in tetrahydrofuran (2 mL) was added, and the resultant mixture was stirred for 1 hour. Thereto, n-butyl lithium (1.6 mol/L hexane solution, 1.2 mL) was further added, and the resultant mixture was stirred under ice cooling for 40 minutes, at room temperature for 10 minutes, at 70° C. for 8 hours, and then at room temperature for 2 days. To this mixture, a saturated aqueous solution of ammonium chloride was added, and the resultant mixture was extracted with diethyl ether. The organic layer was washed with a saturated aqueous solution of ammonium chloride, passed through a phase separator, and concentrated under reduced pressure. The obtained residue was purified by silica gel column chromatography (n-hexane:ethyl acetate=19:1 to 3:2) to give tert-butyl-[[3-[7-(oxan-2-yloxy) heptoxy]oxetan-3-yl]methoxy]-diphenylsilane (630 mg) as a colorless oil.

(7) The compound (630 mg) obtained in (6) above was used to perform the reaction according to the method described in Reference Example 50-1-(3) thereby giving [3-[7-(oxan-2-yloxy)heptoxy]oxetan-3-yl]methanol (360 mg) as a colorless oil.

(8) The compound (360 mg) obtained in (7) above was used to perform the reaction according to the method described in Reference Example 77-1-(4) thereby giving 3-[7-(oxan-2-yloxy)heptoxy]oxetane-3-carboxylic acid (315 mg) as a colorless amorphous substance.

(9) The compound (310 mg) obtained in (8) above was used to perform the reaction according to the method described in Reference Example 12-1-(1) thereby giving a mixture containing methyl 3-[7-(oxan-2-yloxy)heptoxy] oxetane-3-carboxylate.

(10) The mixture obtained in (9) above was used to perform the reaction according to the method described in Reference Example 31-1-(4) thereby giving the title compound (130 mg) as a colorless solid.

¹H NMR (400 MHz, CHLOROFORM-d) δ ppm 1.29-1.75 (m, 10H) 3.37 (t, J=6.5 Hz, 2H) 3.65 (t, J=6.5 Hz, 2H) 3.85 (s, 3H) 4.69 (d, J=6.9 Hz, 2H) 4.86 (d, J=6.9 Hz, 2H).

The compound of Reference Example 106-1 below was synthesized using the corresponding commercially available alcohol, according to the method described in Reference Example 41-1. The structure, NMR data, and MS data of the compound are shown in Table 29-12.

TABLE 29-12

| Reference Example No. | Structure | Analytical Data |
|---|---|---|
| 106-1 | 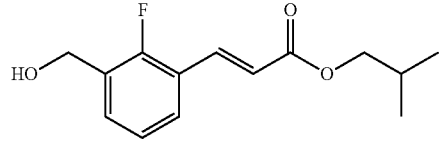 | ¹H NMR (400 MHz, CHLOROFORM-d) δ ppm 1.34 (t, J = 7.1 Hz, 3 H) 1.83 (t, J = 5.9 Hz, 1 H) 4.27 (q, J = 7.1 Hz, 2 H) 4.72 (d, J = 5.9 Hz, 2 H) 6.52 (d, J = 16.2 Hz, 1 H) 7.07-7.20 (m, 2 H) 7.48-7.56 (m, 1 H) 7.79 (d, J = 16.2 Hz, 1 H). MS ESI posi: 225[M + H]⁺. |

Reference Example 107-1

2-Methylpropyl (E)-3-[2-fluoro-3-(hydroxymethyl) phenyl]prop-2-enoate

[Formula 467]

(1) 3-Bromo-2-fluorobenzoic acid (1.0 g) was used to perform the reaction according to the method described in Reference Example 15-1-(1) thereby giving a mixture (1.07 g) containing (3-bromo-2-fluorophenyl)methanol.

(2) The mixture (1.07 g) obtained in (1) above was used to perform the reaction according to the method described in Reference Example 41-1 thereby giving the title compound (640 mg) as a yellow oil.

¹H NMR (400 MHz, CHLOROFORM-d) δ ppm 0.99 (d, J=6.7 Hz, 6H) 1.77-1.83 (m, 1H) 1.94-2.09 (m, 1H) 4.00 (d, J=6.7 Hz, 2H) 4.76-4.83 (m, 2H) 6.55 (d, J=16.2 Hz, 1H) 7.14-7.21 (m, 1H) 7.44-7.54 (m, 2H) 7.83 (d, J=16.2 Hz, 1H).

MS ESI posi: 253 [M+H]⁺, 275 [M+Na]⁺.

The compound of Reference Example 107-2 below was synthesized using commercially available 4-bromo-3-fluorophenylacetic acid, according to the method described in Reference Example 107-1. The structure, NMR data, and MS data of the compound are shown in Table 29-13.

TABLE 29-13

| Reference Example No. | Structure | Analytical Data |
|---|---|---|
| 107-2 | [structure: isobutyl (E)-3-[2-fluoro-4-(2-hydroxyethyl)phenyl]acrylate] | ¹H NMR (400 MHz, CHLOROFORM-d) δ ppm 0.99 (d, J = 6.7 Hz, 6 H) 1.37-1.44 (m, 1 H) 1.93-2.11 (m, 1 H) 2.88 (t, J = 6.4 Hz, 2 H) 3.83-3.93 (m, 2 H) 4.00 (d, J = 6.7 Hz, 2 H) 6.52 (d, J = 16.2 Hz, 1 H) 6.97-7.07 (m, 2 H) 7.43-7.52 (m, 1 H) 7.78 (d, J = 16.2 Hz, 1 H). MS ESI posi: 267[M + H]⁺, 289[M + Na]⁺. |

Reference Example 108-1

Ethyl 2-[4-(hydroxymethyl)phenyl]cyclopropane-1-carboxylate

[Formula 468]

(1) The compound (4.85 g) obtained in Reference Example 44-1-(1) was used to perform the reaction according to the method described in Reference Example 32-1-(1) thereby giving ethyl (E)-3-[4-(oxan-2-yloxymethyl)phenyl]prop-2-enoate (7.49 g) as a colorless oil.

(2) A suspension of trimethylsulfoxonium iodide (4.5 g) in dimethyl sulfoxide (17 mL) was ice-cooled, sodium hydride (60% mineral oil dispersion, 0.83 g) was added thereto under a nitrogen atmosphere, and the mixture was stirred at room temperature for 15 minutes. A solution of the compound (5.0 g) obtained in (1) above in dimethyl sulfoxide (15 mL) was added thereto under ice cooling, and the resultant mixture was stirred at room temperature for 17 hours. A saturated aqueous solution of ammonium chloride was added under ice cooling to stop the reaction, and the resultant mixture was extracted with diethyl ether. The organic layer was passed through a phase separator, and concentrated under reduced pressure. The obtained residue was purified by silica gel column chromatography (n-hexane:ethyl acetate=19:1 to 4:1) to give ethyl 2-[4-(oxan-2-yloxymethyl)phenyl]cyclopropane-1-carboxylate (3.2 g) as a colorless oil.

(3) The compound (3.2 g) obtained in (2) above was used to perform the reaction according to the method described in Reference Example 38-1-(4) thereby giving the title compound (2.05 g) as a colorless solid.

¹H NMR (400 MHz, CHLOROFORM-d) δ ppm 1.28 (t, J=7.1 Hz, 3H) 1.56-1.65 (m, 2H) 1.83-1.93 (m, 1H) 2.47-2.56 (m, 1H) 4.17 (q, J=7.1 Hz, 2H) 4.66 (d, J=5.4 Hz, 2H) 7.10 (d, J=7.9 Hz, 2H) 7.27 (d, J=7.9 Hz, 2H).

MS ESI posi: 203[M-OH]⁺.

Reference Example 109-1

Ethyl 2-[3-fluoro-4-(hydroxymethyl)phenyl]cyclopropane-1-carboxylate

[Formula 469]

(1) 4-Bromo-2-fluorobenzyl alcohol (3.7 g) was used to perform the reaction according to the method described in Reference Example 41-1 thereby giving ethyl (E)-3-[3-fluoro-4-(hydroxymethyl)phenyl]prop-2-enoate (4.0 g) as a yellow solid.

(2) The compound (4.0 g) obtained in (1) above was used to perform the reaction according to the method described in Reference Example 108-1 thereby giving the title compound (1.3 g) as a pale yellow oil.

¹H NMR (400 MHz, CHLOROFORM-d) δ ppm 1.28 (t, J=7.1 Hz, 3H) 1.58-1.64 (m, 1H) 1.67-1.74 (m, 1H) 1.84-1.93 (m, 1H) 2.45-2.54 (m, 1H) 4.17 (q, J=7.1 Hz, 2H) 4.72 (d, J=6.0 Hz, 2H) 6.74-6.82 (m, 1H) 6.84-6.93 (m, 1H) 7.29-7.35 (m, 1H).

MS ESI posi: 221[M-OH]⁺.

Reference Example 109-2

Ethyl 2-[2-fluoro-3-(hydroxymethyl)phenyl]cyclopropane-1-carboxylate (Optically Active Substance)

[Formula 470]

(1) The compound (2.45 g) obtained in Reference Example 107-1-(1) was used to perform the reaction according to the method described in Reference Example 109-1 thereby giving a racemate (360 mg) of the title compound as a colorless oil.

(2) The racemate (115 mg) obtained in (1) above was optically resolved by SFC equipped with a chiral column. A compound (43 mg) of Reference Example 109-2-1, which was a component having a short retention time, was obtained as a colorless solid. A compound (43 mg) of Reference Example 109-2-2, which was a component having a long retention time, was obtained as a colorless solid.

Reference Example 109-2-1 (Isomer Having Short Retention Time, Retention Time 5.27 min)

¹H NMR (400 MHz, CHLOROFORM-d) δ ppm 1.29 (t, J=7.1 Hz, 3H) 1.32-1.38 (m, 1H) 1.57-1.64 (m, 1H) 1.71-1.78 (m, 1H) 1.87-1.97 (m, 1H) 2.62-2.71 (m, 1H) 4.19 (q, J=7.1 Hz, 2H) 4.76 (d, J=4.8 Hz, 2H) 6.87-6.95 (m, 1H) 7.02-7.10 (m, 1H) 7.27-7.32 (m, 1H).

MS ESI posi: 239[M+H]⁺, 261 [M+Na]⁺.

Reference Example 109-2-2 (Isomer Having Long Retention Time, Retention Time: 6.29 min)

¹H NMR (400 MHz, CHLOROFORM-d) δ ppm 1.29 (t, J=7.1 Hz, 3H) 1.32-1.38 (m, 1H) 1.57-1.64 (m, 1H) 1.71-1.78 (m, 1H) 1.87-1.97 (m, 1H) 2.62-2.71 (m, 1H) 4.19 (q, J=7.1 Hz, 2H) 4.76 (d, J=4.8 Hz, 2H) 6.87-6.95 (m, 1H) 7.02-7.10 (m, 1H) 7.27-7.32 (m, 1H).

MS ESI posi: 239[M+H]⁺, 261[M+Na]⁺, 221[M-OH]⁺.

Reference Example 110-1

Ethyl 2-[3-fluoro-4-(2-hydroxyethyl)phenyl]cyclopropane-1-carboxylate

[Formula 471]

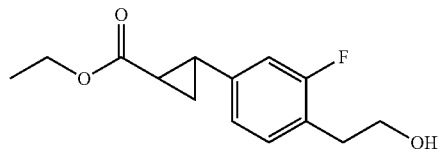

(1) 2-(4-Bromo-2-fluorophenyl)acetic acid (3.0 g) was used to perform the reaction according to the method described in Reference Example 107-1 thereby giving ethyl (E)-3-[3-fluoro-4-(2-hydroxyethyl)phenyl]prop-2-enoate (2.7 g) as a colorless solid.

(2) The compound (1.0 g) obtained in (1) above was used to perform the reaction according to the method described in Reference Example 108-1 thereby giving the title compound (150 mg) as a colorless solid.

¹H NMR (400 MHz, CHLOROFORM-d) δ ppm 1.23-1.39 (m, 5H) 1.56-1.63 (m, 1H) 1.82-1.91 (m, 1H) 2.43-2.53 (m, 1H) 2.88 (t, J=6.5 Hz, 2H) 3.84 (td, J=6.5, 6.1 Hz, 2H) 4.17 (q, J=7.1 Hz, 2H) 6.77 (d, J=10.9 Hz, 1H) 6.85 (d, J=7.9 Hz, 1H) 7.10-7.19 (m, 1H).

MS ESI posi: 253 [M+H]⁺.

The compounds of Reference Examples 110-2 and 110-3 below were synthesized using the corresponding commercially available carboxylic acid, according to the method described in Reference Example 110-1. The structures, NMR data, and MS data of the compounds are shown in Table 29-14.

TABLE 29-14

| Reference Example No. | Structure | Analytical Data |
|---|---|---|
| 110-2 | ethyl 2-[4-fluoro-3-(2-hydroxyethyl)phenyl]cyclopropane-1-carboxylate | ¹H NMR (400 MHz, CHLOROFORM-d) δ ppm 1.29 (t, J = 7.1 Hz, 3 H) 1.31-1.38 (m, 1 H) 1.59 (dt, J = 9.4, 4.9 Hz, 1 H) 1.90-1.98 (m, 1 H) 2.58-2.67 (m, 1 H) 2.80 (t, J = 6.4 Hz, 2 H) 3.78-3.87 (m, 2 H) 4.18 (q, J = 7.1 Hz, 2 H) 6.82 (dd, J = 7.2, 1.5 Hz, 1 H) 6.92-7.00 (m, 1 H) 7.00-7.07 (m, 1 H). MS ESI posi: 253[M + H]⁺, 275[M + Na]⁺. |
| 110-3 | ethyl 2-[2-fluoro-3-(2-hydroxyethyl)phenyl]cyclopropane-1-carboxylate | ¹H NMR (400 MHz, CHLOROFORM-d) δ ppm 1.25-1.40 (m, 5 H) 1.57-1.64 (m, 1 H) 1.87-1.96 (m, 1 H) 2.62-2.72 (m, 1 H) 2.92 (t, J = 6.4 Hz, 2 H) 3.83-3.91 (m, 2 H) 4.18 (q, J = 7.2 Hz, 2 H) 6.80-6.87 (m, 1 H) 6.92-7.05 (m, 1 H) 7.06-7.12 (m, 1 H). MS ESI posi: 253[M + H]⁺, 275[M + Na]⁺. |

Reference Example 110-4

The compound of Reference Example 110-1 was optically resolved by HPLC equipped with a chiral column.

Reference Example 110-4-1 (Isomer Having Short Retention Time, Retention Time: 4.58 min)

¹H NMR (400 MHz, CHLOROFORM-d) δ ppm 1.23-1.39 (m, 5H) 1.56-1.63 (m, 1H) 1.82-1.91 (m, 1H) 2.43-2.53 (m, 1H) 2.88 (t, J=6.5 Hz, 2H) 3.84 (td, J=6.5, 6.1 Hz, 2H) 4.17 (q, J=7.1 Hz, 2H) 6.77 (d, J=10.9 Hz, 1H) 6.85 (d, J=7.9 Hz, 1H) 7.10-7.19 (m, 1H).

MS ESI posi: 253 [M+H]⁺.

Reference Example 110-4-2 (Isomer Having Long Retention Time, Retention Time: 5.40 min)

¹H NMR (400 MHz, CHLOROFORM-d) δ ppm 1.23-1.39 (m, 5H) 1.56-1.63 (m, 1H) 1.82-1.91 (m, 1H) 2.43-2.53

(m, 1H) 2.88 (t, J=6.5 Hz, 2H) 3.84 (td, J=6.5, 6.1 Hz, 2H) 4.17 (q, J=7.1 Hz, 2H) 6.77 (d, J=10.9 Hz, 1H) 6.85 (d, J=7.9 Hz, 1H) 7.10-7.19 (m, 1H).

MS ESI posi: 253 [M+H]⁺.

Reference Example 110-5

The compound of Reference Example 110-3 was optically resolved by HPLC equipped with a chiral column.

Reference Example 110-5-1 (Isomer Having Short Retention Time, Retention Time: 4.62 min)

$^1$H NMR (400 MHz, CHLOROFORM-d) δ ppm 1.24-1.40 (m, 5H) 1.56-1.63 (m, 1H) 1.86-1.97 (m, 1H) 2.61-2.72 (m, 1H) 2.92 (t, J=6.5 Hz, 2H) 3.83-3.91 (m, 2H) 4.18 (q, J=7.2 Hz, 2H) 6.79-6.88 (m, 1H) 6.95-7.04 (m, 1H) 7.05-7.13 (m, 1H).

MS ESI posi: 253 [M+H]⁺, 275 [M+Na]⁺.

Reference Example 110-5-2 (Isomer Having Long Retention Time, Retention Time: 6.37 min)

$^1$H NMR (400 MHz, CHLOROFORM-d) δ ppm 1.24-1.42 (m, 5H) 1.56-1.64 (m, 1H) 1.87-1.96 (m, 1H) 2.62-2.72 (m, 1H) 2.92 (t, J=6.5 Hz, 2H) 3.83-3.92 (m, 2H) 4.18 (q, J=7.2 Hz, 2H) 6.79-6.88 (m, 1H) 6.96-7.03 (m, 1H) 7.05-7.13 (m, 1H).

MS ESI posi: 253 [M+H]⁺, 275 [M+Na]⁺.

Reference Example 111-1

Ethyl cis-2-[4-fluoro-3-(2-hydroxyethyl)phenyl]cyclopropane-1-carboxylate

[Formula 472]

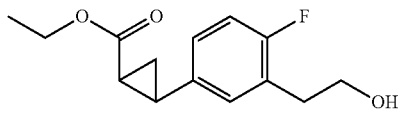

(1) 2-(5-Bromo-2-fluorophenyl)acetic acid (6.0 g) was used to perform the reaction according to the method described in Reference Example 15-1-(1) thereby giving 2-(5-bromo-2-fluorophenyl)ethanol (6.0 g) as a colorless oil.

(2) The compound (6.0 g) obtained in (1) above was used to perform the reaction according to the method described in Reference Example 40-1-(1) thereby giving 2-(5-bromo-2-fluorophenyl)ethoxy-tert-butyl-dimethylsilane (8.6 g) as a colorless oil.

(3) The compound (3.5 g) obtained in (2) above was used to perform the reaction according to the method described in Reference Example 52-1-(2) thereby giving tert-butyl-[2-(5-ethenyl-2-fluorophenyl)ethoxy]-dimethylsilane (1.8 g) as a pale yellow oil.

(4) Palladium(II) acetate (0.15 g) was added to a solution of the compound (1.8 g) obtained in (3) above in tetrahydrofuran (22 mL), the mixture was stirred, and a solution of ethyl diazoacetate (15% toluene solution, 8.3 mL) in diethyl ether (5 mL) was slowly added dropwise thereto under a nitrogen atmosphere over about 25 minutes. After the mixture was stirred at room temperature for 18 hours, palladium (II) acetate (0.15 g) was further added thereto, and a solution of ethyl diazoacetate (15% toluene solution, 8.3 mL) in diethyl ether (5 mL) was added dropwise thereto. The mixture was stirred at room temperature for 20 hours, and then concentrated under reduced pressure. The obtained residue was purified by silica gel column chromatography (n-hexane only to n-hexane:ethyl acetate=9:1) to give a mixture (1.82 g) containing ethyl 2-[3-[2-[tert-butyl(dimethyl)silyl]oxyethyl]-4-fluorophenyl]cyclopropane-1-carboxylate.

(5) Water (3.0 mL) and acetic acid (5.0 mL) were added to a solution of the mixture (1.82 g) obtained in (4) above in tetrahydrofuran (3 mL), and the mixture was stirred at room temperature for 20 hours. The mixture was diluted with water, and adjusted to basic condition with an aqueous solution of 10% sodium hydrogen carbonate, and the resultant mixture was extracted with chloroform. The organic layer was separated by a phase separator, and concentrated under reduced pressure. The obtained residue was repeatedly purified by silica gel column chromatography (n-hexane:ethyl acetate=9:1 to 1:4) to give the title compound (497 mg) as a colorless oil. In addition, a compound (505 mg) of Reference Example 111-1-2, which was the trans isomer, was obtained as a colorless oil.

$^1$H NMR (400 MHz, CHLOROFORM-d) δ ppm 1.03 (t, J=7.1 Hz, 3H) 1.22-1.39 (m, 2H) 1.61-1.70 (m, 1H) 2.00-2.11 (m, 1H) 2.47-2.58 (m, 1H) 2.81-2.94 (m, 2H) 3.76-3.97 (m, 4H) 6.89-6.97 (m, 1H) 7.08-7.17 (m, 2H).

MS ESI posi: 253 [M+H]⁺, 275 [M+Na]⁺.

Reference Example 111-2

Ethyl trans-2-[4-fluoro-3-(2-hydroxyethyl)phenyl]cyclopropane-1-carboxylate (Optically Active Substance)

[Formula 473]

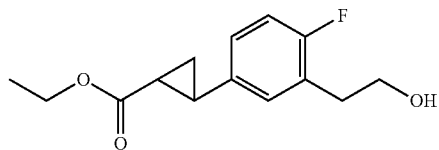 [SMILES: CCOC(=O)C1CC1c1cc(CCO)ccc1F]

The compound of Reference Example 111-1-2 was optically resolved by HPLC equipped with a chiral column.

Reference Example 111-2-1 (Isomer Having Short Retention Time, Retention Time: 6.06 min)

$^1$H NMR (400 MHz, CHLOROFORM-d) δ ppm 1.21-1.32 (m, 4H) 1.53-1.61 (m, 1H) 1.75-1.92 (m, 1H) 2.43-2.54 (m, 1H) 2.88 (t, J=6.5 Hz, 2H) 3.86 (t, J=6.5 Hz, 2H) 4.17 (q, J=7.1 Hz, 2H) 6.90-7.02 (m, 3H).

MS ESI posi: 253 [M+H]⁺, 275 [M+Na]⁺.

Reference Example 111-2-2 (Isomer Having Long Retention Time, Retention Time: 6.81 min)

$^1$H NMR (400 MHz, CHLOROFORM-d) δ ppm 1.21-1.32 (m, 4H) 1.53-1.61 (m, 1H) 1.75-1.92 (m, 1H) 2.43-2.54 (m, 1H) 2.88 (t, J=6.5 Hz, 2H) 3.86 (t, J=6.5 Hz, 2H) 4.17 (q, J=7.1 Hz, 2H) 6.90-7.02 (m, 3H).

MS ESI posi: 253 [M+H]⁺, 275 [M+Na]⁺.

Reference Example 111-3

Ethyl cis-2-[3-fluoro-5-(2-hydroxyethyl)phenyl]cyclopropane-1-carboxylate

[Formula 474]

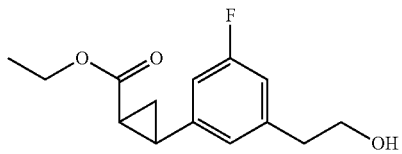

2-(3-Bromo-5-fluorophenyl)acetic acid (4.12 g) was used to perform the synthesis process according to the method described in Reference Example 111-1 thereby giving the title compound (565 mg) as a colorless oil. In addition, a compound (610 mg) of Reference Example 111-3-2, which was the trans isomer, was obtained as a colorless oil.

$^1$H NMR (400 MHz, CHLOROFORM-d) δ ppm 1.04 (t, J=7.1 Hz, 3H) 1.29-1.40 (m, 1H) 1.63-1.73 (m, 1H) 1.99-2.18 (m, 1H) 2.47-2.60 (m, 1H) 2.82 (t, J=6.3 Hz, 2H) 3.75-3.99 (m, 4H) 6.73-6.95 (m, 3H).

MS ESI posi: 253 [M+H]$^+$, 275 [M+Na]$^+$.

Reference Example 111-4

Ethyl trans-2-[3-fluoro-5-(2-hydroxyethyl)phenyl]cyclopropane-1-carboxylate (Optically Active Substance)

[Formula 475]

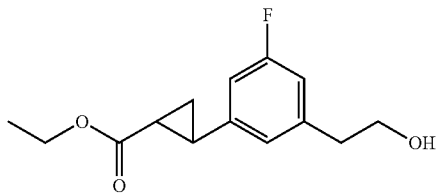

The compound of Reference Example 111-3-2 was optically resolved by HPLC equipped with a chiral column.

Reference Example 111-4-1 (Isomer Having Short Retention Time, Retention Time: 4.51 min)

$^1$H NMR (400 MHz, CHLOROFORM-d) δ ppm 1.28 (t, J=6.9 Hz, 3H) 1.49-1.70 (m, 2H) 1.84-1.93 (m, 1H) 2.44-2.52 (m, 1H) 2.83 (t, J=6.4 Hz, 2H) 3.86 (t, J=6.4 Hz, 2H) 4.17 (q, J=6.9 Hz, 2H) 6.58-6.67 (m, 1H) 6.71-6.86 (m, 2H).

MS ESI posi: 253 [M+H]$^+$, 275 [M+Na]$^+$.

Reference Example 111-4-2 (Isomer Having Long Retention Time, Retention Time: 5.42 min)

$^1$H NMR (400 MHz, CHLOROFORM-d) δ ppm 1.28 (t, J=6.9 Hz, 3H) 1.49-1.70 (m, 2H) 1.84-1.93 (m, 1H) 2.44-2.52 (m, 1H) 2.83 (t, J=6.4 Hz, 2H) 3.86 (t, J=6.4 Hz, 2H) 4.17 (q, J=6.9 Hz, 2H) 6.58-6.67 (m, 1H) 6.71-6.86 (m, 2H).

MS ESI posi: 253 [M+H]$^+$, 275 [M+Na]$^+$.

Reference Example 112-1

Ethyl 6-(5-hydroxypentyl)pyridine-2-carboxylate

[Formula 476]

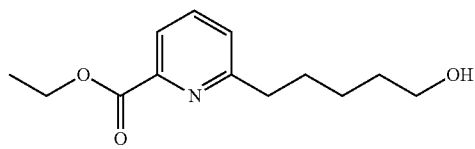

(1) Ethyl 6-bromopyridine-2-carboxylate (800 mg) was used to perform the reaction according to the method described in Reference Example 46-1-(1) in a tetrahydrofuran solvent at room temperature thereby giving ethyl 6-(5-hydroxypent-1-ynyl)pyridine-2-carboxylate (280 mg) as a pale yellow oil.

(2) The compound (280 mg) obtained in (1) above was used to perform the reaction according to the method described in Reference Example 1-1-(3) thereby giving the title compound (130 mg) as a colorless oil.

$^1$H NMR (400 MHz, CHLOROFORM-d) δ ppm 1.37-1.50 (m, 5H) 1.60-1.69 (m, 2H) 1.73-1.87 (m, 2H) 2.92 (t, J=7.8 Hz, 2H) 3.66 (t, J=6.5 Hz, 2H) 4.47 (q, J=7.1 Hz, 2H) 7.33 (d, J=7.8 Hz, 1H) 7.73 (dd, J=7.8, 7.7 Hz, 1H) 7.93 (d, J=7.7 Hz, 1H).

MS ESI posi: 238[M+H]$^+$.

The compounds of Reference Examples 112-2 and 112-3 below were synthesized using the corresponding commercially available aryl bromide, according to the method described in Reference Example 112-1. The structures, NMR data, and MS data of the compounds are shown in Table 29-15.

TABLE 29-15

| Reference Example No. | Structure | Analytical Data |
|---|---|---|
| 112-2 | ![structure] | ¹H NMR (400 MHz, CHLOROFORM-d) δ ppm 1.38-1.49 (m, 2 H) 1.59-1.77 (m, 4 H) 2.71 (t, J = 7.7 Hz, 2 H) 3.65 (t, J = 6.2 Hz, 2 H) 4.00 (s, 3 H) 7.64 (d, J = 7.9 Hz, 1 H) 8.06 (d, J = 7.9 Hz, 1 H) 8.56 (s, 1 H). MS ESI posi: 224[M + H]⁺. |
| 112-3 | ![structure] | ¹H NMR (400 MHz, CHLOROFORM-d) δ ppm 1.30 (t, J = 5.2 Hz, 1 H) 1.82-1.98 (m, 2 H) 2.79 (t, J = 7.8 Hz, 2 H) 3.64-3.75 (m, 2 H) 3.91 (s, 3 H) 7.07 (t, J = 9.2 Hz, 1 H) 7.85-8.01 (m, 2 H). MS ESI posi: 235[M + H]⁺. |

Reference Example 113-1

Ethyl 7-(2-hydroxyethyl)-3,4-dihydro-2H-chromene-2-carboxylate

[Formula 477]

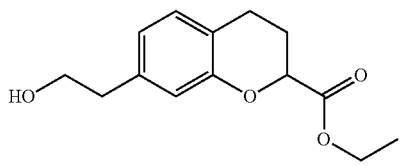

(1) The compound (1.00 g) obtained in Reference Example 53-1 was used to perform the reaction according to the method described in Reference Example 63-1-(1) thereby giving ethyl 7-formyl-3,4-dihydro-2H-chromene-2-carboxylate (962 mg) as a colorless oil.

(2) To a solution of (methoxymethyl)triphenylphosphonium chloride (1.01 g) in toluene (6.5 mL), tert-butoxy potassium (330 mg) was added under an argon atmosphere, and the mixture was stirred at room temperature for 1 hour. To this reaction solution, a solution of the compound (459 mg) obtained in (1) above in toluene (4.0 mL) was added under ice cooling, and the resultant mixture was stirred at room temperature for 1 hour. The reaction system was ice-cooled again, a saturated aqueous solution of ammonium chloride was added to stop the reaction, and the resultant mixture was extracted with ethyl acetate. The organic layer was passed through a phase separator, and concentrated under reduced pressure. The obtained residue was purified by silica gel column chromatography (n-hexane only to n-hexane:ethyl acetate=9:1) to give ethyl 7-[(E)-2-methoxyethenyl]-3,4-dihydro-2H-chromene-2-carboxylate (230 mg) as a colorless oil.

(3) Water (1.0 mL) and concentrated hydrochloric acid (220 μL) were added to a solution of the compound (230 mg) obtained in (2) above in acetonitrile (8.0 mL), and the mixture was stirred at room temperature for 4 hours. A saturated aqueous solution of sodium hydrogen carbonate was added to the mixture, and the organic solvent was distilled off under reduced pressure. The residual aqueous layer was extracted with chloroform. The organic layer was separated by a phase separator and concentrated under reduced pressure to give a mixture (241 mg) containing ethyl 7-(2-oxoethyl)-3,4-dihydro-2H-chromene-2-carboxylate.

(4) The mixture (241 mg) obtained in (3) above was used to perform the reaction according to the method described in Reference Example 53-1-(6) thereby giving the title compound (131 mg) as a colorless solid.

¹H NMR (400 MHz, CHLOROFORM-d) δ ppm 1.30 (t, J=7.1 Hz, 3H) 2.10-2.33 (m, 2H) 2.66-2.90 (m, 4H) 3.71-3.98 (m, 2H) 4.20-4.40 (m, 2H) 4.66-4.74 (m, 1H) 6.74 (d, J=7.8 Hz, 1H) 6.82 (s, 1H) 6.98 (d, J=7.8 Hz, 1H).

MS ESI posi: 251 [M+H]⁺, 273 [M+Na]⁺.

Reference Example 114-1

Ethyl 6-(2-hydroxyethyl)-3,4-dihydro-2H-chromene-2-carboxylate

[Formula 478]

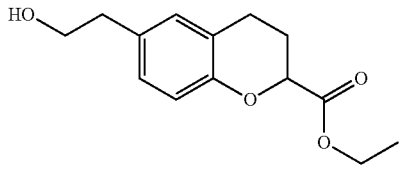

(1) The compound (513 mg) obtained in Reference Example 60-2-(1) was used to perform the reaction according to the method described in Reference Example 52-1-(2) thereby giving ethyl 6-ethenyl-3,4-dihydro-2H-chromene-2-carboxylate (343 mg) as a colorless oil.

(2) The compound (343 mg) obtained in (1) above was used to perform the reaction according to the method described in Reference Example 52-1-(3) thereby giving ethyl 6-(1,2-dihydroxyethyl)-3,4-dihydro-2H-chromene-2-carboxylate (370 mg) as a colorless oil.

(3) The compound (370 mg) obtained in (2) above was used to perform the reaction according to the method described in Reference Example 1-1-(3) thereby giving the title compound (91 mg) as a colorless oil.

¹H NMR (400 MHz, CHLOROFORM-d) δ ppm 1.23-1.33 (m, 4H) 2.12-2.33 (m, 2H) 2.66-2.91 (m, 4H) 3.75-3.90 (m, 2H) 4.20-4.33 (m, 1H) 4.64-4.74 (m, 1H) 6.84-6.92 (m, 2H) 6.98 (d, J=8.1 Hz, 1H).

MS ESI posi: 251 [M+H]⁺, 273 [M+Na]⁺.

427
Reference Example 115-1

Methyl 8-(2-hydroxyethyl)-3,4-dihydro-2H-chromene-3-carboxylate

[Formula 479]

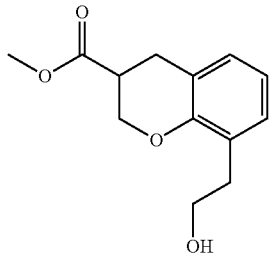

(1) 8-Bromo-3,4-dihydro-2H-chromene-3-carboxylic acid (850 mg) was used to perform the reaction according to the method described in Reference Example 12-1-(1) thereby giving methyl 8-bromo-3,4-dihydro-2H-chromene-3-carboxylate (700 mg) as a pale yellow oil.

(2) The compound (300 mg) obtained in (1) above was used to perform the reaction according to the method described in Reference Example 52-1-(2) thereby giving methyl 8-ethenyl-3,4-dihydro-2H-chromene-3-carboxylate (215 mg) as a pale yellow oil.

(3) The compound (210 mg) obtained in (2) above was dissolved in acetone (971 µL), acetonitrile (971 µL), and water (971 µL). To this mixture, osmium tetroxide (supported by microcapsules, 10% osmium, 124 mg) and 4-methylmorpholine-N-oxide (137 mg) were added under ice cooling, and the resultant mixture was stirred at room temperature for 14 hours, and at 60° C. for 1.5 hours. To the mixture, 4-methylmorpholine-N-oxide (114 mg) was added, and the resultant mixture was stirred at room temperature for 1 hour, and at 80° C. for 3.5 hours. The mixture was cooled to room temperature, and the catalyst was filtered off and washed with ethyl acetate. The filtrate and the washing solution were combined, and the resultant was concentrated under reduced pressure. The obtained residue was purified by silica gel column chromatography (n-hexane:ethyl acetate=22:3 to ethyl acetate only) to give a mixture (30 mg) containing methyl 8-(1,2-dihydroxyethyl)-3,4-dihydro-2H-chromene-3-carboxylate.

(4) The mixture (30 mg) obtained in (3) above was used to perform the reaction according to the method described in Reference Example 45-1-(3) thereby giving the title compound (15 mg) as a colorless solid.

$^1$H NMR (400 MHz, CHLOROFORM-d) δ ppm 2.87 (t, J=6.4 Hz, 2H) 2.98-3.17 (m, 3H) 3.75 (s, 3H) 3.80-3.88 (m, 2H) 4.07-4.18 (m, 1H) 4.44-4.51 (m, 1H) 6.79-6.88 (m, 1H) 6.95-7.06 (m, 2H).

MS ESI posi: 237[M+H]$^+$, 259[M+Na]$^+$, 219[M-OH]$^+$.

428
Reference Example 116-1

Ethyl 7-(hydroxymethyl)-3,4-dihydro-2H-chromene-3-carboxylate

[Formula 480]

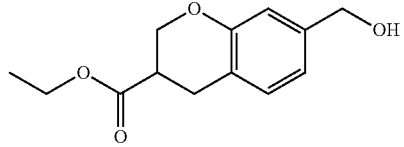

(1) Lithium hexamethyldisilazane (1 mol/L tetrahydrofuran solution, 4.60 mL) was added to a solution of 7-bromo-3,4-dihydro-2H-benzofuran-4-one (950 mg) in tetrahydrofuran (13.9 mL) under a nitrogen atmosphere at −78° C., and the mixture was stirred at the same temperature for 30 minutes. Ethyl cyanoformate (455 µL) was added thereto, and the resultant mixture was stirred under ice cooling for 2 hours. The mixture was cooled to −78° C. again, lithium hexamethyldisilazane (1 mol/L tetrahydrofuran solution, 4.60 mL) was added thereto, and the resultant mixture was stirred under ice cooling for 2 hours. A saturated aqueous solution of ammonium chloride was added to stop the reaction, and the resultant mixture was extracted with chloroform. The organic layer was separated by a phase separator, and concentrated under reduced pressure. The obtained residue was purified by silica gel column chromatography (n-hexane:ethyl acetate=4:1 to 2:3) to give ethyl 7-bromo-4-oxo-2,3-dihydrochromene-3-carboxylate (630 mg) as a colorless solid.

(2) The compound (630 mg) obtained in (1) above was used to perform the reaction according to the method described in Reference Example 53-1-(6) thereby giving ethyl 7-bromo-4-hydroxy-3,4-dihydro-2H-chromene-3-carboxylate (330 mg) as a colorless solid.

(3) A solution of the compound (330 mg) obtained in (2) above in chloroform (11 mL) was ice-cooled under a nitrogen atmosphere, diphenylbis[1-phenyl-1-(trifluoromethyl)-2,2,2-trifluoroethoxy]sulfur(IV) (1.11 g) was added thereto, and the resultant mixture was stirred at room temperature for 5.5 hours. The mixture was concentrated under reduced pressure, and the obtained residue was purified by silica gel column chromatography (n-hexane:ethyl acetate=4:1 to 2:3) to give ethyl 7-bromo-2H-chromene-3-carbosylate (293 mg) as a colorless solid.

(4) In a test tube for microwave reaction, the compound (293 mg) obtained in (3) above, N-formylsaccharin (328 mg), sodium carbonate (165 mg), triethylsilane (215 µL), 1,4-bis(diphenylphosphino)butane (66.2 mg), and palladium (II) acetate (23.2 mg) were mixed in N,N-dimethylformamide (2.59 mL), and the air in the container was purged with nitrogen and the container was sealed. The mixture was stirred at 110° C. for 2.5 hours under microwave irradiation. After cooling to room temperature, the mixture was poured into a saturated aqueous solution of ammonium chloride, and the resultant mixture was extracted with an ethyl acetate:toluene=1:1 mixed solvent. The organic layer was passed through a phase separator, and concentrated under reduced pressure. The obtained residue was purified by silica gel column chromatography (n-hexane:ethyl acetate=9:1 to 3:2) to give ethyl 7-formyl-2H-chromene-3-carboxylate (50 mg) as a yellow solid.

(5) The compound (50 mg) obtained in (4) above was used to perform the reaction according to the method described in Reference Example 54-1-(3) thereby giving the title compound (28 mg) as a colorless oil.

$^1$H NMR (400 MHz, CHLOROFORM-d) δ ppm 1.29 (t, J=7.1 Hz, 3H) 2.94-3.12 (m, 3H) 4.08-4.15 (m, 1H) 4.20 (q, J=7.1 Hz, 2H) 4.38-4.49 (m, 1H) 4.61 (s, 2H) 6.80-6.92 (m, 2H) 7.05-7.11 (m, 1H).

MS ESI posi: 259[M+Na]$^+$, 219[M-OH]$^+$.

Reference Example 117-1

Ethyl 7-(2-hydroxyethyl)-3,4-dihydro-2H-chromene-3-carboxylate

[Formula 481]

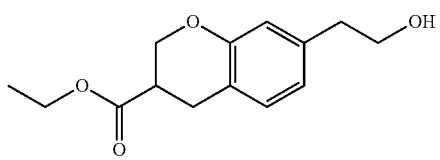

(1) 7-Bromo-3,4-dihydro-2H-benzofuran-4-one (2.5 g) was used to perform the reaction according to the method described in Reference Example 52-1-(2) thereby giving 7-ethenyl-2,3-dihydrochromen-4-one (1.64 g) as a colorless oil.

(2) The compound (1.64 g) obtained in (1) above was used to perform the reaction according to the method described in Reference Example 52-1-(3) thereby giving 7-(1,2-dihydroxyethyl)-2,3-dihydrochromen-4-one (2.18 g) as a colorless solid.

(3) The compound (2.18 g) obtained in (2) above was used to perform the reaction according to the method described in Reference Example 102-2-(1) thereby giving 7-(2,2-dimethyl-1,3-dioxolan-4-yl)-2,3-dihydrochromen-4-one (1.83 g) as a colorless oil.

(4) The compound (1.83 g) obtained in (3) above was used to perform the reaction according to the method described in Reference Example 116-1-(1) thereby giving ethyl 7-(2,2-dimethyl-1,3-dioxolan-4-yl)-4-oxo-2,3-dihydrochromene-3-carboxylate (1.55 g) as a colorless oil.

(5) The compound (1.55 g) obtained in (4) above was used to perform the reaction according to the method described in Reference Example 53-1-(6) thereby giving ethyl 7-(2,2-dimethyl-1,3-dioxolan-4-yl)-4-hydroxy-3,4-dihydro-2H-chromene-3-carboxylate (1.05 g) as a colorless oil.

(6) The compound (120 mg) obtained in (5) above was used to perform the reaction according to the method described in Reference Example 1-1-(3) thereby giving the title compound (92 mg) as a colorless oil.

$^1$H NMR (400 MHz, CHLOROFORM-d) δ ppm 1.29 (t, J=7.1 Hz, 3H) 1.37 (t, J=5.9 Hz, 1H) 2.79 (t, J=6.5 Hz, 2H) 2.95-3.09 (m, 3H) 3.84 (td, J=6.5, 5.9 Hz, 2H) 4.05-4.15 (m, 1H) 4.20 (q, J=7.1 Hz, 2H) 4.38-4.48 (m, 1H) 6.68-6.78 (m, 2H) 7.03 (d, J=7.7 Hz, 1H).

MS ESI posi: 251 [M+H]$^+$, 233 [M-OH]$^+$.

The compound of Reference Example 117-2 below was synthesized using the corresponding commercially available bromo-3,4-dihydro-2H-benzofuranone, according to the method described in Reference Example 117-1. The structure, NMR data, and MS data of the compound are shown in Table 29-16.

TABLE 29-16

| Reference Example No. | Structure | Analytical Data |
|---|---|---|
| 117-2 | 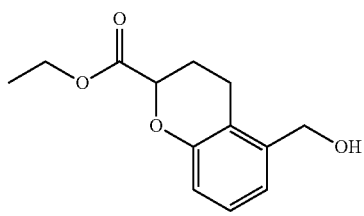 | $^1$H NMR (400 MHz, CHLOROFORM-d) δ ppm 1.29 (t, J = 7.1 Hz, 3 H) 1.36 (t, J = 5.9 Hz, 1 H) 2.78 (t, J = 6.5 Hz, 2 H) 2.94-3.14 (m, 3 H) 3.82 (td, J = 6.5, 5.9 Hz, 2 H) 4.04-4.14 (m, 1 H) 4.20 (q, J = 7.1 Hz, 2 H) 4.37-4.47 (m, 1 H) 6.78 (d, J = 7.9 Hz, 1 H) 6.92-7.00 (m, 2 H). MS ESI posi: 251[M + H]$^+$, 273[M + Na]$^+$. |

Reference Example 118-1

Ethyl 5-(hydroxymethyl)-3,4-dihydro-2H-chromene-2-carboxylate

[Formula 482]

(1) 1-(2,6-Dihydroxyphenyl)ethanone (5.3 g) was used to perform the reaction according to the method described in Reference Example 1-1-(1) thereby giving 1-[2,6-bis(phenylmethoxy)phenyl]ethanone (9.9 g) as a colorless solid.

(2) The compound (8.2 g) obtained in (1) above and ethyl 2-oxoacetate (47% toluene solution, 6.4 mL) were used to perform the reaction according to the method described in

431

Reference Example 29-1-(1) thereby giving ethyl 4-[2,6-bis(phenylmethoxy)phenyl]-2-hydroxy-4-oxobutanoate (8.5 g) as a yellow oil.

(3) The compound (3.0 g) obtained in (2) above was used to perform the reaction according to the method described in Reference Example 28-1 thereby giving ethyl 4-[2,6-bis(phenylmethoxy)phenyl]-2,4-dihydroxybutanoate (1.61 g) as a colorless oil.

(4) The compound (1.61 g) obtained in (3) above was used to perform the reaction according to the method described in Reference Example 1-1-(3) thereby giving ethyl 4-(2,6-dihydroxyphenyl)-2-hydroxybutanoate (382 mg) as a colorless solid.

(5) The compound (340 mg) obtained in (4) above was used to perform the reaction according to the method described in Reference Example 6-2 thereby giving ethyl 5-hydroxy-3,4-dihydro-2H-chromene-2-carboxylate (293 mg) as a colorless solid.

(6) The compound (293 mg) obtained in (5) above was used to perform the reaction according to the method described in Reference Example 53-1-(2) thereby giving ethyl 5-(trifluoromethylsulfonyloxy)-3,4-dihydro-2H-chromene-2-carboxylate (364 mg) as a pale yellow oil.

(7) The compound (364 mg) obtained in (6) above was used to perform the reaction according to the method described in Reference Example 102-1-(2) thereby giving ethyl 5-ethenyl-3,4-dihydro-2H-chromene-2-carboxylate (167 mg) as a colorless oil.

(8) The compound (167 mg) obtained in (7) above was used to perform the reaction according to the method described in Reference Example 52-1-(3) thereby giving ethyl 5-(1,2-dihydroxyethyl)-3,4-dihydro-2H-chromene-2-carboxylate (163 mg) as a colorless solid.

(9) The compound (163 mg) obtained in (8) above was used to perform the reaction according to the method described in Reference Example 102-1-(4) thereby giving the title compound (136 mg) as a colorless oil.

$^1$H NMR (400 MHz, CHLOROFORM-d) δ ppm 1.30 (t, J=7.1 Hz, 3H) 2.15-2.26 (m, 1H) 2.26-2.39 (m, 1H) 2.74-2.93 (m, 2H) 4.26 (q, J=7.1 Hz, 2H) 4.64 (s, 2H) 4.69 (dd, J=7.6, 3.5 Hz, 1H) 6.90-6.98 (m, 2H) 7.09-7.18 (m, 1H).

MS ESI posi: 259[M+Na]$^+$, 219[M-OH]$^+$.

Reference Example 119-1

Methyl 3-[5-(bromomethyl)pyridin-2-yl]oxy-2,2-dimethylpropanoate

[Formula 483]

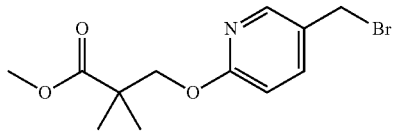

(1) Methyl 3-hydroxy-2,2-dimethylpropanoate (1.40 mL) and 5-methylpyridin-2-ol (1.0 g) were used to perform the reaction according to the method described in Reference Example 6-2 thereby giving methyl 2,2-dimethyl-3-(5-methylpyridin-2-yl)oxypropanoate (1.08 g) as a colorless oil.

(2) The compound (1.08 g) obtained in (1) above was used to perform the reaction according to the method described in

432

Reference Example 12-1-(2) thereby giving a mixture (1.36 g) containing the title compound as a colorless oil.

$^1$H NMR (400 MHz, CHLOROFORM-d) δ ppm 1.30 (s, 6H) 3.69 (s, 3H) 4.33 (s, 2H) 4.45 (s, 2H) 6.70-6.76 (m, 1H) 7.58-7.66 (m, 1H) 8.10-8.16 (m, 1H).

MS ESI/APCI Multi posi: 302[M+H]$^+$, 324[M+Na]$^+$.

The compound of Reference Example 119-2 below was synthesized using the corresponding commercially available alcohol and aryl hydroxide, according to the method described in Reference Example 119-1. The structure, and MS data of the compound are shown in Table 29-17.

TABLE 29-17

| Reference Example No. | Structure | Analytical Data |
|---|---|---|
| 119-2 | 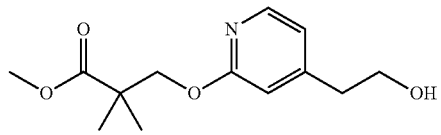 | MS ESI posi: 302[M+H]$^+$ |

Reference Example 120-1

Methyl 3-[4-(2-hydroxyethyl)pyridin-2-yl]oxy-2,2-dimethylpropanoate

[Formula 484]

(1) Methyl 3-hydroxy-2,2-dimethylpropanoate (1.6 g) and 4-bromopyridin-2-ol (2.0 g) were used to perform the reaction according to the method described in Reference Example 6-2 thereby giving methyl 3-(4-bromopyridin-2-yl)oxy-2,2-dimethylpropanoate (2.2 g) as a colorless oil.

(2) The compound (450 mg) obtained in (1) above and allylboronic acid pinacol ester (394 mg) were used to perform the reaction according to the method described in Reference Example 13-1-(1) thereby giving methyl 2,2-dimethyl-3-(4-prop-2-enylpyridin-2-yl)oxypropanoate (358 mg) as a colorless oil.

(3) The compound (358 mg) obtained in (2) above was used to perform the reaction according to the method described in Reference Example 52-1-(3) thereby giving methyl 3-[4-(2,3-dihydroxypropyl)pyridin-2-yl]oxy-2,2-dimethylpropanoate (263 mg) as a colorless oil.

(4) The compound (100 mg) obtained in (3) above was used to perform the reaction according to the method described in Reference Example 102-1-(4) thereby giving the title compound (59 mg) as a colorless oil.

$^1$H NMR (400 MHz, CHLOROFORM-d) δ ppm 1.31 (s, 6H) 1.44 (t, J=5.5 Hz, 1H) 2.81 (t, J=6.4 Hz, 2H) 3.69 (s, 3H) 3.89 (td, J=6.4, 5.5 Hz, 2H) 4.31 (s, 2H) 6.63 (s, 1H) 6.76 (d, J=5.2 Hz, 1H) 8.05 (d, J=5.2 Hz, 1H).

MS ESI posi: 254[M+H]$^+$.

The compounds of Reference Examples 120-2 to 120-6 below were synthesized using the corresponding commercially available alcohol and aryl hydroxide, according to the method described in Reference Example 120-1. The structures, NMR data, and MS data of the compounds are shown in Table 29-18.

was removed, and the mixture was stirred overnight. Sodium perborate tetrahydrate (440 mg) was added thereto under ice cooling, the ice bath was removed, and the mixture was stirred for 5 hours. A saturated aqueous solution of ammonium chloride was added to the reaction solution, and the resultant mixture was extracted with chloroform. The

TABLE 29-18

| Reference Example No. | Structure | Analytical Data |
|---|---|---|
| 120-2 | 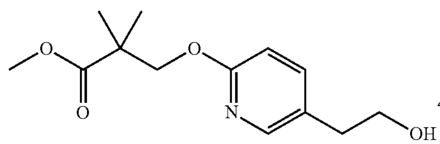 | $^1$H NMR (400 MHz, CHLOROFORM-d) δ ppm 1.30 (s, 6 H) 1.37-1.43 (m, 1 H) 2.78 (t, J = 6.5 Hz, 2 H) 3.69 (s, 3 H) 3.78-3.86 (m, 2 H) 4.29 (s, 2 H) 6.70 (d, J = 8.4 Hz, 1 H) 7.46 (dd, J = 8.4, 2.0 Hz, 1 H) 7.99 (s, 1 H). MS ESI posi: 254[M + H]$^+$. |
| 120-3 | 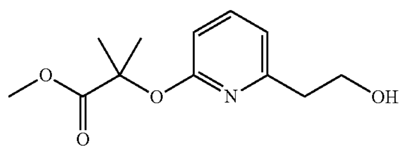 [SMILES: COC(=O)C(C)(C)Oc1cccc(CCO)n1] | $^1$H NMR (400 MHz, CHLOROFORM-d) δ ppm 1.67 (s, 6 H) 2.46-2.55 (m, 1 H) 2.83-2.92 (m, 2 H) 3.71 (s, 3 H) 3.88-3.97 (m, 2 H) 6.58-6.65 (m, 1 H) 6.68-6.27 (m, 1 H) 7.46-7.54 (m, 1 H). MS ESI posi: 240[M + H]$^+$. |
| 120-4 | 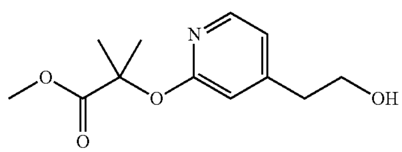 [SMILES: COC(=O)C(C)(C)Oc1cc(CCO)ccn1] | $^1$H NMR (400 MHz, CHLOROFORM-d) δ ppm 1.66 (s, 6 H) 2.81 (t, J = 6.5 Hz, 2 H), 3.66 (s, 3 H), 3.83-3.94 (m, 2 H), 6.64 (s, 1 H), 6.72 (d, J = 5.0 Hz, 1 H) 7.96 (d, J = 5.0 Hz, 1 H). MS ESI posi: 240[M + H]$^+$. |
| 120-5 | 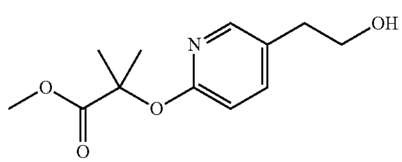 [SMILES: COC(=O)C(C)(C)Oc1ccc(CCO)cn1] | $^1$H NMR (400 MHz, CHLOROFORM-d) δ ppm 1.65 (s, 6 H) 2.72-2.81 (m, 2 H) 3.67 (s, 3 H) 3.76-3.87 (m, 2 H) 6.66-6.74 (m, 1 H) 7.42-7.49 (m, 1 H) 7.86-7.93 (m, 1 H). MS ESI posi: 240[M + H]$^+$. |
| 120-6 | 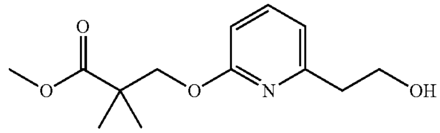 [SMILES: COC(=O)C(C)(C)COc1cccc(CCO)n1] | $^1$H NMR (400 MHz, CHLOROFORM-d) δ ppm 1.31 (s, 6 H) 2.86-2.97 (m, 2 H) 3.68 (s, 3 H) 3.92-4.09 (m, 3 H) 4.26 (s, 2 H) 6.56-6.64 (m, 1 H) 6.69-6.75 (m, 1 H) 7.43-7.53 (m, 1 H). MS ESI posi: 254[M + H]$^+$. |

Reference Example 121-1

Methyl 3-[4-(3-hydroxypropyl)pyridin-2-yl]oxy-2,2-dimethylpropanoate

[Formula 485]

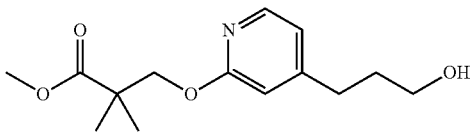

To a solution of the compound (177 mg) obtained in Reference Example 120-1-(1) in tetrahydrofuran (1.4 mL), 9-borabicyclo[3.3.1]nonane (0.5 mol/L tetrahydrofuran solution, 2.2 mL) was added under ice cooling, the ice bath organic layer was separated by a phase separator, and concentrated under reduced pressure. The obtained residue was purified by silica gel column chromatography (n-hexane:ethyl acetate=13:7 to 1:3) to give the title compound (123 mg) as a colorless oil.

$^1$H NMR (400 MHz, CHLOROFORM-d) δ ppm 1.30 (s, 6H) 1.81-1.94 (m, 2H) 2.60-2.70 (m, 2H) 3.56-3.79 (m, 5H) 4.30 (s, 2H) 6.59 (s, 1H) 6.67-6.78 (m, 1H) 7.97-8.07 (m, 1H).

MS ESI posi: 268[M+H]$^+$.

The compounds of Reference Examples 121-2 to 121-6 below were synthesized using the corresponding synthesis intermediates of Reference Examples 120-2 to 120-6, according to the method described in Reference Example 121-1. The structures, NMR data, and MS data of the compounds are shown in Table 29-19.

TABLE 29-19

| Reference Example No. | Structure | Analytical Data |
|---|---|---|
| 121-2 | 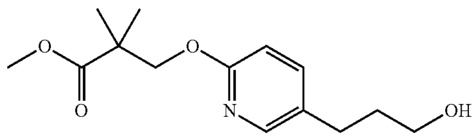 [SMILES: COC(=O)C(C)(C)COc1ccc(CCCO)cn1] | $^1$H NMR (400 MHz, CHLOROFORM-d) δ ppm 1.30 (s, 6 H) 1.78-1.90 (m, 2 H) 2.56-2.68 (m, 2 H) 3.61-3.74 (m, 5 H) 4.29 (s, 2 H) 6.64-6.71 (m, 1 H) 7.37-7.45 (m, 1 H) 7.94-7.98 (m, 1 H). MS ESI posi: 268[M + H]$^+$. |
| 121-3 | 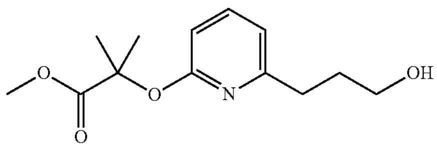 [SMILES: COC(=O)C(C)(C)Oc1cccc(CCCO)n1] | $^1$H NMR (400 MHz, CHLOROFORM-d) δ ppm 1.65 (s, 6 H) 1.86-2.00 (m, 2 H) 2.64-2.77 (m, 2 H) 3.56-3.71 (m, 2 H) 3.67 (s, 3 H) 6.52-6.60 (m, 1 H) 6.66-6.74 (m, 1 H) 7.41-7.51 (m, 1 H). MS ESI posi: 254[M + H]$^+$. |
| 121-4 | 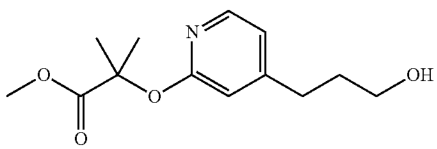 [SMILES: COC(=O)C(C)(C)Oc1cc(CCCO)ccn1] | $^1$H NMR (400 MHz, CHLOROFORM-d) δ ppm 1.66 (s, 6 H) 1.80-1.94 (m, 2 H) 2.59-2.70 (m, 2 H) 3.64-3.72 (m, 2 H) 3.66 (s, 3 H) 6.56-6.62 (m, 1 H) 6.65-6.72 (m, 1 H) 7.88-7.98 (m, 1 H). MS ESI posi: 254[M + H]$^+$. |
| 121-5 | 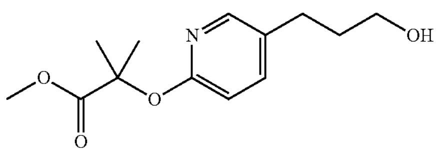 [SMILES: COC(=O)C(C)(C)Oc1ccc(CCCO)cn1] | $^1$H NMR (400 MHz, CHLOROFORM-d) δ ppm 1.65 (s, 6 H) 1.78-1.89 (m, 2 H) 2.54-2.65 (m, 2 H) 3.62-3.72 (m, 2 H) 3.67 (s, 3 H) 6.63-6.73 (m, 1 H) 7.37-7.47 (m, 1 H) 7.82-7.91 (m, 1 H). MS ESI posi: 254[M + H]$^+$. |
| 121-6 | 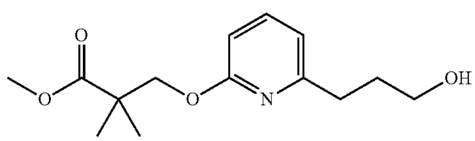 [SMILES: COC(=O)C(C)(C)COc1cccc(CCCO)n1] | $^1$H NMR (400 MHz, CHLOROFORM-d) δ ppm 1.31 (s, 6 H) 1.91-2.02 (m, 2 H) 2.78-2.88 (m, 2 H) 3.04-3.12 (m, 1 H) 3.66-3.75 (m, 2 H) 3.69 (s, 3 H) 4.28 (s, 2 H) 6.51-6.58 (m, 1 H) 6.68-6.75 (m, 1 H) 7.42-7.51 (m, 1 H). MS ESI posi: 268[M + H]$^+$. |

Reference Example 122-1

Methyl 3-[5-(2-hydroxyethyl)pyridin-2-yl]-2,2-dimethylpropanoate

[Formula 486]

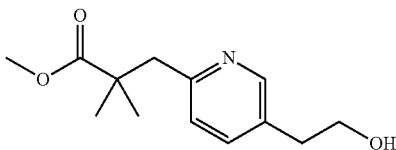

(1) Ethylene glycol (1.4 mL) and p-toluenesulfonic acid monohydrate (307 mg) were added to a solution of 5-bromopyridine-2-carbaldehyde (3.0 g) in toluene (16 mL), and the mixture was heated to reflux for 8 hours. After cooling to room temperature, a saturated aqueous solution of sodium hydrogen carbonate was added to the mixture, and the resultant mixture was extracted with ethyl acetate. The organic layer was washed with brine, then passed through a phase separator, and concentrated under reduced pressure. The obtained residue was purified by silica gel column chromatography (n-hexane:ethyl acetate=4:1 to 11:9) to give 5-bromo-2-(1,3-dioxolan-2-yl)pyridine (3.38 g) as a brown oil.

(2) In a test tube for microwave reaction, the compound (1.69 g) obtained in (1) above, allyltributyltin (2.73 mL), tetrakis(triphenylphosphine)palladium(0) (1.27 g), and 1,4-dioxane (15 mL) were mixed, and the container was sealed. Another such test tube was prepared, providing two test tubes in total. These mixtures were each stirred at 120° C. for 30 minutes under microwave irradiation, cooled to room temperature, and then filtered through Celite. The obtained filtrates were combined, and the resultant was concentrated under reduced pressure. The obtained residue was purified by silica gel column chromatography (n-hexane:ethyl acetate=13:7 to 7:13) to give 2-(1,3-dioxolan-2-yl)-5-prop-2-enylpyridine (2.45 g) as a brown oil.

(3) The compound (2.45 g) obtained in (2) above was used to perform the reaction according to the method described in Reference Example 52-1-(3) thereby giving a mixture (1.56 g) containing 3-[6-(1,3-dioxolan-2-yl)pyridin-3-yl]propane-1,2-diol.

(4) The compound (1.56 g) obtained in (3) above was used to perform the reaction according to the method described in Reference Example 102-1-(4) thereby giving 2-[6-(1,3-dioxolan-2-yl)pyridin-3-yl]ethanol (968 mg) as a brown oil.

(5) The compound (968 mg) obtained in (4) above was used to perform the reaction according to the method described in Reference Example 40-1-(1) thereby giving tert-butyl-[2-[6-(1,3-dioxolan-2-yl)pyridin-3-yl]ethoxy]-dimethylsilane (1.55 g) as a colorless oil.

(6) To a solution of the compound (1.55 g) obtained in (5) above in tetrahydrofuran (44 mL), 2 mol/L hydrochloric acid (8.8 mL) was added under ice cooling, and the mixture was stirred at room temperature for 1 hour, and at 60° C. for 8 hours. After the mixture was ice-cooled, a saturated aqueous solution of sodium hydrogen carbonate was added to the mixture. After salt was added thereto to reach saturation, the resultant mixture was extracted with ethyl acetate. The organic layer was dried over anhydrous magnesium sulfate, the drying agent was filtered off, and the filtrate was concentrated under reduced pressure. The obtained residue was dissolved in chloroform (18 mL), and imidazole (900 mg) and tert-butyldimethylchlorosilane (1.0 g) were added thereto under ice cooling. The mixture was stirred at room temperature overnight, a saturated aqueous solution of sodium hydrogen carbonate was added thereto, the resultant mixture was extracted with chloroform, and the organic layer was separated by a phase separator and concentrated under reduced pressure. The obtained residue was purified by silica gel column chromatography (n-hexane:ethyl acetate=17:3 to 3:2) to give 5-[2-[tert-butyl(dimethyl)silyl]oxyethyl]pyridine-2-carbaldehyde (891 mg) as a colorless oil.

(7) In a microwave reaction container, the compound (891 mg) obtained in (6) above, dimethylketene methyl trimethylsilyl acetal (1.0 mL), lithium chloride (28 mg), 1-methylimidazole (28 µL), and N,N-dimethylformamide (11 mL) were mixed, and the container was sealed. This mixture was stirred at 100° C. for 30 minutes under microwave irradiation. The mixture was cooled to room temperature, water was added thereto, and the resultant mixture was extracted with diethyl ether. The organic layer was sequentially washed with water and brine, passed through a phase separator, and concentrated under reduced pressure. The obtained residue was dissolved in methanol (34 mL), sodium methoxide (406 mg) was added thereto, and the resultant mixture was stirred at room temperature for 4 hours. The mixture was concentrated under reduced pressure, and the obtained residue was purified by silica gel column chromatography (n-hexane:ethyl acetate=4:1 to 1:1) to give methyl 3-[5-[2-[tert-butyl(dimethyl)silyl]oxyethyl]pyridin-2-yl]-3-hydroxy-2,2-dimethylpropanoate (479 mg) as a colorless oil.

(8) The mixture (479 mg) obtained in (7) above was used to perform the reaction according to the method described in Reference Example 42-1-(2) thereby giving methyl 3-[5-[2-[tert-butyl(dimethyl)silyl]oxyethyl]pyridin-2-yl]-2,2-dimethyl-3-methylsulfonyloxypropanoate (302 mg) as a colorless oil.

(9) The compound (302 mg) obtained in (8) above was used to perform the reaction according to the method described in Reference Example 1-1-(3) thereby giving a mixture (277 mg) containing methyl 3-[5-[2-[tert-butyl(dimethyl)silyl]oxyethyl]pyridin-2-yl]-2,2-dimethylpropanoate.

(10) The mixture (277 mg) obtained in (9) above was used to perform the reaction according to the method described in Reference Example 50-1-(3) thereby giving the title compound (41 mg) as a colorless oil.

$^1$H NMR (400 MHz, CHLOROFORM-d) δ ppm 1.23 (s, 6H) 2.77-2.88 (m, 2H) 3.03 (s, 2H) 3.68 (s, 3H) 3.80-3.92 (m, 2H) 7.00-7.07 (m, 1H) 7.40-7.50 (m, 1H) 8.34-8.42 (m, 1H).

MS ESI posi: 238[M+H]$^+$.

Example 1-1

4-[[6-(1H-Pyrazol-5-yl)-3-pyridinyl]oxymethyl]benzoic Acid

[Formula 487]

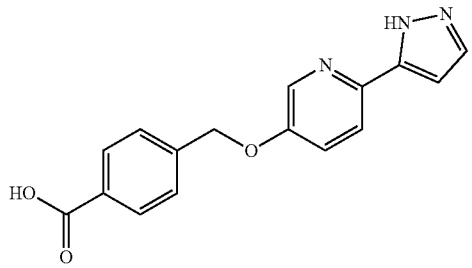

(1) Methyl 4-(hydroxymethyl)benzoate (37 mg) and cyanomethylenetributylphosphorane (0.12 mL) were added to a solution of the compound (50 mg) obtained in Reference Example 1-1 in toluene (1.5 mL), and the mixture was stirred under a nitrogen atmosphere at 100° C. for 2 hours. The reaction solution was cooled, and then concentrated under reduced pressure. The obtained residue was purified by silica gel column chromatography (n-hexane:ethyl acetate=2:1 to 1:2) to give methyl 4-[[6-[2-(2-oxanyl)-3-pyrazolyl]-3-pyridinyl]oxymethyl]benzoate (69 mg) as a yellow oil.

(2) An aqueous solution of 1 mol/L sodium hydroxide (0.39 mL) was added to a solution of the compound (69 mg) obtained in (1) above in tetrahydrofuran (1.8 mL), and the mixture was stirred at an outer temperature of 60° C. for 2 hours to give a solution containing 4-[[6-[2-(2-oxanyl)-3-pyrazolyl]-3-pyridinyl]oxymethyl]benzoic acid.

(3) Water (0.50 mL), methanol (1.50 mL), and trifluoroacetic acid (0.25 mL) were added to the solution obtained in (2) above, and the mixture was stirred at room temperature for 5 hours. After the solvent was distilled off under reduced pressure, the residue was purified by preparative HPLC to give the title compound (18 mg) as a colorless powder.

$^1$H NMR (400 MHz, DMSO-d$_6$) δ ppm 5.31 (s, 2H) 6.73 (d, J=2.1 Hz, 1H) 7.51-7.63 (m, 3H) 7.68 (br s, 1H) 7.86 (d, J=8.7 Hz, 1H) 7.98 (d, J=8.2 Hz, 2H) 8.37 (d, J=2.9 Hz, 1H) 12.87-13.11 (m, 2H).

MS ESI/APCI Multi posi: 296[M+H]$^+$.

MS ESI/APCI Multi nega: 294[M−H]$^-$.

The compounds of Examples 1-2 to 1-10 below were synthesized using any of the compounds obtained in Reference Examples 20-2, 40-1 and 40-2, 44-1 and 44-2, and 46-1 to 46-3, or a commercially available compound, according to the method described in Example 1-1. The structures, NMR data, and MS data of the compounds are shown in Tables 30-1 and 30-2.

TABLE 30-1

| Example No. | Structure | Analytical Data |
|---|---|---|
| 1-2 | (4-(1-((6-(1H-pyrazol-5-yl)pyridin-3-yl)oxy)ethyl)benzoic acid structure) | $^1$H NMR (400 MHz, DMSO-d$_6$) δ ppm 1.61 (d, J = 6.4 Hz, 3 H) 5.74 (q, J = 6.2 Hz, 1 H) 6.70 (d, J = 2.0 Hz, 1 H) 7.39-7.51 (m, 1 H) 7.56 (d, J = 8.3 H, 1 H) 7.67 (s, 1 H) 7.75-7.83 (m, 1 H) 7.93 (d, J = 8.2 Hz, 2 H) 8.26 (d, J = 2.7 Hz, 1 H). MS ESI/APCI Multi posi: 310[M + H]$^+$. |
| 1-3 | (3-(4-(((6-(1H-pyrazol-5-yl)pyridin-3-yl)oxy)methyl)phenyl)propanoic acid structure) | $^1$H NMR (400 MHz, DMSO-d$_6$) δ ppm 2.52-2.58 (m, 2 H) 2.79-2.87 (m, 2 H) 5.19 (s, 2 H) 6.79 (br s, 1 H) 7.27 (d, J = 7.9 Hz, 2 H) 7.39 (d, J = 7.9 Hz, 2 H) 7.62 (br d, J = 8.3 Hz, 1 H) 7.73 (br s, 1 H) 7.85-7.98 (m, 1 H) 8.36 (d, J = 4.0 Hz, 1 H). MS ESI/APCI Muti posi: 324[M + H]$^+$. |
| 1-4 | (3-(2-(((6-(1H-pyrazol-5-yl)pyridin-3-yl)oxy)methyl)phenyl)propanoic acid structure) | $^1$H NMR (400 MHz, DMSO-d$_6$) δ ppm 2.54-2.60 (m, 2 H) 2.92 (t, J = 7.8 Hz, 2 H) 5.15-5.32 (m, 2 H) 6.74 (d, J = 2.1 Hz, 1 H) 7.22-7.35 (m, 3 H) 7.46 (d, J = 7.2 Hz, 1 H) 7.56 (dd, J = 8.8, 2.9 Hz, 1 H) 7.63-7.75 (m, 1 H) 7.87 (d, J = 8.8 Hz, 1 H) 8.36 (d, J = 2.9 Hz, 1 H). MS ESI/APCI Multi posi: 324[M + H]$^+$. |
| 1-5 | (4-(2-((6-(1H-pyrazol-5-yl)pyridin-3-yl)oxy)ethyl)benzoic acid structure) | $^1$H NMR (400 MHz, DMSO-d$_6$) δ ppm 3.15 (t, J = 6.7 Hz, 2 H) 4.35 (t, J = 6.7 Hz, 2 H) 6.72 (d, J = 2.1 Hz, 1 H) 7.43-7.50 (m, 3 H) 7.67 (br s, 1 H) 7.84 (d, J = 8.0 Hz, 1 H) 7.90 (d, J = 8.0 Hz, 2 H) 8.27 (d, J = 2.8 Hz, 1 H) 12.92 (br s, 1 H). MS ESI/APCI Multi posi: 310[M + H]$^+$. MS ESI/APCI Multi nega: 308[M − H]$^-$. |
| 1-6 | (3-(2-((6-(1H-pyrazol-5-yl)pyridin-3-yl)oxy)ethyl)benzoic acid structure) | $^1$H NMR (400 MHz, DMSO-d$_6$) δ ppm 3.15 (t, J = 6.7 Hz, 2 H) 4.34 (t, J = 6.7 Hz, 2 H) 6.72 (d, J = 2.1 Hz, 1 H) 7.41-7.50 (m, 2 H) 7.61 (d, J = 7.2 Hz, 1 H) 7.67 (d, J = 1.8 Hz, 1 H) 7.83 (t, J = 7.6 Hz, 2 H) 7.93 (s, 1 H) 8.13 (s, 1 H) 8.27 (d, J = 2.8 Hz, 1 H) 12.84 (br s, 1 H). MS ESI/APCI Multi posi: 310[M + H]$^+$. |
| 1-7 | (2-(2-((6-(1H-pyrazol-5-yl)pyridin-3-yl)oxy)ethyl)benzoic acid structure) | $^1$H NMR (400 MHz, DMSO-d$_6$) δ ppm 3.18-3.20 (m, 1 H) 3.34-3.47 (m, 2 H) 4.29 (t, J = 7.0 Hz, 2 H) 6.72 (d, J = 2.0 Hz, 1 H) 7.36 (t, J = 7.2 Hz, 1 H) 7.42-7.54 (m, 3 H) 7.61-7.79 (m, 1 H) 7.79-7.89 (m, 2 H) 8.27 (d, J = 2.8 Hz, 1 H). MS ESI/APCI Multi posi: 310[M + H]$^+$. MS ESI/APCI Multi nega: 308[M − H]$^-$. |

TABLE 30-2

| Example No. | Structure | Analytical Data |
|---|---|---|
| 1-8 | 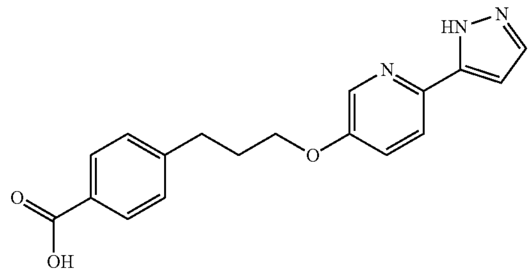 [SMILES: O=C(O)c1ccc(CCCOc2ccc(-c3ccn[nH]3)nc2)cc1] | $^1$H NMR (400 MHz, DMSO-d$_6$) δ ppm 2.00-2.14 (m, 2 H) 2.76-2.89 (m, 2 H) 4.07-4.19 (m, 2 H) 6.77-6.84 (m, 1 H) 7.38 (d, J = 8.2 Hz, 2 H) 7.52-7.70 (m, 1 H) 7.70-7.83 (m, 1 H) 7.82-7.98 (m, 3 H) 8.31 (d, J = 2.8 Hz, 1 H). MS ESI/APCI Multi posi: 324[M + H]$^+$. MS ESI/APCI Multi nega: 322[M − H]$^−$. |
| 1-9 | 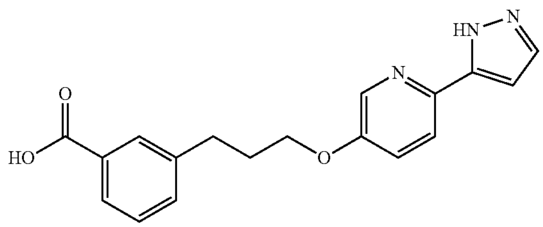 [SMILES: O=C(O)c1cccc(CCCOc2ccc(-c3ccn[nH]3)nc2)c1] | $^1$H NMR (400 MHz, DMSO-d$_6$) δ ppm 2.01-2.14 (m, 2 H) 2.77-2.91 (m, 2 H) 4.07 (s, 2 H) 6.73 (s, 1 H) 7.38-7.54 (m, 3 H) 7.62-7.71 (m, 1 H) 7.74-7.89 (m, 3 H) 8.22-8.34 (m, 1 H) 12.85-13.01 (m, 1 H). MS ESI/APCI Multi posi: 324[M + H]$^+$. MS ESI/APCI Multi nega: 322[M − H]$^−$. |
| 1-10 | 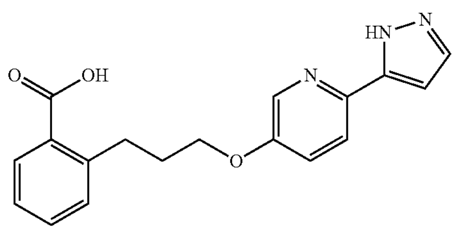 [SMILES: O=C(O)c1ccccc1CCCOc1ccc(-c2ccn[nH]2)nc1] | $^1$H NMR (400 MHz, DMSO-d$_6$) δ ppm 1.99-2.08 (m, 2 H) 3.05-3.13 (m, 2 H) 4.08 (t, J = 6.4 Hz, 2 H) 6.72 (d, J = 2.1 Hz, 1 H) 7.28-7.37 (m, 2 H) 7.40-7.50 (m, 2 H) 7.67 (s, 1 H) 7.75-7.91 (m, 2 H) 8.13 (s, 1 H) 8.27 (d, J = 2.8 Hz, 1 H) 12.84 (br s, 1 H). MS ESI/APCI Multi posi: 324[M + H]$^+$. MS ESI/APCI Multi nega: 322[M − H]$^−$. |

The compounds of Examples 1-11 to 1-39 below were synthesized using a compound obtained in Reference Example 1 or 3, any of the compounds obtained in Reference Examples 15-1 and 15-2, 16-1, 33-4 to 33-6, 44-3 to 44-6, 46-4 to 46-6, 47-1, 49-2, 64-1, 65-1 to 65-3, 66-1 and 66-2, 67-1, 79-1, and 80-1 to 80-3, or a commercially available compound, according to the methods described in Example 1-1-(1) and (2) and by performing the reaction described in Example 1-1-(3) under ice cooling. The structures, NMR data, and MS data of the compounds are shown in Tables 30-3 to 30-7.

TABLE 30-3

| Example No. | Structure | Analytical Data |
|---|---|---|
| 1-11 | 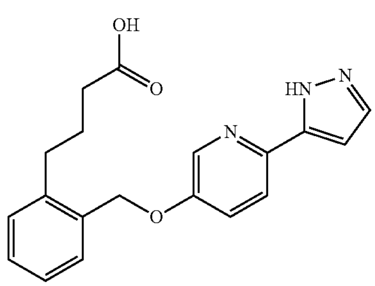 [SMILES: O=C(O)CCCc1ccccc1COc1ccc(-c2ccn[nH]2)nc1] | $^1$H NMR (400 MHz, DMSO-d$_6$) δ ppm 1.80 (quin, J = 7.6 Hz, 2 H) 2.08-2.41 (m, 2 H) 2.60-2.82 (m, 2 H) 5.22 (s, 2 H) 6.74 (d, J = 2.0 Hz, 1 H) 7.20-7.36 (m, 3 H) 7.43-7.51 (m, 1 H) 7.52-7.59 (m, 1 H) 7.68 (br s, 1 H) 7.83-7.92 (m, 1 H) 8.36 (d, J = 2.7 Hz, 1 H) 12.80 (br s, 1 H). MS ESI/APCI Mullti posi: 338[M + H]$^+$. MS ESI/APCI Multi nega: 336[M − H]$^−$. |

TABLE 30-3-continued

| Example No. | Structure | Analytical Data |
|---|---|---|
| 1-12 | 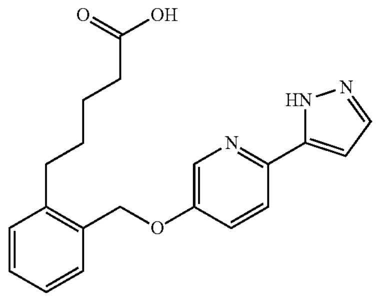 [SMILES: O=C(O)CCCCc1ccccc1COc1ccc(-c2ccn[nH]2)nc1] | ¹H NMR (400 MHz, DMSO-d₆) δ ppm 1.48-1.67 (m, 4 H) 2.17-2.29 (m, 2 H) 2.62-2.74 (m, 2 H) 5.21 (br s, 2 H) 6.74 (br s, 1 H) 7.23-7.32 (m, 2 H) 7.38-7.52 (m, 1 H) 7.53-7.66 (m, 4 H) 7.82-7.95 (m, 1 H) 7.82-7.95 (m, 1 H) 8.37 (br s, 1 H). MS ESI/APCI Multi posi: 352[M + H]⁺. MS ESI/APCI Multi nega: 350[M − H]⁻. |
| 1-13 | 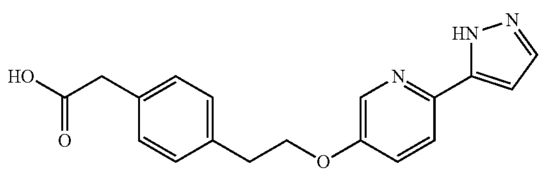 [SMILES: O=C(O)Cc1ccc(CCOc2ccc(-c3ccn[nH]3)nc2)cc1] | ¹H NMR (400 MHz, DMSO-d₆) δ ppm 3.05 (t, J = 6.8 Hz, 2 H) 3.53 (s, 2 H) 4.29 (t, J = 6.8 Hz, 2 H) 6.72 (d, J = 2.2 Hz, 1 H) 7.18-7.23 (m, 2 H) 7.26-7.31 (m, 2 H) 7.46 (dd, J = 8.7, 2.9 Hz, 1 H) 7.67 (br s, 1 H) 7.83 (d, J = 8.7 Hz, 1 H) 8.27 (d, J = 2.9 Hz, 1 H) 12.67 (br s, 1 H). MS ESI/APCI Multi posi: 324[M + H]⁺. MS ESI/APCI Multi nega: 322[M − H]⁻. |
| 1-14 | 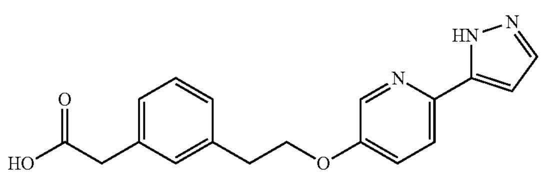 [SMILES: O=C(O)Cc1cccc(CCOc2ccc(-c3ccn[nH]3)nc2)c1] | ¹H NMR (400 MHz, DMSO-d₆) δ ppm 3.05 (t, J = 6.8 Hz, 2 H) 3.55 (s, 2 H) 4.30 (t, J = 6.8 Hz, 2 H) 6.72 (d, J = 2.1 Hz, 1 H) 7.10-7.17 (m, 1 H) 7.20-7.31 (m, 3 H) 7.46 (dd, J = 8.8, 2.8 Hz, 1 H) 7.67 (br s, 1 H). MS ESI/APCI Multi posi: 324[M + H]⁺. MS ESI/APCI Multi nega: 322[M − H]⁻. |
| 1-15 | 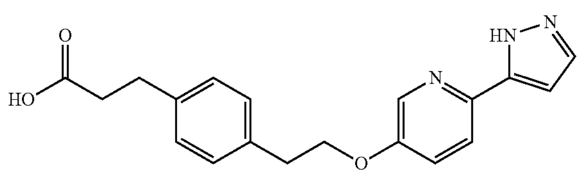 [SMILES: O=C(O)CCc1ccc(CCOc2ccc(-c3ccn[nH]3)nc2)cc1] | ¹H NMR (400 MHz, DMSO-d₆) δ ppm 2.73-2.85 (m, 2 H) 3.02 (t, J = 6.8 Hz, 2 H) 3.34-3.43 (m, 2 H) 4.28 (t, J = 6.8 Hz, 2 H) 6.72 (d, J = 2.1 Hz, 1 H) 7.14-7.21 (m, 2 H) 7.21-7.30 (m, 2 H) 7.45-7.48 (m, 1 H) 7.65 (br s, 1 H) 7.82-7.86 (m, 1 H) 8.27 (d, J = 2.6 Hz, 1 H). MS ESI/APCI Multi posi: 338[M + H]⁺. MS ESI/APCI Multi nega: 336[M − H]⁻. |
| 1-16 | 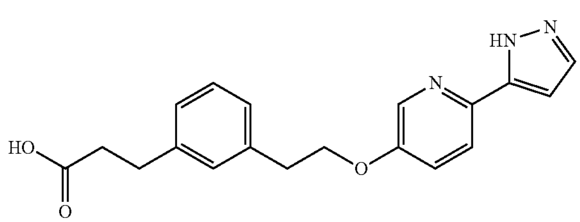 [SMILES: O=C(O)CCc1cccc(CCOc2ccc(-c3ccn[nH]3)nc2)c1] | ¹H NMR (400 MHz, DMSO-d₆) δ ppm 2.54-2.56 (m, 2 H) 2.81 (t, J = 7.6 Hz, 2 H) 3.03 (t, J = 6.9 Hz, 2 H) 4.29 (t, J = 6.9 Hz, 2 H) 6.72 (d, J = 2.1 Hz, 1 H) 7.09 (d, J = 7.6 Hz, 1 H) 7.14-7.26 (m, 3 H) 7.44-7.49 (m, 1 H) 7.68 (br s, 1 H) 7.80-7.86 (m, 1 H) 8.28 (d, J = 2.7 Hz, 1 H). MS ESI/APCI Multi posi: 338[M + H]⁺. MS ESI/APCI Multi nega: 336[M − H]⁻. |

TABLE 30-4

| Example No. | Structure | Analytical Data |
|---|---|---|
| 1-17 | 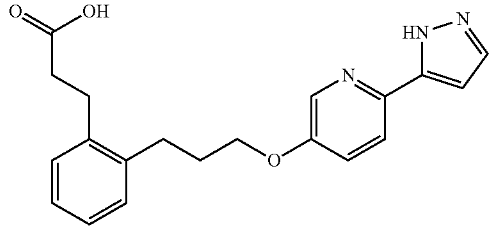 [SMILES: O=C(O)CCc1ccccc1CCCOc1ccc(-c2ccn[nH]2)nc1] | $^1$H NMR (400 MHz, DMSO-d$_6$) δ ppm 1.94-2.08 (m, 2 H) 2.35-2.53 (m, 2 H) 2.73-2.90 (m, 4 H) 4.11 (t, J = 6.1 Hz, 2 H) 6.73 (d, J = 2.1 Hz, 1 H) 7.08-7.23 (m, 4 H) 7.39-7.51 (m, 1 H) 7.60-7.76 (m, 1 H) 7.78-7.91 (m, 1 H) 8.30 (d, J = 3.2 Hz, 1 H). MS ESI/APCI Multi posi: 352[M + H]$^+$. |
| 1-18 | 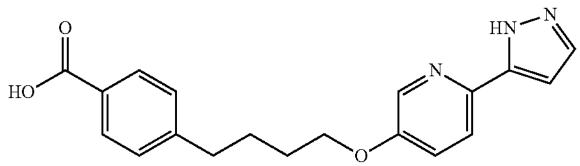 [SMILES: O=C(O)c1ccc(CCCCOc2ccc(-c3ccn[nH]3)nc2)cc1] | $^1$H NMR (400 MHz, DMSO-d$_6$) δ ppm 1.70-1.82 (m, 4 H) 2.70-2.78 (m, 2 H) 4.05-4.18 (m, 2 H) 6.72 (d, J = 2.0 Hz, 1 H) 7.35 (d, J = 8.1 Hz, 2 H) 7.43 (dd, J = 8.7, 2.8 Hz, 1 H) 7.60-7.72 (m, 1 H) 7.81-7.91 (m, 3 H) 8.27 (d, J = 2.8 Hz, 1 H) 12.91 (br s, 1 H). MS ESI/APCI Multi posi: 338[M + H]$^+$. |
| 1-19 | 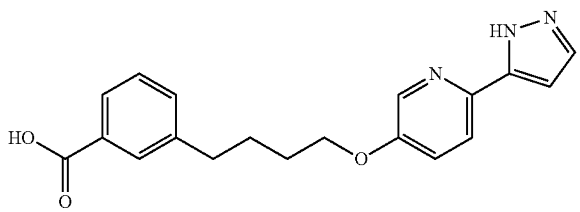 [SMILES: O=C(O)c1cccc(CCCCOc2ccc(-c3ccn[nH]3)nc2)c1] | $^1$H NMR (400 MHz, DMSO-d$_6$) δ ppm 1.71-1.80 (m, 4 H) 2.70-2.77 (m, 2 H) 4.08-4.15 (m, 2 H) 6.72 (d, J = 2.1 Hz, 1 H) 7.37-7.51 (m, 3 H) 7.65-7.71 (m, 1 H) 7.73-7.89 (m, 3 H) 8.27 (d, J = 2.4 Hz, 1 H) 12.90 (br s, 1 H). MS ESI/APCI Multi posi: 338[M + H]$^+$. MS ESI/APCI Multi nega: 336[M − H]$^-$. |
| 1-20 | 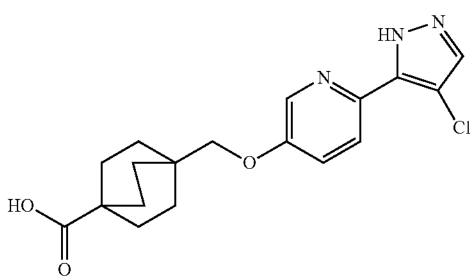 [SMILES: O=C(O)C12CCC(COc3ccc(-c4[nH]ncc4Cl)nc3)(CC1)CC2] | $^1$H NMR (400 MHz, DMSO-d$_6$) δ ppm 1.47-1.61 (m, 6 H) 1.68-1.77 (m, 6 H) 3.76 (s, 2 H) 7.49-7.54 (m, 1 H) 7.61-7.93 (m, 2 H) 8.35 (d, J = 4.0 Hz, 1 H) 13.57 (br s, 1 H). MS ESI/APCI Multi posi: 362[M + H]$^+$. |
| 1-21 | 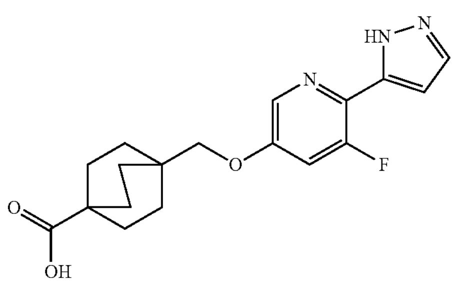 [SMILES: O=C(O)C12CCC(COc3cnc(-c4ccn[nH]4)c(F)c3)(CC1)CC2] | $^1$H NMR (400 MHz, DMSO-d$_6$) δ ppm 1.51-1.59 (m, 6 H) 1.69-1.78 (m, 6 H) 3.77 (s, 2 H) 6.65-6.69 (m, 1 H) 7.46-7.76 (m, 2 H) 8.22 (s, 1 H). MS ESI/APCI Multi posi: 346[M + H]$^+$. |
| 1-22 | 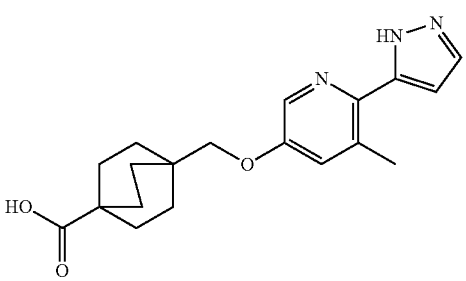 [SMILES: Cc1cc(OCC23CCC(C(=O)O)(CC2)CC3)cnc1-c1ccn[nH]1] | $^1$H NMR (400 MHz, DMSO-d$_6$) δ ppm 1.48-1.60 (m, 6 H) 1.68-1.77 (m, 6 H) 2.53 (s, 3 H) 3.74 (s, 2 H) 6.68 (d, J = 1.7 Hz, 1 H) 7.38-7.48 (m, 1 H) 7.71 (s, 1 H) 8.17 (d, J = 2.6 Hz, 1 H). MS ESI/APCI Multi posi: 342[M + H]$^+$. |

TABLE 30-5

| Example No. | Structure | Analytical Data |
|---|---|---|
| 1-23 | 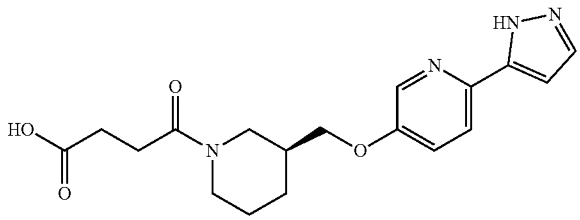 [SMILES: O=C(O)CCC(=O)N1CCC[C@H](COc2ccc(-c3ccn[nH]3)nc2)C1] | ¹H NMR (400 MHz, DMSO-d₆) δ ppm 1.29-1.52 (m, 2 H) 1.56-1.78 (m, 1 H) 1.78-1.95 (m, 2 H) 1.96-2.07 (m, 1 H) 2.39-2.44 (m, 1 H) 2.58-2.64 (m, 1 H) 2.77-2.92 (m, 1 H) 2.97-3.16 (m, 1 H) 3.73-4.07 (m, 4 H) 4.32-4.46 (m, 1 H) 6.73 (s, 1 H) 7.41-7.54 (m, 1 H) 7.59-7.76 (m, 1 H) 7.82-7.89 (m, 1 H) 8.23-8.37 (m, 1 H) 12.82 (br s, 1 H).<br>MS ESI/APCI Multi posi: 359[M + H]⁺.<br>MS ESI/APCI Multi nega: 357[M − H]⁻. |
| 1-24 | 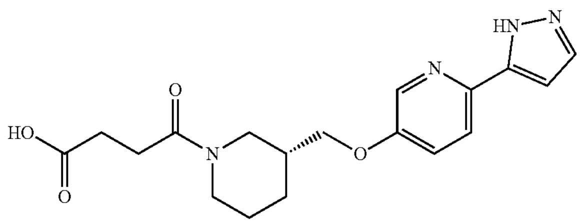 [SMILES: O=C(O)CCC(=O)N1CCC[C@@H](COc2ccc(-c3ccn[nH]3)nc2)C1] | ¹H NMR (400 MHz, DMSO-d₆) δ ppm 1.12-1.21 (m, 1 H) 1.28-1.52 (m, 2 H) 1.59-1.76 (m, 1 H) 1.80-1.92 (m, 2 H) 1.96-2.07 (m, 1 H) 2.80-2.91 (m, 1 H) 2.99-3.13 (m, 1 H) 3.72-4.06 (m, 4 H) 4.30-4.46 (m, 1 H) 6.73 (d, J = 2.0 Hz, 1 H) 7.41-7.50 (m, 1 H) 7.62-7.75 (m, 1 H) 7.81-7.91 (m, 1 H) 8.24-8.33 (m, 1 H).<br>MS ESI/APCI Multi posi: 359[M + H]⁺.<br>MS ESI/APCI Multi nega: 357[M − H]⁻. |
| 1-25 | 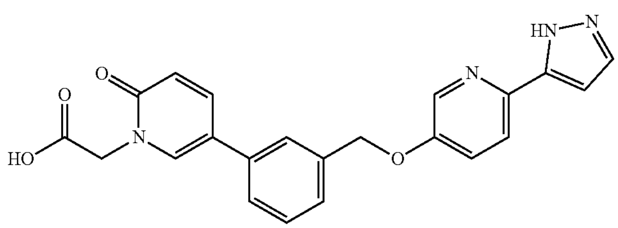 [SMILES: O=C(O)Cn1cc(-c2cccc(COc3ccc(-c4ccn[nH]4)nc3)c2)ccc1=O] | ¹H NMR (400 MHz, DMSO-d₆) δ ppm 4.65 (s, 2 H) 5.25 (s, 2 H) 6.52 (d, J = 9.4 Hz, 1 H) 6.73 (d, J = 2.0 Hz, 1 H) 7.39-7.50 (m, 2 H) 7.55 (dd, J = 8.6, 2.6 Hz, 2 H) 7.63-7.73 (m, 2 H) 7.81-7.95 (m, 2 H) 8.13-8.18 (m, 1 H) 8.38 (d, J = 2.6 Hz, 1 H) 13.04 (br s, 1 H).<br>MS ESI/APCI Multi posi: 403[M + H]⁺.<br>MS ESI/APCI Multi nega: 401[M − H]⁻. |
| 1-26 | 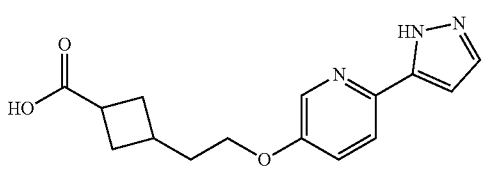 [SMILES: O=C(O)C1CC(CCOc2ccc(-c3ccn[nH]3)nc2)C1] | ¹H NMR (400 MHz, DMSO-d₆) δ ppm 1.77-1.98 (m, 4 H) 2.23-2.45 (m, 3 H) 2.92 (quin, J = 8.9 Hz, 1 H) 3.97-4.07 (m, 2 H) 6.72 (d, J = 2.1 Hz, 1 H) 7.39-7.46 (m, 1 H) 7.62-7.72 (m, 1 H) 7.84 (d, J = 8.7 Hz, 1 H) 8.22-8.29 (m, 1 H) 12.58 (br s, 1 H).<br>MS ESI/APCI Multi posi: 288[M + H]⁺. |
| 1-27 | 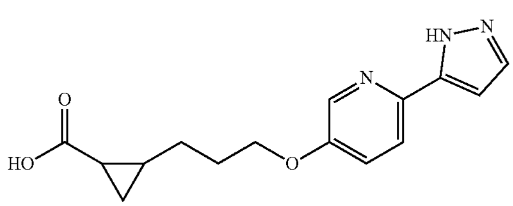 [SMILES: O=C(O)C1CC1CCCOc1ccc(-c2ccn[nH]2)nc1] | ¹H NMR (400 MHz, DMSO-d₆) δ ppm 0.65-0.80 (m, 1 H) 0.94-1.04 (m, 1 H) 1.22-1.37 (m, 2 H) 1.39-1.53 (m, 2 H) 1.75-1.93 (m, 2 H) 4.01-4.21 (m, 2 H) 6.70-6.89 (m, 1 H) 7.42-7.59 (m, 1 H) 7.65-7.79 (m, 1 H) 7.71-7.99 (m, 1 H) 8.21-8.38 (m, 1 H).<br>MS ESI/APCI Multi posi: 288[M + H]⁺.<br>MS ESI/APCI Multi nega: 286[M − H]⁻. |
| 1-28 | 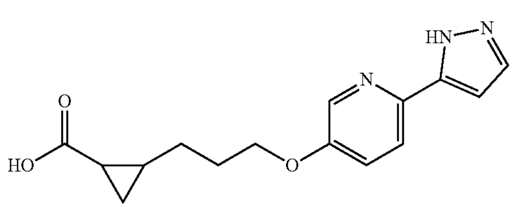 [SMILES: O=C(O)C1CC1CCCOc1ccc(-c2ccn[nH]2)nc1] | ¹H NMR (400 MHz, pyridine-d₅) δ ppm 0.97-1.08 (m, 1 H) 1.09-1.20 (m, 2 H) 1.22-1.35 (m, 1 H) 1.89-2.03 (m, 4 H) 3.95-4.04 (m, 2 H) 7.14-7.20 (m, 1 H) 7.26-7.42 (m, 1 H) 7.95 (d, J = 1.7 Hz, 1 H) 8.05-8.17 (m, 1 H) 8.58 (d, J = 2.8 Hz, 1 H).<br>MS ESI/APCI Multi posi: 288[M + H]⁺. |

TABLE 30-6

| Example No. | Structure | Analytical Data |
|---|---|---|
| 1-29 | 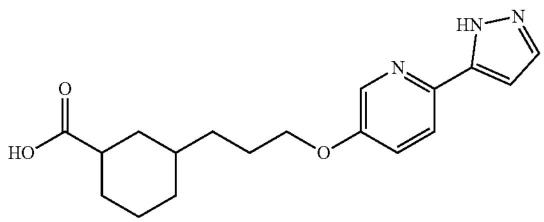 [SMILES: O=C(O)C1CCCC(CCCOc2ccc(-c3ccn[nH]3)nc2)C1] | $^1$H NMR (400 MHz, DMSO-d$_6$) δ ppm 0.79-0.99 (m, 2 H) 1.15-1.39 (m, 5 H) 1.68-1.80 (m, 4 H) 1.82-1.97 (m, 2 H) 2.12-2.22 (m, 1 H) 4.05 (t, J = 6.4 Hz, 2 H) 6.72 (d, J = 1.5 Hz, 1 H) 7.43 (dd, J = 8.8, 2.6 Hz, 1 H) 7.63-7.72 (m, 1 H) 7.75-7.89 (m, 1 H) 8.27 (d, J = 2.6 Hz, 1 H) 12.72 (br s, 1 H).<br>MS ESI/APCI Multi posi: 330[M + H]$^+$.<br>MS ESI/APCI Multi nega: 328[M − H]$^-$. |
| 1-30 | 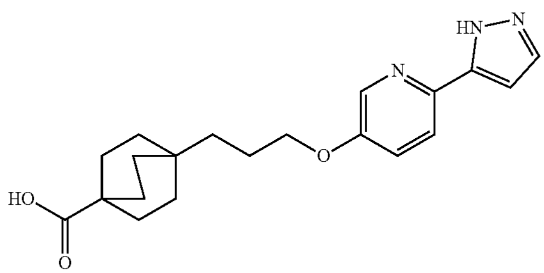 [SMILES: O=C(O)C12CCC(CCCOc3ccc(-c4ccn[nH]4)nc3)(CC1)CC2] | $^1$H NMR (400 MHz, DMSO-d$_6$) δ ppm 1.18-1.27 (m, 2 H) 1.30-1.43 (m, 6 H) 1.55-1.75 (m, 8 H) 4.03 (t, J = 6.4 Hz, 2 H) 6.72 (d, J = 2.1 Hz, 1 H) 7.42 (dd, J = 8.7, 2.8 Hz, 1 H) 7.57-7.75 (m, 1 H) 7.83 (m, 1 H) 8.25 (d, J = 2.8 Hz, 1 H) 12.59 (br s, 1 H).<br>MS ESI/APCI Multi posi: 356[M + H]$^+$. |
| 1-31 | 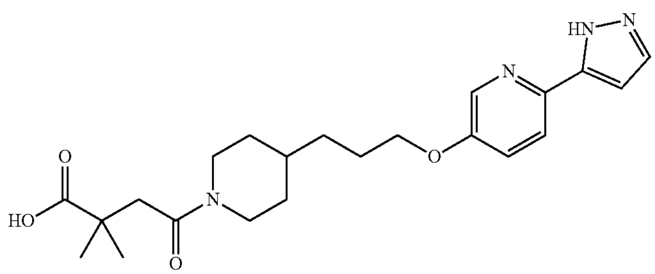 [SMILES: CC(C)(CC(=O)N1CCC(CCCOc2ccc(-c3ccn[nH]3)nc2)CC1)C(=O)O] | $^1$H NMR (400 MHz, DMSO-d$_6$) δ ppm 1.03 (s, 6 H) 1.11-1.28 (m, 4 H) 1.32-1.44 (m, 2 H) 1.45-1.62 (m, 1 H) 1.65-1.87 (m, 4 H) 2.70-2.85 (m, 1 H) 3.17-3.25 (m, 1 H) 3.80-3.88 (m, 2 H) 4.02-4.12 (m, 2 H) 4.40-4.48 (m, 1 H) 6.72 (d, J = 1.8 Hz, 1 H) 7.43 (dd, J = 8.7, 2.8 Hz, 1 H) 7.62-7.71 (m, 1 H) 7.80-7.88 (m, 1 H) 8.23-8.35 (m, 1 H).<br>MS ESI/APCI Multi posi: 415[M + H]$^+$.<br>MS ESI/APCI Multi nega: 413[M − H]$^-$. |
| 1-32 | 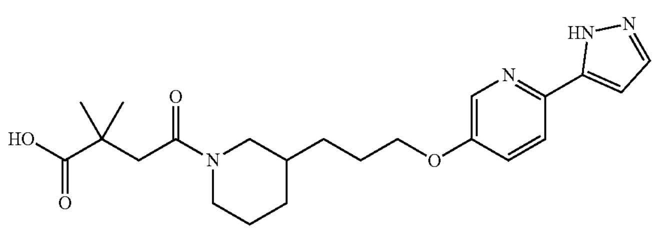 [SMILES: CC(C)(CC(=O)N1CCCC(CCCOc2ccc(-c3ccn[nH]3)nc2)C1)C(=O)O] | $^1$H NMR (400 MHz, DMSO-d$_6$) δ ppm 1.03 (s, 6 H) 1.06-1.21 (m, 2 H) 1.26-1.44 (m, 2 H) 1.52-1.69 (m, 2 H) 1.69-1.87 (m, 4 H) 2.22 (s, 2 H) 2.67-2.79 (m, 1 H) 3.12-3.23 (m, 2 H) 4.04-4.10 (m, 2 H) 6.72 (d, J = 1.8 Hz, 1 H) 7.40-7.47 (m, 1 H) 7.65-7.75 (m, 1 H) 7.82-7.88 (m, 1 H) 8.27 (d, J = 2.7 Hz, 1 H).<br>MS ESI/APCI Multi posi: 415[M + H]$^+$.<br>MS ESI/APCI Multi nega: 413[M − H]$^-$. |
| 1-33 | 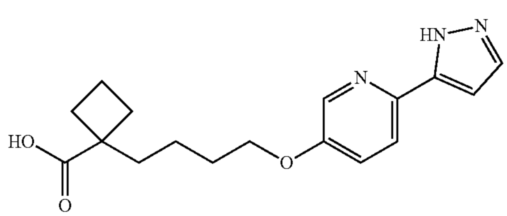 [SMILES: O=C(O)C1(CCCCOc2ccc(-c3ccn[nH]3)nc2)CCC1] | $^1$H NMR (400 MHz, DMSO-d$_6$) δ ppm 1.23-1.41 (m, 2 H) 1.66-1.95 (m, 9 H) 2.20-2.35 (m, 1 H) 4.00-4.15 (m, 2 H) 6.72 (s, 1 H) 7.39-7.50 (m, 1 H) 7.60-7.75 (m, 1 H) 7.80-7.90 (m, 1 H) 8.27 (s, 1 H) 12.63 (br s, 1 H).<br>MS ESI/APCI Multi posi: 316[M + H]$^+$.<br>MS ESI/APCI Multi nega: 314[M − H]$^-$. |
| 1-34 | 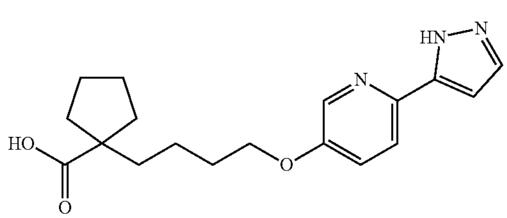 [SMILES: O=C(O)C1(CCCCOc2ccc(-c3ccn[nH]3)nc2)CCCC1] | $^1$H NMR (400 MHz, DMSO-d$_6$) δ ppm 1.30-1.45 (m, 4 H) 1.52-1.64 (m, 6 H) 1.66-1.76 (m, 2 H) 1.96-2.07 (m, 2 H) 4.05 (t, J = 6.4 Hz, 2 H) 6.72 (d, J = 1.8 Hz, 1 H) 7.40-7.50 (m, 1 H) 7.62-7.75 (m, 1 H) 7.75-7.91 (m, 1 H) 8.26 (d, J = 2.9 Hz, 1 H).<br>MS ESI/APCI Multi posi: 330[M + H]$^+$.<br>MS ESI/APCI Multi nega: 328[M − H]$^-$. |

TABLE 30-7

| Example No. | Structure | Analytical Data |
|---|---|---|
| 1-35 | 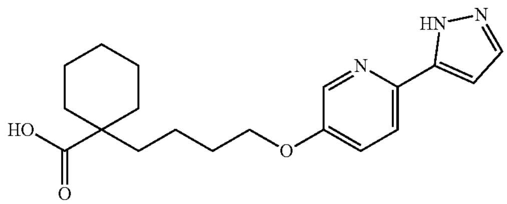 [SMILES: O=C(O)C1(CCCCOc2ccc(-c3ccn[nH]3)nc2)CCCCC1] | ¹H NMR (400 MHz, DMSO-d₆) δ ppm 1.10-1.40 (m, 7 H) 1.45-1.57 (m, 5 H) 1.69 (quin, J = 6.8 Hz, 2 H) 1.90-2.00 (m, 2 H) 4.05 (t, J = 6.4 Hz, 2 H) 6.72 (d, J = 2.0 Hz, 1 H) 7.43 (dd, J = 8.7, 2.8 Hz, 1 H) 7.63-7.75 (m, 1 H) 7.84 (d, J = 8.7 Hz, 1 H) 8.24-8.28 (m, 1 H) 12.60 (br s, 1 H).<br>MS ESI/APCI Multi posi: 344[M + H]⁺.<br>MS ESI/APCI Multi nega: 342[M − H]⁻. |
| 1-36 | 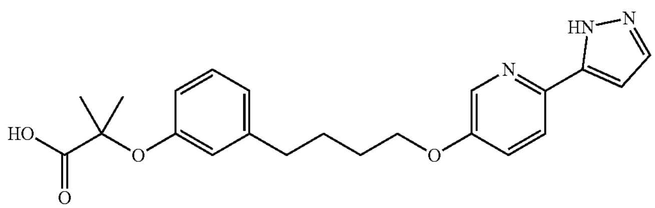 [SMILES: CC(C)(Oc1cccc(CCCCOc2ccc(-c3ccn[nH]3)nc2)c1)C(=O)O] | ¹H NMR (400 MHz, CHLOROFORM-d) δ ppm 1.67 (s, 6 H) 1.69-1.78 (m, 4 H) 2.59-2.68 (m, 2 H) 3.84-3.92 (m, 2 H) 4.72-4.91 (m, 4 H) 6.70 (d, J = 1.7 Hz, 1 H) 6.75-6.88 (m, 3 H) 7.09 (dd, J = 8.6, 2.5 Hz, 1 H) 7.16 (t, J = 7.9 Hz, 1 H) 7.56 (d, J = 8.6 Hz, 1 H) 7.61 (d, J = 1.6 Hz, 1 H) 8.10 (d, J = 2.5 Hz, 1 H).<br>MS ESI/APCI Multi posi: 396[M + H]⁺.<br>MS ESI/APCI Multi nega: 394[M − H]⁻. |
| 1-37 | 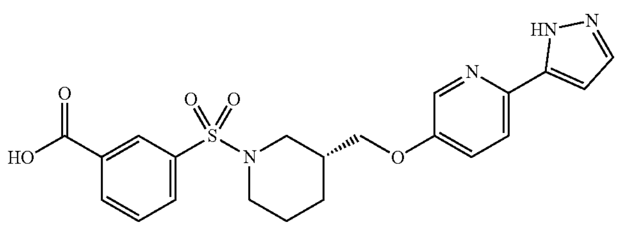 [SMILES: O=C(O)c1cccc(S(=O)(=O)N2CCC[C@@H](COc3ccc(-c4ccn[nH]4)nc3)C2)c1] | ¹H NMR (400 MHz, DMSO-d₆) δ ppm 1.04-1.25 (m, 1 H) 1.48-1.60 (m, 1 H) 1.70-1.80 (m, 2 H) 2.02-2.12 (m, 1 H) 3.48-3.55 (m, 2 H) 3.65-3.71 (m, 2 H) 3.92-4.01 (m, 2 H) 6.73 (s, 1 H) 7.41-7.47 (m, 1 H) 7.62-7.72 (m, 1 H) 7.72-7.80 (m, 1 H) 7.80-7.90 (m, 2 H) 7.93-8.01 (m, 1 H) 8.15-8.30 (m, 3 H).<br>MS ESI/APCI Multi posi: 443[M + H]⁺.<br>MS ESI/APCI Multi nega: 441[M − H]⁻. |
| 1-38 | 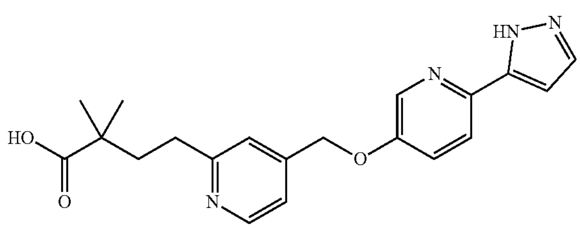 [SMILES: CC(C)(CCc1cc(COc2ccc(-c3ccn[nH]3)nc2)ccn1)C(=O)O] | ¹H NMR (400 MHz, DMSO-d₆) δ ppm 1.15 (s, 6 H) 1.77-1.91 (m, 2 H) 2.63-2.76 (m, 2 H) 5.25 (s, 2 H) 6.73 (s, 1 H) 7.27 (m, 1 H) 7.33 (s, 1 H) 7.49-7.55 (m, 1 H) 7.63-7.72 (m, 1 H) 7.83-7.90 (m, 1 H) 8.37 (d, J = 1.7 Hz, 1 H) 8.47 (d, J = 4.9 Hz, 1 H) 12.68 (br s, 1 H).<br>MS ESI posi: 367[M + H]⁺.<br>MS ESI nega: 365[M − H]⁻. |
| 1-39 | 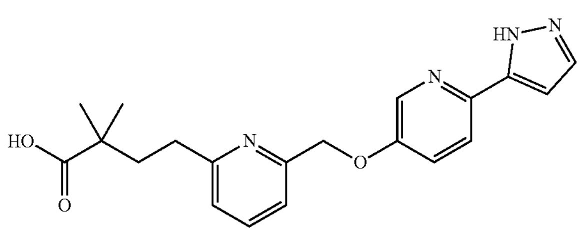 [SMILES: CC(C)(CCc1cccc(COc2ccc(-c3ccn[nH]3)nc2)n1)C(=O)O] | ¹H NMR (400 MHz, DMSO-d₆) δ ppm 1.16 (s, 6 H) 1.80-1.91 (m, 2 H) 2.66-2.76 (m, 2 H) 5.27 (s, 2 H) 6.76 (s, 1 H) 7.22-7.27 (m, 1 H) 7.37-7.42 (m, 1 H) 7.56-7.62 (m, 1 H) 7.68-7.72 (m, 1 H) 7.75-7.81 (m, 1 H) 7.88-7.91 (m, 1 H) 8.39 (d, J = 2.2 Hz, 1 H).<br>MS ESI posi: 367[M + H]⁺.<br>MS ESI nega: 365[M − H]⁻. |

Example 1-40

4-[[6-(1H-Pyrazol-5-yl)-3-pyridinyl]oxymethyl]-2-pyridinecarboxylic Acid

[Formula 488]

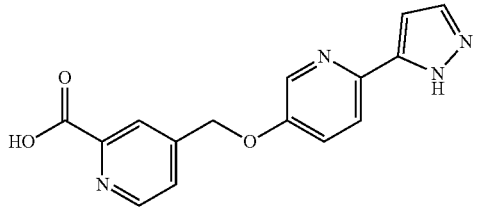

(1) The compound (80 mg) obtained in Reference Example 1-1 and methyl 4-(hydroxymethyl)-2-pyridinecarboxylate (65 mg) were used to perform the synthesis process according to the method described in Example 1-1-(1) thereby giving a crude product (185 mg) containing methyl 4-[[6-[2-(2-oxanyl)-3-pyrazolyl]-3-pyridinyl]oxymethyl]-2-pyridinecarboxylate as a brown oil.

(2) The compound (185 mg) obtained in (1) above was used to perform the method described in Example 1-1-(2) at room temperature thereby giving 4-[[6-[2-(2-oxanyl)-3-pyrazolyl]-3-pyridinyl]oxymethyl]-2-pyridinecarboxylic acid.

(3) The compound obtained in (2) above was used to perform the synthesis process according to the method described in Example 1-1-(3) thereby giving the title compound (8 mg) as a colorless powder.

$^1$H NMR (400 MHz, DMSO-$d_6$) δ ppm 5.40 (s, 2H) 6.71-6.78 (m, 1H) 7.52-7.61 (m, 1H) 7.66-7.75 (m, 2H) 7.84-7.93 (m, 1H) 8.08-8.17 (m, 1H) 8.36-8.44 (m, 1H) 8.68-8.77 (m, 1H).

MS ESI/APCI Multi posi: 297[M+H]$^+$.

Example 1-41

4-[[6-(4-Chloro-1H-pyrazol-3-yl)-3-pyridinyl]oxymethyl]-2-pyridinecarboxylic Acid

[Formula 489]

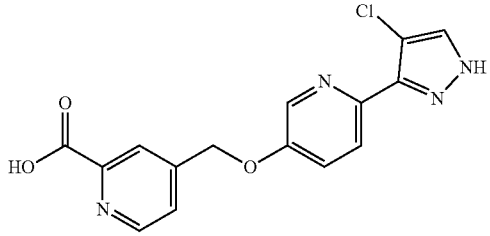

(1) The compound (70 mg) obtained in Reference Example 3-1 was used to perform the synthesis process according to the method described in Example 1-40-(1) thereby giving a crude product (145 mg) containing methyl 4-[[6-[4-chloro-1-(2-oxanyl)-3-pyrazolyl]-3-pyridinyl]oxymethyl]-2-pyridinecarboxylate as a pale brown oil.

(2) The compound (145 mg) obtained in (1) above was used to perform the synthesis process according to the method described in Example 1-40-(2) thereby giving 4-[[6-[4-chloro-1-(2-oxanyl)-3-pyrazolyl]-3-pyridinyl]oxymethyl]-2-pyridinecarboxylic acid.

(3) The compound obtained in (2) above was used to perform the synthesis process according to the method described in Example 1-1-(3) thereby giving the title compound (5 mg) as a colorless powder.

$^1$H NMR (400 MHz, DMSO-$d_6$) δ ppm 5.42 (s, 2H) 7.52-8.03 (m, 4H) 8.07-8.19 (m, 1H) 8.43-8.55 (m, 1H) 8.66-8.76 (m, 1H).

MS ESI/APCI Multi posi: 331 [M+H]$^+$.

The compound of Example 1-42 below was synthesized using a commercially available compound, according to the methods described in Examples 1-1-(1) and 1-40-(2), and by performing the reaction in the method described in Example 1-1-(3) under ice cooling. The structures, NMR data, and MS data of the compounds are shown in Table 30-8.

TABLE 30-8

| Example No. | Structure | Analytical Data |
| --- | --- | --- |
| 1-42 | (structure shown) | $^1$H NMR (400 MHz, DMSO-$d_6$) δ ppm 0.99-1.19 (m, 2 H) 1.25-1.43 (m, 2 H) 1.67-1.80 (m, 1 H) 1.82-2.00 (m, 4 H) 2.10-2.25 (m, 1 H) 3.89 (d, J = 6.4 Hz, 2 H) 6.72 (d, J = 2.0 Hz, 1 H) 7.43 (dd, J = 8.7, 2.8 Hz, 1 H) 7.56-7.75 (m, 1 H) 7.76-7.87 (m, 1 H) 8.27 (d, J = 2.8 Hz, 1 H) 12.48 (br s, 1 H). MS ESI/APCI Multi posi: 302[M + H]$^+$. |

Example 1-43

2,2-Dimethyl-7-[[6-(1H-pyrazol-5-yl)-3-pyridinyl]oxy]heptanoic Acid

[Formula 490]

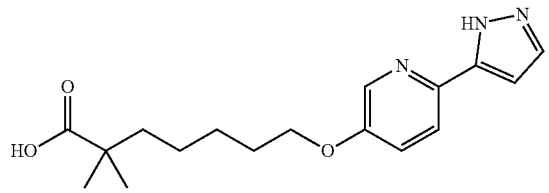

(1) The compound (40 mg) obtained in Reference Example 1-1 and the compound (35 mg) obtained in Reference Example 34-1 were used to perform the synthesis process according to the method described in Example 1-1-(1) thereby giving ethyl 2,2-dimethyl-7-[[6-[2-(2-oxanyl)-3-pyrazolyl]-3-pyridinyl]oxy]heptanoate (47 mg) as a light brown oil.

(2) An aqueous solution of 1 mol/L sodium hydroxide (230 μL) was added to a solution of the compound (47 mg) obtained in (1) above in ethanol (1.5 mL), and the mixture was stirred at 90° C. for 10 hours to give a solution containing 2,2-dimethyl-7-[[6-[2-(2-oxanyl)-3-pyrazolyl]-3-pyridinyl]oxy]heptanoic acid.

(3) The solution obtained in (2) above was ice-cooled, methanol (1.50 mL), trifluoroacetic acid (0.25 mL), and water (0.50 mL) were added thereto, and the mixture was stirred under ice cooling for 0.5 hours. After the solvent was distilled off under reduced pressure, the residue was purified by preparative HPLC to give the title compound (20 mg) as a colorless powder.

$^1$H NMR (400 MHz, DMSO-$d_6$) δ ppm 1.07 (s, 6H) 1.18-1.34 (m, 2H) 1.34-1.54 (m, 4H) 1.68-1.80 (m, 2H) 4.05 (t, J=6.4 Hz, 2H) 6.72 (d, J=2.0 Hz, 1H) 7.38-7.48 (m, 1H) 7.63-7.76 (m, 1H) 7.78-7.91 (m, 1H) 8.21-8.32 (m, 1H).

MS ESI/APCI Multi posi: 318[M+H]$^+$.

MS ESI/APCI Multi nega: 316[M−H]$^−$.

The compounds of Examples 1-44 and 1-45 below were synthesized using any of the compounds obtained in Reference Examples 33-7 and 34-4, according to the method described in Example 1-43. The structures, NMR data, and MS data of the compounds are shown in Table 30-9.

TABLE 30-9

| Example No. | Structure | Analytical Data |
|---|---|---|
| 1-44 | 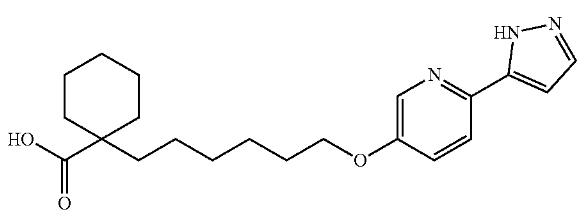 [SMILES: O=C(O)C1(CCCCCCOc2ccc(-c3ccn[nH]3)nc2)CCCCC1] | $^1$H NMR (400 MHz, DMSO-$d_6$) δ ppm 1.07-1.33 (m, 10 H) 1.36-1.45 (m, 3 H) 1.45-1.55 (m, 3 H) 1.66-1.75 (m, 2 H) 1.89-1.98 (m, 2 H) 4.02-4.10 (m, 2 H) 6.72 (d, J = 2.0 Hz, 1 H) 7.40-7.48 (m, 1 H) 7.61-7.76 (m, 1 H) 7.79-7.90 (m, 1 H) 8.26 (d, J = 2.6 Hz, 1 H).<br>MS ESI/APCI Multi posi: 372[M + H]$^+$. |
| 1-45 | 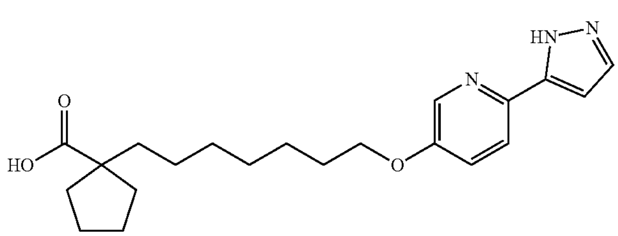 [SMILES: O=C(O)C1(CCCCCCCOc2ccc(-c3ccn[nH]3)nc2)CCCC1] | $^1$H NMR (400 MHz, DMSO-$d_6$) δ ppm 1.16-1.42 (m, 10 H) 1.48-1.59 (m, 6 H) 1.67-1.78 (m, 2 H) 1.95-2.05 (m, 2 H) 4.06 (t, J = 6.4 Hz, 2 H) 6.74 (d, J = 2.1 Hz, 1 H) 7.46 (dd, J = 8.8, 2.9 Hz, 1 H) 7.65-7.72 (m, 1 H) 7.85 (d, J = 8.8 Hz, 1 H) 8.27 (d, J = 2.9 Hz, 1 H).<br>MS ESI/APCI Multi posi: 372[M + H]$^+$.<br>MS ESI/APCI Multi nega: 370[M − H]$^−$. |

Example 1-46

1-[6-[[6-(1H-Pyrazol-5-yl)-3-pyridinyl]oxy]hexyl]-1-cyclopentanecarboxylic Acid

[Formula 491]

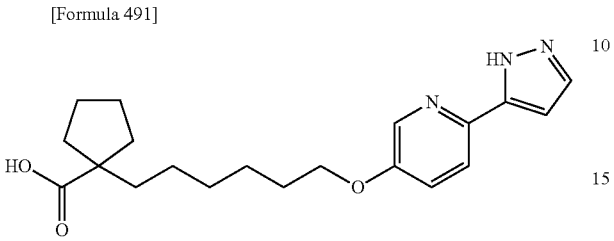

(1) The compound (43 mg) obtained in Reference Example 1-1 and the compound (40 mg) obtained in Reference Example 34-3 were used to perform the synthesis process according to the method described in Example 1-1-(1) thereby giving methyl 1-[6-[[6-[2-(2-oxanyl)-3-pyrazolyl]-3-pyridinyl]oxy]hexyl]-1-cyclopentanecarboxylate (67 mg) as a brown oil.

(2) An aqueous solution of 1 mol/L sodium hydroxide (0.31 mL) was added to the compound (67 mg) obtained in (1) above in ethanol (1.50 mL), and the mixture was stirred at 90° C. for 16 hours. Butanol (2.00 mL) was added to the reaction mixture, and the mixture was stirred at 100° C. for 21 hours. The reaction solution was cooled, and then concentrated under reduced pressure to give 1-[6-[[6-[2-(2-oxanyl)-3-pyrazolyl]-3-pyridinyl]oxy]hexyl]-1-cyclopentanecarboxylic acid as a crude product.

(3) Trifluoroacetic acid (0.25 mL) and water (0.50 mL) were added to a solution of the crude product obtained in (2) above in methanol (1.50 mL) under ice cooling, and the mixture was stirred for 1 hour with ice cooling continued. After the solvent was distilled off under reduced pressure, the residue was purified by preparative HPLC to give the title compound (17 mg) as a colorless powder.

$^1$H NMR (400 MHz, DMSO-d$_6$) δ ppm 1.16-1.25 (m, 2H) 1.27-1.43 (m, 6H) 1.49-1.61 (m, 6H) 1.62-1.76 (m, 2H) 1.94-2.05 (m, 2H) 4.05 (t, J=6.4 Hz, 2H) 6.72 (d, J=1.8 Hz, 1H) 7.43 (dd, J=8.6, 2.5 Hz, 1H) 7.60-7.77 (m, 1H) 7.84 (d, J=8.6 Hz, 1H) 8.26 (d, J=2.5 Hz, 1H) 12.53 (br s, 1H).

MS ESI/APCI Multi posi: 358[M+H]$^+$.
MS ESI/APCI Multi nega: 356[M−H]$^−$.

Example 1-47

6-[[6-(1H-Pyrazol-5-yl)-3-pyridinyl]oxy]hexanoic Acid

[Formula 492]

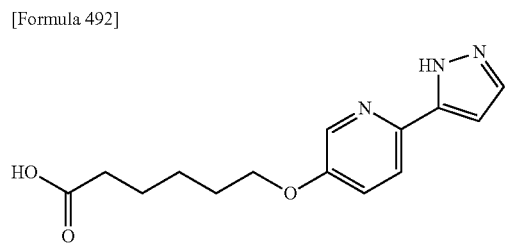 [SMILES: O=C(O)CCCCCOc1ccc(-c2ccn[nH]2)nc1]

(1) The compound (50 mg) obtained in Reference Example 1-1 and ethyl 6-hydroxyhexanoate (40 mg) were used to perform the synthesis process according to the method described in Example 1-1-(1) thereby giving a crude product (68 mg) containing ethyl 6-[[6-[2-(2-oxanyl)-3-pyrazolyl]-3-pyridinyl]oxy]hexanoate as a pale brown oil.

(2) Trifluoroacetic acid (0.25 mL) and water (0.5 mL) were added to a solution of the compound (68 mg) obtained in (1) above in methanol (1 mL), and the mixture was stirred at room temperature overnight. A saturated aqueous solution of sodium hydrogen carbonate was added to the reaction solution, the resultant mixture was extracted with chloroform, and the organic layer was separated by a phase separator, and then concentrated under reduced pressure to give a crude product containing ethyl 6-[[6-(1H-pyrazol-5-yl)-3-pyridinyl]oxy]hexanoate.

(3) An aqueous solution of 6 mol/L sodium hydroxide (0.068 mL) was added to a suspension of the compound (50 mg) obtained in (2) above in methanol (0.83 mL), and the mixture was stirred at room temperature for 2 days. The reaction solution was purified by preparative HPLC to give the title compound (13 mg) as a colorless powder.

$^1$H NMR (400 MHz, DMSO-d$_6$) δ ppm 1.36-1.50 (m, 2H) 1.51-1.64 (m, 2H) 1.67-1.82 (m, 2H) 2.13-2.30 (m, 2H) 3.97-4.14 (m, 2H) 6.67-6.77 (m, 1H) 7.36-7.50 (m, 1H) 7.60-7.75 (m, 1H) 7.79-7.90 (m, 1H) 8.21-8.32 (m, 1H).

MS ESI/APCI Multi posi: 276[M+H]$^+$.

The compounds of Examples 1-48 to 1-56 below were synthesized using any of the compounds obtained in Reference Example 20-1, 59-1, 73-1, and 74-1, or a commercially available compound, according to the method described in Example 1-47. The structures, NMR data, and MS data of the compounds are shown in Tables 30-10 and 30-11.

TABLE 30-10

| Example No. | Structure | Analytical Data |
|---|---|---|
| 1-48 | ![structure] | $^1$H NMR (400 MHz, DMSO-d$_6$) δ ppm 1.20-1.59 (m, 8 H) 1.65-1.80 (m, 2 H) 2.13-2.26 (m, 2 H) 3.99-4.13 (m, 2 H) 6.68-6.77 (m, 1 H) 7.37-7.49 (m, 1 H) 7.61-7.72 (m, 1 H) 7.79-7.89 (m, 1 H) 8.22-8.31 (m, 1 H).<br>MS ESI/APCI Multi posi: 304[M + H]$^+$.<br>MS ESI/APCI Multi nega: 302[M − H]$^−$. |

TABLE 30-10-continued

| Example No. | Structure | Analytical Data |
|---|---|---|
| 1-49 | 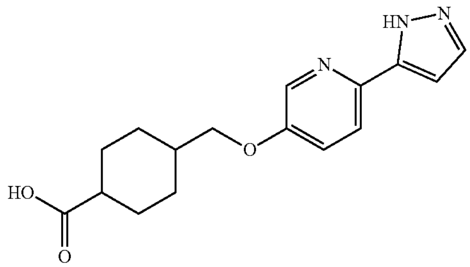 [SMILES: O=C(O)C1CCC(COc2ccc(-c3ccn[nH]3)nc2)CC1] | $^1$H NMR (400 MHz, DMSO-d$_6$) δ ppm 1.00-2.01 (m, 9 H) 3.85-3.99 (m, 2 H) 6.67-6.75 (m, 1 H) 7.39-7.50 (m, 1 H) 7.59-7.73 (m, 1 H) 7.78-7.88 (m, 1 H) 8.24-8.31 (m, 1 H). MS ESI/APCI Multi posi: 302[M + H]$^+$. |
| 1-50 | 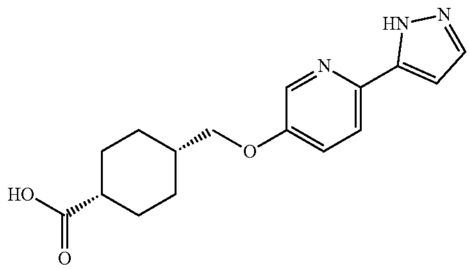 [SMILES: O=C(O)[C@H]1CC[C@@H](COc2ccc(-c3ccn[nH]3)nc2)CC1] | $^1$H NMR (400 MHz, DMSO-d$_6$) δ ppm 1.26-2.00 (m, 9 H) 3.85-3.97 (m, 2 H) 6.68-6.76 (m, 1 H) 7.40-7.49 (m, 1 H) 7.61-7.73 (m, 1 H) 7.78-7.88 (m, 1 H) 8.22-8.32 (m, 1 H). MS ESI/APCI Multi posi: 302[M + H]$^+$. |
| 1-51 | 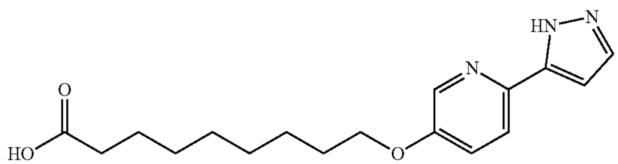 [SMILES: O=C(O)CCCCCCCCOc1ccc(-c2ccn[nH]2)nc1] | $^1$H NMR (400 MHz, DMSO-d$_6$) δ ppm 1.19-1.57 (m, 10 H) 1.65-1.80 (m, 2 H) 2.14-2.24 (m, 2 H) 4.00-4.12 (m, 2 H) 6.67-6.76 (m, 1 H) 7.37-7.48 (m, 1 H) 7.62-7.73 (m, 1 H) 7.79-7.88 (m, 1 H) 8.23-8.31 (m, 1 H). MS ESI/APCI Multi posi: 318[M + H]$^+$. MS ESI/APCI Multi nega: 316[M − H]$^-$. |
| 1-52 | 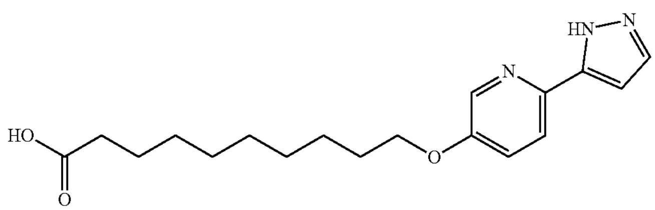 [SMILES: O=C(O)CCCCCCCCCOc1ccc(-c2ccn[nH]2)nc1] | $^1$H NMR (400 MHz, DMSO-d$_6$) δ ppm 1.12-1.59 (m, 12 H) 1.66-1.83 (m, 2 H) 2.18 (t, J = 7.3 Hz, 2 H) 4.06 (t, J = 6.5 Hz, 2 H) 6.66-6.79 (m, 1 H) 7.37-7.50 (m, 1 H) 7.59-7.75 (m, 1 H) 7.79-7.90 (m, 1 H) 8.23-8.32 (m, 1 H). MS ESI/APCI Multi posi: 332[M + H]$^+$. MS ESI/APCI Multi nega: 330[M − H]$^-$. |
| 1-53 | 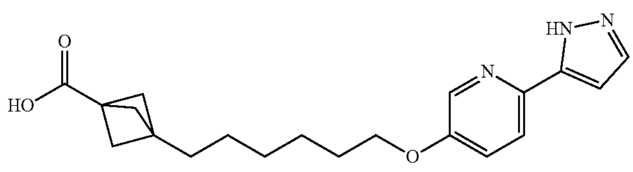 [SMILES: O=C(O)C12CC(CCCCCCOc3ccc(-c4ccn[nH]4)nc3)(C1)C2] | $^1$H NMR (400 MHz, DMSO-d$_6$) δ ppm 1.16-1.49 (m, 8 H) 1.67-1.77 (m, 2 H) 1.79 (s, 6 H) 4.00-4.14 (m, 2 H) 6.68-6.77 (m, 1 H) 7.35-7.49 (m, 1 H) 7.59-7.72 (m, 1 H) 7.79-7.89 (m, 1 H) 8.22-8.30 (m, 1 H). MS ESI/APCI Multi posi: 356[M + H]$^+$. MS ESI/APCI Multi nega: 354[M − H]$^-$. |

TABLE 30-11

| Example No. | Structure | Analytical Data |
|---|---|---|
| 1-54 | 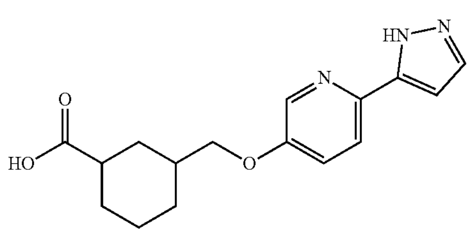 [SMILES: O=C(O)C1CCCC(COc2ccc(-c3ccn[nH]3)nc2)C1] | $^1$H NMR (400 MHz, DMSO-d$_6$) δ ppm 0.95-1.21 (m, 2 H) 1.21-1.35 (m, 2 H) 1.75-1.85 (m, 3 H) 1.85-1.96 (m, 1 H) 2.00-2.10 (m, 1 H) 2.20-2.31 (m, 1 H) 3.88-3.96 (m, 2 H) 6.72 (d, J = 2.1 Hz, 1 H) 7.44 (dd, J = 8.8, 2.8 Hz, 1 H) 7.60-7.78 (m, 1 H) 7.80-7.90 (m, 1 H) 8.28 (d, J = 2.8 Hz, 1 H). MS ESI/APCI Multi posi: 302[M + H]$^+$. |

TABLE 30-11-continued

| Example No. | Structure | Analytical Data |
|---|---|---|
| 1-55 | 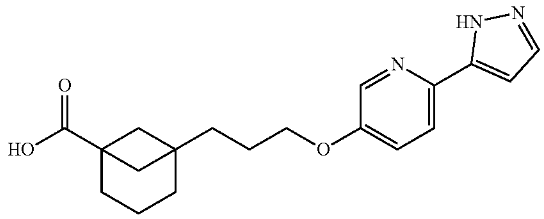 [SMILES: O=C(O)C12CCCC(CCCOc3ccc(-c4ccn[nH]4)nc3)(C1)C2] | $^1$H NMR (400 MHz, DMSO-$d_6$) δ ppm 1.38-1.48 (m, 2 H) 1.51-1.71 (m, 6 H) 1.72-1.88 (m, 6 H) 3.99-4.11 (m, 2 H) 6.67-6.75 (m, 1 H) 7.36-7.48 (m, 1 H) 7.60-7.72 (m, 1 H) 7.77-7.90 (m, 1 H) 8.20-8.32 (m, 1 H). MS ESI/APCI Multi posi: 342[M + H]$^+$. |
| 1-56 | 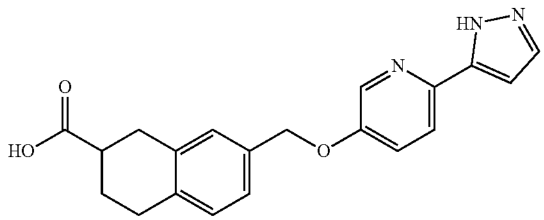 [SMILES: O=C(O)C1CCc2ccc(COc3ccc(-c4ccn[nH]4)nc3)cc2C1] | $^1$H NMR (400 MHz, DMSO-$d_6$) δ ppm 1.64-1.80 (m, 1 H) 2.03-2.15 (m, 1 H) 2.59-3.02 (m, 5 H) 5.13 (s, 2 H) 6.67-6.78 (m, 1 H) 7.05-7.15 (m, 1 H) 7.15-7.27 (m, 2 H) 7.46-7.55 (m, 1 H) 7.63-7.72 (m, 1 H) 7.79-7.90 (m, 1 H) 8.28-8.38 (m, 1 H). MS ESI/APCI Multi posi: 350[M + H]$^+$. MS ESI/APCL Multi nega: 348[M + H]$^-$. |

Example 1-57

2,2-Dimethyl-3-[6-[[6-(1H-pyrazol-5-yl)-3-pyridinyl]oxy]hexoxy]propanoic Acid

[Formula 493]

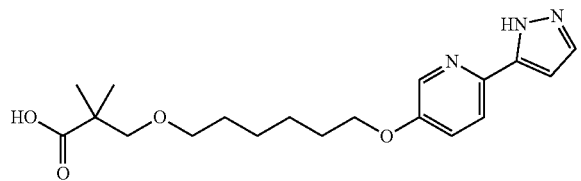

(1) The compound (50 mg) obtained in Reference Example 1-1 and the compound (57 mg) obtained in Reference Example 37-1 were used to perform the synthesis process according to the method described in Example 1-1-(1) thereby giving a crude product (100 mg) containing methyl 2,2-dimethyl-3-[6-[[6-[2-(2-oxanyl)-3-pyrazolyl]-3-pyridinyl]oxy]hexoxy]propanoate as a brown oil.

(2) Trifluoroacetic acid (0.5 mL) and water (1 mL) were added to a solution of the compound (100 mg) obtained in (1) above in methanol (2 mL), and the mixture was stirred at room temperature overnight. A saturated aqueous solution of sodium hydrogen carbonate was added to the reaction solution, the resultant mixture was extracted with chloroform, and the organic layer was separated by a phase separator, and then concentrated under reduced pressure to give a crude product containing methyl 2,2-dimethyl-3-[6-[[6-(1H-pyrazol-5-yl)-3-pyridinyl]oxy]hexoxy]propanoate.

(3) An aqueous solution of 2 mol/L sodium hydroxide (0.26 mL) was added to a solution of the compound (87 mg) obtained in (2) above in methanol (2 mL), and the mixture was stirred for 8 hours while being heated to reflux. The reaction solution was purified by preparative HPLC to give the title compound (23 mg) as a colorless powder.

$^1$H NMR (400 MHz, DMSO-$d_6$) δ ppm 1.07 (s, 6H) 1.25-1.58 (m, 6H) 1.66-1.82 (m, 2H) 3.29-3.47 (m, 4H) 3.98-4.14 (m, 2H) 6.67-6.78 (m, 1H) 7.36-7.49 (m, 1H) 7.62-7.73 (m, 1H) 7.79-7.89 (m, 1H) 8.23-8.32 (m, 1H).
MS ESI/APCI Multi posi: 362[M+H]$^+$.
MS ESI/APCI Multi nega: 360[M−H]$^-$.

The compounds of Examples 1-58 to 1-60 below were synthesized using any of the compounds obtained in Reference Examples 33-1, 49-3, and 75-1, according to the method described in Example 1-57. The structures, NMR data, and MS data of the compounds are shown in Table 30-12.

TABLE 30-12

| Example No. | Structure | Analytical Data |
|---|---|---|
| 1-58 | 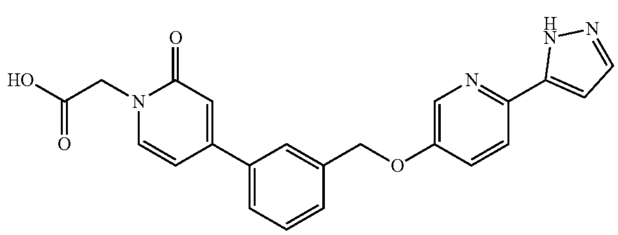 [SMILES: O=C(O)Cn1ccc(-c2cccc(COc3ccc(-c4ccn[nH]4)nc3)c2)cc1=O] | $^1$H NMR (400 MHz, DMSO-$d_6$) δ ppm 4.62 (s, 2 H) 5.29 (s, 2 H) 6.58-6.67 (m, 1 H) 6.68-6.76 (m, 2 H) 7.51-7.62 (m, 3 H) 7.64-7.77 (m, 3 H) 7.83-7.90 (m, 2 H) 8.39 (d, J = 2.8 Hz, 1 H) 13.04 (br s, 1 H). MS ESI/APCI Multi posi: 403[M + H]$^+$. MS ESI/APCI Multi nega: 401[M − H]$^-$. |

TABLE 30-12-continued

| Example No. | Structure | Analytical Data |
|---|---|---|
| 1-59 | 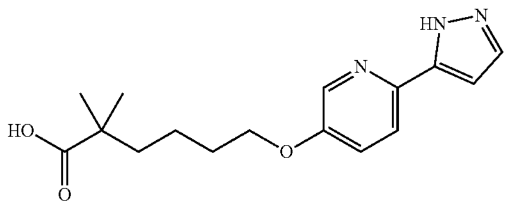 [SMILES: CC(C)(CCCCOc1ccc(-c2ccn[nH]2)nc1)C(=O)O] | $^1$H NMR (400 MHz, DMSO-$d_6$) δ ppm 1.10 (s, 6 H) 1.30-1.42 (m, 2 H) 1.47-1.57 (m, 2 H) 1.63-1.78 (m, 2 H) 4.00-4.13 (m, 2 H) 6.68-6.77 (m, 1 H) 7.38-7.47 (m, 1 H) 7.62-7.72 (m, 1 H) 7.81-7.88 (m, 1 H) 8.24-8.29 (m, 1 H).<br>MS ESI/APCI Multi posi: 304[M + H]$^+$.<br>MS ESI/APCI Multi nega: 302[M − H]$^+$. |
| 1-60 | 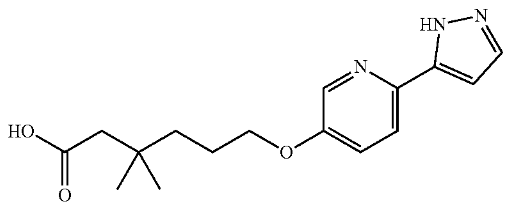 [SMILES: CC(C)(CCCOc1ccc(-c2ccn[nH]2)nc1)CC(=O)O] | $^1$H NMR (400 MHz, DMSO-$d_6$) δ ppm 0.99 (s, 6 H) 1.38-1.49 (m, 2 H) 1.66-1.79 (m, 2 H) 2.13 (s, 2 H) 4.04 (t, J = 6.5 Hz, 2 H) 6.69-6.75 (m, 1 H) 7.39-7.48 (m, 1 H) 7.62-7.73 (m, 1 H) 7.80-7.88 (m, 1 H) 8.24-8.30 (m, 1 H).<br>MS ESI/APCI Multi posi: 304[M + H]$^+$.<br>MS ESI/APCI Multi nega: 302[M − H]$^-$. |

Example 1-61

2,2-Dimethyl-8-[[6-(1H-pyrazol-5-yl)-3-pyridinyl]oxy]octanoic Acid

[Formula 494]

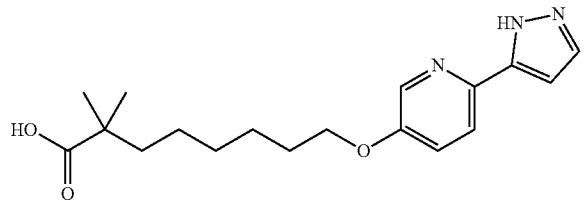

(1) The compound (50 mg) obtained in Reference Example 1-1 and the compound (53 mg) obtained in Reference Example 34-2 were used to perform the synthesis process according to the method described in Example 1-1-(1) thereby giving a crude product (100 mg) containing ethyl 2,2-dimethyl-8-[[6-[2-(2-oxanyl)-3-pyrazolyl]-3-pyridinyl]oxy]octanoate as a brown oil.

(2) Trifluoroacetic acid (0.25 mL) and water (0.5 mL) were added to a solution of the compound (100 mg) obtained in (1) above in ethanol (1 mL), and the mixture was stirred at room temperature overnight. A saturated aqueous solution of sodium hydrogen carbonate was added to the reaction solution, the resultant mixture was extract with chloroform, and the organic layer was separated by a phase separator, and then concentrated under reduced pressure to give a crude product containing ethyl 2,2-dimethyl-8-[[6-(1H-pyrazol-5-yl)-3-pyridinyl]oxy]octanoate.

(3) An aqueous solution of 3 mol/L sodium hydroxide (0.14 mL) was added to a solution of the compound (94 mg) obtained in (2) above in ethanol (1 mL), and the mixture was stirred at room temperature overnight, and for 3 hours while being heated to reflux. An aqueous solution of 3 mol/L sodium hydroxide (0.14 mL) was further added thereto, and the resultant mixture was stirred for 6 hours while being heated to reflux. The reaction solution was purified by preparative HPLC, and the obtained oil was solidified by diethyl ether to give the title compound (33 mg) as a colorless powder.

$^1$H NMR (400 MHz, DMSO-$d_6$) δ ppm 1.07 (s, 6H) 1.16-1.52 (m, 8H) 1.65-1.79 (m, 2H) 4.06 (t, J=6.5 Hz, 2H) 6.67-6.77 (m, 1H) 7.38-7.48 (m, 1H) 7.61-7.73 (m, 1H) 7.79-7.88 (m, 1H) 8.23-8.30 (m, 1H).

MS ESI/APCI Multi posi: 332[M+H]$^+$.
MS ESI/APCI Multi nega: 330[M−H]$^-$.

The compounds of Examples 1-62 and 1-63 below were synthesized using any of the compounds obtained in Reference Examples 32-1 and 33-3, according to the method described in Example 1-61. The structures, NMR data, and MS data of the compounds are shown in Table 30-13.

TABLE 30-13

| Example No. | Structure | Analytical Data |
|---|---|---|
| 1-62 | 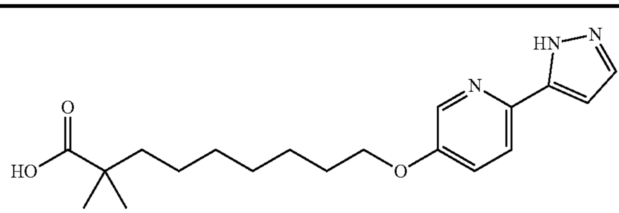 | $^1$H NMR (400 MHz, DMSO-$d_6$) δ ppm 1.07 (s, 6 H) 1.13-1.50 (m, 10 H) 1.67-1.79 (m, 2 H) 4.06 (t, J = 6.4 Hz, 2 H) 6.69-6.76 (m, 1 H) 7.39-7.47 (m, 1 H) 7.61-7.73 (m, 1 H) 7.80-7.88 (m, 1 H) 8.19-8.32 (m, 1 H).<br>MS ESI/APCI Multi posi: 346[M + H]$^+$. |

TABLE 30-13-continued

| Example No. | Structure | Analytical Data |
|---|---|---|
| 1-63 | 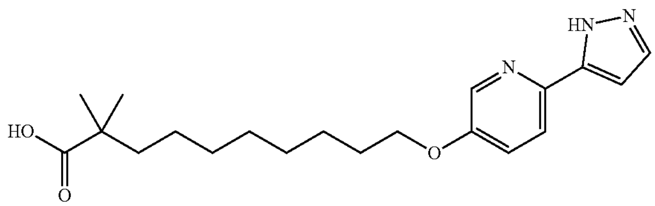 [SMILES: CC(C)(CCCCCCCCOc1ccc(-c2ccn[nH]2)nc1)C(=O)O] | $^1$H NMR (400 MHz, DMSO-$d_6$) δ ppm 1.06 (s, 6 H) 1.13-1.51 (m, 12 H) 1.66-1.80 (m, 2 H) 4.06 (t, J = 6.5 Hz, 2 H) 6.67-6.78 (m, 1 H) 7.37-7.48 (m, 1 H) 7.62-7.72 (m, 1 H) 7.80-7.88 (m, 1 H) 8.23-8.32 (m, 1 H). MS ESI/APCI Multi posi: 360[M + H]$^+$. MS ESI/APCI Multi nega: 358[M − H]$^−$. |

Example 1-64

2,2-Diethyl-6-[[6-(1H-pyrazol-5-yl)-3-pyridinyl]oxy]hexanoic Acid

[Formula 495]

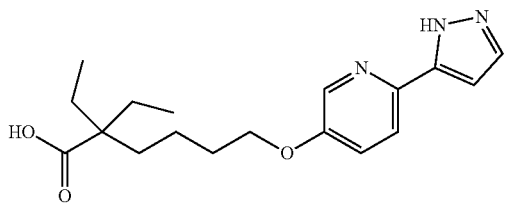

(1) The compound (50 mg) obtained in Reference Example 1-1 and the compound (53 mg) obtained in Reference Example 33-2 were used to perform the synthesis process according to the method described in Example 1-1-(1) thereby giving a crude product (107 mg) containing ethyl 2,2-diethyl-6-[[6-[2-(2-oxanyl)-3-pyrazolyl]-3-pyridinyl]oxy]hexanoate as a brown oil.

(2) The compound (107 mg) obtained in (1) above was used to perform the synthesis process according to the method described in Example 1-61-(2) thereby giving ethyl 2,2-diethyl-6-[[6-(1H-pyrazol-5-yl)-3-pyridinyl]oxy]hexanoate.

(3) An aqueous solution of 3 mol/L sodium hydroxide (0.27 mL) was added to a solution of the compound (83 mg) obtained in (2) above in ethanol (1 mL), the mixture was stirred at 70° C. for 6 hours, an aqueous solution of 3 mol/L sodium hydroxide (0.14 mL) was further added thereto, and the resultant mixture was stirred at 70° C. for 2 hours, at 90° C. for 2 hours, and for 3 hours while being heated to reflux. Further, the mixture was stirred with a microwave reactor at 130° C. for 15 minutes, and at 150° C. for 4 hours. The reaction solution was purified by preparative HPLC, and the obtained oil was solidified by diethyl ether to give the title compound (21 mg) as a colorless powder.

$^1$H NMR (400 MHz, DMSO-$d_6$) δ ppm 0.74 (t, J=7.4 Hz, 6H) 1.19-1.37 (m, 2H) 1.40-1.59 (m, 6H) 1.64-1.81 (m, 2H) 4.07 (t, J=6.4 Hz, 2H) 6.66-6.76 (m, 1H) 7.37-7.48 (m, 1H) 7.59-7.74 (m, 1H) 7.79-7.89 (m, 1H) 8.22-8.31 (m, 1H).

MS ESI/APCI Multi posi: 332[M+H]$^+$.

MS ESI/APCI Multi nega: 330[M−H]$^−$.

Example 1-65

2-Methoxy-5-[[6-(1H-pyrazol-5-yl)-3-pyridinyl]oxymethyl]benzoic Acid

[Formula 496]

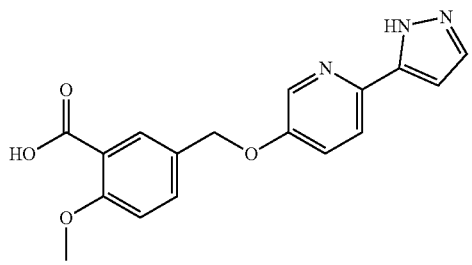

(1) The compound (100 mg) obtained in Reference Example 1-1 and the compound (88 mg) obtained in Reference Example 28-1 were used to perform the synthesis process according to the method described in Example 1-1-(1) thereby giving a crude product (155 mg) containing methyl 2-methoxy-5-[[6-[2-(2-oxanyl)-3-pyrazolyl]-3-pyridinyl]oxymethyl]benzoate as a colorless amorphous substance.

(2) Concentrated hydrochloric acid (0.03 mL) was added to a solution of the compound (155 mg) obtained in (1) above in methanol (3.6 mL), and the mixture was stirred at room temperature for 1.5 hours to give a solution containing methyl 2-methoxy-5-[[6-(1H-pyrazol-5-yl)-3-pyridinyl]oxymethyl]benzoate.

(3) An aqueous solution of 2 mol/L sodium hydroxide (0.89 mL) was added to the solution obtained in (2) above, and the resultant mixture was stirred at 60° C. for 2.5 hours. The reaction solution was concentrated under reduced pressure, and purified by preparative HPLC. The obtained oil was solidified by acetonitrile to give the title compound (68 mg) as a colorless powder.

$^1$H NMR (400 MHz, DMSO-$d_6$) δ ppm 3.83 (s, 3H) 5.17 (s, 2H) 6.66-6.80 (m, 1H) 7.11-7.20 (m, 1H) 7.49-7.55 (m, 1H) 7.58-7.64 (m, 1H) 7.64-7.71 (m, 1H) 7.72-7.77 (m, 1H) 7.82-7.90 (m, 1H) 8.31-8.38 (m, 1H).

MS ESI/APCI Multi posi: 326[M+H]$^+$.

MS ESI/APCI Multi nega: 324[M−H]$^−$.

The compounds of Examples 1-66 to 1-70 below were synthesized using a compound obtained in Reference Example 38-4, 53-1, 60-1 or 60-2, or 81-1, according to the method described in Example 1-65. The structures, NMR data, and MS data of the compounds are shown in Table 30-14.

TABLE 30-14

| Example No. | Structure | Analytical Data |
|---|---|---|
| 1-66 | 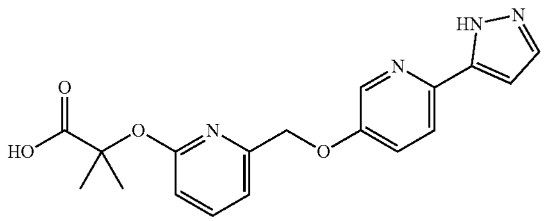 [SMILES: CC(C)(Oc1cccc(COc2ccc(-c3ccn[nH]3)nc2)n1)C(=O)O] | $^1$H NMR (400 MHz, DMSO-d$_6$) δ ppm 1.59 (s, 6 H) 5.08 (s, 2 H) 6.68-6.78 (m, 2 H) 7.04-7.12 (m, 1 H) 7.43-7.52 (m, 1 H) 7.61-7.77 (m, 2 H) 7.81-7.90 (m, 1 H) 8.29-8.36 (m, 1 H). <br> MS ESI/APCI Multi posi: 355[M + H]$^+$. <br> MS ESI/APCI Multi nega: 353[M − H]$^−$. |
| 1-67 | 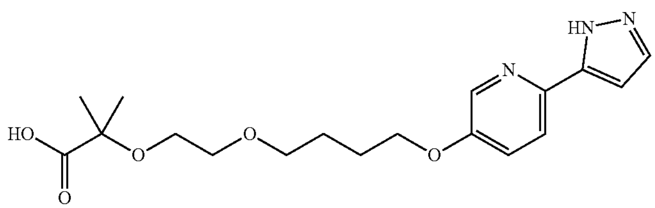 [SMILES: CC(C)(OCCOCCCCOc1ccc(-c2ccn[nH]2)nc1)C(=O)O] | $^1$H NMR (400 MHz, DMSO-d$_6$) δ ppm 1.30 (s, 6 H) 1.55-1.87 (m, 4H) 3.38-3.58 (m, 6H) 4.09 (t, J = 6.4 Hz, 2 H) 6.64-6.80 (m, 1 H) 7.34-7.49 (m, 1 H) 7.61-7.72 (m, 1 H) 7.77-7.90 (m, 1 H) 8.21-8.35 (m, 1 H). <br> MS ESI posi: 364[M + H]$^+$. <br> MS ESI nega: 362[M − H]$^−$. |
| 1-68 | 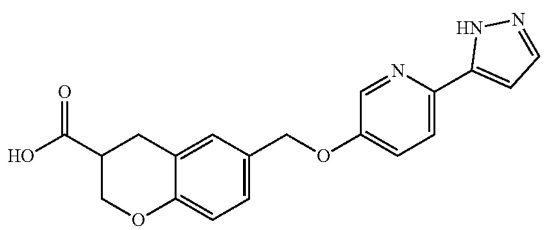 [SMILES: O=C(O)C1COc2ccc(COc3ccc(-c4ccn[nH]4)nc3)cc2C1] | $^1$H NMR (600 MHz, DMSO-d$_6$) δ ppm 2.96 (s, 3 H) 4.10-4.17 (m, 1 H) 4.28-4.34 (m, 1 H) 5.07 (s, 2 H) 6.73 (d, J = 2.1 Hz, 1 H) 6.77 (d, J = 8.3 Hz, 1 H) 7.18 (dd, J = 8.3, 2.1 Hz, 1 H) 7.24 (s, 1 H) 7.51 (dd, J = 8.9, 2.9 Hz, 1 H) 7.63-7.71 (m, 1 H) 7.85 (d, J = 8.9 Hz, 1 H) 8.33 (d, J = 2.9 Hz, 1 H). <br> MS ESI posi: 352[M + H]$^+$. <br> MS ESI nega: 350[M − H]$^−$. |
| 1-69 | 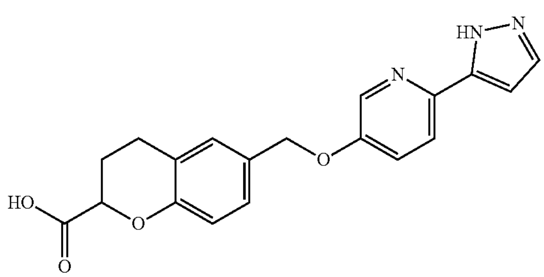 [SMILES: O=C(O)C1CCc2cc(COc3ccc(-c4ccn[nH]4)nc3)ccc2O1] | $^1$H NMR (600 MHz, DMSO-d$_6$) δ ppm 2.02-2.17 (m, 2 H) 2.59-2.69 (m, 1 H) 2.74-2.83 (m, 1 H) 4.72-4.77 (m, 1 H) 5.07 (s, 2 H) 6.72 (d, J = 2.1 Hz, 1 H) 6.81 (d, J = 8.3 Hz, 1 H) 7.15-7.22 (m, 2 H) 7.51 (dd, J = 8.8, 3.0 Hz, 1 H) 7.64-7.72 (m, 1 H) 7.85 (d, J = 8.8 Hz, 1 H) 8.32 (d, J = 3.0 Hz, 1 H). <br> MS ESI posi: 352[M + H]$^+$. <br> MS ESI nega: 350[M − H]$^−$. |
| 1-70 | 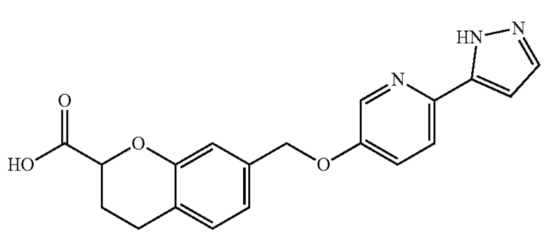 [SMILES: O=C(O)C1CCc2ccc(COc3ccc(-c4ccn[nH]4)nc3)cc2O1] | $^1$H NMR (600 MHz, DMSO-d$_6$) δ ppm 2.02-2.18 (m, 2 H) 2.59-2.67 (m, 1 H) 2.74-2.82 (m, 1 H) 4.76-4.81 (m, 1 H) 5.14 (s, 2 H) 6.72 (d, J = 2.1 Hz, 1 H) 6.90-6.95 (m, 2 H) 7.07 (d, J = 7.8 Hz, 1 H) 7.50 (dd, J = 8.6, 2.8 Hz, 1 H) 7.64-7.70 (m, 1 H) 7.84 (d, J = 8.6 Hz, 1 H) 8.33 (d, J = 2.8 Hz, 1 H). <br> MS ESI posi: 352[M + H]$^+$. <br> MS ESI nega: 350[M − H]$^−$. |

Example 2-1 trans-4-[[6-(1H-Pyrazol-5-yl)-3-pyridinyl]oxymethyl]-1-adamantanecarboxylic Acid

[Formula 497]

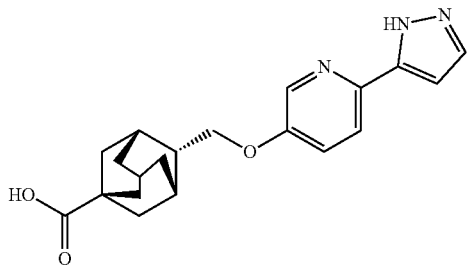

(1) The compound (27 mg) obtained in Reference Example 1-1 and the compound (32 mg) obtained in Reference Example 72-1 were used to perform the synthesis process according to the method described in Example 1-1-(1) thereby giving (phenylmethyl) 4-[[6-[2-(2-oxanyl)-3-pyrazolyl]-3-pyridinyl]oxymethyl]-1-adamantanecarboxylate (41 mg) as a colorless oil.

(2) The compound (41 mg) obtained in (1) above was used to perform the synthesis process according to the method described in Example 1-46-(3) thereby giving a crude product. The obtained crude product was purified by preparative HPLC to give a compound (10 mg) of Example 2-1-(2)-1 (trans form) as a highly polar compound; and a compound (10 mg) of Example 2-1-(2)-2 (cis form) as a less polar compound.

(3) Palladium carbon (110 mg) was added to a solution of the compound (10 mg) of Example 2-1-(2)-1 in ethanol (1.1 mL) under a nitrogen atmosphere, and the mixture was stirred under a hydrogen atmosphere at room temperature for 20 hours. The mixture was filtered through Celite (registered trademark), and the filtrate was concentrated under reduced pressure. The residue was purified by preparative HPLC to give the title compound (5.6 mg) as a colorless powder.

$^1$H NMR (400 MHz, DMSO-$d_6$) δ ppm 1.40-1.51 (m, 2H) 1.77-1.96 (m, 9H) 1.98-2.07 (m, 2H) 2.08-2.15 (m, 1H) 4.19 (d, J=7.3 Hz, 2H) 6.73 (d, J=2.0 Hz, 1H) 7.50 (dd, J=8.7, 2.7 Hz, 1H) 7.62-7.75 (m, 1H) 7.84 (d, J=8.7 Hz, 1H) 8.31 (d, J=2.7 Hz, 1H) 12.67 (br s, 1H).

MS ESI/APCI Multi posi: 354[M+H]$^+$.

Example 2-2 cis-4-[[6-(1H-Pyrazol-5-yl)-3-pyridinyl]oxymethyl]-1-adamantanecarboxylic Acid

[Formula 498]

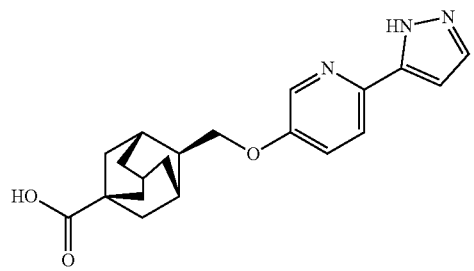

The compound (10 mg) of Example 2-1-(2)-2 was used to perform the synthesis process according to the method described in Example 2-1-(3) thereby giving the title compound (5.3 mg) as a colorless powder.

$^1$H NMR (400 MHz, DMSO-$d_6$) δ ppm 1.55-1.65 (m, 2H) 1.68-1.82 (m, 6H) 1.88-2.07 (m, 5H) 2.07-2.17 (m, 1H) 4.12 (d, J=7.2 Hz, 2H) 6.73 (d, J=2.1 Hz, 1H) 7.50 (dd, J=8.7, 2.7 Hz, 1H) 7.60-7.76 (m, 1H) 7.84 (d, J=8.7 Hz, 1H) 8.30 (d, J=2.7 Hz, 1H) 12.68 (br s, 1H).

MS ESI/APCI Multi posi: 354[M+H]$^+$.

The compounds of Examples 2-3 and 2-4 below were synthesized using a compound obtained in Reference Example 36-1 or 38-3, according to the method described in Example 2-1. The structures, NMR data, and MS data of the compounds are shown in Table 31-1.

TABLE 31-1

| Example No. | Structure | Analytical Data |
| --- | --- | --- |
| 2-3 | ![structure] | $^1$H NMR (400 MHz, DMSO-$d_6$) δ ppm 1.24-1.52 (m, 8 H) 1.55-1.98 (m, 10 H) 3.23-3.35 (m, 2 H) 4.06 (t, J = 6.5 Hz, 2 H) 6.65-6.77 (m, 1 H) 7.35-7.49 (m, 1 H) 7.61-7.73 (m, 1 H) 7.80-7.88 (m, 1 H) 8.21-8.33 (m, 1 H).<br>MS ESI/APCI Multi posi: 388[M + H]$^+$.<br>MS ESI/APCI Multi nega: 386[M − H]$^-$. |
| 2-4 | ![structure] | $^1$H NMR (400 MHz, DMSO-$d_6$) δ ppm 1.50-1.99 (m, 12 H) 3.41-3.55 (m, 6 H) 4.09 (t, J = 6.4 Hz, 2 H) 6.66-6.77 (m, 1 H) 7.34-7.48 (m, 1 H) 7.60-7.72 (m, 1 H) 7.79-7.89 (m, 1 H) 8.21-8.32 (m, 1 H).<br>MS ESI posi: 390[M + H]$^+$.<br>MS ESI nega: 388[M − H]$^-$. |

Example 2-5

3-[2-[2-[[6-(1H-Pyrazol-5-yl)-3-pyridinyl]oxy]ethyl]phenyl]propanoic Acid

[Formula 499]

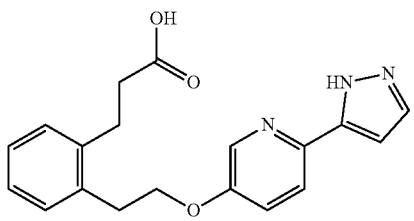

(1) The compound (43 mg) obtained in Reference Example 1-1 and the compound (50 mg) obtained in Reference Example 41-1 were used to perform the synthesis process according to the method described in Example 1-1-(1) thereby giving (phenylmethyl) (E)-3-[2-[2-[[6-[2-(2-oxanyl)-3-pyrazolyl]-3-pyridinyl]oxy]ethyl]phenyl]-2-propenoate (106 mg) as a brown oil.

(2) Palladium carbon (110 mg) was added to a solution of the compound (106 mg) obtained in (1) above in ethanol (1.1 mL) under a nitrogen atmosphere, and the mixture was then stirred under a hydrogen atmosphere at room temperature for 20 hours. The mixture was filtered through Celite (registered trademark), and the filtrate was concentrated under reduced pressure to give (3-[2-[2-[[6-[2-(2-oxanyl)-3-pyrazolyl]-3-pyridinyl]oxy]ethyl]phenyl]propanoic acid as a crude product.

(3) The crude product obtained in (2) above was used to perform the synthesis process according to the method described in Example 1-46-(3) thereby giving the title compound (30 mg) as a colorless powder.

$^1$H NMR (400 MHz, DMSO-$d_6$) δ ppm 2.52-2.57 (m, 2H) 2.84-3.00 (m, 2H) 3.11 (t, J=6.9 Hz, 2H) 4.29 (t, J=7.0 Hz, 2H) 6.72 (d, J=2.0 Hz, 1H) 7.12-7.26 (m, 3H) 7.26-7.37 (m, 1H) 7.46 (dd, J=8.7, 2.6 Hz, 1H) 7.56-7.73 (m, 1H) 7.84 (d, J=8.7 Hz, 1H) 8.28 (d, J=2.6 Hz, 1H) 12.62 (br s, 1H).

MS ESI/APCI Multi posi: 338[M+H]$^+$.
MS ESI/APCI Multi nega: 336[M−H]$^−$.

Example 2-6 cis-3-[3-[[6-(1H-Pyrazol-5-yl)-3-pyridinyl]oxymethyl]cyclohexyl]propanoic Acid (Racemate)

[Formula 500]

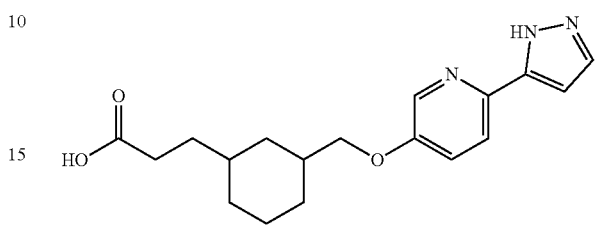

(1) The compound (45 mg) obtained in Reference Example 1-1 and the compound (50 mg) obtained in Reference Example 68-1 were used to perform the synthesis process according to the method described in Example 1-1-(1) thereby giving (phenylmethyl) cis-(E)-3-[3-[[6-[2-(2-oxanyl)-3-pyrazolyl]-3-pyridinyl]oxymethyl]cyclohexyl]-2-propenoate (racemate) (103 mg) as a light yellow oil.

(2) The compound (103 mg) obtained in (1) above was used to perform the synthesis process according to the method described in Example 2-1-(3) thereby giving the title compound (17 mg) as a colorless powder.

$^1$H NMR (400 MHz, DMSO-$d_6$) δ ppm 0.62-0.76 (m, 1H) 0.76-0.89 (m, 1H) 0.89-1.05 (m, 1H) 1.19-1.36 (m, 2H) 1.40-1.50 (m, 2H) 1.67-1.92 (m, 5H) 2.23 (t, J=7.6 Hz, 2H) 3.88 (d, J=6.0 Hz, 2H) 6.72 (d, J=2.0 Hz, 1H) 7.44 (d, J=8.5 Hz, 1H) 7.61-7.78 (m, 1H) 7.83 (d, J=8.5 Hz, 1H) 8.27 (d, J=2.4 Hz, 1H) 12.59 (br s, 1H).

MS ESI/APCI Multi posi: 330[M+H]$^+$.
MS ESI/APCI Multi nega: 328[M−H]$^−$.

The compound of Example 2-7 below was synthesized using the compound obtained in Reference Example 68-2, according to the method described in Example 2-6. The structure, NMR data, and MS data of the compound are shown in Table 31-2.

TABLE 31-2

| Example No. | Structure | Analytical Data |
|---|---|---|
| 2-7 | 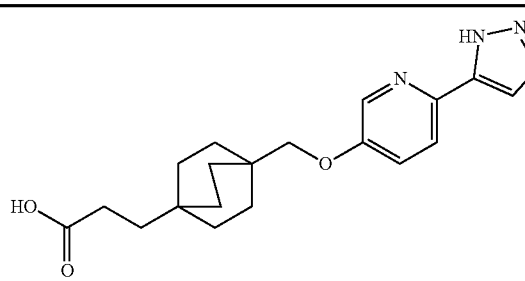 | $^1$H NMR (400 MHz, DMSO-$d_6$) δ ppm 1.28-1.30 (m, 2 H) 1.33-1.39 (m, 6 H) 1.45-1.56 (m, 6 H) 2.08-2.16 (m, 2 H) 3.69 (s, 2 H) 6.72 (d, J = 2.1 Hz, 1 H) 7.38-7.48 (m, 1 H) 7.62-7.74 (m, 1 H) 7.80-7.88 (m, 1 H) 8.25 (d, J = 2.7 Hz, 1 H). MS ESI/APCI Multi posi: 356[M + H]$^+$. |

Example 3-1

4-[8-[[6-(1H-Pyrazol-5-yl)-3-pyridinyl]oxy]octyl]-4-oxanecarboxylic Acid

[Formula 501]

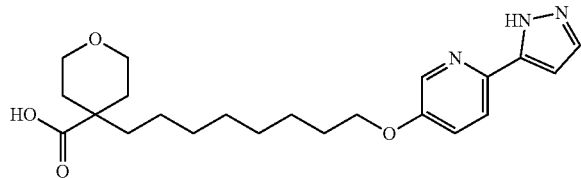

(1) The compound (100 mg) obtained in Reference Example 1-1 and the compound (154 mg) obtained in Reference Example 29-1 were used to perform the synthesis process according to the method described in Example 1-1-(1) thereby giving a crude product (272 mg) containing tert-butyl 4-[8-[[6-[2-(2-oxanyl)-3-pyrazolyl]-3-pyridinyl]oxy]octyl]-4-oxanecarboxylate as a brown oil.

(2) The compound (272 mg) obtained in (1) above was used to perform the synthesis process according to the method described in Example 1-1-(3) thereby giving a crude product (279 mg) containing tert-butyl 4-[8-[[6-(1H-pyrazol-5-yl)-3-pyridinyl]oxy]octyl]-4-oxanecarboxylate as a brown oil.

(3) The compound (279 mg) obtained in (2) above was dissolved in a 4 mol/L hydrogen chloride-1,4-dioxane solution (1.6 mL), and the mixture was stirred at 70° C. for 2.5 hours. The reaction solution was concentrated under reduced pressure, and purified by preparative HPLC to give the title compound (143 mg) as a colorless powder.

$^1$H NMR (400 MHz, DMSO-$d_6$) δ ppm 1.09-1.54 (m, 14H) 1.65-1.80 (m, 2H) 1.83-1.95 (m, 2H) 3.23-3.37 (m, 2H) 3.60-3.77 (m, 2H) 4.06 (t, J=6.5 Hz, 2H) 6.66-6.77 (m, 1H) 7.37-7.48 (m, 1H) 7.63-7.72 (m, 1H) 7.79-7.89 (m, 1H) 8.22-8.31 (m, 1H).

MS ESI/APCI Multi posi: 402[M+H]$^+$.
MS ESI/APCI Multi nega: 400[M−H]$^-$.

The compounds of Examples 3-2 to 3-4 below were synthesized using any of a compound obtained in Reference Example 77-2 or 77-3, or 80-4, according to the method described in Example 3-1. The structures, NMR data, and MS data of the compounds are shown in Table 32-1.

TABLE 32-1

| Example No. | Structure | Analytical Data |
|---|---|---|
| 3-2 | 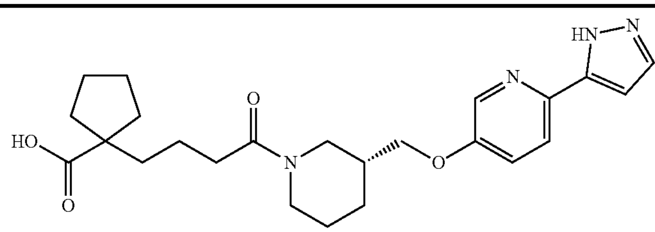 | $^1$H NMR (400 MHz, DMSO-$d_6$) δ ppm 1.14-2.93 (m, 20 H) 2.95-3.18 (m, 1 H) 3.66-4.46 (m, 4H) 6.66-6.77 (m, 1 H) 7.40-7.53 (m, 1 H) 7.61-7.73 (m, 1 H) 7.81-7.90 (m, 1 H) 8.26-8.34 (m, 1 H). MS ESI/APCI Multi posi: 441[M + H]$^+$. MS ESI/APCI Multi nega: 439[M − H]$^-$. |
| 3-3 | 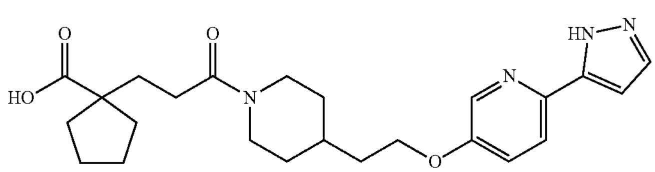 [SMILES: O=C(CCC1(C(=O)O)CCCC1)N1CCC(CCOc2ccc(-c3ccn[nH]3)nc2)CC1] | $^1$H NMR (400 MHz, DMSO-$d_6$) δ ppm 0.96-1.20 (m, 2 H) 1.37-1.47 (m, 2 H) 1.51-1.65 (m, 5 H) 1.67-1.84 (m, 5 H) 1.94-2.03 (m, 3 H) 2.17-2.25 (m, 3 H) 2.94-3.02 (m, 1 H) 3.75-3.82 (m, 1 H) 4.13 (t, J = 6.0 Hz, 2 H) 4.32-4.40 (m, 1 H) 6.73 (d, J = 2.1 Hz, 1 H) 7.45 (dd, J = 8.7, 2.8 Hz, 1 H) 7.65-7.70 (m, 1 H) 7.85 (d, J = 8.7 Hz, 1 H) 8.28 (d, J = 2.8 Hz, 1 H). MS ESI/APCI Multi posi: 441[M + H]$^+$. MS ESI/APCI Multi nega: 439[M − H]$^-$. |
| 3-4 | 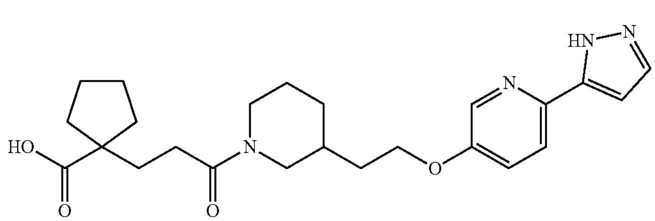 [SMILES: O=C(CCC1(C(=O)O)CCCC1)N1CCCC(CCOc2ccc(-c3ccn[nH]3)nc2)C1] | $^1$H NMR (400 MHz, DMSO-$d_6$) δ ppm 1.17-1.47 (m, 4 H) 1.48-1.79 (m, 10 H) 1.80-2.07 (m, 4 H) 2.11-2.28 (m, 2 H) 2.75-2.86 (m, 0.5 H) 2.97-3.08 (m, 0.5 H) 3.61-3.72 (m, 0.5 H) 3.76-3.87 (m, 0.5 H) 4.06-4.26 (m, 3 H) 6.72 (d, J = 1.6 Hz, 1 H) 7.41-7.51 (m, 1 H) 7.61-7.74 (m, 1 H) 7.85 (d, J = 8.6 Hz, 1 H) 8.23-8.33 (m, 1 H). MS ESI/APCI Multi posi: 441[M + H]$^+$. MS ESI/APCI Multi nega: 439[M − H]$^-$. |

The compounds of Examples 3-5 to 3-8 below were synthesized using a compound obtained in Reference Example 30-1 or 30-2, 31-1, or 35-1, according to the method described in Example 3-1-(1), and then by performing the reaction described in Example 1-1-(3) under ice cooling, and finally by performing the synthesis process according to the method described in Example 3-1-(3). The structures, NMR data, and MS data of the compounds are shown in Table 32-2.

TABLE 32-2

| Example No. | Structure | Analytical Data |
|---|---|---|
| 3-5 | 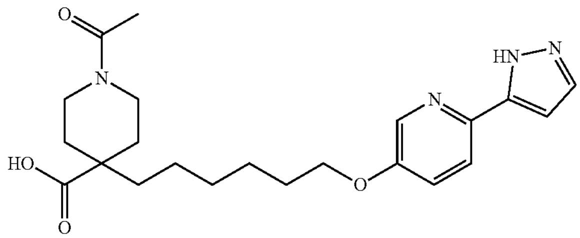 [SMILES: CC(=O)N1CCC(CCCCCCOc2ccc(-c3ccn[nH]3)nc2)(C(=O)O)CC1] | $^1$H NMR (400 MHz, DMSO-d$_6$) δ ppm 1.15-1.47 (m, 10 H) 1.66-1.76 (m, 2 H) 1.89-2.01 (m, 5 H) 2.64-2.75 (m, 1 H) 3.01-3.11 (m, 1 H) 3.60-3.68 (m, 1 H) 4.01-4.11 (m, 3 H) 6.72 (d, J = 1.8 Hz, 1 H) 7.39-7.45 (m, 1 H) 7.63-7.70 (m, 1 H) 7.80-7.87 (m, 1 H) 8.26 (d, J = 2.4 Hz, 1 H) 12.72 (br s, 1 H). MS ESI posi: 415[M + H]$^+$. MS ESI nega: 413[M − H]$^−$. |
| 3-6 | 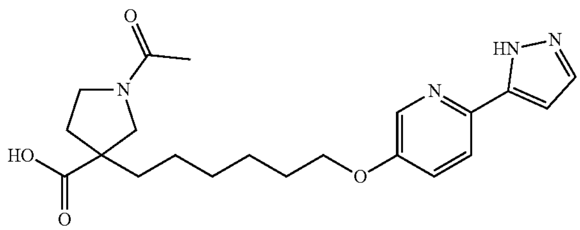 [SMILES: CC(=O)N1CCC(CCCCCCOc2ccc(-c3ccn[nH]3)nc2)(C(=O)O)C1] | $^1$H NMR (400 MHz, DMSO-d$_6$) δ ppm 1.20-1.46 (m, 6 H) 1.59-1.76 (m, 5 H) 1.91 (d, J = 8.8 Hz, 3 H) 2.16-2.34 (m, 1 H) 3.04-3.29 (m, 1 H) 3.34-3.43 (m, 1 H) 3.45-3.53 (m, 1 H) 3.71-3.88 (m, 1 H) 4.02-4.13 (m, 2 H) 6.77 (s, 1 H) 7.47-7.55 (m, 1 H) 7.65-7.73 (m, 1 H) 7.85-7.92 (m, 1 H) 8.28 (d, J = 2.1 Hz, 1 H). MS ESI posi: 401[M + H]$^+$. MS ESI nega: 399[M − H]$^−$. |
| 3-7 | 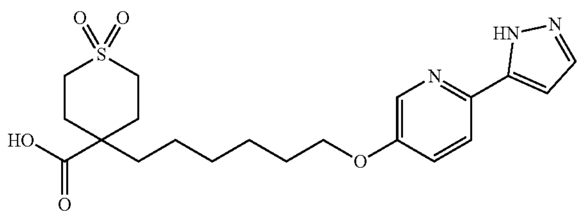 [SMILES: O=C(O)C1(CCCCCCOc2ccc(-c3ccn[nH]3)nc2)CCS(=O)(=O)CC1] | $^1$H NMR (400 MHz, DMSO-d$_6$) δ ppm 1.14-1.25 (m, 2 H) 1.27-1.36 (m, 2 H) 1.38-1.46 (m, 2 H) 1.48-1.59 (m, 2 H) 1.65-1.78 (m, 2 H) 1.80-1.92 (m, 2 H) 2.25-2.35 (m, 2 H) 2.89-3.00 (m, 2 H) 3.04-3.15 (m, 2 H) 4.06 (t, J = 6.4 Hz, 2H) 6.72 (s, 1 H) 7.43 (dd, J = 8.7, 2.7 Hz, 1 H) 7.61-7.70 (m, 1 H) 7.84 (d, J = 8.7 Hz, 1 H) 8.26 (d, J = 2.7 Hz, 1 H) 12.92 (br s, 1 H). MS ESI posi: 422[M + H]$^+$. MS ESI nega: 420[M − H]$^−$. |
| 3-8 | 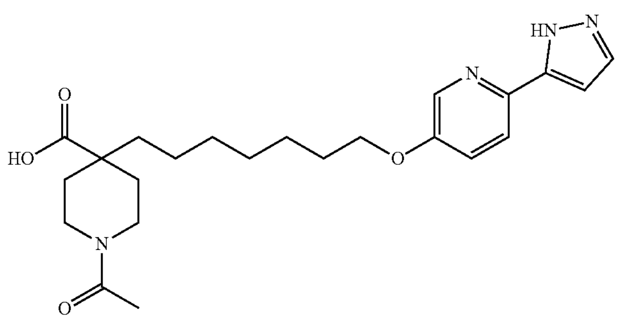 [SMILES: CC(=O)N1CCC(CCCCCCCOc2ccc(-c3ccn[nH]3)nc2)(C(=O)O)CC1] | $^1$H NMR (400 MHz, DMSO-d$_6$) δ ppm 1.13-1.49 (m, 12 H) 1.67-1.78 (m, 2 H) 1.88-2.05 (m, 6 H) 2.62-2.72 (m, 1 H) 3.00-3.10 (m, 1 H) 3.59-3.68 (m, 1 H) 4.00-4.10 (m, 3 H) 6.72 (s, 1 H) 7.39-7.45 (m, 1 H) 7.62-7.70 (m, 1 H) 7.80-7.87 (m, 1 H) 8.26 (s, 1 H) 12.72 (br s, 1 H). MS ESI posi: 429[M + H]$^+$. MS ESI nega: 427[M − H]$^−$. |

The compounds of Examples 3-9 and 3-10 below were synthesized using a compound obtained in Reference Example 78-1 or 78-2, according to the methods described in Example 3-1-(1) and 3-1-(3). The structures, NMR data, and MS data of the compounds are shown in Table 32-3.

TABLE 32-3

| Example No. | Structure | Analytical Data |
|---|---|---|
| 3-9 | 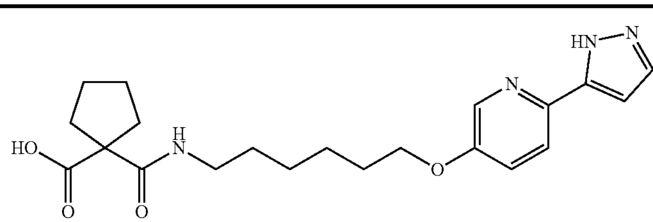 | $^1$H NMR (400 MHz, DMSO-d$_6$) δ ppm 1.26-1.34 (m, 2 H) 1.36-1.47 (m, 4 H) 1.48-1.55 (m, 4 H) 1.66-1.76 (m, 2 H) 1.96-2.06 (m, 4 H) 3.01-3.10 (m, 2 H) 4.06 (t, J = 6.5 Hz, 2 H) 6.72 (d, J = 2.1 Hz, 1 H) 7.43 (dd, J = 8.7, 2.6 Hz, 1 H) 7.60-7.72 (m, 2 H) 7.81-7.87 (m, 1 H) 8.27 (d, J = 2.6 Hz, 1 H). MS ESI/APCI Multi posi: 401[M + H]$^+$. MS ESI/APCI Multi nega: 399[M − H]$^−$. |

TABLE 32-3-continued

| Example No. | Structure | Analytical Data |
|---|---|---|
| 3-10 | 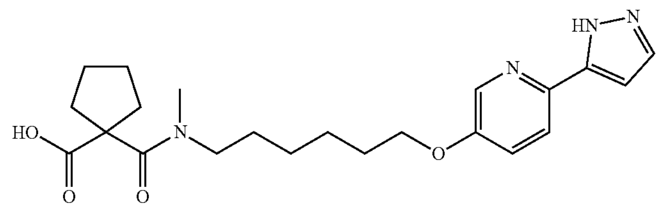 [SMILES: CN(CCCCCCOc1ccc(-c2ccn[nH]2)nc1)C(=O)C1(C(=O)O)CCCC1] | $^1$H NMR (400 MHz, DMSO-$d_6$) δ ppm 1.21-1.36 (m, 2 H) 1.37-1.63 (m, 8 H) 1.68-1.80 (m, 2 H) 1.95-2.06 (m, 2 H) 2.06-2.17 (m, 2 H) 2.72-2.85 (m, 3 H) 3.23-3.29 (m, 2 H) 4.01-4.14 (m, 2 H) 6.72 (d, J = 2.1 Hz, 1 H) 7.43 (dd, H) 8.27 (d, J = 2.6 Hz, 1 H) 12.81 (br s, 1 H). MS ESI/APCI Multi posi: 415[M + H]$^+$. MS ESI/APCI Multi nega: 413[M − H]$^-$. |

The compound of Example 3-11 below was synthesized using the compound obtained in Reference Example 58-1, according to the method described in Example 3-1-(1), and according to the method described in Example 3-1-(2) at a reaction temperature of 60° C. The structure, NMR data, and MS data of the compounds are shown in Table 32-4.

TABLE 32-4

| Example No. | Structure | Analytical Data |
|---|---|---|
| 3-11 | 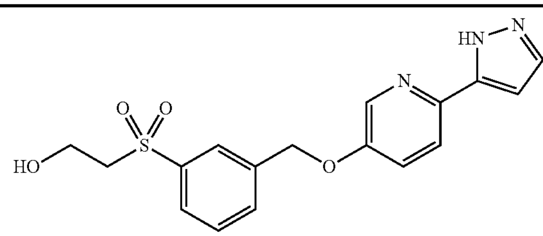 | $^1$H NMR (400 MHz, CHLOROFORM-d) δ ppm 3.35-3.41 (m, 2 H) 3.99-4.05 (m, 2 H) 5.24 (s, 2 H) 6.68-6.74 (m, 1 H) 7.31-7.37 (m, 1 H) 7.61-7.73 (m, 3 H) 7.75-7.81 (m, 1 H) 7.91-7.97 (m, 1 H) 8.02-8.06 (m, 1 H) 8.33-8.39 (m, 1 H). MS ESI/APCI Multi posi: 360 [M + H]$^+$. |

Example 4-1

4-[3-[2-[[6-(1H-Pyrazol-5-yl)-3-pyridinyl]oxy]ethyl]phenyl]butanoic Acid

[Formula 502]

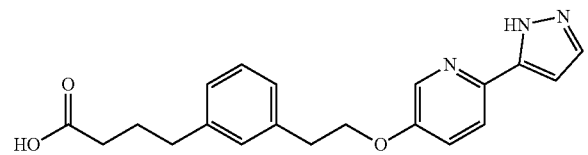

(1) The compound (170 mg) obtained in Reference Example 41-2 was used to perform the synthesis process according to the method described in Example 2-1-(3) thereby giving a crude product (171 mg) containing methyl 4-[3-(2-hydroxyethyl)phenyl]butanoate.

(2) The compound (70 mg) obtained in Reference Example 1-1 and the compound (75 mg) obtained in (1) above were used to perform the synthesis process according to the method described in Example 1-1-(1) thereby giving methyl 4-[3-[2-[[6-[2-(2-oxanyl)-3-pyrazolyl]-3-pyridinyl]oxy]ethyl]phenyl]butanoate (89 mg) as a light yellow oil.

(3) An aqueous solution of 1 mol/L sodium hydroxide (0.42 mL) was added to a solution of the compound (89 mg) obtained in (2) above in methanol (1.0 mL), and the mixture was stirred at an outer temperature of 65° C. for 5 hours to give a solution containing 4-[3-[2-[[6-[2-(2-oxanyl)-3-pyrazolyl]-3-pyridinyl]oxy]ethyl]phenyl]butanoic acid.

(4) The solution obtained in (3) above was used to perform the synthesis process according to the method described in Example 1-43-(3) thereby giving the title compound (31 mg) as a colorless powder.

$^1$H NMR (400 MHz, DMSO-$d_6$) δ ppm 1.76-1.83 (m, 2H) 2.22 (t, J=7.3 Hz, 2H) 2.57 (t, J=7.7 Hz, 2H) 3.04 (t, J=6.9 Hz, 2H) 4.29 (t, J=6.9 Hz, 2H) 6.72 (d, J=2.1 Hz, 1H) 7.06 (d, J=7.5 Hz, 1H) 7.14-7.19 (m, 2H) 7.20-7.26 (m, 1H) 7.46 (dd, J=8.7, 2.8 Hz, 1H) 7.63-7.71 (m, 1H) 7.83 (d, J=8.7 Hz, 1H) 8.27 (d, J=2.8 Hz, 1H).

MS ESI/APCI Multi posi: 352[M+H]$^+$.

MS ESI/APCI Multi nega: 350[M−H]$^-$.

The compound of Example 4-2 below was synthesized using the compound obtained in Reference Example 41-3, according to the method described in Example 4-1. The structure, NMR data, and MS data of the compounds are shown in Table 33-1.

TABLE 33-1

| Example No. | Structure | Analytical Data |
|---|---|---|
| 4-2 | (structure) | ¹H NMR (400 MHz, DMSO-d₆) δ ppm 1.77 (quin, J = 7.4 Hz, 2 H) 2.19 (t, J = 7.4 Hz, 2 H) 2.54-2.59 (m, 2 H) 3.03 (t, J = 6.8 Hz, 2 H) 4.28 (t, J = 6.8 Hz, 2 H) 6.72 (d, J = 2.2 Hz, 1 H) 7.14 (d, J = 8.1 Hz, 2 H) 7.25 (m, J = 8.1 Hz, 2 H) 7.41-7.52 (m, 1 H) 7.63-7.74 (m, 1 H) 7.80-7.88 (m, 1 H) 8.27 (d, J = 2.9 Hz, 1 H). MS ESI/APCI Multi posi: 352 [M + H]⁺. MS ESI/APCI Multi nega: 350 [M − H]⁻ |

Example 5-1

7-[[6-(1H-Pyrazol-5-yl)-3-pyridinyl]oxymethyl]-5,6,7,8-tetrahydronaphthalene-2-carboxylic Acid

[Formula 503]

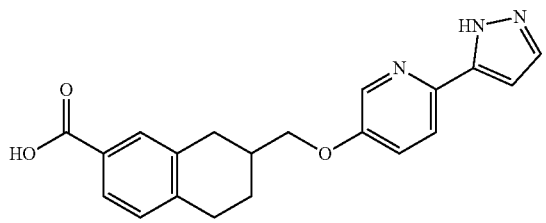

(1) The compound (44 mg) obtained in Reference Example 1-1 and the compound (28 mg) obtained in Reference Example 61-1 were used to perform the synthesis process according to the method described in Example 1-1-(1) thereby giving 7-[[6-[2-(2-oxanyl)-3-pyrazolyl]-3-pyridinyl]oxymethyl]-5,6,7,8-tetrahydronaphthalene-2-carbonitrile (47 mg) as a colorless oil.

(2) The compound (47 mg) obtained in (1) above was used to perform the synthesis process according to the method described in Example 1-1-(3) thereby giving a crude product containing 7-[[6-(1H-pyrazol-5-yl)-3-pyridinyl]oxymethyl]-5,6,7,8-tetrahydronaphthalene-2-carbonitrile (41 mg) as a brown oil.

(3) An aqueous solution of 6 mol/L sodium hydroxide (0.08 mL) was added to a solution of the compound (41 mg) obtained in (2) above in ethanol (0.1 mL), and the mixture was stirred for 8 hours while being heated to reflux. The reaction solution was purified by preparative HPLC to give the title compound (4 mg) as a colorless powder.

¹H NMR (400 MHz, DMSO-d₆) δ ppm 1.44-1.68 (m, 1H) 2.01-2.14 (m, 1H) 2.19-2.33 (m, 1H) 2.58-2.72 (m, 1H) 2.74-3.08 (m, 3H) 3.97-4.16 (m, 2H) 6.64-6.79 (m, 1H) 7.10-7.27 (m, 1H) 7.43-7.57 (m, 1H) 7.58-7.77 (m, 3H) 7.79-7.93 (m, 1H) 8.27-8.37 (m, 1H).

MS ESI/APCI Multi posi: 350[M+H]⁺.

The compound of Example 5-2 below was synthesized using the compound obtained in Reference Example 62-1, according to the method described in Example 5-1. The structure, NMR data, and MS data of the compounds are shown in Table 34-1.

TABLE 34-1

| Example No. | Structure | Analytical Data |
|---|---|---|
| 5-2 | (structure) | ¹H NMR (400 MHz, DMSO-d₆) δ ppm 1.57-2.22 (m, 6 H) 2.67-2.92 (m, 2 H) 3.00-3.16 (m, 1 H) 4.09-4.33 (m, 2 H) 6.71-6.76 (m, 1 H) 7.16-7.22 (m, 1 H) 7.45-7.53 (m, 1 H) 7.61-7.72 (m, 2 H) 7.78-7.82 (m, 1 H) 7.83-7.89 (m, 1 H) 8.29-8.34 (m, 1 H). MS ESI/APCI Multi posi: 364 [M + H]⁺. MS ESI/APCI Multi nega: 362 [M − H]⁻. |

Example 6-1

1-Acetyl-4-[8-[[6-(1H-pyrazol-5-yl)-3-pyridinyl]oxy]octyl]-4-piperidinecarboxylic Acid

[Formula 504]

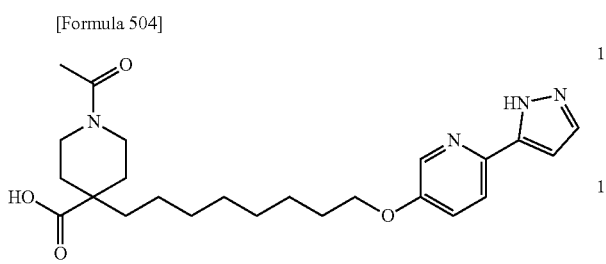

(1) The compound (19 mg) obtained in Reference Example 1-1 and the compound (31 mg) obtained in Reference Example 33-8 were used to perform the synthesis process according to the method described in Example 1-1-(1) thereby giving 04-tert-butyl O1-(phenylmethyl) 4-[8-[[6-[2-(2-oxanyl)-3-pyrazolyl]-3-pyridinyl]oxy]octyl]piperidine-1,4-dicarboxylate (40 mg) as a pale brown oil.

(2) The compound (39 mg) obtained in (1) above was used to perform the synthesis process according to the method described in Example 2-1-(3) thereby giving a crude product (38 mg) containing tert-butyl 4-[8-[[6-[2-(2-oxanyl)-3-pyrazolyl]-3-pyridinyl]oxy]octyl]-4-piperidinecarboxylate.

(3) Triethylamine (18 μL) and acetic anhydride (6.0 μL) were added to a solution of the compound (38 mg) obtained in (2) above in chloroform (0.6 mL), and the mixture was stirred at room temperature overnight. A saturated aqueous solution of sodium hydrogen carbonate was added to the reaction solution, and the resultant mixture was extracted with chloroform. The organic layer was separated by a phase separator, and concentrated under reduced pressure to give a crude product (42 mg) containing tert-butyl 1-acetyl-4-[8-[[6-[2-(2-oxanyl)-3-pyrazolyl]-3-pyridinyl]oxy]octyl]-4-piperidinecarboxylate.

(4) The compound (42 mg) obtained in (3) above was used to perform the synthesis process according to the method described in Example 1-1-(3) thereby giving a crude product (30 mg) containing tert-butyl 1-acetyl-4-[8-[[6-(1H-pyrazol-5-yl)-3-pyridinyl]oxy]octyl]-4-piperidinecarboxylate.

(5) The compound (30 mg) obtained in (4) above was used to perform the synthesis process according to the method described in Example 3-1-(3) thereby giving the title compound (20 mg) as a colorless powder.

$^1$H NMR (400 MHz, DMSO-$d_6$) δ ppm 1.03-1.53 (m, 14H) 1.64-1.81 (m, 2H) 1.86-2.05 (m, 5H) 2.59-2.74 (m, 1H) 2.94-3.15 (m, 1H) 3.54-3.73 (m, 1H) 3.98-4.15 (m, 3H) 6.68-6.76 (m, 1H) 7.35-7.51 (m, 1H) 7.59-7.76 (m, 1H) 7.79-7.88 (m, 1H) 8.23-8.29 (m, 1H).

MS ESI/APCI Multi posi: 443 [M+H]$^+$.

MS ESI/APCI Multi nega: 441[M−H]$^−$.

Example 7-1

4,4-Dimethyl-6-[[6-(1H-pyrazol-5-yl)-3-pyridinyl]oxy]hexanoic Acid

[Formula 505]

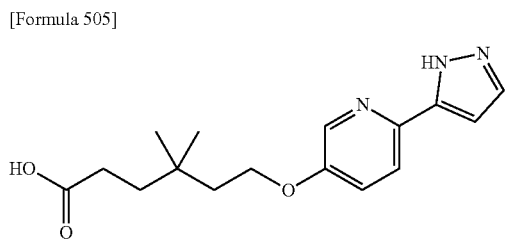

(1) The compound (300 mg) obtained in Reference Example 1-1 and the compound (168 mg) obtained in Reference Example 76-1 were used to perform the synthesis process according to the method described in Example 1-1-(1) thereby giving 5-(3,3-dimethylpent-4-enoxy)-2-[2-(2-oxanyl)-3-pyrazolyl]pyridine (295 mg) as a colorless oil.

(2) To a solution of the compound (295 mg) obtained in (1) above in acetone:water (25:6, 3.1 mL), 2,6-dimethylpyridine (200 μL), 4-methylmorpholine N-oxide (213 mg), and an aqueous solution of 4% osmium tetroxide (1.1 mL) were sequentially added at room temperature, and the mixture was stirred at the same temperature overnight. Subsequently, iodobenzene diacetate (450 mg) was added thereto, and the resultant mixture was stirred at the same temperature for 30 minutes. An aqueous solution of sodium thiosulfate was added to the reaction solution, and the resultant mixture was stirred for a while and then extracted with chloroform, and the organic layer was separated by a phase separator, and concentrated under reduced pressure. The residue was purified by silica gel column chromatography (n-hexane:ethyl acetate=1:1 to 1:3) to give 2,2-dimethyl-4-[[6-[2-(2-oxanyl)-3-pyrazolyl]-3-pyridinyl]oxy]butanal (178 mg) as a colorless oil.

(3) Benzyl (triphenylphosphoranylidene)acetate (255 mg) was added to a solution of the compound (178 mg) obtained in (2) above in tetrahydrofuran (2.6 mL), and the mixture was stirred at room temperature for 3 hours, at 50° C. for 2 hours, and for 13 hours while being heated to reflux. A saturated aqueous solution of ammonium chloride was added to the reaction solution under ice cooling, and the resultant mixture was extracted with chloroform. The organic layer was separated by a phase separator, and concentrated under reduced pressure. The residue was purified by silica gel column chromatography (n-hexane:ethyl acetate=13:7 to 7:13) to give (phenylmethyl) (E)-4,4-dimethyl-6-[[6-[2-(2-oxanyl)-3-pyrazolyl]-3-pyridinyl]oxy]-2-hexenoate (195 mg) as a colorless oil.

(4) The compound (195 mg) obtained in (3) above was used to perform the synthesis process according to the method described in Example 2-1-(3) thereby giving a crude product (170 mg) containing 4,4-dimethyl-6-[[6-[2-(2-oxanyl)-3-pyrazolyl]-3-pyridinyl]oxy]hexanoic acid as a colorless oil.

(5) A solution of the compound (170 mg) obtained in (4) above in 4 mol/L hydrogen chloride-1,4-dioxane (1.6 mL) was stirred at room temperature for 5 hours. An aqueous solution of sodium hydroxide was added thereto under ice cooling to neutralize, and the reaction solution was concentrated under reduced pressure. The resultant was purified by preparative HPLC to give the title compound (28 mg) as a colorless amorphous substance.

$^1$H NMR (400 MHz, DMSO-d$_6$) δ ppm 0.93 (s, 6H) 1.45-1.59 (m, 2H) 1.62-1.75 (m, 2H) 2.13-2.27 (m, 2H) 4.11 (t, J=7.1 Hz, 2H) 6.68-6.78 (m, 1H) 7.38-7.51 (m, 1H) 7.62-7.73 (m, 1H) 7.80-7.88 (m, 1H) 8.22-8.30 (m, 1H).

MS ESI/APCI Multi posi: 304[M+H]$^+$.

Example 8-1 cis-4-[3-[[6-(1H-Pyrazol-5-yl)-3-pyridinyl]oxymethyl]phenyl]-1-cyclohexanecarboxylic Acid

[Formula 506]

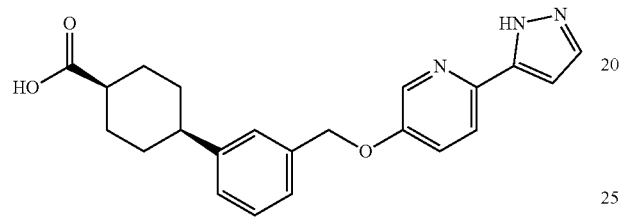

(1) A solution of the compound (73.0 mg) obtained in Reference Example 1-1, the compound (83.0 mg) obtained in Reference Example 54-2, and triphenylphosphine (148 mg) in tetrahydrofuran (1.41 mL) was ice-cooled under a nitrogen flow, bis(2-methoxyethyl) azodicarboxylate (132 mg) wad added thereto, and the mixture was stirred at room temperature overnight. The solvent was distilled off under reduced pressure, and the residue was purified by silica gel column chromatography (n-hexane only to n-hexane:ethyl acetate=3:2) to give ethyl 4-[3-[[6-[2-(2-oxanyl)-3-pyrazolyl]-3-pyridinyl]oxymethyl]phenyl]-1-cyclohexanecarboxylate (33.6 mg) as a colorless oil.

(2) The compound (32.6 mg) obtained in (1) above was used to perform the synthesis process according to the method described in Example 1-65-(2) thereby giving a solution containing ethyl 4-[3-[[6-(1H-pyrazol-5-yl)-3-pyridinyl]oxymethyl]phenyl]-1-cyclohexanecarboxylate.

(3) The solution obtained in (2) above was used to perform the synthesis process according to the method described in Example 1-1-(2), and the reaction mixture was purified by preparative HPLC to give the title compound (3.25 mg), which was a highly polar compound, as a colorless solid; and a compound (8.28 mg) of Example 8-2, which was a less polar compound, as a colorless solid.

$^1$H NMR (400 MHz, DMSO-d$_6$) δ ppm 1.26-1.64 (m, 4H) 1.79-2.05 (m, 4H) 2.25-2.35 (m, 2H) 5.18 (s, 2H) 6.73 (d, J=2.0 Hz, 1H) 7.12-7.42 (m, 4H) 7.49-7.56 (m, 1H) 7.59-7.77 (m, 1H) 7.85 (d, J=8.9 Hz, 1H) 8.35 (d, J=2.8 Hz, 1H).

MS ESI/APCI Multi posi: 378[M+H]$^+$.

Example 8-2 trans-4-[3-[[6-(1H-Pyrazol-5-yl)-3-pyridinyl]oxymethyl]phenyl]-1-cyclohexanecarboxylic Acid

[Formula 507]

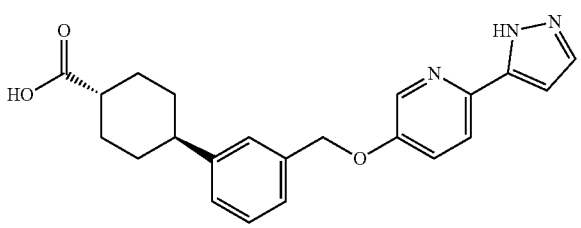

$^1$H NMR (400 MHz, DMSO-d$_6$) δ ppm 1.46-1.79 (m, 6H) 1.98-2.19 (m, 2H) 2.58-2.75 (m, 2H) 5.18 (s, 2H) 6.73 (d, J=2.1 Hz, 1H) 7.16 (d, J=7.2 Hz, 1H) 7.23-7.37 (m, 3H) 7.52 (dd, J=8.7, 2.9 Hz, 1H) 7.59-7.76 (m, 1H) 7.85 (d, J=8.7 Hz, 1H) 8.34 (d, J=2.9 Hz, 1H).

MS ESI/APCI Multi posi: 378[M+H]$^+$.

MS ESI/APCI Multi nega: 376[M−H]$^-$.

The compounds of Examples 8-3 to 8-6 below were synthesized using a compound obtained in Reference Example 27-1, 52-1, 54-1, or 57-1, according to the method described in Example 8-1. The structures, NMR data, and MS data of the compounds are shown in Table 35-1.

TABLE 35-1

| Example No. | Structure | Analytical Data |
|---|---|---|
| 8-3 | ![structure] | $^1$H NMR (400 MHz, DMSO-d$_6$) δ ppm 1.19-1.58 (m, 4 H) 1.69-2.09 (m, 4 H) 2.28-2.42 (m, 1 H) 2.62-2.69 (m, 1 H) 5.18 (s, 2 H) 6.73 (d, J = 2.0 Hz, 1 H) 7.12-7.41 (m, 4 H) 7.53 (dd, J = 8.7, 2.8 Hz, 1 H) 7.60-7.75 (m, 1 H) 7.85 (d, J = 8.2 Hz, 1 H) 8.35 (d, J = 2.8 Hz, 1 H). MS ESI/APCI Multi posi: 378 [M + H]$^+$. |

TABLE 35-1-continued

| Example No. | Structure | Analytical Data |
|---|---|---|
| 8-4 | 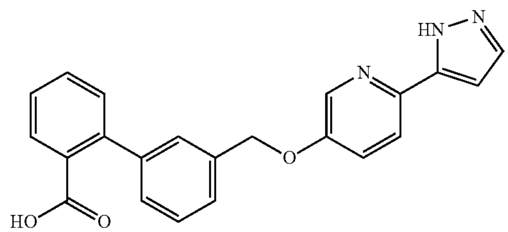 [SMILES: O=C(O)c1ccccc1-c1cccc(COc2ccc(-c3ccn[nH]3)nc2)c1] | ¹H NMR (400 MHz, DMSO-d₆) δ ppm 5.25 (s, 2 H) 6.73 (d, J = 2.1 Hz, 1 H) 7.28-7.34 (m, 1 H) 7.36-7.62 (m, 7 H) 7.64-7.77 (m, 2 H) 7.87 (d, J = 8.7 Hz, 1 H) 8.38 (d, J = 2.8 Hz, 1 H) 12.90 (br s, 1 H). MS ESI/APCI Multi posi: 372 [M + H]⁺. MS ESI/APCI Multi nega; 370 [M − H]⁻. |
| 8-5 | 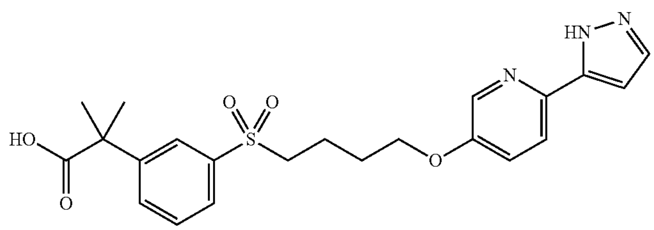 [SMILES: CC(C)(C(=O)O)c1cccc(S(=O)(=O)CCCCOc2ccc(-c3ccn[nH]3)nc2)c1] | ¹H NMR (400 MHz, DMSO-d₆) δ ppm 1.52 (s, 6 H) 1.64-1.91 (m, 4 H) 3.37-3.47 (m, 2 H) 4.06 (t, J = 6.0 Hz, 2 H) 6.72 (d, J = 2.1 Hz, 1 H) 7.40 (dd, J = 8.8, 2.9 Hz, 1 H) 7.60-7.8 (m, 6 H) 8.23 (d, J = 2.9 Hz, 1 H) 12.79 (br s, 1 H). MS ESI/APCI Multi posi: 444 [M + H]⁺. MS ESI/APCI Multi nega: 442 [ M − H]⁻ |
| 8-6 | 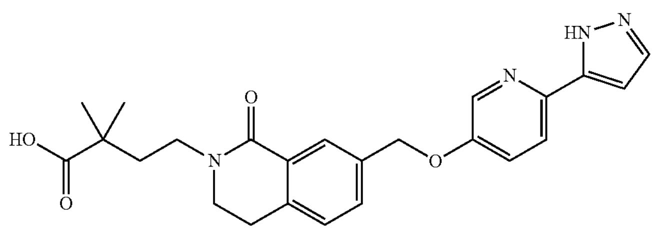 [SMILES: CC(C)(CCN1CCc2ccc(COc3ccc(-c4ccn[nH]4)nc3)cc2C1=O)C(=O)O] | ¹H NMR (400 MHz, DMSO-d₆) δ ppm 1.15 (s, 6 H) 1.69-1.78 (m, 2 H) 2.91-2.99 (m, 2 H) 3.42-3.59 (m, 4 H) 5.26 (s, 2 H) 6.71-6.75 (m, 1 H) 7.32 (d, J = 7.8 Hz, 1 H) 7.46-8.01 (m, 6 H) 8.35 (br s, 1 H). MS ESI posi: 435 [M + H]⁺. MS ESI nega: 433 [M − H]⁻. |

The compounds of Examples 8-7 to 8-17 below were synthesized using any of the compounds obtained in Reference Examples 39-1, 48-3 and 48-4, 50-1 and 50-2, 51-1 and 50-2, 70-1, and 71-1, or a commercially available compound, according to the methods described in Example 8-1-(1) and 8-1-(2), and by performing the reaction described in Example 8-1-(3) at room temperature. The structures, NMR data, and MS data of the compounds are shown in Tables 35-2 and 35-3.

TABLE 35-2

| Example No. | Structure | Analytical Data |
|---|---|---|
| 8-7 | 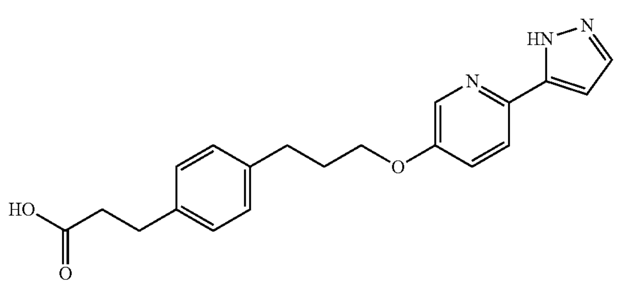 [SMILES: O=C(O)CCc1ccc(CCCOc2ccc(-c3ccn[nH]3)nc2)cc1] | ¹H NMR (400 MHz, DMSO-d₆) δ ppm 1.97-2.08 (m, 2 H) 2.67-2.82 (m, 4 H) 3.20-3.44 (m, 2 H) 4.07 (t, J = 6.4 Hz, 2 H) 6.72 (d, J = 2.1 Hz, 1 H) 7.14 (s, 4 H) 7.43 (dd, J = 8.5, 2.9 Hz, 1 H) 7.60-7.77 (m, 1 H) 7.84 (d, J = 8.5 Hz, 1 H) 8.28 (d, J = 2.9 Hz, 1 H). MS ESI/APCI Multi posi: 352 [M + H]⁺. MS ESI/APCI Multi nega: 350 [M − H]⁻. |
| 8-8 | 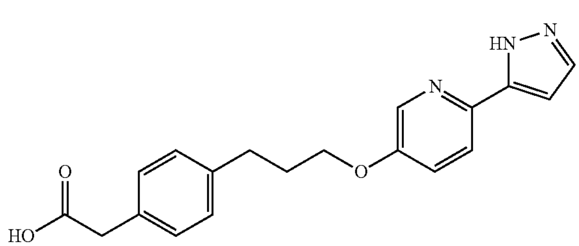 [SMILES: O=C(O)Cc1ccc(CCCOc2ccc(-c3ccn[nH]3)nc2)cc1] | ¹H NMR (400 MHz, DMSO-d₆) δ ppm 1.98-2.10 (m, 2 H) 2.68-2.79 (m, 2 H) 3.51 (s, 2 H) 4.08 (t, J = 6.3 Hz, 2 H) 6.73 (d, J = 2.1 Hz, 1 H) 7.07-7.27 (m, 4 H) 7.44 (dd, J = 8.8, 2.9 Hz, 1 H) 7.68 (d, J = 1.6 Hz, 1 H) 7.84 (d, J = 8.8 Hz, 1 H) 8.29 (d, J = 2.9 Hz, 1 H) 12.66 (br s, 1 H). MS ESI/APCI Multi posi: 338 [M + H]⁺. MS ESI/APCI Multi nega: 336 [M − H]⁻. |

TABLE 35-2-continued

| Example No. | Structure | Analytical Data |
|---|---|---|
| 8-9 | 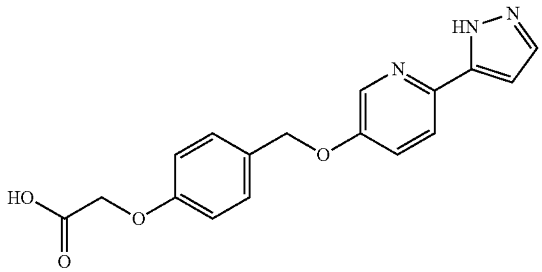 [SMILES: O=C(O)COc1ccc(COc2ccc(-c3ccn[nH]3)nc2)cc1] | $^1$H NMR (400 MHz, DMSO-d$_6$) δ ppm 4.68 (s, 2 H) 5.13 (s, 2 H) 6.74 (d, J = 2.1 Hz, 1 H) 6.94 (d, J = 8.6 Hz, 2 H) 7.41 (d, J = 8.6 Hz, 2 H) 7.50-7.60 (m, 1 H) 7.64-7.80 (m, 1 H) 7.82-7.94 (m, 1 H) 8.30-8.40 (m, 1 H).<br>MS ESI/APCI Multi posi: 326 [M + H]$^+$.<br>MS ESI/APCI Multi nega: 324 [M − H]$^−$. |
| 8-10 | 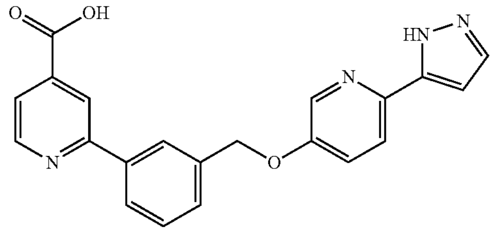 [SMILES: O=C(O)c1ccnc(-c2cccc(COc3ccc(-c4ccn[nH]4)nc3)c2)c1] | $^1$H NMR (400 MHz, DMSO-d$_6$) δ ppm 5.34 (s, 2 H) 6.73 (d, J = 2.1 Hz, 1 H) 7.53-7.62 (m, 3 H) 7.67 (br s, 1 H) 7.79 (d, J = 4.9 Hz, 1 H) 7.87 (d, J = 9.0 Hz, 1 H) 8.12 (d, J = 7.3 Hz, 1 H) 8.28 (s, 1 H) 8.34 (s, 1 H) 8.39 (d, J = 2.8 Hz, 1 H) 8.86 (d, J = 4.9 Hz, 1 H) 13.38 (s, 1 H).<br>MS ESI/APCI Multi posi: 373 [M + H]$^+$.<br>MS ESI/APCI Multi nega: 371 [M − H]$^−$. |
| 8-11 | 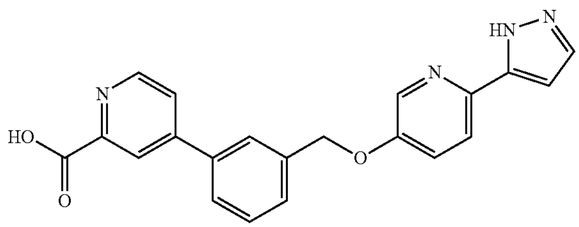 [SMILES: O=C(O)c1cc(-c2cccc(COc3ccc(-c4ccn[nH]4)nc3)c2)ccn1] | $^1$H NMR (400 MHz, DMSO-d$_6$) δ ppm 5.34 (s, 2 H) 6.68-6.83 (m, 1 H) 7.50-8.08 (m, 8 H) 8.29-8.46 (m, 2 H) 8.78 (d, J = 4.9 Hz, 1 H).<br>MS ESI posi: 373 [M + H]$^+$.<br>MS ESI nega: 371 [M − H]$^−$. |
| 8-12 | 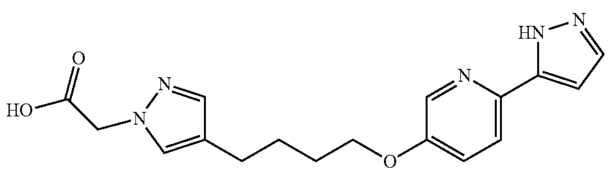 [SMILES: O=C(O)Cn1cc(CCCCOc2ccc(-c3ccn[nH]3)nc2)cn1] | $^1$H NMR (400 MHz, DMSO-d$_6$) δ ppm 1.57-1.90 (m, 4 H), 2.39-2.47 (m, 2 H) 4.09 (t, J = 6.3 Hz, 2 H) 4.85 (s, 2 H) 6.71-6.73 (m, 1 H) 7.29 (s, 1 H) 7.43 (dd, J = 8.7, 2.8 Hz, 1 H) 7.51 (s, 1 H) 7.67 (s, 1 H) 7.84 (d, J = 8.7 Hz, 1 H) 8.27 (d, J = 2.8 Hz, 1 H) 12.88-13.11 (m, 1 H).<br>MS ESI posi: 342 [M + H]$^+$.<br>MS ESI nega: 340 [M − H]$^−$. |

TABLE 35-3

| Example No. | Structure | Analytical Data |
|---|---|---|
| 8-13 | 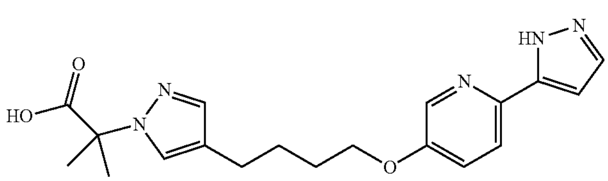 [SMILES: CC(C)(C(=O)O)n1cc(CCCCOc2ccc(-c3ccn[nH]3)nc2)cn1] | $^1$H NMR (400 MHz, CHLOROFORM-d) δ ppm 1.70-1.84 (m, 10 H) 2.58 (t, J = 7.3 Hz, 2 H) 4.06 (t, J = 6.1 Hz, 2 H) 6.67-6.69 (m, 1 H) 7.20-7.26 (m, 1 7.38-7.45 (m, 1 H) 7.46-7.52 (m, 1 H) 7.57-7.71 (m, 2 H) 8.22 (s, 1 H).<br>MS ESI posi: 370 [M + H]$^+$.<br>MS ESI nega: 368 [M − H]$^−$. |
| 8-14 | 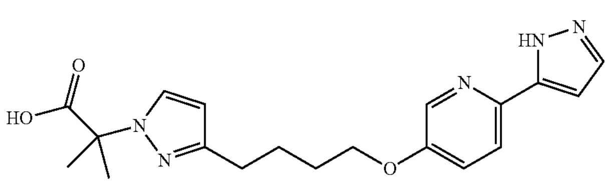 [SMILES: CC(C)(C(=O)O)n1ccc(CCCCOc2ccc(-c3ccn[nH]3)nc2)n1] | $^1$H NMR (400 MHz, DMSO-d$_6$) δ ppm 1.46-2.05 (m, 10 H) 2.59 (br s, 2 H) 4.08 (t, J = 5.4 Hz, 2 H) 5.96-8.51 (m, 7 H) 12.76-13.14 (m, 1 H).<br>MS ESI posi: 370 [M + H]$^+$.<br>MS ESI nega: 368 [M − H]$^−$. |

TABLE 35-3-continued

| Example No. | Structure | Analytical Data |
|---|---|---|
| 8-15 | 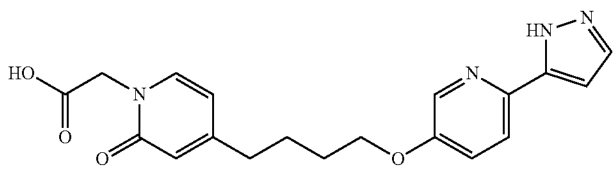 [SMILES: O=C(O)Cn1ccc(CCCCOc2ccc(-c3ccn[nH]3)nc2)cc1=O] | $^1$H NMR (400 MHz, DMSO-d$_6$) δ ppm 1.65-1.80 (m, 4 H) 3.18-3.45 (m, 2 H) 4.05-4.17 (m, 2 H) 4.52 (s, 2 H) 6.15 (d, J = 6.4 Hz, 1 H) 6.23 (s, 1 H) 6.72 (s, 1 H) 7.44 (d, J = 8.3 Hz, 1 H) 7.53 (d, J = 6.7 Hz, 1 H) 7.67 (s, 1 H) 7.84 (d, J = 8.8 Hz, 1 H) 8.28 (d, J = 2.3 Hz, 1 H) 12.97 (br s, 1 H). MS ESI posi: 369 [M + H]$^+$. MS ESI nega: 367 [M − H]$^-$. |
| 8-16 | 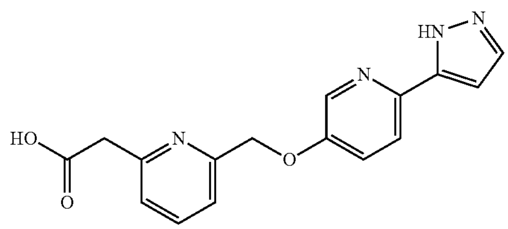 [SMILES: O=C(O)Cc1cccc(COc2ccc(-c3ccn[nH]3)nc2)n1] | $^1$H NMR (400 MHz, DMSO-d$_6$) δ ppm 3.77 (s, 2 H) 5.25 (s, 2 H) 6.73 (d, J = 2.1 Hz, 1 H) 7.33 (d, J = 7.7 Hz, 1 H) 7.45 (d, J = 7.7 Hz, 1 H) 7.55 (dd, J = 8.8, 2.9 Hz, 1 H) 7.61-7.76 (m, 1 H) 7.78-7.90 (m, 2 H) 8.38 (d, J = 2.9 Hz, 1 H) 12.76 (br s, 1 H). MS ESI/APCI Multi posi: 311 [M + H]$^+$. |
| 8-17 | 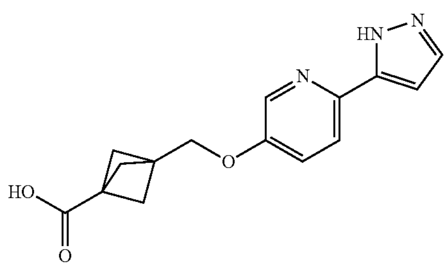 [SMILES: O=C(O)C12CC(COc3ccc(-c4ccn[nH]4)nc3)(C1)C2] | $^1$H NMR (400 MHz, DMSO-d$_6$) δ ppm 1.99 (s, 6 H) 4.14 (s, 2 H) 6.73 (d, J = 2.1 Hz, 1 H) 7.44 (dd, J = 8.8, 2.9 Hz, 1 H) 7.63-7.73 (m, 1 H) 7.84 (d, J = 8.8 Hz, 1 H) 8.28 (d, J = 2.9 Hz, 1 H). MS ESI/APCI Multi posi: 286 [M + H]$^+$. |

The compound of Example 8-18 below was synthesized using a commercially available compound, by performing the reaction described in Example 8-1-(1) with the temperature increased from room temperature to 60° C., and then according to the methods described in Example 8-1-(2) and (3). The structure, NMR data, and MS data of the compounds are shown in Table 35-4.

TABLE 35-4

| Example No. | Structure | Analytical Data |
|---|---|---|
| 8-18 | 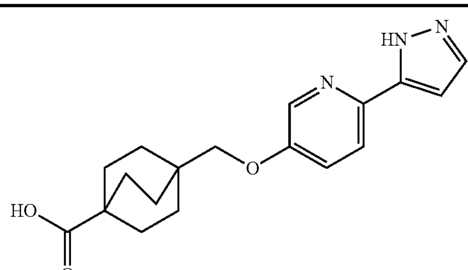 | $^1$H NMR (400 MHz, DMSO-d$_6$) δ ppm 1.47-1.80 (m, 12 H) 3.77 (s, 2 H) 6.80-6.91 (m, 1 H) 7.58-7.72 (m, 1 H) 7.75-7.89 (m, 1 H) 7.92-8.04 (m, 1 H) 8.30 (d, J = 2.6 Hz, 1 H). MS ESI/APCI Multi posi: 328 [M + H]$^+$. |

Example 9-1 trans-3-[[6-(1H-Pyrazol-5-yl)-3-pyridinyl]oxymethyl]-1-cyclohexanecarboxylic Acid (Racemate)

[Formula 508]

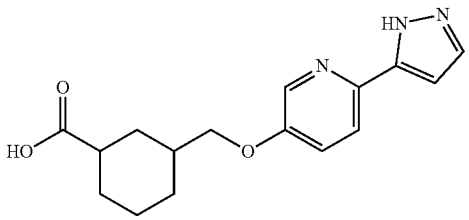

(1) The compound (123 mg) obtained in Reference Example 1-1 and ethyl trans-3-(hydroxymethyl)-1-cyclohexanecarboxylate were used to perform the synthesis process according to the method described in Example 8-1-(1) thereby giving ethyl trans-3-[[6-[2-(2-oxanyl)-3-pyrazolyl]-3-pyridinyl]oxymethyl]-1-cyclohexanecarboxylate (77 mg) as a colorless oil.

(2) The compound (77 mg) obtained in (1) above was used to perform the synthesis process according to the method described in Example 1-61-(2) thereby giving ethyl trans-3-[[6-(1H-pyrazol-5-yl)-3-pyridinyl]oxymethyl]-1-cyclohexanecarboxylate (43 mg).

(3) An aqueous solution of 1 mol/L sodium hydroxide (290 μL) was added to a suspension of the compound (43 mg) obtained in (2) above in ethanol (1.3 mL), and the mixture was stirred at room temperature overnight. This reaction solution was purified by preparative HPLC, and the obtained crude product was solidified by diethyl ether to give the title compound (11 mg) as a colorless powder.

$^1$H NMR (400 MHz, DMSO-d$_6$) δ ppm 0.96-2.73 (m, 9H) 3.31-3.45 (m, 1H) 3.88-4.00 (m, 2H) 6.70-6.74 (m, 1H) 7.39-7.48 (m, 1H) 7.61-7.72 (m, 1H) 7.80-7.87 (m, 1H) 8.24-8.31 (m, 1H).

MS ESI/APCI Multi posi: 302[M+H]$^+$.

MS ESI/APCI Multi nega: 300[M−H]$^−$.

The compounds of Examples 9-2 and 9-3 below were synthesized using a compound obtained in Reference Example 38-1 or 38-2, according to the method described in Example 9-1. The structures, NMR data, and MS data of the compounds are shown in Table 36-1.

TABLE 36-1

| Example No. | Structure | Analytical Data |
|---|---|---|
| 9-2 | 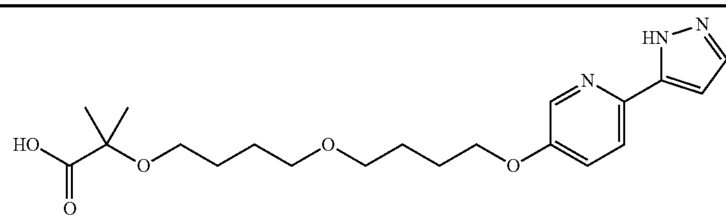 | $^1$H NMR (400 MHz, DMSO-d$_6$) δ ppm 1.28 (s, 6 H) 1.43-1.57 (m, 4 H) 1.60-1.69 (m, 2 H) 1.72-1.83 (m, 2 H) 3.34-3.49 (m, 6 H) 4.09 (t, J = 6.5 Hz, 2 H) 6.70-6.74 (m, 1 H) 7.40-7.47 (m, 1 H) 7.64-7.69 (m, 1 H) 7.82-7.87 (m, 1 H) 8.25-8.29 (m, 1 H) 12.76 (br s, 1 H). MS ESI posi: 392 [M + H]$^+$. MS ESI nega: 390 [M − H]$^−$. |
| 9-3 | 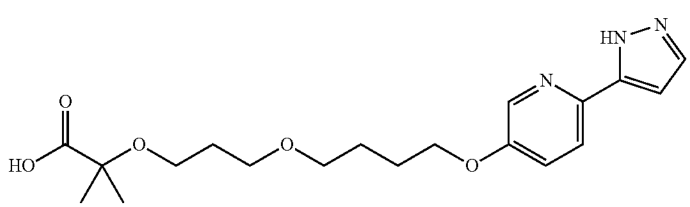 [SMILES: CC(C)(OCCCOCCCCOc1ccc(-c2ccn[nH]2)nc1)C(=O)O] | $^1$H NMR (400 MHz, DMSO-d$_6$) δ ppm 1.28 (s, 6 H) 1.62-1.72 (m, 4 H) 1.73-1.83 (m, 2 H) 3.34-3.45 (m, 6 H) 4.08 (t, J = 6.4 Hz, 2 H) 6.71-6.73 (m, 1 H) 7.41-7.46 (m, 1 H) 7.62-7.69 (m, 1 H) 7.81-7.87 (m, 1 H) 8.25-8.29 (m, 1 H) 12.58-12.96 (m, 1 H). MS ESI posi: 378 [M + H]$^+$. MS ESI nega: 376 [M − H]$^−$. |

Example 9-4

2-[4-[3-[[6-(1H-Pyrazol-5-yl)-6-pyridinyl]oxymethyl]phenyl]-1-pyrazolyl]acetic Acid

[Formula 509]

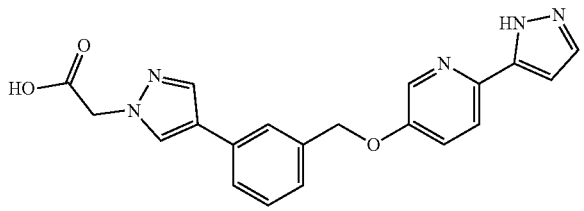

(1) The compound (213 mg) obtained in Reference Example 1-1 and the compound (250 mg) obtained in Reference Example 49-1 were used to perform the synthesis process according to the method described in Example 8-1-(1) thereby giving a mixture (620 mg) containing tert-butyl 2-[4-[3-[[6-[2-(2-oxanyl)-3-pyrazolyl]-3-pyridinyl]oxymethyl]phenyl]-1-pyrazolyl]acetate as a colorless amorphous substance.

(2) To a solution of the mixture (340 mg) obtained in (1) above in tetrahydrofuran (5.0 mL), 2 mol/L hydrochloric acid (5.0 mL) was added, and the mixture was stirred at room temperature for 1 hour, and at an outer temperature of 75° C. for 3.5 hours. After the reaction mixture was cooled to room temperature, an aqueous solution of 1 mol/L sodium hydroxide (5.0 mL) was added thereto, and the resultant mixture was extracted with ethyl acetate. The organic layer was concentrated, an aqueous solution of 1 mol/L sodium hydroxide (0.7 mL) was added to a solution of the obtained residue (140.0 mg) in methanol (1.7 mL), and the resultant mixture was stirred at room temperature for 14 hours. After neutralizing with an aqueous solution of 10% potassium hydrogen sulfate, the solid generated was collected by filtration, and washed with water. The obtained solid was suspended in ethanol (3.0 mL), the suspension was stirred, and the solid was collected by filtration, and washed with ethanol. The solid was dried by heating to give the title compound (110 mg) as a colorless solid.

$^1$H NMR (400 MHz, DMSO-$d_6$) δ ppm 4.96 (s, 2H) 5.23 (s, 2H) 6.73 (d, J=1.7 Hz, 1H) 7.28-7.33 (m, 1H) 7.40 (t, J=7.6 Hz, 1H) 7.50-7.59 (m, 2H) 7.62-7.76 (m, 2H) 7.84-7.89 (m, 1H) 7.92 (s, 1H) 8.18 (s, 1H) 8.38 (d, J=2.8 Hz, 1H) 13.06 (br s, 1H).

MS ESI posi: 376[M+H]$^+$.
MS ESI nega: 374[M−H]$^−$.

Example 10-1

5-[[6-(1H-Pyrazol-5-yl)-3-pyridinyl]oxy]pentanoic Acid

[Formula 510]

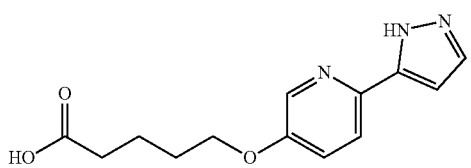

(1) The compound (105 mg) obtained in Reference Example 1-1 and the compound (87.6 mg) obtained in Reference Example 21-1 were used to perform the synthesis process according to the method described in Example 8-1-(1) thereby giving tert-butyl 5-[[6-[2-(2-oxanyl)-3-pyrazolyl]-3-pyridinyl]oxy]pentanoate (87.9 mg) as a colorless oil.

(2) Trifluoroacetic acid (2.00 mL) was added to a solution of the compound (87.9 mg) obtained in (1) above in tetrahydrofuran:water (2:1, 1.5 mL), and the mixture was stirred at room temperature overnight, and at an outer temperature of 60° C. for 5.5 hours. After cooling to room temperature, the mixture was concentrated under reduced pressure. The obtained residue was purified by preparative HPLC-MS to give the title compound (16.9 mg) as a colorless solid.

$^1$H NMR (400 MHz, DMSO-$d_6$) δ ppm 1.57-1.82 (m, 4H) 2.19-2.33 (m, 2H) 4.08 (t, J=6.3 Hz, 2H) 6.72 (d, J=2.1 Hz, 1H) 7.43 (dd, J=8.7, 2.9 Hz, 1H) 7.59-7.78 (m, 1H) 7.84 (d, J=8.7 Hz, 1H) 8.27 (d, J=2.9 Hz, 1H).

MS ESI/APCI Multi posi: 262[M+H]$^+$.

Example 10-2

2-[3-[[6-(1H-Pyrazol-5-yl)-3-pyridinyl]oxymethyl]phenoxy]acetic Acid

[Formula 511]

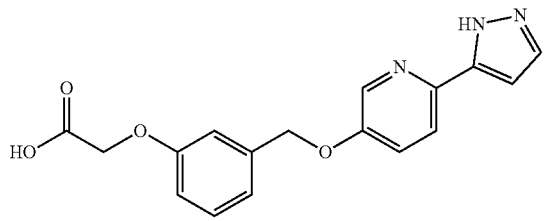

(1) The compound (219 mg) obtained in Reference Example 19-2, triphenylphosphine (321 mg), and diisopropyl azodicarboxylate (40% toluene solution, 0.64 mL) were added to a solution of the compound (150 mg) obtained in Reference Example 1-1 in tetrahydrofuran (5.0 mL), and the mixture was stirred at room temperature for 20 hours. The solvent was distilled off under reduced pressure, and the obtained residue was purified by silica gel column chromatography (n-hexane:ethyl acetate=4:1 to 1:1) to give tert-butyl 2-[3-[[6-[2-(2-oxanyl)-3-pyrazolyl]-3-pyridinyl]oxymethyl]phenoxy] acetate (290 mg) as a colorless oil.

(2) To a solution of the compound (285 mg) obtained in (1) above in tetrahydrofuran (5.0 mL), 2 mol/L hydrochloric acid (5.0 mL) was added, and the mixture was stirred at room temperature for 1 hour, and at an outer temperature of 70° C. for 4 hours. After the reaction solution was cooled, an aqueous solution of 1 mol/L sodium hydroxide was added dropwise thereto to adjust pH to 5 to 6. The solvent was distilled off under reduced pressure, and the residue was then purified by preparative HPLC. An ethanol:diethyl ether (1:1) mixed solution was added to the obtained crude product, and the precipitated solid was collected by filtration. The solid was dried under reduced pressure to give the title compound (32.7 mg) as a colorless powder.

$^1$H NMR (400 MHz, DMSO-$d_6$) δ ppm 4.68 (s, 2H) 5.18 (s, 2H) 6.70-6.75 (m, 1H) 6.85-6.91 (m, 1H) 7.01-7.11 (m, 2H) 7.28-7.35 (m, 1H) 7.48-7.56 (m, 1H) 7.68 (s, 1H) 7.82-7.88 (m, 1H) 8.35 (d, J=2.8 Hz, 1H) 13.01 (br s, 1H).

MS ESI/APCI Multi posi: 326[M+H]$^+$.
MS ESI/APCI Multi nega: 324[M−H]$^−$.

Example 11-1

2,3-Difluoro-5-[3-[[6-(1H-pyrazol-5-yl)-3-pyridinyl]oxy]propyl]phenol

[Formula 512]

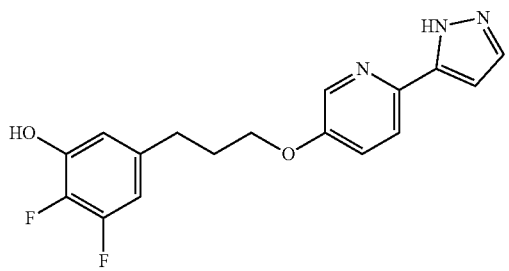

(1) The compound (20.0 mg) obtained in Reference Example 1-1 and the compound (30.0 mg) obtained in Reference Example 45-1 were used to perform the synthesis process according to the method described in Example 8-1-(1) thereby giving 5-[3-[3,4-difluoro-5-[(4-methoxyphenyl)methoxy]phenyl]propoxy]-2-[2-(2-oxanyl)-3-pyrazolyl]pyridine (15.3 mg) as a colorless gum-like substance.

(2) The compound (15.3 mg) obtained in (1) above was dissolved in a 2 mol/L hydrogen chloride-methanol solution (2 mL), and the mixture was stirred at room temperature overnight. The mixture was concentrated under reduced pressure, and the residue was purified by preparative HPLC-MS to give the title compound (3.57 mg) as a colorless solid.

$^1$H NMR (400 MHz, DMSO-$d_6$) δ ppm 1.94-2.05 (m, 2H) 2.59-2.72 (m, 2H) 4.00-4.10 (m, 2H) 6.57-6.79 (m, 3H) 7.39-7.58 (m, 1H) 7.68-7.96 (m, 2H) 8.24-8.53 (m, 1H).

MS ESI/APCI Multi posi: 332[M+H]$^+$.

The compounds of Examples 11-2 and 11-3 below were synthesized using a compound obtained in Reference Example 25-1 or 69-1, according to the method described in Example 11-1. The structures, NMR data, and MS data of the compounds are shown in Table 37-1.

Example 11-4

5-[[6-(1H-Pyrazol-5-yl)-3-pyridinyl]oxy]-1-pentanesulfonamide

[Formula 513]

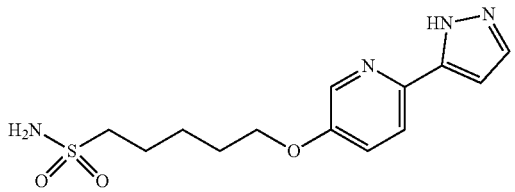

(1) The compound (50 mg) obtained in Reference Example 1-1 and the compound (51 mg) obtained in Reference Example 82-1 were used to perform the synthesis process according to the method described in Example 10-2-(1) thereby giving 5-[[6-[2-(2-oxanyl)-3-pyrazolyl]-3-pyridinyl]oxy]-1-pentanesulfonamide (40 mg) as a colorless oil.

(2) The compound (40 mg) obtained in (1) above was used to perform the synthesis process according to the method described in Example 1-1-(3) thereby giving the title compound (12 mg) as a colorless powder.

$^1$H NMR (400 MHz, DMSO-$d_6$) δ ppm 1.46-1.64 (m, 2H) 1.68-1.90 (m, 4H) 2.88-3.11 (m, 2H) 3.92-4.20 (m, 2H) 6.59-6.85 (m, 3H) 7.31-8.03 (m, 3H) 8.14-8.36 (m, 1H).

MS ESI/APCI Multi posi: 311 [M+H]$^+$.

TABLE 37-1

| Example No. | Structure | Analytical Data |
|---|---|---|
| 11-2 | 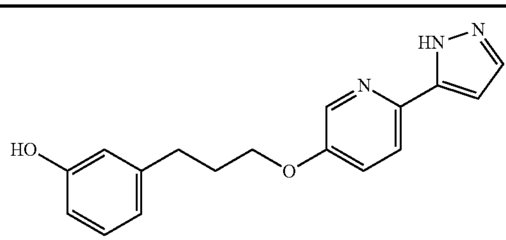 | $^1$H NMR (400 MHz, DMSO-$d_6$) δ ppm 1.94-2.07 (m, 2 H) 2.67 (t, J = 7.6 Hz, 2 H) 4.00-4.14 (m, 2 H) 6.53-6.78 (m, 3 H) 7.02-7.11 (m, 1 H) 7.35-7.57 (m, 2 H) 7.71-7.93 (m, 2 H) 8.28 (s, 1 H) 9.28 (br s, 1 H).<br>MS ESI/APCI Multi posi: 296 [M + H]$^+$. |
| 11-3 | 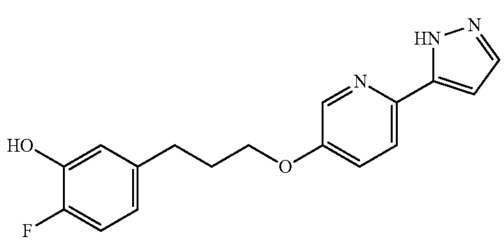 [SMILES: Oc1cc(CCCOc2ccc(-c3ccn[nH]3)nc2)ccc1F] | $^1$H NMR (400 MHz, DMSO-$d_6$) δ ppm 1.93-2.05 (m, 2 H) 2.60-2.71 (m, 2 H) 4.01-4.11 (m, 2 H) 6.58-6.87 (m, 3 H) 7.01 (dd, J = 11.4, 8.3 Hz, 1 H) 7.38-7.60 (m, 1 H) 7.67-7.95 (m, 2 H) 8.28 (s, 1 H) 9.74 (br s, 1 H).<br>MS ESI/APCI Multi posi: 314 [M + H]$^+$. |

Example 12-1

2-Methyl-5-[[6-(1H-pyrazol-5-yl)-3-pyridinyl]oxymethyl]phenol

[Formula 514]

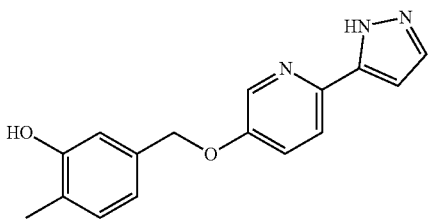

(1) The compound (115 mg) obtained in Reference Example 23-1 was used to perform the synthesis process according to the method described in Example 10-2-(1) thereby giving a mixture (135 mg) containing [2-methyl-5-[[6-[2-(2-oxanyl)-3-pyrazolyl]-3-pyridinyl]oxymethyl]phenyl]acetate.

(2) An aqueous solution of 1 mol/L sodium hydroxide (2 mL) was added to a suspension of the compound (130 mg) obtained in (1) above in methanol (1 mL) and tetrahydrofuran (1 mL), and the mixture was stirred at room temperature for 30 minutes. A saturated aqueous solution of ammonium chloride was added to the mixture to adjust pH to 7, and the resultant mixture was diluted with water, and then extracted twice with chloroform. The organic layer was dried over anhydrous magnesium sulfate, the drying agent was filtered off, and the filtrate was concentrated under reduced pressure to give a mixture (111 mg) containing 2-methyl-5-[[6-[2-(2-oxanyl)-3-pyrazolyl]-3-pyridinyl]oxymethyl]phenol.

(3) To a solution of the compound (22 mg) obtained in (2) above in methanol (1 mL), 2 mol/L hydrochloric acid (0.5 mL) was added, and the mixture was stirred at room temperature for 2 hours. After the end of the reaction was confirmed by LC-MS, triethylamine (140 µL) was added thereto to adjust pH to 8. This mixture was purified by preparative HPLC to give the title compound (15 mg) as a colorless powder.

$^1$H NMR (600 MHz, DMSO-$d_6$) δ ppm 2.10 (s, 3H) 5.09 (s, 2H) 6.71 (br s, 1H) 6.76-6.80 (m, 1H) 6.85 (s, 1H) 7.06 (d, J=7.8 Hz, 1H) 7.41-7.91 (m, 3H) 8.31 (s, 1H) 9.30-9.42 (m, 1H) 12.78-13.37 (m, 1H).

MS ESI/APCI Multi posi: 282[M+H]$^+$.

The compounds of Examples 12-2 and 12-3 below were synthesized using a compound obtained in Reference Example 23-2 or 23-3, according to the method described in Example 12-1. The structures, NMR data, and MS data of the compounds are shown in Table 38-1.

TABLE 38-1

| Example No. | Structure | Analytical Data |
|---|---|---|
| 12-2 | ![structure] | $^1$H NMR (600 MHz, DMSO-$d_6$) δ ppm 5.11 (s, 2 H) 6.73 (br s, 1 H) 6.89 (ddd, J = 8.3, 4.1, 2.1 Hz, 1 H) 7.05 (dd, J = 8.7, 2.1 Hz, 1 H) 7.14 (dd, J = 11.1, 8.3 Hz, 1 H) 7.43-7.94 (m, 3 H) 8.27-8.38 (m, 1 H) 9.84-10.05 (m, 1 H) 12.80-13.42 (m, 1 H). MS ESI/APCI Multi posi: 286 [M + H]$^+$. MS ESI/APCI Multi nega: 284 [M − H]$^-$. |
| 12-3 | ![structure] | MS ESI/APCI Multi posi: 286 [M + H]$^+$. MS ESI/APCI Multi nega: 284 [M − H]$^-$ |

Example 13-1

3-[[6-(1H-Pyrazol-5-yl)-3-pyridinyl]oxymethyl]phenol

[Formula 515]

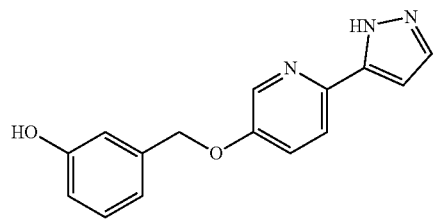

(1) The compound (70 mg) obtained in Reference Example 1-1 was used to perform the synthesis process according to the method described in Example 10-2-(1)

thereby giving 2-[2-(2-oxanyl)-3-pyrazolyl]-5-[(3-phenylmethoxyphenyl)methoxy]pyridine (110 mg).

(2) The compound (110 mg) obtained in (1) above was used to perform the synthesis process according to the method described in Example 12-1-(3) thereby giving a mixture containing 5-[(3-phenylmethoxyphenyl)methoxy]-2-(1H-pyrazol-5-yl)pyridine.

(3) Palladium hydroxide carbon (20 mg) was added to a solution of the mixture obtained in (2) above in ethanol (3 mL), and the mixture was stirred under a hydrogen atmosphere at room temperature overnight. The reaction solution was filtered through Celite (registered trademark), and then concentrated under reduced pressure. After the obtained residue was purified by preparative HPLC, the obtained crude product was recrystallized from a chloroform:hexane mixed solution to give the title compound (15 mg) as a colorless powder.

MS ESI/APCI Multi posi: 268[M+H]⁺.

The compounds of Examples 13-2 and 13-3 below were synthesized using a compound obtained in Reference Example 24-1 or 24-2, according to the method described in Example 13-1. The structures, and MS data of the compounds are shown in Table 39-1.

roform. The organic layer was separated by a phase separator, and concentrated under reduced pressure. The residue was purified by silica gel column chromatography (chloroform:methanol=99:1 to 91:9) to give 3-[(3-ethoxy-3-oxopropyl)thio]benzoic acid (785 mg) as a colorless powder.

(2) Oxone (registered trademark) (1.5 g) was added to a solution of the compound (250 mg) obtained in (1) above in ethanol (6.6 mL) and water (1.3 mL), and the mixture was stirred at room temperature overnight. A saturated aqueous solution of sodium thiosulfate was added to the reaction solution, and the resultant mixture was extracted with chloroform. The organic layer was separated by a phase separator, and concentrated under reduced pressure. The residue was purified by silica gel column chromatography (chloroform:methanol=49:1 to 9:1) to give 3-(3-ethoxy-3-oxopropyl)sulfonylbenzoic acid (234 mg) as a colorless powder.

(3) A borane-tetrahydrofuran complex (0.9 mol/L tetrahydrofuran solution, 1.0 mL) was added dropwise to a solution of the compound (232 mg) obtained in (2) above in tetrahydrofuran (8.1 mL) under ice cooling, and the mixture was stirred at room temperature overnight. A borane-tetrahydrofuran complex (0.9 mol/L tetrahydrofuran solution, 1.0 mL) was further added dropwise thereto under ice

TABLE 39-1

| Example No. | Structure | Analytical Data |
|---|---|---|
| 13-2 | 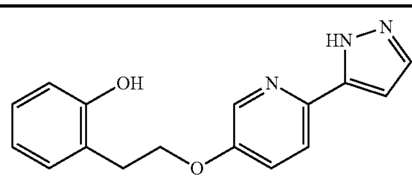 | MS ESI/APCI Multi posi: 282 [M + H]⁺. |
| 13-3 | 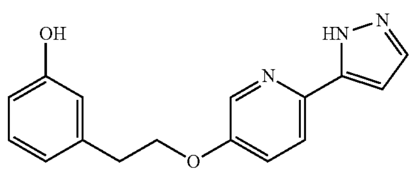 [SMILES: Oc1cccc(CCOc2ccc(-c3ccn[nH]3)nc2)c1] | MS ESI/APCI Multi posi: 282 [M + H]⁺. |

Example 14-1

3-[3-[[6-(1H-Pyrazol-5-yl)-3-pyridinyl]oxymethyl]phenyl]sulfonylpropanoic Acid

[Formula 516]

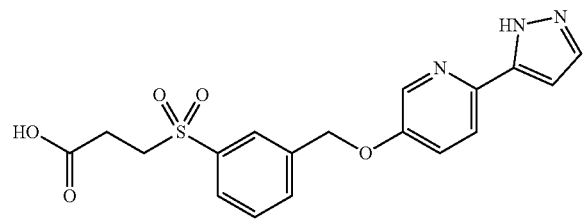

(1) Triethylamine (0.9 mL) and ethyl 2-propenoate (0.43 mL) were added to a solution of 3-mercaptobenzoic acid (500 mg) in tetrahydrofuran (6.5 mL), and the mixture was stirred at room temperature overnight. A saturated aqueous solution of ammonium chloride was added to the reaction solution, and the resultant mixture was extracted with chlocooling, and the resultant mixture was stirred at room temperature for 5 hours. Water and a saturated aqueous solution of ammonium chloride were added thereto under ice cooling, and the resultant mixture was extracted with chloroform. The organic layer was separated by a phase separator, and concentrated under reduced pressure. The residue was purified by silica gel column chromatography (chloroform:methanol=99:1 to 91:9) to give ethyl 3-[3-(hydroxymethyl)phenyl]sulfonylpropanoate (203 mg) as a colorless oil.

(4) The compound (65 mg) obtained in Reference Example 1-1 and the compound (108 mg) obtained in (3) above were used to perform the synthesis process according to the method described in Example 8-1-(1) thereby giving a crude product (207 mg) containing ethyl 3-[3-[[6-[2-(2-oxanyl)-3-pyrazolyl]-3-pyridinyl]oxymethyl]phenyl] sulfonylpropanoate as a colorless oil.

(5) The compound (207 mg) obtained in (4) above was used to perform the synthesis process according to the method described in Example 1-61-(2) thereby giving ethyl 3-[3-[[6-(1H-pyrazol-5-yl)-3-pyridinyl]oxymethyl]phenyl] sulfonylpropanoate (105 mg) as a colorless oil.

(6) The compound (105 mg) obtained in (5) above was used to perform the synthesis process according to the method described in Example 1-47-(3) thereby giving 3-[[6-(1H-pyrazol-5-yl)-3-pyridinyl]oxymethyl]benzenesulfinic acid (55 mg) as a colorless powder.

(7) Acrylic acid (20 μL) was added to a solution of the compound (25 mg) obtained in (6) above in ethanol (0.2 mL) and water (0.2 mL) at room temperature, and the mixture was stirred at the same temperature overnight. The reaction solution was purified by preparative HPLC to give the title compound (4 mg) as a colorless powder.

$^1$H NMR (400 MHz, DMSO-d$_6$) δ ppm 3.53 (t, J=7.3 Hz, 2H) 5.35 (s, 2H) 6.71-6.77 (m, 1H) 7.52-7.60 (m, 1H) 7.63-7.79 (m, 2H) 7.82-7.93 (m, 3H) 7.99-8.07 (m, 1H) 8.33-8.44 (m, 1H).

MS ESI/APCI Multi posi: 388[M+H]$^+$.
MS ESI/APCI Multi nega: 386[M−H]$^-$.

Example 15-1

2-Methyl-2-[7-[[6-(1H-pyrazol-5-yl)-3-pyridinyl]oxy]heptoxy]propanoic Acid

[Formula 517]

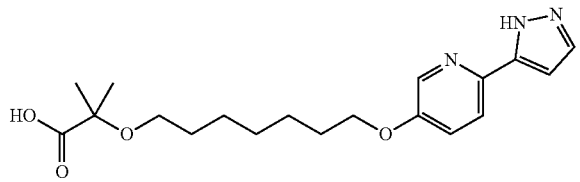

(1) The compound (100 mg) obtained in Reference Example 1-1 and 6-bromo-1-hexanol (0.08 mL) were used to perform the synthesis process according to the method described in Example 8-1-(1) thereby giving 5-(6-bromohexoxy)-2-[2-(2-oxanyl)-3-pyrazolyl]pyridine (125 mg) as a colorless oil.

(2) To a suspension of sodium hydride (60% mineral oil dispersion, 15 mg) in N,N-dimethylformamide (0.5 mL), 2-hydroxy-2-methylpropanoic acid (0.05 mL) was added under ice cooling, the ice bath was removed, and the mixture was stirred for 30 minute. A solution of the compound (116 mg) obtained in (1) above in N,N-dimethylformamide (1.3 mL) was added thereto, and the resultant mixture was stirred at 90° C. for 2 hours. Water was added thereto under ice cooling, the resultant mixture was extracted with a n-hexane:ethyl acetate mixed solution, and the obtained organic layer was sequentially washed with water and brine. The organic layer was separated by a phase separator, and concentrated under reduced pressure. The residue was purified by silica gel column chromatography (n-hexane:ethyl acetate=4:1 to 1:1) to give a crude product (39 mg) containing ethyl 2-methyl-2-[7-[[6-[2-(2-oxanyl)-3-pyrazolyl]-3-pyridinyl]oxy]heptoxy]propanoate as a colorless oil.

(3) The compound (39 mg) obtained in (2) above was used to perform the synthesis process according to the method described in Example 1-1-(3) thereby giving a crude product (37 mg) containing ethyl 2-methyl-2-[7-[[6-(1H-pyrazol-5-yl)-3-pyridinyl]oxy]heptoxy]propanoate.

(4) The compound (37 mg) obtained in (3) above was used to perform the synthesis process according to the method described in Example 1-43-(2) thereby giving the title compound (21 mg) as a colorless powder.

$^1$H NMR (400 MHz, DMSO-d$_6$) δ ppm 1.17-1.56 (m, 14H) 1.66-1.80 (m, 2H) 3.24-3.45 (m, 2H) 4.06 (t, J=6.5 Hz, 2H) 6.67-6.76 (m, 1H) 7.38-7.49 (m, 1H) 7.59-7.74 (m, 1H) 7.79-7.88 (m, 1H) 8.23-8.31 (m, 1H).

MS ESI/APCI Multi posi: 362[M+H]$^+$.
MS ESI/APCI Multi nega: 360[M−H]$^-$.

Example 15-2

1-[3-[[6-(1H-Pyrazol-5-yl)-3-pyridinyl]oxy]propyl]-4-pyrazolecarboxylic Acid

[Formula 518]

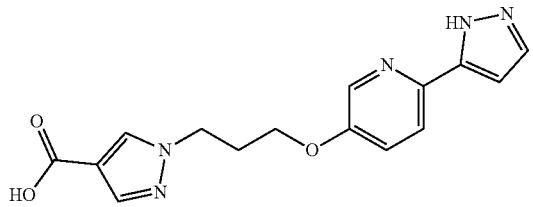

(1) The compound (300 mg) obtained in Reference Example 1-1 and 3-bromo-1-propanol (289 mg) were used to perform the synthesis process according to the method described in Example 8-1-(1) thereby giving 5-(3-bromopropoxy)-2-[2-(2-oxanyl)-3-pyrazolyl]pyridine (400 mg) as a colorless oil.

(2) Potassium carbonate (1.5 g) and ethyl 1H-pyrazole-4-carboxylate (153 mg) were added to a solution of the compound (400 mg) obtained in (1) above in acetone (5.5 mL), and the mixture was stirred at an outer temperature of 60° C. for 6.5 hours, and further stirred at room temperature for 12 hours. The reaction solution was diluted with acetone, and then filtered through Celite (registered trademark) to remove inorganic salts. The filtrate was concentrated under reduced pressure, and then purified by silica gel column chromatography (chloroform:methanol) to give ethyl 1-[3-[[6-[2-(2-oxanyl)-3-pyrazolyl]-3-pyridinyl]oxy]propyl]-4-pyrazolecarboxylate (420 mg) as a colorless oil.

(3) To a solution of the compound (130 mg) obtained in (2) above in ethanol (3 mL), 2 mol/L hydrochloric acid (0.3 mL) was added, and the mixture was stirred at room temperature for 30 minutes to give a solution containing ethyl 1-[3-[[6-(1H-pyrazol-5-yl)-3-pyridinyl]oxy}propyl]-4-pyrazolecarboxylate.

(4) The solution obtained in (3) above was used to perform the synthesis process according to the method described in Example 1-43-(2) thereby giving the title compound (67 mg) as a colorless solid.

$^1$H NMR (400 MHz, DMSO-d$_6$) δ ppm 5.26 (s, 2H) 5.31 (s, 2H) 6.72 (d, J=2.0 Hz, 1H) 7.45-7.62 (m, 2H) 7.65-7.70 (m, 2H) 7.82-7.92 (m, 2H) 8.11 (s, 1H) 8.37 (d, J=2.7 Hz, 1H) 12.92-13.14 (m, 1H).

MS ESI posi: 350[M+H]$^+$.
MS ESI nega: 348[M−H]$^-$.

The compound of Example 15-3 below was synthesized using a commercially available compound, according to the method described in Example 15-2. The structure, NMR data, and MS data of the compounds are shown in Table 40-1.

TABLE 40-1

| Example No. | Structure | Analytical Data |
|---|---|---|
| 15-3 | (structure) | $^1$H NMR (400 MHz, DMSO-d$_6$) δ ppm 1.60-1.75 (m, 2 H) 1.89-2.02 (m, 2 H) 4.08 (t, J = 6.4 Hz, 2 H) 4.22 (t, J = 6.8 Hz, 2 H) 6.72 (d, J = 2.1 Hz, 1 H) 7.43 (dd, J = 8.6, 2.8 Hz, 1 H) 7.57-7.74 (m, 1 H) 7.76-7.89 (m, 2 H) 8.20-8.33 (m, 2 H) 12.39-12.88 (m, 1 H). MS ESI posi: 328 [M + H]$^+$. |

Example 16-1

2-[5-[[6-(1H-Pyrazol-5-yl)-3-pyridinyl]oxymethyl]-1-indazolyl]acetic Acid

[Formula 519]

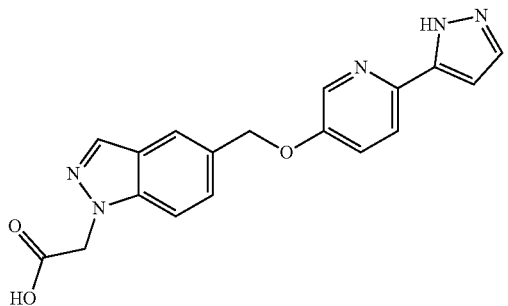

(1) The compound (100 mg) obtained in Reference Example 1-1 and 1H-indazol-5-yl methanol (66 mg) were used to perform the synthesis process according to the method described in Example 8-1-(1) thereby giving 5-[[6-[2-(2-oxanyl)-3-pyrazolyl]-3-pyridinyl]oxymethyl]-1H-indazole (100 mg) as a colorless solid.

(2) Cesium carbonate (130 mg) and tert-butyl 2-bromoacetate (62 mg) were slowly added to a solution of the compound (100 mg) obtained in (1) above in N,N-dimethylformamide (3.0 mL) under ice cooling, and the mixture was then stirred at room temperature for 18 hours. The mixture was diluted with water and extracted with ethyl acetate, and the organic layer was concentrated under reduced pressure. The obtained residue was purified by silica gel column chromatography (chloroform:methanol) to give tert-butyl 2-[5-[[6-[2-(2-oxanyl)-3-pyrazolyl]-3-pyridinyl]oxymethyl]-1-indazolyl]acetate (90 mg) as a light yellow oil.

(3) The compound (90 mg) obtained in (2) above was used to perform the synthesis process according to the method described in Example 12-1-(3) thereby giving a solution containing tert-butyl 2-[5-[[6-(1H-pyrazol-5-yl)-3-pyridinyl]oxymethyl]-1-indazolyl]acetate.

(4) The solution obtained in (3) above was used to perform the synthesis process according to the method described in Example 9-1-(3) thereby giving the title compound (20 mg) as a colorless solid.

$^1$H NMR (400 MHz, DMSO-d$_6$) δ ppm 5.26 (s, 2H) 5.31 (s, 2H) 6.72 (d, J=2.0 Hz, 1H) 7.45-7.62 (m, 2H) 7.65-7.70 (m, 2H) 7.82-7.92 (m, 2H) 8.11 (s, 1H) 8.37 (d, J=2.7 Hz, 1H) 12.92-13.14 (m, 1H).

MS ESI posi: 350[M+H]$^+$.
MS ESI nega: 348[M−H]$^−$.

Example 17-1

2,2-Dimethyl-3-oxo-3-[7-[[6-(1H-pyrazol-5-yl)-3-pyridinyl]oxymethyl]-3,4-dihydro-1H-isoquinolin-2-yl]propanoic Acid

[Formula 520]

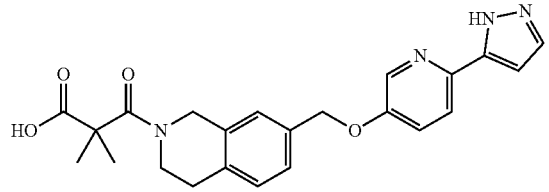

(1) Methyl 1,2,3,4-tetrahydroisoquinoline-7-carboxylate hydrochloride (443 mg) was added little by little to a suspension of lithium aluminum hydride (185 mg) in tetrahydrofuran (6.49 mL) under ice cooling. After the resultant green suspension was stirred at room temperature overnight, water (185 μL), an aqueous solution of 15% sodium hydroxide (185 μL), and water (555 μL) were added to the suspension in this order under ice cooling, and the resultant mixture was stirred at room temperature for 30 minutes. The precipitate generated was filtered off, and washed with diethyl ether. The filtrate and the washing solution were combined, and the solvent was distilled off under reduced pressure. The residue was dissolved in ethanol, and the solution was concentrated under reduced pressure again to give an ethanol adduct (341 mg) of 1,2,3,4-tetrahydroisoquinolin-7-yl methanol as a slightly yellow solid.

(2) The compound (341 mg) obtained in (1) above and trifluoroacetic anhydride (460 μL) were used to perform the synthesis process according to the method described in Example 6-1-(3) thereby giving 2,2,2-trifluoro-1-[7-(hydroxymethyl)-3,4-dihydro-1H-isoquinolin-2-yl]ethanone (118 mg) as a pale yellow oil.

(3) The compound (88.5 mg) obtained in Reference Example 1-1 and the compound (118 mg) obtained in (2) above were used to perform the synthesis process according to the method described in Example 8-1-(1) thereby giving 2,2,2-trifluoro-1-[7-[[6-[2-(2-oxanyl)-3-pyrazolyl]-3-pyridinyl]oxymethyl]-3,4-dihydro-1H-isoquinolin-2-yl]ethanone (158 mg) as a colorless oil.

(4) Potassium carbonate (82.3 mg) was added to a solution of the compound (158 mg) obtained in (3) above in methanol (2.98 mL), and the mixture was stirred at room temperature for 3 hours. The mixture was diluted with chloroform, insolubles were filtered off, and the filtrate was concentrated under reduced pressure. The residue was distributed into ethyl acetate and water, and the aqueous layer was extracted twice with ethyl acetate. The organic layers were combined, and the resultant was washed with brine, separated from the aqueous layer by a phase separator, and concentrated under reduced pressure to give a mixture (126 mg) containing 7-[[6-[2-(2-oxanyl)-3-pyrazolyl]-3-pyridinyl]oxymethyl]-1,2,3,4-tetrahydroisoquinoline.

(5) A solution of the mixture (61.0 mg) obtained in (4) above and N,N-diisopropylethylamine (240 μL) in chloroform (920 μL) was added to a solution of dimethylmalonyl dichloride (91.2 μL) in chloroform (460 μL) under ice cooling, and the mixture was stirred at room temperature overnight. To this mixture, an aqueous solution of 10% potassium hydrogen sulfate was added, and the resultant mixture was vigorously stirred at room temperature for 3.5 hours, and then extracted three times with ethyl acetate. The organic layers were combined, and the resultant was washed with brine, separated from the aqueous layer by a phase separator, and then concentrated under reduced pressure to give a mixture containing 2,2-dimethyl-3-[7-[[6-[2-(2-oxanyl)-3-pyrazolyl]-3-pyridinyl]oxymethyl]-3,4-dihydro-1H-isoquinolin-2-yl]-3-oxopropanoic acid.

(6) Water (500 μL) and acetic acid (2.00 mL) were added to a solution of the mixture obtained in (5) above in tetrahydrofuran (1.00 mL), and the mixture was stirred at room temperature for 2 days. After the mixture was concentrated under reduced pressure, the residue was purified by preparative HPLC, and the obtained crude product was solidified by acetonitrile to give the title compound (14.3 mg) as a pale yellow solid.

$^1$H NMR (400 MHz, DMSO-$d_6$) δ ppm 1.32 (s, 6H) 2.60-2.94 (m, 2H) 3.37-3.87 (m, 2H) 4.21-4.71 (m, 2H) 5.16 (s, 2H) 6.73 (d, J=1.8 Hz, 1H) 7.13-7.37 (m, 3H) 7.52 (dd, J=8.7, 2.7 Hz, 1H) 7.67 (s, 1H) 7.85 (d, J=8.7 Hz, 1H) 8.34 (d, J=2.7 Hz, 1H) 12.98 (br s, 1H).

MS ESI/APCI Multi posi: 421 [M+H]$^+$.
MS ESI/APCI Multi nega: 419[M−H]$^−$.

Example 18-1

6-[3-[[6-(1H-Pyrazol-5-yl)-3-pyridinyl]oxymethyl]phenyl]-2-pyridinecarboxylic Acid

[Formula 521]

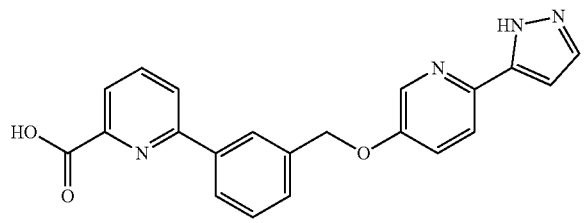

(1) Triethylamine (75 μL) and methanesulfonyl chloride (37 μL) were added to a solution of the compound (120 mg) obtained in Reference Example 48-1 in ethyl acetate (2 mL), and the mixture was stirred at room temperature for 2 hours. The mixture was diluted with ethyl acetate and filtered through Celite (registered trademark), and the obtained solution was concentrated to give a mixture containing ethyl 6-[3-(methylsulfonyloxymethyl)phenyl]-2-pyridinecarboxylate.

(2) Potassium carbonate (113 mg) was added to a solution of the compound (100 mg) obtained in Reference Example 1-1 and the mixture obtained in (1) above in acetone (5 mL), and the mixture was stirred at room temperature for 15 hours. The mixture was diluted with acetone and filtered through Celite (registered trademark), and the filtrate was concentrated. The obtained residue was purified by silica gel column chromatography (n-hexane:ethyl acetate) to give ethyl 6-[3-[[6-[2-(2-oxanyl)-3-pyrazolyl]-3-pyridinyl]oxymethyl]phenyl]-2-pyridinecarboxylate (185 mg) as a colorless amorphous substance.

(3) The compound (185 mg) obtained in (2) above was used to perform the synthesis process according to the method described in Example 15-2-(3) thereby giving ethyl 6-[3-[[6-(1H-pyrazol-5-yl)-3-pyridinyl]oxymethyl]phenyl]-2-pyridinecarboxylate (111 mg) as a colorless amorphous substance.

(4) The compound (110 mg) obtained in (3) above was used to perform the synthesis process according to the method described in Example 12-1-(2) thereby giving the title compound (40 mg) as a colorless solid.

$^1$H NMR (400 MHz, DMSO-$d_6$) δ ppm 5.33 (s, 2H) 6.73 (d, J=2.1 Hz, 1H) 7.47-7.63 (m, 3H) 7.68 (s, 1H) 7.87 (d, J=8.7 Hz, 1H) 7.98-8.04 (m, 1H) 8.05-8.12 (m, 1H) 8.13-8.19 (m, 1H) 8.23 (d, J=7.7 Hz, 1H) 8.30-8.36 (m, 1H) 8.40 (d, J=2.8 Hz, 1H) 12.41-13.63 (m, 1H).

MS ESI posi: 373 [M+H]$^+$.

MS ESI nega: 371[M−H]$^−$.

The compounds of Examples 18-2 to 18-5 below were synthesized using a compound obtained in Reference Example 19-3, 48-2, or 48-5 or 48-6, according to the method described in Example 18-1. The structures, NMR data, and MS data of the compounds are shown in Table 41-1.

TABLE 41-1

| Example No. | Structure | Analytical Data |
|---|---|---|
| 18-2 | 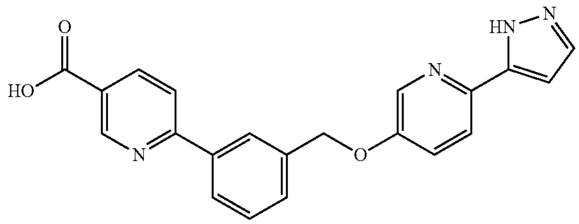 [SMILES: O=C(O)c1ccc(-c2cccc(COc3ccc(-c4ccn[nH]4)nc3)c2)nc1] | $^1$H NMR (400 MHz, DMSO-d$_6$) δ ppm 5.33 (s, 2 H) 6.72 (d, J = 2.0 Hz, 1 H) 7.51-7.78 (m, 4 H) 7.86 (d, J = 8.7 Hz, 1 H) 8.14 (d, J = 8.4 Hz, 2 H) 8.24-8.46 (m, 3 H) 9.15 (d, J = 2.0 Hz, 1 H). MS ESI posi: 373 [M + H]$^+$. |
| 18-3 | 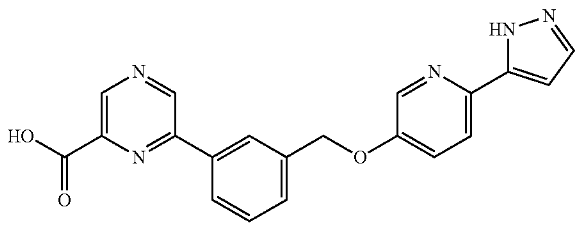 [SMILES: O=C(O)c1cncc(-c2cccc(COc3ccc(-c4ccn[nH]4)nc3)c2)n1] | $^1$H NMR (400 MHz, DMSO-d$_6$) δ pp 5.36 (s, 2 H) 6.76 (s, 1 H) 7.53-7.77 (m, 4 H) 7.90 (d, J = 8.8 Hz, 1 H) 8.23 (d, J = 7.9 Hz, 1 H) 8.33-8.46 (m, 2 H) 9.25 (s, 1 H) 9.42 (s, 1 H). MS ESI/APCI Multi posi: 374 [M + H]$^+$. MS ESI/APCI Multi nega: 372 [M − H]$^-$. |
| 18-4 | 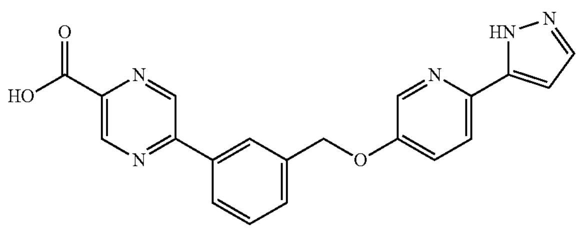 | $^1$H NMR (400 MHz, DMSO-d$_6$) δ ppm 5.34 (s, 2 H) 6.73 (d, J = 2.1 Hz, 1 H) 7.53-7.76 (m, 4 H) 7.87 (d, J = 8.7 Hz, 1 H) 8.21 (d, J = 7.8 Hz, 1 H) 8.32-8.44 (m, 2 H) 9.15 (s, 1 H) 9.49 (s, 1 H) 12.97-13.89 (m, 1 H). MS ESI posi: 374 [M + H]$^+$. MS ESI nega: 372 [M − H]$^-$. |
| 18-5 | 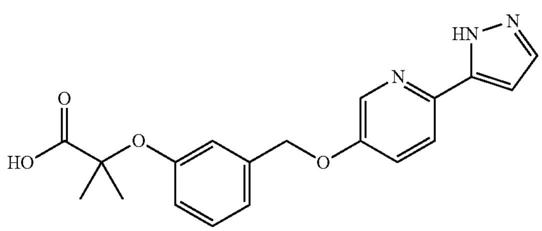 [SMILES: CC(C)(Oc1cccc(COc2ccc(-c3ccn[nH]3)nc2)c1)C(=O)O] | $^1$H NMR (400 MHz, DMSO-d$_6$) δ ppm 1.51 (s, 6 H) 5.17 (s, 2 H) 6.70-6.83 (m, 2 H) 6.93-6.97 (m, 1 H) 7.04-7.10 (m, 1 H) 7.26-7.34 (m, 1 H) 7.47-7.54 (m, 1 H) 7.64 -7.71 (m, 1 H) 7.85 (d, J = 8.6 Hz, 1 H) 8.30-8.36 (m, 1 H) 13.01 (br s, 1 H). MS ESI posi: 354 [M + H]$^+$. MS ESI nega: 352 [M − H]$^-$. |

The compound of Example 18-6 below was synthesized using a commercially available compound, according to the method described in Example 18-1-(1), then by performing the reaction described in Example 18-1-(2) in N,N-dimethylformamide at 60° C., and further according to the methods described in Example 18-1-(3) and (4). The structure, NMR data, and MS data of the compound are shown in Table 41-2.

TABLE 41-2

| Example No. | Structure | Analytical Data |
|---|---|---|
| 18-6 | 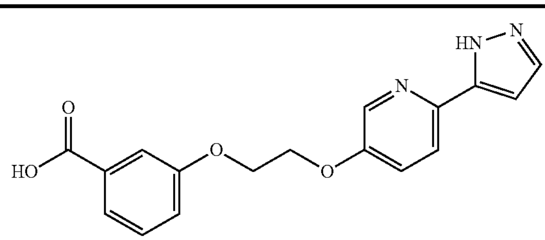 | $^1$H NMR (400 MHz, DMSO-d$_6$) δ ppm 4.38-4.51 (m, 4 H) 6.74 (d, J = 2.1 Hz, 1 H) 7.04-7.13 (m, 2 H) 7.49-7.56 (m, 1 H) 7.65-7.72 (m, 1 H) 7.82-7.95 (m, 3 H) 8.30-8.37 (m, 1 H) 12.86 (br s, 1 H). MS ESI/APCI Multi posi: 326 [M + H]$^+$. MS ESI/APCI Multi nega: 324 [M − H]$^-$. |

Example 19-1

N-[6-[[6-(1H-Pyrazol-5-yl)-3-pyridinyl]oxy]hexyl]methanesulfonamide

[Formula 522]

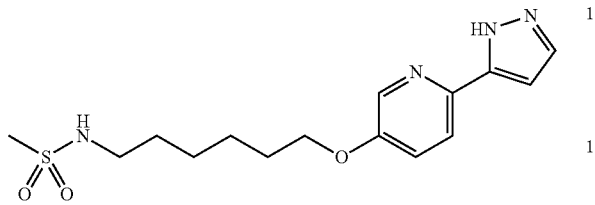

(1) Triethylamine (595 µL) was added to a suspension of 6-amino-1-hexanol (200 mg) in chloroform (5.0 mL), the mixture was ice-cooled, methanesulfonyl chloride (279 µL) was then added dropwise thereto, and the resultant mixture was stirred at room temperature for 2 hours. To the reaction solution, 0.5 mol/L hydrochloric acid was added, and the resultant mixture was extracted with chloroform. The organic layer was separated by a phase separator, and concentrated under reduced pressure. The resultant was dried under reduced pressure to give a mixture (348 mg) containing 6-(methanesulfonamide)hexyl methanesulfonate as a pale yellow oil.

(2) The compound (200 mg) obtained in Reference Example 1-1 and cesium carbonate (531 mg) were added to a solution of the mixture (348 mg) obtained in (1) above in acetonitrile (10 mL), and the resultant mixture was stirred at 80° C. for 6 hours. The reaction solution was cooled, and then filtered through Celite (registered trademark) to remove insolubles. The filtrate was concentrated, and the residue was purified by silica gel column chromatography (chloroform:methanol=19:1). The purified residue was dried under reduced pressure to give N-[6-[[6-[2-(2-oxanyl)-3-pyrazolyl]-3-pyridinyl]oxy]hexyl]methanesulfonamide (118 mg) as a pale yellow oil.

(3) The compound (118 mg) obtained in (2) above was used to perform the synthesis process according to the method described in Example 12-1-(3) thereby giving the title compound (72 mg) as a colorless powder.

$^1$H NMR (400 MHz, DMSO-$d_6$) δ ppm 1.32-1.54 (m, 6H) 1.69-1.79 (m, 2H) 2.87 (s, 3H) 2.90-2.97 (m, 2H) 4.02-4.11 (m, 2H) 6.72 (s, 1H) 6.89-6.96 (m, 1H) 7.36-7.55 (m, 1H) 7.71-7.93 (m, 2H) 8.27 (br s, 1H).

MS ESI/APCI Multi posi: 339[M+H]$^+$.

Example 20-1

2-Methylsulfonyl-4-[[6-(1H-pyrazol-5-yl)-3-pyridinyl]oxymethyl]phenol

[Formula 523]

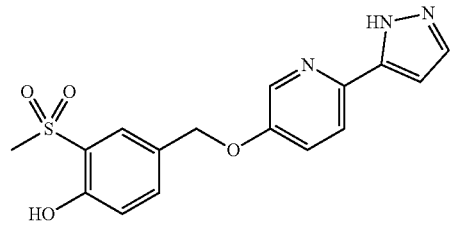

(1) The compound (99.4 mg) obtained in Reference Example 56-1 was used to perform the synthesis process according to the method described in Example 18-1-(1) thereby giving a mixture containing [4-[(4-methoxyphenyl)methoxy]-3-methylsulfonylphenyl]methyl methanesulfonate as a light yellow oil.

(2) Potassium carbonate (85.1 mg) was added to a solution of the compound (75.6 mg) obtained in Reference Example 1-1 and the mixture obtained in (1) above in N,N-dimethylformamide (1.5 mL), and the ressultant mixture was stirred at room temperature for 1 hour. Water was added to the reaction mixture, and the resultant mixture was extracted with ethyl acetate. The organic layer was sequentially washed with water and brine, and then dried over magnesium sulfate. After the drying agent was filtered off, the filtrate was concentrated, and the residue was purified by silica gel column chromatography (n-hexane only to n-hexane:ethyl acetate=1:4), and then dried under reduced pressure to give 5-[[4-[(4-methoxyphenyl)methoxy]-3-methylsulfonylphenyl]methoxy]-2-[2-(2-oxanyl)-3-pyrazolyl]pyridine (148 mg) as a colorless powder.

(3) The compound (164 mg) obtained in (2) above was used to perform the synthesis process according to the method described in Example 1-1-(3) thereby giving 5-[[4-[(4-methoxyphenyl)methoxy]-3-methylsulfonylphenyl]methoxy]-2-(1-H-pyrazol-5-yl)pyridine (58.4 mg) as a colorless powder.

(4) The compound (58.4 mg) obtained in (3) above was used to perform the synthesis process according to the method described in Example 2-1-(3) thereby giving the title compound (7.52 mg) as a colorless amorphous substance.

$^1$H NMR (400 MHz, DMSO-$d_6$) δ ppm 3.25 (s, 3H) 5.14-5.22 (m, 2H) 6.71-6.75 (m, 1H) 7.04-7.09 (m, 1H) 7.47-7.89 (m, 5H) 8.31-8.37 (m, 1H) 10.75-11.56 (m, 1H) 12.79-13.52 (m, 1H).

MS ESI/APCI Multi posi: 346[M+H]$^+$.

The compound of Example 20-2 below was synthesized using the compound obtained in Reference Example 55-1, according to the method described in Example 20-1. The structure, NMR data, and MS data of the compound are shown in Table 42-1.

TABLE 42-1

| Example No. | Structure | Analytical Data |
|---|---|---|
| 20-2 | 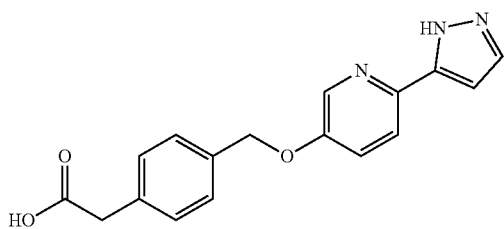 | $^1$H NMR (400 MHz, DMSO-$d_6$) δ ppm 3.19 (s, 3 H) 5.26 (s, 2 H) 6.74 (s, 1 H) 7.19 (s, 1 H) 7.24 (s, 1 H) 7.42-7.63 (m, 2 H) 7.70-7.98 (m, 2 H) 8.30-8.43 (m, 1 H) 10.35 (br s, 1 H). MS ESI/APCI Multi posi: 346 [M + H]$^+$. MS ESI/APCI Multi nega: 344 [M − H]$^-$. |

Example 21-1

2-[4-[[6-(1H-Pyrazol-5-yl)-3-pyridinyl]oxymethyl]phenyl]acetic Acid

[Formula 524]

(1) Potassium carbonate (34 mg) was added to a solution of the compound (50 mg) obtained in Reference Example 1-1 in N,N-dimethylformamide (2.0 mL) under ice cooling, the mixture was stirred at room temperature for 10 minutes, methyl 2-[4-(bromomethyl)phenyl]acetate (52 mg) was then added thereto, and the resultant mixture was stirred at room temperature for 1.5 hours. A saturated aqueous solution of ammonium chloride was added under ice cooling to stop the reaction, and the reaction mixture was extracted three times with ethyl acetate (5.0 mL). The obtained organic layers were combined, and the resultant was dehydrated by passing through a phase separator, and concentrated under reduced pressure. The obtained residue was purified by silica gel column chromatography (n-hexane:ethyl acetate=1:1 to ethyl acetate:methanol=10:1) to give methyl 2-[4-[[6-[2-(2-oxanyl)-3-pyrazolyl]-3-pyridinyl]oxymethyl]phenyl]acetate (94 mg) as a colorless oil.

(2) An aqueous solution of 1 mol/L sodium hydroxide (0.30 mL) was added to a solution of the compound (94 mg) obtained in (1) above in methanol (1.0 mL) and tetrahydrofuran (1.0 mL), and the mixture was stirred at an outer temperature of 60° C. for 2 hours to give a solution containing 2-[4-[[6-[2-(2-oxanyl)-3-pyrazolyl]-3-pyridinyl]oxymethyl]phenyl] acetic acid.

(3) The solution obtained in (2) above was used to perform the synthesis process according to the method described in Example 1-43-(3) thereby giving the title compound (13 mg) as a colorless powder.

$^1$H NMR (400 MHz, DMSO-$d_6$) δ ppm 3.58 (s, 2H) 5.19 (s, 2H) 6.72 (d, J=2.2 Hz, 1H) 7.29 (d, J=8.1 Hz, 2H) 7.42 (d, J=8.1 Hz, 2H) 7.52 (dd, J=8.7, 2.9 Hz, 1H) 7.60-7.74 (m, 1H) 7.85 (d, J=8.7 Hz, 1H) 8.34 (d, J=2.9 Hz, 1H).

MS ESI/APCI Multi posi: 310[M+H]$^+$.

The compound of Example 21-2 below was synthesized using a commercially available compound, according to the method described in Example 21-1. The structure, NMR data, and MS data of the compound are shown in Table 43-1.

TABLE 43-1

| Example No. | Structure | Analytical Data |
|---|---|---|
| 21-2 | 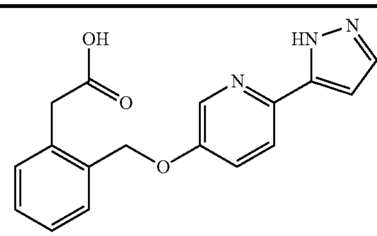 | $^1$H NMR (400 MHz, DMSO-$d_6$) δ ppm 3.72 (s, 2 H) 5.23 (s, 2 H) 6.73 (d, J = 2.1 Hz, 1 H) 7.27-7.35 (m, 3 H) 7.47 (d, J = 6.7 Hz, 1 H) 7.49-7.54 (m, 1 H) 7.54-7.76 (m, 1 H) 7.82-7.88 (m, 1 H) 8.31-8.35 (m, 1 H). MS ESI/APCI Multi posi: 310[M + H]$^+$. MS ESI/APCI Multi nega: 308[M − H]$^-$. |

The compounds of Examples 21-3 to 21-5 below were synthesized using a compound obtained in Reference Example 12-1, 17-1, or 18-1, according to the methods described in Example 21-1-(1) and (2), and then by performing the reaction described in Example 21-1-(3) under ice cooling. The structures, NMR data, and MS data of the compounds are shown in Table 43-2.

TABLE 43-2

| Example No. | Structure | Analytical Data |
|---|---|---|
| 21-3 | 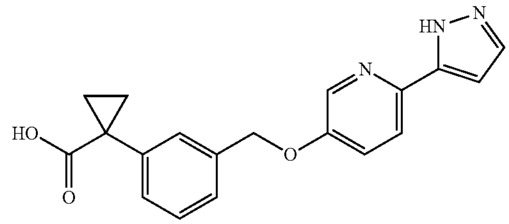 [SMILES: O=C(O)C1(c2cccc(COc3ccc(-c4ccn[nH]4)nc3)c2)CC1] | ¹H NMR (400 MHz, DMSO-d₆) δ ppm 1.12-1.17 (m, 2 H) 1.43-1.48 (m, 2 H) 5.21 (s, 2 H) 6.80 (s, 1 H) 7.29-7.37 (m, 3 H) 7.45 (s, 1 H) 7.59-7.68 (m, 1 H) 7.69-7.76 (m, 1 H) 7.90-7.98 (m, 1 H) 8.38 (d, J = 2.6 Hz, 1 H). MS ESI/APCI Multi posi: 336[M + H]⁺. MS ESI/APCI Multi nega: 334[M – H]⁻. |
| 21-4 | 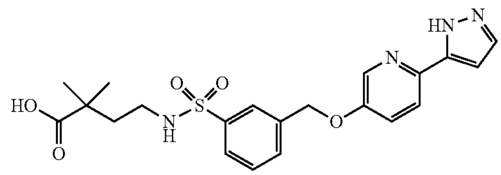 [SMILES: CC(C)(CCNS(=O)(=O)c1cccc(COc2ccc(-c3ccn[nH]3)nc2)c1)C(=O)O] | ¹H NMR (400 MHz, DMSO-d₆) δ ppm 1.00 (s, 6 H) 1.51-1.61 (m, 2 H) 2.69-2.83 (m, 2 H) 5.33 (s, 2 H) 6.69-6.77 (m, 1 H) 7.49-7.58 (m, 1 H) 7.61-7.79 (m, 5 H) 7.84-7.94 (m, 2 H) 8.37 (d, J = 2.7 Hz, 1 H). MS ESI/APCI Multi posi: 445[M + H]⁺. MS ESI/APCI Multi nega: 443[M – H]⁻. |
| 21-5 | 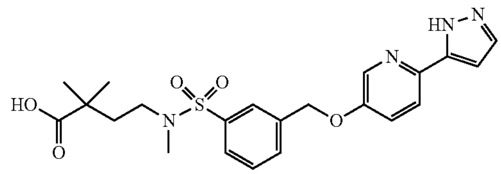 [SMILES: CN(CCC(C)(C)C(=O)O)S(=O)(=O)c1cccc(COc2ccc(-c3ccn[nH]3)nc2)c1] | ¹H NMR (400 MHz, DMSO-d₆) δ ppm 1.07 (s, 6 H) 1.55-1.70 (m, 2 H) 2.61-2.64 (m, 3 H) 2.88-3.03 (m, 2 H) 5.36 (s, 2 H) 6.72 (s, 1 H) 7.51-7.56 (m, 1 H) 7.63-7.75 (m, 3 H) 7.77-7.82 (m, 1 H) 7.84-7.95 (m, 2 H) 8.45-8.48 (m, 1 H). MS ESI/APCI Multi posi: 459[M + H]⁺. MS ESI/APCI Multi nega: 457[M – H]⁻. |

Example 22-1

(2E)-3-[3-[[[6-(1H-Pyrazol-5-yl)pyridin-3-yl]oxy]methyl]phenyl]-2-propenoic Acid

[Formula 525]

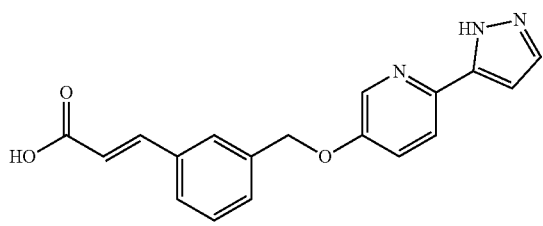

(1) Potassium carbonate (1.47 g) and the compound (1.96 g) obtained in Reference Example 42-1 were added to a solution of the compound (1.30 g) obtained in Reference Example 1-1 in N,N-dimethylformamide (15 mL), and the mixture was stirred at room temperature for 20 hours. Water was added to the reaction mixture, and the resultant mixture was extracted with ethyl acetate. The organic layer was dried over anhydrous sodium sulfate, and the drying agent was filtered off. The filtrate was concentrated under reduced pressure, and the obtained residue was purified by silica gel column chromatography (n-hexane:ethyl acetate=9:1 to 1:1) to give ethyl (E)-3-[3-[[6-[2-(2-oxanyl)-3-pyrazolyl]-3-pyridinyl]oxymethyl]phenyl]-2-propenoate (2.23 g) as a pale yellow oil.

(2) Water (3 mL) and trifluoroacetic acid (2 mL) were added to a solution of the compound (552 mg) obtained in (1) above in ethanol (6 mL), and the mixture was stirred at room temperature for 20 hours. A saturated aqueous solution of sodium hydrogen carbonate was added to the reaction solution, the resultant mixture was extract with chloroform, the organic layer was passed through a phase separator, and the solvent was distilled off under reduced pressure. The obtained residue was purified by silica gel column chromatography (chloroform only to chloroform:methanol=19:1) to give ethyl (E)-3-[3-[[6-(1H-pyrazol-5-yl)-3-pyridinyl]oxymethyl]phenyl]-2-propenoate (423 mg) as a pale yellow oil.

(3) An aqueous solution of 1 mol/L sodium hydroxide (5 mL) was added to a solution of the compound (423 mg) obtained in (2) above in tetrahydrofuran (5 mL) and methanol (5 mL), and the mixture was stirred at room temperature for 20 hours. An aqueous solution of 1 mol/L potassium hydrogen sulfate and water were added to the reaction solution, the resultant mixture was stirred, and the precipitated solid was then collected by filtration to give the title compound (323 mg) as a colorless powder.

¹H NMR (600 MHz, DMSO-d₆) δ ppm 5.24 (s, 2H) 6.56 (d, J=15.9 Hz, 1H) 6.72-6.74 (m, 1H) 7.44-7.49 (m, 1H) 7.51-7.56 (m, 2H) 7.61 (d, J=15.9 Hz, 1H) 7.64-7.71 (m, 2H) 7.81 (s, 1H) 7.84-7.89 (m, 1H) 8.36-8.38 (m, 1H).
MS ESI/APCI Multi posi: 322[M+H]⁺.
MS ESI/APCI Multi nega: 320[M–H]⁻.

The compounds of Examples 22-2 to 22-4 below were synthesized using a compound obtained in Reference Example 11-1 or 43-1, or a commercially available compound, according to the method described in Example 22-1. The structures, NMR data, and MS data of the compounds are shown in Table 44-1.

TABLE 44-1

| Example No. | Structure | Analytical Data |
|---|---|---|
| 22-2 | 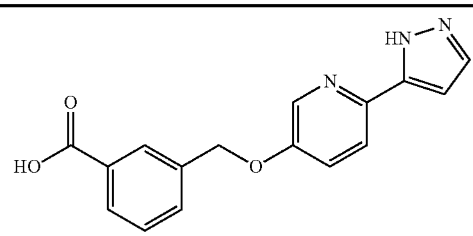 | $^1$H NMR (300 MHz, DMSO-d$_6$) δ ppm 5.30 (s, 2 H) 6.73 (d, J = 2.2 Hz, 1 H) 7.51-7.57 (m, 2 H) 7.65-7.75 (m, 2 H) 7.84-7.95 (m, 2 H) 8.05-8.07 (m, 1 H) 8.37 (d, J = 3.0 Hz, 1 H). MS ESI/APCI Multi posi: 296[M + H]$^+$. MS ESI/APCI Multi nega: 294[M − H]$^−$. |
| 22-3 | 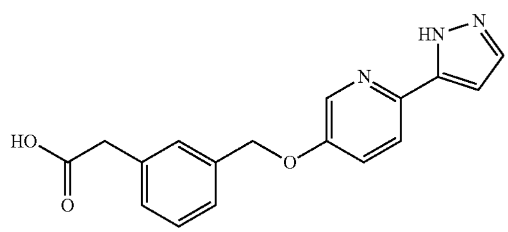 [SMILES: O=C(O)Cc1cccc(COc2ccc(-c3ccn[nH]3)nc2)c1] | $^1$H NMR NMR (600 MHz, DMSO-d$_6$) δ ppm 3.60 (s, 2 H) 5.20 (s, 2 H) 6.73 (d, J = 2.5 Hz, 1 H) 7.22-7.27 (m, 1 H) 7.33-7.40 (m, 3 H) 7.53 (dd, J = 8.7, 2.9 Hz, 1 H) 7.62-7.74 (m, 1 H) 7.86 (d, J = 8.7 Hz, 1 H) 8.35 (d, J = 2.9 Hz, 1 H). MS ESI/APCI Multi posi: 310[M + H]$^+$. MS ESI/APCI Multi nega: 308[M − H]$^−$. |
| 22-4 | 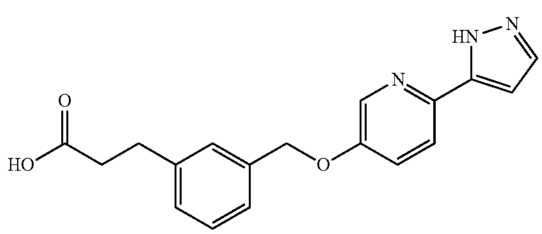 [SMILES: O=C(O)CCc1cccc(COc2ccc(-c3ccn[nH]3)nc2)c1] | $^1$H NMR (600 MHz, DMSO-d$_6$) δ ppm 2.55 (t, J = 7.6 Hz, 2 H) 2.85 (t, J = 7.6 Hz, 2 H) 5.17 (s, 2 H) 6.72-6.74 (m, 1 H) 7.20-7.24 (m, 1 H) 7.27-7.37 (m, 3 H) 7.48-7.57 (m, 1 H) 7.61-7.75 (m, 1 H) 7.80-7.91 (m, 1 H) 8.33-8.37 (m, 1 H). MS ESI/APCI Multi posi: 324[M + H]$^+$. MS ESI/APCI Multi nega: 322[M − H]$^−$. |

Example 22-5

2-[3-[[6-(1H-Pyrazol-5-yl)-3-pyridinyl]oxymethyl]phenyl]-5-pyrimidinecarboxylic Acid

[Formula 526]

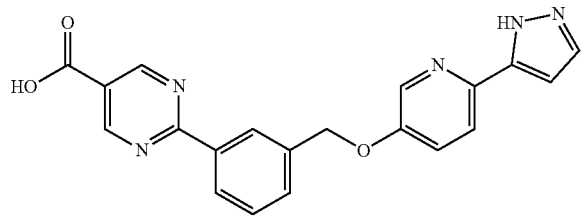

(1) The compound (70 mg) obtained in Reference Example 1-1 and the compound (85 mg) obtained in Reference Example 13-1 were used to perform the synthesis process according to the method described in Example 18-1-(2) thereby giving methyl 2-[3-[[6-[2-(2-oxanyl)-3-pyrazolyl]-3-pyridinyl]oxymethyl]phenyl]-5-pyrimidinecarboxylate (65 mg) as a colorless oil.

(2) The compound (65 mg) obtained in (1) above was used to perform the synthesis process according to the method described in Example 12-1-(3) thereby giving a solution containing methyl 2-[3-[[6-(1H-pyrazol-5-yl)-3-pyridinyl]oxymethyl]phenyl]-5-pyrimidinecarboxylate.

(3) The solution obtained in (2) above was used to perform the synthesis process according to the method described in Example 1-1-(2) thereby giving the title compound (26 mg) as a colorless solid.

$^1$H NMR (400 MHz, DMSO-d$_6$) δ ppm 5.36 (s, 2H) 6.73 (d, J=2.0 Hz, 1H) 7.51-7.77 (m, 4H) 7.87 (d, J=8.8 Hz, 1H) 7.93 (d, J=4.9 Hz, 1H) 8.40 (d, J=2.9 Hz, 1H) 8.45 (d, J=7.7 Hz, 1H) 8.58 (s, 1H) 9.16 (d, J=4.9 Hz, 1H) 13.16-14.01 (m, 1H).

MS ESI posi: 374[M+H]$^+$.
MS ESI nega: 372[M−H]$^−$.

The compounds of Examples 22-6 to 22-12 below were synthesized using any of the compounds obtained in Reference Examples 13-2 and 13-3, and 17-2 to 17-6, according to the method described in Example 22-5. The structures, NMR data, and MS data of the compounds are shown in Tables 44-2 and 44-3.

TABLE 44-2

| Example No. | Structure | Analytical Data |
|---|---|---|
| 22-6 | 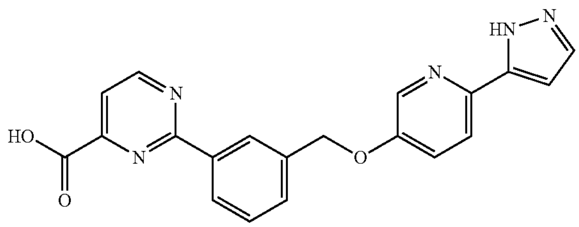 [SMILES: O=C(O)c1ccnc(-c2cccc(COc3ccc(-c4ccn[nH]4)nc3)c2)n1] | $^1$H NMR (400 MHz, DMSO-d$_6$) δ ppm 5.36 (s, 2 H) 6.73 (d, J = 2.1 Hz, 1 H) 7.52-7.75 (m, 4 H) 7.83-7.97 (m, 2 H) 8.40 (d, J = 2.7 Hz, 1 H) 8.44 (d, J = 7.6 Hz, 1 H) 8.57 (s, 1 H) 9.12-9.19 (m, 1 H).<br>MS ESI posi: 374[M + H]$^+$.<br>MS ESI nega: 372[M − H]$^-$. |
| 22-7 | 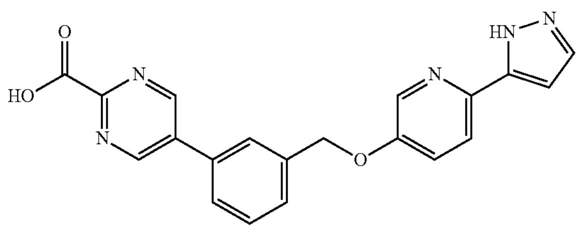 [SMILES: O=C(O)c1ncc(-c2cccc(COc3ccc(-c4ccn[nH]4)nc3)c2)cn1] | $^1$H NMR (400 MHz, DMSO-d$_6$) δ ppm 5.32 (s, 2 H) 6.73 (d, J = 2.1 Hz, 1 H) 7.49-7.79 (m, 4H) 7.82-7.95 (m, 2 H) 7.99-8.08 (m, 1 H) 8.40 (d, J = 2.7 Hz, 1 H) 9.31 (s, 2 H).<br>MS ESI posi: 374[M + H]$^+$.<br>MS ESI nega: 372[M − H]$^-$. |
| 22-8 | 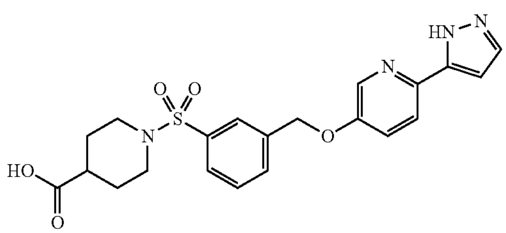 [SMILES: O=C(O)C1CCN(S(=O)(=O)c2cccc(COc3ccc(-c4ccn[nH]4)nc3)c2)CC1] | $^1$H NMR (400 MHz, DMSO-d$_6$) δ ppm 1.46-1.61 (m, 2 H) 1.78-1.92 (m, 2 H) 2.16-2.28 (m, 1 H) 2.30-2.42 (m, 3 H) 3.41-3.52 (m, 1 H) 5.36 (s, 2 H) 6.73 (s, 1 H) 7.52-7.76 (m, 4 H) 7.76-7.92 (m, 3 H) 8.33-8.41 (m, 1 H).<br>MS ESI posi: 443[M + H]$^+$.<br>MS ESI nega: 441[M − H]$^-$. |
| 22-9 | 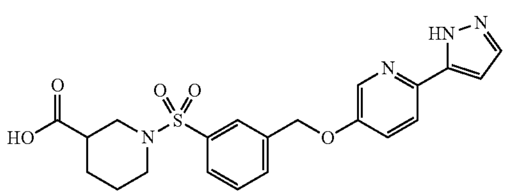 [SMILES: O=C(O)C1CCCN(S(=O)(=O)c2cccc(COc3ccc(-c4ccn[nH]4)nc3)c2)C1] | $^1$H NMR (400 MHz, DMSO-d$_6$) δ ppm 1.23-1.53 (m, 3 H) 1.59-1.79 (m, 3 H) 2.29-2.41 (m, 2 H) 3.45-3.53 (m, 1 H) 5.38 (s, 2 H) 6.73 (s, 1 H) 7.50-7.57 (m, 1 H) 7.64-7.75 (m, 3 H) 7.79-7.90 (m, 3 H) 8.34-8.40 (m, 1 H).<br>MS ESI posi: 443[M + H]$^+$.<br>MS ESI nega: 441[M − H]$^-$. |
| 22-10 | 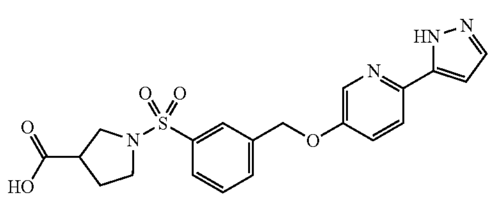 [SMILES: O=C(O)C1CCN(S(=O)(=O)c2cccc(COc3ccc(-c4ccn[nH]4)nc3)c2)C1] | $^1$H NMR (600 MHz, DMSO-d$_6$) δ ppm 1.78-1.94 (m, 2 H) 2.88-2.94 (m, 1 H) 3.10-3.23 (m, 2 H) 3.33-3.38 (m, 2 H) 5.36 (s, 2 H) 6.71-6.74 (m, 1 H) 7.51-7.56 (m, 1 H) 7.66-7.71 (m, 2 H) 7.76-7.92 (m, 4 H) 8.36-8.39 (m, 1 H).<br>MS ESI posi: 429[M + H]$^+$.<br>MS ESI nega: 427[M − H]$^-$. |
| 22-11 | 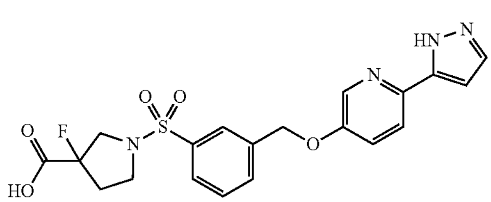 | $^1$H NMR (600 MHz, DMSO-d$_6$) δ ppm 2.13-2.27 (m, 2 H) 3.20-3.27 (m, 1 H) 3.47-3.53 (m, 1 H) 3.57-3.69 (m, 2 H) 5.36 (s, 2 H) 6.73 (d, J = 2.1 Hz, 1 H) 7.54 (dd, J = 9.1, 2.9 Hz, 1 H) 7.66-7.72 (m, 2 H) 7.80-7.88 (m, 3 H) 7.94-7.96 (m, 1 H) 8.38 (d, J = 2.9 Hz, 1 H).<br>MS ESI posi: 447[M + H]$^+$.<br>MS ESI nega: 445[M − H]$^-$. |

TABLE 44-3

| Example No. | Structure | Analytical Data |
|---|---|---|
| 22-12 | 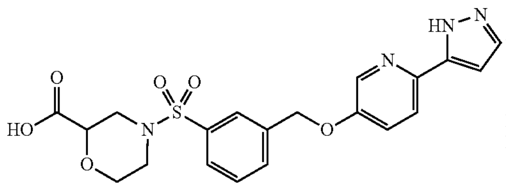 [SMILES: O=C(O)C1CN(S(=O)(=O)c2cccc(COc3ccc(-c4ccn[nH]4)nc3)c2)CCO1] | ¹H NMR (400 MHz, DMSO-d₆) δ ppm 2.70-2.79 (m, 1 H) 3.04-3.12 (m, 1 H) 3.32-3.42 (m, 2 H) 3.54-3.63 (m, 1 H) 3.90 (m, 1 H) 4.14-4.28 (m, 1 H) 5.38 (s, 2 H) 6.69-6.77 (m, 1 H) 7.52-7.77 (m, 4 H) 7.83-7.98 (m, 3 H) 8.34-8.42 (m, 1 H) 12.95-13.21 (m, 1 H).<br>MS ESI posi: 445[M + H]⁺.<br>MS ESI nega: 443[M − H]⁻. |

Example 22-13

2-Methyl-2-[[4-[[6-(1H-pyrazol-5-yl)-3-pyridinyl]oxymethyl]-2-pyridinyl]oxy]propanoic Acid

[Formula 527]

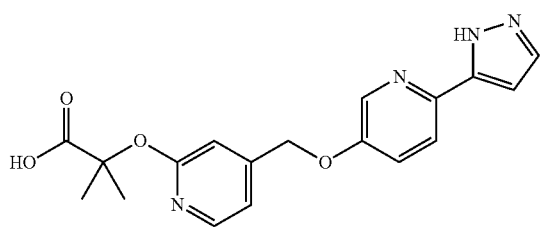

(1) The compound (240 mg) obtained in Reference Example 1-1 and the compound (395 mg) obtained in Reference Example 14-1 were used to perform the synthesis process according to the method described in Example 18-1-(2) thereby giving a mixture (502 mg) containing ethyl 2-methyl-2-[[4-[[6-[2-(2-oxanyl)-3-pyrazolyl]-3-pyridinyl]oxymethyl]-2-pyridinyl]oxy]propanoate as a pale yellow oil.

(2) The compound (502 mg) obtained in (1) above was used to perform the synthesis process according to the method described in Example 12-1-(3) thereby giving a solution containing ethyl 2-methyl-2-[[4-[[6-(1H-pyrazol-5-yl)-3-pyridinyl]oxymethyl]-2-pyridinyl] oxy]propanoate.

(3) The solution obtained in (2) above was used to perform the synthesis process according to the method described in Example 1-1-(2) thereby giving the title compound (315 mg) as a colorless powder.

¹H NMR (400 MHz, DMSO-d₆) δ ppm 1.58 (s, 6H) 5.24 (s, 2H) 6.71-6.76 (m, 1H) 6.85 (s, 1H) 6.98-7.03 (m, 1H) 7.49-7.55 (m, 1H) 7.64-7.72 (m, 1H) 7.84-7.90 (m, 1H) 8.06 (d, J=5.3 Hz, 1H) 8.37 (d, J=2.6 Hz, 1H).
MS ESI posi: 355[M+H]⁺.
MS ESI nega: 353[M−H]⁻.

The compounds of Examples 22-14 to 22-16 below were synthesized using a compound obtained in Reference Example 11-2, 11-3, or 14-2, according to the method described in Example 22-13. The structures, NMR data, and MS data of the compounds are shown in Table 44-4.

TABLE 44-4

| Example No. | Structure | Analytical Data |
|---|---|---|
| 22-14 | 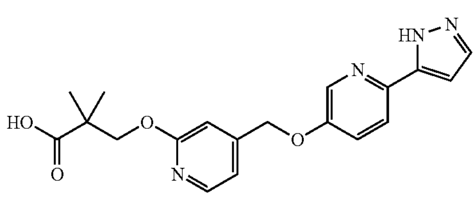 [SMILES: CC(C)(COc1cc(COc2ccc(-c3ccn[nH]3)nc2)ccn1)C(=O)O] | ¹H NMR (400 MHz, DMSO-d₆) δ ppm 1.21 (s, 6 H) 4.25 (s, 2 H) 5.25 (s, 2 H) 6.73 (d, J = 1.8 Hz, 1 H) 6.87 (s, 1 H) 7.01-7.08 (m, 1 H) 7.52 (dd, J = 8.7, 2.8 Hz, 1 H) 7.63-7.72 (m, 1 H) 7.83-7.90 (m, 1 H) 8.15 (d, J = 5.3 Hz, 1 H) 8.37 (d, J = 2.8 Hz, 1 H).<br>MS ESI posi: 369[M + H]⁺.<br>MS ESI nega: 367[M − H]⁻. |
| 22-15 | 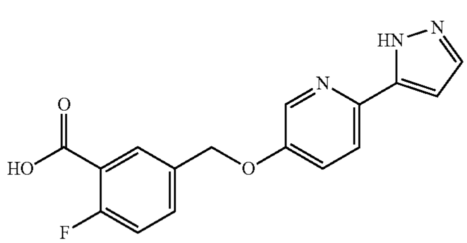 [SMILES: O=C(O)c1cc(COc2ccc(-c3ccn[nH]3)nc2)ccc1F] | ¹H NMR (400 MHz, DMSO-d₆) δ ppm 5.26 (s, 2 H) 6.71-6.80 (m, 1 H) 7.30-7.40 (m, 1 H) 7.52-7.61 (m, 1 H) 7.65-7.81 (m, 2 H) 7.86-7.93 (m, 1 H) 7.95-8.02 (m, 1 H) 8.33-8.41 (m, 1 H).<br>MS ESI/APCI Multi posi: 314[M + H]⁺.<br>MS ESI/APCI Multi nega: 312[M − H]⁻. |

TABLE 44-4-continued

| Example No. | Structure | Analytical Data |
|---|---|---|
| 22-16 | 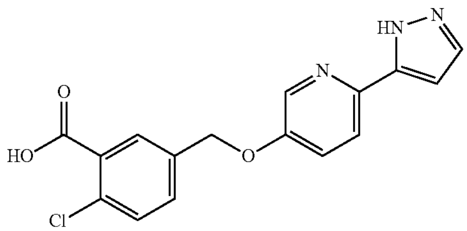 [SMILES: O=C(O)c1cc(COc2ccc(-c3ccn[nH]3)nc2)ccc1Cl] | $^1$H NMR (400 MHz, DMSO-d$_6$) δ ppm 5.29 (s, 2 H) 6.75-6.83 (m, 1 H) 7.53-7.68 (m, 3 H) 7.71-7.76 (m, 1 H) 7.87-7.99 (m, 2 H) 8.35-8.42 (m, 1 H).<br>MS ESI/APCI Multi posi: 330[M + H]$^+$.<br>MS ESI/APCI Multi nega: 328[M − H]$^−$. |

Example 22-17

2-Methoxy-4-[[6-(1H-pyrazol-5-yl)-3-pyridinyl]oxymethyl]benzoic Acid

[Formula 528]

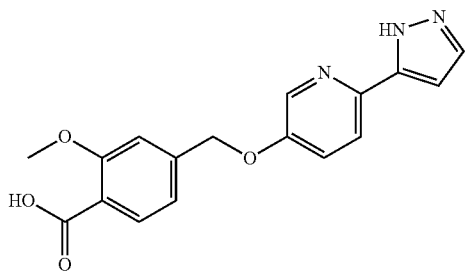

(1) The compound (50.0 mg) obtained in Reference Example 1-1 and methyl 4-(bromomethyl)-2-methoxybenzoate (64.0 mg) were used to perform the synthesis process according to the method described in Example 18-1-(2) thereby giving methyl 2-methoxy-4-[[6-[2-(2-oxanyl)-3-pyrazolyl]-3-pyridinyl]oxymethyl]benzoate (79.8 mg) as a pale yellow gum-like substance.

(2) The compound (79.8 mg) obtained in (1) above was used to perform the synthesis process according to the method described in Example 11-1-(2) thereby giving a mixture (55.8 mg) containing methyl 2-methoxy-4-[[6-(1H-pyrazol-5-yl)-3-pyridinyl]oxymethyl]benzoate hydrochloride.

(3) The mixture (55.8 mg) obtained in (2) above was used to perform the synthesis process according to the method described in Example 1-1-(2) thereby giving the title compound (44.2 mg) as a colorless solid.

$^1$H NMR (400 MHz, DMSO-d$_6$) δ ppm 3.84 (s, 3H) 5.30 (s, 2H) 6.83 (d, J=2.1 Hz, 1H) 7.10 (d, J=7.9 Hz, 1H) 7.25 (s, 1H) 7.63-7.79 (m, 3H) 7.98 (d, J=8.8 Hz, 1H) 8.40 (d, J=2.8 Hz, 1H).

MS ESI/APCI Multi posi: 326[M+H]$^+$.

MS ESI/APCI Multi nega: 324[M−H]$^−$.

The compound of Example 22-18 below was synthesized using a commercially available compound, according to the method described in Example 22-17. The structure, NMR data, and MS data of the compound are shown in Table 44-5.

TABLE 44-5

| Example No. | Structure | Analytical Data |
|---|---|---|
| 22-18 | 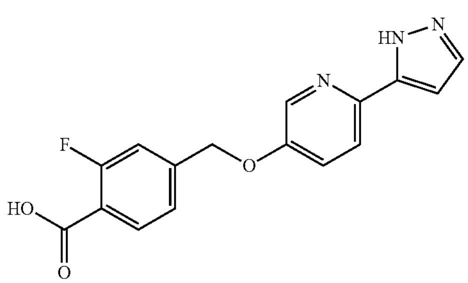 [SMILES: O=C(O)c1ccc(COc2ccc(-c3ccn[nH]3)nc2)cc1F] | $^1$H NMR (400 MHz, DMSO-d$_6$) δ ppm 5.33 (s, 2 H) 6.78 (d, J = 2.0 Hz, 1 H) 7.37-7.47 (m, 2 H) 7.61 (dd, J = 8.8, 2.8 Hz, 1 H) 7.72 (d, J = 1.7 Hz, 1 H) 7.87-7.97 (m, 2 H) 8.39 (d, J = 2.8 Hz, 1 H).<br>MS ESI/APCI Multi posi: 314[M + H]$^+$. |

Example 22-19

2-[3-[2-[[6-(1H-Pyrazol-5-yl)-3-pyridinyl]oxy]ethoxy]phenyl] acetic Acid

[Formula 529]

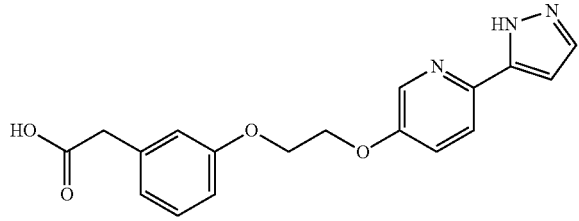

(1) Cesium carbonate (534 mg) was added to a solution of the compound (282 mg) obtained in Reference Example 1-1 and the compound (457 mg) obtained in Reference Example 19-1 in N,N-dimethylformamide (3.64 mL), and the mixture was stirred at an outer temperature of 100° C. for 1.5 hours. After cooling to room temperature, the mixture was diluted with ethyl acetate, and sequentially washed with water and brine. The organic layer was separated by a phase separator, and concentrated under reduced pressure. The obtained residue was purified by silica gel column chromatography (n-hexane:ethyl acetate=19:1 to 2:3) to give methyl 2-[3-[2-[[6-[2-(2-oxanyl)-3-pyrazolyl]-3-pyridinyl]oxy]ethoxy]phenyl]acetate (541 mg) as a pale yellow oil.

(2) The compound (149 mg) obtained in (1) above was used to perform the synthesis process according to the method described in Example 1-65-(2) thereby giving a solution containing methyl 2-[3-[2-[[6-(1H-pyrazol-5-yl)-3-pyridinyl]oxy]ethoxy]phenyl]acetate.

(3) The solution obtained in (2) above was used to perform the synthesis process according to the method described in Example 9-1-(3) thereby giving the title compound (50.2 mg) as a colorless solid.

$^1$H NMR (400 MHz, DMSO-$d_6$) δ ppm 3.52 (s, 2H) 4.27-4.52 (m, 4H) 6.74 (d, J=2.1 Hz, 1H) 6.82-6.93 (m, 3H) 7.17-7.28 (m, 1H) 7.51 (dd, J=8.8, 2.8 Hz, 1H) 7.60-7.78 (m, 1H) 7.87 (d, J=8.8 Hz, 1H) 8.34 (d, J=2.8 Hz, 1H) 12.68 (br s, 1H).

MS ESI/APCI Multi posi: 340[M+H]$^+$.

Example 22-20

7-[[6-(1H-Pyrazol-5-yl)-3-pyridinyl]oxy]heptanoic Acid

[Formula 530]

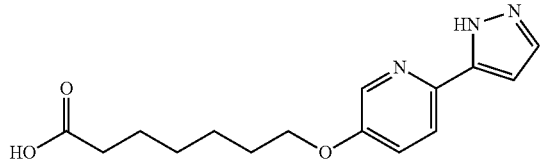

(1) The compound (50 mg) obtained in Reference Example 1-1 and ethyl 7-bromoheptanoate (52 μL) were used to perform the synthesis process according to the method described in Example 19-1-(2) thereby giving ethyl 7-[[6-[2-(2-oxanyl)-3-pyrazolyl]-3-pyridinyl]oxy]heptanoate (84 mg) as a colorless oil.

(2) The compound (84 mg) obtained in (1) above was used to perform the synthesis process according to the method described in Example 1-43-(3) thereby giving a crude product (54 mg) containing ethyl 7-[[6-(1H-pyrazol-5-yl)-3-pyridinyl]oxy]heptanoate as a colorless powder.

(3) The compound (54 mg) obtained in (2) above was used to perform the synthesis process according to the method described in Example 1-47-(3) thereby giving the title compound (18 mg) as a colorless powder.

$^1$H NMR (400 MHz, DMSO-$d_6$) δ ppm 1.27-1.61 (m, 6H) 1.67-1.81 (m, 2H) 2.20 (t, J=7.3 Hz, 2H) 4.06 (t, J=6.5 Hz, 2H) 6.63-6.76 (m, 1H) 7.36-7.48 (m, 1H) 7.58-7.73 (m, 1H) 7.77-7.90 (m, 1H) 8.23-8.33 (m, 1H).

MS ESI/APCI Multi posi: 290[M+H]$^+$.

Example 23-1

N-Methyl-3-[[6-(1-H-pyrazol-5-yl)-3-pyridinyl]oxymethyl]benzenesulfonamide

[Formula 531]

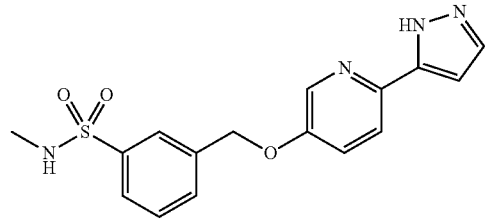

(1) Potassium carbonate (284 mg) and sodium iodide (18.6 mg) were added to a solution of the compound (254 mg) obtained in Reference Example 1-1 and the compound (273 mg) obtained in Reference Example 26-1 in N,N-dimethylformamide (4 mL), and the mixture was stirred at 50° C. for 2 hours. Potassium carbonate (142 mg) was further added thereto, and the resultant mixture was stirred at 50° C. for 6 hours. Water was added to the reaction mixture, and the resultant mixture was extracted with ethyl acetate. The organic layer was washed with brine, and then dried over anhydrous magnesium sulfate. The drying agent was filtered off, and the filtrate was concentrated under reduced pressure. The obtained residue was purified by silica gel column chromatography (chloroform only to chloroform:methanol=13:1) to give N-methyl-3-[[[6-[1-(oxan-2-yl)-1H-pyrazol-5-yl]pyridin-3-yl]oxy]methyl]benzene-1-sulfonamide (193 mg) as a colorless oil. In addition, N-methyl-N-[[3-(methylsulfamoyl)phenyl]methyl]-3-[[[6-[1-(oxan-2-yl)-1H-pyrazol-5-yl]pyridin-3-yl]oxy]methyl]benzene-1-sulfonamide (115 mg), a compound which had undergone two stages of benzylation, was obtained as a colorless oil.

(2) N-Methyl-3-[[[6-[1-(oxan-2-yl)-1H-pyrazol-5-yl]pyridin-3-yl]oxy]methyl]benzene-1-sulfonamide (45.0 mg) obtained in (1) above was used to perform the synthesis process according to the method described in Example 10-1-(2) thereby giving the title compound as a colorless powder (25.4 mg).

$^1$H NMR (300 MHz, DMSO-$d_6$) δ ppm 2.42 (s, 3H) 5.34 (s, 2H) 6.74 (d, J=2.0 Hz, 1H) 7.24-8.12 (m, 7H) 8.38 (d, J=2.5 Hz, 1H) 12.86 (br s, 1H).

MS ESI/APCI Multi posi: 345 [M+H]$^+$.

Example 23-2

N-Methyl-3-[[methyl-[3-[[6-(1-H-pyrazol-5-yl)-3-pyridinyl]oxymethyl]phenyl] sulfonylamino]methyl]benzenesulfonamide

[Formula 532]

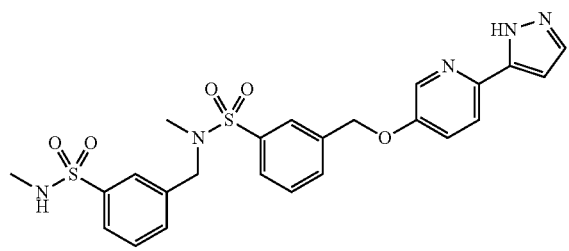

N-Methyl-N-[[3-(methylsulfamoyl)phenyl]methyl]-3-[[[6-[1-(oxan-2-yl)-1H-pyrazol-5-yl]pyridin-3-yl]oxy]methyl]benzene-1-sulfonamide (63.4 mg) obtained in Example 23-1-(1) was used to perform the synthesis process according to the method described in Example 10-1-(2) thereby giving the title compound (42.1 mg) as a colorless amorphous substance.

$^1$H NMR (300 MHz, CHLOROFORM-d) δ ppm 2.59 (s, 3H) 2.66 (d, J=5.2 Hz, 3H) 3.98-4.19 (m, 2H) 5.17 (d, J=5.2 Hz, 1H) 5.24-5.31 (m, 2H) 6.71 (d, J=2.0 Hz, 1H) 7.33 (br s, 1H) 7.47-7.83 (m, 9H) 7.86-7.91 (m, 1H) 8.34 (d, J=2.5 Hz, 1H).

MS ESI/APCI Multi posi: 528[M+H]$^+$.

The compounds of Examples 23-3 to 23-6 below were synthesized using a commercially available compound, according to the method described in Example 23-1. The structures and MS data of the compounds are shown in Table 45-1.

TABLE 45-1

| Example No. | Structure | Analytical Data |
|---|---|---|
| 23-3 | 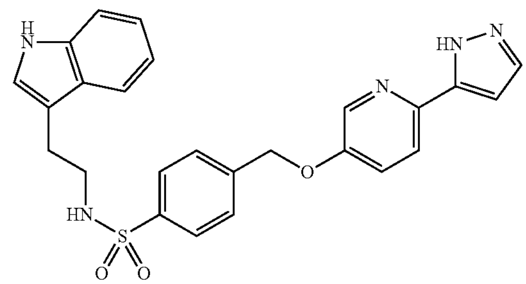 [SMILES: O=S(=O)(NCCc1c[nH]c2ccccc12)c1ccc(COc2ccc(-c3ccn[nH]3)nc2)cc1] | MS ESI posi: 474[M + H]$^+$. |
| 23-4 | 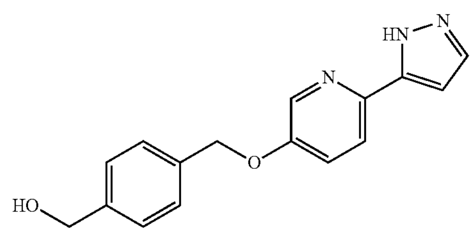 [SMILES: OCc1ccc(COc2ccc(-c3ccn[nH]3)nc2)cc1] | MS ESI posi: 282[M + H]$^+$. |
| 23-5 | 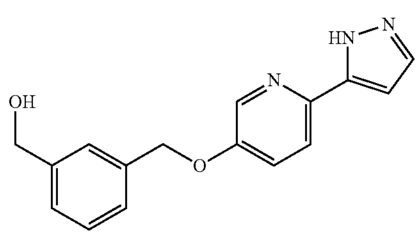 [SMILES: OCc1cccc(COc2ccc(-c3ccn[nH]3)nc2)c1] | MS ESI posi: 282[M + H]$^+$. |
| 23-6 | 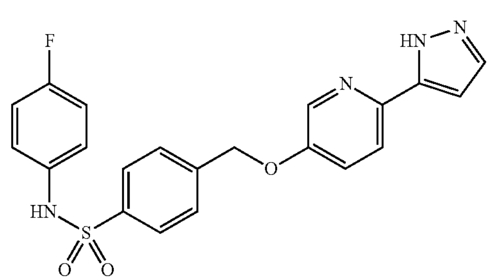 [SMILES: O=S(=O)(Nc1ccc(F)cc1)c1ccc(COc2ccc(-c3ccn[nH]3)nc2)cc1] | MS ESI posi: 425[M + H]$^+$. |

Example 24-1

Sodium 2-[3-[[6-(1H-pyrazol-5-yl)-3-pyridinyl]oxymethyl]phenyl]propanoate

[Formula 533]

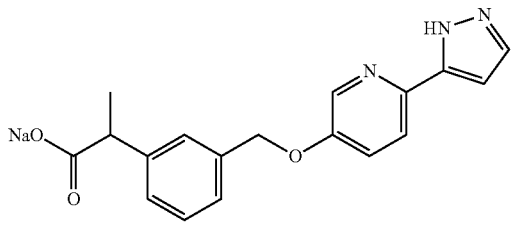

(1) The compound (500 mg) obtained in Reference Example 1-1 and methyl 2-[3-(bromomethyl)phenyl]acetate (568 mg) were used to perform the synthesis process according to the method described in Example 18-1-(2) thereby giving methyl 2-[3-[[6-[2-(2-oxanyl)-3-pyrazolyl]-3-pyridinyl]oxymethyl]phenyl]acetate (567 mg) as a yellow oil.

(2) Sodium hydride (60% mineral oil dispersion, 8.70 mg) was added to a solution of the compound (85.9 mg) obtained in (1) above in N,N-dimethylformamide (989 μL), and the mixture was stirred at room temperature for 5 minutes. To this mixture, methyl iodide (12.3 μL) was added, and the resultant mixture was further stirred for 5 hours. An aqueous solution of 10% ammonium chloride was added to stop the reaction, and the resultant mixture was extracted twice with ethyl acetate. The organic layers were combined, washed with brine, separated from the aqueous layer by a phase separator, and then concentrated under reduced pressure. The obtained residue was purified by silica gel column chromatography (n-hexane only to n-hexane:ethyl acetate=1:1) to give a mixture (67.1 mg) containing methyl 2-[3-[[6-[2-(2-oxanyl)-3-pyrazolyl]-3-pyridinyl]oxymethyl]phenyl]propanoate.

(3) The mixture (67.1 mg) obtained in (2) above was used to perform the synthesis process according to the method described in Example 11-1-(2) thereby giving a mixture (54.4 mg) containing methyl 2-[3-[[6-(1H-pyrazol-5-yl)-3-pyridinyl]oxymethyl]phenyl]propanoate.

(4) The mixture (54.4 mg) obtained in (3) above was used to perform the synthesis process according to the method described in Example 16-1-(4) thereby giving 2-[3-[[6-(1H-pyrazol-5-yl)-3-pyridinyl]oxymethyl]phenyl]propanoic acid (31.4 mg) as a colorless amorphous substance.

(5) An aqueous solution of 1 mol/L sodium hydroxide (109 μL) was added to a solution of the compound (31.4 mg) obtained in (4) above in acetone (1.09 mL), and the mixture was stirred at room temperature for 10 minutes, and then concentrated under reduced pressure. The residue was suspended in ethanol, and the suspension was heated to reflux for 1 hour. After cooling to room temperature, the precipitate was collected by filtration to give the title compound (22.6 mg) as a colorless solid.

$^1$H NMR (400 MHz, D$_2$O) δ ppm 1.41 (d, J=7.1 Hz, 3H) 3.61-3.73 (m, 1H) 5.08-5.33 (m, 2H) 6.71-6.88 (m, 1H) 7.28-7.63 (m, 5H) 7.69-7.90 (m, 2H) 8.20-8.38 (m, 1H).

MS ESI/APCI Multi posi: 324[M+H]$^+$.

MS ESI/APCI Multi nega: 322[M−H]$^−$.

Example 24-2

Sodium 2-methyl-2-[3-[[6-(1H-pyrazol-5-yl)-3-pyridinyl]oxymethyl]phenyl]propanoate

[Formula 534]

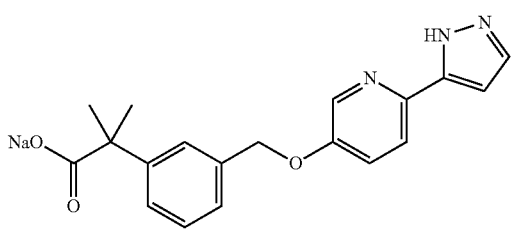

(1) Sodium hydride (60% mineral oil dispersion, 19.9 mg) was added to a solution of the compound (83.2 mg) obtained in Example 24-1-(1) in N,N-dimethylformamide (958 μL), and the mixture was stirred at room temperature for 5 minutes. Methyl iodide (26.2 μL) was added thereto, and the resultant mixture was further stirred for 5 hours. To this mixture, sodium hydride (60% mineral oil dispersion, 19.9 mg) and methyl iodide (26.2 μL) were further added, and the resultant mixture was stirred at room temperature for 1.5 hours. An aqueous solution of 10% ammonium chloride was added to stop the reaction, and the resultant mixture was extracted twice with ethyl acetate. The organic layers were combined, washed with brine, separated from the aqueous layer by a phase separator, and then concentrated under reduced pressure. The obtained residue was purified by silica gel column chromatography (n-hexane only to n-hexane:ethyl acetate=3:2) to give methyl 2-methyl-2-[3-[[6-[2-(2-oxanyl)-3-pyrazolyl]-3-pyridinyl]oxymethyl]phenyl]propanoate (46.1 mg) as a colorless oil.

(2) The compound (46.1 mg) obtained in (1) above was used to perform the synthesis process according to the method described in Example 11-1-(2) thereby giving a mixture (38.2 mg) containing methyl 2-methyl-2-[3-[[6-(1H-pyrazol-5-yl)-3-pyridinyl]oxymethyl]phenyl]propanoate.

(3) The mixture (38.2 mg) obtained in (2) above was used to perform the synthesis process according to the method described in Example 1-1-(2) thereby giving a mixture (38.8 mg) containing 2-methyl-2-[3-[[6-(1H-pyrazol-5-yl)-3-pyridinyl]oxymethyl]phenyl]propanoic acid.

(4) The mixture (38.8 mg) obtained in (3) above was used to perform the synthesis process according to the method described in Example 24-1-(5) thereby giving the title compound (25.6 mg) as a colorless solid.

$^1$H NMR (400 MHz, D$_2$O) δ ppm 1.48 (s, 6H) 5.15-5.29 (m, 2H) 6.75-6.85 (m, 1H) 7.29-7.62 (m, 5H) 7.71-7.89 (m, 2H) 8.22-8.37 (m, 1H).

MS ESI/APCI Multi posi: 338[M+H]$^+$.

MS ESI/APCI Multi nega: 336[M−H]$^−$.

The compound of Example 24-3 below was synthesized using the compounds obtained in Example 22-19-(1) and a commercially available compound, according to the method described in Example 24-2. The structure, NMR data, and MS data of the compound are shown in Table 46-1.

TABLE 46-1

| Example No. | Structure | Analytical Data |
|---|---|---|
| 24-3 | 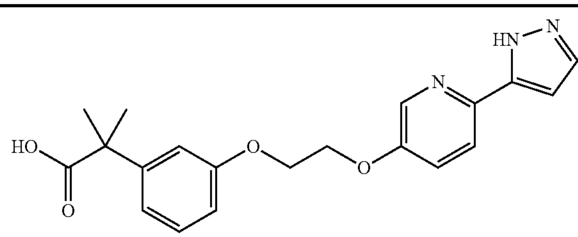 | $^1$H NMR (400 MHz, DMSO-d$_6$) δ ppm 1.46 (s, 6 H) 4.30-4.49 (m, 4 H) 6.74 (d, J = 2.1 Hz, 1 H) 6.84-6.99 (m, 3 H) 7.22-7.32 (m, 1 H) 7.52 (dd, J = 8.7, 2.8 Hz, 1 H) 7.63-7.74 (m, 1 H) 7.87 (d, J = 8.7 Hz, 1 H) 8.34 (d, J = 2.8 Hz, 1 H) 12.68 (br s, 1 H). MS ESI/APCI Multi posi: 368[M + H]$^+$. MS ESI/APCI Multi nega: 366[M − H]$^−$. |

Example 25-1

2-Methyl-4-[[6-(1H-pyrazol-5-yl)-3-pyridinyl]oxymethyl]benzoic Acid

[Formula 535]

(1) The compound (50.0 mg) obtained in Reference Example 1-1 and methyl 2-bromo-4-(bromomethyl)benzoate (92.9 mg) were used to perform the synthesis process according to the method described in Example 18-1-(2) thereby giving methyl 2-bromo-4-[[6-[2-(2-oxanyl)-3-pyrazolyl]-3-pyridinyl]oxymethyl]benzoate (92.2 mg) as a pale yellow oil.

(2) The compound (92.2 mg) obtained in (1) above, potassium methyltrifluoroborate (56.2 mg), [1,1'-bis(diphenylphosphino)ferrocene]palladium(II) dichloride dichloromethane adduct (15.1 mg), and potassium carbonate (191 mg) were mixed in a pressure-resistant tube, and N,N-dimethylformamide (1.84 mL) was added thereto. The tube was sealed, and the mixture was stirred at an outer temperature of 100° C. overnight. After cooling to room temperature, the mixture was poured into water, and the resultant mixture was extracted three times with ethyl acetate. The organic layers were combined, washed with brine, and dried over anhydrous magnesium sulfate, and the solid was filtered off, and the resultant was concentrated under reduced pressure. The obtained residue was purified by silica gel column chromatography (n-hexane:ethyl acetate=9:1 to 3:7) to give methyl 2-methyl-4-[[6-[2-(2-oxanyl)-3-pyrazolyl]-3-pyridinyl]oxymethyl]benzoate (37.3 mg) as a colorless gum-like substance.

(3) The compound (37.3 g) obtained in (2) above was used to perform the synthesis process according to the method described in Example 11-1-(2) thereby giving a mixture containing methyl 2-methyl-4-[[6-(1H-pyrazol-5-yl)-3-pyridinyl]oxymethyl]benzoate.

(4) The mixture obtained in (3) above was used to perform the synthesis process according to the method described in Example 1-1-(2) thereby giving the title compound (18.5 mg) as a colorless solid.

$^1$H NMR (400 MHz, DMSO-d$_6$) δ ppm 2.54 (s, 3H) 5.25 (s, 2H) 6.73 (d, J=2.2 Hz, 1H) 7.31-7.43 (m, 2H) 7.52 (dd, J=8.7, 2.9 Hz, 1H) 7.62-7.76 (m, 1H) 7.79-7.91 (m, 2H) 8.36 (d, J=2.9 Hz, 1H) 12.92 (br s, 1H).
MS ESI/APCI Multi posi: 310[M+H]$^+$.
MS ESI/APCI Multi nega: 308[M−H]$^−$.

Example 26-1 trans-2-[3-[[6-(1H-Pyrazol-5-yl)-3-pyridinyl]oxymethyl]phenyl]-1-cyclopropanecarboxylic Acid

[Formula 536]

(1) Trimethylsulfoxonium iodide (321 mg) was added to a suspension of sodium hydride (60% mineral oil dispersion, 122 mg) in dimethyl sulfoxide (10 mL), and the mixture was stirred at room temperature for 1 hour. A solution of the compound (529 mg) obtained in Example 22-1-(1) in dimethyl sulfoxide (10 mL) was added dropwise to the reaction mixture, and the resultant mixture was stirred at room temperature for 20 hours. An aqueous solution of 2 mol/L potassium hydrogen sulfate was added to the reaction mixture, and the resultant mixture was extracted with ethyl acetate. The organic layer was washed with water and passed through a phase separator, and the filtrate was concentrated. The obtained residue was purified by silica gel column chromatography (chloroform only to chloroform:methanol=19:1) to give 2-[3-[[6-[2-(2-oxanyl)-3-pyrazolyl]-3-pyridinyl]oxymethyl]phenyl]-1-cyclopropanecarboxylic acid (293 mg) as a pale yellow amorphous substance.

(2) Water (2 mL) and trifluoroacetic acid (1 mL) were added to a solution of the compound (293 mg) obtained in (1) above in methanol (4 mL), and the mixture was stirred at room temperature for 20 hours. A saturated aqueous solution of sodium hydrogen carbonate was added to the reaction solution, and the resultant mixture was extracted with chloroform, the organic layer was passed through a phase separator, and the solvent was distilled off under reduced pressure. The obtained residue was purified by preparative HPLC to give the title compound (106 mg) as a colorless amorphous substance.

¹H NMR (600 MHz, CHLOROFORM-d) δ ppm 1.38-1.42 (m, 1H) 1.68-1.72 (m, 1H) 1.95-1.98 (m, 1H) 2.61-2.64 (m, 1H) 5.14 (s, 2H) 6.72-6.73 (m, 1H) 7.06-7.08 (m, 1H) 7.22 (s, 1H) 7.24-7.33 (m, 3H) 7.61-7.66 (m, 2H) 8.36-8.38 (m, 1H).

MS ESI/APCI Multi posi: 336[M+H]⁺.

MS ESI/APCI Multi nega: 334[M−H]⁻.

Example 26-2 trans-2-[3-[[6-(1H-Pyrazol-5-yl)-3-pyridinyl]oxymethyl]phenyl]-1-cyclopropanecarboxylic Acid (Optically Active Substance)

[Formula 537]

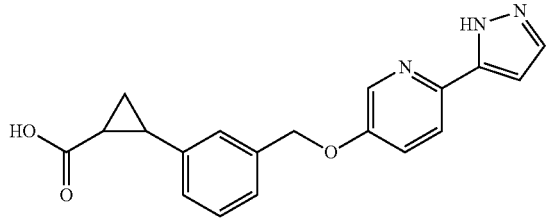

(1) The quenching in Example 26-1-(1) was performed with water under ice cooling thereby giving a crude product (244 mg) containing ethyl 2-[3-[[6-[2-(2-oxanyl)-3-pyrazolyl]-3-pyridinyl]oxymethyl]phenyl]-1-cyclopropanecarboxylate as a colorless oil.

(2) The compound (244 mg) obtained in (1) above was used to perform the synthesis process according to the method described in Example 1-1-(3) thereby giving ethyl 2-[3-[[6-(1H-pyrazol-5-yl)-3-pyridinyl]oxymethyl]phenyl]-1-cyclopropanecarboxylate (107 mg) as a pale brown oil.

(3) The compound obtained in (2) above was purified by preparative HPLC equipped with a chiral column to give a compound (29 mg) of Example 26-2-(3)-1 as a component having a short retention time; and a compound (30 mg) of Example 26-2-(3)-2 as a component having a long retention time.

(4) The compound (29 mg) of Example 26-2-(3)-1 obtained in (3) above was used to perform the synthesis process according to the method described in Example 9-1-(3) thereby giving the title compound (22 mg) as a colorless oil.

¹H NMR (400 MHz, DMSO-d₆) δ ppm 1.23-1.48 (m, 2H) 1.75-1.87 (m, 1H) 5.17 (s, 2H) 6.70-6.74 (m, 1H) 7.09-7.17 (m, 1H) 7.26-7.34 (m, 3H) 7.48-7.57 (m, 1H) 7.63-7.72 (m, 1H) 7.81-7.89 (m, 1H) 8.32-8.37 (m, 1H).

MS ESI/APCI Multi posi: 336[M+H]⁺.

MS ESI/APCI Multi nega: 334[M−H]⁻.

$[\alpha]_D^{25}$=−121 (c=0.112, MeOH)

Example 26-3 trans-2-[3-[[6-(1H-Pyrazol-5-yl)-3-pyridinyl]oxymethyl]phenyl]-1-cyclopropanecarboxylic Acid (Optically Active Substance, Enantiomer of Compound of Example 26-2)

[Formula 538]

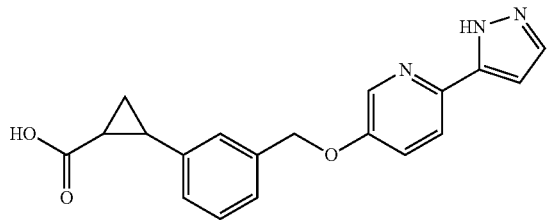

The compound (30 mg) of Example 26-2-(3)-2 was used to perform the synthesis process according to the method described in Example 9-1-(3) thereby giving the title compound (24 mg) as a colorless oil.

¹H NMR (400 MHz, DMSO-d₆) δ ppm 1.23-1.48 (m, 2H) 1.75-1.87 (m, 1H) 5.17 (s, 2H) 6.70-6.74 (m, 1H) 7.09-7.17 (m, 1H) 7.26-7.34 (m, 3H) 7.48-7.57 (m, 1H) 7.63-7.72 (m, 1H) 7.81-7.89 (m, 1H) 8.32-8.37 (m, 1H).

MS ESI/APCI Multi posi: 336[M+H]⁺.

$[\alpha]_D^{25}$=+101 (c=0.115, MeOH)

Example 27-1

2-[3-[[6-(1-H-Pyrazol-5-yl)-3-pyridinyl]oxymethyl]phenyl]-2-propanol

[Formula 539]

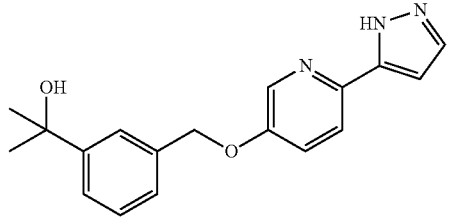

(1) To a solution of the compound (421 mg) obtained in Reference Example 6-1 in tetrahydrofuran (2 mL), n-butyl lithium (2.6 mol/L n-hexane solution, 204 μL) was added dropwise at −78° C., and the mixture was stirred for 1 hour. Acetone (71.1 μL) was slowly added thereto at −78° C., the temperature of the mixture was gradually increased, and the mixture was stirred at room temperature for 18 hours. An aqueous solution of saturated ammonium chloride was added to the reaction mixture, the resultant mixture was extracted with ethyl acetate, and the organic layer was then washed with brine, and dried over anhydrous magnesium sulfate. After the drying agent was filtered off, the filtrate was concentrated under reduced pressure, and the obtained residue was purified by silica gel column chromatography (n-hexane:ethyl acetate=9:1 to 2:3) to give 2-[3-[[6-[2-(2-oxanyl)-3-pyrazolyl]-3-pyridinyl]oxymethyl]phenyl]-2-propanol (98.5 mg) as a colorless oil.

(2) The compound (87.6 mg) obtained in (1) above was used to perform the synthesis process according to the method described in Example 10-1-(2) thereby giving the title compound (48.8 mg) as a colorless powder.

¹H NMR (300 MHz, CHLOROFORM-d) δ ppm 1.60 (s, 6H) 1.71-1.90 (m, 1H) 5.15 (s, 2H) 6.59-6.73 (m, 1H) 7.25-7.53 (m, 4H) 7.54-7.72 (m, 3H) 8.37 (dd, J=3.0, 0.6 Hz, 1H).

MS ESI/APCI Multi posi: 310[M+H]⁺.

The compounds of Examples 27-2 to 27-5 below were synthesized using a compound obtained in Reference Example 6-1 or 8-1, and a commercially available ketone, according to the method described in Example 27-1. The structures, NMR data, and MS data of the compounds are shown in Table 47-1.

Example 28-1

3-Hydroxy-3-[3-[[6-(1-H-pyrazol-5-yl)-3-pyridinyl]oxymethyl]phenyl]-1-cyclobutanecarboxylic Acid

[Formula 540]

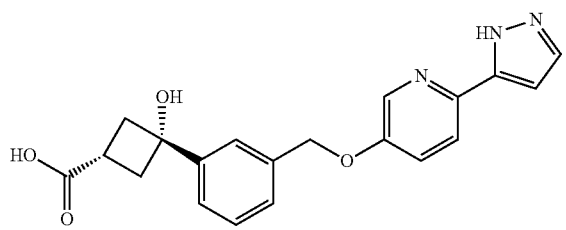

(1) The compound obtained in Reference Example 6-1 and ethyl 3-oxocyclobutylcarboxylate (301 mg) were used to perform the synthesis process according to the method described in Example 27-1 thereby giving ethyl 3-hydroxy-

TABLE 47-1

| Example No. | Structure | Analytical Data |
|---|---|---|
| 27-2 | 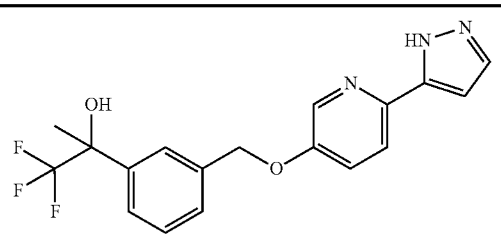 | ¹H NMR (300 MHz, CHLOROFORM-d) δ ppm 1.81 (d, J = 0.9 Hz, 3 H) 2.46-2.61 (m, 1 H) 5.17 (s, 2 H) 6.65-6.73 (m, 1 H) 7.32 (dd, J = 8.7, 3.0 Hz, 1 H) 7.39-7.50 (m, 2 H) 7.51-7.80 (m, 4 H) 8.36 (d, J = 2.8 Hz, 2 H). MS ESI/APCI Multi posi: 364[M + H]⁺. |
| 27-3 | 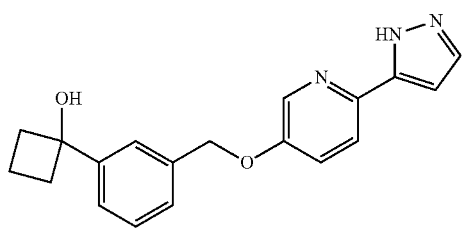 [SMILES: OC1(c2cccc(COc3ccc(-c4ccn[nH]4)nc3)c2)CCC1] | ¹H NMR (600 MHz, CHLOROFORM-d) δ ppm 1.68-1.78 (m, 1 H) 2.00-2.11 (m, 1 H) 2.26-2.43 (m, 2 H) 2.52-2.63 (m, 2 H) 5.16 (s, 2 H) 6.69 (d, J = 1.8 Hz, 1 H) 7.32 (dd, J = 8.7, 2.9 Hz, 1 H) 7.34-7.38 (m, 1 H) 7.39-7.45 (m, 1 H) 7.47-7.53 (m, 1 H) 7.57-7.60 (m, 1 H) 7.62 (d, J = 1.8 Hz, 1 H) 7.66 (d, J = 8.7 Hz, 1 H) 8.37 (d, J = 2.9 Hz, 1 H). MS ESI/APCI Multi posi: 322[M + H]⁺. |
| 27-4 | 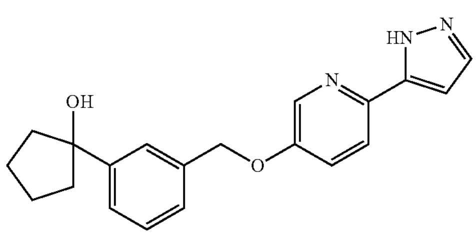 [SMILES: OC1(c2cccc(COc3ccc(-c4ccn[nH]4)nc3)c2)CCCC1] | ¹H NMR (600 MHz, CHLOROFORM-d) δ ppm 1.80-1.94 (m, 3 H) 1.97-2.07 (m, 5 H) 5.16 (s, 2 H) 6.74 (d, J = 2.1 Hz, 1 H) 7.31-7.44 (m, 3 H) 7.45-7.51 (m, 1 H) 7.58-7.62 (m, 1 H) 7.63 (d, J = 2.1 Hz, 1 H) 7.69 (br d, J = 8.7 Hz, 1 H) 8.37 (d, J = 2.9 Hz, 1 H). MS ESI/APCI Multi posi: 336[M + H]⁺. |
| 27-5 | 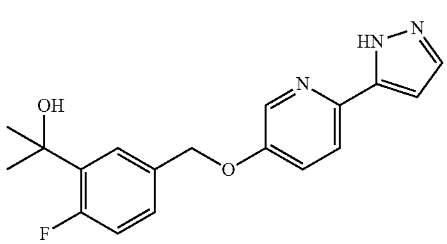 [SMILES: CC(C)(O)c1cc(COc2ccc(-c3ccn[nH]3)nc2)ccc1F] | ¹H NMR (600 MHz, DMSO-d₆) δ ppm 1.49 (s, 6 H) 5.17 (s, 1.4 H) 5.33 (s, 0.6 H) 6.65-8.45 (m, 8 H). MS ESI/APCI Multi posi: 328[M + H]⁺. |

3-[3-[[6-[2-(2-oxanyl)-3-pyrazolyl]-3-pyridinyl]oxymethyl]phenyl]-1-cyclobutanecarboxylate (105 mg) as a colorless oil.

(2) The compound (105 mg) obtained in (1) above was used to perform the synthesis process according to the method described in Example 10-1-(2) thereby giving ethyl 3-hydroxy-3-[3-[[6-(1-H-pyrazol-5-yl)-3-pyridinyl]oxymethyl]phenyl]-1-cyclobutanecarboxylate (69.0 mg) as a colorless oil.

(3) The compound (69.0 mg) obtained in (2) above was used to perform the synthesis process according to the method described in Example 9-1-(3) thereby giving the title compound (37.6 mg) as a colorless powder.

$^1$H NMR (600 MHz, DMSO-d$_6$) δ ppm 2.44-2.54 (m, 2H) 2.58-2.65 (m, 2H) 2.68-2.77 (m, 1H) 5.23 (s, 2H) 5.59-5.96 (m, 1H) 6.73 (d, J=2.1 Hz, 1H) 7.33-7.43 (m, 2H) 7.48-7.51 (m, 1H) 7.54 (dd, J=8.5, 2.8 Hz, 1H) 7.61-7.66 (m, 1H) 7.68 (s, 1H) 7.77-7.95 (m, 1H) 8.36 (d, J=2.8 Hz, 1H) 11.77-13.39 (m, 2H).

MS ESI/APCI Multi posi: 366[M+H]$^+$.

The compound of Example 28-2 below was synthesized using the compound obtained in Reference Example 8-1, according to the method described in Example 28-1. The structure, NMR data, and MS data of the compound are shown in Table 48-1.

extracted with ethyl acetate, and the organic layer was washed with brine. The organic layer was separated by a phase separator, and concentrated under reduced pressure. The residue was purified by silica gel column chromatography (chloroform:methanol=99:1 to 47:3) to give ethyl 6-[3-[[6-[2-(2-oxanyl)-3-pyrazolyl]-3-pyridinyl]oxy]prop-1-inyl]-2-pyridinecarboxylate (93 mg) as a brown oil.

(2) The compound (93 mg) obtained in (1) above was used to perform the synthesis process according to the method described in Example 2-1-(3) thereby giving ethyl 6-[3-[[6-[2-(2-oxanyl)-3-pyrazolyl]-3-pyridinyl]oxy]propyl]-2-pyridinecarboxylate (56 mg) as a colorless oil.

(3) The compound (56 mg) obtained in (2) above was used to perform the synthesis process according to the method described in Example 1-65-(2) thereby giving a solution containing ethyl 6-[3-[[6-(1H-pyrazol-5-yl)-3-pyridinyl]oxy]propyl]-2-pyridinecarboxylate.

(4) The solution obtained in (3) above was used to perform the synthesis process according to the method described in Example 1-1-(2) thereby giving the title compound (27 mg) as a pale brown powder.

$^1$H NMR (400 MHz, DMSO-d$_6$) δ ppm 2.13-2.25 (m, 2H) 2.93-3.04 (m, 2H) 4.10-4.20 (m, 2H) 6.69-6.75 (m, 1H)

TABLE 48-1

| Example No. | Structure | Analytical Data |
|---|---|---|
| 28-2 | 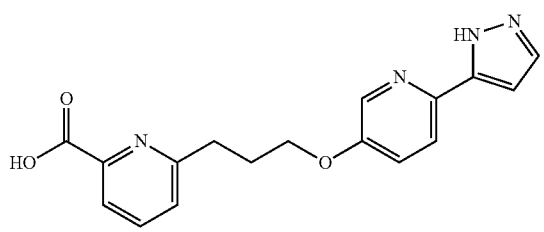 | $^1$H NMR (600 MHz, DMSO-d$_6$) δ ppm 2.43-2.52 (m, 2 H) 2.56-2.66 (m, 1 H) 2.74-2.87 (m, 2 H) 5.15-5.25 (m, 2 H) 6.73 (d, J = 1.7 Hz, 1 H) 7.16-7.24 (m, 1 H) 7.37-7.50 (m, 1 H) 7.51-7.57 (m, 1 H) 7.57-7.73 (m, 2 H) 7.80-7.93 (m, 1 H) 8.35 (d, J = 2.5 Hz, 1 H) 11.93-13.14 (m, 2 H). MS ESI/APCI Multi posi: 384[M + H]$^+$. |

Example 29-1

6-[3-[[6-(1H-Pyrazol-5-yl)-3-pyridinyl]oxy]propyl]-2-pyridinecarboxylic Acid

[Formula 541]

(1) A suspension of the compound (150 mg) obtained in Reference Example 6-4, ethyl 6-bromo-2-pyridinecarboxylate (150 mg), bis(triphenylphosphine)palladium(II) dichloride (38 mg), copper(I) iodide (13 mg), and triethylamine (370 μL) in acetonitrile (2.6 mL) was stirred under a nitrogen atmosphere at room temperature overnight. An aqueous solution of saturated ammonium chloride was added to the reaction solution, the resultant mixture was 7.42-7.50 (m, 1H) 7.51-7.58 (m, 1H) 7.64-7.71 (m, 1H) 7.80-7.94 (m, 3H) 8.24-8.31 (m, 1H).

MS ESI/APCI Multi posi: 325 [M+H]$^+$.
MS ESI/APCI Multi nega: 323[M−H]$^-$.

Example 29-2

2-[3-[[6-(1H-Pyrazol-5-yl)-3-pyridinyl]oxy]propyl]-4-pyridinecarboxylic Acid

[Formula 542]

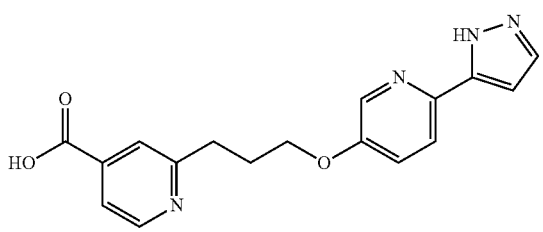

(1) A mixture of the compound (130 mg) obtained in Reference Example 6-4, methyl 2-bromo-4-pyridinecarboxylate (90 mg), bis(triphenylphosphine)palladium(II)

dichloride (29 mg), copper(I) iodide (8 mg), triethylamine (1.4 mL), and tetrahydrofuran (1.4 mL) was stirred at an outer temperature of 70° C. for 3 hours. The mixture was concentrated under reduced pressure, and the residue was purified by silica gel column chromatography (n-hexane:ethyl acetate) to give methyl 2-[3-[[6-[2-(2-oxanyl)-3-pyrazolyl]-3-pyridinyl]oxy]prop-1-inyl]-4-pyridinecarboxylate (115 mg) as a dark yellow solid.

(2) The compound (115 mg) obtained in (1) above was used to perform the synthesis process according to the method described in Example 13-1-(3) thereby giving a mixture containing methyl 2-[3-[[6-[2-(2-oxanyl)-3-pyrazolyl]-3-pyridinyl]oxy]propyl]-4-pyridinecarboxylate.

(3) The mixture obtained in (2) above was used to perform the synthesis process according to the method described in Example 12-1-(3) thereby giving methyl 2-[3-[[6-(1H-pyrazol-5-yl)-3-pyridinyl]oxy]propyl]-4-pyridinecarboxylate (40 mg) as a yellow solid.

(4) The compound (37 mg) obtained in (3) above was used to perform the synthesis process according to the method described in Example 12-1-(2) thereby giving the title compound (20 mg) as a colorless solid.

$^1$H NMR (400 MHz, DMSO-$d_6$) δ ppm 2.11-2.24 (m, 2H) 3.00 (t, J=7.7 Hz, 2H) 4.13 (t, J=6.3 Hz, 2H) 6.72 (s, 1H) 7.38-7.48 (m, 1H) 7.57-7.89 (m, 4H) 8.26 (s, 1H) 8.62-8.70 (m, 1H).

MS ESI posi: 325 [M+H]$^+$.
MS ESI nega: 323[M−H]$^-$.

The compounds of Examples 29-3 to 29-5 below were synthesized using the compound obtained in Reference Example 6-5 and a commercially available compound, according to the method described in Example 29-2. The structures, NMR data, and MS data of the compounds are shown in Table 49-1.

Example 30-1

4-[3-[[6-(1H-Pyrazol-5-yl)-3-pyridinyl]oxymethyl]phenyl]butanoic Acid

[Formula 543]

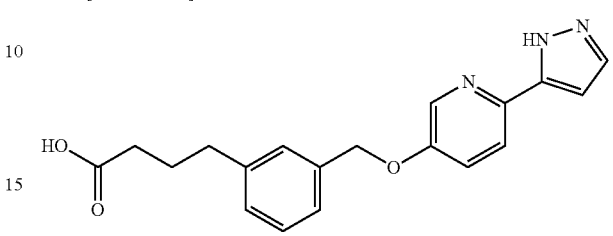

(1) The compound (80.3 mg) obtained in Reference Example 8-3, palladium(II) acetate (3.65 mg), and tri(o-toluyl)phosphine (9.91 mg) were mixed in a three-necked flask. After the air in the flask was purged with nitrogen, acetonitrile (1.63 mL), triethylamine (27.2 μL), and methyl 3-butenoate (20.8 μL) were added thereto, and the resultant mixture was stirred at an outer temperature of 60° C. for 5 hours. To this mixture, methyl 3-butenoate (20.8 μL) was further added, and the resultant mixture was further stirred overnight. After cooling to room temperature, the mixture was poured into water, and the resultant mixture was extracted three times with ethyl acetate. The organic layers were combined and washed twice with brine, and the aqueous layer was separated by a phase separator, and then the resultant was concentrated under reduced pressure. The obtained residue was purified by silica gel column chromatography (n-hexane:ethyl acetate=19:1 to 1:1) to give methyl (E)-4-[3-[[6-[2-(2-oxanyl)-3-pyrazolyl]-3-pyridinyl]oxymethyl]phenyl]-3-butenoate (37.8 mg) as a yellow gum-like substance.

TABLE 49-1

| Example No. | Structure | Analytical Data |
|---|---|---|
| 29-3 | ![structure] | $^1$H NMR (400 MHz, DMSO-$d_6$) δ ppm 1.71-1.89 (m, 4 H) 2.72-2.86 (m, 2 H) 4.05-4.17 (m, 2 H) 6.72 (d, J = 2.1 Hz, 1 H) 7.41-7.47 (m, 1 H) 7.61-7.75 (m, 1 H) 7.84 (d, J = 8.6 Hz, 1 H) 8.28 (d, J = 2.7 Hz, 1 H) 8.86 (s, 2 H) 12.90-13.45 (m, 1 H). MS ESI posi: 340[M + H]$^+$. MS ESI nega: 338[M − H]$^-$. |
| 29-4 | ![structure] | $^1$H NMR (400 MHz, METHANOL-$d_6$) ppm 1.80-2.00 (m, 4 H) 2.79-2.91 (m, 2 H) 4.09-4.20 (m, 2 H) 6.78 (d, J = 2.2 Hz, 1 H) 7.43 (dd, J = 8.8, 2.8 Hz, 1 H) 7.65 (d, J = 2.2 Hz, 1 H) 7.83 (d, J = 8.8 Hz, 1 H) 7.91 (d, J = 8.0 Hz, 1 H) 8.09 (d, J = 8.0 Hz, 1 H) 8.19-8.22 (m, 1 H) 8.23 (d, J = 2.8 Hz, 1 H) 8.50-8.61 (m, 1 H). MS ESI posi: 339[M + H]$^+$. MS ESI nega: 337[M − H]$^-$. |
| 29-5 | ![structure] | $^1$H NMR (400 MHz, DMSO-$d_6$) δ ppm 1.67-1.98 (m, 4 H) 2.88 (t, J = 7.2 Hz, 2 H) 4.12 (t, J = 5.7 Hz, 2 H) 6.72 (s, 1 H) 7.37-7.56 (m, 2 H) 7.62-7.75 (m, 1 H) 7.79-7.98 (m, 3 H) 8.24-8.38 (m, 1 H). MS ESI posi: 339[M + H]$^+$. MS ESI nega: 337[M − H]$^-$. |

(2) A palladium carbon-ethylenediamine complex (15 mg) was added to a solution of the compound (37.8 mg) obtained in (1) above in methanol (3.00 mL), and the mixture was stirred under a hydrogen atmosphere at room temperature overnight. Because the raw materials were found to be remaining, the catalyst was filtered off and washed with ethyl acetate, and then the filtrate and the washing solution were combined and concentrated. The residue was dissolved in methanol (3.00 mL), a palladium carbon-ethylenediamine complex (15 mg) was added thereto, and the resultant mixture was stirred under a hydrogen atmosphere at room temperature for 5 hours. The catalyst was filtered off and washed with ethyl acetate, and the filtrate and the washing solution were combined and concentrated to give a mixture (28.4 mg) containing methyl 4-[3-[[6-[2-(2-oxanyl)-3-pyrazolyl]-3-pyridinyl] oxymethyl]phenyl]butanoate.

(3) The mixture (28.4 mg) obtained in (2) above was used to perform the synthesis process according to the method described in Example 1-65-(2) thereby giving a solution containing methyl 4-[3-[[6-(1H-pyrazol-5-yl)-3-pyridinyl]oxymethyl]phenyl]butanoate.

(4) The solution obtained in (3) above was used to perform the synthesis process according to the method described in Example 16-1-(4) thereby giving the title compound (13.5 mg) as a colorless solid.

$^1$H NMR (400 MHz, DMSO-$d_6$) δ ppm 1.75-1.85 (m, 2H) 2.22 (t, J=7.4 Hz, 2H) 2.56-2.65 (m, 2H) 5.19 (s, 2H) 6.73 (d, J=2.1 Hz, 1H) 7.18 (d, J=6.6 Hz, 1H) 7.26-7.41 (m, 3H) 7.52 (dd, J=8.9, 2.8 Hz, 1H) 7.62-7.78 (m, 1H) 7.85 (d, J=8.9 Hz, 1H) 8.35 (d, J=2.8 Hz, 1H).

MS ESI/APCI Multi posi: 338[M+H]$^+$.

The compound of Example 30-2 below was synthesized using the compound obtained in Reference Examples 8-2 and a commercially available compound, according to the method described in Example 30-1. The structure, NMR data, and MS data of the compound are shown in Table 50-1.

(1) The compound (140 mg) obtained in Reference Example 6-2, palladium(II) acetate (4.37 mg), tri(o-toluyl)phosphine (11.8 mg), N,N-dimethylformamide (1.95 mL), triethylamine (40.7 μL), and ethyl acrylate (52.7 μL) were mixed in a pressure-resistant tube. The air in the container was purged with nitrogen and the container was sealed, and the mixture was stirred at an outer temperature of 100° C. overnight. After cooling to room temperature, palladium(II) acetate (4.37 mg), tri(o-toluyl)phosphine (11.8 mg), and ethyl acrylate (52.7 μL) were added to the mixture, and the air in the container was purged with nitrogen and the container was sealed, and the mixture was stirred at 150° C. for 30 minutes under microwave irradiation. After cooling to room temperature, the mixture was poured into water, and the resultant mixture was extracted three times with ethyl acetate. The organic layers were combined, washed with brine, and dried over anhydrous magnesium sulfate, the solid was filtered off, and the filtrate was concentrated. The obtained residue was purified by silica gel column chromatography (n-hexane:ethyl acetate=17:3 to 3:2) to give ethyl (E)-3-[3-[3-[[6-[2-(2-oxanyl)-3-pyrazolyl]-3-pyridinyl]oxy]propyl]phenyl]-2-propenoate (56.0 mg) as a yellow oil.

(2) The compound (56.0 mg) obtained in (1) above was used to perform the synthesis process according to the method described in Example 30-1-(2) thereby giving a mixture (55.4 mg) containing ethyl 3-[3-[3-[[6-[2-(2-oxanyl)-3-pyrazolyl]-3-pyridinyl]oxy]propyl]phenyl]propanoate.

TABLE 50-1

| Example No. | Structure | Analytical Data |
|---|---|---|
| 30-2 | 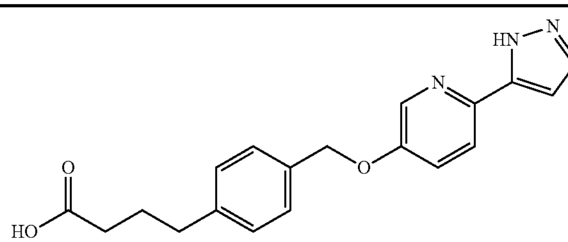 | $^1$H NMR (400 MHz, DMSO-$d_6$) δ ppm 1.73-1.85 (m, 2 H) 2.21 (t, J = 7.3 Hz, 2 H) 2.60 (t, J = 7.6 Hz, 2 H) 5.17 (s, 2 H) 6.73 (d, J = 2.1 Hz, 1 H) 7.23 (d, J = 8.1 Hz, 2 H) 7.40 (d, J = 7.9 Hz, 2 H) 7.52 (dd, J = 8.7, 2.9 Hz, 1 H) 7.62-7.74 (m, 1 H) 7.85 (d, J = 8.7 Hz, 1 H) 8.34 (d, J = 2.9 Hz, 1 H). MS ESI/APCI Multi posi: 338[M + H]$^+$. MS ESI/APCI Multi nega: 336[M − H]$^-$. |

(3) The mixture (55.4 mg) obtained in (2) above was used to perform the synthesis process according to the method described in Example 1-65-(2) thereby giving a solution containing ethyl 3-[3-[3-[[6-(1H-pyrazol-5-yl)-3-pyridinyl]oxy]propyl]phenyl]propanoate.

(4) The solution obtained in (3) above was used to perform the synthesis process according to the method described in Example 16-1-(4) thereby giving the title compound (23.7 mg) as a colorless solid.

$^1$H NMR (400 MHz, DMSO-$d_6$) δ ppm 1.98-2.09 (m, 2H) 2.67-2.83 (m, 4H) 4.08 (t, J=6.4 Hz, 2H) 6.73 (d, J=2.1 Hz, 1H) 7.00-7.13 (m, 3H) 7.15-7.24 (m, 1H) 7.44 (dd, J=8.7, Example 30-3

3-[3-[3-[[6-(1H-Pyrazol-5-yl)-3-pyridinyl]oxy]propyl]phenyl]propanoic Acid

[Formula 544]

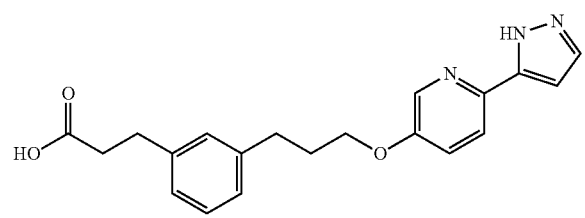

2.9 Hz, 1H) 7.67 (s, 1H) 7.84 (d, J=8.7 Hz, 1H) 8.29 (d, J=2.9 Hz, 1H) 12.59 (br s, 1H).

MS ESI/APCI Multi posi: 352[M+H]⁺.

MS ESI/APCI Multi nega: 350[M−H]⁻.

The compounds of Examples 30-4 and 30-5 below were synthesized using a compound obtained in Reference Example 6-2 or 6-3 and a commercially available compound, according to the method described in Example 30-3. The structures, NMR data, and MS data of the compounds are shown in Table 50-2.

sodium carbonate (37.4 mg) were added to a solution of the compound (87.1 mg) obtained in Reference Example 8-3 in ethylene glycol (2.00 mL) and the container was sealed, and the mixture was stirred at 150° C. for 40 minutes under microwave irradiation. After cooling to room temperature, 3-boronobenzoic acid (38.1 mg), [1,1'-bis(diphenylphosphino)ferrocene]palladium(II) dichloride dichloromethane adduct (14.4 mg), and sodium carbonate (37.4 mg) were further added to the mixture, and the resultant mixture was stirred at 150° C. for 40 minutes under microwave irradia-

TABLE 50-2

| Example No. | Structure | Analytical Data |
|---|---|---|
| 30-4 | 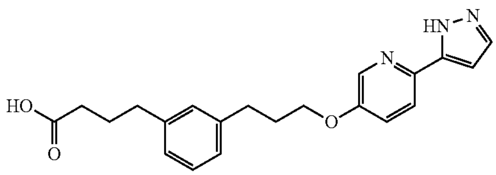 [SMILES: O=C(O)CCCc1cccc(CCCOc2ccc(-c3ccn[nH]3)nc2)c1] | ¹H NMR (400 MHz, DMSO-d₆) δ ppm 1.71-1.83 (m, 2 H) 1.98-2.10 (m, 2 H) 2.20 (t, J = 7.3 Hz, 2 H) 2.47-2.59 (m, 2 H) 2.73 (t, J = 7.7 Hz, 2 H) 4.07 (t, J = 6.3 Hz, 2 H) 6.73 (d, J = 2.1 Hz, 1 H) 6.97-7.10 (m, 3 H) 7.16-7.25 (m, 1 H) 7.43 (dd, J = 8.7, 2.8 Hz, 1 H) 7.59-7.77 (m, 1 H) 7.84 (d, J = 8.8 Hz, 1 H) 8.28 (d, J = 2.9 Hz, 1 H) 12.53 (br s, 1 H). MS ESI/APCI Multi posi: 366[M + H]⁺. MS ESI/APCI Multi nega: 364[M − H]⁻. |
| 30-5 | 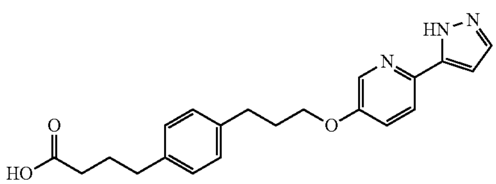 [SMILES: O=C(O)CCCc1ccc(CCCOc2ccc(-c3ccn[nH]3)nc2)cc1] | ¹H NMR (400 MHz, DMSO-d₆) δ ppm 1.70-1.83 (m, 2 H) 1.97-2.08 (m, 2 H) 2.13-2.24 (m, 2 H) 2.45-2.59 (m, 2 H) 2.67 2.77 (m, 2 H) 4.02-4.12 (m, 2 H) 6.73 (d, J = 2.1 Hz, 1 H) 7.05-7.20 (m, 4 H) 7.43 (dd, J = 8.8, 2.9 Hz, 1 H) 7.58-7.73 (m, 1 H) 7.84 (d, J = 8.8 Hz, 1 H) 8.28 (d, J = 2.9 Hz, 1 H) 12.58 (br s, 1 H). MS ESI/APCI Multi posi: 366[M + H]⁺. MS ESI/APCI Multi nega: 364[M − H]⁻. |

Example 31-1

3-[3-[[6-(1H-Pyrazol-5-yl)-3-pyridinyl]oxymethyl]phenyl]benzoic Acid

[Formula 545]

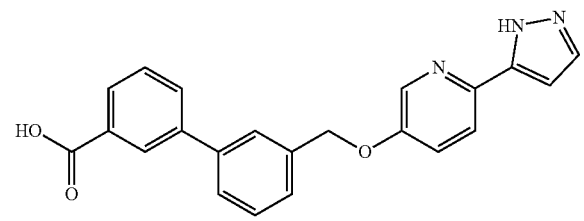

In a microwave reaction container, 3-boronobenzoic acid (38.1 mg), [1,1'-bis(diphenylphosphino)ferrocene]palladium(II) dichloride dichloromethane adduct (14.4 mg), and tion. After cooling to room temperature, the mixture was poured into an aqueous solution of 10% potassium hydrogen sulfate, and the resultant mixture was extracted six times with ethyl acetate. The organic layers were combined, washed with brine, separated from the aqueous layer by a phase separator, and concentrated under reduced pressure. The obtained residue was purified by preparative HPLC to give the title compound (8.1 mg) as a colorless solid.

¹H NMR (400 MHz, DMSO-d₆) δ ppm 5.32 (s, 2H) 6.73 (d, J=2.0 Hz, 1H) 7.42-8.00 (m, 10H) 8.21 (s, 1H) 8.39 (d, J=2.7 Hz, 1H).

MS ESI/APCI Multi posi: 372[M+H]⁺.

MS ESI/APCI Multi nega: 370[M−H]⁻.

The compound of Example 31-2 below was synthesized using a commercially available compound, according to the method described in Example 31-1. The structure, NMR data, and MS data of the compound are shown in Table 51-1.

TABLE 51-1

| Example No. | Structure | Analytical Data |
|---|---|---|
| 31-2 | 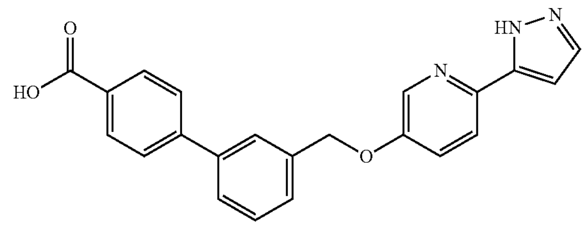 [SMILES: O=C(O)c1ccc(-c2cccc(COc3ccc(-c4ccn[nH]4)nc3)c2)cc1] | $^1$H NMR (400 MHz, DMSO-d$_6$) δ ppm 5.31 (s, 2 H) 6.73 (d, J = 2.0 Hz, 1 H) 7.40-8.07 (m, 11 H) 8.38 (s, 1 H). MS ESI/APCI Multi posi: 372[M + H]$^+$. |

Example 31-3

5-[3-[[6-(1H-Pyrazol-5-yl)-3-pyridinyl]oxymethyl]phenyl]-2-pyridinecarboxylic Acid

[Formula 546]

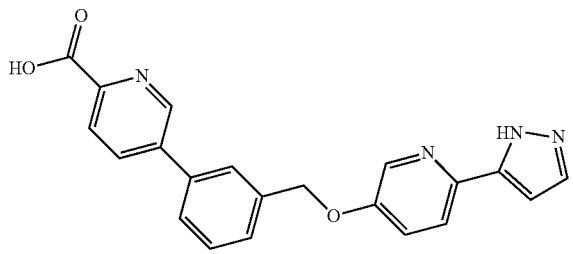

(1) The compound (105 mg) obtained in Reference Example 8-3, (6-methoxycarbonyl-3-pyridinyl)boronic acid (58 mg), [1,1'-bis(diphenylphosphino)ferrocene]palladium(II) dichloride dichloromethane adduct (17 mg), and potassium carbonate (59 mg) were dissolved in 1,4-dioxane:water (4:1, 2.5 mL), and the mixture was stirred at an outer temperature of 90° C. for 3.5 hours. The mixture was cooled to room temperature, diluted with ethyl acetate and filtered through Celite (registered trademark), and the filtrate was concentrated under reduced pressure. The obtained residue was purified by silica gel column chromatography (chloroform:methanol=100:1 to 10:1) to give methyl 5-[3-[[6-[2-(2-oxanyl)-3-pyrazolyl]-3-pyridinyl]oxymethyl]phenyl]-2-pyridinecarboxylate (80 mg) as a colorless oil.

(2) The compound (80 mg) obtained in (1) above was used to perform the synthesis process according to the method described in Example 1-65-(2) thereby giving a solution containing methyl 5-[3-[6-(1H-pyrazol-5-yl)-3-pyridinyl]oxymethyl]phenyl]-2-pyridinecarboxylate.

(3) The solution obtained in (2) above was used to perform the synthesis process according to the method described in Example 9-1-(3) thereby giving the title compound (15 mg) as a colorless solid.

$^1$H NMR (600 MHz, METHANOL-d$_4$) δ ppm 5.35 (s, 2H) 6.77-6.86 (m, 1H) 7.56-7.96 (m, 7H) 8.22-8.32 (m, 2H) 8.35-8.39 (m, 1H) 8.92-8.99 (m, 1H).

MS ESI/APCI Multi posi: 373 [M+H]$^+$.

The compound of Example 31-4 below was synthesized using a commercially available compound, according to the method described in Example 31-3. The structure, NMR data, and MS data of the compound are shown in Table 51-2.

TABLE 51-2

| Example No. | Structure | Analytical Data |
|---|---|---|
| 31-4 | 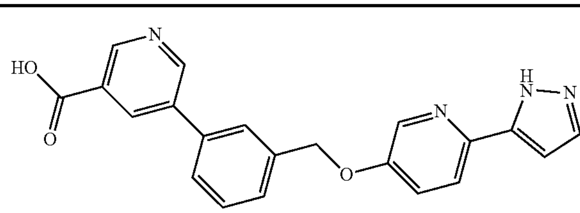 | $^1$H NMR (600 MHz, DMSO-d$_6$) δ ppm 5.32 (s, 2 H) 6.73 (d, J = 1.7 Hz, 1 H) 7.52-7.62 (m, 3 H) 7.77-7.97 (m, 4 H) 8.36-8.42 (m, 1 H) 8.46-8.52 (m, 1 H) 9.05-9.09 (m, 1 H) 9.12-9.16 (m, 1 H) MS ESI/APCI Multi posi: 373 [M + H]$^+$. MS ESI/APCI Multi nega: 371 [M − H]$^-$. |

Example 32-1

2-[3-[3-[[6-(1H-Pyrazol-5-yl)-3-pyridinyl]oxy]propyl]phenyl]acetic Acid

[Formula 547]

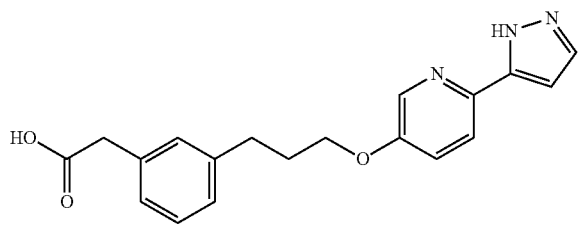

(1) The compound (140 mg) obtained in Reference Example 6-2, bis[tri(tert-butyl)phosphine]palladium(0) (9.95 mg), zinc fluoride (12.1 mg), and N,N-dimethylformamide (1.95 mL) were mixed. After nitrogen was passed through this mixture for 10 minutes, tert-butyl-(1-methoxyethenoxy)-dimethylsilane (84.9 μL) was added thereto, and the resultant mixture was stirred at an outer temperature of 100° C. overnight. Bis[tri(tert-butyl)phosphine]palladium (0) (9.95 mg), zinc fluoride (12.1 mg), and tert-butyl-(1-methoxyethenoxy)-dimethylsilane (84.9 μL) were further added thereto, and the resultant mixture was stirred at 150° C. for 1 hour under microwave irradiation. After cooling to room temperature, 6 mol/L hydrochloric acid (64.9 μL) was added to the mixture, and the resultant mixture was stirred at room temperature for 2.5 hours. Thereto, 6 mol/L hydrochloric acid (1 mL) and methanol (0.5 mL) were further added, and the resultant mixture was stirred at room temperature for 2 hours. An aqueous solution of saturated sodium hydrogen carbonate was added to the mixture, and the resultant mixture was extracted three times with ethyl acetate. The organic layers were combined, washed with brine, and dried over anhydrous sodium sulfate, and the solid was filtered off, and then the filtrate was concentrated under reduced pressure. The obtained residue was purified by silica gel column chromatography (chloroform only to chloroform:methanol=9:1) to give a mixture (52.4 mg) containing methyl 2-[3-[3-[[6-(1H-pyrazol-5-yl)-3-pyridinyl]oxy]propyl]phenyl]acetate.

(2) The compound (52.4 mg) obtained in (1) above was used to perform the synthesis process according to the method described in Example 16-1-(4) thereby giving the title compound (6.1 mg) as a colorless oil.

$^1$H NMR (400 MHz, METHANOL-d$_4$) δ ppm 2.06-2.20 (m, 2H) 2.82 (t, J=7.6 Hz, 2H) 3.56 (s, 2H) 4.08 (t, J=6.2 Hz, 2H) 6.79 (d, J=2.1 Hz, 1H) 7.08-7.27 (m, 4H) 7.41 (dd, J=8.8, 2.8 Hz, 1H) 7.66-7.68 (m, 1H) 7.83 (d, J=8.8 Hz, 1H) 8.23 (d, J=2.8 Hz, 1H).

MS ESI/APCI Multi posi: 338[M+H]$^+$.

MS ESI/APCI Multi nega: 336[M−H]$^−$.

The compound of Example 32-2 below was synthesized using a commercially available compound, according to the method described in Example 32-1. The structure, NMR data, and MS data of the compound are shown in Table 52-1.

TABLE 52-1

| Example No. | Structure | Analytical Data |
|---|---|---|
| 32-2 | 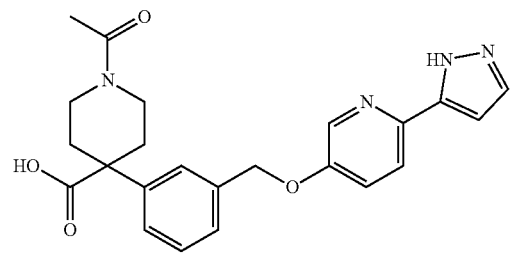 | $^1$H NMR (400 MHz, DMSO-d$_6$) δ ppm 1.44 (s, 6 H) 1.97-2.10 (m, 2 H) 2.76 (t, J = 7.7 Hz, 2 H) 4.08 (t, J = 6.3 Hz, 2 H) 6.73 (d, J = 2.1 Hz, 1 H) 7.07-7.30 (m, 4 H) 7.43 (dd, J = 8.8, 2.9 Hz, 1 H) 7.60-7.75 (m, 1 H) 7.84 (d, J = 8.8 Hz, 1 H) 8.29 (d, J = 2.9 Hz, 1 H) 12.61 (br s, 1 H).<br>MS ESI/APCI Multi posi: 366 [M + H]$^+$.<br>MS ESI/APCI Multi nega: 364 [M − H]$^−$. |

Example 33-1

1-Acetyl-4-[3-[[6-(1H-pyrazol-5-yl)-3-pyridinyl]oxymethyl]phenyl]-4-piperidinecarboxylic Acid

[Formula 548]

(1) To a solution of dicyclohexylamine (216 mg) in toluene (2.37 mL), n-butyl lithium (1.6 mol/L n-hexane solution, 0.74 mL) was added at −78° C., and then the temperature of the mixture was increased to 0° C. over 30 minutes, and the mixture was further stirred at 0° C. for 15 minutes. The mixture was again cooled to −78° C., O1-tert-butyl O4-ethyl piperidine-1,4-dicarboxylate (306 mg) was added thereto, and the resultant mixture was stirred for 30 minutes while the temperature of the mixture was slowly increased to room temperature. A solution of the compound (500 mg) obtained in Reference Example 8-3, tris(dibenzylideneacetone)dipalladium(0) (45 mg), and tri(tert-butyl)phosphine (20 mg) in toluene (2 mL) was added to the reaction solution, and the resultant mixture was stirred at room temperature for 17 hours. Further, the mixture was stirred at an outer temperature of 90° C. for 7 hours. The reaction solution was diluted with water, and then extracted three times with ethyl acetate. The organic layers were collected and washed with brine, and the aqueous layer was separated by a phase separator, and the resultant was concentrated under reduced pressure. The obtained residue was purified by silica gel column chromatography (n-hexane only to n-hexane:ethyl acetate=1:1) to give O1-tert-butyl O4-ethyl 4-[3-[[6-[2-(2-oxanyl)-3-pyrazolyl]-3-pyridinyl]oxymethyl]phenyl]piperidine-1,4-dicarboxylate (231 mg) as a dark orange amorphous substance.

(2) A 4 mol/L hydrogen chloride-ethyl acetate solution (3 mL) was added to a solution of the compound (112 mg) obtained in (1) above in ethanol (1 mL), and the mixture was stirred at room temperature for 3 hours. The reaction solution was diluted with diethyl ether (about 5 mL), and the precipitate generated was collected by filtration. The obtained solid substance was dissolved in water, and the resultant solution was adjusted to basic condition with an aqueous solution of saturated sodium hydroxide, and extracted with ethyl acetate. The organic layers were collected and washed with brine, and the aqueous layer was separated by a phase separator, and then the resultant was concentrated under reduced pressure to give a mixture (75 mg) containing ethyl 4-[3-[[6-(1H-pyrazol-5-yl)-3-pyridinyl]oxymethyl]phenyl]-4-piperidinecarboxylate.

(3) Acetic anhydride (20 mg) was added to a solution of the mixture (75 mg) obtained in (2) above in chloroform (0.9 mL) under ice cooling, and the mixture was stirred at room temperature for 2.5 hours. An aqueous solution of saturated sodium hydrogen carbonate was added thereto, and the resultant mixture was stirred for 10 minutes, and then extracted three times with chloroform. The organic layers were collected and washed with brine, and the aqueous layer was separated by a phase separator, and then the resultant was concentrated under reduced pressure to give a mixture (95 mg) containing ethyl 1-acetyl-4-[3-[[6-(1H-pyrazol-5-yl)-3-pyridinyl]oxymethyl]phenyl]-4-piperidinecarboxylate.

(4) The mixture (95 mg) obtained in (3) above was used to perform the synthesis process according to the method described in Example 1-1-(2) thereby giving the title compound (28 mg) as a light yellow amorphous substance.

$^1$H NMR (400 MHz, DMSO-$d_6$) δ ppm 1.59-1.89 (m, 2H) 2.00 (s, 3H) 2.32-2.43 (m, 2H) 2.75-2.90 (m, 1H) 3.13-3.27 (m, 1H) 3.66-3.81 (m, 1H) 4.11-4.26 (m, 1H) 5.21 (s, 2H) 6.73 (d, J=2.1 Hz, 1H) 7.39 (s, 3H) 7.47-7.59 (m, 2H) 7.68 (s, 1H) 7.86 (d, J=8.9 Hz, 1H) 8.35 (d, J=2.8 Hz, 1H) 12.91 (br s, 1H).

MS ESI/APCI Multi posi: 421 [M+H]$^+$.

Example 33-2

4-[3-[[6-(1H-Pyrazol-5-yl)-3-pyridinyl]oxymethyl]phenyl]-4-oxanecarboxylic Acid

[Formula 549]

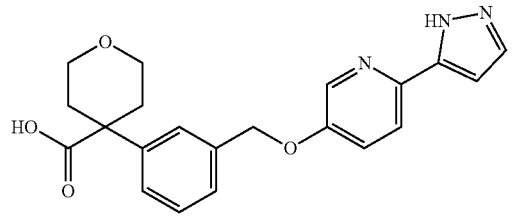

(1) The compound (200 mg) obtained in Reference Example 8-3 and methyl 4-oxanecarboxylate (68.6 mg) were used to perform the synthesis process according to the method described in Example 33-1-(1) thereby giving methyl 4-[3-[[6-[2-(2-oxanyl)-3-pyrazolyl]-3-pyridinyl]oxymethyl]phenyl]-4-oxanecarboxylate (64.1 mg) as a light yellow oil.

(2) The compound (64.1 mg) obtained in (1) above was used to perform the synthesis process according to the method described in Example 1-65-(2) thereby giving a solution containing methyl 4-[3-[[6-(1H-pyrazol-5-yl)-3-pyridinyl]oxymethyl]phenyl]-4-oxanecarboxylate.

(3) The solution obtained in (2) above was used to perform the synthesis process according to the method described in Example 1-1-(2) thereby giving the title compound (23.6 mg) as a colorless solid.

$^1$H NMR (400 MHz, DMSO-$d_6$) δ ppm 1.75-1.93 (m, 2H) 2.32-2.43 (m, 2H) 3.40-3.54 (m, 2H) 3.77-3.93 (m, 2H) 5.22 (s, 2H) 6.73 (d, J=2.1 Hz, 1H) 7.30-7.76 (m, 6H) 7.86 (d, J=8.7 Hz, 1H) 8.35 (d, J=2.8 Hz, 1H).

MS ESI/APCI Multi posi: 380[M+H]$^+$.
MS ESI/APCI Multi nega: 378[M−H]$^-$.

Example 34-1

1-[3-[[6-(1H-Pyrazol-5-yl)-3-pyridinyl]oxymethyl]phenyl]-4-piperidinecarboxylic Acid

[Formula 550]

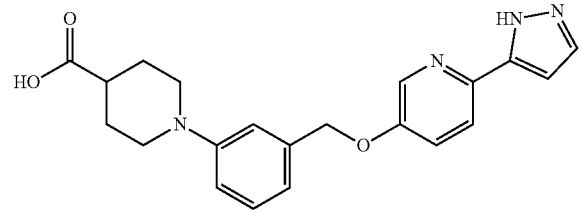

(1) A suspension of the compound (119 mg) obtained in Reference Example 8-3, ethyl 4-piperidinecarboxylate (59 mg), copper(I) iodide (5 mg), L-proline (6 mg), and potassium carbonate (69 mg) in dimethyl sulfoxide (250 μL) was stirred at an outer temperature of 60° C. for 16 hours. The mixture was cooled to room temperature, water was added thereto, and the resultant mixture was extracted twice with ethyl acetate. The organic layers were collected and washed with brine, the aqueous layer was removed by a phase separator, and then the resultant was concentrated under reduced pressure. The obtained residue was purified by silica gel column chromatography (n-hexane:ethyl acetate=9:1 to 3:2) to give ethyl 1-[3-[[6-[2-(2-oxanyl)-3-pyrazolyl]-3-pyridinyl]oxymethyl]phenyl]-4-piperidinecarboxylate (53 mg) as a colorless oil.

(2) The compound (52 mg) obtained in (1) above was used to perform the synthesis process according to the method described in Example 1-65-(2) thereby giving a solution containing ethyl 1-[3-[[6-(1H-pyrazol-5-yl)-3-pyridinyl]oxymethyl]phenyl]-4-piperidinecarboxylate.

(3) The solution obtained in (2) above was used to perform the synthesis process according to the method described in Example 9-1-(3) thereby giving the title compound (27 mg) as a colorless solid.

$^1$H NMR (400 MHz, DMSO-$d_6$) δ ppm 1.56-1.71 (m, 2H) 1.84-1.95 (m, 2H) 2.33-2.44 (m, 1H) 2.71-2.82 (m, 2H) 3.60-3.71 (m, 2H) 5.14 (s, 2H) 6.72 (d, J=2.1 Hz, 1H) 6.82-6.93 (m, 2H) 7.05 (s, 1H) 7.17-7.26 (m, 1H) 7.51 (dd, J=8.7, 2.9 Hz, 1H) 7.67 (s, 1H) 7.84 (d, J=8.7 Hz, 1H) 8.34 (d, J=2.9 Hz, 1H).

MS ESI/APCI Multi posi: 379[M+H]$^+$.

MS ESI/APCI Multi nega: 377[M−H]$^-$.

The compound of Example 34-2 below was synthesized using a commercially available compound, according to the method described in Example 34-1. The structure, NMR data, and MS data of the compound are shown in Table 53-1.

oxanyl)-3-pyrazolyl]-3-pyridinyl]oxymethyl]phenyl]-4-pyrazolecarboxylate (235 mg) as a light yellow oil.

(2) The compound (230 mg) obtained in (1) above was used to perform the synthesis process according to the method described in Example 15-2-(3) thereby giving a solution containing ethyl 1-[3-[[6-(1H-pyrazol-5-yl)-3-pyridinyl]oxymethyl]phenyl]-4-pyrazolecarboxylate.

(3) The solution obtained in (2) above was used to perform the synthesis process according to the method described in Example 9-1-(3) thereby giving the title compound (40 mg) as a colorless solid.

$^1$H NMR (400 MHz, DMSO-$d_6$) δ ppm 5.31 (s, 2H) 6.73 (d, J=2.0 Hz, 1H) 7.45-7.51 (m, 1H) 7.53-7.58 (m, 2H) 7.61-7.76 (m, 1H) 7.80-7.96 (m, 2H) 8.08 (d, J=5.1 Hz, 2H) 8.39 (d, J=2.3 Hz, 1H) 9.04 (s, 1H) 12.66-13.07 (m, 1H).

MS ESI posi: 362[M+H]$^+$.

MS ESI nega: 360[M−H]$^-$.

TABLE 53-1

| Example No. | Structure | Analytical Data |
|---|---|---|
| 34-2 | 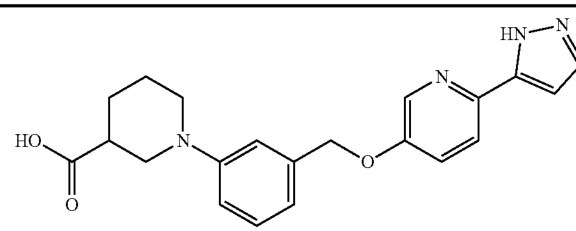 | $^1$H NMR (400 MHz, DMSO-$d_6$) δ ppm 1.47-1.62 (m, 2 H) 1.66-1.77 (m, 1 H) 1.83-1.97 (m, 1 H) 2.70-2.97 (m, 2 H) 3.44-3.54 (m, 1 H) 3.63-3.72 (m, 1 H) 5.14 (s, 2 H) 6.72 (d, J = 2.2 Hz, 1 H) 6.82-6.94 (m, 2 H) 7.04 (s, 1 H) 7.19-7.26 (m, 1 H) 7.47-7.55 (m, 1 H) 7.60-7.90 (m, 2 H) 8.34 (d, J = 2.6 Hz, 1 H).<br>MS ESI/APCI Multi posi: 379 [M + H]$^+$.<br>MS ESI/APCI Multi nega: 377 [M − H]$^-$. |

Example 34-3

1-[3-[[6-(1H-Pyrazol-5-yl)-3-pyridinyl]oxymethyl]phenyl]-4-pyrazolecarboxylic Acid

[Formula 551]

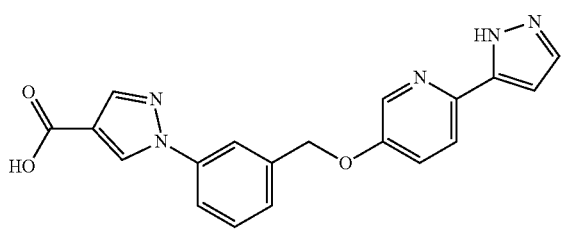

(1) The compound (435 mg) obtained in Reference Example 8-3, ethyl 1H-pyrazole-4-carboxylate (120 mg), copper(I) iodide (33 mg), trans-N,N'-dimethylcyclohexane-1,2-diamine (37 mg), and potassium carbonate (178 mg) were dissolved in N,N-dimethylformamide:water (17:2, 9.5 mL), and the mixture was stirred at an outer temperature of 150° C. for 3 hours. The mixture was cooled to room temperature, water was added thereto, and the resultant mixture was extracted with diethyl ether. The organic layer was concentrated under reduced pressure, and the obtained residue was then purified by silica gel column chromatography (chloroform:methanol) to give ethyl 1-[3-[[6-[2-(2-

Example 35-1

2-[4-[3-[[6-(1H-Pyrazol-5-yl)-3-pyridinyl]oxy]propyl]-1-triazolyl]acetic Acid

[Formula 552]

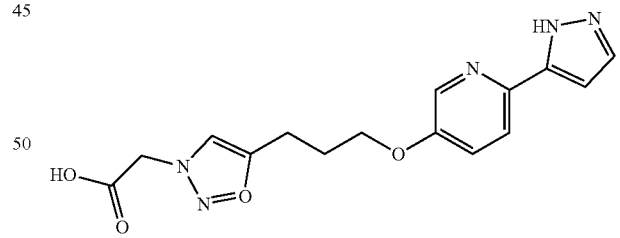

(1) A solution of the compound (150 mg) obtained in Reference Example 6-6, ethyl 2-azidoacetate (68 mg), sodium L-ascorbate (38 mg), and copper(II) sulfate (15 mg) in tert-butanol:water (1:1, 4.8 mL) was stirred at room temperature for 6 hours. Brine was added to stop the reaction, the resultant mixture was extracted with ethyl acetate, and the organic layer was then concentrated. The obtained residue was purified by silica gel column chromatography (chloroform:methanol) to give a mixture (230 mg) containing ethyl 2-[4-[3-[[6-[2-(2-oxanyl)-3-pyrazolyl]-3-pyridinyl]oxy]propyl]-1-triazoly] acetate.

(2) The mixture (230 mg) obtained in (1) above was used to perform the synthesis process according to the method described in Example 15-2-(3) thereby giving a solution containing ethyl 2-[4-[3-[[6-(1H-pyrazol-5-yl)-3-pyridinyl]oxy]propyl]-1-triazolyl]acetate.

(3) The solution obtained in (2) above was used to perform the synthesis process according to the method described in Example 9-1-(3) thereby giving the title compound (47 mg) as a colorless solid.

$^{1}$H NMR (400 MHz, DMSO-$d_6$) δ ppm 2.03-2.19 (m, 2H) 2.82 (t, J=7.5 Hz, 2H) 4.13 (t, J=6.2 Hz, 2H) 5.21 (s, 2H) 6.73 (d, J=1.6 Hz, 1H) 7.44 (dd, J=8.6, 2.8 Hz, 1H) 7.62-7.73 (m, 1H) 7.81-7.87 (m, 1H) 7.90 (s, 1H) 8.29 (d, J=2.8 Hz, 1H) 12.95-13.36 (m, 1H).

MS ESI posi: 329[M+H]$^+$.
MS ESI nega: 327[M−H]$^-$.

The compounds of Examples 35-2 and 35-3 below were synthesized using the compound obtained in Reference Example 6-7 and the compound obtained in Reference Example 84-1 or a commercially available compound, according to the method described in Example 35-1. The structures, NMR data, and MS data of the compounds are shown in Table 54-1.

ide (4 mL), and a nitrogen gas was passed therethrough for 10 minutes. After the test tube was sealed, the mixture was stirred at 100° C. for 15 minutes under microwave irradiation. After cooling to room temperature, the test tube was opened, isobutylene oxide (97.3 µL) was added to the mixture, the test tube was sealed, and the mixture was stirred at 140° C. for 15 minutes, and at 90° C. for 5 hours under microwave irradiation. Thereafter, water was added thereto, and the resultant mixture was extracted with ethyl acetate. The organic layer was washed with water and brine, and then dried over anhydrous magnesium sulfate. After the drying agent was filtered off, the filtrate was concentrated under reduced pressure, and the obtained residue was purified by silica gel column chromatography (chloroform only to chloroform:methanol=9:1) to give 2-methyl-1-[3-[[6-[2-(2-oxanyl)-3-pyrazolyl]-3-pyridinyl]oxymethyl]phenyl]sulfonyl-2-propanol as a yellow oil (59.0 mg).

(2) The compound (59.0 mg) obtained in (1) above was used to perform the synthesis process according to the method described in Example 1-1-(3) thereby giving the title compound (9.8 mg) as a colorless powder.

TABLE 54-1

| Example No. | Structure | Analytical Data |
|---|---|---|
| 35-2 | 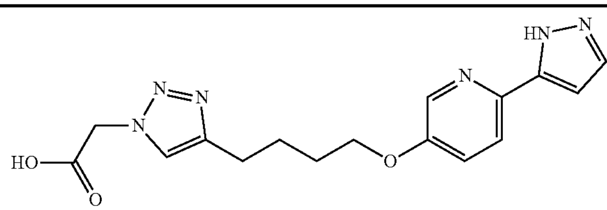 | $^{1}$H NMR (400 MHz, DMSO-$d_6$) δ ppm 1.70-1.98 (m, 4 H) 2.67-2.78 (m, 2 H) 4.05-4.19 (m, 2 H) 5.18 (s, 2 H) 6.71-6.76 (m, 1 H) 7.40-7.51 (m, 1 H) 7.62-7.76 (m, 1 H) 7.82-7.89 (m, 2 H) 8.26-8.31 (m, 1 H) 13.09-13.48 (m, 1 H). MS ESI/APCI Multi posi: 343 [M + H]$^+$. MS ESI/APCI Multi nega: 341 [M − H]$^-$. |
| 35-3 | 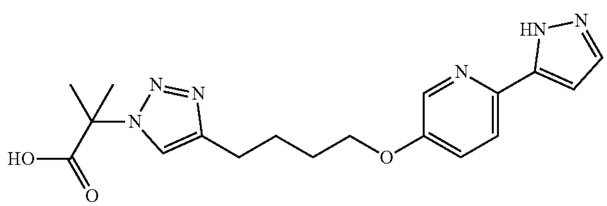 [SMILES: CC(C)(C(=O)O)n1cc(CCCCOc2ccc(-c3ccn[nH]3)nc2)nn1] | $^{1}$H NMR (400 MHz, DMSO-$d_6$) δ ppm 1.71-1.98 (m, 10 H) 2.64-2.80 (m, 2 H) 4.00-4.20 (m, 2 H) 6.72 (d, J = 1.3 Hz, 1 H) 7.44 (dd, J = 8.6, 2.6 Hz, 1 H) 7.62-7.72 (m, 1 H) 7.84 (d, J = 8.6 Hz, 1 H) 8.03 (s, 1 H) 8.27 (d, J = 2.6 Hz, 1 H) 13.14 (br s, 1 H). MS ESI posi: 371 [M + H]$^+$. MS ESI nega: 369 [M − H]$^-$. |

Example 36-1

2-Methyl-1-[3-[[6-(1-H-pyrazol-5-yl)-3-pyridinyl]oxymethyl]phenyl] sulfonyl-2-propanol

[Formula 553]

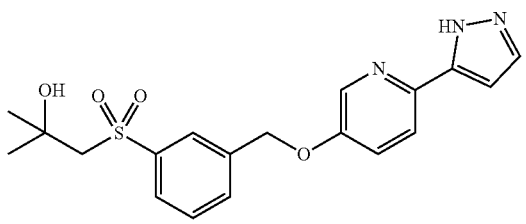

(1) In a test tube for a microwave reaction, potassium disulfite (322 mg), tetrabutylammonium bromide (257 mg), sodium formate (108 mg), palladium(II) acetate (16.3 mg), triphenylphosphine (57.0 mg), and 1,10-phenanthroline (39.2 mg) were added to a solution of the compound (300 mg) obtained in Reference Example 6-1 in dimethyl sulfox- $^{1}$H NMR (600 MHz, CHLOROFORM-d) δ ppm 1.41-1.51 (m, 6H) 3.33 (s, 2H) 3.62 (br s, 1H) 5.23 (s, 2H) 6.72 (s, 1H) 7.34 (dd, J=8.7, 2.9 Hz, 1H) 7.60-7.67 (m, 2H) 7.70 (d, J=8.7 Hz, 1H) 7.73-7.80 (m, 1H) 7.85-7.97 (m, 1H) 7.99-8.08 (m, 1H) 8.37 (d, J=2.9 Hz, 1H).

MS ESI/APCI Multi posi: 388[M+H]$^+$.

Example 37-1

2,2-Dimethyl-5-[3-[[6-(1H-pyrazol-5-yl)-3-pyridinyl]oxymethyl]phenyl] sulfonylpentanoic Acid

[Formula 554]

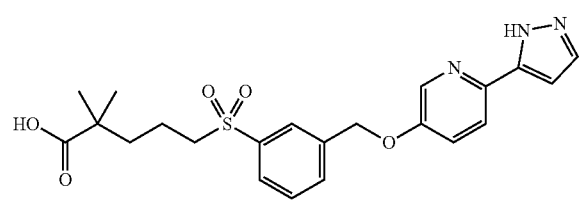

(1) The compound (311 mg) obtained in Reference Example 8-3 was used to perform the synthesis process according to the method described in Example 36-1-(1) thereby giving a suspension containing a sodium sulfinate intermediate. To this suspension, a solution of the compound (160 mg) synthesized in Reference Example 83-1 in dimethyl sulfoxide (1 mL) was added, and the resultant mixture was stirred at room temperature for 13 hours. The reaction solution was diluted with water, and then extracted three times with ethyl acetate. The organic layers were collected, washed with brine, dried over anhydrous magnesium sulfate, and filtered. The filtrate was concentrated under reduced pressure, and the obtained residue was purified by silica gel column chromatography (n-hexane:ethyl acetate=19:1 to 1:3) to give 2,2-dimethyl-5-[3-[[6-[2-(2-oxanyl)-3-pyrazolyl]-3-pyridinyl]oxymethyl]phenyl]sulfonyl-1-cyclopentanone (175 mg) as a light yellow amorphous substance.

(2) The compound (175 mg) obtained in (1) above was used to perform the synthesis process according to the method described in Example 1-65-(2) thereby giving a solution containing 2,2-dimethyl-5-[3-[[6-(1H-pyrazol-5-yl)-3-pyridinyl]oxymethyl]phenyl]sulfonyl-1-cyclopentanone.

(3) The solution obtained in (2) above was used to perform the synthesis process according to the method described in Example 1-1-(2) thereby giving the title compound (88 mg) as a colorless solid.
$^1$H NMR (400 MHz, DMSO-d$_6$) δ ppm 1.02 (s, 6H) 1.41-1.59 (m, 4H) 3.20-3.38 (m, 2H) 5.38 (s, 2H) 6.79-6.89 (m, 1H) 7.60-8.07 (m, 7H) 8.41 (s, 1H).
MS ESI/APCI Multi posi: 444[M+H]$^+$.
MS ESI/APCI Multi nega: 442[M−H]$^−$.

Example 38-1

3-[3-[[5-Fluoro-6-(1H-pyrazol-5-yl)-3-pyridinyl]oxymethyl]phenyl]propanoic Acid

[Formula 555]

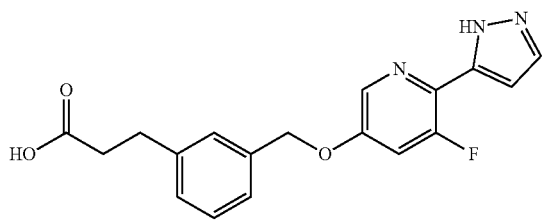

(1) Potassium carbonate (787 mg) and the compound (897 mg) obtained in Reference Example 43-1 were added to a solution of 2-chloro-3-fluoro-5-hydroxypyridine (420 mg) in N,N-dimethylformamide (10 mL), and the mixture was stirred at room temperature for 3 hours. Water was added to the reaction mixture, and the resultant mixture was extracted with ethyl acetate. The organic layer was dried over anhydrous sodium sulfate, and the drying agent was filtered off. The solvent was distilled off under reduced pressure, and the obtained residue was purified by silica gel column chromatography (n-hexane:ethyl acetate=4:1 to 1:1) to give ethyl 3-[3-[(6-chloro-5-fluoro-3-pyridinyl)oxymethyl]phenyl]propanoate (937 mg) as a colorless oil.

(2) To a solution of the compound (549 mg) obtained in (1) above in 1,4-dioxane (10 mL), 1-(2-oxanyl)-5-(4,4,5,5-tetramethyl-1,3,2-dioxaborolan-2-yl)pyrazole (678 mg), [1,1'-bis(diphenylphosphino)ferrocene]palladium(II) dichloride dichloromethane adduct (133 mg), and an aqueous solution of 2 mol/L cesium carbonate (2.4 mL) were added, and the mixture was stirred under heating at 100° C. for 5 hours. Water was added to the reaction solution, and the resultant mixture was extracted with chloroform. The organic layer was passed through a phase separator, and the solvent was distilled off under reduced pressure. The obtained residue was purified by silica gel column chromatography (n-hexane:ethyl acetate=4:1 to 1:1) to give ethyl 3-[3-[[5-fluoro-6-[2-(2-oxanyl)-3-pyrazolyl]-3-pyridinyl]oxymethyl]phenyl]propanoate (693 mg) as an orange oil.

(3) Water (6 mL) and trifluoroacetic acid (3 mL) were added to a solution of the compound (693 mg) obtained in (2) above in ethanol (12 mL), and the mixture was stirred at 50° C. for 1 hour. An aqueous solution of saturated sodium hydrogen carbonate was added to the reaction solution, and the resultant mixture was extracted with chloroform. The organic layer was passed through a phase separator, and the solvent was distilled off under reduced pressure. The obtained residue was purified by silica gel column chromatography (chloroform only to chloroform:methanol=19:1) to give ethyl 3-[3-[[5-fluoro-6-(1H-pyrazol-5-yl)-3-pyridinyl]oxymethyl]phenyl]propanoate (379 mg) as a light purple oil.

(4) An aqueous solution of 1 mol/L sodium hydroxide (3 mL) was added to a solution of the compound (379 mg) obtained in (3) above in tetrahydrofuran:methanol (1:1, 6 mL), and the mixture was stirred at room temperature for 20 hours. An aqueous solution of 1 mol/L potassium hydrogen sulfate and water were added to the reaction solution, and the resultant mixture was extracted with ethyl acetate. The organic layer was passed through a phase separator, and the solvent was distilled off under reduced pressure. Diethyl ether was added to the obtained residue, and the precipitated solid was collected by filtration to give the title compound (300 mg) as a colorless powder.
$^1$H NMR (600 MHz, DMSO-d$_6$) δ ppm 2.55 (t, J=7.6 Hz, 2H) 2.85 (t, J=7.6 Hz, 2H) 5.21 (s, 2H) 6.68-6.70 (m, 1H) 7.22-7.25 (m, 1H) 7.30-7.37 (m, 3H) 7.58-7.74 (m, 2H) 8.29-8.32 (m, 1H).
MS ESI/APCI Multi posi: 342[M+H]$^+$.
MS ESI/APCI Multi nega: 340[M−H]$^−$.

Example 38-2

2-[3-[[6-(1H-Pyrazol-4-yl)-3-pyridinyl]oxymethyl]phenyl]acetic Acid

[Formula 556]

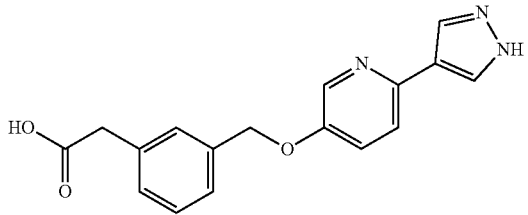

(1) A suspension of the compound (302 mg) obtained in Reference Example 85-1, 4-(5,5-dimethyl-1,3,2-dioxaborinan-2-yl)-1-(2-oxanyl)pyrazole (296 mg), tetrakis(triphenylphosphine)palladium(II) (100 mg), and an aqueous solution of 2 mol/L sodium carbonate (1.3 mL) in ethanol:toluene (1:2, 4.3 mL) was stirred at an outer temperature of 85° C. for 3 hours. The reaction mixture was cooled to room temperature, diluted with water, and then extracted twice with ethyl acetate. The organic layers were collected, washed with brine, dehydrated by a phase separator, and then concentrated under reduced pressure. The obtained residue was purified by silica gel column chromatography (n-hexane:ethyl acetate=19:1 to 7:13) to give ethyl 2-[3-[[6-[1-(2-oxanyl)-4-pyrazolyl]-3-pyridinyl]oxymethyl]phenyl]acetate (463 mg) as a yellow oil.

(2) The compound (108 mg) obtained in (1) above was used to perform the synthesis process according to the method described in Example 11-1-(2) thereby giving methyl 2-[3-[[6-(1H-pyrazol-4-yl)-3-pyridinyl]oxymethyl]phenyl]acetate (50 mg) as a light brown solid.

(3) The compound (49 mg) obtained in (2) above was used to perform the synthesis process according to the method described in Example 9-1-(3) thereby giving the title compound (22 mg) as a light red solid.

$^1$H NMR (400 MHz, DMSO-d$_6$) δ ppm 3.56 (s, 2H) 5.16 (s, 2H) 7.18-7.38 (m, 4H) 7.45 (dd, J=8.7, 2.9 Hz, 1H) 7.62 (d, J=8.7 Hz, 1H) 7.92-8.20 (m, 2H) 8.29 (d, J=2.9 Hz, 1H).

MS ESI/APCI Multi posi: 310[M+H]$^+$.
MS ESI/APCI Multi nega: 308[M−H]$^-$.

Example 38-3

1-[[6-(4-Methyl-1H-pyrazol-5-yl)-3-pyridinyl]oxymethyl]-4-bicyclo[2.2.2]octanecarboxylic Acid

[Formula 557]

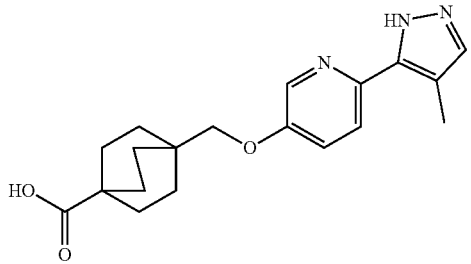

(1) Water (0.5 mL), sodium carbonate (42 mg), and tetrakis(triphenylphosphine)palladium(0) (2 mg) were added to a solution of the compound (47 mg) obtained in Reference Example 86-1 and 4-methyl-1-(2-oxanyl)-5-(4,4,5,5-tetramethyl-1,3,2-dioxaborolan-2-yl)pyrazole (47 mg) in ethanol:toluene (1:1, 2.6 mL) under a nitrogen atmosphere, and the mixture was stirred at 90° C. for 4 hours. The mixture was cooled to room temperature, and water was added to stop the reaction. The reaction mixture was extracted with ethyl acetate, the obtained organic layers were combined and passed through a phase separator to remove the aqueous layer, and concentrated under reduced pressure. The obtained residue was purified by silica gel column chromatography (n-hexane:ethyl acetate=5:1 to 1:2) to give methyl 1-[[6-[4-methyl-2-(2-oxanyl)-3-pyrazolyl]-3-pyridinyl]oxymethyl]-4-bicyclo[2.2.2]octanecarboxylate (63 mg) as a light yellow oil.

(2) The compound (63 mg) obtained in (1) above was used to perform the synthesis process according to the method described in Example 1-1-(2) thereby giving a solution containing 1-[[6-[4-methyl-2-(2-oxanyl)-3-pyrazolyl]-3-pyridinyl]oxymethyl]-4-bicyclo[2.2.2]octanecarboxylic acid.

(3) The solution obtained in (2) above was used to perform the synthesis process according to the method described in Example 1-43-(3) thereby giving the title compound (14 mg) as a colorless powder.

$^1$H NMR (400 MHz, DMSO-d$_6$) δ ppm 1.47-1.61 (m, 6H) 1.65-1.80 (m, 6H) 2.28 (s, 3H) 3.72 (s, 2H) 7.38-7.50 (m, 2H) 7.74 (d, J=8.8 Hz, 1H) 8.29 (d, J=2.9 Hz, 1H) 12.44 (br s, 1H).

MS ESI/APCI Multi posi: 342[M+H]$^+$.

Example 39-1

2-[3-[[6-(5-Isothiazolyl)-3-pyridinyl]oxymethyl]phenyl]acetic Acid

[Formula 558]

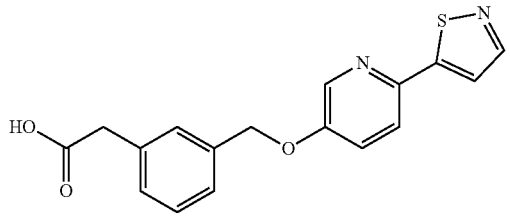

(1) In a test tube for a microwave reaction, hexamethylditin (107 mg) and tetrakis(triphenylphosphine)palladium(0) (34.3 mg) were added to a solution of the compound (100 mg) obtained in Reference Example 85-1 and commercially available 5-bromoisothiazole (73.2 mg) in 1,4-dioxane (10 mL), and the mixture was deaerated under reduced pressure and then placed under a nitrogen atmosphere, and the test tube was sealed. The mixture was stirred at 140° C. for 1 hour, and at 160° C. for 30 minutes under microwave irradiation. The reaction mixture was concentrated, and the residue was purified by silica gel column chromatography (n-hexane only to n-hexane:ethyl acetate=1:1) and then dried under reduced pressure to give methyl 2-[3-[[6-(5-isothiazolyl)-3-pyridinyl]oxymethyl]phenyl]acetate (29.6 mg) as a yellow oil.

(2) The compound (29.6 mg) obtained in (1) above was used to perform the synthesis process according to the method described in Example 12-1-(2) thereby giving the title compound (8.64 mg) as a colorless powder.

$^1$H NMR (400 MHz, DMSO-d$_6$) δ ppm 3.59 (s, 2H) 5.24 (s, 2H) 7.23-7.28 (m, 1H) 7.33-7.40 (m, 3H) 7.63 (dd, J=8.7, 2.9 Hz, 1H) 7.89 (d, J=1.8 Hz, 1H) 8.01 (d, J=8.7 Hz, 1H) 8.40 (d, J=2.9 Hz, 1H) 8.58 (d, J=1.8 Hz, 1H) 12.40 (br s, 1H).

MS ESI/APCI Multi posi: 327[M+H]$^+$.
MS ESI/APCI Multi nega: 325[M−H]$^-$.

The compound of Example 39-2 below was synthesized using the compound obtained in Reference Example 86-1, according to the method described in Example 39-1. The structure, NMR data, and MS data of the compound are shown in Table 55-1.

TABLE 55-1

| Example No. | Structure | Analytical Data |
|---|---|---|
| 39-2 | 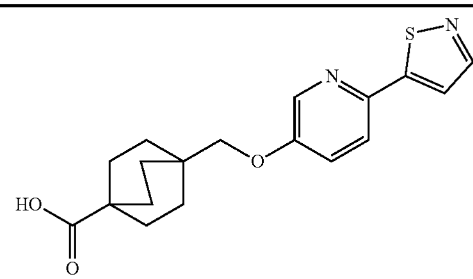 | $^1$H NMR (400 MHz, DMSO-$d_6$) δ ppm 1.42-1.65 (m, 6 H) 1.65-1.78 (m, 6 H) 3.76 (s, 2 H) 7.53 (dd, J = 8.8, 2.8 Hz, 1 H) 7.88 (d, J = 1.7 Hz, 1 H) 7.90-8.02 (m, 1 H) 8.31 (d, J = 2.8 Hz, 1 H) 8.57 (d, J = 1.7 Hz, 1 H). MS ESI/APCI Multi posi: 345 [M + H]$^+$. |

Example 40-1

2-[3-[[6-(5-Oxazolyl)-3-pyridinyl]oxymethyl]phenyl]acetic Acid

[Formula 559]

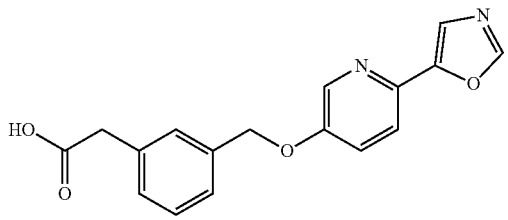

(1) In a test tube for a microwave reaction, tetra-n-butylammonium acetate (269 mg) and palladium acetate (44.6 mg) were added to a solution of the compound (150 mg) obtained in Reference Example 85-1 and oxazole (46.2 mg) in N,N-dimethylacetamide (2 mL), and the mixture was deaerated under reduced pressure and then placed under a nitrogen atmosphere, and the test tube was sealed. The mixture was stirred at 100° C. for 30 minutes under microwave irradiation. The reaction mixture was concentrated, and the residue was purified by silica gel column chromatography (n-hexane only to n-hexane:ethyl acetate=2:3) and then dried under reduced pressure to give methyl 2-[3-[[6-(5-oxazolyl)-3-pyridinyl]oxymethyl]phenyl]acetate (11.4 mg) as a colorless powder.

(2) The compound (11.4 mg) obtained in (1) above was used to perform the synthesis process according to the method described in Example 9-1-(3) thereby giving the title compound (3.45 mg) as a colorless powder.

$^1$H NMR (400 MHz, DMSO-$d_6$) δ ppm 3.52 (s, 2H) 5.21 (s, 2H) 7.22-7.26 (m, 1H) 7.30-7.39 (m, 3H) 7.60 (dd, J=8.8, 2.8 Hz, 1H) 7.64 (s, 1H) 7.73 (d, J=8.8 Hz, 1H) 8.42 (d, J=2.8 Hz, 1H) 8.45-8.47 (m, 1H) 12.02-12.77 (m, 1H).

MS ESI/APCI Multi posi: 311 [M+H]$^+$.

The compound of Example 40-2 below was synthesized using a commercially available compound, according to the method described in Example 40-1. The structure, NMR data, and MS data of the compound are shown in Table 56-1.

TABLE 56-1

| Example No. | Structure | Analytical Data |
|---|---|---|
| 40-2 | 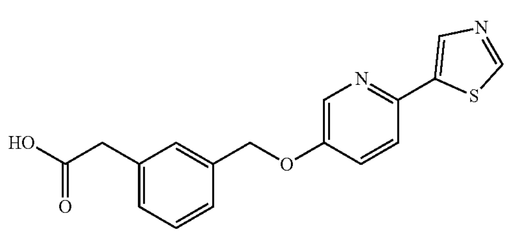 [SMILES: O=C(O)Cc1cccc(COc2ccc(-c3cncs3)nc2)c1] | $^1$H NMR (400 MHz, DMSO-$d_6$) δ ppm 3.58 (s, 2 H) 5.21 (s, 2 H) 7.18-7.28 (m, 1 H) 7.30-7.39 (m, 3 H) 7.58 (dd, J = 8.7, 2.9 Hz, 1 H) 7.97 (d, J = 8.7 Hz, 1 H) 8.36 (d, J = 2.9 Hz, 1 H) 8.42-8.48 (m, 1 H) 9.03-9.09 (m, 1 H) 12.23-12.65 (m, 1 H). MS ESI/APCI Multi posi: 327 [M + H]$^+$. |

Example 41-1

3-[Oxo-[(3R)-3-[[6-(1H-pyrazol-5-yl)-3-pyridinyl]oxymethyl]-1-piperidinyl]methyl]benzenesulfonamide

[Formula 560]

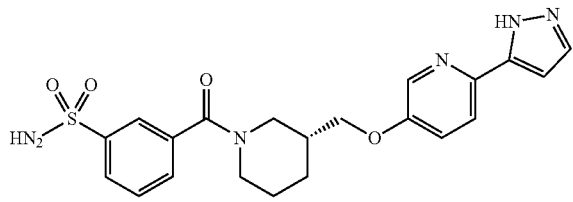

To a solution of the compound (20 mg) obtained in Reference Example 5-1 in N,N-dimethylformamide (1 mL), N,N-diisopropylethylamine (40 μL), 3-sulfamoylbenzoic acid (19 mg), and propylphosphonic anhydride (cyclic trimer) (48% N,N-dimethylformamide solution, about 1.6 mol/L, 96 μL) were added, and the mixture was stirred at room temperature overnight. The mixture was purified by preparative HPLC-MS to give the title compound (6.8 mg) as a colorless amorphous substance.

$^1$H NMR (500 MHz, DMSO-$d_6$, 100° C.) δ ppm 0.90-0.99 (m, 2H) 1.68-1.76 (m, 1H) 1.87-1.96 (m, 1H) 2.01-2.12 (m, 1H) 2.89-3.20 (m, 2H) 3.77-4.17 (m, 3H) 6.70 (s, 1H) 7.11-7.24 (m, 1H) 7.33-7.41 (m, 1H) 7.53-7.63 (m, 3H) 7.76-7.92 (m, 3H) 8.19-8.25 (m, 1H).

MS ESI/APCI Multi posi: 442[M+H]$^+$.
MS ESI/APCI Multi nega: 440[M−H]$^−$.

The compounds of Examples 41-2 to 41-6 below were synthesized using a commercially available carboxylic acid, according to the method described in Example 41-1. The structures, and MS data of the compounds are shown in Table 57-1.

TABLE 57-1

| Example No. | Structure | Analytical Data |
|---|---|---|
| 41-2 | 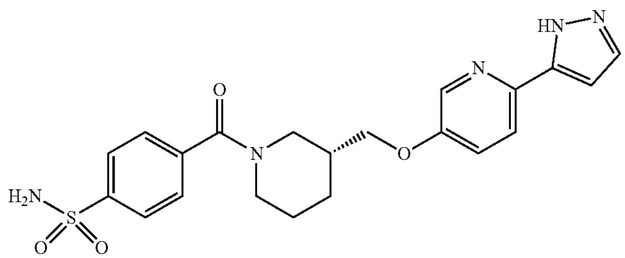 [SMILES: NS(=O)(=O)c1ccc(C(=O)N2CCC[C@@H](COc3ccc(-c4ccn[nH]4)nc3)C2)cc1] | MS ESI/APCI Multi posi: 442 [M + H]$^+$. MS ESI/APCI Multi nega: 440 [M − H]$^−$. |
| 41-3 | 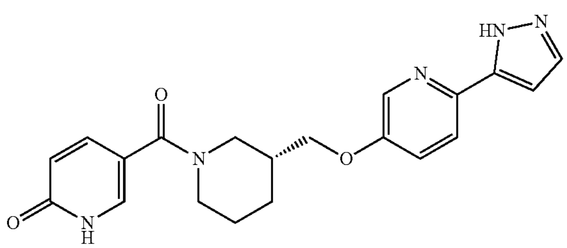 [SMILES: O=C(c1ccc(=O)[nH]c1)N1CCC[C@@H](COc2ccc(-c3ccn[nH]3)nc2)C1] | MS ESI/APCI Multi posi: 380 [M + H]$^+$. MS ESI/APCI Multi nega: 378 [M − H]$^−$. |
| 41-4 | 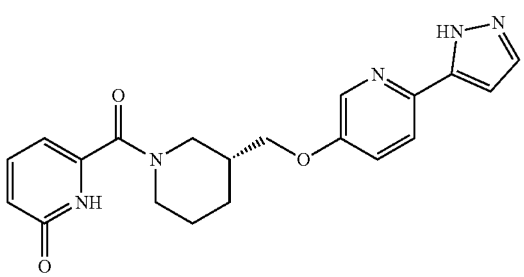 | MS ESI/APCI Multi posi: 380 [M + H]$^+$. MS ESI/APCI Multi nega: 378 [M − H]$^−$. |
| 41-5 | 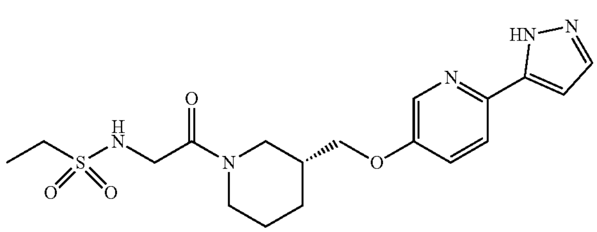 [SMILES: CCS(=O)(=O)NCC(=O)N1CCC[C@@H](COc2ccc(-c3ccn[nH]3)nc2)C1] | MS ESI/APCI Multi posi: 408 [M + H]$^+$. MS ESI/APCI Multi nega: 406 [M − H]$^−$. |

TABLE 57-1-continued

| Example No. | Structure | Analytical Data |
|---|---|---|
| 41-6 | 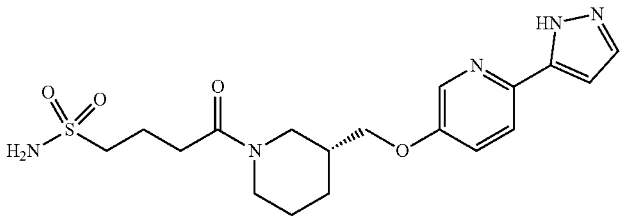 [SMILES: NS(=O)(=O)CCCC(=O)N1CCC[C@@H](COc2ccc(-c3ccn[nH]3)nc2)C1] | MS ESI/APCI Multi posi: 408 [M + H]+.<br>MS ESI/APCI Multi nega: 406 [M − H]−. |

Example 42-1

N-Methyl-3-[[6-(1H-pyrazol-5-yl)-3-pyridinyl]oxymethyl]benzamide

[Formula 561]

To a solution of the compound (50 mg) obtained in Example 22-2 in N,N-dimethylformamide (3 mL), N,N-diisopropylethylamine (115 μL), methylamine hydrochloride (23 mg), and O-(7-azabenzotriazol-1-yl)-N,N,N',N'-tetramethyluronium hexafluorophosphate (HATU) (128 mg) were added, and the mixture was stirred at room temperature for 20 hours. Water was added to the reaction solution, and the resultant mixture was extracted with ethyl acetate. After the obtained organic layer was dried over sodium sulfate, the drying agent was filtered off, and the solvent was distilled off under reduced pressure. The obtained residue was purified by silica gel column chromatography (chloroform only to chloroform:methanol=9:1), and the obtained crude product was then powdered from a n-hexane:diethyl ether (1:1) mixed solution to give the title compound (23 mg) as a colorless powder.

$^1$H NMR (600 MHz, DMSO-$d_6$) δ ppm 2.79 (d, J=4.5 Hz, 3H) 5.27 (s, 2H) 6.71-6.75 (m, 1H) 7.46-7.98 (m, 6H) 8.33-8.40 (m, 1H) 8.43-8.52 (m, 1H).

MS ESI/APCI Multi posi: 309[M+H]+.

The compounds of Examples 42-2 to 42-24 below were synthesized using any of the compounds obtained in Examples 22-1 to 22-4, 24-1 and 24-2, 28-1, and 38-1, and a commercially available amine, according to the method described in Example 42-1. The structures, NMR data, and MS data of the compounds are shown in Tables 58-1 to 58-4.

TABLE 58-1

| Example No. | Structure | Analytical Data |
|---|---|---|
| 42-2 | 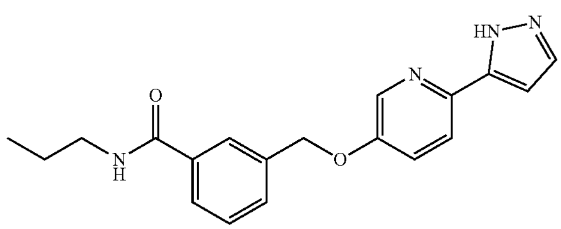 [SMILES: CCCNC(=O)c1cccc(COc2ccc(-c3ccn[nH]3)nc2)c1] | $^1$H NMR (600 MHz, DMSO-$d_6$) δ ppm 0.89 (t, J = 7.4 Hz, 3 H) 1.50-1.57 (m, 2 H) 3.20-3.25 (m, 2 H) 5.27 (s, 2 H) 6.73 (s, 1 H) 7.48-7.57 (m, 2 H) 7.57-7.67 (m, 1 H) 7.70-7.92 (m, 2 H) 7.96 (s, 1 H) 8.34-8.40 (m, 1 H) 8.45-8.54 (m, 1 H).<br>MS ESI/APCI Multi posi: 337 [M + H]+. |
| 42-3 | 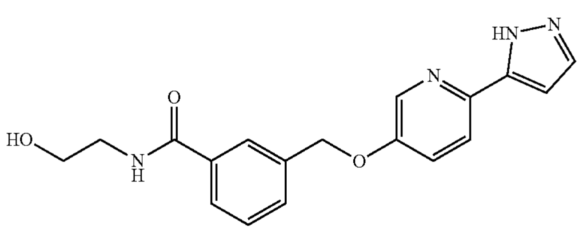 [SMILES: O=C(NCCO)c1cccc(COc2ccc(-c3ccn[nH]3)nc2)c1] | $^1$H NMR (600 MHz, DMSO-$d_6$) δ ppm 3.33-3.39 (m, 2 H) 3.48-3.55 (m, 2 H) 4.70-4.75 (m, 1 H) 5.26 (s, 2 H) 6.73 (s, 1 H) 7.45-7.66 (m, 3 H) 7.72-7.93 (m, 2 H) 7.98 (s, 1 H) 8.34-8.41 (m, 1 H) 8.43-8.55 (m, 1 H).<br>MS ESI/APCI Multi posi: 339 [M + H]+. |

TABLE 58-1-continued

| Example No. | Structure | Analytical Data |
|---|---|---|
| 42-4 | 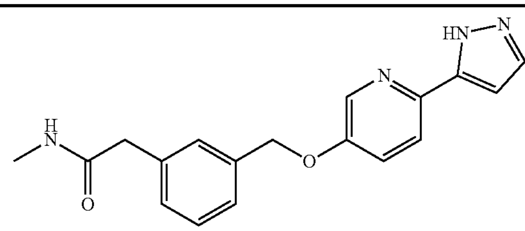 | $^1$H NMR (600 MHz, DMSO-d$_6$) δ ppm 2.57 (d, J = 5.0 Hz, 3 H) 3.41 (s, 2 H) 5.18 (s, 2 H) 6.73 (s, 1 H) 7.22-7.25 (m, 1 H) 7.31-7.37 (m, 3 H) 7.46-7.60 (m, 1 H) 7.72-8.02 (m, 2 H) 8.32-8.39 (m, 1 H) 12.90 (br s, 0.7 H) 13.33 (br s, 0.3 H).<br>MS ESI/APCI Multi posi: 323 [M + H]$^+$. |
| 42-5 | 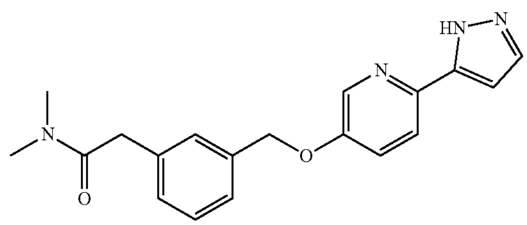 [SMILES: CN(C)C(=O)Cc1cccc(COc2ccc(-c3ccn[nH]3)nc2)c1] | $^1$H NMR (600 MHz, CHLOROFORM-d) δ ppm 2.97 (s, 3 H) 3.01 (s, 3 H) 3.74 (s, 2 H) 5.13 (s, 2 H) 6.69-6.71 (m, 1 H) 7.23-7.26 (m, 1 H) 7.30-7.38 (m, 4 H) 7.61-7.67 (m, 2 H) 8.34-8.37 (m, 1 H).<br>MS ESI/APCI Multi posi: 337 [M + H]$^+$. |
| 42-6 | 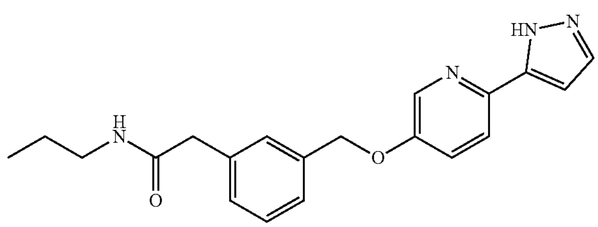 [SMILES: CCCNC(=O)Cc1cccc(COc2ccc(-c3ccn[nH]3)nc2)c1] | $^1$H NMR (600 MHz, DMSO-d$_6$) δ ppm 0.82 (t, J = 7.4 Hz, 3 H) 1.36-1.42 (m, 2 H) 2.96-3.03 (m, 2 H) 3.42 (s, 2 H) 5.19 (s, 2 H) 6.72-6.74 (m, 1 H) 7.22-7.25 (m, 1 H) 7.31-7.37 (m, 3 H) 7.48-7.61 (m, 1 H) 7.81-7.90 (m, 1 H) 7.99-8.07 (m, 1 H) 8.32-8.37 (m, 1 H).<br>MS ESI/APCI Multi posi: 351 [M + H]$^+$. |
| 42-7 | 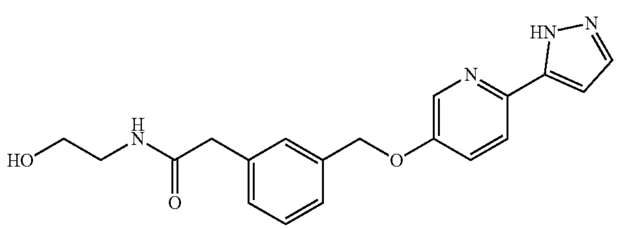 [SMILES: O=C(Cc1cccc(COc2ccc(-c3ccn[nH]3)nc2)c1)NCCO] | $^1$H NMR (600 MHz, DMSO-d$_6$) δ ppm 3.09-3.15 (m, 2 H) 3.37-3.45 (m, 4 H) 4.67-4.70 (m, 1 H) 5.18 (s, 2 H) 6.73 (s, 1 H) 7.23-7.26 (m, 1 H) 7.31-7.38 (m, 3 H) 7.46-7.63 (m, 1 H) 7.73-7.92 (m, 1 H) 8.05-8.11 (m, 1 H) 8.31-8.39 (m, 1 H).<br>MS ESI/APCI Multi posi: 353 [M + H]$^+$. |

TABLE 58-2

| Example No. | Structure | Analytical Data |
|---|---|---|
| 42-8 | 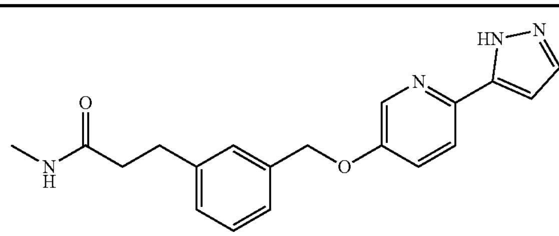 | $^1$H NMR (600 MHz, DMSO-d$_6$) δ ppm 2.34-2.39 (m, 2 H) 2.55 (d, J = 4.5 Hz, 3 H) 2.83 (t, J = 7.8 Hz, 2 H) 5.17 (s, 2 H) 6.73 (s, 1 H) 7.16-7.20 (m, 1 H) 7.27-7.34 (m, 3 H) 7.44-7.61 (m, 1 H) 7.68-7.95 (m, 2 H) 8.31-8.39 (m, 1 H).<br>MS ESI/APCI Multi posi: 337 [M + H]$^+$. |
| 42-9 | 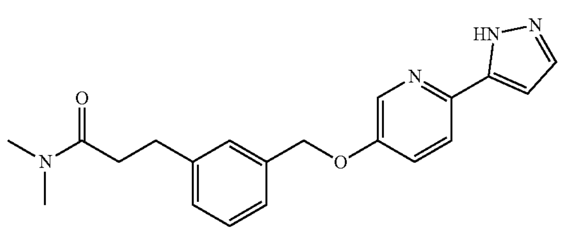 [SMILES: CN(C)C(=O)CCc1cccc(COc2ccc(-c3ccn[nH]3)nc2)c1] | $^1$H NMR (600 MHz, DMSO-d$_6$) δ ppm 2.58-2.62 (m, 2 H) 2.78-2.84 (m, 5 H) 2.89-2.92 (m, 3 H) 5.17 (s, 2 H) 6.73 (s, 1 H) 7.20-7.24 (m, 1 H) 7.27-7.36 (m, 3 H) 7.46-7.62 (m, 1 H) 7.66-7.94 (m, 2 H) 8.30-8.40 (m, 1 H).<br>MS ESI/APCI Multi posi: 351 [M + H]$^+$. |

TABLE 58-2-continued

| Example No. | Structure | Analytical Data |
|---|---|---|
| 42-10 | 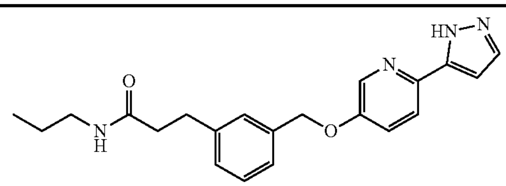 | $^1$H NMR (600 MHz, DMSO-d$_6$) δ ppm 0.78 (t, J = 7.4 Hz, 3 H) 1.32-1.38 (m, 2 H) 2.34-2.40 (m, 2 H) 2.83 (t, J = 7.8 Hz, 2 H) 2.92-3.02 (m, 2 H) 5.16 (s, 2 H) 6.71-6.75 (m, 1 H) 7.17-7.20 (m, 1 H) 7.27-7.33 (m, 3 H) 7.43-7.60 (m, 1 H) 7.72-7.91 (m, 2 H) 8.31-8.38 (m, 1 H).<br>MS ESI/APCI Multi posi: 365 [M + H]$^+$.<br>MS ESI/APCI Multi nega: 363 [M − H]$^−$. |
| 42-11 | 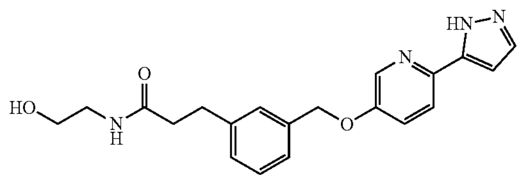 [SMILES: O=C(CCc1cccc(COc2ccc(-c3ccn[nH]3)nc2)c1)NCCO] | $^1$H NMR (600 MHz, DMSO-d$_6$) δ ppm 2.38 (t, J = 7.8 Hz, 2 H) 2.83 (t, J = 7.8 Hz, 2 H) 3.07-3.13 (m, 2 H) 3.33-3.39 (m, 2 H) 4.62-4.66 (m, 1 H) 5.17 (s, 2 H) 6.72-6.74 (m, 1 H) 7.17-7.20 (m, 1 H) 7.28-7.33 (m, 3 H) 7.47-7.60 (m, 1 H) 7.71-7.93 (m, 2 H) 8.32-8.38 (m, 1 H).<br>MS ESI/APCI Multi posi: 367 [M + H]$^+$.<br>MS ESI/APCI Multi nega: 365 [M − H]$^−$. |
| 42-12 | 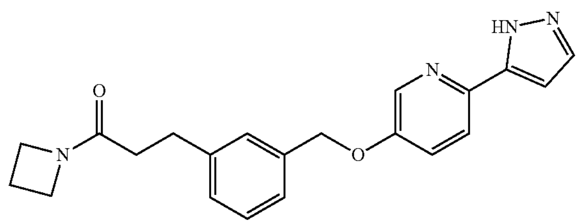 [SMILES: O=C(CCc1cccc(COc2ccc(-c3ccn[nH]3)nc2)c1)N1CCC1] | $^1$H NMR (600 MHz, CHLOROFORM-d) δ ppm 2.15-2.20 (m, 2 H) 2.34-2.38 (m, 2 H) 2.93-3.00 (m, 2 H) 3.93 (t, J = 7.6 Hz, 2 H) 3.99 (t, J = 7.6 Hz, 2 H) 5.12 (s, 2 H) 6.68-6.69 (m, 1 H) 7.20-7.22 (m, 1 H) 7.27-7.35 (m, 5 H) 7.61-7.63 (m, 1 H) 7.64-7.67 (m, 1 H) 8.34-8.36 (m, 1 H).<br>MS ESI/APCI Multi posi: 363 [M + H]$^+$. |
| 42-13 | 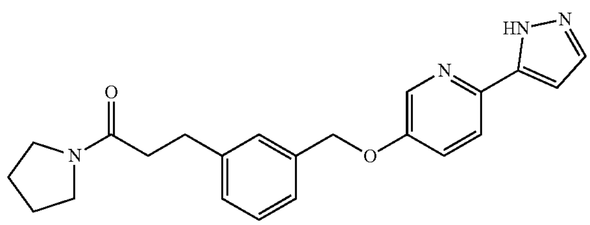 [SMILES: O=C(CCc1cccc(COc2ccc(-c3ccn[nH]3)nc2)c1)N1CCCC1] | $^1$H NMR (600 MHz, DMSO-d$_6$) δ ppm 1.69-1.75 (m, 2 H) 1.77-1.82 (m, 2 H) 2.53 (t, J = 7.8 Hz, 2 H) 2.83 (t, J = 7.8 Hz, 2 H) 3.23-3.32 (m, 4 H) 5.17 (s, 2 H) 6.73 (s, 1 H) 7.20-7.24 (m, 1 H) 7.28-7.35 (m, 3 H) 7.43-7.60 (m, 1 H) 7.70-7.95 (m, 2 H) 8.31-8.39 (m, 1 H) 12.90 (br s, 0.7 H) 13.32 (br s, 0.3 H).<br>MS ESI/APCI Multi posi: 377 [M + H]$^+$. |

TABLE 58-3

| Example No. | Structure | Analytical Data |
|---|---|---|
| 42-14 | 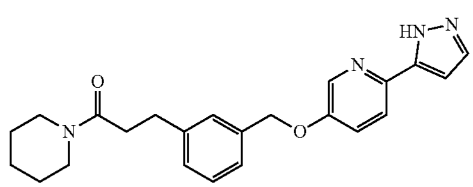 [SMILES: O=C(CCc1cccc(COc2ccc(-c3ccn[nH]3)nc2)c1)N1CCCCC1] | $^1$H NMR (600 MHz, CHLOROFORM-d) δ ppm 1.43-1.54 (m, 4 H) 1.58-1.63 (m, 2 H) 2.61-2.64 (m, 2 H) 2.98-3.02 (m, 2 H) 3.31-3.35 (m, 2 H) 3.53-3.57 (m, 2 H) 5.12 (s, 2 H) 6.68-6.69 (m, 1 H) 7.21-7.23 (m, 1 H) 7.27-7.35 (m, 4 H) 7.60-7.67 (m, 2 H) 8.35-8.37 (m, 1 H).<br>MS ESI/APCI Multi posi: 391 [M + H]$^+$. |
| 42-15 | 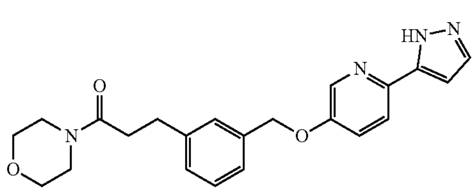 [SMILES: O=C(CCc1cccc(COc2ccc(-c3ccn[nH]3)nc2)c1)N1CCOCC1] | $^1$H NMR (600 MHz, CHLOROFORM-d) δ ppm 2.59-2.67 (m, 2 H) 2.96-3.07 (m, 2 H) 3.32-3.41 (m, 2 H) 3.49-3.58 (m, 2 H) 3.58-3.67 (m, 4 H) 5.12 (s, 2 H) 6.68-6.70 (m, 1 H) 7.19-7.23 (m, 1 H) 7.27-7.35 (m, 4 H) 7.61-7.67 (m, 2 H) 8.33-8.36 (m, 1 H).<br>MS ESI/APCI Multi posi: 393 [M + H]$^+$. |

TABLE 58-3-continued

| Example No. | Structure | Analytical Data |
|---|---|---|
| 42-16 | 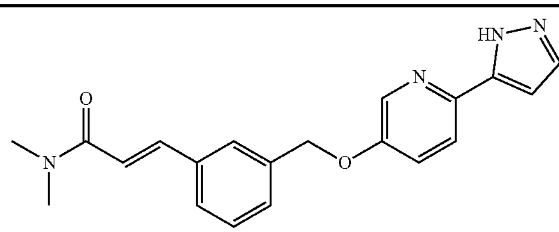 | ¹H NMR (600 MHz, DMSO-d₆) δ ppm 2.93 (s, 3 H) 3.17 (s, 3 H) 5.23 (s, 2 H) 6.72-6.75 (m, 1 H) 7.24 (d, J = 15.7 Hz, 1 H) 7.43-7.51 (m, 3 H) 7.53-7.62 (m, 1 H) 7.64-7.77 (m, 2 H) 7.78-7.92 (m, 2 H) 8.35-8.40 (m, 1 H).<br>MS ESI/APCI Multi posi: 349 [M + H]⁺. |
| 42-17 | 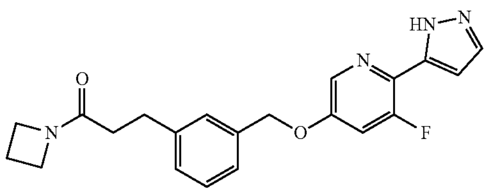 [SMILES: O=C(CCc1cccc(COc2cnc(-c3ccn[nH]3)c(F)c2)c1)N1CCC1] | ¹H NMR (600 MHz, DMSO-d₆) δ ppm 2.07-2.13 (m, 2 H) 2.31 (t, J = 7.6 Hz, 2 H) 2.80 (t, J = 7.6 Hz, 2 H) 3.79 (t, J = 7.6 Hz, 2 H) 3.97 (t, J = 7.6 Hz, 2 H) 5.22 (s, 2 H) 6.68 (s, 1 H) 7.20-7.23 (m, 1 H) 7.29-7.36 (m, 3 H) 7.52-7.87 (m, 2 H) 8.26-8.34 (m, 1 H) 13.02 (br s, 0.4 H) 13.41 (br s, 0.6 H).<br>MS ESI/APCI Multi posi: 381 [M + H]⁺. |
| 42-18 | 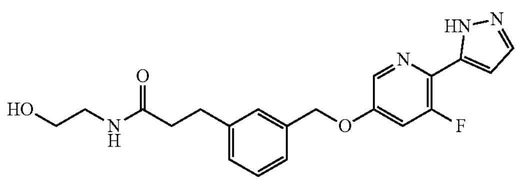 [SMILES: O=C(CCc1cccc(COc2cnc(-c3ccn[nH]3)c(F)c2)c1)NCCO] | ¹H NMR (400 MHz, DMSO-d₆) δ ppm 2.35-2.43 (m, 2 H) 2.80-2.87 (m, 2 H) 3.07-3.14 (m, 2 H) 3.33-3.39 (m, 2 H) 4.59-4.64 (m, 1 H) 5.17-5.24 (m, 2 H) 6.66-6.72 (m, 1 H) 7.17-7.23 (m, 1 H) 7.28-7.35 (m, 3 H) 7.53-7.74 (m, 1 H) 7.77-7.87 (m, 2 H) 8.27-8.34 (m, 1 H) 13.02 (br s, 0.4 H) 13.41 (br s, 0.6 H).<br>MS ESI/APCI Multi posi: 385 [M + H]⁺. |
| 42-19 | 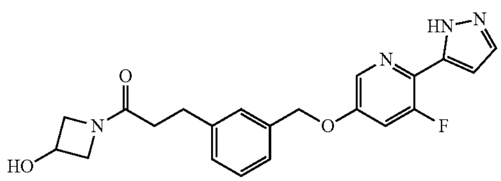 [SMILES: O=C(CCc1cccc(COc2cnc(-c3ccn[nH]3)c(F)c2)c1)N1CC(O)C1] | ¹H NMR (400 MHz, DMSO-d₆) δ ppm 2.31-2.39 (m, 2 H) 2.77-2.83 (m, 2 H) 3.51-3.57 (m, 1 H) 3.73-3.79 (m, 1 H) 3.96-4.02 (m, 1 H) 4.14-4.20 (m, 1 H) 4.35-4.42 (m, 1 H) 5.21 (s, 2 H) 5.66 (d, J = 6.1 Hz, 1 H) 6.67-6.71 (m, 1 H) 7.19-7.25 (m, 1 H) 7.29-7.35 (m, 3 H) 7.53-7.79 (m, 2 H) 8.30 (s, 1 H).<br>MS ESI/APCI Multi posi: 397 [M + H]⁺.<br>MS ESI/APCI Multi nega: 395 [M − H]⁻. |

TABLE 58-4

| Example No. | Structure | Analytical Data |
|---|---|---|
| 42-20 | 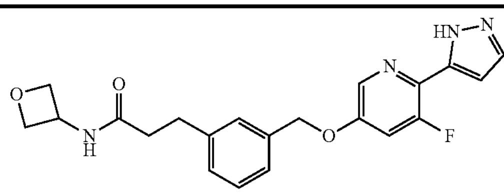 | ¹H NMR (400 MHz, DMSO-d₆) δ ppm 2.38-2.45 (m, 2 H) 2.81-2.89 (m, 2 H) 4.32-4.38 (m, 2 H) 4.62-4.80 (m, 3 H) 5.21 (s, 2 H) 6.69 (s, 1 H) 7.16-7.25 (m, 1 H) 7.28-7.36 (m, 3 H) 7.51-7.89 (m, 2 H) 8.26-8.34 (m, 1 H) 8.52-8.62 (m, 1 H).<br>MS ESI/APCI Multi posi: 397 [M + H]⁺.<br>MS ESI/APCI Multi nega: 395 [M − H]⁻. |
| 42-21 | 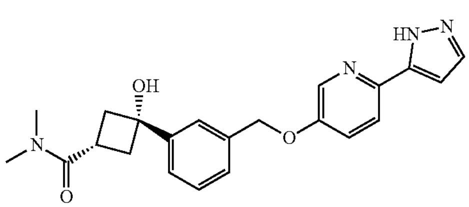 [SMILES: CN(C)C(=O)[C@H]1C[C@](O)(c2cccc(COc3ccc(-c4ccn[nH]4)nc3)c2)C1] | ¹H NMR (600 MHz, CHLOROFORM-d) δ ppm 2.53-2.63 (m, 2 H) 2.82-2.95 (m, 2 H) 3.02 (s, 3 H) 3.03 (s, 3 H) 3.20-3.27 (m, 1 H) 5.16 (s, 2 H) 6.69 (d, J = 1.8 Hz, 1 H) 7.33 (dd, J = 8.7, 2.5 Hz, 1 H) 7.34-7.38 (m, 1 H) 7.39-7.45 (m, 1 H) 7.46-7.52 (m, 1 H) 7.56-7.61 (m, 1 H) 7.62 (d, J = 1.8 Hz, 1 H) 7.66 (d, J = 8.7 Hz, 1 H) 8.37 (br d, J = 2.5 Hz, 1 H).<br>MS ESI/APCI Multi posi: 393 [M + H]⁺. |
| 42-22 | 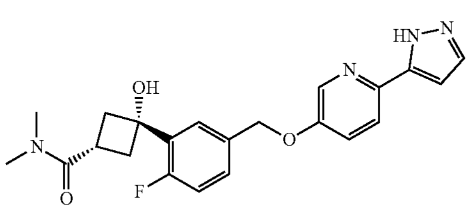 [SMILES: CN(C)C(=O)[C@H]1C[C@](O)(c2cc(COc3ccc(-c4ccn[nH]4)nc3)ccc2F)C1] | ¹H NMR (600 MHz, CHLOROFORM-d) δ ppm 2.51-2.64 (m, 2 H) 3.04 (s, 3 H) 3.04 (s, 3 H) 3.06-3.13 (m, 2 H) 3.34-3.41 (m, 1 H) 5.10 (s, 2 H) 6.69 (d, J = 1.7 Hz, 1 H) 7.05-7.12 (m, 1 H) 7.32 (dd, J = 8.6, 2.6 Hz, 1 H) 7.33-7.38 (m, 1 H) 7.54-7.61 (m, 1 H) 7.63 (d, J = 1.7 Hz, 1 H) 7.67 (d, J = 8.6 Hz, 1 H) 8.35 (d, J = 2.6 Hz, 1 H).<br>MS ESI/APCI Multi posi: 411 [M + H]⁺. |

TABLE 58-4-continued

| Example No. | Structure | Analytical Data |
|---|---|---|
| 42-23 | 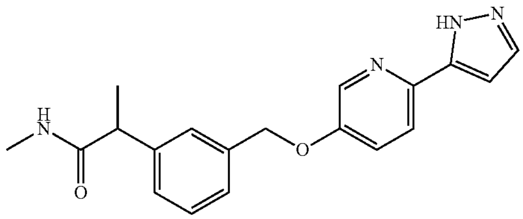 [SMILES: CNC(=O)C(C)c1cccc(COc2ccc(-c3ccn[nH]3)nc2)c1] | ¹H NMR (400 MHz, DMSO-d₆) δ ppm 1.32 (d, J = 7.0 Hz, 3 H) 2.54 (d, J = 4.5 Hz, 3 H) 3.59 (q, J = 7.0 Hz, 1 H) 5.18 (br s, 2 H) 6.64-8.46 (m, 10 H).<br>MS ESI posi: 337 [M + H]⁺. |
| 42-24 | 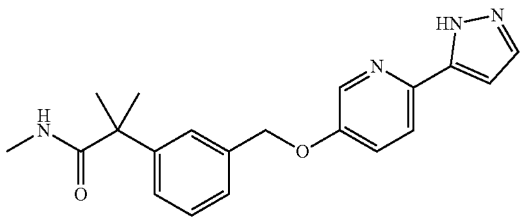 [SMILES: CNC(=O)C(C)(C)c1cccc(COc2ccc(-c3ccn[nH]3)nc2)c1] | ¹H NMR (400 MHz, DMSO-d₆) δ ppm 1.45 (br s, 6 H) 2.50 (br s, 3 H) 5.19 (s, 2 H) 6.13-8.83 (m, 10 H).<br>MS ESI posi: 351 [M + H]⁺. |

Example 43-1

1-(3-Fluoro-1-azetidinyl)-3-[3-[[6-(1H-pyrazol-5-yl)-3-pyridinyl]oxymethyl]phenyl]-1-propanone

[Formula 562]

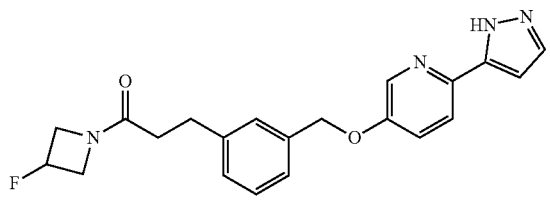

To a solution of the compound (50 mg) obtained in Example 22-4 in N,N-dimethylformamide (1 mL), 3-fluoroazetidine hydrochloride (35 mg), N,N-diisopropylethylamine (105 μL), and propylphosphonic anhydride (48% N,N-dimethylformamide solution, 193 μL) were added, and the mixture was stirred at room temperature for 20 hours. Water was added to the reaction mixture, and the resultant mixture was extracted with ethyl acetate. The organic layer was passed through a phase separator, and the solvent was distilled off under reduced pressure. The obtained residue was purified by silica gel column chromatography (chloroform only to chloroform:methanol=19:1) to give the title compound (18 mg) as a colorless amorphous substance.

¹H NMR (600 MHz, DMSO-d₆) δ ppm 2.32-2.45 (m, 2H) 2.78-2.83 (m, 2H) 3.79-3.89 (m, 1H) 4.04-4.18 (m, 2H) 4.29-4.36 (m, 1H) 5.17 (s, 2H) 5.26-5.40 (m, 1H) 6.73 (s, 1H) 7.19-7.23 (m, 1H) 7.28-7.36 (m, 3H) 7.44-7.61 (m, 1H) 7.67-7.97 (m, 2H) 8.30-8.39 (m, 1H).
MS ESI/APCI Multi posi: 381[M+H]⁺.

The compounds of Examples 43-2 to 43-16 below were synthesized using a compound obtained in Example 22-4 or 26-1 and a compound obtained in Reference Example 87-1 or 88-1, or a commercially available amine, according to the method described in Example 43-1. The structures, NMR data, and MS data of the compounds are shown in Tables 59-1 to 59-3.

TABLE 59-1

| Example No. | Structure | Analytical Data |
|---|---|---|
| 43-2 | 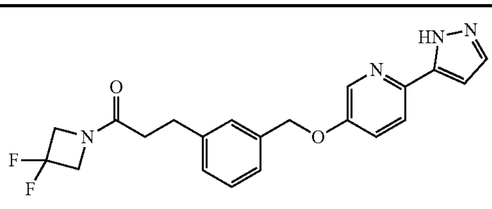 | ¹H NMR (600 MHz, DMSO-d₆) δ ppm 2.45-2.49 (m, 2 H) 2.80-2.85 (m, 2 H) 4.24 (t, J = 12.5 Hz, 2 H) 4.49 (t, J = 12.5 Hz, 2 H) 5.17 (s, 2 H) 6.73 (s, 1 H) 7.19-7.24 (m, 1 H) 7.29-7.36 (m, 3 H) 7.46-7.60 (m, 1 H) 7.72-7.95 (m, 2 H) 8.32-8.39 (m, 1 H) 12.90 (br s, 0.7 H) 13.33 (br s, 0.3 H).<br>MS ESI/APCI Multi posi: 399 [M + H]⁺. |
| 43-3 | 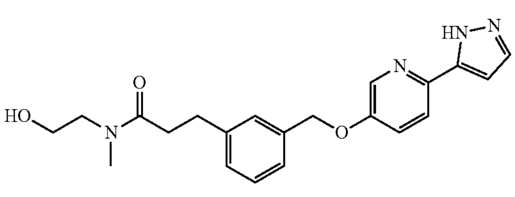 [SMILES: CN(CCO)C(=O)CCc1cccc(COc2ccc(-c3ccn[nH]3)nc2)c1] | ¹H NMR (600 MHz, DMSO-d₆) δ ppm 2.57-2.62 (m, 1 H) 2.63-2.71 (m, 1 H) 2.80-2.84 (m, 4 H) 2.96 (s, 1 H) 3.29-3.35 (m, 2 H) 3.43-3.51 (m, 2 H) 4.61-4.64 (m, 0.5 H) 4.78-4.81 (m, 0.5 H) 5.17 (s, 2 H) 6.73 (s, 1 H) 7.20-7.24 (m, 1 H) 7.27-7.37 (m, 3 H) 7.45-7.60 (m, 1 H) 7.73-7.94 (m, 2 H) 8.31-8.39 (m, 1 H) 12.90 (br s, 0.7 H) 13.33 (br s, 0.3 H).<br>MS ESI/APCI Multi posi: 381 [M + H]⁺. |

TABLE 59-1-continued

| Example No. | Structure | Analytical Data |
|---|---|---|
| 43-4 | 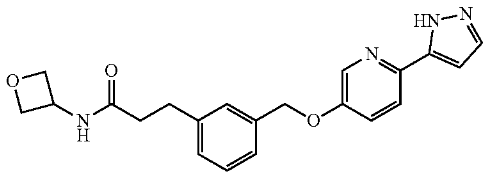 [SMILES: O=C(CCc1cccc(COc2ccc(-c3ccn[nH]3)nc2)c1)NC1COC1] | ¹H NMR (600 MHz, DMSO-d₆) δ ppm 2.41 (t, J = 7.7 Hz, 2 H) 2.84 (t, J = 7.7 Hz, 2 H) 4.33-4.37 (m, 2 H) 4.66-4.70 (m, 2 H) 4.72-4.79 (m, 1 H) 5.17 (s, 2 H) 6.73 (s, 1 H) 7.17-7.21 (m, 1 H) 7.28-7.34 (m, 3 H) 7.43-7.95 (m, 3 H) 8.30-8.39 (m, 1 H) 8.55-8.63 (m, 1 H) 12.90 (br s, 0.7 H) 13.33 (br s, 0.3 H).<br>MS ESI/APCI Multi posi: 379 [M + H]⁺. |
| 43-5 | 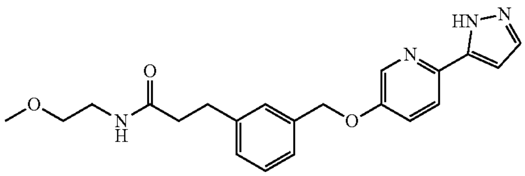 [SMILES: COCCNC(=O)CCc1cccc(COc2ccc(-c3ccn[nH]3)nc2)c1] | ¹H NMR (600 MHz, DMSO-d₆) δ ppm 2.39 (t, J = 7.6 Hz, 2 H) 2.83 (t, J = 7.6 Hz, 2 H) 3.16-3.21 (m, 5 H) 3.27-3.31 (m, 2 H) 5.17 (s, 2 H) 6.73 (s, 1 H) 7.17-7.20 (m, 1 H) 7.27-7.33 (m, 3 H) 7.44-7.65 (m, 1 H) 7.67-7.95 (m, 2 H) 8.31-8.39 (m, 1 H) 12.90 (br s, 0.7 H) 13.33 (br s, 0.3 H).<br>MS ESI/APCI Multi posi: 381 [M + H]⁺. |
| 43-6 | 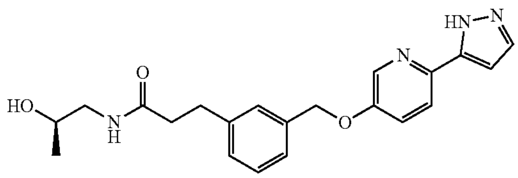 [SMILES: C[C@@H](O)CNC(=O)CCc1cccc(COc2ccc(-c3ccn[nH]3)nc2)c1] | ¹H NMR (600 MHz, DMSO-d₆) δ ppm 0.96 (d, J = 6.2 Hz, 3 H) 2.37-2.43 (m, 2 H) 2.79-2.87 (m, 2 H) 2.94-3.01 (m, 2 H) 3.56-3.62 (m, 1 H) 4.63 (d, J = 4.5 Hz, 1 H) 5.16 (s, 2 H) 6.73 (s, 1 H) 7.17-7.21 (m, 1 H) 7.27-7.33 (m, 3 H) 7.46-7.59 (m, 1 H) 7.74-7.93 (m, 3 H) 8.31-8.39 (m, 1 H) 12.90 (br s, 0.7 H) 13.32 (br s, 0.3 H).<br>MS ESI/APCI Multi posi: 381 [M + H]⁺.<br>MS ESI/APCI Multi nega: 379 [M − H]⁻. |
| 43-7 | 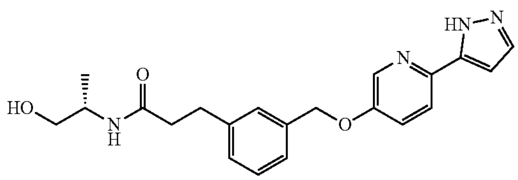 [SMILES: C[C@@H](CO)NC(=O)CCc1cccc(COc2ccc(-c3ccn[nH]3)nc2)c1] | ¹H NMR (600 MHz, DMSO-d₆) δ ppm 0.98 (d, J = 6.6 Hz, 3 H) 2.32-2.41 (m, 2 H) 2.78-2.87 (m, 2 H) 3.11-3.21 (m, 1 H) 3.29-3.32 (m, 1 H) 3.71-3.78 (m, 1 H) 4.61-4.67 (m, 1 H) 5.16 (s, 2 H) 6.73 (s, 1 H) 7.17-7.21 (m, 1 H) 7.27-7.34 (m, 3 H) 7.45-7.65 (m, 2 H) 7.71-7.94 (m, 2 H) 8.31-8.40 (m, 1 H) 12.90 (br s, 0.7 H) 13.33 (br s, 0.3 H).<br>MS ESI/APCI Multi posi: 381 [M + H]⁺.<br>MS ESI/APCI Multi nega: 379 [M − H]⁻. |

TABLE 59-2

| Example No. | Structure | Analytical Data |
|---|---|---|
| 43-8 | 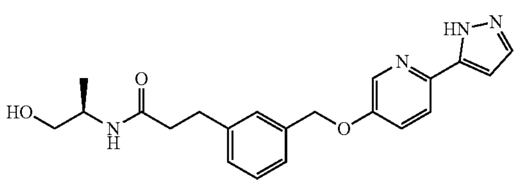 [SMILES: C[C@H](CO)NC(=O)CCc1cccc(COc2ccc(-c3ccn[nH]3)nc2)c1] | ¹H NMR (600 MHz, DMSO-d₆) δ ppm 0.98 (d, J = 6.6 Hz, 3 H) 2.32-2.41 (m, 2 H) 2.78-2.87 (m, 2 H) 3.11-3.21 (m, 1 H) 3.29-3.32 (m, 1 H) 3.71-3.78 (m, 1 H) 4.61-4.67 (m, 1 H) 5.16 (s, 2 H) 6.73 (s, 1 H) 7.17-7.21 (m, 1 H) 7.27-7.34 (m, 3 H) 7.45-7.65 (m, 2 H) 7.71-7.94 (m, 2 H) 8.31-8.40 (m, 1 H) 13.33 (br s, 0.3 H).<br>MS ESI/APCI Multi posi: 381 [M + H]⁺.<br>MS ESI/APCI Multi nega: 379 [M − H]⁻. |
| 43-9 | 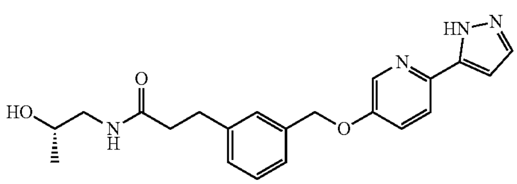 [SMILES: C[C@H](O)CNC(=O)CCc1cccc(COc2ccc(-c3ccn[nH]3)nc2)c1] | ¹H NMR (600 MHz, DMSO-d₆) δ ppm 0.96 (d, J = 6.2 Hz, 3 H) 2.37-2.43 (m, 2 H) 2.79-2.87 (m, 2 H) 2.94-3.01 (m, 2 H) 3.56-3.62 (m, 1 H) 4.63 (d, J = 4.5 Hz, 1 H) 5.16 (s, 2 H) 6.73 (s, 1 H) 7.17-7.21 (m, 1 H) 7.27-7.33 (m, 3 H) 7.46-7.59 (m, 1 H) 7.74-7.93 (m, 3 H) 8.31-8.39 (m, 1 H) 12.90 (br s, 0.7 H) 13.32 (br s, 0.3 H).<br>MS ESI/APCI Multi posi: 381 [M + H]⁺.<br>MS ESI/APCI Multi nega: 379 [M − H]⁻. |
| 43-10 | 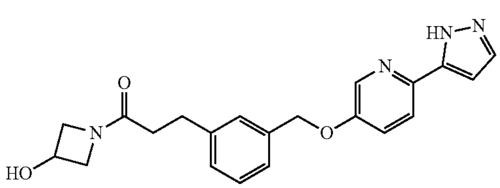 [SMILES: O=C(CCc1cccc(COc2ccc(-c3ccn[nH]3)nc2)c1)N1CC(O)C1] | ¹H NMR (600 MHz, DMSO-d₆) δ ppm 2.32-2.37 (m, 2 H) 2.77-2.82 (m, 2 H) 3.51-3.57 (m, 1 H) 3.74-3.78 (m, 1 H) 3.96-4.02 (m, 1 H) 4.15-4.19 (m, 1 H) 4.36-4.41 (m, 1 H) 5.17 (s, 2 H) 6.72-6.74 (m, 1 H) 7.18-7.22 (m, 1 H) 7.28-7.35 (m, 3 H) 7.50-7.55 (m, 1 H) 7.68 (br s, 1 H) 7.82-7.89 (m, 1 H) 8.33-8.37 (m, 1 H).<br>MS ESI/APCI Multi posi: 379 [M + H]⁺. |

TABLE 59-2-continued

| Example No. | Structure | Analytical Data |
|---|---|---|
| 43-11 | 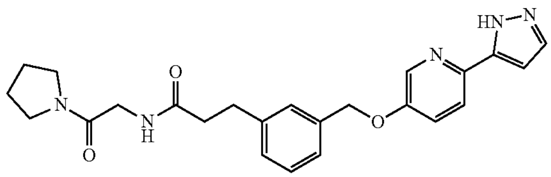 [SMILES: O=C(CCc1cccc(COc2ccc(-c3ccn[nH]3)nc2)c1)NCC(=O)N1CCCC1] | $^1$H NMR (600 MHz, DMSO-d$_6$) δ ppm 1.68-1.74 (m, 2 H) 1.79-1.85 (m, 2 H) 2.42-2.50 (m, 2 H) 2.78-2.83 (m, 2 H) 3.22-3.38 (m, 4 H) 3.79 (d, J = 5.8 Hz, 2 H) 5.14 (s, 2 H) 6.67-6.72 (m, 1 H) 7.15-7.19 (m, 1 H) 7.22-7.33 (m, 3 H) 7.42-7.59 (m, 1 H) 7.63-7.91 (m, 2 H) 7.94-7.99 (m, 1 H) 8.27-8.35 (m, 1 H).<br>MS ESI/APCI Multi posi: 434 [M + H]$^+$. |
| 43-12 | 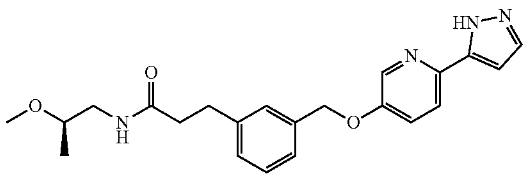 [SMILES: CO[C@H](C)CNC(=O)CCc1cccc(COc2ccc(-c3ccn[nH]3)nc2)c1] | $^1$H NMR (600 MHz, DMSO-d$_6$) δ ppm 0.97 (d, J = 6.2 Hz, 3 H) 2.41 (t, J = 7.7 Hz, 2 H) 2.83 (t, J = 7.7 Hz, 2 H) 3.04-3.08 (m, 2 H) 3.19 (s, 3 H) 3.24-3.29 (m, 1 H) 5.16 (s, 2 H) 6.73 (s, 1 H) 7.18-7.20 (m, 1 H) 7.28-7.33 (m, 3 H) 7.45-7.62 (m, 1 H) 7.72-7.93 (m, 3 H) 8.31-8.38 (m, 1 H) 12.90 (br s, 0.7 H) 13.32 (br s, 0.3 H).<br>MS ESI/APCI Multi posi: 395 [M + H]$^+$. |
| 43-13 | 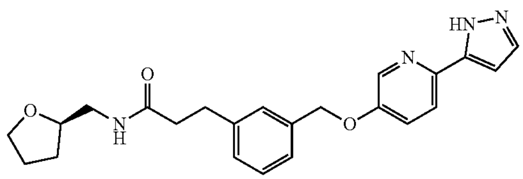 [SMILES: O=C(CCc1cccc(COc2ccc(-c3ccn[nH]3)nc2)c1)NC[C@H]1CCCO1] | $^1$H MR (600 MHz, DMSO-d$_6$) δ ppm 1.37-1.44 (m, 1 H) 1.69-1.81 (m, 3 H) 2.37-2.43 (m, 2 H) 2.78-2.87 (m, 2 H) 3.05-3.13 (m, 2 H) 3.54-3.59 (m, 1 H) 3.68-3.79 (m, 2 H) 5.16 (s, 2 H) 6.73 (s, 1 H) 7.17-7.21 (m, 1 H) 7.27-7.34 (m, 3 H) 7.45-7.59 (m, 1 H) 7.72-7.94 (m, 3 H) 8.31-8.39 (m, 1 H) 12.90 (br s, 0.7 H) 13.32 (br s, 0.3 H).<br>MS ESI/APCI Multi posi: 407 [M + H]$^+$. |

TABLE 59-3

| Example No. | Structure | Analytical Data |
|---|---|---|
| 43-14 | 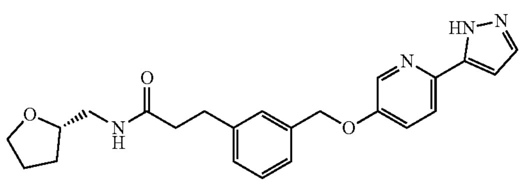 [SMILES: O=C(CCc1cccc(COc2ccc(-c3ccn[nH]3)nc2)c1)NC[C@@H]1CCCO1] | $^1$H NMR (600 MHz, DMSO-d$_6$) δ ppm 1.37-1.44 (m, 1 H) 1.69-1.81 (m, 3 H) 2.37-2.43 (m, 2 H) 2.78-2.87 (m, 2 H) 3.05-3.13 (m, 2 H) 3.54-3.59 (m, 1 H) 3.68-3.79 (m, 2 H) 5.16 (s, 2 H) 6.73 (s, 1 H) 7.17-7.21 (m, 1 H) 7.27-7.34 (m, 3 H) 7.45-7.59 (m, 1 H) 7.72-7.94 (m, 3 H) 8.31-8.39 (m, 1 H) 12.90 (br s, 0.7 H) 13.32 (br s, 0.3 H).<br>MS ESI/APCI Multi posi: 407 [M + H]$^+$. |
| 43-15 | 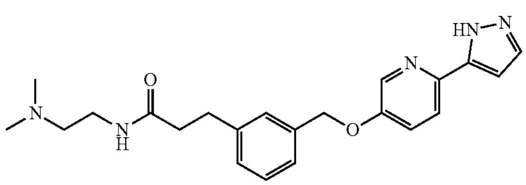 [SMILES: CN(C)CCNC(=O)CCc1cccc(COc2ccc(-c3ccn[nH]3)nc2)c1] | $^1$H NMR (600 MHz, DMSO-d$_6$) δ ppm 2.32-2.45 (m, 2 H) 2.76-2.79 (m, 6 H) 2.83-2.88 (m, 2 H) 3.05-3.14 (m, 2 H) 3.34-3.38 (m, 2 H) 5.18 (s, 2 H) 6.73-6.75 (m, 1 H) 7.18-7.21 (m, 1 H) 7.29-7.34 (m, 3 H) 7.52-7.57 (m, 1 H) 7.66-7.75 (m, 1 H) 7.86-7.90 (m, 1 H) 8.07-8.11 (m, 1 H) 8.34-8.36 (m, 1 H) 9.17 (br s, 1 H).<br>MS ESI/APCI Multi posi: 394 [M + H]$^+$. |
| 43-16 | 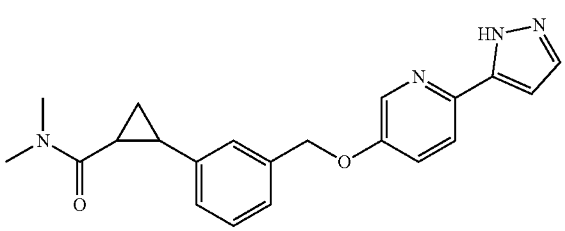 [SMILES: CN(C)C(=O)C1CC1c1cccc(COc2ccc(-c3ccn[nH]3)nc2)c1] | $^1$H NMR (600 MHz, DMSO-d$_6$) δ ppm 1.20-1.25 (m, 1 H) 1.36-1.41 (m, 1 H) 2.22-2.31 (m, 2 H) 2.85 (s, 3 H) 3.08 (s, 3 H) 5.17 (s, 2 H) 6.72 (s, 1 H) 7.13-7.18 (m, 1 H) 7.27-7.32 (m, 3 H) 7.47-7.59 (m, 1 H) 7.72-7.93 (m, 2 H) 8.30-8.38 (m, 1 H) 12.90 (br s, 0.7 H) 13.32 (br s, 0.3 H).<br>MS ESI/APCI Multi posi: 363 [M + H]$^+$. |

Example 44-1

N-Methylsulfonyl-3-[[6-(1H-pyrazol-5-yl)-3-pyridinyl]oxymethyl]benzamide

[Formula 563]

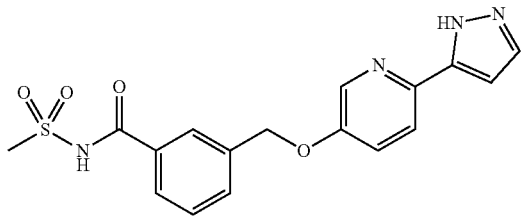

Methanesulfonamide (24 mg), 4-dimethylaminopyridine (31 mg), and 1-(3-dimethylaminopropyl)-3-ethylcarbodiimide hydrochloride (49 mg) were added to a solution of the compound (50 mg) obtained in Example 22-2 in chloroform (2 mL), and the mixture was stirred at room temperature for 20 hours. The solvent was distilled off under reduced pressure, and the obtained residue was purified by preparative HPLC. The obtained compound was solidified from a n-hexane:diethyl ether (1:1) mixed solution to give the title compound (21 mg) as a colorless powder.

$^1$H NMR (600 MHz, DMSO-$d_6$) δ ppm 3.34-3.38 (m, 3H) 5.29 (s, 2H) 6.72-6.74 (m, 1H) 7.50-7.59 (m, 2H) 7.71-7.78 (m, 1H) 7.82-7.95 (m, 2H) 8.07 (s, 1H) 8.36-8.39 (m, 1H).
MS ESI/APCI Multi posi: 373 [M+H]$^+$.
MS ESI/APCI Multi nega: 371[M−H]$^-$.

The compounds of Examples 44-2 to 44-6 below were synthesized using any of the compounds obtained in Examples 22-2 to 22-4, and a commercially available sulfonamide, according to the method described in Example 44-1. The structures, NMR data, and MS data of the compounds are shown in Table 60-1.

TABLE 60-1

| Example No. | Structure | Analytical Data |
|---|---|---|
| 44-2 | 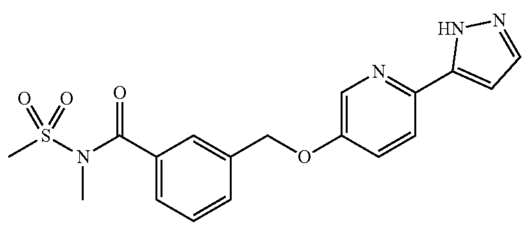 [SMILES: CN(C(=O)c1cccc(COc2ccc(-c3ccn[nH]3)nc2)c1)S(C)(=O)=O] | $^1$H NMR (600 MHz, DMSO-$d_6$) δ ppm 3.17 (s, 3 H) 3.44 (s, 3 H) 5.27-5.33 (m, 2 H) 6.71-6.77 (m, 1 H) 7.50-7.66 (m, 3 H) 7.67-7.73 (m, 1 H) 7.74-7.82 (m, 2 H) 7.86-7.93 (m, 1 H) 8.33-8.42 (m, 1 H).<br>MS ESI/APCI Multi posi: 387 [M + H]$^+$. |
| 44-3 | 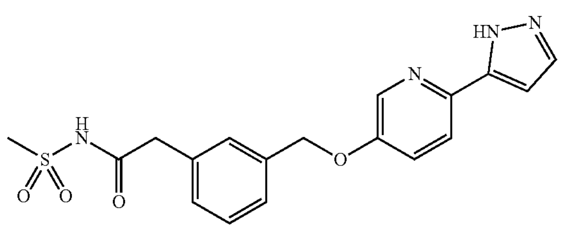 [SMILES: CS(=O)(=O)NC(=O)Cc1cccc(COc2ccc(-c3ccn[nH]3)nc2)c1] | $^1$H NMR (600 MHz, DMSO-$d_6$) δ ppm 3.21 (s, 3 H) 3.64 (s, 2 H) 5.20 (s, 2 H) 6.71-6.76 (m, 1 H) 7.23-7.27 (m, 1 H) 7.35-7.41 (m, 3 H) 7.47-7.64 (m, 1 H) 7.66-7.94 (m, 2 H) 8.32-8.41 (m, 1 H) 11.96 (br s, 1 H).<br>MS ESI/APCI Multi posi: 387 [M + H]$^+$.<br>MS ESI/APCI Multi nega: 385 [M − H]$^-$. |
| 44-4 | 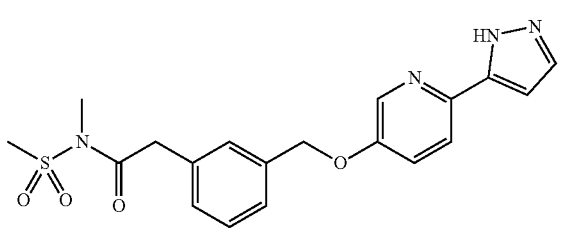 [SMILES: CN(C(=O)Cc1cccc(COc2ccc(-c3ccn[nH]3)nc2)c1)S(C)(=O)=O] | $^1$H NMR (600 MHz, DMSO-$d_6$) δ ppm 3.24 (s, 3 H) 3.36 (s, 3 H) 4.06 (s, 2 H) 5.20 (s, 2 H) 6.73 (s, 1 H) 7.21-7.24 (m, 1 H) 7.35-7.40 (m, 3 H) 7.45-7.61 (m, 1 H) 7.74-7.91 (m, 2 H) 8.32-8.39 (m, 1 H).<br>MS ESI/APCI Multi posi: 401 [M + H]$^+$. |
| 44-5 | 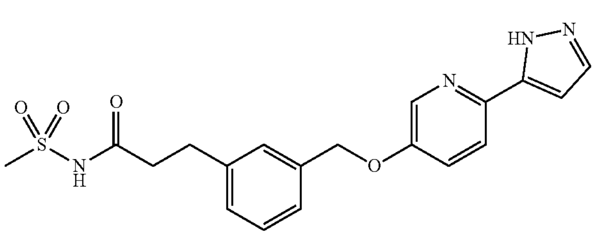 [SMILES: CS(=O)(=O)NC(=O)CCc1cccc(COc2ccc(-c3ccn[nH]3)nc2)c1] | $^1$H NMR (600 MHz, DMSO-$d_6$) δ ppm 2.57 (t, J = 7.6 Hz, 2 H) 2.86 (t, J = 7.6 Hz, 2 H) 3.17 (s, 3 H) 5.17 (s, 2 H) 6.73 (s, 1 H) 7.18-7.23 (m, 1 H) 7.29-7.36 (m, 3 H) 7.46-7.64 (m, 1 H) 7.70-7.94 (m, 2 H) 8.30-8.41 (m, 1 H).<br>MS ESI/APCI Multi posi: 401 [M + H]$^+$.<br>MS ESI/APCI Multi nega: 399 [M − H]$^-$. |

TABLE 60-1-continued

| Example No. | Structure | Analytical Data |
|---|---|---|
| 44-6 | 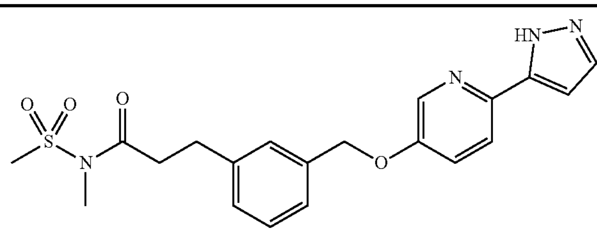 | ¹H NMR (600 MHz, DMSO-d₆) δ ppm 2.84-2.91 (m, 2 H) 2.95-3.00 (m, 2 H) 3.17 (s, 3 H) 3.33 (s, 3 H) 5.18 (s, 2 H) 6.73 (s, 1 H) 7.23-7.27 (m, 1 H) 7.30-7.39 (m, 3 H) 7.44-7.59 (m, 1 H) 7.72-7.93 (m, 2 H) 8.31-8.39 (m, 1 H). MS ESI/APCI Multi posi: 415 [M + H]⁺. |

Example 44-7

4-[[6-(1H-Pyrazol-5-yl)-3-pyridinyl]oxymethyl]-2-pyridinecarboxamide

[Formula 564]

To a suspension of the compound (47 mg) obtained in Example 1-40 in N,N-dimethylformamide (1.6 mL), 1-(3-dimethylaminopropyl)-3-ethylcarbodiimide hydrochloride (61 mg), 1-hydroxybenzotriazole monohydrate (43 mg), triethylamine (88 μL), and ammonium chloride (17 mg) were added, and the mixture was stirred at room temperature overnight. The reaction solution was purified by preparative HPLC to give the title compound (15 mg) as a colorless powder.

¹H NMR (400 MHz, METHANOL-d₄) δ ppm 5.37 (s, 2H) 6.78-6.83 (m, 1H) 7.51-7.58 (m, 1H) 7.63-7.69 (m, 2H) 7.84-7.91 (m, 1H) 8.20-8.25 (m, 1H) 8.35-8.40 (m, 1H) 8.62-8.68 (m, 1H).

MS ESI/APCI Multi posi: 296[M+H]⁺.

Example 45-1

3-[[Oxo-[3-[[6-(1H-pyrazol-5-yl)-3-pyridinyl]oxymethyl]phenyl]methyl]amino]propanoic Acid

[Formula 565]

(1) The compound (50.0 mg) obtained in Reference Example 10-1 was used to perform the synthesis process according to the method described in Example 42-1 thereby giving ethyl 3-[[[3-[[6-[2-(2-oxanyl)-3-pyrazolyl]-3-pyridinyl]oxymethyl]phenyl]-oxomethyl]amino]propanoate (69.0 mg) as a pale brown oil.

(2) The compound (69.0 mg) obtained in (1) above was used to perform the synthesis process according to the method described in Example 1-65-(2) thereby giving a solution containing ethyl 3-[[oxo-[3-[[6-(1H-pyrazol-5-yl)-3-pyridinyl]oxymethyl]phenyl]methyl]amino]propanoate.

(3) The solution obtained in (2) above was used to perform the synthesis process according to the method described in Example 9-1-(3) thereby giving the title compound (35.0 mg) as a colorless powder.

¹H NMR (400 MHz, DMSO-d₆) δ ppm 2.44-2.57 (m, 2H) 3.41-3.51 (m, 2H) 5.26 (s, 2H) 6.73 (d, J=2.0 Hz, 1H) 7.46-7.57 (m, 2H) 7.60-7.74 (m, 2H) 7.78-7.90 (m, 2H) 7.96 (s, 1H) 8.37 (d, J=2.9 Hz, 1H) 8.55-8.63 (m, 1H).

MS ESI/APCI Multi posi: 367[M+H]⁺.

MS ESI/APCI Multi nega: 365[M−H]⁻.

The compounds of Examples 45-2 to 45-47 below were synthesized using any of the compounds obtained in Reference Examples 10-1 to 10-3 or a compound obtained in Example 1-40-(2), and a commercially available compound, according to the method described in Example 45-1. The structures, NMR data, and MS data of the compounds are shown in Tables 61-1 to 61-8.

TABLE 61-1

| Example No. | Structure | Analytical Data |
|---|---|---|
| 45-2 | 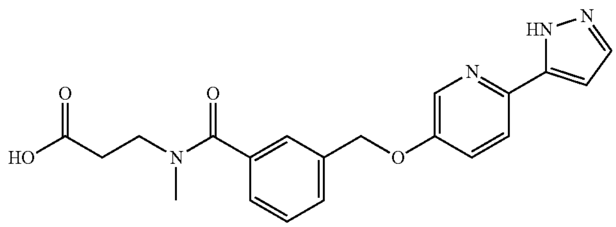 [SMILES: CN(CCC(=O)O)C(=O)c1cccc(COc2ccc(-c3ccn[nH]3)nc2)c1] | ¹H NMR (400 MHz, DMSO-d₆) δ ppm 2.79-3.03 (m, 3 H) 3.29-3.82 (m, 4 H) 5.25 (s, 2 H) 6.73 (d, J = 1.7 Hz, 1 H) 7.35 (d, J = 7.7 Hz, 1 H) 7.43-7.76 (m, 5 H) 7.86 (d, J = 8.7 Hz, 1 H) 8.36 (d, J = 2.9 Hz, 1 H).<br>MS ESI/APCI Multi posi: 381 [M + H]⁺.<br>MS ESI/APCI Multi nega: 379 [M − H]⁻. |
| 45-3 | 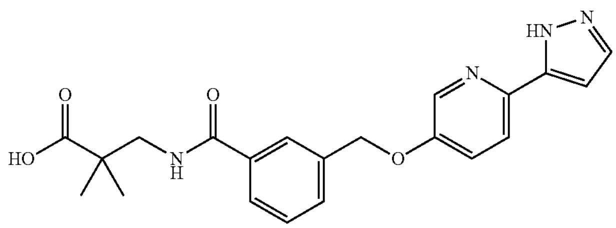 [SMILES: CC(C)(CNC(=O)c1cccc(COc2ccc(-c3ccn[nH]3)nc2)c1)C(=O)O] | ¹H NMR (400 MHz, DMSO-d₆) δ ppm 1.12 (s, 6 H) 3.44 (d, J = 6.2 Hz, 2 H) 5.27 (s, 2 H) 6.73 (d, J = 2.1 Hz, 1 H) 7.45-7.58 (m, 2 H) 7.60-7.73 (m, 2 H) 7.76-7.90 (m, 2 H) 7.95 (s, 1 H) 8.29-8.40 (m, 2 H).<br>MS ESI/APCI Multi posi: 395 [M + H]⁺.<br>MS ESI/APCI Multi nega: 393 [M − H]⁻. |
| 45-4 | 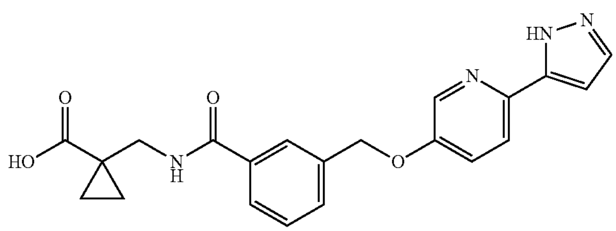 [SMILES: O=C(NCC1(C(=O)O)CC1)c1cccc(COc2ccc(-c3ccn[nH]3)nc2)c1] | ¹H NMR (400 MHz, DMSO-d₆) δ ppm 0.88-0.95 (m, 2 H) 1.01-1.08 (m, 2 H), 3.55 (d, J = 5.5 Hz, 2 H) 5.27 (s, 2 H) 6.73 (d, J = 2.1 Hz, 1 H) 7.41-7.58 (m, 2 H) 7.81 (d, J = 7.7 Hz, 1 H) 7.86 (d, J = 8.7 Hz, 1 H) 7.96 (s, 1 H) 8.34-8.46 (m, 2 H).<br>MS ESI/APCI Multi posi: 393 [M + H]⁺.<br>MS ESI/APCI Multi nega: 391 [M − H]⁻. |
| 45-5 | 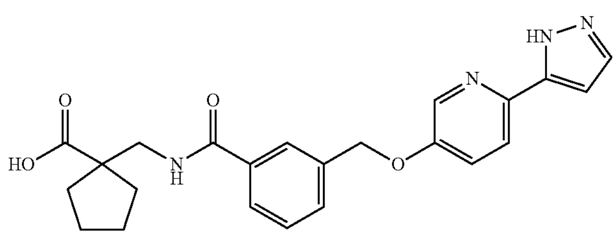 [SMILES: O=C(NCC1(C(=O)O)CCCC1)c1cccc(COc2ccc(-c3ccn[nH]3)nc2)c1] | ¹H NMR (400 MHz, DMSO-d₆) δ ppm 1.41-1.62 (m, 2 H) 1.91 (d, J = 13.3 Hz, 2 H) 3.19-3.37 (m, 2 H) 3.45 (d, J = 6.2 Hz, 2 H) 3.69-3.84 (m, 2 H) 5.27 (s, 2 H) 6.73 (d, J = 2.0 Hz, 1 H) 7.43-7.58 (m, 2 H) 7.59-7.74 (m, 2 H) 7.80 (d, J = 7.7 Hz, 1 H) 7.86 (d, J = 8.7 Hz, 1 H) 7.94 (s, 1 H) 8.37 (d, J = 2.8 Hz, 1 H) 8.43-8.58 (m, 1 H) 12.79 (br s, 1 H)<br>MS ESI/APCI Multi posi: 421 [M + H]⁺.<br>MS ESI/APCI Multi nega: 419 [M − H]⁻. |
| 45-6 | 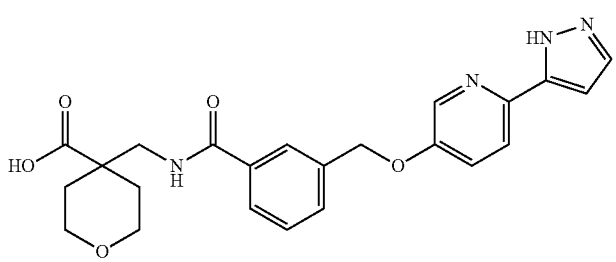 [SMILES: O=C(NCC1(C(=O)O)CCOCC1)c1cccc(COc2ccc(-c3ccn[nH]3)nc2)c1] | ¹H NMR (400 MHz, DMSO-d₆) δ ppm 1.47-1.74 (m, 6 H) 1.81-2.07 (m, 2 H) 3.50 (d, J = 6.0 Hz, 2 H) 5.27 (s, 2 H) 6.73 (d, J = 2.1 Hz, 1 H) 7.40-7.56 (m, 2 H) 7.59-7.73 (m, 2 H) 7.79 (d, J = 7.7 Hz, 1 H) 7.86 (d, J = 8.8 Hz, 1 H) 7.93 (s, 1 H) 8.29-8.49 (m, 2 H).<br>MS ESI/APCI Multi posi: 437 [M + H]⁺.<br>MS ESI/APCI Multi nega: 435 [M − H]⁻. |
| 45-7 | 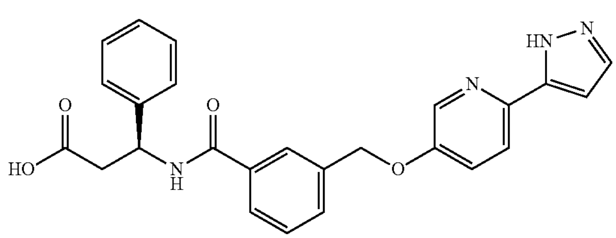 [SMILES: O=C(O)C[C@H](NC(=O)c1cccc(COc2ccc(-c3ccn[nH]3)nc2)c1)c1ccccc1] | ¹H NMR (400 MHz, DMSO-d₆) δ ppm 2.72-3.00 (m, 2 H) 5.27 (s, 2 H) 5.36-5.56 (m, 1 H) 6.73 (d, J = 1.7 Hz, 1 H) 7.15-7.74 (m, 9 H) 7.80-7.89 (m, 2 H) 7.96 (s, 1 H) 8.37 (d, J = 2.8 Hz, 1 H) 8.98 (br s, 1 H).<br>MS ESI/APCI Multi posi: 443 [M + H]⁺.<br>MS ESI/APCI Multi nega: 441 [M − H]⁻. |

TABLE 61-2

| Example No. | Structure | Analytical Data |
|---|---|---|
| 45-8 | 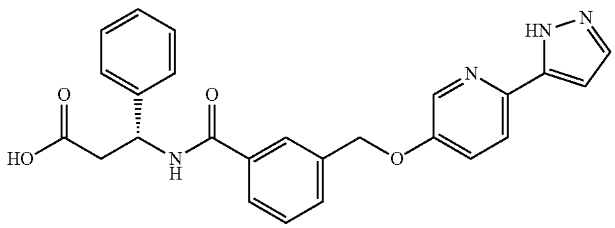 [SMILES: O=C(O)C[C@@H](NC(=O)c1cccc(COc2ccc(-c3ccn[nH]3)nc2)c1)c1ccccc1] | $^1$H NMR (400 MHz, DMSO-d$_6$) δ ppm 2.69-2.97 (m, 2 H) 5.26 (s, 2 H) 5.37-5.51 (m, 1 H) 6.73 (d, J = 2.0 Hz, 1 H) 7.19-7.76 (m, 9 H) 7.79-8.02 (m, 3 H) 8.37 (d, J = 2.8 Hz, 1 H) 9.07 (br s, 1 H).<br>MS ESI/APCI Multi posi: 443 [M + H]$^+$.<br>MS ESI/APCI Multi nega: 441 [M − H]$^−$. |
| 45-9 | 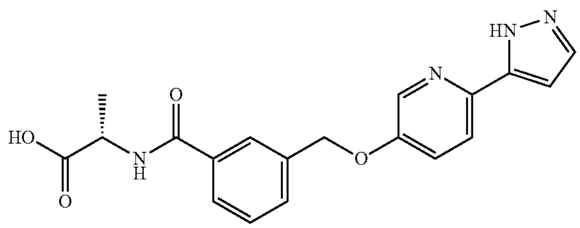 [SMILES: C[C@H](NC(=O)c1cccc(COc2ccc(-c3ccn[nH]3)nc2)c1)C(=O)O] | $^1$H NMR (400 MHz, DMSO-d$_6$) δ ppm 1.40 (d, J = 7.3 Hz, 3 H) 4.43 (quin, J = 7.3 Hz, 1 H) 5.28 (s, 2 H) 6.74 (s, 1 H) 7.47-7.60 (m, 2 H) 7.62-7.73 (m, 2 H) 7.82-7.92 (m, 2 H) 8.01 (s, 1 H) 8.38 (d, J = 2.7 Hz, 1 H) 8.71 (d, J = 7.1 Hz, 1 H).<br>MS ESI/APCI Multi posi: 367 [M + H]$^+$.<br>MS ESI/APCI Multi nega: 365 [M − H]$^−$. |
| 45-10 | 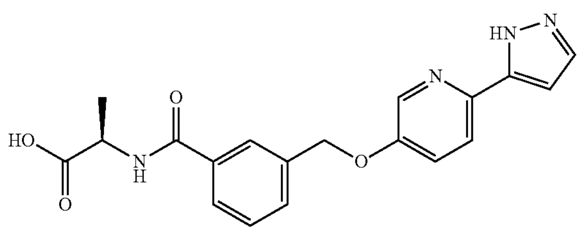 [SMILES: C[C@@H](NC(=O)c1cccc(COc2ccc(-c3ccn[nH]3)nc2)c1)C(=O)O] | $^1$H NMR (400 MHz, DMSO-d$_6$) δ ppm 1.40 (d, J = 7.3 Hz, 3 H) 4.43 (quin, J = 7.3 Hz, 1 H) 5.28 (s, 2 H) 6.73 (d, J = 1.8 Hz, 1 H) 7.48-7.59 (m, 2 H) 7.62-7.72 (m, 2 H) 7.82-7.92 (m, 2 H) 8.01 (s, 1 H) 8.38 (d, J = 2.8 Hz, 1 H) 8.71 (d, J = 7.3 Hz, 1 H).<br>MS ESI/APCI Multi posi: 367 [M + H]$^+$.<br>MS ESI/APCI Multi nega: 365 [M − H]$^−$. |
| 45-11 | 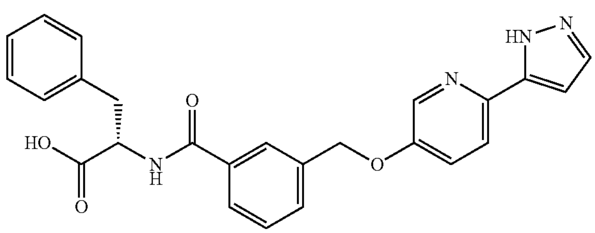 [SMILES: O=C(N[C@@H](Cc1ccccc1)C(=O)O)c1cccc(COc2ccc(-c3ccn[nH]3)nc2)c1] | $^1$H NMR (600 MHz, DMSO-d$_6$) δ ppm 3.07 (dd, J = 13.7, 10.1 Hz, 1 H) 3.19 (dd, J = 13.7, 4.5 Hz, 1 H) 4.54-4.62 (m, 1 H) 5.26 (s, 2 H) 6.73 (d, J = 2.1 Hz, 1 H) 7.13-7.19 (m, 1 H) 7.21-7.32 (m, 4 H) 7.47-7.56 (m, 2 H) 7.60-7.73 (m, 2 H) 7.76 (d, J = 7.8 Hz, 1 H) 7.84-7.88 (m, 1 H) 7.90 (s, 1 H) 8.37 (d, J = 2.9 Hz, 1 H) 8.66 (br s, 1H).<br>MS ESI/APCI Multi posi: 443 [M + H]$^+$.<br>MS ESI/APCI Multi nega: 441 [M − H]$^−$. |
| 45-12 | 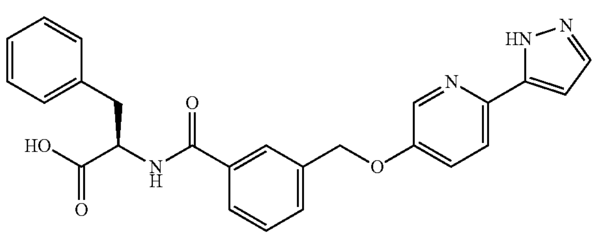 [SMILES: O=C(N[C@H](Cc1ccccc1)C(=O)O)c1cccc(COc2ccc(-c3ccn[nH]3)nc2)c1] | $^1$H NMR (600 MHz, DMSO-d$_6$) δ ppm 3.07 (dd, J = 13.9, 10.3 Hz, 1 H) 3.19 (dd, J = 13.9, 4.3 Hz, 1 H) 4.56-4.64 (m, 1 H) 5.26 (s, 2 H) 6.73 (d, J = 2.1 Hz, 1 H) 7.14-7.18 (m, 1 H) 7.25 (t, J = 7.6 Hz, 2 H) 7.28-7.32 (m, 2 H) 7.49 (t, J = 7.7 Hz, 1 H) 7.51-7.56 (m, 1 H) 7.60-7.73 (m, 2 H) 7.76 (d, J = 7.7 Hz, 1 H) 7.83-7.90 (m, 1 H) 7.91 (s, 1 H) 8.37 (d, J = 2.9 Hz, 1 H) 8.66-8.75 (m, 1 H).<br>MS ESI/APCI Multi posi: 443 [M + H]$^+$.<br>MS ESI/APCI Multi nega: 441 [M − H]$^−$. |
| 45-13 | 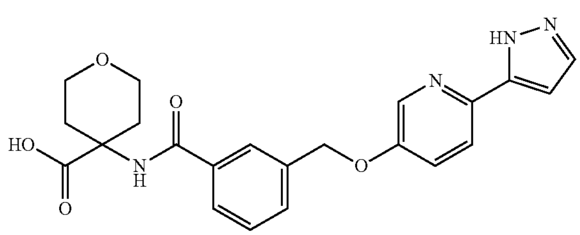 [SMILES: O=C(NC1(C(=O)O)CCOCC1)c1cccc(COc2ccc(-c3ccn[nH]3)nc2)c1] | $^1$H NMR (400 MHz, DMSO-d$_6$) δ ppm 1.82-2.20 (m, 4 H) 3.57-3.81 (m, 4 H) 5.29 (s, 2 H) 6.68-6.76 (m, 1 H) 7.46-7.60 (m, 2 H) 7.63-7.72 (m, 2 H) 7.80-7.92 (m, 2 H) 7.97 (s, 1 H) 8.38 (d, J = 2.7 Hz, 1 H) 8.54 (s, 1 H).<br>MS ESI/APCI Multi posi: 423 [M + H]$^+$.<br>MS ESI/APCI Multi nega: 421 [M − H]$^−$. |

TABLE 61-3

| Example No. | Structure | Analytical Data |
|---|---|---|
| 45-14 | 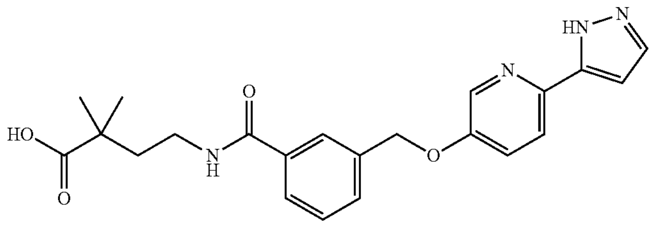 [SMILES: CC(C)(CCNC(=O)c1cccc(COc2ccc(-c3ccn[nH]3)nc2)c1)C(=O)O] | $^1$H NMR (600 MHz, DMSO-d$_6$) δ ppm 1.12-1.16 (m, 6 H) 1.72-1.78 (m, 2 H) 3.22-3.29 (m, 2 H) 5.26 (s, 2 H) 6.72-6.75 (m, 1 H) 7.46-7.51 (m, 1 H) 7.51-7.58 (m, 1 H) 7.59-7.75 (m, 2 H) 7.77-7.83 (m, 1 H) 7.84-7.89 (m, 1 H) 7.93-7.97 (m, 1 H) 8.34-8.39 (m, 1 H) 8.49-8.60 (m, 1 H). <br> MS ESI/APCI Multi posi: 409 [M + H]$^+$. <br> MS ESI/APCI Multi nega: 407 [M − H]$^-$. |
| 45-15 | 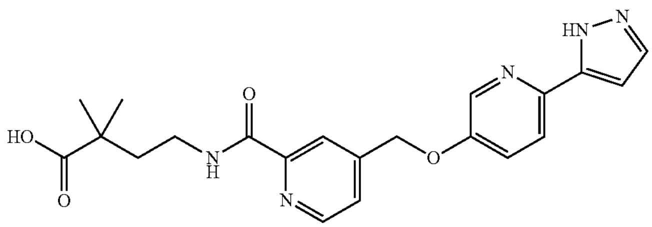 | $^1$H NMR (600 MHz, DMSO-d$_6$) δ ppm 1.14 (s, 6 H) 1.73-1.78 (m, 2 H) 3.27-3.35 (m, 2 H) 5.41 (s, 2 H) 6.74 (d, J = 2.1 Hz, 1 H) 7.54 (dd, J = 8.8, 2.8 Hz, 1 H) 7.63-7.74 (m, 2 H) 7.87 (d, J = 8.8 Hz, 1 H) 8.10 (d, J = 0.8 Hz, 1 H) 8.39 (d, J = 2.8 Hz, 1 H) 8.65 (d, J = 5.0 Hz, 1 H) 8.77 (t, J = 6.0 Hz, 1 H). <br> MS ESI posi: 410 [M + H]$^+$. <br> MS ESI nega: 408 [M − H]$^-$. |
| 45-16 | 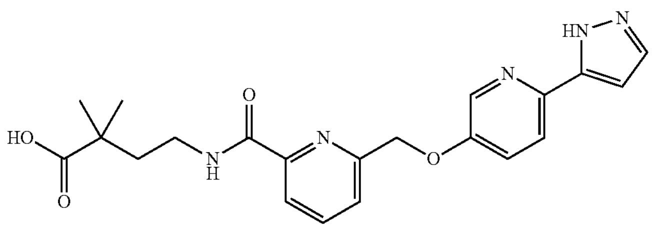 [SMILES: CC(C)(CCNC(=O)c1cccc(COc2ccc(-c3ccn[nH]3)nc2)n1)C(=O)O] | $^1$H NMR (600 MHz, DMSO-d$_6$) δ ppm 1.14 (s, 6 H) 1.72-1.81 (m, 2 H) 3.26-3.36 (m, 2 H) 5.37 (s, 2 H) 6.74 (d, J = 2.1 Hz, 1 H) 7.57 (dd, J = 8.7, 2.9 Hz, 1 H) 7.64-7.74 (m, 1 H) 7.75 (d, J = 7.0 Hz, 1 H) 7.88 (d, J = 8.7 Hz, 1 H) 7.95-7.99 (m, 1 H) 8.01-8.08 (m, 1 H) 8.40 (d, J = 2.9 Hz, 1 H) 8.64 (t, J = 6.0 Hz, 1 H). <br> MS ESI posi: 410 [M + H]$^+$. <br> MS ESI nega: 408 [M − H]$^-$. |
| 45-17 | 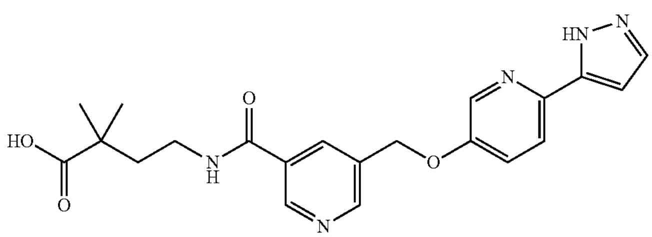 [SMILES: CC(C)(CCNC(=O)c1cncc(COc2ccc(-c3ccn[nH]3)nc2)c1)C(=O)O] | $^1$H NMR (600 MHz, DMSO-d$_6$) δ ppm 1.15 (s, 6 H) 1.73-1.80 (m, 2 H) 3.24-3.40 (m, 2 H) 5.33 (s, 2 H) 6.74 (d, J = 2.1 Hz, 1 H) 7.57 (dd, J = 8.7, 2.9 Hz, 1 H) 7.61-7.75 (m, 1 H) 7.88 (d, J = 8.7 Hz, 1 H) 8.29 (t, J = 2.1 Hz, 1 H) 8.39 (d, J = 2.9 Hz, 1 H) 8.70-8.80 (m, 1 H) 8.82 (d, J = 1.7 Hz, 1 H) 8.96 (d, J = 2.1 Hz, 1 H). <br> MS ESI posi: 410 [M + H]$^+$. <br> MS ESI nega: 408 [M − H]$^-$. |
| 45-18 | 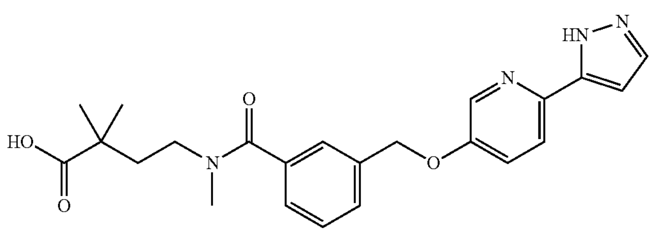 [SMILES: CN(CCC(C)(C)C(=O)O)C(=O)c1cccc(COc2ccc(-c3ccn[nH]3)nc2)c1] | $^1$H NMR (600 MHz, DMSO-d$_6$) δ ppm 0.89 (s, 3 H) 1.17 (s, 3 H) 1.67-1.81 (m, 2 H) 2.81-2.98 (m, 3 H) 3.09-3.16 (m, 1 H) 3.40-3.47 (m, 1 H) 5.26 (s, 2 H) 6.73 (d, J = 2.1 Hz, 1 H) 7.30-7.37 (m, 1 H) 7.46 (t, J = 7.6 Hz, 2 H) 7.51-7.57 (m, 2 H) 7.62-7.76 (m, 1 H) 7.86 (d, J = 7.8 Hz, 1 H) 8.36 (d, J = 2.5 Hz, 1 H). <br> MS ESI/APCI Multi posi: 423 [M + H]$^+$. <br> MS ESI/APCI Multi nega: 421 [M − H]$^-$. |
| 45-19 | 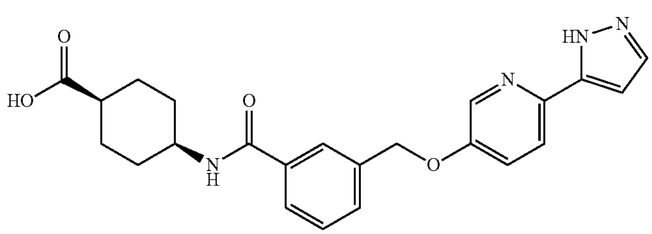 [SMILES: O=C(N[C@H]1CC[C@@H](C(=O)O)CC1)c1cccc(COc2ccc(-c3ccn[nH]3)nc2)c1] | $^1$H NMR (600 MHz, DMSO-d$_6$) δ ppm 1.47-1.76 (m, 6 H) 1.89-2.06 (m, 2 H) 3.79-3.92 (m, 1 H) 5.26 (s, 2 H) 6.73 (d, J = 2.1 Hz, 1 H) 7.35-7.72 (m, 4 H) 7.75-7.91 (m, 2 H) 7.96 (s, 1 H) 8.24 (d, J = 7.8 Hz, 1 H) 8.37 (d, J = 2.8 Hz, 1 H). <br> MS ESI/APCI Multi posi: 421 [M + H]$^+$. <br> MS ESI/APCI Multi nega: 419 [M − H]$^-$. |

TABLE 61-4

| Example No. | Structure | Analytical Data |
|---|---|---|
| 45-20 | 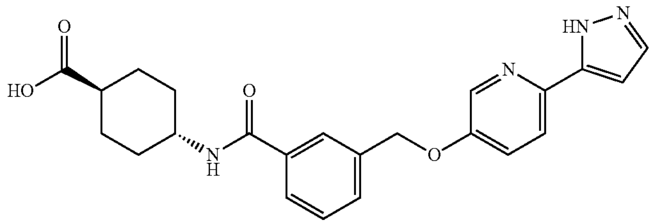 [SMILES: O=C(N[C@H]1CC[C@H](C(=O)O)CC1)c1cccc(COc2ccc(-c3ccn[nH]3)nc2)c1] | ¹H NMR (400 MHz, DMSO-d₆) δ ppm 1.19-1.57 (m, 4 H) 1.78-2.03 (m, 4 H) 2.06-2.23 (m, 1 H) 3.64-3.79 (m, 1 H) 5.26 (s, 2 H) 6.73 (d, J = 2.0 Hz, 1 H) 7.41-7.64 (m, 4 H) 7.77-7.99 (m, 3 H) 8.27 (d, J = 7.2 Hz, 1 H) 8.37 (d, J = 2.7 Hz, 1 H). MS ESI/APCI Multi posi: 421 [M + H]⁺. MS ESI/APCI Multi nega: 419 [M − H]⁻. |
| 45-21 | 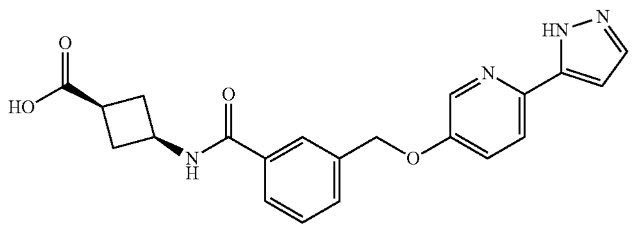 [SMILES: O=C(N[C@H]1C[C@@H](C(=O)O)C1)c1cccc(COc2ccc(-c3ccn[nH]3)nc2)c1] | ¹H NMR (600 MHz, DMSO-d₆) δ ppm 2.21-2.29 (m, 2 H) 2.41-2.47 (m, 2 H) 2.73-2.82 (m, 1 H) 4.33-4.43 (m, 1 H) 5.29 (s, 2 H) 6.81 (d, J = 2.1 Hz, 1 H) 7.50 (t, J = 7.6 Hz, 1 H) 7.62-7.70 (m, 2 H) 7.75 (m, J = 1.7 Hz, 1 H) 7.85 (d, J = 7.8 Hz, 1 H) 7.94-8.00 (m, 2 H) 8.40 (d, J = 2.9 Hz, 1 H) 8.74 (d, J = 7.8 Hz, 1 H). MS ESI/APCI Multi posi: 393 [M + H]⁺. MS ESI/APCI Multi nega: 391 [M − H]⁻. |
| 45-22 | 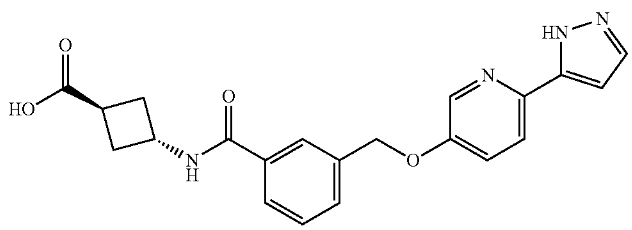 [SMILES: O=C(N[C@H]1C[C@H](C(=O)O)C1)c1cccc(COc2ccc(-c3ccn[nH]3)nc2)c1] | ¹H NMR (600 MHz, DMSO-d₆) δ ppm 2.27-2.36 (m, 2 H) 2.38-2.44 (m, 2 H) 2.89-2.97 (m, 1 H) 4.48-4.57 (m, 1 H) 5.23 (s, 2 H) 6.70 (d, J = 2.1 Hz, 1 H) 7.44-7.53 (m, 2 H) 7.58-7.68 (m, 2 H) 7.77-7.86 (m, 2 H) 7.93 (s, 1 H) 8.33 (d, J = 2.9 Hz, 1 H) 8.71 (d, J = 7.4 Hz, 1 H). MS ESI/APCI Multi posi: 393 [M + H]⁺. MS ESI/APCI Multi nega: 391 [M − H]⁻. |
| 45-23 | 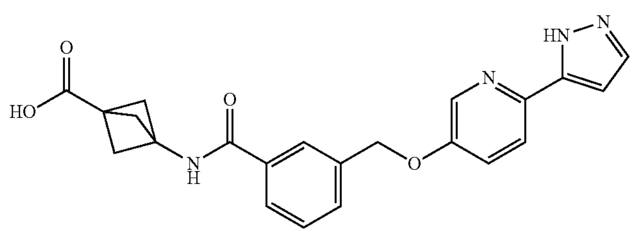 [SMILES: O=C(NC12CC(C(=O)O)(C1)C2)c1cccc(COc2ccc(-c3ccn[nH]3)nc2)c1] | ¹H NMR (600 MHz, DMSO-d₆) δ ppm 2.25 (s, 6 H) 5.24 (s, 2 H) 6.75 (d, J = 2.1 Hz, 1 H) 7.46 (t, J = 7.8 Hz, 1 H) 7.58-7.62 (m, 2 H) 7.69 (s, 1 H) 7.77 (d, J = 7.8 Hz, 1 H) 7.87-7.94 (m, 2 H) 8.35 (d, J = 2.9 Hz, 1 H) 9.08 (s, 1 H). MS ESI/APCI Multi posi: 405 [M + H]⁺. MS ESI/APCI Multi nega: 403 [M − H]⁻. |
| 45-24 | 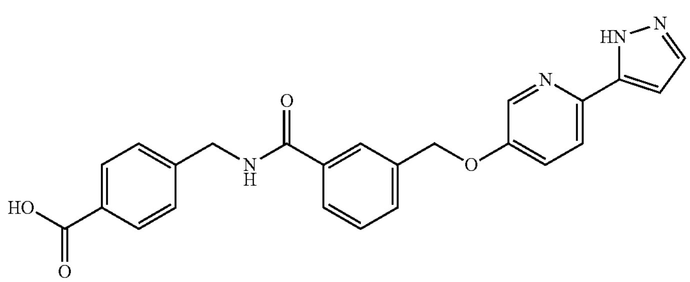 [SMILES: O=C(O)c1ccc(CNC(=O)c2cccc(COc3ccc(-c4ccn[nH]4)nc3)c2)cc1] | ¹H NMR (400 MHz, DMSO-d₆) δ ppm 4.55 (d, J = 5.8 Hz, 2 H) 5.28 (s, 2 H) 6.73 (d, J = 1.6 Hz, 1 H) 7.33-7.73 (m, 6 H) 7.79-7.97 (m, 4 H) 8.03 (s, 1 H) 8.37 (d, J = 2.9 Hz, 1 H) 9.16 (t, J = 5.8 Hz, 1 H) 12.94 (br s, 1 H). MS ESI/APCI Multi posi: 429 [M + H]⁺. MS ESI/APCI Multi nega: 427 [M − H]⁻. |
| 45-25 | 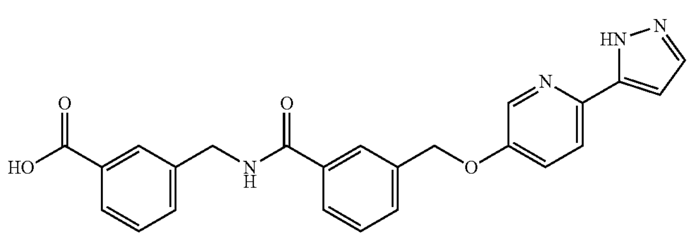 [SMILES: O=C(O)c1cccc(CNC(=O)c2cccc(COc3ccc(-c4ccn[nH]4)nc3)c2)c1] | ¹H NMR (400 MHz, DMSO-d₆) δ ppm 4.54 (d, J = 6.1 Hz, 2 H) 5.28 (s, 2 H) 6.73 (d, J = 2.1 Hz, 1 H) 7.39-7.74 (m, 6 H) 7.76-7.95 (m, 4 H) 8.03 (s, 1 H) 8.37 (d, J = 2.8 Hz, 1 H) 9.17 (t, J = 6.1 Hz, 1 H) 12.97 (br s, 1 H). MS ESI/APCI Multi posi: 429 [M + H]⁺. MS ESI/APCI Multi nega: 427 [M − H]⁻. |

TABLE 61-5

| Example No. | Structure | Analytical Data |
|---|---|---|
| 45-26 | 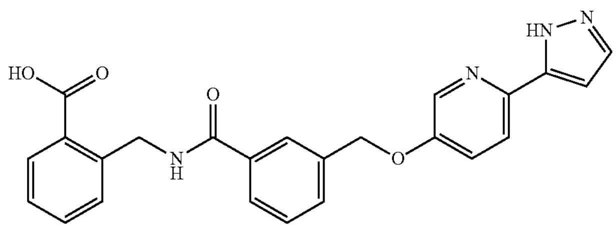 [SMILES: O=C(NCc1ccccc1C(=O)O)c1cccc(COc2ccc(-c3ccn[nH]3)nc2)c1] | $^1$H NMR (400 MHz, DMSO-d$_6$) δ ppm 4.82 (d, J = 5.9 Hz, 2 H) 5.29 (s, 2 H) 6.73 (d, J = 2.1 Hz, 1 H) 7.28-7.44 (m, 2 H) 7.47-7.58 (m, 3 H) 7.66 (d, J = 7.6 Hz, 2 H) 7.83-7.94 (m, 3 H) 8.03 (s, 1 H) 8.38 (d, J = 2.8 Hz, 1 H) 9.05 (br s, 1 H). <br> MS ESI/APCI Multi posi: 429 [M + H]$^+$. <br> MS ESI/APCI Multi nega: 427 [M − H]$^-$. |
| 45-27 | 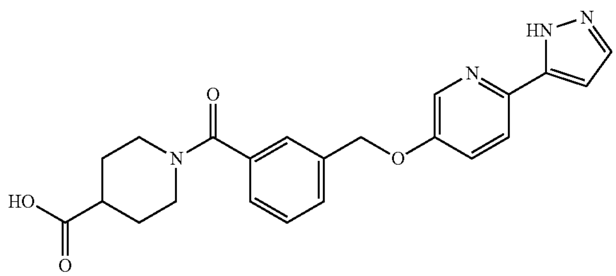 [SMILES: O=C(O)C1CCN(C(=O)c2cccc(COc3ccc(-c4ccn[nH]4)nc3)c2)CC1] | $^1$H NMR (600 MHz, DMSO-d$_6$) δ ppm 1.40-1.60 (m, 2 H) 1.67-1.98 (m, 3 H) 2.86-3.12 (m, 2 H) 3.43-3.60 (m, 1 H) 4.23-4.38 (m, 1 H) 5.26 (s, 2 H) 6.72 (d, J = 2.1 Hz, 1 H) 7.34 (d, J = 7.8 Hz, 1 H) 7.44-7.50 (m, 2 H) 7.51-7.57 (m, 2 H) 7.63-7.75 (m, 1 H) 7.83-7.89 (m, 1 H) 8.35 (d, J = 2.9 Hz, 1 H). <br> MS ESI/APCI Multi posi: 407 [M + H]$^+$. <br> MS ESI/APCI Multi nega: 405 [M − H]$^-$. |
| 45-28 | 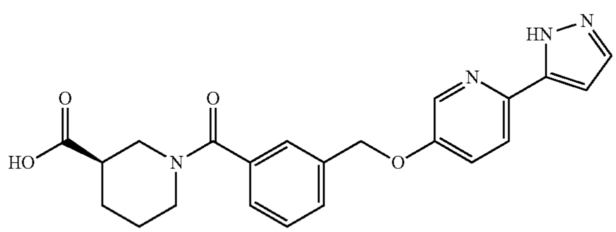 [SMILES: O=C(O)[C@@H]1CCCN(C(=O)c2cccc(COc3ccc(-c4ccn[nH]4)nc3)c2)C1] | $^1$H NMR (600 MHz, DMSO-d$_6$) δ ppm 1.33-1.78 (m, 4 H) 1.93-2.04 (m, 2 H) 2.95-3.09 (m, 2 H) 4.07-4.16 (m, 0.5 H) 4.37-4.47 (m, 0.5 H) 5.27 (s, 2 H) 6.76 (d, J = 2.1 Hz, 1 H) 7.34-7.40 (m, 1 H) 7.45-7.52 (m, 2 H) 7.54-7.61 (m, 2 H) 7.70 (s, 1 H) 7.90 (d, J = 8.7 Hz, 1 H) 8.37 (d, J = 2.5 Hz, 1 H). <br> MS ESI posi: 407 [M + H]$^+$. <br> MS ESI nega: 405 [M − H]$^-$. |
| 45-29 | 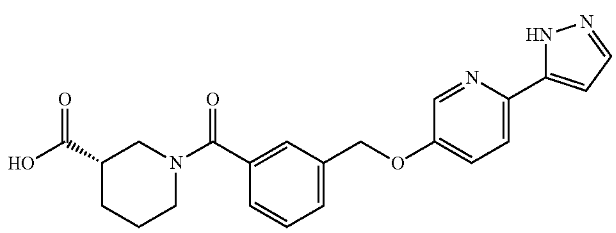 [SMILES: O=C(O)[C@H]1CCCN(C(=O)c2cccc(COc3ccc(-c4ccn[nH]4)nc3)c2)C1] | $^1$H NMR (600 MHz, DMSO-d$_6$) δ ppm 1.33-1.78 (m, 4 H) 1.93-2.03 (m, 2 H) 2.96-3.10 (m, 2 H) 4.05-4.17 (m, 0.5 H) 4.36-4.50 (m, 0.5 H) 5.26 (s, 2 H) 6.73 (d, J = 2.1 Hz, 1 H) 7.30-7.40 (m, 1 H) 7.45-7.58 (m, 4 H) 7.62-7.73 (m, 1 H) 7.86 (d, J = 8.7 Hz, 1 H) 8.36 (d, J = 2.5 Hz, 1 H). <br> MS ESI posi: 407 [M + H]$^+$. <br> MS ESI nega: 405 [M − H]$^-$. |
| 45-30 | 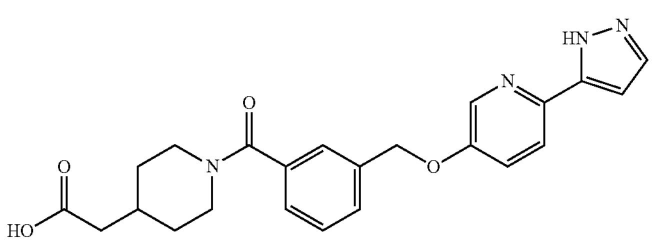 [SMILES: O=C(O)CC1CCN(C(=O)c2cccc(COc3ccc(-c4ccn[nH]4)nc3)c2)CC1] | $^1$H NMR (400 MHz, DMSO-d$_6$) δ ppm 1.02-1.27 (m, 2 H) 1.42-2.01 (m, 3 H) 2.17 (d, J = 6.8 Hz, 2 H) 2.69-3.12 (m, 2 H) 3.43-3.69 (m, 1 H) 4.25-4.64 (m, 1 H) 5.26 (s, 2 H) 6.73 (d, J = 1.7 Hz, 1 H) 7.33 (d, J = 7.3 Hz, 1 H) 7.42-7.61 (m, 4 H) 7.68 (s, 1 H) 7.86 (d, J = 8.8 Hz, 1 H) 8.36 (d, J = 2.8 Hz, 1 H). <br> MS ESI/APCI Multi posi: 421 [M + H]$^+$. <br> MS ESI/APCI Multi nega: 419 [M − H]$^-$. |
| 45-31 | 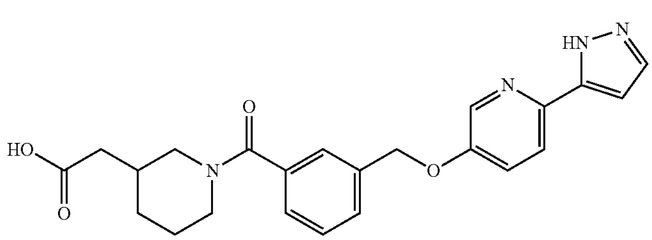 [SMILES: O=C(O)CC1CCCN(C(=O)c2cccc(COc3ccc(-c4ccn[nH]4)nc3)c2)C1] | $^1$H NMR (600 MHz, DMSO-d$_6$) δ ppm 1.19-1.29 (m, 1 H) 1.30-1.74 (m, 2 H) 1.76-1.94 (m, 2 H) 1.96-2.31 (m, 2 H) 2.59-3.04 (m, 2 H) 3.47-3.57 (m, 1 H) 4.16-4.27 (m, 1 H) 5.26 (s, 2 H) 6.73 (d, J = 2.1 Hz, 1 H) 7.34 (d, J = 7.4 Hz, 1 H) 7.41-7.59 (m, 4 H) 7.56-7.64 (m, 1 H) 7.76-7.80 (m, 1 H) 8.36 (d, J = 2.9 Hz, 1 H). <br> MS ESI posi: 421 [M + H]$^+$. <br> MS ESI nega: 419 [M − H]$^-$. |

TABLE 61-6

| Example No. | Structure | Analytical Data |
|---|---|---|
| 45-32 | 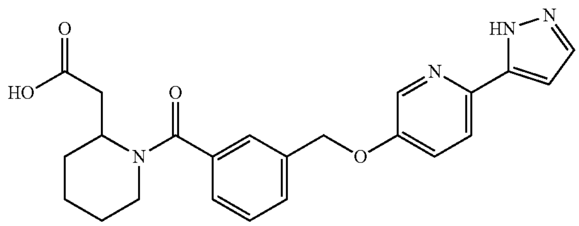 [SMILES: O=C(O)CC1CCCCN1C(=O)c1cccc(COc2ccc(-c3ccn[nH]3)nc2)c1] | $^1$H NMR (600 MHz, DMSO-d$_6$) δ ppm 1.24-1.77 (m, 4 H) 2.53-2.69 (m, 2 H) 2.74-3.14 (m, 2 H) 4.04-4.46 (m, 2 H) 4.98-5.16 (m, 1 H) 5.25 (s, 2 H) 6.73 (d, J = 2.1 Hz, 1 H) 7.28-7.33 (m, 1 H) 7.41-7.49 (m, 2 H) 7.50-7.56 (m, 2 H) 7.65-7.72 (m, 1 H) 7.86 (d, J = 8.7 Hz, 1 H) 8.36 (d, J = 2.9 Hz, 1 H).<br>MS ESI posi: 421 [M + H]$^+$.<br>MS ESI nega: 419 [M − H]$^-$. |
| 45-33 | 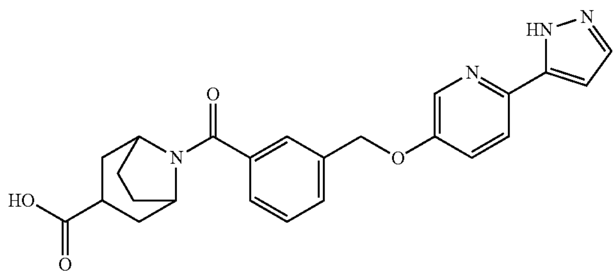 [SMILES: O=C(O)C1CC2CCC(C1)N2C(=O)c1cccc(COc2ccc(-c3ccn[nH]3)nc2)c1] | $^1$H NMR (400 MHz, DMSO-d$_6$) δ ppm 1.48-2.03 (m, 8 H) 2.75-2.92 (m, 1 H) 3.89-4.06 (m, 1 H) 5.54-4.71 (m, 1 H) 5.29 (s, 2 H) 6.73 (d, J = 2.0 Hz, 1 H) 7.38-7.72 (m, 6 H) 7.86 (d, J = 8.7 Hz, 1 H) 8.36 (d, J = 2.9 Hz, 1 H).<br>MS ESI/APCI Multi posi: 433 [M + H]$^+$.<br>MS ESI/APCI Multi nega: 431 [M − H]$^-$. |
| 45-34 | 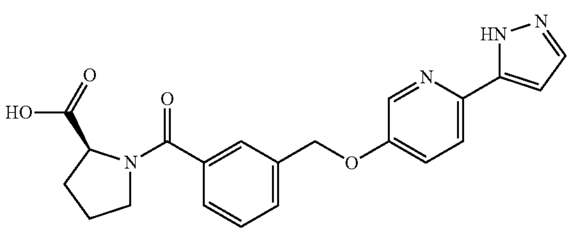 [SMILES: O=C(O)[C@@H]1CCCN1C(=O)c1cccc(COc2ccc(-c3ccn[nH]3)nc2)c1] | $^1$H NMR (600 MHz, DMSO-d$_6$) δ ppm 1.75-2.02 (m, 2 H) 2.19-2.32 (m, 1 H) 3.40-3.61 (m, 3 H) 4.35-4.45 (m, 1 H) 5.21 (s, 0.5 H) 5.28 (s, 1.5 H) 6.73 (d, J = 2.1 Hz, 1 H) 7.33-7.73 (m, 6 H) 7.82-7.90 (m, 1 H) 8.36 (d, J = 2.9 Hz, 1 H).<br>MS ESI/APCI Multi posi: 393 [M + H]$^+$.<br>MS ESI/APCI Multi nega: 391 [M − H]$^-$. |
| 45-35 | 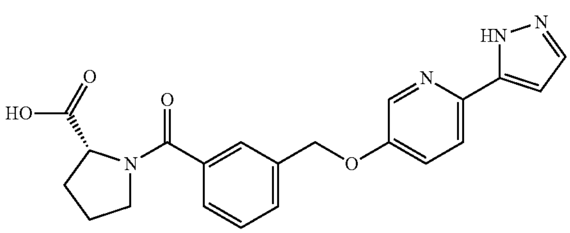 [SMILES: O=C(O)[C@H]1CCCN1C(=O)c1cccc(COc2ccc(-c3ccn[nH]3)nc2)c1] | $^1$H NMR (600 MHz, DMSO-d$_6$) δ ppm 1.74-2.03 (m, 2 H) 2.18-2.31 (m, 1 H) 3.38-3.64 (m, 3 H) 4.32-4.45 (m, 1 H) 5.21 (s, 0.5 H) 5.28 (s, 1.5 H) 6.73 (d, J = 2.1 Hz, 1 H) 7.34-7.73 (m, 6 H) 7.80-7.91 (m, 1 H) 8.37 (d, J = 2.5 Hz, 1 H).<br>MS ESI/APCI Multi posi: 393 [M + H]$^+$.<br>MS ESI/APCI Multi nega: 391 [M − H]$^-$. |
| 45-36 | 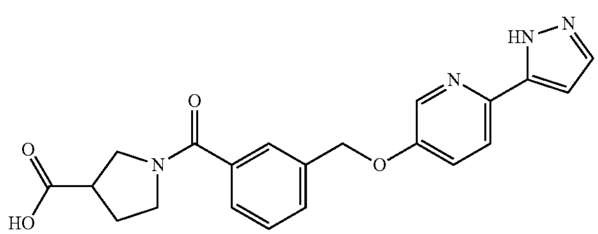 [SMILES: O=C(O)C1CCN(C(=O)c2cccc(COc3ccc(-c4ccn[nH]4)nc3)c2)C1] | $^1$H NMR (400 MHz, DMSO-d$_6$) δ ppm 1.85-2.25 (m, 2 H) 2.94-3.12 (m, 1 H) 3.40-3.74 (m, 3 H) 3.96-4.20 (m, 1 H) 5.27 (s, 2 H) 6.73 (d, J = 1.7 Hz, 1 H) 7.40-7.73 (m, 6 H) 7.86 (d, J = 8.8 Hz, 1 H) 8.36 (s, 1 H) 12.82 (br s, 1 H).<br>MS ESI/APCI Multi posi: 393 [M + H]$^+$.<br>MS ESI/APCI Multi nega: 391 [M − H]$^-$. |
| 45-37 | 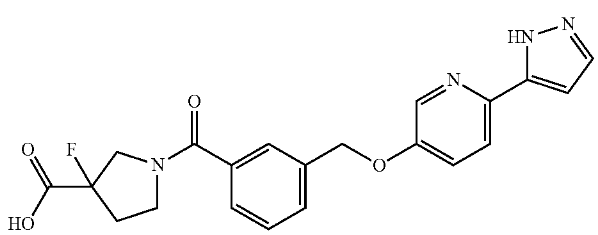 [SMILES: O=C(c1cccc(COc2ccc(-c3ccn[nH]3)nc2)c1)N1CCC(F)(C(=O)O)C1] | $^1$H NMR (600 MHz, DMSO-d$_6$) δ ppm 2.20-2.47 (m, 2 H) 3.60-3.72 (m, 2 H) 3.76-4.11 (m, 2 H) 5.24-5.31 (m, 2 H) 6.73 (d, J = 2.1 Hz, 1 H) 7.47-7.57 (m, 3 H) 7.58-7.62 (m, 1 H) 7.64-7.70 (m, 2 H) 7.86 (d, J = 8.7 Hz, 1 H) 8.36 (d, J = 2.9 Hz, 1 H).<br>MS ESI posi: 411 [M + H]$^+$.<br>MS ESI nega: 409 [M − H]$^-$. |

TABLE 61-7

| Example No. | Structure | Analytical Data |
|---|---|---|
| 45-38 | 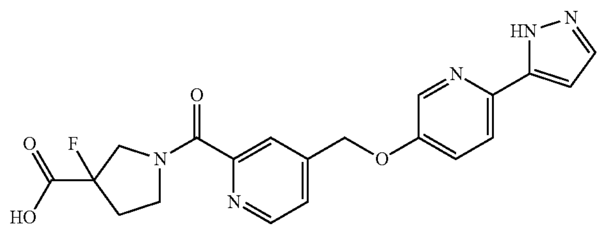 [SMILES: O=C(c1cc(COc2ccc(-c3ccn[nH]3)nc2)ccn1)N1CCC(F)(C(=O)O)C1] | ¹H NMR (600 MHz, DMSO-d₆) δ ppm 2.25-2.47 (m, 2 H) 3.61-4.28 (m, 4 H) 5.35-5.42 (m, 2 H) 6.74 (d, J = 1.7 Hz, 1 H) 7.52-7.57 (m, 1 H) 7.59-7.63 (m, 1 H) 7.65-7.74 (m, 1 H) 7.85-7.94 (m, 2 H) 8.40 (d, J = 2.9 Hz, 1 H) 8.61-8.67 (m, 1 H). MS ESI posi: 412 [M + H]⁺. MS ESI nega: 410 [M − H]⁻. |
| 45-39 | 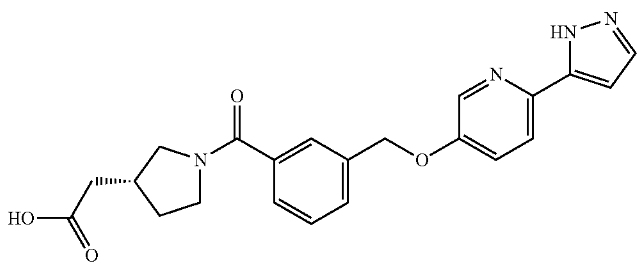 [SMILES: O=C(O)C[C@H]1CCN(C(=O)c2cccc(COc3ccc(-c4ccn[nH]4)nc3)c2)C1] | ¹H NMR (600 MHz, DMSO-d₆) δ ppm 1.49-1.62 (m, 1 H) 1.95-2.10 (m, 1 H) 2.28-2.33 (m, 1 H) 2.37-2.43 (m, 2 H) 3.09-3.14 (m, 1 H) 3.37-3.73 (m, 3 H) 5.26 (s, 2 H) 6.73 (s, 1 H) 7.45-7.51 (m, 2 H) 7.52-7.59 (m, 2 H) 7.59-7.72 (m, 2 H) 7.85-7.91 (m, 1 H) 8.36-8.39 (m, 1 H). MS ESI posi: 407 [M + H]⁺. MS ESI nega: 405 [M − H]⁻. |
| 45-40 | 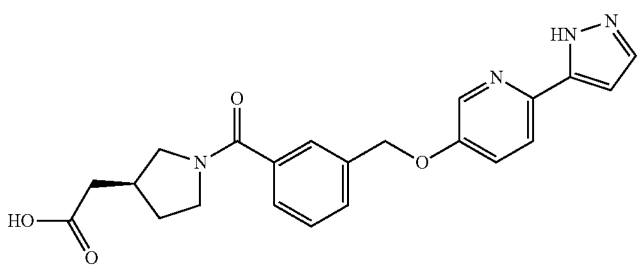 [SMILES: O=C(O)C[C@@H]1CCN(C(=O)c2cccc(COc3ccc(-c4ccn[nH]4)nc3)c2)C1] | ¹H NMR (600 MHz, DMSO-d₆) δ ppm 1.49-1.63 (m, 1 H) 1.95-2.11 (m, 1 H) 2.28-2.34 (m, 1 H) 2.36-2.44 (m, 2 H) 3.08-3.15 (m, 1 H) 3.34-3.73 (m, 3 H) 5.27 (s, 2 H) 6.75 (s, 1 H) 7.44-7.52 (m, 2 H) 7.53-7.65 (m, 3 H) 7.67-7.73 (m, 1 H) 7.88 (d, J = 8.7 Hz, 1 H) 8.35-8.40 (m, 1 H). MS ESI posi: 407 [M + H]⁺. MS ESI nega: 405 [M − H]⁻. |
| 45-41 | 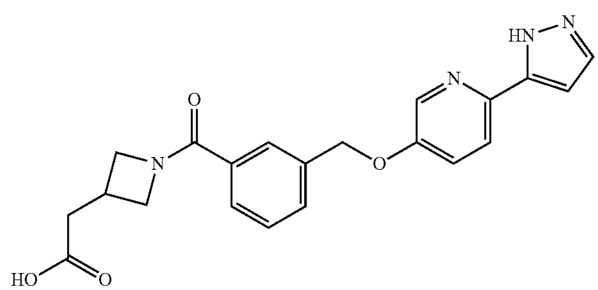 [SMILES: O=C(O)CC1CN(C(=O)c2cccc(COc3ccc(-c4ccn[nH]4)nc3)c2)C1] | ¹H NMR (600 MHz, DMSO-d₆) δ ppm 2.61 (d, J = 7.8 Hz, 2 H) 2.84-2.92 (m, 1 H) 3.69-3.74 (m, 1 H) 3.97-4.01 (m, 1 H) 4.12-4.17 (m, 1 H) 4.37-4.42 (m, 1 H) 5.27 (s, 2 H) 6.73 (d, J = 2.1 Hz, 1 H) 7.46-7.56 (m, 2 H) 7.57-7.63 (m, 2 H) 7.66-7.75 (m, 2 H) 7.86 (d, J = 8.7 Hz, 1 H) 8.36 (d, J = 2.9 Hz, 1 H). MS ESI posi: 393 [M + H]⁺. MS ESI nega: 391 [M − H]⁻. |
| 45-42 | 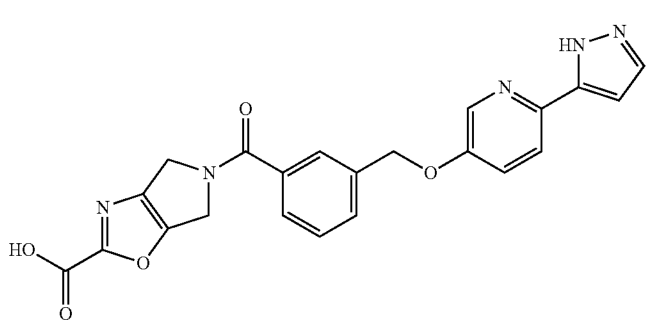 [SMILES: O=C(O)c1nc2c(o1)CN(C(=O)c1cccc(COc3ccc(-c4ccn[nH]4)nc3)c1)C2] | ¹H NMR (400 MHz, DMSO-d₆) δ ppm 4.52-4.65 (m, 2 H) 4.70-4.88 (m, 2 H) 5.29 (s, 2 H) 6.74 (s, 1 H) 7.46-7.78 (m, 6 H) 7.87 (d, J = 8.7 Hz, 1 H) 8.38 (d, J = 2.7 Hz, 1 H). MS ESI/APCI Multi posi: 432 [M + H]⁺. |

TABLE 61-7-continued

| Example No. | Structure | Analytical Data |
|---|---|---|
| 45-43 | 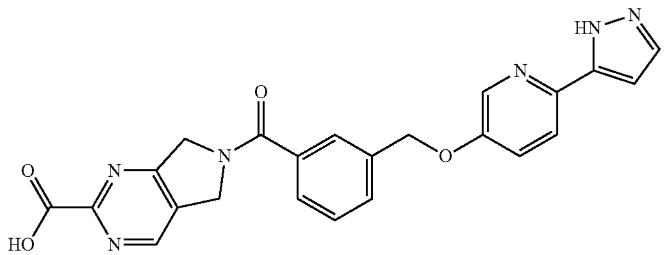 [SMILES: O=C(O)c1ncc2c(n1)CN(C(=O)c1cccc(COc3ccc(-c4ccn[nH]4)nc3)c1)C2] | $^1$H NMR (400 MHz, DMSO-$d_6$) δ ppm 4.75-5.11 (m, 4 H) 5.31 (s, 2 H) 6.74 (d, J = 1.8 Hz, 1 H) 7.48-7.79 (m, 6 H) 7.87 (d, J = 8.8 Hz, 1 H) 8.38 (d, J = 2.8 Hz, 1 H) 8.70-9.08 (m, 1 H). MS ESI/APCI Multi posi: 443 [M + H]$^+$. |

TABLE 61-8

| Example No. | Structure | Analytical Data |
|---|---|---|
| 45-44 | 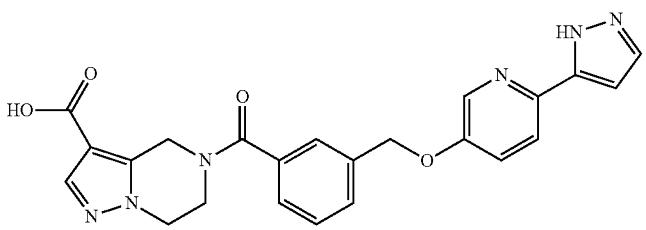 [SMILES: O=C(O)c1cnn2c1CN(C(=O)c1cccc(COc3ccc(-c4ccn[nH]4)nc3)c1)CC2] | $^1$H NMR (400 MHz, DMSO-$d_6$) δ ppm 3.68-4.32 (m, 4 H) 4.77-5.13 (m, 2 H) 5.18-5.42 (m, 2 H) 6.73 (d, J = 1.8 Hz, 1 H) 7.40-7.74 (m, 6 H) 7.80-7.92 (m, 2 H) 8.37 (d, J = 2.9 Hz, 1 H). MS ESI/APCI Multi posi: 445 [M + H]$^+$. MS ESI/APCI Multi nega: 443 [M − H]$^-$. |
| 45-45 | 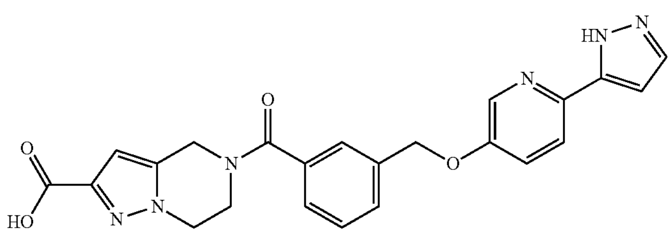 [SMILES: O=C(O)c1cc2n(n1)CCN(C(=O)c1cccc(COc3ccc(-c4ccn[nH]4)nc3)c1)C2] | $^1$H NMR (400 MHz, DMSO-$d_6$) δ ppm 3.62-4.35 (m, 4 H) 4.51-5.01 (m, 2 H) 5.28 (s, 2 H) 6.33-6.67 (m, 1 H) 6.73 (d, J = 1.8 Hz, 1 H) 7.41-7.77 (m, 6 H) 7.87 (d, J = 8.7 Hz, 1 H) 8.37 (d, J = 2.8 Hz, 1 H). MS ESI/APCI Multi posi: 445 [M + H]$^+$. MS ESI/APCI Multi nega: 443 [M − H]$^-$. |
| 45-46 | 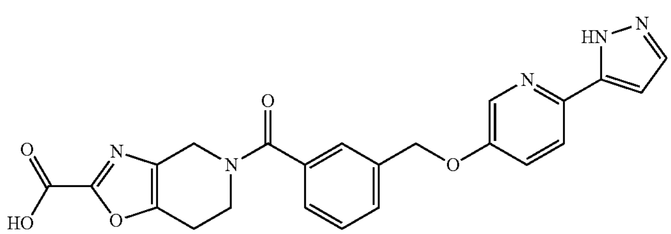 [SMILES: O=C(O)c1nc2c(o1)CCN(C(=O)c1cccc(COc3ccc(-c4ccn[nH]4)nc3)c1)C2] | $^1$H NMR (400 MHz, DMSO-$d_6$) δ ppm 2.71-3.04 (m, 2 H) 3.48-4.84 (m, 4 H) 5.28 (s, 2 H) 6.73 (d, J = 1.7 Hz, 1 H) 7.31-7.73 (m, 6 H) 7.87 (d, J = 8.8 Hz, 1 H) 8.37 (d, J = 2.7 Hz, 1 H). MS ESI/APCI Multi posi: 446 [M + H]$^+$. MS ESI/APCI Multi nega: 444 [M − H]$^-$. |
| 45-47 | 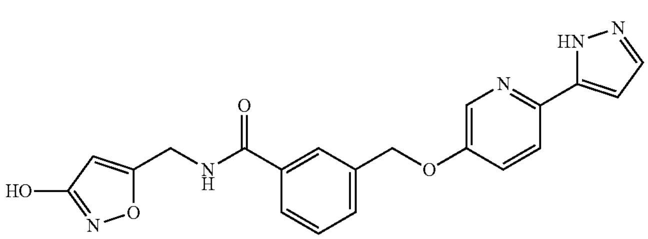 [SMILES: O=C(NCc1cc(O)no1)c1cccc(COc2ccc(-c3ccn[nH]3)nc2)c1] | $^1$H NMR (400 MHz, DMSO-$d_6$) δ ppm 4.46 (d, J = 5.6 Hz, 2 H) 5.28 (s, 2 H) 5.87 (s, 1 H) 6.73 (d, J = 2.1 Hz, 1 H) 7.43-7.75 (m, 5 H) 7.82-7.92 (m, 2 H) 7.95-8.23 (m, 1 H) 8.37 (d, J = 2.7 Hz, 1 H) 9.13 (t, J = 5.6 Hz, 1 H). MS ESI/APCI Multi posi: 392 [M + H]$^+$. MS ESI/APCI Multi nega: 390 [M − H]$^-$. |

Example 46-1

2,2-Dimethyl-4-oxo-4-[4 [[6-(1H-pyrazol-5-yl)-3-pyridinyl]oxymethyl]-1-piperidinyl]butanoic Acid

[Formula 566]

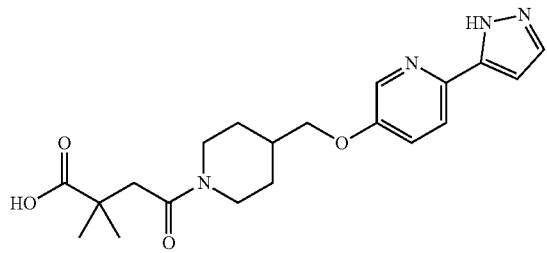

(1) The compound (100 mg) obtained in Reference Example 4-1 and 4-methoxy-3,3-dimethyl-4-oxobutanoic acid (70 mg) were used to perform the synthesis process according to the method described in Example 42-1 thereby giving methyl 2,2-dimethyl-4-[4-[[6-[2-(2-oxanyl)-3-pyrazolyl]-3-pyridinyl]oxymethyl]-1-piperidinyl]-4-oxobutanoate (100 mg) as a colorless oil.

(2) The compound (100 mg) obtained in (1) above was used to perform the synthesis process according to the method described in Example 1-1-(2) thereby giving a mixture containing 2,2-dimethyl-4-[4-[[6-[2-(2-oxanyl)-3-pyrazolyl]-3-pyridinyl]oxymethyl]-1-piperidinyl]-4-oxobutanoic acid.

(3) The mixture obtained in (2) above was used to perform the synthesis process according to the method described in Example 1-43-(3) thereby giving the title compound (35 mg) as a colorless amorphous substance.

$^1$H NMR (400 MHz, DMSO-$d_6$) δ ppm 0.96-1.20 (m, 6H) 2.23 (s, 6H) 2.65-2.71 (m, 1H) 2.72-3.13 (m, 2H) 3.75-4.58 (m, 4H) 6.68-6.77 (m, 1H) 7.41-8.30 (m, 5H).

MS ESI posi: 387[M+H]$^+$.

The compounds of Examples 46-2 to 46-5 below were synthesized using the compound obtained in Reference Example 4-2 and the compound obtained in Reference Example 63-1 or a commercially available compound, according to the method described in Example 46-1. The structures, NMR data, and MS data of the compounds are shown in Table 62-1.

TABLE 62-1

| Example No. | Structure | Analytical Data |
| --- | --- | --- |
| 46-2 | 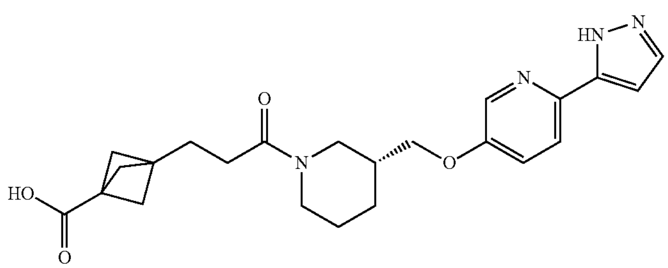 [SMILES: O=C(CCC12CC(C(=O)O)(C1)C2)N1CCC[C@@H](COc2ccc(-c3ccn[nH]3)nc2)C1] | $^1$H NMR (400 MHz, DMSO-$d_6$) δ ppm 1.25-1.50 (m, 2 H) 1.57-1.68 (m, 2 H) 1.70-1.80 (m, 6 H) 1.82-1.93 (m, 2 H) 2.13-2.35 (m, 2 H) 2.97-3.15 (m, 1 H) 3.73-3.87 (m, 1 H) 3.92-4.05 (m, 4 H) 4.38-4.43 (m, 1 H) 6.77 (s, 1 H) 7.50-7.58 (m, 1 H) 7.66-7.75 (m, 1 H) 7.90 (d, J = 8.6 Hz, 1 H) 8.28-8.34 (m, 1 H). MS ESI/APCI Multi posi: 425 [M + H]$^+$. |
| 46-3 | 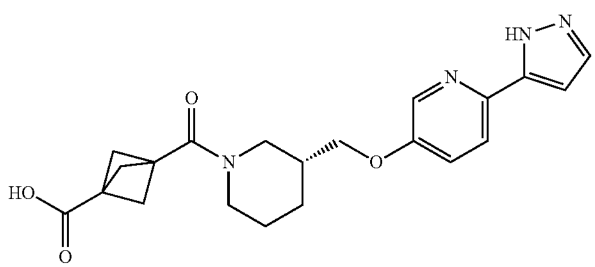 [SMILES: O=C(O)C12CC(C(=O)N3CCC[C@@H](COc4ccc(-c5ccn[nH]5)nc4)C3)(C1)C2] | $^1$H NMR (400 MHz, DMSO-$d_6$) δ ppm 1.29-1.46 (m, 2 H) 1.59-1.79 (m, 1 H) 1.81-1.96 (m, 2 H) 2.16-2.29 (m, 6 H) 2.65-2.82 (m, 1 H) 2.99-3.11 (m, 1 H) 3.86-4.18 (m, 3 H) 4.30-4.43 (m, 1 H) 6.73 (s, 1 H) 7.40-7.51 (m, 1 H) 7.59-7.77 (m, 1 H) 7.80-7.91 (m, 1 H) 8.23-8.34 (m, 1 H). MS ESI/APCI Multi posi: 397 [M + H]$^+$. |
| 46-4 | 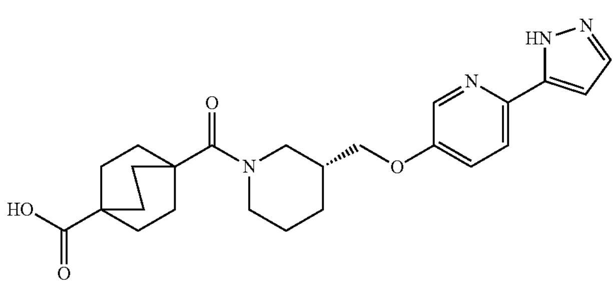 [SMILES: O=C(O)C12CCC(C(=O)N3CCC[C@@H](COc4ccc(-c5ccn[nH]5)nc4)C3)(CC1)CC2] | $^1$H NMR (400 MHz, DMSO-$d_6$) δ ppm 1.27-1.44 (m, 2 H) 1.65-1.82 (m, 12 H) 1.82-1.93 (m, 2 H) 2.67-2.85 (m, 2 H) 3.13-3.20 (m, 1 H) 3.87-4.07 (m, 2 H) 4.16-4.27 (m, 1 H) 4.32-4.43 (m, 1 H) 6.73 (s, 1 H) 7.40-7.54 (m, 1 H) 7.58-7.78 (m, 1 H) 7.80-7.92 (m, 1 H) 8.21-8.35 (m, 1 H). MS ESI/APCI Multi posi: 439 [M + H]$^+$. |

TABLE 62-1-continued

| Example No. | Structure | Analytical Data |
|---|---|---|
| 46-5 | 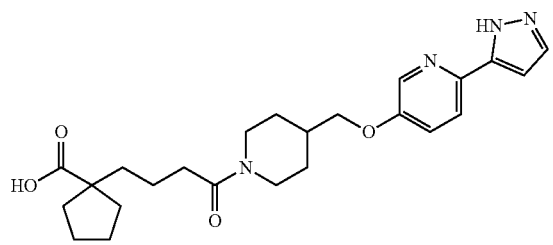 | $^1$H NMR (400 MHz, METHANOL-$d_4$) δ ppm 1.24-2.23 (m, 6 H) 2.90-3.16 (m, 1 H) 3.78-3.99 (m, 3 H) 3.99-4.12 (m, 2 H) 4.26-4.45 (m, 1 H) 6.89-6.98 (m, 1 H) 7.35-7.59 (m, 2 H) 7.74-8.01 (m, 4 H) 8.01-8.22 (m, 1 H) 8.23-8.35 (m, 1 H). MS ESI/APCI Multi posi: 421 [M + H]$^+$. MS ESI/APCI Multi nega: 419 [M − H]$^−$. |

Example 47-1

1-[4-Oxo-4-[4-[[6-(1H-pyrazol-5-yl)-3-pyridinyl]oxymethyl]-1-piperidinyl]butyl]-1-cyclopentanecarboxylic Acid

[Formula 567]

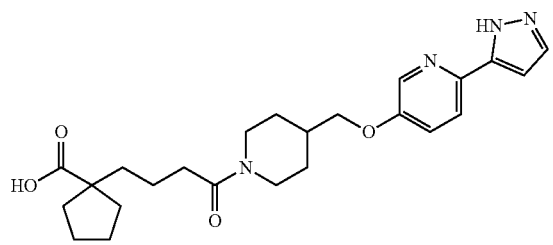

(1) To a solution of the compound (64 mg) obtained in Reference Example 77-1 in N,N-dimethylformamide (2.5 mL), N,N-diisopropylethylamine (0.26 mL), O-(7-azabenzotriazol-1-yl)-N,N,N',N'-tetramethyluronium hexafluorophosphate (HATU) (104 mg), and the compound (164 mg) obtained in Reference Example 4-1 were added under ice cooling, and the mixture was stirred at room temperature for 16 hours. An aqueous solution of saturated ammonium chloride was added to stop the reaction, and the resultant mixture was extracted three times with ethyl acetate (5.0 mL). The obtained organic layers were combined, passed through a phase separator, and concentrated under reduced pressure. The obtained residue was purified by silica gel column chromatography (n-hexane:ethyl acetate=7:3 to 3:7) to give tert-butyl 1-[4-[4-[[6-[2-(2-oxanyl)-3-pyrazolyl]-3-pyridinyl]oxymethyl]-1-piperidinyl]-4-oxobutyl]-1-cyclopentanecarboxylate (120 mg) as a colorless oil.

(2) Trifluoroacetic acid (0.25 mL) and water (0.50 mL) were added to a solution of the compound (120 mg) obtained in (1) above in methanol (1.5 mL) under ice cooling, and the mixture was stirred at the same temperature for 0.5 hours. The reaction mixture was concentrated under reduced pressure to give tert-butyl 1-[4-oxo-4-[4-[[6-(1H-pyrazol-5-yl)-3-pyridinyl]oxymethyl]-1-piperidinyl]butyl]-1-cyclopentanecarboxylate as a crude product.

(3) A 4 mol/L hydrogen chloride-1,4-dioxane solution (1.0 mL) was added to a solution of the crude product obtained in (2) above in 1,4-dioxane (2.1 mL), and the mixture was stirred at room temperature for 14 hours. The solvent was distilled off under reduced pressure, and the resultant was purified by preparative HPLC to give the title compound (32 mg) as a colorless powder.

$^1$H NMR (400 MHz, DMSO-$d_6$) δ ppm 1.09-1.30 (m, 2H) 1.33-1.45 (m, 5H) 1.50-1.60 (m, 6H) 1.72-1.85 (m, 2H) 1.96-2.07 (m, 3H) 2.23-2.30 (m, 2H) 2.96-3.06 (m, 1H) 3.83-3.90 (m, 1H) 3.95 (d, J=6.5 Hz, 2H) 4.37-4.45 (m, 1H) 6.72 (d, J=2.1 Hz, 1H) 7.40-7.47 (m, 1H) 7.61-7.75 (m, 1H) 7.80-7.90 (m, 1H) 8.28 (d, J=2.7 Hz, 1H).

MS ESI/APCI Multi posi: 441 [M+H]$^+$.
MS ESI/APCI Multi nega: 439[M−H]$^−$.

Example 48-1

4-Oxo-4-[4-[[6-(1H-pyrazol-5-yl)-3-pyridinyl]oxymethyl]-1-piperidinyl]butanoic Acid

[Formula 568]

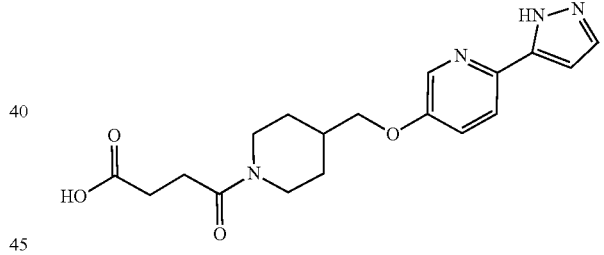

(1) To a solution of the compound (50 mg) obtained in Reference Example 4-1 and 4-oxo-4-phenylmethoxybutanoic acid (30 mg) in chloroform (1.5 mL), N,N-diisopropylethylamine (0.30 mL), 1-ethyl-3-(3-dimethylaminopropyl)carbodiimide hydrochloride (34 mg), and 1-hydroxybenzotriazole monohydrate (29 mg) were added, and the mixture was stirred at room temperature for 3 hours. An aqueous solution of saturated ammonium chloride (5 mL) was added to stop the reaction, and the resultant mixture was extracted three times with chloroform (5 mL). The obtained organic layers were combined, passed through a phase separator, and concentrated under reduced pressure. The obtained residue was purified by silica gel column chromatography (n-hexane:ethyl acetate=3:1 to 1:3 to ethyl acetate:methanol=10:1) to give (phenylmethyl) 4-[4-[[6-[2-(2-oxanyl)-3-pyrazolyl]-3-pyridinyl]oxymethyl]-1-piperidinyl]-4-oxobutanoate (70 mg) as a colorless amorphous substance.

(2) The compound (70 mg) obtained in (1) above was used to perform the synthesis process according to the method described in Example 2-1-(3) thereby giving a crude product of 4-[4-[[6-[2-(2-oxanyl)-3-pyrazolyl]-3-pyridinyl] oxymethyl]-1-piperidinyl]-4-oxobutanoic acid.

(3) The crude product obtained in (2) above was used to perform the synthesis process according to the method described in Example 1-43-(3) thereby giving the title compound (20 mg) as a colorless powder.

$^1$H NMR (400 MHz, DMSO-d$_6$) δ ppm 1.06-1.32 (m, 2H) 1.70-1.87 (m, 2H) 1.94-2.12 (m, 1H) 2.29-2.46 (m, 2H) 2.53-2.68 (m, 3H) 2.94-3.12 (m, 1H) 3.88-4.03 (m, 3H) 4.35-4.45 (m, 1H) 6.73 (d, J=2.1 Hz, 1H) 7.45 (dd, J=8.7, 2.8 Hz, 1H) 7.60-7.72 (m, 1H) 7.84 (d, J=8.7 Hz, 1H) 8.28 (d, J=2.8 Hz, 1H) 12.62 (br s, 1H).

MS ESI/APCI Multi posi: 359[M+H]$^+$.

Example 49-1

3-[[Oxo-[4-[[6-(1H-pyrazol-5-yl)-3-pyridinyl]oxymethyl]-2-pyridinyl]methyl]amino]propanoic Acid

[Formula 569]

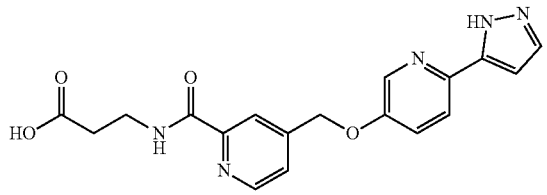

(1) The compound (24 mg) obtained in Example 1-40-(2) and methyl 3-aminopropanoate hydrochloride (10 mg) were used to perform the synthesis process according to the method described in Example 48-1-(1) thereby giving methyl 3-[[[4-[[6-[2-(2-oxanyl)-3-pyrazolyl]-3-pyridinyl] oxymethyl]-2-pyridinyl]-oxomethyl] amino]propanoate (10 mg) as a colorless oil.

(2) An aqueous solution of 1 mol/L sodium hydroxide (0.50 mL) was added to a solution of the compound (10 mg) obtained in (1) above in methanol (0.80 mL), and the mixture was stirred at an outer temperature of 65° C. for 2 hours to give a solution containing 3-[[[4-[[6-[2-(2-oxanyl)-3-pyrazolyl]-3-pyridinyl]oxymethyl]-2-pyridinyl]-oxomethyl] amino]propanoic acid.

(3) The solution obtained in (2) above was used to perform the synthesis process according to the method described in Example 1-43-(3) thereby giving the title compound (5 mg) as a colorless powder.

$^1$H NMR (400 MHz, DMSO-d$_6$) δ ppm 2.56-2.59 (m, 2H) 3.48-3.54 (m, 2H) 5.41 (s, 2H) 6.74 (d, J=2.1 Hz, 1H) 7.50-7.59 (m, 1H) 7.64-7.77 (m, 2H) 7.83-7.92 (m, 1H) 8.12 (s, 1H) 8.39 (d, J=2.7 Hz, 1H) 8.66 (d, J=4.9 Hz, 1H) 8.81-8.90 (m, 1H) 12.87 (br s, 1H).

MS ESI/APCI Multi posi: 368[M+H]$^+$.

Example 50-1

1-[[1-Oxo-7-[[6-(1H-pyrazol-5-yl)-3-pyridinyl]oxy] heptyl]amino]-1-cyclopentanecarboxylic Acid

[Formula 570]

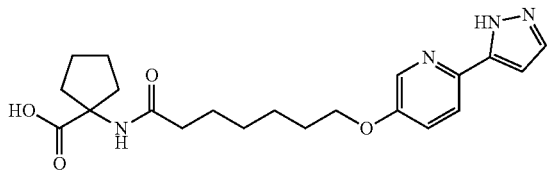

(1) Cesium carbonate (782 mg) and benzyl bromide (0.285 mL) were added to a solution of 1-[[(2-methylpropan-2-yl)oxy-oxomethyl]amino]-1-cyclopentanecarboxylic acid (500 mg) in N,N-dimethylformamide (11 mL), and the mixture was stirred at room temperature for 3 hours. An aqueous solution of saturated ammonium chloride (10 mL) was added to stop the reaction, and the resultant mixture was extracted three times with an ethyl acetate:toluene mixed solution (1:1, 10 mL). The obtained organic layers were combined, passed through a phase separator, and concentrated under reduced pressure to give a crude product. The obtained crude product was purified by silica gel column chromatography (n-hexane:ethyl acetate=5:1 to 1:1) to give (phenylmethyl) 1-[[(2-methylpropan-2-yl)oxy-oxomethyl] amino]-1-cyclopentanecarboxylate (802 mg) as a colorless oil.

(2) Trifluoroacetic acid (1.0 mL) was added to a solution of the compound (300 mg) obtained in (1) above in chloroform (3.1 mL), and the mixture was stirred at room temperature for 2 hours. An aqueous solution of saturated potassium carbonate (10 mL) was added thereto under ice cooling to adjust pH to 9.5, thereby stopping the reaction. The resultant mixture was extracted three times with ethyl acetate (5 mL), and the obtained organic layers were combined, passed through a phase separator, and concentrated under reduced pressure to give (phenylmethyl) 1-amino-1-cyclopentanecarboxylate (262 mg) as a colorless oil.

(3) The compound (254 mg) obtained in Example 22-20-(1) was used to perform the synthesis process according to the method described in Example 1-1-(2) thereby giving 7-[[6-[2-(2-oxanyl)-3-pyrazolyl]-3-pyridinyl]oxy]heptanoic acid (200 mg) as a colorless powder.

(4) The compound (93 mg) obtained in (2) above and the compound (150 mg) obtained in (3) above were used to perform the synthesis process according to the method described in Example 48-1-(1) thereby giving (phenylmethyl) 1-[[7-[[6-[2-(2-oxanyl)-3-pyrazolyl]-3-pyridinyl] oxy]-1-oxoheptyl]amino]-1-cyclopentanecarboxylate (200 mg) as a colorless oil.

(5) The compound (100 mg) obtained in (4) above was used to perform the synthesis process according to the method described in Example 2-1-(3) thereby giving 1-[[7-[[6-[2-(2-oxanyl)-3-pyrazolyl]-3-pyridinyl]oxy]-1-oxoheptyl] amino]-1-cyclopentanecarboxylic acid as a crude product.

(6) The crude product obtained in (5) above was used to perform the synthesis process according to the method described in Example 1-43-(3) thereby giving the title compound (23 mg) as a colorless powder.

$^1$H NMR (400 MHz, DMSO-d$_6$) δ ppm 1.29-1.35 (m, 2H) 1.37-1.47 (m, 2H) 1.47-1.55 (m, 2H) 1.55-1.67 (m, 2H) 1.68-1.77 (m, 3H) 1.78-1.89 (m, 3H) 1.96-2.03 (m, 2H) 2.04-2.08 (m, 2H) 4.06 (t, J=6.4 Hz, 2H) 6.72 (d, J=2.1 Hz, 1H) 7.43 (dd, J=8.7, 2.8 Hz, 1H) 7.61-7.73 (m, 1H) 7.80-7.88 (m, 1H) 8.00 (s, 1H) 8.27 (d, J=2.8 Hz, 1H).

MS ESI/APCI Multi posi: 401 [M+H]$^+$.
MS ESI/APCI Multi nega: 399[M−H]$^-$.

Example 51-1

Methyl 4-hydroxy-4-[3-[[6-(1-H-pyrazol-5-yl)-3-pyridinyl]oxymethyl]phenyl]-1-piperidinecarboxylate

[Formula 571]

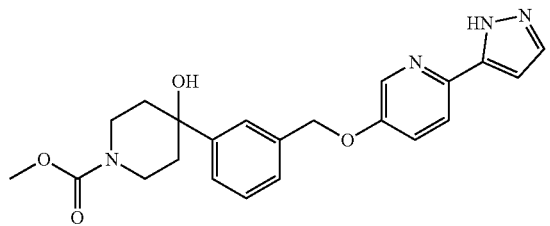

(1) The compound (33.9 mg) obtained in Reference Example 9-1 and methyl chloroformate were used to perform the synthesis process according to the method described in Example 17-1-(5) thereby giving a mixture containing methyl 4-[3-[[6-[2-(2-oxanyl)-3-pyrazolyl]-3-pyridinyl]oxymethyl]phenyl]-4-trimethylsilyloxy-1-piperidinecarboxylate.

(2) The mixture obtained in (1) above was used to perform the synthesis process according to the method described in Example 10-1-(2) thereby giving the title compound (2.5 mg) as a colorless powder.

$^1$H NMR (600 MHz, CHLOROFORM-d) δ ppm 1.23-1.29 (m, 2H) 1.74-1.78 (m, 2H) 1.95-2.11 (m, 1H) 3.23-3.41 (m, 2H) 3.73 (s, 3H) 3.99-4.22 (m, 2H) 5.16 (s, 2H) 6.77 (br s, 1H) 7.35-7.48 (m, 4H) 7.56-7.62 (m, 1H) 7.62-7.66 (m, 1H) 7.67-7.75 (m, 1H) 8.34-8.41 (m, 1H).

MS ESI/APCI Multi posi: 409[M+H]$^+$.

The compound of Example 51-2 below was synthesized using a commercially available compound, according to the method described in Example 51-1. The structure, NMR data, and MS data of the compound are shown in Table 63-1.

Example 52-1

1-[4-Hydroxy-4-[3-[[6-(1-H-pyrazol-5-yl)-3-pyridinyl]oxymethyl]phenyl]-1-piperidinyl]ethanone

[Formula 572]

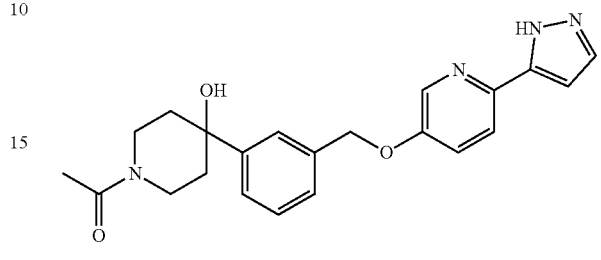

(1) The compound (34.8 mg) obtained in Reference Example 9-1 was used to perform the synthesis process according to the method described in Example 6-1-(3) thereby giving a mixture containing 1-[4-[3-[[6-[2-(2-oxanyl)-3-pyrazolyl]-3-pyridinyl] oxymethyl]phenyl]-4-trimethylsilyloxy-1-piperidinyl]ethanone.

(2) The mixture obtained in (1) above was used to perform the synthesis process according to the method described in Example 10-1-(2) thereby giving the title compound (4.5 mg) as a colorless powder.

$^1$H NMR (600 MHz, CHLOROFORM-d) δ ppm 1.76-1.88 (m, 2H) 1.93-2.01 (m, 1H) 2.01-2.07 (m, 1H) 2.14 (s, 3H) 3.06-3.14 (m, 1H) 3.56-3.68 (m, 1H) 3.68-3.80 (m, 1H) 4.56-4.66 (m, 1H) 5.16 (s, 2H) 6.72 (br s, 1H) 7.31-7.48 (m, 4H) 7.56-7.74 (m, 3H) 8.30-8.42 (m, 1H).

MS ESI/APCI Multi posi: 393 [M+H]$^+$.

The compound of Example 52-2 below was synthesized using the compound obtained in Reference Example 9-2, according to the method described in Example 52-1. The structure, NMR data, and MS data of the compound are shown in Table 64-1.

TABLE 63-1

| Example No. | Structure | Analytical Data |
|---|---|---|
| 51-2 | 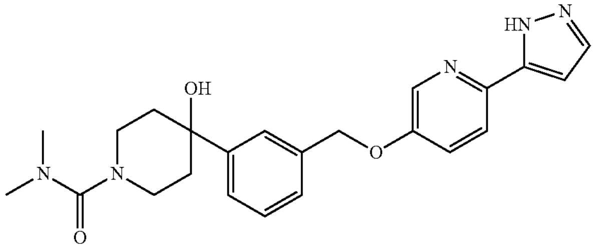 [SMILES: CN(C)C(=O)N1CCC(O)(c2cccc(COc3ccc(-c4ccn[nH]4)nc3)c2)CC1] | $^1$H NMR (600 MHz, CHLOROFORM-d) δ ppm 1.74-1.78 (m, 2 H) 2.07-2.13 (m, 2 H) 2.82-2.90 (m, 6 H) 3.28-3.36 (m, 2 H) 3.58-3.67 (m, 2 H) 5.16 (s, 2 H) 6.78 (br s, 1 H) 7.35-7.51 (m, 4 H) 7.59-7.67 (m, 2 H) 7.68-7.84 (m, 1 H) 8.34-8.41 (m, 1 H).<br>MS ESI/APCI Multi posi: 422 [M + H]$^+$. |

TABLE 64-1

| Example No. | Structure | Analytical Data |
|---|---|---|
| 52-2 | 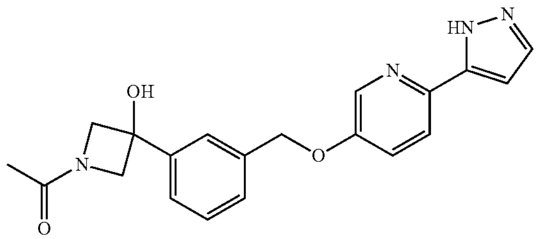 [SMILES: CC(=O)N1CC(O)(c2cccc(COc3ccc(-c4ccn[nH]4)nc3)c2)C1] | $^1$H NMR (600 MHz, CHLOROFORM-d) δ ppm 1.92-1.98 (m, 3 H) 4.27 (d, J = 10.7 Hz, 1 H) 4.36-4.46 (m, 3 H) 5.19 (s, 2 H) 6.74 (br s, 1 H) 7.35-7.52 (m, 4 H) 7.57-7.67 (m, 2 H) 7.70 (d, J = 8.7 Hz, 1 H) 8.37 (d, J = 2.5 Hz, 1H). MS ESI/APCI Multi posi: 365 [M + H]$^+$. |

Example 53-1

3-[[6-(1H-Pyrazol-5-yl)-3-pyridinyl]oxymethyl]benzamide

[Formula 573]

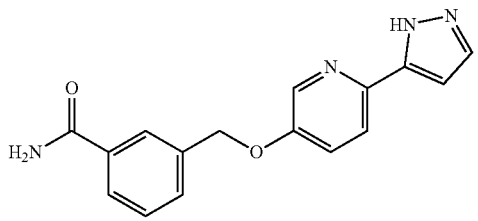

$^1$H NMR (600 MHz, DMSO-d$_6$) δ ppm 5.33 (s, 2H) 6.92 (d, J=2.1 Hz, 1H) 7.42 (br s, 1H) 7.50 (t, J=7.6 Hz, 1H) 7.64 (d, J=7.8 Hz, 1H) 7.79-7.84 (m, 2H) 7.85-7.89 (m, 1H) 8.00-8.04 (m, 2H) 8.06 (d, J=8.7 Hz, 1H) 8.42 (d, J=2.9 Hz, 1H).

MS ESI/APCI Multi posi: 295 [M+H]$^+$.

The compound of Example 53-2 below was synthesized using the compound obtained in Example 1-41-(2), according to the method described in Example 53-1. The structure, NMR data, and MS data of the compound are shown in Table 65-1.

TABLE 65-1

| Example No. | Structure | Analytical Data |
|---|---|---|
| 53-2 | 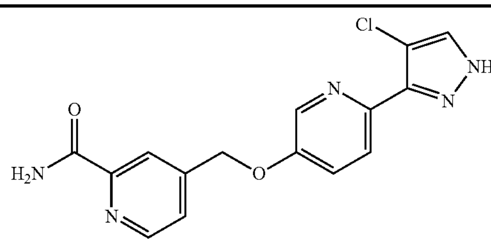 | $^1$H NMR (400 MHz, DMSO-d$_6$) δ ppm 5.44 (s, 2 H) 7.50-8.08 (m, 5 H) 8.09-8.20 (m, 2 H) 8.40-8.56 (m, 1 H) 8.62-8.71 (m, 1 H). MS ESI/APCI Multi posi: 330 [M + H]$^+$. |

(1) The compound (365 mg) obtained in Reference Example 10-1 was used to perform the synthesis process according to the method described in Example 44-7 thereby giving 3-[[6-[2-(2-oxanyl)-3-pyrazolyl]-3-pyridinyl]oxymethyl]benzamide (258 mg).

(2) The compound (258 mg) obtained in (1) above was used to perform the synthesis process according to the method described in Example 12-1-(3) thereby giving the title compound (225 mg) as a colorless solid.

Example 54-1

N-Methylsulfonyl-6-[[6-(1H-pyrazol-5-yl)-3-pyridinyl]oxy]hexanamide

[Formula 574]

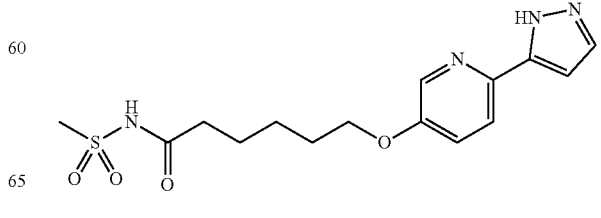

(1) The compound (237 mg) obtained in Example 1-47-(1) was used to perform the synthesis process according to the method described in Example 9-1-(3) thereby giving 6-[[6-[2-(2-oxanyl)-3-pyrazolyl]-3-pyridinyl]oxy]hexanoic acid (220 mg) as a pale yellow oil.

(2) The compound (220 mg) obtained in (1) above and methanesulfonamide (117 mg) were used to perform the synthesis process according to the method described in Example 44-1 thereby giving N-methylsulfonyl-6-[[6-[2-(2-oxanyl)-3-pyrazolyl]-3-pyridinyl]oxy]hexanamide (60 mg).

(3) The compound (60 mg) obtained in (2) above was used to perform the synthesis process according to the method described in Example 12-1-(3) thereby giving the title compound (33 mg) as a colorless powder.

$^1$H NMR (400 MHz, DMSO-$d_6$) δ ppm 1.38-1.48 (m, 2H) 1.54-1.64 (m, 2H) 1.70-1.79 (m, 2H) 2.25-2.31 (m, 2H) 3.20 (s, 3H) 4.03-4.10 (m, 2H) 6.70-6.75 (m, 1H) 7.37-7.50 (m, 1H) 7.63-7.95 (m, 2H) 8.21-8.34 (m, 1H) 11.66 (br s, 1H).

MS ESI/APCI Multi posi: 353 [M+H]$^+$.
MS ESI/APCI Multi nega: 351[M−H]$^−$.

Example 55-1

2,2-Dimethyl-4-[[oxo-[(3R)-3-[[6-(1H-pyrazol-5-yl)-3-pyridinyl]oxymethyl]-1-piperidinyl]methyl]amino]butanoic Acid

[Formula 575]

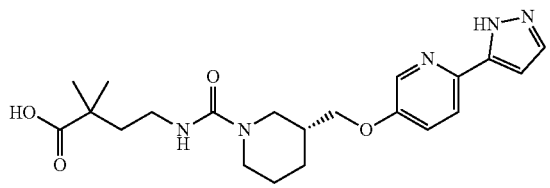

(1) Triethylamine (81 μL) was added to a suspension of methyl 4-amino-2,2-dimethylbutanoate hydrochloride (35 mg) in chloroform (2 mL), the mixture was ice-cooled and triphosgene (23 mg) was then added thereto, and the resultant mixture was stirred for 30 minutes. A solution of triethylamine (54 μL) and the compound (66 mg) obtained in Reference Example 4-2 in chloroform (2 mL) was added to the reaction solution under ice cooling, and the resultant mixture was stirred at room temperature overnight. An aqueous solution of 10% sodium hydrogen carbonate was added to the reaction solution, the organic layer was separated, and the aqueous layer was extracted with chloroform. The organic layers were combined, separated by a phase separator, and concentrated under reduced pressure to give a mixture (67 mg) containing methyl 2,2-dimethyl-4-[[[(3R)-3-[[6-[2-(2-oxanyl)-3-pyrazolyl]-3-pyridinyl]oxymethyl]-1-piperidinyl]-oxomethyl] amino]butanoate.

(2) The mixture (67 mg) obtained in (1) above was dissolved in methanol (5 mL), 2 mol/L hydrochloric acid (0.13 mL) was added thereto, and the resultant mixture was stirred at room temperature for 1 hour. An aqueous solution of 1 mol/L sodium hydroxide (0.52 mL) was added to the reaction solution, and the resultant mixture was stirred at room temperature for 20 hours. Sodium hydroxide (10 mg) was added to the reaction solution, and the resultant mixture was stirred at 65° C. for 5 hours. The solvent was distilled off under reduced pressure, the residue was diluted by adding water thereto, and an aqueous solution of 10% potassium hydrogen sulfate was added thereto to adjust pH to 4 to 5. The resultant was extracted by adding ethyl acetate, and the organic layer was separated by a phase separator, and concentrated under reduced pressure. The obtained residue was purified by preparative HPLC. The purified residue was dried under reduced pressure to give the title compound (34 mg) as a colorless amorphous substance.

$^1$H NMR (600 MHz, DMSO-$d_6$) δ ppm 1.08 (s, 6H) 1.22-1.40 (m, 2H) 1.57-1.64 (m, 3H) 1.80-1.90 (m, 2H) 2.58-2.64 (m, 1H) 2.70-2.77 (m, 1H) 2.94-3.03 (m, 2H) 3.73-3.79 (m, 1H) 3.90-3.96 (m, 2H) 3.98-4.03 (m, 1H) 6.33-6.47 (m, 1H) 6.73 (d, J=2.1 Hz, 1H) 7.43-7.48 (m, 1H) 7.62-7.74 (m, 1H) 7.82-7.88 (m, 1H) 8.29 (d, J=2.9 Hz, 1H).

MS ESI posi: 416[M+H]$^+$.
MS ESI nega: 414[M−H]$^−$.

Example 56-1

N-[3-[[6-(1H-Pyrazol-5-yl)-3-pyridinyl]oxymethyl]phenyl]-2-propanesulfonamide

[Formula 576]

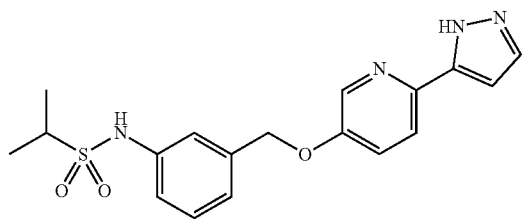

(1) The corresponding commercially available alcohol was used to perform the synthesis process according to the method described in Example 10-2-(1) thereby giving tert-butyl N-[3-[[6-[2-(2-oxanyl)-3-pyrazolyl]-3-pyridinyl]oxymethyl]phenyl]carbamate (202 mg).

(2) The compound (161 mg) obtained in (1) above was dissolved in trifluoroacetic acid (2 mL), water (0.5 mL) was added to this mixture, and the resultant mixture was stirred at room temperature for 8 hours. After confirming the end of the reaction by LC-MS, a nitrogen gas was blown onto the mixture to remove volatiles. An operation of dissolving the residue in methanol and concentrating it under reduced pressure was repeated twice, and the obtained residue was purified by NH silica gel column chromatography (chloroform only to chloroform:methanol=19:1). The resulting compound was recrystallized from a chloroform:methanol:hexane mixed solution to give 3-[[6-(1H-pyrazol-5-yl)-3-pyridinyl]oxymethyl]aniline (35 mg) as a colorless powder.

(3) Isopropylsulfonyl chloride (22 μL), N,N-diisopropylethylamine (47 μL), and a catalytic amount of 4-dimethylaminopyridine were added to a suspension of the compound (35 mg) obtained in (2) above in chloroform (1 mL), and the mixture was stirred at room temperature overnight. To this mixture, isopropylsulfonyl chloride (73 μL) and N,N-diisopropylethylamine (118 μL) were added, and the resultant mixture was further stirred at room temperature for 3 days. An aqueous solution of saturated sodium hydrogen carbonate was added to the reaction solution, and the resultant mixture was extracted twice with chloroform. The organic layers were combined and dried over magnesium sulfate, the drying agent was filtered off, and the filtrate was then concentrated under reduced pressure. The obtained residue was purified by preparative HPLC to give the title compound as a colorless oil (7.5 mg).

$^1$H NMR (600 MHz, DMSO-$d_6$) δ ppm 1.20 (s, 3H) 1.22 (s, 3H) 3.15-3.23 (m, 1H) 5.23 (s, 2H) 6.79 (d, J=2.0 Hz, 1H) 7.16-7.22 (m, 2H) 7.32-7.37 (m, 2H) 7.61 (dd, J=8.7, 2.9 Hz, 1H) 7.73 (d, J=2.0 Hz, 1H) 7.93 (d, J=8.7 Hz, 1H) 8.35 (d, J=2.9 Hz, 1H) 9.82 (s, 1H).

MS ESI/APCI Multi posi: 373 [M+H]$^+$.
MS ESI/APCI Multi nega: 371[M−H]$^−$.

Example 57-1

[2-Methyl-5-[[6-(1H-pyrazol-5-yl)-3-pyridinyl]oxymethyl]phenyl]methanesulfonate

[Formula 577]

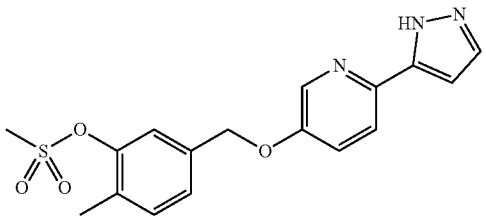

Triethylamine (57.2 μL) and methansulfonyl chloride (25.4 μL) were added to a solution of the compound (30 mg) obtained in Example 12-1-(2) in tetrahydrofuran (1 mL), and the mixture was stirred at room temperature for 1 hour. To this mixture, methanol (1 mL) and 2 mol/L hydrochloric acid (1 mL) were added, and the resultant mixture was stirred at room temperature for 30 minutes. After triethylamine (2 mL) was added thereto, the mixture was concentrated. The obtained residue was purified by silica gel column chromatography (chloroform:methanol=97:3 to 9:1), and the obtained crude product was recrystallized from a chloroform:hexane mixed solution to give the title compound (22 mg) as a colorless powder.

$^1$H NMR (600 MHz, CHLOROFORM-d) δ ppm 2.38 (s, 3H) 3.21 (s, 3H) 5.13 (s, 2H) 6.69 (s, 1H) 7.28-7.34 (m, 3H) 7.39 (s, 1H) 7.62 (d, J=2.1 Hz, 1H) 7.63-7.69 (m, 1H) 8.34 (d, J=2.9 Hz, 1H).

MS ESI/APCI Multi posi: 360[M+H]$^+$.

The compounds of Examples 57-2 and 57-3 below were synthesized using a compound obtained in Reference Example 4-3 or 4-4, according to the method described in Example 57-1. The structures, NMR data, and MS data of the compounds are shown in Table 66-1.

Example 58-1

N-[[3-[[6-(1H-Pyrazol-5-yl)-3-pyridinyl]oxymethyl]-1-bicyclo[1.1.1]pentanyl]methyl]methanesulfonamide

[Formula 578]

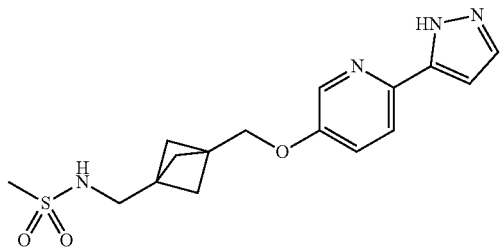

(1) The compound (181 mg) obtained in Reference Example 7-1 and methanesulfonyl chloride were used to perform the synthesis process according to the method described in Example 17-1-(5) thereby giving N-[[3-[[6-[2-(2-oxanyl)-3-pyrazolyl]-3-pyridinyl]oxymethyl]-1-bicyclo[1.1.1]pentanyl]methyl]methanesulfonamide (103 mg) as a colorless oil.

(2) The compound (35.6 mg) obtained in (1) above was used to perform the synthesis process according to the method described in Example 10-1-(2) thereby giving the title compound (17.0 mg) as a colorless powder.

$^1$H NMR (600 MHz, CHLOROFORM-d) δ ppm 1.81 (s, 6H) 2.96 (s, 3H) 3.26 (d, J=6.2 Hz, 2H) 4.07 (s, 2H) 4.12-4.20 (m, 1H) 6.64-6.72 (m, 1H) 7.20-7.25 (m, 1H) 7.57-7.69 (m, 2H) 8.21-8.32 (m, 1H).

MS ESI/APCI Multi posi: 349[M+H]$^+$.

TABLE 66-1

| Example No. | Structure | Analytical Data |
|---|---|---|
| 57-2 | 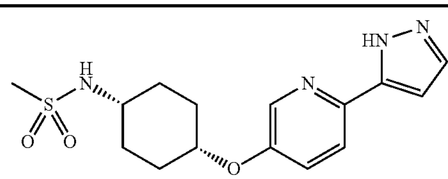 | $^1$H NMR (400 MHz, CHLOROFORM-d) δ ppm 1.67-2.18 (m, 8 H) 3.01 (s, 3 H) 3.43-3.51 (m, 1 H) 4.22-4.28 (m, 1 H) 4.52-4.56 (m, 1 H) 6.69 (d, J = 2.0 Hz, 1 H) 7.24 (dd, J = 8.7, 2.8 Hz, 1 H) 7.62 (d, J = 2.0 Hz, 1 H) 7.65 (d, J = 8.7 Hz, 1 H) 8.28 (d, J = 2.8 Hz, 1 H). MS ESI/APCI Multi posi: 337 [M + H]$^+$. |
| 57-3 | 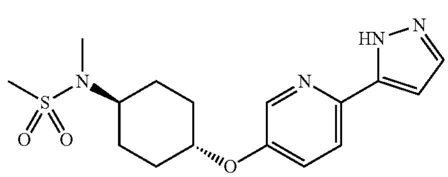 [SMILES: CN([C@H]1CC[C@H](Oc2ccc(-c3ccn[nH]3)nc2)CC1)S(C)(=O)=O] | $^1$H NMR (400 MHz, CHLOROFORM-d) δ ppm 1.56-1.75 (m, 4 H) 1.83-1.95 (m, 2 H) 2.21-2.31 (m, 2 H) 2.82 (s, 3 H) 2.86 (s, 3 H) 3.81-3.89 (m, 1 H) 4.15-4.22 (m, 1 H) 6.69 (d, J = 2.1 Hz, 1 H) 7.23 (dd, J = 8.4, 2.7 Hz, 1 H) 7.62 (d, J = 2.1 Hz, 1 H) 7.64 (d, J = 8.4 Hz, 1 H) 8.26 (d, J = 2.7 Hz, 1 H). MS ESI/APCI Multi posi: 351 [M + H]$^+$. |

Example 58-2

N-Methyl-N-[[3-[[6-(1H-pyrazol-5-yl)-3-pyridinyl]oxymethyl]-1-bicyclo[1.1.1]pentanyl]methyl]methanesulfonamide

[Formula 579]

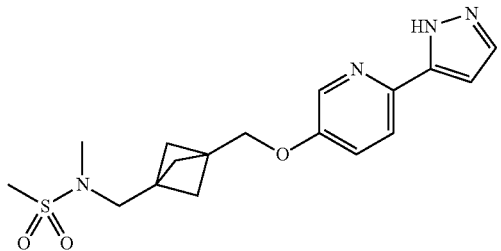

(1) The compound (67.0 mg) obtained in Example 58-1-(1) and methyl iodide were used to perform the synthesis process according to the method described in Example 20-1-(2) thereby giving N-methyl-N-[[3-[[6-[2-(2-oxanyl)-3-pyrazolyl]-3-pyridinyl]oxymethyl]-1-bicyclo[1.1.1]pentanyl]methyl]methanesulfonamide (102 mg) as a yellow oil.

(2) The compound (69.2 mg) obtained in (1) above was used to perform the synthesis process according to the method described in Example 10-1-(2) thereby giving the title compound (25.7 mg) as a colorless powder.

$^1$H NMR (400 MHz, CHLOROFORM-d) δ ppm 1.85 (s, 6H) 2.80 (s, 3H) 2.90 (s, 3H) 3.25 (s, 2H) 4.07 (s, 2H) 6.68 (d, J=2.0 Hz, 1H) 7.22 (dd, J=8.8, 2.9 Hz, 1H) 7.62 (d, J=2.0 Hz, 1H) 7.65 (d, J=8.8 Hz, 1H) 8.27 (d, J=2.9 Hz, 1H).

MS ESI/APCI Multi posi: 363[M+H]$^+$.

Example 59-1

1,1,1-Trifluoro-3-[3-[[6-(1H-pyrazol-5-yl)-3-pyridinyl]oxymethyl]phenyl]-2-propanol

[Formula 580]

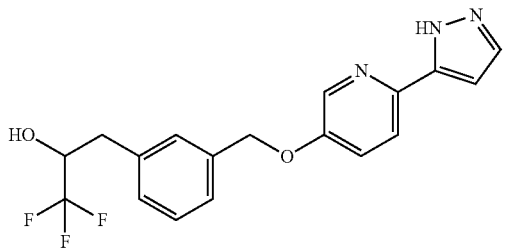

(1) Lithium borohydride (20 mg) was added to a solution of the compound (202 mg) obtained in Example 24-1-(1) in tetrahydrofuran (2.3 mL), and the mixture was stirred at room temperature for 17 hours. Water was added thereto, and the resultant mixture was extracted three times with ethyl acetate. The organic layers were collected, washed with brine, separated by a phase separator, and then concentrated under reduced pressure to give 2-[3-[[6-[2-(2-oxanyl)-3-pyrazolyl]-3-pyridinyl]oxymethyl]phenyl]ethanol (183 mg) as a colorless oil.

(2) Dess-Martin periodinane (273 mg) was added to a suspension of the compound (183 mg) obtained in (1) above and sodium hydrogen carbonate (180 mg) in chloroform (2.2 mL), and the resultant mixture was stirred at room temperature for 2.5 hours. A saturated aqueous solution of sodium hydrogen carbonate and a saturated aqueous solution of sodium thiosulfate were added to the reaction mixture, and the resultant mixture was stirred and then extracted with chloroform. The organic layers were collected, and again sequentially washed with a saturated aqueous solution of sodium hydrogen carbonate, aqueous solution of saturated sodium thiosulfate, and brine, and the aqueous layer was removed by a phase separator. The resultant was concentrated under reduced pressure, and the obtained residue was purified by silica gel column chromatography (n-hexane:ethyl acetate=4:1 to 3:7) to give 2-[3-[[6-[2-(2-oxanyl)-3-pyrazolyl]-3-pyridinyl]oxymethyl]phenyl]acetaldehyde (117 mg) as a colorless oil.

(3) To a suspension of the compound (61 mg) obtained in (3) above and cesium fluoride (47 mg) in tetrahydrofuran (1.5 mL), (trifluoromethyl)trimethylsilane (66 mg) was added, and the mixture was stirred at room temperature for 14 hours. To the reaction mixture, 4 mol/L hydrochloric acid (5 mL) was added, and the resultant mixture was stirred at room temperature for 3 hours. The reaction solution was adjusted to basic condition with an aqueous solution of 1 mol/L sodium hydroxide and a saturated aqueous solution of sodium hydrogen carbonate, and then extracted three times with ethyl acetate. The organic layers were collected and washed with brine, the aqueous layer was removed by a phase separator, and the resultant was concentrated under reduced pressure. The obtained residue was purified by preparative HPLC to give the title compound (24 mg) as a light yellow solid.

$^1$H NMR (400 MHz, DMSO-d$_6$) δ ppm 2.70-2.78 (m, 1H) 2.92-3.00 (m, 1H) 4.09-4.26 (m, 1H) 5.18 (s, 2H) 6.23 (d, J=7.0 Hz, 1H) 6.73 (s, 1H) 7.24-7.62 (m, 5H) 7.72-7.92 (m, 2H) 8.31-8.41 (m, 1H).

MS ESI/APCI Multi posi: 364[M+H]$^+$.

Example 59-2

2,2-Difluoro-1-[4-[[6-(1H-pyrazol-5-yl)-3-pyridinyl]oxymethyl]phenyl]ethanol

[Formula 581]

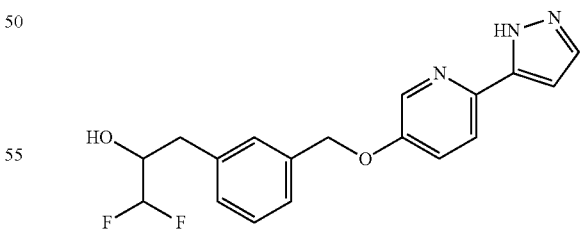

(1) The compound (567 mg) obtained in Example 1-1-(1) was used to perform the synthesis process according to the method described in Example 59-1-(1) thereby giving [4-[[6-[2-(2-oxanyl)-3-pyrazolyl]-3-pyridinyl]oxymethyl]phenyl]methanol (400 mg) as a colorless oil.

(2) The compound (400 mg) obtained in (1) above was used to perform the synthesis process according to the method described in Example 59-1-(2) thereby giving 4-[[6-

[2-(2-oxanyl)-3-pyrazolyl]-3-pyridinyl]oxymethyl]benzaldehyde (358 mg) as a colorless oil.

(3) To a suspension of the compound (205 mg) obtained in (2) above and cesium fluoride (135 mg) in N,N-dimethylformamide (1.3 mL), (difluoromethyl)trimethylsilane (135 mg) was added under ice cooling, and the mixture was stirred at room temperature for 15 hours. Cesium fluoride (135 mg) and (difluoromethyl)trimethylsilane (135 mg) were further added to the reaction mixture, and the resultant mixture was stirred at room temperature for 5 hours. Tetrabutylammonium fluoride (1.2 g) was added thereto, and the resultant mixture was stirred at room temperature for 1 hour. Water was added thereto, and the resultant mixture was extracted three times with a n-hexane:ethyl acetate (1:1) mixed solution. The organic layers were collected and washed with brine, the aqueous layer was removed by a phase separator, and the resultant was then concentrated under reduced pressure. The obtained residue was purified by silica gel column chromatography (n-hexane:ethyl acetate=9:1 to 3:7) to give 2,2-difluoro-1-[4-[[6-[2-(2-oxanyl)-3-pyrazolyl]-3-pyridinyl]oxymethyl]phenyl]ethanol (158 mg) as a colorless oil.

(4) The compound (46 mg) obtained in (3) above was used to perform the synthesis process according to the method described in Example 11-1-(2) thereby giving the title compound (19 mg) as a colorless solid.

$^1$H NMR (400 MHz, DMSO-$d_6$) δ ppm 4.68-4.85 (m, 1H) 5.22 (s, 2H) 5.83-6.26 (m, 2H) 6.72 (s, 1H) 7.37-7.59 (m, 5H) 7.69-7.95 (m, 2H) 8.34 (s, 1H).

MS ESI/APCI Multi posi: 332[M+H]$^+$.

The compound of Example 59-3 below was synthesized using a commercially available compound, according to the method described in Example 59-2. The structure, NMR data, and MS data of the compound are shown in Table 67-1.

(1) Copper (287 mg) was added to a solution of the compound (569 mg) obtained in Reference Example 8-3 and ethyl 2-bromo-2,2-difluoroacetate (302 mg) in dimethyl sulfoxide (4.5 mL) under an argon atmosphere, and the mixture was stirred at an outer temperature of 60° C. for 4 hours. The reaction mixture was cooled to room temperature, a saturated aqueous solution of ammonium chloride was added thereto, and the resultant mixture was extracted three times with ethyl acetate. The organic layers were collected and washed with brine, the aqueous layer was separated by a phase separator, and the resultant was concentrated under reduced pressure. The obtained residue was purified by silica gel column chromatography (n-hexane:ethyl acetate=9:1 to 2:3) to give ethyl 2,2-difluoro-2-[3-[[6-[2-(2-oxanyl)-3-pyrazolyl]-3-pyridinyl]oxymethyl]phenyl]acetate (564 mg) as a light brown oil.

(2) The compound (42 mg) obtained in (1) above was used to perform the synthesis process according to the method described in Example 11-1-(2) thereby giving methyl 2,2-difluoro-2-[3-[[6-(1H-pyrazol-5-yl)-3-pyridinyl]oxymethyl]phenyl]acetate (24 mg) as a light yellow oil.

(3) The compound (24 mg) obtained in (3) above was used to perform the synthesis process according to the method described in Example 9-1-(3) thereby giving the title compound (7.4 mg) as a colorless solid.

$^1$H NMR (400 MHz, DMSO-$d_6$) δ ppm 5.30 (s, 2H) 6.74 (d, J=2.1 Hz, 1H) 7.47-7.78 (m, 6H) 7.87 (d, J=8.6 Hz, 1H) 8.37 (d, J=2.8 Hz, 1H).

MS ESI/APCI Multi posi: 346[M+H]$^+$.

MS ESI/APCI Multi nega: 344[M−H]$^-$.

TABLE 67-1

| Example No. | Structure | Analytical Data |
|---|---|---|
| 59-3 | 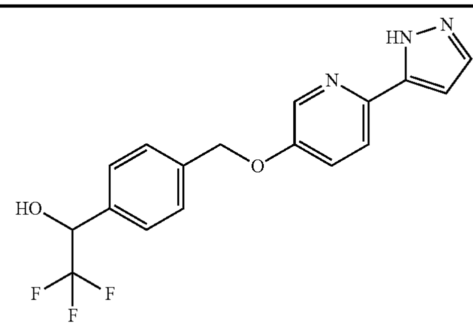 | $^1$H NMR (400 MHz, DMSO-$d_6$) δ ppm 5.11-5.28 (m, 3 H) 6.73 (d, J = 1.7 Hz, 1 H) 6.83 (d, J = 5.5 Hz, 1 H) 7.45-7.58 (m, 5 H) 7.69-7.93 (m, 2 H) 8.35 (s, 1 H). MS ESI/APCI Multi posi: 350 [M + H]$^+$. |

Example 60-1

2,2-Difluoro-2-[3-[[6-(1H-pyrazol-5-yl)-3-pyridinyl]oxymethyl]phenyl]acetic Acid

[Formula 582]

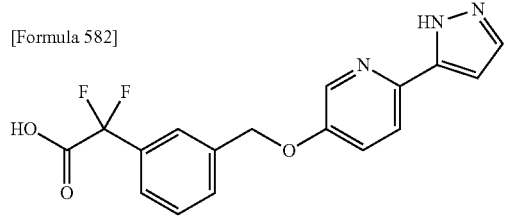

Example 60-2

2,2-Difluoro-2-[3-[[6-(1H-pyrazol-5-yl)-3-pyridinyl]oxymethyl]phenyl]ethanol

[Formula 583]

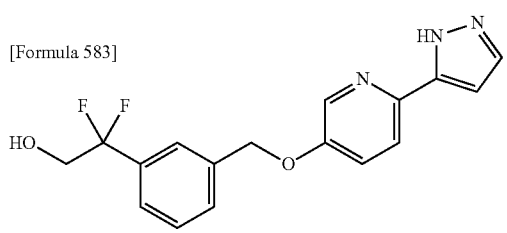

(1) Sodium borohydride (35 mg) was added to a solution of the compound (521 mg) obtained in Example 60-1-(1) in ethanol (3 mL) under ice cooling, and the mixture was stirred at room temperature for 1.5 hours. The reaction mixture was diluted with water, and extracted three times with ethyl acetate. The organic layers were collected and washed with brine, the aqueous layer was removed by a phase separator, and the resultant was then concentrated under reduced pressure. The obtained residue was purified by silica gel column chromatography (n-hexane:ethyl acetate=4:1 to 1:4) to give 2,2-difluoro-2-[3-[[6-[2-(2-oxanyl)-3-pyrazolyl]-3-pyridinyl]oxymethyl]phenyl]ethanol (301 mg) as a light brown gum-like substance.

(2) The compound (41 mg) obtained in (1) above was used to perform the synthesis process according to the method described in Example 11-1-(2) thereby giving the title compound (23 mg) as a colorless solid.

$^1$H NMR (400 MHz, DMSO-$d_6$) δ ppm 3.79-3.94 (m, 2H) 5.28 (s, 2H) 5.64 (t, J=6.3 Hz, 1H) 6.73 (s, 1H) 7.43-7.68 (m, 5H) 7.71-7.96 (m, 2H) 8.36 (br s, 1H).

MS ESI/APCI Multi posi: 332[M+H]$^+$.

Example 61-1

1-Methylsulfonyl-3-[4-[[6-(1-H-pyrazol-5-yl)-3-pyridinyl]oxy]butyl]urea

[Formula 584]

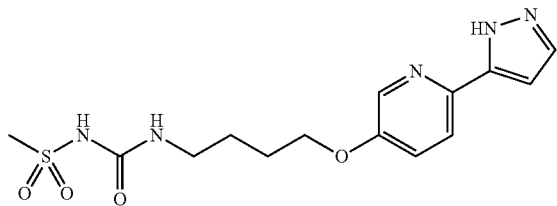

(1) The compound (300 mg) obtained in Reference Example 1-1 and (phenylmethyl) N-(4-hydroxybutyl)carbamate (382 mg) were used to perform the synthesis process according to the method described in Example 8-1-(1) thereby giving (phenylmethyl) N-[4-[[6-[2-(2-oxanyl)-3-pyrazolyl]-3-pyridinyl]oxy]butyl]carbamate (662 mg) as a colorless oil.

(2) The compound (662 mg) obtained in (1) above was used to perform the synthesis process according to the method described in Example 2-1-(3) thereby giving 4-[[6-[2-(2-oxanyl)-3-pyrazolyl]-3-pyridinyl]oxy]-1-butanamine (400 mg) as a colorless oil.

(3) To a solution of the compound (46.0 mg) obtained in (2) above in chloroform (2 mL), 1,1'-carbonyldiimidazole (23.5 mg) was added, and the mixture was stirred for 1.5 hours. Methanesulfonamide (15.2 mg) and 1,8-diazabicyclo[5.4.0]-7-undecene (26.5 mg) were added to the reaction mixture, and the resultant mixture was stirred at room temperature for 65 hours. The reaction mixture was concentrated to give a mixture containing 1-methylsulfonyl-3-[4-[[6-[2-(2-oxanyl)-3-pyrazolyl]-3-pyridinyl]oxy]butyl]urea as a light yellow oil.

(4) The mixture obtained in (3) above was used to perform the synthesis process according to the method described in Example 10-1-(2) thereby giving the title compound (21.3 mg) as a colorless powder.

$^1$H NMR (400 MHz, DMSO-$d_6$) δ ppm 1.49-1.83 (m, 4H) 3.09-3.15 (m, 2H) 3.20 (s, 3H) 4.04-4.13 (m, 2H) 6.35-6.62 (m, 1H) 6.70-6.75 (m, 1H) 7.28-7.98 (m, 3H) 8.24-8.32 (m, 1H) 9.89-10.31 (m, 1H) 12.70-13.59 (m, 1H).

MS ESI/APCI Multi posi: 354[M+H]$^+$.
MS ESI/APCI Multi nega: 352[M−H]$^-$.

Example 61-2

1-[4-[[6-(1-H-pyrazol-5-yl)-3-pyridinyl]oxy]butyl]imidazolidine-2,4-dione

[Formula 585]

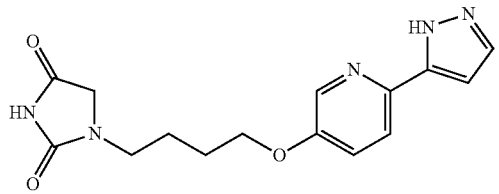

(1) Ethyl N-(2-chloro-1-oxoethyl)carbamate (37.5 mg) was added to a solution of the compound (71.7 mg) obtained in Example 61-1-(2) in N,N-dimethylformamide (3 mL), and the mixture was stirred at 100° C. for 16 hours. The reaction mixture was concentrated, and the residue was purified by preparative HPLC. After the purified residue was dried under reduced pressure, methanol and diethyl ether were added thereto, and the precipitated solid was collected by filtration to give the title compound (5.48 mg) as a colorless powder.

$^1$H NMR (400 MHz, DMSO-$d_6$) δ ppm 1.55-1.84 (m, 4H) 3.23-3.31 (m, 2H) 3.95 (s, 2H) 4.03-4.16 (m, 2H) 6.65-6.77 (m, 1H) 7.29-7.95 (m, 3H) 8.23-8.33 (m, 1H) 10.42-10.91 (m, 1H) 12.63-13.65 (m, 1H).

MS ESI/APCI Multi posi: 316[M+H]$^+$.

Example 62-1

2-(1H-Pyrazol-5-yl)-5-[5-(1H-tetrazol-5-yl)pentoxy]pyridine

[Formula 586]

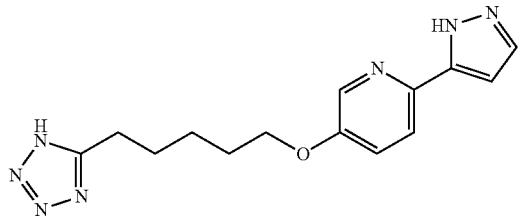

(1) The compound (150 mg) obtained in Reference Example 1-1 and 5-chloro-1-pentanol (190 μL) were used to perform the synthesis process according to the method described in Example 10-2-(1) thereby giving 5-(5-chloropentoxy)-2-[2-(2-oxanyl)-3-pyrazolyl]pyridine (365 mg) as a colorless oil.

(2) Potassium cyanide (213 mg) was added to a solution of the compound (365 mg) obtained in (1) above in dimethyl sulfoxide (2.1 mL), and the mixture was stirred at 100° C.

for 1.5 hours. A saturated aqueous solution of sodium hydrogen carbonate was added to the reaction solution, and the resultant mixture was extracted with ethyl acetate. The organic layer was sequentially washed with water and brine, and anhydrous magnesium sulfate was added thereto. The drying agent was filtered off, and the filtrate was concentrated under reduced pressure. The residue was purified by silica gel column chromatography (n-hexane:ethyl acetate=1:3 to ethyl acetate only) to give 6-[[6-[2-(2-oxanyl)-3-pyrazolyl]-3-pyridinyl]oxy]hexanenitrile (312 mg) as a colorless oil.

(3) A suspension of the compound (150 mg) obtained in (2) above, sodium azide (93 mg), and trimethylamine hydrochloride (126 mg) in toluene (1.5 mL) was stirred at 150° C. for 2 hours under microwave irradiation. Methanol was added to the reaction solution, the solid was filtered off, and the filtrate was concentrated under reduced pressure to give a crude product (232 mg) containing 2-[2-(2-oxanyl)-3-pyrazolyl]-5-[5-(1H-tetrazol-5-yl)pentoxy]pyridine as a pale brown powder.

(4) The compound (232 mg) obtained in (3) above was used to perform the synthesis process according to the method described in Example 10-1-(2) thereby giving the title compound (37 mg) as a colorless powder.

$^1$H NMR (400 MHz, METHANOL-$d_4$) δ ppm 1.47-1.66 (m, 2H) 1.79-1.97 (m, 4H) 2.94-3.06 (m, 2H) 4.03-4.16 (m, 2H) 6.72-6.85 (m, 1H) 7.37-7.49 (m, 1H) 7.58-7.71 (m, 1H) 7.78-7.89 (m, 1H) 8.18-8.28 (m, 1H).

MS ESI/APCI Multi posi: 300[M+H]$^+$.

Example 62-2

3-[5-[[6-(1H-Pyrazol-5-yl)-3-pyridinyl]oxy]pentyl]-4H-1,2,4-oxadiazol-5-one

[Formula 587]

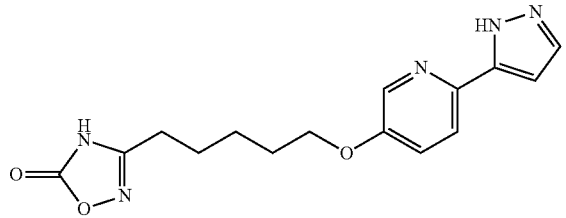

(1) Sodium carbonate (145 mg) and hydroxylamine hydrochloride (95 mg) were added to a solution of the compound (155 mg) obtained in Example 62-1-(2) in ethanol:water (4:1, 2.87 mL), and the mixture was stirred at 75° C. overnight. Water was added to the reaction solution, the resultant mixture was extracted with chloroform, and the organic layer was separated by a phase separator, and concentrated under reduced pressure. The residue was purified by silica gel column chromatography (chloroform:methanol=49:1 to 9:1) to give N'-hydroxy-6-[[6-[2-(2-oxanyl)-3-pyrazolyl]-3-pyridinyl]oxy]hexanimidamide (102 mg) as a colorless oil.

(2) To a solution of the compound (102 mg) obtained in (1) above in tetrahydrofuran (2.7 mL), 1,1'-carbonyldiimidazole (53 mg) and 1,8-diazabicyclo[5.4.0]-7-undecene (45 μL) were added, and the mixture was stirred at room temperature overnight. A saturated aqueous solution of ammonium chloride was added to the reaction solution, and the resultant mixture was extracted with chloroform. The organic layer was separated by a phase separator, and concentrated under reduced pressure. The residue was purified by silica gel column chromatography (chloroform:methanol=49:1 to 9:1) to give 3-[5-[[6-[2-(2-oxanyl)-3-pyrazolyl]-3-pyridinyl]oxy]pentyl]-4H-1,2,4-oxadiazol-5-one (90 mg) as a colorless oil.

(3) The compound (87 mg) obtained in (3) above was used to perform the synthesis process according to the method described in Example 1-1-(3) thereby giving the title compound (22 mg) as a colorless powder.

$^1$H NMR (400 MHz, DMSO-$d_6$) δ ppm 1.40-1.56 (m, 2H) 1.58-1.85 (m, 4H) 4.07 (t, J=6.4 Hz, 2H) 6.67-6.78 (m, 1H) 7.35-7.51 (m, 1H) 7.56-7.97 (m, 2H) 8.23-8.32 (m, 1H).

MS ESI/APCI Multi posi: 316[M+H]$^+$.

MS ESI/APCI Multi nega: 314[M−H]$^-$.

Example 63-1

5-[4-[[6-(1H-Pyrazol-5-yl)-3-pyridinyl]oxy]butyl]oxazolidine-2,4-dione

[Formula 588]

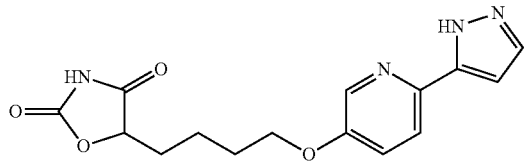

(1) A solution of 5-benzyloxy-1-pentanol (2.0 g) in chloroform (10 mL) was added dropwise to a suspension of Dess-Martin periodinane (5.2 g) in chloroform (41 mL) under ice cooling, and the mixture was stirred at room temperature overnight. A saturated aqueous solution of sodium thiosulfate and a saturated aqueous solution of sodium hydrogen carbonate were added thereto under ice cooling, and the resultant mixture was stirred for a while. The reaction solution was extracted with chloroform, and the organic layer was separated by a phase separator, and concentrated under reduced pressure. The residue was purified by silica gel column chromatography (n-hexane:ethyl acetate=17:3 to 7:3) to give 5-phenylmethoxypentanal (1.67 g) as a colorless oil.

(2) Ethyl cyanoformate (1.0 mL) and 4-dimethylaminopyridine (106 mg) were added to a solution of the compound (1.67 g) obtained in (1) above in acetonitrile (17 mL), and the resultant mixture was stirred at room temperature overnight. Brine was added to the reaction solution, and the resultant mixture was extracted with ethyl acetate. The organic layer was dried over anhydrous magnesium sulfate, the drying agent was filtered off, and the resultant was concentrated under reduced pressure. The residue was purified by NH silica gel column chromatography (n-hexane:ethyl acetate=19:1 to 4:1) to give (1-cyano-5-phenylmethoxypentyl)ethyl carbonate (2.33 g) as a colorless oil.

(3) A 2 mol/L hydrogen chloride-isopropyl alcohol solution (8 mL) and concentrated hydrochloric acid (8 mL) were added to the compound (2.33 g) obtained in (2) above, and the mixture was stirred at room temperature overnight. The reaction solution was concentrated under reduced pressure, brine was added thereto under ice cooling, and the resultant mixture was extracted with ethyl acetate. The organic layer was dried over anhydrous magnesium sulfate, the drying agent was filtered off, and the resultant was concentrated under reduced pressure. The residue was purified by silica gel column chromatography (n-hexane:ethyl acetate=9:1 to 1:9) to give (1-amino-1-oxo-6-phenylmethoxyhexan-2-yl) ethyl carbonate (184 mg) as a colorless oil.

(4) The compound (184 mg) obtained in (3) above was used to perform the synthesis process according to the method described in Example 2-1-(3) thereby giving (1-amino-6-hydroxy-1-oxohexan-2-yl)ethyl carbonate (75 mg) as a colorless powder.

(5) The compound (163 mg) obtained in Reference Example 1-1 and the compound (73 mg) obtained in (4) above were used to perform the synthesis process according to the method described in Example 10-2-(1) thereby giving [1-amino-6-[[6-[2-(2-oxanyl)-3-pyrazolyl]-3-pyridinyl] oxy]-1-oxohexan-2-yl]ethyl carbonate (103 mg) as a colorless oil.

(6) To a solution of the compound (103 mg) obtained in (5) above in acetonitrile (2.3 mL), 1,8-diazabicyclo[5.4.0]-7-undecene (38 μL) was added, and the mixture was stirred at room temperature for 3 days. The reaction solution was concentrated under reduced pressure, and the residue was purified by silica gel column chromatography (chloroform:methanol=49:1 to 91:9) to give 5-[4-[[6-[2-(2-oxanyl)-3-pyrazolyl]-3-pyridinyl]oxy]butyl]oxazolidine-2,4-dione (108 mg) as a colorless oil.

(7) The compound (108 mg) obtained in (6) above was used to perform the synthesis process according to the method described in Example 1-1-(3) thereby giving the title compound (48 mg) as a pale yellow powder.

$^1$H NMR (400 MHz, DMSO-$d_6$) δ ppm 1.41-1.66 (m, 2H) 1.70-2.01 (m, 4H) 4.09 (t, J=6.3 Hz, 2H) 4.89-5.04 (m, 1H) 6.63-6.80 (m, 1H) 7.36-7.50 (m, 1H) 7.52-7.96 (m, 2H) 8.21-8.35 (m, 1H).

MS ESI/APCI Multi posi: 317[M+H]$^+$.
MS ESI/APCI Multi nega: 315[M−H]$^−$.

Example 64-1

5-[4-[[6-(1H-Pyrazol-5-yl)-3-pyridinyl]oxy]butyl]-3-isoxazole

[Formula 589]

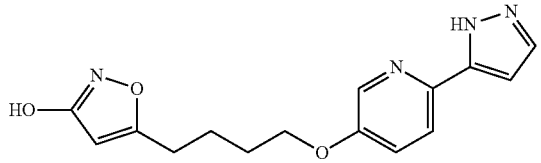

(1) The compound (300 mg) obtained in Reference Example 1-1 and ethyl 5-bromopentanoate (232 μL) were used to perform the synthesis process according to the method described in Example 19-1-(2) thereby giving ethyl 5-[[6-[2-(2-oxanyl)-3-pyrazolyl]-3-pyridinyl]oxy]pentanoate (459 mg) as a pale yellow oil.

(2) The compound (459 mg) obtained in (1) above was used to perform the synthesis process according to the method described in Example 1-47-(3) thereby giving 5-[[6-[2-(2-oxanyl)-3-pyrazolyl]-3-pyridinyl]oxy]pentanoic acid (483 mg) as a colorless powder.

(3) The compound (483 mg) obtained in (2) above and Meldrum's acid (213 mg) were used to perform the synthesis process according to the method described in Example 44-1 thereby giving 5-[1-hydroxy-5-[[6-[2-(2-oxanyl)-3-pyrazolyl]-3-pyridinyl]oxy]pentylidene]-2,2-dimethyl-1,3-dioxane-4,6-dione (462 mg) as a pale yellow oil.

(4) To a solution of the compound (462 mg) obtained in (3) above in toluene (9.8 mL), N,O-bis(tert-butoxycarbonyl) hydroxylamine (229 mg) was added, and the mixture was stirred at 90° C. for 2 hours. The reaction solution was concentrated under reduced pressure to give a crude product containing tert-butyl[[(2-methylpropan-2-yl)oxy-oxomethyl]-[7-[[6-[2-(2-oxanyl)-3-pyrazolyl]-3-pyridinyl]oxy]-1,3-dioxoheptyl]amino]carbonate.

(5) To a solution of the compound obtained in (4) above in methanol (2.0 mL), 6 mol/L hydrochloric acid (3.3 mL) was added under ice cooling, and the mixture was stirred at room temperature for 2 hours, and at 60° C. for 2 hours. The reaction solution was concentrated under reduced pressure, a saturated aqueous solution of sodium hydrogen carbonate was added to the residue, and the resultant mixture was washed with chloroform. The aqueous layer was concentrated under reduced pressure, a chloroform:methanol mixed solution was added to the residue to suspend, the suspension was stirred, and the solid was filtered off. The filtrate was concentrated under reduced pressure, and the residue was purified by preparative HPLC to give the title compound (83 mg) as a yellow powder.

$^1$H NMR (400 MHz, DMSO-$d_6$) δ ppm 1.67-1.88 (m, 4H) 2.63-2.76 (m, 2H) 3.98-4.19 (m, 2H) 5.80 (s, 1H) 6.63-6.81 (m, 1H) 7.31-7.52 (m, 1H) 7.56-7.98 (m, 2H) 8.19-8.36 (m, 1H) 11.02 (br s, 1H).

MS ESI/APCI Multi posi: 301[M+H]$^+$.
MS ESI/APCI Multi nega: 299[M−H]$^−$.

Example 65-1

1,1,1-Trifluoro-N-[[3-[[6-(1-H-pyrazol-5-yl)-3-pyridinyl]oxymethyl]phenyl]methyl]methanesulfonamide

[Formula 590]

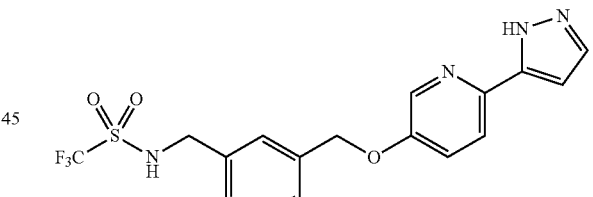

(1) The compound (200 mg) obtained in Reference Example 1-1 and 3-(bromomethyl)benzonitrile (175 mg) were used to perform the synthesis process according to the method described in Example 18-1-(2) thereby giving 3-[[6-[2-(2-oxanyl)-3-pyrazolyl]-3-pyridinyl]oxymethyl]benzonitrile (276 mg) as a colorless oil.

(2) Lithium aluminum hydride (58.1 mg) was slowly added to a solution of the compound (276 mg) obtained in (1) above in tetrahydrofuran (8 mL) under ice cooling, and the mixture was stirred at room temperature for 3 hours. After the mixture was ice-cooled, sodium sulfate decahydrate was slowly added thereto, and the resultant mixture was stirred at room temperature for 30 minutes. The reaction mixture was filtered, the residue was washed with ethyl acetate, and the filtrate and the washing solution were then combined and concentrated. The residue was purified by NH silica gel column chromatography (chloroform only to chloroform:methanol=19:1), and then by silica gel column chromatography (chloroform only to chloroform:methanol=4:1), and thereafter dried under reduced pressure to give a mixture (98.1 mg) containing [3-[[6-[2-(2-oxanyl)-3-pyrazolyl]-3-pyridinyl]oxymethyl]phenyl]methanamine as a colorless oil.

(3) Triethylamine (62.6 µL) was added to a solution of the mixture (98.1 mg) obtained in (2) above in chloroform (2 mL). After cooling to −50° C., trifluoromethanesulfonic anhydride (56.6 µL) was added thereto, and the resultant mixture was stirred at −50 to −30° C. for 2 hours. Water was added thereto at −30° C., the temperature of the resultant mixture was slowly increased to room temperature, and the mixture was concentrated under reduced pressure to give a mixture containing 1,1,1-trifluoro-N-[[3-[[6-[2-(2-oxanyl)-3-pyrazolyl]-3-pyridinyl]oxymethyl]phenyl]methyl]methanesulfonamide.

(4) The mixture obtained in (3) above was used to perform the synthesis process according to the method described in Example 1-1-(3) thereby giving the title compound (51.8 mg) as a colorless powder.

$^1$H NMR (400 MHz, CHLOROFORM-d) δ ppm 4.49 (s, 2H) 5.15 (s, 2H) 6.67-6.69 (m, 1H) 7.28-7.36 (m, 2H) 7.42-7.46 (m, 3H) 7.59-7.65 (m, 2H) 8.31-8.33 (m, 1H).

MS ESI/APCI Multi posi: 413 [M+H]$^+$.

MS ESI/APCI Multi nega: 411[M−H]$^−$.

Example 66-1

3-[[6-(4-Chloro-1H-pyrazol-5-yl)-3-pyridinyl]oxymethyl]-5-methylsulfonylphenol

[Formula 591]

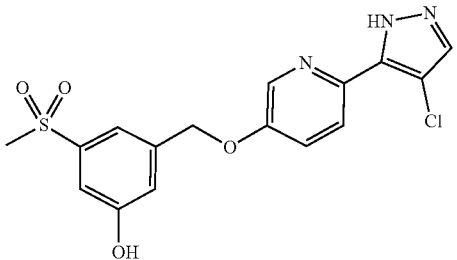

To a suspension of the compound (50 mg) obtained in Example 20-2 in chloroform:N,N-dimethylformamide (1:1, 3.0 mL), N-chlorosuccinimide (21 mg) was added, and the mixture was stirred at 60° C. for 5 hours. The solvent was distilled off under reduced pressure, and the residue was purified by preparative HPLC. The fraction containing the target substance was concentrated under reduced pressure, diethyl ether was added to the residue, and the precipitated solid was collected by filtration. The solid was dried under reduced pressure to give the title compound (16 mg) as a colorless powder.

$^1$H NMR (600 MHz, DMSO-d$_6$) δ ppm 3.20 (s, 3H) 5.30 (s, 2H) 7.18-7.21 (m, 1H) 7.23-7.26 (m, 1H) 7.47 (s, 1H) 7.53-7.73 (m, 2H) 7.80-8.11 (m, 1H) 8.39-8.53 (m, 1H) 10.42 (br s, 1H).

MS ESI/APCI Multi posi: 380[M+H]$^+$.

MS ESI/APCI Multi nega: 378[M−H]$^−$.

Example 67-1

4-[[6-[4-(Difluoromethyl)-1H-pyrazol-5-yl]-3-pyridinyl]oxymethyl]-2-pyridinecarboxamide

[Formula 522]

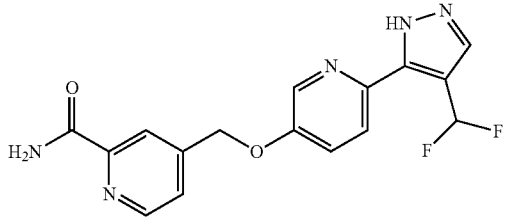

(1) Commercially available methyl 4-(hydroxymethyl)-2-pyridinecarboxylate (37 mg) was used to perform the synthesis process according to the method described in Example 18-1-(1) thereby giving methyl 4-(methylsulfonyloxymethyl)-2-pyridinecarboxylate as a crude product.

(2) The compound (35 mg) obtained in Reference Example 2-1 and the crude product obtained in (1) above were used to perform the synthesis process according to the method described in Example 21-1-(1) thereby giving methyl 4-[[6-[4-(difluoromethyl)-2-(2-oxanyl)-3-pyrazolyl]-3-pyridinyl]oxymethyl]-2-pyridinecarboxylate (35 mg) as a colorless powder.

(3) The compound (35 mg) obtained in (2) above was used to perform the synthesis process according to the method described in Example 12-1-(2) thereby giving a crude product of 4-[[6-[4-(difluoromethyl)-2-(2-oxanyl)-3-pyrazolyl]-3-pyridinyl]oxymethyl]-2-pyridinecarboxylic acid.

(4) Ammonium chloride (8 mg), triethylamine (0.06 mL), 1-ethyl-3-(3-dimethylaminopropyl)carbodiimide hydrochloride (47 mg), and 1-hydroxybenzotriazole monohydrate (31 mg) were added to a solution of the crude product obtained in (3) above in N,N-dimethylformamide (0.80 mL), and the mixture was stirred at room temperature for 13 hours. The reaction was stopped with a saturated aqueous solution of ammonium chloride (3 mL), and the reaction mixture was extracted three times with ethyl acetate (10 mL). The obtained organic layers were combined and washed with brine, and dehydrated with anhydrous sodium sulfate. The resultant was filtered, and the obtained solution was concentrated under reduced pressure to give 4-[[6-[4-(difluoromethyl)-2-(2-oxanyl)-3-pyrazolyl]-3-pyridinyl]oxymethyl]-2-pyridinecarboxamide (30 mg) as a colorless oil.

(5) The compound (30 mg) obtained in (4) above was used to perform the synthesis process according to the method described in Example 1-43-(3) thereby giving the title compound (5 mg) as a colorless powder.

$^1$H NMR (400 MHz, DMSO-d$_6$) δ ppm 3.12-3.19 (m, 1H) 5.42 (s, 2H) 7.55-7.62 (m, 1H) 7.63-7.71 (m, 2H) 7.88-7.98 (m, 1H) 8.04-8.17 (m, 3H) 8.39-8.48 (m, 1H) 8.61-8.70 (m, 1H).

MS ESI/APCI Multi posi: 346[M+H]$^+$.

Example 68-1

4-[8-[[6-(1H-Pyrazol-5-yl)-3-pyridinyl]oxy]octoxy]-4-oxanecarboxylic Acid

[Formula 593]

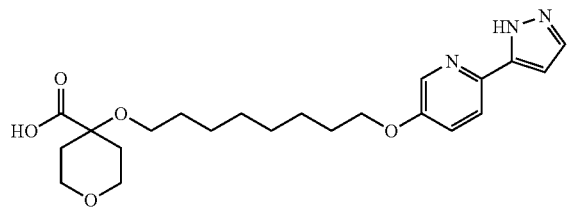

(1) The compound (2.0 g) obtained in Reference Example 1-1 and 8-bromo-1-octanol (1.9 mL) were used to perform the synthesis process according to the method described in Example 20-1-(2) thereby giving 8-[[6-[2-(2-oxanyl)-3-pyrazolyl]-3-pyridinyl]oxy]-1-octanol (3.6 g) as a colorless oil.

(2) Triethylamine (750 µL), trimethylamine hydrochloride (26 mg), and p-toluenesulfonyl chloride (664 mg) were added to a solution of the compound (1.0 g) obtained in (1) above in toluene (14 mL), and the mixture was stirred at room temperature overnight. Water was added to the reaction solution under ice cooling, and the resultant mixture was extracted with chloroform, and the organic layer was separated by a phase separator, and concentrated under reduced pressure. The residue was purified by silica gel column chromatography (n-hexane:ethyl acetate=13:7 to 7:3) to give 8-[[6-[2-(2-oxanyl)-3-pyrazolyl]-3-pyridinyl]oxy]octyl 4-methylbenzenesulfonate (1.38 g) as a colorless oil.

(3) Sodium hydride (60% mineral oil dispersion, 139 mg) was added to a suspension of the compound (774 mg) obtained in Reference Example 22-1 in N,N-dimethylformamide (1.6 mL) under ice cooling, and the mixture was stirred at room temperature for 1 hour. Thereto, a solution of the compound (673 mg) obtained in (2) above in N,N-dimethylformamide (1 mL) was added under ice cooling, and the resultant mixture was stirred at 90° C. for 3 hours. A saturated aqueous solution of ammonium chloride was added thereto under ice cooling, and the resultant mixture was extracted with ethyl acetate. The organic layer was sequentially washed with water and brine, and the organic layer was separated by a phase separator, and concentrated under reduced pressure. The residue was purified by silica gel column chromatography (n-hexane:ethyl acetate=4:1 to 1:1) to give tert-butyl 4-[8-[[6-[2-(2-oxanyl)-3-pyrazolyl]-3-pyridinyl]oxy]octoxy]-4-oxanecarboxylate (410 mg) as a colorless oil.

(4) The compound (410 mg) obtained in (3) above was used to perform the synthesis process according to the method described in Example 1-65-(2) thereby giving a crude product (398 mg) containing tert-butyl 4-[8-[[6-(1H-pyrazol-5-yl)-3-pyridinyl]oxy]octoxy]-4-oxanecarboxylate as a colorless oil.

(5) The compound (398 mg) obtained in (4) above was used to perform the synthesis process according to the method described in Example 3-1-(3) thereby giving the title compound (68 mg) as a colorless powder.

$^1$H NMR (400 MHz, DMSO-d$_6$) δ ppm 1.17-1.58 (m, 10H) 1.62-1.98 (m, 6H) 3.51-3.68 (m, 4H) 3.99-4.14 (m, 2H) 6.66-6.77 (m, 1H) 7.37-7.48 (m, 1H) 7.61-7.72 (m, 1H) 7.79-7.89 (m, 1H) 8.22-8.31 (m, 1H).

MS ESI posi: 418[M+H]$^+$.
MS ESI nega: 416[M−H]$^-$.

With a supercritical fluid chromatography (SFC) apparatus equipped with a chiral column, separation of isomers was found for the compounds of Examples 1-56, 1-68, 1-70, 22-9, and 22-11. The conditions are shown in Example 69.

Example 69-1

Analysis of the compound of Example 1-56 using an SFC apparatus under the following conditions found separation of optical isomers.

Column: CHIRALCEL ODH, 5 m, 4.6×250 mm (Daicel Corporation)
Solvent: solution A; methanol, solution B; carbon dioxide
Elution condition: solution A/solution B=40/60
Flow rate: 3.0 mL/min, temperature: 40° C.
Analysis time: 10 min Example 69-1-1 (Isomer Having Short Retention Time, Retention Time: 3.24 min)

Example 69-1-2 (Isomer Having Long Retention Time, Retention Time: 3.92 min)

The compounds of Examples 69-1-1 and 69-1-2 were obtained by using the method described in the following.

(1) The compound obtained according to the methods described in Example 1-47-(1) and (2) using the compounds of Reference Examples 1-1 and 59-1 was optically resolved by an SFC apparatus equipped with a chiral column. A component having a short retention time was obtained as a compound of Example 69-1-(1)-1, and a component having a long retention time was obtained as a compound of Example 69-1-(1)-2.

(2) An aqueous solution of 0.6 mol/L lithium hydroxide (530 µL) was added to a solution of the compound (40 mg) of Example 69-1-(1)-1 in ethanol (530 µL) under ice cooling, and the mixture was stirred at the same temperature for 15 minutes, and at room temperature for 5 minutes. Tetrahydrofuran (530 µL) was added thereto to dissolve the precipitate, and the resultant mixture was stirred at room temperature for 2 hours. An aqueous solution of 10% potassium hydrogen sulfate was added to the mixture under ice cooling, and the resultant mixture was extracted three times with chloroform. The organic layers were combined, washed with water, passed through a phase separator, and concentrated under reduced pressure. The residue was purified by preparative HPLC to give the compound of Example 69-1-1 (10 mg) as a colorless solid.

$^1$H NMR (400 MHz, DMSO-d$_6$) δ ppm 1.66-1.83 (m, 1H) 2.01-2.15 (m, 1H) 2.63-3.01 (m, 5H) 5.13 (s, 2H) 6.72 (s, 1H) 7.09 (d, J=7.8 Hz, 1H) 7.15-7.27 (m, 2H) 7.46-7.56 (m, 1H) 7.67 (s, 1H) 7.84 (d, J=8.7 Hz, 1H) 8.33 (s, 1H).

MS ESI posi: 350[M+H]$^+$.
MS ESI nega: 348[M−H]$^-$.

In the same manner, the compound (65 mg) of Example 69-1-(1)-2 was used to obtain the compound (25 mg) of Example 69-1-2 as a colorless solid.

$^1$H NMR (400 MHz, DMSO-d$_6$) δ ppm 1.66-1.81 (m, 1H) 2.01-2.14 (m, 1H) 2.63-3.01 (m, 5H) 5.13 (s, 2H) 6.72 (s, 1H) 7.09 (d, J=7.8 Hz, 1H) 7.14-7.27 (m, 2H) 7.42-7.55 (m, 1H) 7.68 (s, 1H) 7.85 (d, J=8.8 Hz, 1H) 8.33 (s, 1H) 12.11-13.21 (m, 2H).
MS ESI posi: 350[M+H]$^+$.
MS ESI nega: 348[M−H]$^-$.

Example 69-2

Analysis of the compound of Example 1-68 using an SFC apparatus under the following conditions found separation of optical isomers.
Column: CHIRALCEL OD3, 3 μm, 4.6×250 mm (Daicel Corporation)
Solvent: solution A; ethanol, solution B; carbon dioxide
Elution condition: solution A/solution B=25/75
Flow rate: 3.0 mL/min, temperature: 40° C.
Analysis time: 15 min Example 69-2-1 (Isomer Having Short Retention Time, Retention Time: 11.32 min)

Example 69-2-2 (Isomer Having Long Retention Time, Retention Time: 12.50 min)

The compounds of Examples 69-2-1 and 69-2-2 were obtained by using the method described in the following.
(1) The compound obtained according to the methods described in Example 1-47-(1) and (2) using the compounds of Reference Examples 1-1 and 60-1 was optically resolved by an HPLC apparatus equipped with a chiral column. A component having a short retention time was obtained as a compound of Example 69-2-(1)-1, and a component having a long retention time was obtained as a compound of Example 69-2-(1)-2.
(2) The compound of Example 69-2-(1)-2 was used to perform the reaction according to the method described in Example 69-1-(2) thereby giving the compound of Example 69-2-1 as a colorless solid.
$^1$H NMR (400 MHz, DMSO-d$_6$) δ ppm 2.73-2.90 (m, 2H) 3.74-3.90 (m, 1H) 4.24-4.44 (m, 1H) 5.05 (s, 2H) 6.63-6.84 (m, 2H) 7.07-7.29 (m, 2H) 7.40-8.04 (m, 3H) 8.24-8.45 (m, 1H).
MS ESI posi: 352[M+H]$^+$.
MS ESI nega: 350[M−H]$^-$.
In the same manner, the compound of Example 69-2-(1)-1 was used to obtain the compound of Example 69-2-2 as a colorless solid.
$^1$H NMR (400 MHz, DMSO-d$_6$) δ ppm 2.79-2.93 (m, 2H) 3.87-4.02 (m, 1H) 4.23-4.38 (m, 1H) 5.06 (s, 2H) 6.65-6.82 (m, 2H) 7.07-7.27 (m, 2H) 7.45-7.55 (m, 1H) 7.58-7.74 (m, 1H) 7.85 (m, J=8.3 Hz, 1H) 8.26-8.38 (m, 1H).
MS ESI posi: 352[M+H]$^+$.
MS ESI nega: 350[M−H]$^-$.

Example 69-3

Analysis of the compound of Example 1-70 using an SFC apparatus under the following conditions found separation of optical isomers.
Column: CHIRALPAK AY-H, 5 m, 4.6×250 mm (Daicel Corporation)
Solvent: solution A; methanol, solution B; carbon dioxide
Elution condition: solution A/solution B=50/50
Flow rate: 3.0 mL/min, temperature: 40° C.
Analysis time: 10 min Example 69-3-1 (Isomer Having Short Retention Time, Retention Time: 2.96 min)

Example 69-3-2 (Isomer Having Long Retention Time, Retention Time: 4.57 min)

The isomers were separately collected under the following conditions.
Column: CHIRALPAK AY-H, 5 m, 20×250 mm (Daicel Corporation)
Solvent: solution A; methanol, solution B; carbon dioxide
Elution condition: solution A/solution B=40/60
Flow rate: 30 mL/min, temperature: 40° C.
Analysis time: 27 min Example 69-4

Analysis of the compound of Example 22-9 using an SFC apparatus under the following conditions found separation of optical isomers.
Column: CHIRALPAK AY-H, 5 m, 4.6×250 mm (Daicel Corporation)
Solvent: solution A; methanol, solution B; carbon dioxide
Elution condition: solution A/solution B=40/60
Flow rate: 3.0 mL/min, temperature: 40° C.
Analysis time: 10 min Example 69-4-1 (Isomer Having Short Retention Time, Retention Time: 3.29 min)

Example 69-4-2 (Isomer Having Long Retention Time, Retention Time: 4.93 min)

The compound of Example 69-4-1 was obtained by using the method described in the following.
(1) The compound (349 mg) obtained in Reference Example 91-2 was used to perform the reaction according to the method described in Example 18-1-(1) thereby giving a mixture (438 mg) containing ethyl (3S)-1-[3-(methylsulfonyloxymethyl)phenyl]sulfonylpiperidine-3-carboxylate.
(2) The mixture (432 mg) obtained in (1) above was used to perform the reaction according to the method described in Example 18-1-(2) thereby giving ethyl (3S)-1-[3-[[6-[2-(oxan-2-yl)pyrazol-3-yl]pyridin-3-yl]oxymethyl]phenyl]sulfonylpiperidine-3-carboxylate (494 mg) as a colorless amorphous substance.
(3) The compound (494 mg) obtained in (2) above was used to perform the reaction according to the method described in Example 12-1-(3) thereby giving ethyl (3S)-1-[3-[[6-(1H-pyrazol-5-yl)pyridin-3-yl]oxymethyl]phenyl]sulfonylpiperidine-3-carboxylate (353 mg) as a colorless amorphous substance.
(4) An aqueous solution of 1 mol/L lithium hydroxide (0.6 mL) was added dropwise to a solution of the compound (133 mg) obtained in (3) above in tetrahydrofuran (3.0 mL) under ice cooling, and the mixture was stirred at the same temperature for 1 hour, and at room temperature for 4 hours. The reaction solution was diluted with water, an aqueous solution of 0.5 mol/L potassium hydrogen sulfate was used to adjust pH to 2 to 3, and the resultant mixture was extracted three times with ethyl acetate. The organic layers were combined, passed through a phase separator, and concentrated under reduced pressure. Diethyl ether was added to the obtained residue, and the precipitated solid was collected by filtration and dried under air flow to give the compound (65.7 mg) of Example 69-4-1 as a colorless solid.

¹H NMR (400 MHz, DMSO-d₆) δ ppm 1.23-1.53 (m, 3H) 1.59-1.79 (m, 3H) 2.29-2.41 (m, 2H) 3.45-3.53 (m, 1H) 5.38 (s, 2H) 6.73 (s, 1H) 7.50-7.57 (m, 1H) 7.64-7.75 (m, 3H) 7.79-7.90 (m, 3H) 8.34-8.40 (m, 1H).
MS ESI posi: 443[M+H]⁺.
MS ESI nega: 441[M−H]⁻.

The compound of Reference Example 91-1 was used to perform the synthesis process according to the methods described in (1) to (4) above thereby giving the compound of Example 69-4-2 as a colorless solid.

¹H NMR (400 MHz, DMSO-d₆) δ ppm 1.23-1.53 (m, 3H) 1.59-1.79 (m, 3H) 2.29-2.41 (m, 2H) 3.45-3.53 (m, 1H) 5.38 (s, 2H) 6.73 (s, 1H) 7.50-7.57 (m, 1H) 7.64-7.75 (m, 3H) 7.79-7.90 (m, 3H) 8.34-8.40 (m, 1H).
MS ESI posi: 443[M+H]⁺.
MS ESI nega: 441[M−H]⁻.

Example 69-5

Analysis of the compound of Example 22-11 using an SFC apparatus under the following conditions found separation of optical isomers.
Column: CHIRALPAK AD-H, 5 m, 4.6×250 mm (Daicel Corporation)
Solvent: solution A; methanol, solution B; carbon dioxide
Elution condition: solution A/solution B=60/40
Flow rate: 3.0 mL/min, temperature: 40° C.
Analysis time: 10 min Example 69-5-1 (Isomer Having Short Retention Time, Retention Time: 2.72 min)

Example 69-5-2 (Isomer Having Long Retention Time, Retention Time: 6.56 min)

The isomers can be separately collected by applying the above conditions to a preparative column.

Example 70-1

(E)-3-[2-Fluoro-3-[[6-(1H-pyrazol-5-yl)pyridin-3-yl] oxymethyl]phenyl]prop-2-enoic Acid

[Formula 594]

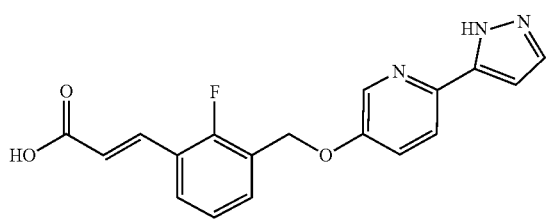

(1) The compound (640 mg) obtained in Reference Example 107-1 was used to perform the reaction according to the method described in Example 8-1-(1) thereby giving 2-methylpropyl (E)-3-[2-fluoro-3-[[6-[2-(oxan-2-yl)pyrazol-3-yl]pyridin-3-yl]oxymethyl]phenyl]prop-2-enoate (988 mg) as a colorless oil.
(2) The compound (70 mg) obtained in (1) above was used to perform the reaction according to the method described in Example 12-1-(3) thereby giving a solution containing 2-methylpropyl (E)-3-[2-fluoro-3-[[6-(1H-pyrazol-5-yl)pyridin-3-yl]oxymethyl]phenyl]prop-2-enoate.

(3) The solution obtained in (2) above was used to perform the reaction according to the method described in Example 9-1-(3) thereby giving the title compound (15 mg) as a colorless solid.
¹H NMR (400 MHz, DMSO-d₆) δ ppm 5.30 (s, 2H) 6.56-6.82 (m, 2H) 7.24-7.37 (m, 1H) 7.52-7.74 (m, 4H) 7.80-7.97 (m, 2H) 8.28-8.44 (m, 1H).
MS ESI posi: 340[M+H]⁺.

Example 70-2

3-[2-Fluoro-3-[[6-(1H-pyrazol-5-yl)pyridin-3-yl] oxymethyl]phenyl]propanoic Acid

[Formula 595]

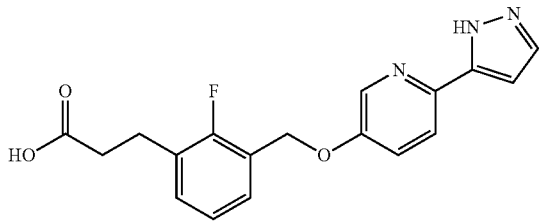

(1) The compound (230 mg) obtained in Example 70-1-(1) was used to perform the reaction described in Example 2-1-(3) at 60° C. thereby giving 2-methylpropyl 3-[2-fluoro-3-[[6-(1H-pyrazol-5-yl)pyridin-3-yl]oxymethyl]phenyl]propanoate (34 mg) as a colorless oil.
(2) The compound (30 mg) obtained in (1) above was used to perform the reaction according to the method described in Example 9-1-(3) thereby giving the title compound (12 mg) as a colorless solid.
¹H NMR (400 MHz, DMSO-d₆) δ ppm 2.88 (t, J=7.5 Hz, 2H) 5.24 (s, 2H) 6.69-6.78 (m, 1H) 7.11-7.21 (m, 1H) 7.34 (t, J=7.3 Hz, 1H) 7.43 (t, J=7.0 Hz, 1H) 7.56 (dd, J=8.8, 2.6 Hz, 1H) 7.63-7.74 (m, 1H) 7.87 (d, J=8.4 Hz, 1H) 8.36 (d, J=2.6 Hz, 1H).
MS ESI posi: 342[M+H]⁺.
MS ESI nega: 340[M−H]⁻.

Example 70-3

2-[2-Fluoro-3-[[6-(1H-pyrazol-5-yl)pyridin-3-yl] oxymethyl]phenyl]cyclopropane-1-carboxylic Acid

[Formula 596]

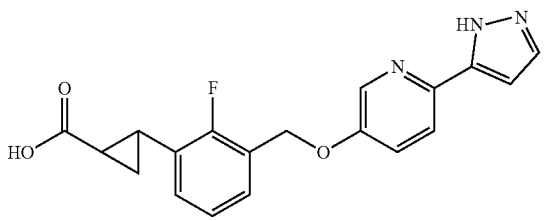

(1) The compound (200 mg) obtained in Example 70-1-(1) was used to perform the reaction according to the method described in Example 26-2-(1) thereby giving 2-methylpropyl 2-[2-fluoro-3-[[6-[2-(oxan-2-yl)pyrazol-3-yl]pyridin-3-yl]oxymethyl]phenyl]cyclopropane-1-carboxylate (128 mg) as a colorless oil.

(2) The compound (128 mg) obtained in (1) above was used to perform the reaction according to the method described in Example 12-1-(3) thereby giving a solution containing 2-methylpropyl 2-[2-fluoro-3-[[6-(1H-pyrazol-5-yl)pyridin-3-yl]oxymethyl]phenyl]cyclopropane-1-carboxylate.

(3) The solution obtained in (2) above was used to perform the reaction according to the method described in Example 9-1-(3) thereby giving the title compound (21 mg) as a colorless solid.

¹H NMR (400 MHz, DMSO-d₆) δ ppm 1.36-1.50 (m, 2H) 1.78-1.93 (m, 1H) 5.25 (s, 2H) 6.74 (d, J=2.1 Hz, 1H) 7.09-7.21 (m, 2H) 7.38-7.46 (m, 1H) 7.56 (dd, J=8.6, 2.2 Hz, 1H) 7.61-7.77 (m, 1H) 7.87 (d, J=8.6 Hz, 1H) 8.37 (d, J=2.2 Hz, 1H).
MS ESI posi: 354[M+H]⁺.
MS ESI nega: 352[M–H]⁻.

The compounds of Examples 70-4 and 70-5 below were synthesized using a compound obtained in Reference Example 44-5-(1) or 107-2, according to the method described in Example 70-1, and the compound of Example 70-6 below was synthesized using the synthesis intermediate of Reference Example 44-6, according to the method described in Example 70-1. The structures, NMR data, and MS data of the compounds are shown in Table 67-2.

TABLE 67-2

| Example No. | Structure | Analytical Data |
|---|---|---|
| 70-4 | 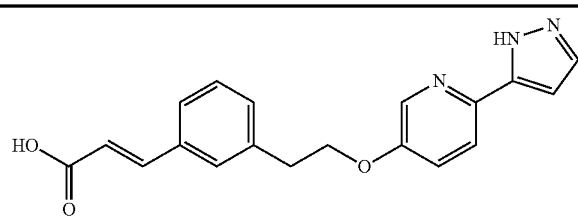 | ¹H NMR (400 MHz, DMSO-d₆) δ ppm 3.10 (t, J = 6.9 Hz, 2 H) 4.34 (t, J = 6.9 Hz, 2 H) 6.55 (d, J = 16.0 Hz, 1 H) 6.72 (d, J = 2.1 Hz, 1 H) 7.32-7.42 (m, 2 H) 7.47 (dd, J = 8.7, 2.8 Hz, 1 H) 7.51-7.61 (m, 2 H) 7.63-7.74 (m, 2 H) 7.84 (d, J = 8.7 Hz, 1 H) 8.28 (d, J = 2.8 Hz, 1 H).<br>MS ESI posi: 336 [M + H]⁺.<br>MS ESI nega: 334 [M − H]⁻. |
| 70-5 | 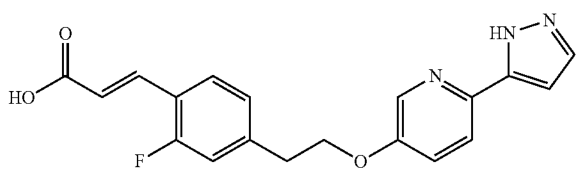 [SMILES: O=C(O)/C=C/c1ccc(CCOc2ccc(-c3ccn[nH]3)nc2)cc1F] | ¹H NMR (400 MHz, DMSO-d₆) δ ppm 3.12 (t, J = 6.6 Hz, 2 H) 4.34 (t, J = 6.6 Hz, 2 H) 6.50-6.60 (m, 1 H) 6.69-6.76 (m, 1 H) 7.20-7.35 (m, 2 H) 7.42-7.51 (m, 1 H) 7.52-7.90 (m, 4 H) 8.24-8.31 (m, 1 H).<br>MS ESI posi: 354 [M + H]⁺.<br>MS ESI nega: 352 [M − H]⁻. |
| 70-6 | 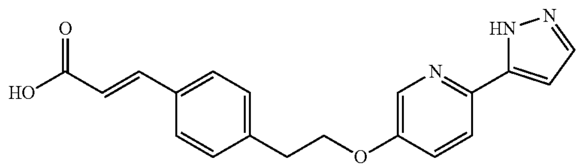 [SMILES: O=C(O)/C=C/c1ccc(CCOc2ccc(-c3ccn[nH]3)nc2)cc1] | ¹H NMR (400 MHz, DMSO-d₆) δ ppm 3.10 (t, J = 6.7 Hz, 2 H) 4.32 (t, J = 6.7 Hz, 2 H) 6.49 (d, J = 16.0 Hz, 1 H) 6.72 (d, J = 2.1 Hz, 1 H) 7.39 (d, J = 8.0 Hz, 2 H) 7.46 (dd, J = 8.7, 2.7 Hz, 1 H) 7.55 (d, J = 16.0 Hz, 1 H) 7.63 (d, J = 8.0 Hz, 2 H) 7.64-7.72 (m, 1 H) 7.84 (d, J = 8.7 Hz, 1 H) 8.27 (d, J = 2.7 Hz, 1 H).<br>MS ESI posi: 336 [M + H]⁺.<br>MS ESI nega: 334 [M − H]⁻. |

The compounds of Examples 70-7 to 70-9 below were synthesized using any of the synthesis intermediates obtained in Examples 70-4 to 70-6, according to the method described in Example 70-3. The structures, NMR data, and MS data of the compounds are shown in Table 67-3.

TABLE 67-3

| Example No. | Structure | Analytical Data |
|---|---|---|
| 70-7 | 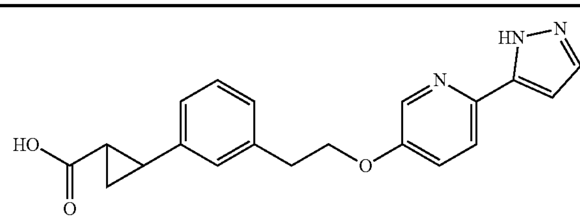 | ¹H NMR (400 MHz, DMSO-d₆) δ ppm 1.29-1.51 (m, 2 H) 1.75-1.89 (m, 1 H) 2.32-2.41 (m, 1 H) 3.03 (t, J = 6.9 Hz, 2 H) 4.29 (t, J = 6.9 Hz, 2 H) 6.72 (d, J = 2.0 Hz, 1 H) 7.02 (d, J = 7.5 Hz, 1 H) 7.10-7.26 (m, 3 H) 7.46 (dd, J = 8.7, 2.5 Hz, 1 H) 7.64-7.69 (m, 1 H) 7.84 (d, J = 8.7 Hz, 1 H) 8.27 (d, J = 2.5 Hz, 1 H). MS ESI posi: 350[M + H]⁺. MS ESI nega: 348[M − H]⁻. |
| 70-8 | 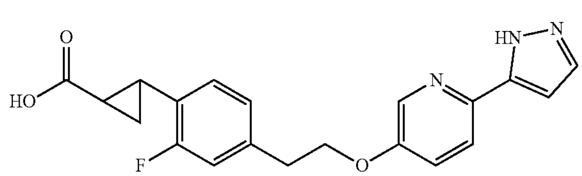 [SMILES: O=C(O)C1CC1c1ccc(CCOc2ccc(-c3ccn[nH]3)nc2)cc1F] | ¹H NMR (400 MHz, DMSO-d₆) δ ppm 1.31-1.43 (m, 2 H) 1.75-1.86 (m, 1 H), 2.39-2.44 (m, 1 H) 3.05 (t, J = 6.7 Hz, 2 H) 4.29 (t, J = 6.7 Hz, 2 H) 6.72 (d, J = 2.1 Hz, 1 H), 7.01-7.13 (m, 2 H) 7.18 (d, J = 11.6 Hz, 1 H) 7.45 (dd, J = 8.7, 2.7 Hz, 1 H) 7.67 (s, 1 H) 7.84 (d, J = 8.7 Hz, 1 H) 8.27 (d, J = 2.7 Hz, 1 H). MS ESI posi: 368[M + H]⁺. MS ESI |

TABLE 67-3-continued

| Example No. | Structure | Analytical Data |
|---|---|---|
| 70-9 | 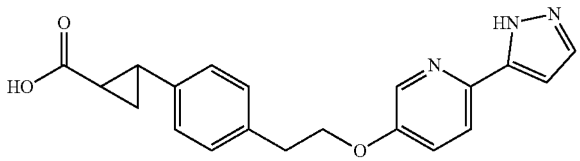 [SMILES: O=C(O)C1CC1c1ccc(CCOc2ccc(-c3ccn[nH]3)nc2)cc1] | nega: 366[M – H]⁻.<br>¹H NMR (400 MHz, DMSO-d₆) δ ppm 1.26-1.45 (m, 2 H) 1.73-1.83 (m, 1 H) 2.30-2.40 (m, 1 H) 3.03 (t, J = 6.4 Hz, 2 H), 4.27 (t, J = 6.6 Hz, 2 H) 6.72 (s, 1 H), 7.11 (d, J = 7.8 Hz, 2 H) 7.24 (d, J = 7.8 Hz, 2 H) 7.44 (dd, J = 8.7, 2.4 Hz, 1 H) 7.67 (s, 1 H) 7.83 (d, J = 8.7 Hz, 1 H) 8.26 (d, J = 2.4 Hz, 1 H).<br>MS ESI posi: 350[M + H]⁺. MS ESI nega: 348[M – H]⁻. |

Example 70-10

With an HPLC equipped with a chiral column, separation of optical isomers was found for the compound of Example 70-9.

Example 70-10-1 (Isomer Having Short Retention Time, Retention Time: 6.11 min)

Example 70-10-2 (Isomer Having Long Retention Time, Retention Time: 11.48 min)

Separation of the isomers was performed by SFC.

Example 70-11

2-[2-Fluoro-4-[[6-(1H-pyrazol-5-yl)pyridin-3-yl]oxymethyl]phenyl]cyclopropane-1-carboxylic Acid

[Formula 597]

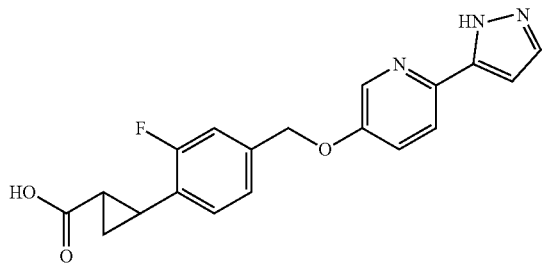

(1) The compound (400 mg) obtained in Reference Example 106-1 was used to perform the reaction according to the method described in Example 1-1-(1) thereby giving ethyl (E)-3-[2-fluoro-4-[[6-[2-(oxan-2-yl)pyrazol-3-yl]pyridin-3-yl]oxymethyl]phenyl]prop-2-enoate (701 mg) as a brown oil.

(2) The compound (701 mg) obtained in (1) above was used to perform the reaction according to the method described in Example 26-1-(1) thereby giving ethyl 2-[2-fluoro-4-[[6-[2-(oxan-2-yl)pyrazol-3-yl]pyridin-3-yl]oxymethyl]phenyl]cyclopropane-1-carboxylate (428 mg) as a brown oil.

(3) The compound (428 mg) obtained in (2) above was used to perform the reaction according to the method described in Example 12-1-(3) thereby giving a solution containing ethyl 2-[2-fluoro-4-[[6-(1H-pyrazol-5-yl)pyridin-3-yl]oxymethyl]phenyl]cyclopropane-1-carboxylate.

(4) The solution obtained in (3) above was used to perform the reaction according to the method described in Example 1-1-(2) thereby giving the title compound (20 mg) as a colorless solid.

¹H NMR (400 MHz, DMSO-d₆) δ ppm 1.34-1.46 (m, 2H) 1.77-1.87 (m, 1H) 5.20 (s, 2H) 6.66-6.82 (m, 1H) 7.08-7.33 (m, 3H) 7.46-7.58 (m, 1H) 7.59-7.75 (m, 1H) 7.79-7.92 (m, 1H) 8.29-8.39 (m, 1H).

MS ESI posi: 354[M+H]⁺.

MS ESI nega: 352[M–H]⁻.

Example 71-1

2-[7-[6-(1H-Pyrazol-5-yl)pyridin-3-yl]oxyheptoxy]butanoic Acid

[Formula 598]

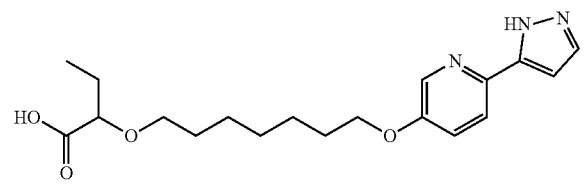

(1) The compound (45 mg) obtained in Reference Example 104-2 was used to perform the reaction according to the method described in Example 1-1-(1) thereby giving ethyl 2-[7-[6-[2-(oxan-2-yl)pyrazol-3-yl]pyridin-3-yl]oxyheptoxy]butanoate (90 mg) as a pale yellow oil.

(2) The compound (85 mg) obtained in (1) above was used to perform the reaction according to the method described in Example 1-1-(3) thereby giving a mixture containing ethyl 2-[7-[6-(1H-pyrazol-5-yl)pyridin-3-yl]oxyheptoxy]butanoate.

(3) The mixture obtained in (2) above was used to perform the reaction according to the method described in Example 9-1-(3) thereby giving the title compound (30 mg) as a colorless solid.

¹H NMR (400 MHz, DMSO-d₆) δ ppm 0.87 (t, J=7.4 Hz, 3H) 1.21-1.91 (m, 12H) 3.20-3.30 (m, 1H) 3.46-3.55 (m, 1H) 3.62-3.69 (m, 1H) 4.06 (t, J=6.5 Hz, 2H) 6.66-6.75 (m, 1H) 7.43 (dd, J=8.7, 2.8 Hz, 1H) 7.67 (s, 1H) 7.84 (d, J=8.7 Hz, 1H) 8.20-8.30 (m, 1H) 12.55-13.07 (m, 2H).

MS ESI posi: 362[M+H]⁺.

MS ESI nega: 360[M–H]⁻.

Example 71-2

With HPLC equipped with a chiral column, separation of optical isomers was found for the compound of Example 71-1.

Example 71-2-1 (Isomer Having Short Retention Time, Retention Time: 3.17 min)

Example 71-2-2 (Isomer Having Long Retention Time, Retention Time: 5.49 min)

Separation of the isomers was performed also by HPLC.

The compounds of Examples 71-3 to 71-6 below were synthesized using a compound obtained in Reference Example 103-1, 104-1, 104-5, or 105-1, according to the method described in Example 71-1. The structures, NMR data, and MS data of the compounds are shown in Table 67-4.

Example 71-7

6-[2-[6-(1H-Pyrazol-5-yl)pyridin-3-yl]oxyethyl]-3,4-dihydro-2H-chromene-2-carboxylic Acid

[Formula 599]

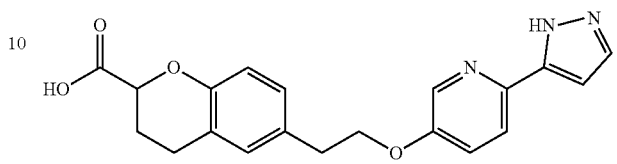

(1) The compound (90 mg) obtained in Reference Example 114-1 was used to perform the reaction according to the method described in Example 1-1-(1) thereby giving ethyl 6-[2-[6-[2-(oxan-2-yl)pyrazol-3-yl]pyridin-3-yl]oxyethyl]-3,4-dihydro-2H-chromene-2-carboxylate (158 mg) as a yellow oil.

(2) The compound (158 mg) obtained in (1) above was used to perform the reaction according to the method

TABLE 67-4

| Example No. | Structure | Analytical Data |
|---|---|---|
| 71-3 | 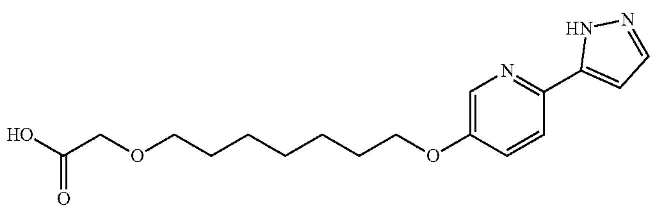 [SMILES: O=C(O)COCCCCCCCOc1ccc(-c2ccn[nH]2)nc1] | $^1$H NMR (400 MHz, DMSO-$d_6$) δ ppm 1.21-1.58 (m, 8 H) 1.67-1.80 (m, 2 H) 3.43 (t, J = 6.5 Hz, 2 H) 3.95 (s, 2 H) 4.06 (t, J = 6.4 Hz, 2 H) 6.72 (d, J = 2.0 Hz, 1 H) 7.44 (dd, J = 8.7, 2.7 Hz, 1 H) 7.67 (s, 1 H) 7.84 (d, J = 8.7 Hz, 1 H) 8.27 (d, J = 2.7 Hz, 1 H). MS ESI posi: 334[M + H]$^+$. MS ESI nega: 332[M − H]$^−$. |
| 71-4 | 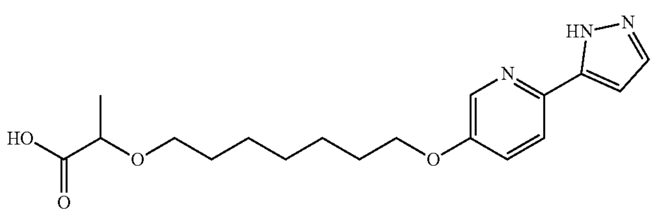 [SMILES: CC(OCCCCCCCOc1ccc(-c2ccn[nH]2)nc1)C(=O)O] | $^1$H NMR (400 MHz, DMSO-$d_6$) δ ppm 1.24 (d, J = 6.9 Hz, 3 H) 1.29-1.60 (m, 8 H) 1.68-1.79 (m, 2 H) 3.23-3.34 (m, 1 H) 3.42-3.53 (m, 1 H) 3.85 (q, J = 6.9 Hz, 1 H), 4.06 (t, J = 6.5 Hz, 2 H) 6.66-6.75 (m, 1 H) 7.43 (dd, J = 8.8, 2.8 Hz, 1 H) 7.67 (s, 1 H) 7.84 (d, J = 8.8 Hz, 1 H) 8.27 (d, J = 2.8 Hz, 1 H). MS ESI posi: 348[M + H]$^+$. MS ESI nega: 346[M − H]$^−$. |
| 71-5 | 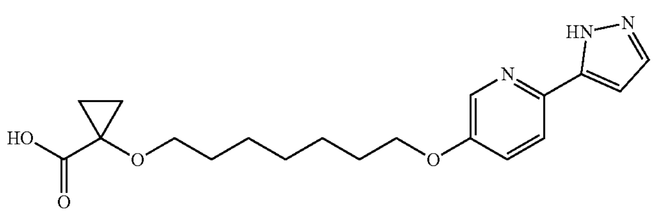 [SMILES: O=C(O)C1(OCCCCCCCOc2ccc(-c3ccn[nH]3)nc2)CC1] | $^1$H NMR (400 MHz, DMSO-$d_6$) δ ppm 0.96-1.15 (m, 4 H) 1.26-1.51 (m, 8 H) 1.64-1.82 (m, 2 H) 3.51 (t, J = 6.4 Hz, 2 H) 4.06 (t, J = 6.4 Hz, 2 H) 6.63-6.77 (m, 1 H) 7.43 (dd, J = 8.7, 2.8 Hz, 1 H) 7.67 (s, 1 H) 7.84 (d, J = 8.7 Hz, 1 H) 8.19-8.35 (m, 1 H). MS ESI posi: 360[M + H]$^+$. MS ESI nega: 358[M − H]$^−$. |
| 71-6 | | $^1$H NMR (400 MHz, DMSO-$d_6$) δ ppm 1.30-1.63 (m, 8 H) 1.66-1.82 (m, 2 H) 3.33-3.40 (m, 2 H) 4.07 (t, J = 6.4 Hz, 2 H) 4.51 (d, J = 6.9 Hz, 2 H) 4.71 (d, J = 6.9 Hz, 2 H) 6.72 (d, J = 1.8 Hz, 1 H) 7.44 (dd, J = 8.7, 2.7 Hz, 1 H) 7.67 (s, 1 H) 7.84 (d, J = 8.7 Hz, 1 H) 8.27 (d, J = 2.7 Hz, 1 H). MS ESI posi: 376[M + H]$^+$. MS ESI nega: 374[M − H]$^−$. | described in Example 12-1-(3) thereby giving a solution containing ethyl 6-[2-[6-(1H-pyrazol-5-yl)pyridin-3-yl]oxy-ethyl]-3,4-dihydro-2H-chromene-2-carboxylate.

(3) The solution obtained in (2) above was used to perform the reaction according to the method described in Example 9-1-(3) thereby giving the title compound (65 mg) as a colorless solid.

$^1$H NMR (400 MHz, DMSO-$d_6$) δ ppm 1.97-2.21 (m, 2H) 2.54-2.70 (m, 1H) 2.71-2.85 (m, 1H) 2.95 (t, J=6.9 Hz, 2H) 4.24 (t, J=6.9 Hz, 2H) 4.72-4.78 (m, 1H) 6.70-6.78 (m, 2H) 7.00-7.08 (m, 2H) 7.46 (dd, J=8.9, 2.6 Hz, 1H) 7.65-7.71 (m, 1H) 7.84 (d, J=8.9 Hz, 1H) 8.27 (d, J=2.6 Hz, 1H) 12.89-13.12 (m, 2H).

MS ESI posi: 366[M+H]$^+$.
MS ESI nega: 364[M–H]$^-$.

Example 71-8

With SFC equipped with a chiral column, separation of optical isomers was found for the compound of Example 71-7.

Example 71-8-1 (Isomer Having Short Retention Time, Retention Time: 5.84 min)

Example 71-8-2 (Isomer Having Long Retention Time, Retention Time: 7.47 min)

Separation of the isomers was performed also by SFC.

The compounds of Examples 71-9 to 71-20 below were synthesized using a compound obtained in Reference Example 95-1, 95-2-1, 95-2-2, 108-1, 110-1, 110-4, 112-1, 112-3, 115-1, 117-1 or 117-2, or 118-1, according to the method described in Example 71-7. The structures, NMR data, and MS data of the compounds are shown in Tables 67-5 and 67-6.

The compounds of Examples 71-17 and 71-18 are optically active compounds.

TABLE 67-5

| Example No. | Structure | Analytical Data |
|---|---|---|
| 71-9 | 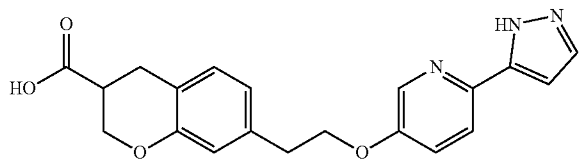 [SMILES: O=C(O)C1COc2cc(CCOc3ccc(-c4ccn[nH]4)nc3)ccc2C1] | $^1$H NMR (400 MHz, DMSO-$d_6$) δ ppm 2.85-3.03 (m, 5 H) 4.02-4.15 (m, 1 H) 4.20-4.35 (m, 3 H) 6.69-6.76 (m, 2 H) 6.78-6.84 (m, 1 H) 7.04 (d, J = 7.8 Hz, 1 H) 7.41-7.48 (m, 1 H) 7.60-7.77 (m, 1 H) 7.83 (d, J = 8.2 Hz, 1 H) 8.26 (d, J = 2.3 Hz, 1 H). MS ESI posi: 366[M + H]$^+$. MS ESI nega: 364[M – H]$^-$. |
| 71-10 | 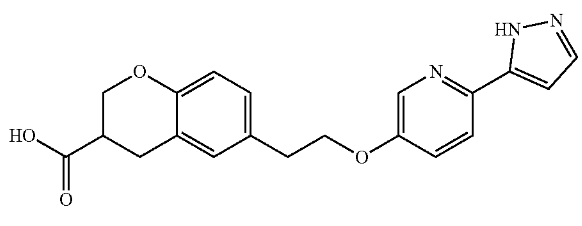 [SMILES: O=C(O)C1COc2ccc(CCOc3ccc(-c4ccn[nH]4)nc3)cc2C1] | $^1$H NMR (400 MHz, DMSO-$d_6$) δ ppm 2.87-3.02 (m, 5 H) 3.99-4.08 (m, 1 H) 4.19-4.32 (m, 3 H) 6.69 (d, J = 8.3 Hz, 1 H) 6.72 (d, J = 1.6 Hz, 1 H) 7.02 (d, J = 8.3 Hz, 1 H) 7.07 (s, 1 H) 7.46 (dd, J = 8.6, 2.6 Hz, 1 H) 7.67 (s, 1 H) 7.83 (d, J = 8.6 Hz, 1 H) 8.27 (d, J = 2.6 Hz, 1 H). MS ESI posi: 366[M + H]$^+$. MS ESI nega: 364[M – H]$^-$. |
| 71-11 | 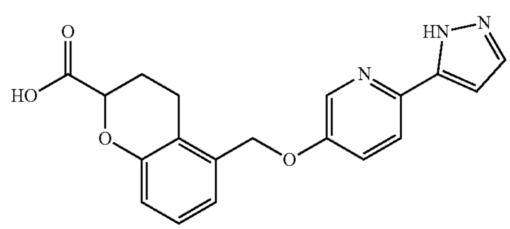 [SMILES: O=C(O)C1CCc2c(COc3ccc(-c4ccn[nH]4)nc3)cccc2O1] | $^1$H NMR (400 MHz, DMSO-$d_6$) δ ppm 2.03-2.13 (m, 1 H) 2.13-2.24 (m, 1 H) 2.68-2.72 (m, 1 H) 2.78-2.90 (m, 1 H) 4.70-4.79 (m, 1 H) 5.16 (s. 2 H) 6.73 (d, J = 2.1 Hz, 1 H) 6.81-6.86 (m, 1 H) 7.00-7.04 (m, 1 H) 7.09-7.16 (m, 1 H) 7.54 (dd, J = 8.7, 2.8 Hz, 1 H) 7.63-7.72 (m, 1 H) 7.86 (d, J = 8.7 Hz, 1 H) 8.35 (d, J = 2.8 Hz, 1 H). MS ESI posi: 352[M + H]$^+$. MS ESI nega: 350[M – H]$^-$. |
| 71-12 | 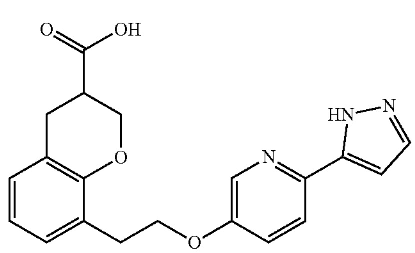 [SMILES: O=C(O)C1COc2c(CCOc3ccc(-c4ccn[nH]4)nc3)cccc2C1] | $^1$H NMR (400 MHz, DMSO-$d_6$) δ ppm 2.88-3.06 (m, 6 H) 4.18-4.26 (m, 2 H) 4.35-4.46 (m, 1 H) 6.70-6.74 (m, 1 H) 6.75-6.83 (m, 1 H) 6.96-7.11 (m, 2 H) 7.39-7.50 (m, 1 H) 7.57-7.91 (m, 2 H) 8.22-8.32 (m, 1 H). MS ESI posi: 366[M + H]$^+$. MS ESI nega: 364[M – H]$^-$. |

TABLE 67-5-continued

| Example No. | Structure | Analytical Data |
|---|---|---|
| 71-13 | 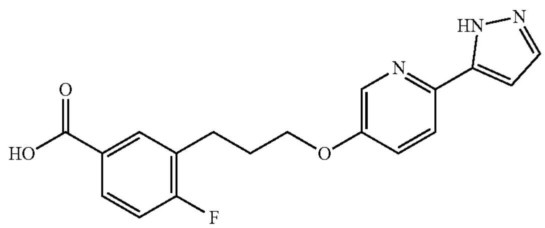 [SMILES: O=C(O)c1ccc(F)c(CCCOc2ccc(-c3ccn[nH]3)nc2)c1] | $^1$H NMR (400 MHz, DMSO-d$_6$) δ ppm 1.94-2.12 (m, 2 H) 2.86 (t, J = 7.3 Hz, 2 H) 4.11 (t, J = 5.9 Hz, 2 H) 6.72 (s, 1 H) 7.28 (t, J = 9.4 Hz, 1 H) 7.37-7.48 (m, 1 H) 7.58-7.74 (m, 1 H) 7.76-7.88 (m, 2 H) 7.93 (d, J = 7.6 Hz, 1 H) 8.21-8.33 (m, 1 H) 12.55-13.23 (m, 2 H). MS ESI posi: 342[M + H]$^+$. MS ESI nega: 340[M − H]$^−$. |
| 71-14 | 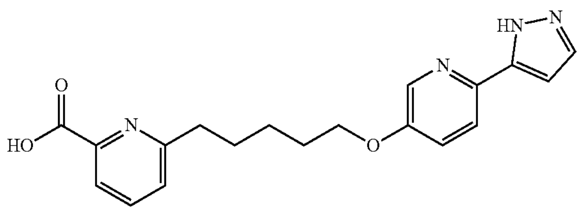 [SMILES: O=C(O)c1cccc(CCCCCOc2ccc(-c3ccn[nH]3)nc2)n1] | $^1$H NMR (400 MHz, DMSO-d$_6$) δ ppm 1.38-1.56 (m, 2 H) 1.67-1.88 (m, 4 H) 2.83 (t, J = 7.6 Hz, 2 H) 4.07 (t, J = 6.4 Hz, 2 H) 6.72 (s, 1 H) 7.43 (d, J = 8.3 Hz, 1 H) 7.49 (d, J = 6.2 Hz, 1 H) 7.61-7.77 (m, 1H) 7.78-7.94 (m, 3 H) 8.21-8.30 (m, 1 H). MS ESI posi: 353[M + H]$^+$. MS ESI nega: 351[M − H]$^−$. |

TABLE 67-6

| Example No. | Structure | Analytical Data |
|---|---|---|
| 71-15 | 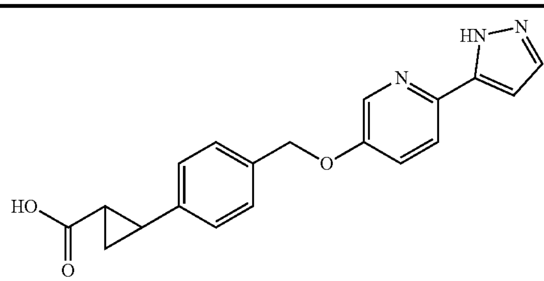 | $^1$H NMR (400 MHz, DMSO-$_6$) δ ppm 1.27-1.46 (m, 2 H) 1.74-1.86 (m, 1 H) 5.17 (s, 2 H) 6.69-6.75 (m, 1 H) 7.19 (d, J = 8.1 Hz, 2 H) 7.38 (d, J = 7.8 Hz, 2 H) 7.46-7.53 (m, 1 H) 7.63-7.72 (m, 1 H) 7.81-7.88 (m, 1 H) 8.30-8.36 (m, 1 H). MS ESI posi: 336[M + H]$^+$. MS ESI nega: 334[M − H]$^−$. |
| 71-16 | 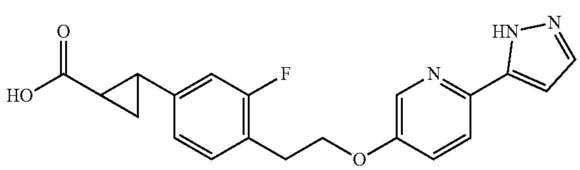 [SMILES: O=C(O)C1CC1c1ccc(CCOc2ccc(-c3ccn[nH]3)nc2)c(F)c1] | $^1$H NMR (400 MHz, DMSO-d$_6$) δ ppm 1.29-1.44 (m, 2 H) 1.79-1.87 (m, 1 H) 2.35-2.43 (m, 1 H) 3.05 (t, J = 6.4 Hz, 2 H) 4.27 (t, J = 6.4 Hz, 2 H) 6.69-6.75 (m, 1 H) 6.96-7.06 (m, 2 H) 7.28-7.35 (m, 1 H) 7.40-7.48 (m, 1 H) 7.67 (s, 1 H) 7.80-7.87 (m, 1 H) 8.25 (s, 1 H) 12.72 (br s, 1 H). MS ESI posi: 368[M + H]$^+$. MS ESI nega: 366[M − H]$^−$. |
| 71-17 | 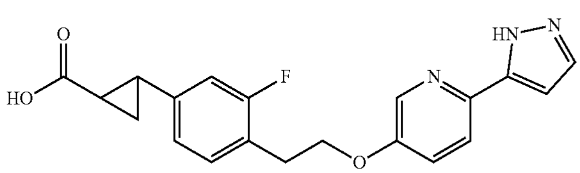 [SMILES: O=C(O)C1CC1c1ccc(CCOc2ccc(-c3ccn[nH]3)nc2)c(F)c1] | $^1$H NMR (400 MHz, DMSO-d$_6$) δ ppm 1.29-1.44 (m, 2 H) 1.79-1.87 (m, 1 H) 2.35-2.43 (m, 1 H) 3.05 (t, J = 6.4 Hz, 2 H) 4.27 (t, J = 6.4 Hz, 2 H) 6.69-6.75 (m, 1 H) 6.96-7.06 (m, 2 H) 7.28-7.35 (m, 1 H) 7.40-7.48 (m, 1 H) 7.67 (s, 1 H) 7.80-7.87 (m, 1 H) 8.25 (s, 1 H). MS ESI posi: 368[M + H]$^+$. MS ESI nega: 366[M − H]$^−$. Retention time: 6.03 min (S F C) |
| 71-18 | 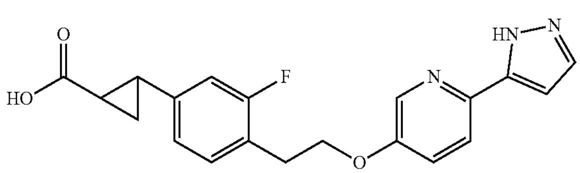 [SMILES: O=C(O)C1CC1c1ccc(CCOc2ccc(-c3ccn[nH]3)nc2)c(F)c1] | $^1$H NMR (400 MHz, DMSO-d$_6$) δ ppm 1.31-1.46 (m, 2 H) 1.79-1.87 (m, 1 H) 2.37-2.39 (m, 1 H) 3.02-3.09 (m, 2 H) 4.24-4.31 (m, 2 H) 6.69-6.75 (m, 1 H) 6.96-7.06 (m, 2 H) 7.27-7.35 (m, 1 H) 7.41-7.49 (m, 1 H) 7.62-7.71 (m, 1 H) 7.80-7.87 (m, 1 H) 8.22-8.29 (m, 1 H). MS ESI posi: 368[M + H]+. MS ESI nega: 366[M − H]$^−$. Retention time 3.54 min (S F C) |

TABLE 67-6-continued

| Example No. | Structure | Analytical Data |
|---|---|---|
| 71-19 | 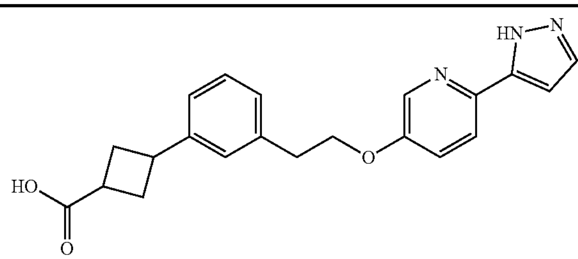 | $^1$H NMR (400 MHz, DMSO-d$_6$) δ ppm 2.17-2.26 (m, 2 H) 2.97-3.10 (m, 4 H) 3.34-3.47 (m, 2 H) 4.29 (t, J = 6.8 Hz, 2 H) 6.68-6.76 (m, 1 H) 7.06-7.30 (m, 4 H) 7.42-7.49 (m, 1 H) 7.62-7.74 (m, 1 H) 7.84 (d, J = 8.6 Hz, 1 H) 8.24-8.31 (m, 1 H). MS ESI posi: 364[M + H]$^+$. MS ESI nega: 362[M − H]$^−$. |
| 71-20 | 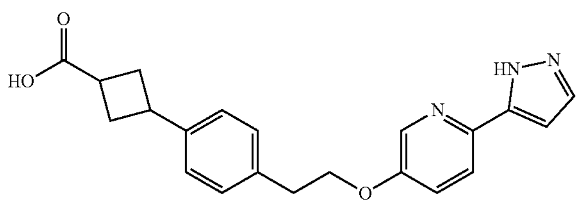 [SMILES: O=C(O)C1CC(c2ccc(CCOc3ccc(-c4ccn[nH]4)nc3)cc2)C1] | $^1$H NMR (400 MHz, DMSO-d$_6$) δ ppm 2.10-2.24 (m, 2 H) 2.94-3.08 (m, 4 H) 3.35-3.45 (m, 2 H) 4.27 (t, J = 6.9 Hz, 2 H) 6.72 (d, J = 2.1 Hz, 1 H) 7.17 (d, J = 7.9 Hz, 2 H) 7.28 (d, J = 7.9 Hz, 2 H) 7.45 (dd, J = 8.6, 2.7 Hz, 1 H) 7.58-7.76 (m, 1 H) 7.83 (d, J = 8.6 Hz, 1 H) 8.27 (d, J = 2.7 Hz, 1 H). MS ESI posi: 364[M + H]$^+$. MS ESI nega: 362[M − H]$^−$. |

Example 71-21

7-[2-[6-(1H-Pyrazol-5-yl)pyridin-3-yl]oxyethyl]-3,4-dihydro-2H-chromene-2-carboxylic Acid

[Formula 600]

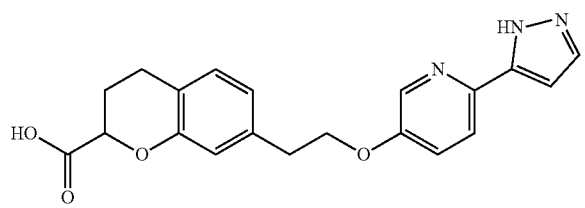

(1) The compound (130 mg) obtained in Reference Example 113-1 was used to perform the reaction according to the method described in Example 1-1-(1) thereby giving a mixture (201 mg) containing ethyl 7-[2-[6-[2-(oxan-2-yl)pyrazol-3-yl]pyridin-3-yl]oxyethyl]-3,4-dihydro-2H-chromene-2-carboxylate.

(2) The mixture (200 mg) obtained in (1) above was used to perform the reaction according to the method described in Example 12-1-(3) thereby giving ethyl 7-[2-[6-(1H-pyrazol-5-yl)pyridin-3-yl]oxyethyl]-3,4-dihydro-2H-chromene-2-carboxylate (71 mg) as a yellow high-viscosity substance.

(3) The compound (70 mg) obtained in (2) above was used to perform the reaction according to the method described in Example 1-1-(2) thereby giving the title compound (45 mg) as a colorless solid.

$^1$H NMR (400 MHz, DMSO-d$_6$) δ ppm 1.97-2.19 (m, 2H) 2.54-2.82 (m, 2H) 2.98 (t, J=6.7 Hz, 2H) 4.27 (t, J=6.7 Hz, 2H) 4.69-4.79 (m, 1H) 6.72 (d, J=2.0 Hz, 1H) 6.76-6.84 (m, 2H) 6.98 (d, J=7.8 Hz, 1H) 7.46 (dd, J=8.7, 2.9 Hz, 1H) 7.62-7.74 (m, 1H) 7.84 (d, J=8.7 Hz, 1H) 8.27 (d, J=2.9 Hz, 1H) 12.90-13.15 (m, 2H).

MS ESI posi: 366[M+H]$^+$.
MS ESI nega: 364[M−H]$^−$.

Example 71-22

With SFC equipped with a chiral column, separation of optical isomers was found for the compound of Example 71-21.

Example 71-22-1 (Isomer Having Short Retention Time, Retention Time: 3.20 min)

Example 71-22-2 (Isomer Having Long Retention Time, Retention Time: 5.20 min)

Separation of the isomers was performed also by SFC.

The compounds of Examples 71-23 to 71-44 below were synthesized using any of the compounds obtained in Reference Example 94-1 and 94-2, 96-2, 100-1, 102-1, 102-3, 109-1, 112-2, 116-1, 120-1 to 120-6, 121-1 to 121-6, and 122-1, according to the method described in Example 71-21. The structures, NMR data, and MS data of the compounds are shown in Tables 67-7 to 67-9.

TABLE 67-7

| Example No. | Structure | Analytical Data |
|---|---|---|
| 71-23 | 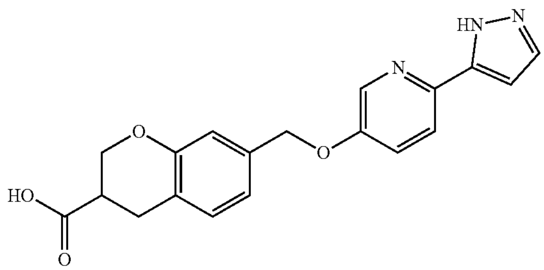 [SMILES: O=C(O)C1COc2cc(COc3ccc(-c4ccn[nH]4)nc3)ccc2C1] | $^1$H NMR (400 MHz, DMSO-d$_6$) δ ppm 2.87-3.01 (m, 3 H) 4.06-4.16 (m, 1 H) 4.31 (d, J = 11.1 Hz, 1 H) 5.12 (s, 2 H) 6.72 (d, J = 2.0 Hz, 1 H) 6.83-6.88 (m, 1 H) 6.94 (d, J = 7.6 Hz, 1 H) 7.13 (d, J = 7.6 Hz, 1 H) 7.49 (dd, J = 8.7, 2.7 Hz, 1 H) 7.61-7.75 (m, 1 H) 7.84 (d, J = 8.7 Hz, 1 H) 8.32 (d, J = 2.7 Hz, 1 H). MS ESI posi: 352[M + H]$^+$. MS ESI nega: 350[M − H]$^−$. |
| 71-24 | 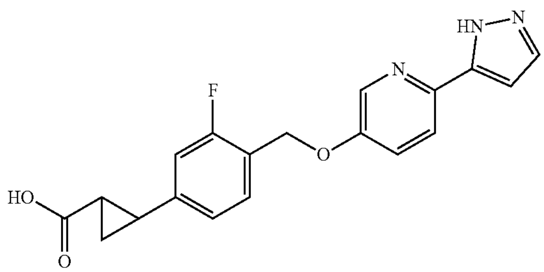 [SMILES: O=C(O)C1CC1c1ccc(COc2ccc(-c3ccn[nH]3)nc2)c(F)c1] | $^1$H NMR (400 MHz, DMSO-d$_6$) δ ppm 1.32-1.48 (m, 2 H) 1.81-1.93 (m, 1 H) 5.20 (s, 2 H) 6.73 (s, 1 H) 7.01-7.17 (m, 2 H) 7.47 (t, J = 7.8 Hz, 1 H) 7.51-7.58 (m, 1 H) 7.68 (s, 1 H) 7.86 (d, J = 8.4 Hz, 1 H) 8.34 (s, 1 H). MS ESI posi: 354[M + H]$^+$. MS ESI nega: 352[M − H]$^−$. |
| 71-25 | 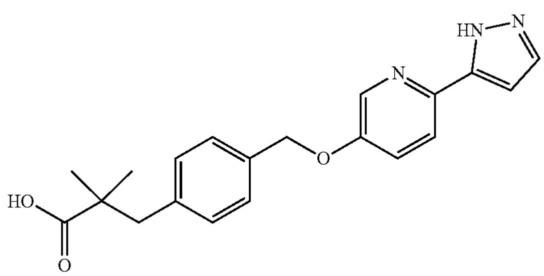 [SMILES: CC(C)(Cc1ccc(COc2ccc(-c3ccn[nH]3)nc2)cc1)C(=O)O] | $^1$H NMR (400 MHz, DMSO-d$_6$) δ ppm 1.07 (s, 6 H) 2.80 (s, 2 H) 5.16 (s, 2 H) 6.73 (s, 1 H) 7.18 (d, J = 7.7 Hz, 2 H) 7.38 (d, J = 7.7 Hz, 2 H) 7.48-7.55 (m, 1 H) 7.63-7.71 (m, 1 H) 7.81-7.89 (m, 1 H) 8.32-8.36 (m, 1 H). MS ESI posi: 352[M + H]$^+$. MS ESI nega: 350[M − H]$^−$. |
| 71-26 | 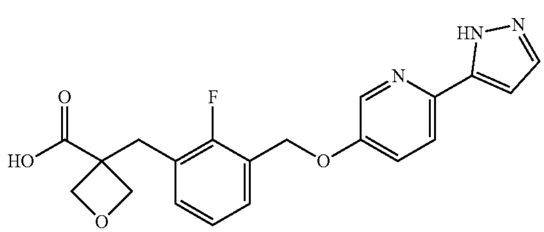 [SMILES: O=C(O)C1(Cc2cccc(COc3ccc(-c4ccn[nH]4)nc3)c2F)COC1] | $^1$H NMR (400 MHz, DMSO-d$_6$) δ ppm 4.51 (d, J = 6.0 Hz, 2 H) 4.73 (d, J = 6.0 Hz, 2 H) 5.23 (s, 2 H) 6.74 (s, 1 H) 7.13-7.26 (m, 2 H) 7.42-7.50 (m, 1 H) 7.52-7.60 (m, 1 H) 7.64-7.74 (m, 1 H) 7.87 (d, J = 8.1 Hz, 1 H) 8.36 (s, 1 H) 12.89-13.12 (m, 2 H). MS ESI posi: 384[M + H]$^+$. MS ESI nega: 382[M − H]$^−$. |
| 71-27 | 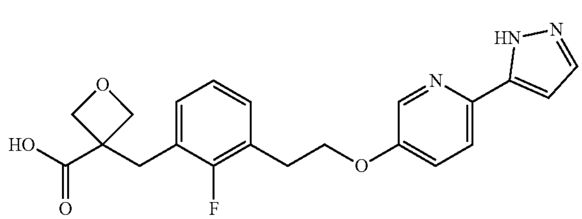 [SMILES: O=C(O)C1(Cc2cccc(CCOc3ccc(-c4ccn[nH]4)nc3)c2F)COC1] | $^1$H NMR (400 MHz, DMSO-d$_6$) δ ppm 3.09 (t, J = 6.5 Hz, 2 H) 3.28 (s, 2 H) 4.29 (t, J = 6.5 Hz, 2 H) 4.50 (d, J = 6.0 Hz, 2 H) 4.72 (d, J = 6.0 Hz, 2 H) 6.72 (s, 1 H) 7.09 (d, J = 5.4 Hz, 2 H) 7.27-7.35 (m, 1 H) 7.45 (d, J = 8.3 Hz, 1 H) 7.63-7.72 (m, 1 H) 7.84 (d, J = 8.3 Hz, 1 H) 8.27 (s, 1 H) 12.88-13.08 (m, 2 H). MS ESI posi: 398[M + H]$^+$. MS ESI nega: 396[M − H]$^−$. |

TABLE 67-8

| Example No. | Structure | Analytical Data |
|---|---|---|
| 71-28 | 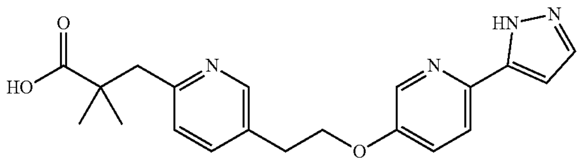 [SMILES: CC(C)(Cc1ccc(CCOc2ccc(-c3ccn[nH]3)nc2)cn1)C(=O)O] | $^1$H NMR (400 MHz, DMSO-d$_6$) δ ppm 1.09 (s, 6 H) 2.93 (s, 2 H) 3.01-3.11 (m, 2 H) 4.24-4.36 (m, 2 H) 6.67-6.77 (m, 1 H) 7.11-7.19 (m, 1 H) 7.41-7.49 (m, 1 H) 7.62-7.73 (m, 2 H) 7.79-7.88 (m, 1 H) 8.23-8.31 (m, 1 H) 8.40-8.47 (m, 1 H). MS ESI posi: 367[M + H]$^+$. |
| 71-29 | 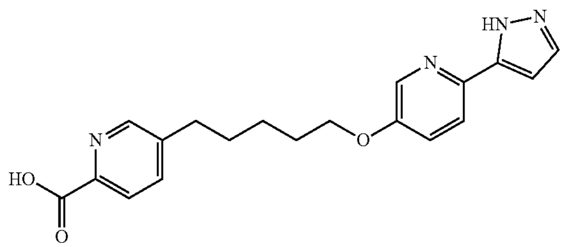 [SMILES: O=C(O)c1ccc(CCCCCOc2ccc(-c3ccn[nH]3)nc2)cn1] | $^1$H NMR (400 MHz, DMSO-d$_6$) δ ppm 1.41-1.54 (m, 2 H) 1.64-1.87 (m, 4 H) 2.73 (t, J = 7.7 Hz, 2 H) 4.08 (t, J = 6.4 Hz, 2 H) 6.74 (s, 1 H) 7.42-7.50 (m, 1 H) 7.64-7.75 (m, 1 H) 7.76-7.92 (m, 2 H) 7.98 (d, J = 7.7 Hz, 1 H) 8.23-8.30 (m, 1 H) 8.58 (s, 1 H). MS ESI posi: 353[M + H]$^+$. MS ESI nega: 351[M − H]$^-$. |
| 71-30 | 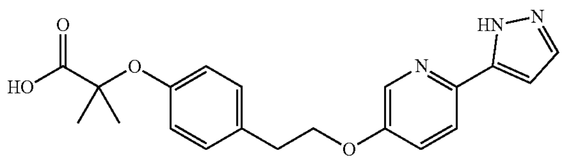 [SMILES: CC(C)(Oc1ccc(CCOc2ccc(-c3ccn[nH]3)nc2)cc1)C(=O)O] | $^1$H NMR (400 MHz, DMSO-d$_6$) δ ppm 1.48 (s, 6 H) 2.99 (t, J = 6.9 Hz, 2 H) 4.26 (t, J = 6.9 Hz, 2 H) 6.72 (d, J = 2.1 Hz, 1 H) 6.78 (d, J = 8.4 Hz, 2 H) 7.23 (d, J = 8.4 Hz, 2 H) 7.46 (dd, J = 8.7, 2.7 Hz, 1 H) 7.65-7.69 (m, 1 H) 7.83 (d, J = 8.7 Hz, 1 H) 8.27 (d, J = 2.7 Hz, 1 H). MS ESI posi: 368[M + H]$^+$. MS ESI nega: 366[M − H]$^-$. |
| 71-31 | 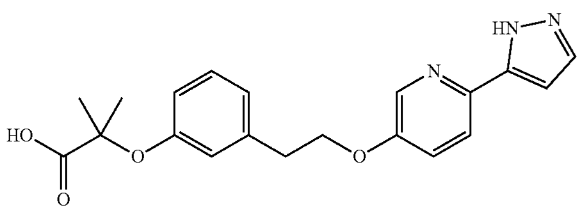 [SMILES: CC(C)(Oc1cccc(CCOc2ccc(-c3ccn[nH]3)nc2)c1)C(=O)O] | $^1$H NMR (400 MHz, DMSO-d$_6$) δ ppm 1.50 (s, 6 H) 3.01 (t, J = 6.7 Hz, 2 H) 4.27 (t, J = 6.7 Hz, 2 H) 6.67 (dd, J = 8.1, 2.1 Hz, 1 H) 6.72 (d, J = 2.1 Hz, 1 H) 6.83 (s, 1 H) 6.93 (d, J = 7.7 Hz, 1 H), 7.14-7.24 (m, 1 H) 7.45 (dd, J = 8.7, 2.7 Hz, 1 H) 7.61-7.69 (m, 1 H) 7.83 (d, J = 8.7 Hz, 1 H) 8.27 (d, J = 2.7 Hz, 1 H). MS ESI posi: 368[M + H]$^+$. MS ESI nega: 366[M − H]$^-$. |
| 71-32 | 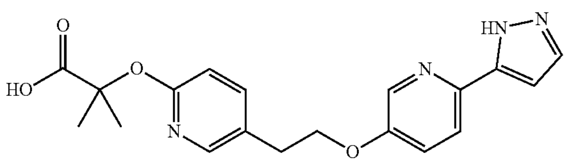 [SMILES: CC(C)(Oc1ccc(CCOc2ccc(-c3ccn[nH]3)nc2)cn1)C(=O)O] | $^1$H NMR (400 MHz, DMSO-d$_6$) δ ppm 1.56 (s, 6 H) 2.93-3.05 (m, 2 H) 4.19-4.33 (m, 2 H) 6.66-6.80 (m, 2 H) 7.38-7.51 (m, 1 H) 7.59-7.74 (m, 2 H) 7.79-7.89 (m, 1 H) 7.98-8.05 (m, 1 H) 8.23-8.31 (m, 1 H). MS ESI posi: 369[M + H]$^+$. MS ESI nega: 367[M − H]$^-$. |
| 71-33 | 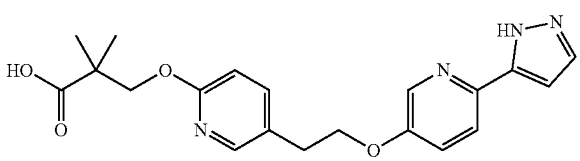 [SMILES: CC(C)(COc1ccc(CCOc2ccc(-c3ccn[nH]3)nc2)cn1)C(=O)O] | $^1$H NMR (400 MHz, DMSO-d$_6$) δ ppm 1.19 (s, 6 H) 3.01 (t, J = 6.4 Hz, 2 H) 4.21 (s, 2 H) 4.27 (t, J = 6.4 Hz, 2 H) 6.69-6.81 (m, 2 H) 7.40-7.50 (m, 1 H) 7.61-7.74 (m, 2 H) 7.84 (d, J = 8.8 Hz, 1 H) 8.10 (s, 1 H) 8.27 (d, J = 2.6 Hz, 1 H). MS ESI posi: 383[M + H]$^+$. MS ESI nega: 381[M − H]$^-$. |
| 71-34 | 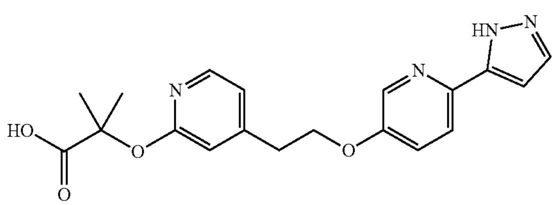 [SMILES: CC(C)(Oc1cc(CCOc2ccc(-c3ccn[nH]3)nc2)ccn1)C(=O)O] | $^1$H NMR (400 MHz, DMSO-d$_6$) δ ppm 1.57 (s, 6 H) 3.00-3.10 (m, 2 H) 4.30-4.41 (m, 2 H) 6.69-6.81 (m, 2 H) 6.89-6.97 (m, 1 H) 7.43-7.51 (m, 1 H) 7.62-7.74 (m, 1 H) 7.81-7.88 (m, 1 H) 7.93-8.00 (m, 1 H) 8.25-8.31 (m, 1 H). MS ESI posi: 369[M + H]$^+$. MS ESI nega: 367[M − H]$^-$. |
| 71-35 | 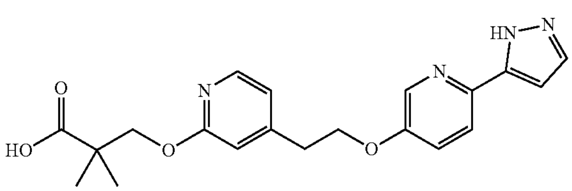 [SMILES: CC(C)(COc1cc(CCOc2ccc(-c3ccn[nH]3)nc2)ccn1)C(=O)O] | $^1$H NMR (400 MHz, DMSO-d$_6$) δ ppm 1.19 (s, 6 H) 3.05 (t, J = 6.6 Hz, 2 H) 4.21 (s, 2 H) 4.35 (t, J = 6.6 Hz, 2 H) 6.69-6.84 (m, 2 H) 6.91-7.03 (m, 1 H) 7.43-7.52 (m, 1 H) 7.68 (br s, 1 H) 7.80-7.89 (m, 1 H) 8.06 (d, J = 5.3 Hz, 1 H) 8.23-8.31 (m, 1 H). MS ESI posi: 383[M + H]$^+$. MS ESI nega: 381[M − H]$^-$. |

TABLE 67-8-continued

| Example No. | Structure | Analytical Data |
|---|---|---|
| 71-36 | 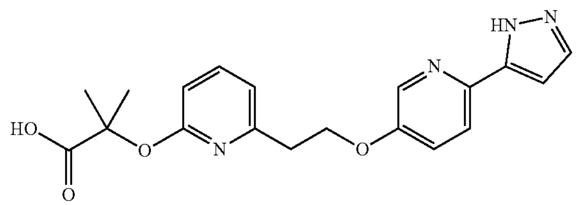 [SMILES: CC(C)(Oc1cccc(CCOc2ccc(-c3ccn[nH]3)nc2)n1)C(=O)O] | $^1$H NMR (400 MHz, DMSO-$d_6$) δ ppm 1.55 (s, 6 H) 2.99-3.24 (m, 2 H) 4.33-4.52 (m, 2 H) 6.60-6.69 (m, 1 H) 6.69-6.79 (m, 1 H) 6.81-6.98 (m, 1 H) 7.43-7.55 (m, 1 H) 7.58-7.76 (m, 2 H) 7.76-7.96 (m, 1 H) 8.25-8.35 (m, 1 H). MS ESI posi: 369[M + H]$^+$. MS ESI nega: 367[M − H]$^-$. |
| 71-37 | 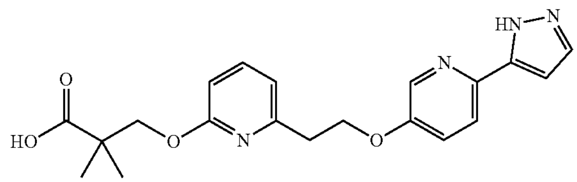 [SMILES: CC(C)(COc1cccc(CCOc2ccc(-c3ccn[nH]3)nc2)n1)C(=O)O] | $^1$H NMR (400 MHz, DMSO-$d_6$) δ ppm 1.18 (s, 6 H) 3.08-3.18 (m, 2 H) 4.22 (s, 2 H) 4.40-4.51 (m, 2 H) 6.61-6.67 (m, 1 H) 6.70-6.75 (m, 1 H) 6.92-6.99 (m, 1 H) 7.42-7.51 (m, 1 H) 7.59-7.71 (m, 2 H) 7.80-7.87 (m, 1 H) 8.23-8.32 (m, 1 H). MS ESI posi: 383[M + H]$^+$. MS ESI nega: 381[M − H]$^-$. |
| 71-38 | 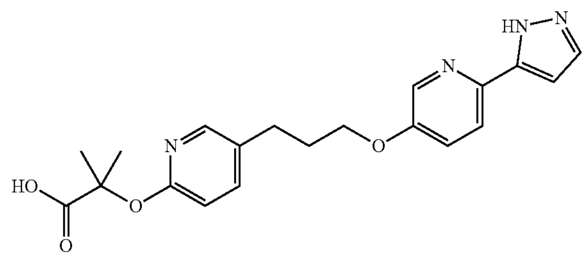 [SMILES: CC(C)(Oc1ccc(CCCOc2ccc(-c3ccn[nH]3)nc2)cn1)C(=O)O] | $^1$H NMR (400 MHz, DMSO-$d_6$) δ ppm 1.56 (s, 6 H) 1.94-2.12 (m, 2 H) 2.61-2.73 (m, 2 H) 4.02-4.13 (m, 2 H) 6.67-6.78 (m, 2 H) 7.39-7.48 (m, 1 H) 7.56-7.62 (m, 1 H) 7.63-7.74 (m, 1 H) 7.80-7.88 (m, 1 H) 7.89-7.95 (m, 1 H) 8.24-8.32 (m, 1 H). MS ESI posi: 383[M + H]$^+$. MS ESI nega: 381[M − H]$^-$. |

TABLE 67-9

| Example No. | Structure | Analytical Data |
|---|---|---|
| 71-39 | 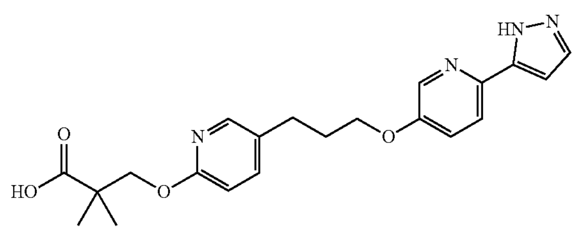 [SMILES: CC(C)(COc1ccc(CCCOc2ccc(-c3ccn[nH]3)nc2)cn1)C(=O)O] | $^1$H NMR (400 MHz, DMSO-$d_6$) δ ppm 1.19 (s, 6 H) 1.93-2.12 (m, 2 H) 2.62-2.80 (m, 2 H) 4.00-4.12 (m, 2 H) 4.19 (s, 2 H) 6.67-6.79 (m, 2 H) 7.39-7.48 (m, 1 H) 7.55-7.73 (m, 2 H) 7.80-7.89 (m, 1 H) 7.96-8.04 (m, 1 H) 8.24-8.33 (m, 1 H). MS ESI posi: 397[M + H]$^+$. MS ESI nega: 395[M − H]$^-$. |
| 71-40 | 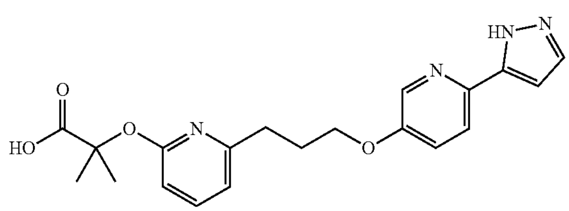 [SMILES: CC(C)(Oc1cccc(CCCOc2ccc(-c3ccn[nH]3)nc2)n1)C(=O)O] | $^1$H NMR (400 MHz, DMSO-$d_6$) δ ppm 1.58 (s, 6 H) 2.04-2.22 (m, 2 H) 2.70-2.85 (m, 2 H) 3.98-4.15 (m, 2 H) 6.54-6.65 (m, 1 H) 6.68-6.76 (m, 1 H) 6.77-6.87 (m, 1 H) 7.37-7.48 (m, 1 H) 7.51-7.62 (m, 1 H) 7.63-7.73 (m, 1 H) 7.76-7.92 (m, 1 H) 8.18-8.37 (m, 1 H). MS ESI posi: 383[M + H]$^+$. MS ESI nega: 381[M − H]$^-$. |
| 71-41 | 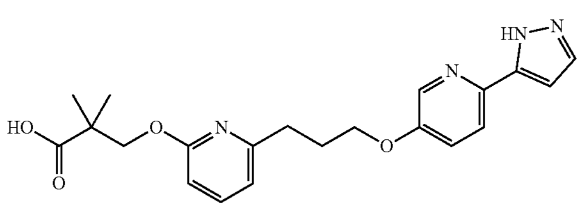 [SMILES: CC(C)(COc1cccc(CCCOc2ccc(-c3ccn[nH]3)nc2)n1)C(=O)O] | $^1$H NMR (400 MHz, DMSO-$d_6$) δ ppm 1.17 (s, 6 H) 2.07-2.23 (m, 2 H) 2.75-2.90 (m, 2 H) 4.07-4.19 (m, 2 H) 4.20 (s, 2 H) 6.54-6.65 (m, 1 H) 6.68-6.78 (m, 1 H) 6.81-6.92 (m, 2 H) 7.38-7.50 (m, 1 H) 7.53-7.75 (m, 2 H) 7.79-7.91 (m, 1 H) 8.24-8.33 (m, 1 H). MS ESI posi: 397[M + H]$^+$. |

TABLE 67-9-continued

| Example No. | Structure | Analytical Data |
|---|---|---|
| 71-42 | 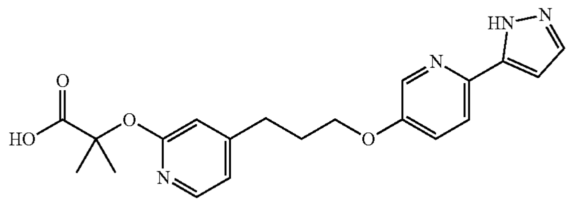 [SMILES: CC(C)(Oc1cc(CCCOc2ccc(-c3ccn[nH]3)nc2)ccn1)C(=O)O] | $^1$H NMR (400 MHz, DMSO-$d_6$) δ ppm 1.56 (s, 6 H) 1.96-2.14 (m, 2 H) 2.63-2.82 (m, 2 H) 3.98-4.19 (m, 2 H) 6.58-6.92 (m, 3 H) 7.35-7.52 (m, 1 H) 7.60-7.76 (m, 1 H) 7.78-8.01 (m, 2 H) 8.21-8.36 (m, 1 H). MS ESI posi: 383[M + H]$^+$. MS ESI nega: 381[M − H]$^−$. |
| 71-43 | 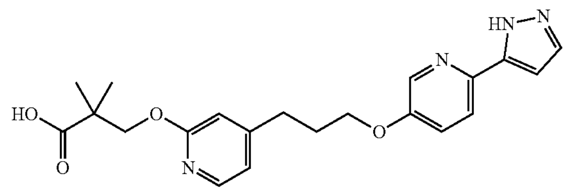 [SMILES: CC(C)(COc1cc(CCCOc2ccc(-c3ccn[nH]3)nc2)ccn1)C(=O)O] | $^1$H NMR (400 MHz, DMSO-$d_6$) δ ppm 1.19 (s, 6 H) 1.96-2.14 (m, 2 H) 2.65-2.81 (m, 2 H) 4.01-4.13 (m, 2 H) 4.21 (s, 2 H) 6.62-6.78 (m, 2 H) 6.84-6.92 (m, 1 H) 7.38-7.49 (m, 1 H) 7.62-7.72 (m, 1 H) 7.79-7.89 (m, 1 H) 7.99-8.08 (m, 1 H) 8.23-8.32 (m, 1 H). MS ESI posi: 419[M + Na]$^+$. MS ESI nega: 395[M − H]$^−$. |
| 71-44 | 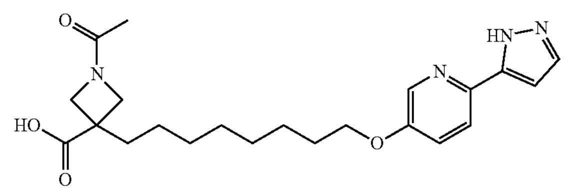 [SMILES: CC(=O)N1CC(CCCCCCCCOc2ccc(-c3ccn[nH]3)nc2)(C(=O)O)C1] | $^1$H NMR (400 MHz, DMSO-$d_6$) δ ppm 1.08-1.52 (m, 14 H) 2.50 (s, 3 H) 3.57 (d, J = 8.6 Hz, 1 H) 3.78-3.97 (m, 2 H) 4.06 (t, J = 6.4 Hz, 2 H) 4.23 (d, J = 7.8 Hz, 1 H) 6.72 (d, J = 2.0 Hz, 1 H) 7.37-7.50 (m, 1 H) 7.57-7.75 (m, 1 H) 7.84 (d, J = 8.4 Hz, 1 H) 8.26 (d, J = 2.8 Hz, 1 H). MS ESI posi: 415[M + H]$^+$. MS ESI nega: 413[M − H]$^−$. |

Example 71-45

2-[2-Fluoro-3-[[6-(1H-pyrazol-5-yl)pyridin-3-yl]oxymethyl]phenyl]cyclopropane-1-carboxylic Acid (Optically Active Substance)

[Formula 601]

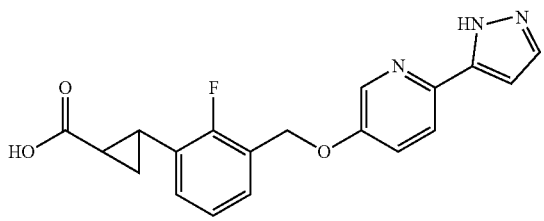

(1) The compound (43 mg) obtained in Reference Example 109-2-1 was used to perform the reaction according to the method described in Example 1-1-(1) thereby giving ethyl 2-[2-fluoro-3-[[6-[2-(oxan-2-yl)pyrazol-3-yl]pyridin-3-yl]oxymethyl]phenyl]cyclopropane-1-carboxylate (76 mg) as a colorless oil.

(2) To a solution of the compound (76 mg) obtained in (1) above in tetrahydrofuran (3.27 mL), 2 mol/L hydrochloric acid (245 μL) was added under ice cooling, and the mixture was stirred at room temperature for 3.5 hours. An aqueous solution of 1 mol/L lithium hydroxide (980 μL) was added to the mixture, and the resultant mixture was stirred at room temperature for 12 hours. An aqueous solution of 10% potassium hydrogen sulfate was added to the mixture, and the resultant mixture was extracted with ethyl acetate. The organic layer was passed through a phase separator, and concentrated under reduced pressure. The obtained residue was purified by preparative HPLC to give the title compound (19 mg) as a pale yellow solid.

$^1$H NMR (400 MHz, DMSO-$d_6$) δ ppm 1.38-1.49 (m, 2H) 1.81-1.90 (m, 1H) 5.25 (s, 2H) 6.74 (s, 1H) 7.10-7.20 (m, 2H) 7.39-7.47 (m, 1H) 7.56 (dd, J=8.6, 2.2 Hz, 1H) 7.68 (s, 1H) 7.87 (d, J=8.6 Hz, 1H) 8.37 (d, J=2.2 Hz, 1H).

MS ESI posi: 354[M+H]$^+$.

MS ESI nega: 352[M−H]$^−$.

Retention time: 4.17 min (SFC)

The compound of Example 71-46 below was synthesized using the compound obtained in Reference Example 109-2-2, according to the method described in Example 71-45. The structure, NMR data, and MS data of the compound are shown in Table 67-10.

The compound of Example 71-46 is an optically active compound. The compound of Example 71-46 was synthesized from the compound of Reference Example 109-2-2, an optically active starting material, and isomerization was not found during the synthesis.

TABLE 67-10

| Example No. | Structure | Analytical Data |
|---|---|---|
| 71-46 | 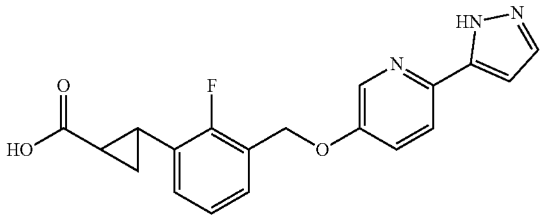 [SMILES: O=C(O)C1CC1c1cccc(COc2ccc(-c3ccn[nH]3)nc2)c1F] | ¹H NMR (400 MHz, DMSO-d₆) δ ppm 1.38-1.49 (m, 2 H) 1.81-1.90 (m, 1 H) 5.25 (s, 2 H) 6.74 (s, 1 H) 7.10-7.20 (m, 2 H) 7.39-7.47 (m, 1 H) 7.56 (dd, J = 8.6, 2.2 Hz, 1 H) 7.68 (s, 1 H) 7.87 (d, J = 8.6 Hz, 1 H) 8.37 (d, J = 2.2 Hz, 1 H). MS ESI posi: 354[M + H]⁺. MS ESI nega: 352[M − H]⁻. Retention time: 2.96 min (S F C) |

The compounds of Examples 72-1 to 72-9 below were synthesized using any of the compounds obtained in Reference Examples 96-1, 97-1, 99-1 to 99-3, 102-2, 102-4, 104-4, and 104-6, according to the method described in Example 3-1. The structures, NMR data, and MS data of the compounds are shown in Tables 67-11 and 67-12.

TABLE 67-11

| Example No. | Structure | Analytical Data |
|---|---|---|
| 72-1 | 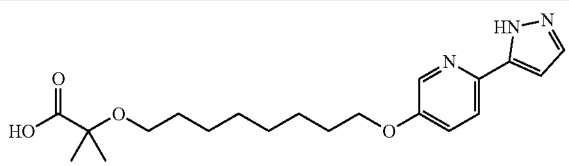 [SMILES: CC(C)(OCCCCCCCCOc1ccc(-c2ccn[nH]2)nc1)C(=O)O] | ¹H NMR (400 MHz, DMSO-d₆) δ ppm 1.18-1.35 (m, 12 H) 1.38-1.51 (m, 4 H) 1.67-1.79 (m, 2 H) 3.30 (t, J = 6.4 Hz, 2 H) 4.06 (t, J = 6.4 Hz, 2 H) 6.72 (d, J = 1.6 Hz, 1 H) 7.43 (dd, J = 8.7, 2.6 Hz, 1 H) 7.67 (s, 1 H) 7.84 (d, J = 8.7 Hz, 1 H) 8.27 (d, J = 2.6 Hz, 1 H). MS ESI posi: 376[M + H]⁺. MS ESI nega: 374[M − H]⁻. |
| 72-2 | 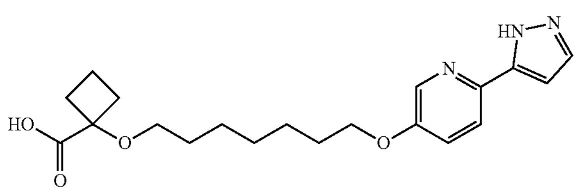 [SMILES: O=C(O)C1(OCCCCCCCOc2ccc(-c3ccn[nH]3)nc2)CCC1] | ¹H NMR (400 MHz, DMSO-d₆) δ ppm 1.20-1.56 (m, 8 H) 1.64-1.85 (m, 4 H) 1.97-2.14 (m, 2 H) 2.24-2.39 (m, 2 H) 3.23 (t, J = 6.3 Hz, 2 H) 4.06 (t, J = 6.4 Hz, 2 H) 6.73 (d, J = 1.7 Hz, 1 H) 7.43 (dd, J = 8.7, 2.5 Hz, 1 H) 7.67 (s, 1 H) 7.84 (d, J = 8.7 Hz, 1 H) 8.27 (d, J = 2.5 Hz, 1 H). MS ESI posi: 374[M + H]⁺. MS ESI nega: 372[M − H]⁻. |
| 72-3 | 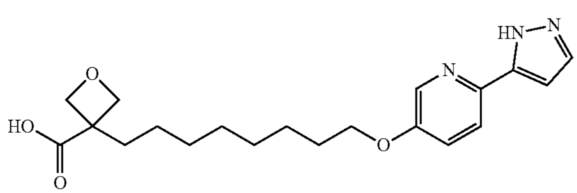 [SMILES: O=C(O)C1(CCCCCCCCOc2ccc(-c3ccn[nH]3)nc2)COC1] | ¹H NMR (400 MHz, DMSO-d₆) δ ppm 1.13-1.48 (m, 10 H) 1.73-1.79 (m, 2 H) 1.82-1.96 (m, 2 H) 4.06 (t, J = 6.5 Hz, 2 H) 4.33 (d, J = 5.9 Hz, 2 H) 4.68 (d, J = 5.9 Hz, 2 H) 6.72 (d, J = 2.0 Hz, 1 H) 7.43 (dd, J = 8.7, 2.8 Hz, 1 H) 7.67 (s, 1 H) 7.84 (d, J = 8.7 Hz, 1 H) 8.27 (d, J = 2.8 Hz, 1 H). MS ESI posi: 374[M + H]⁺. MS ESI nega: 372[M − H]⁻. |
| 72-4 | 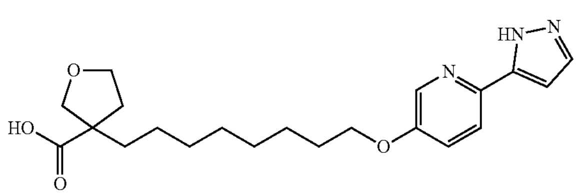 [SMILES: O=C(O)C1(CCCCCCCCOc2ccc(-c3ccn[nH]3)nc2)CCOC1] | ¹H NMR (400 MHz, DMSO-d₆) δ ppm 1.03-1.79 (m, 15 H) 2.21-2.37 (m, 1 H) 3.41 (d, J = 8.6 Hz, 1 H) 3.58-3.77 (m, 2 H) 3.95 (d, J = 8.6 Hz, 1 H) 4.06 (t, J = 6.4 Hz, 2 H) 6.72 (d, J = 2.0 Hz, 1 H) 7.43 (dd, J = 8.7, 2.6 Hz, 1 H) 7.67 (s, 1 H) 7.84 (d, J = 8.7 Hz, 1 H) 8.27 (d, J = 2.6 Hz, 1 H). MS ESI posi: 388[M + H]⁺. MS ESI nega: 386[M − H]⁻. |
| 72-5 | 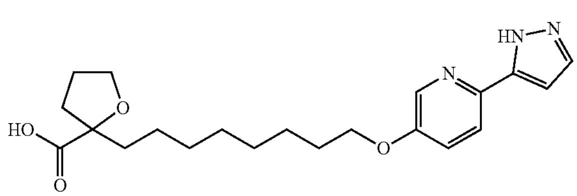 [SMILES: O=C(O)C1(CCCCCCCCOc2ccc(-c3ccn[nH]3)nc2)CCCO1] | ¹H NMR (400 MHz, CHLOROFORM-d) δ ppm 1.17-2.04 (m, 17 H), 2.30-2.40 (m, 1 H) 3.87-4.12 (m, 4 H) 6.69 (d, J = 1.6 Hz, 1 H) 7.19-7.26 (m, 1 H) 7.57-7.69 (m, 2 H) 8.27 (d, J = 2.6 Hz, 1 H). MS ESI posi: 388[M + H]⁺. MS ESI nega: 386[M − H]⁻. |

TABLE 67-12

| Example No. | Structure | Analytical Data |
|---|---|---|
| 72-6 | 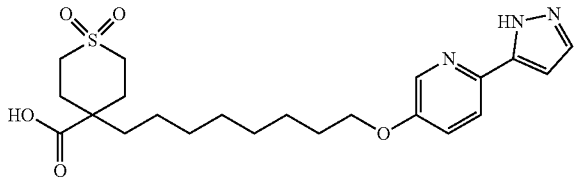 [SMILES: O=C(O)C1(CCCCCCCCOc2ccc(-c3ccn[nH]3)nc2)CCS(=O)(=O)CC1] | ¹H NMR (400 MHz, DMSO-d₆) δ ppm 1.12-1.54 (m, 14 H) 1.68-1.84 (m, 4 H) 2.93-3.08 (m, 4 H) 4.06 (t, J = 6.1 Hz, 2 H) 6.72 (d, J = 2.0 Hz, 1 H) 7.38-7.47 (m, 1 H) 7.53-7.92 (m, 2 H) 8.22-8.31 (m, 1 H). MS ESI posi: 450[M + H]⁺. MS ESI nega: 448[M − H]⁻. |
| 72-7 | 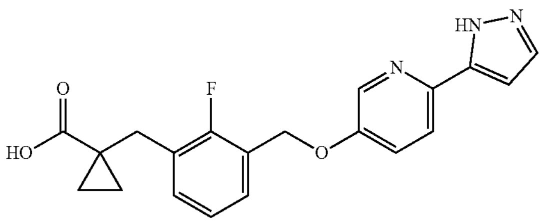 [SMILES: O=C(O)C1(Cc2cccc(COc3ccc(-c4ccn[nH]4)nc3)c2F)CC1] | ¹H NMR (400 MHz, DMSO-d₆) δ ppm 0.80 (s, 2 H) 1.16 (s, 2 H) 2.96 (s, 2 H) 5.23 (s, 2 H) 6.74 (s, 1 H) 7.17 (t, J = 7.8 Hz, 1 H) 7.37-7.46 (m, 2 H) 7.56 (d, J = 8.6 Hz, 1 H) 7.64-7.73 (m, 1 H) 7.87 (d, J = 7.8 Hz, 1 H) 8.36 (s, 1 H). MS ESI posi: 368[M + H]⁺. MS ESI nega: 366[M − H]⁻. |
| 72-8 | 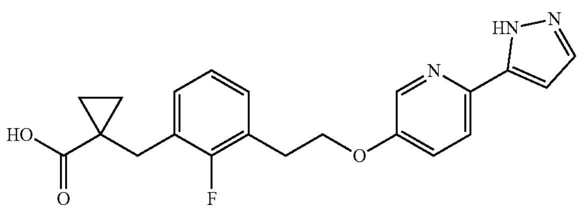 [SMILES: O=C(O)C1(Cc2cccc(CCOc3ccc(-c4ccn[nH]4)nc3)c2F)CC1] | ¹H NMR (400 MHz, DMSO-d₆) δ ppm 0.76 (s, 2 H) 1.13 (s, 2 H) 2.95 (s, 2 H) 3.04-3.13 (m, 2 H) 4.30 (t, J = 6.5 Hz, 2 H) 6.72 (s, 1 H) 7.08 (t, J = 7.5 Hz, 1 H) 7.21-7.31 (m, 2 H) 7.45 (d, J = 8.8 Hz, 1 H) 7.62-7.73 (m, 1 H) 7.84 (d, J = 8.8 Hz, 1 H) 8.27 (s, 1 H). MS ESI posi: 382[M + H]⁺. MS ESI nega: 380[M − H]⁻. |
| 72-9 | 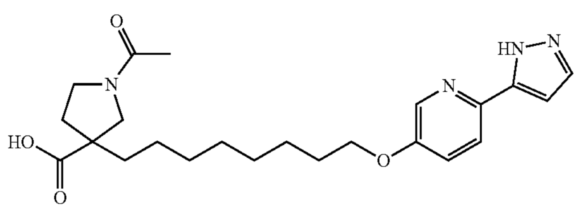 [SMILES: CC(=O)N1CCC(CCCCCCCCOc2ccc(-c3ccn[nH]3)nc2)(C(=O)O)C1] | ¹H NMR (400 MHz, CHLOROFORM-d) δ ppm 1.20-1.53 (m, 11 H) 1.64-2.20 (m, 7 H) 2.39-2.59 (m, 1 H) 3.21-3.38 (m, 1 H) 3.45-3.65 (m, 2 H) 3.98-4.18 (m, 3 H) 6.71-6.76 (m, 1 H) 7.29 (dd, J = 8.9, 2.4 Hz, 1 H) 7.63 (s, 1 H) 7.65-7.73 (m, 1 H) 8.26 (s, 1 H). MS ESI posi: 429[M + H]⁺. MS ESI nega: 427[M − H]⁻. |

Example 73-1

1,1-Dioxo-3-[8-[6-(1H-pyrazol-5-yl)pyridin-3-yl]oxyoctyl]thietane-3-carboxylic Acid

[Formula 602]

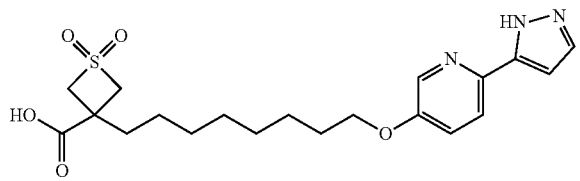

(1) The compound (15 mg) obtained in Reference Example 98-1 was used to perform the reaction according to the method described in Example 1-1-(1) thereby giving 3-[8-[6-[2-(oxan-2-yl)pyrazol-3-yl]pyridin-3-yl]oxyoctyl]-1,1-dioxothietane-3-carbonitrile (31 mg) as a brown oil.

(2) The compound (31 mg) obtained in (1) above was used to perform the reaction according to the method described in Example 1-1-(3) thereby giving a mixture (28 mg) containing 1,1-dioxo-3-[8-[6-(1H-pyrazol-5-yl)pyridin-3-yl]oxyoctyl]thietane-3-carbonitrile.

(3) The mixture (28 mg) obtained in (2) above was suspended in 6 mol/L hydrochloric acid (1.2 mL), the container was sealed, and the mixture was then stirred at 100° C. for 16 hours. To the mixture, 6 mol/L hydrochloric acid (0.6 mL) was added, and the resultant mixture was heated to reflux for 6 hours. The mixture was cooled to room temperature, and purified by preparative HPLC. The fractions containing the target substance were collected and concentrated under reduced pressure, and the residue was solidified by diethyl ether to give the title compound (15 mg) as a colorless solid.

¹H NMR (400 MHz, DMSO-d₆) δ ppm 1.03-1.53 (m, 10H) 1.63-1.80 (m, 2H) 1.83-1.99 (m, 2H) 3.96-4.20 (m, 4H) 4.34-4.48 (m, 2H) 6.66-6.78 (m, 1H) 7.35-7.49 (m, 1H) 7.59-7.74 (m, 1H) 7.77-7.91 (m, 1H) 8.22-8.31 (m, 1H).

MS ESI posi: 422[M+H]⁺.

MS ESI nega: 420[M−H]⁻.

The compound of Example 74-1 below was synthesized using the compound obtained in Reference Example 101-2, according to the method described in Example 8-1. The structure, NMR data, and MS data of the compound are shown in Table 67-13.

TABLE 67-13

| Example No. | Structure | Analytical Data |
|---|---|---|
| 74-1 | 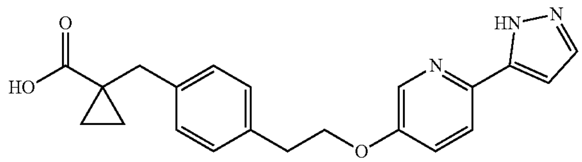 [SMILES: O=C(O)C1(Cc2ccc(CCOc3ccc(-c4ccn[nH]4)nc3)cc2)CC1] | $^1$H NMR (400 MHz, DMSO-d$_6$) δ ppm 0.75-0.82 (m, 2 H) 1.05-1.14 (m, 2 H) 2.85 (s, 2 H) 3.02 (t, J = 6.8 Hz, 2 H) 4.28 (t, J = 6.8 Hz, 2 H) 6.72 (s, 1 H) 7.15-7.27 (m, 4 H) 7.46 (d, J = 8.6 Hz, 1 H) 7.60-7.73 (m, 1 H) 7.83 (d, J = 8.6 Hz, 1 H) 8.27 (s, 1 H). MS ESI posi: 364[M + H]$^+$. MS ESI nega: 362[M − H]$^-$. |

The compounds of Examples 74-2 to 74-11 below were synthesized using a compound obtained in Reference Example 110-2 or 110-3, 110-5, or 111, according to the method described in Example 8-7. The structures, NMR data, and MS data of the compounds are shown in Tables 67-14 and 67-15.

The compounds of Examples 74-7, 74-8, 74-10, and 74-11 are optically active compounds. These compounds were synthesized from the compounds of Reference Examples 111-2-1, 111-2-2, 111-4-1, and 111-4-2, each being an optically active compound, and lowering of optical purity was not found during each synthesis.

TABLE 67-14

| Example No. | Structure | Analytical Data |
|---|---|---|
| 74-2 | 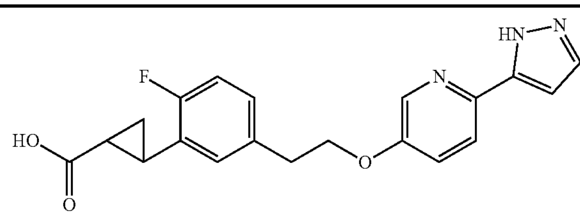 | $^1$H NMR (400 MHz, DMSO-d$_6$) δ ppm 1.37-1.47 (m, 2 H) 1.82-1.92 (m, 1 H) 2.42-2.47 (m, 1 H) 3.02 (t, J = 6.6 Hz, 2 H) 4.24-4.39 (m, 2 H) 6.75-6.92 (m, 1 H) 7.03-7.16 (m, 2 H) 7.17-7.27 (m, 1 H) 7.49-8.05 (m, 3 H) 8.25-8.35 (m, 1 H). MS ESI posi: 368[M + H]$^+$. |
| 74-3 | 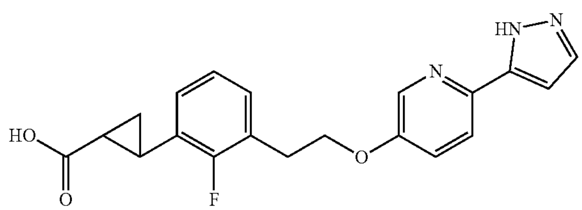 [SMILES: O=C(O)C1CC1c1cccc(CCOc2ccc(-c3ccn[nH]3)nc2)c1F] | $^1$H NMR (400 MHz, DMSO-d$_6$) δ ppm 1.35-1.48 (m, 2 H) 1.78-1.86 (m, 1 H) 3.11 (t, J = 6.3 Hz, 2 H) 4.26-4.36 (m, 2 H) 6.71-6.82 (m, 1 H) 6.99 (t, J = 7.6 Hz, 1 H) 7.04-7.13 (m, 1 H) 7.28 (t, J = 7.1 Hz, 1 H) 7.45-7.61 (m, 1 H) 7.65-7.76 (m, 1 H) 7.83-7.94 (m, 1 H) 8.28 (s, 1 H). MS ESI posi: 368[M + H]$^+$. |
| 74-4 | 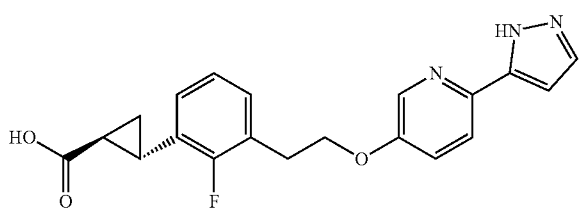 [SMILES: O=C(O)[C@H]1C[C@@H]1c1cccc(CCOc2ccc(-c3ccn[nH]3)nc2)c1F] | $^1$H NMR (400 MHz, DMSO-d$_6$) δ ppm 1.36-1.47 (m, 2 H) 1.78-1.87 (m, 1 H) 3.11 (t, J = 6.6 Hz, 2 H) 4.31 (t, J = 6.6 Hz, 2 H) 6.70-6.76 (m, 1 H) 6.99 (t, J = 7.3 Hz, 1 H) 7.04-7.13 (m, 1 H) 7.24-7.32 (m, 1 H) 7.42-7.51 (m, 1 H) 7.63-7.72 (m, 1 H) 7.84 (d, J = 8.7 Hz, 1 H) 8.24-8.30 (m, 1 H). MS ESI posi: 368[M + H]$^+$. MS ESI nega: 366[M − H]$^-$. Retention time: 11.38 min (H P L C) |
| 74-5 | 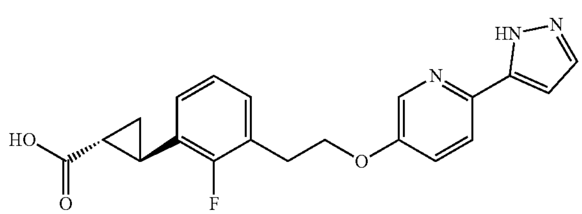 [SMILES: O=C(O)[C@@H]1C[C@H]1c1cccc(CCOc2ccc(-c3ccn[nH]3)nc2)c1F] | $^1$H NMR (400 MHz, DMSO-d$_6$) δ ppm 1.35-1.46 (m, 2 H) 1.78-1.85 (m, 1 H) 3.11 (t, J = 6.6 Hz, 2 H) 4.31 (t, J = 6.6 Hz, 2 H) 6.69-6.75 (m, 1 H) 6.95-7.03 (m, 1 H) 7.04-7.13 (m, 1 H) 7.23-7.32 (m, 1 H) 7.42-7.50 (m, 1 H) 7.62-7.72 (m, 1 H) 7.84 (d, J = 8.7 Hz, 1 H) 8.24-8.30 (m, 1 H). MS ESI posi: 368[M + H]$^+$. MS ESI nega: 366[M − H]$^-$. Retention time 8.31 min (H P L C) |
| 74-6 | 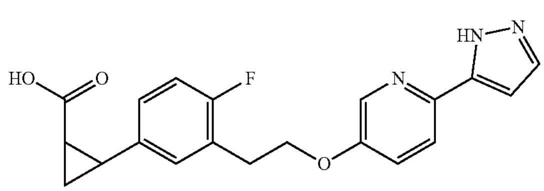 [SMILES: O=C(O)C1CC1c1ccc(F)c(CCOc2ccc(-c3ccn[nH]3)nc2)c1] | $^1$H NMR (400 MHz, DMSO-d$_6$) δ ppm 1.22-1.33 (m, 1 H) 1.43-1.53 (m, 1 H) 1.93-2.06 (m, 1 H) 3.00-3.12 (m, 2 H) 4.22-4.35 (m, 2 H) 6.73 (s, 1 H) 7.01-7.17 (m, 2 H) 7.26-7.34 (m, 1 H) 7.41-7.50 (m, 1 H) 7.61-7.74 (m, 1 H) 7.77-7.90 (m, 1 H) 8.28 (s, 1 H). MS ESI posi: 368[M + H]$^+$. MS ESI nega: 366[M − H]$^-$. |

TABLE 67-14-continued

| Example No. | Structure | Analytical Data |
| --- | --- | --- |
| 74-7 | 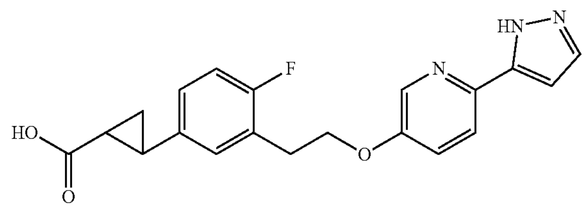 [SMILES: O=C(O)C1CC1c1ccc(F)c(CCOc2ccc(-c3ccn[nH]3)nc2)c1] | $^1$H NMR (400 MHz, DMSO-$d_6$) δ ppm 1.26-1.46 (m, 2 H) 1.73-1.85 (m, 1 H) 2.98-3.13 (m, 2 H) 4.21-4.39 (m, 2 H) 6.73 (s, 1 H) 7.02-7.13 (m, 2 H) 7.17-7.30 (m, 1 H) 7.40-7.50 (m, 1 H) 7.63-7.71 (m, 1 H) 7.79-7.88 (m, 1 H) 8.27 (s, 1 H). MS ESI posi: 368[M + H]$^+$. MS ESI nega: 366[M − H]$^-$. |
| 74-8 | 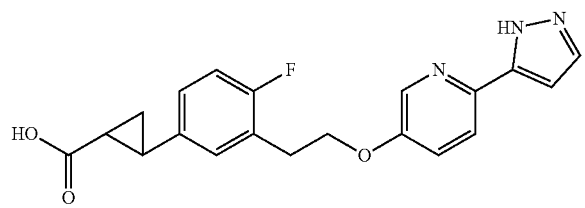 [SMILES: O=C(O)C1CC1c1ccc(F)c(CCOc2ccc(-c3ccn[nH]3)nc2)c1] | $^1$H NMR (400 MHz, DMSO-$d_6$) δ ppm 1.26-1.46 (m, 2 H) 1.73-1.85 (m, 1 H) 2.98-3.13 (m, 2 H) 4.21-4.39 (m, 2 H) 6.73 (s, 1 H) 7.02-7.13 (m, 2 H) 7.17-7.30 (m, 1 H) 7.40-7.50 (m, 1 H) 7.63-7.71 (m, 1 H) 7.79-7.88 (m, 1 H) 8.27 (s, 1 H). MS ESI posi: 368[M + H]$^+$. MS ESI nega: 366[M − H]$^-$. |

TABLE 67-15

| Example No. | Structure | Analytical Data |
| --- | --- | --- |
| 74-9 | 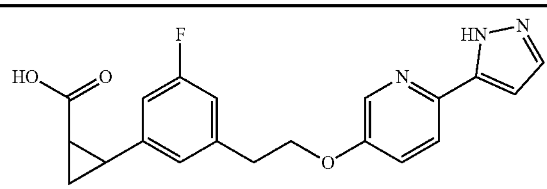 | $^1$H NMR (400 MHz, DMSO-$d_6$) δ ppm 1.25-1.36 (m, 1 H) 1.47-1.57 (m, 1 H) 1.98-2.09 (m, 1 H) 2.98-3.10 (m, 2 H) 4.22-4.37 (m, 2 H) 6.73 (s, 1 H) 6.85-6.93 (m, 1 H) 6.98-7.05 (m, 1 H) 7.09 (s, 1 H) 7.41-7.51 (m, 1 H) 7.61-7.73 (m, 1 H) 7.80-7.89 (m, 1 H) 8.28 (s, 1 H). MS ESI posi: 368[M + H]$^+$. MS ESI nega: 366[M − H]$^-$. |
| 74-10 | 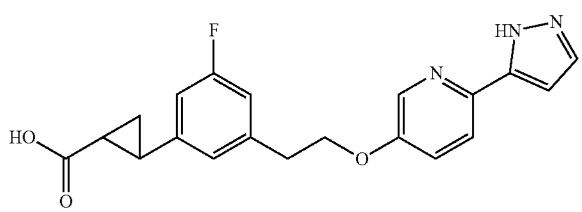 [SMILES: O=C(O)C1CC1c1cc(F)cc(CCOc2ccc(-c3ccn[nH]3)nc2)c1] | $^1$H NMR (400 MHz, DMSO-$d_6$) δ ppm 1.33-1.47 (m, 2 H) 1.83-1.91 (m, 1 H) 3.00-3.09 (m, 2 H) 4.26-4.36 (m, 2 H) 6.73 (s, 1 H) 6.85-6.93 (m, 1 H) 6.98-7.06 (m, 2 H) 7.43-7.50 (m, 1 H) 7.67 (s, 1 H) 7.80-7.88 (m, 1 H) 8.24-8.32 (m, 1 H). MS ESI posi: 368[M + H]$^+$. MS ESI nega: 366[M − H]$^-$. |
| 74-11 | 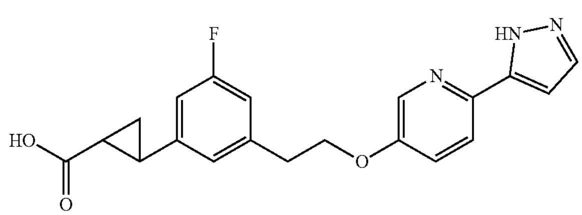 [SMILES: O=C(O)C1CC1c1cc(F)cc(CCOc2ccc(-c3ccn[nH]3)nc2)c1] | $^1$H NMR (400 MHz, DMSO-$d_6$) δ ppm 1.33-1.47 (m, 2 H) 1.83-1.91 (m, 1 H) 3.00-3.09 (m, 2 H) 4.26-4.36 (m, 2 H) 6.73 (s, 1 H) 6.85-6.93 (m, 1 H) 6.98-7.06 (m, 2 H) 7.43-7.50 (m, 1 H) 7.67 (s, 1 H) 7.80-7.88 (m, 1 H) 8.24-8.32 (m, 1 H). MS ESI posi: 368[M + H]$^+$. MS ESI nega: 366[M − H]$^-$. |

Example 74-12

3-[[4-[2-[6-(1H-Pyrazol-5-yl)pyridin-3-yl]oxyethyl]phenyl]methyl]oxetane-3-carboxylic Acid

[Formula 603]

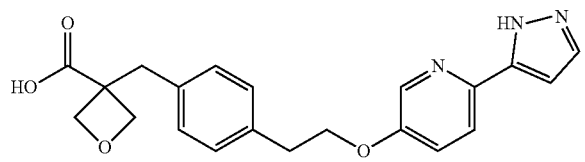

(1) The compound (41.9 mg) obtained in Reference Example 101-1 was used to perform the reaction according to the method described in Example 8-1-(1) thereby giving methyl 3-[[4-[2-[6-[2-(oxan-2-yl)pyrazol-3-yl]pyridin-3-yl]oxyethyl]phenyl]methyl]oxetane-3-carboxylate (49.8 mg) as a colorless oil.

(2) Piperidinium p-toluenesulfonate (71.8 mg) was added to a solution of the compound (49.8 mg) obtained in (1) above in methanol (953 μL), and the mixture was stirred at room temperature for 18.5 hours. A saturated aqueous solution of sodium hydrogen carbonate was added to the mixture, and the resultant mixture was extracted three times with ethyl acetate. The organic layers were combined, washed with brine, passed through a phase separator, and concentrated under reduced pressure to give a mixture (41.7 mg) containing methyl 3-[[4-[2-[6-(1H-pyrazol-5-yl)pyridin-3-yl]oxyethyl]phenyl]methyl]oxetane-3-carboxylate.

(3) The mixture (41.7 mg) obtained in (2) above was used to perform the reaction according to the method described in Example 9-1-(3) thereby giving the title compound (17.3 mg) as a colorless high-viscosity substance.

$^1$H NMR (400 MHz, DMSO-$d_6$) δ ppm 3.02 (t, J=6.7 Hz, 2H) 3.21 (s, 2H) 4.28 (t, J=6.7 Hz, 2H) 4.43-4.52 (m, 2H) 4.68 (d, J=6.0 Hz, 2H) 6.72 (s, 1H) 7.08-7.15 (m, 2H) 7.21-7.28 (m, 2H) 7.40-7.49 (m, 1H) 7.60-7.74 (m, 1H) 7.79-7.89 (m, 1H) 8.27 (s, 1H).

MS ESI posi: 380[M+H]$^+$.
MS ESI nega: 378[M−H]$^−$.

The compounds of Examples 75-1 to 75-6 below were synthesized using any of the compounds obtained in Reference Examples 92-1 to 92-3, 93-1, and 119-1 and 119-2, according to the method described in Example 22-13. The structures, NMR data, and MS data of the compounds are shown in Table 67-16.

TABLE 67-16

| Example No. | Structure | Analytical Data |
|---|---|---|
| 75-1 | 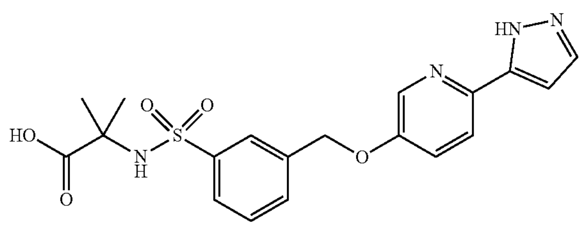 [SMILES: CC(C)(NS(=O)(=O)c1cccc(COc2ccc(-c3ccn[nH]3)nc2)c1)C(=O)O] | $^1$H NMR (400 MHz, DMSO-$d_6$) δ ppm 1.22 (s, 6 H) 5.33 (s, 2 H) 6.73 (d, J = 2.0 Hz, 1 H) 7.50-7.56 (m, 1 H) 7.57-7.63 (m, 1 H) 7.66-7.73 (m, 2 H) 7.78 (d, J = 8.1 Hz, 1 H) 7.84-7.93 (m, 3 H) 8.02 (s, 1 H) 8.37 (d, J = 2.7 Hz, 1 H) 12.63-12.96 (m, 1 H). MS ESI posi: 417[M + H]$^+$. MS ESI nega: 415[M − H]$^−$. |
| 75-2 | 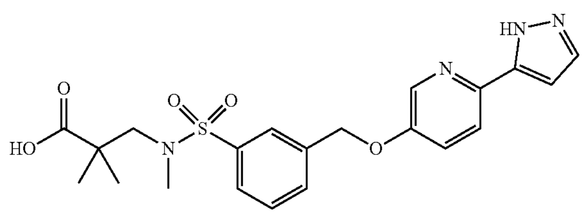 [SMILES: CN(CC(C)(C)C(=O)O)S(=O)(=O)c1cccc(COc2ccc(-c3ccn[nH]3)nc2)c1] | $^1$H NMR (400 MHz, DMSO-$d_6$) δ ppm 1.13 (s, 6 H) 2.64 (s, 3 H) 3.13 (s, 2 H) 5.36 (s, 2 H) 6.73 (s, 1 H) 7.50-7.59 (m, 1 H) 7.64-7.92 (m, 6 H) 8.37 (s, 1 H) 12.54-13.01 (m, 1 H). MS ESI posi: 445[M + H]$^+$. MS ESI nega: 443[M − H]$^−$. |
| 75-3 | 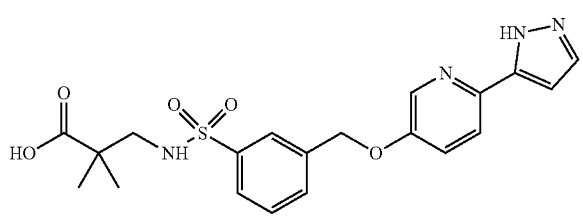 [SMILES: CC(C)(CNS(=O)(=O)c1cccc(COc2ccc(-c3ccn[nH]3)nc2)c1)C(=O)O] | $^1$H NMR (400 MHz, DMSO-$d_6$) δ ppm 1.04 (s, 6 H) 2.81 (d, J = 6.8 Hz, 2 H) 5.35 (s, 2 H) 6.77 (d, J = 2.0 Hz, 1 H) 7.56-7.83 (m, 6 H) 7.87-7.96 (m, 2 H) 8.39 (d, J = 2.7 Hz, 1 H). MS ESI posi: 431[M + H]$^+$. |
| 75-4 | 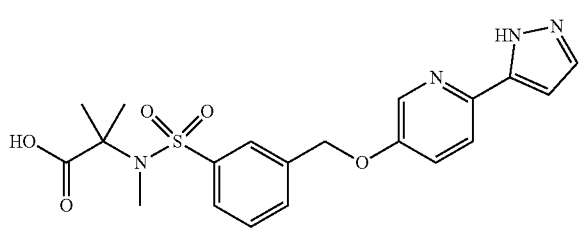 [SMILES: CN(C(C)(C)C(=O)O)S(=O)(=O)c1cccc(COc2ccc(-c3ccn[nH]3)nc2)c1] | $^1$H NMR (400 MHz, DMSO-$d_6$) δ ppm 1.38 (s, 6 H) 2.70 (s, 3 H) 5.33 (s, 2 H) 6.73 (s, 1 H) 7.51-7.58 (m, 1 H) 7.59-7.78 (m, 3 H) 7.83-7.94 (m, 2 H) 8.02 (s, 1 H) 8.38 (d, J = 2.4 Hz, 1 H) 12.71-13.07 (m, 1 H). MS ESI posi: 431[M + H]$^+$. MS ESI nega: 429[M − H]$^−$. |

TABLE 67-16-continued

| Example No. | Structure | Analytical Data |
|---|---|---|
| 75-5 | 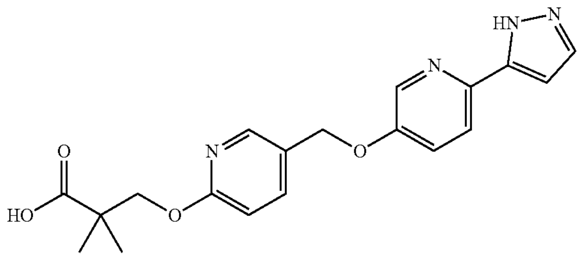 [SMILES: CC(C)(COc1ccc(COc2ccc(-c3ccn[nH]3)nc2)cn1)C(=O)O] | $^1$H NMR (400 MHz, DMSO-d$_6$) δ ppm 1.19 (s, 6 H) 4.25 (s, 2 H) 5.15 (s, 2 H) 6.64-6.90 (m, 2 H) 7.43-7.95 (m, 4 H) 8.21-8.41 (m, 2 H). MS ESI posi: 369[M + H]$^+$. MS ESI nega: 367[M − H]$^-$. |
| 75-6 | 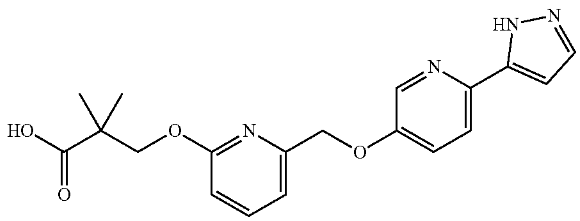 [SMILES: CC(C)(COc1cccc(COc2ccc(-c3ccn[nH]3)nc2)n1)C(=O)O] | $^1$H NMR (400 MHz, DMSO-d$_6$) δ ppm 1.20 (s, 6 H) 4.22 (s, 2 H) 5.20 (s, 2 H) 6.59-6.85 (m, 2 H) 7.04-7.22 (m, 1 H) 7.44-7.96 (m, 4 H) 8.31-8.45 (m, 1 H). MS ESI posi: 369[M + H]$^+$. MS ESI nega: 367[M − H]$^-$. |

The compounds of Examples 75-7 and 75-8 below were synthesized using the compounds obtained in Reference Example 3-1 and Reference Examples 90-1 and 90-2, according to the methods described in Example 22-13-(1) and Example 71-45-(2). The structures, NMR data, and MS data of the compounds are shown in Table 67-17.

The compounds of Examples 75-7 and 75-8 are optically active compounds.

TABLE 67-17

| Example No. | Structure | Analytical Data |
|---|---|---|
| 75-7 | 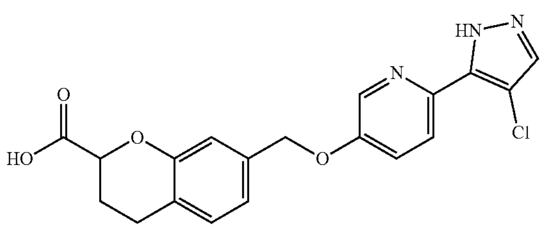 [SMILES: O=C(O)C1CCc2ccc(COc3ccc(-c4[nH]ncc4Cl)nc3)cc2O1] | $^1$H NMR (400 MHz, DMSO-d$_6$) δ ppm 1.99-2.20 (m, 2 H) 2.64-2.85 (m, 2 H) 4.71-4.80 (m, 1 H) 5.17 (s, 2 H) 6.87-6.98 (m, 2 H) 7.07 (d, J = 7.6 Hz, 1 H) 7.49-8.06 (m, 3 H) 8.38-8.50 (m, 1 H). MS ESI posi: 386[M + H]$^+$. Retention time 5.99 min (S F C) |
| 75-8 | 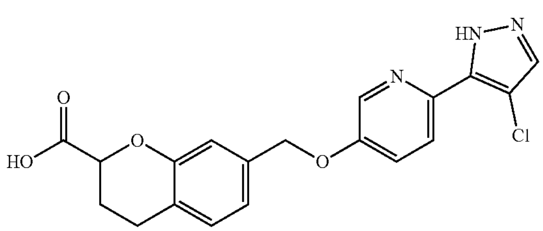 [SMILES: O=C(O)C1CCc2ccc(COc3ccc(-c4[nH]ncc4Cl)nc3)cc2O1] | $^1$H NMR (400 MHz, DMSO-d$_6$) δ ppm 2.02-2.20 (m, 2 H) 2.60-2.85 (m, 2 H) 4.73-4.82 (m, 1 H) 5.17 (s, 2 H) 6.89-6.97 (m, 2 H) 7.07 (d, J = 7.6 Hz, 1 H) 7.48-8.02 (m, 3 H) 8.43 (s, 1 H). MS ESI posi: 386[M + H]$^+$. MS ESI nega: 384[M − H]$^-$. Retention time 7.60 min (S F C) |

Example 76-1

2-Methyl-2-[7-[6-(1,3-oxazol-5-yl)pyridin-3-yl]oxyheptoxy]propanoic Acid

[Formula 604]

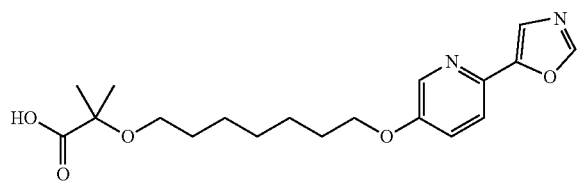

(1) The compound (700 mg) obtained in Reference Example 104-3 and 6-methylpyridin-3-ol (334 mg) were used to perform the reaction according to the method described in Example 1-1-(1) thereby giving tert-butyl 2-methyl-2-[7-(6-methylpyridin-3-yl)oxyheptoxy]propanoate (810 mg) as a colorless oil.

(2) Meta-chloroperbenzoic acid (734 mg) was added to a solution of the compound (810 mg) obtained in (1) above in chloroform (13 mL) under ice cooling, and the mixture was stirred at room temperature for 5 hours. A saturated aqueous solution of sodium hydroxide was added thereto under ice cooling, and the resultant mixture was extracted with chloroform. The organic layer was passed through a phase separator, and concentrated under reduced pressure. The obtained residue was purified by silica gel column chromatography (chloroform:methanol=99:1 to 91:9) to give tert-butyl 2-methyl-2-[7-(6-methyl-1-oxidepyridin-1-ium-3-yl)oxyheptoxy]propanoate (838 mg) as a pale brown solid.

(3) A solution of the compound (838 mg) obtained in (2) above in acetic anhydride (2.2 mL) was stirred at 120° C. for 1.5 hours. The reaction solution was concentrated under reduced pressure, a saturated aqueous solution of sodium bicarbonate was added thereto, and the resultant mixture was extracted with chloroform. The organic layer was passed through a phase separator, and concentrated under reduced pressure. The residue was dissolved in methanol (22 mL), water (4.4 mL) and potassium carbonate (607 mg) were added thereto, and the resultant mixture was stirred at 70° C. for 1 hour. The organic solvent was distilled off under reduced pressure, and the residual aqueous layer was extracted with chloroform. The organic layer was separated by a phase separator, and concentrated under reduced pressure. The obtained residue was purified by silica gel column chromatography (chloroform:methanol=99:1 to 91:9) to give tert-butyl 2-[7-[6-(hydroxymethyl)pyridin-3-yl]oxyheptoxy]-2-methylpropanoate (645 mg) as a brown oil.

(4) Manganese dioxide (2.2 g) was added to a solution of the compound (645 mg) obtained in (3) above in chloroform (9 mL), and the mixture was stirred at room temperature overnight. The mixture was filtered through Celite (registered trademark), and the filtrate was concentrated under reduced pressure. The obtained residue was purified by silica gel column chromatography (n-hexane:ethyl acetate=9:1 to 7:3) to give tert-butyl 2-[7-(6-formylpyridin-3-yl)oxyheptoxy]-2-methylpropanoate (497 mg) as a colorless oil.

(5) Potassium carbonate (280 mg) and 1-(isocyanomethylsulfonyl)-4-methylbenzene (396 mg) were added to a solution of the compound (497 mg) obtained in (4) above in methanol (8.5 mL), and the mixture was stirred at room temperature for 4 hours. The mixture was concentrated under reduced pressure, a saturated aqueous solution of sodium hydrogen carbonate was added to the residue, and the resultant mixture was extracted with chloroform. The organic layer was separated by a phase separator, and concentrated under reduced pressure. The obtained residue was purified by silica gel column chromatography (n-hexane:ethyl acetate=13:7 to 7:13) to give tert-butyl 2-methyl-2-[7-[6-(1,3-oxazol-5-yl)pyridin-3-yl]oxyheptoxy]propanoate (419 mg) as a pale yellow oil.

(6) The compound (419 mg) obtained in (5) above was used to perform the reaction according to the method described in Example 3-1-(3) thereby giving the title compound (255 mg) as a pale brown solid.

$^1$H NMR (400 MHz, DMSO-$d_6$) δ ppm 1.00-1.84 (m, 10H) 1.29 (s, 6H) 3.27-3.31 (m, 2H) 3.95-4.21 (m, 2H) 7.51 (m, 1H) 7.62 (s, 1H) 7.71 (m, 1H) 8.34 (m, 1H) 8.45 (s, 1H) 12.49 (br s, 1H).

MS ESI posi: 363[M+H]$^+$.
MS ESI nega: 361[M−H]$^-$.

The inhibitory action of the compound of the present invention against 20-HETE producing enzymes was measured by the method described in Test Example 1 below.

Test Example 1

(1) Inhibition Test for Each Compound of the Present Invention Against 20-HETE Producing Enzymes (CYP4F2 and CYP4A11)

In the CYP4F2 inhibition test, the reaction solution containing each compound [final concentration of 50 mM, KPO$_4$ (pH 7.4), 2.5 μM luciferine derivative, and 1 mM NADPH] was added to an *Escherichia coli* membrane fraction (100 μg/mL protein) in which human CYP4F2 had been expressed. In the CYP4A11 inhibition test, the reaction solution containing each compound [final concentration of 100 mM, Tris-HCl (pH 7.5), 60 μM luciferine derivative, 1.3 mM NADP$^+$, 3.3 mM Glucose 6-Phosphate, 3.3 mM MgCl$_2$, and 0.4 U/mL Glucose 6-Phosphate dehydrogenase] was added to an *Escherichia coli* membrane fraction (100 μg/mL protein) in which human CYP4A11 had been expressed. Following this, the membrane fraction was left to stand at room temperature for 60 minutes to perform an enzymatic reaction. After the reaction, a luciferine detection reagent was added, and the luminescence value was measured using a plate reader. By using that value, the percent inhibition of 20-HETE producing enzyme (%) was calculated according to the equation described below, and the 50% inhibitory concentration (IC$_{50}$ value) for each compound was calculated.

Percent inhibition of 20-HETE producing enzyme (%)=[1−(A−B)/(C−B)]*100

A: Luminescence value with addition of compound
B: Luminescence value without addition of compound and enzyme
C: Luminescence value without addition of compound (2) Results The inhibitory activity of each compound of the present invention against CYP4F2 and CYP4A11 is shown in Tables 68-1 to 68-7 below.

TABLE 68-1

| | IC$_{50}$ value [nM] | |
|---|---|---|
| Example No. | Human CYP4F2 | Human CYP4A11 |
| 1-1 | 15000 | 37 |
| 1-2 | 42000 | 250 |

TABLE 68-1-continued

| | IC$_{50}$ value [nM] | |
|---|---|---|
| Example No. | Human CYP4F2 | Human CYP4A11 |
| 1-3 | 220 | 79 |
| 1-4 | 16000 | 110 |
| 1-5 | 3500 | 150 |
| 1-6 | 2300 | 340 |
| 1-7 | 11000 | 2400 |
| 1-8 | 2600 | 78 |
| 1-9 | 480 | 79 |
| 1-10 | 27000 | 4200 |
| 1-11 | 43000 | 24 |
| 1-12 | >50000 | 170 |
| 1-13 | 2700 | 31 |
| 1-14 | 7800 | 21 |
| 1-15 | 670 | 210 |
| 1-16 | 1100 | 36 |
| 1-17 | 5100 | 16 |
| 1-18 | 330 | 14 |
| 1-19 | 220 | 9.5 |
| 1-20 | 9200 | 16 |
| 1-21 | 31000 | 29 |
| 1-22 | >50000 | 38 |
| 1-23 | 20000 | 320 |
| 1-24 | 15000 | 170 |
| 1-25 | 1600 | 120 |
| 1-26 | 14000 | 43 |
| 1-27 | 41000 | 38 |
| 1-28 | 19000 | 74 |
| 1-29 | 360 | 30 |
| 1-30 | 4100 | 34 |
| 1-31 | 160 | 1700 |
| 1-32 | 3800 | 9300 |
| 1-33 | 15000 | 74 |
| 1-34 | 1800 | 38 |
| 1-35 | 2200 | 84 |
| 1-36 | 1300 | 110 |
| 1-37 | 94 | 21 |
| 1-38 | 1200 | 42 |
| 1-39 | 9800 | 420 |
| 1-40 | 15000 | 580 |
| 1-41 | 3700 | 97 |
| 1-42 | 25000 | 52 |
| 1-43 | 18000 | 46 |
| 1-44 | 510 | 110 |
| 1-45 | 19 | 46 |
| 1-46 | 370 | 66 |
| 1-47 | 14000 | 68 |
| 1-48 | 2000 | 44 |
| 1-49 | 24000 | 140 |
| 1-50 | 23000 | 170 |
| 1-51 | 200 | 54 |
| 1-52 | 41 | 44 |
| 1-53 | 330 | 61 |
| 1-54 | 3400 | 57 |
| 1-55 | 3700 | 30 |
| 1-56 | 170 | 27 |
| 1-57 | 340 | 110 |
| 1-58 | 650 | 86 |
| 1-59 | 17000 | 42 |
| 1-60 | 31000 | 38 |
| 1-61 | 1900 | 26 |
| 1-62 | 96 | 23 |
| 1-63 | 8.9 | 36 |
| 1-64 | 7500 | 28 |
| 1-65 | 24000 | 1200 |
| 1-66 | >50000 | 330 |
| 1-67 | 10000 | 120 |
| 1-68 | 640 | 28 |
| 1-69 | 3000 | 75 |
| 1-70 | 140 | 62 |
| 2-1 | 24000 | 23 |
| 2-2 | >50000 | 130 |
| 2-3 | 75 | 99 |
| 2-4 | 1800 | 200 |
| 2-5 | 8600 | 15 |
| 2-6 | 1300 | 25 |
| 2-7 | 4400 | 35 |
| 3-1 | 24 | 190 |

TABLE 68-1-continued

| | IC$_{50}$ value [nM] | |
|---|---|---|
| Example No. | Human CYP4F2 | Human CYP4A11 |
| 3-2 | 440 | 120 |
| 3-3 | 2300 | 390 |

TABLE 68-2

| | IC$_{50}$ value [nM] | |
|---|---|---|
| Example No. | Human CYP4F2 | Human CYP4A11 |
| 3-4 | 260 | 1800 |
| 3-5 | 3000 | 2200 |
| 3-6 | 2700 | 810 |
| 3-7 | 5700 | 1600 |
| 3-8 | 250 | 1200 |
| 3-9 | 430 | 240 |
| 3-10 | 250 | 92 |
| 3-11 | 290 | 55 |
| 4-1 | 830 | 22 |
| 4-2 | 160 | 250 |
| 5-1 | 33 | 22 |
| 5-2 | 1700 | 73 |
| 6-1 | 7.9 | 770 |
| 7-1 | 48000 | 34 |
| 8-1 | 790 | 20 |
| 8-2 | 6500 | 19 |
| 8-3 | 860 | 28 |
| 8-4 | 4300 | 250 |
| 8-5 | 2300 | 560 |
| 8-6 | 53 | 2500 |
| 8-7 | 280 | 440 |
| 8-8 | 1100 | 260 |
| 8-9 | 6200 | 29 |
| 8-10 | 1300 | 35 |
| 8-11 | 120 | 14 |
| 8-12 | 5000 | 100 |
| 8-13 | 8300 | 120 |
| 8-14 | 11000 | 68 |
| 8-15 | 1400 | 530 |
| 8-16 | 680 | 750 |
| 8-17 | 22000 | 520 |
| 8-18 | 16000 | 52 |
| 9-1 | 1900 | 51 |
| 9-2 | 1100 | 1800 |
| 9-3 | 490 | 1400 |
| 9-4 | 740 | 43 |
| 10-1 | 19000 | 560 |
| 10-2 | 1100 | 23 |
| 11-1 | 5.1 | 140 |
| 11-2 | 19 | 520 |
| 11-3 | 7.3 | 270 |
| 11-4 | 1300 | 4500 |
| 12-1 | 6.2 | 260 |
| 12-2 | 11 | 310 |
| 12-3 | 25 | 290 |
| 13-1 | 34 | 610 |
| 13-2 | 13 | 400 |
| 13-3 | 19 | 300 |
| 14-1 | 2200 | 30 |
| 15-1 | 220 | 120 |
| 15-2 | 25000 | 690 |
| 15-3 | 6300 | 130 |
| 16-1 | 1400 | 53 |
| 17-1 | 180 | 1400 |
| 18-1 | 460 | 13 |
| 18-2 | 230 | 12 |
| 18-3 | 510 | 24 |
| 18-4 | 490 | 22 |
| 18-5 | 5200 | 32 |
| 18-6 | 6100 | 310 |
| 19-1 | 22 | 1700 |
| 20-1 | 1100 | 28000 |
| 20-2 | 69 | 210 |
| 21-1 | 15000 | 43 |

TABLE 68-2-continued

| Example No. | IC$_{50}$ value [nM] | |
|---|---|---|
| | Human CYP4F2 | Human CYP4A11 |
| 21-2 | >50000 | 3800 |
| 21-3 | 21000 | 16 |
| 21-4 | 1500 | 25 |
| 21-5 | 430 | 29 |
| 22-1 | 140 | 15 |
| 22-2 | 1400 | 42 |
| 22-3 | 17000 | 16 |
| 22-4 | 1400 | 20 |
| 22-5 | 3100 | 120 |
| 22-6 | 3100 | 110 |
| 22-7 | 1200 | 38 |
| 22-8 | 1500 | 68 |
| 22-9 | 180 | 45 |
| 22-10 | 2000 | 24 |
| 22-11 | 700 | 28 |
| 22-12 | 2000 | 53 |

TABLE 68-3

| Example No. | IC$_{50}$ value [nM] | |
|---|---|---|
| | Human CYP4F2 | Human CYP4A11 |
| 22-13 | 11000 | 380 |
| 22-14 | 380 | 70 |
| 22-15 | 14000 | 92 |
| 22-16 | 33000 | 780 |
| 22-17 | 19000 | 62 |
| 22-18 | 18000 | 35 |
| 22-19 | 1500 | 49 |
| 22-20 | 9600 | 76 |
| 23-1 | 220 | 36 |
| 23-2 | 3.0 | 13 |
| 23-3 | 49 | 1700 |
| 23-4 | 51 | 2000 |
| 23-5 | 130 | 480 |
| 23-6 | 6.4 | 270 |
| 24-1 | 13000 | 16 |
| 24-2 | 3500 | 16 |
| 24-3 | 3200 | 60 |
| 25-1 | 16000 | 33 |
| 26-1 | 400 | 20 |
| 26-2 | 890 | 23 |
| 26-3 | 1500 | 24 |
| 27-1 | 400 | 44 |
| 27-2 | 300 | 15 |
| 27-3 | 350 | 120 |
| 27-4 | 120 | 110 |
| 27-5 | 900 | 79 |
| 28-1 | 470 | 61 |
| 28-2 | 1000 | 100 |
| 29-1 | 4000 | 650 |
| 29-2 | 2700 | 1300 |
| 29-3 | 84 | 380 |
| 29-4 | 240 | 42 |
| 29-5 | 690 | 29 |
| 30-1 | 1400 | 17 |
| 30-2 | 190 | 160 |
| 30-3 | 370 | 150 |
| 30-4 | 350 | 140 |
| 30-5 | 74 | 420 |
| 31-1 | 110 | 9.3 |
| 31-2 | 100 | 9.8 |
| 31-3 | 180 | 25 |
| 31-4 | 390 | 12 |
| 32-1 | 430 | 33 |
| 32-2 | 1300 | 22 |
| 33-1 | 7000 | 180 |
| 33-2 | 14000 | 130 |
| 34-1 | 4100 | 42 |
| 34-2 | 11000 | 50 |
| 34-3 | 390 | 26 |
| 35-1 | 20000 | 3000 |

TABLE 68-3-continued

| Example No. | IC$_{50}$ value [nM] | |
|---|---|---|
| | Human CYP4F2 | Human CYP4A11 |
| 35-2 | 5700 | 360 |
| 35-3 | 7400 | 290 |
| 36-1 | 93 | 82 |
| 37-1 | 32 | 46 |
| 38-1 | 1100 | 20 |
| 38-2 | 19000 | 11 |
| 38-3 | 17000 | 35 |
| 39-1 | 13000 | 5.3 |
| 39-2 | 22000 | 18 |
| 40-1 | 28000 | 9.9 |
| 40-2 | 8200 | 6.9 |
| 41-1 | 590 | 250 |
| 41-2 | 450 | 330 |
| 41-3 | 4300 | 570 |
| 41-4 | 1500 | 710 |
| 41-5 | 550 | 1100 |
| 41-6 | 320 | 440 |
| 42-1 | 76 | 420 |
| 42-2 | 25 | 110 |
| 42-3 | 210 | 350 |
| 42-4 | 12 | 540 |
| 42-5 | 260 | 200 |
| 42-6 | 97 | 300 |
| 42-7 | 1100 | 760 |
| 42-8 | 70 | 120 |
| 42-9 | 76 | 67 |
| 42-10 | 15 | 46 |
| 42-11 | 95 | 100 |
| 42-12 | 42 | 44 |
| 42-13 | 15 | 150 |

TABLE 68-4

| Example No. | IC$_{50}$ value [nM] | |
|---|---|---|
| | Human CYP4F2 | Human CYP4A11 |
| 42-14 | 30 | 240 |
| 42-15 | 140 | 400 |
| 42-16 | 5.7 | 210 |
| 42-17 | 12 | 35 |
| 42-18 | 21 | 58 |
| 42-19 | 47 | 110 |
| 42-20 | 11 | 76 |
| 42-21 | 28 | 430 |
| 42-22 | 99 | 270 |
| 42-23 | 55 | 160 |
| 42-24 | 150 | 39 |
| 43-1 | 52 | 58 |
| 43-2 | 48 | 59 |
| 43-3 | 170 | 310 |
| 43-4 | 45 | 150 |
| 43-5 | 40 | 82 |
| 43-6 | 92 | 56 |
| 43-7 | 63 | 320 |
| 43-8 | 120 | 120 |
| 43-9 | 73 | 130 |
| 43-10 | 190 | 140 |
| 43-11 | 32 | 280 |
| 43-12 | 40 | 76 |
| 43-13 | 21 | 48 |
| 43-14 | 18 | 52 |
| 43-15 | 280 | 910 |
| 43-16 | 22 | 190 |
| 44-1 | 7500 | 49 |
| 44-2 | 73 | 340 |
| 44-3 | 11000 | 44 |
| 44-4 | 290 | 410 |
| 44-5 | 2700 | 31 |
| 44-6 | 45 | 230 |
| 44-7 | 85 | 3800 |
| 45-1 | 7600 | 120 |
| 45-2 | 3200 | 150 |

TABLE 68-4-continued

| Example No. | IC$_{50}$ value [nM] Human CYP4F2 | Human CYP4A11 |
|---|---|---|
| 45-3 | 6100 | 91 |
| 45-4 | 6400 | 86 |
| 45-5 | 750 | 74 |
| 45-6 | 4500 | 250 |
| 45-7 | 2900 | 780 |
| 45-8 | 1900 | 130 |
| 45-9 | 4800 | 82 |
| 45-10 | 10000 | 180 |
| 45-11 | 1200 | 23 |
| 45-12 | 890 | 220 |
| 45-13 | 6800 | 240 |
| 45-14 | 410 | 51 |
| 45-15 | 180 | 1200 |
| 45-16 | 3400 | 120 |
| 45-17 | 1000 | 510 |
| 45-18 | 270 | 440 |
| 45-19 | 13000 | 1000 |
| 45-20 | 2100 | 410 |
| 45-21 | 6100 | 580 |
| 45-22 | 2800 | 97 |
| 45-23 | 3900 | 710 |
| 45-24 | 830 | 56 |
| 45-25 | 370 | 40 |
| 45-26 | 880 | 31 |
| 45-27 | 2200 | 510 |
| 45-28 | 3700 | 270 |
| 45-29 | 4900 | 170 |
| 45-30 | 4000 | 290 |
| 45-31 | 2500 | 370 |
| 45-32 | 6800 | 660 |
| 45-33 | 19000 | 2000 |
| 45-34 | 17000 | 220 |
| 45-35 | 13000 | 3200 |
| 45-36 | 1100 | 230 |
| 45-37 | 720 | 120 |
| 45-38 | 300 | 310 |
| 45-39 | 1400 | 470 |
| 45-40 | 1400 | 410 |
| 45-41 | 1800 | 200 |
| 45-42 | 34 | 450 |
| 45-43 | 5200 | 1700 |
| 45-44 | 3500 | 110 |
| 45-45 | 1600 | 1700 |
| 45-46 | 54 | 160 |

TABLE 68-5

| Example No. | IC$_{50}$ value [nM] Human CYP4F2 | Human CYP4A11 |
|---|---|---|
| 45-47 | 970 | 190 |
| 46-1 | 7600 | 3200 |
| 46-2 | 470 | 730 |
| 46-3 | >50000 | 1500 |
| 46-4 | 18000 | 1000 |
| 46-5 | 7500 | 280 |
| 47-1 | 150 | 830 |
| 48-1 | 11000 | 620 |
| 49-1 | 1100 | 1200 |
| 50-1 | 2800 | 75 |
| 51-1 | 3.0 | 270 |
| 51-2 | 3.5 | 310 |
| 52-1 | 4.4 | 710 |
| 52-2 | 50 | 520 |
| 53-1 | 190 | 110 |
| 53-2 | 16 | 950 |
| 54-1 | 21000 | 70 |
| 55-1 | 6500 | 200 |
| 56-1 | 450 | 140 |
| 57-1 | 140 | 220 |
| 57-2 | 7300 | 6700 |
| 57-3 | 2000 | 2000 |

TABLE 68-5-continued

| Example No. | IC$_{50}$ value [nM] Human CYP4F2 | Human CYP4A11 |
|---|---|---|
| 58-1 | 120 | 580 |
| 58-2 | 5.1 | 240 |
| 59-1 | 10 | 130 |
| 59-2 | 100 | 1800 |
| 59-3 | 41 | 1500 |
| 60-1 | 37000 | 8.2 |
| 60-2 | 130 | 29 |
| 61-1 | 8000 | 72 |
| 61-2 | 280 | 750 |
| 62-1 | 3500 | 28 |
| 62-2 | 1900 | 27 |
| 63-1 | 12000 | 31 |
| 64-1 | 780 | 41 |
| 65-1 | 63 | 8.1 |
| 66-1 | 16 | 33 |
| 67-1 | 2700 | >50000 |
| 68-1 | 39 | 620 |

TABLE 68-6

| Example No. | IC$_{50}$ value [nM] Human CYP4F2 | Human CYP4A11 |
|---|---|---|
| 69-1-1 | 240 | 21 |
| 69-1-2 | 200 | 25 |
| 69-2-1 | 600 | 37 |
| 69-2-2 | 1100 | 36 |
| 69-3-1 | 110 | 23 |
| 69-3-2 | 300 | 220 |
| 69-4-1 | 86 | 27 |
| 69-4-2 | 670 | 40 |
| 70-1 | 49 | 27 |
| 70-2 | 1100 | 28 |
| 70-3 | 280 | 28 |
| 70-4 | 56 | 150 |
| 70-5 | 27 | 43 |
| 70-6 | 47 | 76 |
| 70-7 | 320 | 50 |
| 70-8 | 120 | 130 |
| 70-9 | 200 | 210 |
| 70-10-1 | 120 | 160 |
| 70-10-2 | 340 | 450 |
| 70-11 | 330 | 43 |
| 71-1 | 140 | 110 |
| 71-2-1 | 300 | 170 |
| 71-2-2 | 90 | 87 |
| 71-3 | 320 | 230 |
| 71-4 | 200 | 270 |
| 71-5 | 39 | 96 |
| 71-6 | 100 | 230 |
| 71-7 | 550 | 82 |
| 71-8-1 | 430 | 1000 |
| 71-8-2 | 560 | 48 |
| 71-9 | 870 | 310 |
| 71-10 | 260 | 140 |
| 71-11 | 29000 | 22 |
| 71-12 | 1300 | 18 |
| 71-13 | 770 | 51 |
| 71-14 | 1300 | 150 |
| 71-15 | 1200 | 84 |
| 71-16 | 91 | 190 |
| 71-17 | 520 | 250 |
| 71-18 | 83 | 110 |
| 71-19 | 540 | 53 |
| 71-20 | 190 | 500 |
| 71-21 | 190 | 330 |
| 71-22-1 | 310 | 250 |
| 71-22-2 | 160 | 1000 |
| 71-23 | 550 | 50 |
| 71-24 | 2100 | 72 |
| 71-25 | 4800 | 300 |
| 71-26 | 9700 | 39 |

TABLE 68-6-continued

| | IC$_{50}$ value [nM] | |
|---|---|---|
| Example No. | Human CYP4F2 | Human CYP4A11 |
| 71-27 | 15000 | 94 |
| 71-28 | 6200 | 1600 |
| 71-29 | 260 | 110 |
| 71-30 | 11000 | 1900 |
| 71-31 | 15000 | 300 |
| 71-32 | 23000 | 6200 |
| 71-33 | 600 | 1600 |
| 71-34 | 36000 | 1100 |
| 71-35 | 1900 | 1400 |
| 71-36 | >50000 | 260 |
| 71-37 | 3500 | 160 |
| 71-38 | 1900 | 1400 |
| 71-39 | 51 | 780 |
| 71-40 | 8700 | 450 |
| 71-41 | 660 | 160 |
| 71-42 | 2100 | 630 |
| 71-43 | 250 | 870 |
| 71-44 | 37 | 1000 |
| 71-45 | 210 | 15 |
| 71-46 | 240 | 19 |
| 72-1 | 54 | 450 |
| 72-2 | 97 | 120 |
| 72-3 | 43 | 130 |
| 72-4 | 14 | 150 |
| 72-5 | 43 | 260 |
| 72-6 | 9.4 | 270 |
| 72-7 | 15000 | 14 |
| 72-8 | 1700 | 15 |
| 72-9 | 18 | 230 |
| 73-1 | 12 | 160 |
| 74-1 | 1100 | 130 |

TABLE 68-7

| | IC$_{50}$ value [nM] | |
|---|---|---|
| Example No. | Human CYP4F2 | Human CYP4A11 |
| 74-2 | 130 | 53 |
| 74-3 | 60 | 88 |
| 74-4 | 58 | 82 |
| 74-5 | 80 | 88 |
| 74-6 | 16000 | 35 |
| 74-7 | 1300 | 78 |
| 74-8 | 410 | 77 |
| 74-9 | 19000 | 47 |
| 74-10 | 2600 | 56 |
| 74-11 | 1200 | 78 |
| 74-12 | 13000 | 510 |
| 75-1 | 9300 | 21 |
| 75-2 | 130 | 38 |
| 75-3 | 490 | 36 |
| 75-4 | 29000 | 43 |
| 75-5 | 780 | 720 |
| 75-6 | 1700 | 180 |
| 75-7 | 20 | 7.7 |
| 75-8 | 67 | 67 |
| 76-1 | 1500 | 740 |

(3) Inhibition Test for Compound a and Compound B Disclosed in WO03/022821 Against 20-HETE Producing Enzymes (CYP4F2 and CYP4A11)

For compound A (Example 402) and compound B (Example 754) described below, whose inhibitory activity against 20-HETE producing enzymes using human kidney microsomes is disclosed in WO03/022821, the 50% inhibitory concentration (IC$_{50}$ value) against CYP4F2 and CYP4A11 was calculated according to the method described in Test Example 1.

Note that compound A and compound B disclosed in WO03/022821 are as follows:

[Formula 605]

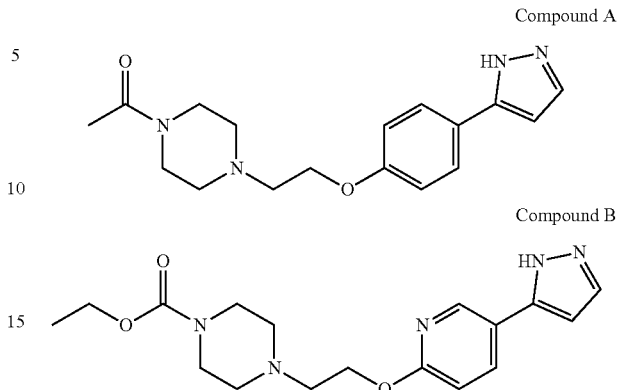

(4) Results

The inhibitory activity of compound A and compound B against CYP4F2 and CYP4A11 is shown in Table 68-8 below.

TABLE 68-8

| | IC$_{50}$ value [nM] | |
|---|---|---|
| Example No. | Human CYP4F2 | Human CYP4A11 |
| Compound A | 1000 | 11000 |
| Compound B | 36000 | >50000 |

Furthermore, the inhibitory action of the compound of the present invention against 20-HETE producing enzymes was also measured by the method described in Test Example 2 below.

Test Example 2

(1) Inhibition Test for Each Compound of the Present Invention Against 20-HETE Producing Enzymes Using Human Kidney Microsomes The reaction solution containing each compound [final concentration of 100 mM, KPO$_4$ (pH 7.4), 20 µM Arachidonic acid, 4 mM NADPH] was added to the human kidney microsome (250 µg/mL protein). Following this, the microsome was left to stand at 37° C. for 45 minutes to perform 20-HETE producing reaction. After adding formic acid to stop the reaction, 9 times amount of acetonitrile was added, and deproteinization was carried out by centrifugation (1000 rpm, 4° C., 10 minutes). After that, the peak area value of 20-HETE was measured using a liquid chromatograph-tandem mass spectrometer (LC-MS/MS), and by using that value, the percent inhibition of 20-HETE producing enzyme (%) was calculated according to the equation described below, and the 50% inhibitory concentration (IC$_{50}$ value) for each compound was calculated.

Percent inhibition of 20-HETE producing enzyme (%)=[1−(A−B)/(C−B)]*100

A: Peak area value of 20-HETE/peak area value of internal standard substance with addition of compound
B: Peak area value of 20-HETE/peak area value of internal standard substance without addition of compound and NADPH
C: Peak area value of 20-HETE/peak area value of internal standard substance without addition of compound (2) Results The inhibitory activity of each compound of the present invention against 20-HETE producing enzymes is shown in Tables 69-1 and 69-2 below.

TABLE 69-1

| Example No. | $IC_{50}$ value [nM] |
|---|---|
| 1-53 | 14 |
| 1-56 | 20 |
| 1-57 | 19 |
| 1-68 | 26 |
| 1-70 | 37 |
| 3-1 | 10 |
| 5-1 | 8.2 |
| 15-1 | 18 |
| 22-9 | 15 |
| 22-11 | 15 |
| 22-14 | 32 |
| 26-2 | 26 |
| 26-3 | 30 |
| 68-1 | 6.9 |

TABLE 69-2

| Example No. | $IC_{50}$ value [nM] |
|---|---|
| 70-7 | 16 |
| 70-10-1 | 6.4 |
| 71-6 | 11 |
| 71-18 | 6.0 |
| 71-46 | 12 |
| 72-2 | 4.7 |
| 72-3 | 4.0 |
| 73-1 | 1.7 |
| 74-2 | 20 |
| 74-4 | 4.4 |
| 74-5 | 9.1 |

(3) Inhibition Test for Compound a and Compound B Disclosed in WO03/022821 Against 20-HETE Producing Enzymes Using Human Kidney Microsomes For compound A and compound B disclosed in WO03/022821, which have been described above, the 50% inhibitory concentration ($IC_{50}$ value) against 20-HETE producing enzymes was calculated according to the method described in Test Example 2.

(4) Results

The inhibitory activity of compound A and compound B against 20-HETE producing enzymes is shown in Table 69-3 below.

TABLE 69-3

| Example No. | $IC_{50}$ value [nM] |
|---|---|
| Compound A | 408 |
| Compound B | 15600 |

(5) Comparison of Inhibitory Activities Against 20-HETE Producing Enzymes Between Compound a and Compound B Disclosed in WO03/022821, which have been Described Above, and the Compound of the Present Invention Compared to compound A and compound B described above, 15 compounds from Examples of the present inventive compounds (Example 1-53, Example 1-56, Example 1-57, Example 1-68, Example 1-70, Example 3-1, Example 5-1, Example 15-1, Example 22-9, Example 22-11, Example 22-14, Example 26-2, Example 26-3, and Example 68-1) have stronger inhibitory activities against 20-HETE producing enzymes.

Now, explanation will be given regarding the inhibition test against 20-HETE producing enzymes using human kidney microsomes, disclosed in WO03/022821, and Test Example 2 described above.

In the test disclosed in WO03/022821, radiolabelled arachidonic acid is used as a substrate, and the amount of 20-HETE produced is measured using a radio-HPLC. In this case, the concentration of arachidonic acid, the substrate, is 0.01 µM.

On the other hand, as described above, in Test Example 2, nonradioactive arachidonic acid was used as a substrate for 20-HETE producing reaction, and the amount of 20-HETE produced was measured using LC-MS/MS. In this case, the concentration of arachidonic acid, the substrate, is 20 µM.

In recent years, it is recommended that the substrate concentration for calculating the $IC_{50}$ value be set at the Km value (Assay Guidance Manual, Sittampalam et. al. (URL: http://www.ncbi.nlm.nih.gov/books/NBK53196/)). According to this, in Test Example 2 described above, human kidney microsomes were used to calculate the Km value, and the calculated Km value of 20 µM was set as the concentration of the substrate, arachidonic acid.

From the above, in the light of the current science level, the conditions used for the test in Test Example 2 described above are believed to be more appropriate, compared to the conditions of the test disclosed in WO03/022821, and thus the $IC_{50}$ value calculated under the conditions of Test Example 2 is believed to be more reasonable than the value disclosed in WO03/022821.

Test Example 3: CYP Selectivity Test for Each Compound of the Present Invention (1) CYP4F22 Selectivity Test for Each Compound of the Present Invention The reaction solution containing each compound [final concentration of 100 mM $KPO_4$ (pH 7.4), 14 µM luciferine derivative, and 1 mM NADPH] was added to a cell membrane fraction (30 µg/mL protein) in which human CYP4F22 had been expressed. Following this, the cell membrane fraction was left to stand at room temperature for 50 minutes to perform an enzymatic reaction. After the reaction, a luciferine detection reagent was added, and the luminescence value was measured using a plate reader. By using that value, the percent inhibition of the enzymatic reaction of CYP4F22(%) was calculated according to the equation described below, and the 50% inhibitory concentration ($IC_{50}$ value) for each compound was calculated.

Percent inhibition of CYP4F22 enzyme (%)=[1−(A−B)/(C−B)]*100

A: Luminescence value with addition of compound

B: Luminescence value without addition of compound and enzyme

C: Luminescence value without addition of compound (2) Results

The inhibitory activity of each compound of the present invention against CYP4F22 is shown in Table 70-1 below.

TABLE 70-1

| Example No. | $IC_{50}$ value [nM] |
|---|---|
| 15-1 | 2900 |
| 70-7 | 1400 |
| 70-10-1 | 2300 |
| 71-6 | 370 |
| 71-18 | 1900 |

TABLE 70-1-continued

| Example No. | IC$_{50}$ value [nM] |
|---|---|
| 71-46 | 1300 |
| 72-2 | 2500 |
| 72-3 | 3800 |
| 73-1 | 2300 |
| 74-2 | 280 |
| 74-4 | 480 |
| 74-5 | 3000 |

(3) CYP4V2 Selectivity Test for Each Compound of the Present Invention

The reaction solution containing each compound [final concentration of 100 mM KPO$_4$ (pH 7.4), 7 μM luciferine derivative, and 1 mM NADPH] was added to a cell membrane fraction (38 μg/mL protein) in which human CYP4V2 had been expressed. Following this, the cell membrane fraction was left to stand at room temperature for 40 minutes to perform an enzymatic reaction. After the reaction, a luciferine detection reagent was added, and the luminescence value was measured using a plate reader. By using that value, the percent inhibition of the enzymatic reaction of CYP4V2(%) was calculated according to the equation described below, and the 50% inhibitory concentration (IC$_{50}$ value) for each compound was calculated.

Percent inhibition of *CYP4V2* enzyme (%)=[1−(*A*−*B*)/(*C*−*B*)]*100

A: Luminescence value with addition of compound
B: Luminescence value without addition of compound and enzyme
C: Luminescence value without addition of compound (4) Results The inhibitory activity of each compound of the present invention against CYP4V2 is shown in Table 71-1 below.

TABLE 71-1

| Example No. | IC$_{50}$ value [nM] |
|---|---|
| 15-1 | 1000 |
| 70-7 | 2900 |
| 70-10-1 | 3300 |
| 71-6 | 1200 |
| 71-18 | 2100 |
| 71-46 | 620 |
| 72-2 | 510 |
| 72-3 | 1500 |
| 73-1 | 660 |
| 74-2 | 2300 |
| 74-4 | 2300 |
| 74-5 | 5000 |

The 90% inhibitory concentration (IC$_{90}$ value) for each compound can be calculated using the same method. It is desirable in some cases to use 90% inhibitory concentration as an index.

Test Example 4

(1) Evaluation Test for In Vivo Stability of Each Compound of the Present Invention Each compound was dissolved in an aqueous solution of 10% HP-β-CD (0.5 mg/mL), and intravenously administered to rats (Sprague-Dawley (SD), male, 7-week-old, fasted, dose: 0.5 mg/kg). Blood was collected from the tail vein at each time of blood collection, and the plasma was collected by centrifugation. Quantitative analysis of each compound in plasma was performed using LC-MS/MS. Half-life in plasma ($t_{1/2eff}$) was calculated from clearance (CL) and distribution volume ($Vd_{ss}$) calculated through noncompartmental analysis with Phoenix WinNonlin (Certara, L.P.), according to the equation described below.

$$t_{1/2eff}=LN(2)/(CL/Vd_{ss})$$

(2) Results

The half-life, $t_{1/2}$, of each compound of the present invention is shown in Table 72-1 below.

TABLE 72-1

| Example No. | $t_{1/2}$eff [h] |
|---|---|
| 15-1 | 2.4 |
| 71-46 | 3.6 |
| 72-2 | 2.4 |
| 72-3 | 1.4 |
| 74-4 | 3.5 |

Some of the compounds of the present invention have high selectivity to CYP4F22 and CYP4V2, which belong to the same family as 20-HETE producing enzymes (CYP4F2 and CYP4A11).

Those compounds are expected to be provided as a medical product having strong drug effect with a small risk of adverse effect.

The efficacy of each compound of the present invention can be confirmed by using a model animal such as a mouse and a rat, for example, by checking suppression of 20-HETE production in the kidney or amelioration of polycystic kidney disease.

INDUSTRIAL APPLICABILITY

The compound of the present invention has an excellent effect of inhibiting 20-HETE producing enzymes, and thus the present invention makes it possible to provide a medical product effective in preventing or treating diseases derived from polycystic kidney disease or the like, and is expected to relieve a burden on the patient and contribute to the development of the pharmaceutical industry.

The invention claimed is:
1. A compound represented by formula [I] shown below:

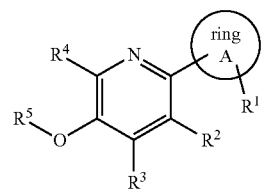

[I]

wherein
the structure represented by formula [II] shown below:

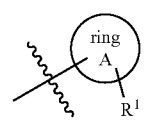

[II]

represents any of the structures represented by formula group [III] shown below:

[III]

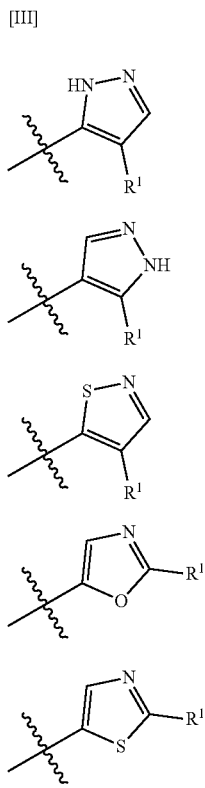

[III-1]

[III-2]

[III-3]

[III-4]

[III-5]

R¹ represents a hydrogen atom, a fluorine atom, a chlorine atom, methyl, or difluoromethyl;

R², R³, and R⁴ each independently represent a hydrogen atom, a fluorine atom, or methyl;

R⁵ represents any of the structures represented by formula group [IV] shown below:

[IV]

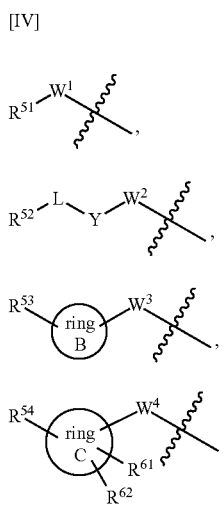

[IV-1]

[IV-2]

[IV-3]

[IV-4]

(A)
when R⁵ represents the structure represented by formula [IV-1],
R⁵¹ represents any of the structures represented by formula group [V] shown below:

[V]

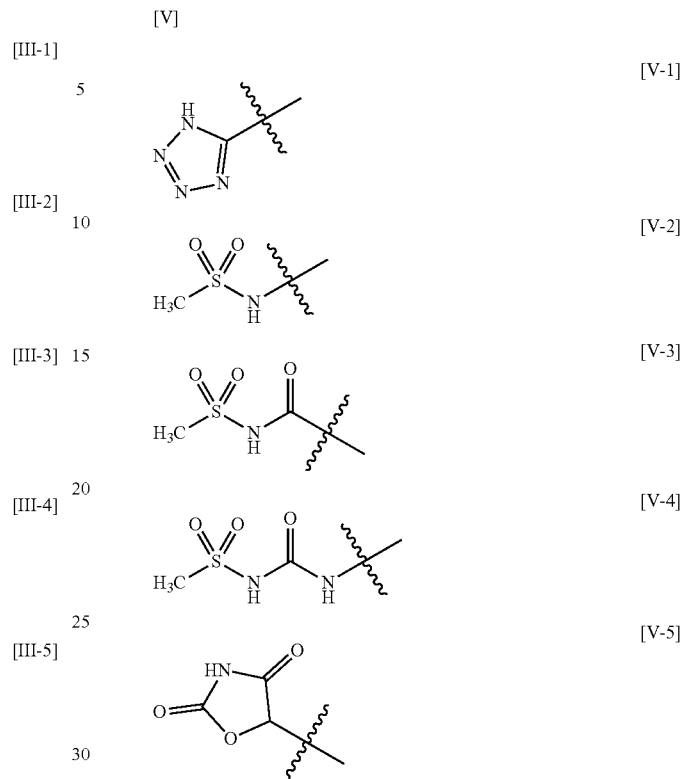

[V-1]

[V-2]

[V-3]

[V-4]

[V-5]

[V-6]

[V-7]

[V-8]

[V-10]

$W^1$ represents $C_{4-10}$alkanediyl;

(B)
when R⁵ represents the structure represented by formula [IV-2],
R⁵² represents carboxy;
L represents any of the structures represented by formula group [VI] shown below:

[VI]

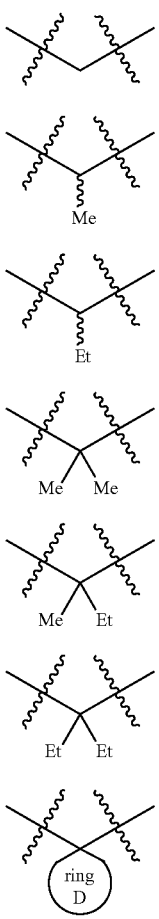

(VI-1)

(VI-2)
Me (VI-3)
Et (VI-4)
Me Me (VI-5)
Me Et (VI-6)
Et Et (VI-7)
ring D wherein
ring D represents
(i) $C_{3-6}$cycloalkane,
(ii) 4- to 6-membered saturated oxygen-containing hetero ring,
(iii) 4- to 6-membered saturated sulfur-containing hetero ring (the sulfur atom of the 4- to 6-membered saturated sulfur-containing hetero ring is unsubstituted or is substituted with one or two oxo),
(iv) 4- to 6-membered saturated nitrogen-containing hetero ring (the nitrogen atom of the 4- to 6-membered nitrogen-containing hetero ring is unsubstituted or is substituted with one $C_{1-4}$alkylcarbonyl);
Y represents the formula —$CH_2$—, the formula —$CMe_2$-, the formula —O—, the formula —NHCO—, the formula —NMeCO—, the formula —CONH—, or the formula —CONMe-;
$W^2$ represents $C_{2-10}$alkanediyl, wherein one of the carbon atoms that constitute the $C_{2-10}$alkanediyl represented by $W^2$ is carbon or is replaced with an oxygen atom;
(C)
when $R^5$ represents the structure represented by formula [IV-3] above,
$R^{53}$ represents carboxy, carboxymethyl, or carboxymethoxy, wherein the methylene moiety of the carboxymethyl or carboxymethoxy that is represented by $R^{53}$ is a methylene or is replaced with a structure selected from structure group α below, structure group α represents any of the structures represented by formula group [VII] below:

[VII]

(VII-1)
Me (VII-2)
Me Me (VII-3)
ring D' wherein
ring D' represents
(i) $C_{3-6}$cycloalkane,
(ii) 4- to 6-membered saturated oxygen-containing hetero ring,
(iii) 4- to 6-membered saturated sulfur-containing hetero ring (the sulfur atom of the 4- to 6-membered saturated sulfur-containing hetero ring is unsubstituted or is substituted with one or two oxo),
(iv) 4- to 6-membered saturated nitrogen-containing hetero ring (the nitrogen atom of the 4- to 6-membered saturated nitrogen-containing hetero ring is unsubstituted or is substituted with one $C_{1-4}$alkylcarbonyl);
ring B represents any of the structures represented by formula group [VIII] below:

[VIII]

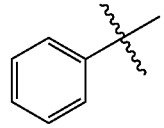

(VIII-1)

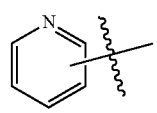

(VIII-2)

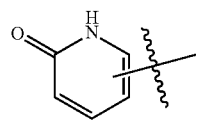

(VIII-3)

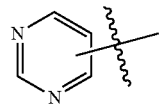

(VIII-4)

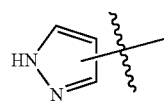

(VIII-5)

-continued

[VIII-6]

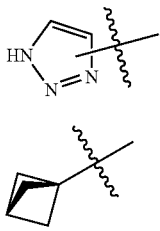

[VIII-7]

$W^3$ represents $C_{4-8}$alkanediyl, the formula —O—$W^{31}$—, or the formula —$SO_2$—$W^{33}$—, wherein $W^{31}$ represents $C_{3-7}$alkanediyl, W33 represents $C_{3-7}$alkanediyl;

(D)

when $R^5$ represents the structure represented by formula [IV-4] above, ring C represents
(a) $C_{3-6}$cycloalkyl,
(b) 4- to 6-membered saturated nitrogen-containing heterocyclyl,
(c) phenyl,
(d) pyridyl,
(e) pyrazolyl,
(f) triazolyl,
(g) tetrahydronaphthyl,
(h) chromanyl,
(j) indazolyl,
(k) tetrahydroisoquinolyl,
(m) 2-oxotetrahydroisoquinolyl,
(n) the structure represented by formula [IX-1] below,
(p) the structure represented by formula [IX-2] below,
(q) the structure represented by formula [IX-3] below, or
(r) the structure represented by formula [IX-4] below:

[IX]

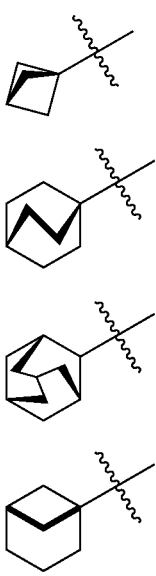

[IX-1]

[IX-2]

[IX-3]

[IX-4]

(a) when ring C represents $C_{3-6}$cycloalkyl,
$R^{54}$ is selected from the group consisting of:
(i) carboxy,
(ii) $C_{1-4}$alkylsulfonylamino,
(iii) $C_{1-4}$alkylsulfonyl($C_{1-4}$alkyl)amino, and
(iv) $C_{1-4}$alkyl substituted with carboxy;
$R^{61}$ and $R^{62}$ represent a hydrogen atom;

(b) when ring C represents 4- to 6-membered saturated nitrogen-containing heterocyclyl,
$R^{54}$ is selected from the group consisting of:
(i) $C_{1-4}$alkylcarbonyl substituted with carboxy,
(ii) $C_{1-4}$alkylcarbonyl substituted with sulfamoyl,
(iii) $C_{1-4}$alkylcarbonyl substituted with $C_{1-4}$alkylsulfonylamino,
(iv) phenylmethylcarbonyl substituted with carboxy,
(v) phenylcarbonyl substituted with sulfamoyl,
(vi) dihydopyridinylcarbonyl substituted with oxo,
(vii) phenylsulfonyl substituted with carboxy,
(viii) mono$C_{1-4}$alkylaminocarbonyl substituted with carboxy,
(ix) the structure represented by formula [X-1] below, which is substituted with carboxy,
(x) the structure represented by formula [X-2] below, which is substituted with carboxy,
(xi) the structure represented by formula [X-3] below, which is substituted with carboxy,

[X]

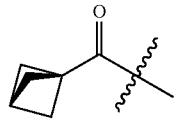

[X-1]

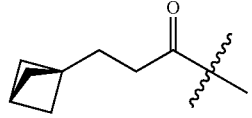

[X-2]

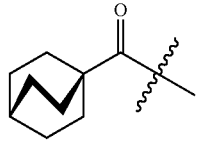

[X-3]

when position α of the carboxy of the $C_{1-4}$alkylcarbonyl substituted with carboxy, the $C_{1-4}$alkylsulfonyl substituted with carboxy, or the mono$C_{1-4}$alkylaminocarbonyl substituted with carboxy is a methylene moiety, said methylene moiety is a methylene or is replaced with a structure selected from structure group α above;

wherein $R^{61}$ and $R^{62}$ represent a hydrogen atom;

(c) when ring C is phenyl,
$R^{54}$ is selected from the group consisting of:
(i) carboxy,
(ii) carbamoyl,
(iii) mono$C_{1-4}$alkylaminocarbonyl (the $C_{1-4}$alkyl of the mono$C_{1-4}$alkylaminocarbonyl is unsubstituted or is substituted with one hydroxy),
(iv) mono$C_{1-4}$alkylaminosulfonyl (the $C_{1-4}$alkyl of the mono$C_{1-4}$alkylaminosulfonyl is unsubstituted or is substituted with one indolyl),
(v) di($C_{1-4}$alkyl)aminosulfonyl (one $C_{1-4}$alkyl of the di($C_{1-4}$alkyl)aminosulfonyl is unsubstituted or is substituted with one phenyl, and the phenyl is unsubstituted or is substituted with one mono$C_{1-4}$alkylaminosulfonyl),
(vi) phenylaminosulfonyl (the phenyl of the phenylaminosulfonyl is unsubstituted or is substituted with one fluorine atom), (vii) $C_{1-4}$alkylsulfonylamino,
(viii) $C_{1-4}$alkylsulfonylaminocarbonyl,
(ix) $C_{1-4}$alkylsulfonyl($C_{1-4}$alkyl)aminocarbonyl,
(x) $C_{1-4}$alkyl substituted with carboxy (when position α of the carboxy of the $C_{1-4}$alkyl substituted with carboxy is a methylene moiety, said methylene moiety is a methylene or is replaced with a structure selected from structure group α above),
(xi) $C_{1-4}$alkyl substituted with methylsulfonylaminocarbonyl,
(xii) $C_{1-4}$alkyl substituted with trifluoromethylsulfonylamino,
(xiii) $C_{1-4}$alkyl substituted with methylsulfonyl(methyl)aminocarbonyl,
(xiv) $C_{1-4}$alkyl substituted with mono$C_{1-4}$alkylaminocarbonyl (the $C_{1-4}$alkyl of the mono$C_{1-4}$alkylaminocarbonyl of the $C_{1-4}$alkyl substituted with mono$C_{1-4}$alkylaminocarbonyl is unsubstituted or is substituted with one group selected from the group consisting of hydroxy, $C_{1-4}$alkoxy, 4- to 6-membered saturated oxygen-containing heterocyclyl, di($C_{1-4}$alkyl)amino, and 4- to 6-membered saturated nitrogen-containing heterocyclylcarbonyl),
(xv) $C_{1-4}$alkyl substituted with di($C_{1-4}$alkyl)aminocarbonyl (one $C_{1-4}$alkyl of the di($C_{1-4}$alkyl)aminocarbonyl of the $C_{1-4}$alkyl substituted with di($C_{1-4}$alkyl)aminocarbonyl is unsubstituted or is substituted with one hydroxy),
(xvi) $C_{1-4}$alkyl substituted with 4- to 6-membered saturated oxygen-containing heterocyclylaminocarbonyl,
(xvii) $C_{1-4}$alkyl substituted with 4- to 6-membered saturated nitrogen-containing heterocyclylcarbonyl (the 4- to 6-membered saturated nitrogen-containing heterocyclyl of the $C_{1}$ 4alkyl substituted with 4- to 6-membered saturated nitrogen-containing heterocyclylcarbonyl is unsubstituted or is substituted with one to two groups selected from the group consisting of hydroxy and a fluorine atom),
(xviii) halo-$C_{1-4}$alkyl substituted with carboxy,
(xix) $C_{2-4}$alkenyl substituted with carboxy,
(xx) $C_{2-4}$alkenyl substituted with di($C_{1-4}$alkyl)aminocarbonyl,
(xxi) $C_{3-6}$cycloalkyl substituted with carboxy,
(xxii) $C_{3-6}$cycloalkyl substituted with di($C_{1-4}$alkyl)aminocarbonyl,
(xxiii) 4- to 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl (the methylene moiety at position α of the carboxy of the pyrazolyl substituted with carboxymethyl is a methylene or is replaced with a structure selected from structure group α above),
(xxviii) pyrimidinyl substituted with carboxy,
(xxix) pyrazinyl substituted with carboxy,
(xxx) 2-oxodihydropyridinyl substituted with carboxymethyl (the methylene moiety at position ca of the carboxy of the 2-oxodihydropyridinyl substituted with carboxymethyl is a methylene or is replaced with a structure selected from structure group α above),
(xxxi) mono$C_{1-4}$alkylaminocarbonyl substituted with carboxy (the $C_{1-4}$alkyl of the mono$C_{1-4}$alkylaminocarbonyl substituted with carboxy is unsubstituted or is substituted with one group selected from the group consisting of phenyl and benzyl, and when position α of the carboxy of the mono$C_{1-4}$alkylaminocarbonyl substituted with carboxy is a methylene moiety, said methylene moiety is a methylene or is replaced with a structure selected from formula group α above),
(xxxii) phenyl$C_{1-4}$alkylaminocarbonyl substituted with carboxy,
(xxxiii) mono$C_{1-4}$alkylaminocarbonyl substituted with the structure represented by formula [V-6] below,

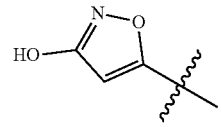

[V-6]

(xxxiv) di($C_{1-4}$alkyl)aminocarbonyl substituted with carboxy (when position α of the carboxy of the di($C_{1-4}$alkyl)aminocarbonyl substituted with carboxy is a methylene moiety, said methylene moiety is a methylene or is replaced with a structure selected from formula group α above),
(xxxv) $C_{3-6}$cycloalkylaminocarbonyl substituted with carboxy,
(xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy is unsubstituted or is substituted with one fluorine atom),
(xxxvii) 4- to 6-membered saturated nitrogen-containing heterocyclylcarbonyl substituted with carboxymethyl (the methylene moiety at position α of the carboxy of the 4- to 6-membered saturated nitrogen-containing heterocyclylcarbonyl substituted with carboxymethyl is a methylene or is replaced with a structure selected from structure group α above),
(xxxviii) the structure represented by formula [XI-1] below, which is substituted with carboxy,
(xxxix) the structure represented by formula [XI-2] below, which is substituted with carboxy,
(xxxx) the structure represented by formula [XI-3] below, which is substituted with carboxy,
(xxxxi) the structure represented by formula [XI-4] below, which is substituted with carboxy,
(xxxxii) the structure represented by formula [XI-5] below, which is substituted with carboxy,
(xxxxiii) the structure represented by formula [XI-6] below, which is substituted with carboxy,

[XI]

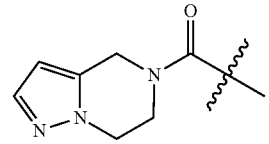

[XI-1]

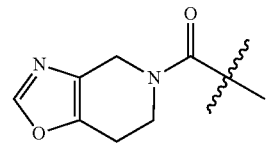

[XI-2]

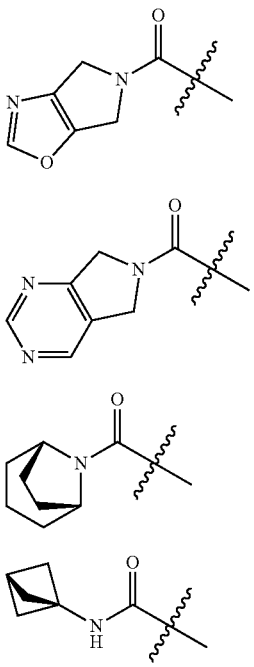

(xxxiv) $C_{1-4}$alkylsulfonyl substituted with carboxy (when position α of the carboxy of the $C_{1-4}$alkylsulfonyl substituted with carboxy is a methylene moiety, said methylene moiety is a methylene or is replaced with a structure selected from structure group α above), (xxxv) mono$C_{1-4}$alkylaminosulfonyl substituted with carboxy (when position α of the carboxy of the mono$C_{1-4}$alkylaminosulfonyl substituted with carboxy is a methylene moiety, said methylene moiety is a methylene or is replaced with a structure selected from structure group cc above), (xxxvi) di($C_{1-4}$alkyl)aminosulfonyl substituted with carboxy (when position α of the carboxy of the di($C_{1-4}$alkyl)aminosulfonyl substituted with carboxy is a methylene moiety, said methylene moiety is a methylene or is replaced with the structure selected from structure group α above), (xxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy is unsubstituted or is substituted with one fluorine atom), (xxxviii) $C_{1-4}$alkoxy substituted with carboxy (when position α of the carboxy of the $C_{1-4}$alkoxy substituted with carboxy is a methylene moiety, said methylene moiety is a methylene or is replaced with a structure selected from structure group α above), (xxxix) hydroxy, (xxxxx) $C_{1-4}$alkylsulfonyloxy, (xxxxxi) $C_{1-4}$alkyl substituted with hydroxy, (xxxxxii) halo-$C_{1-4}$alkyl substituted with hydroxy, (xxxxxiii) $C_{1-4}$alkylsulfonyl substituted with hydroxy, (xxxxxiv) $C_{3-6}$cycloalkyl substituted with hydroxy (the $C_{3-6}$cycloalkyl of the $C_{3-6}$cycloalkyl substituted with hydroxy is unsubstituted or is substituted with one group selected from the group consisting of carboxy and di($C_{1-4}$alkyl)aminocarbonyl), or (xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy is unsubstituted or is substituted with one group selected from the group consisting of $C_{1-4}$alkylcarbonyl, $C_{1-4}$alkoxycarbonyl, and di($C_{1-4}$alkyl)aminocarbonyl);

wherein $R^{61}$ and $R^{62}$ each independently represent a hydrogen atom, a fluorine atom, a chlorine atom, methyl, methoxy, or methylsulfonyl;

(d) when ring C is pyridyl, $R^{54}$ is selected from the group consisting of:

(i) carboxy, (ii) carbamoyl, (iii) $C_{1-4}$alkyl substituted with carboxy, (iv) $C_{1-4}$alkoxy substituted with carboxy, (v) mono$C_{1-4}$alkylaminocarbonyl substituted with carboxy, and (vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy is unsubstituted or is substituted with one fluorine atom), wherein when position α of the carboxy of the $C_{1-4}$alkyl substituted with carboxy, the $C_{1-4}$alkoxy substituted with carboxy, or the mono$C_{1-4}$alkylaminocarbonyl substituted with carboxy is a methylene moiety, said methylene moiety is a methylene or is replaced with a structure selected from structure group α above);

and wherein $R^{61}$ and $R^{62}$ represent a hydrogen atom;

(e) when ring C is pyrazolyl, $R^{54}$ represents carboxy;

wherein $R^{61}$ and $R^{62}$ represent a hydrogen atom;

(f) when ring C is triazolyl, $R^{54}$ represents $C_{1-4}$alkyl substituted with carboxy, wherein when position α of the carboxy of the $C_{1-4}$alkyl substituted with carboxy is a methylene moiety, said methylene moiety is a methylene or is replaced with a structure selected from structure group α above;

wherein $R^{61}$ and $R^{62}$ represent a hydrogen atom;

(g) when ring C is tetrahydronaphthyl, $R^{54}$ is carboxy;

wherein $R^{61}$ and $R^{62}$ represent a hydrogen atom;

(h) when ring C is chromanyl, $R^{54}$ is carboxy;

wherein $R^{61}$ and $R^{62}$ represent a hydrogen atom;

(j) when ring C is indazolyl, $R^{54}$ represents $C_{1-4}$alkyl substituted with carboxy, wherein when position α of the carboxy of the $C_{1-4}$alkyl substituted with carboxy is a methylene moiety, said methylene moiety is a methylene or is replaced with a structure selected from structure group α above;

wherein $R^{61}$ and $R^{62}$ represent a hydrogen atom;

(k) when ring C is tetrahydroisoquinolyl, $R^{54}$ represents $C_{1-4}$alkylcarbonyl substituted with carboxy, wherein position α of the carboxy of the $C_{1-4}$alkylcarbonyl substituted with carboxy is a methylene moiety, said methylene moiety is a methylene or is replaced with a structure selected from structure group α above;

wherein $R^{61}$ and $R^{62}$ represent a hydrogen atom;

(m) when ring C is 2-oxotetrahydroisoquinolyl, $R^{54}$ represents $C_{1-4}$alkyl substituted with carboxy, wherein position α of the carboxy of the $C_{1-4}$alkyl substituted with carboxy is a methylene moiety, said methylene moiety is a methylene or is replaced with a structure selected from structure group α above;
wherein R⁶¹ and R⁶² represent a hydrogen atom;
(n) when ring C is the structure represented by formula [IX-1] above,
R⁵⁴ is selected from the group consisting of:
(i) carboxy,
(ii) $C_{1-4}$alkyl substituted with $C_{1-4}$alkylsulfonylamino, and
(iii) $C_{1-4}$alkyl substituted with $C_{1-4}$alkylsulfonyl($C_{1-4}$alkyl)amino
wherein when R⁵⁴ represents (ii) $C_{1-4}$alkyl substituted with $C_{1-4}$alkylsulfonylamino and the $C_{1-4}$alkyl of the $C_{1-4}$alkylsulfonylamino of the $C_{1-4}$alkyl substituted with $C_{1-4}$alkylsulfonylamino is substituted with one carboxy and if position α of the carboxy of the $C_{1-4}$alkylsulfonylamino substituted with carboxy is a methylene moiety, said methylene moiety is a methylene or is replaced with a structure selected from structure group α above;
wherein R⁶¹ and R⁶² represent a hydrogen atom;
(p) when ring C is the structure represented by formula [IX-2] above,
R⁵⁴ is selected from the group consisting of:
(i) carboxy, and
(ii) $C_{1-4}$alkyl substituted with carboxy,
wherein when position α of the carboxy of the $C_{1-4}$alkyl substituted with carboxy is a methylene moiety, said methylene moiety is a methylene or is replaced with a structure selected from structure group α above;
and wherein R⁶¹ and R⁶² represent a hydrogen atom;
(q) when ring C is the structure represented by formula [IX-3] above,
R⁵⁴ represents carboxy;
wherein R⁶¹ and R⁶² represent a hydrogen atom;
(r) when ring C is the structure represented by formula [IX-4] above,
R⁵⁴ represents carboxy;
wherein R⁶¹ and R⁶² represent a hydrogen atom;
W⁴ represents a single bond, $C_{1-3}$alkanediyl, or the formula —O—CH₂CH₂—;
or a pharmaceutically acceptable salt thereof.

2. The compound according to claim 1,
wherein as regards R⁵ of formula [I] above,
(A)
when R⁵ is the structure represented by formula [IV-1] above,
R⁵¹ represents any of the structures represented by formula group [V''] below:

[V'']

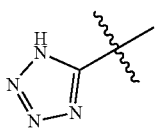

[V-1]

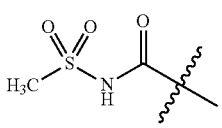

[V-3]

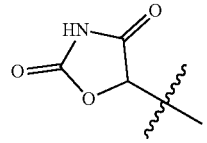

[V-5]

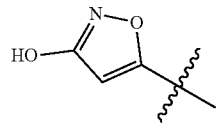

[V-6]

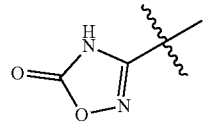

[V-7]

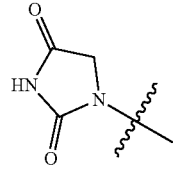

[V-8]

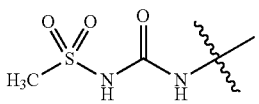

[V-4]

W¹ represents $C_{4-10}$alkanediyl;
(B)
when R⁵ represents the structure represented by formula [IV-2] above,
R⁵² represents carboxy,
L represents any of the structures represented by formula group [VI'] below:

[VI']

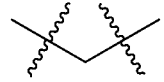

(VI-1)

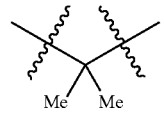

[VI-4]

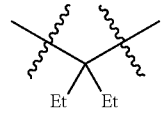

[VI-6]

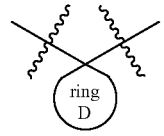

[VI-7]

wherein ring D is $C_{3-6}$cycloalkane, 4- to 6-membered saturated oxygen-containing hetero ring, or 4- to 6-membered saturated nitrogen-containing hetero ring (the nitrogen atom of the 4- to 6-membered saturated nitrogen-containing hetero ring is unsubstituted or is substituted with $C_{1-4}$alkylcarbonyl);
Y represents the formula —CH₂—, the formula —CMe₂-, the formula —O—, the formula —NHCO—, the formula —CONH—, or the formula —CONMe-, W² represents C₂₋₈alkanediyl, wherein one of the carbon atoms that constitute the C₂₋₈alkanediyl represented by W² is a carbon atom or is replaced with an oxygen atom;

(C)

when R⁵ represents the structure represented by formula [IV-3] above,

R⁵³ represents carboxy, carboxymethyl, or carboxymethoxy, wherein the methylene moiety of the carboxymethyl and carboxymethoxy represented by R⁵³ is a methylene or is replaced with propane-2,2-diyl;

ring B represents any of the structures represented by formula group [VIII] below:

[VIII]

[VIII-1]

[VIII-2]

[VIII-3]

[VIII-4]

[VIII-5]

[VIII-6]

[VIII-7]

W³ represents C₄₋₈alkanediyl, or the formula —SO₂—W³³—,

W³³ represents C₃₋₇alkanediyl;

(D)

when R⁵ is the structure represented by formula [IV-4] above, ring C represents:

(a) C₃₋₆cycloalkyl,
(b) 4- to 6-membered saturated nitrogen-containing heterocyclyl,
(c) phenyl,
(d) pyridyl,
(e) pyrazolyl,
(g) tetrahydronaphthyl,
(h) chromanyl,
(j) indazolyl,
(n) the structure represented by formula [IX-1] below,
(p) the structure represented by formula [IX-2] below,
(q) the structure represented by formula [IX-3] below, or
(r) the structure represented by formula [IX-4] below,

[IX]

[IX-1]

[IX-2]

[IX-3]

[IX-4]

wherein
(a) when ring C represents C₃₋₆cycloalkyl,
R⁵⁴ represents
(i) carboxy or
(iv) C₁₋₄alkyl substituted with carboxy,
wherein R⁶¹ and R⁶² represent a hydrogen atom;
(b) when ring C represents 4- to 6-membered saturated nitrogen-containing heterocyclyl,
R⁵⁴ represents:
(i) C₁₋₄alkylcarbonyl substituted with carboxy (when position α of the carboxy of the C₁₋₄alkylcarbonyl substituted with carboxy is a methylene moiety, said methylene moiety is a methylene or is replaced with C₅cycloalkanediyl),
(ii) C₁₋₄alkylcarbonyl substituted with sulfamoyl,
(iv) phenylmethylcarbonyl substituted with carboxy,
(v) phenylcarbonyl substituted with sulfamoyl,
(vi) dihydropyridinylcarbonyl substituted with oxo,
(vii) phenylsulfonyl substituted with carboxy,
(viii) mono-C₁₋₄alkylaminocarbonyl substituted with carboxy (when position α of the carboxy of mono-C₁₋₄alkylaminocarbonyl substituted with carboxy is a methylene moiety, said methylene moiety is a methylene or is replaced with propane-2,2-diyl), and
(x) the structure represented by formula [X-2] below, which is substituted with carboxy:

[X-2]

wherein R⁶¹ and R⁶² represent a hydrogen atom;
(c) when ring C is phenyl,
R⁵⁴ represents:
(i) carboxy,
(ii) carbamoyl,
(iii) mono-$C_{1-4}$alkylaminocarbonyl (the $C_{1-4}$alkyl of the mono-$C_{1-4}$alkylaminocarbonyl is unsubstituted or is substituted with one hydroxy),
(iv) mono-$C_{1-4}$alkylaminosulfonyl,
(v) di($C_{1-4}$alkyl)aminosulfonyl (one $C_{1-4}$alkyl of the di($C_{1-4}$alkyl)aminosulfonyl is substituted with one phenyl, wherein said phenyl is unsubstituted or is substituted with one mono-$C_{1-4}$alkylaminosulfonyl),
(vi) phenylaminosulfonyl (the phenyl of the phenylaminosulfonyl is unsubstituted or is substituted with one fluorine atom),
(vii) $C_{1-4}$alkylsulfonylamino,
(viii) $C_{1-4}$alkylsulfonylaminocarbonyl,
(ix) $C_{1-4}$alkylsulfonyl($C_{1-4}$alkyl)aminocarbonyl,
(x) $C_{1-4}$alkyl substituted with carboxy (when position α of the carboxy of the $C_{1-4}$alkyl substituted with carboxy is a methylene moiety, said methylene moiety is a methylene or is replaced with a structure selected from the group consisting of ethane-1,1-diyl, propane-2,2-diyl, cyclopropane-1,1-diyl, tetrahydropyran-4,4-diyl, and piperidine-4,4-diyl (the nitrogen atom of the piperidine-4,4-diyl is substituted with methylcarbonyl)),
(xi) $C_{1-4}$alkyl substituted with methylsulfonylaminocarbonyl,
(xii) $C_{1-4}$alkyl substituted with trifluoromethylsulfonylamino,
(xiii) $C_{1-4}$alkyl substituted with methylsulfonyl(methyl)aminocarbonyl,
(xiv) $C_{1-4}$alkyl substituted with mono-$C_{1-4}$alkylaminocarbonyl (the $C_{1-4}$alkyl of the mono-$C_{1-4}$alkylaminocarbonyl of the $C_{1-4}$alkyl substituted with mono-$C_{1-4}$alkylaminocarbonyl is unsubstituted or is substituted with one group selected from the group consisting of hydroxy, $C_{1-4}$alkoxy, 4- to 6-membered saturated oxygen-containing heterocyclyl, di($C_{1-4}$alkyl)amino, and 4- to 6-membered saturated nitrogen-containing heterocyclylcarbonyl),
(xv) $C_{1-4}$alkyl substituted with di($C_{1-4}$alkyl)aminocarbonyl (one $C_{1-4}$alkyl of the di($C_{1-4}$alkyl)aminocarbonyl of the $C_{1-4}$alkyl substituted with di($C_{1-4}$alkyl)aminocarbonyl is unsubstituted or is substituted with one hydroxy),
(xvi) $C_{1-4}$alkyl substituted with 4- to 6-membered saturated oxygen-containing heterocyclylaminocarbonyl,
(xvii) $C_{1-4}$alkyl substituted with 4- to 6-membered saturated nitrogen-containing heterocyclylcarbonyl (the 4- to 6-membered saturated nitrogen-containing heterocyclyl of the $C_{1-4}$alkyl substituted with 4- to 6-membered saturated nitrogen-containing heterocyclylcarbonyl is unsubstituted or is substituted with one to two groups selected from the group consisting of hydroxy and a fluorine atom),
(xviii) halo-$C_{1-4}$alkyl substituted with carboxy,
(xix) $C_{2-4}$alkenyl substituted with carboxy,
(xx) $C_{2-4}$alkenyl substituted with di($C_{1-4}$alkyl)aminocarbonyl,
(xxi) $C_{3-6}$cycloalkyl substituted with carboxy,
(xxii) $C_{3-6}$cycloalkyl substituted with di($C_{1-4}$alkyl)aminocarbonyl,
(xxiii) 4- to 6-membered saturated nitrogen-containing heterocyclyl substituted with carboxy,
(xxiv) phenyl substituted with carboxy,
(xxv) pyridyl substituted with carboxy,
(xxvi) pyrazolyl substituted with carboxy,
(xxvii) pyrazolyl substituted with carboxymethyl,
(xxviii) pyrimidinyl substituted with carboxy,
(xxix) pyrazinyl substituted with carboxy,
(xxx) 2-oxodihydropyridinyl substituted with carboxymethyl,
(xxxi) mono-$C_{1-4}$alkylaminocarbonyl substituted with carboxy (the $C_{1-4}$ alkyl of the mono-$C_{1-4}$alkylaminocarbonyl substituted with carboxy is unsubstituted or is substituted with one group selected from the group consisting of phenyl and benzyl, wherein when position α of the carboxy of the mono-$C_{1-4}$alkylaminocarbonyl substituted with carboxy is a methylene moiety, said methylene moiety is a methylene or is replaced with a structure selected from the group consisting of ethane-1,1-diyl, propane-2,2-diyl, cyclopropane-1,1-diyl, cyclopentane-1,1-diyl, and tetrahydropyran-4,4-diyl),
(xxxii) phenyl$C_{1-4}$alkylaminocarbonyl substituted with carboxy,
(xxxiii) mono-$C_{1-4}$alkylaminocarbonyl substituted with the structure represented by formula [V-6] below:

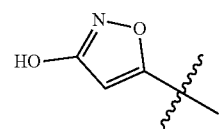

[V-6]

(xxxiv) di($C_{1-4}$alkyl)aminocarbonyl substituted with carboxy (when position α of the carboxy of the di($C_{1-4}$alkyl)aminocarbonyl substituted with carboxy is a methylene moiety, said methylene moiety is a methylene or is replaced with propane-2,2-diyl),
(xxxv) $C_{3-6}$cycloalkylaminocarbonyl substituted with carboxy,
(xxxvi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy is unsubstituted or is substituted with one fluorine atom),
(xxxvii) 4- to 6-membered saturated nitrogen-containing heterocyclylcarbonyl substituted with carboxymethyl,
(xxxviii) the structure represented by formula [XI-1] below, which is substituted with carboxy,
(xxxix) the structure represented by formula [XI-2] below, which is substituted with carboxy,
(xxxx) the structure represented by formula [XI-3] below, which is substituted with carboxy,
(xxxxiii) the structure represented by formula [XI-6] below, which is substituted with carboxy,

[XI']

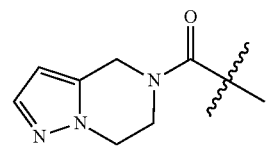

[XI-1]

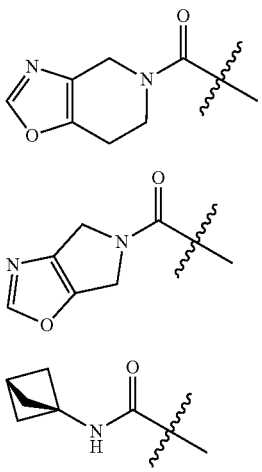

[XI-2]

[XI-3]

[XI-6]

(xxxiv) $C_{1-4}$alkylsulfonyl substituted with carboxy (when position α of the carboxy of the $C_{1-4}$alkylsulfonyl substituted with carboxy is a methylene moiety, said methylene moiety is a methylene or is replaced with propane-2,2-diyl), (xxxv) mono-$C_{1-4}$alkylaminosulfonyl substituted with carboxy (when position α of the carboxy of the mono-$C_{1-4}$alkylaminosulfonyl substituted with carboxy is a methylene moiety, said methylene moiety is a methylene or is replaced with propane-2,2-diyl), (xxxvi) di($C_{1-4}$alkyl)aminosulfonyl substituted with carboxy (when position α of the carboxy of the di($C_{1-4}$alkyl)aminosulfonyl substituted with carboxy is a methylene moiety, said methylene moiety is a methylene or is replaced with propane-2,2-diyl), (xxxvii) 4- to 6-membered saturated nitrogen-containing heterocyclylsulfonyl substituted with carboxy (the 4- to 6-membered saturated nitrogen-containing heterocyclyl of the 4- to 6-membered saturated nitrogen-containing heterocyclylsulfonyl substituted with carboxy is unsubstituted or is substituted with one fluorine atom), (xxxviii) $C_{1-4}$alkoxy substituted with carboxy (when position α of the carboxy of the $C_{1-4}$alkoxy substituted with carboxy is a methylene moiety, said methylene moiety is a methylene or is replaced with propane-2, 2-diyl), (xxxix) hydroxy, (xxxxx) $C_{1-4}$alkylsulfonyloxy, (xxxxxi) $C_{1-4}$alkyl substituted with hydroxy, (xxxxxii) halo-$C_{1-4}$alkyl substituted with hydroxy, (xxxxxiii) $C_{1-4}$alkylsulfonyl substituted with hydroxy, (xxxxxiv) $C_{3-6}$cycloalkyl substituted with hydroxy (the $C_{3-6}$cycloalkyl of the $C_{3-6}$cycloalkyl substituted with hydroxy is unsubstituted or is substituted with one group selected from the group consisting of carboxy and di($C_{1-4}$alkyl)aminocarbonyl), or (xxxxxv) 4- to 6-membered saturated nitrogen-containing heterocyclyl substituted with hydroxy (the nitrogen atom of the 4- to 6-membered saturated nitrogen-containing heterocyclyl substituted with hydroxy is unsubstituted or is substituted with one group selected from the group consisting of $C_{1-4}$alkylcarbonyl, $C_{1-4}$alkoxycarbonyl, and di($C_{1-4}$alkyl)aminocarbonyl), wherein $R^{61}$ and $R^{62}$ each independently represent a hydrogen atom, a fluorine atom, a chlorine atom, methyl, methoxy, or methylsulfonyl;

(d) when ring C is pyridyl, $R^{54}$ represents:
(i) carboxy,
(ii) carbamoyl,
(iii) $C_{1-4}$alkyl substituted with carboxy (when position α of the carboxy of the $C_{1-4}$alkyl substituted with carboxy is a methylene moiety, said methylene moiety is a methylene or is replaced with propane-2,2-diyl),
(iv) $C_{1-4}$alkoxy substituted with carboxy (when position α of the carboxy of the $C_{1-4}$alkoxy substituted with carboxy is a methylene moiety, said methylene moiety is a methylene or is replaced with propane-2,2-diyl),
(v) mono-$C_{1-4}$alkylaminocarbonyl substituted with carboxy (when position α of the carboxy of the mono-$C_{1-4}$alkylaminocarbonyl substituted with carboxy is a methylene moiety, said methylene moiety is a methylene or is replaced with propane-2,2-diyl) or,
(vi) 4- to 6-membered saturated nitrogen-containing heterocyclylcarbonyl substituted with carboxy (the 4- to 6-membered saturated nitrogen-containing heterocyclyl of the 4- to 6-membered saturated nitrogen-containing heterocyclylcarbonyl substituted with carboxy is unsubstituted or is substituted with one fluorine atom),
wherein $R^{61}$ and $R^{62}$ represent a hydrogen atom;
(e) when ring C is pyrazolyl,
$R^{54}$ represents carboxy,
wherein $R^{61}$ and $R^{62}$ represent a hydrogen atom;
(g) when ring C is tetrahydronaphthyl,
$R^{54}$ represents carboxy,
wherein $R^{61}$ and $R^{62}$ represent a hydrogen atom;
(h) when ring C is chromanyl,
$R^{54}$ represents carboxy,
wherein $R^{61}$ and $R^{62}$ represent a hydrogen atom;
(j) when ring C is indazolyl,
$R^{54}$ represents $C_{1-4}$alkyl substituted with carboxy,
wherein $R^{61}$ and $R^{62}$ represent a hydrogen atom;
(n) when ring C is the structure represented by formula [IX-1] above,
$R^{54}$ represents:
(i) carboxy,
(ii) $C_{1-4}$alkyl substituted with $C_{1-4}$alkylsulfonylamino, or
(iii) $C_{1-4}$alkyl substituted with $C_{1-4}$alkylsulfonyl($C_{1-4}$alkyl)amino,
wherein $R^{61}$ and $R^{62}$ represent a hydrogen atom;
(p) when ring C is the structure represented by formula [IX-2] above,
$R^{54}$ is selected from the group consisting of:
(i) carboxy, and
(ii) $C_{1-4}$alkyl substituted with carboxy,
wherein $R^{61}$ and $R^{62}$ represent a hydrogen atom;
(q) when ring C is the structure represented by formula [IX-3] above,
$R^{54}$ represents carboxy,
wherein $R^{61}$ and $R^{62}$ represent a hydrogen atom;
(r) when ring C is the structure represented by formula [IX-4] above,
$R^{54}$ represents carboxy,
wherein $R^{61}$ and $R^{62}$ represent a hydrogen atom;
$W^4$ is $C_{1-3}$alkanediyl or the formula —O—$CH_2CH_2$—;
or a pharmaceutically acceptable salt thereof.

3. The compound according to claim 1,
wherein as regards $R^5$ of formula [I] above,
(A) when $R^5$ represents the structure represented by formula [IV-1] above,
$R^{51}$ represents any of the structures represented by formula group [V'''] below,

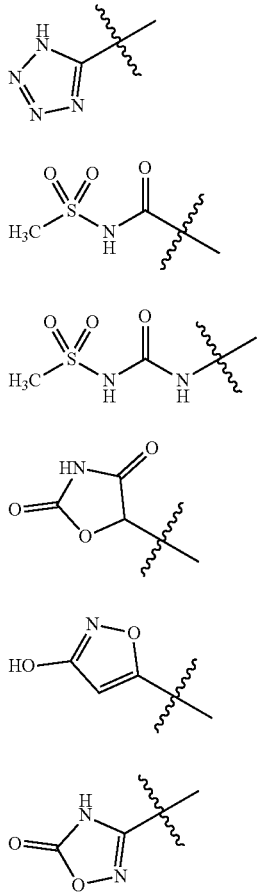

[V″′]

[V-1]

[V-3]

[V-4]

[V-5]

[V-6]

[V-7]

W$^1$ represents butane-1,4-diyl, or pentane-1,5-diyl;

(B) when R$^5$ represents the structure represented by formula [IV-2] above,

R$^{52}$ represents carboxy,

L represents the structure represented by formula [VI-1], formula [VI-4], formula [VI-8], formula [VI-9], formula [VI-10], or formula [VI-12] below:

[VI-1]

[VI-4]

[VI-8]

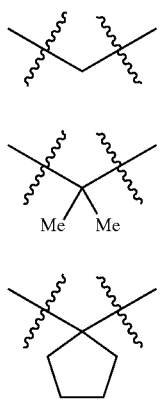

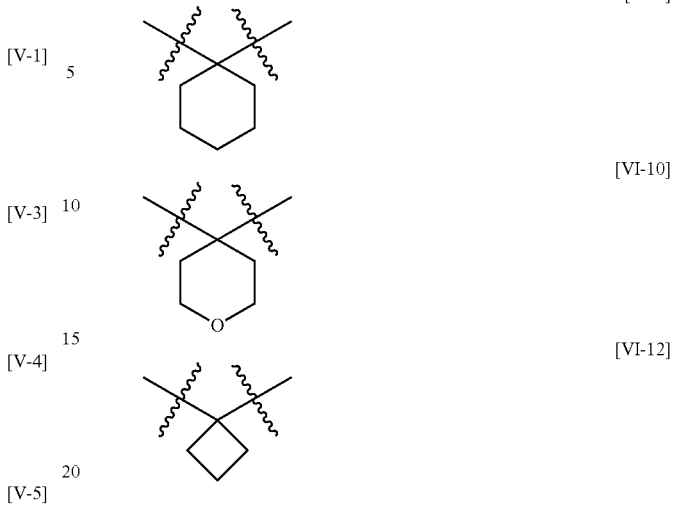

[VI-9]

[VI-10]

[VI-12]

Y represents the formula —CH$_2$—, the formula —CMe$_2$-, the formula —O—, the formula —NHCO—, or the formula —CONMe-, W$^2$ represents propane-1,3-diyl, butane-1,4-diyl, pentane-1,5-diyl, hexane-1,6-diyl, heptane-1,7-diyl, or the formula —O—(CH$_2$)$_6$—;

(C) when R$^5$ represents the structure represented by formula [IV-3] above,

R$^{53}$ represents carboxy, carboxymethyl (the methylene moiety of the carboxymethyl is a methylene or is replaced with propane-2,2-diyl) or carboxymethoxy (the methylene moiety of the carboxymethoxy is substituted with propane-2,2-diyl);

ring B represents the structure represented by formula [VIII-1], formula [VIII-8], formula [VIII-9], formula [VIII-11], formula [VIII-12], formula [VIII-14], formula [VIII-13], or formula [VIII-7] below,

[VIII-1]

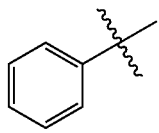

[VIII-8]

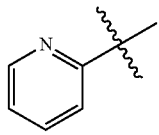

[VIII-9]

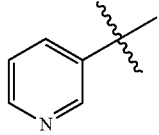

[VIII-11]

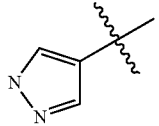

-continued

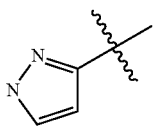
[VIII-12]

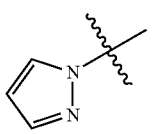
[VI-14]

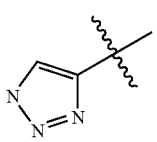
[VIII-13]

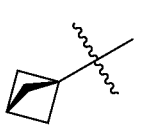
[VIII-7]

W³ represents butane-1,4-diyl, or hexane-1,6-diyl;

(D) when R⁵ represents the structure represented by formula [IV-4] above, ring C represents:

(a) $C_{3-6}$cycloalkyl, (b) 4- to 6-membered saturated nitrogen-containing heterocyclyl, (c) phenyl, (d) pyridyl, (g) tetrahydronaphthyl, (h) chromanyl, (j) indazolyl, (p) the structure represented by formula [IX-2] below, (q) the structure represented by formula [IX-3] below, or (r) the structure represented by formula [IX-4] below,

[IX']

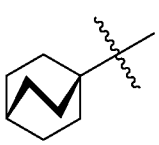
[IX-2]

[IX-3]

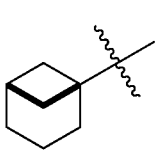
[IX-4]

wherein (a) when ring C is $C_{3-6}$cycloalkyl,
ring C is cyclopropyl, cyclobutyl, or cyclohexyl,
R⁵⁴ represents:
(i) carboxy, or
(iv) methyl substituted with carboxy, or ethyl substituted with carboxy,
wherein R⁶¹ and R⁶² represent a hydrogen atom;

(b) when ring C is 4- to 6-membered saturated nitrogen-containing heterocyclyl,
ring C is pipieridin-3-yl;
R⁵⁴ represents:
(i) ethylcarbonyl substituted with carboxy, n-butylcarbonyl substituted with carboxy (the methylene moiety at position α of the carboxy of the n-butylcarbonyl substituted with carboxy is replaced with cyclopentane-1,1-diyl)
or
(vii) phenylsulfonyl substituted with carboxy;
wherein R⁶¹ and R⁶² represent a hydrogen atom;

(c) when ring C is phenyl,
R⁵⁴ represents:
(i) carboxy,
(ii) carbamoyl,
(iii) n-propylaminocarbonyl,
(iv) methylaminosulfonyl,
(v) dimethylaminosulfonyl (one methyl of the dimethylaminosuflonyl is substituted with one phenyl, wherein the phenyl is substituted with one methylaminosulfonyl),
(vii) isopropylsulfonylamino,
(viii) methylsulfonylaminocarbonyl,
(x) methyl substituted with carboxy (the methylene moiety at position α of the carboxy of the methyl substituted with carboxy is a methylene or is replaced with ethane-1,1-diyl, propane-2,2-diyl, cyclopropane-1,1-diyl, tetrahydropyran-4,4-diyl, or piperidine-4,4-diyl, wherein the nitrogen atom of the piperidine-4,4-diyl is substituted with one methylcarbonyl), ethyl substituted with carboxy, n-propyl substituted with carboxy, or n-butyl substituted with carboxy,
(xi) methyl substituted with methylsulfonylaminocarbonyl, or ethyl substituted with methylsulfonylaminocarbonyl,
(xii) methyl substituted with trifluoromethylsulfonylamino,
(xiv) ethyl substituted with methylaminocarbonyl (the methyl of the ethyl substituted with methylaminocarbonyl is unsubstituted or is substituted with tetrahydrofuranyl), ethyl substituted with ethylaminocarbonyl (the ethyl of the ethylaminocarbonyl of the ethyl substituted with ethylaminocarbonyl is substituted with one group selected from the group consisting of hydroxy and methoxy), ethyl substituted with n-propylaminocarbonyl (the n-propyl of the ethyl substituted with n-propylaminocarbonyl is unsubstituted or is substituted with one group selected from the group consisting of hydroxy and methoxy), or ethyl substituted with isopropylaminocarbonyl (the isopropyl of the ethyl substituted with isopropylaminocarbonyl is substituted with one hydroxy),
(xv) ethyl substituted with dimethylaminocarbonyl,
(xvi) ethyl substituted with oxetanylaminocarbonyl,
(xvii) ethyl substituted with azetidinylcarbonyl (the azetidinyl of the ethyl substituted with azetidinylcarbonyl is unsubstituted or is substituted with one to two groups selected from the group consisting of hydroxy and a fluorine atom) or ethyl substituted with pyrrolidinylcarbonyl, (xviii) halo-methyl substituted with carboxy, (xix) ethenyl substituted with carboxy, (xxi) cyclopropyl substituted with carboxy, or cyclohexyl substituted with carboxy, (xxii) cyclopropyl substituted with dimethylaminocarbonyl, (xxiii) piperidinyl substituted with carboxy, (xxiv) phenyl substituted with carboxy, (xxv) pyridyl substituted with carboxy, (xxvi) pyrazolyl substituted with carboxy, (xxvii) pyrazolyl substituted with carboxymethyl, (xxviii) pyrimidinyl substituted with carboxy, (xxix) pyrazinyl substituted with carboxy, (xxx) 2-oxodihydropyridinyl substituted with carboxymethyl, (xxxi) methylaminocarbonyl substituted with carboxy (the methyl of the methylaminocarbonyl substituted with carboxy is unsubstituted or is substituted with one benzyl, and the methylene moiety at position α of the carboxy of the methylaminocarbonyl substituted with carboxy is a methylene or is replaced with ethane-1,1-diyl), ethylaminocarbonyl substituted with carboxy (the ethyl of the ethylaminocarbonyl substituted with carboxy is unsubstituted or is substituted with one phenyl, and the methylene moiety at position α of the carboxy of the ethylaminocarbonyl substituted with carboxy is a methylene or is replaced with a structure selected from the group consisting of propane-2,2-diyl, cyclopropane-1,1-diyl, and cyclopentane-1,1-diyl), or n-propylaminocarbonyl substituted with carboxy (the methylene moiety at position α of the carboxy of the n-propylaminocarbonyl substituted with carboxy is replaced with propane-2,2-diyl), (xxxii) phenylmethylaminocarbonyl substituted with carboxy, (xxxiii) monomethylaminocarbonyl substituted with the structure represented by formula [V-6] below,

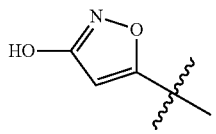

[V-6]

(xxxiv) ethyl(methyl)aminocarbonyl substituted with carboxy, (xxxv) cyclobutylaminocarbonyl substituted with carboxy, (xxxvi) pyrrolidinylcarbonyl substituted with carboxy (the pyrrolidinyl of the pyrrolidinylcarbonyl substituted with carboxy is substituted with one fluorine atom), or piperidinylcarbonyl substituted with carboxy, (xxxviii) the structure represented by formula [XI-1] below, which is substituted with carboxy, (xxxix) the structure represented by formula [XI-2] below, which is substituted with carboxy,

[XI″]

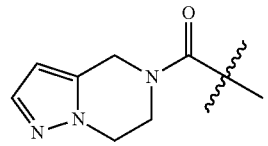

[XI-1]

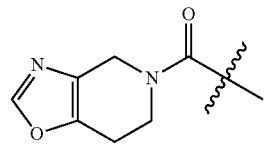

[XI-2]

(xxxiv) ethylsulfonyl substituted with carboxy, or n-butylsulfonyl substituted with carboxy (the methylene moiety at position α of carboxy of the n-butylsulfonyl substituted with carboxy is replaced with propane-2,2-diyl), (xxxv) mono-n-propylaminosulfonyl substituted with carboxy (the methylene moiety at position α of the carboxy of the mono-n-propylaminosuflonyl substituted with carboxy is replaced with propane-2,2-diyl), (xxxvi) n-propyl(methyl)aminosulfonyl substituted with carboxy (the methylene moiety at position α of the carboxy of the n-propyl(methyl)aminosulfonyl substituted with carboxy is replaced with propane-2,2-diyl), (xxxvii) pyrrolidinylsulfonyl substituted with carboxy (the pyrrolidinyl of the pyrrolidinylsulfonyl substituted with carboxy is unsubstituted or is substituted with one fluorine atom), piperidinylsulfonyl substituted with carboxy, or morpholinylsulfonyl substituted with carboxy, (xxxviii) methoxy substituted with carboxy (the methylene moiety at position α of the carboxy of the methoxy substituted with carboxy is a methylene or is replaced with propane-2,2-diyl), (xxxix) hydroxy, (xxxxi) isopropyl substituted with hydroxy, (xxxxii) haloethyl substituted with hydroxy, halo-n-propyl substituted with hydroxy, or haloisopropyl substituted with hydroxy, (xxxxiii) ethylsulfonyl substituted with hydroxy, isobutylsulfonyl substituted with hydroxy, or (xxxxiv) cyclobutyl substituted with hydroxy (the cyclobutyl of the cyclobutyl substituted with hydroxy is unsubstituted or is substituted with one carboxy), cyclopentyl substituted with hydroxy, wherein $R^{61}$ and $R^{62}$ each independently represent a hydrogen atom, a fluorine atom, methyl, methoxy, or methylsulfonyl;

(d) when ring C is pyridyl, ring C is pyridin-2-yl or pyridin-4-yl;

$R^{54}$ represents:

(i) carboxy, (iii) n-propyl substituted with carboxy (the methylene moiety at position α of the carboxy of the n-propyl substituted with carboxy is replaced with propane-2,2-diyl), (iv) ethoxy substituted with carboxy (the methylene moiety at position α of the carboxy of the ethoxy substituted with carboxy is replaced with propane-2,2-diyl), (v) mono-n-propylaminocarbonyl substituted with carboxy (the methylene moiety at position ca of the carboxy of the mono-n-propylaminocarbonyl substituted with carboxy is replaced with propane-2,2-diyl);
wherein $R^{61}$ and $R^{62}$ represent a hydrogen atom;
(g) when ring C is tetrahydronaphthyl,
ring C represents the structure represented by formula [XII-1], formula [XII-2], or formula [XII-3] below,

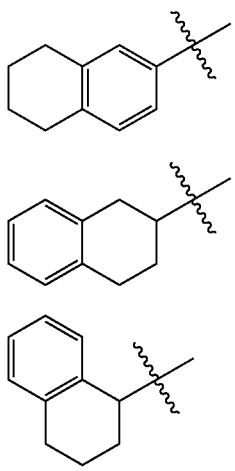

[XII-1]

[XII-2]

[XII-3]

$R^{54}$ represents carboxy, wherein $R^{61}$ and $R^{62}$ represent a hydrogen atom;
(h) when ring C is chromanyl,
ring C represents the structure represented by formula [XIII-1] or formula [XIII-2] below

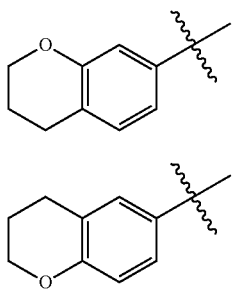

[XIII-1]

[XIII-2]

$R^{54}$ represents carboxy, wherein $R^{61}$ and $R^{62}$ represent a hydrogen atom;
(j) when ring C is indazolyl,
$R^{54}$ represents methyl substituted with carboxy, wherein $R^{61}$ and $R^{62}$ represent a hydrogen atom;
(p) when ring C is the structure represented by formula [IX-2] above,
$R^{54}$ represents
(i) carboxy, or
(ii) ethyl substituted with carboxy, wherein $R^{61}$ and $R^{62}$ represent a hydrogen atom;
(q) when ring C is the structure represented by formula [IX-3] above,
$R^{54}$ represents carboxy, wherein $R^{61}$ and $R^{62}$ represent a hydrogen atom;
(r) when ring C is the structure represented by formula [IX-4] above,
$R^{54}$ represents carboxy, wherein $R^{61}$ and $R^{62}$ represent a hydrogen atom;

$W^4$ represents methanediyl, ethane-1,2-diyl, propane-1,3-diyl, or the formula —O—CH$_2$CH$_2$—;
or a pharmaceutically acceptable salt thereof.

4. The compound according to claim 1, wherein the structure represented by formula [II] below is the structure represented by formula [III-1] below:

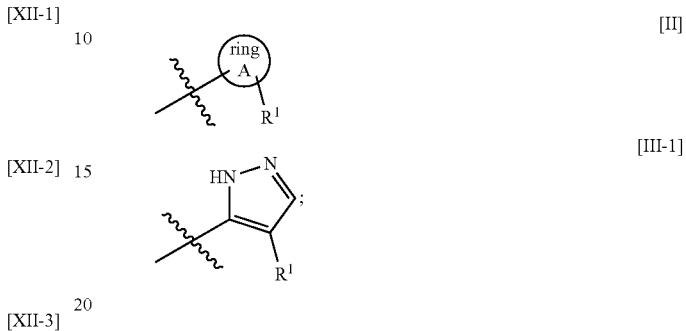

[II]

[III-1]

or a pharmaceutically acceptable salt thereof.

5. The compound according to claim 1, wherein
$R^1$ represents a hydrogen atom;
$R^2$ represents a hydrogen atom;
$R^3$ represents a hydrogen atom;
$R^4$ represents a hydrogen atom;
wherein (B) when $R^5$ represents the structure represented by formula [IV-2] below

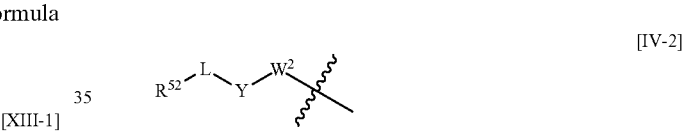

[IV-2]

$R^{52}$ represents carboxy,
L represents the structure represented by formula [VI-4] or formula [VI-7] below

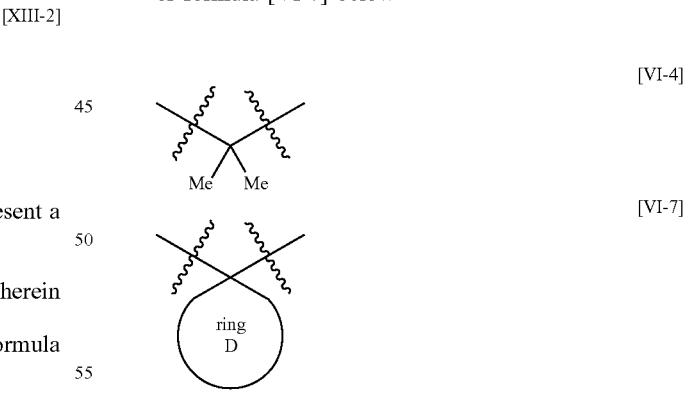

[VI-4]

[VI-7]

wherein ring D represents (ii) 4- to 6-membered saturated oxygen-containing hetero ring,
Y represents the formula —CH$_2$—, or the formula —O—,
$W^2$ represents C$_{7-8}$alkanediyl, wherein one of the carbon atoms that constitute the C$_{7-8}$alkanediyl represented by $W^2$ is a carbon atom or is replaced with one oxygen atom;
(C) when $R^5$ represents the structure represented by formula [IV-3] below

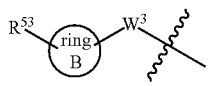

$R^{53}$ represents carboxy, ring B represents the structure represented by formula [VIII-7] below

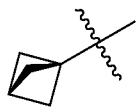

$W^3$ represents hexane-1,6-diyl;

(D) when $R^5$ represents the structure represented by formula [IV-4] below

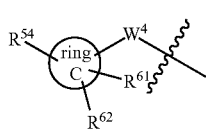

ring C represents (c) phenyl, (d) pyridyl, (g) tetrahydronaphthyl or (h) chromanyl, $W^4$ represents methanediyl;

(c) when ring C is phenyl, $R^{54}$ represents (xxi) $C_{3-6}$cycloalkyl substituted with carboxy, or
(xxxxvii) 4- to 6-membered saturated nitrogen-containing heterocyclylsulfonyl, which is substituted with carboxy (the 4- to 6-membered saturated nitrogen-containing heterocyclyl of the 4- to 6-membered saturated nitrogen-containing heterocyclylsulfonyl substituted with carboxy is unsubstituted or is substituted with one fluorine atom), wherein $R^{61}$ represents a hydrogen atom and $R^{62}$ represents a hydrogen atom;

(d) when ring C is pyridyl, $R^{54}$ represents (iv) $C_{1-4}$alkoxy substituted with carboxy, wherein $R^{61}$ represents a hydrogen atom and $R^{62}$ represents a hydrogen atom;

(g) when ring C is tetrahydronaphthyl, $R^{54}$ represents carboxy, wherein $R^{61}$ represents a hydrogen atom and $R^{62}$ represents a hydrogen atom;

(h) when ring C is chromanyl, $R^{54}$ represents carboxy, wherein $R^{61}$ represents a hydrogen atom and $R^{62}$ represents a hydrogen atom;

or a pharmaceutically acceptable salt thereof.

6. The compound according to claim 1,
wherein formula [I] is formula [I-D'] below,

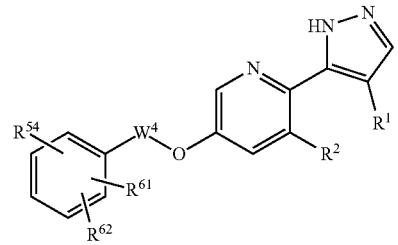

wherein
$R^1$ represents a hydrogen atom;
$R^2$ represents a hydrogen atom;
$R^{54}$ represents $C_{3-6}$cycloalkyl substituted with carboxy,
wherein $R^{61}$ and $R^{62}$ each independently represent a hydrogen atom, a fluorine atom, methyl, or methylsulfonyl;
$W^4$ represents $C_{1-3}$alkanediyl;
or a pharmaceutically acceptable salt thereof.

7. The compound according to claim 6,
wherein formula [I] is formula [I-D'] below,

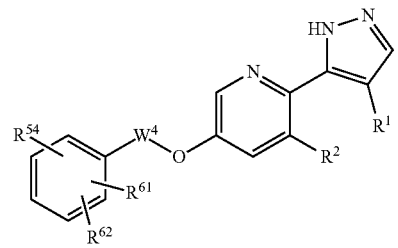

wherein
$R^1$ represents a hydrogen atom;
$R^2$ represents a hydrogen atom;
$R^{54}$ represents cyclopropyl substituted with carboxy,
wherein
$R^{61}$ represents a fluorine atom that substitutes the benzene ring at ortho position with respect to —$W^4$—,
$R^{62}$ represents a hydrogen atom;
$W^4$ represents methanediyl or ethane-1,2-diyl;
or a pharmaceutically acceptable salt thereof.

8. The compound according to claim 7,
wherein formula [I] is formula [I-D'] below,

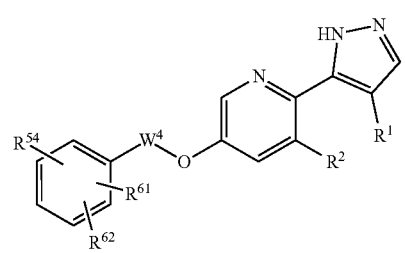

wherein
R¹ represents a hydrogen atom;
R² represents a hydrogen atom;
R⁵⁴ represents cyclopropyl substituted with carboxy, which substitutes the benzene ring at meta position with respect to —W⁴—,
wherein R⁶¹ represents a fluorine atom that substitutes the benzene ring at ortho position with respect to —W⁴—,
R⁶² represents a hydrogen atom;
W⁴ represents methanediyl or ethane-1,2-diyl;
or a pharmaceutically acceptable salt thereof.

9. The compound according to claim 6, wherein formula [I] is formula [I-D'] below,

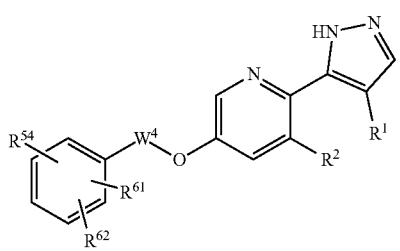

[I-D']

wherein
R¹ represents a hydrogen atom;
R² represents a hydrogen atom;
R⁵⁴ represents cyclopropyl substituted with carboxy, which substitutes the benzene ring at meta position with respect to —W⁴—,
wherein R⁶¹ and R⁶² each independently represent a hydrogen atom or a fluorine atom;
W⁴ represents ethane-1,2-diyl;
or a pharmaceutically acceptable salt thereof.

10. The compound according to claim 9, wherein formula [I] is formula [I-D'] below,

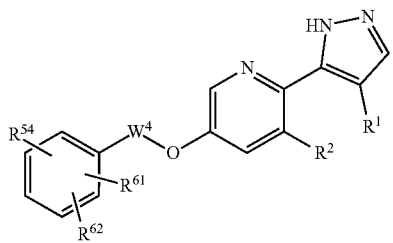

[I-D']

wherein
R¹ represents a hydrogen atom;
R² represents a hydrogen atom;
R⁵⁴ represents cyclopropyl substituted with carboxy, which substitutes the benzene ring at meta position with respect to —W⁴—,
wherein R⁶¹ represents a fluorine atom,
R⁶² represents a hydrogen atom;
W⁴ represents ethane-1,2-diyl;
or a pharmaceutically acceptable salt thereof.

11. The compound according to claim 6, wherein formula [I] is formula [I-D'] below,

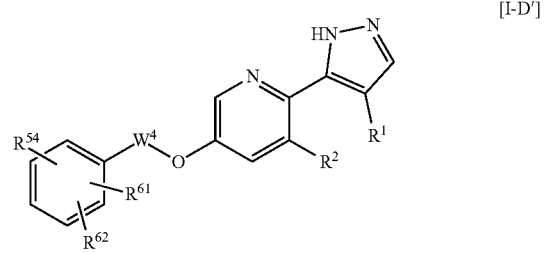

[I-D']

wherein
R¹ represents a hydrogen atom;
R² represents a hydrogen atom;
R⁵⁴ represents cyclopropyl substituted with carboxy,
wherein R⁶¹ and R⁶² each identically represent a hydrogen atom;
W⁴ represents ethane-1,2-diyl;
or a pharmaceutically acceptable salt thereof.

12. The compound according to claim 1, wherein formula [I] is formula [I-B] below,

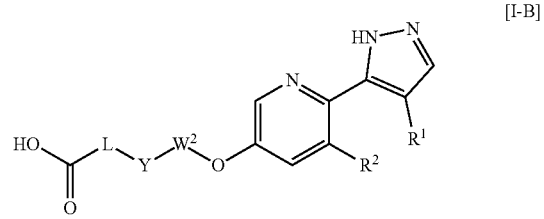

[I-B]

wherein
R¹ represents a hydrogen atom;
R² represents a hydrogen atom;
L is the structure represented by formula [VI-1], formula [VI-4], or [VI-7] below,

[VI-1]

[VI-4]

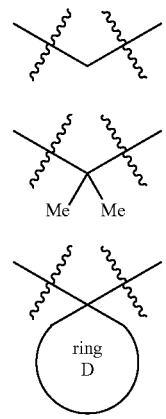

[VI-7]

wherein ring D represents
(i) C₃₋₆cycloalkane,
(ii) 4- to 6-membered saturated oxygen-containing hetero ring, or
(iv) 6-membered saturated nitrogen-containing hetero ring (the nitrogen atom of the 6-membered saturated nitrogen-containing hetero ring is unsubstituted or is substituted with one $C_{1-4}$alkylcarbonyl);

Y represents the formula —$CH_2$—, the formula —O—, or the formula —CONMe-;

$W^2$ represents $C_{2-10}$alkanediyl, wherein one of the carbon atoms that constitute $C_{2-10}$alkanediyl represented by $W^2$ is a carbon atom or is replaced with one oxygen atom;

or a pharmaceutically acceptable salt thereof.

13. The compound according to claim 12, wherein formula [I] is formula [I-B] below,

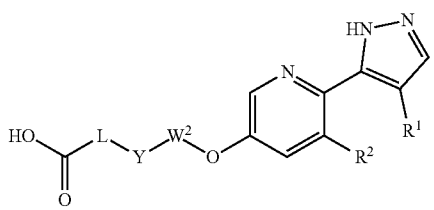
[I-B]

wherein $R^1$ represents a hydrogen atom;

$R^2$ represents a hydrogen atom;

L represents the structure represented by formula [VI-7] below

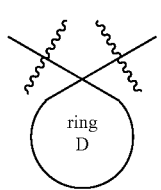
[VI-7]

wherein ring D represents (i) $C_4$cycloalkane, or (ii) 4-membered saturated oxygen-containing hetero ring;

Y represents the formula —$CH_2$— or the formula —O—;

$W^2$ represents heptane-1,7-diyl;

or a pharmaceutically acceptable salt thereof.

14. The compound according to claim 1, wherein formula [I] is formula [I-B] below,

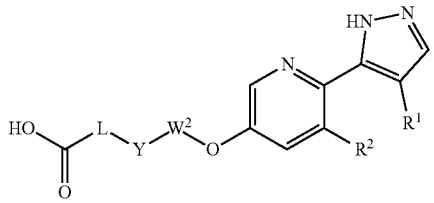
[I-B]

wherein $R^1$ represents a hydrogen atom;

$R^2$ represents a hydrogen atom;

L represents the structure represented by formula [VI-7] below

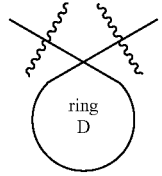
[VI-7]

wherein ring D represents (i) $C_4$cycloalkane, (ii) 4-membered saturated oxygen-containing hetero ring, or (iii) 4-membered saturated sulfur-containing hetero ring (the sulfur atom of the 4-membered saturated sulfur-containing hetero ring is substituted with two oxo), Y represents the formula —$CH_2$— or the formula —O—;

$W^2$ represents heptane-1,7-diyl;

or a pharmaceutically acceptable salt thereof.

15. The compound according to claim 1, which is shown below:

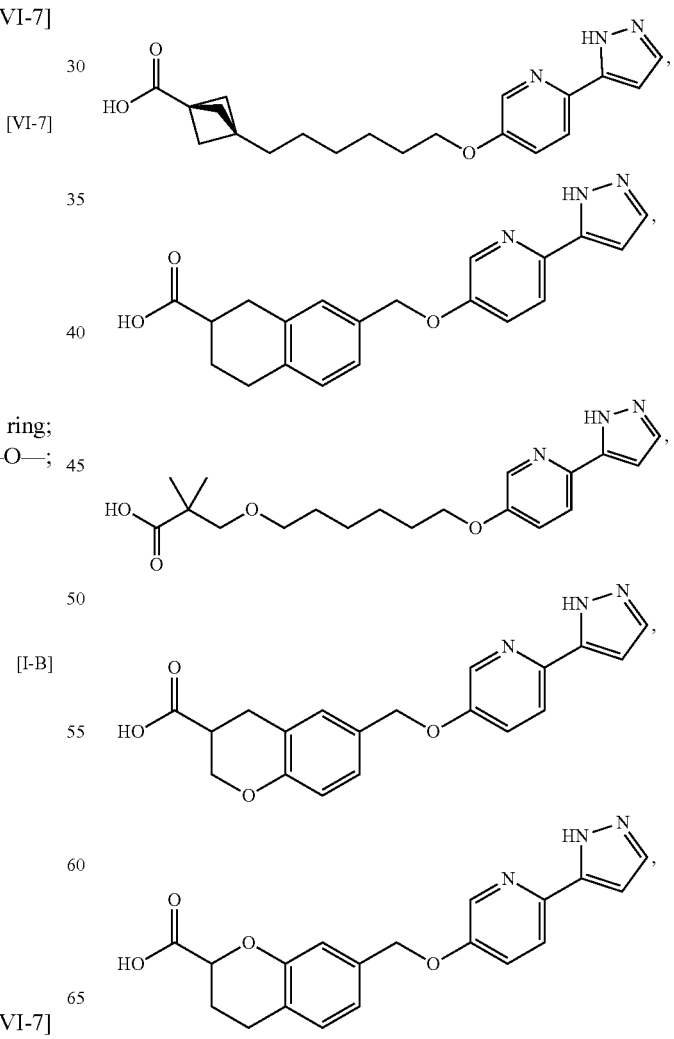

705
-continued
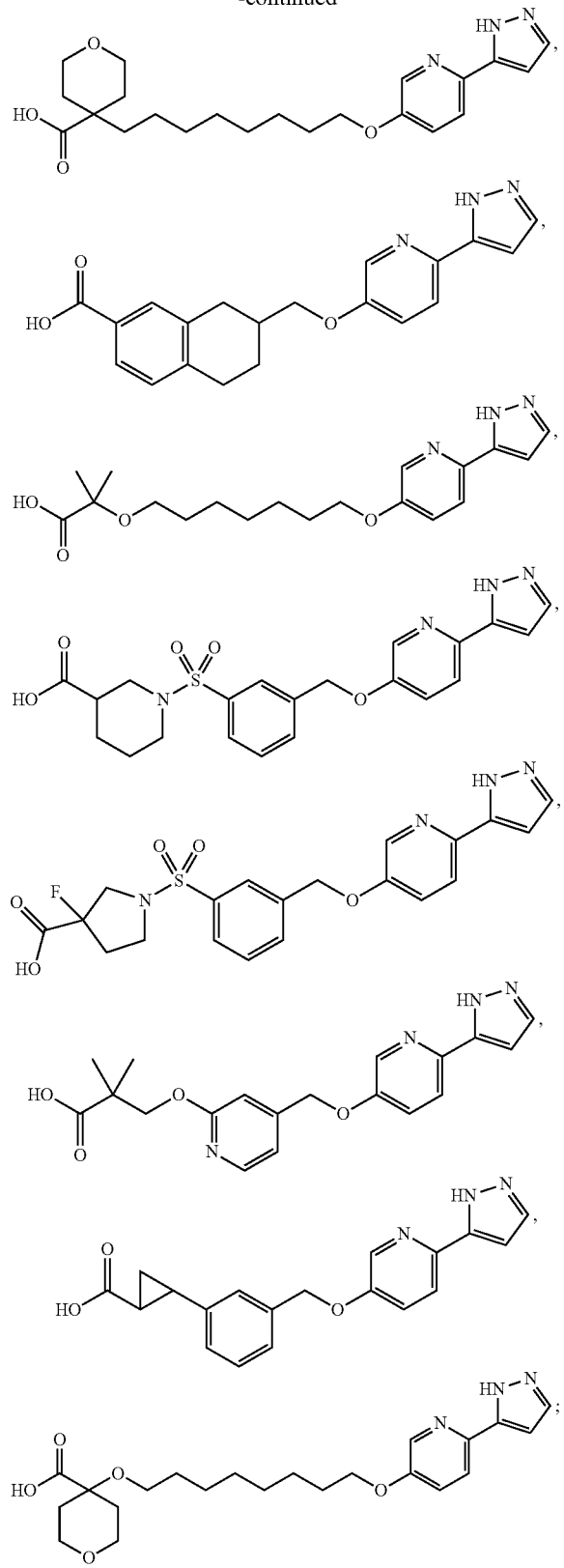
or a pharmaceutically acceptable salt thereof.
16. The compound according to claim 1, which is shown below:
706
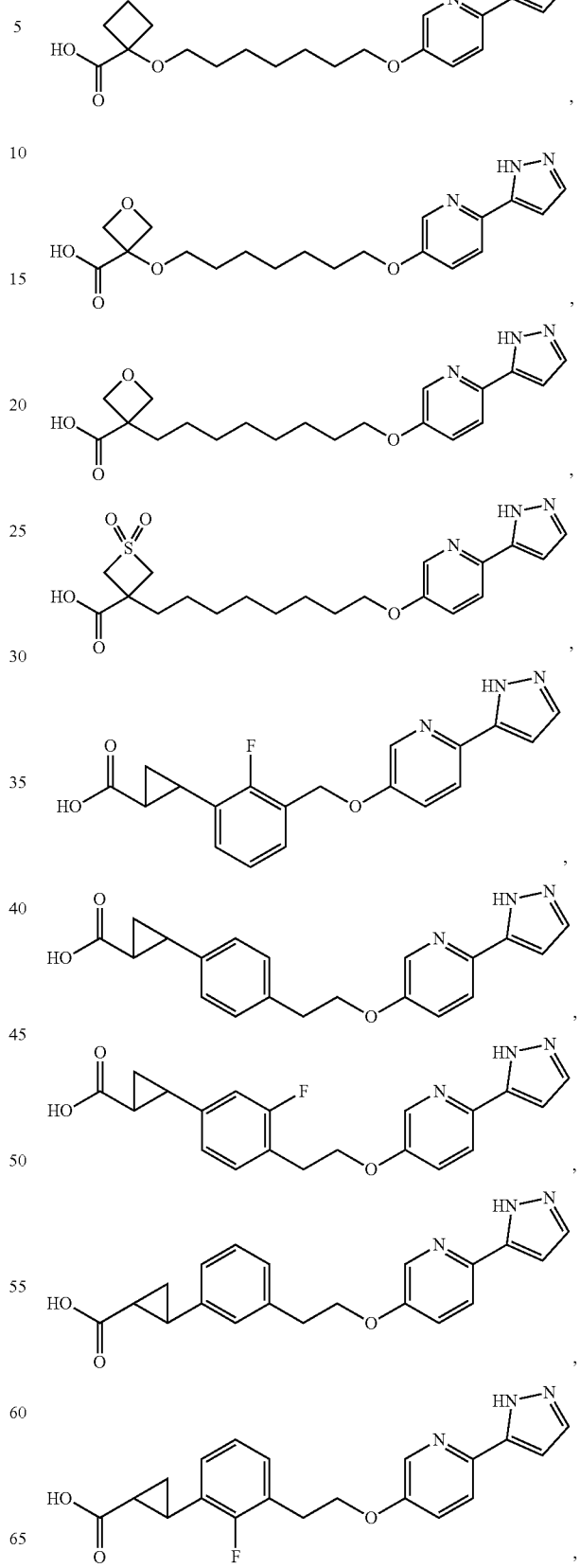

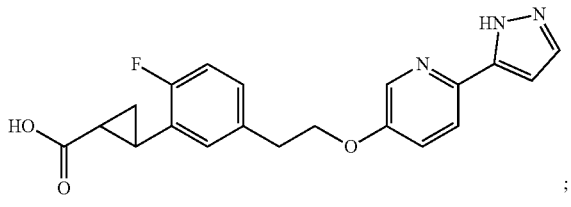

or a pharmaceutically acceptable salt thereof.

17. The compound according to claim 1, which is shown below:

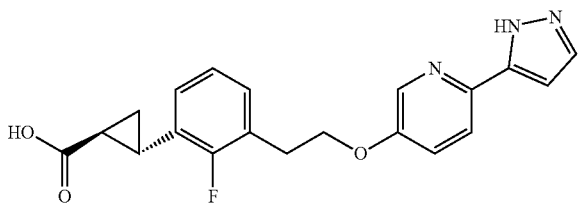 [SMILES: O=C(O)[C@H]1C[C@@H]1c1cccc(CCOc2ccc(-c3ccn[nH]3)nc2)c1F]

or a pharmaceutically acceptable salt thereof.

18. The compound according to claim 1, which is shown below:

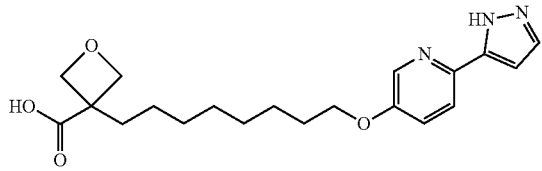 [SMILES: O=C(O)C1(CCCCCCCCOc2ccc(-c3ccn[nH]3)nc2)COC1]

or a pharmaceutically acceptable salt thereof.

19. The compound according to claim 1, which is shown below:

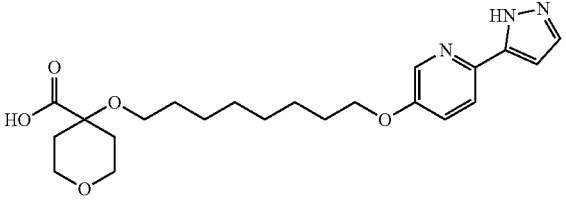 [SMILES: O=C(O)C1(OCCCCCCCCOc2ccc(-c3ccn[nH]3)nc2)CCOCC1]

or a pharmaceutically acceptable salt thereof.

20. The compound according to claim 1, which is shown below:

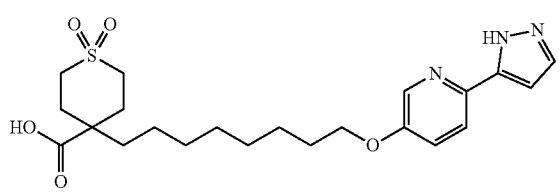 [SMILES: O=C(O)C1(CCCCCCCCOc2ccc(-c3ccn[nH]3)nc2)CCS(=O)(=O)CC1]

or a pharmaceutically acceptable salt thereof.

21. A pharmaceutical comprising the compound or pharmaceutically acceptable salt thereof according to claim 1 an active ingredient.

22. A method of inhibiting 20-HETE producing enzyme in a subject in need thereof, the method comprising administering to the subject an effective amount of the compound or pharmaceutically acceptable salt thereof according to claim 1 for inhibiting the 20-HETE producing enzyme.

23. A method of treating polycystic kidney disease in a subject in need thereof, the method comprising administering to the subject an effective amount of the compound or pharmaceutically acceptable salt thereof according to claim 1 as an active ingredient for treating the polycystic kidney disease.

* * * * *

UNITED STATES PATENT AND TRADEMARK OFFICE
CERTIFICATE OF CORRECTION

PATENT NO. : 11,365,192 B2
APPLICATION NO. : 16/637595
DATED : June 21, 2022
INVENTOR(S) : Hiroaki Tanaka et al.

It is certified that error appears in the above-identified patent and that said Letters Patent is hereby corrected as shown below:

In the Claims

Claim 1, Column 677, Line 14, "$W_{33}$" should read as --$W^{33}$--.

Claim 1, Column 679, Line 34, "$C_1$ 4alkyl" should read as --$C_{1-4}$alkyl--.

Claim 1, Column 679, Line 59, "ca" should read as --α--.

Claim 1, Column 681, Line 40, "cc" should read as --α--.

Claim 3, Column 696, Line 67, "ca" should read as --α--.

Signed and Sealed this
First Day of November, 2022

*Katherine Kelly Vidal*

Katherine Kelly Vidal
*Director of the United States Patent and Trademark Office*

Page 1 of 1